US012281057B2

(12) United States Patent
Ahmad et al.

(10) Patent No.: US 12,281,057 B2
(45) Date of Patent: Apr. 22, 2025

(54) CARBOXAMIDES AS MODULATORS OF SODIUM CHANNELS

(71) Applicant: VERTEX PHARMACEUTICALS INCORPORATED, Boston, MA (US)

(72) Inventors: Nadia M. Ahmad, Didcot (GB); Corey Anderson, Brighton, MA (US); Vijayalaksmi Arumugam, San Marcos, CA (US); Iuliana Luci Asgian, San Diego, CA (US); Joanne Louise Camp, Didcot (GB); Lev Tyler Dewey Fanning, San Marcos, CA (US); Sara Sabina Hadida Ruah, La Jolla, CA (US); Dennis Hurley, San Marcos, CA (US); Yvonne Schmidt, San Diego, CA (US); David Shaw, Oxford (GB); Urvi Patel, San Diego, CA (US); Stephen Andrew Thomson, Del Mar, CA (US); Lidio Marx Carvalho Meireles, San Marcos, CA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

(21) Appl. No.: 18/065,208

(22) Filed: Dec. 13, 2022

(65) Prior Publication Data

US 2023/0286907 A1    Sep. 14, 2023

Related U.S. Application Data

(62) Division of application No. 16/824,255, filed on Mar. 19, 2020, now Pat. No. 11,603,351, which is a division of application No. 16/032,799, filed on Jul. 11, 2018, now Pat. No. 10,647,661.

(60) Provisional application No. 62/608,283, filed on Dec. 20, 2017, provisional application No. 62/531,313, filed on Jul. 11, 2017.

(51) Int. Cl.
| | |
|---|---|
| *C07C 235/64* | (2006.01) |
| *A61K 31/165* | (2006.01) |
| *C07C 237/42* | (2006.01) |
| *C07D 213/69* | (2006.01) |
| *C07D 213/81* | (2006.01) |
| *C07D 213/82* | (2006.01) |
| *C07D 213/89* | (2006.01) |
| *C07D 239/34* | (2006.01) |
| *C07D 239/42* | (2006.01) |
| *C07D 307/79* | (2006.01) |
| *C07D 307/86* | (2006.01) |
| *C07D 317/46* | (2006.01) |
| *C07D 405/12* | (2006.01) |

(52) U.S. Cl.
CPC .......... *C07C 235/64* (2013.01); *A61K 31/165* (2013.01); *C07C 237/42* (2013.01); *C07D 213/69* (2013.01); *C07D 213/81* (2013.01); *C07D 213/82* (2013.01); *C07D 213/89* (2013.01); *C07D 239/34* (2013.01); *C07D 239/42* (2013.01); *C07D 307/79* (2013.01); *C07D 307/86* (2013.01); *C07D 317/46* (2013.01); *C07D 405/12* (2013.01); *C07B 2200/05* (2013.01); *C07C 2601/02* (2017.05)

(58) Field of Classification Search
CPC ... C07C 237/42; C07C 235/64; C07D 239/34; C07D 239/42; C07D 307/79; C07D 307/86; C07D 317/46; C07D 405/12; C07D 213/69; C07D 213/81; C07D 213/82; C07D 213/89
See application file for complete search history.

(56) References Cited

U.S. PATENT DOCUMENTS

| | | | |
|---|---|---|---|
| 2,511,231 | A | 6/1950 | Weissberger et al. |
| 2,657,134 | A | 10/1953 | Graham et al. |
| 2,688,617 | A | 9/1954 | Hein et al. |
| 2,694,718 | A | 11/1954 | Salminen et al. |
| 2,710,802 | A | 6/1955 | Parmerter et al. |
| 2,710,803 | A | 6/1955 | Salminen et al. |
| 2,721,798 | A | 10/1955 | Loria et al. |
| 2,725,292 | A | 11/1955 | Graham et al. |
| 2,772,163 | A | 11/1956 | Tong |
| 4,146,637 | A | 3/1979 | Metz et al. |
| 4,218,765 | A | 8/1980 | Kinkade |
| 4,639,273 | A | 1/1987 | Gilmore et al. |
| 5,258,407 | A | 11/1993 | Washburn et al. |
| 5,304,121 | A | 4/1994 | Sahatjian |
| 5,310,760 | A | 5/1994 | Washburn et al. |
| 5,312,960 | A | 5/1994 | Kramer et al. |

(Continued)

FOREIGN PATENT DOCUMENTS

| | | |
|---|---|---|
| BE | 854683 | 11/1977 |
| CA | 1091247 | 12/1980 |

(Continued)

OTHER PUBLICATIONS

Akopian, A.N., L. Sivilotti, and J.N. Wood, A tetrodotoxin-resistant voltage-gated sodium channel expressed by sensory neurons. Nature, 1996. 379(6562): p. 257-62.

(Continued)

*Primary Examiner* — Rebecca L Anderson
(74) *Attorney, Agent, or Firm* — Barnes & Thornburg, LLP

(57) ABSTRACT

Compounds, and pharmaceutically acceptable salts thereof, useful as inhibitors of sodium channels are provided. Also provided are pharmaceutical compositions comprising the compounds or pharmaceutically acceptable salts and methods of using the compounds, pharmaceutically acceptable salts, and pharmaceutical compositions in the treatment of various disorders, including pain.

15 Claims, No Drawings

(56) References Cited

U.S. PATENT DOCUMENTS

| | | |
|---|---|---|
| 5,532,235 A | 7/1996 | Albright et al. |
| 5,536,718 A | 7/1996 | Albright et al. |
| 5,886,026 A | 3/1999 | Hunter et al. |
| 6,099,562 A | 8/2000 | Ding et al. |
| 6,211,242 B1 | 4/2001 | Setoi et al. |
| 6,235,680 B1 | 5/2001 | Ziemer et al. |
| 6,531,291 B1 | 3/2003 | Kabbash et al. |
| 6,699,994 B1 | 3/2004 | Babu et al. |
| 6,936,719 B2 | 8/2005 | Babu et al. |
| 7,056,910 B2 | 6/2006 | Koshio et al. |
| 7,374,749 B2 | 5/2008 | Haase et al. |
| 7,863,280 B2 | 1/2011 | Paukert et al. |
| 8,389,734 B2 | 3/2013 | Chen et al. |
| 8,466,188 B2 | 6/2013 | Chafeev et al. |
| 8,481,479 B1 | 7/2013 | Mousa |
| 8,519,137 B2 | 8/2013 | Joshi et al. |
| 8,779,197 B2 | 7/2014 | Chen et al. |
| 8,841,483 B2 | 9/2014 | Joshi et al. |
| 8,865,771 B2 | 10/2014 | Chen et al. |
| 8,883,840 B2 | 11/2014 | Chafeev et al. |
| 9,051,270 B2 | 6/2015 | Hadida-Ruah et al. |
| 9,108,903 B2 | 8/2015 | Hadida-Ruah et al. |
| 9,139,529 B2 | 9/2015 | Hadida-Ruah et al. |
| 9,163,042 B2 | 10/2015 | Anderson et al. |
| 9,169,246 B2 | 10/2015 | Benazet et al. |
| 9,393,235 B2 | 7/2016 | Hadida-Ruah et al. |
| 9,421,196 B2 | 8/2016 | Hadida-Ruah et al. |
| 9,464,102 B2 | 10/2016 | Anderson et al. |
| 9,758,483 B2 | 9/2017 | Hadida-Ruah et al. |
| 9,783,501 B2 | 10/2017 | Hadida-Ruah et al. |
| 9,828,397 B2 | 11/2017 | Anderson et al. |
| 10,087,143 B2 | 10/2018 | Hadida-Ruah et al. |
| 10,253,054 B2 | 4/2019 | Anderson et al. |
| 10,647,661 B2 | 5/2020 | Ahmad et al. |
| 11,603,351 B2 | 3/2023 | Ahmad et al. |
| 2002/0002183 A1 | 1/2002 | Zhu et al. |
| 2002/0032238 A1 | 3/2002 | Priepke et al. |
| 2002/0173656 A1 | 11/2002 | Peyman et al. |
| 2003/0225158 A1 | 12/2003 | Auerbach et al. |
| 2004/0058903 A1 | 3/2004 | Takasugi et al. |
| 2004/0132745 A1 | 7/2004 | Bertinato et al. |
| 2004/0186148 A1 | 9/2004 | Shankar et al. |
| 2005/0038035 A1 | 2/2005 | Takasugi et al. |
| 2005/0207972 A1 | 9/2005 | Friebe et al. |
| 2007/0237840 A1 | 10/2007 | Chern et al. |
| 2007/0238733 A1 | 10/2007 | Joshi et al. |
| 2008/0192127 A1 | 8/2008 | Sakai et al. |
| 2008/0312235 A1 | 12/2008 | Lane et al. |
| 2009/0012091 A1 | 1/2009 | Yu |
| 2009/0029994 A1 | 1/2009 | Nakamura et al. |
| 2009/0048306 A1 | 2/2009 | Bagal et al. |
| 2009/0074884 A1 | 3/2009 | Chesney et al. |
| 2009/0099233 A1 | 4/2009 | Joshi et al. |
| 2009/0118333 A1 | 5/2009 | Chen et al. |
| 2009/0118338 A1 | 5/2009 | Chen et al. |
| 2009/0163545 A1 | 6/2009 | Goldfarb |
| 2009/0326020 A1 | 12/2009 | Miller et al. |
| 2010/0009970 A1 | 1/2010 | Johansen et al. |
| 2010/0075948 A1 | 3/2010 | Ding et al. |
| 2010/0152190 A1 | 6/2010 | Bartkovitz et al. |
| 2011/0046370 A1 | 2/2011 | Sim et al. |
| 2011/0178089 A1 | 7/2011 | Bissantz et al. |
| 2011/0257196 A1 | 10/2011 | Lu et al. |
| 2011/0306607 A1 | 12/2011 | Hadida-Ruah et al. |
| 2012/0196869 A1 | 8/2012 | Hadida Ruah et al. |
| 2012/0220605 A1 | 8/2012 | Pajouhesh et al. |
| 2012/0245136 A1 | 9/2012 | Hadida-Ruah et al. |
| 2012/0264749 A1 | 10/2012 | Hadida-Ruah et al. |
| 2013/0150339 A1 | 6/2013 | Boezio et al. |
| 2013/0231370 A1 | 9/2013 | Chen et al. |
| 2013/0274243 A1 | 10/2013 | Bagal et al. |
| 2013/0295187 A1 | 11/2013 | Mousa |
| 2013/0303535 A1 | 11/2013 | Tsuboi et al. |
| 2014/0094457 A1 | 4/2014 | Gardner et al. |
| 2014/0187533 A1 | 7/2014 | Pajouhesh et al. |
| 2014/0200215 A1 | 7/2014 | Buckman et al. |
| 2014/0213616 A1 | 7/2014 | Hadida-Ruah et al. |
| 2014/0221435 A1 | 8/2014 | Hadida-Ruah et al. |
| 2014/0228371 A1 | 8/2014 | Hadida-Ruah et al. |
| 2014/0296313 A1 | 10/2014 | Bagal et al. |
| 2015/0005304 A1 | 1/2015 | Hadida-Ruah et al. |
| 2015/0166589 A1 | 6/2015 | Anderson et al. |
| 2015/0245028 A1 | 8/2015 | Choi et al. |
| 2015/0328196 A1 | 11/2015 | Hadida-Ruah et al. |
| 2015/0336945 A1 | 11/2015 | Hadida-Ruah et al. |
| 2016/0009743 A1 | 1/2016 | Anderson et al. |
| 2016/0152561 A1 | 6/2016 | Hadida-Ruah et al. |
| 2016/0376295 A1 | 12/2016 | Anderson et al. |
| 2017/0037009 A1 | 2/2017 | Hadida-Ruah et al. |
| 2018/0016235 A1 | 1/2018 | Hadida-Ruah et al. |
| 2018/0044361 A1 | 2/2018 | Anderson et al. |
| 2019/0005521 A1 | 1/2019 | Nobe |
| 2019/0016671 A1 | 1/2019 | Ahmad et al. |
| 2019/0248745 A1 | 8/2019 | Hadida Ruah et al. |
| 2019/0276483 A1 | 9/2019 | Anderson et al. |
| 2019/0343817 A1 | 11/2019 | Agarwal et al. |

FOREIGN PATENT DOCUMENTS

| | | |
|---|---|---|
| CA | 2109195 | 2/1993 |
| CA | 2512582 | 7/2004 |
| CA | 2851462 | 7/2004 |
| CN | 101838264 | 9/2010 |
| CN | 101855210 A | 10/2010 |
| CN | 101883758 A | 11/2010 |
| CN | 103012397 | 4/2013 |
| CN | 103961348 | 8/2014 |
| CN | 104968647 A | 10/2015 |
| CN | 106317027 | 1/2017 |
| DE | 2623228 | 12/1977 |
| DE | 4023008 | 1/1991 |
| DE | 4019307 | 12/1991 |
| DE | 19523640 | 1/1997 |
| DE | 102004009238 | 9/2005 |
| DE | 102004050196 | 4/2006 |
| EP | 407217 | 1/1991 |
| EP | 569912 | 11/1993 |
| EP | 1217000 | 6/2002 |
| EP | 2573073 | 3/2013 |
| EP | 2606726 | 6/2013 |
| EP | 2997966 | 3/2016 |
| FR | 2628864 | 9/1989 |
| GB | 1555723 | 11/1979 |
| IT | 1349739 | 12/2008 |
| JP | 63-182182 | 7/1988 |
| JP | 05313169 | 11/1993 |
| JP | H 09-512528 A | 12/1997 |
| JP | 10-191842 | 7/1998 |
| JP | 10-213820 | 8/1998 |
| JP | 2003342175 | 12/2003 |
| JP | 2004502749 A | 1/2004 |
| JP | 2004043456 | 2/2004 |
| JP | 2004175739 | 6/2004 |
| JP | 2004315395 | 11/2004 |
| JP | 2006514032 A | 4/2006 |
| JP | 2008106017 | 5/2008 |
| JP | 2009108152 | 5/2009 |
| JP | 2009149754 | 7/2009 |
| JP | 2009209090 | 9/2009 |
| JP | 2009242540 | 10/2009 |
| JP | 2010001284 | 1/2010 |
| JP | 2010059131 | 3/2010 |
| JP | 2010066630 | 3/2010 |
| JP | 2010126651 | 6/2010 |
| JP | 2011006360 | 1/2011 |
| JP | 2011500599 | 1/2011 |
| JP | 2011500599 A | 1/2011 |
| JP | 2011500600 | 1/2011 |
| JP | 2011500600 A | 1/2011 |
| JP | 2011162678 | 8/2011 |
| JP | 2011207765 | 10/2011 |
| JP | 2014232188 | 12/2014 |
| JP | 2016506964 | 3/2016 |
| JP | 2016506964 A | 3/2016 |

(56) References Cited

FOREIGN PATENT DOCUMENTS

| | | |
|---|---|---|
| JP | 2016508500 | 3/2016 |
| JP | 2016508500 A | 3/2016 |
| WO | WO 1993016684 | 9/1993 |
| WO | WO 1995029152 | 11/1995 |
| WO | WO 1995032943 | 12/1995 |
| WO | WO 1996022282 | 7/1996 |
| WO | WO 1997001542 | 1/1997 |
| WO | WO 1997045016 | 12/1997 |
| WO | WO 1997049707 | 12/1997 |
| WO | WO 1998047879 | 10/1998 |
| WO | WO 1999047529 | 9/1999 |
| WO | WO 1999055663 | 11/1999 |
| WO | WO 1999065874 | 12/1999 |
| WO | WO 2000024707 | 5/2000 |
| WO | WO 2000064876 | 11/2000 |
| WO | WO 2001007028 | 2/2001 |
| WO | WO 2001019788 | 3/2001 |
| WO | WO 2001043732 | 6/2001 |
| WO | WO 2001056989 | 8/2001 |
| WO | WO 2001064642 | 9/2001 |
| WO | WO 2001064643 | 9/2001 |
| WO | WO 2001066098 | 9/2001 |
| WO | WO 2001070671 | 9/2001 |
| WO | WO 2001080894 | 11/2001 |
| WO | WO 2002004403 | 1/2002 |
| WO | WO 2002028835 | 4/2002 |
| WO | WO 2002034711 | 5/2002 |
| WO | WO 2002042273 | 5/2002 |
| WO | WO 2002046159 | 6/2002 |
| WO | WO 2002051397 | 7/2002 |
| WO | WO 2002054077 | 7/2002 |
| WO | WO 2002070483 | 9/2002 |
| WO | WO 2002090347 | 11/2002 |
| WO | WO 2002098839 | 12/2002 |
| WO | WO 2002101007 | 12/2002 |
| WO | WO 2003003008 | 1/2003 |
| WO | WO 2003003009 | 1/2003 |
| WO | WO 2003004020 | 1/2003 |
| WO | WO 2003007955 | 1/2003 |
| WO | WO 2003013516 | 2/2003 |
| WO | WO 2003018536 | 3/2003 |
| WO | WO 2003045921 | 6/2003 |
| WO | WO 2003055477 | 7/2003 |
| WO | WO 2003057205 | 7/2003 |
| WO | WO 2003062221 | 7/2003 |
| WO | WO 2003072532 | 9/2003 |
| WO | WO 2003075907 | 9/2003 |
| WO | WO 2004000820 | 12/2003 |
| WO | WO 2004014844 | 2/2004 |
| WO | WO 2004018428 | 3/2004 |
| WO | WO 2004052837 | 6/2004 |
| WO | WO 2004056777 | 7/2004 |
| WO | WO 2004062601 | 7/2004 |
| WO | WO 2005000309 | 1/2005 |
| WO | WO 2005023761 | 3/2005 |
| WO | WO 2005033079 | 4/2005 |
| WO | WO 2005040135 | 5/2005 |
| WO | WO 2005073165 | 8/2005 |
| WO | WO 2005085202 | 9/2005 |
| WO | WO 2006007864 | 1/2006 |
| WO | WO 2006011050 | 2/2006 |
| WO | WO 2006058905 | 6/2006 |
| WO | WO 2006067445 | 6/2006 |
| WO | WO 2006068199 | 6/2006 |
| WO | WO 2006137376 | 12/2006 |
| WO | WO 2007008627 | 1/2007 |
| WO | WO 2007013332 | 2/2007 |
| WO | WO 2007030567 | 3/2007 |
| WO | WO 2007052843 | 5/2007 |
| WO | WO 2007056143 | 5/2007 |
| WO | WO 2007071632 | 6/2007 |
| WO | WO 2007088996 | 8/2007 |
| WO | WO 2008044767 | 4/2008 |
| WO | WO 2008073670 | 6/2008 |
| WO | WO 2008074997 | 6/2008 |
| WO | WO 2008104994 | 9/2008 |
| WO | WO 2008135826 | 11/2008 |
| WO | WO 2008140810 | 11/2008 |
| WO | WO 2009000413 | 12/2008 |
| WO | WO 2009047105 | 4/2009 |
| WO | WO 2009047151 | 4/2009 |
| WO | WO 2009049180 | 4/2009 |
| WO | WO 2009049181 | 4/2009 |
| WO | WO 2009049183 | 4/2009 |
| WO | WO 2009070533 | 6/2009 |
| WO | WO 2010027746 | 3/2010 |
| WO | WO 2010031713 | 3/2010 |
| WO | WO 2010048149 | 4/2010 |
| WO | WO 2010133312 | 11/2010 |
| WO | WO 2010133748 | 11/2010 |
| WO | WO 2010138901 | 12/2010 |
| WO | WO 2011026240 | 3/2011 |
| WO | WO 2011032169 | 3/2011 |
| WO | WO 2011109059 | 9/2011 |
| WO | WO 2011133729 | 10/2011 |
| WO | WO 2011139765 | 11/2011 |
| WO | WO 2011140425 | 11/2011 |
| WO | WO 2012016133 | 2/2012 |
| WO | WO 2012026931 | 3/2012 |
| WO | WO 2012027392 | 3/2012 |
| WO | WO 2012106499 | 3/2012 |
| WO | WO 2012080729 | 6/2012 |
| WO | WO 2012112743 | 8/2012 |
| WO | WO 2012116440 | 9/2012 |
| WO | WO 2012125613 | 9/2012 |
| WO | WO 2012129562 | 9/2012 |
| WO | WO 2012166951 | 12/2012 |
| WO | WO 2012177668 | 12/2012 |
| WO | WO 2013003112 | 1/2013 |
| WO | WO 2013045400 | 4/2013 |
| WO | WO 2013061205 | 5/2013 |
| WO | WO 2013072502 | 5/2013 |
| WO | WO 2013092350 | 6/2013 |
| WO | WO 2013096060 | 6/2013 |
| WO | WO 2013109521 | 7/2013 |
| WO | WO 2013114250 | 8/2013 |
| WO | WO 2013131018 | 9/2013 |
| WO | WO 2014041125 | 3/2014 |
| WO | WO 2014055634 | 4/2014 |
| WO | WO 2014120808 | 8/2014 |
| WO | WO 2014120815 | 8/2014 |
| WO | WO 2014120820 | 8/2014 |
| WO | WO 2014134127 | 9/2014 |
| WO | WO 2014149207 | 9/2014 |
| WO | WO 2014157267 | 10/2014 |
| WO | WO 2014192681 | 12/2014 |
| WO | WO 2014204831 | 12/2014 |
| WO | WO 2015003816 | 1/2015 |
| WO | WO 2015010065 | 1/2015 |
| WO | WO 2015011284 | 1/2015 |
| WO | WO 2015014900 | 2/2015 |
| WO | WO 2015030898 | 3/2015 |
| WO | WO 2015046827 | 4/2015 |
| WO | WO 2015085238 | 6/2015 |
| WO | WO 2015089361 | 6/2015 |
| WO | WO 2015196072 | 12/2015 |
| WO | WO 2016022626 | 1/2016 |
| WO | WO 2016040449 | 3/2016 |
| WO | WO 2017040982 | 3/2017 |
| WO | WO 2017062751 | 4/2017 |
| WO | WO 2017066705 | 4/2017 |
| WO | WO 2017161028 | 9/2017 |
| WO | WO 2018060110 | 4/2018 |
| WO | WO 2018064119 | 4/2018 |
| WO | WO 2018161033 | 9/2018 |
| WO | WO 2018195439 | 10/2018 |
| WO | WO 2018202681 | 11/2018 |
| WO | WO 2019014352 | 1/2019 |
| WO | WO 2019018119 | 1/2019 |
| WO | WO 2019036657 | 2/2019 |
| WO | WO 2019150220 | 8/2019 |
| WO | WO 2019206925 | 10/2019 |
| WO | WO 2019207081 | 10/2019 |
| WO | WO 2019241787 | 12/2019 |

(56) References Cited

FOREIGN PATENT DOCUMENTS

| | | |
|---|---|---|
| WO | WO 2020051207 | 3/2020 |
| WO | WO 2020081572 | 4/2020 |
| WO | WO 2020123675 | 6/2020 |
| WO | WO 2020139748 | 7/2020 |
| WO | WO 2020146612 | 7/2020 |
| WO | WO 2020146682 | 7/2020 |
| WO | WO 2020152079 | 7/2020 |
| WO | WO 2020159576 | 8/2020 |
| WO | WO 2020176763 | 9/2020 |
| WO | WO 2020190774 | 9/2020 |
| WO | WO 2020198712 | 10/2020 |
| WO | WO 2020219867 | 10/2020 |
| WO | WO 2020221677 | 11/2020 |
| WO | WO 2020251974 | 12/2020 |

OTHER PUBLICATIONS

Balasegaram, T. et al., "Structure-Activity Relations. Part 9. The Biological Activity and Mode of Action of Substituted 2-Phenoxy-N'phenyl-pyridine-3-carboxamides," J. Chem. Research (S), (1991), pp. 234.

Berge, S.M., et al. describe pharmaceutically acceptable salts in detail in J. Pharmaceutical Sciences, 1977, 66, 1-19.

Black, J.A., et al., Multiple sodium channel isoforms and mitogen-activated protein kinases are present in painful human neuromas. Ann. Neurol., 2008. 64(6): p. 644-53.

Blair, N.T. and B.P. Bean, Roles of tetrodotoxin (TTX)-sensitive Na+ current, TTX-resistant Na+ current, and Ca2+ current in the action potentials of nociceptive sensory neurons. J. Neurosci., 2002. 22(23): p. 10277-90.

Bolton et al., "Discovery of nonbenzamidine factor VIIa inhibitors using a biaryl acid scaffold," Bioorganic & Medicinal Chemistry Letters, vol. 23, Iss. 18, (Sep. 15, 2013), pp. 5239-5243.

Catterall, W. A., Goldin, A. L., and Waxman, S. G., International Union of Pharmacology. XLVII. Nomenclature and structure-function relationships of voltage- gated sodium channels. Pharmacol. Rev. 57 (4), p. 397 (2005).

Chahine, M., Chatelier, A., Babich, O., and Krupp, J. J., Voltage-gated sodium channels in neurological disorders. CNS Neurol. Disord. Drug Targets 7 (2), p. 144-58 (2008).

Cheney et al., "Discovery of Novel P1 Groups for Coagulation Factor VIIa Inhibition Using Fragment-Based Screening," J. med. Chem., (2015), 58, 6, pp. 2799-2808.

Coward, K., et al., Immunolocalization of SNS/PN3 and NaN/SNS2 sodium channels in human pain states. Pain, 2000. 85(1-2): p. 41-50.

Deak HL, et al., "N-(3-(Phenylcarbamoyl)arylpyrimidine)-5-carboxamides as potent and selective inhibitors of Lck: Structure, synthesis and SAR." Bioorg. Med. Chem. Lett., (Feb. 1, 2008); 18(3); pp. 1172-1176.

Dieleman, J.P., et al., Incidence rates and treatment of neuropathic pain conditions in the general population. Pain, 2008. 137(3): p. 681-8.

Dong, X.W., et al., Small interfering RNA-mediated selective knockdown of Na(V)1.8 tetrodotoxin-resistant sodium channel reverses mechanical allodynia in neuropathic rats. Neuroscience, 2007. 146(2): p. 812-21.

England, S., Voltage-gated sodium channels: the search for subtype-selective analgesics. Expert Opin. Investig. Drugs 17 (12), p. 1849-64 (2008).

Harbeson, S.L., and Tung, Deuterium in Drug Discovery and Development, Ann. Rep. Med. Chem. 2011, 46, 403-417.

Huang, H.L., et al., Proteomic profiling of neuromas reveals alterations in protein composition and local protein synthesis in hyperexcitable nerves. Mol. Pain, 2008. 4: p. 33.

Jarvis, M.F., et al., A-803467, a potent and selective NaV1.8 sodium channel blocker, attenuates neuropathic and inflammatory pain in the rat. Proc. Natl. Acad. Sci. U S A, 2007. 104(20): p. 8520-5.

Joshi, S.K., et al., Involvement of the TTX-resistant sodium channel Nav1.8 in inflammatory and neuropathic, but not post-operative, pain states. Pain, 2006. 123(1-2): pp. 75-82.

Kassah, E.A. et al., "Synthesis and behavior of a static benzoxazinone derivative towards nitrogen and sulphur nucleophieles," Egyptian Journal of Chemistry, 44, (2001); pp. 169-180.

Krafte, D. S. and Bannon, A. W., Sodium channels and nociception: recent concepts and therapeutic opportunities. Curr. Opin. Pharmacol. 8 (1), p. 50-56 (2008).

Lai, J., et al., Inhibition of neuropathic pain by decreased expression of the tetrodotoxin-resistant sodium channel, NaV1.8. Pain, 2002. 95(1-2): p. 143-52.

Lambeng et al., "Arylsulfonamides as a new class of cannabinoid CB1 receptor ligands: Identification of a lead and initial SAR studies," Bioorganic & Medicinal Chemistry Letters, vol. 17, Iss. 1, (Jan. 1, 2007), pp. 272-277.

Li, J., et al., "Discovery of potent and orally active MTP inhibitors as potential anti-obesity agents," Bioorganic & Medicinal Chemistry Letters, vol. 16, Iss. 11, 16 (Jun. 2006), pp. 3039-3042.

Liew et al., "SVM Model for Virtual Screening of Lck Inhibitors," J. Chem. Inf. Model. (2009), 44, 4, pp. 877-885.

Mehta et al., "Synthesis, characterization and antimicrobial activity of 1, 3, 4,-oxadiazoles derivatives of benzimidazoles," Chem. Sci. Rev. & Lett., 2014, 3(11), pp. 522-528.

Mehta et al., "Synthesis, characterization and antimicrobial evaluation of some novel benzenesulfonylhydrazone derivatives of benzimidazole," Der ChemicaSinica, 2015, 6(2): pp. 29-34.

Micronized amino-substituted hydroxyphenylbenzophenone derivatives IP.com Journal (Feb. 24, 2006) IP134143D.

Miura et al., "Design, synthesis and biological activity of selective and orally available TF/FVIIa complex inhibitors containing non-amidine P1 ligands," Bioorg. Med. Chem. (Jan. 1, 2007); 15(1): pp. 160-173.

Miura et la., "Potent and selective TF/FVIIa inhibitors containing a neutral P1 ligand," Bioorg. Med. Chem. (Dec. 1, 2006); 14(23): pp. 7688-7705.

Naruto et al., "Synthesis of yokonoside and its related compounds," Yakugaku Zassh (Aug. 1976); 96(8): pp. 945-951.

Nielsen et la., "2-(4-Methoxyphenoxy)-5-nitro-N-(4-sulfamoylphenyl)benzamide activates Kir6.2/SUR1 KATP channels," Bioorg. Med. Chem. Lett. (Dec. 6, 2004); 14(23): pp. 5727-5730.

Preparation of amino substituted hydroxyl phenyl benzophenone derivatives and their uses as UV filters in sunscreen formulations, IP.com Journal (Aug. 4, 2003) IP 18721D.

Renganathan, M., T.R. Cummins, and S.G. Waxman, Contribution of Na(V)1.8 sodium channels to action potential electrogenesis in DRG neurons. J. Neurophysiol., 2001. 86(2): p. 629-40.

Roza, C., et al., The tetrodotoxin-resistant Na+ channel NaV1.8 is essential for the expression of spontaneous activity in damaged sensory axons of mice. J. Physiol., 2003. 550(Pt 3): p. 921-6.

Rush, A.M. and T.R. Cummins, Painful Research: Identification of a Small-Molecule Inhibitor that Selectively Targets NaV1.8 Sodium Channels. Mol. Interv., 2007. 7(4): p. 192-5).

Rush, A.M., et al., A single sodium channel mutation produces hyper- or hypoexcitability in different types of neurons. Proc. Natl. Acad. Sci. USA, 2006. 103(21): p. 8245-50).

Shirley, V.S., & Lederer, C.M., Isotopes Project, Nuclear Science Division, Lawrence Berkeley Laboratory, Table of Nuclides (Jan. 1980).

Soderpalm, B., Anticonvulsants: aspects of their mechanisms of action. Eur. J. Pain 6 Suppl. A, p. 3-9 (2002).

Strickland, I.T., et al., Changes in the expression of NaV1.7, NaV1.8 and NaV1.9 in a distinct population of dorsal root ganglia innervating the rat knee joint in a model of chronic inflammatory joint pain. Eur. J. Pain, 2008. 12(5): p. 564-72.

Use of amino hydroxy benzophenone derivatives for protecting human hair and skin, IP.com Journal (Aug. 10, 2006) IP 138915D.

Use of aminohydroxybenzophenone derivatives in sunscreen preparations, IP.com Journal (Aug. 24, 2006) IP139425D.

Vertex Announces Treatment with the NaV1.8 Inhibitor VX-150 Showed Significant Relief of Acute Pain in Phase 2 Study (Feb. 14, 2018).

(56) References Cited

OTHER PUBLICATIONS

Wang et al., "Kinetics of extractable residue, bound residue and mineralization of a novel herbicide, ZJ0273, in aerobic soils," Chemosphere, vol. 76, Iss. 8, (Aug. 2009), pp. 1036-1040.

Wang et al., "Studies on the anoxic dissipation and metabolism of pyribambenz propyl (ZJ0273) in soils using position-specific radiolabeling," Science of the Total Environment 472, (2014), pp. 582-589.

Wang et al., "Transformation of 14C-pyrimidynyloxybenzoic herbicide ZJ0273 in aerobic soils," Science of The Total Environment, vol. 408, Iss. 10, (Apr. 15, 2010); pp. 2239-2244.

Wang, G. K., Mitchell, J., and Wang, S. Y., Block of persistent late Na+ currents by antidepressant sertraline and paroxetine. J. Membr. Biol. 222 (2), p. 79-90 (2008).

Written Opinion of the International Searching Authority and International Search Report for PCT/US2018/041649 dated Oct. 17, 2018.

Yiangou, Y., et al., SNS/PN3 and SNS2/NaN sodium channel-like immunoreactivity in human adult and neonate injured sensory nerves. FEBS Lett., 2000. 467(2-3): p. 249-52.

Yu et al., "The metabolism of a novel herbicide ZJ0273 in oilseed rape and crickweed," Pesticide Biochemistry and Physiology, vol. 104, Iss. 3, (Sep. 2012), pp. 44-49.

Choi, U.S. and S.G. Waxman, Physiological interactions between NaV1.7 and NaV1.8 sodium channels: a computer simulation study. J. Neurophysiol. 106(6): pp. 3173-3184 (2011).

List of Registry Compounds from CAS STN® Registry Database, with dates of entry in database—(May 2016).

Qiu, F., et al., Increased expression of tetrodotoxin-resistant sodium channels NaV1.8 and NaV1.9 within dorsal root ganglia in a rat model of bone cancer pain. Neurosci. Lett., 512(2): pp. 61-66 (2012).

Ruangsri, S., et al., Relationship of axonal voltage-gated sodium channel 1.8 (NaV1.8) MRNA accumulation to sciatic nerve injury-induced painful neuropathy in rats. J. Biol. Chem. 286(46): pp. 39836-39847 (Nov. 2011).

Sun. W., et al., Reduced conduction failure of the main axon of polymodal nociceptive C-fibers contributes to painful diabetic neuropathy in rats. Brain, 135(Pt 2): pp. 359-375 (Jan. 2012).

CARBOXAMIDES AS MODULATORS OF SODIUM CHANNELS

CROSS-REFERENCE TO RELATED APPLICATIONS

This application is a division of U.S. patent application Ser. No. 16/824,255, filed Mar. 19, 2020, which is a division of U.S. patent application Ser. No. 16/032,799, filed Jul. 11, 2018, which claims the benefit of U.S. Provisional Application No. 62/531,313, filed Jul. 11, 2017, and U.S. Provisional Application No. 62/608,283, filed Dec. 20, 2017, each of which is incorporated by reference in its entirety.

BACKGROUND

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain*, 2008. 137(3): p. 681-8). Neuropathic pain can be divided into two categories, pain caused by generalized metabolic damage to the nerve and pain caused by a discrete nerve injury. The metabolic neuropathies include post herpetic neuropathy, diabetic neuropathy, and drug-induced neuropathy. Discrete nerve injury indications include post amputation pain, post-surgical nerve injury pain, and nerve entrapment injuries like neuropathic back pain.

Voltage-gated sodium channels ($Na_V$'s) are involved in pain signaling. $Na_V$'s are biological mediators of electrical signaling as they mediate the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_V$'s in pain sensation (Rush, A. M. and T. R. Cummins, *Painful Research: Identification of a Small-Molecule Inhibitor that Selectively Targets $Na_V$1.8 Sodium Channels*. Mol. Interv., 2007. 7(4): p. 192-5); England, S., Voltage-gated sodium channels: the search for subtype-selective analgesics. *Expert Opin. Investig. Drugs* 17 (12), p. 1849-64 (2008); Krafte, D. S. and Bannon, A. W., Sodium channels and nociception: recent concepts and therapeutic opportunities. *Curr. Opin. Pharmacol.* 8 (1), p. 50-56 (2008)). $Na_V$'s mediate the rapid upstroke of the action potential of many excitable cell types (e.g. neurons, skeletal myocytes, cardiac myocytes), and thus are involved in the initiation of signaling in those cells (Hille, Bertil, *Ion Channels of Excitable Membranes*, Third ed. (Sinauer Associates, Inc., Sunderland, MA, 2001)). Because of the role $Na_V$'s play in the initiation and propagation of neuronal signals, antagonists that reduce $Na_V$ currents can prevent or reduce neural signaling and $Na_V$ channels have been considered likely targets to reduce pain in conditions where hyper-excitability is observed (Chahine, M., Chatelier, A., Babich, O., and Krupp, J. J., Voltage-gated sodium channels in neurological disorders. *CNS Neurol. Disord. Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur. J. Pain* 6 Suppl. A, p. 3-9 (2002); Wang, G. K., Mitchell, J., and Wang, S. Y., Block of persistent late $Na^+$ currents by antidepressant sertraline and paroxetine. *J. Membr. Biol.* 222 (2), p. 79-90 (2008)).

The $Na_V$'s form a subfamily of the voltage-gated ion channel super-family and comprises 9 isoforms, designated $Na_V1.1$-$Na_V1.9$. The tissue localizations of the nine isoforms vary. $Na_V1.4$ is the primary sodium channel of skeletal muscle, and $Na_V1.5$ is primary sodium channel of cardiac myocytes. $Na_V$'s 1.7, 1.8 and 1.9 are primarily localized to the peripheral nervous system, while $Na_V$'s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol. Rev.* 57 (4), p. 397 (2005)).

Upon their discovery, $Na_V1.8$ channels were identified as likely targets for analgesia (Akopian, A. N., L. Sivilotti, and J. N. Wood, A tetrodotoxin-resistant voltage-gated sodium channel expressed by sensory neurons. *Nature*, 1996. 379 (6562): p. 257-62). Since then, $Na_V1.8$ has been shown to be a carrier of the sodium current that maintains action potential firing in small DRG neurons (Blair, N. T. and B. P. Bean, Roles of tetrodotoxin (TTX)-sensitive Na+ current, TTX-resistant $Na^+$ current, and $Ca^{2+}$ current in the action potentials of nociceptive sensory neurons. *J. Neurosci.*, 2002. 22(23): p. 10277-90). $Na_V1.8$ is involved in spontaneous firing in damaged neurons, like those that drive neuropathic pain (Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6; Jarvis, M. F., et al., A-803467, a potent and selective $Na_V1.8$ sodium channel blocker, attenuates neuropathic and inflammatory pain in the rat. *Proc. Natl. Acad. Sci. USA*, 2007. 104(20): p. 8520-5; Joshi, S. K., et al., Involvement of the TTX-resistant sodium channel Nav1.8 in inflammatory and neuropathic, but not post-operative, pain states. *Pain*, 2006. 123(1-2): pp. 75-82; Lai, J., et al., Inhibition of neuropathic pain by decreased expression of the tetrodotoxin-resistant sodium channel, $Na_V1.8$. *Pain*, 2002. 95(1-2): p. 143-52; Dong, X. W., et al., Small interfering RNA-mediated selective knockdown of $Na(_V)1.8$ tetrodotoxin-resistant sodium channel reverses mechanical allodynia in neuropathic rats. *Neuroscience*, 2007. 146(2): p. 812-21; Huang, H. L., et al., Proteomic profiling of neuromas reveals alterations in protein composition and local protein synthesis in hyper-excitable nerves. *Mol. Pain*, 2008. 4: p. 33; Black, J. A., et al., Multiple sodium channel isoforms and mitogen-activated protein kinases are present in painful human neuromas. *Ann. Neurol.*, 2008. 64(6): p. 644-53; Coward, K., et al., Immunolocalization of SNS/PN3 and NaN/SNS2 sodium channels in human pain states. *Pain*, 2000. 85(1-2): p. 41-50; Yiangou, Y., et al., SNS/PN3 and SNS2/NaN sodium channel-like immunoreactivity in human adult and neonate injured sensory nerves. *FEBS Lett.*, 2000. 467(2-3): p. 249-52; Ruangsri, S., et al., Relationship of axonal voltage-gated sodium channel 1.8 ($Na_V1.8$) mRNA accumulation to sciatic nerve injury-induced painful neuropathy in rats. *J. Biol. Chem.* 286(46): p. 39836-47). The small DRG neurons where $Na_V1.8$ is expressed include the nociceptors involved in pain signaling. $Na_V1.8$ mediates large amplitude action potentials in small neurons of the dorsal root ganglia (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J. Neurosci.*, 2002. 22(23): p. 10277-90). $Na_V1.8$ is necessary for rapid repetitive action potentials in nociceptors, and for spontaneous activity of damaged neurons. (Choi, J. S. and S. G. Waxman, Physiological interactions between $Na_V1.7$ and $Na_V1.8$ sodium channels: a computer simulation study. *J. Neurophysiol.* 106(6): p. 3173-84; Renganathan, M., T. R. Cummins, and S. G. Waxman, Contribution of $Na(_V)1.8$ sodium channels to action potential electrogenesis in DRG neurons. *J. Neurophysiol.*, 2001. 86(2): p. 629-40; Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6). In depolarized or damaged DRG neurons, $Na_V1.8$ appears to be a driver of hyper-excitablility (Rush, A. M., et al., A single sodium channel mutation produces hyper- or hypoexcitability in different types of neurons. *Proc. Natl. Acad. Sci. USA*, 2006. 103(21): p. 8245-50). In some animal pain models, $Na_V1.8$ mRNA expression levels have been shown to increase in the DRG (Sun, W., et al., Reduced conduction failure of the main axon of polymodal nociceptive C-fibers contributes to painful diabetic neuropathy in rats. *Brain*, 135(Pt 2): p. 359-75; Strickland, I. T., et al., Changes in the expression of NaV1.7, $Na_V1.8$ and $Na_V1.9$ in a distinct population of dorsal root ganglia innervating the rat knee joint in a model of chronic inflammatory joint pain. *Eur. J Pain*, 2008. 12(5): p. 564-72; Qiu, F., et al., Increased expression of tetrodotoxin-resistant sodium channels $Na_V1.8$ and $Na_V1.9$ within dorsal root ganglia in a rat model of bone cancer pain. *Neurosci. Lett.*, 512(2): p. 61-6).

The primary drawback to some known $Na_V$ inhibitors is their poor therapeutic window, and this is likely a consequence of their lack of isoform selectivity. Since $Na_V1.8$ is primarily restricted to the neurons that sense pain, selective $Na_V1.8$ blockers are unlikely to induce the adverse events common to non-selective $Na_V$ blockers. Accordingly, there remains a need to develop additional $Na_V$ channel modulators, preferably those that are more potent and selective for $Na_V1.8$.

SUMMARY

In one aspect, the invention relates to a compound described herein, or a pharmaceutically acceptable salt thereof.

In another aspect, the invention relates to a pharmaceutical composition comprising the compound, or a pharmaceutically acceptable salt thereof, and one or more pharmaceutically acceptable carriers or vehicles.

In still another aspect, the invention relates to a method of inhibiting a voltage gated sodium channel in a subject by administering the compound, pharmaceutically acceptable salt, or pharmaceutical composition to the subject.

In yet another aspect, the invention relates to a method of treating or lessening the severity in a subject of a variety of diseases, disorders, or conditions, including, but not limited to, chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, and cardiac arrhythmia, by administering the compound, pharmaceutically acceptable salt, or pharmaceutical composition to the subject.

DETAILED DESCRIPTION

In one aspect, the invention relates to a compound of formula (I-A)

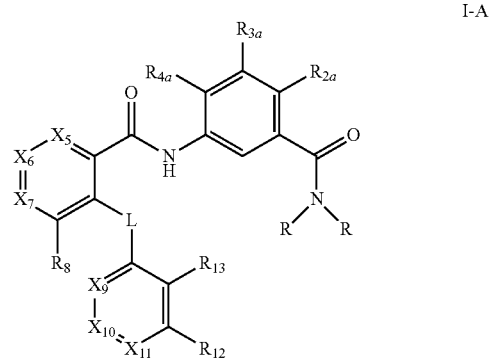

I-A or a pharmaceutically acceptable salt thereof, wherein:

L is O, $C(R)_2$, or a single bond;

$X_5$ is N or $CR_5$;

$X_6$ is N or $CR_6$;

$X_7$ is N or $CR_7$;

$X_9$ is N or $CR_9$;

$X_{10}$ is N or $CR_{10}$;

$X_{11}$ is N or $CR_{11}$;

each R is independently H or $C_1$-$C_6$ alkyl;

$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$, $R_6$, and $R_7$ are defined as follows:

(i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;

(ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

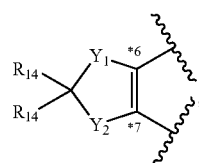

or (iii) $R_5$ and $R_6$, together with the carbon atoms to which they are attached, form a ring of formula:

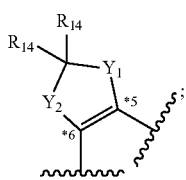

and

R$_7$ is H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

R$_8$ is H or —O—(CH$_2$)$_n$—R$_w$;

R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$; or R$_{12}$ and R$_{13}$, together with the carbon atoms to which they are attached, form a ring of formula:

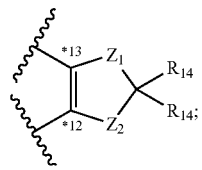

Y$_1$, Y$_2$, Z$_1$, and Z$_2$ are each independently O or C(R$_{14}$)$_2$;

each R$_{14}$ is independently H, halo, C$_1$-C$_4$ alkyl, or C$_1$-C$_4$ haloalkyl;

each W is independently O or a single bond;

each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, C$_1$-C$_6$ alkyl, and C$_1$-C$_6$ haloalkyl; and n is 0 or 1;

wherein when R$_8$ is H, then at least one of X$_5$, X$_6$, and X$_7$ is not N or CH;

wherein when X$_7$ is CR$_7$ and R$_7$ is C$_1$-C$_6$ alkyl, then R$_{2a}$ is not H;

wherein when R$_{4a}$ is halo, then R$_{2a}$ is not H;

wherein no more than one of X$_5$, X$_6$, and X$_7$ is N;

wherein no more than one of X$_9$, X$_{10}$, and X$_{11}$ is N; or a compound of formula (I-B)

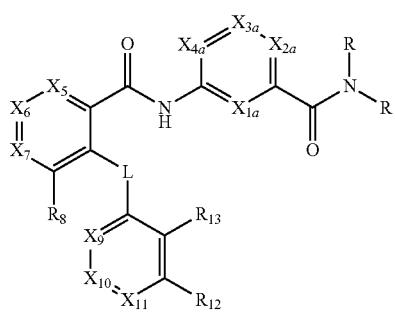

I-B or a pharmaceutically acceptable salt thereof, wherein:

L is O, C(R)$_2$, or a single bond;

X$_{1a}$ is N or CH;

X$_{2a}$ is N, N$^+$—O$^-$, or CR$_{2a}$;

X$_{3a}$ is N or CR$_{3a}$;

X$_{4a}$ is N or CR$_{4a}$;

X$_5$ is N or CR$_5$;

X$_6$ is N or CR$_6$;

X$_7$ is N or CR$_7$;

X$_9$ is N or CR$_9$;

X$_{10}$ is N or CR$_{10}$;

X$_{11}$ is N or CR$_{11}$;

each R is independently H or C$_1$-C$_6$ alkyl;

R$_{2a}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{3a}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{4a}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_5$, R$_6$, and R$_7$ are defined as follows:

(i) R$_5$, R$_6$, and R$_7$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$;

(ii) R$_5$ is H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$; and R$_6$ and R$_7$, together with the carbon atoms to which they are attached, form a ring of formula:

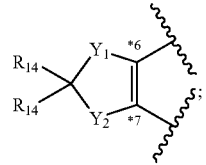

or (iii) R$_5$ and R$_6$, together with the carbon atoms to which they are attached, form a ring of formula:

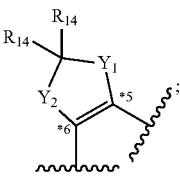

and

R$_7$ is H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

R$_8$ is H or —O—(CH$_2$)$_n$—R$_w$;

R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$; or R$_{12}$ and R$_{13}$, together with the carbon atoms to which they are attached, form a ring of formula:

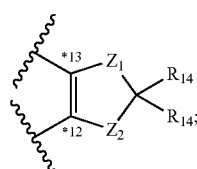

$Y_1$, $Y_2$, $Z_1$, and $Z_2$ are each independently O or $C(R_{14})_2$;
each $R_{14}$ is independently H, halo, $C_1$-$C_4$ alkyl, or $C_1$-$C_4$ haloalkyl;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein when $R_8$ is H, then at least one of $X_5$, $X_6$, and $X_7$ is not N or CH;
wherein one or two of $X_{1a}$, $X_{2a}$, $X_{3a}$, and $X_{4a}$ is N or $N^+$—$O^-$;
wherein no more than one of $X_5$, $X_6$, and $X_7$ is N;
wherein no more than one of $X_9$, $X_{10}$, and $X_{11}$ is N; or
a compound of formula (II)

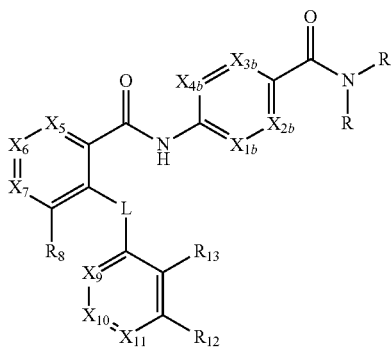

II or a pharmaceutically acceptable salt thereof, wherein:
L is O, $C(R)_2$, or a single bond;
$X_{1b}$ is N or $CR_{1b}$;
$X_{2b}$ is N or $CR_{2b}$;
$X_{3b}$ is N or $CR_{3b}$;
$X_{4b}$ is N or $CR_{4b}$;
$X_5$ is N or $CR_5$;
$X_6$ is N or $CR_6$;
$X_7$ is N or $CR_7$;
$X_9$ is N or $CR_9$;
$X_{10}$ is N or $CR_{10}$;
$X_{11}$ is N or $CR_{11}$;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{2b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are defined as follows:

(i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
(ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

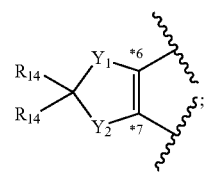

or
(iii) $R_5$ and $R_6$, together with the carbon atoms to which they are attached, form a ring of formula:

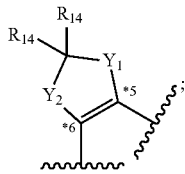

and
$R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

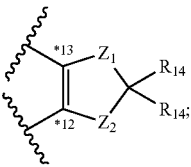

$Y_1$, $Y_2$, $Z_1$, and $Z_2$ are each independently O or $C(R_{14})_2$;
each $R_{14}$ is independently H, halo, $C_1$-$C_4$ alkyl, or $C_1$-$C_4$ haloalkyl;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein when $R_8$ is H, then at least one of $X_5$, $X_6$, and $X_7$ is not N or CH;

wherein no more than two of $X_{1b}$, $X_{2b}$, $X_{3b}$, and $X_{4b}$ is N;
wherein no more than one of $X_5$, $X_6$, and $X_7$ is N;
wherein no more than one of $X_9$, $X_{10}$, and $X_{11}$ is N.

For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry," Thomas Sorrell, University Science Books, Sausalito: 1999, and "March's Advanced Organic Chemistry," 5$^{th}$ Ed., Ed.: Smith, M. B. and March, J., John Wiley & Sons, New York: 2001, the entire contents of which are hereby incorporated by reference.

As used herein, the term "compounds of the invention" refers to the compounds of formulas (I-A), (I-A-1), (I-A-2), (I-A-3), (I-A-4), (I-A-5), (I-A-6), (I-A-7), (I-A-8), (I-B), (I-B-1), (I-B-2), (I-B-3), (I-B-4), (I-B-5), (I-B-6), (I-B-7), (I-B-8), (I-B-9), (I-B-10), (II), (II-A-1), (II-A-2), (II-B3-1), (II-B3-2), (II-B-3), (II-B-4), and (II-B-5), and all of the embodiments thereof, as described herein, and to the compounds identified in Tables 1, 1A, 1B, and 1C.

As described herein, the compounds of the invention comprise multiple variable groups (e.g., L, R, $X_{2a}$, $R_5$, etc.). As one of ordinary skill in the art will recognize, combinations of groups envisioned by this invention are those combinations that result in the formation of stable or chemically feasible compounds. The term "stable," in this context, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

As used herein, the term "substituted," refers to a group in which one or more hydrogen radicals has been replaced with a specified substituent. Unless otherwise indicated, a substituted group can have a substituent at any substitutable position of the group, and when more than one position in any given structure can be substituted with more than one substituent selected from a specified group, the substituent can be either the same or different at every position. As one of ordinary skill in the art will recognize, substituted groups envisioned by this invention are those that result in the formation of stable or chemically feasible compounds.

As used herein, the term "halo" means F, Cl, Br or I.

As used herein, the term "alkyl" refers to a straight or branched hydrocarbon chain radical group consisting solely of carbon and hydrogen atoms, containing no unsaturation, and having the specified number of carbon atoms, which is attached to the rest of the molecule by a single bond. For example, a "$C_1$-$C_6$ alkyl" group is an alkyl group having between one and six carbon atoms.

As used herein, the term "haloalkyl" refers to an alkyl group having the specified number of carbon atoms, wherein one or more of the hydrogen atoms of the alkyl group are replaced by halo groups. For example, a "$C_1$-$C_6$ haloalkyl" group is an alkyl group having between one and six carbon atoms, wherein one or more of the hydrogen atoms of the alkyl group are replaced by halo groups.

As used herein, the term "alkoxy" refers to a radical of the formula —$OR_a$ where $R_a$ is an alkyl group having the specified number of carbon atoms. For example, a "$C_1$-$C_6$ alkoxy" group is a radical of the formula —$OR_a$ where $R_a$ is an alkyl group having the between one and six carbon atoms.

As used herein, the term "haloalkoxy" refers to an alkoxy group having the specified number of carbon atoms, wherein one or more of the hydrogen atoms of the of the alkyl group are replaced by halo groups.

As used herein, the term "cycloalkyl" refers to a stable, non-aromatic, mono- or bicyclic (fused, bridged, or spiro) saturated hydrocarbon radical consisting solely of carbon and hydrogen atoms, having the specified number of carbon ring atoms, and which is attached to the rest of the molecule by a single bond.

As used herein, the term "heteroaryl" refers to a stable, aromatic, mono- or bicyclic ring radical having the specified number of ring atoms and comprising one or more heteroatoms individually selected from nitrogen, oxygen and sulfur.

As used herein, "*5," "*6," "*7," "*12," and "*13" in the following structures designate the carbon atom in formula (I-A), (I-A-1), (I-A-2), (I-A-3), (I-A-4), (I-A-5), (I-A-6), (I-A-7), (I-A-8), (I-B), (I-B-1), (I-B-2), (I-B-3), (I-B-4), (I-B-5), (I-B-6), (I-B-7), (I-B-8), (I-B-9), (I-B-10), (II), (II-A-1), (II-A-2), (II-B-1), (II-B-2), (II-B-3), (II-B-4), or (II-B-5) to which the corresponding R group is attached. For example, "*5" designates the carbon atom to which $R_5$ is attached.

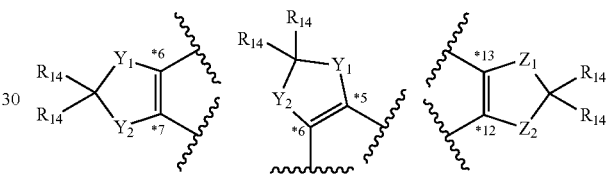

Unless otherwise specified, the compounds of the invention, whether identified by chemical name or chemical structure, include all stereoisomers (e.g., enantiomers and diastereomers), double bond isomers (e.g., (Z) and (E)), conformational isomers, and tautomers, of the compounds identified by the chemical names and chemical structures provided herein. In addition, single stereoisomers, double bond isomers, conformation isomers, and tautomers as well as mixtures of stereoisomers, double bond isomers, conformation isomers, and tautomers are within the scope of the invention.

As used herein, in any chemical structure or formula, a bold or hashed straight bond attached to a stereocenter of a compound, such as in

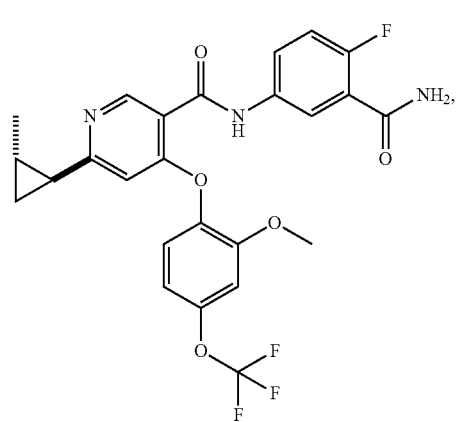

denotes the relative stereochemistry of the stereocenter, relative to other stereocenter(s) to which bold or hashed straight bonds are attached.

As used herein, in any chemical structure or formula, a bold or hashed wedge bond attached to a stereocenter of a compound, such as in

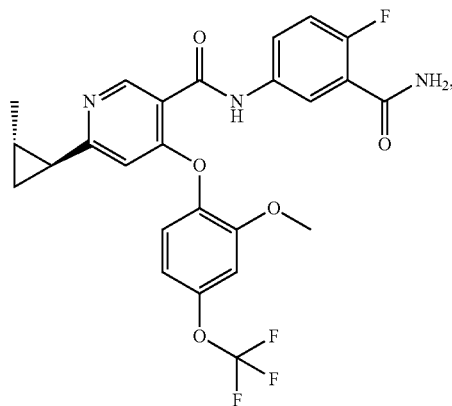 [SMILES: COc1cc(OC(F)(F)F)ccc1Oc1cc([C@H]2C[C@@H]2C)ncc1C(=O)Nc1ccc(F)c(C(N)=O)c1]

denotes the absolute stereochemistry of the stereocenter, as well as the relative stereochemistry of the stereocenter, relative to other stereocenter(s) to which bold or hashed wedge bonds are attached.

As used herein, the prefix "rel-," when used in connection with a chiral compound, means that the compound was obtained as substantially a single enantiomer, but that the absolute stereochemistry was not determined. In a compound bearing the "rel-" prefix, the absolute stereochemistry indicated by each bold or hashed wedge bond in the chemical structure and each (R)- and (S)-designator in the chemical name was arbitrarily assigned. Unless otherwise specified, the relative stereochemistry indicated by such bonds and designators in a compound bearing the "rel-" prefix reflects the relative stereochemistry of the compound.

As used herein, the term "compound," when referring to the compounds of the invention, refers to a collection of molecules having identical chemical structures, except that there may be isotopic variation among the constituent atoms of the molecules. The term "compound" includes such a collection of molecules without regard to the purity of a given sample containing the collection of molecules. Thus, the term "compound" includes such a collection of molecules in pure form, in a mixture (e.g., solution, suspension, or colloid) with one or more other substances, or in the form of a hydrate, solvate, or co-crystal.

In the specification and claims, unless otherwise specified, any atom not specifically designated as a particular isotope in any compound of the invention is meant to represent any stable isotope of the specified element. In the Examples, where an atom is not specifically designated as a particular isotope in any compound of the invention, no effort was made to enrich that atom in a particular isotope, and therefore a person of ordinary skill in the art would understand that such atom likely was present at approximately the natural abundance isotopic composition of the specified element.

As used herein, the term "stable," when referring to an isotope, means that the isotope is not known to undergo spontaneous radioactive decay. Stable isotopes include, but are not limited to, the isotopes for which no decay mode is identified in V. S. Shirley & C. M. Lederer, Isotopes Project, Nuclear Science Division, Lawrence Berkeley Laboratory, Table of Nuclides (January 1980).

As used herein in the specification and claims, "H" refers to hydrogen and includes any stable isotope of hydrogen, namely $^1$H and D. In the Examples, where an atom is designated as "H," no effort was made to enrich that atom in a particular isotope of hydrogen, and therefore a person of ordinary skill in the art would understand that such hydrogen atom likely was present at approximately the natural abundance isotopic composition of hydrogen.

As used herein, "$^1$H" refers to protium. Where an atom in a compound of the invention, or a pharmaceutically acceptable salt thereof, is designated as protium, protium is present at the specified position at least the natural abundance concentration of protium.

As used herein, "D," "d," and "$^2$H" refer to deuterium.

In some embodiments, the compounds of the invention, and pharmaceutically acceptable salts thereof, include each constituent atom at approximately the natural abundance isotopic composition of the specified element.

In some embodiments, the compounds of the invention, and pharmaceutically acceptable salts thereof, include one or more atoms having an atomic mass or mass number which differs from the atomic mass or mass number of the most abundant isotope of the specified element ("isotope-labelled" compounds and salts). Examples of stable isotopes which are commercially available and suitable for the invention include without limitation isotopes of hydrogen, carbon, nitrogen, oxygen, and phosphorus, for example $^2$H, $^{13}$C, $^{15}$N, $^{18}$O, $^{17}$O, and $^{31}$P, respectively.

The isotope-labelled compounds and salts can be used in a number of beneficial ways, including as medicaments. In some embodiments, the isotope-labelled compounds and salts are deuterium ($^2$H)-labelled. Deuterium ($^2$H)-labelled compounds and salts are therapeutically useful with potential therapeutic advantages over the non-$^2$H-labelled compounds. In general, deuterium ($^2$H)-labelled compounds and salts can have higher metabolic stability as compared to those that are not isotope-labelled owing to the kinetic isotope effect described below. Higher metabolic stability translates directly into an increased in vivo half-life or lower dosages, which under most circumstances would represent a preferred embodiment of the present invention. The isotope-labelled compounds and salts can usually be prepared by carrying out the procedures disclosed in the synthesis schemes, the examples and the related description, replacing a non-isotope-labelled reactant by a readily available isotope-labelled reactant.

The deuterium ($^2$H)-labelled compounds and salts can manipulate the rate of oxidative metabolism of the compound by way of the primary kinetic isotope effect. The primary kinetic isotope effect is a change of the rate for a chemical reaction that results from exchange of isotopic nuclei, which in turn is caused by the change in ground state energies of the covalent bonds involved in the reaction. Exchange of a heavier isotope usually results in a lowering of the ground state energy for a chemical bond and thus causes a reduction in the rate-limiting bond breakage. If the bond breakage occurs in or in the vicinity of a saddle-point region along the coordinate of a multi-product reaction, the product distribution ratios can be altered substantially. For explanation: if deuterium is bonded to a carbon atom at a non-exchangeable position, rate differences of $k_H/k_D$=2-7 are typical. For a further discussion, see S. L. Harbeson and R. D. Tung, *Deuterium In Drug Discovery and Development*, Ann. Rep. Med. Chem. 2011, 46, 403-417, incorporated in its entirety herein by reference.

The concentration of an isotope (e.g., deuterium) incorporated at a given position of an isotope-labelled compound of the invention, or a pharmaceutically acceptable salt thereof, may be defined by the isotopic enrichment factor. The term "isotopic enrichment factor," as used herein, means the ratio between the abundance of an isotope at a given position in an isotope-labeled compound (or salt) and the natural abundance of the isotope.

Where an atom in a compound of the invention, or a pharmaceutically acceptable salt thereof, is designated as deuterium, such compound (or salt) has an isotopic enrichment factor for such atom of at least 3000 (45% deuterium incorporation). In some embodiments, the isotopic enrichment factor is at least 3500 (52.5% deuterium incorporation), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

When discovering and developing therapeutic agents, the person skilled in the art attempts to optimize pharmacokinetic parameters while retaining desirable in vitro properties. It may be reasonable to assume that many compounds with poor pharmacokinetic profiles are susceptible to oxidative metabolism.

In one aspect, the invention relates to a compound of formula (I-A)

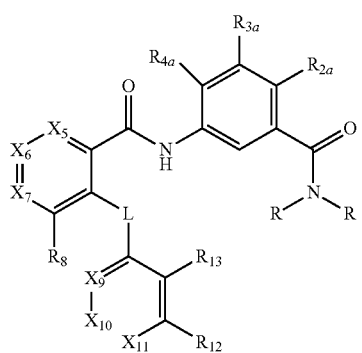

I-A or a pharmaceutically acceptable salt thereof, wherein:
L is O, C(R)$_2$, or a single bond;
X$_5$ is N or CR$_5$;
X$_6$ is N or CR$_6$;
X$_7$ is N or CR$_7$;
X$_9$ is N or CR$_9$;
X$_{10}$ is N or CR$_{10}$;
X$_{11}$ is N or CR$_{11}$;
each R is independently H or C$_1$-C$_6$ alkyl;
R$_{2a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_{3a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_{4a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_5$, R$_6$, and R$_7$ are defined as follows:
(i) R$_5$, R$_6$, and R$_7$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$;

(ii) R$_5$ is H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$; and R$_6$ and R$_7$, together with the carbon atoms to which they are attached, form a ring of formula:

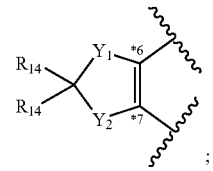

or (iii) R$_5$ and R$_6$, together with the carbon atoms to which they are attached, form a ring of formula:

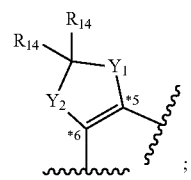

and

R$_7$ is H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
R$_8$ is H or —O—(CH$_2$)$_n$—R$_w$;
R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$; or R$_{12}$ and R$_{13}$, together with the carbon atoms to which they are attached, form a ring of formula:

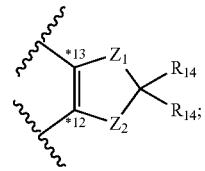

Y$_1$, Y$_2$, Z$_1$, and Z$_2$ are each independently O or C(R$_{14}$)$_2$;
each R$_{14}$ is independently H, halo, C$_1$-C$_4$ alkyl, or C$_1$-C$_4$ haloalkyl;
each W is independently O or a single bond;
each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, C$_1$-C$_6$ alkyl, and C$_1$-C$_6$ haloalkyl; and
n is 0 or 1;
wherein when R$_8$ is H, then at least one of X$_5$, X$_6$, and X$_7$ is not N or CH;
wherein when X$_7$ is CR$_7$ and R$_7$ is C$_1$-C$_6$ alkyl, then R$_{2a}$ is not H;
wherein when R$_{4a}$ is halo, then R$_{2a}$ is not H;

wherein no more than one of $X_5$, $X_6$, and $X_7$ is N;
wherein no more than one of $X_9$, $X_{10}$, and $X_{11}$ is N.

In some embodiments, the invention relates to a compound of formula (I-A), or a pharmaceutically acceptable salt thereof, wherein L is O or a single bond. In other embodiments, L is O. In other embodiments, L is a single bond.

In some embodiments, the invention relates to a compound of formula (I-A), or a pharmaceutically acceptable salt thereof, wherein $X_5$ is N. In other embodiments, $X_5$ is $CR_5$.

In some embodiments, the invention relates to a compound of formula (I-A), or a pharmaceutically acceptable salt thereof, wherein $X_6$ is N. In other embodiments, $X_6$ is $CR_6$.

In some embodiments, the invention relates to a compound of formula (I-A), or a pharmaceutically acceptable salt thereof, wherein $X_7$ is N. In other embodiments, $X_7$ is $CR_7$.

In some embodiments, the invention relates to a compound of formula (I-A), or a pharmaceutically acceptable salt thereof, wherein $X_9$ is N. In other embodiments, $X_9$ is $CR_9$.

In some embodiments, the invention relates to a compound of formula (I-A), or a pharmaceutically acceptable salt thereof, wherein $X_{10}$ is N. In other embodiments, $X_{10}$ is $CR_{10}$.

In some embodiments, the invention relates to a compound of formula (I-A), or a pharmaceutically acceptable salt thereof, wherein $X_{11}$ is N. In other embodiments, $X_{11}$ is $CR_{11}$.

In some embodiments, the invention relates to a compound of formula (I-A), or a pharmaceutically acceptable salt thereof, wherein each R is independently H or $CH_3$. In other embodiments, each R is H. In other embodiments, each R is $CH_3$.

In some embodiments, the invention relates to a compound of formula (I-A), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is H, F, Cl, OH, $CH_3$, or $OCH_3$. In other embodiments, $R_{2a}$ is H. In other embodiments, $R_{2a}$ is F. In other embodiments, $R_{2a}$ is Cl. In other embodiments, $R_{2a}$ is OH. In other embodiments, $R_{2a}$ is $CH_3$. In other embodiments, $R_{2a}$ is $OCH_3$.

In some embodiments, the invention relates to a compound of formula (I-A), or a pharmaceutically acceptable salt thereof, wherein $R_{3a}$ is H or halo. In other embodiments, $R_{3a}$ is halo. In other embodiments, $R_{3a}$ is H or F. In other embodiments, $R_{3a}$ is H. In other embodiments, $R_{3a}$ is F.

In some embodiments, the invention relates to a compound of formula (I-A), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H or $CH_3$. In other embodiments, $R_{4a}$ is H. In other embodiments, $R_{4a}$ is $^1H$. In other embodiments, $R_{4a}$ is D. In other embodiments, $R_{4a}$ is $CH_3$.

In some embodiments, the invention relates to a compound of formula (I-A), or a pharmaceutically acceptable salt thereof, wherein $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H, F, $CF_3$, or $OCH_3$. In other embodiments, $R_5$ is H. In other embodiments, $R_5$ is F. In other embodiments, $R_5$ is $CF_3$. In other embodiments, $R_5$ is $OCH_3$.

In some embodiments, the invention relates to a compound of formula (I-A), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H, F, Cl, $CHF_2$, $CF_3$, $CF_2CF_3$, $OCF_3$, or cyclopropyl. In other embodiments, $R_6$ is H. In other embodiments, $R_6$ is F. In other embodiments, $R_6$ is Cl. In other embodiments, $R_6$ is $CHF_2$. In other embodiments, $R_6$ is $CF_3$. In other embodiments, $R_6$ is $CF_2CF_3$. In other embodiments, $R_6$ is $OCF_3$. In other embodiments, $R_6$ is cyclopropyl.

In some embodiments, the invention relates to a compound of formula (I-A), or a pharmaceutically acceptable salt thereof, wherein $R_5$ and $R_6$, together with the carbon atoms to which they are attached, form a ring of formula:

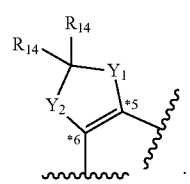

In some embodiments, the invention relates to a compound of formula (I-A), or a pharmaceutically acceptable salt thereof, wherein $R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, or —W—$(CH_2)_n$—$R_w$. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is —W—$(CH_2)_n$—$R_w$. In other embodiments, $R_7$ is —W—$(CH_2)_n$—$R_w$, wherein W is O, n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H, F, Cl, $CH(CH_3)_2$, $C(CH_3)_3$, $CF(CH_3)_2$, $CF_3$, $OCH_3$, $OCH_2Ph$, cyclopropyl, 1-methylcylopropyl, 2-methylcyclopropyl, or 2,2-difluorocyclopropyl. In other embodiments, $R_7$ is H. In other embodiments, $R_7$ is F. In other embodiments, $R_7$ is Cl. In other embodiments, $R_7$ is $CH(CH_3)_2$. In other embodiments, $R_7$ is $C(CH_3)_3$. In other embodiments, $R_7$ is $CF(CH_3)_2$. In other embodiments, $R_7$ is $CF_3$. In other embodiments, $R_7$ is $OCH_3$. In other embodiments, $R_7$ is $OCH_2Ph$. In other embodiments, $R_7$ is cyclopropyl. In other embodiments, $R_7$ is 1-methylcylopropyl. In other embodiments, $R_7$ is 2-methylcyclopropyl. In other embodiments, $R_7$ is 2,2-difluorocyclopropyl.

In some embodiments, the invention relates to a compound of formula (I-A), or a pharmaceutically acceptable salt thereof, wherein $R_6$ and $R_7$, together with the carbon atoms to which they are attached, form a ring of formula:

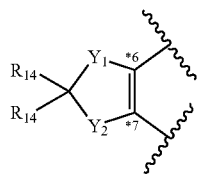

In some embodiments, the invention relates to a compound of formula (I-A), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H or $OCH_2Ph$. In other embodiments, $R_8$ is H. In other embodiments, $R_8$ is $OCH_2Ph$.

In some embodiments, the invention relates to a compound of formula (I-A), or a pharmaceutically acceptable salt thereof, wherein $R_9$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, halo, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H, F, Cl, OH, $CH_3$, $OCH_3$, or 1-methylpyrazol-5-yl. In other embodiments, $R_9$ is H. In other embodiments, $R_9$ is $^1H$. In other embodiments, $R_9$ is D. In other embodiments, $R_9$ is F. In other embodiments, $R_9$ is Cl. In other embodiments, $R_9$ is OH. In other embodiments, $R_9$ is $CH_3$. In other embodiments, $R_9$ is $OCH_3$. In other embodiments, $R_9$ is $OC(^1H)_3$. In other embodiments, $R_9$ is $OCD_3$. In other embodiments, $R_9$ is 1-methylpyrazol-5-yl.

In some embodiments, the invention relates to a compound of formula (I-A), or a pharmaceutically acceptable salt thereof, wherein $R_{10}$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_{10}$ is H, halo, OH, or $C_1$-$C_6$ alkoxy. In other embodiments, $R_{10}$ is halo, OH, or $C_1$-$C_6$ alkoxy. In other embodiments, $R_{10}$ is H, OH, or $C_1$-$C_6$ alkoxy. In other embodiments, $R_{10}$ is H, halo, or $C_1$-$C_6$ alkoxy. In other embodiments, $R_{10}$ is H, halo, or OH. In other embodiments, $R_{10}$ is halo. In other embodiments, $R_{10}$ is $C_1$-$C_6$ alkoxy. In other embodiments, $R_{10}$ is H, F, Cl, OH, or $OCH_3$. In other embodiments, $R_{10}$ is H. In other embodiments, $R_{10}$ is $^1H$. In other embodiments, $R_{10}$ is D. In other embodiments, $R_{10}$ is F. In other embodiments, $R_{10}$ is Cl. In other embodiments, $R_{10}$ is OH. In other embodiments, $R_{10}$ is $OCH_3$.

In some embodiments, the invention relates to a compound of formula (I-A), or a pharmaceutically acceptable salt thereof, wherein $R_{11}$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkyl. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H, F, Cl, $OCH_3$, or $OCF_3$. In other embodiments, $R_{11}$ is H. In other embodiments, $R_{11}$ is $^1H$. In other embodiments, $R_{11}$ is D. In other embodiments, $R_{11}$ is F. In other embodiments, $R_{11}$ is Cl. In other embodiments, $R_{11}$ is $OCH_3$. In other embodiments, $R_{11}$ is $OCF_3$.

In some embodiments, the invention relates to a compound of formula (I-A), or a pharmaceutically acceptable salt thereof, wherein $R_{12}$ is H. In other embodiments, $R_{12}$ is $^1H$. In other embodiments, $R_{12}$ is D.

In some embodiments, the invention relates to a compound of formula (I-A), or a pharmaceutically acceptable salt thereof, wherein $R_{13}$ is H. In other embodiments, $R_{13}$ is $^1H$. In other embodiments, $R_{13}$ is D.

In some embodiments, the invention relates to a compound of formula (I-A), or a pharmaceutically acceptable salt thereof, wherein $R_{12}$ and $R_{13}$, together with the carbon atoms to which they are attached, form a ring of formula:

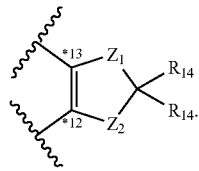

In some embodiments, the invention relates to a compound of formula (I-A), or a pharmaceutically acceptable salt thereof, wherein $Y_1$ is O, and $Y_2$ is $C(R_{14})_2$. In other embodiments, $Y_1$ is $C(R_{14})_2$, and $Y_2$ is O. In other embodiments, $Y_1$ is O, and $Y_2$ is O. In other embodiments, $Y_1$ is $C(R_{14})_2$, and $Y_2$ is $C(R_{14})_2$.

In some embodiments, the invention relates to a compound of formula (I-A), or a pharmaceutically acceptable salt thereof, wherein $Z_1$ is O, and $Z_2$ is $C(R_{14})_2$. In other embodiments, $Z_1$ is $C(R_{14})_2$, and $Z_2$ is O. In other embodiments, $Z_1$ is O, and $Z_2$ is O. In other embodiments, $Z_1$ is $C(R_{14})_2$, and $Z_2$ is $C(R_{14})_2$.

In some embodiments, the invention relates to a compound of formula (I-A), or a pharmaceutically acceptable salt thereof, wherein each $R_{14}$ is independently H or F. In other embodiments, each $R_{14}$ is H. In other embodiments, $R_{14}$ is $^1$H. In other embodiments, $R_{14}$ is D.

In other embodiments, each $R_{14}$ is F.

In some embodiments, the invention relates to a compound of formula (I-A), i.e., the compound in non-salt form.

In another aspect, the invention relates to a compound of formula (I-A-1)

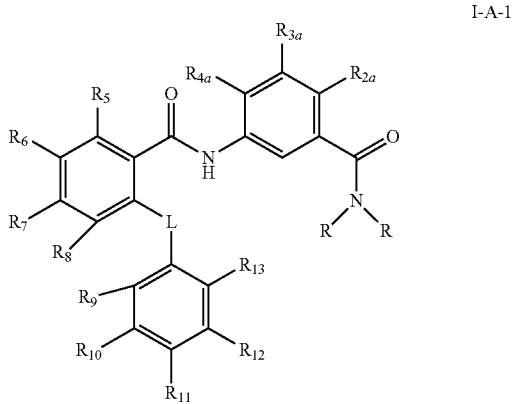

I-A-1 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, $R_7$, and $R_8$ is not H;
wherein when $R_7$ is $C_1$-$C_6$ alkyl, then $R_{2a}$ is not H;
wherein when $R_{4a}$ is halo, then $R_{2a}$ is not H.

In some embodiments, the invention relates to a compound of formula (I-A-1), or a pharmaceutically acceptable salt thereof, wherein L is O or a single bond. In other embodiments, L is O. In other embodiments, L is a single bond.

In some embodiments, the invention relates to a compound of formula (I-A-1), or a pharmaceutically acceptable salt thereof, wherein each R is independently H or $CH_3$. In other embodiments, each R is H. In other embodiments, each R is $CH_3$.

In some embodiments, the invention relates to a compound of formula (I-A-1), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is H, F, Cl, OH, or $CH_3$. In other embodiments, $R_{2a}$ is H. In other embodiments, $R_{2a}$ is F. In other embodiments, $R_{2a}$ is Cl. In other embodiments, $R_{2a}$ is OH. In other embodiments, $R_{2a}$ is $CH_3$.

In some embodiments, the invention relates to a compound of formula (I-A-1), or a pharmaceutically acceptable salt thereof, wherein $R_{3a}$ is H or halo. In other embodiments, $R_{3a}$ is halo. In other embodiments, $R_{3a}$ is H or F. In other embodiments, $R_{3a}$ is H. In other embodiments, $R_{3a}$ is F.

In some embodiments, the invention relates to a compound of formula (I-A-1), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H or $CH_3$. In other embodiments, $R_{4a}$ is H. In other embodiments, $R_{4a}$ is $^1$H. In other embodiments, $R_{4a}$ is D. In other embodiments, $R_{4a}$ is $CH_3$.

In some embodiments, the invention relates to a compound of formula (I-A-1), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H, F, $CF_3$, or $OCH_3$. In other embodiments, $R_5$ is H. In other embodiments, $R_5$ is F. In other embodiments, $R_5$ is $CF_3$. In other embodiments, $R_5$ is $OCH_3$.

In some embodiments, the invention relates to a compound of formula (I-A-1), or a pharmaceutically acceptable salt thereof, wherein $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H, F, Cl, $CHF_2$, $CF_3$, $CF_2CF_3$, $OCF_3$, or cyclopropyl. In other embodiments, $R_6$ is H. In other embodiments, $R_6$ is F. In other embodiments, $R_6$ is Cl. In other embodiments, $R_6$ is $CHF_2$. In other embodiments, $R_6$ is $CF_3$. In other embodiments, $R_6$ is $CF_2CF_3$. In other embodiments, $R_6$ is $OCF_3$. In other embodiments, $R_6$ is cyclopropyl.

In some embodiments, the invention relates to a compound of formula (I-A-1), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, or —W—$(CH_2)_n$—$R_w$. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is —W—$(CH_2)_n$—$R_w$. In other embodiments, $R_7$ is —W—$(CH_2)_n$—$R_w$, wherein W is O, n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H, F, $CF_3$, $OCH_3$, or $OCH_2Ph$. In other embodiments, $R_7$ is H. In other embodiments, $R_7$ is F. In other embodiments, $R_7$ is $CF_3$. In other embodiments, $R_7$ is $OCH_3$. In other embodiments, $R_7$ is $OCH_2Ph$.

In some embodiments, the invention relates to a compound of formula (I-A-1), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H or $OCH_2Ph$. In other embodiments, $R_8$ is H. In other embodiments, $R_8$ is $OCH_2Ph$.

In some embodiments, the invention relates to a compound of formula (I-A-1), or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, halo, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H, F, Cl, OH, $CH_3$, $OCH_3$, or 1-methylpyrazol-5-yl. In other embodiments, $R_9$ is H. In other embodiments, $R_9$ is $^1$H. In other embodiments, $R_9$ is D. In other embodiments, $R_9$ is F. In other embodiments, $R_9$ is Cl. In other embodiments, $R_9$ is OH. In other embodiments, $R_9$ is $CH_3$. In other embodiments, $R_9$ is $OCH_3$. In other embodiments, $R_9$ is $OC(^1H)_3$. In other embodiments, $R_9$ is $OCD_3$. In other embodiments, $R_9$ is 1-methylpyrazol-5-yl.

In some embodiments, the invention relates to a compound of formula (I-A-1), or a pharmaceutically acceptable salt thereof, wherein $R_{10}$ is H, halo, OH, or $C_1$-$C_6$ alkoxy. In other embodiments, $R_{10}$ is halo, OH, or $C_1$-$C_6$ alkoxy. In other embodiments, $R_{10}$ is H, OH, or $C_1$-$C_6$ alkoxy. In other embodiments, $R_{10}$ is H, halo, or $C_1$-$C_6$ alkoxy. In other embodiments, $R_{10}$ is H, halo, or OH. In other embodiments, $R_{10}$ is halo. In other embodiments, $R_{10}$ is $C_1$-$C_6$ alkoxy. In other embodiments, $R_{10}$ is H, F, Cl, OH, or $OCH_3$. In other embodiments, $R_{10}$ is H. In other embodiments, $R_{10}$ is $^1$H. In other embodiments, $R_{10}$ is D. In other embodiments, $R_{10}$ is F. In other embodiments, $R_{10}$ is Cl. In other embodiments, $R_{10}$ is OH. In other embodiments, $R_{10}$ is $OCH_3$.

In some embodiments, the invention relates to a compound of formula (I-A-1), or a pharmaceutically acceptable salt thereof, wherein $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is F, $OCH_3$, or $OCF_3$. In other embodiments, $R_{11}$ is H. In other embodiments, $R_{11}$ is $^1$H. In other embodiments, $R_{11}$ is D. In other embodiments, $R_{11}$ is F. In other embodiments, $R_{11}$ is $OCH_3$. In other embodiments, $R_{11}$ is $OCF_3$.

In some embodiments, the invention relates to a compound of formula (I-A-1), or a pharmaceutically acceptable salt thereof, wherein $R_{12}$ is H.

In some embodiments, the invention relates to a compound of formula (I-A-1), or a pharmaceutically acceptable salt thereof, wherein $R_{13}$ is H. In other embodiments, $R_{13}$ is $^1$H. In other embodiments, $R_{13}$ is D.

In some embodiments, the invention relates to a compound of formula (I-A-1), i.e., the compound in non-salt form.

In another aspect, the invention relates to a compound of formula (I-A-2)

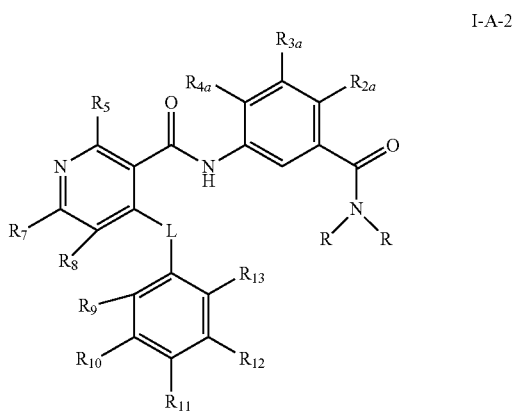

I-A-2 or a pharmaceutically acceptable salt thereof, wherein:
L is O, C(R)$_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_6$ and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—(CH$_2$)$_n$—$R_w$;
$R_8$ is H or —O—(CH$_2$)$_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_7$, and $R_8$ is not H;
wherein when $R_7$ is $C_1$-$C_6$ alkyl, then $R_{2a}$ is not H;
wherein when $R_{4a}$ is halo, then $R_{2a}$ is not H.

In some embodiments, the invention relates to a compound of formula (I-A-2), or a pharmaceutically acceptable salt thereof, wherein L is O or a single bond. In other embodiments, L is O. In other embodiments, L is a single bond.

In some embodiments, the invention relates to a compound of formula (I-A-2), or a pharmaceutically acceptable salt thereof, wherein each R is independently H or CH$_3$. In other embodiments, each R is H. In other embodiments, each R is CH$_3$.

In some embodiments, the invention relates to a compound of formula (I-A-2), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, F, CH$_3$, or OCH$_3$. In other embodiments, $R_{2a}$ is H. In other embodiments, $R_{2a}$ is F. In other embodiments, $R_{2a}$ is CH$_3$. In other embodiments, $R_{2a}$ is OCH$_3$.

In some embodiments, the invention relates to a compound of formula (I-A-2), or a pharmaceutically acceptable salt thereof, wherein $R_{3a}$ is H or halo. In other embodiments, $R_{3a}$ is halo. In other embodiments, $R_{3a}$ is H.

In some embodiments, the invention relates to a compound of formula (I-A-2), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H.

In some embodiments, the invention relates to a compound of formula (I-A-2), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H.

In some embodiments, the invention relates to a compound of formula (I-A-2), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or —W—(CH$_2$)$_n$—$R_w$. In other embodiments, $R_7$ is halo, $C_1$-$C_6$ alkyl, $C_1$-$C_6$ haloalkyl, $C_1$-$C_6$ alkoxy, or —W—(CH$_2$)$_n$—$R_w$. In other embodiments, $R_7$ is H, $C_1$-$C_6$ alkyl, $C_1$-$C_6$ haloalkyl, $C_1$-$C_6$ alkoxy, or —W—(CH$_2$)$_n$—$R_w$. In other embodiments, $R_7$ is H, halo, $C_1$-$C_6$ haloalkyl, $C_1$-$C_6$ alkoxy, or —W—(CH$_2$)$_n$—$R_w$. In other embodiments, $R_7$ is H, halo, $C_1$-$C_6$ alkyl, $C_1$-$C_6$ alkoxy, or —W—(CH$_2$)$_n$—$R_w$. In other embodiments, $R_7$ is H, halo, $C_1$-$C_6$ alkyl, $C_1$-$C_6$ haloalkyl, or —W—(CH$_2$)$_n$—$R_w$. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is —W—(CH$_2$)$_n$—$R_w$. In other embodiments, $R_7$ is —W—(CH$_2$)$_n$—$R_w$, wherein W is O, n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_7$ is —W—(CH$_2$)$_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is $CH(CH_3)_2$, $C(CH_3)_3$, $CF(CH_3)_2$, $CF_3$, cyclopropyl, 1-methylcylopropyl, 2-methylcyclopropyl, or 2,2-difluorocyclopropyl. In other embodiments, $R_7$ is $CH(CH_3)_2$. In other embodiments, $R_7$ is $C(CH_3)_3$. In other embodiments, $R_7$ is $CF(CH_3)_2$. In other embodiments, $R_7$ is $CF_3$. In other embodiments, $R_7$ is cyclopropyl. In other embodiments, $R_7$ is 1-methylcylopropyl. In other embodiments, $R_7$ is 2-methylcyclopropyl. In other embodiments, $R_7$ is 2,2-difluorocyclopropyl.

In some embodiments, the invention relates to a compound of formula (I-A-2), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H.

In some embodiments, the invention relates to a compound of formula (I-A-2), or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, halo, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H or $C_1$-$C_6$ alkoxy. In other embodiments, $R_9$ is H or $OCH_3$. In other embodiments, $R_9$ is H. In other embodiments, $R_9$ is $^1$H. In other embodiments, $R_9$ is D. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (I-A-2), or a pharmaceutically acceptable salt thereof, wherein $R_{10}$ is H, halo, OH, or $C_1$-$C_6$ alkoxy. In other embodiments, $R_{10}$ is halo, OH, or $C_1$-$C_6$ alkoxy. In other embodiments, $R_{10}$ is H, OH, or $C_1$-$C_6$ alkoxy. In other embodiments, $R_{10}$ is H, halo, or $C_1$-$C_6$ alkoxy. In other embodiments, $R_{10}$ is H, halo, or OH. In other embodiments, $R_{10}$ is halo. In other embodiments, $R_{10}$ is $C_1$-$C_6$ alkoxy. In other embodiments, $R_{10}$ is H or halo. In other embodiments, $R_{10}$ is H, F or Cl. In other embodiments, $R_{10}$ is H. In other embodiments, $R_{10}$ is $^1$H. In other embodiments, $R_{10}$ is D. In other embodiments, $R_{10}$ is F. In other embodiments, $R_{10}$ is Cl.

In some embodiments, the invention relates to a compound of formula (I-A-2), or a pharmaceutically acceptable salt thereof, wherein $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is halo or $C_1$-$C_6$ haloalkoxy. In other embodiments, $R_{11}$ is F or $OCF_3$. In other embodiments, $R_{11}$ is H. In other embodiments, $R_{11}$ is $^1$H. In other embodiments, $R_{11}$ is D. In other embodiments, $R_{11}$ is F. In other embodiments, $R_{11}$ is $OCF_3$.

In some embodiments, the invention relates to a compound of formula (I-A-2), or a pharmaceutically acceptable salt thereof, wherein $R_{12}$ is H.

In some embodiments, the invention relates to a compound of formula (I-A-2), or a pharmaceutically acceptable salt thereof, wherein $R_{13}$ is H.

In some embodiments, the invention relates to a compound of formula (I-A-2), i.e., the compound in non-salt form.

In another aspect, the invention relates to a compound of formula (I-A-3)

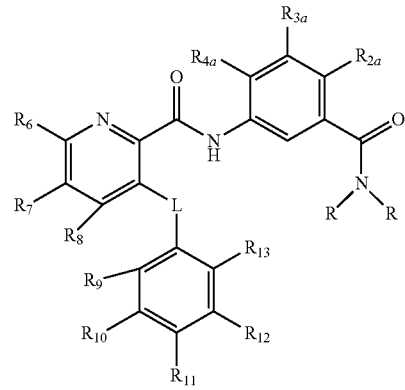

I-A-3 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_6$ and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_6$, $R_7$, and $R_8$ is not H;
wherein when $R_7$ is $C_1$-$C_6$ alkyl, then $R_{2a}$ is not H;
wherein when $R_{4a}$ is halo, then $R_{2a}$ is not H.

In some embodiments, the invention relates to a compound of formula (I-A-3), or a pharmaceutically acceptable salt thereof, wherein L is O.

In some embodiments, the invention relates to a compound of formula (I-A-3), or a pharmaceutically acceptable salt thereof, wherein each R is independently H or $CH_3$. In other embodiments, each R is H. In other embodiments, each R is $CH_3$.

In some embodiments, the invention relates to a compound of formula (I-A-3), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is H or halo. In other embodiments, $R_{2a}$ is H or F. In other embodiments, $R_{2a}$ is H. In other embodiments, $R_{2a}$ is F.

In some embodiments, the invention relates to a compound of formula (I-A-3), or a pharmaceutically acceptable salt thereof, wherein $R_{3a}$ is H or halo. In other embodiments, $R_{3a}$ is halo. In other embodiments, $R_{3a}$ is H.

In some embodiments, the invention relates to a compound of formula (I-A-3), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H.

In some embodiments, the invention relates to a compound of formula (I-A-3), or a pharmaceutically acceptable salt thereof, wherein $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—R. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H.

In some embodiments, the invention relates to a compound of formula (I-A-3), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, or —W—$(CH_2)_n$—$R_w$. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is —W—$(CH_2)_n$—$R_w$. In other embodiments, $R_7$ is —W—$(CH_2)_n$—$R_w$, wherein W is O, n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is $CF_3$.

In some embodiments, the invention relates to a compound of formula (I-A-3), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H.

In some embodiments, the invention relates to a compound of formula (I-A-3), or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, halo, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-A-3), or a pharmaceutically acceptable salt thereof, wherein $R_{10}$ is H, halo, OH, or $C_1$-$C_6$ alkoxy. In other embodiments, $R_{10}$ is halo, OH, or $C_1$-$C_6$ alkoxy. In other embodiments, $R_{10}$ is H, OH, or $C_1$-$C_6$ alkoxy. In other embodiments, $R_{10}$ is H, halo, or $C_1$-$C_6$ alkoxy. In other embodiments, $R_{10}$ is H, halo, or OH. In other embodiments, $R_{10}$ is halo. In other embodiments, $R_{10}$ is $C_1$-$C_6$ alkoxy. In other embodiments, $R_{10}$ is H. In other embodiments, $R_{10}$ is $^1$H. In other embodiments, $R_{10}$ is D.

In some embodiments, the invention relates to a compound of formula (I-A-3), or a pharmaceutically acceptable salt thereof, wherein $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{10}$ is $^1$H. In other embodiments, $R_{11}$ is D. In other embodiments, $R_{11}$ is $OCF_3$.

In some embodiments, the invention relates to a compound of formula (I-A-3), or a pharmaceutically acceptable salt thereof, wherein $R_{12}$ is H.

In some embodiments, the invention relates to a compound of formula (I-A-3), or a pharmaceutically acceptable salt thereof, wherein $R_{13}$ is H.

In some embodiments, the invention relates to a compound of formula (I-A-3), i.e., the compound in non-salt form.

In another aspect, the invention relates to a compound of formula (I-A-4)

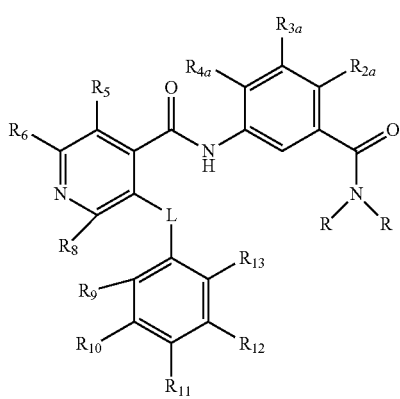

I-A-4 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$ and $R_6$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, and $R_8$ is not H;
wherein when $R_{4a}$ is halo, then $R_{2a}$ is not H.

In some embodiments, the invention relates to a compound of formula (I-A-4), or a pharmaceutically acceptable salt thereof, wherein L is O or a single bond. In other embodiments, L is O. In other embodiments, L is a single bond.

In some embodiments, the invention relates to a compound of formula (I-A-4), or a pharmaceutically acceptable salt thereof, wherein each R is independently H or $CH_3$. In other embodiments, each R is H. In other embodiments, each R is $CH_3$.

In some embodiments, the invention relates to a compound of formula (I-A-4), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is F.

In some embodiments, the invention relates to a compound of formula (I-A-4), or a pharmaceutically acceptable salt thereof, wherein $R_{3a}$ is H or halo. In other embodiments, $R_{3a}$ is halo. In other embodiments, $R_{3a}$ is H.

In some embodiments, the invention relates to a compound of formula (I-A-4), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H.

In some embodiments, the invention relates to a compound of formula (I-A-4), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H, halo, or $C_1$-$C_6$ alkoxy. In other embodiments, $R_5$ is H, F, or $OCH_3$. In other embodiments, $R_5$ is H. In other embodiments, $R_5$ is F. In other embodiments, $R_5$ is $OCH_3$.

In some embodiments, the invention relates to a compound of formula (I-A-4), or a pharmaceutically acceptable salt thereof, wherein $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—

$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H, $C_1$-$C_6$ alkyl, $C_1$-$C_6$ haloalkyl, or —W—$(CH_2)_n$—$R_w$. In other embodiments, $R_6$ is H, $CF_3$, or cyclopropyl. In other embodiments, $R_6$ is H. In other embodiments, $R_6$ is $CF_3$. In other embodiments, $R_6$ is cyclopropyl.

In some embodiments, the invention relates to a compound of formula (I-A-4), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H.

In some embodiments, the invention relates to a compound of formula (I-A-4), or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, halo, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H or $C_1$-$C_6$ alkoxy. In other embodiments, $R_9$ is H or $OCH_3$. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-A-4), or a pharmaceutically acceptable salt thereof, wherein $R_{10}$ is H, halo, OH, or $C_1$-$C_6$ alkoxy. In other embodiments, $R_{10}$ is halo, OH, or $C_1$-$C_6$ alkoxy. In other embodiments, $R_{10}$ is H, OH, or $C_1$-$C_6$ alkoxy. In other embodiments, $R_{10}$ is H, halo, or $C_1$-$C_6$ alkoxy. In other embodiments, $R_{10}$ is H, halo, or OH. In other embodiments, $R_{10}$ is halo. In other embodiments, $R_{10}$ is $C_1$-$C_6$ alkoxy. In other embodiments, $R_{10}$ is H. In other embodiments, $R_{10}$ is $^1$H. In other embodiments, $R_{10}$ is D.

In some embodiments, the invention relates to a compound of formula (I-A-4), or a pharmaceutically acceptable salt thereof, wherein $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is halo or $C_1$-$C_6$ haloalkoxy. In other embodiments, $R_{11}$ is F or $OCF_3$. In other embodiments, $R_{11}$ is H. In other embodiments, $R_{11}$ is $^1$H. In other embodiments, $R_{11}$ is D. In other embodiments, $R_{11}$ is F. In other embodiments, $R_{11}$ is $OCF_3$.

In some embodiments, the invention relates to a compound of formula (I-A-4), or a pharmaceutically acceptable salt thereof, wherein $R_{12}$ is H.

In some embodiments, the invention relates to a compound of formula (I-A-4), or a pharmaceutically acceptable salt thereof, wherein $R_{13}$ is H.

In some embodiments, the invention relates to a compound of formula (I-A-4), i.e., the compound in non-salt form.

In another aspect, the invention relates to a compound of formula (I-A-5)

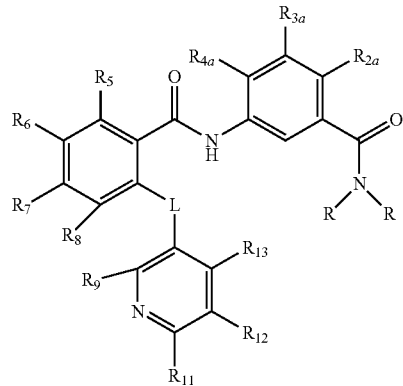

I-A-5 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$ and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, $R_7$, and $R_8$ is not H;
wherein when $R_7$ is $C_1$-$C_6$ alkyl, then $R_{2a}$ is not H;
wherein when $R_{4a}$ is halo, then $R_{2a}$ is not H.

In some embodiments, the invention relates to a compound of formula (I-A-5), or a pharmaceutically acceptable salt thereof, wherein L is O.

In some embodiments, the invention relates to a compound of formula (I-A-5), or a pharmaceutically acceptable salt thereof, wherein each R is independently H or $CH_3$. In other embodiments, each R is H. In other embodiments, each R is $CH_3$.

In some embodiments, the invention relates to a compound of formula (I-A-5), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is F.

In some embodiments, the invention relates to a compound of formula (I-A-5), or a pharmaceutically acceptable salt thereof, wherein $R_{3a}$ is H or halo. In other embodiments, $R_{3a}$ is halo. In other embodiments, $R_{3a}$ is H.

In some embodiments, the invention relates to a compound of formula (I-A-5), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H.

In some embodiments, the invention relates to a compound of formula (I-A-5), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H or halo. In other embodiments, $R_5$ is H or F. In other embodiments, $R_5$ is H. In other embodiments, $R_5$ is F.

In some embodiments, the invention relates to a compound of formula (I-A-5), or a pharmaceutically acceptable salt thereof, wherein $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is halo, $C_1$-$C_6$ alkyl, or $C_1$-$C_6$ haloalkyl. In other embodiments, $R_6$ is Cl or $CF_3$. In other embodiments, $R_6$ is Cl. In other embodiments, $R_6$ is $CF_3$.

In some embodiments, the invention relates to a compound of formula (I-A-5), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, or —W—$(CH_2)_n$—$R_w$. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is —W—$(CH_2)_n$—$R_w$. In other embodiments, $R_7$ is —W—$(CH_2)_n$—$R_w$, wherein W is O, n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H or halo. In other embodiments, $R_7$ is H or Cl. In other embodiments, $R_7$ is H. In other embodiments, $R_7$ is Cl.

In some embodiments, the invention relates to a compound of formula (I-A-5), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H.

In some embodiments, the invention relates to a compound of formula (I-A-5), or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, halo, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H or $C_1$-$C_6$ alkoxy. In other embodiments, $R_9$ is H or $OCH_3$. In other embodiments, $R_9$ is H. In other embodiments, $R_9$ is $^1H$. In other embodiments, $R_9$ is D. In other embodiments, $R_9$ is $OCH_3$.

In some embodiments, the invention relates to a compound of formula (I-A-5), or a pharmaceutically acceptable salt thereof, wherein $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H, Cl, $OCH_3$, or $OCF_3$. In other embodiments, $R_{11}$ is H. In other embodiments, $R_{11}$ is $^1H$. In other embodiments, $R_{11}$ is D. In other embodiments, $R_{11}$ is Cl. In other embodiments, $R_{11}$ is $OCH_3$. In other embodiments, $R_{11}$ is $OCF_3$.

In some embodiments, the invention relates to a compound of formula (I-A-5), or a pharmaceutically acceptable salt thereof, wherein $R_{12}$ is H.

In some embodiments, the invention relates to a compound of formula (I-A-5), or a pharmaceutically acceptable salt thereof, wherein $R_{13}$ is H.

In some embodiments, the invention relates to a compound of formula (I-A-5), i.e., the compound in non-salt form.

In another aspect, the invention relates to a compound of formula (I-A-6)

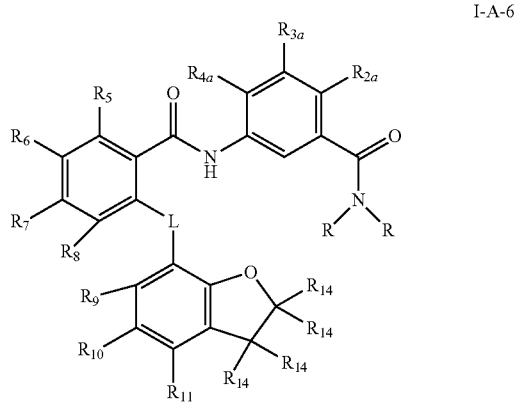

I-A-6 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each $R_{14}$ is independently H, halo, $C_1$-$C_4$ alkyl, or $C_1$-$C_4$ haloalkyl;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, $R_7$, and $R_8$ is not H;
wherein when $R_7$ is $C_1$-$C_6$ alkyl, then $R_{2a}$ is not H;
wherein when $R_{4a}$ is halo, then $R_{2a}$ is not H.

In some embodiments, the invention relates to a compound of formula (I-A-6), or a pharmaceutically acceptable salt thereof, wherein L is O.

In some embodiments, the invention relates to a compound of formula (I-A-6), or a pharmaceutically acceptable salt thereof, wherein each R is independently H or $CH_3$. In other embodiments, each R is H. In other embodiments, each R is $CH_3$.

In some embodiments, the invention relates to a compound of formula (I-A-6), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is F.

In some embodiments, the invention relates to a compound of formula (I-A-6), or a pharmaceutically acceptable salt thereof, wherein $R_{3a}$ is H or halo. In other embodiments, $R_{3a}$ is halo. In other embodiments, $R_{3a}$ is H.

In some embodiments, the invention relates to a compound of formula (I-A-6), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H.

In some embodiments, the invention relates to a compound of formula (I-A-6), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is F.

In some embodiments, the invention relates to a compound of formula (I-A-6), or a pharmaceutically acceptable salt thereof, wherein $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—

$R_w$, wherein W is a single bond, n is 0, and $R_w$ is unsubstituted 3-6 membered cycloalkyl. In other embodiments, $R_6$ is $CF_3$.

In some embodiments, the invention relates to a compound of formula (I-A-6), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, or —W—$(CH_2)_n$—$R_w$. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is —W—$(CH_2)_n$—$R_w$. In other embodiments, $R_7$ is —W—$(CH_2)_n$—$R_w$, wherein W is O, n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H.

In some embodiments, the invention relates to a compound of formula (I-A-6), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H.

In some embodiments, the invention relates to a compound of formula (I-A-6), or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, halo, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H. In other embodiments, $R_9$ is $^1$H. In other embodiments, $R_9$ is D.

In some embodiments, the invention relates to a compound of formula (I-A-6), or a pharmaceutically acceptable salt thereof, wherein $R_{10}$ is H, halo, OH, or $C_1$-$C_6$ alkoxy. In other embodiments, $R_{10}$ is halo, OH, or $C_1$-$C_6$ alkoxy. In other embodiments, $R_{10}$ is H, OH, or $C_1$-$C_6$ alkoxy. In other embodiments, $R_{10}$ is H, halo, or $C_1$-$C_6$ alkoxy. In other embodiments, $R_{10}$ is H, halo, or OH. In other embodiments, $R_{10}$ is halo. In other embodiments, $R_{10}$ is $C_1$-$C_6$ alkoxy. In other embodiments, $R_{10}$ is H. In other embodiments, $R_{10}$ is $^1$H. In other embodiments, $R_{10}$ is D.

In some embodiments, the invention relates to a compound of formula (I-A-6), or a pharmaceutically acceptable salt thereof, wherein $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D.

In some embodiments, the invention relates to a compound of formula (I-A-6), or a pharmaceutically acceptable salt thereof, wherein each $R_{14}$ is H.

In some embodiments, the invention relates to a compound of formula (I-A-6), i.e., the compound in non-salt form.

In another aspect, the invention relates to a compound of formula (I-A-7)

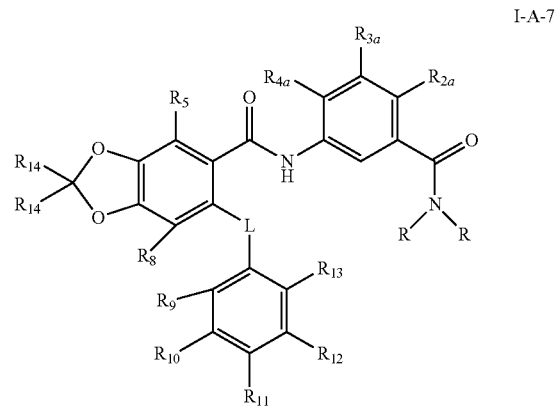

I-A-7 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each $R_{14}$ is independently H, halo, $C_1$-$C_4$ alkyl, or $C_1$-$C_4$ haloalkyl;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein when $R_{4a}$ is halo, then $R_{2a}$ is not H.

In some embodiments, the invention relates to a compound of formula (I-A-7), or a pharmaceutically acceptable salt thereof, wherein L is O.

In some embodiments, the invention relates to a compound of formula (I-A-7), or a pharmaceutically acceptable salt thereof, wherein each R is independently H or $CH_3$. In other embodiments, each R is H. In other embodiments, each R is $CH_3$.

In some embodiments, the invention relates to a compound of formula (I-A-7), or a pharmaceutically acceptable salt thereof, wherein $R_{2a}$ is H, halo, OH, $C_1$-$C_6$ alkyl, or $C_1$-$C_6$ alkoxy. In other embodiments, $R_{2a}$ is halo, OH, $C_1$-$C_6$ alkyl, or $C_1$-$C_6$ alkoxy. In other embodiments, $R_{2a}$ is H, OH, $C_1$-$C_6$ alkyl, or $C_1$-$C_6$ alkoxy. In other embodiments, $R_{2a}$ is H, halo, $C_1$-$C_6$ alkyl, or $C_1$-$C_6$ alkoxy. In other embodiments, $R_{2a}$ is H, halo, OH, or $C_1$-$C_6$ alkoxy. In other embodiments, $R_{2a}$ is H, halo, OH, or $C_1$-$C_6$ alkyl. In other embodiments, $R_{2a}$ is halo. In other embodiments, $R_{2a}$ is $C_1$-$C_6$ alkyl. In other embodiments, $R_{2a}$ is $C_1$-$C_6$ alkoxy. In other embodiments, $R_{2a}$ is F.

In some embodiments, the invention relates to a compound of formula (I-A-7), or a pharmaceutically acceptable salt thereof, wherein $R_{3a}$ is H or halo. In other embodiments, $R_{3a}$ is halo. In other embodiments, $R_{3a}$ is H.

In some embodiments, the invention relates to a compound of formula (I-A-7), or a pharmaceutically acceptable salt thereof, wherein $R_{4a}$ is H or $C_1$-$C_6$ alkyl. In other embodiments, $R_{4a}$ is $C_1$-$C_6$ alkyl. In other embodiments, $R_{4a}$ is H.

In some embodiments, the invention relates to a compound of formula (I-A-7), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H.

In some embodiments, the invention relates to a compound of formula (I-A-7), or a pharmaceutically acceptable salt thereof, wherein $R_8$ is —O—$(CH_2)_n$—$R_w$. In other embodiments, $R_8$ is —O—$(CH_2)_n$—$R_w$, wherein n is 1, and $R_w$ is phenyl, wherein said phenyl may be unsubstituted or may be substituted with 1-3 substituents selected from a group consisting of halo, $C_1$-$C_6$ alkyl, and $C_1$-$C_6$ haloalkyl. In other embodiments, $R_8$ is H.

In some embodiments, the invention relates to a compound of formula (I-A-7), or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$. In other embodiments, $R_9$ is halo, OH, $C_1$-$C_6$ alkyl, $C_1$-$C_6$ alkoxy, or —W—$(CH_2)_n$—$R_w$. In other embodiments, $R_9$ is H, OH, $C_1$-$C_6$ alkyl, $C_1$-$C_6$ alkoxy, or —W—$(CH_2)_n$—$R_w$. In other embodiments, $R_9$ is H, $C_1$-$C_6$ alkyl, $C_1$-$C_6$ alkoxy, or —W—$(CH_2)_n$—$R_w$. In other embodiments, $R_9$ is H, halo, OH, $C_1$-$C_6$ alkoxy, or —W—$(CH_2)_n$—$R_w$. In other embodiments, $R_9$ is H, halo, OH, $C_1$-$C_6$ alkyl, or —W—$(CH_2)_n$—$R_w$. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is —W—$(CH_2)_n$—$R_w$. In other embodiments, $R_9$ is —W—$(CH_2)_n$—$R_w$, wherein W is a single bond, n is 0, and $R_w$ is 5-6 membered heteroaryl, wherein said 5-6 membered heteroaryl may be unsubstituted or may be substituted with 1-3 substituents selected from a group consisting of halo, $C_1$-$C_6$ alkyl, and $C_1$-$C_6$ haloalkyl. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-A-7), or a pharmaceutically acceptable salt thereof, wherein $R_{10}$ is H, halo, OH, or $C_1$-$C_6$ alkoxy. In other embodiments, $R_{10}$ is halo, OH, or $C_1$-$C_6$ alkoxy. In other embodiments, $R_{10}$ is H, OH, or $C_1$-$C_6$ alkoxy. In other embodiments, $R_{10}$ is H, halo, or $C_1$-$C_6$ alkoxy. In other embodiments, $R_{10}$ is H, halo, or OH. In other embodiments, $R_{10}$ is halo. In other embodiments, $R_{10}$ is $C_1$-$C_6$ alkoxy. In other embodiments, $R_{10}$ is H. In other embodiments, $R_{10}$ is $^1$H. In other embodiments, $R_{10}$ is D.

In some embodiments, the invention relates to a compound of formula (I-A-7), or a pharmaceutically acceptable salt thereof, wherein $R_{11}$ is H, halo, $C_1$-$C_6$ alkoxy, or $C_1$-$C_6$ haloalkoxy. In other embodiments, $R_{11}$ is halo, $C_1$-$C_6$ alkoxy, or $C_1$-$C_6$ haloalkoxy. In other embodiments, $R_{11}$ is H, $C_1$-$C_6$ alkoxy, or $C_1$-$C_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{10}$ is $^1$H. In other embodiments, $R_{11}$ is D. In other embodiments, $R_{11}$ is $OCF_3$.

In some embodiments, the invention relates to a compound of formula (I-A-7), or a pharmaceutically acceptable salt thereof, wherein $R_{12}$ is H.

In some embodiments, the invention relates to a compound of formula (I-A-7), or a pharmaceutically acceptable salt thereof, wherein $R_{13}$ is H.

In some embodiments, the invention relates to a compound of formula (I-A-7), or a pharmaceutically acceptable salt thereof, wherein each $R_{14}$ is F.

In some embodiments, the invention relates to a compound of formula (I-A-7), i.e., the compound in non-salt form.

In another aspect, the invention relates to a compound of formula (I-A-8)

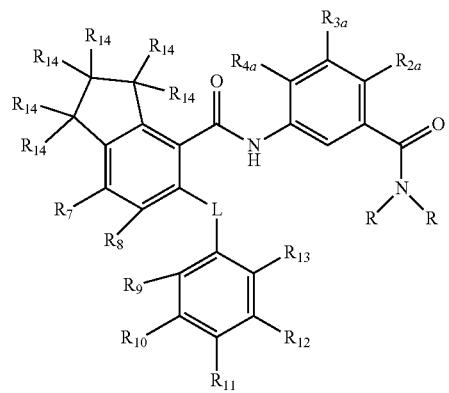

I-A-8 or a pharmaceutically acceptable salt thereof, wherein:

L is O, C(R)$_2$, or a single bond;

each R is independently H or C$_1$-C$_6$ alkyl;

R$_{2a}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{3a}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{4a}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_7$ is H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

R$_8$ is H or —O—(CH$_2$)$_n$—R$_w$;

R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

each R$_{14}$ is independently H, halo, C$_1$-C$_4$ alkyl, or C$_1$-C$_4$ haloalkyl;

each W is independently O or a single bond;

each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, C$_1$-C$_6$ alkyl, and C$_1$-C$_6$ haloalkyl; and n is 0 or 1;

wherein when R$_7$ is C$_1$-C$_6$ alkyl, then R$_{2a}$ is not H;

wherein when R$_{4a}$ is halo, then R$_{2a}$ is not H.

In some embodiments, the invention relates to a compound of formula (I-A-8), or a pharmaceutically acceptable salt thereof, wherein L is O.

In some embodiments, the invention relates to a compound of formula (I-A-8), or a pharmaceutically acceptable salt thereof, wherein each R is independently H or CH$_3$. In other embodiments, each R is H. In other embodiments, each R is CH$_3$.

In some embodiments, the invention relates to a compound of formula (I-A-8), or a pharmaceutically acceptable salt thereof, wherein R$_{2a}$ is H, halo, OH, C$_1$-C$_6$ alkyl, or C$_1$-C$_6$ alkoxy. In other embodiments, R$_{2a}$ is halo, OH, C$_1$-C$_6$ alkyl, or C$_1$-C$_6$ alkoxy. In other embodiments, R$_{2a}$ is H, OH, C$_1$-C$_6$ alkyl, or C$_1$-C$_6$ alkoxy. In other embodiments, R$_{2a}$ is H, halo, C$_1$-C$_6$ alkyl, or C$_1$-C$_6$ alkoxy. In other embodiments, R$_{2a}$ is H, halo, OH, or C$_1$-C$_6$ alkoxy. In other embodiments, R$_{2a}$ is H, halo, OH, or C$_1$-C$_6$ alkyl. In other embodiments, R$_{2a}$ is halo. In other embodiments, R$_{2a}$ is C$_1$-C$_6$ alkyl. In other embodiments, R$_{2a}$ is C$_1$-C$_6$ alkoxy. In other embodiments, R$_{2a}$ is F.

In some embodiments, the invention relates to a compound of formula (I-A-8), or a pharmaceutically acceptable salt thereof, wherein R$_{3a}$ is H or halo. In other embodiments, R$_{3a}$ is halo. In other embodiments, R$_{3a}$ is H.

In some embodiments, the invention relates to a compound of formula (I-A-8), or a pharmaceutically acceptable salt thereof, wherein R$_{4a}$ is H or C$_1$-C$_6$ alkyl. In other embodiments, R$_{4a}$ is C$_1$-C$_6$ alkyl. In other embodiments, R$_{4a}$ is H.

In some embodiments, the invention relates to a compound of formula (I-A-8), or a pharmaceutically acceptable salt thereof, wherein R$_7$ is H, halo, C$_1$-C$_6$ alkyl, C$_1$-C$_6$ haloalkyl, C$_1$-C$_6$ alkoxy, or —W—(CH$_2$)$_n$—R$_w$. In other embodiments, R$_7$ is halo, C$_1$-C$_6$ alkyl, C$_1$-C$_6$ haloalkyl, C$_1$-C$_6$ alkoxy, or —W—(CH$_2$)$_n$—R$_w$. In other embodiments, R$_7$ is H, C$_1$-C$_6$ alkyl, C$_1$-C$_6$ haloalkyl, C$_1$-C$_6$ alkoxy, or —W—(CH$_2$)$_n$—R$_w$. In other embodiments, R$_7$ is H, halo, C$_1$-C$_6$ haloalkyl, C$_1$-C$_6$ alkoxy, or —W—(CH$_2$)$_n$—R$_w$. In other embodiments, R$_7$ is H, halo, C$_1$-C$_6$ alkyl, C$_1$-C$_6$ alkoxy, or —W—(CH$_2$)$_n$—R$_w$. In other embodiments, R$_7$ is H, halo, C$_1$-C$_6$ alkyl, C$_1$-C$_6$ haloalkyl, or —W—(CH$_2$)$_n$—R$_w$. In other embodiments, R$_7$ is H, halo, C$_1$-C$_6$ alkyl, C$_1$-C$_6$ haloalkyl, or C$_1$-C$_6$ alkoxy. In other embodiments, R$_7$ is halo. In other embodiments, R$_7$ is C$_1$-C$_6$ alkyl. In other embodiments, R$_7$ is C$_1$-C$_6$ haloalkyl. In other embodiments, R$_7$ is C$_1$-C$_6$ alkoxy. In other embodiments, R$_7$ is —W—(CH$_2$)$_n$—R$_w$. In other embodiments, R$_7$ is —W—(CH$_2$)$_n$—R$_w$, wherein W is O, n is 1, and R$_w$ is phenyl, wherein said phenyl may be unsubstituted or may be substituted with 1-3 substituents selected from a group consisting of halo, C$_1$-C$_6$ alkyl, and C$_1$-C$_6$ haloalkyl. In other embodiments, R$_7$ is —W—(CH$_2$)$_n$—R$_w$, wherein W is a single bond, n is 0, and R$_w$ is 3-6 membered cycloalkyl, wherein said 3-6 membered cycloalkyl may be unsubstituted or may be substituted with 1-3 substituents selected from a group consisting of halo, C$_1$-C$_6$ alkyl, and C$_1$-C$_6$ haloalkyl. In other embodiments, R$_7$ is H.

In some embodiments, the invention relates to a compound of formula (I-A-8), or a pharmaceutically acceptable salt thereof, wherein R$_8$ is —O—(CH$_2$)$_n$—R$_w$. In other embodiments, R$_8$ is —O—(CH$_2$)$_n$—R$_w$, wherein n is 1, and R$_w$ is phenyl, wherein said phenyl may be unsubstituted or may be substituted with 1-3 substituents selected from a group consisting of halo, C$_1$-C$_6$ alkyl, and C$_1$-C$_6$ haloalkyl. In other embodiments, R$_8$ is H.

In some embodiments, the invention relates to a compound of formula (I-A-8), or a pharmaceutically acceptable salt thereof, wherein R$_9$ is H, halo, OH, C$_1$-C$_6$ alkyl, C$_1$-C$_6$ alkoxy, or —W—(CH$_2$)$_n$—R$_w$. In other embodiments, R$_9$ is halo, OH, C$_1$-C$_6$ alkyl, C$_1$-C$_6$ alkoxy, or —W—(CH$_2$)$_n$—R$_w$. In other embodiments, R$_9$ is H, OH, C$_1$-C$_6$ alkyl, C$_1$-C$_6$ alkoxy, or —W—(CH$_2$)$_n$—R$_w$. In other embodiments, R$_9$ is H, halo, C$_1$-C$_6$ alkyl, C$_1$-C$_6$ alkoxy, or —W—(CH$_2$)$_n$—R$_w$. In other embodiments, R$_9$ is H, halo, OH, C$_1$-C$_6$ alkoxy, or —W—(CH$_2$)$_n$—R$_w$. In other embodiments, R$_9$ is H, halo, OH, C$_1$-C$_6$ alkyl, or —W—(CH$_2$)$_n$—R$_w$. In other embodiments, R$_9$ is H, halo, OH, C$_1$-C$_6$ alkyl, or C$_1$-C$_6$ alkoxy. In other embodiments, R$_9$ is halo. In other embodiments, R$_9$ is C$_1$-C$_6$ alkyl. In other embodiments, R$_9$ is C$_1$-C$_6$ alkoxy. In other embodiments, R$_9$ is —W—(CH$_2$)$_n$—R$_w$. In other embodiments, R$_9$ is —W—(CH$_2$)$_n$—R$_w$, wherein W is a single bond, n is 0, and R$_w$ is 5-6 membered heteroaryl, wherein said 5-6 membered heteroaryl may be unsubstituted or may be substituted with 1-3 substituents selected from a group consisting of halo, C$_1$-C$_6$ alkyl, and C$_1$-C$_6$ haloalkyl. In other embodiments, R$_9$ is H. In other embodiments, R$_9$ is $^1$H. In other embodiments, R$_9$ is D.

In some embodiments, the invention relates to a compound of formula (I-A-8), or a pharmaceutically acceptable salt thereof, wherein R$_{10}$ is H, halo, OH, or C$_1$-C$_6$ alkoxy. In other embodiments, R$_{10}$ is halo, OH, or C$_1$-C$_6$ alkoxy. In other embodiments, R$_{10}$ is H, OH, or C$_1$-C$_6$ alkoxy. In other embodiments, R$_{10}$ is H, halo, or C$_1$-C$_6$ alkoxy. In other embodiments, R$_{10}$ is H, halo, or OH. In other embodiments, R$_{10}$ is halo. In other embodiments, R$_{10}$ is C$_1$-C$_6$ alkoxy. In other embodiments, R$_{10}$ is H. In other embodiments, R$_{10}$ is $^1$H. In other embodiments, R$_{10}$ is D.

In some embodiments, the invention relates to a compound of formula (I-A-8), or a pharmaceutically acceptable salt thereof, wherein R$_{11}$ is H, halo, C$_1$-C$_6$ alkoxy, or C$_1$-C$_6$ haloalkoxy. In other embodiments, R$_{11}$ is halo, C$_1$-C$_6$ alkoxy, or C$_1$-C$_6$ haloalkoxy. In other embodiments, R$_{11}$ is H, C$_1$-C$_6$ alkoxy, or C$_1$-C$_6$ haloalkoxy. In other embodiments, $R_{11}$ is H, halo, or $C_1$-$C_6$ haloalkoxy. In other embodiments, $R_{11}$ is H, halo, or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (I-A-8), or a pharmaceutically acceptable salt thereof, wherein $R_{12}$ is H.

In some embodiments, the invention relates to a compound of formula (I-A-8), or a pharmaceutically acceptable salt thereof, wherein $R_{13}$ is H.

In some embodiments, the invention relates to a compound of formula (I-A-8), or a pharmaceutically acceptable salt thereof, wherein each $R_{14}$ is independently H or F.

In some embodiments, the invention relates to a compound of formula (I-A-8), i.e., the compound in non-salt form.

In another aspect, the invention relates to a compound of formula (I-B)

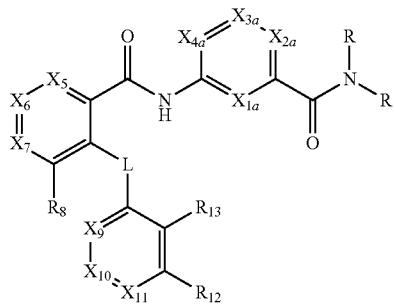

I-B or a pharmaceutically acceptable salt thereof, wherein:
L is O, $C(R)_2$, or a single bond;
$X_{1a}$ is N or CH;
$X_{2a}$ is N, $N^+$—$O^-$, or $CR_{2a}$;
$X_{3a}$ is N or $CR_{3a}$;
$X_{4a}$ is N or $CR_{4a}$;
$X_5$ is N or $CR_5$;
$X_6$ is N or $CR_6$;
$X_7$ is N or $CR_7$;
$X_9$ is N or $CR_9$;
$X_{10}$ is N or $CR_{10}$;
$X_{11}$ is N or $CR_{11}$;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are defined as follows:
(i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
(ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

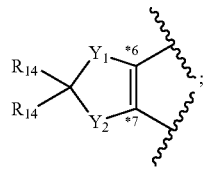

or
(iii) $R_5$ and $R_6$, together with the carbon atoms to which they are attached, form a ring of formula:

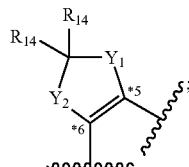

and
$R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

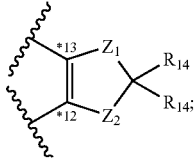

$Y_1$, $Y_2$, $Z_1$, and $Z_2$ are each independently O or $C(R_{14})_2$;
each $R_{14}$ is independently H, halo, $C_1$-$C_4$ alkyl, or $C_1$-$C_4$ haloalkyl;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein when $R_8$ is H, then at least one of $X_5$, $X_6$, and $X_7$ is not N or CH;
wherein one or two of $X_{1a}$, $X_{2a}$, $X_{3a}$, and $X_{4a}$ is N or $N^+$—$O^-$;
wherein no more than one of $X_5$, $X_6$, and $X_7$ is N;
wherein no more than one of $X_9$, $X_{10}$, and $X_{11}$ is N.

In some embodiments, the invention relates to a compound of formula (I-B), or a pharmaceutically acceptable salt thereof, wherein L is O.

In some embodiments, the invention relates to a compound of formula (I-B), or a pharmaceutically acceptable salt thereof, wherein $X_{1a}$ is N. In other embodiments, $X_{1a}$ is CH.

In some embodiments, the invention relates to a compound of formula (I-B), or a pharmaceutically acceptable salt thereof, wherein $X_{2a}$ is N or $N^+$—$O^-$. In other embodiments, $X_{2a}$ is N. In other embodiments, $X_{2a}$ is $N^+$—$O^-$. In other embodiments, $X_{2a}$ is $CR_{2a}$.

In some embodiments, the invention relates to a compound of formula (I-B), or a pharmaceutically acceptable salt thereof, wherein $X_{3a}$ is N. In other embodiments, $X_{3a}$ is $CR_{3a}$.

In some embodiments, the invention relates to a compound of formula (I-B), or a pharmaceutically acceptable salt thereof, wherein $X_{4a}$ is N. In other embodiments, $X_{4a}$ is $CR_{4a}$.

In some embodiments, the invention relates to a compound of formula (I-B), or a pharmaceutically acceptable salt thereof, wherein $X_5$ is N. In other embodiments, $X_5$ is $CR_5$.

In some embodiments, the invention relates to a compound of formula (I-B), or a pharmaceutically acceptable salt thereof, wherein $X_6$ is N. In other embodiments, $X_6$ is $CR_6$.

In some embodiments, the invention relates to a compound of formula (I-B), or a pharmaceutically acceptable salt thereof, wherein $X_7$ is N. In other embodiments, $X_7$ is $CR_7$.

In some embodiments, the invention relates to a compound of formula (I-B), or a pharmaceutically acceptable salt thereof, wherein $X_9$ is N. In other embodiments, $X_9$ is $CR_9$.

In some embodiments, the invention relates to a compound of formula (I-B), or a pharmaceutically acceptable salt thereof, wherein $X_{10}$ is N. In other embodiments, $X_{10}$ is $CR_{10}$.

In some embodiments, the invention relates to a compound of formula (I-B), or a pharmaceutically acceptable salt thereof, wherein $X_{11}$ is N. In other embodiments, $X_{11}$ is $CR_{11}$.

In some embodiments, the invention relates to a compound of formula (I-B), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B), or a pharmaceutically acceptable salt thereof, wherein $R_{2a}$ is H or halo. In other embodiments, $R_{2a}$ is halo. In other embodiments, $R_{2a}$ is H or F. In other embodiments, $R_{2a}$ is H. In other embodiments, $R_{2a}$ is F.

In some embodiments, the invention relates to a compound of formula (I-B), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H or $CH_3$. In other embodiments, $R_{3a}$ is H. In other embodiments, $R_{3a}$ is $CH_3$.

In some embodiments, the invention relates to a compound of formula (I-B), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H, F, Cl, or $CH_3$. In other embodiments, $R_{4a}$ is H. In other embodiments, $R_{4a}$ is F. In other embodiments, $R_{4a}$ is Cl. In other embodiments, $R_{4a}$ is $CH_3$.

In some embodiments, the invention relates to a compound of formula (I-B), or a pharmaceutically acceptable salt thereof, wherein $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is H, F, Cl, $NHCH_3$, $CF_3$, $OCH_3$, or $OCH_2CH_3$. In other embodiments, $R_5$ is H. In other embodiments, $R_5$ is F. In other embodiments, $R_5$ is Cl. In other embodiments, $R_5$ is $NHCH_3$. In other embodiments, $R_5$ is $CF_3$. In other embodiments, $R_5$ is $OCH_3$. In other embodiments, $R_5$ is $OCH_2CH_3$.

In some embodiments, the invention relates to a compound of formula (I-B), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H, F, Cl, $CH_3$, $CHF_2$, $CF_3$, $CF_2CF_3$, $OCHF_2$, $OCF_3$, or cyclopropyl. In other embodiments, $R_6$ is H. In other embodiments, $R_6$ is F. In other embodiments, $R_6$ is Cl. In other embodiments, $R_6$ is $CH_3$. In other embodiments, $R_6$ is $C(^1H)_3$. In other embodiments, $R_6$ is $CD_3$. In other embodiments, $R_6$ is $CHF_2$. In other embodiments, $R_6$ is $CF_3$. In other embodiments, $R_6$ is $CF_2CF_3$. In other embodiments, $R_6$ is $OCHF_2$. In other embodiments, $R_6$ is $OCF_3$. In other embodiments, $R_6$ is cyclopropyl.

In some embodiments, the invention relates to a compound of formula (I-B), or a pharmaceutically acceptable salt thereof, wherein $R_5$ and $R_6$, together with the carbon atoms to which they are attached, form a ring of formula:

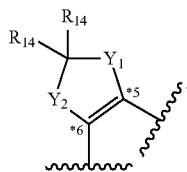

In some embodiments, the invention relates to a compound of formula (I-B), or a pharmaceutically acceptable salt thereof, wherein $R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is —W—$(CH_2)_n$—$R_w$. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H, Cl, $C(CH_3)_3$, $CF(CH_3)_2$, $CF_3$, $OCHF_2$, $OCF_3$, cyclopropyl, 1-methylcyclopropyl, 2-methylcyclopropyl, 2,2-difluorocyclopropyl, or 1-trifluoromethylcyclopropyl. In other embodiments, $R_7$ is H. In other embodiments, $R_7$ is Cl. In other embodiments, $R_7$ is $C(CH_3)_3$. In other embodiments, $R_7$ is $CF(CH_3)_2$. In other embodiments, $R_7$ is $CF_3$. In other embodiments, $R_7$ is $OCHF_2$. In other embodiments, $R_7$ is $OCF_3$. In other embodiments, $R_7$ is cyclopropyl. In other embodiments, $R_7$ is 1-methylcyclopropyl. In other embodiments, $R_7$ is 2-methylcyclopropyl. In other embodiments, $R_7$ is 2,2-difluorocyclopropyl. In other embodiments, $R_7$ is 1-trifluoromethylcyclopropyl.

In some embodiments, the invention relates to a compound of formula (I-B), or a pharmaceutically acceptable salt thereof, wherein $R_6$ and $R_7$, together with the carbon atoms to which they are attached, form a ring of formula:

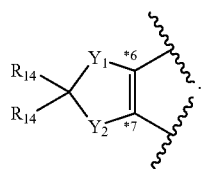

In some embodiments, the invention relates to a compound of formula (I-B), or a pharmaceutically acceptable salt thereof, wherein $R_8$ is H.

In some embodiments, the invention relates to a compound of formula (I-B), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H, F, Cl, OH, $CH_3$, $OCH_3$, $OCHF_2$, or $OCF_3$. In other embodiments, $R_9$ is H. In other embodiments, $R_9$ is $^1H$. In other embodiments, $R_9$ is D. In other embodiments, $R_9$ is F. In other embodiments, $R_9$ is Cl. In other embodiments, $R_9$ is OH. In other embodiments, $R_9$ is $CH_3$. In other embodiments, $R_9$ is $C(^1H)_3$. In other embodiments, $R_9$ is $CD_3$. In other embodiments, $R_9$ is $OCH_3$. In other embodiments, $R_9$ is $OC(^1H)_3$. In other embodiments, $R_9$ is $OCD_3$. In other embodiments, $R_9$ is $OCHF_2$. In other embodiments, $R_9$ is $OCF_3$.

In some embodiments, the invention relates to a compound of formula (I-B), or a pharmaceutically acceptable salt thereof, wherein $R_{10}$ is H or halo. In other embodiments, $R_{10}$ is halo. In other embodiments, $R_{10}$ is H, F, or Cl. In other embodiments, $R_{10}$ is H. In other embodiments, $R_{10}$ is $^1H$. In other embodiments, $R_{10}$ is D. In other embodiments, $R_{10}$ is F. In other embodiments, $R_{10}$ is Cl.

In some embodiments, the invention relates to a compound of formula (I-B), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is F, $OCH_3$, $OCHF_2$, or $OCF_3$. In other embodiments, $R_{11}$ is H. In other embodiments, $R_{11}$ is $^1H$. In other embodiments, $R_{11}$ is D. In other embodiments, $R_{11}$ is F. In other embodiments, $R_{11}$ is $OCH_3$. In other embodiments, $R_{11}$ is $OCHF_2$. In other embodiments, $R_{11}$ is $OCF_3$.

In some embodiments, the invention relates to a compound of formula (I-B), or a pharmaceutically acceptable salt thereof, wherein $R_{12}$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_{12}$ is H.

In some embodiments, the invention relates to a compound of formula (I-B), or a pharmaceutically acceptable salt thereof, wherein $R_{13}$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_{13}$ is H.

In some embodiments, the invention relates to a compound of formula (I-B), or a pharmaceutically acceptable salt thereof, wherein $Y_1$ is O, and $Y_2$ is $C(R_{14})_2$. In other embodiments, $Y_1$ is $C(R_{14})_2$, and $Y_2$ is O. In other embodiments, $Y_1$ is O, and $Y_2$ is O. In other embodiments, $Y_1$ is $C(R_{14})_2$, and $Y_2$ is $C(R_{14})_2$.

In some embodiments, the invention relates to a compound of formula (I-B), or a pharmaceutically acceptable salt thereof, wherein $Z_1$ is O, and $Z_2$ is $C(R_{14})_2$. In other embodiments, $Z_1$ is $C(R_{14})_2$, and $Z_2$ is O. In other embodiments, $Z_1$ is O, and $Z_2$ is O. In other embodiments, $Z_1$ is $C(R_{14})_2$, and $Z_2$ is $C(R_{14})_2$.

In some embodiments, the invention relates to a compound of formula (I-B), or a pharmaceutically acceptable salt thereof, wherein each $R_{14}$ is independently H or F. In other embodiments, each $R_{14}$ is H. In other embodiments, each $R_{14}$ is F.

In some embodiments, the invention relates to a compound of formula (I-B), i.e., the compound in non-salt form.

In another aspect, the invention relates to a compound of formula (I-B-1)

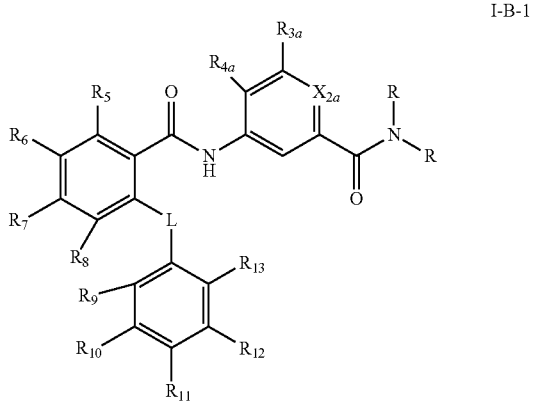

I-B-1 or a pharmaceutically acceptable salt thereof, wherein:
L is O, $C(R)_2$, or a single bond;
$X_{2a}$ is N or $N^+$—$O^-$;
each R is independently H or $C_1$-$C_6$ alkyl;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, $R_7$, and $R_8$ is not H.

In some embodiments, the invention relates to a compound of formula (I-B-1), or a pharmaceutically acceptable salt thereof, wherein L is O.

In some embodiments, the invention relates to a compound of formula (I-B-1), or a pharmaceutically acceptable salt thereof, wherein $X_{2a}$ is N. In other embodiments, $X_{2a}$ is $N^+$—$O^-$.

In some embodiments, the invention relates to a compound of formula (I-B-1), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B-1), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H or $CH_3$. In other embodiments, $R_{3a}$ is H. In other embodiments, $R_{3a}$ is $CH_3$.

In some embodiments, the invention relates to a compound of formula (I-B-1), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H, F, Cl, or $CH_3$. In other embodiments, $R_{4a}$ is H. In other embodiments, $R_{4a}$ is F. In other embodiments, $R_{4a}$ is Cl. In other embodiments, $R_{4a}$ is $CH_3$.

In some embodiments, the invention relates to a compound of formula (I-B-1), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, F, Cl, $NHCH_3$, $CF_3$, or $OCH_3$. In other embodiments, $R_5$ is H. In other embodiments, $R_5$ is F. In other embodiments, $R_5$ is Cl. In other embodiments, $R_5$ is $NHCH_3$. In other embodiments, $R_5$ is $CF_3$. In other embodiments, $R_5$ is $OCH_3$.

In some embodiments, the invention relates to a compound of formula (I-B-1), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H, F, Cl, $CH_3$, $CHF_2$, $CF_3$, $CF_2CF_3$, $OCHF_2$, $OCF_3$, or cyclopropyl. In other embodiments, $R_6$ is H. In other embodiments, $R_6$ is F. In other embodiments, $R_6$ is Cl. In other embodiments, $R_6$ is $CH_3$. In other embodiments, $R_6$ is $C(^1H)_3$. In other embodiments, $R_6$ is $CD_3$. In other embodiments, $R_6$ is $CHF_2$. In other embodiments, $R_6$ is $CF_3$. In other embodiments, $R_6$ is $CF_2CF_3$. In other embodiments, $R_6$ is $OCHF_2$. In other embodiments, $R_6$ is $OCF_3$. In other embodiments, $R_6$ is cyclopropyl.

In some embodiments, the invention relates to a compound of formula (I-B-1), or a pharmaceutically acceptable salt thereof, wherein $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is —W—$(CH_2)_n$—$R_w$. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is halo, $C_1$-$C_6$ haloalkyl, $C_1$-$C_6$ haloalkoxy, or —W—$(CH_2)_n$—$R_w$. In other embodiments, $R_7$ is H, Cl, $CF_3$, $OCHF_2$, $OCF_3$, or cyclopropyl. In other embodiments, $R_7$ is H. In other embodiments, $R_7$ is Cl. In other embodiments, $R_7$ is $CF_3$. In other embodiments, $R_7$ is $OCHF_2$. In other embodiments, $R_7$ is $OCF_3$. In other embodiments, $R_7$ is cyclopropyl.

In some embodiments, the invention relates to a compound of formula (I-B-1), or a pharmaceutically acceptable salt thereof, wherein $R_8$ is H.

In some embodiments, the invention relates to a compound of formula (I-B-1), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is $C_1$-$C_6$ halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H, F, Cl, OH, $CH_3$, $OCH_3$, $OCHF_2$, or $OCF_3$. In other embodiments, $R_9$ is H. In other embodiments, $R_9$ is $^1H$. In other embodiments, $R_9$ is D. In other embodiments, $R_9$ is F. In other embodiments, $R_9$ is Cl. In other embodiments, $R_9$ is OH. In other embodiments, $R_9$ is $CH_3$. In other embodiments, $R_9$ is $C(^1H)_3$. In other embodiments, $R_9$ is $CD_3$. In other embodiments, $R_9$ is $OCH_3$. In other embodiments, $R_9$ is $OC(^1H)_3$. In other embodiments, $R_9$ is $OCD_3$. In other embodiments, $R_9$ is $OCHF_2$. In other embodiments, $R_9$ is $OCF_3$.

In some embodiments, the invention relates to a compound of formula (I-B-1), or a pharmaceutically acceptable salt thereof, wherein $R_{10}$ is H or halo. In other embodiments, $R_{10}$ is halo. In other embodiments, $R_{10}$ is H, F, or Cl. In other embodiments, $R_{10}$ is H. In other embodiments, $R_{10}$ is $^1H$. In other embodiments, $R_{10}$ is D. In other embodiments, $R_{10}$ is F. In other embodiments, $R_{10}$ is Cl.

In some embodiments, the invention relates to a compound of formula (I-B-1), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is F, $OCH_3$, $OCHF_2$, or $OCF_3$. In other embodiments, $R_{11}$ is H. In other embodiments, $R_{11}$ is $^1H$. In other embodiments, $R_{11}$ is D. In other embodiments, $R_{11}$ is F. In other embodiments, $R_{11}$ is $OCH_3$. In other embodiments, $R_{11}$ is $OCHF_2$. In other embodiments, $R_{11}$ is $OCF_3$.

In some embodiments, the invention relates to a compound of formula (I-B-1), or a pharmaceutically acceptable salt thereof, wherein $R_{12}$ is H.

In some embodiments, the invention relates to a compound of formula (I-B-1), or a pharmaceutically acceptable salt thereof, wherein $R_{13}$ is H.

In some embodiments, the invention relates to a compound of formula (I-B-1), i.e., the compound in non-salt form.

In another aspect, the invention relates to a compound of formula (I-B-2)

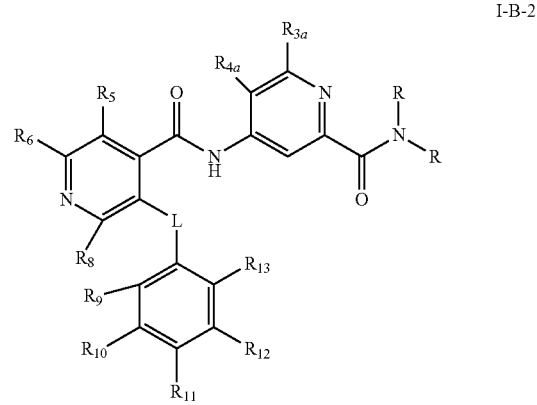

I-B-2 or a pharmaceutically acceptable salt thereof, wherein:
L is O, $C(R)_2$, or a single bond;
each R is independently H or $C_1$-$C_6$ alkyl;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$ and $R_6$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; or $R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein at least one of $R_5$, $R_6$, and $R_8$ is not H.

In some embodiments, the invention relates to a compound of formula (I-B-2), or a pharmaceutically acceptable salt thereof, wherein L is O.

In some embodiments, the invention relates to a compound of formula (I-B-2), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B-2), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H.

In some embodiments, the invention relates to a compound of formula (I-B-2), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H or $CH_3$. In other embodiments, $R_{4a}$ is H. In other embodiments, $R_{4a}$ is $CH_3$.

In some embodiments, the invention relates to a compound of formula (I-B-2), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is halo or $C_1$-$C_6$ alkoxy. In other embodiments, $R_5$ is F, $OCH_3$, or $OCH_2CH_3$. In other embodiments, $R_5$ is F. In other embodiments, $R_5$ is $OCH_3$. In other embodiments, $R_5$ is $OCH_2CH_3$.

In some embodiments, the invention relates to a compound of formula (I-B-2), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H or $C_1$-$C_6$ haloalkyl. In other embodiments, $R_6$ is H or $CF_3$. In other embodiments, $R_6$ is H. In other embodiments, $R_6$ is $CF_3$.

In some embodiments, the invention relates to a compound of formula (I-B-2), or a pharmaceutically acceptable salt thereof, wherein $R_8$ is H.

In some embodiments, the invention relates to a compound of formula (I-B-2), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H or $C_1$-$C_6$ alkoxy. In other embodiments, $R_9$ is H or $OCH_3$. In other embodiments, $R_9$ is H. In other embodiments, $R_9$ is $^1H$. In other embodiments, $R_9$ is D. In other embodiments, $R_9$ is $OCH_3$.

In some embodiments, the invention relates to a compound of formula (I-B-2), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1H$. In other embodiments, $R_{10}$ is D.

In some embodiments, the invention relates to a compound of formula (I-B-2), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1H$. In other embodiments, $R_{11}$ is D. In other embodiments, $R_{11}$ is $OCF_3$.

In some embodiments, the invention relates to a compound of formula (I-B-2), or a pharmaceutically acceptable salt thereof, wherein $R_{12}$ is H.

In some embodiments, the invention relates to a compound of formula (I-B-2), or a pharmaceutically acceptable salt thereof, wherein $R_{13}$ is H.

In some embodiments, the invention relates to a compound of formula (I-B-2), i.e., the compound in non-salt form.

In another aspect, the invention relates to a compound of formula (I-B-3)

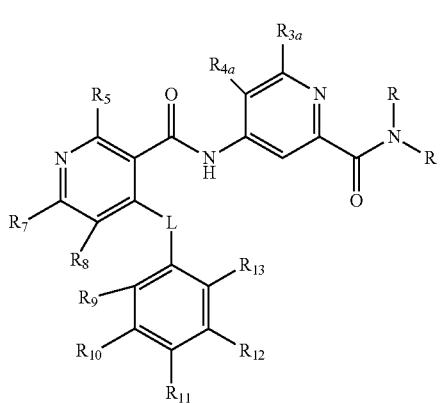

I-B-3 or a pharmaceutically acceptable salt thereof, wherein:

L is O, C(R)$_2$, or a single bond;

each R is independently H or $C_1$-$C_6$ alkyl;

$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$ and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—(CH$_2$)$_n$—R$_w$;

$R_8$ is H or —O—(CH$_2$)$_n$—R$_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—R$_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—R$_w$;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein at least one of $R_5$, $R_7$, and $R_8$ is not H.

In some embodiments, the invention relates to a compound of formula (I-B-3), or a pharmaceutically acceptable salt thereof, wherein L is O.

In some embodiments, the invention relates to a compound of formula (I-B-3), or a pharmaceutically acceptable salt thereof, wherein each R is independently H or CH$_3$. In other embodiments, each R is H. In other embodiments, each R is CH$_3$.

In some embodiments, the invention relates to a compound of formula (I-B-3), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H or CH$_3$. In other embodiments, $R_{3a}$ is H. In other embodiments, $R_{3a}$ is CH$_3$.

In some embodiments, the invention relates to a compound of formula (I-B-3), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H.

In some embodiments, the invention relates to a compound of formula (I-B-3), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is H.

In some embodiments, the invention relates to a compound of formula (I-B-3), or a pharmaceutically acceptable salt thereof, wherein $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—R$_w$. In other embodiments, $R_7$ is halo, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—R$_w$. In other embodiments, $R_7$ is H, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—R$_w$. In other embodiments, $R_7$ is H, halo, $C_1$-$C_6$ haloalkyl, $C_1$-$C_6$ alkoxy, $C_1$-$C_6$ haloalkoxy, or —W—(CH$_2$)$_n$—R$_w$. In other embodiments, $R_7$ is H, halo, $C_1$-$C_6$ alkyl, $C_1$-$C_6$ alkoxy, $C_1$-$C_6$ haloalkoxy, or —W—(CH$_2$)$_n$—R$_w$. In other embodiments, $R_7$ is H, halo, $C_1$-$C_6$ alkyl, $C_1$-$C_6$ haloalkyl, $C_1$-$C_6$ haloalkoxy, or —W—(CH$_2$)$_n$—R$_w$. In other embodiments, $R_7$ is H, halo, $C_1$-$C_6$ alkyl, $C_1$-$C_6$ haloalkyl, $C_1$-$C_6$ alkoxy, or —W—(CH$_2$)$_n$—R$_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is —W—(CH$_2$)$_n$—R$_w$. In other embodiments, $R_7$ is —W—(CH$_2$)$_n$—R$_w$, wherein W is a single bond, n is 0, and R$_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is $C_1$-$C_6$ alkyl, $C_1$-$C_6$ haloalkyl, or —W—(CH$_2$)$_n$—R$_w$. In other embodiments, $R_7$ is C(CH$_3$)$_3$, CF(CH$_3$)$_2$, CF$_3$, cyclopropyl, 1-methylcyclopropyl, 2-methylcyclopropyl, 2,2-difluorocyclopropyl, or 1-trifluoromethylcyclopropyl. In other embodiments, $R_7$ is C(CH$_3$)$_3$. In other embodiments, $R_7$ is CF(CH$_3$)$_2$. In other embodiments, $R_7$ is CF$_3$. In other embodiments, $R_7$ is cyclopropyl. In other embodiments, $R_7$ is 1-methylcyclopropyl. In other embodiments, $R_7$ is 2-methylcyclopropyl. In other embodiments, $R_7$ is 2,2-difluorocyclopropyl. In other embodiments, $R_7$ is 1-trifluoromethylcyclopropyl.

In some embodiments, the invention relates to a compound of formula (I-B-3), or a pharmaceutically acceptable salt thereof, wherein $R_8$ is H.

In some embodiments, the invention relates to a compound of formula (I-B-3), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-B-3), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-3), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (I-B-3), or a pharmaceutically acceptable salt thereof, wherein $R_{12}$ is H.

In some embodiments, the invention relates to a compound of formula (I-B-3), or a pharmaceutically acceptable salt thereof, wherein $R_{13}$ is H.

In some embodiments, the invention relates to a compound of formula (I-B-3), i.e., the compound in non-salt form.

In another aspect, the invention relates to a compound of formula (I-B-4)

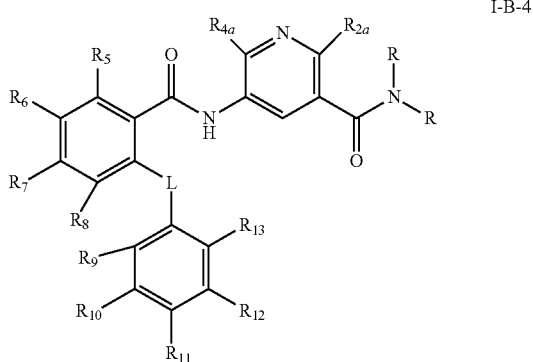

I-B-4 or a pharmaceutically acceptable salt thereof, wherein:
L is O, $C(R)_2$, or a single bond;

each R is independently H or $C_1$-$C_6$ alkyl;

$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein at least one of $R_5$, $R_6$, $R_7$, and $R_8$ is not H.

In some embodiments, the invention relates to a compound of formula (I-B-4), or a pharmaceutically acceptable salt thereof, wherein L is O.

In some embodiments, the invention relates to a compound of formula (I-B-4), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B-4), or a pharmaceutically acceptable salt thereof, wherein $R_{2a}$ is H.

In some embodiments, the invention relates to a compound of formula (I-B-4), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H.

In some embodiments, the invention relates to a compound of formula (I-B-4), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is F.

In some embodiments, the invention relates to a compound of formula (I-B-4), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is $CF_3$.

In some embodiments, the invention relates to a compound of formula (I-B-4), or a pharmaceutically acceptable salt thereof, wherein $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is —W—$(CH_2)_n$—$R_w$. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H.

In some embodiments, the invention relates to a compound of formula (I-B-4), or a pharmaceutically acceptable salt thereof, wherein $R_8$ is H.

In some embodiments, the invention relates to a compound of formula (I-B-4), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-B-4), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-4), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is $OCF_3$. In other embodiments, $R_{11}$ is H. In other embodiments, $R_{11}$ is $^1$H. In other embodiments, $R_{11}$ is D.

In some embodiments, the invention relates to a compound of formula (I-B-4), or a pharmaceutically acceptable salt thereof, wherein $R_{12}$ is H.

In some embodiments, the invention relates to a compound of formula (I-B-4), or a pharmaceutically acceptable salt thereof, wherein $R_{13}$ is H.

In some embodiments, the invention relates to a compound of formula (I-B-4), i.e., the compound in non-salt form.

In another aspect, the invention relates to a compound of formula (I-B-5)

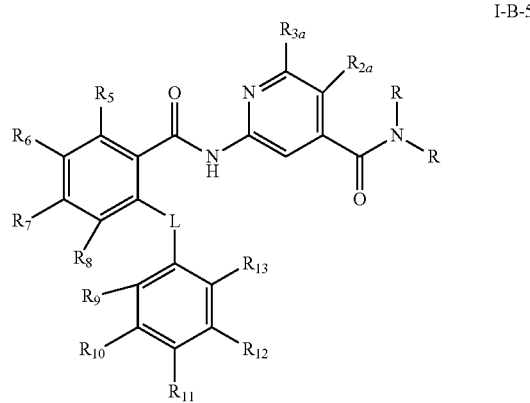

I-B-5 or a pharmaceutically acceptable salt thereof, wherein:
L is O, $C(R)_2$, or a single bond;
each R is independently H or $C_1$-$C_6$ alkyl;
$R_{2a}$ is H, halo, OH, or $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, or $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein at least one of $R_5$, $R_6$, $R_7$, and $R_8$ is not H.

In some embodiments, the invention relates to a compound of formula (I-B-5), or a pharmaceutically acceptable salt thereof, wherein L is O.

In some embodiments, the invention relates to a compound of formula (I-B-5), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B-5), or a pharmaceutically acceptable salt thereof, wherein $R_{2a}$ is H.

In some embodiments, the invention relates to a compound of formula (I-B-5), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H.

In some embodiments, the invention relates to a compound of formula (I-B-5), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is F.

In some embodiments, the invention relates to a compound of formula (I-B-5), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is $CF_3$.

In some embodiments, the invention relates to a compound of formula (I-B-5), or a pharmaceutically acceptable salt thereof, wherein $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is —W—$(CH_2)_n$—$R_w$. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H.

In some embodiments, the invention relates to a compound of formula (I-B-5), or a pharmaceutically acceptable salt thereof, wherein $R_8$ is H.

In some embodiments, the invention relates to a compound of formula (I-B-5), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-B-5), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-5), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (I-B-5), or a pharmaceutically acceptable salt thereof, wherein $R_{12}$ is H.

In some embodiments, the invention relates to a compound of formula (I-B-5), or a pharmaceutically acceptable salt thereof, wherein $R_{13}$ is H.

In some embodiments, the invention relates to a compound of formula (I-B-5), i.e., the compound in non-salt form.

In another aspect, the invention relates to a compound of formula (I-B-6)

I-B-6 or a pharmaceutically acceptable salt thereof, wherein:
L is O, C(R)$_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—(CH$_2$)$_n$—R$_w$;
$R_8$ is H or —O—(CH$_2$)$_n$—R$_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—R$_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—(CH$_2$)$_n$—R$_w$;
each $R_{14}$ is independently H, halo, $C_1$-$C_4$ alkyl, or $C_1$-$C_4$ haloalkyl;
each W is independently O or a single bond;
each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1.

In some embodiments, the invention relates to a compound of formula (I-B-6), or a pharmaceutically acceptable salt thereof, wherein L is O.

In some embodiments, the invention relates to a compound of formula (I-B-6), or a pharmaceutically acceptable salt thereof, wherein each R is independently H or CH$_3$. In other embodiments, each R is H. In other embodiments, each R is CH$_3$.

In some embodiments, the invention relates to a compound of formula (I-B-6), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H.

In some embodiments, the invention relates to a compound of formula (I-B-6), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H.

In some embodiments, the invention relates to a compound of formula (I-B-6), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is H.

In some embodiments, the invention relates to a compound of formula (I-B-6), or a pharmaceutically acceptable salt thereof, wherein $R_8$ is H.

In some embodiments, the invention relates to a compound of formula (I-B-6), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D. In other embodiments, $R_9$ is OCH$_3$.

In some embodiments, the invention relates to a compound of formula (I-B-6), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-6), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is OCF$_3$.

In some embodiments, the invention relates to a compound of formula (I-B-6), or a pharmaceutically acceptable salt thereof, wherein $R_{12}$ is H.

In some embodiments, the invention relates to a compound of formula (I-B-6), or a pharmaceutically acceptable salt thereof, wherein $R_{13}$ is H.

In some embodiments, the invention relates to a compound of formula (I-B-6), or a pharmaceutically acceptable salt thereof, wherein each $R_{14}$ is F.

In some embodiments, the invention relates to a compound of formula (I-B-6), i.e., the compound in non-salt form.

In another aspect, the invention relates to a compound of formula (I-B-7)

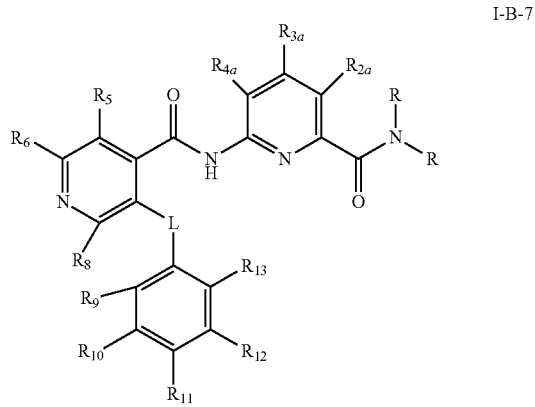

I-B-7 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$ and $R_6$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, and $R_8$ is not H.

In some embodiments, the invention relates to a compound of formula (I-B-7), or a pharmaceutically acceptable salt thereof, wherein L is O.

In some embodiments, the invention relates to a compound of formula (I-B-7), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B-7), or a pharmaceutically acceptable salt thereof, wherein $R_{2a}$ is F.

In some embodiments, the invention relates to a compound of formula (I-B-7), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H.

In some embodiments, the invention relates to a compound of formula (I-B-7), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H.

In some embodiments, the invention relates to a compound of formula (I-B-7), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is F.

In some embodiments, the invention relates to a compound of formula (I-B-7), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is H.

In some embodiments, the invention relates to a compound of formula (I-B-7), or a pharmaceutically acceptable salt thereof, wherein $R_8$ is H.

In some embodiments, the invention relates to a compound of formula (I-B-7), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-B-7), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-7), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (I-B-7), or a pharmaceutically acceptable salt thereof, wherein $R_{12}$ is H.

In some embodiments, the invention relates to a compound of formula (I-B-7), or a pharmaceutically acceptable salt thereof, wherein $R_{13}$ is H.

In some embodiments, the invention relates to a compound of formula (I-B-7), i.e., the compound in non-salt form.

In another aspect, the invention relates to a compound of formula (I-B-8)

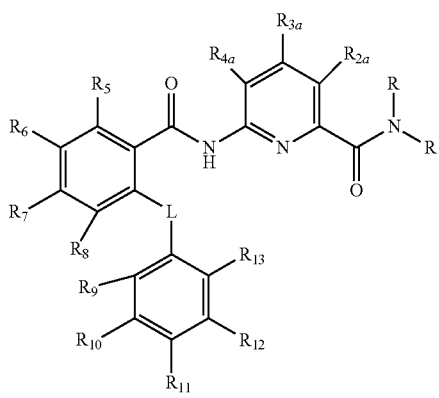

I-B-8 or a pharmaceutically acceptable salt thereof, wherein:
L is O, $C(R)_2$, or a single bond;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, $R_7$, and $R_8$ is not H.

In some embodiments, the invention relates to a compound of formula (I-B-8), or a pharmaceutically acceptable salt thereof, wherein L is O.

In some embodiments, the invention relates to a compound of formula (I-B-8), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B-8), or a pharmaceutically acceptable salt thereof, wherein $R_{2a}$ is F.

In some embodiments, the invention relates to a compound of formula (I-B-8), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H.

In some embodiments, the invention relates to a compound of formula (I-B-8), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H.

In some embodiments, the invention relates to a compound of formula (I-B-8), or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is halo, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, $C_1$-$C_6$ alkyl, $C_1$-$C_6$ haloalkyl, $C_1$-$C_6$ alkoxy, or $C_1$-$C_6$ alkylamino. In other embodiments, $R_5$ is H, halo, $C_1$-$C_6$ haloalkyl, $C_1$-$C_6$ alkoxy, or $C_1$-$C_6$ alkylamino. In other embodiments, $R_5$ is H, halo, $C_1$-$C_6$ alkyl, $C_1$-$C_6$ alkoxy, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkylamino. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is $C_1$-$C_6$ alkylamino. In other embodiments, $R_5$ is F.

In some embodiments, the invention relates to a compound of formula (I-B-8), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is —W—$(CH_2)_n$—$R_w$. In other embodiments, $R_6$ is —W—$(CH_2)_n$—$R_w$, wherein W is a single bond, n is 0, and $R_w$ is unsubstituted 3-6 membered cycloalkyl. In other embodiments, $R_6$ is $CF_3$.

In some embodiments, the invention relates to a compound of formula (I-B-8), or a pharmaceutically acceptable salt thereof, wherein $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is —W—$(CH_2)_n$—$R_w$. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H.

In some embodiments, the invention relates to a compound of formula (I-B-8), or a pharmaceutically acceptable salt thereof, wherein $R_8$ is H.

In some embodiments, the invention relates to a compound of formula (I-B-8), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (I-B-8), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-8), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (I-B-8), or a pharmaceutically acceptable salt thereof, wherein $R_{12}$ is H.

In some embodiments, the invention relates to a compound of formula (I-B-8), or a pharmaceutically acceptable salt thereof, wherein $R_{13}$ is H.

In some embodiments, the invention relates to a compound of formula (I-B-8), i.e., the compound in non-salt form.

In another aspect, the invention relates to a compound of formula (I-B-9)

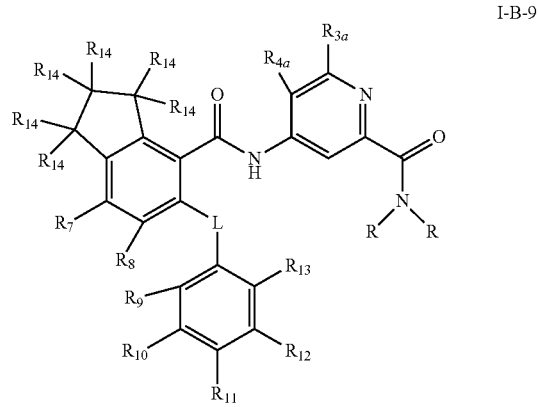

I-B-9 or a pharmaceutically acceptable salt thereof, wherein:
L is O, $C(R)_2$, or a single bond;
each R is independently H or $C_1$-$C_6$ alkyl;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

each $R_{14}$ is independently H, halo, $C_1$-$C_4$ alkyl, or $C_1$-$C_4$ haloalkyl;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1.

In some embodiments, the invention relates to a compound of formula (I-B-9), or a pharmaceutically acceptable salt thereof, wherein L is O.

In some embodiments, the invention relates to a compound of formula (I-B-9), or a pharmaceutically acceptable salt thereof, wherein each R is independently H or $CH_3$. In other embodiments, each R is H. In other embodiments, each R is $CH_3$.

In some embodiments, the invention relates to a compound of formula (I-B-9), or a pharmaceutically acceptable salt thereof, wherein $R_{3a}$ is H or $C_1$-$C_6$ alkyl. In other embodiments, $R_{3a}$ is $C_1$-$C_6$ alkyl. In other embodiments, $R_{3a}$ is H.

In some embodiments, the invention relates to a compound of formula (I-B-9), or a pharmaceutically acceptable salt thereof, wherein $R_{4a}$ is H, halo, or $C_1$-$C_6$ alkyl. In other embodiments, $R_{4a}$ is halo or $C_1$-$C_6$ alkyl. In other embodiments, $R_{4a}$ is H or $C_1$-$C_6$ alkyl. In other embodiments, $R_{4a}$ is H or halo. In other embodiments, $R_{4a}$ is halo. In other embodiments, $R_{4a}$ is $C_1$-$C_6$ alkyl. In other embodiments, $R_{4a}$ is H.

In some embodiments, the invention relates to a compound of formula (I-B-9), or a pharmaceutically acceptable salt thereof, wherein $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ haloalkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ alkoxy, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ haloalkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is —W—$(CH_2)_n$—$R_w$. In other embodiments, $R_7$ is —W—$(CH_2)_n$—$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H.

In some embodiments, the invention relates to a compound of formula (I-B-9), or a pharmaceutically acceptable salt thereof, wherein $R_8$ is H.

In some embodiments, the invention relates to a compound of formula (I-B-9), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D.

In some embodiments, the invention relates to a compound of formula (I-B-9), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-9), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (I-B-9), or a pharmaceutically acceptable salt thereof, wherein $R_{12}$ is H.

In some embodiments, the invention relates to a compound of formula (I-B-9), or a pharmaceutically acceptable salt thereof, wherein $R_{13}$ is H.

In some embodiments, the invention relates to a compound of formula (I-B-9), or a pharmaceutically acceptable salt thereof, wherein each $R_{14}$ is independently H or F.

In some embodiments, the invention relates to a compound of formula (I-B-9), i.e., the compound in non-salt form.

In another aspect, the invention relates to a compound of formula (I-B-10)

I-B-10

[Structure diagram of formula I-B-10 showing a pyrimidine with R$_{3a}$, R$_{4a}$ substituents, connected via NH-C(O) to a benzene ring with R$_5$, R$_6$, R$_7$, R$_8$, and L linking to another phenyl with R$_9$-R$_{13}$, and a C(O)-NR-R group]

or a pharmaceutically acceptable salt thereof, wherein:
L is O, C(R)$_2$, or a single bond;
each R is independently H or C$_1$-C$_6$ alkyl;
R$_{3a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_{4a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_5$, R$_6$, and R$_7$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$;
R$_8$ is H or —O—(CH$_2$)$_n$—R$_w$;
R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
each W is independently O or a single bond;
each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, C$_1$-C$_6$ alkyl, and C$_1$-C$_6$ haloalkyl; and
n is 0 or 1;
wherein at least one of R$_5$, R$_6$, R$_7$, and R$_8$ is not H.

In some embodiments, the invention relates to a compound of formula (I-B-10), or a pharmaceutically acceptable salt thereof, wherein L is O.

In some embodiments, the invention relates to a compound of formula (I-B-10), or a pharmaceutically acceptable salt thereof, wherein each R is independently H or CH$_3$. In other embodiments, each R is H. In other embodiments, each R is CH$_3$.

In some embodiments, the invention relates to a compound of formula (I-B-10), or a pharmaceutically acceptable salt thereof, wherein R$_{3a}$ is H or C$_1$-C$_6$ alkyl. In other embodiments, R$_{3a}$ is C$_1$-C$_6$ alkyl. In other embodiments, R$_{3a}$ is H.

In some embodiments, the invention relates to a compound of formula (I-B-10), or a pharmaceutically acceptable salt thereof, wherein R$_{4a}$ is H, halo, or C$_1$-C$_6$ alkyl. In other embodiments, R$_{4a}$ is halo or C$_1$-C$_6$ alkyl. In other embodiments, R$_{4a}$ is H or C$_1$-C$_6$ alkyl. In other embodiments, R$_{4a}$ is H or halo. In other embodiments, R$_{4a}$ is halo. In other embodiments, R$_{4a}$ is C$_1$-C$_6$ alkyl. In other embodiments, R$_{4a}$ is H.

In some embodiments, the invention relates to a compound of formula (I-B-10), or a pharmaceutically acceptable salt thereof, wherein R$_5$ is H, halo, C$_1$-C$_6$ alkyl, C$_1$-C$_6$ haloalkyl, C$_1$-C$_6$ alkoxy, or C$_1$-C$_6$ alkylamino. In other embodiments, R$_5$ is halo, C$_1$-C$_6$ alkyl, C$_1$-C$_6$ haloalkyl, C$_1$-C$_6$ alkoxy, or C$_1$-C$_6$ alkylamino. In other embodiments, R$_5$ is H, C$_1$-C$_6$ alkyl, C$_1$-C$_6$ haloalkyl, C$_1$-C$_6$ alkoxy, or C$_1$-C$_6$ alkylamino. In other embodiments, R$_5$ is H, halo, C$_1$-C$_6$ haloalkyl, C$_1$-C$_6$ alkoxy, or C$_1$-C$_6$ alkylamino. In other embodiments, R$_5$ is H, halo, C$_1$-C$_6$ alkyl, C$_1$-C$_6$ alkoxy, or C$_1$-C$_6$ alkylamino. In other embodiments, R$_5$ is H, halo, C$_1$-C$_6$ alkyl, C$_1$-C$_6$ haloalkyl, or C$_1$-C$_6$ alkylamino. In other embodiments, R$_5$ is H, halo, C$_1$-C$_6$ alkyl, C$_1$-C$_6$ haloalkyl, or C$_1$-C$_6$ alkoxy. In other embodiments, R$_5$ is halo. In other embodiments, R$_5$ is C$_1$-C$_6$ alkyl. In other embodiments, R$_5$ is C$_1$-C$_6$ haloalkyl. In other embodiments, R$_5$ is C$_1$-C$_6$ alkoxy. In other embodiments, R$_5$ is C$_1$-C$_6$ alkylamino. In other embodiments, R$_5$ is F.

In some embodiments, the invention relates to a compound of formula (I-B-10), or a pharmaceutically acceptable salt thereof, wherein R$_6$ is H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$. In other embodiments, R$_6$ is H, halo, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_6$ is halo, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_6$ is H, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_6$ is H, halo, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_6$ is H, halo, C$_1$-C$_6$ alkyl, C$_1$-C$_6$ alkoxy, C$_1$-C$_6$ haloalkoxy, or —W—(CH$_2$)$_n$—R$_w$. In other embodiments, R$_6$ is H, halo, C$_1$-C$_6$ alkyl, C$_1$-C$_6$ haloalkyl, C$_1$-C$_6$ haloalkoxy, or —W—(CH$_2$)$_n$—R$_w$. In other embodiments, R$_6$ is H, halo, C$_1$-C$_6$ alkyl, C$_1$-C$_6$ haloalkyl, C$_1$-C$_6$ alkoxy, or —W—(CH$_2$)$_n$—R$_w$. In other embodiments, R$_6$ is H, halo, C$_1$-C$_6$ alkyl, C$_1$-C$_6$ haloalkyl, C$_1$-C$_6$ alkoxy, or C$_1$-C$_6$ haloalkoxy. In other embodiments, R$_6$ is halo. In other embodiments, R$_6$ is C$_1$-C$_6$ alkyl. In other embodiments, R$_6$ is C$_1$-C$_6$ haloalkyl. In other embodiments, R$_6$ is C$_1$-C$_6$ alkoxy. In other embodiments, R$_6$ is C$_1$-C$_6$ haloalkoxy. In other embodiments, R$_6$ is —W—(CH$_2$)$_n$—R$_w$. In other embodiments, R$_6$ is —W—(CH$_2$)$_n$—R$_w$, wherein W is a single bond, n is 0, and R$_w$ is unsubstituted 3-6 membered cycloalkyl. In other embodiments, R$_6$ is CF$_3$.

In some embodiments, the invention relates to a compound of formula (I-B-10), or a pharmaceutically acceptable salt thereof, wherein R$_7$ is H, halo, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_7$ is halo, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_7$ is H, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_7$ is H, halo, C$_1$-C$_6$ haloalkyl, C$_1$-C$_6$ alkoxy, C$_1$-C$_6$ haloalkoxy, or —W—(CH$_2$)$_n$—R$_w$. In other embodiments, R$_7$ is H, halo, C$_1$-C$_6$ alkyl, C$_1$-C$_6$ alkoxy, C$_1$-C$_6$ haloalkoxy, or —W—(CH$_2$)$_n$—R$_w$. In other embodiments, R$_7$ is H, halo, C$_1$-C$_6$ alkyl, C$_1$-C$_6$ haloalkyl, C$_1$-C$_6$ haloalkoxy, or —W—(CH$_2$)$_n$—R$_w$. In other embodiments, R$_7$ is H, halo, C$_1$-C$_6$ alkyl, C$_1$-C$_6$ haloalkyl, C$_1$-C$_6$ alkoxy, or —W—(CH$_2$)$_n$—R$_w$. In other embodiments, R$_7$ is H, halo, C$_1$-C$_6$ alkyl, C$_1$-C$_6$ haloalkyl, C$_1$-C$_6$ alkoxy, or C$_1$-C$_6$ haloalkoxy. In other embodiments, R$_7$ is halo. In other embodiments, R$_7$ is C$_1$-C$_6$ alkyl. In other embodiments, R$_7$ is C$_1$-C$_6$ haloalkyl. In other embodiments, R$_7$ is C$_1$-C$_6$ alkoxy. In other embodiments, R$_7$ is C$_1$-C$_6$ haloalkoxy. In other embodiments, R$_7$ is —W—(CH$_2$)$_n$—R$_w$. In other embodiments, R$_7$ is —W—(CH$_2$)$_n$—

$R_w$, wherein W is a single bond, n is 0, and $R_w$ is 3-6 membered cycloalkyl, wherein said 3-6 membered cycloalkyl may be unsubstituted or may be substituted with 1-3 substituents selected from a group consisting of halo, $C_1$-$C_6$ alkyl, and $C_1$-$C_6$ haloalkyl. In other embodiments, $R_7$ is H.

In some embodiments, the invention relates to a compound of formula (I-B-10), or a pharmaceutically acceptable salt thereof, wherein $R_8$ is H.

In some embodiments, the invention relates to a compound of formula (I-B-10), or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy. In other embodiments, $R_9$ is halo, OH, $C_1$-$C_6$ alkyl, $C_1$-$C_6$ alkoxy, or $C_1$-$C_6$ haloalkoxy. In other embodiments, $R_9$ is H, OH, $C_1$-$C_6$ alkyl, $C_1$-$C_6$ alkoxy, or $C_1$-$C_6$ haloalkoxy. In other embodiments, $R_9$ is H, halo, $C_1$-$C_6$ alkyl, $C_1$-$C_6$ alkoxy, or $C_1$-$C_6$ haloalkoxy. In other embodiments, $R_9$ is H, halo, OH, $C_1$-$C_6$ alkoxy, or $C_1$-$C_6$ haloalkoxy. In other embodiments, $R_9$ is H, halo, OH, $C_1$-$C_6$ alkyl, or $C_1$-$C_6$ haloalkoxy. In other embodiments, $R_9$ is H, halo, OH, $C_1$-$C_6$ alkyl, or $C_1$-$C_6$ alkoxy. In other embodiments, $R_9$ is halo. In other embodiments, $R_9$ is $C_1$-$C_6$ alkyl. In other embodiments, $R_9$ is $C_1$-$C_6$ alkoxy. In other embodiments, $R_9$ is $C_1$-$C_6$ haloalkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (I-B-10), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (I-B-10), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (I-B-10), or a pharmaceutically acceptable salt thereof, wherein $R_{12}$ is H.

In some embodiments, the invention relates to a compound of formula (I-B-10), or a pharmaceutically acceptable salt thereof, wherein $R_{13}$ is H.

In some embodiments, the invention relates to a compound of formula (I-B-10), i.e., the compound in non-salt form.

In another aspect, the invention relates to a compound of formula (II)

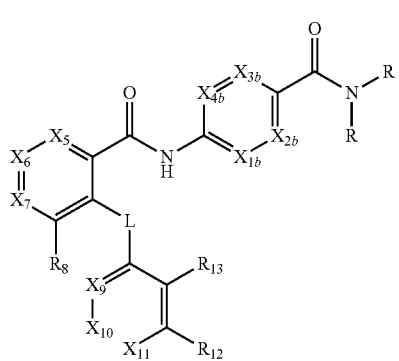

II or a pharmaceutically acceptable salt thereof, wherein:
L is O, $C(R)_2$, or a single bond;
$X_{1b}$ is N or $CR_{1b}$;
$X_{2b}$ is N or $CR_{2b}$;
$X_{3b}$ is N or $CR_{3b}$;
$X_{4b}$ is N or $CR_{4b}$;
$X_5$ is N or $CR_5$;
$X_6$ is N or $CR_6$;
$X_7$ is N or $CR_7$;
$X_9$ is N or $CR_9$;
$X_{10}$ is N or $CR_{10}$;
$X_{11}$ is N or $CR_{11}$;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{2b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are defined as follows:
(i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
(ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

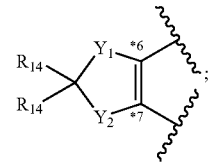

or
(iii) $R_5$ and $R_6$, together with the carbon atoms to which they are attached, form a ring of formula:

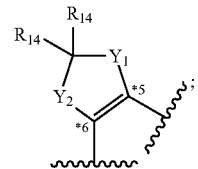

and
$R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

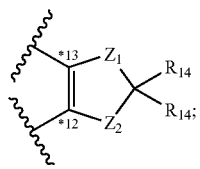

$Y_1$, $Y_2$, $Z_1$, and $Z_2$ are each independently O or $C(R_{14})_2$;

each $R_{14}$ is independently H, halo, $C_1$-$C_4$ alkyl, or $C_1$-$C_4$ haloalkyl;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein when $R_8$ is H, then at least one of $X_5$, $X_6$, and $X_7$ is not N or CH;

wherein no more than two of $X_{1b}$, $X_{2b}$, $X_{3b}$, and $X_{4b}$ is N;

wherein no more than one of $X_5$, $X_6$, and $X_7$ is N;

wherein no more than one of $X_9$, $X_{10}$, and $X_{11}$ is N.

In some embodiments, the invention relates to a compound of formula (II), or a pharmaceutically acceptable salt thereof, wherein L is O.

In some embodiments, the invention relates to a compound of formula (II), or a pharmaceutically acceptable salt thereof, wherein $X_{1b}$ is N. In other embodiments, $X_{1b}$ is $CR_{1b}$.

In some embodiments, the invention relates to a compound of formula (II), or a pharmaceutically acceptable salt thereof, wherein $X_{2b}$ is N. In other embodiments, $X_{2b}$ is $CR_{2b}$.

In some embodiments, the invention relates to a compound of formula (II), or a pharmaceutically acceptable salt thereof, wherein $X_{3b}$ is N. In other embodiments, $X_{3b}$ is $CR_{3b}$.

In some embodiments, the invention relates to a compound of formula (II), or a pharmaceutically acceptable salt thereof, wherein $X_{4b}$ is N. In other embodiments, $X_{4b}$ is $CR_{4b}$.

In some embodiments, the invention relates to a compound of formula (II), or a pharmaceutically acceptable salt thereof, wherein $X_5$ is N. In other embodiments, $X_5$ is $CR_5$.

In some embodiments, the invention relates to a compound of formula (II), or a pharmaceutically acceptable salt thereof, wherein $X_6$ is N. In other embodiments, $X_6$ is $CR_6$.

In some embodiments, the invention relates to a compound of formula (II), or a pharmaceutically acceptable salt thereof, wherein $X_7$ is N. In other embodiments, $X_7$ is $CR_7$.

In some embodiments, the invention relates to a compound of formula (II), or a pharmaceutically acceptable salt thereof, wherein $X_9$ is N. In other embodiments, $X_9$ is $CR_9$.

In some embodiments, the invention relates to a compound of formula (II), or a pharmaceutically acceptable salt thereof, wherein $X_{10}$ is N. In other embodiments, $X_{10}$ is $CR_{10}$.

In some embodiments, the invention relates to a compound of formula (II), or a pharmaceutically acceptable salt thereof, wherein $X_{11}$ is N. In other embodiments, $X_{11}$ is $CR_{11}$.

In some embodiments, the invention relates to a compound of formula (II), or a pharmaceutically acceptable salt thereof, wherein each R is independently H or $CH_3$. In other embodiments, each R is H. In other embodiments, each R is $CH_3$.

In some embodiments, the invention relates to a compound of formula (II), or a pharmaceutically acceptable salt thereof, wherein $R_{1b}$ is H, halo, or $C_1$-$C_6$ alkyl. In other embodiments, $R_{1b}$ is halo or $C_1$-$C_6$ alkyl. In other embodiments, $R_{1b}$ is H or $C_1$-$C_6$ alkyl. In other embodiments, $R_{1b}$ is H or halo. In other embodiments, $R_{1b}$ is halo. In other embodiments, $R_{1b}$ is $C_1$-$C_6$ alkyl. In other embodiments, $R_{1b}$ is H, F, or $CH_3$. In other embodiments, $R_{1b}$ is H. In other embodiments, $R_{1b}$ is F. In other embodiments, $R_{1b}$ is $CH_3$.

In some embodiments, the invention relates to a compound of formula (II), or a pharmaceutically acceptable salt thereof, wherein $R_{2b}$ is H or halo. In other embodiments, $R_{2b}$ is halo. In other embodiments, $R_{2b}$ is H or F. In other embodiments, $R_{2b}$ is H. In other embodiments, $R_{2b}$ is F.

In some embodiments, the invention relates to a compound of formula (II), or a pharmaceutically acceptable salt thereof, wherein $R_{3b}$ is H.

In some embodiments, the invention relates to a compound of formula (II), or a pharmaceutically acceptable salt thereof, wherein $R_{4b}$ is H or $C_1$-$C_6$ alkyl. In other embodiments, $R_{4b}$ is $C_1$-$C_6$ alkyl. In other embodiments, $R_{4b}$ is H or $CH_3$. In other embodiments, $R_{4b}$ is H. In other embodiments, $R_{4b}$ is $CH_3$.

In some embodiments, the invention relates to a compound of formula (II), or a pharmaceutically acceptable salt thereof, wherein $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H, F, Cl, $CF_3$, or $OCH_3$. In other embodiments, $R_5$ is H. In other embodiments, $R_5$ is F. In other embodiments, $R_5$ is Cl. In other embodiments, $R_5$ is $CF_3$. In other embodiments, $R_5$ is $OCH_3$.

In some embodiments, the invention relates to a compound of formula (II), or a pharmaceutically acceptable salt thereof, wherein $R_6$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ alkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is H, F, Cl, $OCHF_2$, $CF_3$, $CHF_2$, or $OCF_3$. In other embodiments, $R_6$ is H. In other embodiments, $R_6$ is F. In other embodiments, $R_6$ is Cl. In other embodiments, $R_6$ is $OCHF_2$. In other embodiments, $R_6$ is $CF_3$. In other embodiments, $R_6$ is $CHF_2$. In other embodiments, $R_6$ is $OCF_3$.

In some embodiments, the invention relates to a compound of formula (II), or a pharmaceutically acceptable salt thereof, wherein $R_5$ and $R_6$, together with the carbon atoms to which they are attached, form a ring of formula:

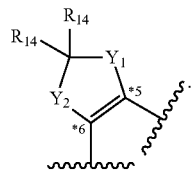

In some embodiments, the invention relates to a compound of formula (II), or a pharmaceutically acceptable salt thereof, wherein $R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$. In other embodiments, $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is H, Cl, $CF_3$, $OCHF_2$, or $OCF_3$. In other embodiments, $R_7$ is H. In other embodiments, $R_7$ is Cl. In other embodiments, $R_7$ is $CF_3$. In other embodiments, $R_7$ is $OCHF_2$. In other embodiments, $R_7$ is $OCF_3$.

In some embodiments, the invention relates to a compound of formula (II), or a pharmaceutically acceptable salt thereof, wherein $R_6$ and $R_7$, together with the carbon atoms to which they are attached, form a ring of formula:

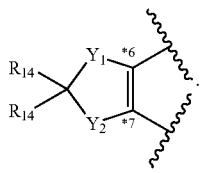

In some embodiments, the invention relates to a compound of formula (II), or a pharmaceutically acceptable salt thereof, wherein $R_8$ is H.

In some embodiments, the invention relates to a compound of formula (II), or a pharmaceutically acceptable salt thereof, wherein $R_9$ is H, $C_1$-$C_6$ alkyl, or $C_1$-$C_6$ alkoxy. In other embodiments, $R_9$ is $C_1$-$C_6$ alkyl or $C_1$-$C_6$ alkoxy. In other embodiments, $R_9$ is H or $C_1$-$C_6$ alkoxy. In other embodiments, $R_9$ is H or $C_1$-$C_6$ alkyl. In other embodiments, $R_9$ is $C_1$-$C_6$ alkyl. In other embodiments, $R_9$ is $C_1$-$C_6$ alkoxy. In other embodiments, $R_9$ is H, $CH_3$, or $OCH_3$. In other embodiments, $R_9$ is H. In other embodiments, $R_9$ is $^1$H. In other embodiments, $R_9$ is D. In other embodiments, $R_9$ is $CH_3$. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (II), or a pharmaceutically acceptable salt thereof, wherein $R_{10}$ is H or halo. In other embodiments, $R_{10}$ is halo. In other embodiments, $R_{10}$ is H or F. In other embodiments, $R_{10}$ is H. In other embodiments, $R_{10}$ is $^1$H. In other embodiments, $R_{10}$ is D. In other embodiments, $R_{10}$ is F.

In some embodiments, the invention relates to a compound of formula (II), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is F, Cl, or $OCF_3$. In other embodiments, $R_{11}$ is H. In other embodiments, $R_{11}$ is $^1$H. In other embodiments, $R_{11}$ is D. In other embodiments, $R_{11}$ is F. In other embodiments, $R_{11}$ is Cl. In other embodiments, $R_{11}$ is $OCF_3$.

In some embodiments, the invention relates to a compound of formula (II), or a pharmaceutically acceptable salt thereof, wherein $R_{12}$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_{12}$ is H.

In some embodiments, the invention relates to a compound of formula (II), or a pharmaceutically acceptable salt thereof, wherein $R_{13}$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$. In other embodiments, $R_{13}$ is H.

In some embodiments, the invention relates to a compound of formula (II), or a pharmaceutically acceptable salt thereof, wherein $Y_1$ is O, and $Y_2$ is $C(R_{14})_2$. In other embodiments, $Y_1$ is $C(R_{14})_2$, and $Y_2$ is O. In other embodiments, $Y_1$ is O, and $Y_2$ is O. In other embodiments, $Y_1$ is $C(R_{14})_2$, and $Y_2$ is $C(R_{14})_2$.

In some embodiments, the invention relates to a compound of formula (II), or a pharmaceutically acceptable salt thereof, wherein each $R_{14}$ is independently H or F. In other embodiments, each $R_{14}$ is H. In other embodiments, each $R_{14}$ is F.

In some embodiments, the invention relates to a compound of formula (II), i.e., the compound in non-salt form.

In another aspect, the invention relates to a compound of formula (II-A-1)

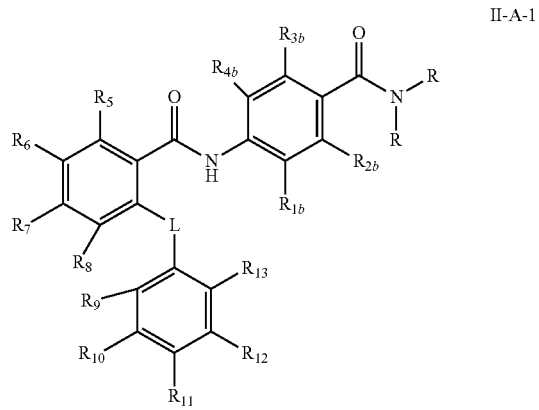

or a pharmaceutically acceptable salt thereof, wherein:

L is O, C(R)$_2$, or a single bond;

each R is independently H or C$_1$-C$_6$ alkyl;

R$_{1b}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{2b}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{3b}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{4b}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_5$, R$_6$, and R$_7$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$;

R$_8$ is H or —O—(CH$_2$)$_n$—R$_w$;

R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;

each W is independently O or a single bond;

each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, C$_1$-C$_6$ alkyl, and C$_1$-C$_6$ haloalkyl; and n is 0 or 1;

wherein at least one of R$_5$, R$_6$, R$_7$, and R$_8$ is not H.

In some embodiments, the invention relates to a compound of formula (II-A-1), or a pharmaceutically acceptable salt thereof, wherein L is O.

In some embodiments, the invention relates to a compound of formula (II-A-1), or a pharmaceutically acceptable salt thereof, wherein each R is independently H or CH$_3$. In other embodiments, each R is H. In other embodiments, each R is CH$_3$.

In some embodiments, the invention relates to a compound of formula (II-A-1), or a pharmaceutically acceptable salt thereof, wherein R$_{1b}$ is H, halo, or C$_1$-C$_6$ alkyl. In other embodiments, R$_{1b}$ is halo or C$_1$-C$_6$ alkyl. In other embodiments, R$_{1b}$ is H or C$_1$-C$_6$ alkyl. In other embodiments, R$_{1b}$ is H or halo. In other embodiments, R$_{1b}$ is halo. In other embodiments, R$_{1b}$ is C$_1$-C$_6$ alkyl. In other embodiments, R$_{1b}$ is H or F. In other embodiments, R$_{1b}$ is H. In other embodiments, R$_{1b}$ is F.

In some embodiments, the invention relates to a compound of formula (II-A-1), or a pharmaceutically acceptable salt thereof, wherein R$_{2b}$ is H or halo. In other embodiments, R$_{2b}$ is halo. In other embodiments, R$_{2b}$ is H or F. In other embodiments, R$_{2b}$ is H. In other embodiments, R$_{2b}$ is F.

In some embodiments, the invention relates to a compound of formula (II-A-1), or a pharmaceutically acceptable salt thereof, wherein R$_{3b}$ is H.

In some embodiments, the invention relates to a compound of formula (II-A-1), or a pharmaceutically acceptable salt thereof, wherein R$_{4b}$ is H or C$_1$-C$_6$ alkyl. In other embodiments, R$_{4b}$ is C$_1$-C$_6$ alkyl. In other embodiments, R$_{4b}$ is H.

In some embodiments, the invention relates to a compound of formula (II-A-1), or a pharmaceutically acceptable salt thereof, wherein R$_5$ is H, halo, C$_1$-C$_6$ alkyl, C$_1$-C$_6$ haloalkyl, or C$_1$-C$_6$ alkoxy. In other embodiments, R$_5$ is halo, C$_1$-C$_6$ alkyl, C$_1$-C$_6$ haloalkyl, or C$_1$-C$_6$ alkoxy. In other embodiments, R$_5$ is H, C$_1$-C$_6$ alkyl, C$_1$-C$_6$ haloalkyl, or C$_1$-C$_6$ alkoxy. In other embodiments, R$_5$ is H, halo, C$_1$-C$_6$ haloalkyl, or C$_1$-C$_6$ alkoxy. In other embodiments, R$_5$ is H, halo, C$_1$-C$_6$ alkyl, or C$_1$-C$_6$ alkoxy. In other embodiments, R$_5$ is H, halo, C$_1$-C$_6$ alkyl, or C$_1$-C$_6$ haloalkyl. In other embodiments, R$_5$ is halo. In other embodiments, R$_5$ is C$_1$-C$_6$ alkyl. In other embodiments, R$_5$ is C$_1$-C$_6$ haloalkyl. In other embodiments, R$_5$ is C$_1$-C$_6$ alkoxy. In other embodiments, R$_5$ is halo or C$_1$-C$_6$ alkoxy. In other embodiments, R$_5$ is F or OCH$_3$. In other embodiments, R$_5$ is F. In other embodiments, R$_5$ is OCH$_3$.

In some embodiments, the invention relates to a compound of formula (II-A-1), or a pharmaceutically acceptable salt thereof, wherein R$_6$ is H, halo, C$_1$-C$_6$ alkyl, C$_1$-C$_6$ haloalkyl, C$_1$-C$_6$ alkoxy, or C$_1$-C$_6$ haloalkoxy. In other embodiments, R$_6$ is halo, C$_1$-C$_6$ alkyl, C$_1$-C$_6$ haloalkyl, C$_1$-C$_6$ alkoxy, or C$_1$-C$_6$ haloalkoxy. In other embodiments, R$_6$ is H, C$_1$-C$_6$ alkyl, C$_1$-C$_6$ haloalkyl, C$_1$-C$_6$ alkoxy, or C$_1$-C$_6$ haloalkoxy. In other embodiments, R$_6$ is H, halo, C$_1$-C$_6$ haloalkyl, C$_1$-C$_6$ alkoxy, or C$_1$-C$_6$ haloalkoxy. In other embodiments, R$_6$ is H, halo, C$_1$-C$_6$ alkyl, C$_1$-C$_6$ alkoxy, or C$_1$-C$_6$ haloalkoxy. In other embodiments, R$_6$ is H, halo, C$_1$-C$_6$ alkyl, C$_1$-C$_6$ haloalkyl, or C$_1$-C$_6$ haloalkoxy. In other embodiments, R$_6$ is H, halo, C$_1$-C$_6$ alkyl, C$_1$-C$_6$ haloalkyl, or C$_1$-C$_6$ alkoxy. In other embodiments, R$_6$ is halo. In other embodiments, R$_6$ is C$_1$-C$_6$ alkyl. In other embodiments, R$_6$ is C$_1$-C$_6$ haloalkyl. In other embodiments, R$_6$ is C$_1$-C$_6$ alkoxy. In other embodiments, R$_6$ is C$_1$-C$_6$ haloalkoxy. In other embodiments, R$_6$ is CF$_3$.

In some embodiments, the invention relates to a compound of formula (II-A-1), or a pharmaceutically acceptable salt thereof, wherein R$_7$ is H, halo, C$_1$-C$_6$ alkyl, C$_1$-C$_6$ haloalkyl, C$_1$-C$_6$ alkoxy, or C$_1$-C$_6$ haloalkoxy. In other embodiments, R$_7$ is halo, C$_1$-C$_6$ alkyl, C$_1$-C$_6$ haloalkyl, C$_1$-C$_6$ alkoxy, or C$_1$-C$_6$ haloalkoxy. In other embodiments, R$_7$ is H, C$_1$-C$_6$ alkyl, C$_1$-C$_6$ haloalkyl, C$_1$-C$_6$ alkoxy, or C$_1$-C$_6$ haloalkoxy. In other embodiments, R$_7$ is H, halo, C$_1$-C$_6$ haloalkyl, C$_1$-C$_6$ alkoxy, or C$_1$-C$_6$ haloalkoxy. In other embodiments, R$_7$ is H, halo, C$_1$-C$_6$ alkyl, C$_1$-C$_6$ alkoxy, or C$_1$-C$_6$ haloalkoxy. In other embodiments, R$_7$ is H, halo, C$_1$-C$_6$ alkyl, C$_1$-C$_6$ haloalkyl, or C$_1$-C$_6$ haloalkoxy. In other embodiments, R$_7$ is H, halo, C$_1$-C$_6$ alkyl, C$_1$-C$_6$ haloalkyl, or C$_1$-C$_6$ alkoxy. In other embodiments, R$_7$ is halo. In other embodiments, R$_7$ is C$_1$-C$_6$ alkyl. In other embodiments, Rn is C$_1$-C$_6$ haloalkyl. In other embodiments, Rn is C$_1$-C$_6$ alkoxy. In other embodiments, R$_7$ is C$_1$-C$_6$ haloalkoxy. In other embodiments, R$_7$ is H.

In some embodiments, the invention relates to a compound of formula (II-A-1), or a pharmaceutically acceptable salt thereof, wherein R$_8$ is H.

In some embodiments, the invention relates to a compound of formula (II-A-1), or a pharmaceutically acceptable salt thereof, wherein R$_9$ is H, C$_1$-C$_6$ alkyl, or C$_1$-C$_6$ alkoxy. In other embodiments, R$_9$ is C$_1$-C$_6$ alkyl or C$_1$-C$_6$ alkoxy. In other embodiments, R$_9$ is H or C$_1$-C$_6$ alkoxy. In other embodiments, R$_9$ is H or C$_1$-C$_6$ alkyl. In other embodiments, R$_9$ is C$_1$-C$_6$ alkyl. In other embodiments, R$_9$ is C$_1$-C$_6$ alkoxy. In other embodiments, R$_9$ is H, CH$_3$, or OCH$_3$. In other embodiments, R$_9$ is H. In other embodiments, R$_9$ is $^1$H. In other embodiments, R$_9$ is D. In other embodiments, R$_9$ is CH$_3$. In other embodiments, R$_9$ is OCH$_3$. In other embodiments, R$_9$ is OC($^1$H)$_3$. In other embodiments, R$_9$ is OCD$_3$.

In some embodiments, the invention relates to a compound of formula (II-A-1), or a pharmaceutically acceptable salt thereof, wherein R$_{10}$ is H or halo. In other embodiments, R$_{10}$ is halo. In other embodiments, R$_{10}$ is H. In other embodiments, R$_{10}$ is $^1$H. In other embodiments, R$_{10}$ is D.

In some embodiments, the invention relates to a compound of formula (II-A-1), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (II-A-1), or a pharmaceutically acceptable salt thereof, wherein $R_{12}$ is H.

In some embodiments, the invention relates to a compound of formula (II-A-1), or a pharmaceutically acceptable salt thereof, wherein $R_{13}$ is H.

In some embodiments, the invention relates to a compound of formula (II-A-1), i.e., the compound in non-salt form.

In another aspect, the invention relates to a compound of formula (II-A-2)

II-A-2 or a pharmaceutically acceptable salt thereof, wherein:
L is O, $C(R)_2$, or a single bond;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{2b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$ and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, $R_7$, and $R_8$ is not H.

In some embodiments, the invention relates to a compound of formula (II-A-2), or a pharmaceutically acceptable salt thereof, wherein L is O.

In some embodiments, the invention relates to a compound of formula (II-A-2), or a pharmaceutically acceptable salt thereof, wherein each R is independently H or $CH_3$. In other embodiments, each R is H. In other embodiments, each R is $CH_3$.

In some embodiments, the invention relates to a compound of formula (II-A-2), or a pharmaceutically acceptable salt thereof, wherein $R_{1b}$ is H, halo, or $C_1$-$C_6$ alkyl. In other embodiments, $R_{1b}$ is halo or $C_1$-$C_6$ alkyl. In other embodiments, $R_{1b}$ is H or $C_1$-$C_6$ alkyl. In other embodiments, $R_{1b}$ is H or halo. In other embodiments, $R_{1b}$ is halo. In other embodiments, $R_{1b}$ is $C_1$-$C_6$ alkyl. In other embodiments, $R_{1b}$ is H.

In some embodiments, the invention relates to a compound of formula (II-A-2), or a pharmaceutically acceptable salt thereof, wherein $R_{2b}$ is H or halo. In other embodiments, $R_{2b}$ is halo. In other embodiments, $R_{2b}$ is F.

In some embodiments, the invention relates to a compound of formula (II-A-2), or a pharmaceutically acceptable salt thereof, wherein $R_{3b}$ is H.

In some embodiments, the invention relates to a compound of formula (II-A-2), or a pharmaceutically acceptable salt thereof, wherein $R_{4b}$ is H or $C_1$-$C_6$ alkyl. In other embodiments, $R_{4b}$ is $C_1$-$C_6$ alkyl. In other embodiments, $R_{4b}$ is H.

In some embodiments, the invention relates to a compound of formula (II-A-2), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is F.

In some embodiments, the invention relates to a compound of formula (II-A-2), or a pharmaceutically acceptable salt thereof, wherein $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ alkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is $CF_3$.

In some embodiments, the invention relates to a compound of formula (II-A-2), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is H.

In some embodiments, the invention relates to a compound of formula (II-A-2), or a pharmaceutically acceptable salt thereof, wherein $R_8$ is H.

In some embodiments, the invention relates to a compound of formula (II-A-2), or a pharmaceutically acceptable salt thereof, wherein $R_9$ is H, $C_1$-$C_6$ alkyl, or $C_1$-$C_6$ alkoxy. In other embodiments, $R_9$ is $C_1$-$C_6$ alkyl or $C_1$-$C_6$ alkoxy. In other embodiments, $R_9$ is H or $C_1$-$C_6$ alkoxy. In other embodiments, $R_9$ is H or $C_1$-$C_6$ alkyl. In other embodiments, $R_9$ is $C_1$-$C_6$ alkyl. In other embodiments, $R_9$ is $C_1$-$C_6$ alkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (II-A-2), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is Cl.

In some embodiments, the invention relates to a compound of formula (II-A-2), or a pharmaceutically acceptable salt thereof, wherein $R_{12}$ is H.

In some embodiments, the invention relates to a compound of formula (II-A-2), or a pharmaceutically acceptable salt thereof, wherein $R_{13}$ is H.

In some embodiments, the invention relates to a compound of formula (II-A-2), i.e., the compound in non-salt form.

In another aspect, the invention relates to a compound of formula (II-B-1)

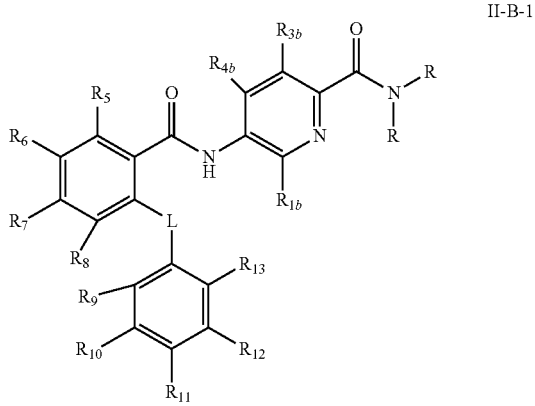

or a pharmaceutically acceptable salt thereof, wherein:
L is O, $C(R)_2$, or a single bond;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, $R_7$, and $R_8$ is not H.

In some embodiments, the invention relates to a compound of formula (II-B-1), or a pharmaceutically acceptable salt thereof, wherein L is O.

In some embodiments, the invention relates to a compound of formula (II-B-1), or a pharmaceutically acceptable salt thereof, wherein each R is independently H or $CH_3$. In other embodiments, each R is H. In other embodiments, each R is $CH_3$.

In some embodiments, the invention relates to a compound of formula (II-B-1), or a pharmaceutically acceptable salt thereof, wherein $R_{1b}$ is H, halo, or $C_1$-$C_6$ alkyl. In other embodiments, $R_{1b}$ is halo or $C_1$-$C_6$ alkyl. In other embodiments, $R_{1b}$ is H or $C_1$-$C_6$ alkyl. In other embodiments, $R_{1b}$ is H or halo. In other embodiments, $R_{1b}$ is halo. In other embodiments, $R_{1b}$ is $C_1$-$C_6$ alkyl. In other embodiments, $R_{1b}$ is H or $CH_3$. In other embodiments, $R_{1b}$ is H. In other embodiments, $R_{1b}$ is $CH_3$.

In some embodiments, the invention relates to a compound of formula (II-B-1), or a pharmaceutically acceptable salt thereof, wherein $R_{3b}$ is H.

In some embodiments, the invention relates to a compound of formula (II-B-1), or a pharmaceutically acceptable salt thereof, wherein $R_{4b}$ is H or $C_1$-$C_6$ alkyl. In other embodiments, $R_{4b}$ is $C_1$-$C_6$ alkyl. In other embodiments, $R_{4b}$ is H or $CH_3$. In other embodiments, $R_{4b}$ is H. In other embodiments, $R_{4b}$ is $CH_3$.

In some embodiments, the invention relates to a compound of formula (II-B-1), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H, F, Cl, $CF_3$, or $OCH_3$. In other embodiments, $R_5$ is H. In other embodiments, $R_5$ is F. In other embodiments, $R_5$ is Cl. In other embodiments, $R_5$ is $CF_3$. In other embodiments, $R_5$ is $OCH_3$.

In some embodiments, the invention relates to a compound of formula (II-B-1), or a pharmaceutically acceptable salt thereof, wherein $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ alkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is H, halo, $C_1$-$C_6$ haloalkyl, or $C_1$-$C_6$ haloalkoxy. In other embodiments, $R_6$ is H, F, Cl, $OCHF_2$, $CF_3$, $CHF_2$, or $OCF_3$. In other embodiments, $R_6$ is H. In other embodiments, $R_6$ is F. In other embodiments, $R_6$ is Cl. In other embodiments, $R_6$ is $OCHF_2$. In other embodiments, $R_6$ is $CF_3$. In other embodiments, $R_6$ is $CHF_2$. In other embodiments, $R_6$ is $OCF_3$.

In some embodiments, the invention relates to a compound of formula (II-B-1), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is H, halo, $C_1$-$C_6$ haloalkyl, or $C_1$-$C_6$ haloalkoxy. In other embodiments, $R_7$ is H, Cl, $CF_3$, $OCHF_2$, or $OCF_3$. In other embodiments, $R_7$ is H. In other embodiments, $R_7$ is Cl. In other embodiments, $R_7$ is $CF_3$. In other embodiments, $R_7$ is $OCHF_2$. In other embodiments, $R_7$ is $OCF_3$.

In some embodiments, the invention relates to a compound of formula (II-B-1), or a pharmaceutically acceptable salt thereof, wherein $R_8$ is H.

In some embodiments, the invention relates to a compound of formula (II-B-1), or a pharmaceutically acceptable salt thereof, wherein $R_9$ is H, $C_1$-$C_6$ alkyl, or $C_1$-$C_6$ alkoxy. In other embodiments, $R_9$ is $C_1$-$C_6$ alkyl or $C_1$-$C_6$ alkoxy. In other embodiments, $R_9$ is H or $C_1$-$C_6$ alkoxy. In other embodiments, $R_9$ is H or $C_1$-$C_6$ alkyl. In other embodiments, $R_9$ is $C_1$-$C_6$ alkyl. In other embodiments, $R_9$ is $C_1$-$C_6$ alkoxy. In other embodiments, $R_9$ is H or $OCH_3$. In other embodiments, $R_9$ is H. In other embodiments, $R_9$ is $^1H$. In other embodiments, $R_9$ is D. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (II-B-1), or a pharmaceutically acceptable salt thereof, wherein $R_{10}$ is H or halo. In other embodiments, $R_{10}$ is halo. In other embodiments, $R_{10}$ is H or F. In other embodiments, $R_{10}$ is H. In other embodiments, $R_{10}$ is $^1H$. In other embodiments, $R_{10}$ is D. In other embodiments, $R_{10}$ is F.

In some embodiments, the invention relates to a compound of formula (II-B-1), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is F or $OCF_3$. In other embodiments, $R_{11}$ is H. In other embodiments, $R_{11}$ is $^1H$. In other embodiments, $R_{11}$ is D. In other embodiments, $R_{11}$ is F. In other embodiments, $R_{11}$ is $OCF_3$.

In some embodiments, the invention relates to a compound of formula (II-B-1), or a pharmaceutically acceptable salt thereof, wherein $R_{12}$ is H.

In some embodiments, the invention relates to a compound of formula (II-B-1), or a pharmaceutically acceptable salt thereof, wherein $R_{13}$ is H.

In some embodiments, the invention relates to a compound of formula (II-B-1), i.e., the compound in non-salt form.

In another aspect, the invention relates to a compound of formula (II-B-2)

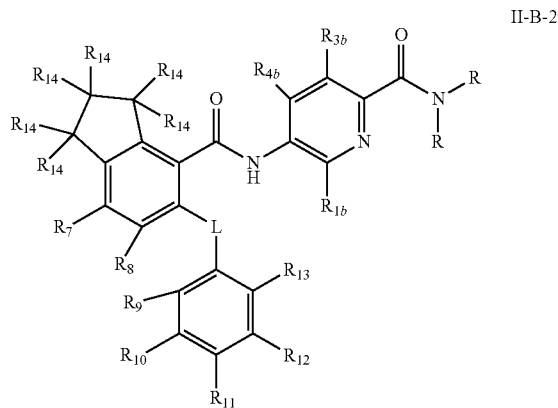

II-B-2 or a pharmaceutically acceptable salt thereof, wherein:
L is O, $C(R)_2$, or a single bond;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

each $R_{14}$ is independently H, halo, $C_1$-$C_4$ alkyl, or $C_1$-$C_4$ haloalkyl;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1.

In some embodiments, the invention relates to a compound of formula (II-B-2), or a pharmaceutically acceptable salt thereof, wherein L is O.

In some embodiments, the invention relates to a compound of formula (II-B-2), or a pharmaceutically acceptable salt thereof, wherein each R is independently H or $CH_3$. In other embodiments, each R is H. In other embodiments, each R is $CH_3$.

In some embodiments, the invention relates to a compound of formula (II-B-2), or a pharmaceutically acceptable salt thereof, wherein $R_{1b}$ is H, halo, or $C_1$-$C_6$ alkyl. In other embodiments, $R_{1b}$ is halo or $C_1$-$C_6$ alkyl. In other embodiments, $R_{1b}$ is H or $C_1$-$C_6$ alkyl. In other embodiments, $R_{1b}$ is H or halo. In other embodiments, $R_{1b}$ is halo. In other embodiments, $R_{1b}$ is $C_1$-$C_6$ alkyl. In other embodiments, $R_{1b}$ is H.

In some embodiments, the invention relates to a compound of formula (II-B-2), or a pharmaceutically acceptable salt thereof, wherein $R_{3b}$ is H.

In some embodiments, the invention relates to a compound of formula (II-B-2), or a pharmaceutically acceptable salt thereof, wherein $R_{4b}$ is H or $C_1$-$C_6$ alkyl. In other embodiments, $R_{4b}$ is $C_1$-$C_6$ alkyl. In other embodiments, $R_{4b}$ is H.

In some embodiments, the invention relates to a compound of formula (II-B-2), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is H.

In some embodiments, the invention relates to a compound of formula (II-B-2), or a pharmaceutically acceptable salt thereof, wherein $R_8$ is H.

In some embodiments, the invention relates to a compound of formula (II-B-2), or a pharmaceutically acceptable salt thereof, wherein $R_9$ is H, $C_1$-$C_6$ alkyl, or $C_1$-$C_6$ alkoxy. In other embodiments, $R_9$ is $C_1$-$C_6$ alkyl or $C_1$-$C_6$ alkoxy. In other embodiments, $R_9$ is H or $C_1$-$C_6$ alkoxy. In other embodiments, $R_9$ is H or $C_1$-$C_6$ alkyl. In other embodiments, $R_9$ is $C_1$-$C_6$ alkyl. In other embodiments, $R_9$ is $C_1$-$C_6$ alkoxy. In other embodiments, $R_9$ is H. In other embodiments, $R_9$ is $^1H$. In other embodiments, $R_9$ is D.

In some embodiments, the invention relates to a compound of formula (II-B-2), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1H$. In other embodiments, $R_{10}$ is D.

In some embodiments, the invention relates to a compound of formula (II-B-2), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1H$. In other embodiments, $R_{11}$ is D. In other embodiments, $R_{11}$ is $OCF_3$.

In some embodiments, the invention relates to a compound of formula (II-B-2), or a pharmaceutically acceptable salt thereof, wherein $R_{12}$ is H.

In some embodiments, the invention relates to a compound of formula (II-B-2), or a pharmaceutically acceptable salt thereof, wherein $R_{13}$ is H.

In some embodiments, the invention relates to a compound of formula (II-B-2), or a pharmaceutically acceptable salt thereof, wherein each $R_{14}$ is independently H or F.

In some embodiments, the invention relates to a compound of formula (II-B-2), i.e., the compound in non-salt form.

In another aspect, the invention relates to a compound of formula (II-B-3)

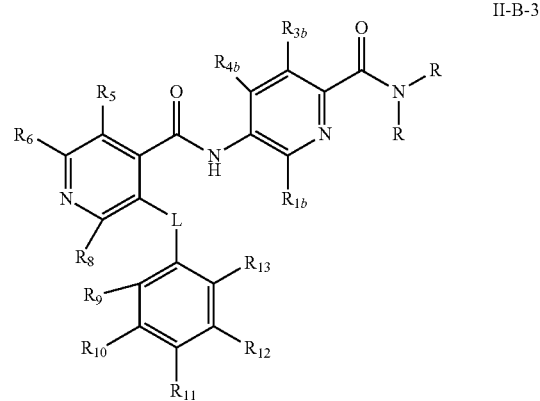

II-B-3 or a pharmaceutically acceptable salt thereof, wherein:

L is O, C(R)$_2$, or a single bond;

each R is independently H or $C_1$-$C_6$ alkyl;

$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$ and $R_6$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein at least one of $R_5$, $R_6$, and $R_8$ is not H.

In some embodiments, the invention relates to a compound of formula (II-B-3), or a pharmaceutically acceptable salt thereof, wherein L is O.

In some embodiments, the invention relates to a compound of formula (II-B-3), or a pharmaceutically acceptable salt thereof, wherein each R is independently H or $CH_3$. In other embodiments, each R is H. In other embodiments, each R is $CH_3$.

In some embodiments, the invention relates to a compound of formula (II-B-3), or a pharmaceutically acceptable salt thereof, wherein $R_{1b}$ is H, halo, or $C_1$-$C_6$ alkyl. In other embodiments, $R_{1b}$ is halo or $C_1$-$C_6$ alkyl. In other embodiments, $R_{1b}$ is H or $C_1$-$C_6$ alkyl. In other embodiments, $R_{1b}$ is H or halo. In other embodiments, $R_{1b}$ is halo. In other embodiments, $R_{1b}$ is $C_1$-$C_6$ alkyl. In other embodiments, $R_{1b}$ is H.

In some embodiments, the invention relates to a compound of formula (II-B-3), or a pharmaceutically acceptable salt thereof, wherein $R_{3b}$ is H.

In some embodiments, the invention relates to a compound of formula (II-B-3), or a pharmaceutically acceptable salt thereof, wherein $R_{4b}$ is H or $C_1$-$C_6$ alkyl. In other embodiments, $R_{4b}$ is $C_1$-$C_6$ alkyl. In other embodiments, $R_{4b}$ is H.

In some embodiments, the invention relates to a compound of formula (II-B-3), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is halo or $C_1$-$C_6$ alkoxy. In other embodiments, $R_5$ is F or $OCH_3$. In other embodiments, $R_5$ is F. In other embodiments, $R_5$ is $OCH_3$.

In some embodiments, the invention relates to a compound of formula (II-B-3), or a pharmaceutically acceptable salt thereof, wherein $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ alkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is $CF_3$.

In some embodiments, the invention relates to a compound of formula (II-B-3), or a pharmaceutically acceptable salt thereof, wherein $R_8$ is H.

In some embodiments, the invention relates to a compound of formula (II-B-3), or a pharmaceutically acceptable salt thereof, wherein $R_9$ is H, $C_1$-$C_6$ alkyl, or $C_1$-$C_6$ alkoxy. In other embodiments, $R_9$ is $C_1$-$C_6$ alkyl or $C_1$-$C_6$ alkoxy. In other embodiments, $R_9$ is H or $C_1$-$C_6$ alkoxy. In other embodiments, $R_9$ is H or $C_1$-$C_6$ alkyl. In other embodiments, $R_9$ is $C_1$-$C_6$ alkyl. In other embodiments, $R_9$ is $C_1$-$C_6$ alkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (II-B-3), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (II-B-3), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (II-B-3), or a pharmaceutically acceptable salt thereof, wherein $R_{12}$ is H.

In some embodiments, the invention relates to a compound of formula (II-B-3), or a pharmaceutically acceptable salt thereof, wherein $R_{13}$ is H.

In some embodiments, the invention relates to a compound of formula (II-B-3), i.e., the compound in non-salt form.

In another aspect, the invention relates to a compound of formula (II-B-4)

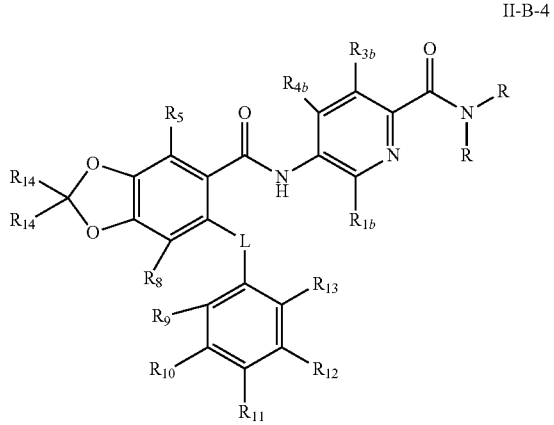

II-B-4 or a pharmaceutically acceptable salt thereof, wherein:
L is O, $C(R)_2$, or a single bond;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

each $R_{14}$ is independently H, halo, $C_1$-$C_4$ alkyl, or $C_1$-$C_4$ haloalkyl;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1.

In some embodiments, the invention relates to a compound of formula (II-B-4), or a pharmaceutically acceptable salt thereof, wherein L is O.

In some embodiments, the invention relates to a compound of formula (II-B-4), or a pharmaceutically acceptable salt thereof, wherein each R is independently H or $CH_3$. In other embodiments, each R is H. In other embodiments, each R is $CH_3$.

In some embodiments, the invention relates to a compound of formula (II-B-4), or a pharmaceutically acceptable salt thereof, wherein $R_{1b}$ is H, halo, or $C_1$-$C_6$ alkyl. In other embodiments, $R_{1b}$ is halo or $C_1$-$C_6$ alkyl. In other embodiments, $R_{1b}$ is H or $C_1$-$C_6$ alkyl. In other embodiments, $R_{1b}$ is H or halo. In other embodiments, $R_{1b}$ is halo. In other embodiments, $R_{1b}$ is $C_1$-$C_6$ alkyl. In other embodiments, $R_{1b}$ is H.

In some embodiments, the invention relates to a compound of formula (II-B-4), or a pharmaceutically acceptable salt thereof, wherein $R_{3b}$ is H.

In some embodiments, the invention relates to a compound of formula (II-B-4), or a pharmaceutically acceptable salt thereof, wherein $R_{4b}$ is H or $C_1$-$C_6$ alkyl. In other embodiments, $R_{4b}$ is $C_1$-$C_6$ alkyl. In other embodiments, $R_{4b}$ is H.

In some embodiments, the invention relates to a compound of formula (II-B-4), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is H In some embodiments, the invention relates to a compound of formula (II-B-4), or a pharmaceutically acceptable salt thereof, wherein $R_8$ is H In some embodiments, the invention relates to a compound of formula (II-B-4), or a pharmaceutically acceptable salt thereof, wherein $R_9$ is H, $C_1$-$C_6$ alkyl, or $C_1$-$C_6$ alkoxy. In other embodiments, $R_9$ is $C_1$-$C_6$ alkyl or $C_1$-$C_6$ alkoxy. In other embodiments, $R_9$ is H or $C_1$-$C_6$ alkoxy. In other embodiments, $R_9$ is H or $C_1$-$C_6$ alkyl. In other embodiments, $R_9$ is $C_1$-$C_6$ alkyl. In other embodiments, $R_9$ is $C_1$-$C_6$ alkoxy. In other embodiments, $R_9$ is H. In other embodiments, $R_9$ is $^1$H. In other embodiments, $R_9$ is D. In other embodiments, $R_9$ is $OCH_3$.

In some embodiments, the invention relates to a compound of formula (II-B-4), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (II-B-4), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (II-B-4), or a pharmaceutically acceptable salt thereof, wherein $R_{12}$ is H.

In some embodiments, the invention relates to a compound of formula (II-B-4), or a pharmaceutically acceptable salt thereof, wherein $R_{13}$ is H.

In some embodiments, the invention relates to a compound of formula (II-B-4), or a pharmaceutically acceptable salt thereof, wherein each $R_{14}$ is F.

In some embodiments, the invention relates to a compound of formula (II-B-4), i.e., the compound in non-salt form.

In another aspect, the invention relates to a compound of formula (II-B-5)

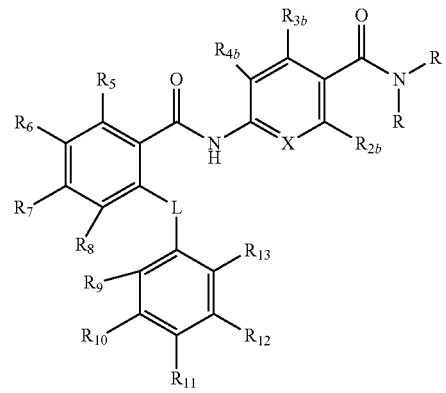

II-B-5 or a pharmaceutically acceptable salt thereof, wherein:

L is O, $C(R)_2$, or a single bond;

each R is independently H or $C_1$-$C_6$ alkyl;

$R_{2b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein at least one of $R_5$, $R_6$, $R_7$, and $R_8$ is not H.

In some embodiments, the invention relates to a compound of formula (II-B-5), or a pharmaceutically acceptable salt thereof, wherein L is O.

In some embodiments, the invention relates to a compound of formula (II-B-5), or a pharmaceutically acceptable salt thereof, wherein each R is independently H or $CH_3$. In other embodiments, each R is H. In other embodiments, each R is $CH_3$.

In some embodiments, the invention relates to a compound of formula (II-B-5), or a pharmaceutically acceptable salt thereof, wherein $R_{2b}$ is H or halo. In other embodiments, $R_{2b}$ is halo. In other embodiments, $R_{2b}$ is H.

In some embodiments, the invention relates to a compound of formula (II-B-5), or a pharmaceutically acceptable salt thereof, wherein $R_{3b}$ is H.

In some embodiments, the invention relates to a compound of formula (II-B-5), or a pharmaceutically acceptable salt thereof, wherein $R_{4b}$ is H or $C_1$-$C_6$ alkyl. In other embodiments, $R_{4b}$ is $C_1$-$C_6$ alkyl. In other embodiments, $R_{4b}$ is H.

In some embodiments, the invention relates to a compound of formula (II-B-5), or a pharmaceutically acceptable salt thereof, wherein $R_5$ is H, halo, $C_1$-$C_6$ alkyl, $C_1$-$C_6$ haloalkyl, or $C_1$-$C_6$ alkoxy. In other embodiments, $R_5$ is halo, $C_1$-$C_6$ alkyl, $C_1$-$C_6$ haloalkyl, or $C_1$-$C_6$ alkoxy. In other embodiments, $R_5$ is H, $C_1$-$C_6$ alkyl, $C_1$-$C_6$ haloalkyl, or $C_1$-$C_6$ alkoxy. In other embodiments, $R_5$ is H, halo, $C_1$-$C_6$ haloalkyl, or $C_1$-$C_6$ alkoxy. In other embodiments, $R_5$ is H, halo, $C_1$-$C_6$ alkyl, or $C_1$-$C_6$ alkoxy. In other embodiments, $R_5$ is H, halo, $C_1$-$C_6$ alkyl, or $C_1$-$C_6$ haloalkyl. In other embodiments, $R_5$ is halo. In other embodiments, $R_5$ is $C_1$-$C_6$ alkyl. In other embodiments, $R_5$ is $C_1$-$C_6$ haloalkyl. In other embodiments, $R_5$ is $C_1$-$C_6$ alkoxy. In other embodiments, $R_5$ is halo or $C_1$-$C_6$ alkoxy. In other embodiments, $R_5$ is F or $OCH_3$. In other embodiments, $R_5$ is F. In other embodiments, $R_5$ is $OCH_3$.

In some embodiments, the invention relates to a compound of formula (II-B-5), or a pharmaceutically acceptable salt thereof, wherein $R_6$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ haloalkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ alkoxy, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ haloalkoxy. In other embodiments, $R_6$ is H, halo, $C_1$-$C_6$ alkyl, $C_1$-$C_6$ haloalkyl, or $C_1$-$C_6$ alkoxy. In other embodiments, $R_6$ is halo. In other embodiments, $R_6$ is $C_1$-$C_6$ alkyl. In other embodiments, $R_6$ is $C_1$-$C_6$ haloalkyl. In other embodiments, $R_6$ is $C_1$-$C_6$ alkoxy. In other embodiments, $R_6$ is $C_1$-$C_6$ haloalkoxy. In other embodiments, $R_6$ is $CF_3$.

In some embodiments, the invention relates to a compound of formula (II-B-5), or a pharmaceutically acceptable salt thereof, wherein $R_7$ is H, halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is halo, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, $C_1$-$C_6$ alkyl, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ haloalkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ alkoxy, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ haloalkoxy. In other embodiments, $R_7$ is H, halo, $C_1$-$C_6$ alkyl, $C_1$-$C_6$ haloalkyl, or $C_1$-$C_6$ alkoxy. In other embodiments, $R_7$ is halo. In other embodiments, $R_7$ is $C_1$-$C_6$ alkyl. In other embodiments, $R_7$ is $C_1$-$C_6$ haloalkyl. In other embodiments, $R_7$ is $C_1$-$C_6$ alkoxy. In other embodiments, $R_7$ is $C_1$-$C_6$ haloalkoxy. In other embodiments, $R_7$ is H.

In some embodiments, the invention relates to a compound of formula (II-B-5), or a pharmaceutically acceptable salt thereof, wherein $R_8$ is H.

In some embodiments, the invention relates to a compound of formula (II-B-5), or a pharmaceutically acceptable salt thereof, wherein $R_9$ is H, $C_1$-$C_6$ alkyl, or $C_1$-$C_6$ alkoxy. In other embodiments, $R_9$ is $C_1$-$C_6$ alkyl or $C_1$-$C_6$ alkoxy. In other embodiments, $R_9$ is H or $C_1$-$C_6$ alkoxy. In other embodiments, $R_9$ is H or $C_1$-$C_6$ alkyl. In other embodiments, $R_9$ is $C_1$-$C_6$ alkyl. In other embodiments, $R_9$ is $C_1$-$C_6$ alkoxy. In other embodiments, $R_9$ is H. In other embodiments, $R_9$ is $^1$H. In other embodiments, $R_9$ is D. In other embodiments, $R_9$ is $OCH_3$. In other embodiments, $R_9$ is $OC(^1H)_3$. In other embodiments, $R_9$ is $OCD_3$.

In some embodiments, the invention relates to a compound of formula (II-B-5), or a pharmaceutically acceptable salt thereof, wherein $R_{10}$ is H or halo. In other embodiments, $R_{10}$ is halo. In other embodiments, $R_{10}$ is H. In other embodiments, $R_{10}$ is $^1$H. In other embodiments, $R_{10}$ is D.

In some embodiments, the invention relates to a compound of formula (II-B-5), or a pharmaceutically acceptable salt thereof, wherein $R_{11}$ is halo, $C_1$-$C_6$ alkoxy, or $C_1$-$C_6$ haloalkoxy. In other embodiments, $R_{11}$ is $C_1$-$C_6$ alkoxy or $C_1$-$C_6$ haloalkoxy. In other embodiments, $R_{11}$ is halo or $C_1$-$C_6$ haloalkoxy. In other embodiments, $R_{11}$ is halo or $C_1$-$C_6$ alkoxy. In other embodiments, $R_{11}$ is halo. In other embodiments, $R_{11}$ is $C_1$-$C_6$ alkoxy. In other embodiments, $R_{11}$ is $C_1$-$C_6$ haloalkoxy. In other embodiments, $R_{11}$ is H. In other embodiments, $R_{11}$ is $^1$H. In other embodiments, $R_{11}$ is D. In other embodiments, $R_{11}$ is $OCF_3$.

In some embodiments, the invention relates to a compound of formula (II-B-5), or a pharmaceutically acceptable salt thereof, wherein $R_{12}$ is H.

In some embodiments, the invention relates to a compound of formula (II-B-5), or a pharmaceutically acceptable salt thereof, wherein $R_{13}$ is H.

In some embodiments, the invention relates to a compound of formula (II-B-5), i.e., the compound in non-salt form.

In some embodiments, the invention relates to a compound selected from Table 1, 1A, or 1B, or a pharmaceutically acceptable salt thereof. In other embodiments, the invention relates to a compound selected from Table 1, 1A, or 1B, i.e., the compound in non-salt form.

TABLE 1

| Compound Number | Compound Structure and Chemical Name |
|---|---|
| 1 | 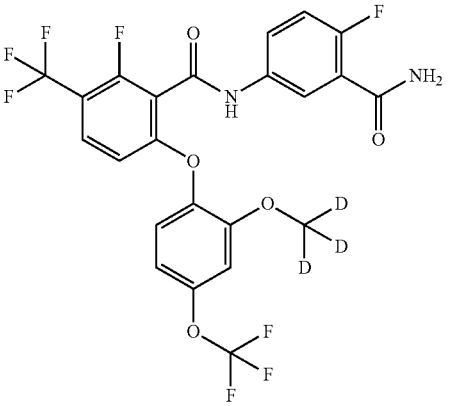<br>N-(3-carbamoyl-4-fluoro-phenyl)-2-fluoro-6-[2-(trideuteriomethoxy)-4-(trifluoromethoxy)phenoxy]-3-(trifluoromethyl)benzamide |
| 2 | 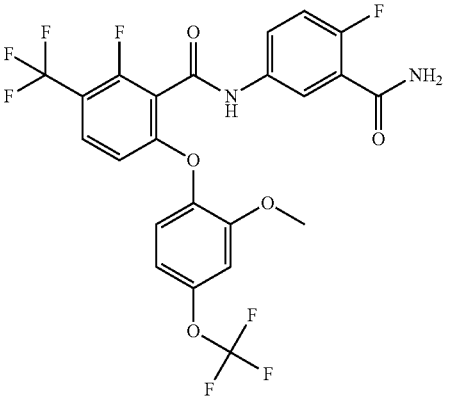<br>N-(3-carbamoyl-4-fluoro-phenyl)-2-fluoro-6-[2-methoxy-4-(trifluoromethoxy)phenoxy]-3-(trifluoromethyl)benzamide |
| 3 | 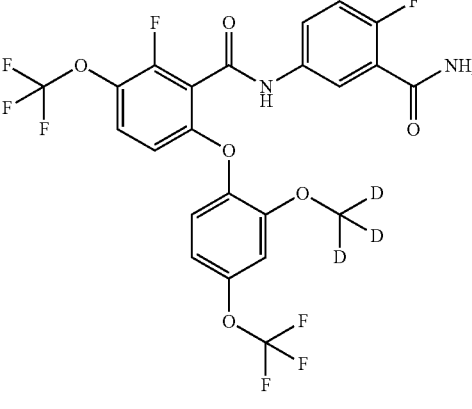<br>N-(3-carbamoyl-4-fluoro-phenyl)-2-fluoro-6-[2-(trideuteriomethoxy)-4-(trifluoromethoxy)phenoxy]-3-(trifluoromethoxy)benzamide |

TABLE 1-continued

| Compound Number | Compound Structure and Chemical Name |
|---|---|
| 4 | 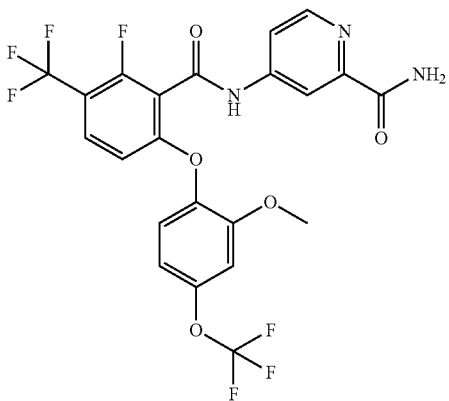<br>4-[[2-fluoro-6-[2-methoxy-4-(trifluoromethoxy)phenoxy]-3-(trifluoromethyl)benzoyl]amino]pyridine-2-carboxamide |
| 5 | 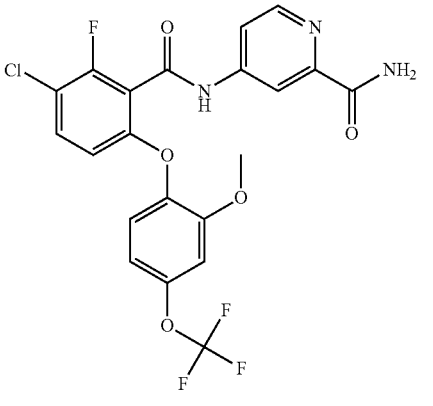<br>4-[[3-chloro-2-fluoro-6-[2-methoxy-4-(trifluoromethoxy)phenoxy]benzoyl]amino]pyridine-2-carboxamide |
| 6 | 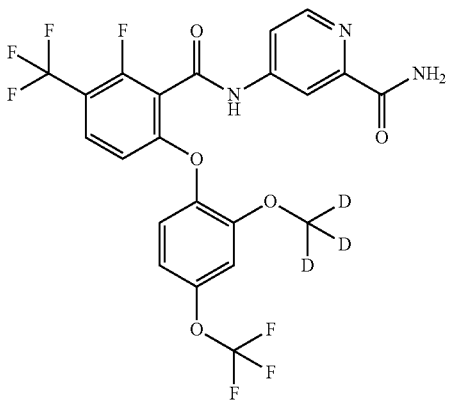<br>4-[[2-fluoro-6-[2-(trideuteriomethoxy)-4-(trifluoromethoxy)phenoxy]-3-(trifluoromethyl)benzoyl]amino]pyridine-2-carboxamide |

TABLE 1-continued

Compound Numbers, Structures, and Chemical Names

| Compound Number | Compound Structure and Chemical Name |
|---|---|
| 7 | 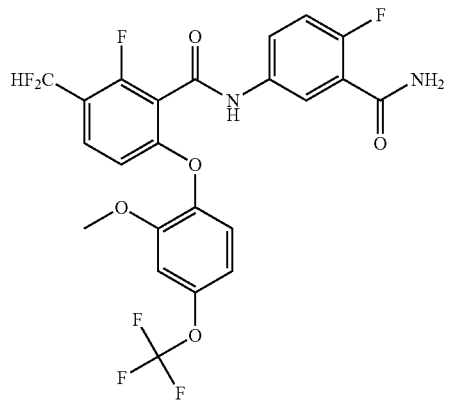<br>N-(3-carbamoyl-4-fluoro-phenyl)-3-(difluoromethyl)-2-fluoro-6-[2-methoxy-4-(trifluoromethoxy)phenoxy]benzamide |
| 8 | 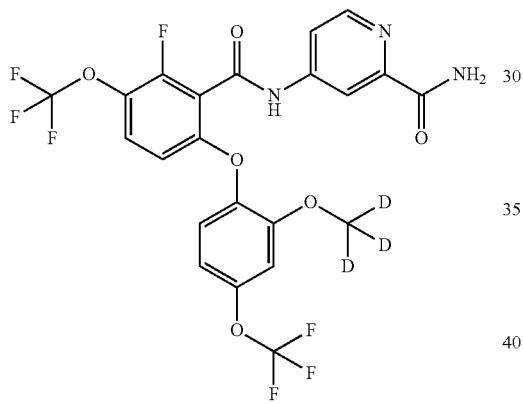<br>4-[[2-fluoro-6-[2-(trideuteriomethoxy)-4-(trifluoromethoxy)phenoxy]-3-(trifluoromethoxy)benzoyl]amino]pyridine-2-carboxamide |
| 9 | 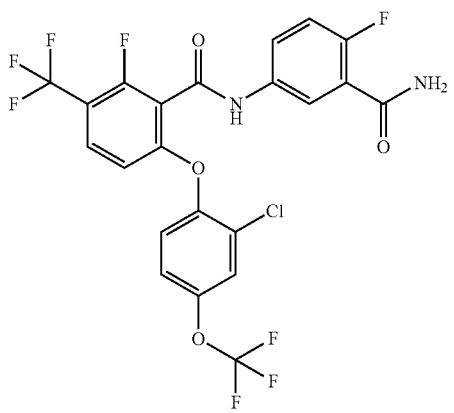<br>N-(3-carbamoyl-4-fluoro-phenyl)-6-[2-chloro-4-(trifluoromethoxy)phenoxy]-2-fluoro-3-(trifluoromethyl)benzamide |
| 10 | 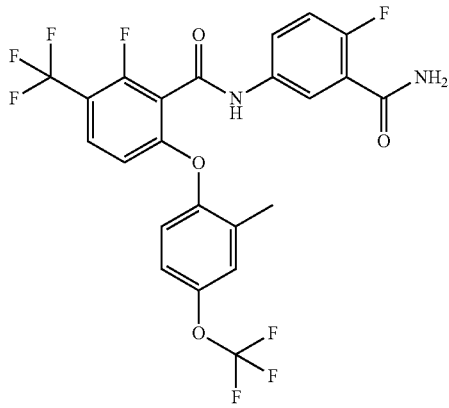<br>N-(3-carbamoyl-4-fluoro-phenyl)-2-fluoro-6-[2-methyl-4-(trifluoromethoxy)phenoxy]-3-(trifluoromethyl)benzamide |
| 11 | 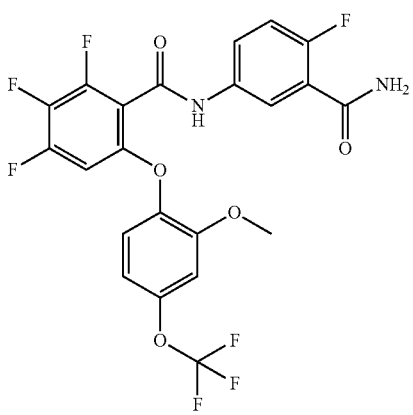<br>N-(3-carbamoyl-4-fluoro-phenyl)-2,3,4-trifluoro-6-[2-methoxy-4-(trifluoromethoxy)phenoxy]benzamide |
| 12 | 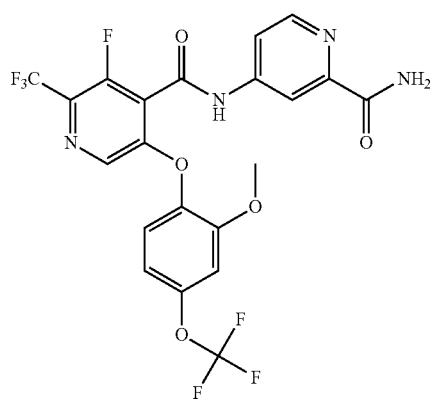<br>N-(2-carbamoyl-4-pyridyl)-3-fluoro-5-[2-methoxy-4-(trifluoromethoxy)phenoxy]-2-(trifluoromethyl)pyridine-4-carboxamide |

TABLE 1-continued

Compound Numbers, Structures, and Chemical Names

| Compound Number | Compound Structure and Chemical Name |
|---|---|
| 13 | 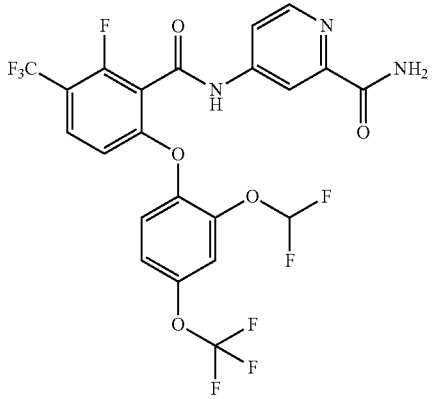<br>4-[[6-2-(difluoromethoxy)-4-(trifluoromethoxy)phenoxy]-2-fluoro-3-(trifluoromethyl)benzoyl]amino]pyridine-2-carboxamide |
| 14 | 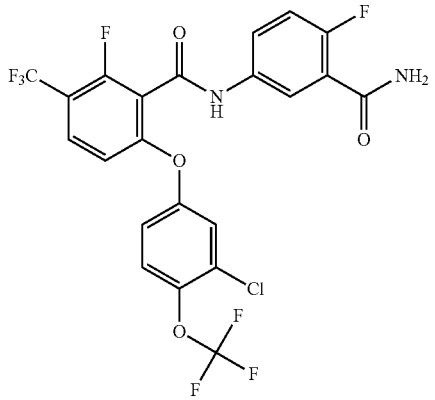<br>N-(3-carbamoyl-4-fluoro-phenyl)-6-[3-chloro-4-(trifluoromethoxy)phenoxy]-2-fluoro-3-(trifluoromethyl)benzamide |
| 15 | 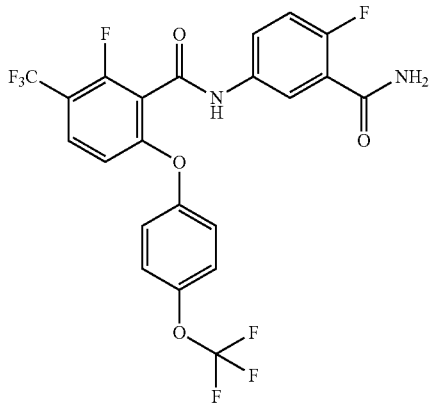<br>N-(3-carbamoyl-4-fluoro-phenyl)-2-fluoro-6-[4-(trifluoromethoxy)phenoxy]-3-(trifluoromethyl)benzamide |
| 16 | 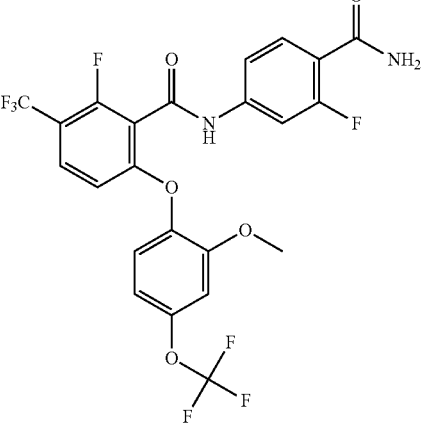<br>N-(4-carbamoyl-3-fluoro-phenyl)-2-fluoro-6-[2-methoxy-4-(trifluoromethoxy)phenoxy]-3-(trifluoromethyl)benzamide |
| 17 | 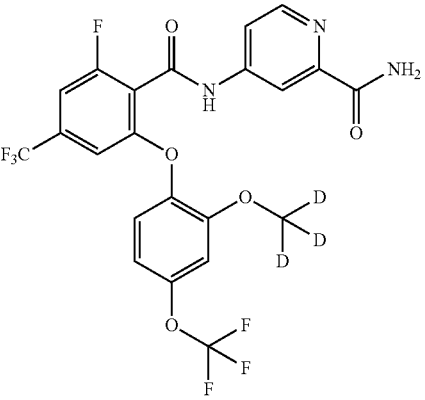<br>4-[[2-fluoro-6-[2-(trideuteriomethoxy)-4-(trifluoromethoxy)phenoxy]-4-(trifluoromethyl)benzoyl]amino]pyridine-2-carboxamide |
| 18 | 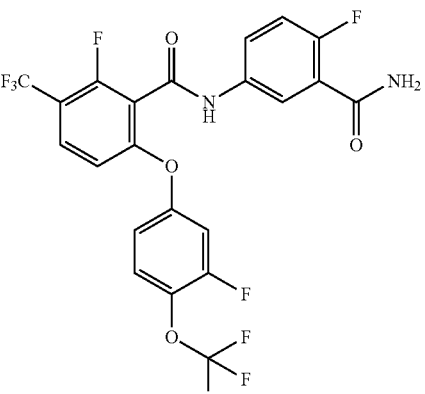<br>N-(3-carbamoyl-4-fluoro-phenyl)-2-fluoro-6-[3-fluoro-4-(trifluoromethoxy)phenoxy]-3-(trifluoromethyl)benzamide |

TABLE 1-continued

Compound Numbers, Structures, and Chemical Names

| Compound Number | Compound Structure and Chemical Name |
|---|---|
| 19 | N-(3-carbamoyl-4-fluoro-phenyl)-2-[2-methoxy-4-(trifluoromethoxy)phenoxy]-5-(1,1,2,2,2-pentafluoroethyl)benzamide |
| 20 | 4-[[4-(difluoromethoxy)-2-fluoro-6-[2-methoxy-4-(trifluoromethoxy)phenoxy]benzoyl]amino]pyridine-2-carboxamide |
| 21 | N-(3-carbamoyl-4-fluoro-phenyl)-2-fluoro-6-[2-fluoro-4-(trifluoromethoxy)phenoxy]-3-(trifluoromethyl)benzamide |
| 22 | 4-[[4-cyclopropyl-2-fluoro-6-[2-methoxy-4-(trifluoromethoxy)phenoxy]benzoyl]amino]pyridine-2-carboxamide |
| 23 | N-(3-carbamoyl-4-fluoro-phenyl)-5-fluoro-2-[2-methoxy-4-(trifluoromethoxy)phenoxy]-4-(trifluoromethyl)benzamide |
| 24 | 5-[[2-fluoro-6-[2-(trideuteriomethoxy)-4-(trifluoromethoxy)phenoxy]-3-(trifluoromethyl)benzoyl]amino]pyridine-2-carboxamide |

TABLE 1-continued
Compound Numbers, Structures, and Chemical Names
| Compound Number | Compound Structure and Chemical Name |
|---|---|
| 25 | 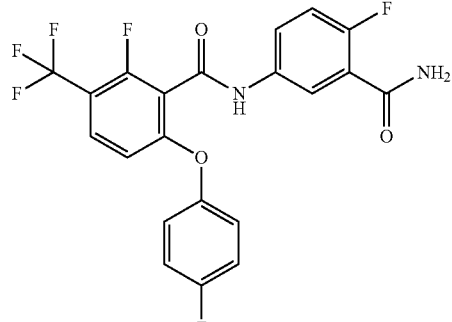<br>N-(3-carbamoyl-4-fluoro-phenyl)-2-fluoro-6-(4-fluorophenoxy)-3-(trifluoromethyl)benzamide |
| 26 | 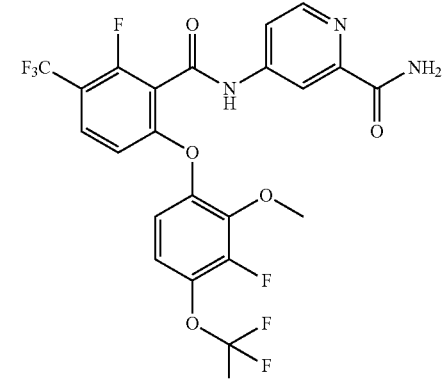<br>4-[[2-fluoro-6-[3-fluoro-2-methoxy-4-(trifluoromethoxy)phenoxy]-3-(trifluoromethyl)benzoyl]amino]pyridine-2-carboxamide |
TABLE 1A
Compound Numbers and Structures.
| 27 | 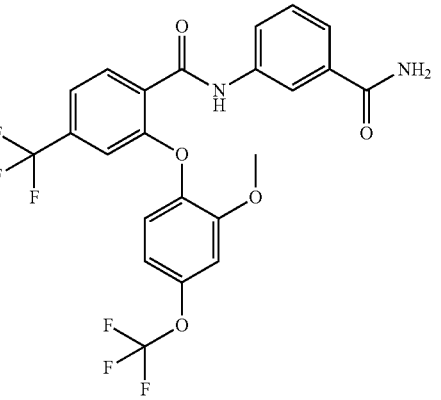 |
| 28 | 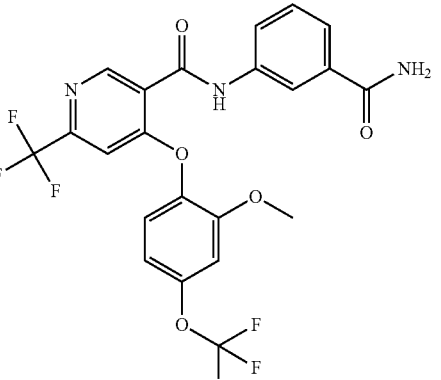 |
| 29 | 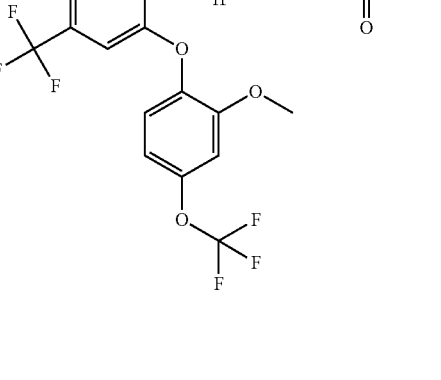 |
| 30 | 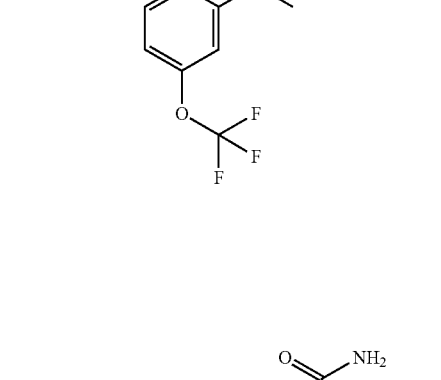 |

TABLE 1A-continued
Compound Numbers and Structures.
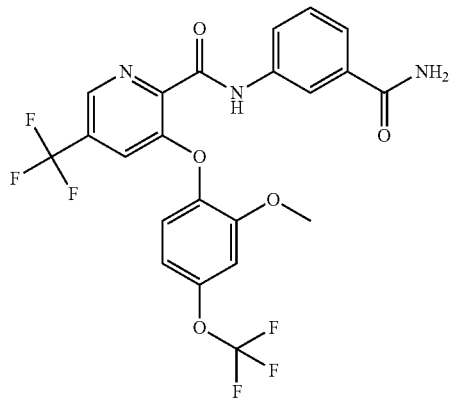 [SMILES: COc1cc(OC(F)(F)F)ccc1Oc1cc(C(F)(F)F)cnc1C(=O)Nc1cccc(C(N)=O)c1]
31
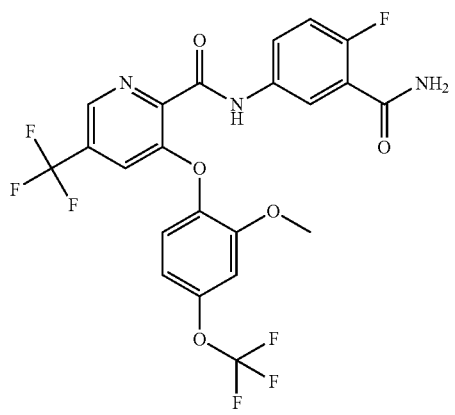 [SMILES: COc1cc(OC(F)(F)F)ccc1Oc1cc(C(F)(F)F)cnc1C(=O)Nc1ccc(F)c(C(N)=O)c1]
32
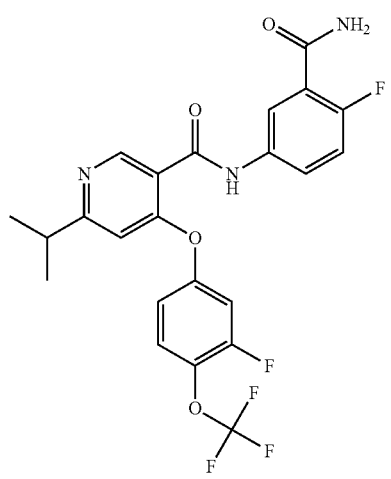 [SMILES: CC(C)c1cc(Oc2ccc(OC(F)(F)F)c(F)c2)c(C(=O)Nc2ccc(F)c(C(N)=O)c2)cn1]
33
TABLE 1A-continued
Compound Numbers and Structures.
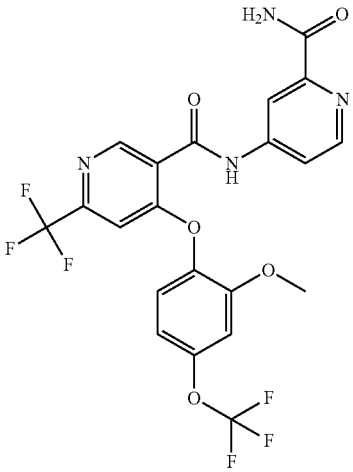 [SMILES: COc1cc(OC(F)(F)F)ccc1Oc1cc(C(F)(F)F)ncc1C(=O)Nc1ccnc(C(N)=O)c1]
34
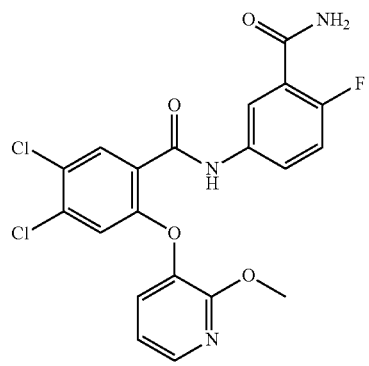 [SMILES: COc1ncccc1Oc1cc(Cl)c(Cl)cc1C(=O)Nc1ccc(F)c(C(N)=O)c1]
35
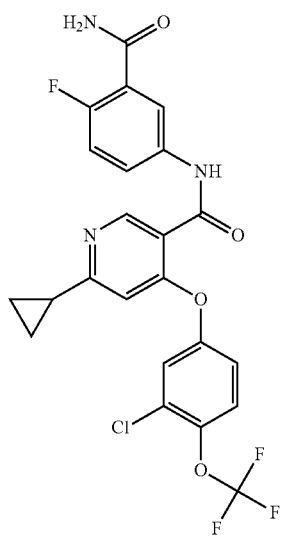 [SMILES: NC(=O)c1cc(NC(=O)c2cnc(C3CC3)cc2Oc2ccc(OC(F)(F)F)c(Cl)c2)ccc1F]
36

TABLE 1A-continued
Compound Numbers and Structures.
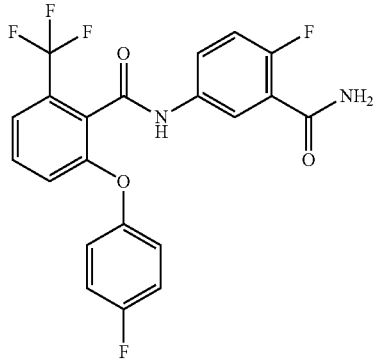 [SMILES: NC(=O)c1cc(NC(=O)c2c(Oc3ccc(F)cc3)cccc2C(F)(F)F)ccc1F]
37
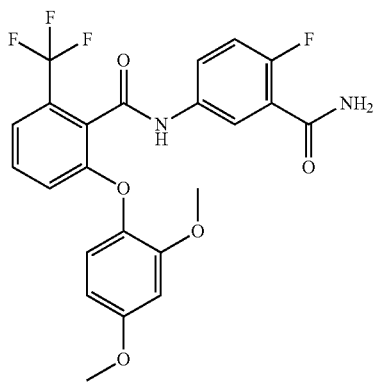 [SMILES: COc1ccc(Oc2cccc(C(F)(F)F)c2C(=O)Nc2ccc(F)c(C(N)=O)c2)c(OC)c1]
38
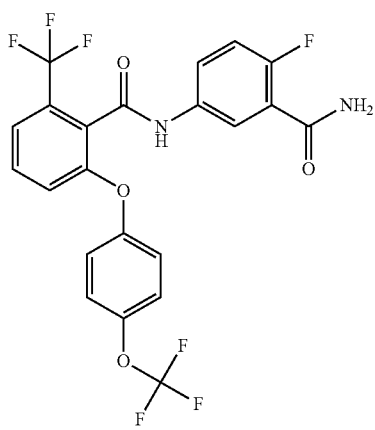 [SMILES: NC(=O)c1cc(NC(=O)c2c(Oc3ccc(OC(F)(F)F)cc3)cccc2C(F)(F)F)ccc1F]
39
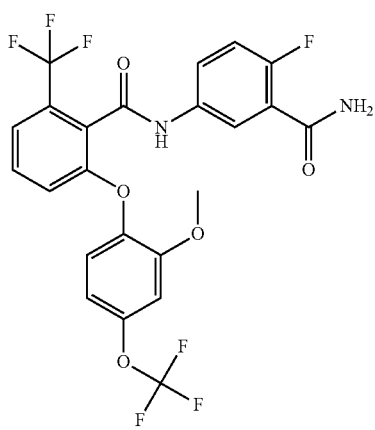 [SMILES: COc1cc(OC(F)(F)F)ccc1Oc1cccc(C(F)(F)F)c1C(=O)Nc1ccc(F)c(C(N)=O)c1]
40
TABLE 1A-continued
Compound Numbers and Structures.
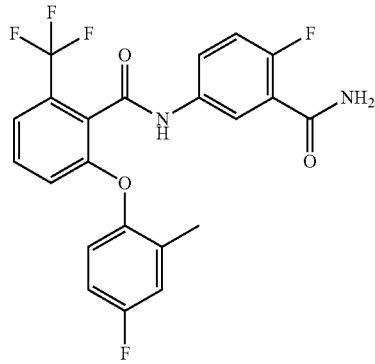
41
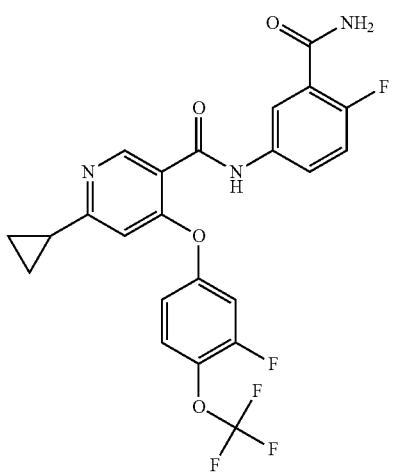 [SMILES: NC(=O)c1cc(NC(=O)c2cnc(C3CC3)cc2Oc2ccc(OC(F)(F)F)c(F)c2)ccc1F]
42
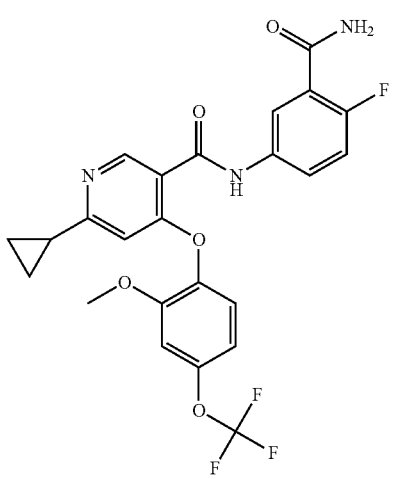 [SMILES: COc1cc(OC(F)(F)F)ccc1Oc1cc(C2CC2)ncc1C(=O)Nc1ccc(F)c(C(N)=O)c1]
43

TABLE 1A-continued
Compound Numbers and Structures.
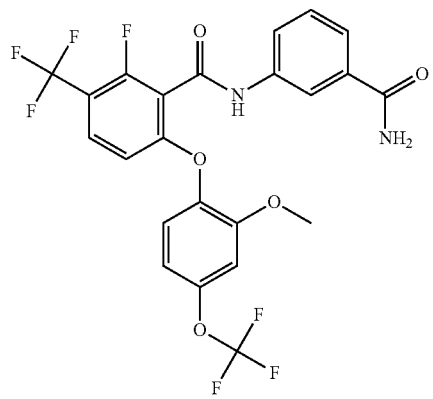 [SMILES: COc1cc(OC(F)(F)F)ccc1Oc1ccc(C(F)(F)F)c(F)c1C(=O)Nc1cccc(C(N)=O)c1]
44
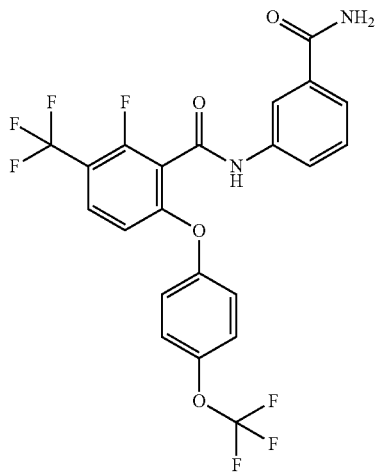
47
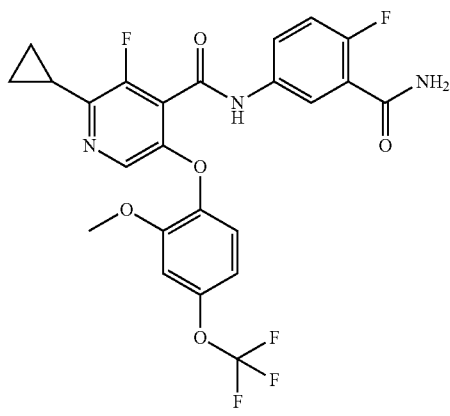 [SMILES: COc1cc(OC(F)(F)F)ccc1Oc1cnc(C2CC2)c(F)c1C(=O)Nc1ccc(F)c(C(N)=O)c1]
45
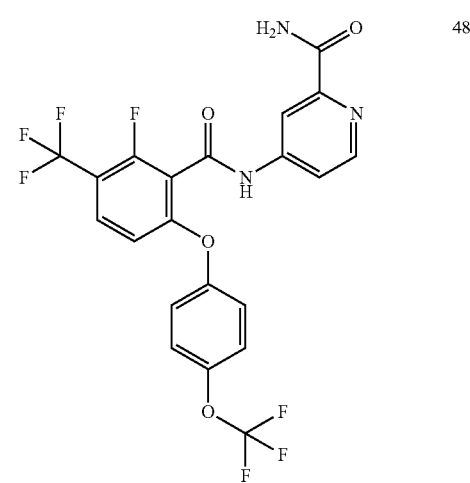
48
46
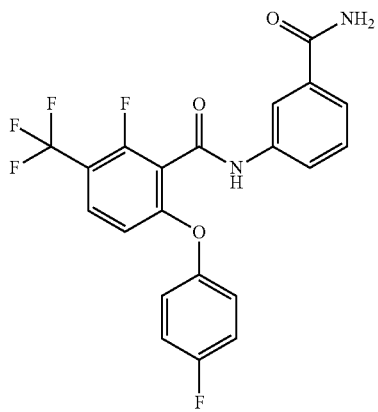 [SMILES: NC(=O)c1cccc(NC(=O)c2c(Oc3ccc(F)cc3)ccc(C(F)(F)F)c2F)c1]
49

TABLE 1A-continued
Compound Numbers and Structures.
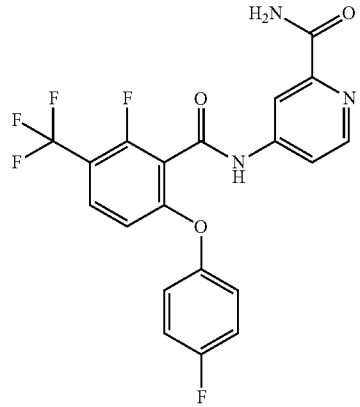 [SMILES: NC(=O)c1cc(NC(=O)c2c(Oc3ccc(F)cc3)ccc(C(F)(F)F)c2F)ccn1]
50
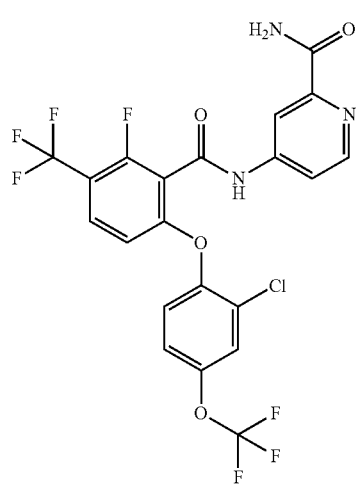 [SMILES: NC(=O)c1cc(NC(=O)c2c(Oc3ccc(OC(F)(F)F)cc3Cl)ccc(C(F)(F)F)c2F)ccn1]
51
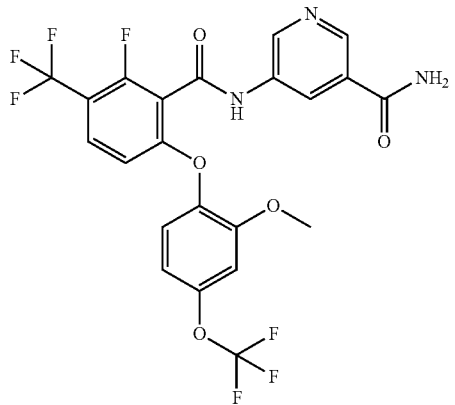 [SMILES: COc1cc(OC(F)(F)F)ccc1Oc1ccc(C(F)(F)F)c(F)c1C(=O)Nc1cncc(C(N)=O)c1]
52
TABLE 1A-continued
Compound Numbers and Structures.
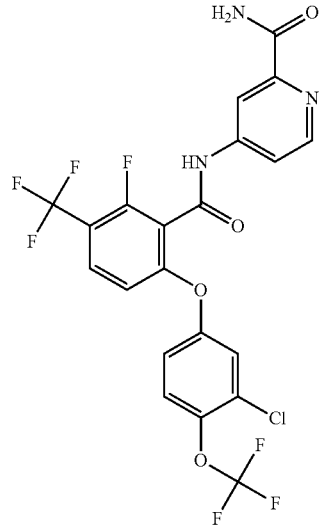 [SMILES: NC(=O)c1cc(NC(=O)c2c(Oc3ccc(OC(F)(F)F)c(Cl)c3)ccc(C(F)(F)F)c2F)ccn1]
53
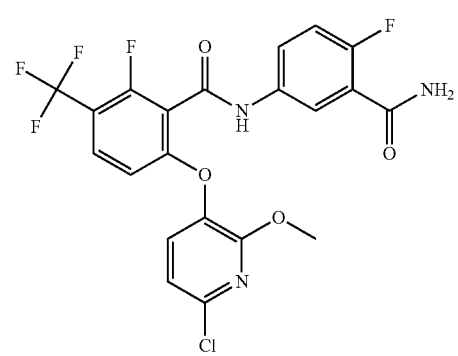 [SMILES: COc1nc(Cl)ccc1Oc1ccc(C(F)(F)F)c(F)c1C(=O)Nc1ccc(F)c(C(N)=O)c1]
54
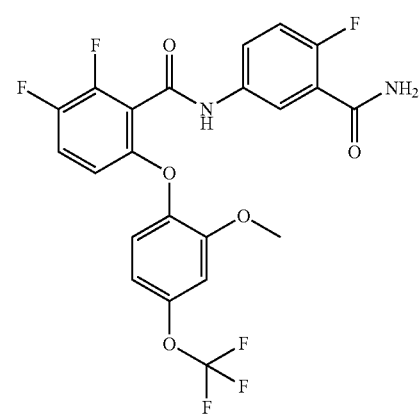 [SMILES: COc1cc(OC(F)(F)F)ccc1Oc1ccc(F)c(F)c1C(=O)Nc1ccc(F)c(C(N)=O)c1]
55

TABLE 1A-continued

Compound Numbers and Structures.

TABLE 1A-continued
Compound Numbers and Structures.
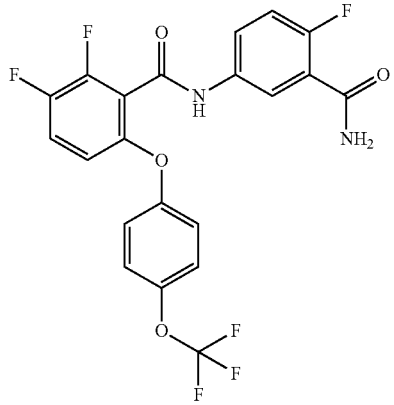
63
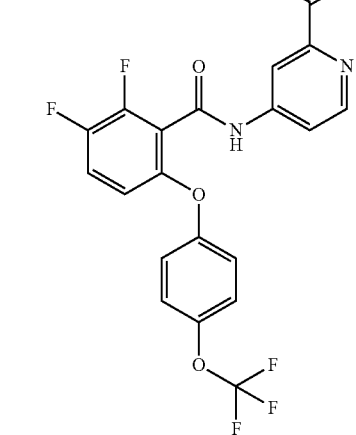
64
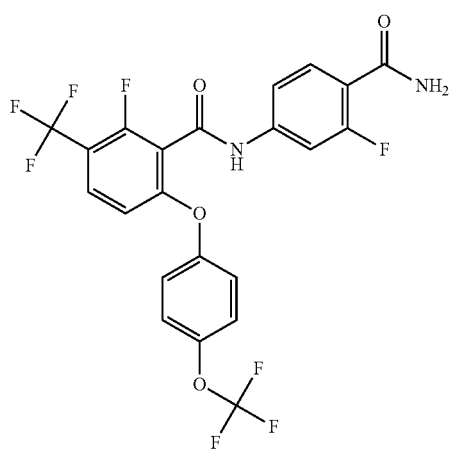 [SMILES: NC(=O)c1ccc(NC(=O)c2c(Oc3ccc(OC(F)(F)F)cc3)ccc(C(F)(F)F)c2F)cc1F]
65
TABLE 1A-continued
Compound Numbers and Structures.
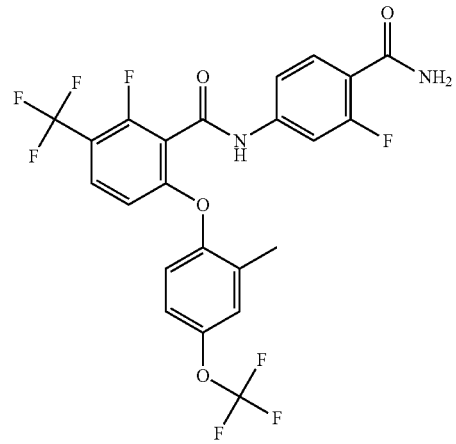 [SMILES: Cc1cc(OC(F)(F)F)ccc1Oc1ccc(C(F)(F)F)c(F)c1C(=O)Nc1ccc(C(N)=O)c(F)c1]
66
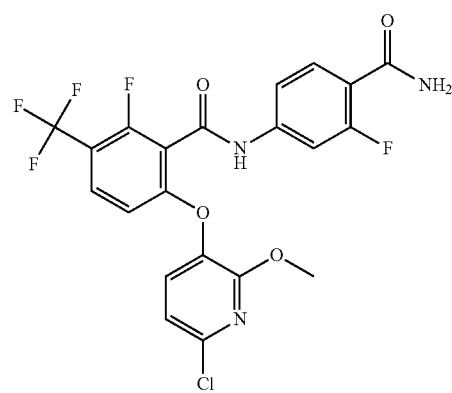 [SMILES: COc1nc(Cl)ccc1Oc1ccc(C(F)(F)F)c(F)c1C(=O)Nc1ccc(C(N)=O)c(F)c1]
67
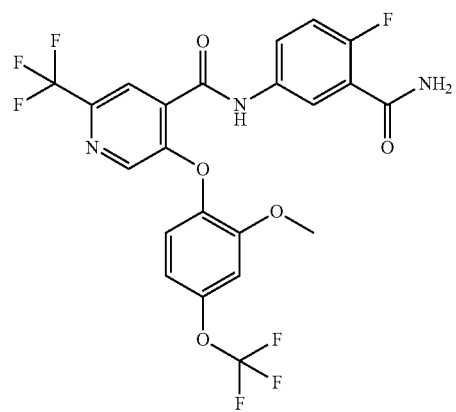 [SMILES: COc1cc(OC(F)(F)F)ccc1Oc1cnc(C(F)(F)F)cc1C(=O)Nc1ccc(F)c(C(N)=O)c1]
68

TABLE 1A-continued
Compound Numbers and Structures.
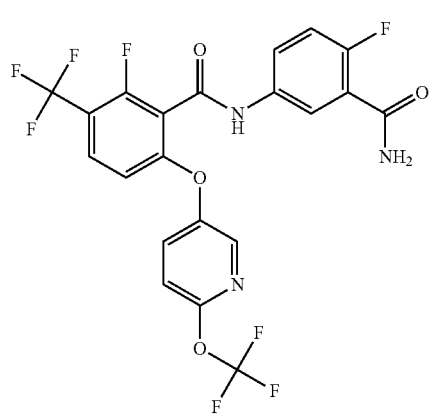 [SMILES: NC(=O)c1cc(NC(=O)c2c(Oc3ccc(OC(F)(F)F)nc3)ccc(C(F)(F)F)c2F)ccc1F]
69
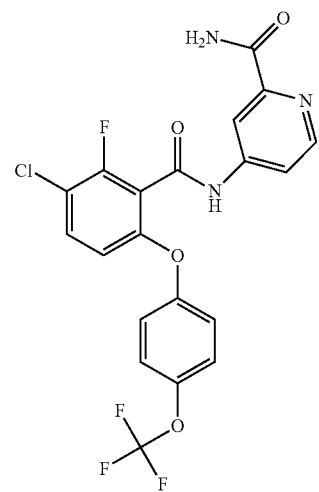 [SMILES: NC(=O)c1cc(NC(=O)c2c(Oc3ccc(OC(F)(F)F)cc3)ccc(Cl)c2F)ccn1]
70
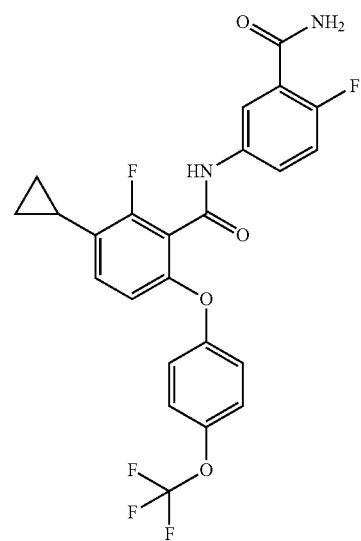 [SMILES: NC(=O)c1cc(NC(=O)c2c(Oc3ccc(OC(F)(F)F)cc3)ccc(C3CC3)c2F)ccc1F]
71
TABLE 1A-continued
Compound Numbers and Structures.
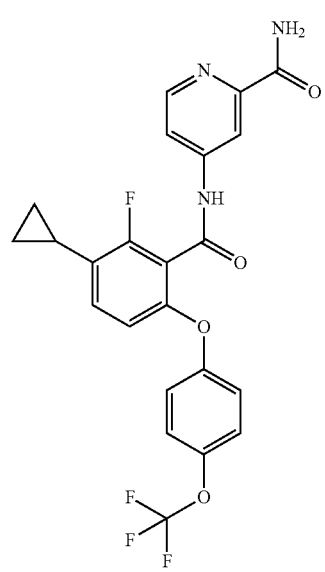 [SMILES: NC(=O)c1cc(NC(=O)c2c(Oc3ccc(OC(F)(F)F)cc3)ccc(C3CC3)c2F)ccn1]
72
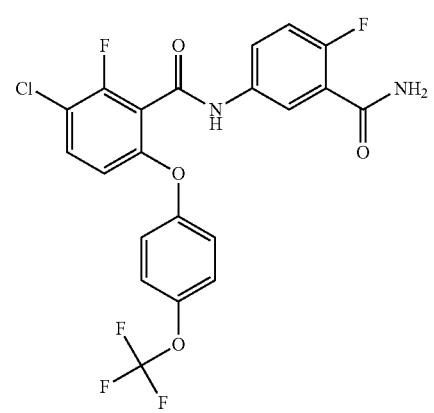 [SMILES: NC(=O)c1cc(NC(=O)c2c(Oc3ccc(OC(F)(F)F)cc3)ccc(Cl)c2F)ccc1F]
73
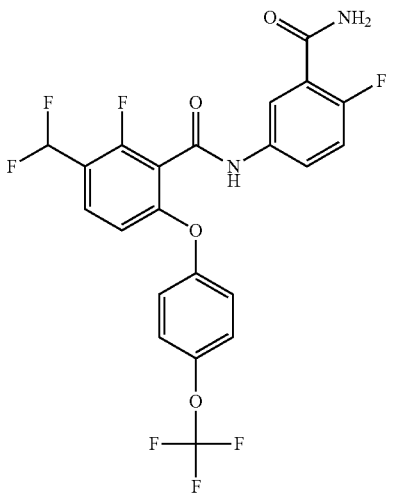 [SMILES: NC(=O)c1cc(NC(=O)c2c(Oc3ccc(OC(F)(F)F)cc3)ccc(C(F)F)c2F)ccc1F]
74

TABLE 1A-continued
Compound Numbers and Structures.
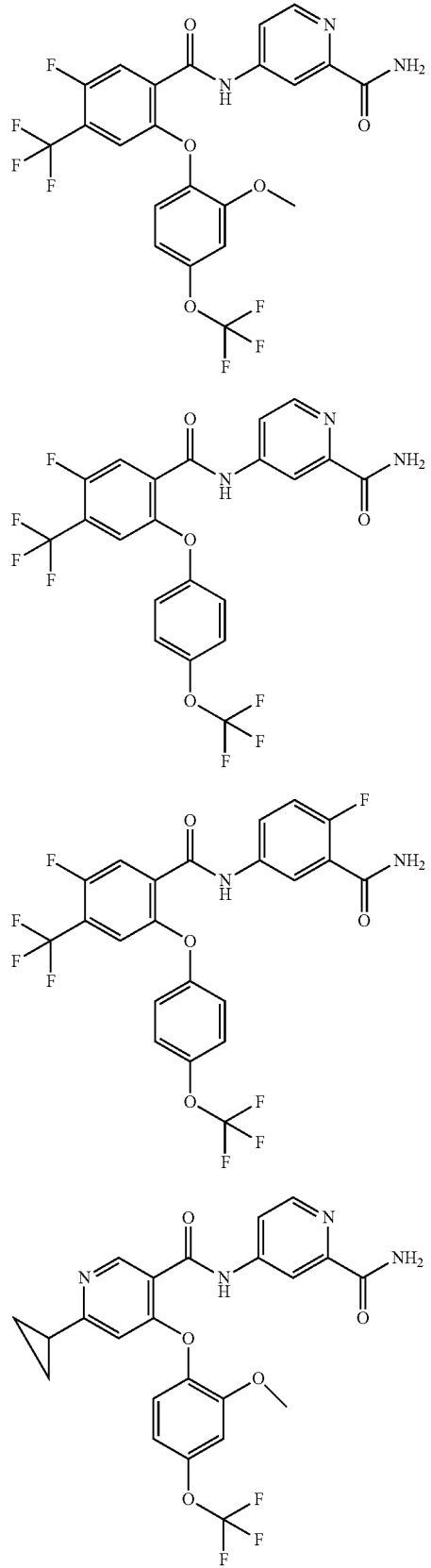
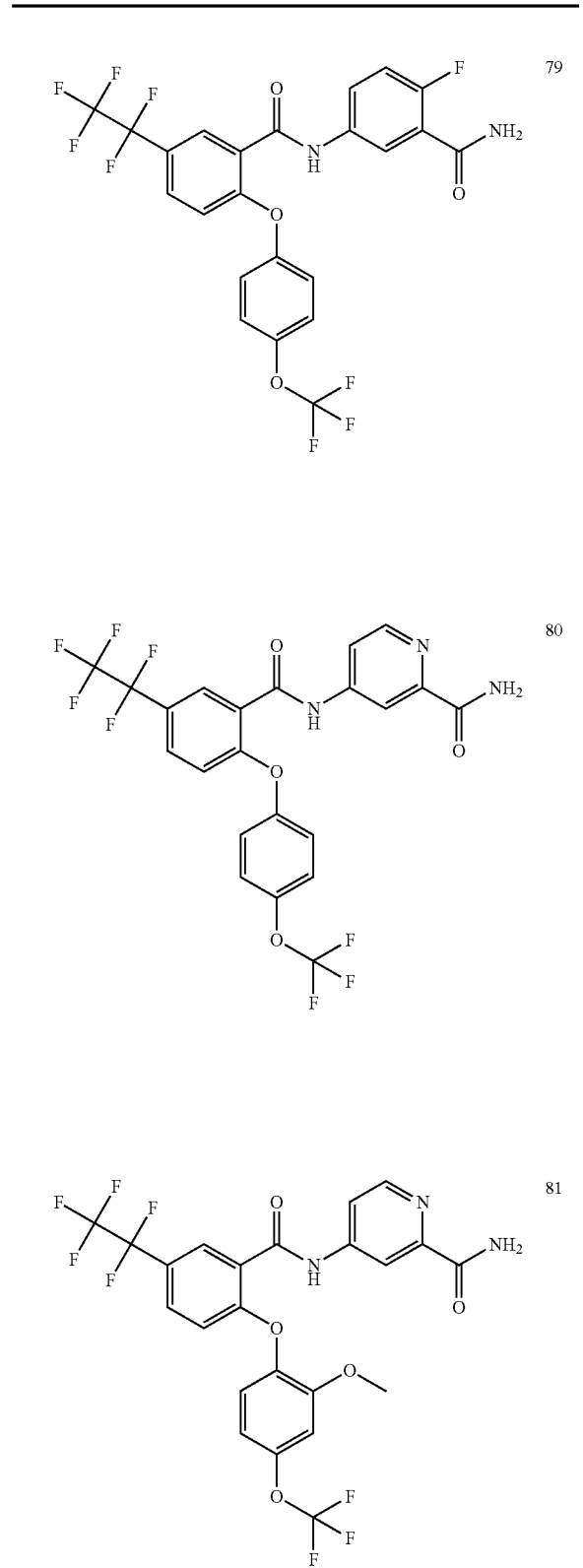

TABLE 1A-continued
Compound Numbers and Structures.
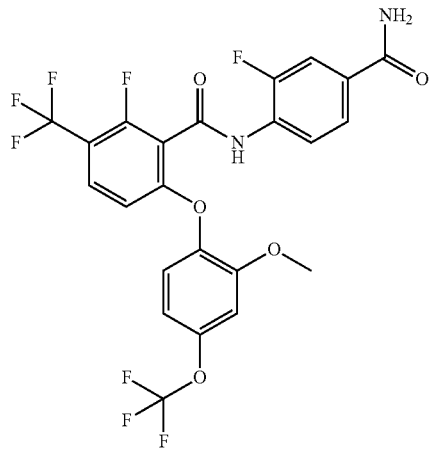 [SMILES: COc1cc(OC(F)(F)F)ccc1Oc1ccc(C(F)(F)F)c(F)c1C(=O)Nc1ccc(C(N)=O)cc1F]
82
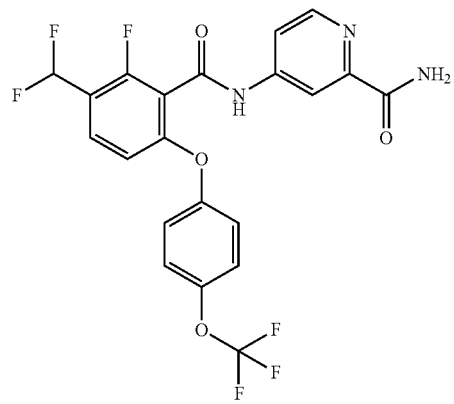 [SMILES: NC(=O)c1cc(NC(=O)c2c(Oc3ccc(OC(F)(F)F)cc3)ccc(C(F)F)c2F)ccn1]
83
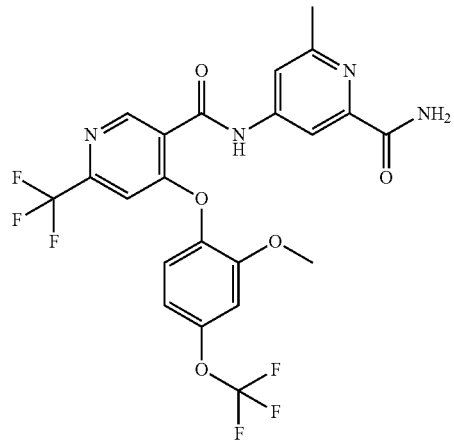 [SMILES: COc1cc(OC(F)(F)F)ccc1Oc1cc(C(F)(F)F)ncc1C(=O)Nc1cc(C)nc(C(N)=O)c1]
84
TABLE 1A-continued
Compound Numbers and Structures.
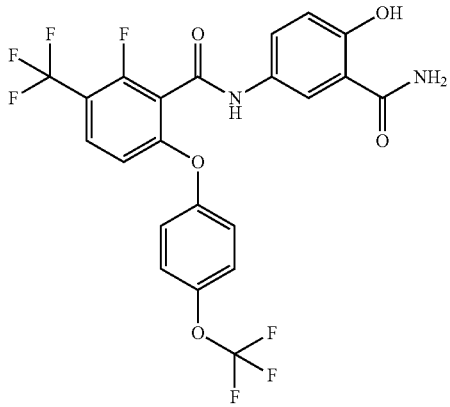 [SMILES: NC(=O)c1cc(NC(=O)c2c(Oc3ccc(OC(F)(F)F)cc3)ccc(C(F)(F)F)c2F)ccc1O]
85
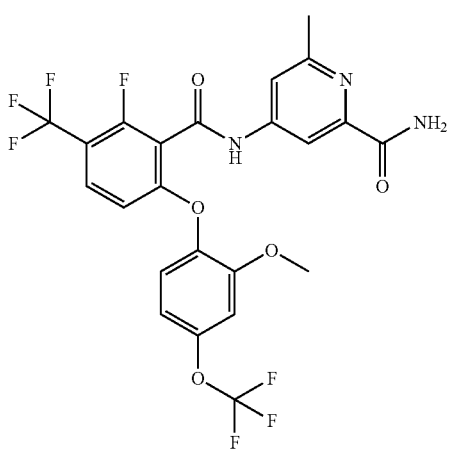 [SMILES: COc1cc(OC(F)(F)F)ccc1Oc1ccc(C(F)(F)F)c(F)c1C(=O)Nc1cc(C)nc(C(N)=O)c1]
86
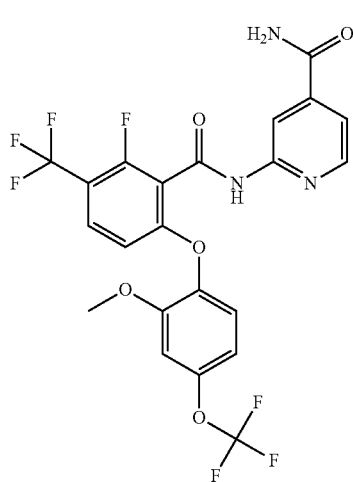 [SMILES: COc1cc(OC(F)(F)F)ccc1Oc1ccc(C(F)(F)F)c(F)c1C(=O)Nc1cc(C(N)=O)ccn1]
87

TABLE 1A-continued
Compound Numbers and Structures.
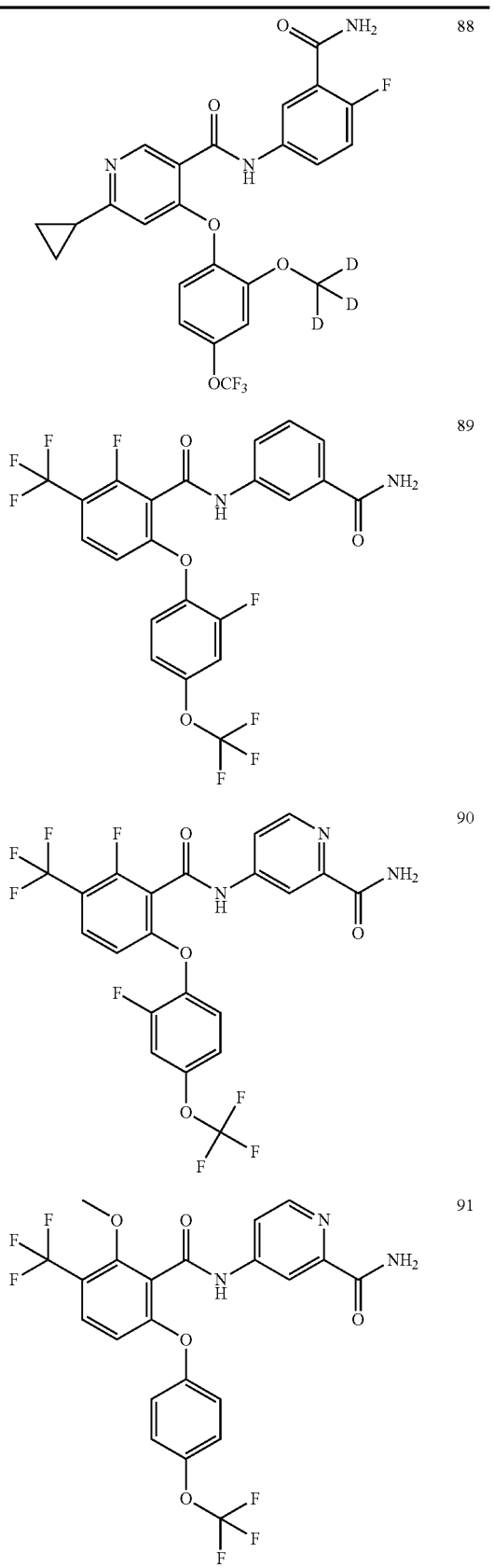
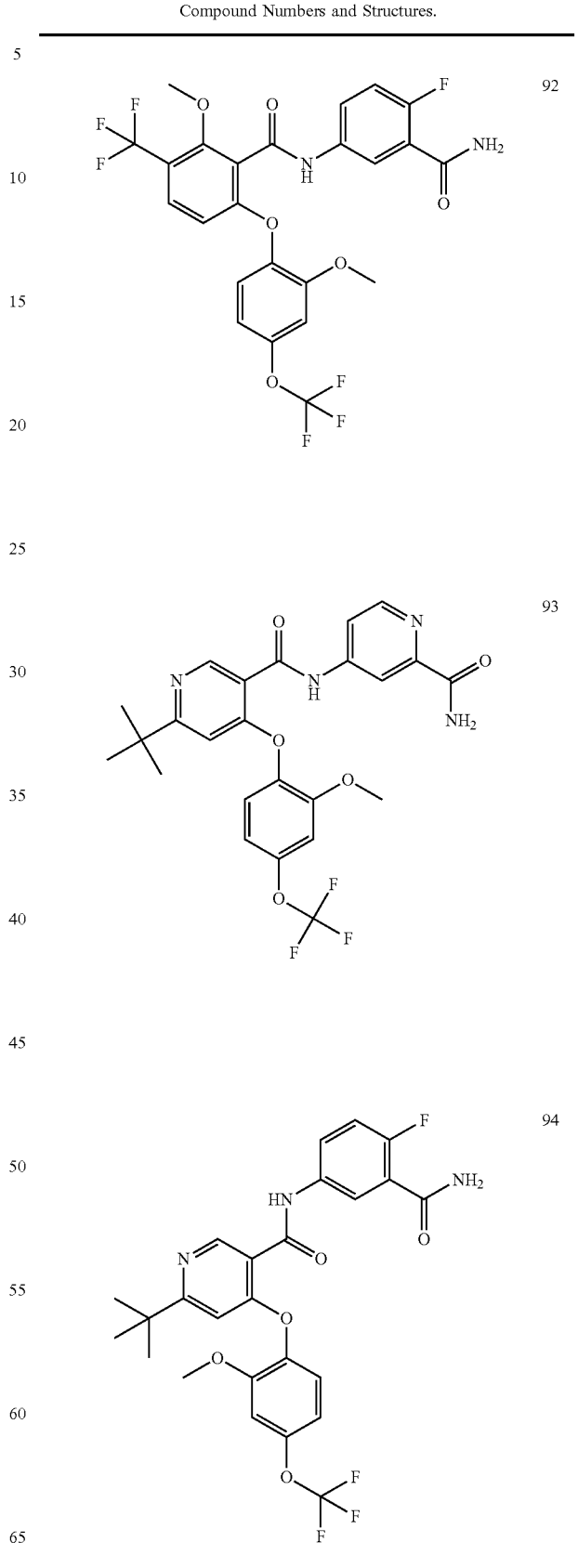

TABLE 1A-continued
Compound Numbers and Structures.
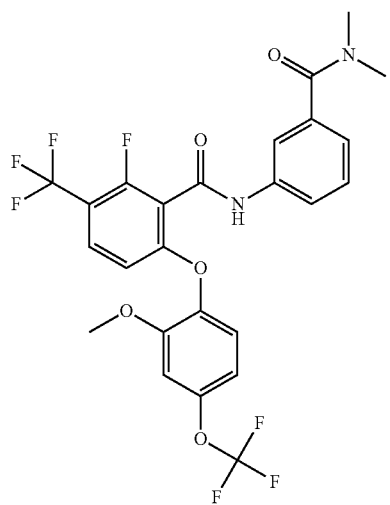 [SMILES: COc1cc(OC(F)(F)F)ccc1Oc1ccc(C(F)(F)F)c(F)c1C(=O)Nc1cccc(C(=O)N(C)C)c1]
95
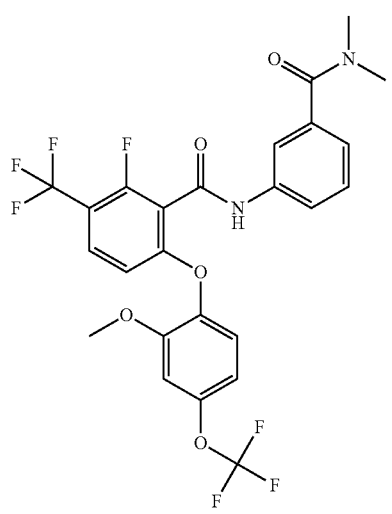 [SMILES: COc1cc(OC(F)(F)F)ccc1Oc1ccc(C(F)(F)F)c(F)c1C(=O)Nc1cccc(C(=O)N(C)C)c1]
96
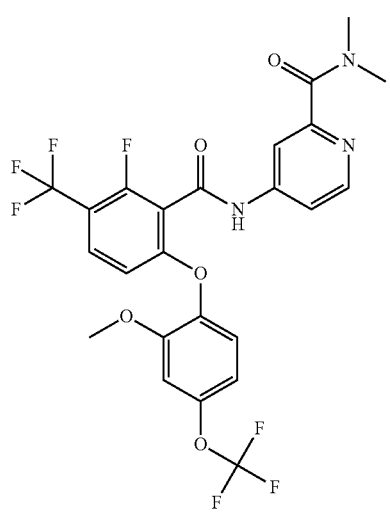 [SMILES: COc1cc(OC(F)(F)F)ccc1Oc1ccc(C(F)(F)F)c(F)c1C(=O)Nc1ccnc(C(=O)N(C)C)c1]
97
TABLE 1A-continued
Compound Numbers and Structures.
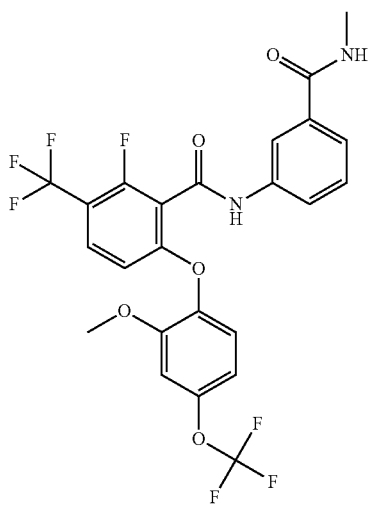 [SMILES: CNC(=O)c1cccc(NC(=O)c2c(Oc3ccc(OC(F)(F)F)cc3OC)ccc(C(F)(F)F)c2F)c1]
98
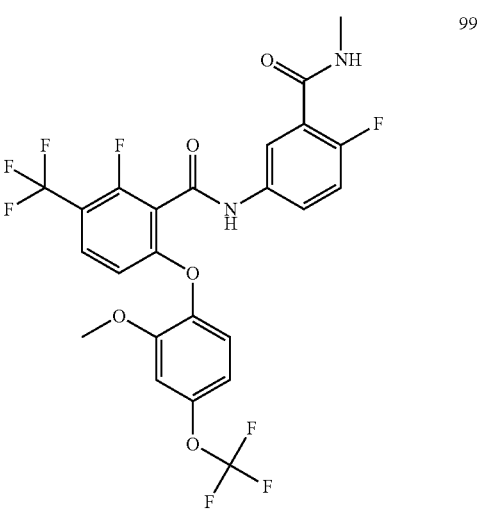
99
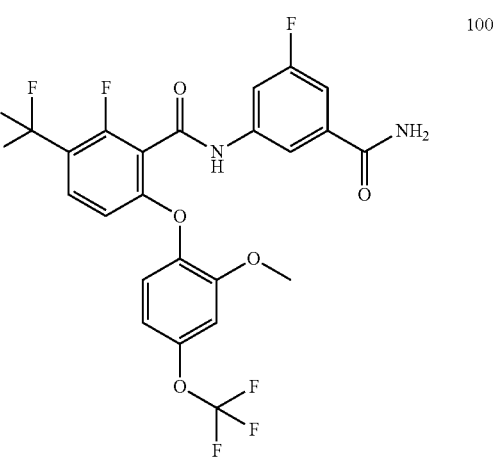
100

TABLE 1A-continued

Compound Numbers and Structures.

TABLE 1A-continued

Compound Numbers and Structures.

TABLE 1A-continued
Compound Numbers and Structures.
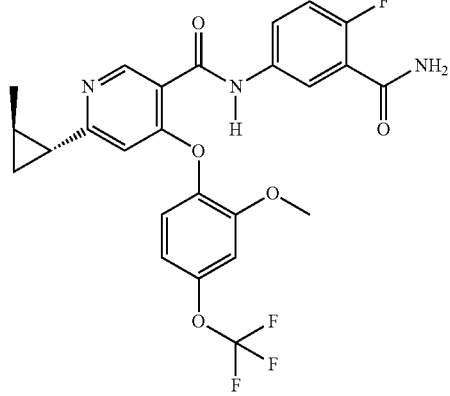
114
(rel-(R,R))
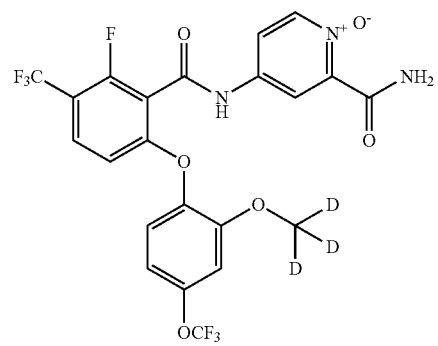
115
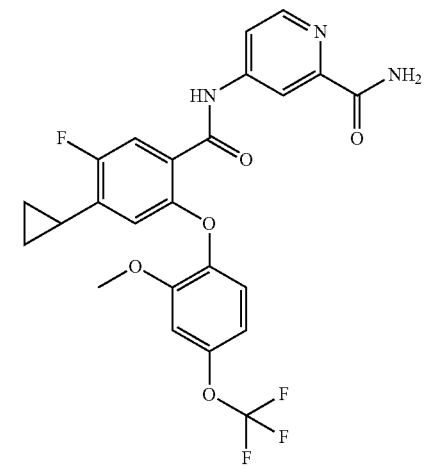 [SMILES: COc1cc(OC(F)(F)F)ccc1Oc1cc(C2CC2)c(F)cc1C(=O)Nc1ccnc(C(N)=O)c1]
116
TABLE 1A-continued
Compound Numbers and Structures.
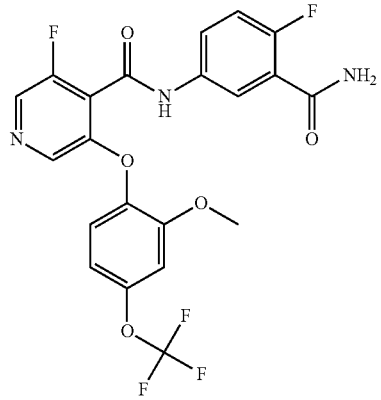 [SMILES: COc1cc(OC(F)(F)F)ccc1Oc1cncc(F)c1C(=O)Nc1ccc(F)c(C(N)=O)c1]
117
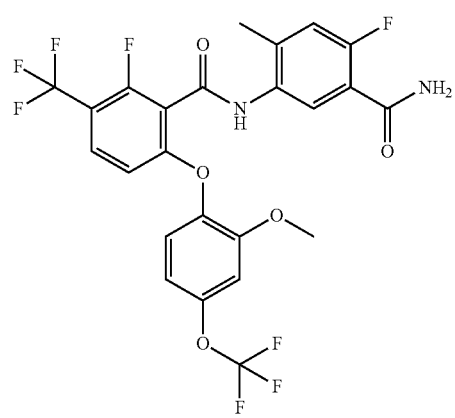 [SMILES: COc1cc(OC(F)(F)F)ccc1Oc1ccc(C(F)(F)F)c(F)c1C(=O)Nc1cc(C(N)=O)c(F)cc1C]
118
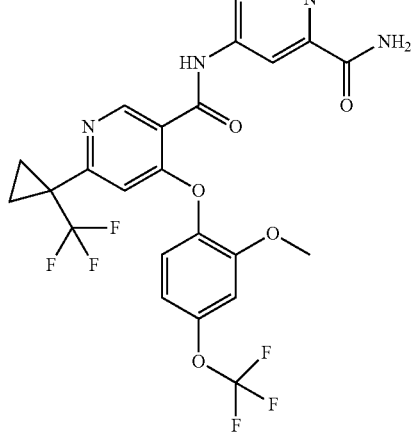
119

TABLE 1A-continued

Compound Numbers and Structures.

TABLE 1A-continued
Compound Numbers and Structures.
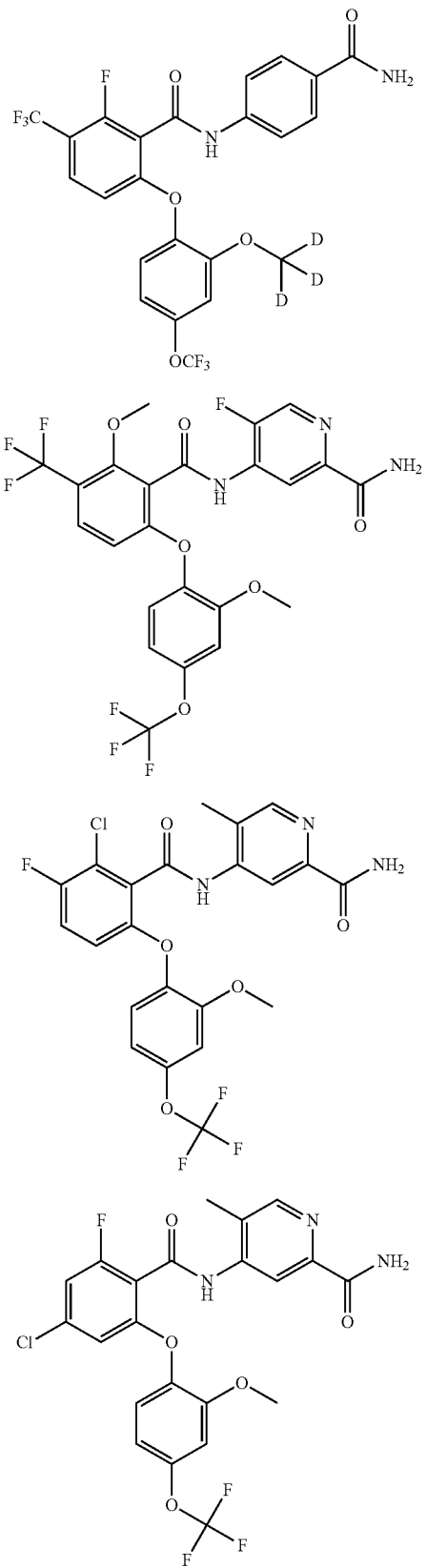
127
128
129
130
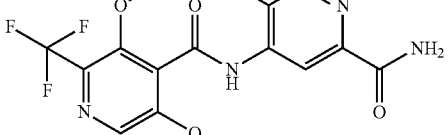
131
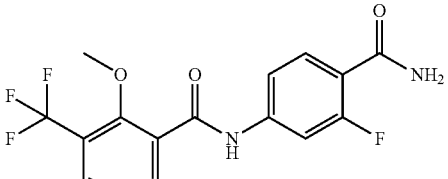
132
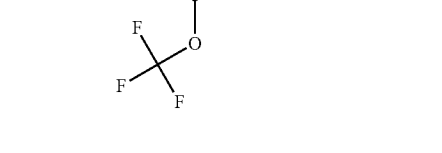
133

TABLE 1A-continued
Compound Numbers and Structures.
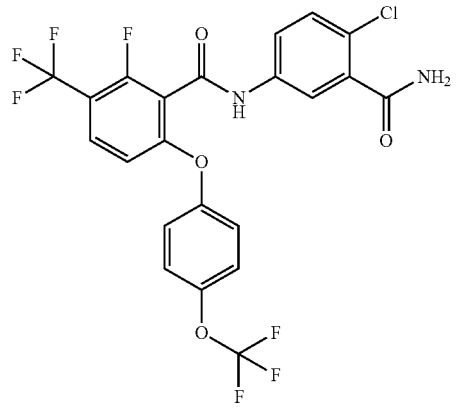 [SMILES: NC(=O)c1cc(NC(=O)c2c(Oc3ccc(OC(F)(F)F)cc3)ccc(C(F)(F)F)c2F)ccc1Cl]
134
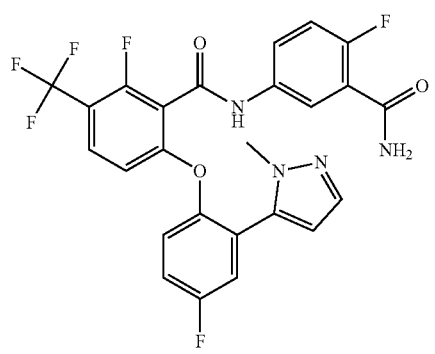 [SMILES: Cn1nccc1-c1cc(F)ccc1Oc1ccc(C(F)(F)F)c(F)c1C(=O)Nc1ccc(F)c(C(N)=O)c1]
135
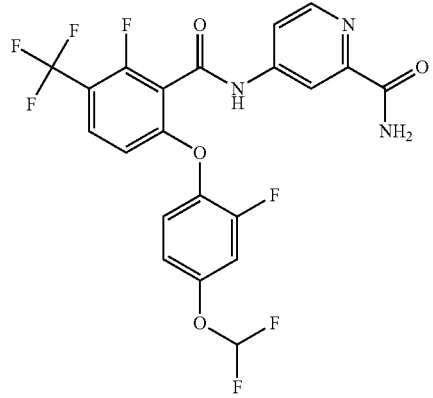 [SMILES: NC(=O)c1cc(NC(=O)c2c(Oc3ccc(OC(F)F)cc3F)ccc(C(F)(F)F)c2F)ccn1]
136
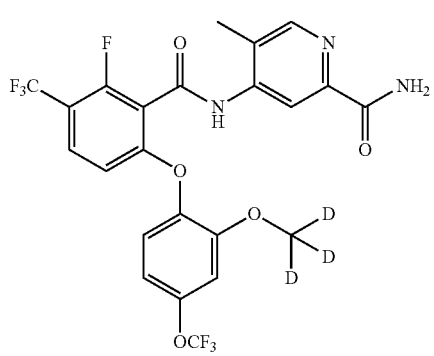 [SMILES: [2H]C([2H])([2H])Oc1cc(OC(F)(F)F)ccc1Oc1ccc(C(F)(F)F)c(F)c1C(=O)Nc1cc(C(N)=O)ncc1C]
137
TABLE 1A-continued
Compound Numbers and Structures.
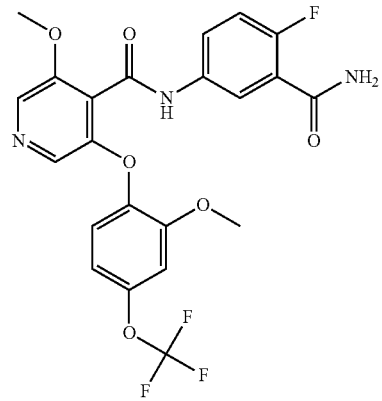 [SMILES: COc1cc(OC(F)(F)F)ccc1Oc1cncc(OC)c1C(=O)Nc1ccc(F)c(C(N)=O)c1]
138
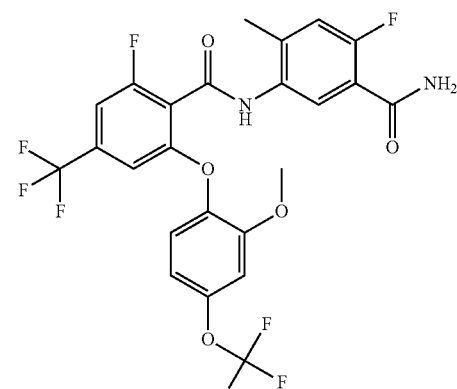
139
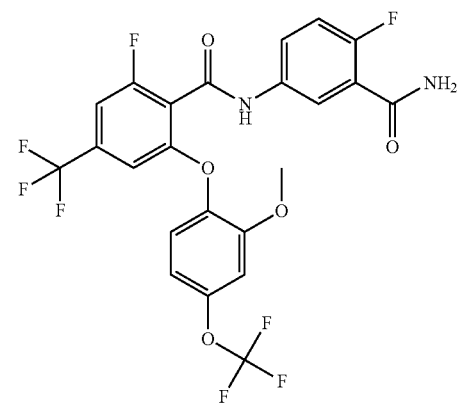 [SMILES: COc1cc(OC(F)(F)F)ccc1Oc1cc(C(F)(F)F)cc(F)c1C(=O)Nc1ccc(F)c(C(N)=O)c1]
140
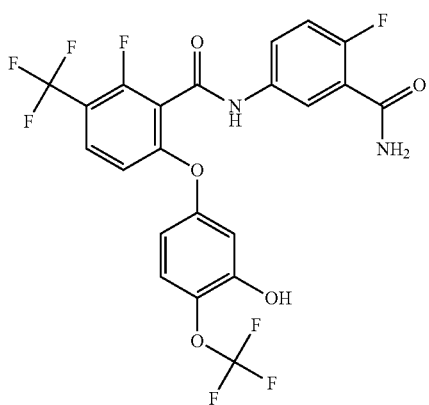 [SMILES: NC(=O)c1cc(NC(=O)c2c(Oc3ccc(OC(F)(F)F)c(O)c3)ccc(C(F)(F)F)c2F)ccc1F]
141

TABLE 1A-continued
Compound Numbers and Structures.
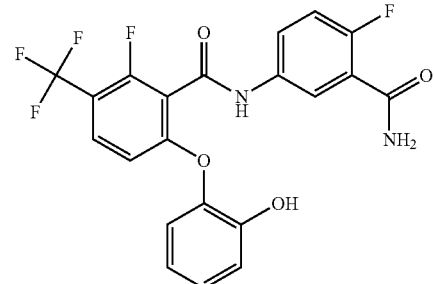
142
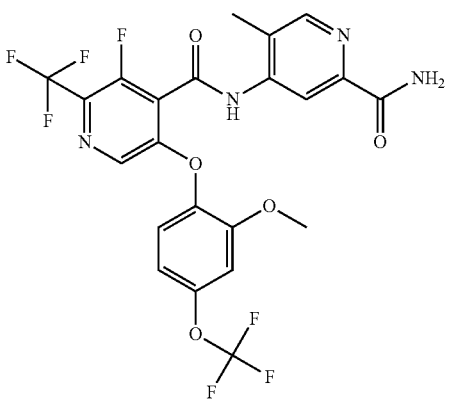 [SMILES: COc1cc(OC(F)(F)F)ccc1Oc1cnc(C(F)(F)F)c(F)c1C(=O)Nc1cc(C(N)=O)ncc1C]
143
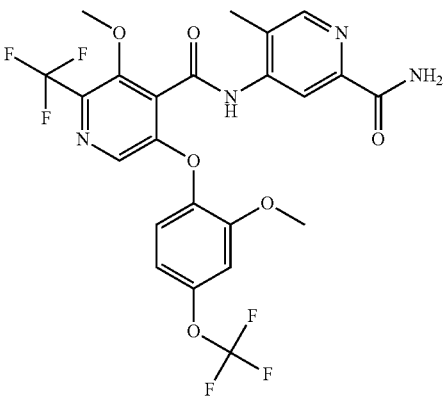 [SMILES: COc1cc(OC(F)(F)F)ccc1Oc1cnc(C(F)(F)F)c(OC)c1C(=O)Nc1cc(C(N)=O)ncc1C]
144
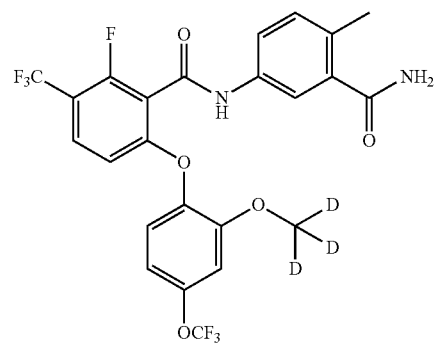 [SMILES: [2H]C([2H])([2H])Oc1cc(OC(F)(F)F)ccc1Oc1ccc(C(F)(F)F)c(F)c1C(=O)Nc1ccc(C)c(C(N)=O)c1]
145
TABLE 1A-continued
Compound Numbers and Structures.
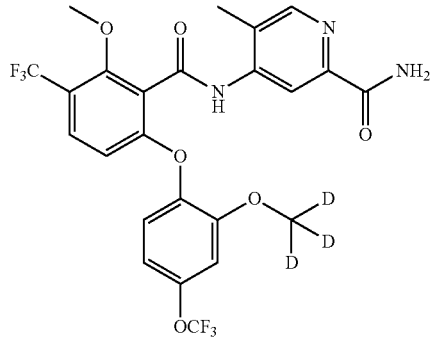 [SMILES: [2H]C([2H])([2H])Oc1cc(OC(F)(F)F)ccc1Oc1ccc(C(F)(F)F)c(OC)c1C(=O)Nc1cc(C(N)=O)ncc1C]
146
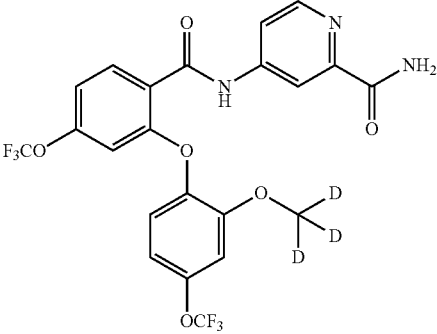 [SMILES: [2H]C([2H])([2H])Oc1cc(OC(F)(F)F)ccc1Oc1cc(OC(F)(F)F)ccc1C(=O)Nc1ccnc(C(N)=O)c1]
147
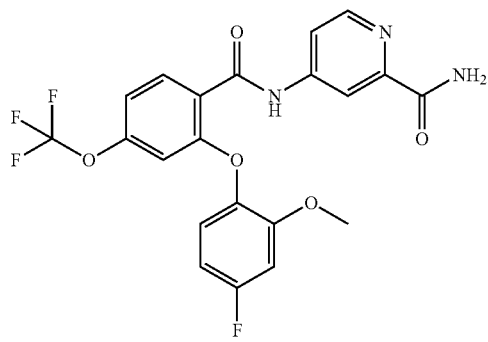 [SMILES: COc1cc(F)ccc1Oc1cc(OC(F)(F)F)ccc1C(=O)Nc1ccnc(C(N)=O)c1]
148
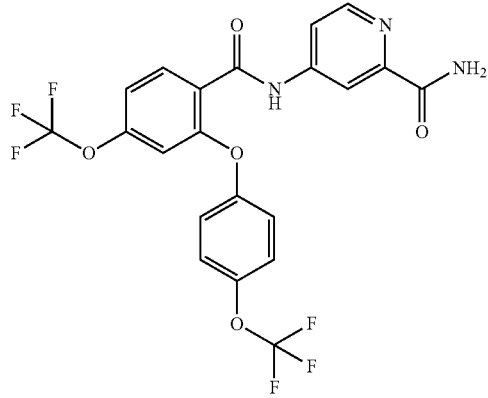 [SMILES: NC(=O)c1cc(NC(=O)c2ccc(OC(F)(F)F)cc2Oc2ccc(OC(F)(F)F)cc2)ccn1]
149

TABLE 1A-continued
Compound Numbers and Structures.
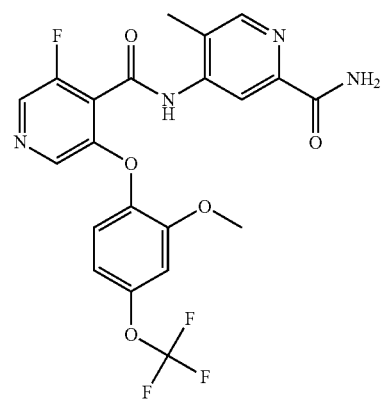 [SMILES: COc1cc(OC(F)(F)F)ccc1Oc1cncc(F)c1C(=O)Nc1cc(C(N)=O)ncc1C]
150
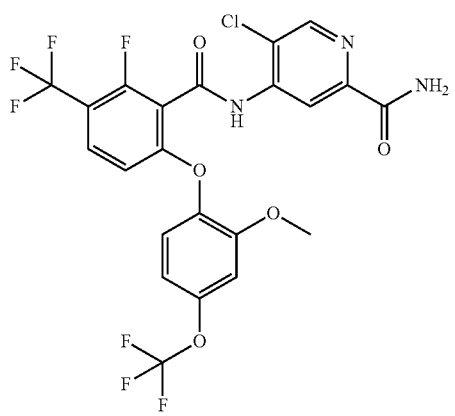 [SMILES: COc1cc(OC(F)(F)F)ccc1Oc1ccc(C(F)(F)F)c(F)c1C(=O)Nc1cc(C(N)=O)ncc1Cl]
151
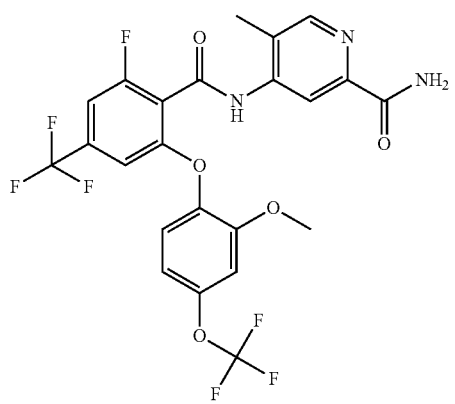 [SMILES: COc1cc(OC(F)(F)F)ccc1Oc1cc(C(F)(F)F)cc(F)c1C(=O)Nc1cc(C(N)=O)ncc1C]
152
153
TABLE 1A-continued
Compound Numbers and Structures.
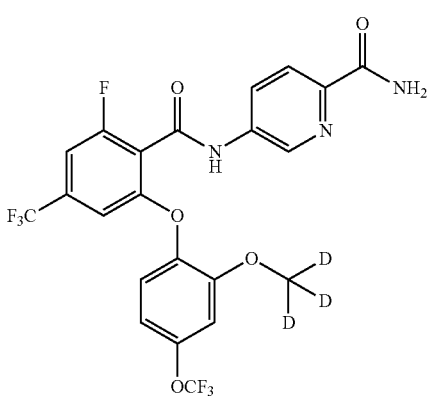 [SMILES: [2H]C([2H])([2H])Oc1cc(OC(F)(F)F)ccc1Oc1cc(C(F)(F)F)cc(F)c1C(=O)Nc1ccc(C(N)=O)nc1]
154
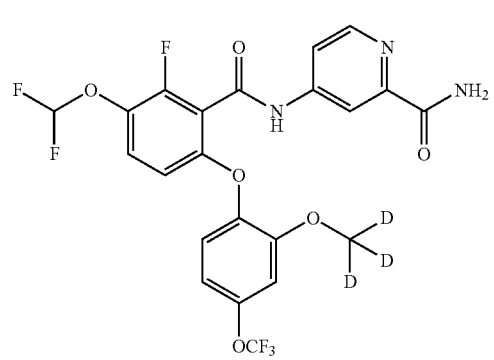 [SMILES: [2H]C([2H])([2H])Oc1cc(OC(F)(F)F)ccc1Oc1ccc(OC(F)F)c(F)c1C(=O)Nc1ccnc(C(N)=O)c1]
155
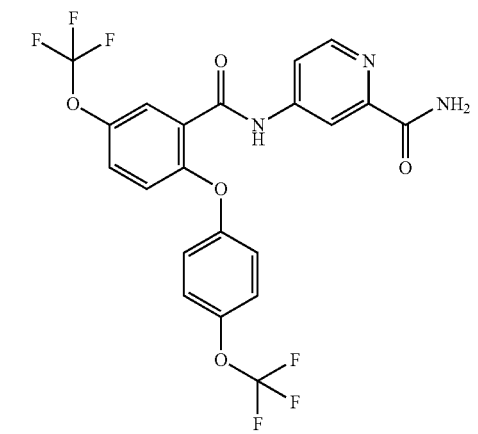 [SMILES: NC(=O)c1cc(NC(=O)c2cc(OC(F)(F)F)ccc2Oc2ccc(OC(F)(F)F)cc2)ccn1]
156
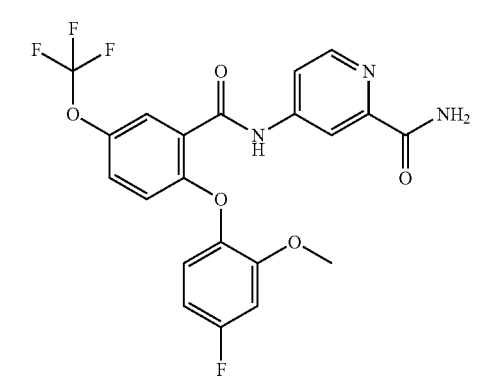 [SMILES: COc1cc(F)ccc1Oc1ccc(OC(F)(F)F)cc1C(=O)Nc1ccnc(C(N)=O)c1]
157

TABLE 1A-continued

Compound Numbers and Structures.

TABLE 1A-continued
Compound Numbers and Structures.
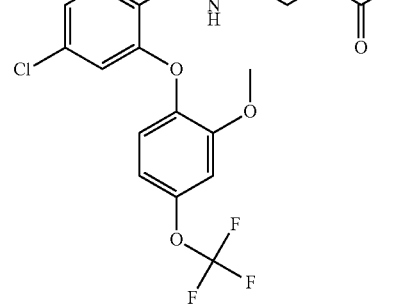

TABLE 1A-continued
Compound Numbers and Structures.
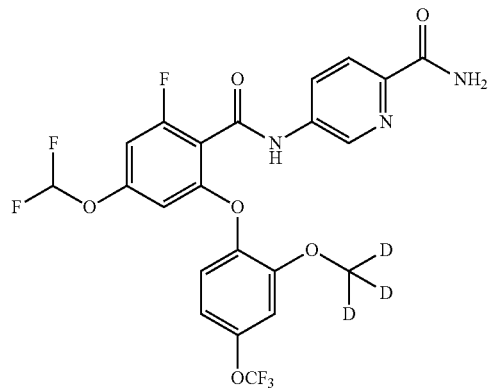 [SMILES: [2H]C([2H])([2H])Oc1cc(OC(F)(F)F)ccc1Oc1cc(OC(F)F)cc(F)c1C(=O)Nc1ccc(C(N)=O)nc1]
174
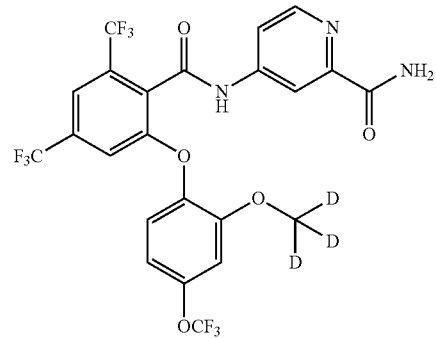 [SMILES: [2H]C([2H])([2H])Oc1cc(OC(F)(F)F)ccc1Oc1cc(C(F)(F)F)cc(C(F)(F)F)c1C(=O)Nc1ccnc(C(N)=O)c1]
175
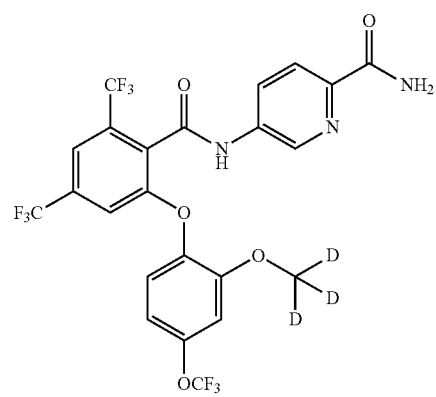 [SMILES: [2H]C([2H])([2H])Oc1cc(OC(F)(F)F)ccc1Oc1cc(C(F)(F)F)cc(C(F)(F)F)c1C(=O)Nc1ccc(C(N)=O)nc1]
176
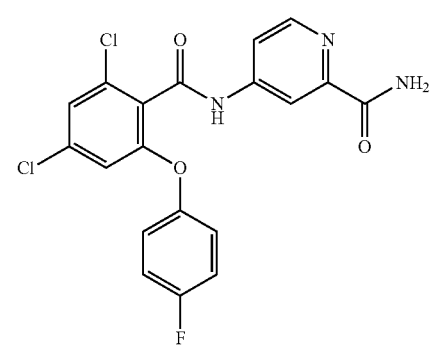 [SMILES: NC(=O)c1cc(NC(=O)c2c(Cl)cc(Cl)cc2Oc2ccc(F)cc2)ccn1]
177
TABLE 1A-continued
Compound Numbers and Structures.
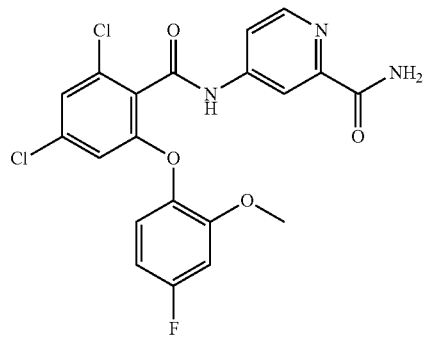 [SMILES: COc1cc(F)ccc1Oc1cc(Cl)cc(Cl)c1C(=O)Nc1ccnc(C(N)=O)c1]
178
179
180
181

TABLE 1A-continued
Compound Numbers and Structures.
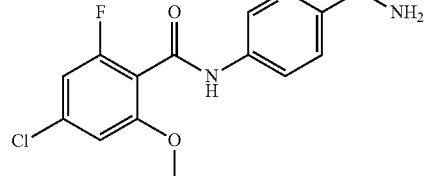

TABLE 1A-continued
Compound Numbers and Structures.
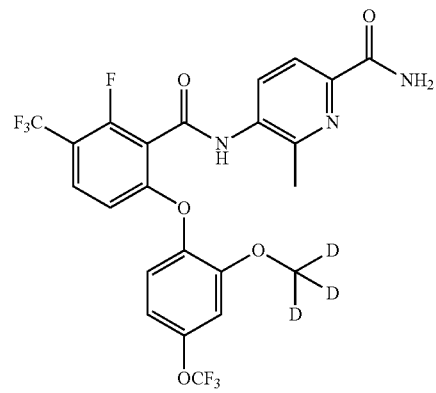 [SMILES: [2H]C([2H])([2H])Oc1cc(OC(F)(F)F)ccc1Oc1ccc(C(F)(F)F)c(F)c1C(=O)Nc1ccc(C(N)=O)nc1C]
188
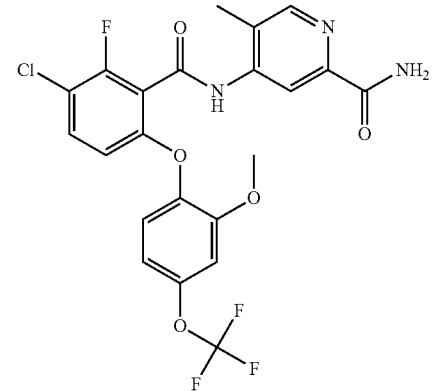 [SMILES: COc1cc(OC(F)(F)F)ccc1Oc1ccc(Cl)c(F)c1C(=O)Nc1cc(C(N)=O)ncc1C]
189
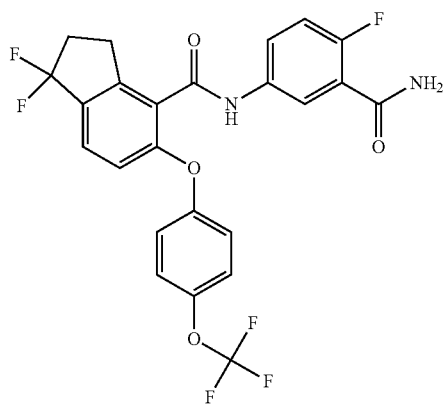 [SMILES: NC(=O)c1cc(NC(=O)c2c(Oc3ccc(OC(F)(F)F)cc3)ccc3c2CCC3(F)F)ccc1F]
190
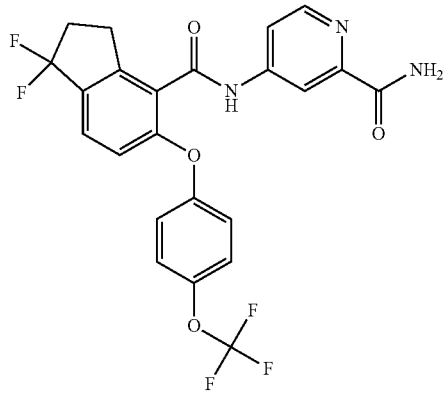 [SMILES: NC(=O)c1cc(NC(=O)c2c(Oc3ccc(OC(F)(F)F)cc3)ccc3c2CCC3(F)F)ccn1]
191
TABLE 1A-continued
Compound Numbers and Structures.
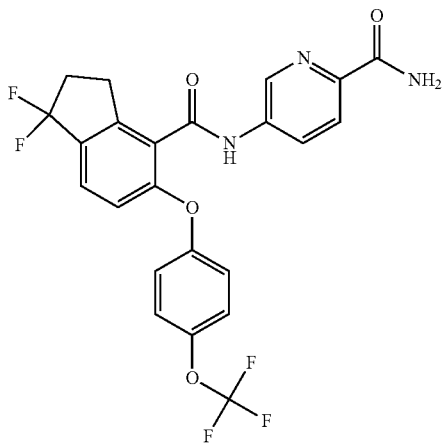 [SMILES: NC(=O)c1ccc(NC(=O)c2c(Oc3ccc(OC(F)(F)F)cc3)ccc3c2CCC3(F)F)cn1]
192
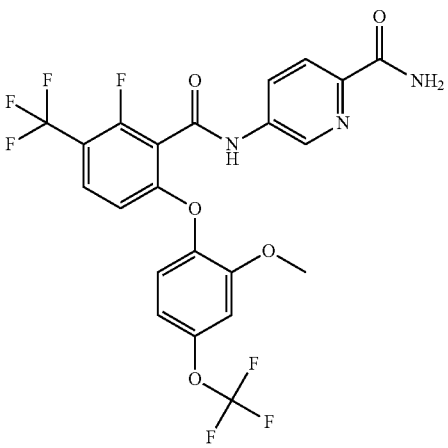 [SMILES: COc1cc(OC(F)(F)F)ccc1Oc1ccc(C(F)(F)F)c(F)c1C(=O)Nc1ccc(C(N)=O)nc1]
193
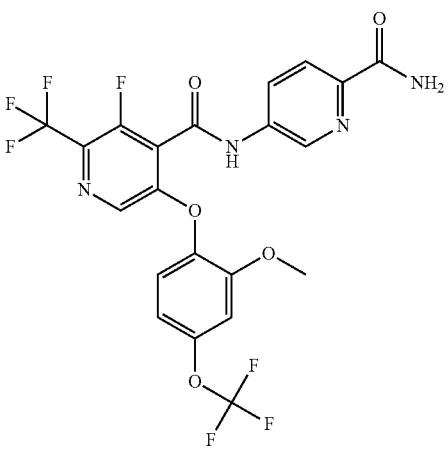 [SMILES: COc1cc(OC(F)(F)F)ccc1Oc1cnc(C(F)(F)F)c(F)c1C(=O)Nc1ccc(C(N)=O)nc1]
194

TABLE 1A-continued
Compound Numbers and Structures.
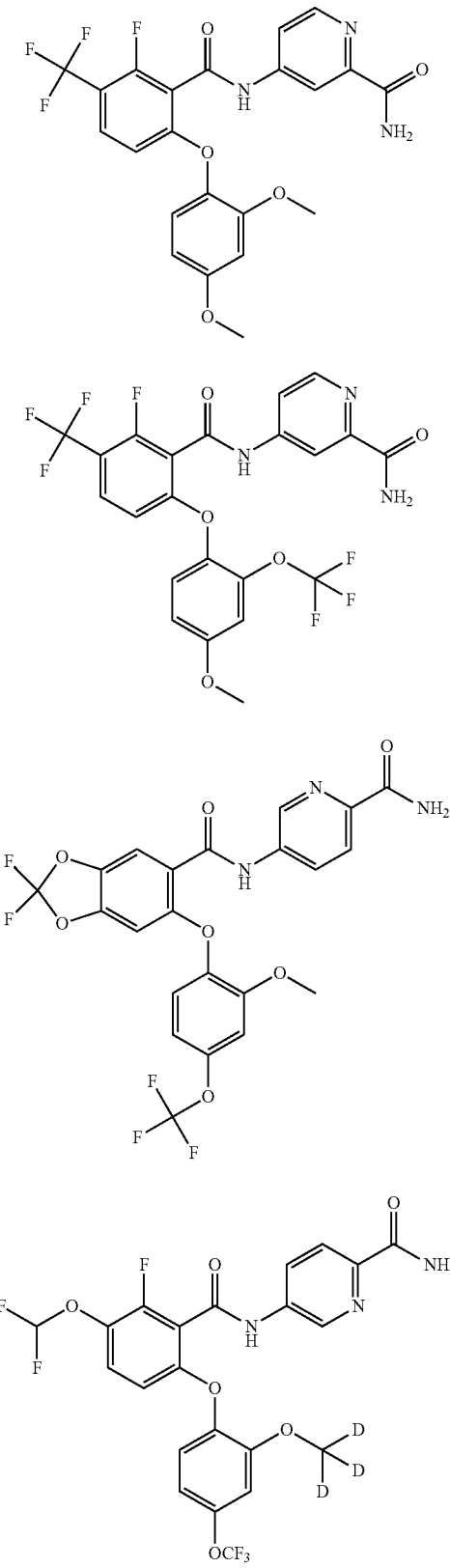
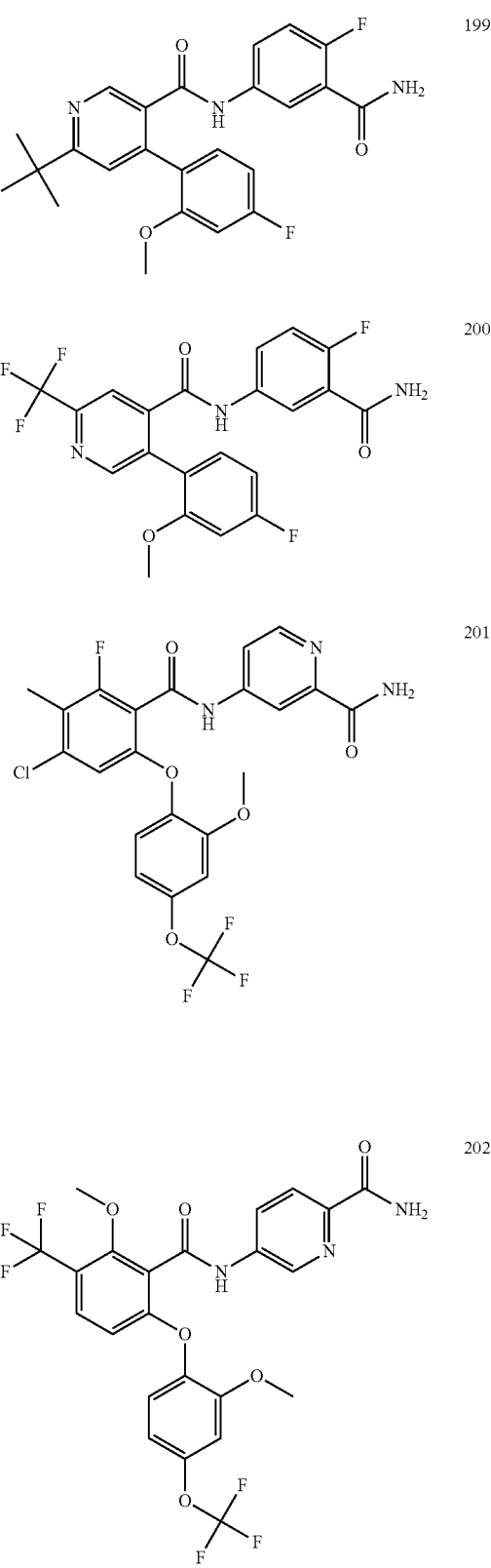

TABLE 1A-continued
Compound Numbers and Structures.
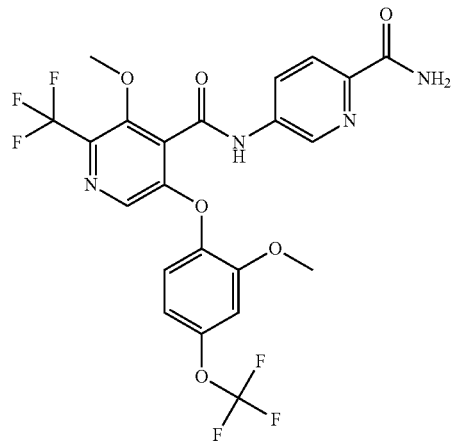 [SMILES: COc1cc(OC(F)(F)F)ccc1Oc1cnc(C(F)(F)F)c(OC)c1C(=O)Nc1ccc(C(N)=O)nc1]
203
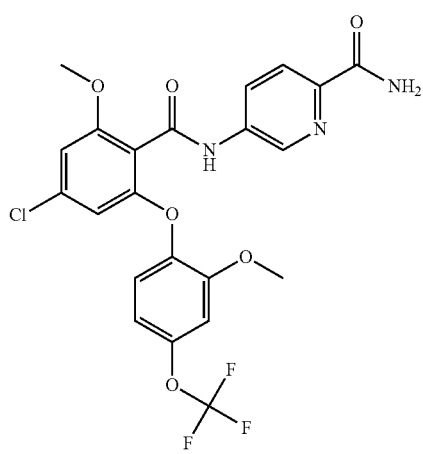 [SMILES: COc1cc(OC(F)(F)F)ccc1Oc1cc(Cl)cc(OC)c1C(=O)Nc1ccc(C(N)=O)nc1]
204
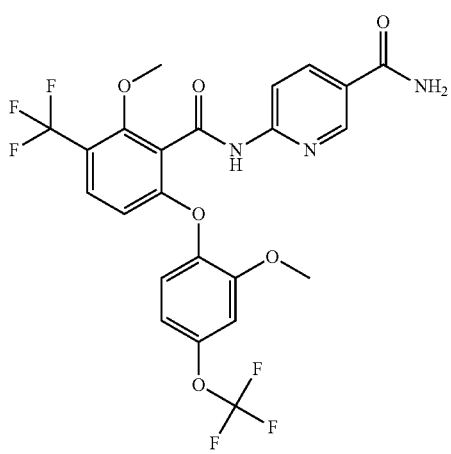 [SMILES: COc1cc(OC(F)(F)F)ccc1Oc1ccc(C(F)(F)F)c(OC)c1C(=O)Nc1ccc(C(N)=O)cn1]
205
TABLE 1A-continued
Compound Numbers and Structures.
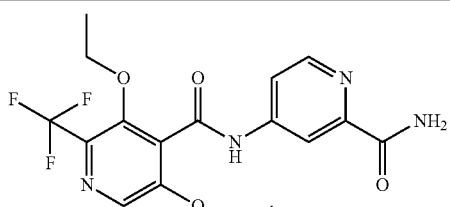
206
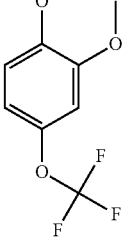
207
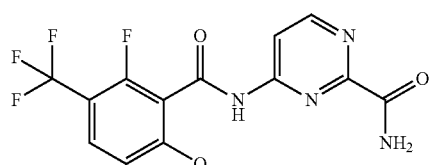
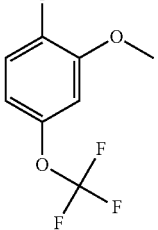
208
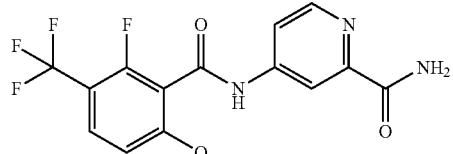
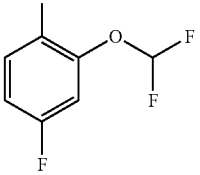
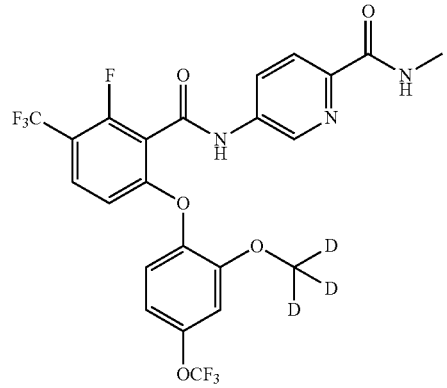 [SMILES: [2H]C([2H])([2H])Oc1cc(OC(F)(F)F)ccc1Oc1ccc(C(F)(F)F)c(F)c1C(=O)Nc1ccc(C(=O)NC)nc1]
209

TABLE 1A-continued
Compound Numbers and Structures.
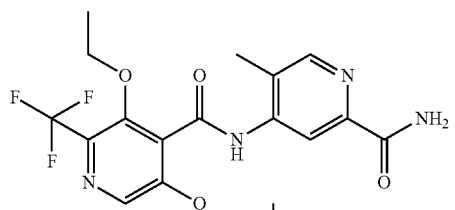
210
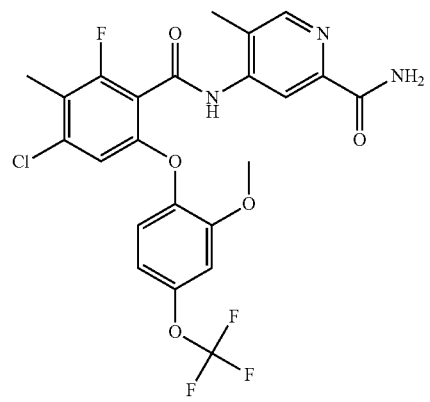 [SMILES: COc1cc(OC(F)(F)F)ccc1Oc1cc(Cl)c(C)c(F)c1C(=O)Nc1cc(C(N)=O)ncc1C]
211
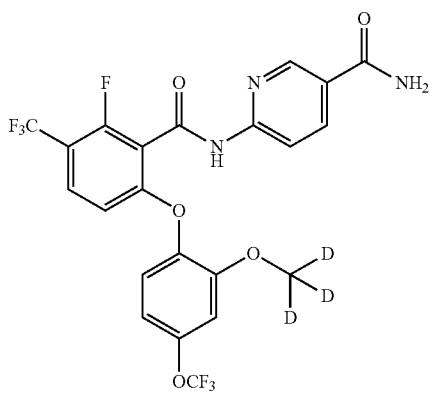
212
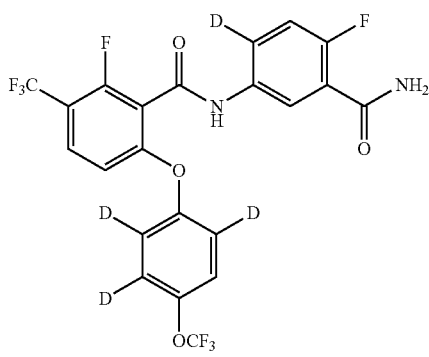 [SMILES: [2H]c1cc(F)c(C(N)=O)cc1NC(=O)c1c(Oc2c([2H])cc(OC(F)(F)F)c([2H])c2[2H])ccc(C(F)(F)F)c1F]
213
TABLE 1A-continued
Compound Numbers and Structures.
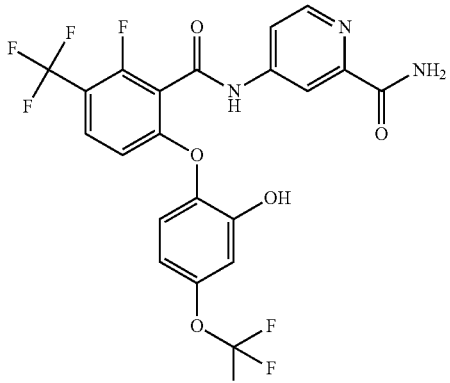
214
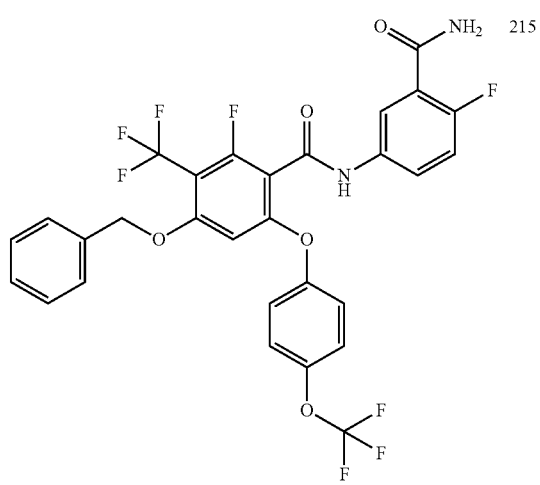
215
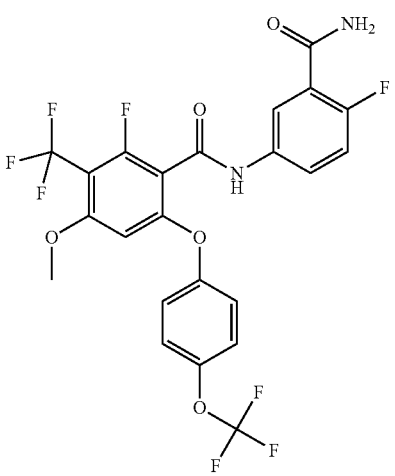 [SMILES: COc1cc(Oc2ccc(OC(F)(F)F)cc2)c(C(=O)Nc2ccc(F)c(C(N)=O)c2)c(F)c1C(F)(F)F]
216

TABLE 1A-continued
Compound Numbers and Structures.
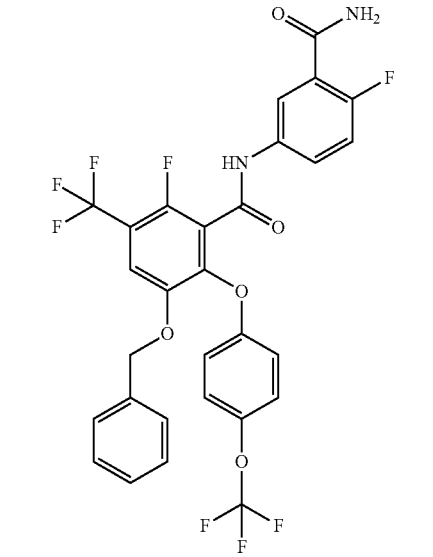 [SMILES: NC(=O)c1cc(NC(=O)c2c(F)c(C(F)(F)F)cc(OCc3ccccc3)c2Oc2ccc(OC(F)(F)F)cc2)ccc1F]
217
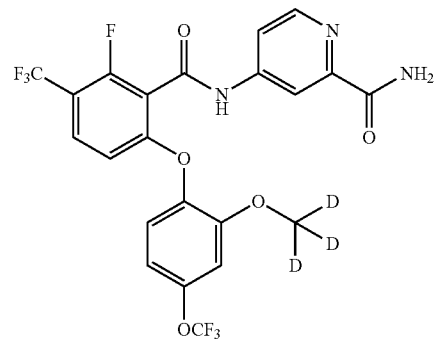
218
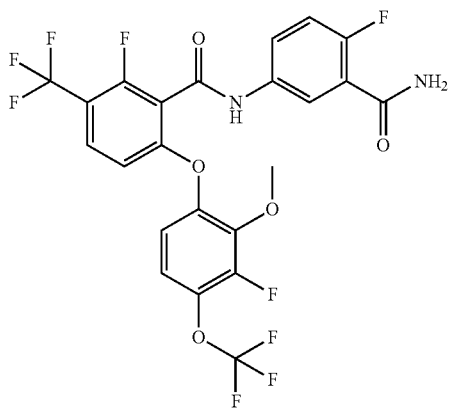 [SMILES: COc1c(Oc2ccc(C(F)(F)F)c(F)c2C(=O)Nc2ccc(F)c(C(N)=O)c2)ccc(OC(F)(F)F)c1F]
219
TABLE 1A-continued
Compound Numbers and Structures.
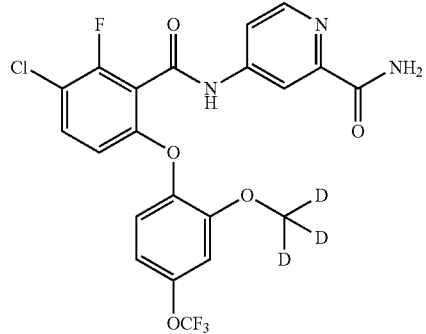 [SMILES: [2H]C([2H])([2H])Oc1cc(OC(F)(F)F)ccc1Oc1ccc(Cl)c(F)c1C(=O)Nc1ccnc(C(N)=O)c1]
220
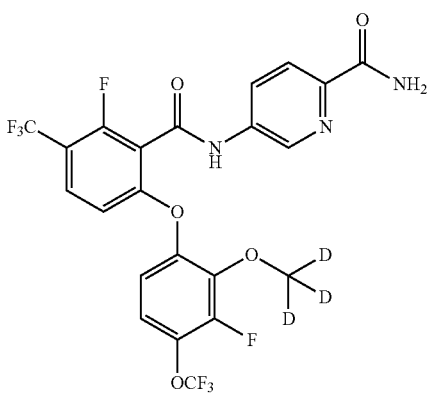
221
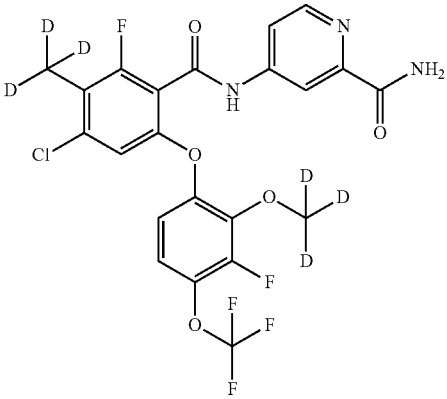 [SMILES: [2H]C([2H])([2H])Oc1c(Oc2cc(Cl)c(C([2H])([2H])[2H])c(F)c2C(=O)Nc2ccnc(C(N)=O)c2)ccc(OC(F)(F)F)c1F]
222
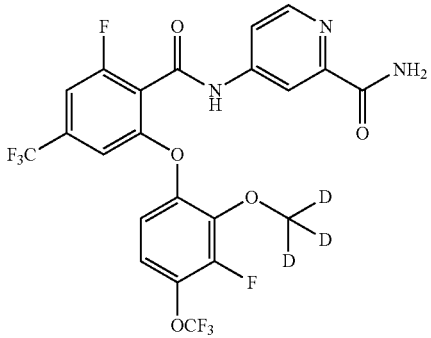 [SMILES: [2H]C([2H])([2H])Oc1c(Oc2cc(C(F)(F)F)cc(F)c2C(=O)Nc2ccnc(C(N)=O)c2)ccc(OC(F)(F)F)c1F]
223

TABLE 1A-continued
Compound Numbers and Structures.
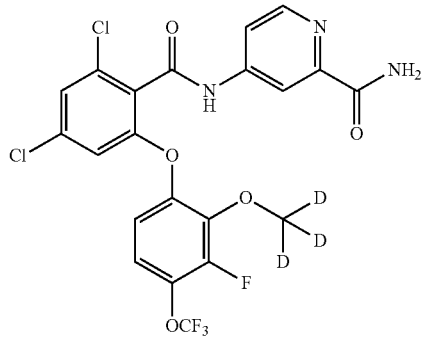 [SMILES: [2H]C([2H])([2H])Oc1c(Oc2cc(Cl)cc(Cl)c2C(=O)Nc2ccnc(C(N)=O)c2)ccc(OC(F)(F)F)c1F]
224
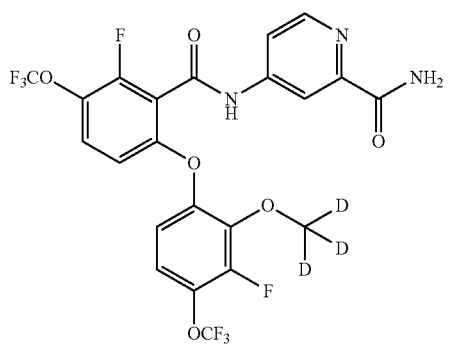
225
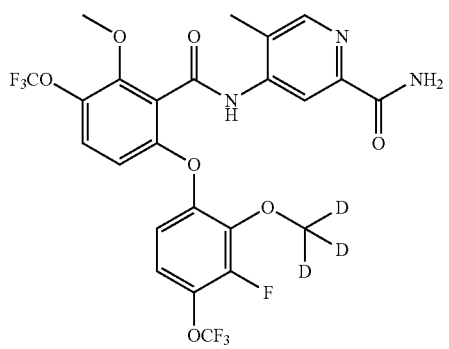 [SMILES: [2H]C([2H])([2H])Oc1c(Oc2ccc(OC(F)(F)F)c(OC)c2C(=O)Nc2cc(C(N)=O)ncc2C)ccc(OC(F)(F)F)c1F]
226
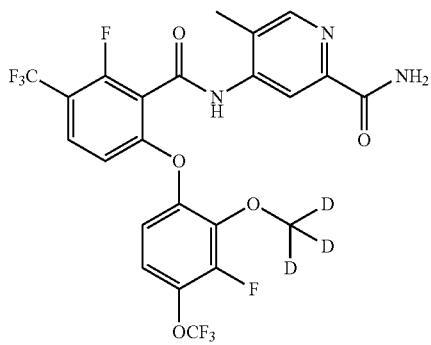 [SMILES: [2H]C([2H])([2H])Oc1c(Oc2ccc(C(F)(F)F)c(F)c2C(=O)Nc2cc(C(N)=O)ncc2C)ccc(OC(F)(F)F)c1F]
227
TABLE 1A-continued
Compound Numbers and Structures.
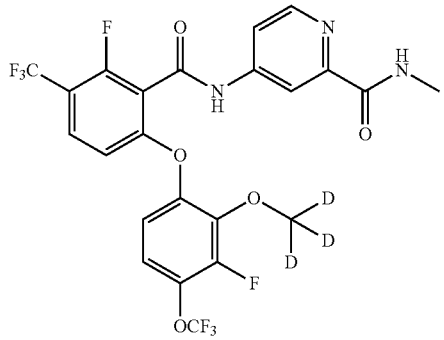 [SMILES: [2H]C([2H])([2H])Oc1c(Oc2ccc(C(F)(F)F)c(F)c2C(=O)Nc2ccnc(C(=O)NC)c2)ccc(OC(F)(F)F)c1F]
228
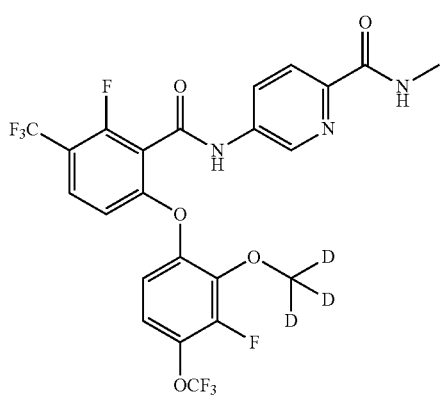 [SMILES: [2H]C([2H])([2H])Oc1c(Oc2ccc(C(F)(F)F)c(F)c2C(=O)Nc2ccc(C(=O)NC)nc2)ccc(OC(F)(F)F)c1F]
229
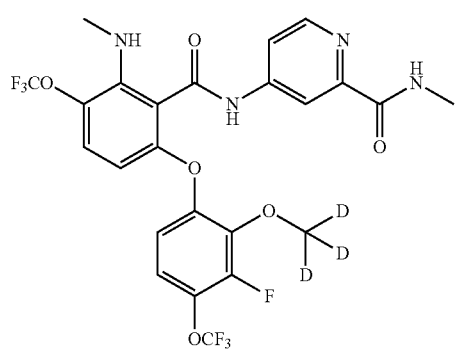 [SMILES: [2H]C([2H])([2H])Oc1c(Oc2ccc(OC(F)(F)F)c(NC)c2C(=O)Nc2ccnc(C(=O)NC)c2)ccc(OC(F)(F)F)c1F]
230
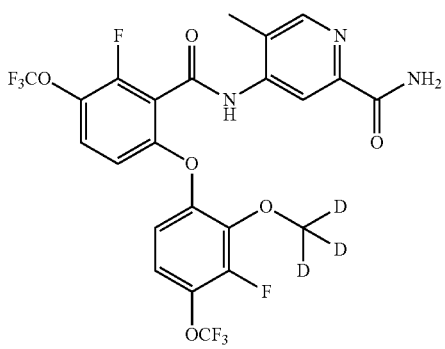 [SMILES: [2H]C([2H])([2H])Oc1c(Oc2ccc(OC(F)(F)F)c(F)c2C(=O)Nc2cc(C(N)=O)ncc2C)ccc(OC(F)(F)F)c1F]
231

TABLE 1A-continued
Compound Numbers and Structures.
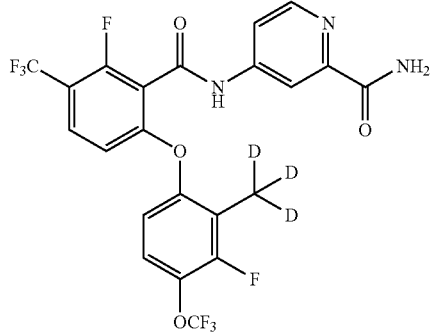 [SMILES: [2H]C([2H])([2H])c1c(Oc2ccc(C(F)(F)F)c(F)c2C(=O)Nc2ccnc(C(N)=O)c2)ccc(OC(F)(F)F)c1F]
232
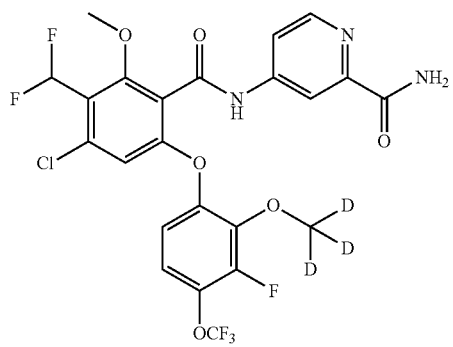 [SMILES: [2H]C([2H])([2H])Oc1c(Oc2cc(Cl)c(C(F)F)c(OC)c2C(=O)Nc2ccnc(C(N)=O)c2)ccc(OC(F)(F)F)c1F]
233
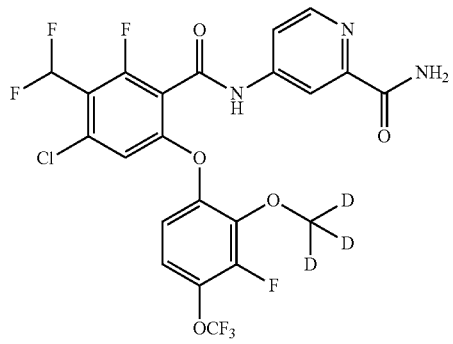 [SMILES: [2H]C([2H])([2H])Oc1c(Oc2cc(Cl)c(C(F)F)c(F)c2C(=O)Nc2ccnc(C(N)=O)c2)ccc(OC(F)(F)F)c1F]
234
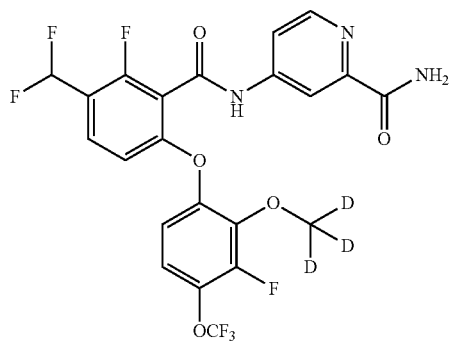
235
TABLE 1A-continued
Compound Numbers and Structures.
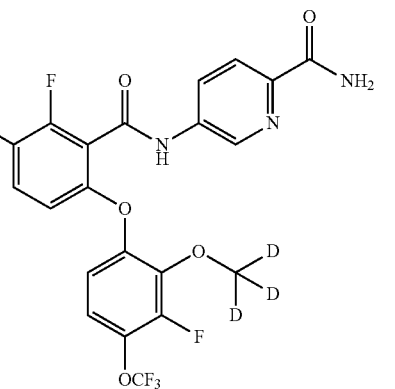
236
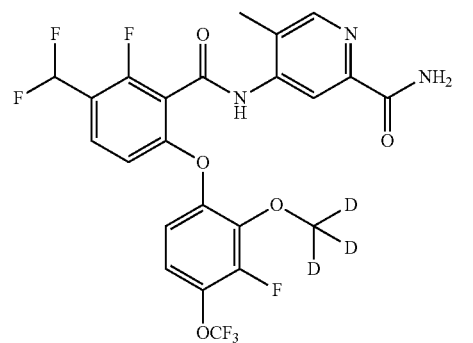 [SMILES: [2H]C([2H])([2H])Oc1c(Oc2ccc(C(F)F)c(F)c2C(=O)Nc2cc(C(N)=O)ncc2C)ccc(OC(F)(F)F)c1F]
237
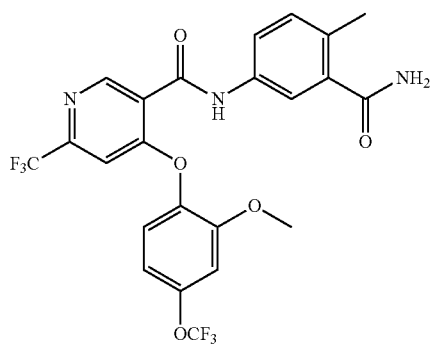 [SMILES: COc1cc(OC(F)(F)F)ccc1Oc1cc(C(F)(F)F)ncc1C(=O)Nc1ccc(C)c(C(N)=O)c1]
238
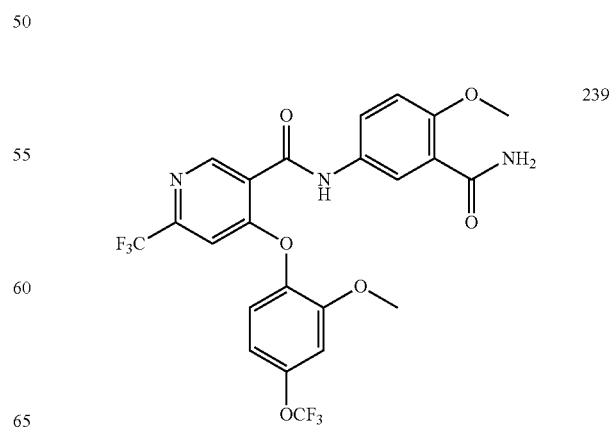
239

TABLE 1A-continued
Compound Numbers and Structures.
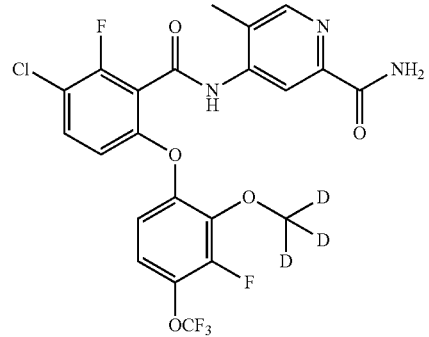 [SMILES: [2H]C([2H])([2H])Oc1c(Oc2ccc(Cl)c(F)c2C(=O)Nc2cc(C(N)=O)ncc2C)ccc(OC(F)(F)F)c1F]
240
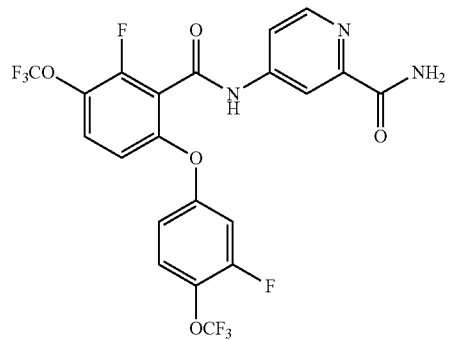 [SMILES: NC(=O)c1cc(NC(=O)c2c(Oc3ccc(OC(F)(F)F)c(F)c3)ccc(OC(F)(F)F)c2F)ccn1]
241
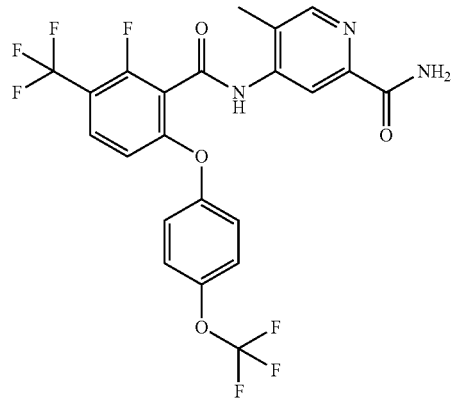 [SMILES: Cc1cnc(C(N)=O)cc1NC(=O)c1c(Oc2ccc(OC(F)(F)F)cc2)ccc(C(F)(F)F)c1F]
242
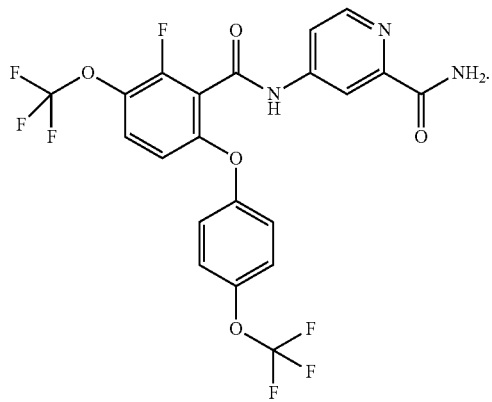 [SMILES: NC(=O)c1cc(NC(=O)c2c(Oc3ccc(OC(F)(F)F)cc3)ccc(OC(F)(F)F)c2F)ccn1]
243
TABLE 1B
Compound Numbers and Structures.
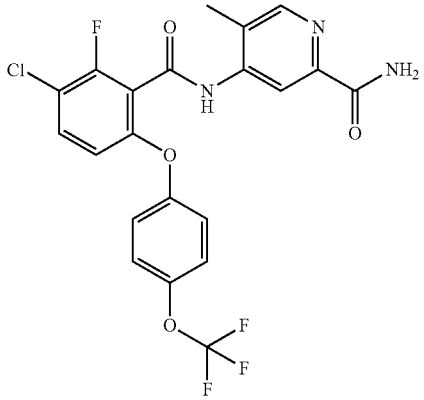 [SMILES: Cc1cnc(C(N)=O)cc1NC(=O)c1c(Oc2ccc(OC(F)(F)F)cc2)ccc(Cl)c1F]
244
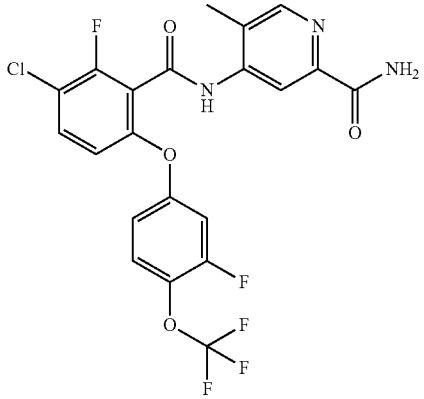 [SMILES: Cc1cnc(C(N)=O)cc1NC(=O)c1c(Oc2ccc(OC(F)(F)F)c(F)c2)ccc(Cl)c1F]
245
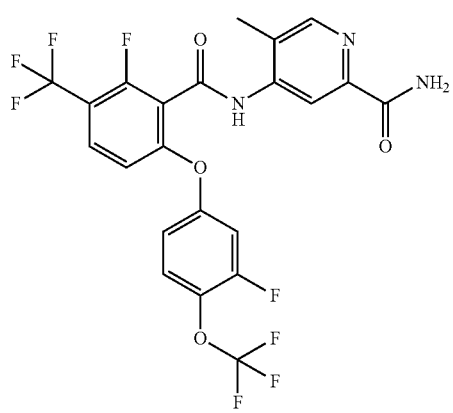 [SMILES: Cc1cnc(C(N)=O)cc1NC(=O)c1c(Oc2ccc(OC(F)(F)F)c(F)c2)ccc(C(F)(F)F)c1F]
246
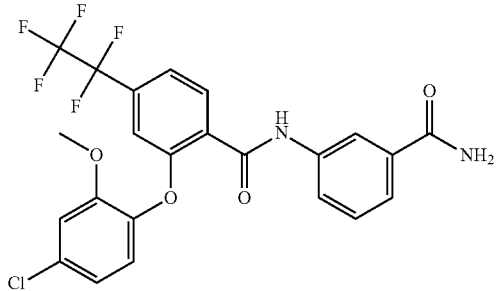 [SMILES: COc1cc(Cl)ccc1Oc1cc(C(F)(F)C(F)(F)F)ccc1C(=O)Nc1cccc(C(N)=O)c1]
247

TABLE 1B-continued
Compound Numbers and Structures.
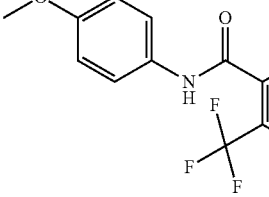 248
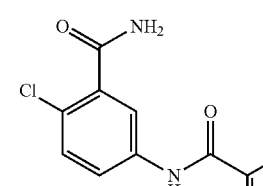 249
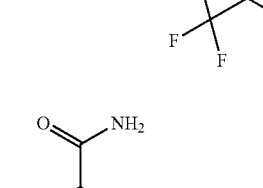 250
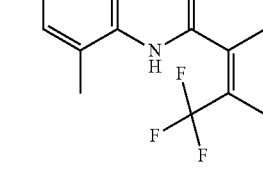 251
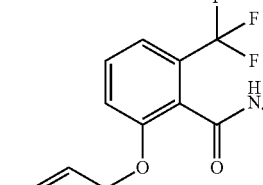 252
TABLE 1B-continued
Compound Numbers and Structures.
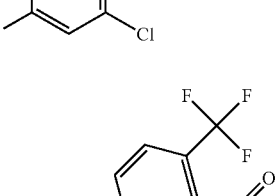 253
254
255
256
257

TABLE 1B-continued

Compound Numbers and Structures.

258

259

260

261

262

263

264

TABLE 1B-continued
Compound Numbers and Structures.
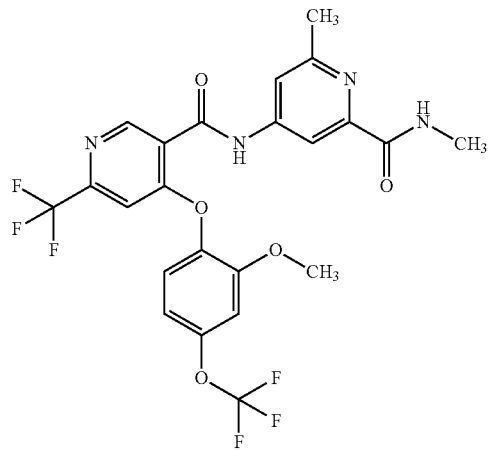 [SMILES: CNC(=O)c1cc(NC(=O)c2cnc(C(F)(F)F)cc2Oc2ccc(OC(F)(F)F)cc2OC)cc(C)n1]
265
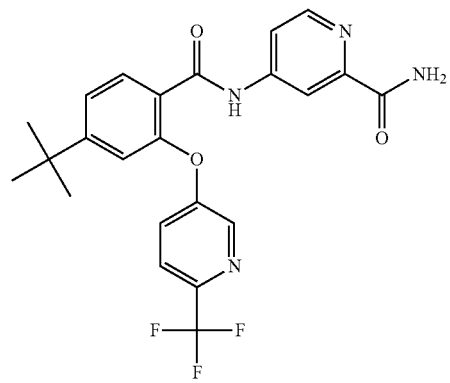 [SMILES: CC(C)(C)c1ccc(C(=O)Nc2ccnc(C(N)=O)c2)c(Oc2ccc(C(F)(F)F)nc2)c1]
266
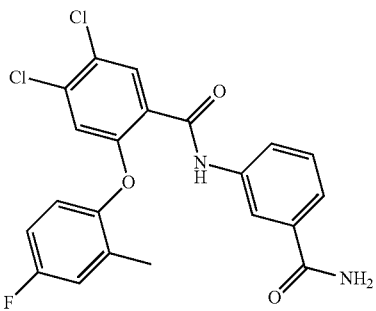 [SMILES: Cc1cc(F)ccc1Oc1cc(Cl)c(Cl)cc1C(=O)Nc1cccc(C(N)=O)c1]
267
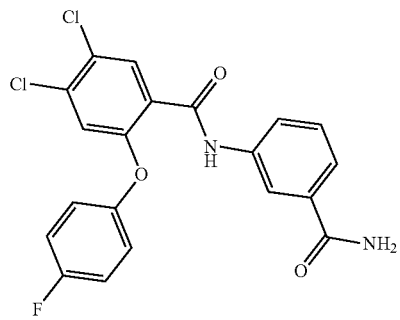 [SMILES: NC(=O)c1cccc(NC(=O)c2cc(Cl)c(Cl)cc2Oc2ccc(F)cc2)c1]
268
TABLE 1B-continued
Compound Numbers and Structures.
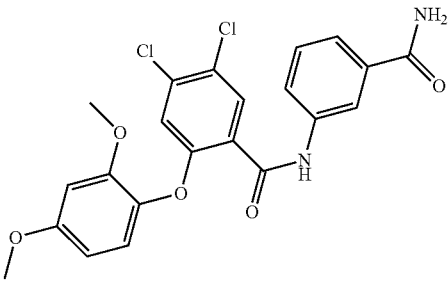 [SMILES: COc1ccc(Oc2cc(Cl)c(Cl)cc2C(=O)Nc2cccc(C(N)=O)c2)c(OC)c1]
269
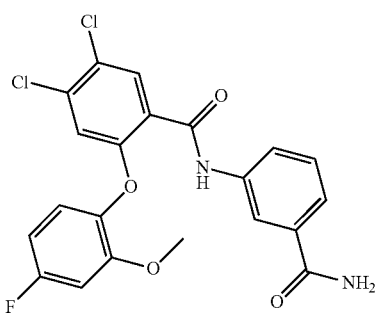 [SMILES: COc1cc(F)ccc1Oc1cc(Cl)c(Cl)cc1C(=O)Nc1cccc(C(N)=O)c1]
270
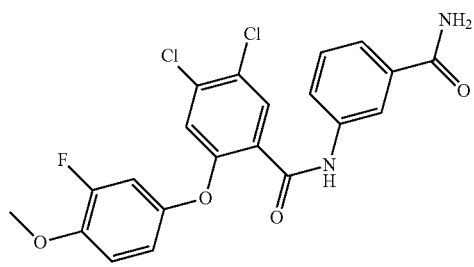 [SMILES: COc1ccc(Oc2cc(Cl)c(Cl)cc2C(=O)Nc2cccc(C(N)=O)c2)cc1F]
271
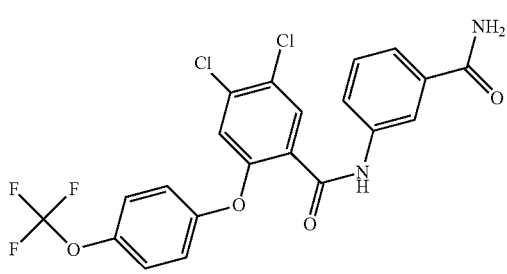 [SMILES: NC(=O)c1cccc(NC(=O)c2cc(Cl)c(Cl)cc2Oc2ccc(OC(F)(F)F)cc2)c1]
272
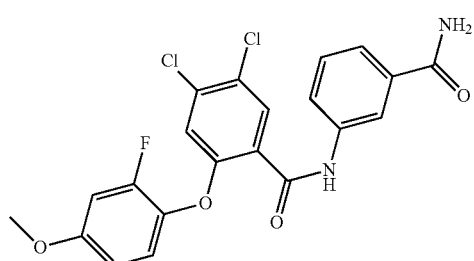
273

TABLE 1B-continued
Compound Numbers and Structures.
274
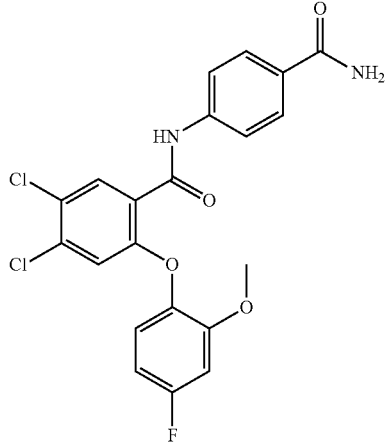 [SMILES: COc1cc(F)ccc1Oc1cc(Cl)c(Cl)cc1C(=O)Nc1ccc(C(N)=O)cc1]
275
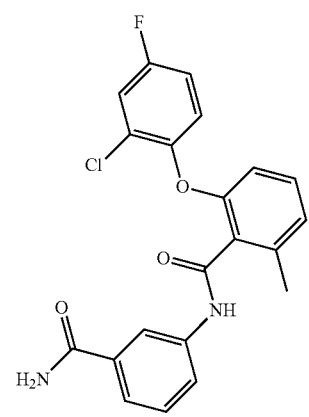 [SMILES: Cc1cccc(Oc2ccc(F)cc2Cl)c1C(=O)Nc1cccc(C(N)=O)c1]
276
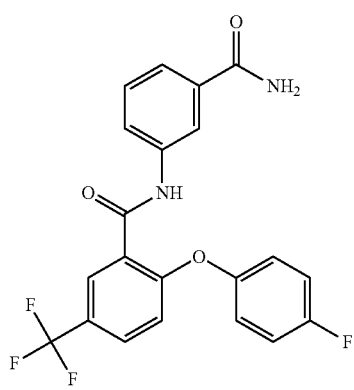 [SMILES: NC(=O)c1cccc(NC(=O)c2cc(C(F)(F)F)ccc2Oc2ccc(F)cc2)c1]
TABLE 1B-continued
Compound Numbers and Structures.
277
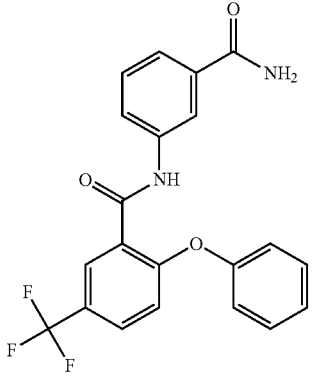 [SMILES: NC(=O)c1cccc(NC(=O)c2cc(C(F)(F)F)ccc2Oc2ccccc2)c1]
278
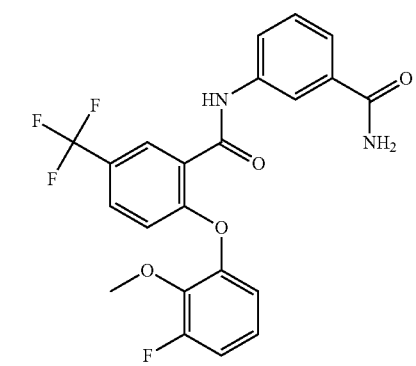 [SMILES: COc1c(F)cccc1Oc1ccc(C(F)(F)F)cc1C(=O)Nc1cccc(C(N)=O)c1]
279
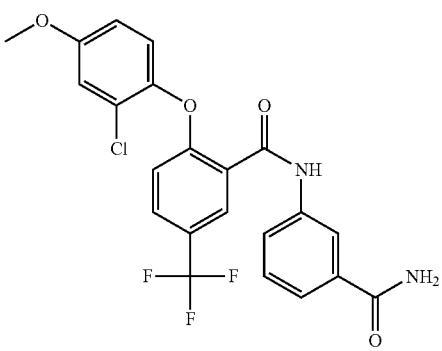 [SMILES: COc1ccc(Oc2ccc(C(F)(F)F)cc2C(=O)Nc2cccc(C(N)=O)c2)c(Cl)c1]
280
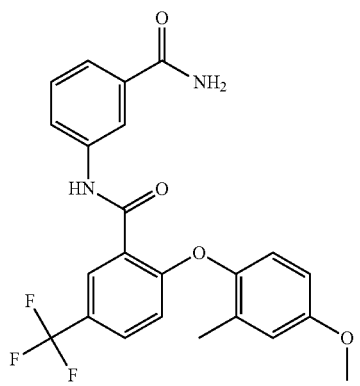 [SMILES: COc1ccc(Oc2ccc(C(F)(F)F)cc2C(=O)Nc2cccc(C(N)=O)c2)c(C)c1]

TABLE 1B-continued
Compound Numbers and Structures.
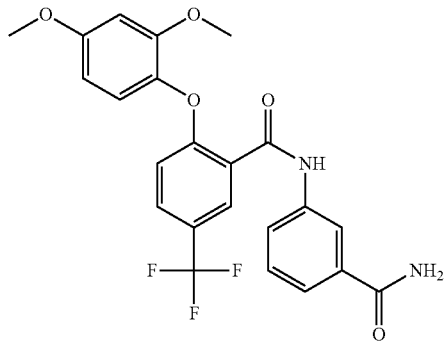 [SMILES: COc1ccc(Oc2ccc(C(F)(F)F)cc2C(=O)Nc2cccc(C(N)=O)c2)c(OC)c1]
281
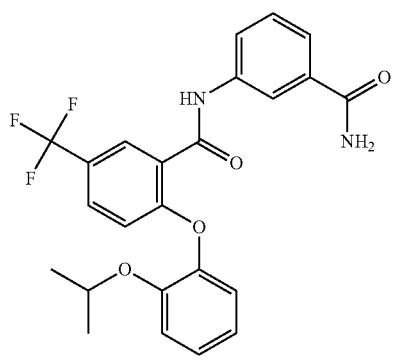 [SMILES: CC(C)Oc1ccccc1Oc1ccc(C(F)(F)F)cc1C(=O)Nc1cccc(C(N)=O)c1]
282
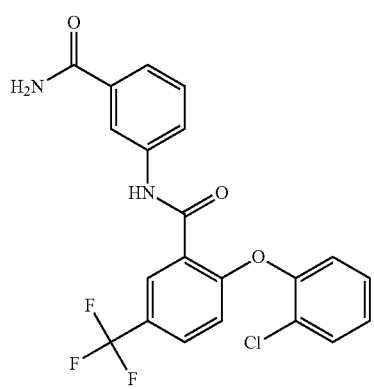 [SMILES: NC(=O)c1cccc(NC(=O)c2cc(C(F)(F)F)ccc2Oc2ccccc2Cl)c1]
283
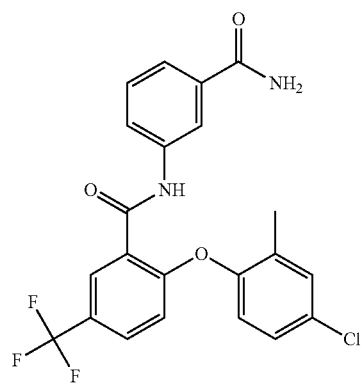 [SMILES: Cc1cc(Cl)ccc1Oc1ccc(C(F)(F)F)cc1C(=O)Nc1cccc(C(N)=O)c1]
284
TABLE 1B-continued
Compound Numbers and Structures.
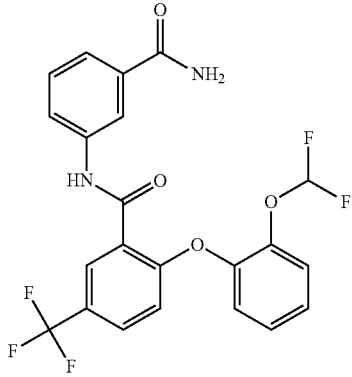 [SMILES: NC(=O)c1cccc(NC(=O)c2cc(C(F)(F)F)ccc2Oc2ccccc2OC(F)F)c1]
285
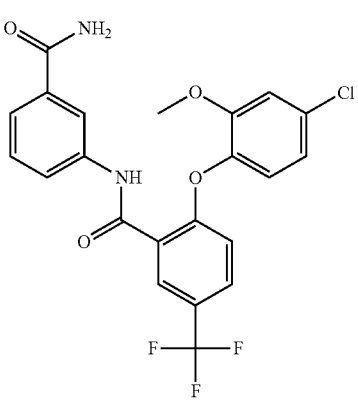 [SMILES: COc1cc(Cl)ccc1Oc1ccc(C(F)(F)F)cc1C(=O)Nc1cccc(C(N)=O)c1]
286
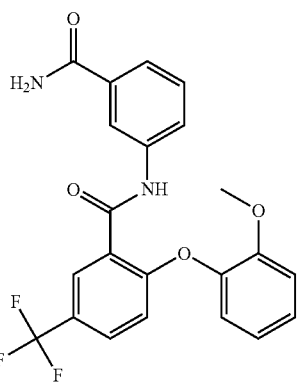
287
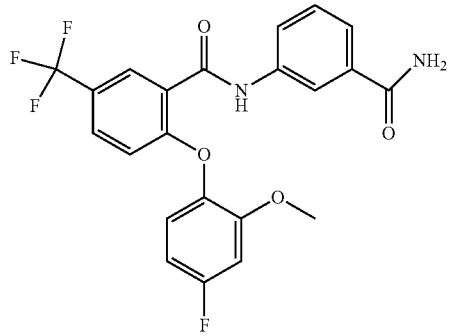 [SMILES: COc1cc(F)ccc1Oc1ccc(C(F)(F)F)cc1C(=O)Nc1cccc(C(N)=O)c1]
288

TABLE 1B-continued
Compound Numbers and Structures.
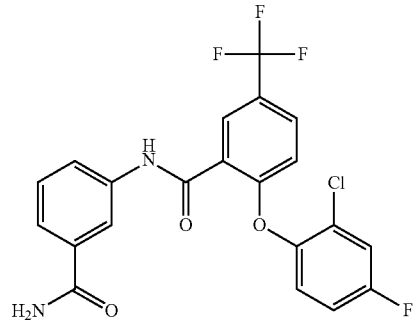 [SMILES: NC(=O)c1cccc(NC(=O)c2cc(C(F)(F)F)ccc2Oc2ccc(F)cc2Cl)c1]
289
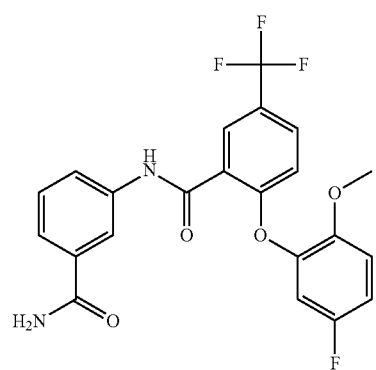 [SMILES: COc1ccc(F)cc1Oc1ccc(C(F)(F)F)cc1C(=O)Nc1cccc(C(N)=O)c1]
290
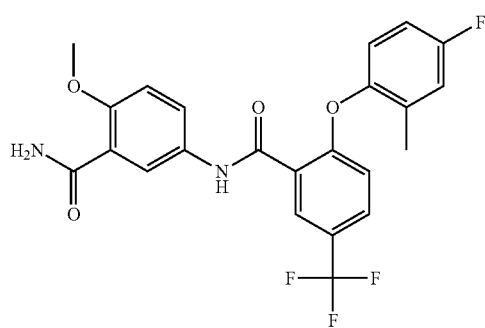 [SMILES: COc1ccc(NC(=O)c2cc(C(F)(F)F)ccc2Oc2ccc(F)cc2C)cc1C(N)=O]
292
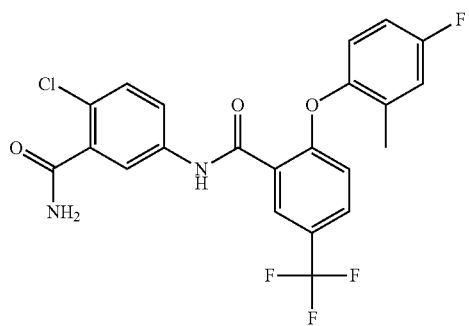 [SMILES: Cc1cc(F)ccc1Oc1ccc(C(F)(F)F)cc1C(=O)Nc1ccc(Cl)c(C(N)=O)c1]
293
TABLE 1B-continued
Compound Numbers and Structures.
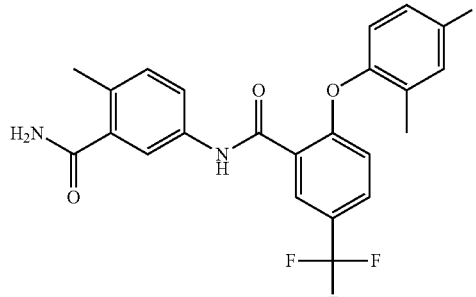
294
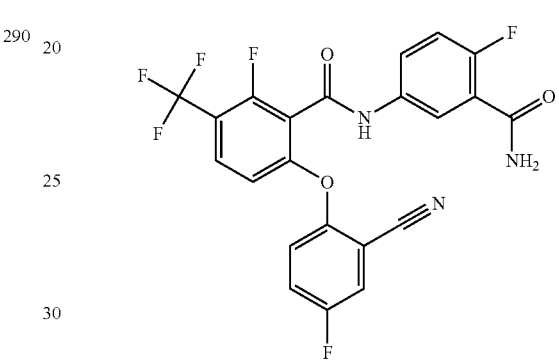
295
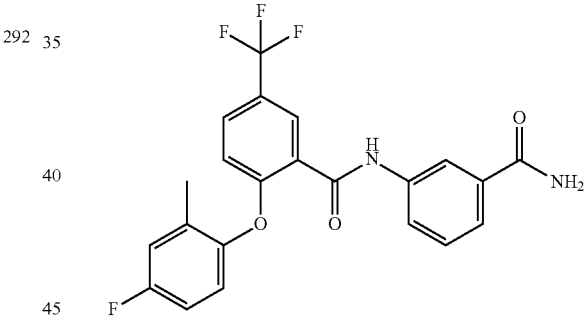
296
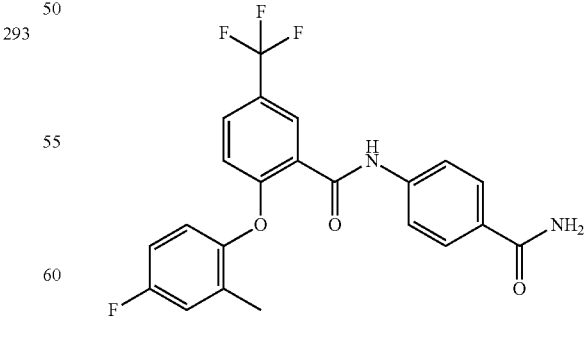
297

TABLE 1B-continued

Compound Numbers and Structures.

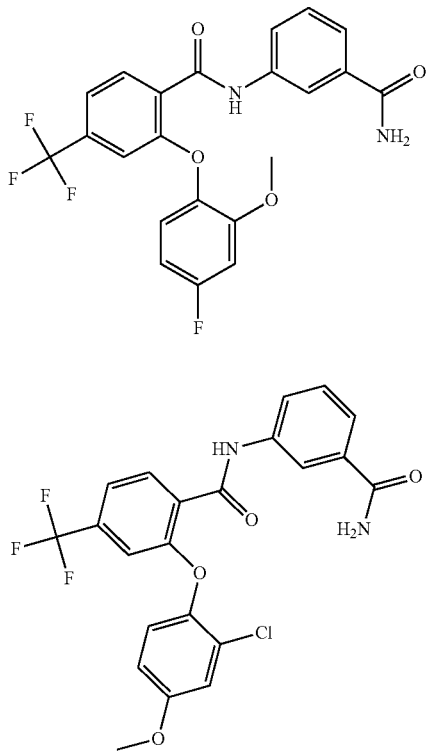

298

299

300

301

TABLE 1B-continued

Compound Numbers and Structures.

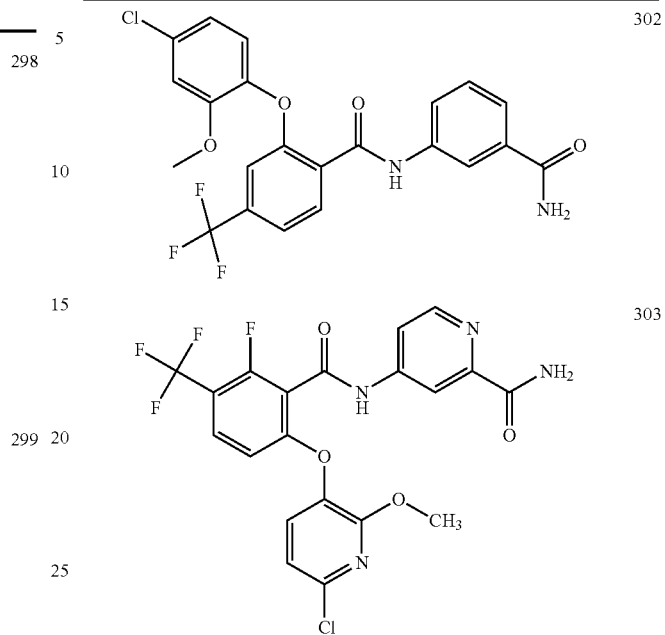

302

303

In some embodiments, the invention relates to the compound identified in Table 1C, or a pharmaceutically acceptable salt thereof. In other embodiments, the invention relates to the compound identified in Table 1C, i.e., the compound in non-salt form.

TABLE 1C

Compound Number and Structure.

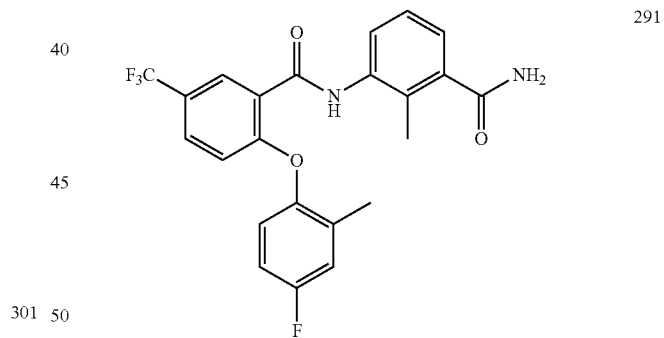

291

Salts, Compositions, Uses, Formulation, Administration and Additional Agents

Pharmaceutically Acceptable Salts and Compositions

As discussed herein, the invention provides compounds, and pharmaceutically acceptable salts thereof, that are inhibitors of voltage-gated sodium channels, and thus the present compounds, and pharmaceutically acceptable salts thereof, are useful for the treatment of diseases, disorders, and conditions including, but not limited to chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia. Accordingly, in another aspect of the invention, pharmaceutical compositions are provided, wherein these compositions comprise a compound as described herein, or a pharmaceutically acceptable salt thereof, and optionally comprise a pharmaceutically acceptable carrier, adjuvant or vehicle. In certain embodiments, these compositions optionally further comprise one or more additional therapeutic agents. In some embodiments, the additional therapeutic agent is a sodium channel inhibitor.

As used herein, the term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" of a compound of this invention includes any non-toxic salt that, upon administration to a recipient, is capable of providing, either directly or indirectly, a compound of this invention or an inhibitorily active metabolite or residue thereof. The salt may be in pure form, in a mixture (e.g., solution, suspension, or colloid) with one or more other substances, or in the form of a hydrate, solvate, or co-crystal. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences*, 1977, 66, 1-19, incorporated herein by reference. Pharmaceutically acceptable salts of the compound of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}$ alkyl$)_4$ salts. Representative alkali or alkaline earth metal salts include sodium, lithium, potassium, calcium, magnesium, and the like. Further pharmaceutically acceptable salts include, when appropriate, non-toxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising a compound of the invention, or a pharmaceutically acceptable salt thereof, and a pharmaceutically acceptable carrier.

In another aspect, the invention features a pharmaceutical composition comprising a therapeutically effective amount of a compound, or a pharmaceutically acceptable salt thereof, and one or more pharmaceutically acceptable carriers or vehicles.

Uses of Compounds and Pharmaceutically Acceptable Salts and Compositions

In another aspect, the invention features a method of inhibiting a voltage-gated sodium channel in a subject comprising administering to the subject a compound of the invention or a pharmaceutically acceptable salt thereof or a pharmaceutical composition thereof. In another aspect, the voltage-gated sodium channel is Nav1.8.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of chronic pain, gut pain, neuropathic pain, musculoskeletal pain, acute pain, inflammatory pain, cancer pain, idiopathic pain, postsurgical pain, bunionectomy pain, multiple sclerosis, Charcot-Marie-Tooth syndrome, incontinence, or cardiac arrhythmia comprising administering an effective amount of a compound of the invention, a pharmaceutically acceptable salt thereof or a pharmaceutical composition thereof.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound of the invention, a pharmaceutically acceptable salt thereof or a pharmaceutical composition thereof.

In yet another aspect, the invention features a method of treating or lessening the severity in a subject of neuropathic pain comprising administering an effective amount of a compound of the invention, a pharmaceutically acceptable salt thereof or a pharmaceutical composition thereof. In some aspects, the neuropathic pain comprises post-herpetic neuralgia or idiopathic small-fiber neuropathy. As used herein, the phrase "idiopathic small-fiber neuropathy" shall be understood to include any small fiber neuropathy.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic cephalalgia wherein said method comprises administering an effective amount of a compound of the invention, a pharmaceutically acceptable salt thereof or a pharmaceutical composition thereof.

In yet another aspect, the invention features a method of treating or lessening the severity in a subject of musculoskeletal pain comprising administering an effective amount of a compound of the invention, a pharmaceutically acceptable salt thereof or a pharmaceutical composition thereof. In some aspects, the musculoskeletal pain comprises osteoarthritis pain.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound of the invention, a pharmaceutically acceptable salt thereof or a pharmaceutical composition thereof.

In yet another aspect, the invention features a method of treating or lessening the severity in a subject of inflammatory pain, wherein inflammatory pain comprises rheumatoid arthritis pain wherein said method comprises administering an effective amount of a compound of the invention, a pharmaceutically acceptable salt thereof or a pharmaceutical composition thereof.

In yet another aspect, the invention features a method of treating or lessening the severity in a subject of idiopathic pain, wherein idiopathic pain comprises fibromyalgia pain wherein said method comprises administering an effective amount of a compound of the invention, a pharmaceutically acceptable salt thereof or a pharmaceutical composition thereof.

In yet another aspect, the invention features a method of treating or lessening the severity in a subject of pathological cough wherein said method comprises administering an effective amount of a compound of the invention, a pharmaceutically acceptable salt thereof or a pharmaceutical composition thereof.

In yet another aspect, the invention features a method of treating or lessening the severity in a subject of acute pain comprising administering an effective amount of a compound of the invention, a pharmaceutically acceptable salt thereof or a pharmaceutical composition thereof. In some aspects, the acute pain comprises acute post-operative pain.

In yet another aspect, the invention features a method of treating or lessening the severity in a subject of postsurgical pain (e.g., bunionectomy pain or abdominoplasty pain) comprising administering an effective amount of a compound of the invention, a pharmaceutically acceptable salt thereof or a pharmaceutical composition thereof.

In yet another aspect, the invention features a method of treating or lessening the severity in a subject of bunionectomy pain comprising administering an effective amount of a compound of the invention, a pharmaceutically acceptable salt thereof or a pharmaceutical composition thereof.

In yet another aspect, the invention features a method of treating or lessening the severity in a subject of abdominoplasty pain comprising administering an effective amount of a compound of the invention, a pharmaceutically acceptable salt thereof or a pharmaceutical composition thereof.

In yet another aspect, the invention features a method of treating or lessening the severity in a subject of visceral pain comprising administering an effective amount of a compound of the invention, a pharmaceutically acceptable salt thereof or a pharmaceutical composition thereof. In some aspects, the visceral pain comprises visceral pain from abdominoplasty.

In yet another aspect, the invention features a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is Nav1.8.

In another aspect, the invention features a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility, comprising administering an effective amount of a compound of the invention, a pharmaceutically acceptable salt thereof or a pharmaceutical composition thereof.

In another aspect, the invention features a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain, comprising administering an effective amount of a compound of the invention, a pharmaceutically acceptable salt thereof or a pharmaceutical composition thereof.

Compounds, Pharmaceutically Acceptable Salts, and Compositions for Use

In another aspect, the invention features a compound of the invention, or a pharmaceutically acceptable salt or pharmaceutical composition thereof, for use as a medicament.

In another aspect, the invention features a compound of the invention, or a pharmaceutically acceptable salt or pharmaceutical composition thereof, for use in a method of inhibiting a voltage-gated sodium channel in a subject. In another aspect, the voltage-gated sodium channel is Nav1.8.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia.

In another aspect, the invention features a compound of the invention, or a pharmaceutically acceptable salt or pharmaceutical composition thereof, for use in a method of treating or lessening the severity in a subject of chronic pain, gut pain, neuropathic pain, musculoskeletal pain, acute pain, inflammatory pain, cancer pain, idiopathic pain, postsurgical pain, bunionectomy pain, multiple sclerosis, Charcot-Marie-Tooth syndrome, incontinence, or cardiac arrhythmia.

In another aspect, the invention features a compound of the invention, or a pharmaceutically acceptable salt or pharmaceutical composition thereof, for use in a method of treating or lessening the severity in a subject of gut pain, wherein gut pain comprises inflammatory bowel disease pain, Crohn's disease pain or interstitial cystitis pain.

In another aspect, the invention features a compound of the invention, or a pharmaceutically acceptable salt or pharmaceutical composition thereof, for use in a method of treating or lessening the severity in a subject of neuropathic pain. In some aspects, the neuropathic pain comprises post-herpetic neuralgia or idiopathic small-fiber neuropathy. As used herein, the phrase "idiopathic small-fiber neuropathy" shall be understood to include any small fiber neuropathy.

In another aspect, the invention features a compound of the invention, or a pharmaceutically acceptable salt or pharmaceutical composition thereof, for use in a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, anti-retroviral therapy induced neuralgia; post spinal cord injury pain, idiopathic small-fiber neuropathy, idiopathic sensory neuropathy or trigeminal autonomic cephalalgia.

In another aspect, the invention features a compound of the invention, or a pharmaceutically acceptable salt or pharmaceutical composition thereof, for use in a method of treating or lessening the severity in a subject of musculoskeletal pain. In some aspects, the musculoskeletal pain comprises osteoarthritis pain.

In another aspect, the invention features a compound of the invention, or a pharmaceutically acceptable salt or pharmaceutical composition thereof, for use in a method of treating or lessening the severity in a subject of musculoskeletal pain, wherein musculoskeletal pain comprises osteoarthritis pain, back pain, cold pain, burn pain or dental pain.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain or vulvodynia.

In another aspect, the invention features a compound of the invention, or a pharmaceutically acceptable salt or pharmaceutical composition thereof, for use in a method of treating or lessening the severity in a subject of inflammatory pain, wherein inflammatory pain comprises rheumatoid arthritis pain.

In another aspect, the invention features a compound of the invention, or a pharmaceutically acceptable salt or pharmaceutical composition thereof, for use in a method of treating or lessening the severity in a subject of idiopathic pain, wherein idiopathic pain comprises fibromyalgia pain.

In another aspect, the invention features a compound of the invention, or a pharmaceutically acceptable salt or pharmaceutical composition thereof, for use in a method of treating or lessening the severity in a subject of pathological cough.

In another aspect, the invention features a compound of the invention, or a pharmaceutically acceptable salt or pharmaceutical composition thereof, for use in a method of treating or lessening the severity in a subject of acute pain. In some aspects, the acute pain comprises acute postoperative pain.

In another aspect, the invention features a compound of the invention, or a pharmaceutically acceptable salt or pharmaceutical composition thereof, for use in a method of treating or lessening the severity in a subject of postsurgical pain (e.g., bunionectomy pain or abdominoplasty pain).

In another aspect, the invention features a compound of the invention, or a pharmaceutically acceptable salt or pharmaceutical composition thereof, for use in a method of treating or lessening the severity in a subject of bunionectomy pain.

In another aspect, the invention features a compound of the invention, or a pharmaceutically acceptable salt or pharmaceutical composition thereof, for use in a method of treating or lessening the severity in a subject of abdominoplasty pain.

In another aspect, the invention features a compound of the invention, or a pharmaceutically acceptable salt or pharmaceutical composition thereof, for use in a method of treating or lessening the severity in a subject of visceral pain. In some aspects, the visceral pain comprises visceral pain from abdominoplasty.

In another aspect, the invention features a compound of the invention, or a pharmaceutically acceptable salt or pharmaceutical composition thereof, for use in a method wherein the subject is treated with one or more additional therapeutic agents administered concurrently with, prior to, or subsequent to treatment with an effective amount of the compound, pharmaceutically acceptable salt or pharmaceutical composition. In some embodiments, the additional therapeutic agent is a sodium channel inhibitor.

In another aspect, the invention features a compound of the invention, or a pharmaceutically acceptable salt or pharmaceutical composition thereof, for use in a method of inhibiting a voltage-gated sodium channel in a biological sample comprising contacting the biological sample with an effective amount of a compound of the invention, a pharmaceutically acceptable salt thereof or a pharmaceutical composition thereof. In another aspect, the voltage-gated sodium channel is Nav1.8.

In another aspect, the invention features a compound of the invention, or a pharmaceutically acceptable salt or pharmaceutical composition thereof, for use in a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention features a compound of the invention, or a pharmaceutically acceptable salt or pharmaceutical composition thereof, for use in a method of treating or lessening the severity in a subject of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory pain, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence, pathological cough; hyperactive bladder; painful bladder syndrome; interstitial cystitis (IC); prostatitis; complex regional pain syndrome (CRPS), type I, complex regional pain syndrome (CRPS) type II; widespread pain, paroxysmal extreme pain, pruritus, tinnitus, or angina-induced pain.

Manufacture of Medicaments

In another aspect, the invention provides the use of a compound of the invention, or a pharmaceutically acceptable salt or pharmaceutical composition thereof, for the manufacture of a medicament.

In another aspect, the invention provides the use of a compound of the invention, a pharmaceutically acceptable salt thereof, or a pharmaceutical composition thereof for the manufacture of a medicament for use in inhibiting a voltage-gated sodium channel. In another aspect, the voltage-gated sodium channel is Nav1.8.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain (e.g., bunionectomy pain or abdominoplasty pain), visceral pain, multiple sclerosis, Charcot-Marie-Tooth syndrome, incontinence, pathological cough, or cardiac arrhythmia.

In yet another aspect, the invention provides the use of a compound of the invention, a pharmaceutically acceptable salt thereof, or a pharmaceutical composition thereof for the manufacture of a medicament for use in treating or lessening the severity in a subject of chronic pain, gut pain, neuropathic pain, musculoskeletal pain, acute pain, inflammatory pain, cancer pain, idiopathic pain, postsurgical pain, bunionectomy pain, multiple sclerosis, Charcot-Marie-Tooth syndrome, incontinence, or cardiac arrhythmia.

In yet another aspect, the invention provides the use of the compound, pharmaceutically acceptable salt, or pharmaceutical composition described herein for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides a compound of the invention, a pharmaceutically acceptable salt thereof, or a pharmaceutical composition thereof for the manufacture of a medicament for use in treating or lessening the severity in a subject of neuropathic pain. In some aspects, the neuropathic pain comprises post-herpetic neuralgia or idiopathic small-fiber neuropathy.

In yet another aspect, the invention provides the use of a compound of the invention, a pharmaceutically acceptable salt thereof, or a pharmaceutical composition thereof for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma; Morton's neuroma; nerve entrapment injury, spinal stenosis, carpal tunnel syndrome, radicular pain, sciatica pain; nerve avulsion injury, brachial plexus avulsion injury; complex regional pain syndrome, drug therapy induced neuralgia, cancer chemotherapy induced neuralgia, antiretroviral therapy induced neuralgia; post spinal cord injury pain, idiopathic small-fiber neuropathy, idiopathic sensory neuropathy or trigeminal autonomic neuropathy.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain. In some aspects the musculoskeletal pain comprises osteoarthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain or vulvodynia.

In yet another aspect, the invention provides the use of a compound of the invention, a pharmaceutically acceptable salt thereof, or a pharmaceutical composition thereof for the manufacture of a medicament for use in treating or lessening the severity in a subject of inflammatory pain, wherein inflammatory pain comprises rheumatoid arthritis pain.

In yet another aspect, the invention provides the use of a compound of the invention, a pharmaceutically acceptable salt thereof, or a pharmaceutical composition thereof for the manufacture of a medicament for use in treating or lessening the severity in a subject of idiopathic pain, wherein idiopathic pain comprises fibromyalgia pain.

In yet another aspect, the invention provides the use of a compound of the invention, a pharmaceutically acceptable salt thereof, or a pharmaceutical composition thereof for the manufacture of a medicament for use in treating or lessening the severity in a subject of pathological cough.

In yet another aspect, the invention provides the use of a compound of the invention, a pharmaceutically acceptable salt thereof, or a pharmaceutical composition thereof for the manufacture of a medicament for use in treating or lessening the severity in a subject of acute pain. In some aspects, the acute pain comprises acute post-operative pain.

In yet another aspect, the invention provides the use of a compound of the invention, a pharmaceutically acceptable salt thereof, or a pharmaceutical composition thereof for the manufacture of a medicament for use in treating or lessening the severity in a subject of postsurgical pain (e.g., bunionectomy pain or abdominoplasty pain).

In yet another aspect, the invention provides the use of a compound of the invention, a pharmaceutically acceptable salt thereof, or a pharmaceutical composition thereof for the manufacture of a medicament for use in treating or lessening the severity in a subject of bunionectomy pain.

In yet another aspect, the invention provides the use of a compound of the invention, a pharmaceutically acceptable salt thereof, or a pharmaceutical composition thereof for the manufacture of a medicament for use in treating or lessening the severity in a subject of abdominoplasty pain.

In yet another aspect, the invention provides the use of a compound of the invention, a pharmaceutically acceptable salt thereof, or a pharmaceutical composition thereof for the manufacture of a medicament for use in treating or lessening the severity in a subject of visceral pain. In some aspects, the visceral pain comprises visceral pain from abdominoplasty.

In yet another aspect, the invention provides the use of a compound of the invention, a pharmaceutically acceptable salt thereof, or a pharmaceutical composition thereof for the manufacture of a medicament for use in combination with one or more additional therapeutic agents administered concurrently with, prior to, or subsequent to treatment with the compound or pharmaceutical composition. In some embodiments, the additional therapeutic agent is a sodium channel inhibitor.

In another aspect, the invention provides the use of a compound of the invention, a pharmaceutically acceptable salt thereof, or a pharmaceutical composition thereof for the manufacture of a medicament for use in treating or lessening the severity of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, bipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain (e.g., bunionectomy pain or abdominoplasty pain), cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound of the invention, a pharmaceutically acceptable salt thereof, or a pharmaceutical composition thereof for the manufacture of a medicament for use in treating or lessening the severity of femur cancer pain; non-malignant chronic bone pain; rheumatoid arthritis; osteoarthritis; spinal stenosis; neuropathic low back pain; myofascial pain syndrome; fibromyalgia; temporomandibular joint pain; chronic visceral pain, abdominal pain; pancreatic pain; IBS pain; chronic and acute headache pain; migraine; tension headache; cluster headaches; chronic and acute neuropathic pain, post-herpetic neuralgia; diabetic neuropathy; HIV-associated neuropathy; trigeminal neuralgia; Charcot-Marie-Tooth neuropathy; hereditary sensory neuropathy; peripheral nerve injury; painful neuromas; ectopic proximal and distal discharges; radiculopathy; chemotherapy induced neuropathic pain; radiotherapy-induced neuropathic pain; post-mastectomy pain; central pain; spinal cord injury pain; post-stroke pain; thalamic pain; complex regional pain syndrome; phantom pain; intractable pain; acute pain, acute post-operative pain; acute musculoskeletal pain; joint pain; mechanical low back pain; neck pain; tendonitis; injury pain; exercise pain; acute visceral pain; pyelonephritis; appendicitis; cholecystitis; intestinal obstruction; hernias; chest pain, cardiac pain; pelvic pain, renal colic pain, acute obstetric pain, labor pain; cesarean section pain; acute inflammatory, burn pain, trauma pain; acute intermittent pain, endometriosis; acute herpes zoster pain; sickle cell anemia; acute pancreatitis; breakthrough pain; orofacial pain; sinusitis pain; dental pain; multiple sclerosis (MS) pain; pain in depression; leprosy pain; Behcet's disease pain; adiposis dolorosa; phlebitic pain; Guillain-Barre pain; painful legs and moving toes; Haglund syndrome; erythromelalgia pain; Fabry's disease pain; bladder and urogenital disease; urinary incontinence; pathological cough; hyperactive bladder; painful bladder syndrome; interstitial cystitis (IC); prostatitis; complex regional pain syndrome (CRPS) type I; complex regional pain syndrome (CRPS) type II; widespread pain, paroxysmal extreme pain, pruritus, tinnitus, or angina-induced pain. Administration of Pharmaceutically Acceptable Salts and Compositions.

In certain embodiments of the invention an "effective amount" of a compound of the invention, a pharmaceutically acceptable salt thereof, or a pharmaceutical composition thereof is that amount effective for treating or lessening the severity of one or more of the conditions recited above.

The compounds, salts, and compositions, according to the method of the invention, may be administered using any amount and any route of administration effective for treating or lessening the severity of one or more of the pain or non-pain diseases recited herein. The exact amount required will vary from subject to subject, depending on the species, age, and general condition of the subject, the severity of the condition, the particular agent, its mode of administration, and the like. The compounds, salts, and compositions of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds, salts, and compositions of the invention will be decided by the attending physician within the scope of sound medical judgment. The specific effective dose level for any particular subject or organism will depend upon a variety of factors including the disorder being treated and the severity of the disorder; the activity of the specific compound or salt employed; the specific composition employed; the age, body weight, general health, sex and diet of the subject; the time of administration, route of administration, and rate of excretion of the specific compound or salt employed; the duration of the treatment; drugs used in combination or coincidental with the specific compound or salt employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the condition being treated. In certain embodiments, the compound, salts, and compositions of the invention may be administered orally or parenterally at dosage levels of about 0.001 mg/kg to about 100 mg/kg, or about 0.01 mg/kg to about 50 mg/kg, of subject body weight per day, one or more times a day, effective to obtain the desired therapeutic effect.

Liquid dosage forms for oral administration include, but are not limited to, pharmaceutically acceptable emulsions, microemulsions, solutions, suspensions, syrups and elixirs. In addition to the active compound or salt, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of the compounds of the invention, it is often desirable to slow the absorption of the compounds from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compound or salt of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound or salt is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compound or salt can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound or salt may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound or salt of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds are inhibitors of $Na_V1.8$ and thus, without wishing to be bound by any particular theory, the compounds, salts, and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in International Publication No. WO 2014/120808 A9 and U.S. Publication No. 2014/0213616 A1, both of which are incorporated by reference in their entirety, methods described herein, and other methods known and available to one of ordinary skill in the art.

Additional Therapeutic Agents

It will also be appreciated that the compounds, salts, and pharmaceutically acceptable compositions of the invention can be employed in combination therapies, that is, the compounds, salts, and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Aspirin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blockade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp &Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine, pentazocine, or difelikefalin;

(2) a nonsteroidal antiinflammatory drug (NSAID), e.g. aspirin, diclofenac, diflunisal, etodolac, fenbufen, fenoprofen, flufenisal, flurbiprofen, ibuprofen (including without limitation intravenous ibuprofen (e.g., Caldolor®)), indomethacin, ketoprofen, ketorolac (including without limitation ketorolac tromethamine (e.g., Toradol®)), meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butalbital, mephobarbital, metharbital, methohexital, pentobarbital, phenobarbital, secobarbital, talbutal, thiamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphenadrine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)-(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmedetomidine, modafinil, or 4-amino-6,7-dimethoxy-2-(5-methane-sulfonamido-1, 2,3,4-tetrahydroisoquinolin-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis (trifluoromethyl)benzyl]-8,9,10,11-tetrahydro-9-methyl-5-(4-methylphenyl)-7H-[1,4]diazocino[2,1-g] [1,7]-naphthyridine-6-13-dione (TAK-637), 5-[[(2R, 3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-HT$_{1B/1D}$ agonist such as eletriptan, sumatriptan, naratriptan, zolmitriptan or rizatriptan;
(22) a 5-HT$_{2A}$ receptor antagonist such as R(+)-alpha-(2,3-dimethoxy-phenyl)-1-[2-(4-fluorophenylethyl)]-4-piperidinemethanol (MDL-100907);
(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;
(24) Tramadol®, Tramadol ER (Ultram ER®), Tapentadol ER (Nucynta®);
(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethyl-piperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;
(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-aminomethyl-bicyclo[3.2.0]hept-3-yl)-acetic acid, (3S,5R)-3-aminomethyl-5-methyl-heptanoic acid, (3S,5R)-3-amino-5-methyl-heptanoic acid, (3S,5R)-3-amino-5-methyl-octanoic acid, (2S,4S)-4-(3-chlorophenoxy) proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4] oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;
(27) a cannabinoid such as KHK-6188;
(28) metabotropic glutamate subtype 1 receptor (mGluR1) antagonist;
(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;
(30) a noradrenaline (norepinephrine) reuptake inhibitor, such as maprotiline, lofepramine, mirtazepine, oxaprotiline, fezolamine, tomoxetine, mianserin, bupropion, bupropion metabolite hydroxybupropion, nomifensine and viloxazine (Vivalan®), especially a selective noradrenaline reuptake inhibitor such as reboxetine, in particular (S,S)-reboxetine;
(31) a dual serotonin-noradrenaline reuptake inhibitor, such as venlafaxine, venlafaxine metabolite O-desmethylvenlafaxine, clomipramine, clomipramine metabolite desmethylclomipramine, duloxetine (Cymbalta®), milnacipran and imipramine;
(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, NXN-462, or guanidinoethyldisulfide;
(33) an acetylcholinesterase inhibitor such as donepezil;
(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methyl-benzenesulfonamide or 4-[(15)-1-({[5-chloro-2-(3-fluorophenoxy)pyridin-3-yl]carbonyl}amino)ethyl] benzoic acid;
(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;
(36) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);
(37) a sodium channel blocker, such as lidocaine, lidocaine plus tetracaine cream (ZRS-201) or eslicarbazepine acetate;
(38) an Na$_V$1.7 blocker, such as XEN-402, XEN403, TV-45070, PF-05089771, CNV1014802, GDC-0276, RG7893 and such as those disclosed in WO2011/140425 (US2011/306607); WO2012/106499 (US2012196869); WO2012/112743 (US2012245136); WO2012/125613 (US2012264749), WO2012/116440 (US2014187533), WO2011026240 (US2012220605), U.S. Pat. Nos. 8,883,840, 8,466,188, or WO2013/109521 (US2015005304), the entire contents of each application hereby incorporated by reference.
(38a) an Na$_V$1.7 blocker such as (2-benzylspiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl] ethanone, [8-fluoro-2-methyl-6-(trifluoromethyl)spiro [3,4-dihydropyrrolo[1,2-a]pyrazine-1,4'-piperidine]-1'-yl]-(4-isobutoxy-3-methoxy-phenyl)methanone, 1-(4-benzhydrylpiperazin-1-yl)-3-[2-(3,4-dimethylphenoxy)ethoxy]propan-2-ol, (4-butoxy-3- methoxy-phenyl)-[2-methyl-6-(trifluoromethyl)spiro[3,4-dihydropyrrolo[1,2-a]pyrazine-1,4'-piperidine]-1'-yl]methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro[3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl]ethanone, 2,2,2-trifluoro-1-[1'-(5-isopentyloxypyridine-2-carbonyl)-2-methyl-spiro[3,4-dihydropyrrolo[1,2-a]pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl]methanone, 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone, 1-[(3S)-2,3-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy]phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl]ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl]methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) an $Na_V1.8$ blocker, such as PF-04531083, PF-06372865 and such as those disclosed in WO2008/135826 (US2009048306), WO2006/011050 (US2008312235), WO2013/061205 (US2014296313), US20130303535, WO2013131018, U.S. Pat. No. 8,466,188, WO2013114250 (US2013274243), WO2014/120808 (US2014213616), WO2014/120815 (US2014228371) WO2014/120820 (US2014221435), WO2015/010065 (US20160152561), and WO2015/089361 (US20150166589), the entire contents of each application hereby incorporated by reference.

(39a) an $Na_V1.8$ blocker such as 4,5-dichloro-2-(4-fluoro-2-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-4-(perfluoroethyl)benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy)phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl)benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl)benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl)benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl)benzamide, 2-(4-fluorophenoxy)-N-(2-oxo-1,2-dihydropyridin-4-yl)-5-(trifluoromethyl)benzamide, In one embodiment, the compound is 3-(4-fluoro-2-methoxyphenoxy)-N-(3-(methylsulfonyl)phenyl)quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl)quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy)quinoxaline-2-carboxamido)picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy)quinoline-3-carboxamide, N-(3-sulfamoylphenyl)-3-(4-(trifluoromethoxy)phenoxy)quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy)quinoxaline-2-carboxamido)picolinic acid, 3-(4-fluoro-2-methoxyphenoxy)-N-(2-oxo-2,3-dihydro-1H-benzo[d]imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl)quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy)quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido)picolinic acid, 4-(4,5-dichloro-2-(4-fluoro- 2-methoxyphenoxy)benzamido)benzoic acid, 5-(2-(4-fluoro-2-methoxyphenoxy)-4,6-bis(trifluoromethyl)benzamido)picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl)benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methylphenoxy)-4-(perfluoroethyl)benzamido)benzoic acid, 4-(4,5-dichloro-2-(4-(trifluoromethoxy)phenoxy)benzamido)benzoic acid, 4-(4,5-dichloro-2-(4-chloro-2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methylphenoxy)benzamido)benzoic acid, 5-(4,5-dichloro-2-(2,4-dimethoxyphenoxy)benzamido)picolinic acid, 5-(4,5-dichloro-2-(2-chloro-4-fluorophenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido)benzoic acid, 5-(4,5-dichloro-2-(2,4-difluorophenoxy)benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl)benzamide, 2-(2-chloro-4-fluorophenoxy)-N-(3-sulfamoylphenyl)-6-(trifluoromethyl)benzamide, 2-(2-chloro-4-fluorophenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis(trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl)benzamide or N-(3-sulfamoylphenyl)-2-(4-(trifluoromethoxy)phenoxy)-4-(trifluoromethyl)benzamide.

(40) a combined $Na_V1.7$ and $Na_V1.8$ blocker, such as DSP-2230 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof,

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

(48) acetaminophen (including without limitation intravenous acetaminophen (e.g., Ofirmev®));

(49) bupivacaine (including without limitation bupivacaine liposome injectable suspension (e.g., Exparel®) and transdermal bupivacaine (Eladur®)); and

(50) bupivacaine and meloxicam combination (e.g., HTX-011).

In one embodiment, the additional appropriate therapeutic agents are selected from V-116517, Pregabalin, controlled release Pregabalin, Ezogabine (Potiga®). Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

In another embodiment, the additional therapeutic agent is a sodium channel inhibitor (also know as a sodium channel blocker), such as the Nav1.7 and Nav1.8 blockers identified above.

The amount of additional therapeutic agent present in the compositions of this invention may be no more than the amount that would normally be administered in a composition comprising that therapeutic agent as the only active agent. The amount of additional therapeutic agent in the presently disclosed compositions may range from about 10% to 100% of the amount normally present in a composition comprising that agent as the only therapeutically active agent.

The compounds and salts of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound or salt of the invention as described generally above, and in classes and subclasses herein, and a carrier suitable for coating said implantable device. In still another aspect, the invention includes an implantable device coated with a composition comprising a compound or salt of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccharides, polyethylene glycol, phospholipids or combinations thereof to impart controlled release characteristics in the composition.

Another aspect of the invention relates to inhibiting $Na_V1.8$ activity in a biological sample or a subject, which method comprises administering to the subject, or contacting said biological sample with a compound of the invention, a pharmaceutically acceptable salt thereof, or a pharmaceutical composition thereof. The term "biological sample," as used herein, includes, without limitation, cell cultures or extracts thereof, biopsied material obtained from a mammal or extracts thereof, and blood, saliva, urine, feces, semen, tears, or other body fluids or extracts thereof.

Inhibition of $Na_V1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

skilled in the art would appreciate, the functional groups of the intermediate compounds in the methods described below may need to be protected by suitable protecting groups. Protecting groups may be added or removed in accordance with standard techniques, which are well-known to those skilled in the art. The use of protecting groups is described in detail in T. G. M. Wuts et al., *Greene's Protective Groups in Organic Synthesis* (4th ed. 2006).

In general, the compounds of formula (I-A) where L is O can be synthesized according to the general methods outlined in Scheme 1 and the specific procedures discussed in the Examples. The starting materials for the synthesis described in Scheme 1 are commercially available or can be prepared according to methods known to one skilled in the art.

Scheme 1. Synthesis of Compounds of Formula (I-a) (L = O)

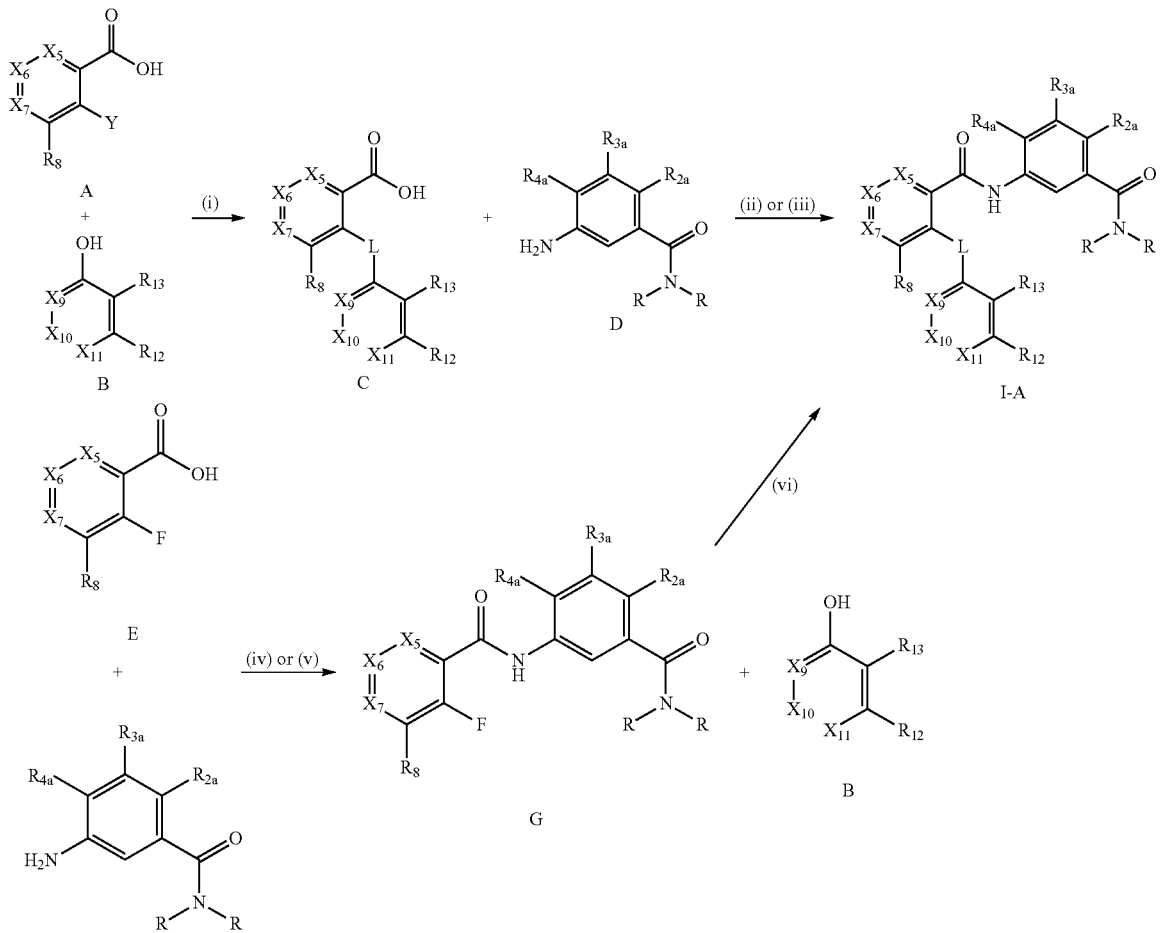

(i) base (e.g., $Cs_2CO_3$), solvent (e.g., toluene), and catalyst (e.g., CuI) (Y = Br); or base (e.g., $K_2CO_3$), solvent (e.g., DMF), and heat (Y = F); (ii) oxalyl chloride/thionyl chloride, DMF, and solvent (e.g., $CH_2Cl_2$), then D, base (e.g., DIEA), and solvent (e.g., THF); (iii) coupling agent (e.g., HATU, EDCI, HOBT), base (e.g., N-methylmorpholine, $Et_3N$), solvent (e.g., DMF, dichloromethane); (iv) oxalyl chloride/thionyl chloride, DMF and solvent (e.g., $CH_2Cl_2$), then F, base (e.g, DIPEA), and solvent (e.g., THF, $CH_2Cl_2$); (v) coupling agent (e.g., HATU, EDCI, HOBT), base (e.g., N-methylmorpholine, $Et_3N$), solvent (e.g., DMF, dichloromethane); (vi) base (e.g., $K_2CO_3$), solvent (e.g., DMF), and heat.

Synthesis of the Compounds of the Invention

The compounds of the invention can be prepared from known materials by the following methods, similar methods, and other methods known to one skilled in the art. As one In general, the compounds of formulas (I-B) and (II) where L is O can be synthesized by methods analogous to the general methods outlined in Scheme 1, and by the specific procedures discussed in the Examples.

In general, the compounds of formula (I-A) where L is a single bond can be synthesized according to the general methods outlined in Scheme 2 and the specific procedures discussed in the Examples. The starting materials for the synthesis described in Scheme 2 are commercially available or can be prepared according to methods known to one skilled in the art.

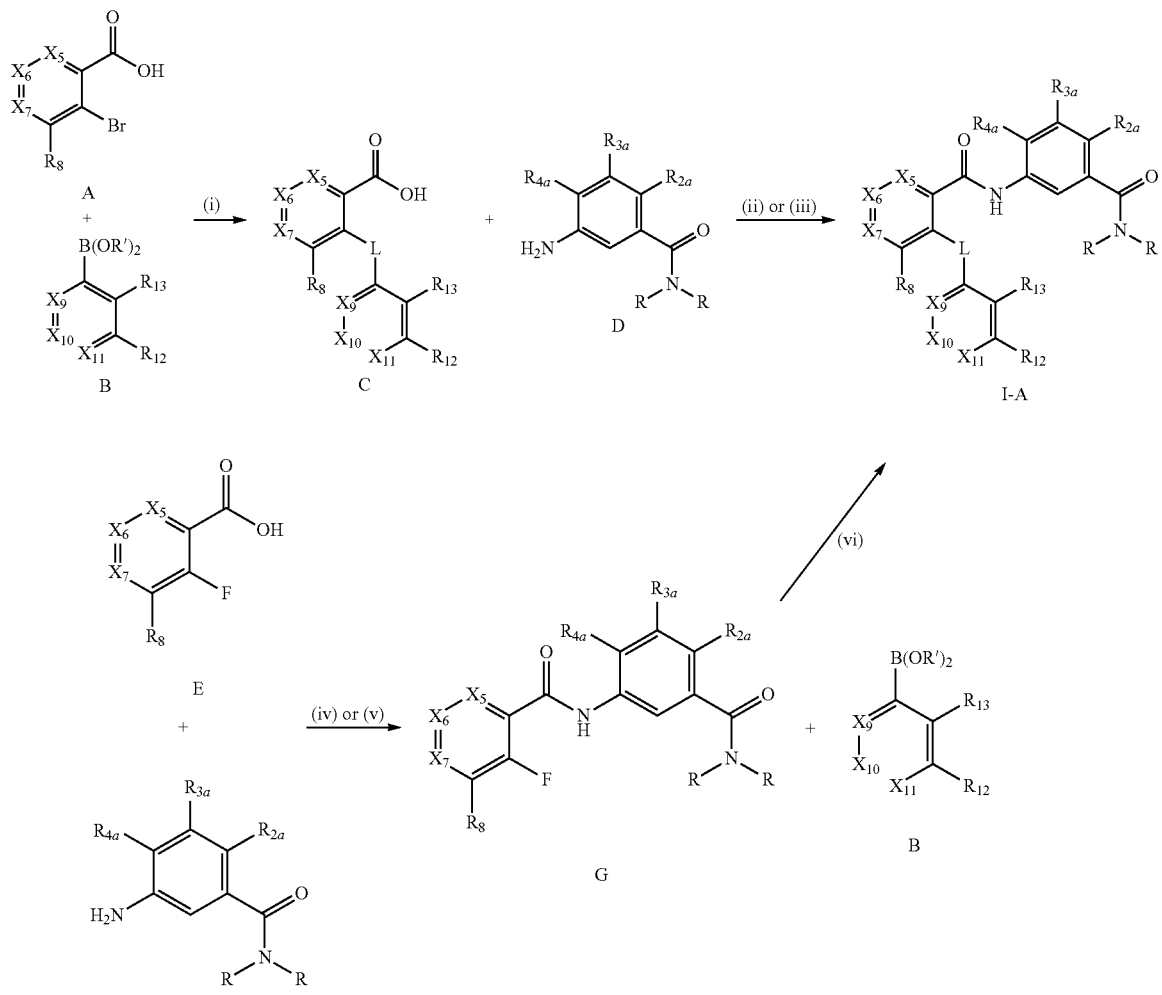

Scheme 2. Synthesis of Compounds of Formula (I-A) (L = single bond)

R' = H or CH₃
(i) palladium catalyst (e.g., Pd(PPh₃)₄), base (e.g., Na₂CO₃), and solvent (e.g., dioxane); (ii) oxalyl chloride/thionyl chloride, DMF and solvent (e.g., CH₂Cl₂), then D, base (e.g., DIEA) and solvent (e.g., THF); (iii) coupling agent (e.g., HATU, EDCl, HOBT, T3P), base (e.g., N-methylmorpholine, Et₃N), solvent (e.g., DMF, dichloromethane, isopropyl acetate); (iv) oxalyl chloride/thionyl chloride, DMF and solvent (e.g., CH₂Cl₂), then F, base (e.g., DIPEA), and solvent (e.g., THF, CH₂Cl₂); (v) coupling agent (e.g., HATU, EDCl, HOBT, T3P), base (e.g., N-methylmorpholine, Et₃N), solvent (e.g., DMF, dichloromethane, isopropyl acetate); (vi) palladium catalyst (e.g., Pd(PPh₃)₄), base (e.g., Na₂CO₃), and solvent (e.g., dioxane).

In general, the compounds of formulas (I-B) and (II) where L is a single bond can be synthesized by methods analogous to the general methods outlined in Scheme 2, and by the specific procedures discussed in the Examples.

In general, the compounds of formula (I-A) where L is $CR_2$ can be synthesized according to the general methods outlined in Scheme 3. The starting materials for the synthesis described in Scheme 3 are commercially available or can be prepared according to methods known to one skilled in the art.

209

Scheme 3. Synthesis of Compounds of Formula (I-A) (L = CR$_2$)

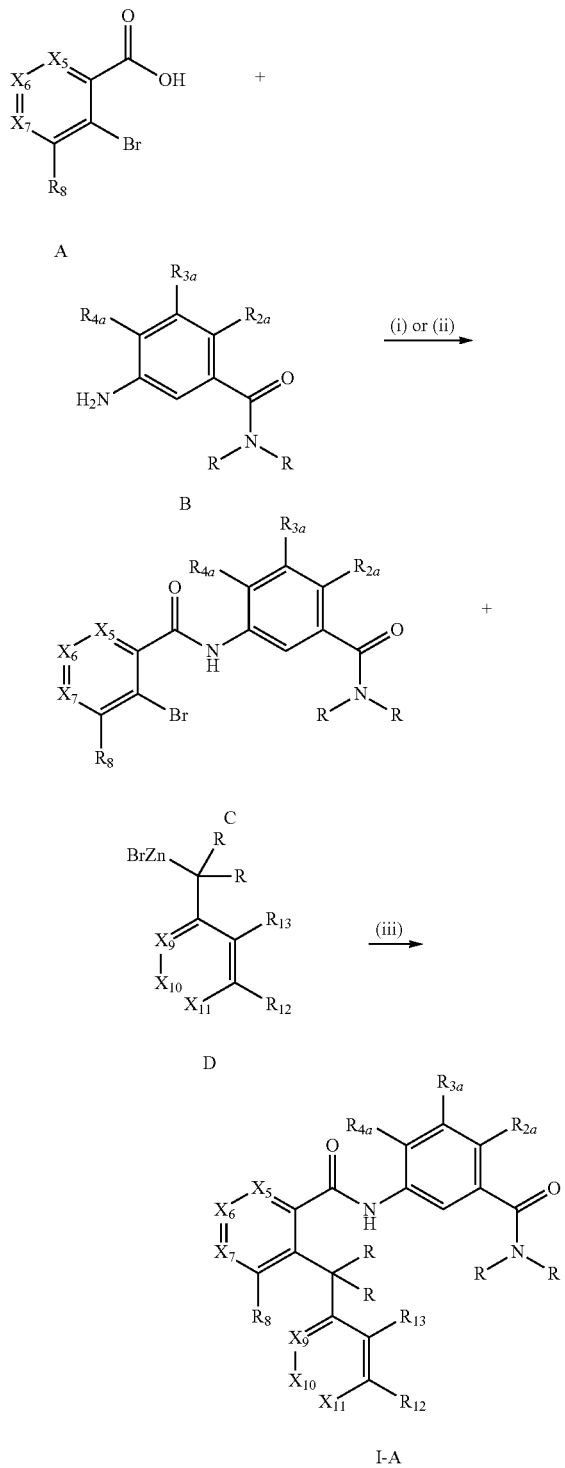

I-A (i) oxalyl chloride/thionyl chloride, DMF and solvent (e.g. CH$_2$Cl$_2$) then B, base (e.g. DIEA, pyridine) and solvent (e.g. THF); (ii) coupling agent (e.g. HATU, EDCI, HOBT, T$_3$P), base (e.g. N-methylmorpholine, Et$_3$N), solvent (e.g. DMF, dichloromethane, isopropyl acetate); (iii) palladium catalyst (e.g. Pd$_2$(dba)$_3$, ligand (e.g. X-Phos) and solvent (e.g. THF)

In general, the compounds of formulas (I-B) and (II) where L is CR$_2$ can be synthesized by methods analogous to the general methods outlined in Scheme 3.

210

Radiolabeled Analogs of the Compounds of the Invention

In another aspect, the invention relates to radiolabeled analogs of the compounds of the invention. As used herein, the term "radiolabeled analogs of the compounds of the invention" refers to compounds that are identical to the compounds of the invention, including the compounds of formulas (I-B-4), (I-B-5), (I-B-6), (I-B-7), (I-B-8), (I-B-9), (I-B-10), (II), (II-A-1), (II-A-2), (II-B-1), (II-B-2), (II-B3-3), (II-B-4), and (II-B-5), and all of the embodiments thereof, as described herein, and the compounds identified in Tables 1, 1A, 1B, and 1C, except that one or more atoms has been replaced with a radioisotope of the atom present in the compounds of the invention.

As used herein, the term "radioisotope" refers to an isolope of an element that is known to undergo spontaneous radioactive decay. Examples of radioisotopes include $^3$H, $^{14}$C, $^{32}$P $^{35}$S, $^{18}$F, $^{36}$Cl, and the like, as well as the isotopes for which no decay mode is identified in V. S. Shirley & C. M. Lederer, Isotopes Project, Nuclear Science Division, Lawrence Berkeley Laboratory, Table of Nuclides (January 1980).

The radiolabeled analogs can be used in a number of beneficial ways, including in various types of assays, such as substrate tissue distribution assays. For example, tritium ($^3$H)- and/or carbon-14 ($^{14}$C)-labelled compounds are particularly useful for various types of assays, such as substrate tissue distribution assays, due to relatively simple preparation and excellent detectability.

In another aspect, the invention relates to pharmaceutically acceptable salts of the radiolabeled analogs, in accordance with any of the embodiments described herein in connection with the compounds of the invention.

In another aspect, the invention relates to pharmaceutical compositions comprising the radiolabeled analogs, or pharmaceutically acceptable salts thereof, and a pharmaceutically acceptable carrier, adjuvant or vehicle, in accordance with any of the embodiments described herein in connection with the compounds of the invention.

In another aspect, the invention relates to methods of inhibiting voltage-gated sodium channels and methods of treating or lessening the severity of various diseases and disorders, including pain, in a subject comprising administering an effective amount of the radiolabeled analogs, pharmaceutically acceptable salts thereof, and pharmaceutical compositions thereof, in accordance with any of the embodiments described herein in connection with the compounds of the invention.

In another aspect, the invention relates to radiolabeled analogs, pharmaceutically acceptable salts thereof, and pharmaceutical compositions thereof, for use, in accordance with any of the embodiments described herein in connection with the compounds of the invention.

In another aspect, the invention relates to the use of the radiolabeled analogs, or pharmaceutically acceptable salts thereof, and pharmaceutical compositions thereof, for the manufacture of medicaments, in accordance with any of the embodiments described herein in connection with the compounds of the invention.

In another aspect, the radiolabeled analogs, pharmaceutically acceptable salts thereof, and pharmaceutical compositions thereof, can be employed in combination therapies, in accordance with any of the embodiments described herein in connection with the compounds of the invention.

ENUMERATED EMBODIMENTS

Further embodiments of the disclosure are set out in the following numbered clauses:

1. A compound of formula (I-A)

I-A or a pharmaceutically acceptable salt thereof, wherein:
L is O, C(R)$_2$, or a single bond;
X$_5$ is N or CR$_5$;
X$_6$ is N or CR$_6$;
X$_7$ is N or CR$_7$;
X$_9$ is N or CR$_9$;
X$_{10}$ is N or CR$_{10}$;
X$_{11}$ is N or CR$_{11}$;
each R is independently H or C$_1$-C$_6$ alkyl;
R$_{2a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_{3a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_{4a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_5$, R$_6$, and R$_7$ are defined as follows:
  (i) R$_5$, R$_6$, and R$_7$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$;
  (ii) R$_5$ is H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$; and R$_6$ and R$_7$, together with the carbon atoms to which they are attached, form a ring of formula:

or
  (iii) R$_5$ and R$_6$, together with the carbon atoms to which they are attached, form a ring of formula:

and
R$_7$ is H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
R$_8$ is H or —O—(CH$_2$)$_n$—R$_w$;
R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$; or R$_{12}$ and R$_{13}$, together with the carbon atoms to which they are attached, form a ring of formula:

Y$_1$, Y$_2$, Z$_1$, and Z$_2$ are each independently O or C(R$_4$)$_2$;
each R$_{14}$ is independently H, halo, C$_1$-C$_4$ alkyl, or C$_1$-C$_4$ haloalkyl;
each W is independently O or a single bond;
each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, C$_1$-C$_6$ alkyl, and C$_1$-C$_6$ haloalkyl; and
n is 0 or 1;
wherein when R$_8$ is H, then at least one of X$_5$, X$_6$, and X$_7$ is not N or CH;
wherein when X$_7$ is CR$_7$ and R$_7$ is C$_1$-C$_6$ alkyl, then R$_{2a}$ is not H;
wherein when R$_{4a}$ is halo, then R$_{2a}$ is not H;
wherein no more than one of X$_5$, X$_6$, and X$_7$ is N;
wherein no more than one of X$_9$, X$_{10}$, and X$_{11}$ is N; or
a compound of formula (I-B)

I-B or a pharmaceutically acceptable salt thereof, wherein:
L is O, C(R)$_2$, or a single bond;
X$_{1a}$ is N or CH;
X$_{2a}$ is N, N$^+$—O$^-$, or CR$_{2a}$;
X$_{3a}$ is N or CR$_{3a}$;
X$_{4a}$ is N or CR$_{4a}$;
X$_5$ is N or CR$_5$;
X$_6$ is N or CR$_6$;
X$_7$ is N or CR$_7$;
X$_9$ is N or CR$_9$;

$X_{10}$ is N or $CR_{10}$;
$X_{11}$ is N or $CR_{11}$;
each R is independently H or $C_1$-$C_6$ alkyl;
$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are defined as follows:
  (i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
  (ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

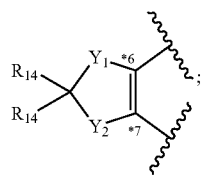

or
  (iii) $R_5$ and $R_6$, together with the carbon atoms to which they are attached, form a ring of formula:

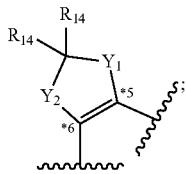

and
$R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_8$ is H or —O—$(CH_2)_n$—$R_w$;
$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

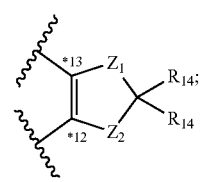

$Y_1$, $Y_2$, $Z_1$, and $Z_2$ are each independently O or $C(R_{14})_2$;
each $R_{14}$ is independently H, halo, $C_1$-$C_4$ alkyl, or $C_1$-$C_4$ haloalkyl;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein when $R_8$ is H, then at least one of $X_5$, $X_6$, and $X_7$ is not N or CH;
wherein one or two of $X_{1a}$, $X_{2a}$, $X_{3a}$, and $X_{4a}$ is N or $N^+$—$O^-$;
wherein no more than one of $X_5$, $X_6$, and $X_7$ is N;
wherein no more than one of $X_9$, $X_{10}$, and $X_{11}$ is N; or
a compound of formula (II)

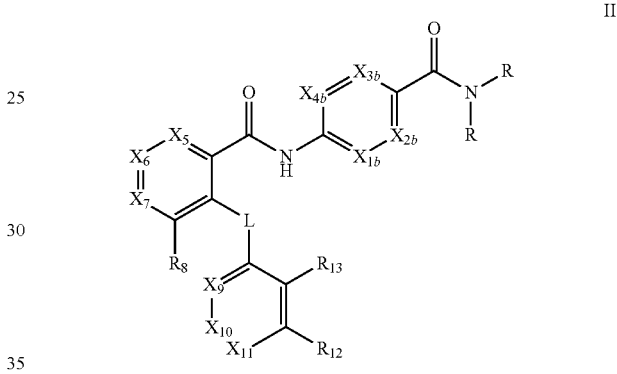

or a pharmaceutically acceptable salt thereof, wherein:
L is O, $C(R)_2$, or a single bond;
$X_{1b}$ is N or $CR_{1b}$;
$X_{2b}$ is N or $CR_{2b}$;
$X_{3b}$ is N or $CR_{3b}$;
$X_{4b}$ is N or $CR_{4b}$;
$X_5$ is N or $CR_5$;
$X_6$ is N or $CR_6$;
$X_7$ is N or $CR_7$;
$X_9$ is N or $CR_9$;
$X_{10}$ is N or $CR_{10}$;
$X_{11}$ is N or $CR_{11}$;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{2b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are defined as follows:
  (i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
  (ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

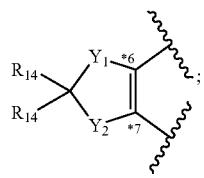

or (iii) $R_5$ and $R_6$, together with the carbon atoms to which they are attached, form a ring of formula:

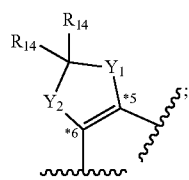

and $R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

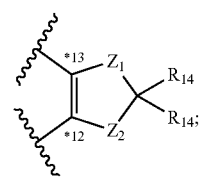

$Y_1$, $Y_2$, $Z_1$, and $Z_2$ are each independently O or $C(R_{14})_2$;

each $R_{14}$ is independently H, halo, $C_1$-$C_4$ alkyl, or $C_1$-$C_4$ haloalkyl;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein when $R_8$ is H, then at least one of $X_5$, $X_6$, and $X_7$ is not N or CH;

wherein no more than two of $X_{1b}$, $X_{2b}$, $X_{3b}$, and $X_{4b}$ is N;

wherein no more than one of $X_5$, $X_6$, and $X_7$ is N;

wherein no more than one of $X_9$, $X_{10}$, and $X_{11}$ is N.

2. A compound of formula (I-A)

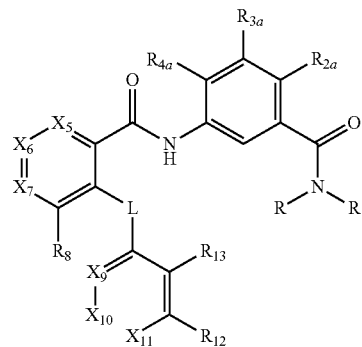

I-A or a pharmaceutically acceptable salt thereof, wherein:

L is O, $C(R)_2$, or a single bond;

$X_5$ is N or $CR_5$;

$X_6$ is N or $CR_6$;

$X_7$ is N or $CR_7$;

$X_9$ is N or $CR_9$;

$X_{10}$ is N or $CR_{10}$;

$X_1$ is N or $CR_{11}$;

each R is independently H or $C_1$-$C_6$ alkyl;

$R_{2a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{3a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_{4a}$ is H, halo, OH, $C_1$-$C_6$ alkyl, $C_1$-$C_6$ haloalkyl, $C_1$-$C_6$ alkoxy, or $C_1$-$C_6$ haloalkoxy;

$R_5$, $R_6$, and $R_7$ are defined as follows:

(i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;

(ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

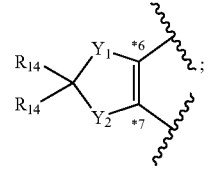

or (iii) $R_5$ and $R_6$, together with the carbon atoms to which they are attached, form a ring of formula:

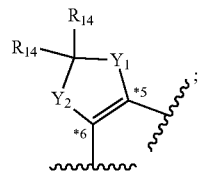

and $R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

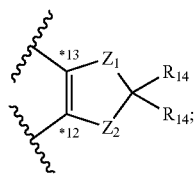

$Y_1$, $Y_2$, $Z_1$, and $Z_2$ are each independently O or $C(R_{14})_2$;

each $R_{14}$ is independently H, halo, $C_1$-$C_4$ alkyl, or $C_1$-$C_4$ haloalkyl;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein when $R_8$ is H, then at least one of $X_5$, $X_6$, and $X_7$ is not N or CH;

wherein when $X_7$ is $CR_7$ and $R_7$ is $C_1$-$C_6$ alkyl, then $R_{2a}$ is not H;

wherein when $R_{4a}$ is halo, then $R_{2a}$ is not H;

wherein no more than one of $X_5$, $X_6$, and $X_7$ is N;

wherein no more than one of $X_9$, $X_{10}$, and $X_{11}$ is N.

3. The compound of clause 2, wherein the compound has formula (I-A-1)

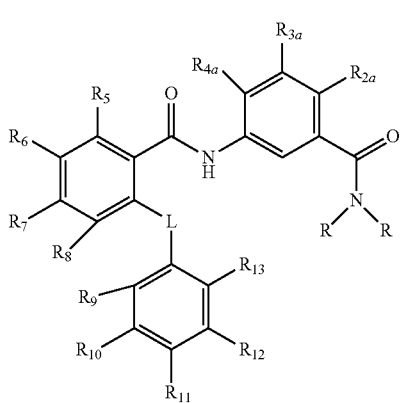

I-A-1 or a pharmaceutically acceptable salt thereof, wherein:

L, R, $R_{2a}$, $R_{3a}$, $R_{4a}$, $R_8$, $R_9$, $R_{10}$, and $R_{11}$ are as defined in clause 2;

$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$.

4. The compound of clause 2 or 3, or a pharmaceutically acceptable salt thereof, wherein L is O.

5. The compound of any one of clauses 2-4, or a pharmaceutically acceptable salt thereof, wherein each R is H.

6. The compound of any one of clauses 2-5, or a pharmaceutically acceptable salt thereof, wherein $R_{2a}$ is H, halo, OH, $C_1$-$C_6$ alkyl, or $C_1$-$C_6$ alkoxy.

7. The compound of any one of clauses 2-6, or a pharmaceutically acceptable salt thereof, wherein $R_{3a}$ is H or halo.

8. The compound of any one of clauses 2-7, or a pharmaceutically acceptable salt thereof, wherein $R_{4a}$ is H or $C_1$-$C_6$ alkyl.

9. The compound of any one of clauses 2-8, or a pharmaceutically acceptable salt thereof, wherein $R_5$ is H, halo, $C_1$-$C_6$ alkyl, $C_1$-$C_6$ haloalkyl, or $C_1$-$C_6$ alkoxy.

10. The compound of any one of clauses 2-9, or a pharmaceutically acceptable salt thereof, wherein $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$.

11. The compound of any one of clauses 2-10, or a pharmaceutically acceptable salt thereof, wherein $R_7$ is H, halo, $C_1$-$C_6$ alkyl, $C_1$-$C_6$ haloalkyl, $C_1$-$C_6$ alkoxy, or —W—$(CH_2)_n$—$R_w$.

12. The compound of any one of clauses 2-11, or a pharmaceutically acceptable salt thereof, wherein $R_8$ is H or $OCH_2Ph$.

13. The compound of any one of clauses 2-12, or a pharmaceutically acceptable salt thereof, wherein $R_9$ is H, halo, OH, $C_1$-$C_6$ alkyl, $C_1$-$C_6$ alkoxy, or —W—$(CH_2)_n$—$R_w$.

14. The compound of any one of clauses 2-13, or a pharmaceutically acceptable salt thereof, wherein $R_{10}$ is H, halo, OH, or $C_1$-$C_6$ alkoxy.

15. The compound of any one of clauses 2-14, or a pharmaceutically acceptable salt thereof, wherein $R_{11}$ is H, halo, $C_1$-$C_6$ alkoxy, or $C_1$-$C_6$ haloalkoxy.

16. The compound of any one of clauses 2-15, or a pharmaceutically acceptable salt thereof, wherein $R_{12}$ is H, and $R_{13}$ is H.

17. The compound of clause 2, wherein the compound is selected from the group of compounds identified in Tables 1, 1A, and 1B, or a pharmaceutically acceptable salt thereof.

18. The compound of any one of clauses 1-17.

19. A pharmaceutical composition comprising a therapeutically effective amount of the compound of any one of clauses 1-17, or a pharmaceutically acceptable salt thereof, or the compound of clause 18 and one or more pharmaceutically acceptable carriers or vehicles.

20. A pharmaceutical composition comprising the compound of any one of clauses 1-17, or a pharmaceutically acceptable salt thereof, or the compound of clause 18 and one or more pharmaceutically acceptable carriers or vehicles.

21. A method of inhibiting a voltage-gated sodium channel in a subject comprising administering to the subject the compound of any one of clauses 1-17, or a pharmaceutically acceptable salt thereof, the compound of clause 18, or the pharmaceutical composition of clause 19 or 20.

22. The method of clause 21, wherein the voltage-gated sodium channel is Nav1.8.

23. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of any one of clauses 1-17, or a pharmaceutically acceptable salt thereof, the compound of clause 18, or the pharmaceutical composition of clause 19 or 20.

24. The method of clause 23, where the method comprises treating or lessening the severity in the subject of neuropathic pain.

25. The method of clause 24, wherein the neuropathic pain comprises post-herpetic neuralgia.

26. The method of clause 24, wherein the neuropathic pain comprises idiopathic small-fiber neuropathy.

27. The method of clause 23, wherein the method comprises treating or lessening the severity in the subject of musculoskeletal pain.

28. The method of clause 27, wherein the musculoskeletal pain comprises osteoarthritis pain.

29. The method of clause 23, wherein the method comprises treating or lessening the severity in the subject of acute pain.

30. The method of clause 29, wherein the acute pain comprises acute post-operative pain.

31. The method of clause 23, wherein the method comprises treating or lessening the severity in the subject of postsurgical pain.

32. The method of clause 31, wherein the postsurgical pain comprises bunionectomy pain.

33. The method of clause 31, wherein the postsurgical pain comprises abdominoplasty pain.

34. The method of clause 23, wherein the method comprises treating or lessening the severity in the subject of visceral pain.

35. The method of any one of clauses 21-34, wherein said subject is treated with one or more additional therapeutic agents administered concurrently with, prior to, or subsequent to treatment with the compound, pharmaceutically acceptable salt, or pharmaceutical composition.

36. A compound of formula (I-B)

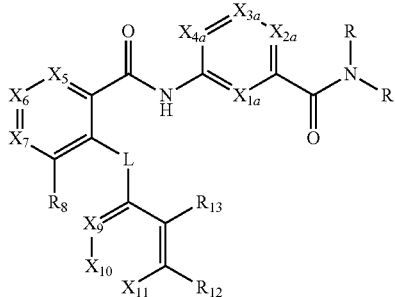

I-B or a pharmaceutically acceptable salt thereof, wherein:
L is O, C(R)$_2$, or a single bond;
X$_{1a}$ is N or CH;
X$_{2a}$ is N, N$^+$—O$^-$, or CR$_{2a}$;
X$_{3a}$ is N or CR$_{3a}$;
X$_{4a}$ is N or CR$_{4a}$;
X$_5$ is N or CR$_5$;
X$_6$ is N or CR$_6$;
X$_7$ is N or CR$_7$;
X$_9$ is N or CR$_9$;
X$_{10}$ is N or CR$_{10}$;
X$_{11}$ is N or CR$_{11}$;
each R is independently H or C$_1$-C$_6$ alkyl;
R$_{2a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_{3a}$ is H, halo, OH, C$_1$-C$_6$ alkyl, C$_1$-C$_6$ haloalkyl, C$_1$-C$_6$ alkoxy, or C$_1$-C$_6$ haloalkoxy;

R$_{4a}$ is H, halo, OH, C$_1$-C$_6$ alkyl, C$_1$-C$_6$ haloalkyl, C$_1$-C$_6$ alkoxy, or C$_1$-C$_6$ haloalkoxy;
R$_5$, R$_6$, and R$_7$ are defined as follows:
  (i) R$_5$, R$_6$, and R$_7$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$;
  (ii) R$_5$ is H, halo, CN, OH, C$_1$-C$_6$ alkyl, C$_1$-C$_6$ haloalkyl, C$_1$-C$_6$ alkoxy, C$_1$-C$_6$ haloalkoxy, C$_1$-C$_6$ alkylamino, or —W—(CH$_2$)$_n$—R$_w$; and R$_6$ and R$_7$, together with the carbon atoms to which they are attached, form a ring of formula:

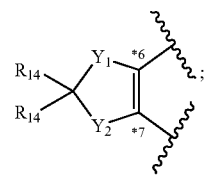

or
  (iii) R$_5$ and R$_6$, together with the carbon atoms to which they are attached, form a ring of formula:

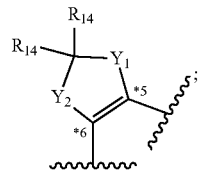

and
R$_7$ is H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
R$_8$ is H or —O—(CH$_2$)$_n$—R$_w$;
R$_9$, R$_{10}$, and R$_{11}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$;
R$_{12}$ and R$_{13}$ are each independently H, halo, CN, OH, C$_1$-C$_6$ alkyl, C$_1$-C$_6$ haloalkyl, C$_1$-C$_6$ alkoxy, C$_1$-C$_6$ haloalkoxy, or —W—(CH$_2$)$_n$—R$_w$; or R$_{12}$ and R$_{13}$, together with the carbon atoms to which they are attached, form a ring of formula:

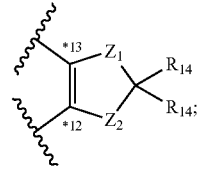

Y$_1$, Y$_2$, Z$_1$, and Z$_2$ are each independently O or C(R$_{14}$)$_2$;
each R$_{14}$ is independently H, halo, C$_1$-C$_4$ alkyl, or C$_1$-C$_4$ haloalkyl;
each W is independently O or a single bond;
each R$_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein when $R_8$ is H, then at least one of $X_5$, $X_6$, and $X_7$ is not N or CH;

wherein one or two of $X_{1a}$, $X_{2a}$, $X_{3a}$, and $X_{4a}$ is N or $N^+$—$O^-$;

wherein no more than one of $X_5$, $X_6$, and $X_7$ is N;

wherein no more than one of $X_9$, $X_{10}$, and $X_{11}$ is N.

37. The compound of clause 36, wherein the compound has formula (I-B-1)

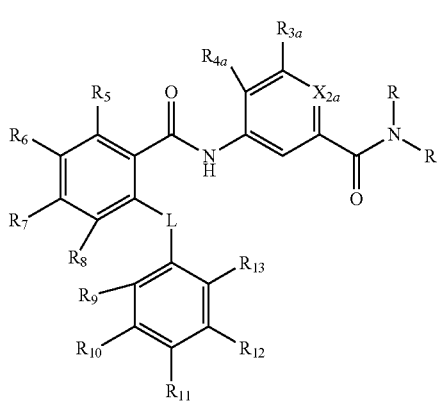

I-B-1 or a pharmaceutically acceptable salt thereof, wherein:

L, R, $R_{2a}$, $R_{3a}$, $R_{4a}$, $R_8$, $R_9$, $R_{10}$, and $R_{11}$ are as defined in clause 36;

$X_{2a}$ is N or $N^+$—$O^-$;

$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$.

38. The compound of clause 36 or 37, or a pharmaceutically acceptable salt thereof, wherein L is O.

39. The compound of any one of clauses 36-38, or a pharmaceutically acceptable salt thereof, wherein $X_{2a}$ is N.

40. The compound of any one of clauses 36-38, or a pharmaceutically acceptable salt thereof, wherein $X_{2a}$ is $N^+$—$O^-$.

41. The compound of any one of clauses 36-40, or a pharmaceutically acceptable salt thereof, wherein each R is independently H or $CH_3$.

42. The compound of any one of clauses 36-41, or a pharmaceutically acceptable salt thereof, wherein $R_{2a}$ is H or halo.

43. The compound of any one of clauses 36-42, or a pharmaceutically acceptable salt thereof, wherein $R_{3a}$ is H or $C_1$-$C_6$ alkyl.

44. The compound of any one of clauses 36-43, or a pharmaceutically acceptable salt thereof, wherein $R_{4a}$ is H, halo, or $C_1$-$C_6$ alkyl.

45. The compound of any one of clauses 36-44, or a pharmaceutically acceptable salt thereof, wherein $R_5$ is H, halo, $C_1$-$C_6$ alkyl, $C_1$-$C_6$ haloalkyl, $C_1$-$C_6$ alkoxy, or $C_1$-$C_6$ alkylamino.

46. The compound of any one of clauses 36-45, or a pharmaceutically acceptable salt thereof, wherein $R_6$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$.

47. The compound of any one of clauses 36-46, or a pharmaceutically acceptable salt thereof, wherein $R_7$ is H, halo, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$.

48. The compound of any one of clauses 36-47, or a pharmaceutically acceptable salt thereof, wherein $R_8$ is H.

49. The compound of any one of clauses 36-48, or a pharmaceutically acceptable salt thereof, wherein $R_9$ is H, halo, OH, $C_1$-$C_6$ alkyl, $C_1$-$C_6$ alkoxy, or $C_1$-$C_6$ haloalkoxy.

50. The compound of any one of clauses 36-49, or a pharmaceutically acceptable salt thereof, wherein $R_{10}$ is H or halo.

51. The compound of any one of clauses 36-50, or a pharmaceutically acceptable salt thereof, wherein $R_{11}$ is halo, $C_1$-$C_6$ alkoxy, or $C_1$-$C_6$ haloalkoxy.

52. The compound of any one of clauses 36-51, or a pharmaceutically acceptable salt thereof, wherein $R_{12}$ is H, and $R_{13}$ is H.

53. The compound of clause 36, wherein the compound is selected from the group of compounds identified in Tables 1, 1A, and 1B, or a pharmaceutically acceptable salt thereof.

54. The compound of any one of clauses 36-53.

55. A pharmaceutical composition comprising a therapeutically effective amount of the compound of any one of clauses 36-53, or a pharmaceutically acceptable salt thereof, or the compound of clause 54 and one or more pharmaceutically acceptable carriers or vehicles.

56. A pharmaceutical composition comprising the compound of any one of clauses 36-53, or a pharmaceutically acceptable salt thereof, or the compound of clause 54 and one or more pharmaceutically acceptable carriers or vehicles.

57. A method of inhibiting a voltage-gated sodium channel in a subject comprising administering to the subject the compound of any one of clauses 36-53, or a pharmaceutically acceptable salt thereof, or the compound of clause 54, or the pharmaceutical composition of clause 55 or 56.

58. The method of clause 57, wherein the voltage-gated sodium channel is Nav1.8.

59. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of any one of clauses 36-53, or a pharmaceutically acceptable salt thereof, or the compound of clause 54, or the pharmaceutical composition of clause 55 or 56.

60. The method of clause 59, where the method comprises treating or lessening the severity in the subject of neuropathic pain.

61. The method of clause 60, wherein the neuropathic pain comprises post-herpetic neuralgia.

62. The method of clause 60, wherein the neuropathic pain comprises idiopathic small-fiber neuropathy.

63. The method of clause 59 wherein the method comprises treating or lessening the severity in the subject of musculoskeletal pain.

64. The method of clause 63, wherein the musculoskeletal pain comprises osteoarthritis pain.

65. The method of clause 59, wherein the method comprises treating or lessening the severity in the subject of acute pain.

66. The method of clause 65, wherein the acute pain comprises acute post-operative pain.

67. The method of clause 59, wherein the method comprises treating or lessening the severity in the subject of postsurgical pain.

68. The method of clause 67, wherein the postsurgical pain comprises bunionectomy pain.

69. The method of clause 67, wherein the postsurgical pain comprises abdominoplasty pain.

70. The method of clause 59, wherein the method comprises treating or lessening the severity in the subject of visceral pain.

71. The method of any one of clauses 57-70, wherein said subject is treated with one or more additional therapeutic agents administered concurrently with, prior to, or subsequent to treatment with the compound, pharmaceutically acceptable salt, or pharmaceutical composition.

72. A compound of formula (II)

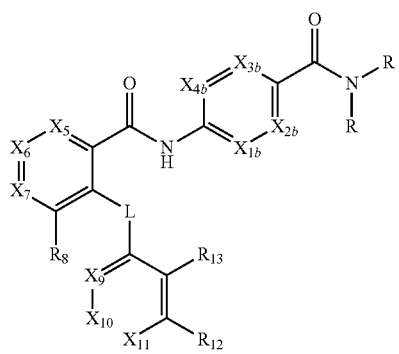

II or a pharmaceutically acceptable salt thereof, wherein:
L is O, $C(R)_2$, or a single bond;
$X_{1b}$ is N or $CR_{1b}$;
$X_{2b}$ is N or $CR_{2b}$;
$X_{3b}$ is N or $CR_{3b}$;
$X_{4b}$ is N or $CR_{4b}$;
$X_5$ is N or $CR_5$;
$X_6$ is N or $CR_6$;
$X_7$ is N or $CR_7$;
$X_9$ is N or $CR_9$;
$X_{10}$ is N or $CR_{10}$;
$X_{11}$ is N or $CR_{11}$;
each R is independently H or $C_1$-$C_6$ alkyl;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{2b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are defined as follows:
(i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
(ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

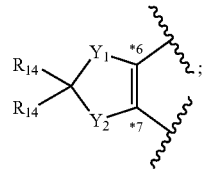

or (iii) $R_5$ and $R_6$, together with the carbon atoms to which they are attached, form a ring of formula:

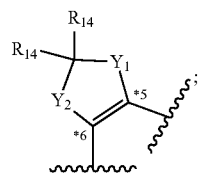

and $R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

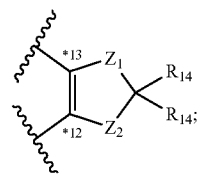

$Y_1$, $Y_2$, $Z_1$, and $Z_2$ are each independently O or $C(R_{14})_2$;
each $R_{14}$ is independently H, halo, $C_1$-$C_4$ alkyl, or $C_1$-$C_4$ haloalkyl;
each W is independently O or a single bond;
each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and
n is 0 or 1;
wherein when $R_8$ is H, then at least one of $X_5$, $X_6$, and $X_7$ is not N or CH;
wherein no more than two of $X_{1b}$, $X_{2b}$, $X_{3b}$, and $X_{4b}$ is N;
wherein no more than one of $X_5$, $X_6$, and $X_7$ is N;
wherein no more than one of $X_9$, $X_{10}$, and $X_{11}$ is N.

73. The compound of clause 36, wherein the compound has formula (II-B-1)

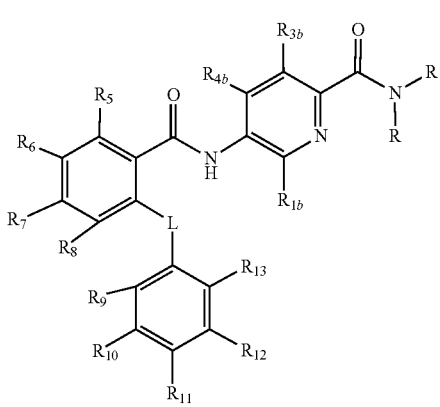

II-B-1 or a pharmaceutically acceptable salt thereof, wherein:
L, R, $R_{1b}$, $R_{3b}$, $R_{4b}$, $R_8$, $R_9$, $R_{10}$, and $R_{11}$ are as defined in clause 73;
$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and
$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$.

74. The compound of clause 72 or 73, or a pharmaceutically acceptable salt thereof, wherein L is O.

75. The compound of any one of clauses 72-74, or a pharmaceutically acceptable salt thereof, wherein each R is independently H or $CH_3$.

76. The compound of any one of clauses 72-75, or a pharmaceutically acceptable salt thereof, wherein $R_{1b}$ is H, halo, or $C_1$-$C_6$ alkyl.

77. The compound of any one of clauses 72-76, or a pharmaceutically acceptable salt thereof, wherein $R_{2b}$ is H or halo.

78. The compound of any one of clauses 72-77, or a pharmaceutically acceptable salt thereof, wherein $R_{3b}$ is H.

79. The compound of any one of clauses 72-78, or a pharmaceutically acceptable salt thereof, wherein $R_{4b}$ is H or $C_1$-$C_6$ alkyl.

80. The compound of any one of clauses 72-79, or a pharmaceutically acceptable salt thereof, wherein $R_5$ is H, halo, $C_1$-$C_6$ alkyl, $C_1$-$C_6$ haloalkyl, or $C_1$-$C_6$ alkoxy.

81. The compound of any one of clauses 72-80, or a pharmaceutically acceptable salt thereof, wherein $R_6$ is H, halo, $C_1$-$C_6$ alkyl, $C_1$-$C_6$ haloalkyl, $C_1$-$C_6$ alkoxy, or $C_1$-$C_6$ haloalkoxy.

82. The compound of any one of clauses 72-81, or a pharmaceutically acceptable salt thereof, wherein $R_7$ is H, halo, $C_1$-$C_6$ alkyl, $C_1$-$C_6$ haloalkyl, $C_1$-$C_6$ alkoxy, or $C_1$-$C_6$ haloalkoxy.

83. The compound of any one of clauses 72-82, or a pharmaceutically acceptable salt thereof, wherein $R_8$ is H.

84. The compound of any one of clauses 72-83, or a pharmaceutically acceptable salt thereof, wherein $R_9$ is H, $C_1$-$C_6$ alkyl, or $C_1$-$C_6$ alkoxy.

85. The compound of any one of clauses 72-84, or a pharmaceutically acceptable salt thereof, wherein $R_{10}$ is H or halo.

86. The compound of any one of clauses 72-85, or a pharmaceutically acceptable salt thereof, wherein $R_{11}$ is halo, $C_1$-$C_6$ alkoxy, or $C_1$-$C_6$ haloalkoxy.

87. The compound of any one of clauses 72-86, or a pharmaceutically acceptable salt thereof, wherein $R_{12}$ is H, and $R_{13}$ is H.

88. The compound of clause 72, wherein the compound is selected from the group of compounds identified in Tables 1, 1A, and 1B, or a pharmaceutically acceptable salt thereof.

89. The compound of any one of clauses 72-88.

90. A pharmaceutical composition comprising a therapeutically effective amount of the compound of any one of clauses 72-88, or a pharmaceutically acceptable salt thereof, or the compound of clause 89 and one or more pharmaceutically acceptable carriers or vehicles.

91. A pharmaceutical composition comprising the compound of any one of clauses 72-88, or a pharmaceutically acceptable salt thereof, or the compound of clause 89 and one or more pharmaceutically acceptable carriers or vehicles.

92. A method of inhibiting a voltage-gated sodium channel in a subject comprising administering to the subject the compound of any one of clauses 72-88, or a pharmaceutically acceptable salt thereof, or the compound of clause 89, or the pharmaceutical composition of clause 90 or 91.

93. The method of clause 92, wherein the voltage-gated sodium channel is Nav1.8.

94. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of any one of clauses 72-88, or a pharmaceutically acceptable salt thereof, or the compound of clause 89, or the pharmaceutical composition of clause 90 or 91.

95. The method of clause 94, where the method comprises treating or lessening the severity in the subject of neuropathic pain.

96. The method of clause 95, wherein the neuropathic pain comprises post-herpetic neuralgia.

97. The method of clause 95, wherein the neuropathic pain comprises idiopathic small-fiber neuropathy.

98. The method of clause 94 wherein the method comprises treating or lessening the severity in the subject of musculoskeletal pain.

99. The method of clause 98, wherein the musculoskeletal pain comprises osteoarthritis pain.

100. The method of clause 94, wherein the method comprises treating or lessening the severity in the subject of acute pain.

101. The method of clause 100, wherein the acute pain comprises acute post-operative pain.

102. The method of clause 94, wherein the method comprises treating or lessening the severity in the subject of postsurgical pain.

103. The method of clause 102, wherein the postsurgical pain comprises bunionectomy pain.

104. The method of clause 102, wherein the postsurgical pain comprises abdominoplasty pain.

105. The method of clause 94, wherein the method comprises treating or lessening the severity in the subject of visceral pain.

106. The method of any one of clauses 92-105, wherein said subject is treated with one or more additional therapeutic agents administered concurrently with, prior to, or subsequent to treatment with the compound, pharmaceutically acceptable salt, or pharmaceutical composition.

EXAMPLES

General methods. $^1$H NMR (400 MHz) spectra were obtained as solutions in an appropriate deuterated solvent such as dimethyl sulfoxide-d$_6$ (DMSO-d6).

Compound purity, retention time, and electrospray mass spectrometry (ESI-MS) data were determined by LC/MS analysis using one of 9 methods: Methods A-I.

LC/MS Method A. LC/MS analysis was conducted using a Waters Acquity Ultra Performance LC system by reverse phase UPLC using an Acquity UPLC BEH C18 column (30×2.1 mm, 1.7 m particle) made by Waters (pn: 186002349), and a dual gradient run from 1-99% mobile phase B over 1.2 minutes. Mobile phase A=H$_2$O (0.05% CF$_3$CO$_2$H). Mobile phase B=CH$_3$CN (0.035% CF$_3$CO$_2$H). Flow rate=1.5 mL/min, injection volume=1.5 µL, and column temperature=60° C.

LC/MS Method B. LC/MS analysis was conducted using a Waters Acquity Ultra Performance LC system by reverse phase UPLC using an Acquity UPLC BEH C18 column (50×2.1 mm, 1.7 m particle) made by Waters (pn: 186002350), and a dual gradient run from 1-99% mobile phase B over 3.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 µL, and column temperature=60° C.

LC/MS Method C. LC/MS analysis was conducted using a Waters Acquity Ultra Performance LC system by reverse phase UPLC using an Acquity UPLC BEH C18 column (50×2.1 mm, 1.7 m particle) made by Waters (pn: 186002350), and a dual gradient run from 1-99% mobile phase B over 5.0 minutes. Mobile phase A=H$_2$O (0.05% CF$_3$CO$_2$H). Mobile phase B=CH$_3$CN (0.035% CF$_3$CO$_2$H). Flow rate=1.2 mL/min, injection volume=1.5 µL, and column temperature=60° C.

LC/MS Method D. LC/MS analysis was conducted using an Acquity UPLC BEH C$_8$ column (50×2.1 mm, 1.7 m particle) made by Waters (pn: 186002877) with a (2.1×5 mm, 1.7 m particle) guard column (pn: 186003978), and a dual gradient run from 2-98% mobile phase B over 1.15 minutes. Mobile phase A=H$_2$O (10 mM ammonium formate with 0.05% ammonium hydroxide). Mobile phase B=acetonitrile. Flow rate=1.0 mL/min, injection volume=2 µL, and column temperature=45° C.

LC/MS Method E. LC/MS analysis was conducted using an Acquity UPLC BEH C$_8$ column (50×2.1 mm, 1.7 m particle) made by Waters (pn: 186002877) with a (2.1×5 mm, 1.7 m particle) guard column (pn: 186003978), and a dual gradient run from 2-98% mobile phase B over 4.45 minutes. Mobile phase A=H$_2$O (10 mM ammonium formate with 0.05% ammonium hydroxide). Mobile phase B=acetonitrile. Flow rate=0.6 mL/min, injection volume=2 µL, and column temperature=45° C.

LC/MS Method F. LC/MS analysis was conducted using an Acquity UPLC BEH C$_8$ column (50×2.1 mm, 1.7 µm particle) made by Waters (pn: 186002877) with a (2.1×5 mm, 1.7 m particle) guard column (pn: 186003978), and a dual gradient run from 2-98% mobile phase B over 1.5 minutes. Mobile phase A=H$_2$O (10 mM ammonium formate with 0.05% ammonium hydroxide). Mobile phase B=acetonitrile. Flow rate=0.6 mL/min, injection volume=2 µL, and column temperature=45° C.

LC/MS Method G. LC/MS analysis was conducted using a Shimadzu 10-A LC system by reverse phase HPLC using an Onyx Monolithic C18 column (50×4.6 mm) made by Phenomenex (pn:CH0-7644), and a dual gradient run from 5-100% mobile phase B over 4.2 minutes. Mobile phase A=H$_2$O (0.1% CF$_3$CO$_2$H). Mobile phase B=CH$_3$CN (0.1% CF$_3$CO$_2$H). Flow rate=1.5 mL/min, injection volume 10 µL and with the column at ambient temperature.

LC/MS Method H. LC/MS analysis was conducted using a Shimadzu 10-A LC system by reverse phase HPLC using an Onyx Monolithic C18 column (50×4.6 mm) made by Phenomenex (pn:CH0-7644), and a dual gradient run from 5-100% mobile phase B over 12 minutes. Mobile phase A=H$_2$O (0.1% CF$_3$CO$_2$H). Mobile phase B=CH$_3$CN (0.1% CF$_3$CO$_2$H). Flow rate=1.5 mL/min, injection volume 10 µL and with the column at ambient temperature.

LC/MS Method I. LC/MS analysis was conducted using an Acquity UPLC HSS T3 C$_8$ column (50×2.1 mm, 1.8 m particle) made by Waters (pn: 186003538), and a dual gradient run from 1-99% mobile phase B over 2.90 minutes. Mobile phase A=H$_2$O (10 mM ammonium formate). Mobile phase B=acetonitrile. Flow rate=1.2 mL/min, injection volume=1.5 µL, and column temperature=60° C.

Unless otherwise noted, where purification by reverse phase HPLC is indicated in the Examples below, samples were purified using a reverse phase HPLC-MS method using a Luna C$_{18}$ (2) column (75×30 mm, 5 µm particle size) sold by Phenomenex (pn: 00C-4252-U0-AX), and a dual gradient run from 1-99% mobile phase B over 15.0 minutes. Mobile phase A=H$_2$O (5 mM HCl). Mobile phase B=CH$_3$CN. Flow rate=50 mL/min, injection volume=950 µL, and column temperature=25° C.

Abbreviations

Unless otherwise noted, or where the context dictates otherwise, the following abbreviations shall be understood to have the following meanings:

| Abbreviation | Meaning |
| --- | --- |
| NMR | Nuclear magnetic resonance |
| ESI-MS | Electrospray mass spectrometry |
| LC/MS | Liquid chromatograph-mass spectrometry |
| UPLC | Ultra performance liquid chromatography |
| HPLC/MS/MS | High performance liquid chromatography/tandem mass spectrometry |
| IS | Internal standard |
| HPLC | High performance liquid chromatography |
| SFC | Supercritical fluid chromatography |
| ESI | Electrospray ionization |
| g | grams |
| mg | milligrams |
| L | Liter(s) |
| mL | Milliliters |
| µL | Microliters |
| nL | nanoliters |
| mmol | millimoles |
| hr, h | hours |
| min | Minutes |
| ms | millisecond |
| mm | Millimeters |
| µm | Micrometers |
| nm | nanometer |
| MHz | Megahertz |
| Hz | Hertz |
| N | Normal (concentration) |
| M | Molar (concentration) |
| mM | Millimolar (concentration) |
| µM | Micromolar (concentration) |
| ppm | Parts per million |
| % w/v | Weight-volume concentration |
| t-BuOH | tert-butyl alcohol |
| DCM | Dichloromethane |

-continued

| Abbreviation | Meaning |
|---|---|
| DIEA, DIPEA | N,N-Diisopropyl ethyl amine |
| DMA | N,N-Dimethylacetamide |
| DMF | N,N-Dimethylformamide |
| DMSO | Dimethyl sulfoxide |
| EtOH | Ethanol |
| HATU | 1-[Bis(dimethylamino)methylene]-1H-1,2,3-triazolo[4,5-b]pyridinium 3-oxide hexafluorophosphate |
| EDCI | 1-Ethyl-3-(3-dimethylaminopropyl)carbodiimide |
| T3P | Propylphosphonic anhydride, i.e., 2,4,6-tripropyl-1,3,5,2,4,6-trioxatriphosphinane 2,4,6-trioxide |
| MeOH | Methanol |
| MTBE | Methyl tert-butyl ether |
| NMP | N-Methylpyrrolidone |
| THF | Tetrahydrofuran |
| TEA | triethylamine |
| RB | Round bottom (flask) |
| RT | Room temperature |
| ca. | Circa (approximately) |
| E-VIPR | Electrical stimulation voltage ion probe reader |
| HEK | Human embryonic kidney |
| KIR2.1 | Inward-rectifier potassium ion channel 2.1 |
| DMEM | Dulbecco's Modified Eagle's Medium |
| FBS | Fetal bovine serum |
| NEAA | Non-essential amino acids |
| HEPES | 2-[4-(2-hydroxyethyl)piperazin-1-yl]ethanesulfonic acid |
| DiSBAC$_6$(3) | Bis-(1,3-dihexyl-thiobarbituric acid) trimethine oxonol |
| CC2-DMPE | Chlorocoumarin-2-dimyristoyl phosphatidylethanolamine |
| VABSC-1 | Voltage Assay Background Suppression Compound |
| HS | Human serum |
| BSA | Bovine Serum Albumin |

Preparation 1

4-[(Z)-[(tert-Butylamino)-phenylsulfanyl-methylene]amino]pyridine-2-carboxamide

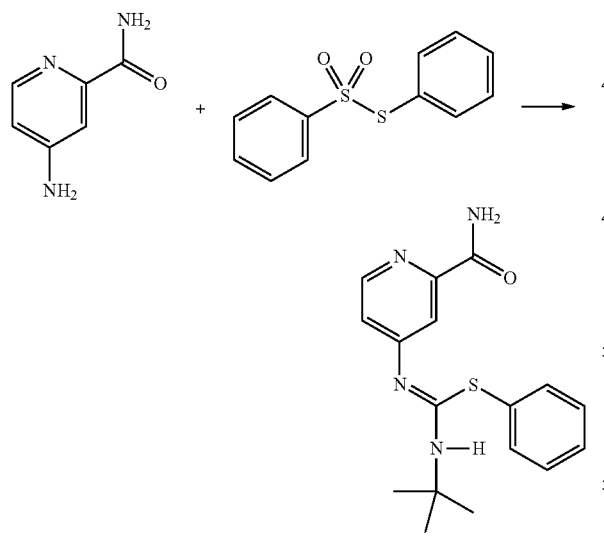

A flask equipped with a reflux condenser was charged with 4-aminopyridine-2-carboxamide (1.12 g, 8.17 mmol), benzenesulfonylsulfanylbenzene (1.85 g, 7.39 mmol), 2-isocyano-2-methyl-propane (3.0 mL, 27 mmol), copper (I) iodide (60 mg, 0.32 mmol) and molecular sieves (2.2 g) in 2-methyltetrahydrofuran (10 mL), and the mixture was heated at 75° C. for 24 hours. The reaction mixture was filtered through Celite and the cake was rinsed with ethyl acetate. The filtrate was concentrated and dried under vacuum. The residue was purified by silica gel chromatography (0-60% ethyl acetate/hexanes) to obtain 4-[(Z)-[(tert-butylamino)-phenylsulfanyl-methylene]amino]pyridine-2-carboxamide (1.25 g, 51%). ESI-MS m/z calc. 328.14, found 329.2 (M+1)+; retention time (Method B): 1.07 minutes (3 minute run). $^1$H NMR (400 MHz, DMSO-d6) δ 8.17 (dd, J=5.3, 0.6 Hz, 1H), 7.94 (d, J=3.0 Hz, 1H), 7.49 (s, 1H), 7.28 (dd, J=2.2, 0.6 Hz, 1H), 7.25-7.17 (m, 5H), 6.74 (dd, J=5.3, 2.2 Hz, 1H), 6.66 (s, 1H), 1.35 (s, 9H) ppm.

Preparation 2

Methyl 4-[(Z)-[tert-butylamino)-phenylsulfanyl-methylene]amino]-5-fluoro-pyridine-2-carboxylate

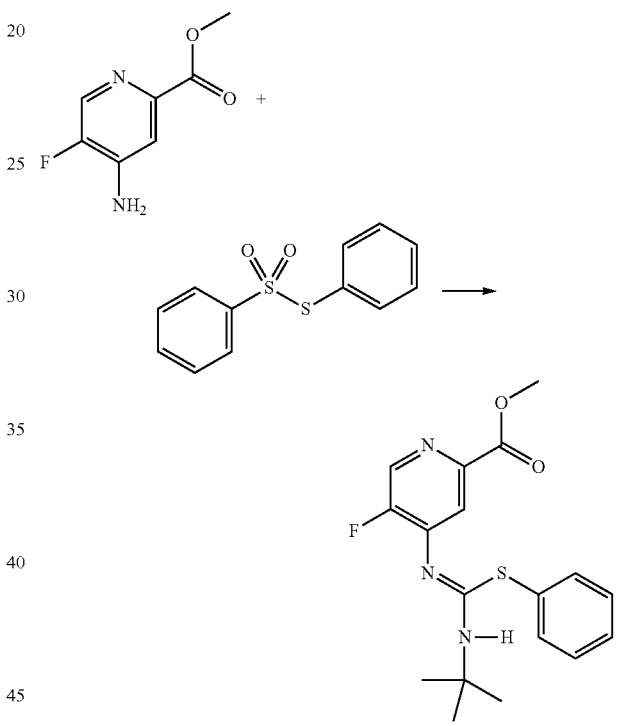

Methyl 4-amino-5-fluoro-pyridine-2-carboxylate (105 mg, 0.617 mmol), 2-isocyano-2-methyl-propane (154 mg, 1.85 mmol), benzenesulfonylsulfanylbenzene (158 mg, 0.631 mmol) and copper (I) iodide (3.0 mg, 0.016 mmol) and 4 Å molecular sieves (300 mg/mmol) in 2-methyltetrahydrofuran (1.5 mL) were heated in a sealed vial at 75° C. for 24 hours. The mixture was filtered through Celite, washed with ethyl acetate and concentrated in vacuo. Purification by silica gel chromatography (0-100% ethyl acetate/petroleum ether) afforded methyl 4-[(Z)-[(tert-butylamino)-phenylsulfanyl-methylene]amino]-5-fluoro-pyridine-2-carboxylate as a yellow oil (84 mg, 37%). ESI-MS m/z calc. 361.13, found 362.22 (M+1)+; retention time (Method F): 1.01 minutes. $^1$H NMR (500 MHz, CDCl$_3$) δ 8.34 (d, J=2.1 Hz, 1H), 7.73 (d, J=6.8 Hz, 1H), 7.46-7.42 (m, 2H), 7.41-7.32 (m, 3H), 3.98 (s, 3H), 1.33 (s, 9H) ppm.

231

Preparation 3

4-Amino-6-methyl-pyridine-2-carboxamide

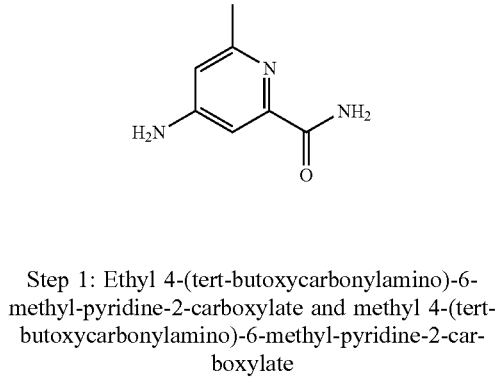

Step 1: Ethyl 4-(tert-butoxycarbonylamino)-6-methyl-pyridine-2-carboxylate and methyl 4-(tert-butoxycarbonylamino)-6-methyl-pyridine-2-carboxylate

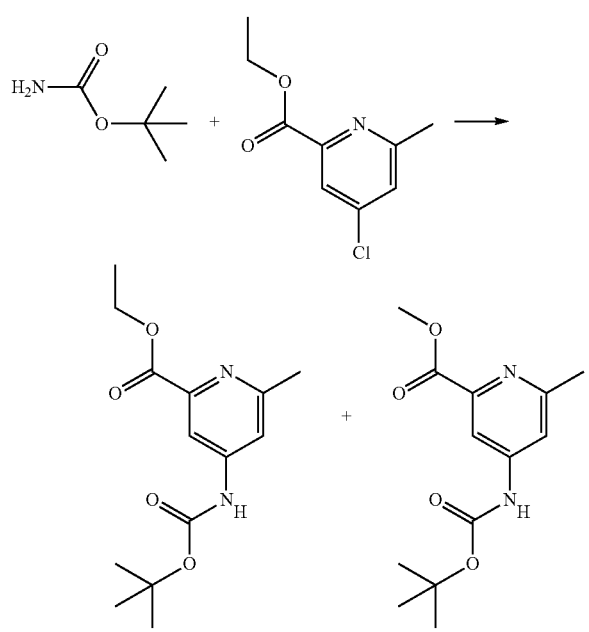

A mixture of tert-butyl carbamate (352 mg, 3.01 mmol), ethyl 4-chloro-6-methyl-pyridine-2-carboxylate (500 mg, 2.51 mmol), dicyclohexyl-[2-(2,4,6-triisopropylphenyl)phenyl]phosphane (120 mg, 0.252 mmol), $Cs_2CO_3$ (1.15 g, 3.530 mmol) and $Pd(OAc)_2$ (18 mg, 0.08 mmol) in dioxane (20 mL) was heated at 100° C. for 16 hours. The reaction mixture was cooled to room temperature, filtered through Celite and rinsed with methanol. The filtrate was concentrated in vacuo to provide the desired product as a mixture of methyl and ethyl esters which were taken directly to the next step. Methyl 4-(tert-butoxycarbonylamino)-6-methyl-pyridine-2-carboxylate (333 mg). ESI-MS m/z calc. 266.13, found 267.1 (M+1)+; 265.0 (M−1)−; retention time (Method F): 0.77 minutes (1.5 minute run). Ethyl 4-(tert-butoxycarbonylamino)-6-methyl-pyridine-2-carboxylate (351 mg). ESI-MS m/z calc. 280.14, found 281.1 (M+1)+; 279.0 (M−1)−; retention time (Method F): 0.83 minutes (1.5 minute run).

232

Step 2: tert-Butyl N-(2-carbamoyl-6-methyl-4-pyridyl)carbamate

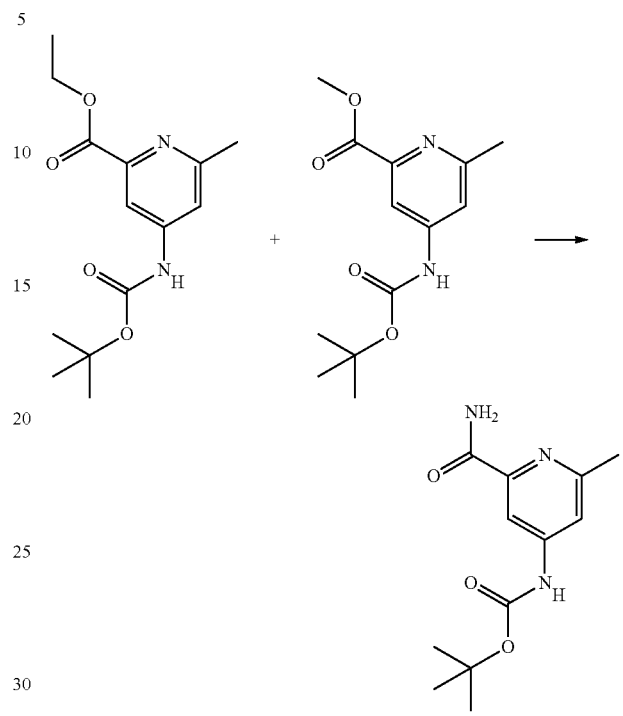

A solution of ammonia (16 mL of 7 M in methanol, 112 mmol) was added to a mixture of ethyl 4-(tert-butoxycarbonylamino)-6-methyl-pyridine-2-carboxylate (315 mg, 1.12 mmol) and methyl 4-(tert-butoxycarbonylamino)-6-methyl-pyridine-2-carboxylate (300 mg, 1.13 mmol) and the resulting mixture was stirred at room temperature for 3 days. The reaction mixture was concentrated in vacuo to provide tert-butyl N-(2-carbamoyl-6-methyl-4-pyridyl)carbamate (560 mg, 99%) as a creamy solid. ESI-MS m/z calc. 251.13, found 252.1 (M+1)+; 250.0 (M−1)−; retention time (Method F): 0.73 minutes (1.5 minute run).

Step 3: 4-Amino-6-methyl-pyridine-2-carboxamide

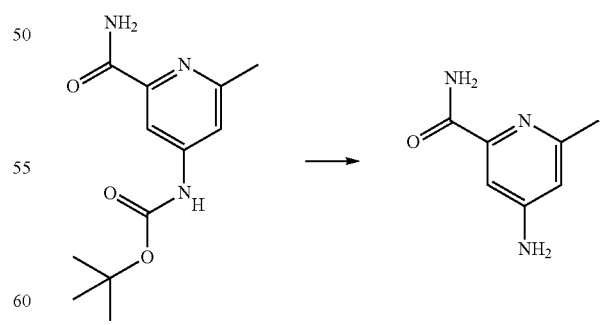

Trifluoroacetic acid (200 µL, 2.60 mmol) was added to a solution of tert-butyl N-(2-carbamoyl-6-methyl-4-pyridyl)carbamate (65 mg, 0.26 mmol) in dichloromethane (5 mL) and the mixture was stirred for 16 hours. The reaction mixture was concentrated in vacuo and the residue was dissolved in dichloromethane and passed through a bicarbonate filter cartridge flushing with additional dichloromethane and methanol. The combined fractions were concentrated to provide 4-amino-6-methyl-pyridine-2-carboxamide (38 mg, 97%) as a pale yellow oil that solidified on standing. ESI-MS m/z calc. 151.07, found 152.0 (M+1)+; retention time (Method F): 0.36 minutes (1.5 minute run).

Preparation 4

5-Amino-2-fluoro-4-methyl-benzamide

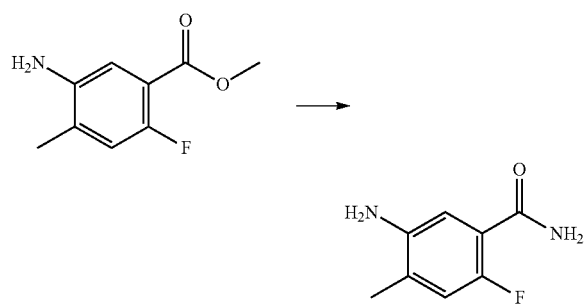

To a solution of methyl 5-amino-2-fluoro-4-methyl-benzoate (500 mg, 2.73 mmol) in methanol (3 mL) was added ammonia (2 mL of 7 M, 14 mmol), and the mixture was stirred for 16 hours at room temperature. Additional ammonia (2 mL of 7 M, 14 mmol) was added and the reaction was stirred for 6 hours. The reaction mixture was concentrated in vacuo to afford 5-amino-2-fluoro-4-methyl-benzamide (390 mg, 85%) as a yellow solid. ESI-MS m/z calc. 168.07, found 169.0 (M+1)+; retention time (Method F): 0.42 minutes (1.5 minute run).

Preparation 5

5-Amino-4-deuterio-2-fluoro-benzamide

Step 1: 4-chloro-2-fluoro-5-nitro-benzamide

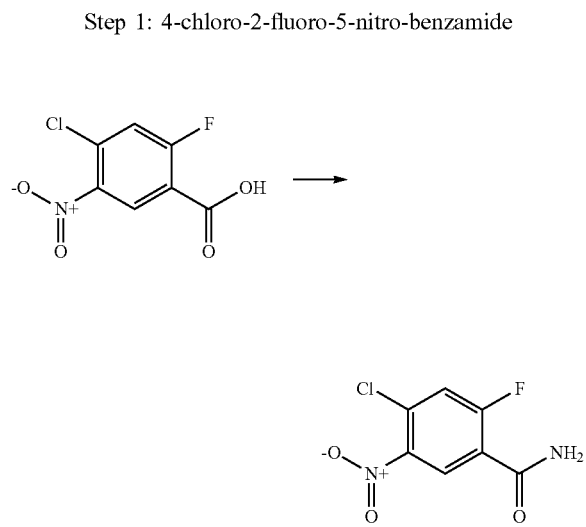

To a solution of 4-chloro-2-fluoro-5-nitro-benzoic acid (4.00 g, 18.2 mmol) and HATU (7.45 g, 19.6 mmol) in DMF (40 mL) was added a solution of ammonia (60 mL of 0.5 M in dioxane, 30 mmol) dropwise and the reaction mixture was stirred at room temperature for 20 hours. The reaction mixture was diluted with water and extracted with ethyl acetate. The organic layer was extracted with 1 M NaOH to remove any unreacted acid. The organic layer was then washed with brine, dried over MgSO$_4$, filtered and concentrated in vacuo. The solid was dissolved in warm dichloromethane and the solution was allowed to cool to room temperature. The resulting crystals were filtered, washed with minimal dichloromethane and air dried to provide the desired product (0.73 g). The mother liquor was purified using silica gel chromatography (0-10% methanol/dichloromethane) to provide an additional 0.37 g of 4-chloro-2-fluoro-5-nitro-benzamide (combined yield 1.100 g, 28%) as a white solid. ESI-MS m/z calc. 217.99, found 219.1 (M+1)+; retention time (Method A): 0.39 minutes (1 minute run). $^1$H NMR (400 MHz, DMSO-d6) δ 8.37 (d, J=6.7 Hz, 1H), 8.00 (br s, 1H), 7.98 (d, J=9.7 Hz, 1H), 7.96 (br s, 1H) ppm.

Step 2: 5-Amino-4-deuterio-2-fluoro-benzamide

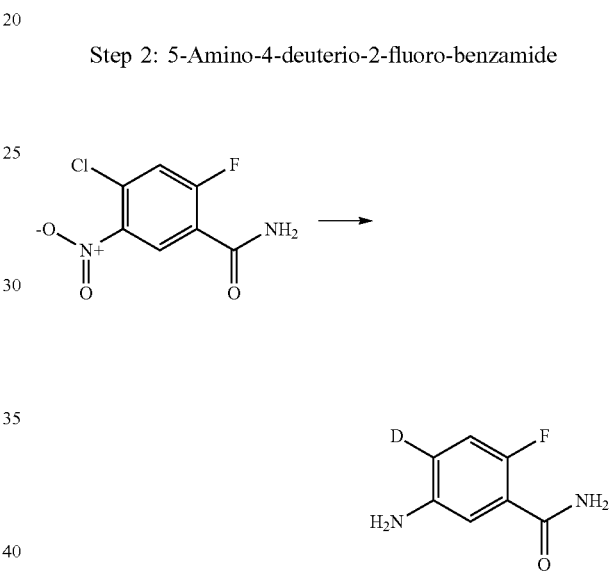

A flask charged with 4-chloro-2-fluoro-5-nitro-benzamide (1.63 g, 7.46 mmol) and dry 10% Pd/C (800 mg, 0.752 mmol) was put under high vacuum for 1 hour then backfilled with N$_2$. Methanol-d4 (20 mL) and triethylamine (1.25 mL, 8.97 mmol) were added under N$_2$ atmosphere. The flask was fixed with a deuterium balloon and stirred vigorously at room temperature, then cooled to 0° C. due to a rapid exotherm. The flask was removed from the ice bath after 10 minutes and allowed to warm to room temperature over 1 hour with continued stirring. The reaction mixture was filtered through Celite and rinsed with methanol-d4. The filtrate was again filtered (0.45 micron syringe filter) and concentrated in vacuo. Silica gel chromatography (5-10% methanol/dichloromethane) provided 5-amino-4-deuterio-2-fluoro-benzamide (845 mg, 73%) as a white solid. ESI-MS m/z calc. 155.06, found 156.1 (M+1)+; retention time (Method I): 0.52 minutes (3 minute run). $^1$H NMR (400 MHz, DMSO-d6) δ 7.44 (d, J=9.7 Hz, 2H), 6.90 (d, J=10.6 Hz, 1H), 6.83 (d, J=6.1 Hz, 1H), 5.09 (s, 2H) ppm.

Example 1

N-(3-carbamoyl-4-fluoro-phenyl)-2-fluoro-6-[2-(trideuteriomethoxy)-4-(trifluoromethoxy)phenoxy]-3-(trifluoromethyl)benzamide (1)

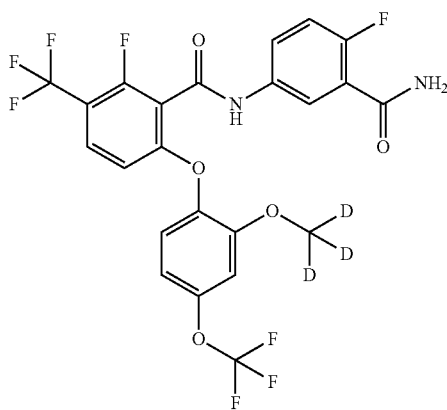 [SMILES: [2H]C([2H])([2H])Oc1cc(OC(F)(F)F)ccc1Oc1ccc(C(F)(F)F)c(F)c1C(=O)Nc1ccc(F)c(C(N)=O)c1]

Step 1: 1-bromo-2-(trideuteriomethoxy)-4-(trifluoromethoxy)benzene 2-bromo-5-(trifluoromethoxy)phenol (57.5 g, 223.7 mmol) in DMF (400 mL) was treated with $K_2CO_3$ (62 g, 448.6 mmol), stirred for 15 minutes, and cooled in an ice bath, and iodomethane-d3 (Aldrich, >99.5% D, 15.3 mL, 245.8 mmol) was added dropwise. The pale yellow suspension was removed from the ice bath and stirred at room temperature for 16 hours. The suspension was partitioned between water (2 L) and MTBE (500 mL) and separated. The organic phase was washed with 0.5M NaOH (500 mL) and brine (2×300 mL) and the aqueous phases were back extracted once with MTBE (250 ml). The combined organic phases were dried, filtered and evaporated to give 1-bromo-2-(trideuteriomethoxy)-4-(trifluoromethoxy)benzene (62.4 g, 97%) as a pale yellow liquid. LC/MS retention time (Method B): 1.84 minutes (3 minute run). $^1$H NMR (400 MHz, DMSO-d6) δ 7.71 (d, J=8.7 Hz, 1H), 7.14 (d, J=2.6 Hz, 1H), 6.92 (ddq, J=8.7, 2.5, 1.3 Hz, 1H) ppm.

Step 2: 2-(trideuteriomethoxy)-4-(trifluoromethoxy)phenol

A 1000 mL 3 neck RB flask was fitted with a mechanical stirrer, a heating mantle, a water cooled reflux condenser, temperature probe/controller and a nitrogen inlet/outlet was charged under a nitrogen atmosphere with tetrabutylammonium hydroxide (354.8 mL of 55% w/w, 729.5 mmol) and 1-bromo-2-(trideuteriomethoxy)-4-(trifluoromethoxy)benzene (50 g, 182.4 mmol). With stirring, the solution was degassed with nitrogen for 15 minutes. 1,10-phenanthroline-4,7-diol (3.871 g, 18.24 mmol) was then added as a solid in one portion followed by copper (I) oxide (1.305 g, 9.120 mmol) added as a solid in one portion. After these additions, the gas dispersion tube was removed and the vessel was fitted with a septum. The resulting mixture was then heated to a pot temperature of 100° C. for 15 hours. After cooling to RT, the reaction mixture was poured into ice cold hydrochloric acid (912 mL of 1 M, 912.0 mmol). The mixture was diluted with ethyl acetate (500 ml) and mixed for several minutes. The phases were separated and the aqueous phase was extracted with ethyl acetate (2×200 mL). The combined organic phases were washed with brine (2×250 mL), dried over sodium sulfate (200 g), filtered and concentrated. The residue was purified by silica gel chromatography (ethyl acetate/hexane gradient) to provide 2-(trideuteriomethoxy)-4-(trifluoromethoxy)phenol (33 g, 86%) as a clear pale yellow oil. LC/MS retention time (Method B): 1.38 minutes (3 minute run). $^1$H NMR (400 MHz, DMSO-d6) δ 9.31 (s, 1H), 6.91 (dd, J=2.8, 0.9 Hz, 1H), 6.82 (d, J=8.6 Hz, 1H), 6.79-6.70 (m, 1H) ppm.

Step 3: 2-fluoro-6-[2-(trideuteriomethoxy)-4-(trifluoromethoxy)phenoxy]-3-(trifluoromethyl)benzoic acid A pressure bottle was charged with 2-(trideuteriomethoxy)-4-(trifluoromethoxy)phenol (2 g, 9.472 mmol), cesium carbonate (6.50 g, 19.94 mmol) and 6-bromo-2-fluoro-3-(trifluoromethyl)benzoic acid (2.81 g, 9.97 mmol) in toluene (71 mL). The mixture was degassed with nitrogen. After ca. 2 minutes, copper (I) iodide (380 mg, 1.99 mmol) was added, the bottle was sealed, and the reaction was stirred at 110° C. for 40 minutes. After cooling to RT, the reaction was diluted with ethyl acetate and water. The organic phase was washed with brine and dried over sodium sulfate. Trituration with hexane and filtration gave 2-fluoro-6-[2-(trideuteriomethoxy)-4-(trifluoromethoxy)phenoxy]-3-(trifluoromethyl)benzoic acid (2.8 g, 67%). ESI-MS m/z calc. 417.05, found 418.1 (M+1)+; retention time (Method A): 0.73 minutes (1.2 minute run). $^1$H NMR (400 MHz, DMSO-d6) δ 7.35 (t, J=8.5 Hz, 1H), 7.20 (d, J=2.7 Hz, 1H), 7.13 (d, J=8.7 Hz, 1H), 6.97 (ddt, J=8.8, 2.7, 1.2 Hz, 1H), 6.39 (d, J=8.6 Hz, 1H) ppm.

Step 4: 2-fluoro-6-[2-(trideuteriomethoxy)-4-(trifluoromethoxy)phenoxy]-3-(trifluoromethyl)benzoyl chloride To a solution of 2-fluoro-6-[2-(trideuteriomethoxy)-4-(trifluoromethoxy)phenoxy]-3-(trifluoromethyl)benzoic acid (600 mg, 1.44 mmol) and DMF (20 µL, 0.26 mmol) in DCM (6.5 mL) at 0° C. was added oxalyl chloride (800 µL, 9.17 mmol) dropwise. The ice bath was removed and the reaction was stirred under $N_2$ atmosphere for 45 minutes. The solvent was evaporated under reduced pressure to afford 2-fluoro-6-[2-(trideuteriomethoxy)-4-(trifluoromethoxy)phenoxy]-3-(trifluoromethyl)benzoyl chloride. The intermediate was used in the next step without further purification.

Step 5: N-(3-carbamoyl-4-fluoro-phenyl)-2-fluoro-6-[2-(trideuteriomethoxy)-4-(trifluoromethoxy)phenoxy]-3-(trifluoromethyl)benzamide (1)

To 5-amino-2-fluoro-benzamide (212 mg, 1.38 mmol) and diisopropylethylamine (719 µL, 4.13 mmol) in dichloromethane (6 mL) cooled at 0° C. was added dropwise a solution of 2-fluoro-6-[2-(trideuteriomethoxy)-4-(trifluoromethoxy)phenoxy]-3-(trifluoromethyl)benzoyl chloride (600 mg, 1.377 mmol) in THF (6 mL). The reaction was stirred at room temperature overnight. The mixture was concentrated and the residue was purified by silica gel chromatography (ethyl acetate/hexane gradient) to provide N-(3-carbamoyl-4-fluoro-phenyl)-2-fluoro-6-[2-(trideuteriomethoxy)-4-(trifluoromethoxy)phenoxy]-3-(trifluoromethyl)benzamide (329 mg, 42%). ESI-MS m/z calc. 553.0963, found 554.1 (M+1)+; Retention time (Method B):

1.83 minutes (3 minute run). $^1$H NMR (400 MHz, DMSO-d6) δ 11.02 (s, 1H), 8.00 (dd, J=6.4, 2.8 Hz, 1H), 7.84-7.73 (m, 3H), 7.70 (s, 1H), 7.36 (d, J=8.8 Hz, 1H), 7.33-7.26 (m, 2H), 7.05 (ddd, J=8.8, 2.7, 1.3 Hz, 1H), 6.65 (d, J=8.9 Hz, 1H) ppm.

The compounds set forth in Table 2 were prepared by methods analogous to the preparation of compound 1.

TABLE 2

Additional Compounds Prepared By Methods Analogous to Example 1

| Cmpd No | Compound Name | LC/MS | NMR (shifts in ppm) |
|---|---|---|---|
| 127 | N-(4-carbamoylphenyl)-2-fluoro-6-[2-(trideuteriomethoxy)-4-(trifluoromethoxy)phenoxy]-3-(trifluoromethyl)benzamide | ESI-MS m/z calc. 535.09, found 535.9 (M + 1)+; Retention time (Method B): 2.48 minutes (3 minute run). | $^1$H NMR (400 MHz, DMSO-d6) δ 11.08 (s, 1H), 7.93 (s, 1H), 7.92-7.8 7 (m, 2H), 7.79 (t, J = 8.7 Hz, 1H), 7.74 (d, J = 8.8 Hz, 2H), 7.36 (d, J = 8.8 Hz, 1H), 7.32 (s, 1H), 7.27 (d, J = 2.8 Hz, 1H), 7.05 (ddd, J = 8.8, 2.7, 1.3 Hz, 1H), 6.65 (d, J = 8.9 Hz, 1H) |
| 145 | N-(3-carbamoyl-4-methyl-phenyl)-2-fluoro-6-[2-(trideuteriomethoxy)-4-(trifluoromethoxy)phenoxy]-3-(trifluoromethyl)benzamide | ESI-MS m/z calc. 549.12, found 551.0 (M + 1)+; Retention time (Method C): 2.53 minutes (5 minute run). | $^1$H NMR (400 MHz, DMSO-d6) δ 10.84 (s, 1H), 7.78 (d, J = 8.7 Hz, 1H), 7.74 (d, J = 4.0 Hz, 1H), 7.69 (d, J = 2.3 Hz, 1H), 7.61 (dd, J = 8.3, 2.3 Hz, 1H), 7.37 (s, 1H), 7.34 (d, J = 8.8 Hz, 1H), 7.26 (d, J = 2.8 Hz, 1H), 7.21 (d, J = 8.4 Hz, 1H), 7.08-7.02 (m, 1H), 6.63 (d, J = 8.9 Hz, 1H), 2.31 (s, 3H). |
| 209 | 5-[[2-fluoro-6-[2-(trideuteriomethoxy)-4-(trifluoromethoxy)phenoxy]-3-(trifluoromethyl)benzoyl]amino]-N-methyl-pyridine-2-carboxamide | ESI-MS m/z calc. 550.12, found 551.0 (M + 1)+; Retention time (Method B): 2.60 minutes (3 minute run). | $^1$H NMR (400 MHz, DMSO-d6) δ 11.35 (s, 1H), 8.89 (d, J = 2.4 Hz, 1H), 8.73-8.57 (m, 1H), 8.28 (dd, J = 8.6, 2.5 Hz, 1H), 8.05 (d, J = 8.5 Hz, 1H), 7.81 (t, J = 8.7 Hz, 1H), 7.36 (d, J = 8.7 Hz, 1H), 7.26 (d, J = 2.7 Hz, 1H), 7.04 (d, J = 9.2 Hz, 1H), 6.68 (d, J = 8.9 Hz, 1H), 2.81 (d, J = 4.8 Hz, 3H). |

Example 2

N-(3-carbamoyl-4-fluoro-phenyl)-2-fluoro-6-[2-methoxy-4-(trifluoromethoxy)phenoxy]-3-(trifluoromethyl)benzamide (2)

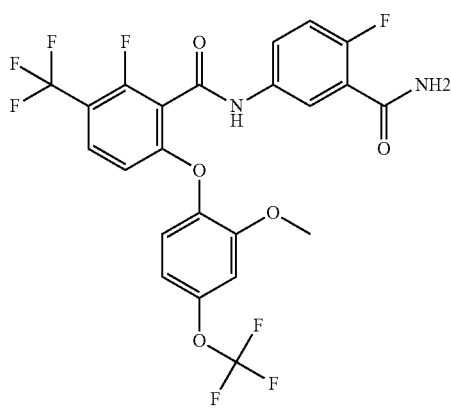 [SMILES: COc1cc(OC(F)(F)F)ccc1Oc1ccc(C(F)(F)F)c(F)c1C(=O)Nc1ccc(F)c(C(N)=O)c1]

Step 1:
1-bromo-2-methoxy-4-(trifluoromethoxy)benzene

A 500 mL 3 neck RB flask was fitted with a mechanical stirrer, a cooling bath, an addition funnel, temperature probe and a nitrogen inlet/outlet. The vessel was charged under a nitrogen atmosphere with 2-bromo-5-(trifluoromethoxy) phenol (80 g, 311.3 mmol), N,N-dimethylformamide (800 mL) and was treated with $K_2CO_3$ (56.05 g, 405.6 mmol). The mixture was stirred at RT for 15 minutes and then cooled in an ice bath and methyl iodide (19.38 mL, 311.3 mmol) was added dropwise over 5 minutes. The cooling bath was removed and the resulting suspension was allowed to slowly warm to RT and continue to stir at RT for 10 hours. The reaction mixture was then poured into crushed ice/water (1000 mL) and stirred for 5 minutes. The mixture was diluted with methyl tert-butyl ether (1000 mL) and transferred to a separatory funnel and allowed to stand for 10 minutes. The organic phase was separated and the aqueous was extracted with methyl tert-butyl ether (2×500 ml). The combined organic phases were washed with brine, dried over sodium sulfate (500 g), filtered and concentrated. The crude product was purified by silica gel chromatography (starting with hexane, then 9:1 hexane:dichloromethane and finally 8:1:1 hexane:dichloromethane:ethyl acetate) to give 1-bromo-2-methoxy-4-(trifluoromethoxy)benzene (82 g, 97%) as a pale yellow oil. $^1$H NMR (400 MHz, DMSO-d6) δ 7.71 (d, J=8.7 Hz, 1H), 7.25-7.06 (m, 1H), 6.93 (ddq, J=8.7, 2.5, 1.2 Hz, 1H), 3.89 (s, 3H) ppm.

Step 2: 2-methoxy-4-(trifluoromethoxy)phenol

A 1000 mL 3 neck RB flask was fitted with a mechanical stirrer, a heating mantle, a water cooled reflux condenser, a temperature probe/controller and a nitrogen inlet/outlet. The vessel was charged under a nitrogen atmosphere with tetrabutylammonium hydroxide (287.2 mL of 40% w/v, 442.7 mmol) in water and 1-bromo-2-methoxy-4-(trifluoromethoxy)benzene (30 g, 110.7 mmol). With stirring the solution was degassed with nitrogen for 15 minutes. The vessel was then charged with 1,10-phenanthroline-4,7-diol (2.349 g, 11.07 mmol) added as a solid in one portion followed by copper (I) oxide (792 mg, 5.54 mmol) added as a solid in one portion. After these additions the gas dispersion tube was removed and the vessel was fitted with a septum. The mixture was then heated to a pot temperature of 100° C. for 15 hours. After cooling to RT the reaction mixture was poured into ice cold hydrochloric acid (553.5 mL of 1 M, 553.5 mmol). The mixture was diluted with ethyl acetate (500 mL) and mixed for several minutes. The biphasic mixture was transferred to a separatory funnel and allowed to stand for 5 minutes. The phases were separated and the aqueous was extracted with ethyl acetate (2×200 mL). The combined organic phases were washed with saturated brine (2×250 mL), dried over sodium sulfate, filtered and concentrated. The residue was purified by silica gel chromatography (ethyl acetate/hexane gradient) to provide 2-methoxy-4-(trifluoromethoxy)phenol (18 g, 78%) as a pale yellow oil. LC/MS retention time (Method B): 1.34 minutes (3 minute run). $^1$H NMR (400 MHz, DMSO-d6) δ 9.35 (s, 1H), 6.92 (dd, J=2.7, 0.8 Hz, 1H), 6.82 (d, J=8.6 Hz, 1H), 6.79-6.70 (m, 1H), 3.79 (s, 3H) ppm.

Step 3: 2-fluoro-6-[2-methoxy-4-(trifluoromethoxy) phenoxy]-3-(trifluoromethyl)benzoic acid A pressure flask was charged with 6-bromo-2-fluoro-3-(trifluoromethyl)benzoic acid (5 g, 17.42 mmol), 2-methoxy-4-(trifluoromethoxy)phenol (4.35 g, 20.90 mmol), cesium carbonate (11.35 g, 34.84 mmol) and toluene (50 mL). The mixture was degassed with nitrogen. After ca. 2 minutes, copper (I) iodide (663 mg, 3.48 mmol) was added and the reaction was stirred at 100° C. for 1 hr. The reaction was diluted with 300 mL ethyl acetate and 200 mL of water and the phases were separated. The aqueous layer was acidified to pH-3 and extracted with ethyl acetate. The combined organic phases were dried over sodium sulfate, filtered and concentrated. The residue was purified by silica gel chromatography (ethyl acetate/hexane gradient, followed by 9:1 dichloromethane:methanol) to afford 2-fluoro-6-[2-methoxy-4-(trifluoromethoxy)phenoxy]-3-(trifluoromethyl)benzoic acid (5.4503 g, 76%) as a pale green solid. ESI-MS m/z calc. 414.03, found 415.0 (M+1)+; retention time (Method B): 1.94 minutes (3 minute run). $^1$H NMR (400 MHz, DMSO-d6) δ 7.53 (t, J=8.4 Hz, 1H), 7.27-7.11 (m, 2H), 6.99 (ddd, J=8.8, 2.7, 1.3 Hz, 1H), 6.49 (d, J=8.8 Hz, 1H), 3.80 (s, 3H) ppm.

Step 4: 2-fluoro-6-[2-methoxy-4-(trifluoromethoxy) phenoxy]-3-(trifluoromethyl)benzoyl chloride To a slurry of 2-fluoro-6-[2-methoxy-4-(trifluoromethoxy)phenoxy]-3-(trifluoromethyl)benzoic acid (660 mg, 1.59 mmol) and N,N-dimethylformamide (10 µL, 0.13 mmol) in dichloromethane (6.5 mL) at 0° C. was added oxalyl chloride (550 µL, 6.30 mmol) dropwise. The mixture was stirred at 50° C. for 40 minutes under N$_2$ atmosphere. The solvent was evaporated under reduced pressure to afford 2-fluoro-6-[2-methoxy-4-(trifluoromethoxy)phenoxy]-3-(trifluoromethyl)benzoyl chloride which was used in the next step without further purification.

Step 5: N-(3-carbamoyl-4-fluoro-phenyl)-2-fluoro-6-[2-methoxy-4-(trifluoromethoxy)phenoxy]-3-(trifluoromethyl)benzamide (2)

To a solution of 5-amino-2-fluoro-benzamide (111 mg, 0.724 mmol) and DIEA (378 µL, 2.17 mmol) in dichloromethane (2 mL) at 0° C. was added a solution of 2-fluoro-6-[2-methoxy-4-(trifluoromethoxy)phenoxy]-3-(trifluoromethyl)benzoyl chloride (313 mg, 0.723 mmol) in dichloromethane (2 mL) slowly, and the reaction was stirred at room temperature for 2 hours. The solvent was evaporated by blowing down with nitrogen. The crude product was dissolved in DMSO, filtered and purified by reverse phase HPLC to yield N-(3-carbamoyl-4-fluoro-phenyl)-2-fluoro-6-[2-methoxy-4-(trifluoromethoxy)phenoxy]-3-(trifluoromethyl)benzamide (234 mg, 59%). ESI-MS m/z calc. 550.0775, found 551.0 (M+1)+; retention time (Method C): 2.56 minutes (5 minute run).

The compounds set forth in Table 3 were prepared by methods analogous to the preparation of compound 2.

TABLE 3

Additional Compounds Prepared By Methods Analogous to Example 2

| Cmpd No. | Compound Name | LC/MS | NMR (shifts in ppm) |
|---|---|---|---|
| 99 | 2-fluoro-N-[4-fluoro-3-(methylcarbamoyl)phenyl]-6-[2-methoxy-4-(trifluoromethoxy)phenoxy]-3-(trifluoromethyl)benzamide | ESI-MS m/z calc. 564.09, found 565.0 (M + 1)+; Retention time (Method C): 2.67 minutes (5 minute run). | $^1$H NMR (400 MHz, DMSO-d6) δ 11.03 (s, 1H), 8.34-8.24 (m, 1H), 7.98 (dd, J = 6.3, 2.8 Hz, 1H), 7.84-7.68 (m, 2H), 7.37-7.26 (m, 3H), 7.14-6.97 (m, 1H), 6.64 (d, J = 8.9 Hz, 1H), 3.79 (s, 3H), 2.78 (d, J = 4.6 Hz, 3H). |
| 44 | N-(3-carbamoylphenyl)-2-fluoro-6-[2-methoxy-4-(trifluoromethoxy)phenoxy]-3-(trifluoromethyl)benzamide | ESI-MS m/z calc. 532.09, found 533.1 (M + 1)+; Retention time (Method B): 1.73 minutes (3 minute run). | $^1$H NMR (400 MHz, DMSO-d6) δ 10.98 (s, 1H), 8.17 (t, J = 1.9 Hz, 1H), 8.00 (s, 1H), 7.82 (ddd, J = 8.2, 2.3, 1.1 Hz, 1H), 7.77 (d, J = 8.7 Hz, 1H), 7.62 (dt, J = 7.7, 1.2 Hz, 1H), 7.44 (t, J = 7.9 Hz, 1H), 7.39 (s, 1H), 7.36 (d, J = 8.8 Hz, 1H), 7.27 (d, J = 2.7 Hz, 1H), 7.05 (ddd, J = 8.8, 2.7, 1.3 Hz, 1H), 6.64 (d, J = 8.9 Hz, 1H), 3.80 (s, 3H) |

TABLE 3-continued

Additional Compounds Prepared By Methods Analogous to Example 2

| Cmpd No. | Compound Name | LC/MS | NMR (shifts in ppm) |
|---|---|---|---|
| 100 | N-(3-carbamoyl-5-fluoro-phenyl)-2-fluoro-6-[2-methoxy-4-(trifluoromethoxy)phenoxy]-3-(trifluoromethyl)benzamide | ESI-MS m/z calc. 550.08, found 551.1 (M + 1)+; Retention time (Method B): 1.85 minutes (3 minute run). | $^1$H NMR (400 MHz, DMSO-d6) δ 11.22 (s, 1H), 8.07 (s, 1H), 7.93 (t, J = 1.6 Hz, 1H), 7.83-7.76 (m, 2H), 7.55 (s, 1H), 7.47 (ddd, J = 9.3, 2.4, 1.4 Hz, 1H), 7.37 (d, J = 8.8 Hz, 1H), 7.28 (dd, J = 6.1, 2.7 Hz, 1H), 7.05 (ddq, J = 7.6, 2.4, 1.2 Hz, 1H), 6.66 (d, J = 8.9 Hz, 1H), 3.79 (s, 3H). |
| 52 | 5-[[2-fluoro-6-[2-methoxy-4-(trifluoromethoxy)phenoxy]-3-(trifluoromethyl)benzoyl]amino]pyridine-3-carboxamide | ESI-MS m/z calc. 533.08, found 534.0 (M + 1)+; Retention time (Method B): 1.63 minutes (3 minute run). | $^1$H NMR (400 MHz, DMSO-d6) δ 11.27 (s, 1H), 8.91 (d, J = 2.4 Hz, 1H), 8.80 (d, J = 2.0 Hz, 1H), 8.57 (t, J = 2.2 Hz, 1H), 8.22 (s, 1H), 7.80 (t, J = 8.6 Hz, 1H), 7.64 (s, 1H), 7.37 (d, J = 8.8 Hz, 1H), 7.27 (d, J = 2.7 Hz, 1H), 7.08-7.00 (m, 1H), 6.67 (d, J = 8.9 Hz, 1H), 3.80 (s, 3H). |
| 98 | 2-fluoro-6-[2-methoxy-4-(trifluoromethoxy)phenoxy]-N-[3-(methylcarbamoyl)phenyl]-3-(trifluoromethyl)benzamide | ESI-MS m/z calc. 546.10, found 546.9 (M + 1)+; Retention time (Method C): 2.59 minutes (5 minute run). | $^1$H NMR (400 MHz, DMSO-d6) δ 10.99 (s, 1H), 8.51-8.40 (m, 1H), 8.16 (t, J = 1.9 Hz, 1H), 7.86-7.72 (m, 2H), 7.61-7.51 (m, 1H), 7.44 (t, J = 7.9 Hz, 1H), 7.36 (d, J = 8.8 Hz, 1H), 7.27 (d, J = 2.8 Hz, 1H), 7.10-6.99 (m, 1H), 6.64 (d, J = 8.8 Hz, 1H), 3.79 (s, 3H), 2.78 (d, J = 4.5 Hz, 3H). |
| 193 | 5-[[2-fluoro-6-[2-methoxy-4-(trifluoromethoxy)phenoxy]-3-(trifluoromethyl)benzoyl]amino]pyridine-2-carboxamide | ESI-MS m/z calc. 533.08, found 534.0 (M + 1)+; Retention time (Method E): 3.25 minutes (5 minute run). | $^1$H NMR (500 MHz, DMSO-d6) δ 11.35 (s, 1H), 8.87 (d, J = 2.4 Hz, 1H), 8.30 (dd, J = 8.5, 2.5 Hz, 1H), 8.10-8.00 (m, 2H), 7.82 (t, J = 8.6 Hz, 1H), 7.56 (s, 1H), 7.37 (d, J = 8.8 Hz, 1H), 7.27 (d, J = 2.7 Hz, 1H), 7.08-7.02 (m, 1H), 6.69 (d, J = 8.9 Hz, 1H), 3.79 (s, 3H). |
| 97 | 4-[[2-fluoro-6-[2-methoxy-4-(trifluoromethoxy)phenoxy]-3-(trifluoromethyl)benzoyl]amino]-N,N-dimethyl-pyridine-2-carboxamide | ESI-MS m/z calc. 561.11, found 562.0 (M + 1)+; Retention time (Method C): 2.47 minutes (5 minute run). | $^1$H NMR (400 MHz, DMSO-d6) δ 11.43 (s, 1H), 8.51 (d, J = 5.5 Hz, 1H), 7.86-7.78 (m, 2H), 7.67 (dd, J = 5.6, 2.2 Hz, 1H), 7.37 (d, J = 8.8 Hz, 1H), 7.27 (d, J = 2.7 Hz, 1H), 7.05 (ddd, J = 8.8, 2.7, 1.3 Hz, 1H), 6.67 (d, J = 8.9 Hz, 1H), 3.79 (s, 3H), 3.00 (s, 3H), 2.95 (s, 3H). |
| 86 | 4-[[2-fluoro-6-[2-methoxy-4-(trifluoromethoxy)phenoxy]-3-(trifluoromethyl)benzoyl]amino]-6-methyl-pyridine-2-carboxamide | ESI-MS m/z calc. 547.10, found 548.0 (M + 1)+; Retention time (Method E): 3.37 minutes (5 minute run). | $^1$H NMR (500 MHz, DMSO-d6) δ 11.37-11.31 (m, 1H), 8.13-8.09 (m, 1H), 7.97 (d, J = 3.1 Hz, 1H), 7.81 (t, J = 8.6 Hz, 1H), 7.74 (d, J = 1.9 Hz, 1H), 7.62 (d, J = 3.1 Hz, 1H), 7.37 (d, J = 8.8 Hz, 1H), 7.26 (d, J = 2.7 Hz, 1H), 7.05 (ddt, J = 8.8, 2.3, 1.2 Hz, 1H), 6.71-6.65 (m, 1H), 3.79 (s, 3H), 3.29 (s, 3H). |
| 95 | N-[3-(dimethylcarbamoyl)-4-fluoro-phenyl]-2-fluoro-6-[2-methoxy-4-(trifluoromethoxy)phenoxy]-3-(trifluoromethyl)benzamide | ESI-MS m/z calc. 578.11, found 578.9 (M + 1)+; Retention time (Method B): 1.93 minutes (3 minute run). | $^1$H NMR (400 MHz, DMSO-d6) δ 11.05 (s, 1H), 7.82-7.74 (m, 2H), 7.69 (ddd, J = 9.0, 4.7, 2.7 Hz, 1H), 7.38-7.29 (m, 2H), 7.27 (d, J = 2.8 Hz, 1H), 7.11-7.02 (m, 1H), 6.65 (d, J = 8.9 Hz, 1H), 3.79 (s, 3H), 3.00 (s, 3H), 2.87 (d, J = 1.3 Hz, 3H). |
| 96 | N-[3-(dimethylcarbamoyl)phenyl]-2-fluoro-6-[2-methoxy-4-(trifluoromethoxy)phenoxy]-3-(trifluoromethyl)benzamide | ESI-MS m/z calc. 560.12, found 561.0 (M + 1)+; Retention time (Method C): 2.69 minutes (5 minute run). | $^1$H NMR (400 MHz, DMSO-d6) δ 10.99 (s, 1H), 7.82-7.75 (m, 2H), 7.68 (ddd, J = 8.2, 2.2, 1.1 Hz, 1H), 7.43 (t, J = 7.9 Hz, 1H), 7.36 (d, J = 8.8 Hz, 1H), 7.27 (d, J = 2.8 Hz, 1H), 7.16 (dt, J = 7.7, 1.3 Hz, 1H), 7.05 (ddd, J = 8.8, 2.7, 1.3 Hz, 1H), 6.65 (d, J = 8.9 Hz, 1H), 3.79 (s, 3H), 2.98 (s, 3H), 2.92 (s, 3H). |

TABLE 3-continued

Additional Compounds Prepared By Methods Analogous to Example 2

| Cmpd No. | Compound Name | LC/MS | NMR (shifts in ppm) |
|---|---|---|---|
| 82 | N-(4-carbamoyl-2-fluoro-phenyl)-2-fluoro-6-[2-methoxy-4-(trifluoromethoxy)phenoxy]-3-(trifluoromethyl)benzamide | ESI-MS m/z calc. 550.08, found 551.2 (M + 1)+; Retention time (Method B): 1.81 minutes (3 minute run). | $^1$H NMR (400 MHz, DMSO-d6) δ 10.9 1 (s, 1H), 8.13 (t, J = 8.3 Hz, 1H), 8.04 (s, 1H), 7.82-7.74 (m, 3H), 7.50 (s, 1H), 7.36 (d, J = 8.8 Hz, 1H), 7.27 (d, J = 2.7 Hz, 1H), 7.06 (ddd, J = 8.8, 2.7, 1.3 Hz, 1H), 6.64 (d, J = 8.9 Hz, 1H), 3.80 (s, 3H). |
| 118 | [N-(5-carbamoyl-4-fluoro-2-methyl-phenyl)-2-fluoro-6-[2-methoxy-4-(trifluoromethoxy)phenoxy]-3-(trifluoromethyl)benzamide | ESI-MS m/z calc. 564.09, found 565.2 (M + 1)+; Retention time (Method E): 3.41 minutes (5 minute run). | $^1$H NMR (500 MHz, DMSO-d6) δ 10.37 (s, 1H), 7.81-7.70 (m, 2H), 7.63 (d, J = 13.7 Hz, 2H), 7.36 (d, J = 8.8 Hz, 1H), 7.31-7.27 (m, 1H), 7.23 (d, J = 11.3 Hz, 1H), 7.07 (ddt, J = 8.7, 2.3, 1.2 Hz, 1H), 6.65 (d, J = 8.9 Hz, 1H), 3.82 (s, 3H), 2.28 (s, 3H). |
| 87 | 2-[[2-fluoro-6-[2-methoxy-4-(trifluoromethoxy)phenoxy]-3-(trifluoromethyl)benzoyl]amino]pyridine-4-carboxamide | ESI-MS m/z calc. 533.08, found 533.9 (M + 1)+; Retention time (Method B): 1.75 minutes (3 minute run). | $^1$H NMR (500 MHz, DMSO-d6 ) δ 11.53 (s, 1H), 8.57 (s, 1H), 8.49 (d, J = 5.1 Hz, 1H), 8.28 (d, J = 12.3 Hz, 1H), 7.81-7.70 (m, 2H), 7.59-7.55 (m, 1H), 7.37 (d, J = 8.8 Hz, 1H), 7.26 (d, J = 2.8 Hz, 1H), 7.05 (d, J = 8.8 Hz, 1H), 6.63 (d, J = 9.0 Hz, 1H), 3.80 (s, 3H) |

Example 3

N-(3-carbamoyl-4-fluoro-phenyl)-2-fluoro-6-[2-(trideuteriomethoxy)-4-(trifluoromethoxy)phenoxy]-3-(trifluoromethoxy)benzamide (3)

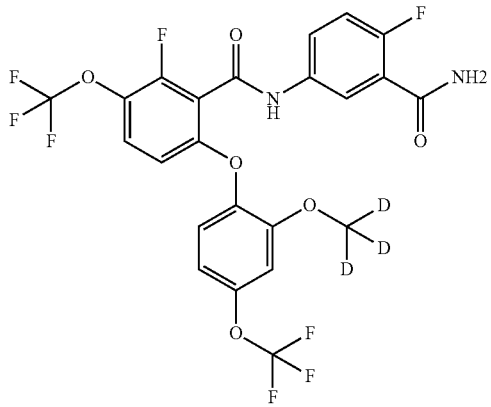 [SMILES: [2H]C([2H])([2H])Oc1cc(OC(F)(F)F)ccc1Oc1ccc(OC(F)(F)F)c(F)c1C(=O)Nc1ccc(F)c(C(N)=O)c1]

Step 1:
6-bromo-2-fluoro-3-(trifluoromethoxy)benzoic acid

To a suspension of 6-bromo-2-fluoro-3-(trifluoromethoxy)benzaldehyde (2.8 g, 9.76 mmol) in t-butanol (15 mL), water (15 mL) and acetonitrile (15 mL) was added sodium dihydrogen phosphate (3.53 g, 29.42 mmol) and 2-methyl-2-butene (5.6 mL, 52.94 mmol). Sodium chlorite (2.7 g, 29.85 mmol) was added portion wise with cooling in an ice bath and an exotherm and bubbling was observed during the addition. The reaction was removed from the ice bath and allowed to warm warmed to room temperature. After 20 minutes the mixture was acidified with aqueous HCl (140 mL, 1 M, 140.0 mmol) and diluted with ethyl acetate. The layers were separated and the organic layer was washed with brine, dried over sodium sulfate, filtered and concentrated. Silica gel chromatography (dichloromethane/methanol gradient with 0.2% acetic acid) provided 6-bromo-2-fluoro-3-(trifluoromethoxy)benzoic acid (2.10 g, 71%). ESI-MS m/z calc. 301.92, found 304.0 (M+1)+; retention time (Method A): 0.52 minutes (1.2 minute run). $^1$H NMR (400 MHz, DMSO-d6) δ 14.52 (br s, 1H), 7.78-7.56 (m, 2H) ppm.

Step 2: 2-fluoro-6-[2-(trideuteriomethoxy)-4-(trifluoromethoxy)phenoxy]-3-(trifluoromethoxy)benzoic acid To a pressure flask was added 6-bromo-2-fluoro-3-(trifluoromethoxy)benzoic acid (600 mg, 1.98 mmol), 2-(trideuteriomethoxy)-4-(trifluoromethoxy)phenol (prepared as described in Example 1, 420 mg, 1.99 mmol), cesium carbonate (1.29 g, 3.96 mmol), and toluene (15 mL). The reaction mixture was degassed with $N_2$ for 10 min, then copper (I) iodide (75 mg, 0.39 mmol) was added. The flask was flushed with $N_2$, capped, and heated at 100° C. with vigorous stirring for 2 h. The mixture was allowed to cool to RT and was then diluted with ethyl acetate and water. The water layer was acidified with 1M HCl and was extracted with ethyl acetate. The combined organic layers were washed with brine, dried over sodium sulfate, filtered and concentrated. Silica gel chromatography (dichloromethane/methanol gradient with 0.5% acetic acid) provided 2-fluoro-6-[2-(trideuteriomethoxy)-4-(trifluoromethoxy)phenoxy]-3-(trifluoromethoxy)benzoic acid (672 mg, 78%). ESI-MS m/z calc. 433.05, found 434.2 (M+1)+; retention time (Method B): 1.83 minutes (3 minute run). $^1$H NMR (400 MHz, DMSO-d6) δ 14.02 (s, 1H), 7.56 (td, J=9.0, 1.2 Hz, 1H), 7.29-7.18 (m, 2H), 7.00 (ddd, J=8.8, 2.7, 1.2 Hz, 1H), 6.58 (dd, J=9.3, 1.7 Hz, 1H) ppm.

Step 3: N-(3-carbamoyl-4-fluoro-phenyl)-2-fluoro-6-[2-(trideuteriomethoxy)-4-(trifluoromethoxy)phenoxy]-3-(trifluoromethoxy)benzamide (3)

2-Fluoro-6-[2-(trideuteriomethoxy)-4-(trifluoromethoxy) phenoxy]-3-(trifluoromethoxy)benzoic acid (55 mg, 0.13 mmol) and HATU (49 mg, 0.13 mmol) were combined in DMF (1 mL) and DIEA (90 μL, 0.5167 mmol), stirred for 5 min, and then treated with 5-amino-2-fluoro-benzamide (24 mg, 0.16 mmol). The reaction was stirred at 45° C. for 30 min. Reverse phase HPLC purification provided N-(3-carbamoyl-4-fluoro-phenyl)-2-fluoro-6-[2-(trideuteriomethoxy)-4-(trifluoromethoxy)phenoxy]-3-(trifluoromethoxy)benzamide (11.6 mg, 16%). ESI-MS m/z calc. 569.09, found 570.2 (M+1)+; retention time (Method B): 1.8 minutes (3 minute run). $^1$H NMR (400 MHz, DMSO-d6) δ 10.98 (s, 1H), 7.99 (dd, J=6.4, 2.8 Hz, 1H), 7.78 (ddd, J=9.0, 4.4, 2.8 Hz, 1H), 7.72 (s, 1H), 7.67 (s, 1H), 7.59 (t, J=9.0 Hz, 1H), 7.30 (dd, J=9.2, 1.7 Hz, 2H), 7.22 (d, J=2.8 Hz, 1H), 7.05-6.99 (m, 1H), 6.61 (dd, J=9.2, 1.6 Hz, 1H) ppm.

The compounds set forth in Table 4 were prepared by methods analogous to the preparation of compound 3.

TABLE 4

Additional Compounds Prepared By Methods Analogous to Example 3

| Cmpd No. | Compound Name | LC/MS | NMR (shifts in ppm) |
|---|---|---|---|
| 167 | 5-[[2-fluoro-6-[2-(trideuteriomethoxy)-4-(trifluoromethoxy)phenoxy]-3-(trifluoromethoxy)benzoyl]amino]pyridine-2-carboxamide | ESI-MS m/z calc. 552.10, found 553.3 (M + 1)+; Retention time (Method B): 1.77 minutes (3 minute run). | $^1$H NMR (400 MHz, DMSO-d6) δ 11.33 (s, 1H), 8.86 (dd, J = 2.5, 0.7 Hz, 1H), 8.28 (dd, J = 8.6, 2.5 Hz, 1H), 8.06 (dd, J = 8.5, 0.7 Hz, 1H), 8.02 (d, J = 2.3 Hz, 2H), 7.63 (td, J = 9.1, 1.2 Hz, 1H), 7.57 (d, J = 2.0 Hz, 1H), 7.32 (d, J = 8.8 Hz, 1H), 7.22 (dd, J = 2.8, 0.8 Hz, 1H), 7.02 (ddd, J = 8.8, 2.7, 1.2 Hz, 1H), 6.65 (dd, J = 9.2, 1.6 Hz, 1H). |

Example 4

4-[[2-fluoro-6-[2-methoxy-4-(trifluoromethoxy)phenoxy]-3-(trifluoromethyl)benzoyl]amino]pyridine-2-carboxamide (4)

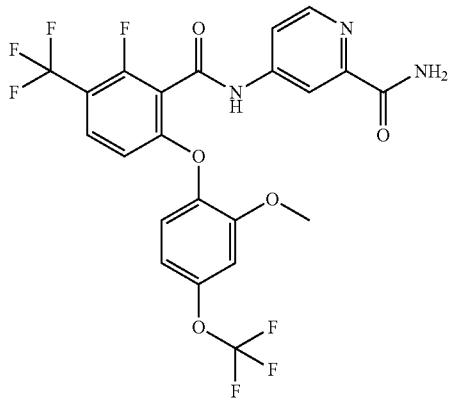 [SMILES: COc1cc(OC(F)(F)F)ccc1Oc1ccc(C(F)(F)F)c(F)c1C(=O)Nc1ccnc(C(N)=O)c1]

A microwave vial charged with 4-[(Z)-[(tert-butylamino)-phenylsulfanyl-methylene]amino]pyridine-2-carboxamide (75 mg, 0.29 mmol, prepared as described in Preparation 1), tris[(Z)-1-methyl-3-oxo-but-1-enoxy]iron (approximately 2 mg, 0.0057 mmol) and 2-fluoro-6-[2-methoxy-4-(trifluoromethoxy)phenoxy]-3-(trifluoromethyl)benzoic acid (prepared as described in Example 2, 94 mg, 0.29 mmol) in isopropanol (2 mL) was heated at 83° C. for 16 hours. The reaction mixture was cooled to room temperature and the solvent evaporated. The crude material was taken up in dichloromethane and washed with 1N HCl. The organic layer was dried over MgSO$_4$, filtered and concentrated. The residue was purified by silica gel chromatography (ethyl acetate/hexane gradient) to afford 4-[[2-fluoro-6-[2-methoxy-4-(trifluoromethoxy)phenoxy]-3-(trifluoromethyl)benzoyl]amino]pyridine-2-carboxamide (80 mg, 64%). ESI-MS m/z calc. 533.08215, found 534.1 (M+1)+; retention time (Method B): 1.77 minutes (3 minute run). $^1$H NMR (400 MHz, DMSO-d6) δ 11.45 (s, 1H), 8.56 (d, J=5.5 Hz, 1H), 8.32 (d, J=2.2 Hz, 1H), 8.12 (d, J=2.7 Hz, 1H), 7.86-7.77 (m, 2H), 7.72-7.64 (m, 1H), 7.38 (d, J=8.8 Hz, 1H), 7.27 (d, J=2.8 Hz, 1H), 7.08-7.01 (m, 1H), 6.68 (d, J=8.9 Hz, 1H), 3.79 (s, 3H) ppm.

Example 5

4-[[3-chloro-2-fluoro-6-[2-methoxy-4-(trifluoromethoxy)phenoxy]benzoyl]amino]pyridine-2-carboxamide (5)

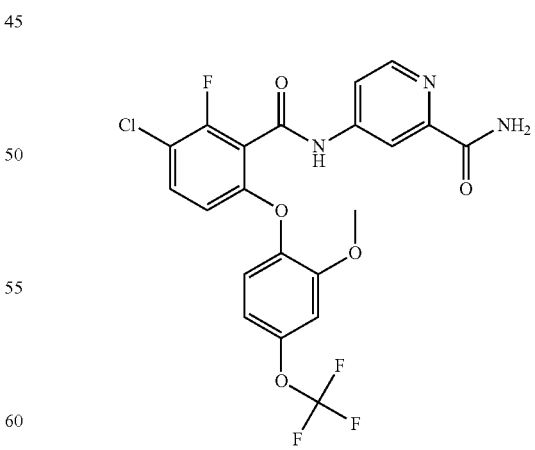

Step 1: 6-bromo-3-chloro-2-fluoro-benzoic acid

To a solution of 6-bromo-3-chloro-2-fluoro-benzaldehyde (1000 mg, 4.21 mmol) in a mixture of t-BuOH (7 mL) and water (5 mL) was added sodium dihydrogenphosphate (600 mg, 5.00 mmol) and 2-methyl-2-butene (9.5 mL of 2 M, 19.00 mmol). NaClO$_2$ (600 mg, 5.31 mmol) was then added in 1 portion. After 2 hours, the reaction mixture was acidified with 1M HCl, and extracted with ethyl acetate. The combined organic phases were dried over MgSO$_4$, filtered and concentrated under reduced pressure to afford 6-bromo-3-chloro-2-fluoro-benzoic acid (900 mg, 84%), which was used in the next step without further purification. ESI-MS m/z calc. 251.90, found 209.0 (M+1)+(decarboxylated fragment); retention time (Method D): 0.36 minutes (1.15 minute run).

Step 2: 3-chloro-2-fluoro-6-[2-methoxy-4-(trifluoromethoxy)phenoxy]benzoic acid

To a mixture of 6-bromo-3-chloro-2-fluoro-benzoic acid (900 mg, 3.55 mmol), 2-methoxy-4-(trifluoromethoxy)phenol (prepared as described in Example 2, 1 g, 4.80 mmol) and cesium carbonate (2.5 g, 7.67 mmol) in toluene (20 mL) was added copper (I) iodide (220 mg, 1.16 mmol). The resulting mixture was heated at 100° C. for 4 hours. The mixture was cooled to RT, the pH was adjusted to ~2 by addition of 2M HCl (aq) and the mixture was then extracted with ethyl acetate (2×30 mL). The organic phases were combined, washed with water (20 mL), brine (2×20 mL), dried (phase separation cartridge) and concentrated to afford a yellow-orange solid. The crude product was purified by reverse phase chromatography (ISCO 120 g C18 column, 0-100% CH$_3$CN:water-0.1% TFA gradient) to afford 3-chloro-2-fluoro-6-[2-methoxy-4-(trifluoromethoxy)phenoxy]benzoic acid (680 mg, 50%) as a cream-colored solid. ESI-MS m/z calc. 380.01, found 378.9 (M−1)−; retention time (Method D): 0.69 minutes (1.15 minute run).

Step 3: methyl 4-aminopyridine-2-carboxylate

To 4-aminopyridine-2-carboxylic acid (665 mg, 4.815 mmol) in methanol (25 mL) was added conc. sulfuric acid (257 μL, 4.82 mmol) and the mixture was heated at reflux overnight. The mixture was cooled to RT and concentrated under reduced pressure. The residue was diluted with saturated NaHCO$_3$ and extracted with dichloromethane (2×) followed by chloroform (3×). The combined organic phases were dried (MgSO$_4$), filtered and evaporated to dryness to give methyl 4-aminopyridine-2-carboxylate (370 mg, 51%) as a yellow solid. ESI-MS m/z calc. 151.06, found 152.85 (M+1)+; retention time (Method UK2): 1.55 minutes (4.55 minute run).

Step 4: methyl 4-[[3-chloro-2-fluoro-6-[2-methoxy-4-(trifluoromethoxy)phenoxy]benzoyl]amino]pyridine-2-carboxylate To an ice-cooled solution of 3-chloro-2-fluoro-6-[2-methoxy-4-(trifluoromethoxy)phenoxy]benzoic acid (180 mg, 0.47 mmol) in dichloromethane (3 mL) was added DMF (3.9 μL, 0.05 mmol), followed by dropwise addition of oxalyl chloride (141 μL, 1.616 mmol). The mixture was warmed to room temperature over 3 hours. The reaction mixture was then concentrated, dissolved in dichloromethane (3 mL) and cooled in an ice bath. Methyl 4-aminopyridine-2-carboxylate (94 mg, 0.62 mmol) was added followed by TEA (253 μL, 1.82 mmol). The resulting mixture was stirred and warmed to ambient temperature over 16 hours. The reaction mixture was quenched with water (10 mL) and extracted with dichloromethane (2×10 mL). The combined organic phases were dried (MgSO$_4$), filtered and concentrated. The residue was purified by silica gel chromatography (ethyl acetate/petroleum ether gradient) to give methyl 4-[[3-chloro-2-fluoro-6-[2-methoxy-4-(trifluoromethoxy)phenoxy]benzoyl]amino]pyridine-2-carboxylate (200 mg, 82%). ESI-MS m/z calc. 514.0555, found 515.0 (M+1)+; retention time (Method D): 1.0 minutes (1.15 minute run).

Step 5: 4-[[3-chloro-2-fluoro-6-[2-methoxy-4-(trifluoromethoxy)phenoxy]benzoyl]amino]pyridine-2-carboxamide (5)

Methyl 4-[[3-chloro-2-fluoro-6-[2-methoxy-4-(trifluoromethoxy)phenoxy]benzoyl]amino]pyridine-2-carboxylate (200 mg, 0.3885 mmol) was stirred in aqueous ammonia (6.3 mL of 7 M, 44.10 mmol) overnight. The reaction was concentrated and residue was triturated from ethyl acetate and ether to give 4-[[3-chloro-2-fluoro-6-[2-methoxy-4-(trifluoromethoxy)phenoxy]benzoyl]amino]pyridine-2-carboxamide (173.3 mg, 88%). ESI-MS m/z calc. 499.05, found 500.0 (M+1)+; retention time (Method E): 3.3 minutes (4.45 minute run). $^1$H NMR (400 MHz, DMSO-d6) δ 11.36 (s, 1H), 8.56 (d, J=5.5 Hz, 1H), 8.33 (d, J=2.2 Hz, 1H), 8.11 (d, J=2.9 Hz, 1H), 7.84 (dd, J=5.5, 2.2 Hz, 1H), 7.74-7.55 (m, 1H), 7.39-7.12 (m, 2H), 7.00 (ddd, J=8.8, 2.7, 1.3 Hz, 2H), 6.64 (dd, J=9.0, 1.4 Hz, 1H), 3.78 (s, 3H) ppm.

Example 6

4-[[2-fluoro-6-[2-(trideuteriomethoxy)-4-(trifluoromethoxy)phenoxy]-3-(trifluoromethyl)benzoyl]amino]pyridine-2-carboxamide (6)

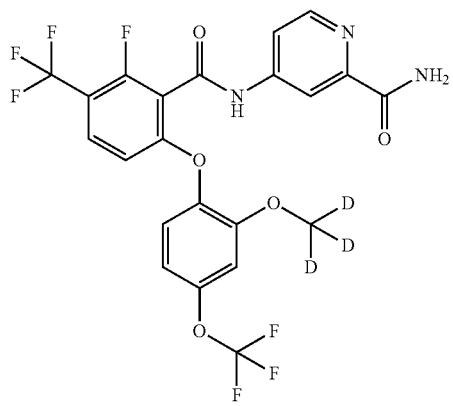 [SMILES: [2H]C([2H])([2H])Oc1cc(OC(F)(F)F)ccc1Oc1ccc(C(F)(F)F)c(F)c1C(=O)Nc1ccnc(C(N)=O)c1]

To an ice cold solution of 2-fluoro-6-[2-(trideuteriomethoxy)-4-(trifluoromethoxy)phenoxy]-3-(trifluoromethyl)benzoic acid (prepared as described in Example 1, 5 g, 11.98 mmol) and DMF (46 μL, 0.5941 mmol) in anhydrous dichloromethane (50 mL) under nitrogen was added oxalyl chloride (1.7 mL, 19.49 mmol) dropwise. Five minutes after the addition the ice bath was removed and the mixture was stirred at room temperature for 1 hour and at 35° C. for 15 min. The mixture was concentrated under reduced pressure and the residue was dissolved in dichloromethane (12.5 mL) and the resulting solution was added dropwise to a cold solution of 4-aminopyridine-2-carboxamide (1.97 g, 14.36 mmol) and DIEA (5.2 mL, 29.85 mmol) in NMP (50 mL) keeping the internal temperature between 1 and 5° C. The mixture was stirred for 10 minutes, and then the ice bath was removed and the mixture was stirred at room temperature for 2 hours. The reaction was partitioned between water (250 mL) and dichloromethane (50 mL) and the dichloromethane phase was washed with water (250 mL) and brine (100 mL) and the combined aqueous phases were back extracted with dichloromethane (25 mL). The combined organic phases were dried, filtered and evaporated. The residue was purified by silica gel chromatography (dichloromethane/methanol gradient) to give 5.75 g of an oil which was dissolved in ethyl acetate (50 mL), washed three times with water (3×50 mL) and once with brine (50 mL). The aqueous phases were back extracted once with ethyl acetate (25 mL) and the combined organic phases were dried, filtered, and concentrated under reduced pressure to give 4-[[2-fluoro-6-[2-(trideuteriomethoxy)-4-(trifluoromethoxy)phenoxy]-3-(trifluoromethyl)benzoyl]amino]pyridine-2-carboxamide (3.7 g, 57%) as a cream colored foam. ESI-MS m/z calc. 536.10, found 537.0 (M+1)+; retention time (Method B): 1.81 (3 minute run). $^1$H NMR (400 MHz, DMSO-d6) δ 11.43 (s, 1H), 8.56 (d, J=5.5 Hz, 1H), 8.33 (d, J=2.1 Hz, 1H), 8.10 (d, J=2.8 Hz, 1H), 7.88-7.77 (m, 2H), 7.66 (d, J=2.8 Hz, 1H), 7.37 (d, J=8.8 Hz, 1H), 7.26 (d, J=2.8 Hz, 1H), 7.08-7.01 (m, 1H), 6.68 (d, J=8.9 Hz, 1H) ppm.

Example 7

N-(3-carbamoyl-4-fluoro-phenyl)-3-(difluoromethyl)-2-fluoro-6-[2-methoxy-4-(trifluoromethoxy)phenoxy]benzamide (7)

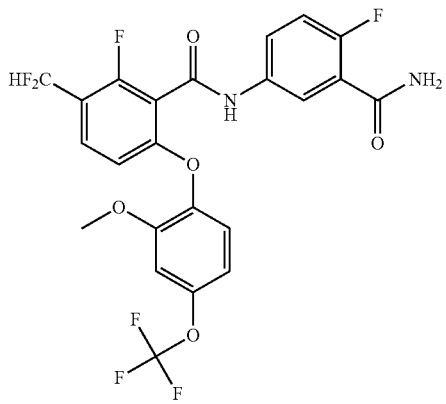

Step 1: methyl 3-bromo-2-fluoro-6-[2-methoxy-4-(trifluoromethoxy)phenoxy]benzoate A vial charged with methyl 3-bromo-2,6-difluoro-benzoate (1 g, 3.98 mmol), 2-methoxy-4-(trifluoromethoxy)phenol (prepared as described in Example 2, 830 mg, 3.988 mmol) and Cs$_2$CO$_3$ (2.5 g, 7.67 mmol) in DMF (20 mL) was stirred at room temperature overnight. The reaction mixture was quenched with water and the aqueous layer was extracted with ethyl acetate. The organic phase was washed with brine, dried over MgSO$_4$, filtered and concentrated. The resulting residue was purified by silica gel chromatography (ethyl acetate/hexane gradient) to give methyl 3-bromo-2-fluoro-6-[2-methoxy-4-(trifluoromethoxy)phenoxy]benzoate (250 mg, 14%). ESI-MS m/z calc. 439.97, found 440.9 (M+1)+; retention time (Method A): 0.83 minutes (1.2 minute run). $^1$H NMR (400 MHz, DMSO-d6) δ 7.73 (dd, J=9.0, 8.1 Hz, 1H), 7.27-7.23 (m, 2H), 7.00 (ddq, J=8.7, 2.4, 1.1 Hz, 1H), 6.54 (dd, J=9.0, 1.4 Hz, 1H), 3.86 (s, 3H), 3.78 (s, 3H) ppm.

Step 2: methyl 2-fluoro-3-formyl-6-[2-methoxy-4-(trifluoromethoxy)phenoxy]benzoate A solution of methyl 3-bromo-2-fluoro-6-[2-methoxy-4-(trifluoromethoxy)phenoxy]benzoate (250 mg, 0.57 mmol) in dry THF (2.5 mL) was purged with N$_2$. The solution was cooled to −70° C., iPrMgCl (350 μL of 2 M in diethyl ether, 0.70 mmol), was added dropwise while maintaining the reaction temperature below −60° C. DMF (500 μL, 6.457 mmol) was added immediately after (maintain temp below −40° C.) and the reaction was stirred for 20 minutes at −70° C. and then warmed to 25° C. and allowed to stir for an additional 30 minutes. The reaction was quenched with aqueous 1N HCl and extracted with ethyl acetate. The organic phase was washed with brine, dried over magnesium sulfate, filtered and concentrated. The resulting residue was purified by silica gel chromatography (ethyl acetate/hexane gradient) to give methyl 2-fluoro-3-formyl-6-[2-methoxy-4-(trifluoromethoxy)phenoxy]benzoate (135 mg, 61%). ESI-MS m/z calc. 388.06, found 389.0 (M+1)+; retention time (Method A): 0.73 minutes (1.2 minute run). $^1$H NMR (400 MHz, DMSO-d6) δ 10.09 (s, 1H), 7.87 (dd, J=8.9, 8.1 Hz, 1H), 7.35 (d, J=8.8 Hz, 1H), 7.29 (d, J=2.8 Hz, 1H), 7.04 (ddd, J=8.8, 2.7, 1.2 Hz, 1H), 6.64 (d, J=8.8 Hz, 1H), 3.90 (s, 3H), 3.78 (s, 3H) ppm.

Step 3: methyl 3-(difluoromethyl)-2-fluoro-6-[2-methoxy-4-(trifluoromethoxy)phenoxy]benzoate Deoxo-fluor® (Bis(2-methoxyethyl)aminosulfur trifluoride) (350 μL, 1.90 mmol) was added to methyl 2-fluoro-3-formyl-6-[2-methoxy-4-(trifluoromethoxy)phenoxy]benzoate (130 mg, 0.33 mmol) followed by 2 drops of EtOH and the mixture was stirred at RT overnight. The mixture was cooled to 0° C. and quenched with sat. aqueous sodium bicarbonate (gas evolution) and then extracted with ethyl acetate (3×). The combined organic phases were washed with water and brine, dried (MgSO$_4$) and evaporated to dryness. The crude material was again treated with Deoxo-fluor® (200 μL) and stirred for 2 hours. The mixture was cooled to 0° C. and quenched with sat. aqueous sodium bicarbonate (gas evolution) and then extracted with ethyl acetate (3×). The combined organic phases were washed with water and brine, dried (MgSO$_4$) and evaporated to dryness. The residue was purified by silica gel chromatography (ethyl acetate/hexane gradient) to give methyl 3-(difluoromethyl)-2-fluoro-6-[2-methoxy-4-(trifluoromethoxy)phenoxy]benzoate (90 mg, 66%). ESI-MS m/z calc. 410.06, found 411.0 (M+1)+; retention time (Method B): 2.01 minutes (3 minute run). $^1$H NMR (400 MHz, DMSO-d6) δ 7.66 (t, J=8.5 Hz, 1H), 7.30 (d, J=8.8 Hz, 1H), 7.27 (d, J=2.8 Hz, 1H), 7.13 (t, J=54.2 Hz, 1H), 7.02 (ddd, J=8.8, 2.7, 1.2 Hz, 1H), 6.63 (d, J=8.7 Hz, 1H), 3.88 (s, 3H), 3.78 (s, 3H) ppm.

Step 4: 3-(difluoromethyl)-2-fluoro-6-[2-methoxy-4-(trifluoromethoxy)phenoxy]benzoic acid To a flask charged with methyl 3-(difluoromethyl)-2-fluoro-6-[2-methoxy-4-(trifluoromethoxy)phenoxy]benzoate (175 mg, 0.43 mmol) in MeOH (2 mL) was added NaOH (1.5 mL of 3M, 4.50 mmol), and the mixture was stirred for 4 hours at room temperature. The solvent was evaporated, the reaction mixture was cooled to 0° C. and quenched with 6N HCl, and was extracted with dichloromethane. The organic layer was dried over MgSO$_4$, filtered and concentrated to obtain 3-(difluoromethyl)-2-fluoro-6-[2-methoxy-4-(trifluoromethoxy)phenoxy]benzoic acid (150 mg, 89%). ESI-MS m/z calc. 396.04324, found 397.0 (M+1)+; retention time (Method B): 1.74 minutes (3 minute run).

Step 5: 3-(difluoromethyl)-2-fluoro-6-[2-methoxy-4-(trifluoromethoxy)phenoxy]benzoyl chloride To a solution of 3-(difluoromethyl)-2-fluoro-6-[2-methoxy-4-(trifluoromethoxy)phenoxy]benzoic acid (150 mg, 0.38 mmol) and DMF (10 μL, 0.13 mmol) in dichloromethane (2 mL) at 0° C. was added oxalyl chloride (50 μL, 0.5732 mmol) dropwise. The mixture was stirred at room temperature for 30 minutes. The solvent was evaporated under reduced pressure to afford 3-(difluoromethyl)-2-fluoro-6-[2-methoxy-4-(trifluoromethoxy)phenoxy]benzoyl chloride, which was used without purification in the next step.

Step 6: N-(3-carbamoyl-4-fluoro-phenyl)-3-(difluoromethyl)-2-fluoro-6-[2-methoxy-4-(trifluoromethoxy)phenoxy]benzamide (7)

A solution of 5-amino-2-fluoro-benzamide (29 mg, 0.19 mmol) and DIEA (100 μL, 0.57 mmol) in THF (1 mL) was cooled to 0° C. To this solution was added a suspension of 3-(difluoromethyl)-2-fluoro-6-[2-methoxy-4-(trifluoromethoxy)phenoxy]benzoyl chloride (75 mg, 0.1809 mmol) in THF (1 mL) and dichloromethane (1 mL). The reaction mixture was gradually warmed to room temperature and stirred for 16 hours. The reaction mixture was quenched with water and the aqueous layer was extracted with dichloromethane. The organic phase was washed with 1N HCl (2×), dried over MgSO$_4$, filtered and concentrated. The residue was purified by silica gel chromatography (ethyl acetate/hexane gradient) to afford N-(3-carbamoyl-4-fluoro-phenyl)-3-(difluoromethyl)-2-fluoro-6-[2-methoxy-4-(trifluoromethoxy)phenoxy]benzamide (29 mg, 29%). ESI-MS m/z calc. 532.09, found 533.1 (M+1)+; retention time (Method B): 1.72 minutes (3 minute run). $^1$H NMR (400 MHz, DMSO-d6) δ 10.95 (s, 1H), 8.00 (dd, J=6.4, 2.8 Hz, 1H), 7.78 (ddd, J=8.9, 4.4, 2.8 Hz, 1H), 7.73 (s, 1H), 7.65 (dd, J=17.3, 9.0 Hz, 2H), 7.34-7.23 (m, 3H), 7.15 (t, J=54.2 Hz, 1H), 7.03 (ddd, J=8.8, 2.7, 1.2 Hz, 1H), 6.62 (d, J=8.7 Hz, 1H), 3.79 (s, 3H) ppm.

Example 8

4-[[2-fluoro-6-[2-(trideuteriomethoxy)-4-(trifluoromethoxy)phenoxy]-3-(trifluoromethoxy)benzoyl]amino]pyridine-2-carboxamide (8)

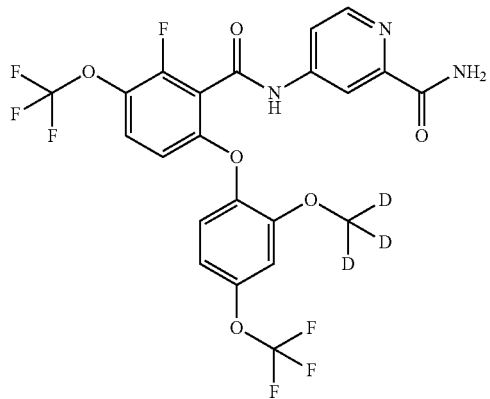 [SMILES: [2H]C([2H])([2H])Oc1cc(OC(F)(F)F)ccc1Oc1ccc(OC(F)(F)F)c(F)c1C(=O)Nc1ccnc(C(N)=O)c1]

A solution of 2-fluoro-6-[2-(trideuteriomethoxy)-4-(trifluoromethoxy)phenoxy]-3-(trifluoromethoxy)benzoic acid (prepared as described in Example 3, 600 mg, 1.39 mmol) in dichloromethane (12 mL) was cooled using an ice-bath. To this was added DMF (20 μL, 0.26 mmol) followed by careful addition of oxalyl chloride (275 μL, 3.15 mmol). The solution was stirred for 10 minutes then removed from the ice bath and allowed to warm to room temperature over 1 h. The reaction was concentrated under reduced pressure and azeotroped with dichloromethane to afford 2,5-difluoro-4-(trifluoromethyl)benzoyl chloride, which was used without purification. An ice cold solution of this material in dichloromethane (6 mL) was added to an ice cold solution of 4-aminopyridine-2-carboxamide (190 mg, 1.39 mmol), dichloromethane (6 mL), NMP (2 mL) and DIEA (725 μL, 4.16 mmol). The reaction was stirred for 10 minutes then removed from the ice bath and allowed to come to room temperature over 1 hour. The reaction was concentrated and purified by reverse phase HPLC to provide 4-[[2-fluoro-6-[2-(trideuteriomethoxy)-4-(trifluoromethoxy)phenoxy]-3-(trifluoromethoxy)benzoyl]amino]pyridine-2-carboxamide (316 mg, 41%). ESI-MS m/z calc. 552.10, found 553.2 (M+1)+; retention time (Method B): 1.77 minutes (3 minute run). $^1$H NMR (400 MHz, DMSO-d6) δ 11.41 (s, 1H), 8.55 (d, J=5.4 Hz, 1H), 8.31 (d, J=2.1 Hz, 1H), 8.10 (d, J=2.8 Hz, 1H), 7.83 (dd, J=5.5, 2.2 Hz, 1H), 7.69-7.58 (m, 2H), 7.32 (d, J=8.8 Hz, 1H), 7.22 (dd, J=2.8, 0.8 Hz, 1H), 7.02 (ddd, J=8.8, 2.7, 1.2 Hz, 1H), 6.65 (dd, J=9.2, 1.6 Hz, 1H) ppm.

Example 9

N-(3-carbamoyl-4-fluoro-phenyl)-6-[2-chloro-4-(trifluoromethoxy)phenoxy]-2-fluoro-3-(trifluoromethyl)benzamide (9)

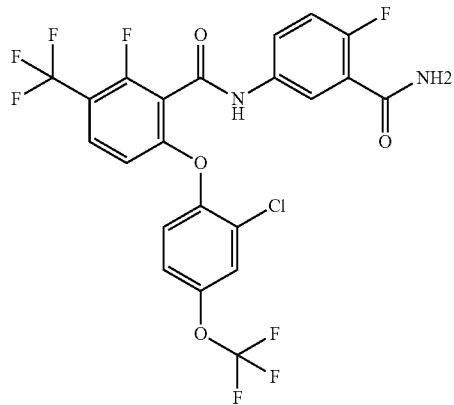 [SMILES: NC(=O)c1cc(NC(=O)c2c(Oc3ccc(OC(F)(F)F)cc3Cl)ccc(C(F)(F)F)c2F)ccc1F]

Step 1: 6-[2-chloro-4-(trifluoromethoxy)phenoxy]-2-fluoro-3-(trifluoromethyl)benzoic acid A pressure flask was charged with 6-bromo-2-fluoro-3-(trifluoromethyl)benzoic acid (3.24 g, 11.29 mmol), cesium carbonate (7.357 g, 22.58 mmol) and 2-chloro-4-(trifluoromethoxy)phenol (2.4 g, 11.29 mmol) in toluene (24.3 mL). The mixture was degassed with nitrogen. After ca. 2 minutes, copper (I) iodide (430 mg, 2.258 mmol) was added and the reaction was stirred at 100° C. for 10 minutes. The reaction was diluted with ethyl acetate and water. The phases were separated and the organic phase was washed with brine and dried over sodium sulfate. Trituration with hexane (2×) and filtration gave 6-[2-chloro-4-(trifluoromethoxy)phenoxy]-2-fluoro-3-(trifluoromethyl)benzoic acid (3.54 g, 75%). ESI-MS m/z calc. 417.98, found 419.2 (M+1)+; retention time (Method B): 1.9 minutes (3 minute run). $^1$H NMR (400 MHz, DMSO-d6) δ 7.74 (d, J=2.8 Hz, 1H), 7.46 (t, J=8.3 Hz, 1H), 7.42-7.34 (m, 1H), 7.15 (d, J=9.0 Hz, 1H), 6.69 (d, J=8.6 Hz, 1H) ppm.

Step 2: 6-[2-chloro-4-(trifluoromethoxy)phenoxy]-2-fluoro-3-(trifluoromethyl)benzoyl chloride To 6-[2-chloro-4-(trifluoromethoxy)phenoxy]-2-fluoro-3-(trifluoromethyl)benzoic acid (600 mg, 1.43 mmol) and N,N-dimethylformamide (10 µL, 0.13 mmol) in dichloromethane (7 mL) at 0° C. was added oxalyl chloride (609 µL, 6.99 mmol) dropwise. The mixture was stirred at room temperature for 15 minutes under a N$_2$ atmosphere. The solvent was evaporated under reduced pressure to afford 6-[2-chloro-4-(trifluoromethoxy)phenoxy]-2-fluoro-3-(trifluoromethyl)benzoyl chloride (626 mg, 100%), which was used in the next step without further purification.

Step 3: N-(3-carbamoyl-4-fluoro-phenyl)-6-[2-chloro-4-(trifluoromethoxy)phenoxy]-2-fluoro-3-(trifluoromethyl)benzamide (9)

To 5-amino-2-fluoro-benzamide (70.54 mg, 0.4576 mmol) and diisopropylethylamine (178 mg, 1.37 mmol) in dichloromethane (2.4 mL) cooled at 0° C. was added dropwise a solution of 6-[2-chloro-4-(trifluoromethoxy)phenoxy]-2-fluoro-3-(trifluoromethyl)benzoyl chloride (200 mg, 0.46 mmol) in dichloromethane (2.4 mL). The reaction was stirred at room temperature overnight. The crude material was purified by silica gel chromatography (ethyl acetate/hexane gradient) to obtain N-(3-carbamoyl-4-fluoro-phenyl)-6-[2-chloro-4-(trifluoromethoxy)phenoxy]-2-fluoro-3-(trifluoromethyl)benzamide (85 mg, 33%). ESI-MS m/z calc. 554.03, found 555.0 (M+1)+; retention time (Method B): 1.9 minutes (3 minute run). $^1$H NMR (400 MHz, DMSO-d6) δ 11.06 (s, 1H), 7.98 (dd, J=6.4, 2.8 Hz, 1H), 7.95-7.82 (m, 2H), 7.80-7.59 (m, 3H), 7.52 (d, J=2.4 Hz, 2H), 7.30 (dd, J=10.0, 9.1 Hz, 1H), 6.85 (d, J=8.8 Hz, 1H) ppm.

The compounds set forth in Table 5 were prepared by methods analogous to the preparation of compound 9.

TABLE 5

Additional Compounds Prepared By Methods Analogous to Example 9

| Cmpd No. | Compound Name | LC/MS | NMR (shifts in ppm) |
|---|---|---|---|
| 51 | 4-[[6-[2-chloro-4-(trifluoromethoxy)phenoxy]-2-fluoro-3-(trifluoromethyl)benzoyl]amino]pyridine-2-carboxamide | ESI-MS m/z calc. 537.03 found 538.0 (M + 1)+; Retention time (Method B): 1.84 minutes (3 minute run). | $^1$H NMR (400 MHz, DMSO-d6) δ 11.50 (s, 1H), 8.57 (d, J = 5.5 Hz, 1H), 8.31 (d, J = 2.1 Hz, 1H), 8.12 (d, J = 2.7 Hz, 1H), 7.94-7.77 (m, 3H), 7.68 (d, J = 2.7 Hz, 1H), 7.53 (t, J = 1.3 Hz, 2H), 6.88 (d, J = 8.8 Hz, 1H). |

Example 10

N-(3-carbamoyl-4-fluoro-phenyl)-2-fluoro-6-[2-methyl-4-(trifluoromethoxy)phenoxy]-3-(trifluoromethyl)benzamide (10)

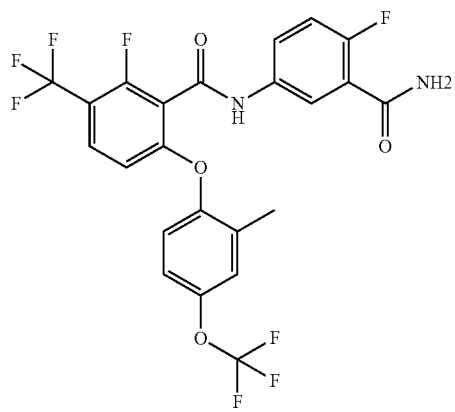 [SMILES: Cc1cc(OC(F)(F)F)ccc1Oc1ccc(C(F)(F)F)c(F)c1C(=O)Nc1ccc(F)c(C(N)=O)c1]

Step 1: 2-fluoro-6-[2-methyl-4-(trifluoromethoxy)phenoxy]-3-(trifluoromethyl)benzoic acid To a pressure flask was added 6-bromo-2-fluoro-3-(trifluoromethyl)benzoic acid (4.48 g, 15.61 mmol), 2-methyl-4-(trifluoromethoxy)phenol (3 g, 15.61 mmol), cesium carbonate (5.1 g, 15.65 mmol), and toluene (90 mL). The mixture was degassed with N$_2$ for 10 min, then copper (I) iodide (600 mg, 3.15 mmol) added. The flask was flushed with N$_2$, sealed, and heated at 100° C. with vigorous stirring for 1 hour. The mixture was allowed to cool to RT and then diluted with ethyl acetate and water. The water layer was acidified with HCl (32 mL of 1 M, 32.00 mmol) and the product extracted into ethyl acetate. The organic phase was washed with brine, dried over sodium sulfate, filtered and concentrated. To the resulting the oil was added minimal dichloromethane and hexane to form an off white precipitate. The solid was filtered, washed with hexane and dried to provide 2-fluoro-6-[2-methyl-4-(trifluoromethoxy)phenoxy]-3-(trifluoromethyl)benzoic acid (6.1 g, 98%) as a white solid. ESI-MS m/z calc. 398.04, found 399.0 (M+1)+; retention time (Method A): 0.76 minutes (1.2 minute run). $^1$H NMR (400 MHz, DMSO-d6) δ 14.17 (s, 1H), 7.80 (t, J=8.6 Hz, 1H), 7.46 (d, J=2.9 Hz, 1H), 7.31 (dd, J=8.9, 2.9 Hz, 1H), 7.23 (d, J=8.8 Hz, 1H), 6.68 (d, J=8.9 Hz, 1H), 2.18 (s, 3H) ppm.

Step 2: 2-fluoro-6-[2-methyl-4-(trifluoromethoxy) phenoxy]-3-(trifluoromethyl)benzoyl chloride To a solution of 2-fluoro-6-[2-methyl-4-(trifluoromethoxy)phenoxy]-3-(trifluoromethyl)benzoic acid (800 mg, 2.01 mmol) and N,N-dimethylformamide (35 µL, 0.45 mmol) in dichloromethane (8 mL) at 0° C. was added oxalyl chloride (900 µL, 10.32 mmol) dropwise. The mixture was allowed to warm to room temperature and stirred 30 minutes. The solvent was evaporated under reduced pressure to afford 2-fluoro-6-[2-methyl-4-(trifluoromethoxy)phenoxy]-3-(trifluoromethyl)benzoyl chloride as a yellow solid, which was used in the next step without further purification.

Step 3: N-(3-carbamoyl-4-fluoro-phenyl)-2-fluoro-6-[2-methyl-4-(trifluoromethoxy)phenoxy]-3-(trifluoromethyl)benzamide (10)

To a solution of 5-amino-2-fluoro-benzamide (37 mg, 0.24 mmol) in dichloromethane (1 mL) was added DIEA (approximately 93.06 mg, 125.4 µL, 0.7200 mmol) and the mixture was cooled to 0° C. To this solution was added a cold solution of 2-fluoro-6-[2-methyl-4-(trifluoromethoxy)phenoxy]-3-(trifluoromethyl)benzoyl chloride (100 mg, 0.24 mmol) in dichloromethane (1 mL) dropwise. The reaction was allowed to come to room temperature then stirred for 16 hours. The mixture was concentrated, then dissolved in 2 mL DMSO and purified by reverse phase HPLC to provide N-(3-carbamoyl-4-fluoro-phenyl)-2-fluoro-6-[2-methyl-4-(trifluoromethoxy)phenoxy]-3-(trifluoromethyl)benzamide (551 mg, 48%). ESI-MS m/z calc. 534.0826, found 535.1 (M+1)+; retention time (Method B): 1.9 minutes (3 minute run). $^1$H NMR (400 MHz, DMSO-d6) δ 11.06 (s, 1H), 7.98 (dd, J=6.4, 2.8 Hz, 1H), 7.82 (t, J=8.7 Hz, 1H), 7.76 (ddd, J=9.2, 4.5, 3.0 Hz, 2H), 7.70 (s, 1H), 7.43 (d, J=2.8 Hz, 1H), 7.36-7.24 (m, 3H), 6.70 (d, J=8.9 Hz, 1H), 2.18 (s, 3H) ppm.

The compounds set forth in Table 6 were prepared by methods analogous to the preparation of compound 10.

Example 11

N-(3-carbamoyl-4-fluoro-phenyl)-2,3,4-trifluoro-6-[2-methoxy-4-(trifluoromethoxy)phenoxy]benzamide (11)

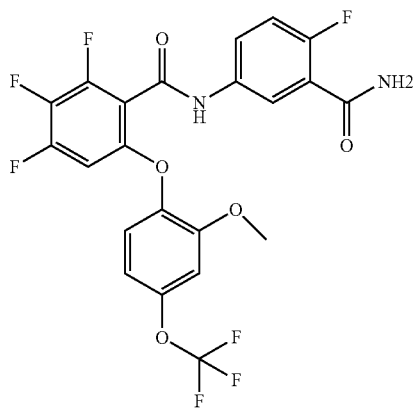 [SMILES: COc1cc(OC(F)(F)F)ccc1Oc1cc(F)c(F)c(F)c1C(=O)Nc1ccc(F)c(C(N)=O)c1]

Step 1: 2,3,4-trifluoro-6-[2-methoxy-4-(trifluoromethoxy)phenoxy]benzoic acid A solution of 6-bromo-2,3,4-trifluoro-benzoic acid (544 mg, 2.13 mmol), $Cs_2CO_3$ (1.4 g, 4.30 mmol), copper (I) iodide (92.3 mg, 0.4846 mmol), 2-methoxy-4-(trifluoromethoxy)phenol (prepared as described in Example 2, 675 mg, 3.24 mmol) and toluene (5.5 mL) was flushed with $N_2$ and stirred at 100° C. for 6 hours. After cooling to RT, water and ethyl acetate were added to the mixture and the layers were separated. The aqueous layer was acidified with concentrated HCl to ~pH 1 and extracted with ethyl acetate (3×). The combined organic phases were dried over sodium sulfate, filtered and concentrated under reduced pressure. The crude material was purified by silica gel chromatography (ethyl acetate/hexane gradient) to yield 2,3,4-trifluoro-6-[2-methoxy-4-(trifluoromethoxy)phenoxy]benzoic acid

TABLE 6

Additional Compounds Prepared By Methods Analogous to Example 10

| Cmpd No. | Compound Name | LC/MS | NMR (shifts in ppm) |
|---|---|---|---|
| 59 | 4-[[2-fluoro-6-[2-methyl-4-(trifluoromethoxy)phenoxy]-3-(trifluoromethyl)benzoyl]amino]pyridine-2-carboxamide | ESI-MS m/z calc. 517.09, found 518.1 (M + 1)+; Retention time (Method B): 1.87 minutes (3 minute run). | $^1$H NMR (400 MHz, DMSO-d6) δ 11.50 (s, 1H), 8.56 (d, J = 5.5 Hz, 1H), 8.32 (d, J = 2.1 Hz, 1H), 8.13 (d, J = 2.7 Hz, 1H), 7.86 (t, J = 8.7 Hz, 1H), 7.82 (dd, J = 5.5, 2.2 Hz, 1H), 7.69 (d, J = 2.9 Hz, 1H), 7.46-7.41 (m, 1H), 7.35-7.25 (m, 2H), 6.74 (d, J = 8.9 Hz, 1H), 2.18 (s, 3H). |
| 66 | N-(4-carbamoyl-3-fluoro-phenyl)-2-fluoro-6-[2-methyl-4-(trifluoromethoxy)phenoxy]-3-(trifluoromethyl)benzamide | ESI-MS m/z calc. 534.08, found 535.1 (M + 1)+; Retention time (Method B): 1.92 minutes (3 minute run). | $^1$H NMR (400 MHz, DMSO-d6) δ 11.30 (s, 1H), 7.84 (t, J = 8.6 Hz, 1H), 7.73 (d, J = 8.5 Hz, 1H), 7.71-7.64 (m, 1H), 7.60 (s, 1H), 7.56 (s, 1H), 7.46-7.39 (m, 2H), 7.32 (dd, J = 8.9, 2.7 Hz, 1H), 7.27 (d, J = 8.9 Hz, 1H), 6.73 (d, J = 8.8 Hz, 1H), 2.18 (s, 3H). |

(143.6 mg, 18%). ESI-MS m/z calc. 382.0276, found 383.1 (M+1)+; retention time (Method B): 1.82 minutes (3 minute run).

Step 2: N-(3-carbamoyl-4-fluoro-phenyl)-2,3,4-trifluoro-6-[2-methoxy-4-(trifluoromethoxy)phenoxy]benzamide (11)

2,3,4-trifluoro-6-[2-methoxy-4-(trifluoromethoxy)phenoxy]benzoic acid (140 mg, 0.37 mmol) and HATU (145 mg, 0.38 mmol) were combined in N,N-dimethylformamide (1.5 mL) and DIEA (128 μL, 0.73 mmol) and stirred for 5 minutes. 5-Amino-2-fluoro-benzamide (57.1 mg, 0.3704 mmol) was added in one portion and the reaction was stirred at RT for 2.5 hours. The reaction was diluted with ethyl acetate and washed with saturated aqueous sodium bicarbonate and brine. The organic layer was dried over sodium sulfate, filtered, and concentrated. The crude material was purified by silica gel chromatography (ethyl acetate/hexane gradient) and re-purified using a reverse phase HPLC to yield N-(3-carbamoyl-4-fluoro-phenyl)-2,3,4-trifluoro-6-[2-methoxy-4-(trifluoromethoxy)phenoxy]benzamide (18.1 mg, 10%) as a white solid. ESI-MS m/z calc. 518.07, found 519.1 (M+1)+; retention time (Method B): 1.73 minutes (3 minute run). $^1$H NMR (400 MHz, DMSO-d6) δ 10.92 (s, 1H), 7.96 (dd, J=6.4, 2.8 Hz, 1H), 7.80-7.60 (m, 3H), 7.28 (dd, J=10.1, 8.9 Hz, 1H), 7.24 (d, J=8.8 Hz, 1H), 7.18 (d, J=2.8 Hz, 1H), 7.06-6.90 (m, 1H), 6.90-6.76 (m, 1H), 3.78 (s, 3H) ppm.

Example 12

N-(2-Carbamoyl-4-pyridyl)-3-fluoro-5-[2-methoxy-4-(trifluoromethoxy)phenoxy]-2-(trifluoromethyl)pyridine-4-carboxamide (12)

N-(2-Carbamoyl-4-pyridyl)-3-methoxy-5-[2-methoxy-4-(trifluoromethoxy)phenoxy]-2-(trifluoromethyl)pyridine-4-carboxamide (166)

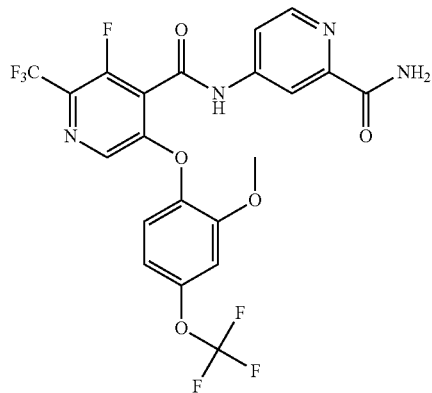

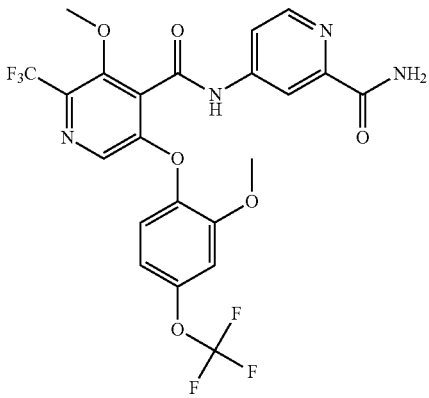

Step 1: ethyl 3,5-difluoro-2-(trifluoromethyl)pyridine-4-carboxylate 3,5-difluoro-2-(trifluoromethyl)pyridine (4.87 g, 26.57 mmol) was dissolved in anhydrous THF (20 mL) under a nitrogen atmosphere and cooled in a dry ice acetone bath (internal temperature −75° C.). Lithium diisopropylamide (15.94 mL of 2 M, 31.88 mmol) as a solution in THF/heptane/benzene was further diluted with anhydrous THF (50 mL) and this solution was added dropwise via pressure equalized addition funnel to the reaction mixture, not letting the internal temperature rise above −70° C. After complete addition the reaction mixture continued to stir for 1 h with cooling resulting in a dark orange solution. Ethyl chloroformate (6.9 mL, 72.16 mmol) as solution in THF (10 mL) was then added dropwise via pressure equalized addition funnel to the reaction mixture maintaining and internal temperature below −70° C. and stirred for an additional 5 minutes at this temperature. The cooling bath was removed and the reaction was allowed to warm to warm to room temperature. After 25 minutes at room temperature the reaction was quenched with saturated aqueous ammonium chloride. The mixture was extracted with ethyl acetate, and the organic layer was washed with water. The organic layer was dried over sodium sulfate, filtered and concentrated under reduced pressure. The crude material was purified by silica gel chromatography (ethyl acetate/hexane gradient) to provide ethyl 3,5-difluoro-2-(trifluoromethyl)pyridine-4-carboxylate (3.2 g, 47%) as a clear liquid. ESI-MS m/z calc. 255.03, found 256.0 (M+1)+; retention time (Method A): 0.68 minutes (1.2 minute run). $^1$H NMR (400 MHz, DMSO-d6) δ 8.90 (s, 1H), 4.46 (q, J=7.1 Hz, 2H), 1.34 (t, J=7.1 Hz, 3H) ppm.

Step 2: ethyl 3-fluoro-5-[2-methoxy-4-(trifluoromethoxy)phenoxy]-2-(trifluoromethyl)pyridine-4-carboxylate Ethyl 3,5-difluoro-2-(trifluoromethyl)pyridine-4-carboxylate (634 mg, 2.49 mmol) was dissolved in anhydrous DMA (6 mL) under a nitrogen atmosphere and then cooled in an ice water bath. 2-Methoxy-4-(trifluoromethoxy)phenol (prepared as described in Example 2, 517 mg, 2.48 mmol) was added in one portion followed by Cs$_2$CO$_3$ (1.62 g, 4.97 mmol). The reaction mixture was allowed to warm to room temperature and was stirred for 2 hours. The reaction mixture was partitioned between ethyl acetate and water and the layers were separated. The organic layer was then washed with brine (3×), dried over sodium sulfate, filtered and concentrated under reduced pressure. The crude material was purified by silica gel chromatography (ethyl acetate/hexane gradient) to yield ethyl 3-fluoro-5-[2-methoxy-4-(trifluoromethoxy)phenoxy]-2-(trifluoromethyl)pyridine-4-carboxylate (818 mg, 74%) as a white solid. ESI-MS m/z calc. 443.06, found 444.07 (M+1)+; retention time (Method A): 0.85 minutes (1.2 minute run). $^1$H NMR (400 MHz, DMSO-d6) δ 8.20 (s, 1H), 7.40 (d, J=8.8 Hz, 1H), 7.28 (d, J=2.7 Hz, 1H), 7.04 (ddd, J=8.8, 2.7, 1.3 Hz, 1H), 4.37 (q, J=7.1 Hz, 2H), 3.81 (s, 3H), 1.27 (t, J=7.1 Hz, 3H) ppm.

Step 3: 3-fluoro-5-[2-methoxy-4-(trifluoromethoxy)phenoxy]-2-(trifluoromethyl)pyridine-4-carboxylic acid Ethyl 3-fluoro-5-[2-methoxy-4-(trifluoromethoxy)phenoxy]-2-(trifluoromethyl)pyridine-4-carboxylate (620 mg, 1.40 mmol) was dissolved in methanol (9 mL) and then cooled in an ice water bath. Water (3 mL) was added followed by the addition of NaOH (800 mg, 20.00 mmol) and the reaction was stirred with cooling for 5 minutes. The cooling bath was removed and stirring continued as the reaction mixture was allowed to warm to room temperature and continued to stir for 30 minutes. The solvents were removed under reduced pressure and the resulting solid was dissolved in water, cooled in an ice water bath and treated with the dropwise addition of 6 M aqueous HCl until a white solid formed. The resulting solid was collected by vacuum filtration, washed with water and then further dried under reduced pressure to yield 3-fluoro-5-[2-methoxy-4-(trifluoromethoxy)phenoxy]-2-(trifluoromethyl)pyridine-4-carboxylic acid (470 mg, 81%). ESI-MS m/z calc. 415.02908, found 416.1 (M+1)+; retention time (Method C): 2.41 minutes (5 minute run). $^1$H NMR (400 MHz, DMSO-d6) δ 8.08 (s, 1H), 7.39 (d, J=8.8 Hz, 1H), 7.28 (d, J=2.8 Hz, 1H), 7.03 (ddd, J=8.8, 2.8, 1.3 Hz, 1H), 3.81 (s, 3H) ppm.

Step 4: methyl 4-[[3-fluoro-5-[2-methoxy-4-(trifluoromethoxy)phenoxy]-2-(trifluoromethyl)pyridine-4-carbonyl]amino]pyridine-2-carboxylate To an ice-cooled solution of 3-fluoro-5-[2-methoxy-4-(trifluoromethoxy)phenoxy]-2-(trifluoromethyl)pyridine-4-carboxylic acid (240 mg, 0.58 mmol) in dichloromethane (4 mL) was added DMF (5 µL, 0.065 mmol) and carefully oxalyl chloride (173 µL, 1.98 mmol) and the mixture was allowed to warmed to room temperature over 3 hours. The reaction mixture was concentrated under reduced pressure, dissolved in dichloromethane (4 mL) and cooled in an ice bath. Methyl 4-aminopyridine-2-carboxylate (prepared as described in Example 5, 115 mg, 0.76 mmol) was added followed by triethylamine (431 µL, 3.09 mmol). The resulting mixture was allowed to warm to RT and stirred for 16 hours. The reaction mixture was quenched with water (10 mL) and extracted with dichloromethane (2×10 mL). The combined organics were dried (MgSO$_4$), filtered and concentrated under reduced pressure. The residue was purified by silica gel chromatography (ethyl acetate/petroleum ether gradient) to give methyl 4-[[3-fluoro-5-[2-methoxy-4-(trifluoromethoxy)phenoxy]-2-(trifluoromethyl)pyridine-4-carbonyl]amino]pyridine-2-carboxylate (182 mg, 57%). ESI-MS m/z calc. 549.0771, found 550.0 (M+1)+; retention time (Method D): 1.01 minutes (1.15 run).

Step 5: N-(2-carbamoyl-4-pyridyl)-3-fluoro-5-[2-methoxy-4-(trifluoromethoxy)phenoxy]-2-(trifluoromethyl)pyridine-4-carboxamide (12) and N-(2-Carbamoyl-4-pyridyl)-3-methoxy-5-[2-methoxy-4-(trifluoromethoxy)phenoxy]-2-(trifluoromethyl)pyridine-4-carboxamide (166)

A solution of methyl 4-[[3-fluoro-5-[2-methoxy-4-(trifluoromethoxy)phenoxy]-2-(trifluoromethyl)pyridine-4-carbonyl]amino]pyridine-2-carboxylate (182 mg, 0.33 mmol) in ammonia (5.3 mL of 7 M, 37.10 mmol) was stirred at RT overnight. The reaction was concentrated and the crude material was purified by achiral, normal phase SFC (DEAP Column (250×21.2 mm, 6 Å 5 µm particle) made by Princeton (pn: 250212-01575) with a Gemini-NX (10×10 mm) guard column), isocratic run over 15.5 minutes. Mobile phase A=Supercritical Liquid Carbon Dioxide (58-60 bar); Mobile phase B=5% Methanol with 20 mM Ammonium hydroxide; Flow rate=100 mL/min; injection volume=600 µL; Mass load 44 mg/injection; column temperature=40° C. Two products were obtained as white solids:

N-(2-carbamoyl-4-pyridyl)-3-fluoro-5-[2-methoxy-4-(trifluoromethoxy)phenoxy]-2-(trifluoromethyl)pyridine-4-carboxamide (12, 17.53 mg, 10%). ESI-MS m/z calc. 534.08, found 535.0 (M+1)+; retention time (Method E): 3.22 minutes (4.45 minute run). $^1$H NMR (400 MHz, DMSO-d6) δ 11.58 (s, 1H), 8.58 (d, J=5.5 Hz, 1H), 8.40-8.06 (m, 3H), 7.78 (dd, J=5.5, 2.2 Hz, 1H), 7.69 (d, J=2.8 Hz, 1H), 7.42 (d, J=8.8 Hz, 1H), 7.24 (d, J=2.7 Hz, 1H), 7.12-6.89 (m, 1H), 3.80 (s, 3H) ppm.

N-(2-Carbamoyl-4-pyridyl)-3-methoxy-5-[2-methoxy-4-(trifluoromethoxy)phenoxy]-2-(trifluoromethyl)pyridine-4-carboxamide (166, 50 mg, 27%). ESI-MS m/z calc. 546.10, found 547.0 (M+1)+; retention time (Method E): 3.17 minutes (5 minute run). $^1$H NMR (400 MHz, DMSO-d6) δ 11.50 (s, 1H), 8.58 (s, 1H), 8.33 (d, J=2.1 Hz, 1H), 8.12 (d, J=2.9 Hz, 1H), 7.97 (s, 1H), 7.82 (dd, J=5.5, 2.2 Hz, 1H), 7.68 (d, J=2.9 Hz, 1H), 7.36 (d, J=8.8 Hz, 1H), 7.23 (d, J=2.7 Hz, 1H), 7.01 (ddd, J=8.8, 2.8, 1.3 Hz, 1H), 3.97 (s, 3H), 3.80 (s, 3H) ppm.

Example 13

4-[[6-[2-(difluoromethoxy)-4-(trifluoromethoxy)phenoxy]-2-fluoro-3-(trifluoromethyl)benzoyl]amino]pyridine-2-carboxamide (13)

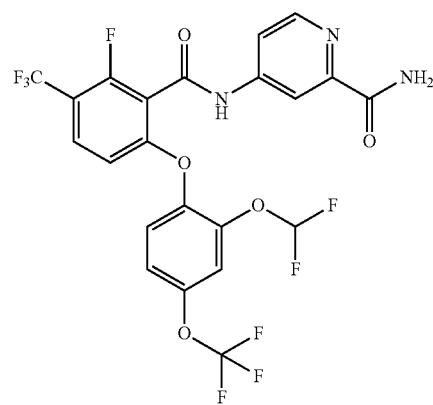 [SMILES: NC(=O)c1cc(NC(=O)c2c(Oc3ccc(OC(F)(F)F)cc3OC(F)F)ccc(C(F)(F)F)c2F)ccn1]

Step 1: 6-bromo-2-fluoro-3-(trifluoromethyl)benzoyl chloride

To 6-bromo-2-fluoro-3-(trifluoromethyl)benzoic acid (5.4 g, 18.81 mmol) and N,N-dimethylformamide (125.9 mg, 1.722 mmol) in dichloromethane (54 mL) at 0° C. was added oxalyl chloride (11.46 g, 90.29 mmol) dropwise. The mixture was stirred at room temperature for 5 hours under $N_2$ atmosphere. The solvent was evaporated under reduced pressure to afford 6-bromo-2-fluoro-3-(trifluoromethyl)benzoyl chloride, which was used in the next step without further purification.

Step 2: 4-[[6-bromo-2-fluoro-3-(trifluoromethyl)benzoyl]amino]pyridine-2-carboxamide To 4-aminopyridine-2-carboxamide (2.559 g, 18.66 mmol) and diisopropylethylamine (6.03 g, 46.65 mmol) in dichloromethane (28.5 mL) cooled at 0° C. was added dropwise a solution of 6-bromo-2-fluoro-3-(trifluoromethyl)benzoyl chloride (5.7 g, 18.66 mmol) in dichloromethane (28.5 mL). The mixture was stirred at room temperature overnight. Ethyl acetate (150 ml) was added to the mixture was washed with water. The organic layer was dried over sodium sulfate and concentrated. Purification by silica gel chromatography (dichloromethane/methanol gradient) gave 4-[[6-bromo-2-fluoro-3-(trifluoromethyl)benzoyl]amino]pyridine-2-carboxamide (800 mg, 11%). ESI-MS m/z calc. 406.97, found 408.2 (M+1)+; retention time (Method A): 0.58 minutes (1.2 minute run).

Step 3: 1-bromo-2-(difluoromethoxy)-4-(trifluoromethoxy)benzene

A mixture of 2-bromo-5-(trifluoromethoxy)phenol (5.5 g, 21.40 mmol), 2-chloro-2,2-difluoro-acetate (sodium salt) (6.525 g, 42.80 mmol) and cesium carbonate (10.46 g, 32.10 mmol) in DMF (82.5 mL) was heated to 100° C. for 2 hours. The mixture was diluted with dichloromethane, filtered, and the filtrate was washed with water and brine. The organic layer was dried over $MgSO_4$, concentrated and purified by silica gel chromatography (ethyl acetate/hexane gradient) to give 1-bromo-2-(difluoromethoxy)-4-(trifluoromethoxy)benzene (4.4 g, 67%) as a pale yellow liquid, which was used in the next step without purification.

Step 4: 2-(difluoromethoxy)-4-(trifluoromethoxy)phenol

To 1-bromo-2-(difluoromethoxy)-4-(trifluoromethoxy)benzene (1.024 g, 3.34 mmol) in dioxane (2.25 mL), in a microwave vial, was added KOH (562 mg, 10.01 mmol) and water (1.126 mL). The mixture was degassed with $N_2$, and stirred under $N_2$ for ca. 2 minutes. Then di-tert-butyl-[2-(2,4,6-triisopropylphenyl)phenyl]phosphane (113.3 mg, 0.267 mmol) and (1E,4E)-1,5-diphenylpenta-1,4-dien-3-one:palladium (61 mg, 0.067 mmol) were added. The mixture was purged with nitrogen, the vial capped and heated at 100° C. for 1 day. After cooling to RT, ethyl ether (30 mL) was added and the mixture was extracted with water. The water layer was acidified to approximately pH of 4 using 1N HCl and extracted with ether. The combined organic phases were washed with brine, dried over sodium sulfate and concentrated to dryness under reduced pressure to obtain 2-(difluoromethoxy)-4-(trifluoromethoxy)phenol (350 mg, 43%) as a dark oil, which was used in the next step without further purification.

Step 5: 4-[[6-[2-(difluoromethoxy)-4-(trifluoromethoxy)phenoxy]-2-fluoro-3-(trifluoromethyl)benzoyl]amino]pyridine-2-carboxamide (13)

A microwave vial was charged with toluene (490 µL) (which was degassed prior to use with $N_2$ purge), 4-[[6-bromo-2-fluoro-3-(trifluoromethyl)benzoyl]amino]pyridine-2-carboxamide (49 mg, 0.121 mmol), cesium carbonate (78.65 mg, 0.241 mmol) and 2-(difluoromethoxy)-4-(trifluoromethoxy)phenol (29.46 mg, 0.121 mmol). The mixture was degassed with nitrogen. After ca. 2 minutes, copper (I) iodide (13.79 mg, 0.07241 mmol) was added and the reaction was stirred at 100° C. for 20 minutes. After cooling to RT, the reaction was diluted with ethyl acetate and water and the layers separated. The organic layer was concentrated and dissolved in 2 mL of DMSO. Purification by reverse phase HPLC gave 4-[[6-[2-(difluoromethoxy)-4-(trifluoromethoxy)phenoxy]-2-fluoro-3-(trifluoromethyl)benzoyl]amino]pyridine-2-carboxamide (8.4 mg, 12%). ESI-MS m/z calc. 569.06, found 570.2 (M+1)+; retention time (Method B): 1.82 minutes (3 minute run).

Example 14

N-(3-carbamoyl-4-fluoro-phenyl)-6-[3-chloro-4-(trifluoromethoxy)phenoxy]-2-fluoro-3-(trifluoromethyl)benzamide (14)

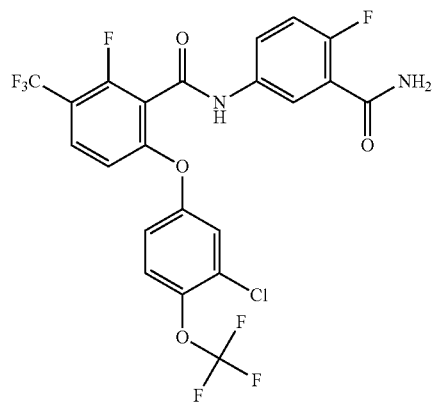 [SMILES: NC(=O)c1cc(NC(=O)c2c(Oc3ccc(OC(F)(F)F)c(Cl)c3)ccc(C(F)(F)F)c2F)ccc1F]

Step 1: 6-[3-chloro-4-(trifluoromethoxy)phenoxy]-2-fluoro-3-(trifluoromethyl)benzoic acid A pressure bottle was charged with 6-bromo-2-fluoro-3-(trifluoromethyl)benzoic acid (5 g, 17.42 mmol), cesium carbonate (11.35 g, 34.84 mmol), 3-chloro-4-(trifluoromethoxy)phenol (3.70 g, 17.42 mmol) and toluene (150 mL). The mixture was degassed with nitrogen. After ca. 2 minutes, copper (I) iodide (663.5 mg, 3.484 mmol) was added and the reaction was stirred at 100° C. for 20 minutes. The mixture was diluted with ethyl acetate and water, and the organic layer was washed with brine and dried over sodium sulfate. Trituration with hexane and filtration yielded 6-[3-chloro-4-(trifluoromethoxy)phenoxy]-2-fluoro-3-(trifluoromethyl)benzoic acid (6.27 g, 86%). ESI-MS m/z calc. 417.98, found 419.1 (M+1)+; retention time (Method B): 1.93 minutes (3 minute run).

Step 2: 6-[3-chloro-4-(trifluoromethoxy)phenoxy]-2-fluoro-3-(trifluoromethyl)benzoyl chloride To a slurry of 6-[3-chloro-4-(trifluoromethoxy)phenoxy]-2-fluoro-3-(trifluoromethyl)benzoic acid (1.31 g, 3.13 mmol) and N,N-dimethylformamide (20 µL, 0.2583 mmol) in dichloromethane (13 mL) at 0° C. was added oxalyl chloride (1.5 mL, 17.20 mmol) dropwise. The mixture was stirred at 0° C. for 20 minutes under $N_2$ atmosphere. The ice bath was removed and the reaction was stirred at room temperature for 35 minutes. The solvent was evaporated under reduced pressure to afford 6-[3-chloro-4-(trifluoromethoxy)phenoxy]-2-fluoro-3-(trifluoromethyl)benzoyl chloride, which was used in the next step without further purification.

Step 3: N-(3-carbamoyl-4-fluoro-phenyl)-6-[3-chloro-4-(trifluoromethoxy)phenoxy]-2-fluoro-3-(trifluoromethyl)benzamide (14)

To a solution of 5-amino-2-fluoro-benzamide (53 mg, 0.34 mmol) and diisopropylethylamine (179 µL, 1.03 mmol) in dichloromethane (1 mL) at 0° C. was added a slurry 6-[3-chloro-4-(trifluoromethoxy)phenoxy]-2-fluoro-3-(trifluoromethyl)benzoyl chloride (150 mg, 0.34 mmol) in dichloromethane (1 mL) slowly and the mixture was stirred at room temperature for 1 hour. The solvent was evaporated by blowing down with nitrogen. The crude product was dissolved in DMSO, filtered and purified using a reverse phase HPLC to yield N-(3-carbamoyl-4-fluoro-phenyl)-6-[3-chloro-4-(trifluoromethoxy)phenoxy]-2-fluoro-3-(trifluoromethyl)benzamide (49.5 mg, 26%). ESI-MS m/z calc. 554.03, found 555.0 (M+1)+; retention time (Method C): 2.58 minutes (5 minute run). $^1$H NMR (400 MHz, DMSO-d6) δ 11.02 (s, 1H), 7.94 (dd, J=6.4, 2.8 Hz, 1H), 7.90 (t, J=8.6 Hz, 1H), 7.76-7.69 (m, 3H), 7.69-7.64 (m, 1H), 7.63 (d, J=2.9 Hz, 1H), 7.34-7.25 (m, 2H), 7.06 (d, J=8.8 Hz, 1H) ppm.

The compounds set forth in Table 7 were prepared by methods analogous to the preparation of compound 14.

Example 15

N-(3-carbamoyl-4-fluoro-phenyl)-2-fluoro-6-[4-(trifluoromethoxy)phenoxy]-3-(trifluoromethyl)benzamide (15)

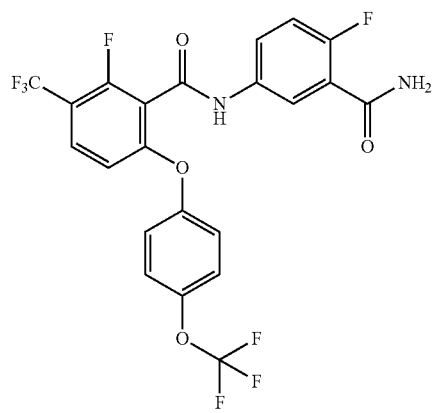 [SMILES: NC(=O)c1cc(NC(=O)c2c(Oc3ccc(OC(F)(F)F)cc3)ccc(C(F)(F)F)c2F)ccc1F]

Step 1: 2-fluoro-6-[4-(trifluoromethoxy)phenoxy]-3-(trifluoromethyl)benzoic acid To a solution of 4-(trifluoromethoxy)phenol (5.5 mL, 42.46 mmol), 6-bromo-2-fluoro-3-(trifluoromethyl)benzoic acid (10.0 g, 34.84 mmol), and cesium carbonate (22.73 g, 69.76 mmol) in toluene (75.0 mL, degassed with $N_2$ purge prior to use) was added copper (I) iodide (1.6 g, 8.40 mmol). The mixture was stirred at 100° C. for 1 hour. The mixture was cooled to RT and diluted with cold water (150 mL). The mixture was acidified with 6N HCl (slight foaming) and diluted with ethyl acetate (150 mL). The biphasic mixture was filtered through celite to remove insoluble inorganics. The aqueous phase was separated and extracted with ethyl acetate (150 mL). The combined organic phases were washed with 150 mL of brine, dried over $MgSO_4$, filtered and concentrated under reduced pressure affording an oil. The crude material was purified by silica gel chromatography (dichloromethane/methanol gradient), followed by crystallization from heptane affording 2-fluoro-6-[4-(trifluoromethoxy)phenoxy]-3-(trifluoromethyl)benzoic acid (7.0 g, 52%) as an off-white solid. ESI-MS m/z calc. 384.02, found 385.1 (M+1)+; retention time (Method B): 1.78 minutes (3 minute run). $^1$H NMR (400 MHz, Chloroform-d3) δ 7.67-7.58 (m, 1H), 7.28 (dt, J=9.1, 1.0 Hz, 2H), 7.19-7.10 (m, 2H), 6.70 (dd, J=8.9, 1.1 Hz, 1H) ppm.

TABLE 7

Additional Compounds Prepared By Methods Analogous to Example 14

| Cmpd No. | Compound Name | LC/MS | NMR (shifts in ppm) |
|---|---|---|---|
| 53 | 4-[[6-[3-chloro-4-(trifluoromethoxy)phenoxy]-2-fluoro-3-(trifluoromethyl)benzoyl]amino]pyridine-2-carboxamide | ESI-MS m/z calc. 537.03, found 538.0 (M + 1)+; Retention time (Method C): 2.54 minutes (5 minute run). | $^1$H NMR (500 MHz, DMSO-d$_6$) δ 11.50 (s, 1H), 8.56 (d, J = 5.5 Hz, 1H), 8.29 (d, J = 2.2 Hz, 1H), 8.13 (s, 1H), 7.93 (t, J = 8.6 Hz, 1H), 7.80 (dd, J = 5.6, 2.3 Hz, 1H), 7.71-7.63 (m, 3H), 7.34 (dd, J = 9.1, 2.9 Hz, 1H), 7.08 (d, J = 8.8 Hz, 1H) |

Step 2: 2-fluoro-6-[4-(trifluoromethoxy)phenoxy]-3-(trifluoromethyl)benzoyl chloride To a solution of 2-fluoro-6-[4-(trifluoromethoxy)phenoxy]-3-(trifluoromethyl)benzoic acid (700 mg, 1.82 mmol) and N,N-dimethylformamide (32 µL, 0.41 mmol) in dichloromethane (7 mL) at 0° C. was added oxalyl chloride (800 µL, 9.17 mmol) dropwise. The mixture was allowed to warm to room temperature and stirred for 30 minutes. The solvent was evaporated under reduced pressure to afford 2-fluoro-6-[4-(trifluoromethoxy)phenoxy]-3-(trifluoromethyl)benzoyl chloride, which was used in the next step without further purification.

Step 3: N-(3-carbamoyl-4-fluoro-phenyl)-2-fluoro-6-[4-(trifluoromethoxy)phenoxy]-3-(trifluoromethyl)benzamide (15)

A vial charged with 5-amino-2-fluoro-benzamide (218 mg, 1.41 mmol) and DIEA (750 µL, 4.31 mmol) in THF (6 mL) was cooled at 0° C. under an atmosphere of $N_2$. A solution of 2-fluoro-6-[4-(trifluoromethoxy)phenoxy]-3-(trifluoromethyl)benzoyl chloride (570 mg, 1.42 mmol) in THF (4 mL) and dichloromethane (3 mL) was added. The reaction mixture was gradually warmed to room temperature and stirred for 1 hour. The mixture was quenched with water, and the aqueous layer was extracted with dichloromethane. The combined organic layers were washed with 1N HCl (4×), dried over $MgSO_4$, filtered and concentrated. The crude material was purified via silica gel chromatography (ethyl acetate/hexane gradient) to obtain N-(3-carbamoyl-4-fluoro-phenyl)-2-fluoro-6-[4-(trifluoromethoxy)phenoxy]-3-(trifluoromethyl)benzamide (420 mg, 57%). ESI-MS m/z calc. 520.07, found 521.1 (M+1)+; retention time (Method B): 1.82 minutes (3 minute run). $^1$H NMR (400 MHz, DMSO-d6) δ 11.05 (s, 1H), 7.96 (dd, J=6.3, 2.8 Hz, 1H), 7.87 (t, J=8.6 Hz, 1H), 7.75 (ddd, J=9.0, 4.5, 2.9 Hz, 2H), 7.69 (s, 1H), 7.49 (dq, J=7.8, 0.9 Hz, 2H), 7.37-7.25 (m, 3H), 6.90 (d, J=8.8 Hz, 1H) ppm.

The compounds set forth in Table 8 were prepared by methods analogous to the preparation of compound 15.

TABLE 8

Additional Compounds Prepared By Methods Analogous to Example 15

| Cmpd No. | Compound Name | LC/MS | NMR (shifts in ppm) |
|---|---|---|---|
| 47 | N-(3-carbamoylphenyl)-2-fluoro-6-[4-(trifluoromethoxy)phenoxy]-3-(trifluoromethyl)benzamide | ESI-MS m/z calc. 502.08, found 503.0 (M + 1)+; Retention time (Method B): 1.79 minutes (3 minute run). | $^1$H NMR (400 MHz, DMSO-d6) δ 11.01 (s, 1H), 8.13 (t, J = 1.9 Hz, 1H), 7.99 (s, 1H), 7.86 (t, J = 8.7 Hz, 1H), 7.79 (ddd, J = 8.0, 2.2, 1.0 Hz, 1H), 7.62 (dt, J = 7.8, 1.2 Hz, 1H), 7.52-7.46 (m, 2H), 7.43 (t, J = 7.9 Hz, 1H), 7.39 (s, 1H), 7.35 (d, J = 9.1 Hz, 1H), 6.90 (d, J = 8.8 Hz, 1H) |
| 48 | 4-[[2-fluoro-6-[4-(trifluoromethoxy)phenoxy]-3-(trifluoromethyl)benzoyl]amino]pyridine-2-carboxamide | ESI-MS m/z calc. 503.07, found 504.0 (M + 1)+; Retention time (Method B): 1.79 minutes (3 minute run). | $^1$H NMR (400 MHz, DMSO-d6) δ 11.47 (s, 1H), 8.55 (d, J = 5.4 Hz, 1H), 8.29 (d, J = 2.1 Hz, 1H), 8.11 (d, J = 2.9 Hz, 1H), 7.90 (t, J = 8.7 Hz, 1H), 7.81 (dd, J = 5.5, 2.2 Hz, 1H), 7.67 (d, J = 2.8 Hz, 1H), 7.49 (dd, J = 9.2, 1.0 Hz, 2H), 7.36 (d, J = 9.1 Hz, 2H), 6.92 (d, J = 8.9 Hz, 1H) |
| 134 | N-(3-carbamoyl-4-chloro-phenyl)-2-fluoro-6-[4-(trifluoromethoxy)phenoxy]-3-(trifluoromethyl)benzamide | ESI-MS m/z calc. 536.04, found 537.2 (M + 1)+; Retention time (Method B): 1.78 minutes (3 minute run). | $^1$H NMR (400 MHz, DMSO-d6) δ 11.13 (s, 1H), 7.93 (s, 1H), 7.87 (t, J = 8.6 Hz, 1H), 7.76 (d, J = 2.6 Hz, 1H), 7.68 (dd, J = 8.7, 2.6 Hz, 1H), 7.64 (s, 1H), 7.52-7.45 (m, 3H), 7.35 (d, J = 9.1 Hz, 2H), 6.89 (d, J = 8.9 Hz, 1H) |
| 101 | N-(3-carbamoyl-5-fluoro-phenyl)-2-fluoro-6-[4-(trifluoromethoxy)phenoxy]-3-(trifluoromethyl)benzamide | ESI-MS m/z calc. 520.07, found 521.1 (M + 1)+; Retention time (Method B): 1.83 minutes (3 minute run). | $^1$H NMR (400 MHz, DMSO-d6) δ 11.24 (s, 1H), 8.06 (s, 1H), 7.91-7.85 (m, 2H), 7.75 (dt, J = 10.6, 2.2 Hz, 1H), 7.55 (s, 1H), 7.51-7.44 (m, 3H), 7.38-7.27 (m, 2H), 6.91 (d, J = 8.8 Hz, 1H) |
| 60 | 5-[[2-fluoro-6-[4-(trifluoromethoxy)phenoxy]-3-(trifluoromethyl)benzoyl]amino]pyridine-2-carboxamide | ESI-MS m/z calc. 503.07, found 504.1 (M + 1)+; Retention time (Method B): 1.77 minutes (3 minute run). | $^1$H NMR (400 MHz, DMSO-d6) δ 11.41 (s, 1H), 8.84 (dd, J = 2.5, 0.7 Hz, 1H), 8.27 (dd, J = 8.6, 2.5 Hz, 1H), 8.09-8.02 (m, 2H), 7.90 (t, J = 8.6 Hz, 1H), 7.60 (d, J = 2.8 Hz, 1H), 7.52-7.45 (m, 2H), 7.40-7.32 (m, 2H), 6.94 (d, J = 8.8 Hz, 1H). |
| 85 | N-(3-carbamoyl-4-hydroxy-phenyl)-2-fluoro-6-[4-(trifluoromethoxy)phenoxy]-3-(trifluoromethyl)benzamide | ESI-MS m/z calc. 518.07, found 519.2 (M + 1)+; Retention time (Method B): 1.77 minutes (3 minute run). | $^1$H NMR (400 MHz, DMSO-d6) δ 12.41 (s, 1H), 10.72 (s, 1H), 8.32 (s, 1H), 8.04 (d, J = 2.7 Hz, 1H), 7.84 (t, J = 8.6 Hz, 2H), 7.57-7.46 (m, 3H), 7.40-7.30 (m, 2H), 6.89 (dd, J = 8.8, 4.5 Hz, 2H). |

TABLE 8-continued

Additional Compounds Prepared By Methods Analogous to Example 15

| Cmpd No. | Compound Name | LC/MS | NMR (shifts in ppm) |
|---|---|---|---|
| 264 | N-(4-carbamoylphenyl)-2-fluoro-6-(4-(trifluoromethoxy)phenoxy)-3-(trifluoromethyl)benzamide | ESI-MS m/z calc. 502.34, found 503.1 (M + 1)+; Retention time (Method B): 1.76 minutes (3 minute run). | $^1$H NMR (400 MHz, DMSO-d6) δ 11.10 (s, 1H), 7.92 (br s, 1H), 7.91-7.84 (m, 3H), 7.74-7.68 (m, 2H), 7.53-7.45 (m, 2H), 7.38-7.34 (m, 2H), 7.32 (br s, 1H), 6.91 (d, J = 8.8 Hz, 1H). |

Example 16

N-(4-carbamoyl-3-fluoro-phenyl)-2-fluoro-6-[2-methoxy-4-(trifluoromethoxy)phenoxy]-3-(trifluoromethyl)benzamide (16)

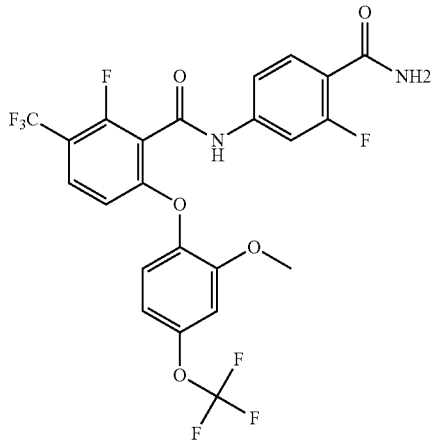 [SMILES: COc1cc(OC(F)(F)F)ccc1Oc1ccc(C(F)(F)F)c(F)c1C(=O)Nc1ccc(C(N)=O)c(F)c1]

2-fluoro-6-[2-methoxy-4-(trifluoromethoxy)phenoxy]-3-(trifluoromethyl)benzoic acid (prepared as described in Example 2, 109 mg, 0.26 mmol) and HATU (111 mg, 0.29 mmol) were dissolved in DMF (1.5 mL) and DIEA (102 μL, 0.58 mmol) and the mixture was stirred for 10 minutes. 4-Amino-2-fluoro-benzamide (45 mg, 0.29 mmol) was then added and the reaction was stirred at 45° C. for 16 h. The crude material was purified by silica gel chromatography (dichloromethane/methanol gradient), and further purified using reverse phase HPLC to provide N-(4-carbamoyl-3-fluoro-phenyl)-2-fluoro-6-[2-methoxy-4-(trifluoromethoxy)phenoxy]-3-(trifluoromethyl)benzamide (6.4 mg, 4%). ESI-MS m/z calc. 550.0775, found 551.1 (M+1)+; retention time (Method B): 1.85 minutes (3 minute run).

Example 17

4-[[2-fluoro-6-[2-(trideuteriomethoxy)-4-(trifluoromethoxy)phenoxy]-4-(trifluoromethyl)benzoyl]amino]pyridine-2-carboxamide (17)

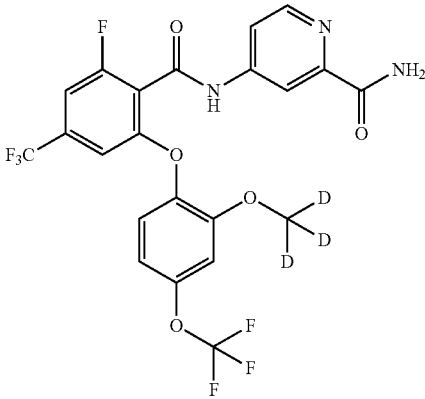 [SMILES: [2H]C([2H])([2H])Oc1cc(OC(F)(F)F)ccc1Oc1cc(C(F)(F)F)cc(F)c1C(=O)Nc1ccnc(C(N)=O)c1]

Step 1: 2-fluoro-6-[2-(trideuteriomethoxy)-4-(trifluoromethoxy)phenoxy]-4-(trifluoromethyl)benzoic acid To a solution of methyl 2,6-difluoro-4-(trifluoromethyl)benzoate (1000 mg, 4.16 mmol) in DMF (12 mL) was added 2-(trideuteriomethoxy)-4-(trifluoromethoxy)phenol (prepared as described in Example 1, 880 mg, 4.168 mmol) and Cs$_2$CO$_3$ (4.10 g, 12.58 mmol) and the mixture was heated at 70° C. for 20 minutes. The reaction was diluted with ethyl acetate and washed with water and brine. The organic layer was dried over sodium sulfate, filtered and concentrated under reduced pressure. The crude product was purified by silica gel chromatography (ethyl acetate/hexane gradient) to yield methyl 2-fluoro-6-[2-(trideuteriomethoxy)-4-(trifluoromethoxy)phenoxy]-4-(trifluoromethyl)benzoate. ESI-MS m/z calc. 431.0683, found 432.2 (M+1)+; Retention time: 0.81 minutes. A solution of this material in cold methanol (8 mL) was treated with cold aqueous NaOH (8.5 mL of 1 M, 8.500 mmol). The cloudy white reaction mixture was allowed to come to room temperature then heated at 55° C. for 1 h. The crude reaction was partitioned between 1 N HCl and dichloromethane. The dichloromethane phase was dried over sodium sulfate, filtered and concentrated to a viscous oil. The oil was suspended in hexane and stirred to form a thick precipitate. The solid was filtered and air dried to provide 2-fluoro-6-[2-(trideuteriomethoxy)-4-(trifluoromethoxy)phenoxy]-4-(trifluoromethyl)benzoic acid (1.321 g, 75%) as a white solid. ESI-MS m/z calc. 417.05, found 418.1 (M+1)+; retention time (Method B): 1.82 minutes (3 minute run). ¹H NMR (400 MHz, DMSO-d6) δ 14.09 (s, 1H), 7.57 (dd, J=8.9, 1.4 Hz, 1H), 7.29-7.22 (m, 2H), 7.01 (ddd, J=8.8, 2.7, 1.2 Hz, 1H), 6.77 (s, 1H) ppm.

Step 2: 2-fluoro-6-[2-(trideuteriomethoxy)-4-(trifluoromethoxy)phenoxy]-4-(trifluoromethyl)benzoyl chloride A solution of 2-fluoro-6-[2-(trideuteriomethoxy)-4-(trifluoromethoxy)phenoxy]-4-(trifluoromethyl)benzoic acid (400 mg, 0.94 mmol) in dichloromethane (8 mL) was cooled using an ice-bath. To this was added DMF (15 µL, 0.194 mmol) followed by careful addition of oxalyl chloride (200 µL, 2.29 mmol). The solution was stirred for 10 min then removed from the ice bath and allowed to warm to room temperature over 20 minutes. The reaction was concentrated under reduced pressure and azeotroped with dichloromethane to afford 2-fluoro-6-[2-(trideuteriomethoxy)-4-(trifluoromethoxy)phenoxy]-4-(trifluoromethyl)benzoyl chloride, which was used directly in the next step.

Step 3: 4-[[2-fluoro-6-[2-(trideuteriomethoxy)-4-(trifluoromethoxy)phenoxy]-4-(trifluoromethyl)benzoyl]amino]pyridine-2-carboxamide (17)

4-Aminopyridine-2-carboxamide (32 mg, 0.23 mmol) was dissolved in NMP (1 mL) and DIEA (100 µL, 0.57 mmol) and then cooled to 0° C. To this was added dropwise a cold solution of freshly prepared 2-fluoro-6-[2-(trideuteriomethoxy)-4-(trifluoromethoxy)phenoxy]-4-(trifluoromethyl)benzoyl chloride (100 mg, 0.23 mmol) in dichloromethane (3 mL). The reaction was allowed to warm to room temperature and stirred for 16 hours. Reverse phase HPLC purification provided 4-[[2-fluoro-6-[2-(trideuteriomethoxy)-4-(trifluoromethoxy)phenoxy]-4-(trifluoromethyl)benzoyl]amino]pyridine-2-carboxamide (30.3 mg, 25%). ESI-MS m/z calc. 536.101, found 537.2 (M+1)+; retention time (Method B): 1.75 minutes (3 minute run). ¹H NMR (400 MHz, DMSO-d6) δ 11.41 (s, 1H), 8.55 (d, J=5.4 Hz, 1H), 8.30 (d, J=2.1 Hz, 1H), 8.10 (d, J=2.7 Hz, 1H), 7.82 (dd, J=5.5, 2.2 Hz, 1H), 7.72-7.62 (m, 2H), 7.33 (d, J=8.8 Hz, 1H), 7.22 (d, J=2.7, 0.8 Hz, 1H), 7.01 (ddd, J=8.8, 2.8, 1.3 Hz, 1H), 6.86 (s, 1H) ppm.

The compounds set forth in Table 9 were prepared by methods analogous to the preparation of compound 17.

TABLE 9

Additional Compounds Prepared By Methods Analogous to Example 17

| Cmpd No. | Compound Name | LC/MS | NMR (shifts in ppm) |
|---|---|---|---|
| 154 | 5-[[2-fluoro-6-[2-(trideuteriomethoxy)-4-(trifluoromethoxy)phenoxy]-4-(trifluoromethyl)benzoyl]amino]pyridine-2-carboxamide | ESI-MS m/z calc. 536.10, found 537.2 (M + 1)+; Retention time (Method B): 1.75 minutes (3 minute run). | ¹H NMR (400 MHz, DMSO-d6) δ 11.33 (s, 1H), 8.85 (dd, J = 2.5, 0.7 Hz, 1H), 8.26 (dd, J = 8.6, 2.5 Hz, 1H), 8.08-8.04 (m, 1H), 8.02 (d, J = 2.3 Hz, 1H), 7.68 (d, J = 8.4 Hz, 1H), 7.57 (d, J = 1.7 Hz, 1H), 7.32 (d, J = 8.8 Hz, 1H), 7.22 (d, J = 2.8 Hz, 1H), 7.01 (ddd, J = 8.8, 2.7, 1.2 Hz, 1H), 6.87 (s, 1H). |

Example 18

N-(3-carbamoyl-4-fluoro-phenyl)-2-fluoro-6-[3-fluoro-4-(trifluoromethoxy)phenoxy]-3-(trifluoromethyl)benzamide (18)

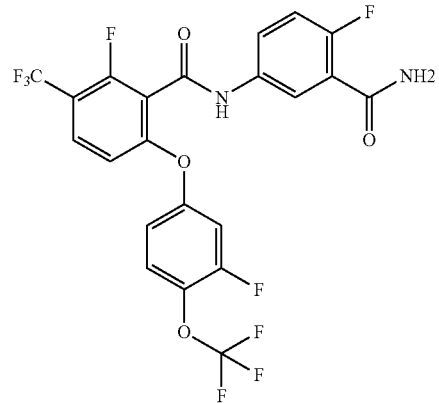 [SMILES: NC(=O)c1cc(NC(=O)c2c(Oc3ccc(OC(F)(F)F)c(F)c3)ccc(C(F)(F)F)c2F)ccc1F]

Step 1: 2-fluoro-6-[3-fluoro-4-(trifluoromethoxy)phenoxy]-3-(trifluoromethyl)benzoic acid A pressure bottle was charged with 6-bromo-2-fluoro-3-(trifluoromethyl)benzoic acid (5 g, 17.42 mmol), cesium carbonate (11.35 g, 34.84 mmol) and 3-fluoro-4-(trifluoromethoxy)phenol (3.416 g, 17.42 mmol) in toluene (125 mL). The mixture was degassed with nitrogen. After ca. 2 minutes, copper (I) iodide (664 mg, 3.48 mmol) was added and the reaction was stirred at 100° C. for 20 minutes. The reaction was diluted with ethyl acetate and water. The phases were separated and the organic phase was washed with brine and dried over sodium sulfate. Trituration with hexane and filtration gave 2-fluoro-6-[3-fluoro-4-(trifluoromethoxy)phenoxy]-3-(trifluoromethyl)benzoic acid (4.7 g, 67%), which was used without further purification. ESI-MS m/z calc. 402.01, found 403.2 (M+1)+; retention time (Method B): 1.86 minutes (3 minute run).

Step 2: 2-fluoro-6-[3-fluoro-4-(trifluoromethoxy) phenoxy]-3-(trifluoromethyl)benzoyl chloride To 2-fluoro-6-[3-fluoro-4-(trifluoromethoxy)phenoxy]-3-(trifluoromethyl)benzoic acid (900 mg, 2.24 mmol) and N,N-dimethylformamide (16 μL, 0.21 mmol) in dichloromethane (10.5 mL) at 0° C. was added oxalyl chloride (952 μL, 10.91 mmol) dropwise. The mixture was stirred at room temperature for 20 minutes at 50° C. under a $N_2$ atmosphere. The solvent was evaporated under reduced pressure to afford 2-fluoro-6-[3-fluoro-4-(trifluoromethoxy)phenoxy]-3-(trifluoromethyl)benzoyl chloride (940 mg, 100%), which was used in the next step without further purification.

Step 3: N-(3-carbamoyl-4-fluoro-phenyl)-2-fluoro-6-[3-fluoro-4-(trifluoromethoxy)phenoxy]-3-(trifluoromethyl)benzamide (18)

To 5-amino-2-fluoro-benzamide (55 mg, 0.36 mmol) and diisopropylethylamine (186 μL, 1.07 mmol) in dichloromethane (1.5 mL) cooled at 0° C. was added dropwise a solution of 2-fluoro-6-[3-fluoro-4-(trifluoromethoxy)phenoxy]-3-(trifluoromethyl)benzoyl chloride (150 mg, 0.3566 mmol) in dichloromethane (1.5 mL). The reaction was stirred at room temperature overnight. The mixture as diluted with ethyl acetate (30 mL) washed with water, saturated aqueous sodium bicarbonate and brine, dried over sodium sulfate and concentrated to dryness. Purification by silica gel chromatography (ethyl acetate/hexane gradient) yielded N-(3-carbamoyl-4-fluoro-phenyl)-2-fluoro-6-[3-fluoro-4-(trifluoromethoxy)phenoxy]-3-(trifluoromethyl)benzamide (117.5 mg, 60%). ESI-MS m/z calc. 538.06, found 539.1 (M+1)+; retention time (Method B): 1.82 minutes (3 minute run). $^1$H NMR (400 MHz, DMSO-d6) δ 11.03 (s, 1H), 8.03-7.84 (m, 2H), 7.82-7.61 (m, 4H), 7.49 (dd, J=11.0, 2.9 Hz, 1H), 7.34-7.22 (m, 1H), 7.19-7.11 (m, 1H), 7.07 (d, J=8.8 Hz, 1H) ppm.

Example 19

N-(3-carbamoyl-4-fluoro-phenyl)-2-[2-methoxy-4-(trifluoromethoxy)phenoxy]-5-(1,1,2,2,2-pentafluoroethyl)benzamide (19)

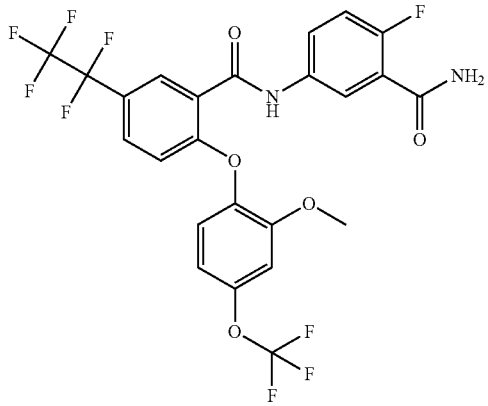 [SMILES: COc1cc(OC(F)(F)F)ccc1Oc1ccc(C(F)(F)C(F)(F)F)cc1C(=O)Nc1ccc(F)c(C(N)=O)c1]

Step 1:
2-fluoro-5-(1,1,2,2,2-pentafluoroethyl)benzoic acid

Bronze copper powder (20 g) was stirred in a solution of iodine (4 g) in acetone (250 mL) for 15 minutes until the iodine solution was decolorized. The product was collected in a filter funnel and added to a solution of concentrate HCL in acetone (1:1, v/v, 80 mL). After stirring for 5 minutes, it was filtered and the solids were washed with acetone (8×40 ml) and dried for 30 minutes. The material was used directly in the next step.

5-bromo-2-fluoro-benzoic acid (5 g, 22.83 mmol) was dissolved in dimethyl sulfoxide (100 mL) at RT under a $N_2$ atmosphere and cooled to 0° C. A tank of 1,1,1,2,2-pentafluoro-2-iodo-ethane was cooled and then 1,1,1,2,2-pentafluoro-2-iodo-ethane (39.3 g, 159.8 mmol) was transferred into the reaction flask under $N_2$. A mixture of activated copper (freshly prepared, 12.25 g, 192.8 mmol) was added and the flask was sealed under $N_2$ and heated for 30 minutes at 100° C. The temperature was raised to 120° C. and stirred for 48 h. The mixture was cooled to RT and was filtered. The cake was washed with 60 mL DMSO and the filtrate was diluted with ethyl acetate (450 mL) and re-filtered through a plug of Celite (3×). To the filtrate was added 1 N HCl and the layers were separated. The aqueous phase was extracted several times with ethyl acetate. The organic phases were combined, dried over $Na_2SO_4$, filtered and the solvent was evaporated under reduced pressure. The residue was dissolved in ethyl acetate, washed with water (2×) and brine, dried over $Na_2SO_4$, filtered and the solvent was evaporated under reduced pressure. The crude material was purified by silica gel chromatography (ethyl acetate/dichloromethane gradient) to yield 2-fluoro-5-(1,1,2,2,2-pentafluoroethyl)benzoic acid (2.06 g, 35%) as a light brown solid. ESI-MS m/z calc. 258.01, found 259.2 (M+1)+; retention time (Method B): 1.36 minutes (3 minute run). $^1$H NMR (400 MHz, DMSO-d6) δ 13.84 (s, 1H), 8.11 (dd, J=6.6, 2.7 Hz, 1H), 8.07-7.96 (m, 1H), 7.81-7.41 (m, 1H) ppm.

Step 2: 2-[2-methoxy-4-(trifluoromethoxy)phenoxy]-5-(1,1,2,2,2-pentafluoroethyl)benzoic acid A mixture of 2-fluoro-5-(1,1,2,2,2-pentafluoroethyl)benzoic acid (500 mg, 1.94 mmol), cesium carbonate (1.358 g, 4.16 mmol), N,N-dimethylformamide (10 mL) and 2-methoxy-4-(trifluoromethoxy)phenol (prepared as described in Example 2, 448 mg, 2.15 mmol) was heated at 150° C. for 6 hours. The mixture was diluted with water and ethyl acetate and the layers were separated. The aqueous layer was acidified with 1 N HCl and extracted with ethyl acetate. The combined organic phases were washed with water and brine, dried over $Na_2SO_4$, filtered and concentrated. The crude material was purified by silica gel chromatography (ethyl acetate/dichloromethane gradient) to yield 2-[2-methoxy-4-(trifluoromethoxy)phenoxy]-5-(1,1,2,2,2-pentafluoroethyl)benzoic acid (272.9 mg, 32%) as a yellow viscous solid. ESI-MS m/z calc. 446.04, found 447.0 (M+1)+; retention time (Method B): 2.01 minutes (3 minute run).

Step 3: 2-[2-methoxy-4-(trifluoromethoxy)phenoxy]-5-(1,1,2,2,2-pentafluoroethyl)benzoyl chloride To a solution of 2-[2-methoxy-4-(trifluoromethoxy)phenoxy]-5-(1,1,2,2,2-pentafluoroethyl)benzoic acid (257 mg, 0.58 mmol) and N,N-dimethylformamide (10 μL, 0.13 mmol) in dichloromethane (3 mL) at 0° C. was added oxalyl chloride (350 μL, 4.01 mmol) dropwise. The ice bath was removed and the reaction was stirred under a $N_2$ atmosphere for 35 min. The solvent was evaporated under reduced pressure to afford 2-[2-methoxy-4-(trifluoromethoxy)phenoxy]-5-(1,1,2,2,2-pentafluoroethyl)benzoyl chloride, which was used in the next step without further purification.

Step 4: N-(3-carbamoyl-4-fluoro-phenyl)-2-[2-methoxy-4-(trifluoromethoxy)phenoxy]-5-(1,1,2,2,2-pentafluoroethyl)benzamide (19)

A solution of 5-amino-2-fluoro-benzamide (30 mg, 0.19 mmol) and diisopropylethylamine (100 µL, 0.5766 mmol) in tetrahydrofuran (1 mL) at 0° C. was added to a slurry of 2-[2-methoxy-4-(trifluoromethoxy)phenoxy]-5-(1,1,2,2,2-pentafluoroethyl)benzoyl chloride (89 mg, 0.19 mmol) in tetrahydrofuran (1 mL) slowly at 0° C. and the reaction was stirred at room temperature for 4 hours. The solvent was evaporated by blowing down with nitrogen. The crude product was dissolved in DMSO, filtered and purified by reverse phase HPLC to yield N-(3-carbamoyl-4-fluoro-phenyl)-2-[2-methoxy-4-(trifluoromethoxy)phenoxy]-5-(1,1,2,2,2-pentafluoroethyl)benzamide (25.7 mg, 23%). ESI-MS m/z calc. 582.08, found 583.0 (M+1)+; retention time (Method B): 2.04 minutes (3 minute run). $^1$H NMR (400 MHz, DMSO-d6) δ 10.62 (s, 1H), 8.00 (dd, J=6.5, 2.8 Hz, 1H), 7.91 (d, J=2.4 Hz, 1H), 7.83 (ddd, J=9.0, 4.4, 2.8 Hz, 1H), 7.78-7.62 (m, 3H), 7.44 (d, J=8.8 Hz, 1H), 7.32-7.24 (m, 2H), 7.07 (ddd, J=8.8, 2.8, 1.3 Hz, 1H), 6.87 (d, J=8.8 Hz, 1H), 3.78 (s, 3H) ppm.

The compounds set forth in Table 10 were prepared by methods analogous to the preparation of compound 19.

TABLE 10

Additional Compounds Prepared By Methods Analogous to Example 19

| Cmpd No. | Compound Name | LC/MS | NMR (shifts in ppm) |
|---|---|---|---|
| 81 | 4-[[2-[2-methoxy-4-(trifluoromethoxy)phenoxy]-5-(1,1,2,2,2-pentafluoroethyl)benzoyl]amino]pyridine-2-carboxamide | ESI-MS m/z calc. 565.09, found 566.0 (M + 1)+; Retention time (Method B): 199 minutes (3 minute run). | $^1$H NMR (400 MHz, DMSO-d6) δ 11.07 (s, 1H), 8.54 (d, J = 5.5 Hz, 1H), 8.34 (d, J = 2.2 Hz, 1H), 8.12 (d, J = 2.9 Hz, 1H), 7.96 (d, J = 2.5 Hz, 1H), 7.90 (dd, J = 5.5, 2.2 Hz, 1H), 7.77 (dd, J = 8.9, 2.5 Hz, 1H), 7.66 (d, J = 2.7 Hz, 1H), 7.45 (d, J = 8.8 Hz, 1H), 7.25 (d, J = 2.6 Hz, 1H), 7.12-7.03 (m, 1H), 6.90 (d, J = 8.6 Hz, 1H), 3.78 (s, 3H). |

Example 20

4-[[4-(difluoromethoxy)-2-fluoro-6-[2-methoxy-4-(trifluoromethoxy)phenoxy]benzoyl]amino]pyridine-2-carboxamide (20)

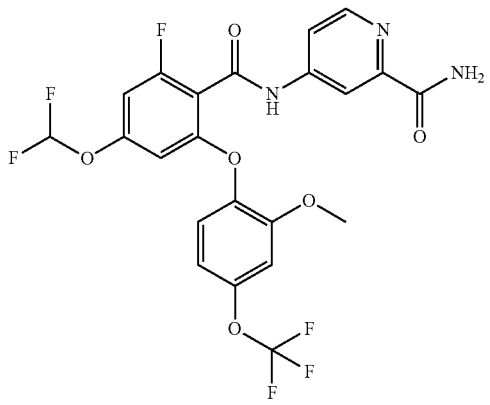 [SMILES: COc1cc(OC(F)(F)F)ccc1Oc1cc(OC(F)F)cc(F)c1C(=O)Nc1ccnc(C(N)=O)c1]

Step 1: methyl 4-(difluoromethoxy)-2,6-difluoro-benzoate

To a suspension of 4-(difluoromethoxy)-2,6-difluoro-benzoic acid (900 mg, 4.02 mmol) in dichloromethane (10 mL) and MeOH (3.5 mL, 86.40 mmol) under N$_2$ at 0° C. was added diazomethyl(trimethyl)silane (3.4 mL of 2 M solution in hexanes, 6.80 mmol) dropwise (persistent yellow color). The mixture was stirred for 10 minutes then several drops of acetic acid were added to quench excess reagent (resulting in a colorless solution). The mixture was concentrated, dissolved in dichloromethane and washed with saturated aqueous NaHCO$_3$, dried over MgSO$_4$ and concentrated. The crude material was purified by silica gel column chromatography (ethyl acetate/dichloromethane gradient) to yield methyl 4-(difluoromethoxy)-2,6-difluoro-benzoate (746 mg, 74%). $^1$H NMR (400 MHz, DMSO-d6) δ 7.43 (t, J=72.6 Hz, 1H), 7.23 (d, J=1.8 Hz, 1H), 7.21 (d, J=1.9 Hz, 1H), 3.88 (s, 3H) ppm.

Step 2: methyl 4-(difluoromethoxy)-2-fluoro-6-[2-methoxy-4-(trifluoromethoxy)phenoxy]benzoate A vial charged with 2-methoxy-4-(trifluoromethoxy)phenol (prepared as described in Example 2, 442 mg, 2.12 mmol), methyl 4-(difluoromethoxy)-2,6-difluoro-benzoate (505 mg, 2.12 mmol), Cs$_2$CO$_3$ (2 g, 6.14 mmol) and DMF (7 mL) was heated at 80° C. for 30 minutes. The reaction mixture was quenched with ethyl acetate and brine and the layers were separated. The organic layer was washed with brine (3×), dried over sodium sulfate, filtered and concentrated under reduced pressure. The crude material was purified by silica gel chromatography (ethyl acetate/hexane gradient) to yield methyl 4-(difluoromethoxy)-2-fluoro-6-[2-methoxy-4-(trifluoromethoxy)phenoxy]benzoate (640 mg, 71%). ESI-MS m/z calc. 426.05, found 427.2 (M+1)+; retention time (Method B): 1.98 minutes (3 minute run).

Step 3: 4-(difluoromethoxy)-2-fluoro-6-[2-methoxy-4-(trifluoromethoxy)phenoxy]benzoic acid To a solution of methyl 4-(difluoromethoxy)-2-fluoro-6-[2-methoxy-4-(trifluoromethoxy)phenoxy]benzoate (640 mg, 1.50 mmol) in MeOH (6 mL) was added NaOH (1.1 g, 27.50 mmol) in water (6 mL). The reaction mixture was stirred at room temperature for 15 hours. The solvent was evaporated and the reaction mixture was quenched with 6N HCl. The aqueous layer was extracted with ethyl acetate, dried over MgSO$_4$, filtered and concentrated to give 4-(difluoromethoxy)-2-fluoro-6-[2-methoxy-4-(trifluoromethoxy)phenoxy]benzoic acid (550 mg, 89%), which was used in the next step without further purification. ESI-MS m/z calc. 412.04, found 413.0 (M+1)+; retention time (Method A): 0.67 minutes (1.2 minute run).

Step 4: 4-[[4-(difluoromethoxy)-2-fluoro-6-[2-methoxy-4-(trifluoromethoxy)phenoxy]benzoyl]amino]pyridine-2-carboxamide (20)

A vial was charged with 4-(difluoromethoxy)-2-fluoro-6-[2-methoxy-4-(trifluoromethoxy)phenoxy]benzoic acid (100 mg, 0.24 mmol), 4-[(Z)-[(tert-butylamino)-phenylsulfanyl-methylene]amino]pyridine-2-carboxamide (prepared as described in Example 2, 81 mg, 0.25 mmol), tris[(Z)-1-methyl-3-oxo-but-1-enoxy]iron (4.2 mg, 0.0118 mmol) in 2-propanol (1.5 mL) and was heated at 83° C. under an air atmosphere for 24 hours. The reaction mixture was cooled to room temperature, the solvent evaporated and the residue was taken up in dichloromethane and washed with 1N HCl. The organic layer was dried over MgSO$_4$, filtered and concentrated. The crude material was purified by silica gel chromatography (ethyl acetate/hexane gradient) to yield 4-[[4-(difluoromethoxy)-2-fluoro-6-[2-methoxy-4-(trifluoromethoxy)phenoxy]benzoyl]amino]pyridine-2-carboxamide (75 mg, 58%). ESI-MS m/z calc. 531.09, found 532.2 (M+1)+; retention time (Method B): 1.65 minutes (3 minute run). $^1$H NMR (400 MHz, DMF-d7) δ 11.69 (s, 1H), 8.96 (d, J=5.5 Hz, 1H), 8.72 (d, J=2.1 Hz, 1H), 8.51 (d, J=2.9 Hz, 1H), 8.25 (dd, J=5.5, 2.2 Hz, 1H), 8.07 (d, J=2.8 Hz, 1H), 7.96-7.54 (m, 3H), 7.50 (dd, J=10.1, 2.2 Hz, 1H), 7.43 (ddd, J=8.7, 2.7, 1.3 Hz, 1H), 6.79 (d, J=1.8 Hz, 1H), 4.20 (s, 3H) ppm.

Example 21

N-(3-carbamoyl-4-fluoro-phenyl)-2-fluoro-6-[2-fluoro-4-(trifluoromethoxy)phenoxy]-3-(trifluoromethyl)benzamide (21)

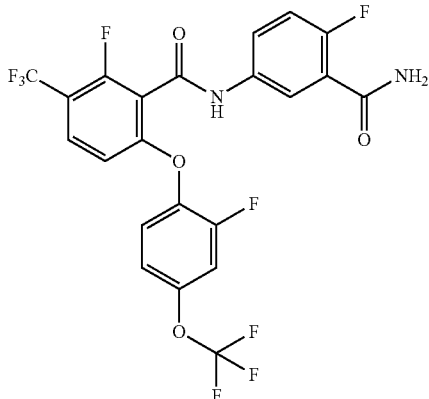 [SMILES: NC(=O)c1cc(NC(=O)c2c(Oc3ccc(OC(F)(F)F)cc3F)ccc(C(F)(F)F)c2F)ccc1F]

Step 1: 2-fluoro-6-[2-fluoro-4-(trifluoromethoxy)phenoxy]-3-(trifluoromethyl)benzoic acid A pressure bottle was charged with 2-fluoro-4-(trifluoromethoxy)phenol (1.23 g, 6.29 mmol), cesium carbonate (4.31 g, 13.24 mmol) and 6-bromo-2-fluoro-3-(trifluoromethyl)benzoic acid (1.9 g, 6.62 mmol) in toluene (47 mL). The mixture was degassed with nitrogen. After ca. 2 minutes, copper (I) iodide (252.2 mg, 1.324 mmol) was added and the reaction was stirred at 110° C. for 40 minutes. The reaction was diluted with ethyl acetate (100 mL) and water (30 mL) and the layers separated. The organic layer was washed with brined and dried over sodium sulfate. Trituration with hexane and filtration of the solid yielded 2-fluoro-6-[2-fluoro-4-(trifluoromethoxy)phenoxy]-3-(trifluoromethyl)benzoic acid (2.1 g, 79%). ESI-MS m/z calc. 402.01, found 403.1 (M+1)+; retention time (Method A): 0.73 minutes (1.2 minute run). $^1$H NMR (400 MHz, DMSO-d6) δ 7.76-7.46 (m, 1H), 7.42 (s, 1H), 7.25 (s, 2H), 6.76 (d, J=8.6 Hz, 1H) ppm.

Step 2: N-(3-carbamoyl-4-fluoro-phenyl)-2-fluoro-6-[2-fluoro-4-(trifluoromethoxy)phenoxy]-3-(trifluoromethyl)benzamide (21)

2-fluoro-6-[2-fluoro-4-(trifluoromethoxy)phenoxy]-3-(trifluoromethyl)benzoic acid (1.45 g, 3.60 mmol) in dichloromethane (14.5 mL) was treated with DMF (14 µL, 0.18 mmol), cooled in an ice bath and treated dropwise with oxalyl chloride (505 µL, 5.79 mmol). The yellow solution was stirred at room temperature for 1 hour and in a warm water bath for 0.5 hour till no further gas evolution was observed. The solution was evaporated, and the residue dissolved in dry dichloromethane (14.5 mL) to give a pale yellow solution of the acid chloride, which was used directly in the next step.

5-Amino-2-fluoro-benzamide (667 mg, 4.33 mmol) in dichloromethane (14.5 mL) was treated with diisopropylethylamine (1.6 mL, 9.19 mmol) and the suspension was cooled in an ice bath and treated dropwise with the acid chloride solution. The fine suspension was stirred in the ice bath for 1 hour and at room temperature for 1 h. The solution was washed with water (2×50 mL) and the aqueous phases were back extracted once with dichloromethane (20 mL). The combined organic phases were dried, filtered and evaporated. The crude material was purified by silica gel chromatography (ethyl acetate/hexane gradient) to give N-(3-carbamoyl-4-fluoro-phenyl)-2-fluoro-6-[2-fluoro-4-(trifluoromethoxy)phenoxy]-3-(trifluoromethyl)benzamide (1089 mg, 56%) as a white solid. ESI-MS m/z calc. 538.06, found 539.0 (M+1)+; retention time (Method C): 2.55 minutes (5 minute run). $^1$H NMR (400 MHz, DMSO-d6) δ 11.07 (s, 1H), 7.97 (dd, J=6.3, 2.8 Hz, 1H), 7.86 (t, J=8.6 Hz, 1H), 7.80-7.62 (m, 4H), 7.52 (t, J=9.0 Hz, 1H), 7.36 (ddt, J=8.9, 2.5, 1.3 Hz, 1H), 7.29 (dd, J=10.1, 9.0 Hz, 1H), 6.94 (d, J=8.8 Hz, 1H) ppm.

The compounds set forth in Table 11 were prepared by methods analogous to the preparation of compound 21.

TABLE 11

Additional Compounds Prepared By Methods Analogous to Example 21

| Cmpd No. | Compound Name | LC/MS | NMR (shifts in ppm) |
|---|---|---|---|
| 90 | 4-[[2-fluoro-6-[2-fluoro-4-(trifluoromethoxy)phenoxy]-3-(trifluoromethyl)benzoyl]amino]pyridine-2-carboxamide | ESI-MS m/z calc. 521.06, found 521.9 (M + 1)+; Retention time (Method B): 1.77 minutes (3 minute run). | $^1$H NMR (400 MHz, DMSO-d6) δ 11.52 (s, 1H), 8.56 (d, J = 5.5 Hz, 1H), 8.30 (d, J = 2.1 Hz, 1H), 8.12 (d, J = 2.9 Hz, 1H), 7.90 (t, J = 8.6 Hz, 1H), 7.82 (dd, J = 5.5, 2.2 Hz, 1H), 7.77-7.62 (m, 2H), 7.55 (t, J = 9.0 Hz, 1H), 7.44-7.31 (m, 1H), 6.97 (d, J = 8.8 Hz, 1H). |
| 89 | N-(3-carbamoylphenyl)-2-fluoro-6-[2-fluoro-4-(trifluoromethoxy)phenoxy]-3-(trifluoromethyl)benzamide | ESI-MS m/z calc. 520.07, found 521.2 (M + 1)+; Retention time (Method B): 1.77 minutes (3 minute run). | $^1$H NMR (400 MHz, DMSO-d6) δ 11.05 (s, 1H), 8.14 (t, J = 2.0 Hz, 1H), 8.00 (s, 1H), 7.86 (t, J = 8.7 Hz, 1H), 7.82-7.76 (m, 1H), 7.72 (dd, J = 10.8, 2.7 Hz, 1H), 7.68-7.59 (m, 1H), 7.53 (t, J = 9.0 Hz, 1H), 7.44 (t, J = 7.9 Hz, 1H), 7.41-7.34 (m, 2H), 6.93 (d, J = 8.7 Hz, 1H). |

Example 22

4-[[4-cyclopropyl-2-fluoro-6-[2-methoxy-4-(trifluoromethoxy)phenoxy]benzoyl]amino]pyridine-2-carboxamide (22)

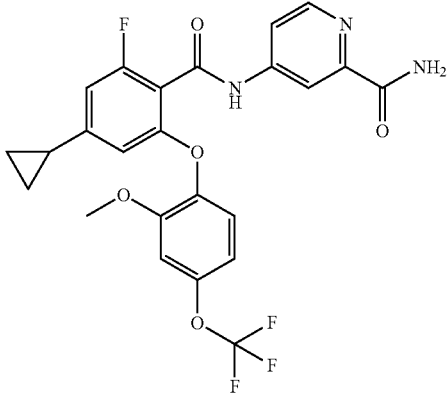 [SMILES: COc1cc(OC(F)(F)F)ccc1Oc1cc(C2CC2)cc(F)c1C(=O)Nc1ccnc(C(N)=O)c1]

Step 1: methyl 4-bromo-2-fluoro-6-[2-methoxy-4-(trifluoromethoxy)phenoxy]benzoate A vial charged with methyl 4-bromo-2,6-difluoro-benzoate (500 mg, 1.99 mmol), 2-methoxy-4-(trifluoromethoxy) phenol (prepared as described in Example 2, 415 mg, 1.99 mmol), Cs$_2$CO$_3$ (1.948 g, 5.98 mmol) and DMF (5 mL) was heated at 80° C. for 1 hour. Ethyl acetate and brine were added and the phases were separated. The organic phase was washed with brine (3×), dried over sodium sulfate, filtered and concentrated under reduced pressure. The crude material was purified by silica gel chromatography (ethyl acetate/hexane gradient) to yield methyl 4-bromo-2-fluoro-6-[2-methoxy-4-(trifluoromethoxy)phenoxy]benzoate (465 mg, 53%). ESI-MS m/z calc. 437.9726, found 441.2 (M+2)+; retention time (Method A): 0.83 minutes (1.2 minute run).

Step 2: methyl 4-cyclopropyl-2-fluoro-6-[2-methoxy-4-(trifluoromethoxy)phenoxy]benzoate A round bottom flask under a N$_2$ atmosphere, was charged with methyl 4-bromo-2-fluoro-6-[2-methoxy-4-(trifluoromethoxy)phenoxy]benzoate (465 mg, 1.06 mmol), bis(tri-t-butylphosphine)palladium(0) (180 mg, 0.35 mmol), and THF (4.65 mL). The reaction mixture was cooled in an ice bath and bromo(cyclopropyl)zinc (4.3 mL of 0.5 M, 2.15 mmol), as a solution in THF, was then added dropwise and the reaction was stirred for 30 minutes. The reaction was quenched with saturated aqueous ammonium chloride and the mixture was diluted with ethyl acetate. The layers were separated and the organic layer was dried over anhydrous sodium sulfate, filtered and concentrated under reduced pressure. The crude material was purified by silica gel chromatography (ethyl acetate/hexane gradient) to yield methyl 4-cyclopropyl-2-fluoro-6-[2-methoxy-4-(trifluoromethoxy)phenoxy]benzoate (325 mg, 77%) as an off white. ESI-MS m/z calc. 400.09, found 401.3 (M+1)+; retention time (Method B): 2.11 minutes (3 minute run).

Step 3: 4-cyclopropyl-2-fluoro-6-[2-methoxy-4-(trifluoromethoxy)phenoxy]benzoic acid To a slurry of methyl 4-cyclopropyl-2-fluoro-6-[2-methoxy-4-(trifluoromethoxy)phenoxy]benzoate (325 mg, 0.81 mmol) in MeOH (3.2 mL) and water (3.2 mL) was added NaOH (350 mg, 8.75 mmol). The reaction mixture was stirred at room temperature for 5 hours. The solvent was evaporated and the residue was taken up in water, cooled in an ice bath and quenched with 6N HCl slowly. The resulting precipitated solid was filtered and washed with water. The residue was dissolved in dichloromethane and ethyl acetate, dried over MgSO$_4$, filtered and concentrated. The filtrate was extracted with ethyl acetate, dried over MgSO$_4$, concentrated and combined with the residue to yield 4-cyclopropyl-2-fluoro-6-[2-methoxy-4-(trifluoromethoxy)phenoxy]benzoic acid (275 mg, 88%). ESI-MS m/z calc. 386.08, found 387.3 (M+1)+; retention time (Method B): 1.87 minutes (3 minute run).

Step 4: 4-[[4-cyclopropyl-2-fluoro-6-[2-methoxy-(trifluoromethoxy)phenoxy]benzoyl]amino]pyridine-2-carboxamide (22)

A vial was charged with 4-cyclopropyl-2-fluoro-6-[2-methoxy-4-(trifluoromethoxy)phenoxy]benzoic acid (80 mg, 0.207 mmol), 4-[(Z)-[(tert-butylamino)-phenylsulfanyl-methylene]amino]pyridine-2-carboxamide (prepared as described in Example 4, 69 mg, 0.21 mmol), tris[(Z)-1-methyl-3-oxo-but-1-enoxy]iron (3 mg, 0.008 mmol) in 2-propanol (1.2 mL) and was heated at 80° C. under an atmosphere of air for 20 hours. The mixture was cooled to room temperature, the solvent evaporated and the residue was taken up in dichloromethane and washed with 1N HCl. The organic layer was dried over MgSO$_4$, filtered and concentrated. The crude material was purified by silica gel chromatography (ethyl acetate/hexane gradient) to yield 4-[[4-cyclopropyl-2-fluoro-6-[2-methoxy-4-(trifluoromethoxy)phenoxy]benzoyl]amino]pyridine-2-carboxamide (68 mg, 64%). ESI-MS m/z calc. 505.13, found 506.3 (M+1)+; retention time (Method B): 1.73 minutes (3 minute run). $^1$H NMR (400 MHz, DMSO-d6) δ 11.14 (s, 1H), 8.50 (d, J=5.5 Hz, 1H), 8.28 (d, J=2.1 Hz, 1H), 8.07 (d, J=2.8 Hz, 1H), 7.80 (dd, J=5.5, 2.2 Hz, 1H), 7.62 (d, J=2.9 Hz, 1H), 7.23-7.10 (m, 2H), 7.01-6.89 (m, 1H), 6.75 (dd, J=10.6, 1.4 Hz, 1H), 6.42 (d, J=1.2 Hz, 1H), 3.76 (s, 3H), 2.01-1.78 (m, 1H), 0.99-0.94 (m, 2H), 0.78-0.51 (m, 2H) ppm.

Example 23

N-(3-carbamoyl-4-fluoro-phenyl)-5-fluoro-2-[2-methoxy-4-(trifluoromethoxy)phenoxy]-4-(trifluoromethyl)benzamide (23)

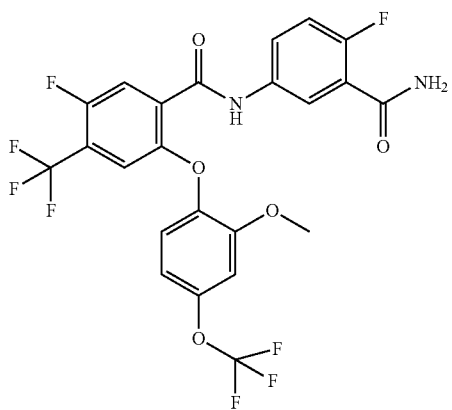 [SMILES: COc1cc(OC(F)(F)F)ccc1Oc1cc(C(F)(F)F)c(F)cc1C(=O)Nc1ccc(F)c(C(N)=O)c1]

Step 1: 2,5-difluoro-4-(trifluoromethyl)benzoyl chloride

To 2,5-difluoro-4-(trifluoromethyl)benzoic acid (2.00 g, 8.85 mmol) and N,N-dimethylformamide (63 μL, 0.81 mmol) in dichloromethane (23 mL) at 0° C. was added oxalyl chloride (3.76 mL, 43.13 mmol) dropwise. The mixture was stirred at 50° C. for 40 minutes under a N$_2$ atmosphere. The solvent was evaporated under reduced pressure to afford 2,5-difluoro-4-(trifluoromethyl)benzoyl chloride (1.9 g, 88%), which was used in the next step without further purification.

Step 2: N-(3-carbamoyl-4-fluoro-phenyl)-2,5-difluoro-4-(trifluoromethyl)benzamide To 5-amino-2-fluoro-benzamide (441 mg, 2.86 mmol) and diisopropylethylamine (1.50 mL, 8.59 mmol) in dichloromethane (7 mL), cooled at 0° C., was added dropwise a solution of 2,5-difluoro-4-(trifluoromethyl)benzoyl chloride (700 mg, 2.862 mmol) in THF (7 mL). The reaction was stirred at room temperature overnight. The mixture was diluted with ethyl acetate (100 mL) and washed with saturated aqueous NaHCO$_3$, water, and brine. The organic phase was dried over sodium sulfate and concentrated to dryness. The crude material was purified by silica gel chromatography (ethyl acetate/hexane gradient) to yield N-(3-carbamoyl-4-fluoro-phenyl)-2,5-difluoro-4-(trifluoromethyl)benzamide (1 g, 89%). ESI-MS m/z calc. 362.049, found 363.2 (M+1)+; retention time (Method A): 0.55 minutes (1.2 minute run).

Step 3: N-(3-carbamoyl-4-fluoro-phenyl)-5-fluoro-2-[2-methoxy-4-(trifluoromethoxy)phenoxy]-4-(trifluoromethyl)benzamide (23)

A mixture of N-(3-carbamoyl-4-fluoro-phenyl)-2,5-difluoro-4-(trifluoromethyl)benzamide (90 mg, 0.23 mmol), 2-methoxy-4-(trifluoromethoxy)phenol (prepared as described in Example 2, 48 mg, 0.23 mmol), potassium carbonate (95 mg, 0.69 mmol) and N,N-dimethylformamide (828 μL) was heated at 100° C. overnight. The mixture was filtered, and diluted with DMSO (1 mL). The crude material was purified by reverse phase HPLC to yield N-(3-carbamoyl-4-fluoro-phenyl)-5-fluoro-2-[2-methoxy-4-(trifluoromethoxy)phenoxy]-4-(trifluoromethyl)benzamide (21.9 mg, 17%) as a white solid. ESI-MS m/z calc. 550.08, found 551.2 (M+1)+; retention time (Method B): 1.86 minutes (3 minute run). $^1$H NMR (400 MHz, DMSO-d6) δ 10.71 (s, 1H), 7.96 (dd, J=6.4, 2.8 Hz, 1H), 7.90 (d, J=10.0 Hz, 1H), 7.79-7.64 (m, 3H), 7.28 (dd, J=10.1, 8.9 Hz, 1H), 7.22 (d, J=8.8 Hz, 1H), 7.18 (d, J=2.7 Hz, 1H), 7.15 (d, J=5.6 Hz, 1H), 6.98 (ddd, J=8.9, 2.7, 1.3 Hz, 1H), 3.77 (s, 3H) ppm.

Example 24

5-[[2-fluoro-6-[2-(trideuteriomethoxy)-4-(trifluoromethoxy)phenoxy]-3-(trifluoromethyl)benzoyl]amino]pyridine-2-carboxamide (24)

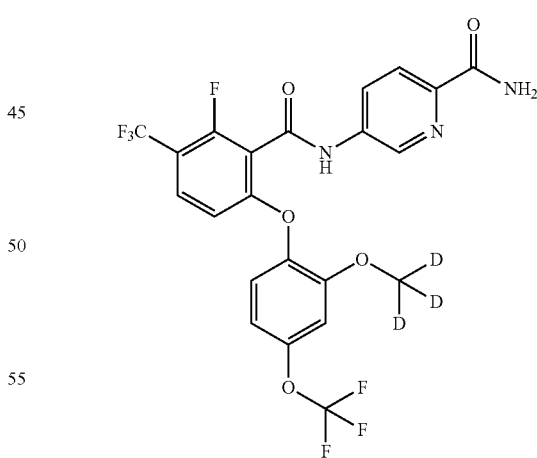

Step 1: 2-fluoro-6-[2-(trideuteriomethoxy)-4-(trifluoromethoxy)phenoxy]-3-(trifluoromethyl)benzoyl chloride To a solution of 2-fluoro-6-[2-(trideuteriomethoxy)-4-(trifluoromethoxy)phenoxy]-3-(trifluoromethyl)benzoic acid (prepared as described in Example 1, 500 mg, 1.20 mmol) and N,N-dimethylformamide (20 µL, 0.26 mmol) in dichloromethane (5 mL) at 0° C. was added oxalyl chloride (650 µL, 7.45 mmol) dropwise under N₂ atmosphere. The reaction was removed from the ice bath after 10 min and stirred at RT for 30 minutes. The solvent was evaporated under reduced pressure to afford 2-fluoro-6-[2-(trideuteriomethoxy)-4-(trifluoromethoxy)phenoxy]-3-(trifluoromethyl)benzoyl chloride which was used in the next step without further purification.

Step 2: 5-[[2-fluoro-6-[2-(trideuteriomethoxy)-4-(trifluoromethoxy)phenoxy]-3-(trifluoromethyl)benzoyl]amino]pyridine-2-carboxamide (24)

A solution of 5-aminopyridine-2-carboxamide (248.6 mg, 1.813 mmol) in dichloromethane (2.50 mL) and N,N-diisopropylethylamine (420 µL, 2.41 mmol) was cooled to 0° C. A solution of ice cold 2-fluoro-6-[2-(trideuteriomethoxy)-4-(trifluoromethoxy)phenoxy]-3-(trifluoromethyl)benzoyl chloride in dichloromethane (2.5 mL) was added slowly dropwise to the stirring amine solution. The mixture was removed from the ice bath after 1 hour and stirred at RT for 69 hours. The reaction was diluted with dichloromethane and washed with water, 1 N HCl, saturated aqueous sodium bicarbonate and brine. The organic layer was dried over Na₂SO₄, filtered and the solvent was evaporated under reduced pressure. The crude material was purified by silica gel chromatography (ethyl acetate/hexane gradient) to yield 5-[[2-fluoro-6-[2-(trideuteriomethoxy)-4-(trifluoromethoxy)phenoxy]-3-(trifluoromethyl)benzoyl]amino]pyridine-2-carboxamide (326 mg, 51%) as a white solid. ESI-MS m/z calc. 536.10, found 537.0 (M+1)+; retention time (Method C): 2.48 minutes (5 minute run). ¹H NMR (400 MHz, DMSO-d6) δ 11.36 (s, 1H), 8.88 (d, J=2.5 Hz, 1H), 8.31 (dd, J=8.6, 2.5 Hz, 1H), 8.07 (d, J=8.6 Hz, 1H), 8.03 (d, J=2.8 Hz, 1H), 7.81 (t, J=8.6 Hz, 1H), 7.57 (d, J=2.8 Hz, 1H), 7.37 (d, J=8.7 Hz, 1H), 7.25 (d, J=2.8 Hz, 1H), 7.12-6.92 (m, 1H), 6.69 (d, J=8.9 Hz, 1H) ppm.

Example 25

N-(3-carbamoyl-4-fluoro-phenyl)-2-fluoro-6-(4-fluorophenoxy)-3-(trifluoromethyl)benzamide (25)

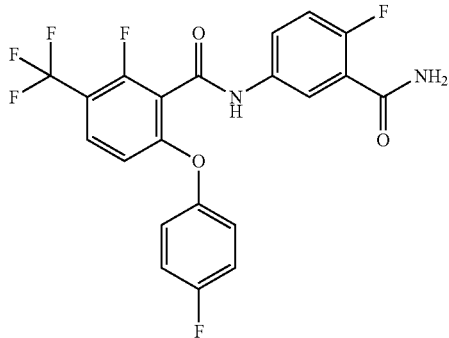 [SMILES: NC(=O)c1cc(NC(=O)c2c(Oc3ccc(F)cc3)ccc(C(F)(F)F)c2F)ccc1F]

Step 1: 2-fluoro-6-(4-fluorophenoxy)-3-(trifluoromethyl)benzoic acid

A microwave vial was charged 6-bromo-2-fluoro-3-(trifluoromethyl)benzoic acid (2.5 g, 8.71 mmol), cesium carbonate (5.676 g, 17.42 mmol) and 4-fluorophenol (1.171 g, 10.45 mmol) in toluene (18.75 mL). The mixture was degassed with nitrogen. After ca. 2 minutes, copper (I) iodide (332 mg, 1.74 mmol) was added and the reaction was stirred at 100° C. for 25 minutes. The reaction was diluted with 300 mL ethyl acetate and 200 mL of water and the phases were separated. The aqueous layer was acidified to approximately pH 3 and extracted with ethyl acetate. The combined organic phases were dried over sodium sulfate and concentrated. The crude material was purified by silica gel chromatography (ethyl acetate/hexane gradient) to afford 2-fluoro-6-(4-fluorophenoxy)-3-(trifluoromethyl)benzoic acid (1.2 g, 43%). ESI-MS m/z calc. 318.03, found 319.0 (M+1)+; retention time (Method A): 0.67 minutes (1.2 minute run).

Step 2: 2-fluoro-6-(4-fluorophenoxy)-3-(trifluoromethyl)benzoyl chloride

To 2-fluoro-6-(4-fluorophenoxy)-3-(trifluoromethyl)benzoic acid (570 mg, 1.79 mmol) and N,N-dimethylformamide (11 µL, 0.141 mmol) in dichloromethane (5.6 mL) at 0° C. was added oxalyl chloride (655 µL, 7.51 mmol) dropwise. The mixture was stirred at 50° C. for 40 minutes under an N₂ atmosphere. The solvent was evaporated under reduced pressure to afford 2-fluoro-6-(4-fluorophenoxy)-3-(trifluoromethyl)benzoyl chloride, which was used in the next step without further purification.

Step 3: N-(3-carbamoyl-4-fluoro-phenyl)-2-fluoro-6-(4-fluorophenoxy)-3-(trifluoromethyl)benzamide (25)

To 5-amino-2-fluoro-benzamide (37 mg, 0.24 mmol) and diisopropylethylamine (124 µL, 0.71 mmol) in dichloromethane (390 µL) cooled at 0° C. was added dropwise a solution of 2-fluoro-6-(4-fluorophenoxy)-3-(trifluoromethyl)benzoyl chloride (80 mg, 0.24 mmol) in dichloromethane (390 µL). The reaction was stirred at room temperature for 1 hour. The solvent was evaporated and the residue was partitioned between water and ethyl acetate. The organic phase was concentrated to dryness. The residue was dissolved in 1 ml of DMSO and purified by reverse phase HPLC to afford N-(3-carbamoyl-4-fluoro-phenyl)-2-fluoro-6-(4-fluorophenoxy)-3-(trifluoromethyl)benzamide (25.5 mg, 24%). ESI-MS m/z calc. 454.08, found 455.1 (M+1)+; retention time (Method B): 1.63 minutes (3 minute run). ¹H NMR (400 MHz, DMSO-d6) δ 11.05 (s, 1H), 7.98 (dd, J=6.4, 2.8 Hz, 1H), 7.89-7.74 (m, 3H), 7.71 (s, 1H), 7.40-7.25 (m, 5H), 6.79 (d, J=8.9 Hz, 1H) ppm.

The compounds set forth in Table 12 were prepared by methods analogous to the preparation of compound 15.

TABLE 12

Additional Compounds Prepared By Methods Analogous to Example 15

| Cmpd No. | Compound Name | LC/MS | NMR (shifts in ppm) |
|---|---|---|---|
| 50 | 4-[[2-fluoro-6-(4-fluorophenoxy)-3-(trifluoromethyl)benzoyl]amino]pyridine-2-carboxamide | ESI-MS m/z calc. 437.08, found 438.1 (M + 1)+; Retention time (Method B): 1.61 minutes (3 minute run). | $^1$H NMR (400 MHz, DMSO-d6) δ 11.54 (s, 1H), 8.57 (d, J = 5.5 Hz, 1H), 8.33 (d, J = 2.2 Hz, 1H), 8.16 (s, 1H), 7.92-7.82 (m, 2H), 7.71 (s, 1H), 7.39-7.26 (m, 4H), 6.80 (d, J = 8.9 Hz, 1H). |
| 49 | N-(3-carbamoylphenyl)-2-fluoro-6-(4-fluorophenoxy)-3-(trifluoromethyl)benzamide | ESI-MS m/z calc. 436.08, found 437.1 (M + 1)+; Retention time (Method B): 1.59 minutes (3 minute run). | $^1$H NMR (400 MHz, DMSO-d6) δ 11.00 (s, 1H), 8.15 (t, J = 1.9 Hz, 1H), 8.00 (s, 1H), 7.88-7.77 (m, 2H), 7.62 (dt, J = 7.9, 1.2 Hz, 1H), 7.44 (t, J = 7.9 Hz, 1H), 7.40 (s, 1H), 7.36-7.25 (m, 4H), 6.78 (d, J = 8.9 Hz, 1H). |

Example 26

4-[[2-fluoro-6-[3-fluoro-2-methoxy-4-(trifluoromethoxy)phenoxy]-3-(trifluoromethyl)benzoyl]amino]pyridine-2-carboxamide (26)

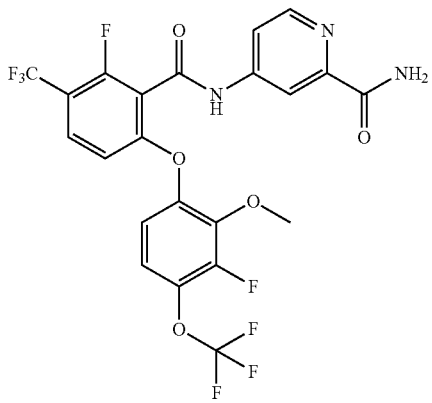 [SMILES: COc1c(Oc2ccc(C(F)(F)F)c(F)c2C(=O)Nc2ccnc(C(N)=O)c2)ccc(OC(F)(F)F)c1F]

Step 1:
6-bromo-2-fluoro-3-(trifluoromethoxy)phenol

To a solution of 2-fluoro-3-(trifluoromethoxy)phenol (3 g, 15.30 mmol) in dichloromethane (10 mL) and heptane (20 mL) cooled in an ice-bath was added 1-bromopyrrolidine-2,5-dione (3 g, 16.86 mmol) in 6 portions over 1 hour. The reaction was stirred for a further hour at 0° C. and then allowed to warm to RT. The reaction was filtered and the filtrate was concentrated under reduced pressure to yield 6-bromo-2-fluoro-3-(trifluoromethoxy)phenol (3.7 g, 88%), which was used without further purification. ESI-MS m/z calc. 275.925, found 274.8 (M−1)−; retention time (Method D): 0.65 minutes (1.15 minute run).

Step 2: 1-bromo-3-fluoro-2-methoxy-4-(trifluoromethoxy)benzene

To a solution of 6-bromo-2-fluoro-3-(trifluoromethoxy)phenol (3 g, 10.91 mmol) in acetone (3 mL) was added iodomethane (2.38 g, 16.77 mmol) and potassium carbonate (2.26 g, 16.35 mmol) and the mixture heated to 60° C. for 1 hour. The mixture was allowed to cool to RT and was diluted with dichloromethane (15 mL) and filtered. The filtrate was concentrated under reduced pressure to yield an oil. The crude material was purified by silica gel chromatography (ethyl acetate/petroleum ether gradient) to yield 1-bromo-3-fluoro-2-methoxy-4-(trifluoromethoxy)benzene (2.35 g, 75%) as a white solid. $^1$H NMR (500 MHz, Chloroform-d3) δ 7.36 (dd, J=9.1, 2.4 Hz, 1H), 6.97 (ddq, J=8.6, 7.2, 1.3 Hz, 1H), 4.05-4.00 (m, 3H) ppm.

Step 3:
3-fluoro-2-methoxy-4-(trifluoromethoxy)phenol

To a solution of 1-bromo-3-fluoro-2-methoxy-4-(trifluoromethoxy)benzene (1 g, 3.460 mmol) in dioxane (5 mL) was added di-tert-butyl-[2-(2,4,6-triisopropylphenyl)phenyl]phosphane (75 mg, 0.18 mmol), (1E,4E)-1,5-diphenylpenta-1,4-dien-3-one; palladium (80 mg, 0.087 mmol) and KOH (582 mg, 10.37 mmol) followed by water (5 mL) and the mixture heated to 90° C. for 3 hours. The reaction mixture was allowed to cool to RT and filtered. The aqueous layer was acidified to approximately pH 1 with 2M HCl and was extracted with ethyl acetate (2×10 mL). The combined organic phases were washed with brine (5 mL), dried over magnesium sulfate and concentrated to dryness. The product was purified by silica gel chromatography (ethyl acetate/petroleum ether gradient) to yield 3-fluoro-2-methoxy-4-(trifluoromethoxy)phenol (514 mg, 66%) as an oil. ESI-MS m/z calc. 226.025, found 224.9 (M−1)−; retention time (Method D): 0.87 minutes (1.15 minute run).

Step 4: 2-fluoro-6-[3-fluoro-2-methoxy-4-(trifluoromethoxy)phenoxy]-3-(trifluoromethyl)benzoic acid To a solution of 3-fluoro-2-methoxy-4-(trifluoromethoxy)phenol (40 mg, 0.18 mmol) in toluene (1 mL) was added copper (I) iodide (7 mg, 0.03676 mmol), cesium carbonate (113 mg, 0.3468 mmol) and 6-bromo-2-fluoro-3-(trifluoromethyl)benzoic acid (50 mg, 0.1742 mmol) and the mixture heated to 100° C. for 6 hours. The reaction mixture was allowed to cool to RT and HCl (270 µL of 2 M, 0.54 mmol) added slowly. The mixture was extracted with ethyl acetate (10 mL). The organic phase was washed with brine (20 mL), dried over magnesium sulfate and concentrated to dryness. The product was purified by silica gel chromatography (ethyl acetate/petroleum ether gradient) to yield 2-fluoro-6-[3-fluoro-2-methoxy-4-(trifluoromethoxy)phenoxy]-3-(trifluoromethyl)benzoic acid (52 mg, 69%) as a white solid.

ESI-MS m/z calc. 432.02, found 430.9 (M−1)−; retention time (Method D): 0.76 minutes (1.15 minute run).

Step 5: 4-[[2-fluoro-6-[3-fluoro-2-methoxy-4-(trifluoromethoxy)phenoxy]-3-(trifluoromethyl)benzoyl]amino]pyridine-2-carboxamide (26)

To an ice-cooled solution of 2-fluoro-6-[3-fluoro-2-methoxy-4-(trifluoromethoxy)phenoxy]-3-(trifluoromethyl)benzoic acid (60 mg, 0.14 mmol) in dichloromethane (10 mL) and DMF (6 µL, 0.077 mmol) was carefully added oxalyl chloride (25 µL, 0.29 mmol) and the mixture was warmed to room temperature over 30 minutes and stirred for a further hour. The reaction mixture was concentrated under reduced pressure to afford a yellow solid. The residue was dissolved in dichloromethane (10 mL) followed by the addition of 4-aminopyridine-2-carboxamide (25 mg, 0.18 mmol) and triethylamine (60 µL, 0.43 mmol). The resulting mixture was stirred at RT for 45 minutes and then concentrated under reduced pressure. The residue was purified by silica gel chromatography (ethyl acetate/petroleum ether gradient) to yield 4-[[2-fluoro-6-[3-fluoro-2-methoxy-4-(trifluoromethoxy)phenoxy]-3-(trifluoromethyl)benzoyl]amino]pyridine-2-carboxamide (4 mg, 4%) as a white solid. ESI-MS m/z calc. 551.07, found 552.0 (M+1)+; retention time (Method E): 3.36 minutes (4.45 minute run).

Example 27

4-[[2-Fluoro-6-[2-(trideuteriomethoxy)-4-(trifluoromethoxy)phenoxy]-3-(trifluoromethyl)benzoyl]amino]-1-oxido-pyridin-1-ium-2-carboxamide (115)

To a stirring solution of 4-[[2-fluoro-6-[2-(trideuteriomethoxy)-4-(trifluoromethoxy)phenoxy]-3-(trifluoromethyl)benzoyl]amino]pyridine-2-carboxamide (prepared as described in Example 6, 112 mg, 0.209 mmol) in anhydrous dichloromethane (1 mL) under $N_2$ atmosphere at 0° C. was added 3-chloroperoxybenzoic acid (140 mg, 0.627 mmol). The reaction mixture was allowed to warm to room temperature and stirred for 1 hour. The reaction mixture was then cooled to 0° C., treated with additional 3-chloroperoxybenzoic acid (70 mg, 0.31 mmol) and stirred at room temperature for 5 hours. The reaction mixture was again cooled to 0° C., treated with 3-chloroperoxybenzoic acid (30 mg, 0.13 mmol) and stirred for an additional 16 hours at room temperature. Dichloromethane was added to clarify the reaction and the resulting solution was stirred for 1 hour. The solvent was removed in vacuo and the residue was purified by silica gel chromatography (0-100% ethyl acetate/hexanes) to provide 4-[[2-fluoro-6-[2-(trideuteriomethoxy)-4-(trifluoromethoxy)phenoxy]-3-(trifluoromethyl)benzoyl]amino]-1-oxido-pyridin-1-ium-2-carboxamide (80 mg, 69%) as a white solid. ESI-MS m/z calc. 552.10, found 553.0 (M+1)+; retention time (Method B): 1.66 minutes (3 minute run). $^1$H NMR (400 MHz, DMSO-d6) δ 11.56 (s, 1H), 10.59 (d, J=4.6 Hz, 1H), 8.55 (d, J=3.3 Hz, 1H), 8.38 (d, J=7.1 Hz, 1H), 8.27 (d, J=4.6 Hz, 1H), 7.87 (dd, J=7.1, 3.3 Hz, 1H), 7.82 (t, J=8.7 Hz, 1H), 7.37 (d, J=8.8 Hz, 1H), 7.26 (d, J=2.8 Hz, 1H), 7.10-6.96 (m, 1H), 6.69 (d, J=8.9 Hz, 1H) ppm.

Example 28

4-[[2-Fluoro-6-[2-(trideuteriomethoxy)-4-(trifluoromethoxy)phenoxy]-3-(trifluoromethyl)benzoyl]amino]-5-methyl-pyridine-2-carboxamide (137)

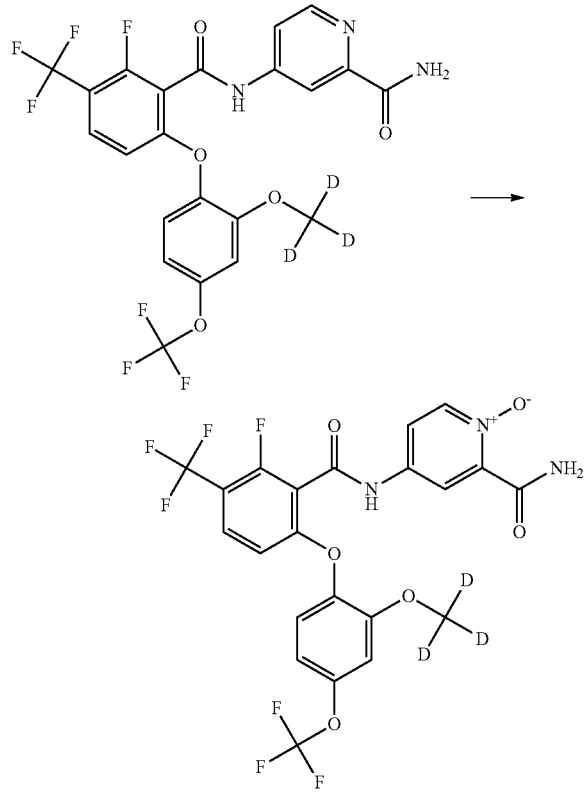

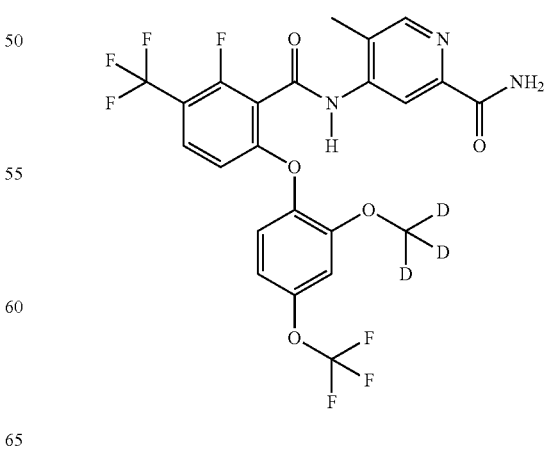

287

Step 1: N-(2-Bromo-5-methyl-4-pyridyl)-2-fluoro-6-[2-(trideuteriomethoxy)-4-(trifluoromethoxy)phenoxy]-3-(trifluoromethyl)benzamide

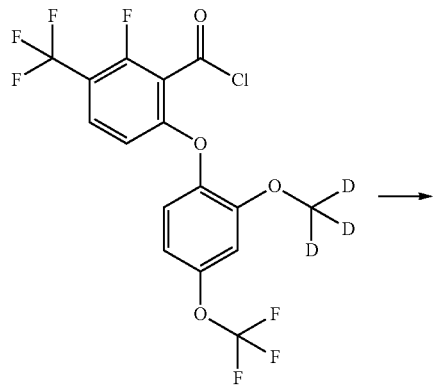

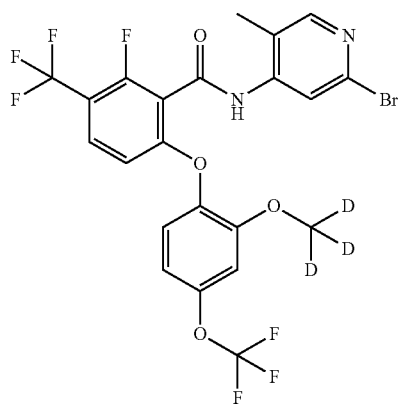

A solution of 2-bromo-5-methyl-pyridin-4-amine (406 mg, 2.17 mmol) in dichloromethane (3 mL) and DIEA (500 µL, 2.87 mmol) was cooled to 0° C. A solution of cold 2-fluoro-6-[2-(trideuteriomethoxy)-4-(trifluoromethoxy)phenoxy]-3-(trifluoromethyl)benzoyl chloride (prepared as described in Example 1, Step 4) in dichloromethane (3 mL) was added dropwise to the stirring amine solution. The reaction mixture was removed from the ice bath after 30 minutes and stirred at room temperature for 24 hours. The reaction was diluted with dichloromethane and washed with water, 1 M HCl, saturated aqueous NaHCO₃, and brine. The organic layer was dried over Na₂SO₄, filtered and concentrated in vacuo. Silica gel chromatography (0-20% ethyl acetate/hexanes) provided N-(2-bromo-5-methyl-4-pyridyl)-2-fluoro-6-[2-(trideuteriomethoxy)-4-(trifluoromethoxy)phenoxy]-3-(trifluoromethyl)benzamide (551 mg, 65%) as a yellow solid. ESI-MS m/z calc. 585.02, found 586.0 (M+1)+; retention time (Method C): 3.06 minutes (5 minute run).

288

Step 2: Methyl 4-[[2-fluoro-6-[2-(trideuteriomethoxy)-4-(trifluoromethoxy)phenoxy]-3-(trifluoromethyl)benzoyl]amino]-5-methyl-pyridine-2-carboxylate

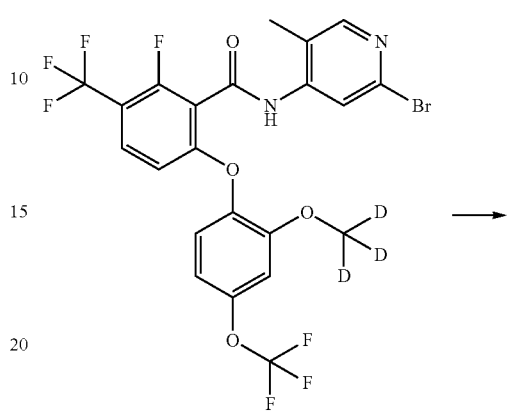

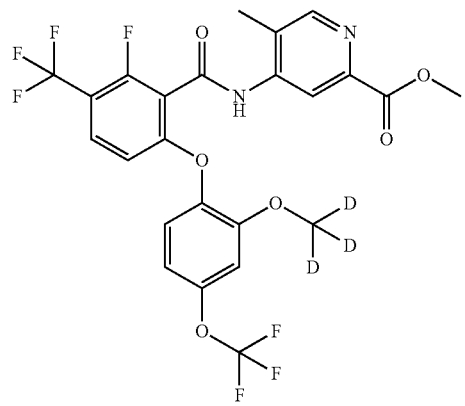

In a pressure tube, N-(2-bromo-5-methyl-4-pyridyl)-2-fluoro-6-[2-(trideuteriomethoxy)-4-(trifluoromethoxy)phenoxy]-3-(trifluoromethyl)benzamide (550 mg, 0.938 mmol) was dissolved in methanol (15 mL), and triethylamine (277 µL, 1.99 mmol) and Pd(dppf)Cl₂·DCM (152 mg, 0.186 mmol) were added. Carbon monoxide was bubbled through the vigorously stirring mixture for ~16 minutes. The reaction vessel was sealed and heated to 75° C. for 22 hours. The reaction mixture was cooled, filtered through a pad of Celite eluting with methanol and concentrated in vacuo. Silica gel chromatography (0-100% ethyl acetate/dichloromethane) provided methyl 4-[[2-fluoro-6-[2-(trideuteriomethoxy)-4-(trifluoromethoxy)phenoxy]-3-(trifluoromethyl)benzoyl]amino]-5-methyl-pyridine-2-carboxylate (383 mg, 72%). ESI-MS m/z calc. 565.12, found 566.0 (M+1)+; retention time (Method C): 2.62 minutes (5 minute run).

289

Step 3: 4-[[2-Fluoro-6-[2-(trideuteriomethoxy)-4-(trifluoromethoxy)phenoxy]-3-(trifluoromethyl)benzoyl]amino]-5-methyl-pyridine-2-carboxamide (137)

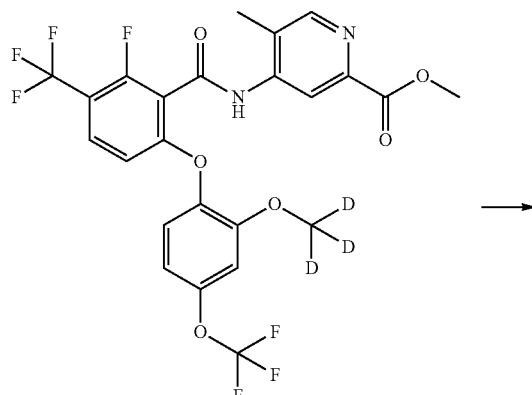

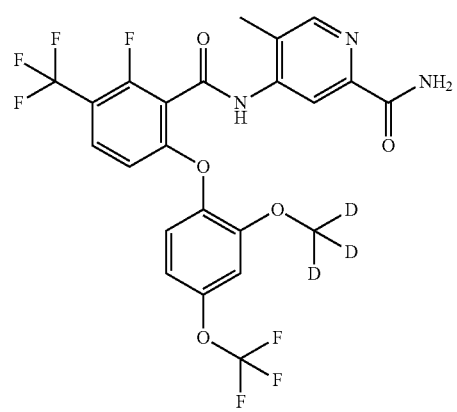 [SMILES: [2H]C([2H])([2H])Oc1cc(OC(F)(F)F)ccc1Oc1ccc(C(F)(F)F)c(F)c1C(=O)Nc1cc(C(N)=O)ncc1C]

A mixture of methyl 4-[[2-fluoro-6-[2-(trideuteriomethoxy)-4-(trifluoromethoxy)phenoxy]-3-(trifluoromethyl)benzoyl]amino]-5-methyl-pyridine-2-carboxylate (283 mg, 0.501 mmol) and ammonia (8 mL of 7 M in methanol, 56 mmol) was stirred at room temperature for 23 hours. The reaction was concentrated in vacuo. Silica gel chromatography (0-30% ethyl acetate/dichloromethane) provided 4-[[2-fluoro-6-[2-(trideuteriomethoxy)-4-(trifluoromethoxy)phenoxy]-3-(trifluoromethyl)benzoyl]amino]-5-methyl-pyridine-2-carboxamide (195 mg, 71%) as a white solid. ESI-MS m/z calc. 550.12, found 551.0 (M+1)+; retention time (Method C): 2.5 minutes (5 minute run). $^1$H NMR (400 MHz, DMSO-d6) δ 10.58 (s, 1H), 8.48 (d, J=4.8 Hz, 2H), 8.06 (d, J=2.8 Hz, 1H), 7.80 (t, J=8.6 Hz, 1H), 7.61 (d, J=2.7 Hz, 1H), 7.38 (d, J=8.8 Hz, 1H), 7.28 (d, J=2.6 Hz, 1H), 7.16-6.95 (m, 1H), 6.65 (d, J=8.9 Hz, 1H), 2.32 (s, 3H) ppm.

290

Example 29

6-[[2-Fluoro-6-[2-(trideuteriomethoxy)-4-(trifluoromethoxy)phenoxy]-3-(trifluoromethyl)benzoyl]amino]pyridine-3-carboxamide (212)

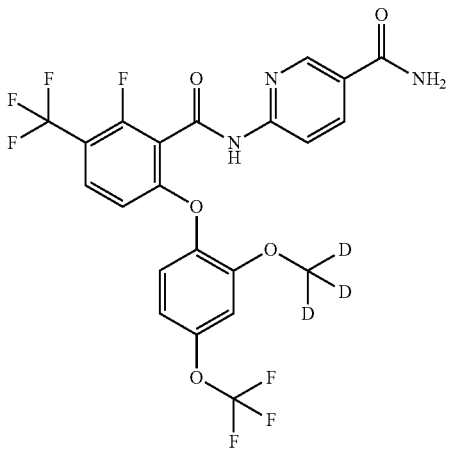 [SMILES: [2H]C([2H])([2H])Oc1cc(OC(F)(F)F)ccc1Oc1ccc(C(F)(F)F)c(F)c1C(=O)Nc1ccc(C(N)=O)cn1]

Step 1: Methyl 6-[[2-fluoro-6-[2-(trideuteriomethoxy)-4-(trifluoromethoxy)phenoxy]-3-(trifluoromethyl)benzoyl]amino]pyridine-3-carboxylate

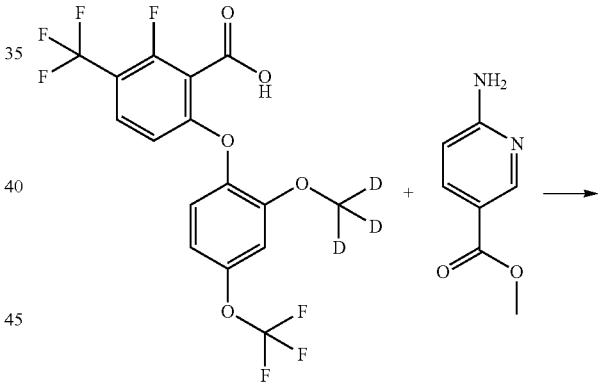

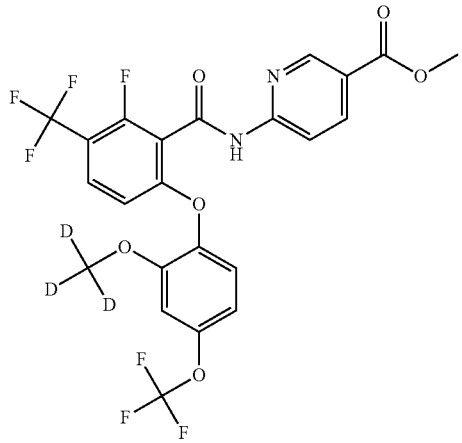

2-Fluoro-6-[2-(trideuteriomethoxy)-4-(trifluoromethoxy)phenoxy]-3-(trifluoromethyl)benzoic acid (prepared as described in Example 1, Step 3, 200 mg, 0.479 mmol) and HATU (201 mg, 0.527 mmol) were combined in DMF (2 mL) and DIEA (186 mg, 251 µL, 1.44 mmol), and the mixture was stirred for 5 minutes. Methyl 6-aminopyridine-3-carboxylate (73 mg, 0.48 mmol) was added in one portion and the reaction was stirred for 21 hours. Additional methyl 6-aminopyridine-3-carboxylate (146 mg, 0.96 mmol) was added and the reaction mixture was heated at 80° C. for 3 hours. The reaction mixture was filtered and purified by HPLC (10-99% acetonitrile/5 mM HCl) to provide methyl 6-[[2-fluoro-6-[2-(trideuteriomethoxy)-4-(trifluoromethoxy)phenoxy]-3-(trifluoromethyl)benzoyl]amino]pyridine-3-carboxylate (56 mg, 21%). ESI-MS m/z calc. 551.10, found 552.0 (M+1)+; retention time (Method A): 0.79 minutes (1 minute run).

Step 2: 6-[[2-Fluoro-6-[2-(trideuteriomethoxy)-4-(trifluoromethoxy)phenoxy]-3-(trifluoromethyl)benzoyl]amino]pyridine-3-carboxamide (212)

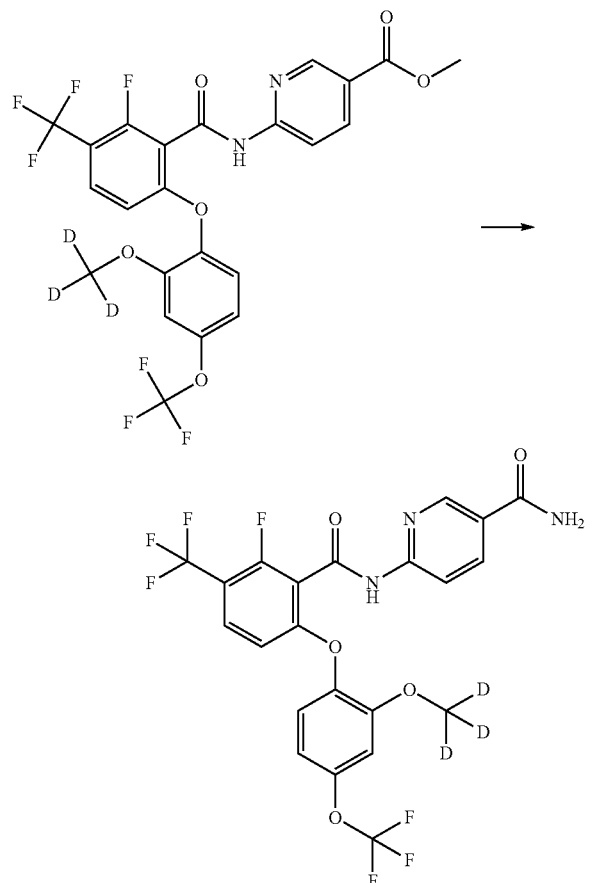

A mixture of methyl 6-[[2-fluoro-6-[2-(trideuteriomethoxy)-4-(trifluoromethoxy)phenoxy]-3-(trifluoromethyl)benzoyl]amino]pyridine-3-carboxylate (56 mg, 0.10 mmol) and ammonia (6 mL of 7 M in methanol, 42 mmol) was stirred at 60° C. for 17 hours. The reaction mixture was concentrated in vacuo. The crude product was dissolved in DMSO, filtered and purified using by HPLC (10-99% acetonitrile/5 mM HCl) to provide 6-[[2-fluoro-6-[2-(trideuteriomethoxy)-4-(trifluoromethoxy)phenoxy]-3-(trifluoromethyl)benzoyl]amino]pyridine-3-carboxamide (16 mg, 29%). ESI-MS m/z calc. 536.10, found 537.0 (M+1)+; retention time (method C): 2.46 minutes (5 minutes run). $^1$H NMR (400 MHz, DMSO-d6) δ 11.60 (s, 1H), 8.96-8.61 (m, 1H), 8.30 (dd, J=9.0, 2.3 Hz, 1H), 8.23 (d, J=8.8 Hz, 1H), 8.07 (s, 1H), 7.76 (t, J=8.6 Hz, 1H), 7.50 (s, 1H), 7.36 (d, J=8.8 Hz, 1H), 7.24 (d, J=2.8 Hz, 1H), 7.12-6.90 (m, 1H), 6.64 (d, J=8.9 Hz, 1H) ppm.

Example 30

6-[[2-Fluoro-6-[2-(trideuteriomethoxy)-4-(trifluoromethoxy)phenoxy]-3-(trifluoromethyl)benzoyl]amino]pyridine-2-carboxamide (168)

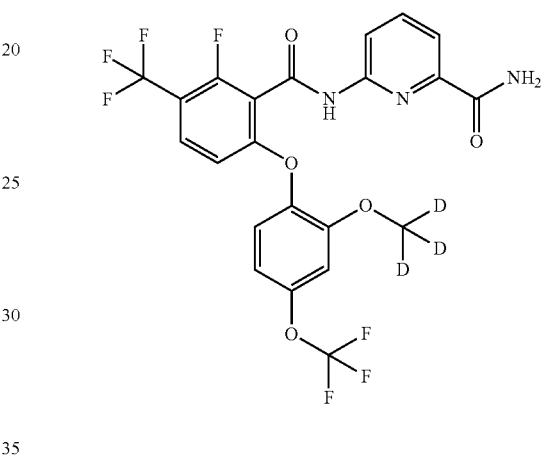

Step 1: N-(6-Bromo-2-pyridyl)-2-fluoro-6-[2-(trideuteriomethoxy)-4-(trifluoromethoxy)phenoxy]-3-(trifluoromethyl)benzamide

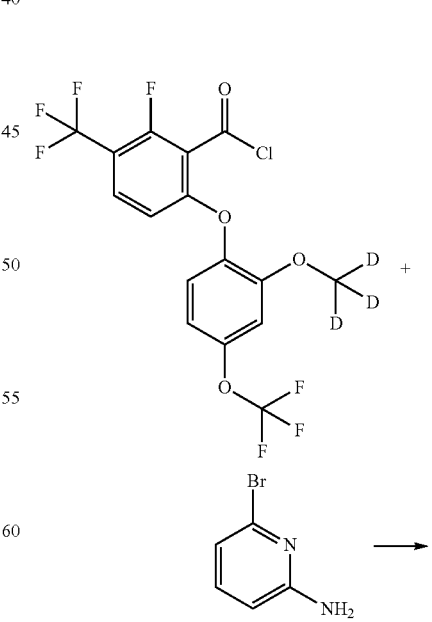

293

-continued

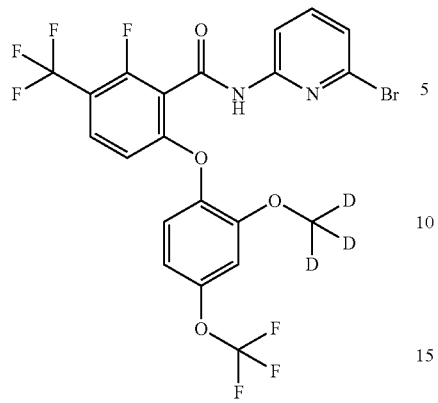

294

-continued

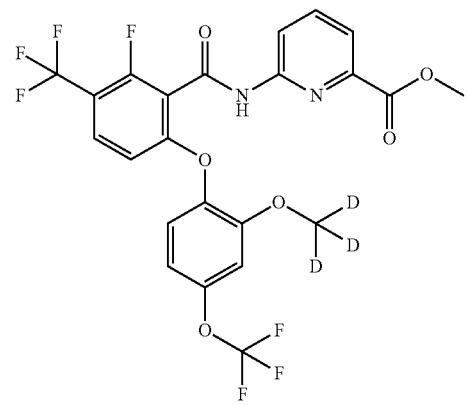

To a stirring slurry of 6-bromopyridin-2-amine (191 mg, 1.10 mmol) in dichloromethane (3 mL) and DIEA (190 mg, 256 µL, 1.47 mmol) at 0° C. was added slurry of cold 2-fluoro-6-[2-(trideuteriomethoxy)-4-(trifluoromethoxy) phenoxy]-3-(trifluoromethyl)benzoyl chloride (prepared as described in Example 1, Step 4, 320 mg, 0.735 mmol) in dichloromethane (3 mL) dropwise. The reaction mixture was removed from the ice bath after 10 min and stirred at room temperature for 18 hours. The solvent was evaporated in vacuo and the crude product was dissolved in DMSO, filtered and purified by HPLC (10-99% acetonitrile/5 mM HCl) to provide N-(6-bromo-2-pyridyl)-2-fluoro-6-[2-(trideuteriomethoxy)-4-(trifluoromethoxy)phenoxy]-3-(trifluoromethyl)benzamide (172 mg, 41%). ESI-MS m/z calc. 571.01, found 571.8 (M+1); retention time (Method A): 0.84 minutes (1 minute run).

Step 2: Methyl 6-[[2-fluoro-6-[2-(trideuteriomethoxy)-4-(trifluoromethoxy)phenoxy]-3-(trifluoromethyl)benzoyl]amino]pyridine-2-carboxylate In a pressure tube, N-(6-bromo-2-pyridyl)-2-fluoro-6-[2-(trideuteriomethoxy)-4-(trifluoromethoxy)phenoxy]-3-(trifluoromethyl)benzamide (171 mg, 0.299 mmol) was dissolved in methanol (6 mL) and triethylamine (84 µL, 0.60 mmol), and Pd(dppf)Cl$_2$·DCM (50 mg, 0.061 mmol) was added. Carbon monoxide was bubbled through the vigorously stirring reaction mixture for 15 minutes. The reaction vessel was sealed and heated to 75° C. for 14 hours. The reaction mixture was cooled, filtered through a pad of Celite eluting with methanol and concentrated in vacuo. The crude material was purified by silica gel chromatography (0-30% ethyl acetate/dichloromethane) to provide methyl 6-[[2-fluoro-6-[2-(trideuteriomethoxy)-4-(trifluoromethoxy)phenoxy]-3-(trifluoromethyl)benzoyl]amino]pyridine-2-carboxylate (126.9 mg, 77%) as a white solid. ESI-MS m/z calc. 551.10, found 552.0 (M+1)+; retention time (Method C): 2.93 minutes (5 minute run).

Step 3: 6-[[2-Fluoro-6-[2-(trideuteriomethoxy)-4-(trifluoromethoxy)phenoxy]-3-(trifluoromethyl)benzoyl]amino]pyridine-2-carboxamide (168)

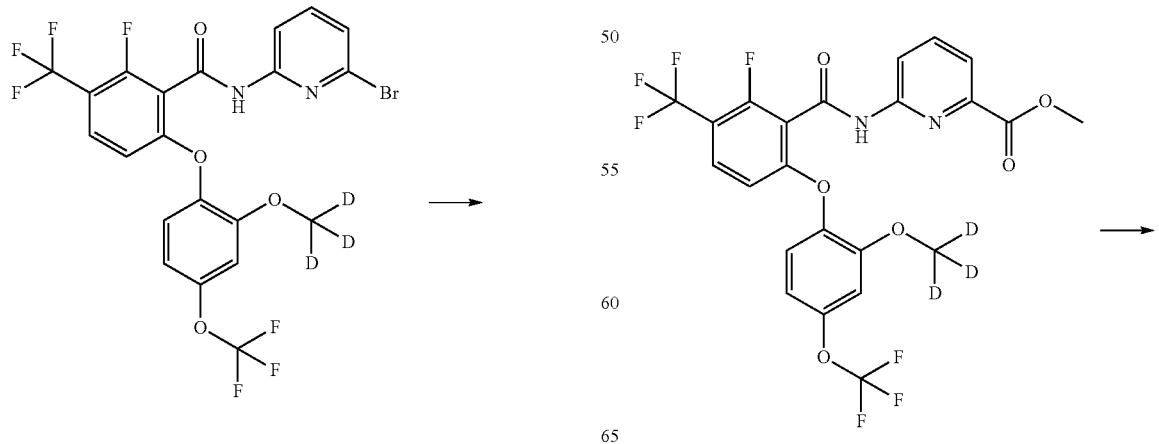

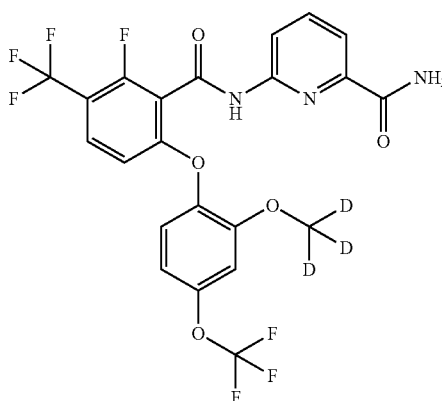

A solution of methyl 6-[[2-fluoro-6-[2-(trideuteriomethoxy)-4-(trifluoromethoxy)phenoxy]-3-(trifluoromethyl)benzoyl]amino]pyridine-2-carboxylate (127 mg, 0.2303 mmol) and ammonia (3.6 mL of 7 M in methanol, 25.20 mmol) was stirred at ambient temperature for 4 hours. The reaction was concentrated in vacuo. The crude material was purified by silica gel chromatography (0-30% ethyl acetate/dichloromethane) to provide 6-[[2-fluoro-6-[2-(trideuteriomethoxy)-4-(trifluoromethoxy)phenoxy]-3-(trifluoromethyl)benzoyl]amino]pyridine-2-carboxamide (99 mg, 80%) as a white solid. ESI-MS m/z calc. 536.10, found 537.0 (M+1)+; retention time (Method C): 2.59 minutes (5 minute run). $^1$H NMR (400 MHz, DMSO-d6) δ 11.45 (s, 1H), 8.32 (d, J=8.2 Hz, 1H), 8.05 (t, J=7.9 Hz, 1H), 7.91-7.66 (m, 3H), 7.59 (s, 1H), 7.36 (d, J=8.8 Hz, 1H), 7.25 (d, J=2.7 Hz, 1H), 7.03 (d, J=8.5 Hz, 1H), 6.66 (d, J=8.8 Hz, 1H) ppm.

Example 31

5-[[2-fluoro-6-[2-(trideuteriomethoxy)-4-(trifluoromethoxy)phenoxy]-3-(trifluoromethyl)benzoyl]amino]-4-methyl-pyridine-2-carboxamide (161)

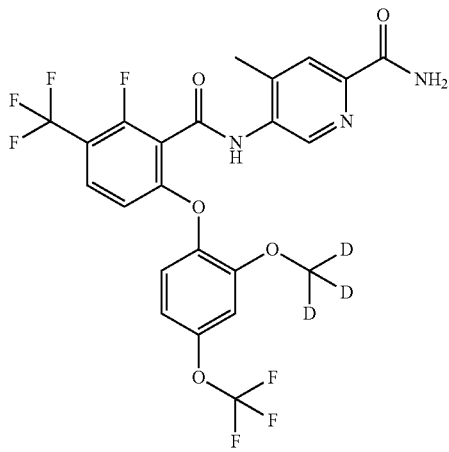 [SMILES: [2H]C([2H])([2H])Oc1cc(OC(F)(F)F)ccc1Oc1ccc(C(F)(F)F)c(F)c1C(=O)Nc1cnc(C(N)=O)cc1C]

Step 1: Methyl 5-[[2-fluoro-6-[2-(trideuteriomethoxy)-4-(trifluoromethoxy)phenoxy]-3-(trifluoromethyl)benzoyl]amino]-4-methyl-pyridine-2-carboxylate

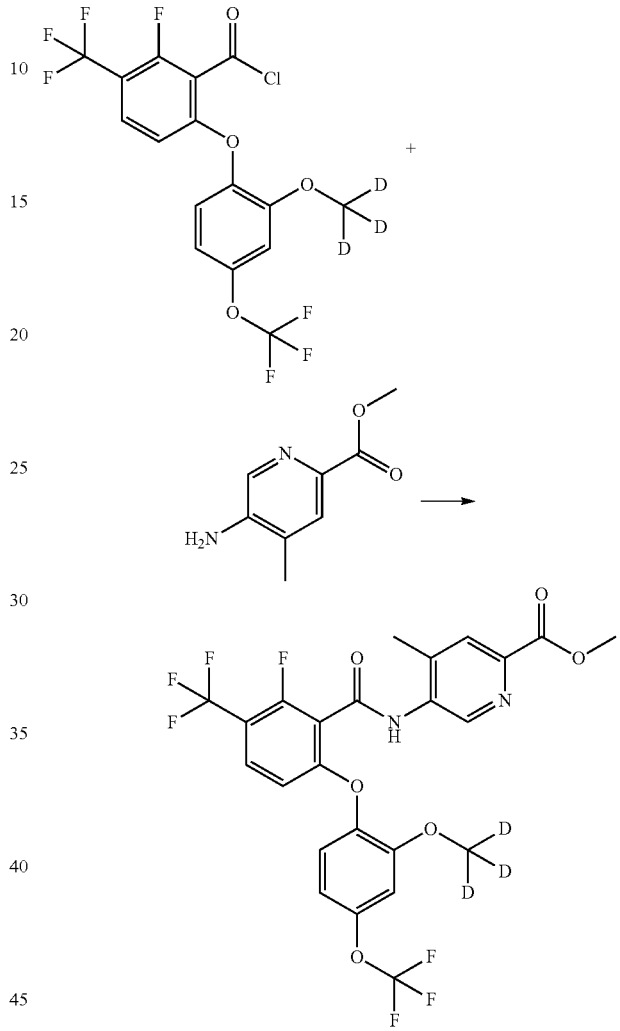

To a stirring slurry of methyl 5-amino-4-methyl-pyridine-2-carboxylate (183 mg, 1.10 mmol) in dichloromethane (3 mL) and DIEA (190 mg, 256 µL, 1.47 mmol) at 0° C. was added slurry of cold 2-fluoro-6-[2-(trideuteriomethoxy)-4-(trifluoromethoxy)phenoxy]-3-(trifluoromethyl)benzoyl chloride (prepared as described in Example 1, Step 4, 320 mg, 0.735 mmol) in dichloromethane (3 mL) dropwise. The reaction mixture was removed from the ice bath after 10 min and stirred at room temperature for 18 hours. The solvent was evaporated in vacuo and the crude product was dissolved in DMSO, filtered and purified by HPLC (10-99% acetonitrile/5 mM HCl) to provide methyl 5-[[2-fluoro-6-[2-(trideuteriomethoxy)-4-(trifluoromethoxy)phenoxy]-3-(trifluoromethyl)benzoyl]amino]-4-methyl-pyridine-2-carboxylate (360 mg, 87%). ESI-MS m/z calc. 565.12, found 566.0 (M+1)+; retention time (Method A): 0.72 minutes (1 minute run).

297

Step 2: 5-[[2-Fluoro-6-[2-(trideuteriomethoxy)-4-(trifluoromethoxy)phenoxy]-3-(trifluoromethyl)benzoyl]amino]-4-methyl-pyridine-2-carboxamide (161)

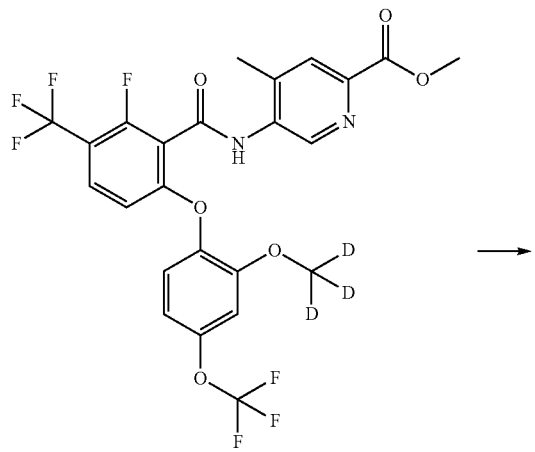

A solution of methyl 5-[[2-fluoro-6-[2-(trideuteriomethoxy)-4-(trifluoromethoxy)phenoxy]-3-(trifluoromethyl)benzoyl]amino]-4-methyl-pyridine-2-carboxylate (360 mg, 0.637 mmol) and ammonia (10 mL of 7 M in methanol, 70 mmol) was stirred at room temperature for 16 hours. The reaction was concentrated in vacuo. The crude material was purified by silica gel chromatography (0-30% ethyl acetate/dichloromethane) to provide 5-[[2-fluoro-6-[2-(trideuteriomethoxy)-4-(trifluoromethoxy)phenoxy]-3-(trifluoromethyl)benzoyl]amino]-4-methyl-pyridine-2-carboxamide (199 mg, 57%) as a white solid. ESI-MS m/z calc. 550.12, found 551.0 (M+1)+; retention time (Method C): 2.5 minutes (5 minute run). $^1$H NMR (400 MHz, DMSO-d6) δ 10.66 (s, 1H), 8.71 (s, 1H), 8.06 (s, 1H), 7.97 (s, 1H), 7.80 (t, J=8.6 Hz, 1H), 7.59 (s, 1H), 7.39 (d, J=8.7 Hz, 1H), 7.29 (d, J=2.8 Hz, 1H), 7.15-6.94 (m, 1H), 6.67 (d, J=8.8 Hz, 1H), 2.35 (s, 3H) ppm.

298

Example 32

5-[[2-Fluoro-6-[2-(trideuteriomethoxy)-4-(trifluoromethoxy)phenoxy]-3-(trifluoromethyl)benzoyl]amino]-6-methyl-pyridine-2-carboxamide (188)

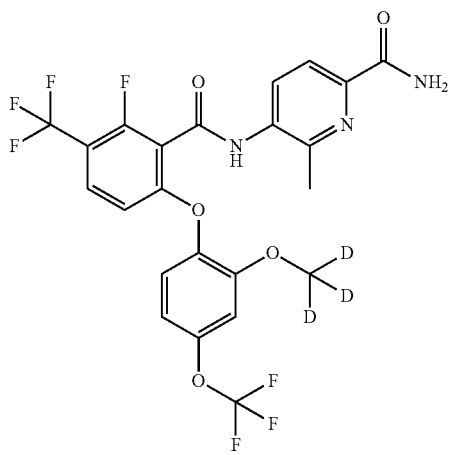 [SMILES: [2H]C([2H])([2H])Oc1cc(OC(F)(F)F)ccc1Oc1ccc(C(F)(F)F)c(F)c1C(=O)Nc1ccc(C(N)=O)nc1C]

Step 1: N-(6-Bromo-2-methyl-3-pyridyl)-2-fluoro-6-[2-(trideuteriomethoxy)-4-(trifluoromethoxy)phenoxy]-3-(trifluoromethyl)benzamide

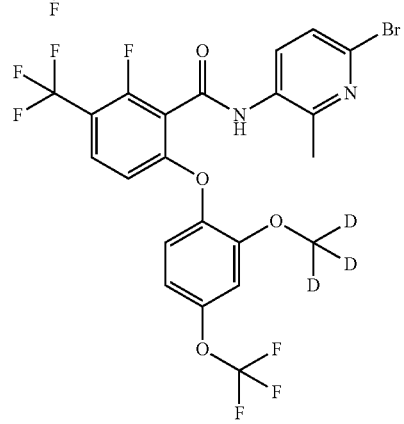

To a stirring solution of 2-fluoro-6-[2-(trideuteriomethoxy)-4-(trifluoromethoxy)phenoxy]-3-(trifluoromethyl)benzoic acid (prepared as described in Example 1, Step 3, 200 mg, 0.479 mmol) in dichloromethane (4 mL) at 0° C. was added DMF (6 μL, 0.08 mmol) followed by the dropwise addition of oxalyl chloride (84 μL, 0.96 mmol). The solution was stirred for 10 minutes then removed from the ice bath and allowed to warm to room temperature over 20 minutes. The reaction was concentrated in vacuo and azeotroped with dichloromethane to afford 2-fluoro-6-[2-(trideuteriomethoxy)-4-(trifluoromethoxy)phenoxy]-3-(trifluoromethyl)benzoyl chloride as a white solid. The solid was redissolved in cold dichloromethane (2 mL) and added dropwise to a stirring solution of 6-bromo-2-methyl-pyridin-3-amine (99 mg, 0.53 mmol) in NMP (1 mL) and DIEA (250 μL, 1.44 mmol) at 0° C. The reaction was allowed to warm to room temperature and was then diluted with dichloromethane and washed with water and brine, dried over $Na_2SO_4$, filtered and concentrated in vacuo. Silica gel chromatography (0-10% methanol/dichloromethane) provided N-(6-bromo-2-methyl-3-pyridyl)-2-fluoro-6-[2-(trideuteriomethoxy)-4-(trifluoromethoxy)phenoxy]-3-(trifluoromethyl)benzamide (250 mg, 89%). ESI-MS m/z calc. 585.02, found 588.2 (M+1)+; retention time (Method B): 2.07 minutes (3 minute run). $^1$H NMR (400 MHz, DMSO-d6) δ 10.58 (s, 1H), 7.86 (d, J=8.4 Hz, 1H), 7.79 (t, J=8.7 Hz, 1H), 7.53 (d, J=8.4 Hz, 1H), 7.37 (d, J=8.8 Hz, 1H), 7.29 (d, J=2.7 Hz, 1H), 7.07 (ddd, J=8.7, 2.6, 1.3 Hz, 1H), 6.65 (d, J=8.9 Hz, 1H), 2.44 (s, 3H) ppm.

Step 2: Methyl 5-[[2-fluoro-6-[2-(trideuteriomethoxy)-4-(trifluoromethoxy)phenoxy]-3-(trifluoromethyl)benzoyl]amino]-6-methyl-pyridine-2-carboxylate

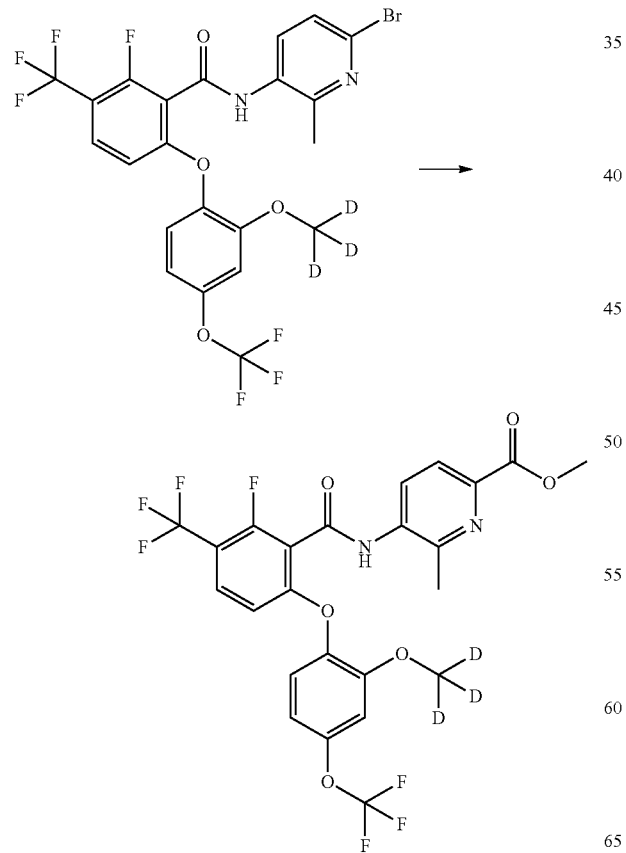

N-(6-Bromo-2-methyl-3-pyridyl)-2-fluoro-6-[2-(trideuteriomethoxy)-4-(trifluoromethoxy)phenoxy]-3-(trifluoromethyl)benzamide (230 mg, 0.392 mmol) was dissolved in methanol (8 mL) and triethylamine (115 μL, 0.825 mmol) in a pressure tube and Pd(dppf)Cl$_2$·DCM (65 mg, 0.07959 mmol) was added. Carbon monoxide was vigorously bubbled through the reaction mixture for 5 minutes. The reaction vessel was sealed and heated to 75° C. for 2 hours. The reaction was cooled to room temperature and concentrated in vacuo. Purification by silica gel chromatography (0-30% ethyl acetate/dichloromethane) provided methyl 5-[[2-fluoro-6-[2-(trideuteriomethoxy)-4-(trifluoromethoxy)phenoxy]-3-(trifluoromethyl)benzoyl]amino]-6-methyl-pyridine-2-carboxylate as a white solid. ESI-MS m/z calc. 565.11, found 566.3 (M+1)+; retention time (Method A): 0.74 minutes (1 minute run).

Step 3: 5-[[2-Fluoro-6-[2-(trideuteriomethoxy)-4-(trifluoromethoxy)phenoxy]-3-(trifluoromethyl)benzoyl]amino]-6-methyl-pyridine-2-carboxamide (188)

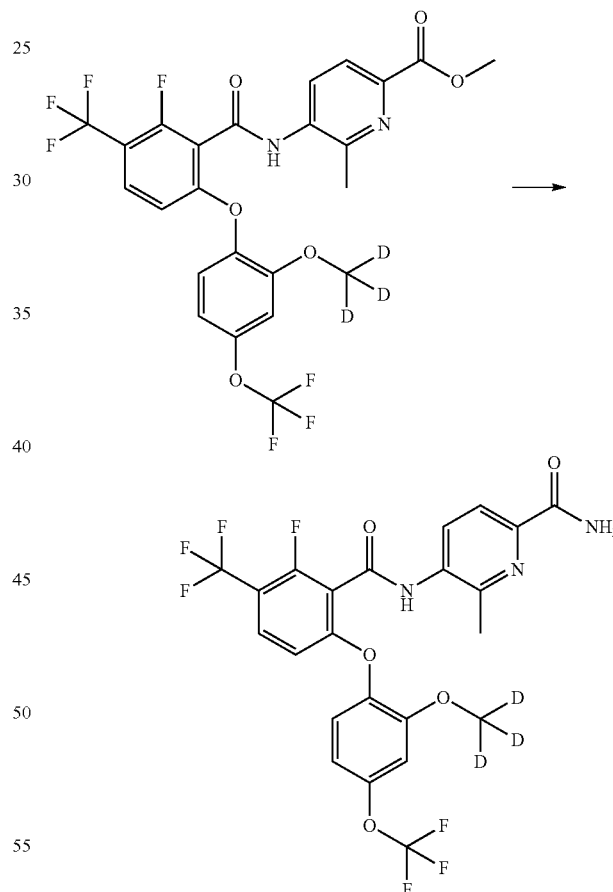

A solution of methyl 5-[[2-fluoro-6-[2-(trideuteriomethoxy)-4-(trifluoromethoxy)phenoxy]-3-(trifluoromethyl)benzoyl]amino]-6-methyl-pyridine-2-carboxylate (from Step 2) in methanol (4 mL) and ammonia (5.6 mL of 7 M in methanol, 39.2 mmol) was stirred at room temperature for 16 hours. The reaction was concentrated in vacuo and purified by silica gel chromatography (0-30% ethyl acetate/dichloromethane) to provide 5-[[2-fluoro-6-[2-(trideuteriomethoxy)-4-(trifluoromethoxy)phenoxy]-3-(trifluoromethyl)benzoyl]amino]-6-methyl-pyridine-2-carboxamide (180 mg, 83% over 2 steps). ESI-MS m/z calc. 550.12, found 551.3 (M+1)+; retention time (Method B): 1.77 minutes (3 minute run). $^1$H NMR (400 MHz, DMSO-d6) δ 10.63 (s, 1H), 8.11 (d, J=8.3 Hz, 1H), 7.96 (d, J=2.8 Hz, 1H), 7.92 (d, J=8.2 Hz, 1H), 7.80 (t, J=8.7 Hz, 1H), 7.59 (s, 1H), 7.38 (d, J=8.8 Hz, 1H), 7.29 (d, J=2.7 Hz, 1H), 7.07 (ddd, J=8.8, 2.8, 1.2 Hz, 1H), 6.66 (d, J=8.9 Hz, 1H), 2.53 (s, 3H) ppm.

Example 33

5-Fluoro-4-[[2-fluoro-6-[2-methoxy-4-(trifluoromethoxy)phenoxy]-3-(trifluoromethyl)benzoyl]amino]pyridine-2-carboxamide (123) and 5-Fluoro-4-(2-methoxy-6-(2-methoxy-4-(trifluoromethoxy)phenoxy)-3-(trifluoromethyl)benzamido)picolinamide (128)

123

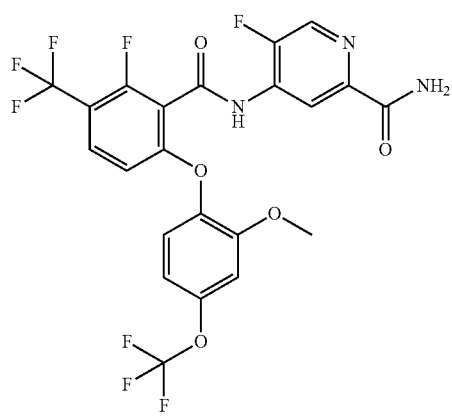

128

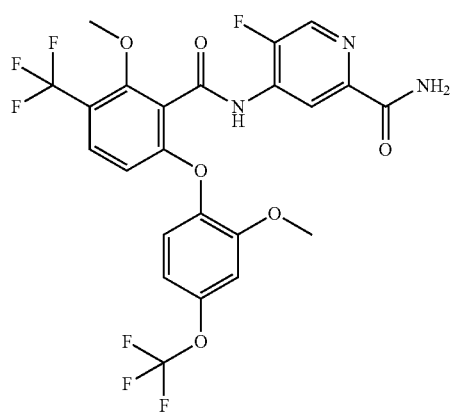

Step 1: Isopropyl 5-fluoro-4-[[2-fluoro-6-[2-methoxy-4-(trifluoromethoxy)phenoxy]-3-(trifluoromethyl)benzoyl]amino]pyridine-2-carboxylate

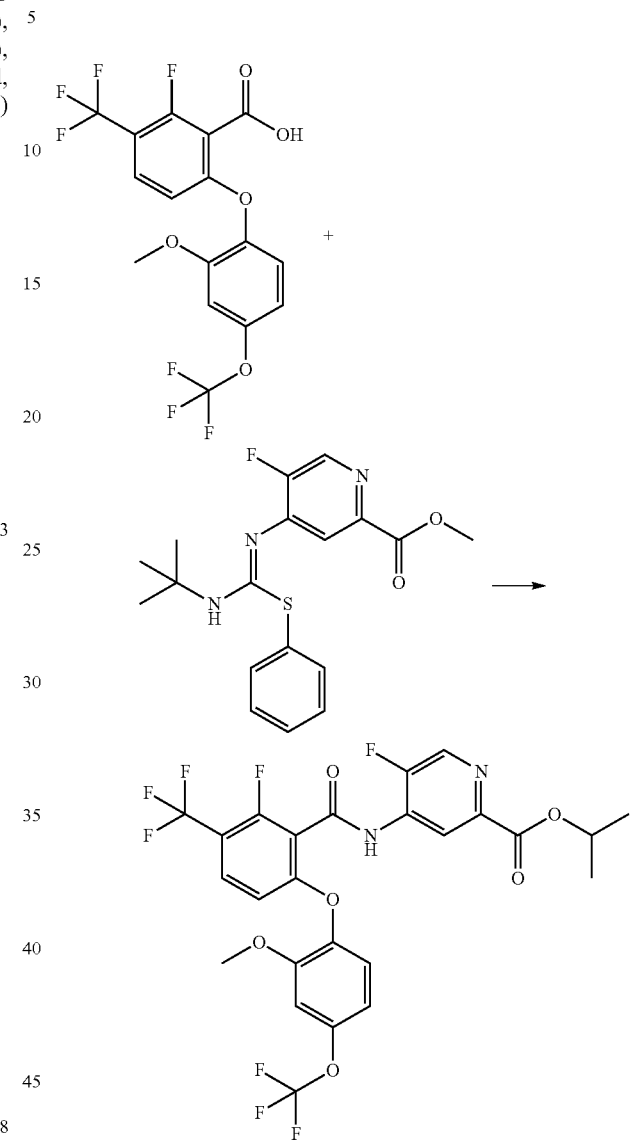

Methyl 4-[(Z)-[(tert-butylamino)-phenylsulfanyl-methylene]amino]-5-fluoro-pyridine-2-carboxylate (prepared as described in Preparation 2, 84 mg, 0.23 mmol), 2-fluoro-6-[2-methoxy-4-(trifluoromethoxy)phenoxy]-3-(trifluoromethyl)benzoic acid (prepared as described in Example 2, Step 3, 123 mg, 0.279 mmol) and tris[(Z)-1-methyl-3-oxobut-1-enoxy]iron (2 mg, 0.006 mmol) were combined in 2-propanol (1.6 mL) and heated at reflux for 7 days. The reaction mixture was concentrated in vacuo directly onto silica gel and purified by silica gel chromatography (0-80% ethyl acetate/petroleum ether) to provide isopropyl 5-fluoro-4-[[2-fluoro-6-[2-methoxy-4-(trifluoromethoxy)phenoxy]-3-(trifluoromethyl)benzoyl]amino]pyridine-2-carboxylate (42 mg, 30%). ESI-MS m/z calc. 594.10, found 595.3 (M+1)+; 593.3 (M−1)−; retention time (Method F): 1.13 minutes (1.5 minute run).

Step 2: 5-Fluoro-4-[[2-fluoro-6-[2-methoxy-4-(trifluoromethoxy)phenoxy]-3-(trifluoromethyl)benzoyl]amino]pyridine-2-carboxamide (123) and 5-Fluoro-4-(2-methoxy-6-(2-methoxy-4-(trifluoromethoxy)phenoxy)-3-(trifluoromethyl)benzamido)picolinamide (128)

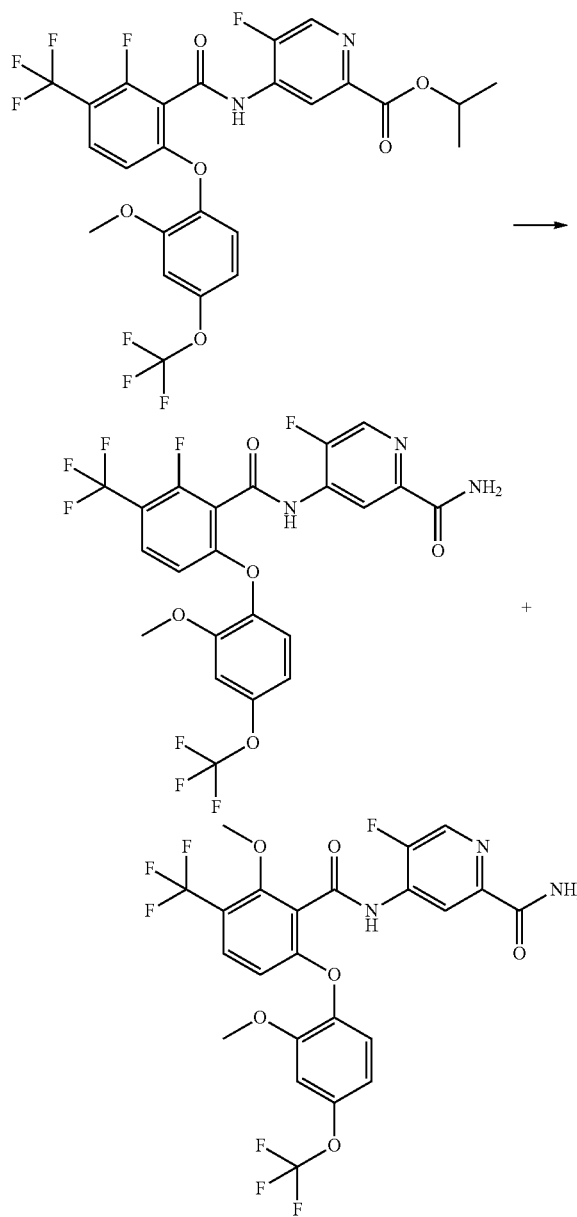

A solution of isopropyl 5-fluoro-4-[[2-fluoro-6-[2-methoxy-4-(trifluoromethoxy)phenoxy]-3-(trifluoromethyl)benzoyl]amino]pyridine-2-carboxylate (40 mg, 0.07 mmol) in ammonia (850 µL of 4 M in methanol, 3.4 mmol) was stirred at room temperature for 24 hours then at 50° C. for 24 hours. The cooled reaction mixture was filtered and purified directly by HPLC (0-100% acetonitrile/0.05% TFA) to provide 5-fluoro-4-[[2-fluoro-6-[2-methoxy-4-(trifluoromethoxy)phenoxy]-3-(trifluoromethyl)benzoyl]amino]pyridine-2-carboxamide (123, 14 mg, 35%) ESI-MS m/z calc. 551.07, found 551.8 (M+1)+; 549.9 (M−1)−; Retention time (Method E): 3.34 minutes (5 minutes run). $^1$H NMR (500 MHz, DMSO-d6) δ 11.36 (s, 1H), 8.92 (d, J=6.4 Hz, 1H), 8.63 (d, J=2.2 Hz, 1H), 8.07 (d, J=2.6 Hz, 1H), 7.80 (t, J=8.6 Hz, 1H), 7.68 (d, 1H), 7.36 (d, J=8.8 Hz, 1H), 7.25 (d, J=2.7 Hz, 1H), 7.07-7.01 (m, 1H), 6.66 (d, J=8.9 Hz, 1H), 3.80 (s, 3H) ppm and 5-fluoro-4-[[2-methoxy-6-[2-methoxy-4-(trifluoromethoxy)phenoxy]-3-(trifluoromethyl)benzoyl]amino]pyridine-2-carboxamide (128, 6 mg, 15%) ESI-MS m/z calc. 563.09, found 563.9 (M+1)+; 561.9 (M−1)−; Retention time (Method E): 3.37 minutes (5 minutes run). $^1$H NMR (500 MHz, DMSO-d$_6$) δ 11.23 (s, 1H), 8.91 (d, J=6.4 Hz, 1H), 8.62 (d, J=2.2 Hz, 1H), 8.09-8.05 (m, 1H), 7.69 (d, J=7.9 Hz, 2H), 7.33 (d, J=8.8 Hz, 1H), 7.24 (d, J=2.7 Hz, 1H), 7.04 (dd, J=9.1, 2.4 Hz, 1H), 6.53 (d, J=8.9 Hz, 1H), 3.94 (s, 3H), 3.81 (s, 3H) ppm.

Example 34

4-[[2-Fluoro-6-[2-methoxy-4-(trifluoromethoxy)phenoxy]-3-(trifluoromethyl)benzoyl]amino]-5-methyl-pyridine-2-carboxamide (120)

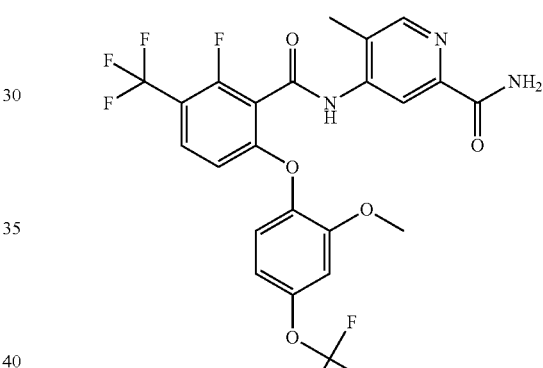

Step 1: N-(2-Bromo-5-methyl-4-pyridyl)-2-fluoro-6-[2-methoxy-4-(trifluoromethoxy)phenoxy]-3-(trifluoromethyl)benzamide

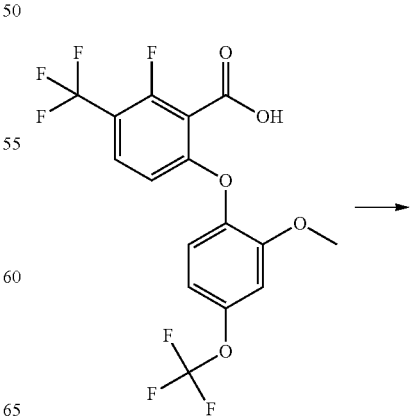

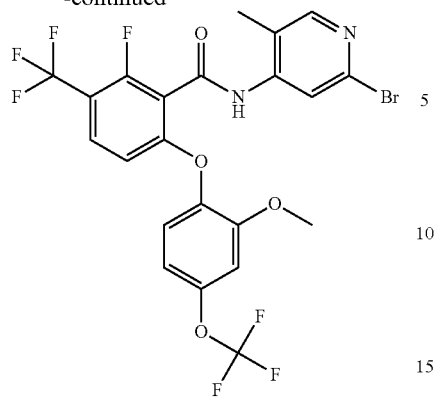

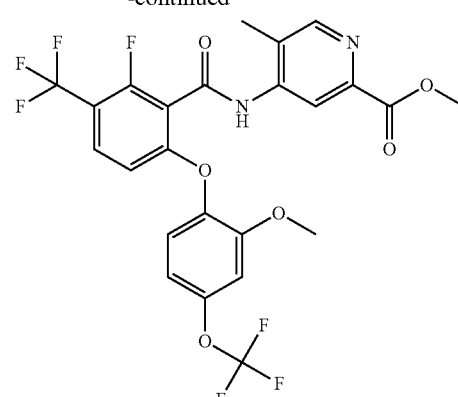

To solution of 2-fluoro-6-[2-methoxy-4-(trifluoromethoxy)phenoxy]-3-(trifluoromethyl)benzoic acid (prepared as described in Example 2, Step 3, 300 mg, 0.681 mmol) in dichloromethane (5 mL) at 0° C. was added DMF (6 μL, 0.08 mmol) and oxalyl chloride (200 μL, 2.29 mmol) dropwise. The reaction mixture was allowed to warm to room temperature over 3.5 hours then concentrated in vacuo. The residue was dissolved in dichloromethane (5 mL) and cooled to 0° C. The solution was treated with 2-bromo-5-methyl-pyridin-4-amine (165 mg, 0.882 mmol) followed by triethylamine (500 μL, 3.59 mmol). The resulting mixture was allowed to warm to room temperature and stirred for 48 hours. The reaction mixture was diluted with water (10 mL) and extracted with dichloromethane (2×10 mL). The combined organics were dried over MgSO₄, filtered and concentrated in vacuo. Silica gel chromatography (0-20% ethyl acetate/petroleum ether) provided N-(2-bromo-5-methyl-4-pyridyl)-2-fluoro-6-[2-methoxy-4-(trifluoromethoxy)phenoxy]-3-(trifluoromethyl)benzamide (217 mg, 55%) as an off-white solid. ESI-MS m/z calc. 582.00, found 585.1 (M+1)+; 583.1 (M−1)−; retention time (Method E): 1.15 minutes (5 minute run). ¹H NMR (500 MHz, CDCl₃) δ 8.61 (s, 1H), 8.15 (s, 2H), 7.60-7.57 (m, 1H), 7.23 (d, J=8.7 Hz, 1H), 6.98-6.96 (m, 1H), 6.94 (d, J=2.4 Hz, 1H), 6.53 (d, J=9.0 Hz, 1H), 3.82 (s, 3H), 2.17 (s, 3H); ¹⁹F NMR (471 MHz, CDCl₃) δ −58.01, −60.82 (d, J=13.0 Hz), −112.20 (q, J=14.3, 13.3 Hz) ppm.

Step 2: Methyl 4-[[2-fluoro-6-[2-methoxy-4-(trifluoromethoxy)phenoxy]-3-(trifluoromethyl)benzoyl]amino]-5-methyl-pyridine-2-carboxylate

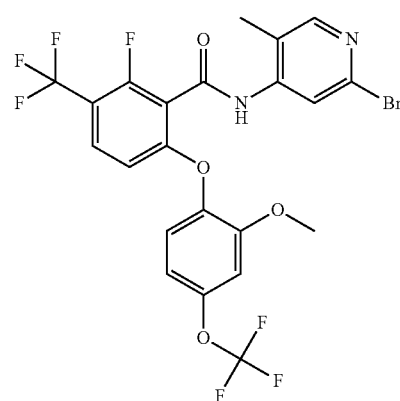

In a pressure tube N-(2-bromo-5-methyl-4-pyridyl)-2-fluoro-6-[2-methoxy-4-(trifluoromethoxy)phenoxy]-3-(trifluoromethyl)benzamide (217 mg, 0.372 mmol) was dissolved in methanol (10 mL) and triethylamine (110 μL, 0.789 mmol) and Pd(dppf)Cl₂·DCM (60 mg, 0.074 mmol) were added. Carbon monoxide was bubbled through the vigorously stirring reaction mixture for 5 minutes. The reaction vessel was sealed and heated to 75° C. for 16 hours. The reaction mixture was cooled to room temperature, filtered through a pad of Celite eluting with methanol and concentrated in vacuo. Silica gel chromatography (0-100% ethyl acetate/petroleum ether) provided methyl 4-[[2-fluoro-6-[2-methoxy-4-(trifluoromethoxy)phenoxy]-3-(trifluoromethyl)benzoyl]amino]-5-methyl-pyridine-2-carboxylate (178.6 mg, 85%). ESI-MS m/z calc. 562.10, found 563.2 (M+1)+; 561.2 (M−1)−; retention time (Method F): 1.04 minutes (1.5 minute run). ¹H NMR (500 MHz, CDCl₃) δ 9.06 (s, 1H), 8.54 (s, 1H), 8.20 (s, 1H), 7.59 (d, J=17.0 Hz, 1H), 7.24 (d, J=8.7 Hz, 1H), 6.98-6.96 (m, 1H), 6.94-6.93 (m, 1H), 6.55 (d, J=9.4 Hz, 1H), 4.03 (s, 3H), 3.83 (s, 3H), 2.30 (s, 3H) ppm. ¹⁹F NMR (471 MHz, CDCl₃) δ −58.01, −60.82 (d, J=12.9 Hz), −112.16--112.24 (m) ppm.

Step 3: 4-[[2-Fluoro-6-[2-methoxy-4-(trifluoromethoxy)phenoxy]-3-(trifluoromethyl)benzoyl]amino]-5-methyl-pyridine-2-carboxamide (120)

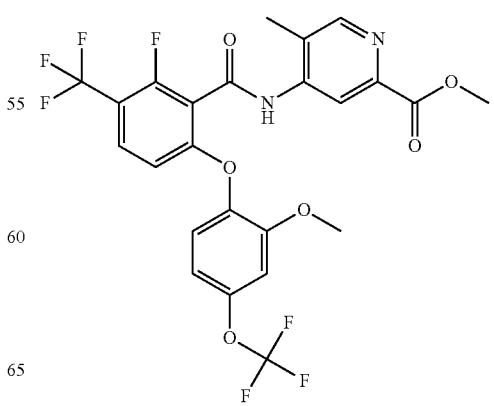

307

-continued

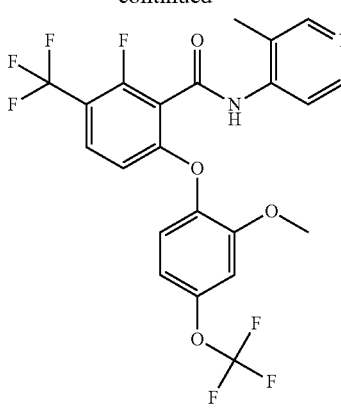

A mixture of methyl 4-[[2-fluoro-6-[2-methoxy-4-(trifluoromethoxy)phenoxy]-3-(trifluoromethyl)benzoyl]amino]-5-methyl-pyridine-2-carboxylate (178 mg, 0.317 mmol) and ammonia (5 mL of 7 M in methanol, 35 mmol) was stirred at room temperature for 16 hours. SPM32 silica metal scavenger (150 mg) was added and the reaction was stirred for 15 minutes. The mixture was filtered and the filtrate was concentrated in vacuo. Silica gel chromatography (0-100% ethyl acetate/petroleum ether) provided 4-[[2-fluoro-6-[2-methoxy-4-(trifluoromethoxy)phenoxy]-3-(trifluoromethyl)benzoyl]amino]-5-methyl-pyridine-2-carboxamide (54.5 mg, 31%) as a white solid. ESI-MS m/z calc. 547.10, found 548.1 (M+1)+; 546.0 (M−1)−; retention time (Method E): 3.32 minutes (5 minute run). $^1$H NMR (500 MHz, DMSO-d6) δ 10.58 (s, 1H), 8.49-8.48 (m, 2H), 8.06 (d, J=2.9 Hz, 1H), 7.81 (t, J=8.6 Hz, 1H), 7.61-7.60 (m, 1H), 7.39 (d, J=8.8 Hz, 1H), 7.29 (d, J=2.7 Hz, 1H), 7.09-7.06 (m, 1H), 6.66 (d, J=8.9 Hz, 1H), 3.82 (s, 3H), 2.33 (s, 3H) ppm. $^{19}$F NMR (471 MHz, DMSO-d6) δ −56.85, −59.11 (d, J=12.2 Hz), −117.84 (q, J=12.5 Hz) ppm.

Example 35

5-Chloro-4-[[2-fluoro-6-[2-methoxy-4-(trifluoromethoxy)phenoxy]-3-(trifluoromethyl)benzoyl]amino]pyridine-2-carboxamide (152)

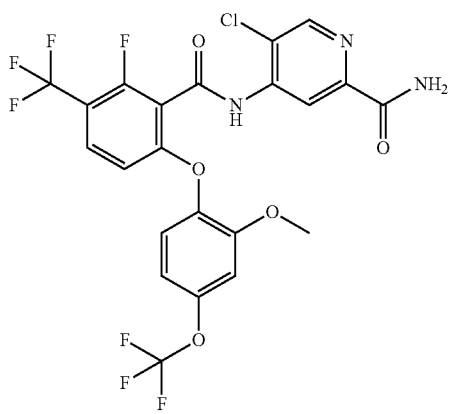

308

Step 1: N-(2,5-Dichloro-4-pyridyl)-2-fluoro-6-[2-methoxy-4-(trifluoromethoxy)phenoxy]-3-(trifluoromethyl)benzamide

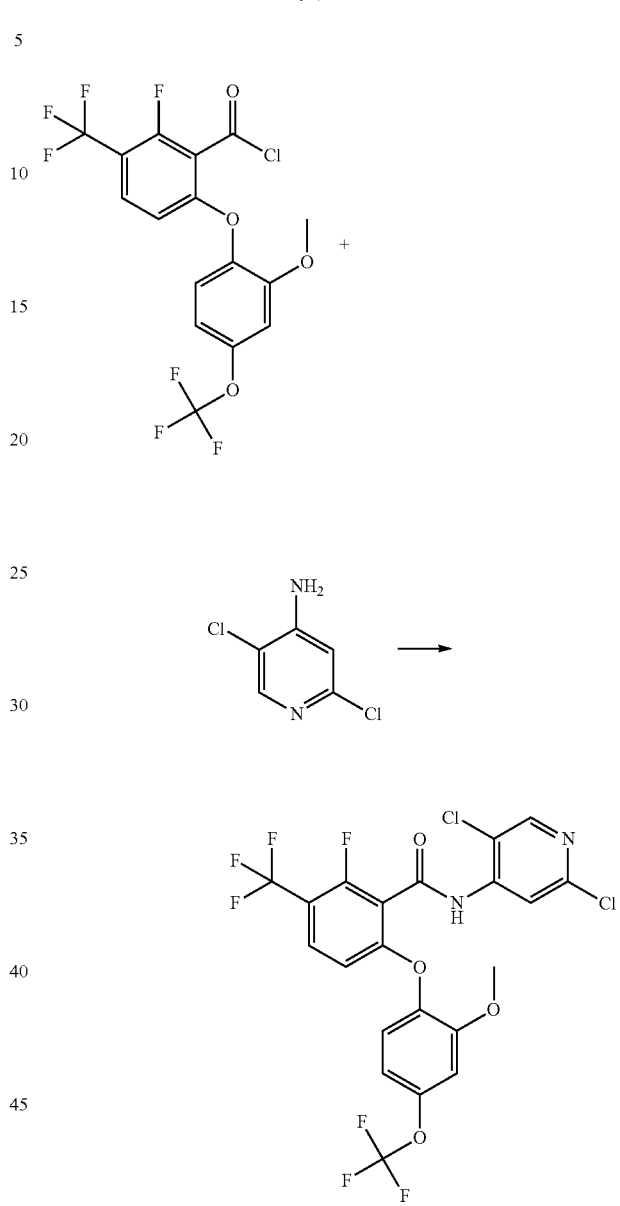

NaH (90 mg, 2.3 mmol) was added to 2,5-dichloropyridin-4-amine (125 mg, 0.767 mmol) in DMF (1.5 mL) at 0° C. and was stirred for 10 minutes. A solution of 2-fluoro-6-[2-methoxy-4-(trifluoromethoxy)phenoxy]-3-(trifluoromethyl)benzoyl chloride (prepared as described in Example 2, Step 4, 365 mg, 0.844 mmol) in DMF (1.5 mL) was then added dropwise and warmed to room temperature and stirred for 16 hours. The reaction was quenched with saturated aqueous NH$_4$Cl and diluted with ethyl acetate. The organic layer was separated and washed with brine (3×), dried over MgSO$_4$, filtered and concentrated in vacuo to afford a light brown oil. Silica gel chromatography (0-40% ethyl acetate/petroleum ether) afforded N-(2,5-dichloro-4-pyridyl)-2-fluoro-6-[2-methoxy-4-(trifluoromethoxy)phenoxy]-3-(trifluoromethyl)benzamide (190 mg, 44%). ESI-MS m/z calc. 558.00, found 558.8 (M+1)+; 556.8 (M−1)−; retention time (Method F): 1.18 minutes (1.5 minute run).

309

Step 2: Methyl 5-chloro-4-[[2-fluoro-6-[2-methoxy-4-(trifluoromethoxy)phenoxy]-3-(trifluoromethyl)benzoyl]amino]pyridine-2-carboxylate

310

Step 3: 5-Chloro-4-[[2-fluoro-6-[2-methoxy-4-(trifluoromethoxy)phenoxy]-3-(trifluoromethyl)benzoyl]amino]pyridine-2-carboxamide (152)

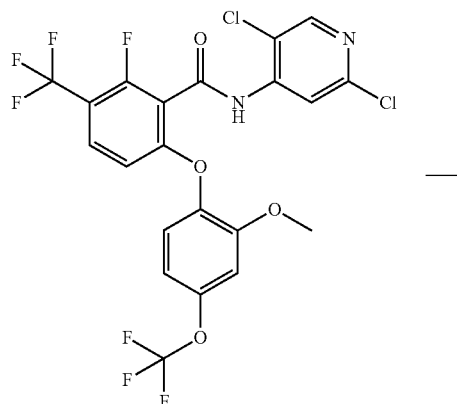

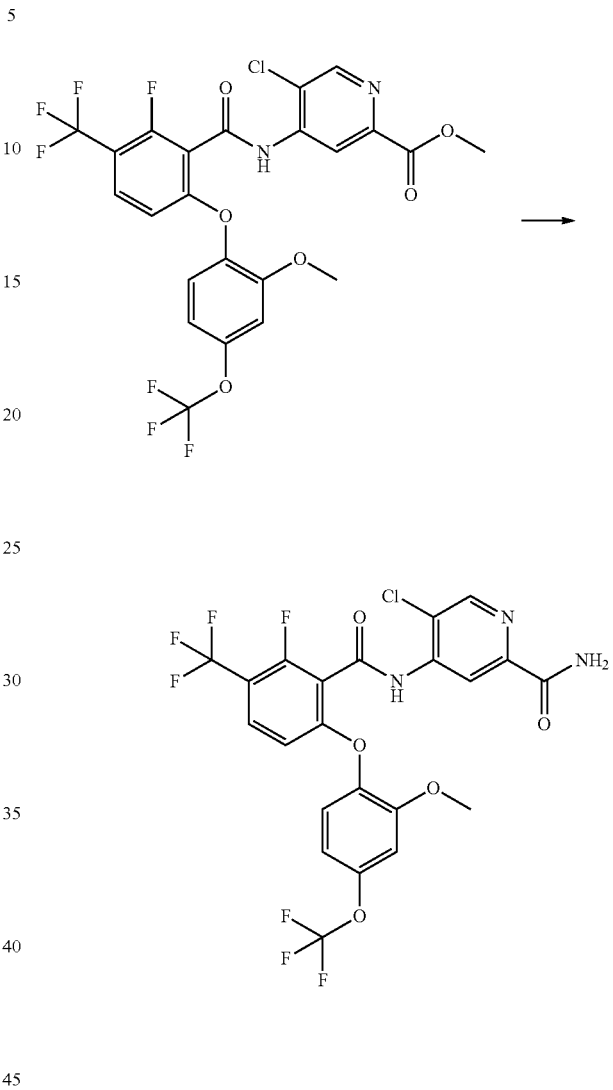

A mixture of N-(2,5-dichloro-4-pyridyl)-2-fluoro-6-[2-methoxy-4-(trifluoromethoxy)phenoxy]-3-(trifluoromethyl)benzamide (190.0 mg, 0.3398 mmol), Pd(dppf)Cl$_2$·DCM (27 mg, 0.033 mmol) and triethylamine (100 µL, 0.718 mmol) in DMF (2.2 mL)/methanol (1.1 mL) was bubbled with excess carbon monoxide in a pressure vessel. The vessel was sealed and heated to 80° C. for 24 hours. The reaction mixture was filtered, concentrated in vacuo and the crude methyl 5-chloro-4-[[2-fluoro-6-[2-methoxy-4-(trifluoromethoxy)phenoxy]-3-(trifluoromethyl)benzoyl]amino]pyridine-2-carboxylate was used directly in the next step. ESI-MS m/z calc. 582.81, found 583.2 (M+1)+; retention time (Method F): 1.10 minutes (1.5 minute run).

A solution of crude methyl 5-chloro-4-[[2-fluoro-6-[2-methoxy-4-(trifluoromethoxy)phenoxy]-3-(trifluoromethyl)benzoyl]amino]pyridine-2-carboxylate (198.0 mg, 0.3398 mmol) from Step 2 in ammonia (2.5 mL of 7 M in methanol, 17.5 mmol) was stirred at room temperature for 24 hours. The reaction mixture was reduced in volume in vacuo, filtered (0.45 µM PTFE syringe filter) and purified by HPLC (10-95% acetonitrile/0.05% TFA) to provide 5-chloro-4-[[2-fluoro-6-[2-methoxy-4-(trifluoromethoxy)phenoxy]-3-(trifluoromethyl)benzoyl]amino]pyridine-2-carboxamide (103 mg, 53%). ESI-MS m/z calc. 567.04, found 568.2 (M+1)+; 566.1 (M−1)−; retention time (Method E): 3.62 minutes (5 minute run). $^1$H NMR (400 MHz, DMSO-d6) δ 10.94 (s, 1H), 8.77 (s, 1H), 8.70 (s, 1H), 8.14 (d, J=2.5 Hz, 1H), 7.87-7.71 (m, 2H), 7.39 (d, J=8.8 Hz, 1H), 7.27 (d, J=2.7 Hz, 1H), 7.05 (ddd, J=8.8, 2.7, 1.2 Hz, 1H), 6.65 (d, J=8.9 Hz, 1H), 3.80 (s, 3H) ppm.

Example 36

4-[[2-Fluoro-6-[2-methoxy-4-(trifluoromethoxy) phenoxy]-3-(trifluoromethyl)benzoyl]amino]pyrimidine-2-carboxamide (207)

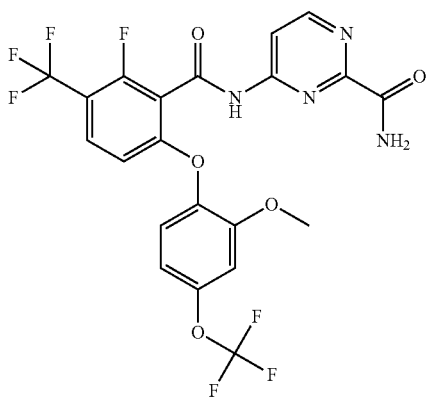 [SMILES: COc1cc(OC(F)(F)F)ccc1Oc1ccc(C(F)(F)F)c(F)c1C(=O)Nc1ccnc(C(N)=O)n1]

Step 1: Methyl 4-[[2-fluoro-6-[2-methoxy-4-(trifluoromethoxy)phenoxy]-3-(trifluoromethyl)benzoyl]amino]pyrimidine-2-carboxylate

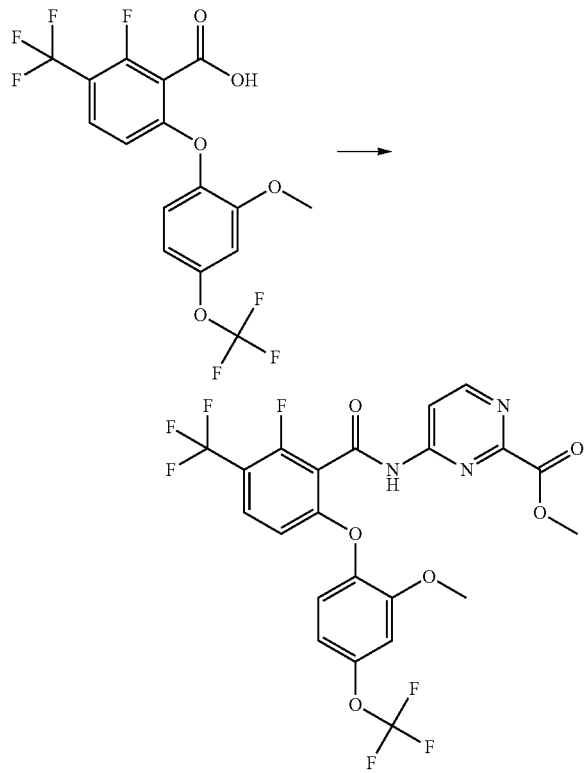

To a solution of 2-fluoro-6-[2-methoxy-4-(trifluoromethoxy)phenoxy]-3-(trifluoromethyl)benzoic acid (prepared as described in Example 2, Step 3, 150 mg, 0.362 mmol) in dichloromethane (2 mL) at 0° C. was added DMF (3 μL, 0.04 mmol) and oxalyl chloride (95 μL, 1.09 mmol) dropwise. The reaction was stirred for 2 hours then concentrated in vacuo to afford the acid chloride as a pale yellow oil. The oil was dissolved in dichloromethane (2 mL) and added dropwise to a stirring solution of methyl 4-aminopyrimidine-2-carboxylate (61 mg, 0.40 mmol) and triethylamine (300 μL, 2.15 mmol) in dichloromethane at 0° C. (3 mL). The resulting mixture was allowed to warm to room temperature and stirred for 16 hours. The reaction was concentrated in vacuo and purified by HPLC (37-100% acetonitrile/ 0.1% ammonium hydroxide) to provide methyl 4-[[2-fluoro-6-[2-methoxy-4-(trifluoromethoxy)phenoxy]-3-(trifluoromethyl)benzoyl]amino]pyrimidine-2-carboxylate (10 mg, 5%). ESI-MS m/z calc. 549.08, found 550.0 (M+1)+; 547.9 (M−1)−; retention time (Method F): 1.04 minutes (1.5 minute run). $^1$H NMR (400 MHz, CD$_3$OD) δ 8.86 (dd, J=5.7, 1.8 Hz, 1H), 8.48 (s, 1H), 7.72 (t, J=8.4 Hz, 1H), 7.33 (dd, J=8.9, 1.9 Hz, 1H), 7.11 (d, J=2.5 Hz, 1H), 7.01-6.93 (m, 1H), 6.68 (d, J=8.8 Hz, 1H), 4.00 (d, J=1.8 Hz, 3H), 3.84 (d, J=1.8 Hz, 4H) ppm.

Step 2: 4-[[2-Fluoro-6-[2-methoxy-4-(trifluoromethoxy)phenoxy]-3-(trifluoromethyl)benzoyl]amino]pyrimidine-2-carboxamide (207)

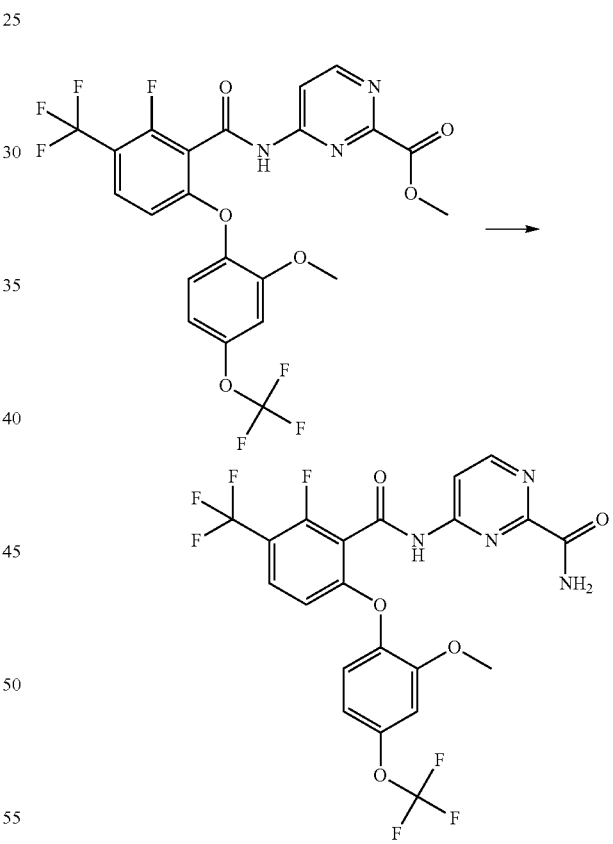

Methyl 4-[[2-fluoro-6-[2-methoxy-4-(trifluoromethoxy)phenoxy]-3-(trifluoromethyl)benzoyl]amino]pyrimidine-2-carboxylate (15 mg, 0.027 mmol) was dissolved in ammonia (1 mL of 7 M in methanol, 7 mmol) and stirred at room temperature for 3 hours. The reaction mixture was concentrated in vacuo, dissolved in DMSO, and purified by HPLC (37-100% acetonitrile/0.1% ammonium hydroxide) to provide 4-[[2-fluoro-6-[2-methoxy-4-(trifluoromethoxy)phenoxy]-3-(trifluoromethyl)benzoyl]amino]pyrimidine-2-carboxamide (3.8 mg, 26%) as a white solid. ESI-MS m/z calc.

534.08, found 534.96 (M+1)+; 532.86 (M−1)−; retention time (Method E): 3.18 minutes (5 minute run). ¹H NMR (400 MHz, MeOD) δ 8.74 (dd, J=5.8, 2.7 Hz, 1H), 8.32 (d, J=5.5 Hz, 1H), 7.60 (td, J=8.6, 2.6 Hz, 1H), 7.21 (dd, J=8.8, 2.7 Hz, 1H), 6.99 (d, J=2.8 Hz, 1H), 6.85 (ddt, J=9.2, 3.0, 1.5 Hz, 1H), 6.56 (dd, J=8.9, 2.5 Hz, 1H), 3.71 (d, J=2.6 Hz, 3H) ppm.

Example 37

6-[[2-Fluoro-6-[2-methoxy-4-(trifluoromethoxy)phenoxy]-3-(trifluoromethyl)benzoyl]amino]pyridine-2-carboxamide (169)

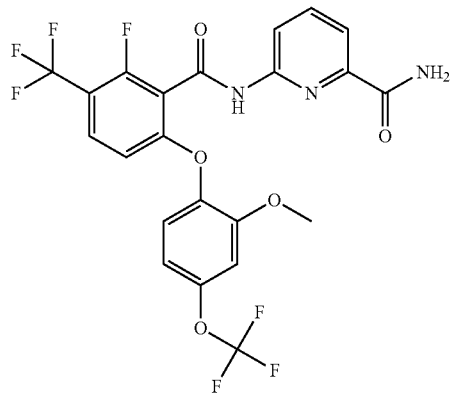

Step 1: Methyl 6-[[2-fluoro-6-[2-methoxy-4-(trifluoromethoxy)phenoxy]-3-(trifluoromethyl)benzoyl]amino]pyridine-2-carboxylate

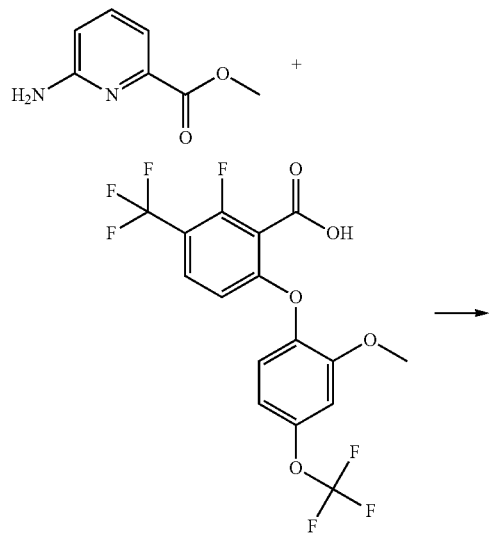

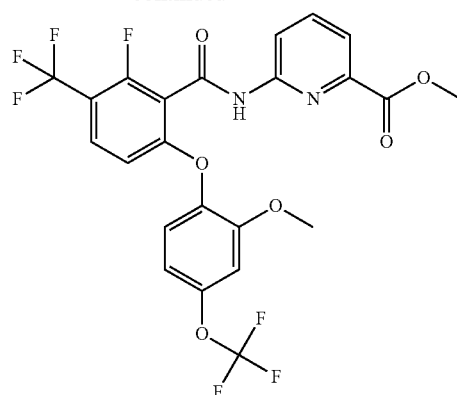

To a solution of 2-fluoro-6-[2-methoxy-4-(trifluoromethoxy)phenoxy]-3-(trifluoromethyl)benzoic acid (prepared as described in Example 2, Step 3, 100 mg, 0.241 mmol) in dichloromethane (2 mL) at 0° C. was added DMF (10 μL, 0.13 mmol) and oxalyl chloride (70 μL, 0.8024 mmol) dropwise. The reaction mixture was stirred for 2 hours then concentrated in vacuo to afford the acid chloride as a pale yellow oil. The oil was dissolved in dichloromethane (2 mL) and added dropwise to a solution of methyl 6-aminopyridine-2-carboxylate (37 mg, 0.24 mmol) and triethylamine (210 μL, 1.51 mmol) in dichloromethane (2 mL) at 0° C. The resulting mixture was allowed to warm to room temperature and stirred for 16 hours. The reaction mixture was concentrated in vacuo and purified by silica gel chromatography (0-50% ethyl acetate/petroleum ether) to provide methyl 6-[[2-fluoro-6-[2-methoxy-4-(trifluoromethoxy)phenoxy]-3-(trifluoromethyl)benzoyl]amino]pyridine-2-carboxylate (40 mg, 30%). ESI-MS m/z calc. 548.08, found 549.0 (M+1)+; 547.0 (M−1)−; retention time (Method F): 1.1 minutes (1.5 minute run). ¹H NMR (400 MHz, CDCl₃) δ 9.16 (s, 1H), 8.63 (dd, J=7.1, 2.2 Hz, 1H), 7.98-7.88 (m, 2H), 7.60-7.51 (m, 1H), 7.29-7.22 (m, 1H), 6.95-6.85 (m, 2H), 6.59 (d, J=9.0 Hz, 1H), 3.97 (d, J=12.0 Hz, 6H) ppm.

Step 2: 6-[[2-Fluoro-6-[2-methoxy-4-(trifluoromethoxy)phenoxy]-3-(trifluoromethyl)benzoyl]amino]pyridine-2-carboxamide (169)

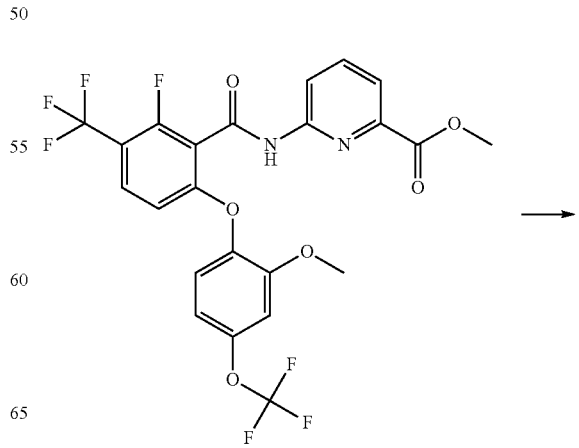

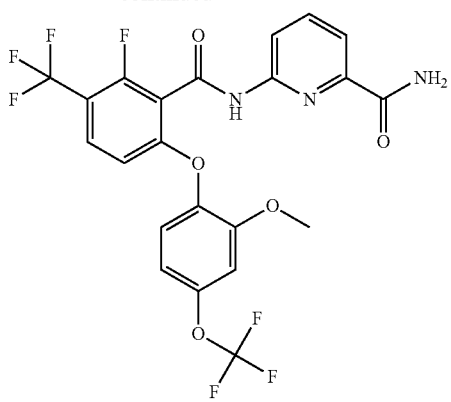 [SMILES: COc1cc(OC(F)(F)F)ccc1Oc1ccc(C(F)(F)F)c(F)c1C(=O)Nc1cccc(C(N)=O)n1]

Methyl 6-[[2-fluoro-6-[2-methoxy-4-(trifluoromethoxy)phenoxy]-3-(trifluoromethyl)benzoyl]amino]pyridine-2-carboxylate (40 mg, 0.073 mmol) was dissolved in ammonia (2 mL of 7 M in methanol, 14 mmol) and stirred at 45° C. temperature in a sealed tube for 16 hours. The reaction was concentrated in vacuo, dissolved in DMSO (1 mL) and purified by HPLC (29-100% acetonitrile/0.1% ammonium hydroxide) to provide 6-[[2-fluoro-6-[2-methoxy-4-(trifluoromethoxy)phenoxy]-3-(trifluoromethyl)benzoyl]amino]pyridine-2-carboxamide (9 mg, 22%) as an off-white solid. ESI-MS m/z calc. 533.08, found 534.31 (M+1)+; retention time (Method E): 3.32 minutes (5 minute run). $^1$H NMR (400 MHz, CD$_3$OD) δ 8.48 (d, J=8.3 Hz, 1H), 8.03 (t, J=7.9 Hz, 1H), 7.92 (dd, J=7.6, 0.9 Hz, 1H), 7.70 (t, J=8.5 Hz, 1H), 7.32 (d, J=8.8 Hz, 1H), 7.10 (d, J=2.6 Hz, 1H), 6.96 (ddd, J=8.9, 2.8, 1.3 Hz, 1H), 6.67 (d, J=8.9 Hz, 1H), 3.82 (s, 3H), 3.33 (p, J=1.6 Hz, 2H) ppm.

Example 38

4-[[3-Chloro-2-fluoro-6-[2-methoxy-4-(trifluoromethoxy)phenoxy]benzoyl]amino]-5-methyl-pyridine-2-carboxamide (189)

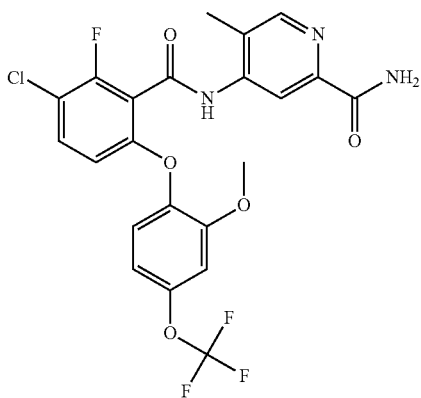

Step 1: N-(2-bromo-5-methyl-4-pyridyl)-3-chloro-2-fluoro-6-[2-methoxy-4-(trifluoromethoxy)phenoxy]benzamide

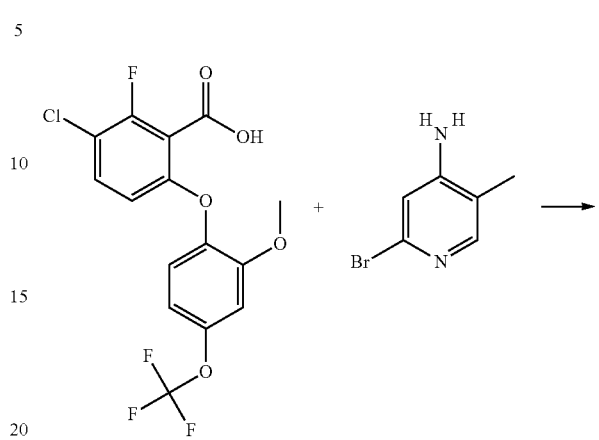

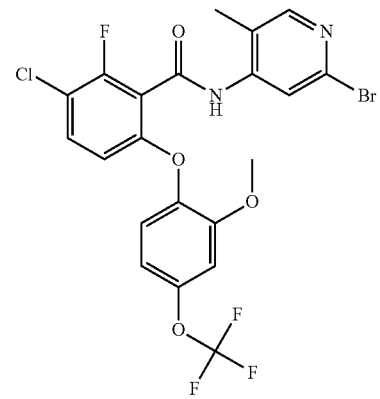

To a solution of 3-chloro-2-fluoro-6-[2-methoxy-4-(trifluoromethoxy)phenoxy]benzoic acid (prepared as described in Example 5, Step 2, 300 mg, 0.788 mmol) in dichloromethane (5 mL) at 0° C. was added DMF (7 μL, 0.08 mmol) and oxalyl chloride (235 μL, 2.69 mmol) dropwise. The reaction was allowed to warm to room temperature over 3 hours and then concentrated in vacuo. The residue was dissolved in dichloromethane (5 mL), cooled to 0° C. and treated with 2-bromo-5-methyl-pyridin-4-amine (221 mg, 1.18 mmol) followed by triethylamine (980 μL, 7.03 mmol). The resulting mixture was stirred and warmed to ambient temperature over 16 hours. The reaction mixture was diluted with water (10 mL) and extracted with dichloromethane (2×10 mL). The combined organics were dried over MgSO$_4$, filtered and concentrated in vacuo. Silica gel chromatography (0-60% ethyl acetate/petroleum ether) provided N-(2-bromo-5-methyl-4-pyridyl)-3-chloro-2-fluoro-6-[2-methoxy-4-(trifluoromethoxy)phenoxy]benzamide (140 mg, 32%). ESI-MS m/z calc. 547.98, found 551.0 (M+1)+; retention time (Method F): 1.12 minutes (1.5 minute run).

Step 2: Methyl 4-[[3-chloro-2-fluoro-6-[2-methoxy-4-(trifluoromethoxy)phenoxy]benzoyl]amino]-5-methyl-pyridine-2-carboxylate

Step 3: 4-[[3-Chloro-2-fluoro-6-[2-methoxy-4-(trifluoromethoxy)phenoxy]benzoyl]amino]-5-methyl-pyridine-2-carboxamide (189)

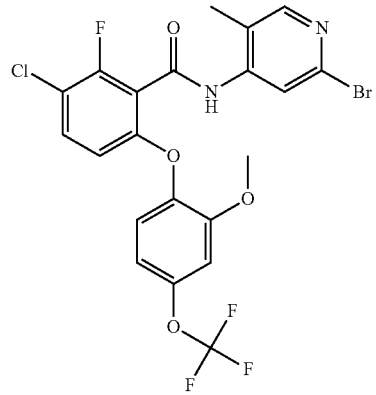

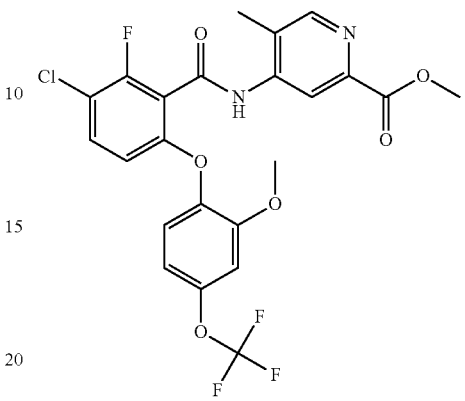

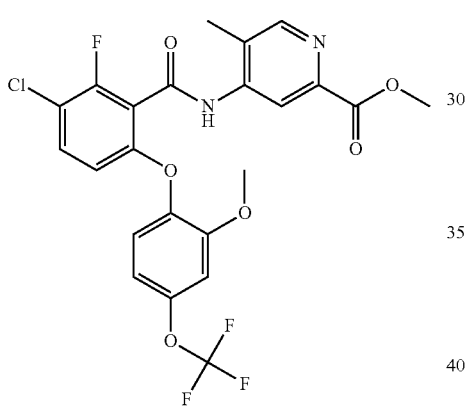

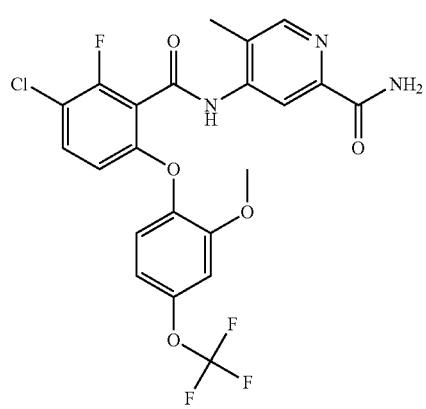 [SMILES: COc1cc(OC(F)(F)F)ccc1Oc1ccc(Cl)c(F)c1C(=O)Nc1cc(C(N)=O)ncc1C]

N-(2-Bromo-5-methyl-4-pyridyl)-3-chloro-2-fluoro-6-[2-methoxy-4-(trifluoromethoxy)phenoxy]benzamide (140 mg, 0.255 mmol) was dissolved in methanol (2.5 mL) and triethylamine (81 µL, 0.58 mmol), and Pd(dppf)Cl$_2$·DCM (43 mg, 0.053 mmol) was added. Carbon monoxide was bubbled through the vigorously stirring reaction mixture for 5 minutes. The reaction mixture was then heated at 75° C. under carbon monoxide atmosphere for 16 hours. The reaction was cooled to room temperature, filtered through a pad of Celite eluting with methanol and concentrated in vacuo. Silica gel chromatography (30-80% ethyl acetate/petroleum ether) provided methyl 4-[[3-chloro-2-fluoro-6-[2-methoxy-4-(trifluoromethoxy)phenoxy]benzoyl]amino]-5-methyl-pyridine-2-carboxylate (100 mg, 74%). ESI-MS m/z calc. 528.07, found 529.0 (M+1)+; retention time (Method F): 1.02 minutes (0.5 minute run).

Methyl 4-[[3-chloro-2-fluoro-6-[2-methoxy-4-(trifluoromethoxy)phenoxy]benzoyl]amino]-5-methyl-pyridine-2-carboxylate (100 mg, 0.189 mmol) and ammonia (3 mL of 7 M, 21 mmol) were stirred at room temperature under N$_2$ atmosphere for 16 hours. Additional ammonia (3 mL of 7 M in methanol, 21 mmol) was added and the reaction was stirred for 24 hours. The reaction mixture was concentrated in vacuo and purified by silica gel chromatography (0-100% ethyl acetate/petroleum ether) to provide 4-[[3-chloro-2-fluoro-6-[2-methoxy-4-(trifluoromethoxy)phenoxy]benzoyl]amino]-5-methyl-pyridine-2-carboxamide (34 mg, 35%) as a white solid. ESI-MS m/z calc. 513.07, found 514.0 (M+1)+; retention time: 3.33 minutes (5 minute run). $^1$H NMR (400 MHz, DMSO-d6) δ 10.50 (s, 1H), 8.47 (s, 2H), 8.09-8.04 (m, 1H), 7.67-7.58 (m, 2H), 7.30 (d, J=8.8 Hz, 1H), 7.23 (d, J=2.8 Hz, 1H), 7.06-6.98 (m, 1H), 6.62 (d, J=9.0 Hz, 1H), 3.81 (s, 3H), 2.31 (s, 3H) ppm.

Example 39

N-(5-Carbamoyl-2-deuterio-4-fluoro-phenyl)-2-fluoro-6-[2,3,6-trideuterio-4-(trifluoromethoxy)phenoxy]-3-(trifluoromethyl)benzamide (213)

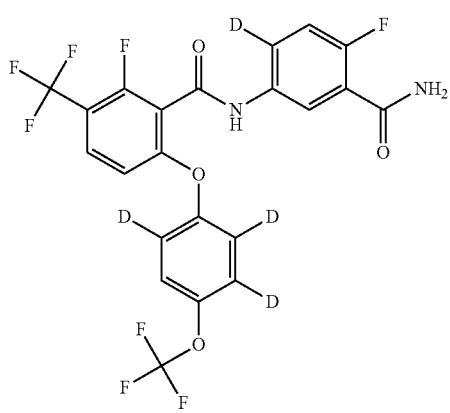 [SMILES: [2H]c1cc(F)c(C(N)=O)cc1NC(=O)c1c(Oc2c([2H])cc(OC(F)(F)F)c([2H])c2[2H])ccc(C(F)(F)F)c1F]

Step 1: 2,3,6-Tribromo-4-(trifluoromethoxy)phenol

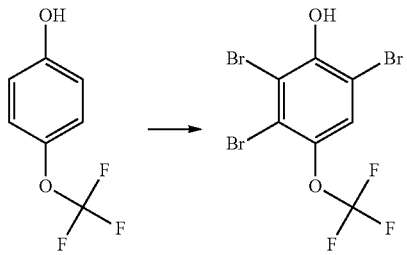 [SMILES: Oc1ccc(OC(F)(F)F)cc1 ; Oc1c(Br)cc(OC(F)(F)F)c(Br)c1Br]

A stirring mixture of 4-(trifluoromethoxy)phenol (2.0 g, 11 mmol) and Fe (44 mg, 0.79 mmol) in $CHCl_3$ (20 mL) was slowly treated with $Br_2$ (2.3 mL, 44.64 mmol) (exothermic, strong gas evolution). The deep red mixture was stirred for 16 hours at room temperature. The mixture was diluted with dichloromethane and water, and treated with solid sodium bisulfite until the color had changed from orange to almost colorless. The phases were separated and the organic phase was washed twice with water. The aqueous phase was extracted with dichloromethane and the combined organic phases were dried over $MgSO_4$, filtered and concentrated in vacuo. The solid was crystallized from heptane to provide 2,3,6-tribromo-4-(trifluoromethoxy)phenol (3.3 g, 70%). $^1$H NMR (400 MHz, DMSO-d6) δ 10.80 (s, 1H), 7.86 (q, J=1.1 Hz, 1H) ppm.

Step 2: 2,3,6-Trideuterio-4-(trifluoromethoxy)phenol

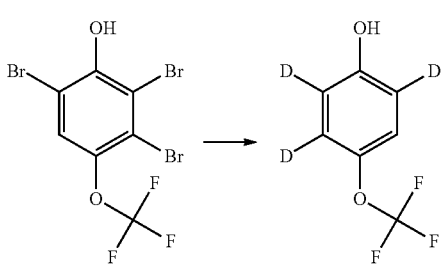 [SMILES: Oc1c(Br)cc(OC(F)(F)F)c(Br)c1Br ; [2H]c1cc(OC(F)(F)F)c([2H])c([2H])c1O]

2,3,6-Tribromo-4-(trifluoromethoxy)phenol (250 mg, 0.603 mmol) was added to a round bottom flask and evaporated with methanol-d4 (3×3 mL). The flask was charged with dry 10% Pd/C (130 mg, 0.061 mmol) under N2 atmosphere, followed by methanol-d4 (5 mL) and triethylamine (336 µL, 2.411 mmol). The flask was flushed with deuterium gas and the reaction was stirred vigorously under deuterium atmosphere for 90 minutes. The reaction mixture was filtered (fritted funnel, followed 0.4 micron syringe filter) then diluted with diethyl ether and washed with 0.5 M HCl (2×5 mL) and brine. The ether layer was dried over $MgSO_4$, filtered, and carefully concentrated in vacuo to provide 2,3,6-trideuterio-4-(trifluoromethoxy)phenol (109 mg, 100%). $^1$H NMR (400 MHz, DMSO-d6) δ 9.75 (s, 1H), 7.19-7.10 (m, 1H) ppm.

Step 3: 2-Fluoro-6-[2,3,6-trideuterio-4-(trifluoromethoxy)phenoxy]-3-(trifluoromethyl)benzoic acid

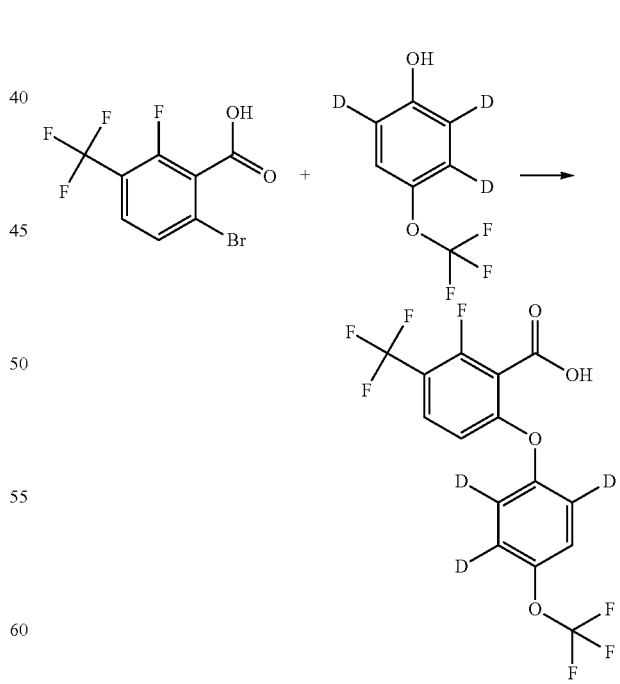

6-Bromo-2-fluoro-3-(trifluoromethyl)benzoic acid (3.27 g, 11.4 mmol) in a 100-mL round bottom flask was evaporated sequentially with methanol-d4 (4×2 mL) and benzene-d6 (2 mL). Anhydrous cesium carbonate (4.0 g, 12 mmol)

was added and the mixture was stored under high vacuum for 16 hours. The flask was repressurized under N₂, and a solution of 2,3,6-trideuterio-4-(trifluoromethoxy)phenol (2.07 g, 11.4 mmol) in benzene-d6 (50 mL) was added. The solution was bubbled with N₂ for 10 minutes then treated with copper (I) iodide (415 mg, 2.18 mmol). The flask was flushed with N₂ and heated at 75° C. for 2.5 hours. The reaction mixture was cooled to room temperature then diluted with D₂O (~10 mL). The mixture was stirred for 10 minutes, then further diluted with ether and acidified with cold 1 M HCl. The ether layer was separated, washed with brine, dried over MgSO₄, filtered and concentrated. Purification using silica gel chromatography (0-5% methanol/dichloromethane) followed by trituration of the resulting solid with hexanes provide 2-fluoro-6-[2,3,6-trideuterio-4-(trifluoromethoxy)phenoxy]-3-(trifluoromethyl)benzoic acid (3.20 g, 73%) as a white solid. ESI-MS m/z calc. 387.04, found 388.1 (M+1)+; retention time (Method A): 0.72 minutes (1 minute run). ¹H NMR (400 MHz, DMSO-d6) δ 14.15 (br s, 1H), 7.84 (t, J=8.7 Hz, 1H), 7.47 (d, J=0.9 Hz, 1H), 6.98-6.88 (m, 1H) ppm.

Step 4: N-(5-Carbamoyl-2-deuterio-4-fluoro-phenyl)-2-fluoro-6-[2,3,6-trideuterio-4-(trifluoromethoxy)phenoxy]-3-(trifluoromethyl)benzamide (213)

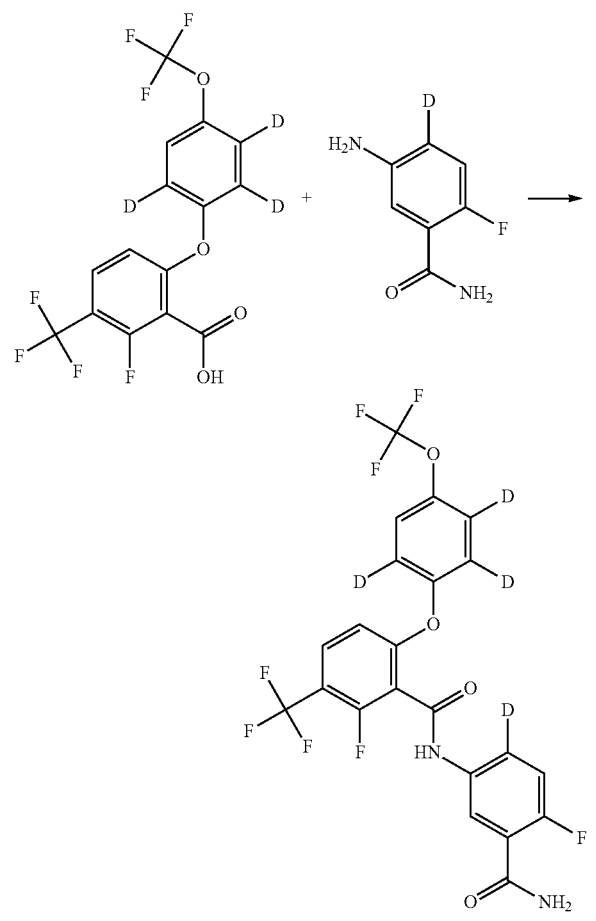

A solution of 2-fluoro-6-[2,3,6-trideuterio-4-(trifluoromethoxy)phenoxy]-3-(trifluoromethyl)benzoic acid (2.00 g, 5.17 mmol), 5-amino-4-deuterio-2-fluoro-benzamide (prepared as described in Preparation 5, 0.801 g, 5.16 mmol) and triethylamine (1.44 mL, 10.33 mmol) in NMP (20 mL) was treated with HATU (2.16 g, 5.68 mmol) and stirred at room temperature for 16 hours. The reaction mixture was partitioned between ethyl acetate (100 mL) and water (300 mL) and the layers separated. The organic layer was washed with 0.5 M citric acid, saturated sodium carbonate/water (1:1) and brine. The aqueous phases were back-extracted once with ethyl acetate and the combined organic phases were dried over MgSO₄, filtered and concentrated in vacuo. The crude was dissolved in ethyl acetate, filtered (0.45 μm syringe filter) and evaporated to provide a pale yellow foam. The foam was dissolved in dichloromethane (10-20 mL) and stirred at room temperature for 1 hour to give a colorless suspension. The solid was collected by filtration, washed with cold dichloromethane and dried under vacuum at 40-45° C. to provide N-(5-carbamoyl-2-deuterio-4-fluoro-phenyl)-2-fluoro-6-[2,3,6-trideuterio-4-(trifluoromethoxy)phenoxy]-3-(trifluoromethyl)benzamide (2.4 g, 88%) as an off-white solid. ESI-MS m/z calc. 524.09, found 525.1 (M+1)+; retention time (Method B): 1.82 minutes (3 minute run). ¹H NMR (400 MHz, DMSO-d6) δ 11.03 (s, 1H), 7.95 (d, J=6.4 Hz, 1H), 7.86 (t, J=8.6 Hz, 1H), 7.70 (d, J=16.3 Hz, 2H), 7.48 (s, 1H), 7.28 (d, J=10.1 Hz, 1H), 6.90 (d, J=8.8 Hz, 1H) ppm.

Example 40

4-[[2-Fluoro-6-[4-(trifluoromethoxy)phenoxy]-3-(trifluoromethyl)benzoyl]amino]-1-oxido-pyridin-1-ium-2-carboxamide (110)

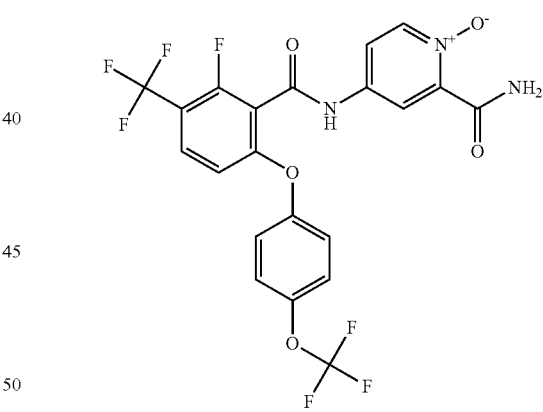

To a stirring solution of 4-[[2-fluoro-6-[4-(trifluoromethoxy)phenoxy]-3-(trifluoromethyl)benzoyl]amino]pyridine-2-carboxamide (48, 521 mg, 1.04 mmol) in anhydrous dichloromethane (5 mL) at 0° C. under N₂ atmosphere was added 3-chloroperoxybenzoic acid (790 mg, 3.53 mmol). The reaction was allowed to warm to room temperature and stirred for 4 hours. The reaction was cooled to 0° C. and additional 3-chloroperoxybenzoic acid (348 mg, 1.56 mmol) was added. The reaction was warmed to room temperature for an additional 2.5 hours, then filtered and concentrated in vacuo. Silica gel chromatography (0-100% ethyl acetate/hexanes) provided 4-[[2-fluoro-6-[4-(trifluoromethoxy)phenoxy]-3-(trifluoromethyl)benzoyl]amino]-1-oxido-pyridin-1-ium-2-carboxamide (358 mg, 67%) as a white solid. ESI-MS m/z calc. 519.07, found 520.0 (M+1)+;

retention time (Method B): 1.65 minutes (3 minute run). $^1$H NMR (400 MHz, DMSO-d6) δ 11.60 (s, 1H), 10.58 (d, J=4.6 Hz, 1H), 8.51 (d, J=3.2 Hz, 1H), 8.37 (d, J=7.1 Hz, 1H), 8.29 (d, J=4.7 Hz, 1H), 7.90 (t, J=8.7 Hz, 1H), 7.84 (dd, J=7.1, 3.3 Hz, 1H), 7.55-7.43 (m, 2H), 7.41-7.30 (m, 2H), 6.92 (d, J=8.9 Hz, 1H) ppm.

Example 41

N-(5-Carbamoyl-4-fluoro-2-methyl-phenyl)-2-fluoro-6-[4-(trifluoromethoxy)phenoxy]-3-(trifluoromethyl)benzamide (124)

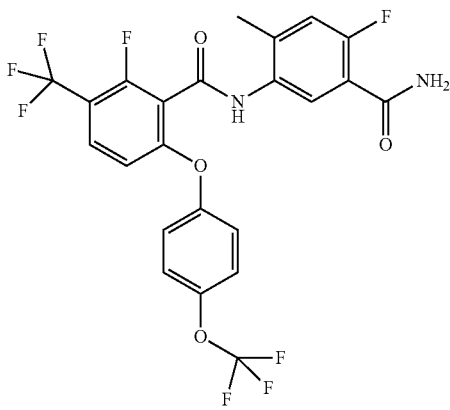 [SMILES: Cc1cc(F)c(C(N)=O)cc1NC(=O)c1c(Oc2ccc(OC(F)(F)F)cc2)ccc(C(F)(F)F)c1F]

Step 1: N-(5-Carbamoyl-4-fluoro-2-methyl-phenyl)-2,6-difluoro-3-(trifluoromethyl)benzamide

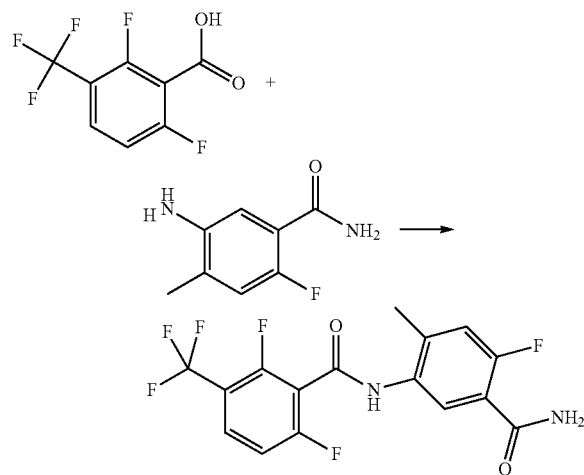

To a solution of 2,6-difluoro-3-(trifluoromethyl)benzoic acid (200 mg, 0.885 mmol) in dichloromethane (5 mL) at 0° C. was added DMF (40 μL, 0.52 mmol) and oxalyl chloride (230 μL, 2.64 mmol) dropwise. The reaction was allowed to warm to room temperature and stirred for 1 hour. The reaction mixture was concentrated in vacuo to afford a yellow solid. The solid was dissolved in dichloromethane (2 mL) and treated with 5-amino-2-fluoro-4-methyl-benzamide (150 mg, 0.892 mmol) and triethylamine (250 μL, 1.79 mmol). The reaction mixture was stirred at room temperature for 45 minutes, then washed with water (10 mL) and brine (2 mL), dried over MgSO$_4$, filtered and concentrated in vacuo. Silica gel chromatography (0-100% ethyl acetate/petroleum ether) provided N-(5-carbamoyl-4-fluoro-2-methyl-phenyl)-2,6-difluoro-3-(trifluoromethyl)benzamide (120 mg, 36%). ESI-MS m/z calc. 376.07, found 377.0 (M+1)+; retention time (Method F): 0.77 minutes (1.5 minute run).

Step 2: N-(5-Carbamoyl-4-fluoro-2-methyl-phenyl)-2-fluoro-6-[4-(trifluoromethoxy)phenoxy]-3-(trifluoromethyl)benzamide (124)

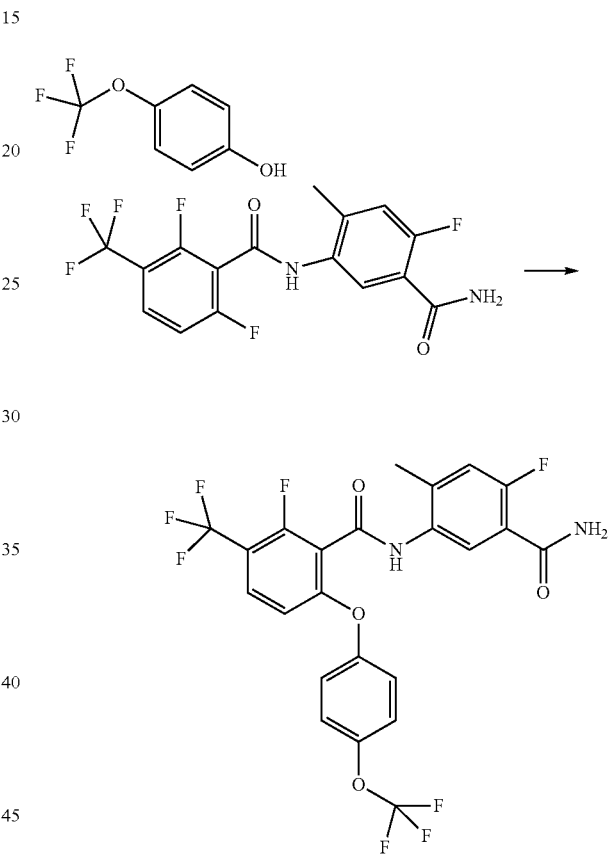

N-(5-Carbamoyl-4-fluoro-2-methyl-phenyl)-2,6-difluoro-3-(trifluoromethyl)benzamide (88 mg, 0.23 mmol), 4-(trifluoromethoxy)phenol (70 mg, 0.39 mmol) and Cs$_2$CO$_3$ (100 mg, 0.307 mmol) were combined in acetonitrile (1 mL) and the mixture was stirred for 16 hours. The reaction mixture was partitioned between ethyl acetate and water and the layers separated. The aqueous layer was further extracted with ethyl acetate and the combined organics were washed with brine, dried over MgSO$_4$, and concentrated in vacuo. Silica gel chromatography (0-100% ethyl acetate/petroleum ether) provided N-(5-carbamoyl-4-fluoro-2-methyl-phenyl)-2-fluoro-6-[4-(trifluoromethoxy)phenoxy]-3-(trifluoromethyl)benzamide (41 mg, 32%) as a white solid. ESI-MS m/z calc. 534.08, found 535.0 (M+1)+; retention time (Method E): 3.3 minutes (5 minute run). $^1$H NMR (500 MHz, DMSO-d6) δ 10.41 (s, 1H), 7.87 (t, J=8.6 Hz, 1H), 7.70 (d, J=7.1 Hz, 1H), 7.63 (d, J=15.0 Hz, 2H), 7.55-7.44 (m, 2H), 7.40-7.33 (m, 2H), 7.26-7.20 (m, 1H), 6.92 (d, J=8.8 Hz, 1H), 2.24 (s, 3H) ppm.

Example 42

4-[[5-Fluoro-2-[2-methoxy-4-(trifluoromethoxy)phenoxy]-4-(trifluoromethyl)benzoyl]amino]pyridine-2-carboxamide (75)

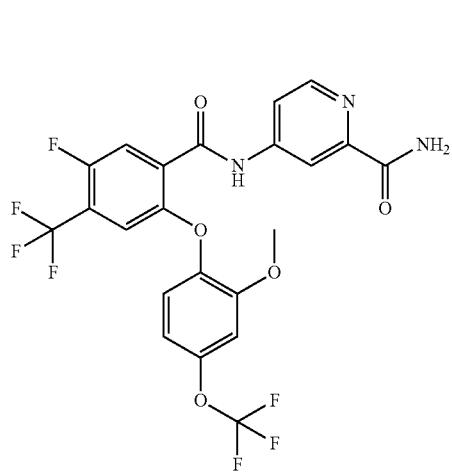 [SMILES: COc1cc(OC(F)(F)F)ccc1Oc1cc(C(F)(F)F)c(F)cc1C(=O)Nc1ccnc(C(N)=O)c1]

Step 1: Methyl 4-[[2,5-difluoro-4-(trifluoromethyl)benzoyl]amino]pyridine-2-carboxylate

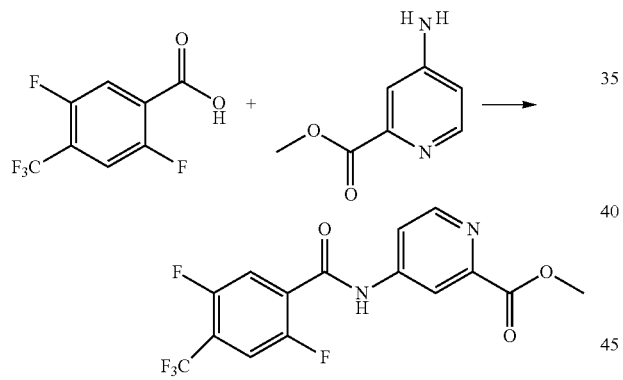

Step 2: Methyl 4-[[5-fluoro-2-[2-methoxy-4-(trifluoromethoxy)phenoxy]-4-(trifluoromethyl)benzoyl]amino]pyridine-2-carboxylate

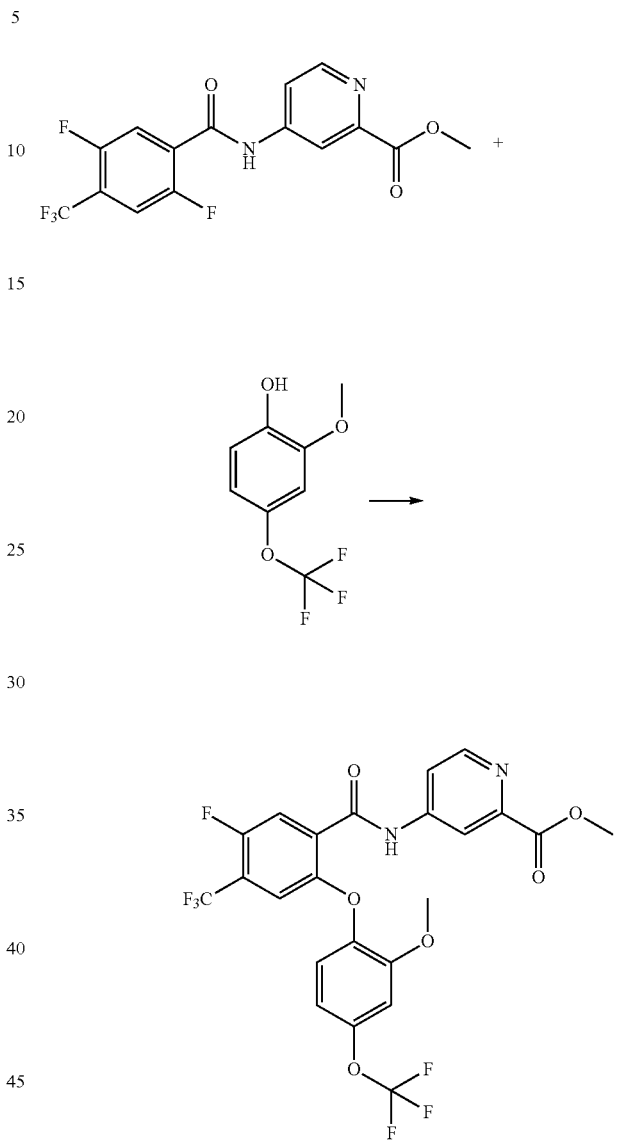

To a solution of 2,5-difluoro-4-(trifluoromethyl)benzoic acid (200 mg, 0.885 mmol) in dichloromethane (4 mL) at 0° C. was added DMF (7 μL, 0.1 mmol) and oxalyl chloride (265 μL, 3.04 mmol) dropwise. The reaction was allowed to warm to room temperature and stirred for 3 hours. The reaction mixture was concentrated in vacuo, dissolved in dichloromethane (3 mL) and cooled to 0° C. Methyl 4-aminopyridine-2-carboxylate (185 mg, 1.22 mmol) was added followed by triethylamine (652 μL, 4.68 mmol) and the resulting mixture was allowed to warm to room temperature and stirred for 16 hours. The reaction mixture was diluted with water (10 mL) and extracted with dichloromethane (2×10 mL). The combined organics were dried over $MgSO_4$, filtered and concentrated in vacuo. Silica gel chromatography (0-60% ethyl acetate/petroleum ether) provided methyl 4-[[2,5-difluoro-4-(trifluoromethyl)benzoyl]amino]pyridine-2-carboxylate (217 mg, 68%). ESI-MS m/z calc. 360.05, found 361.0 (M+1)+; retention time (Method F): 0.78 minutes (1.5 minute run).

Methyl 4-[[2,5-difluoro-4-(trifluoromethyl)benzoyl]amino]pyridine-2-carboxylate (215 mg, 0.597 mmol), $Cs_2CO_3$ (292 mg, 0.896 mmol) and 2-methoxy-4-(trifluoromethoxy)phenol (149 mg, 0.716 mmol) were heated in acetonitrile (5 mL) at 75° C. under $N_2$ atmosphere for 10 hours. The reaction mixture was cooled and partitioned between ethyl acetate and water. The layers were separated and the aqueous layer was extracted with ethyl acetate. The combined organic extracts were washed with brine, dried over $MgSO_4$, filtered and concentrated in vacuo. Purification by silica gel chromatography (0-50% ethyl acetate/petroleum ether) provided methyl 4-[[5-fluoro-2-[2-methoxy-4-(trifluoromethoxy)phenoxy]-4-(trifluoromethyl)benzoyl]amino]pyridine-2-carboxylate (143 mg, 44%) as a white solid. ESI-MS m/z calc. 548.08, found 549.0 (M+1)+; retention time (Method F): 1.02 minutes (1.5 minute run).

327

Step 3: 4-[[5-Fluoro-2-[2-methoxy-4-(trifluoromethoxy)phenoxy]-4-(trifluoromethyl)benzoyl]amino]pyridine-2-carboxamide (75)

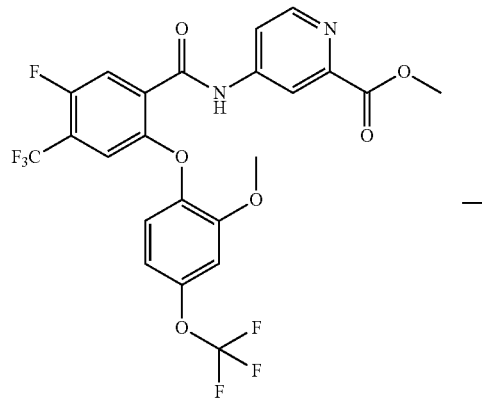

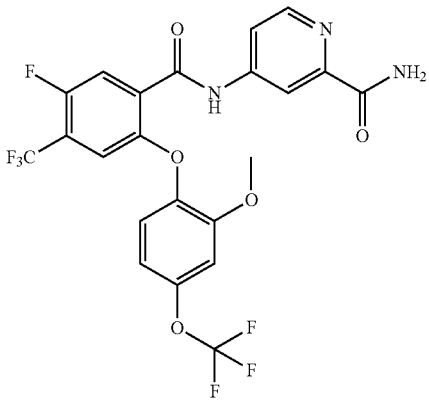

A solution of methyl 4-[[5-fluoro-2-[2-methoxy-4-(trifluoromethoxy)phenoxy]-4-(trifluoromethyl)benzoyl]amino]pyridine-2-carboxylate (143 mg, 0.2608 mmol) in ammonia (4 mL of 7 M in methanol, 28 mmol) was stirred for 16 hours under $N_2$ atmosphere. The reaction mixture was filtered to provide 4-[[5-fluoro-2-[2-methoxy-4-(trifluoromethoxy)phenoxy]-4-(trifluoromethyl)benzoyl]amino]pyridine-2-carboxamide (106 mg, 75%) as a white solid. ESI-MS m/z calc. 533.08, found 534.0 (M+1)+; retention time (Method E): 3.55 minutes (5 minute run). $^1$H NMR (500 MHz, DMSO-d6) δ 11.11 (s, 1H), 8.53 (d, J=5.4 Hz, 1H), 8.29 (d, J=2.1 Hz, 1H), 8.08 (s, 1H), 7.95 (d, J=10.0 Hz, 1H), 7.84-7.76 (m, 1H), 7.71-7.55 (m, 1H), 7.32-7.08 (m, 3H), 6.97 (ddd, J=8.8, 2.7, 1.2 Hz, 1H), 3.75 (s, 3H) ppm.

328

Example 43

4-[[4-Chloro-2-fluoro-6-[2-methoxy-4-(trifluoromethoxy)phenoxy]-3-methyl-benzoyl]amino]-5-methyl-pyridine-2-carboxamide (211)

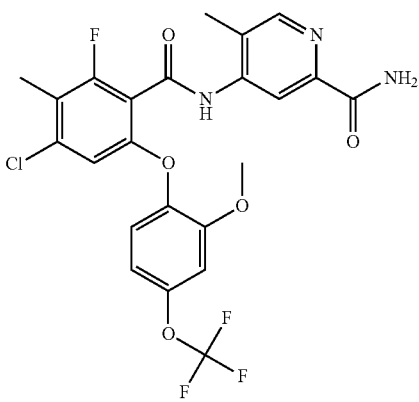 [SMILES: COc1cc(OC(F)(F)F)ccc1Oc1cc(Cl)c(C)c(F)c1C(=O)Nc1cc(C(N)=O)ncc1C]

Step 1: Methyl 4-chloro-2,6-difluoro-benzoate

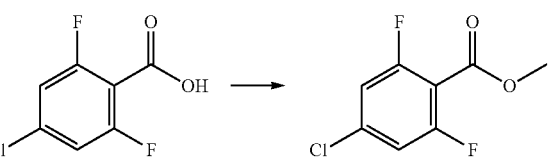

Methyl iodide (1.3 mL, 20.9 mmol) was added to a stirred suspension of 4-chloro-2,6-difluoro-benzoic acid (4.0 g, 20.8 mmol) and $Cs_2CO_3$ (3.4 g, 10.44 mmol) in DMF (40 mL), and the reaction mixture was stirred at ambient temperature for 16.5 hours. The reaction mixture was added to water (150 mL) with stirring and the resulting precipitate was filtered and dried to provide methyl 4-chloro-2,6-difluoro-benzoate (3.7 g, 86%) as a white solid. $^1$H NMR (500 MHz, DMSO-d6) δ 7.59-7.58 (m, 1H), 7.56-7.55 (m, 1H), 3.90 (s, 3H) ppm. $^{19}$F NMR (471 MHz, DMSO-d$_6$) δ −109.07 ppm.

Step 2: Methyl 4-chloro-2-fluoro-6-[2-methoxy-4-(trifluoromethoxy)phenoxy]benzoate

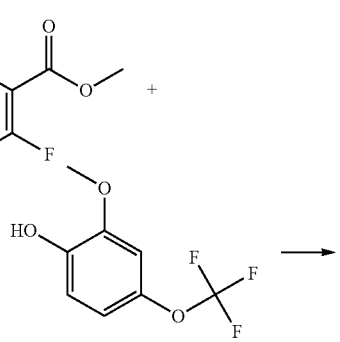

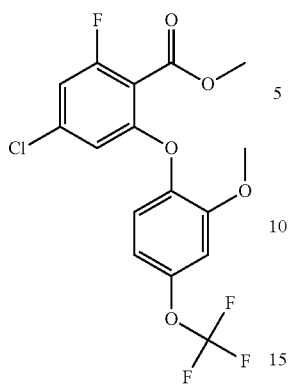

A mixture of Cs₂CO₃ (690 mg, 2.12 mmol), 2-methoxy-4-(trifluoromethoxy)phenol (305 mg, 1.47 mmol) and methyl 4-chloro-2,6-difluoro-benzoate (288 mg, 1.39 mmol) in DMF (5 mL) was stirred at ambient temperature for 22.5 hours. The reaction was diluted with ethyl acetate and washed with water (3×) and brine. The organic layer was dried over MgSO₄, filtered and concentrated in vacuo. The residue was purified by silica gel column chromatography (0-10% ethyl acetate/petroleum ether) to provide methyl 4-chloro-2-fluoro-6-[2-methoxy-4-(trifluoromethoxy)phenoxy]benzoate (468 mg, 85%) as a colorless oil. ESI-MS m/z calc. 394.02, found 395.1 (M+1)+; retention time (Method F): 1.13 minutes (1.5 minute run). ¹H NMR (400 MHz, CDCl₃) δ 7.12-7.09 (m, 1H), 6.89-6.85 (m, 3H), 6.47 (t, J=1.6 Hz, 1H), 3.93 (s, 3H), 3.83 (s, 3H) ppm. ¹⁹F NMR (376 MHz, CDCl₃) δ −58.01, −111.00 ppm.

Step 3: methyl 4-chloro-2-fluoro-6-[2-methoxy-4-(trifluoromethoxy)phenoxy]-3-methyl-benzoate

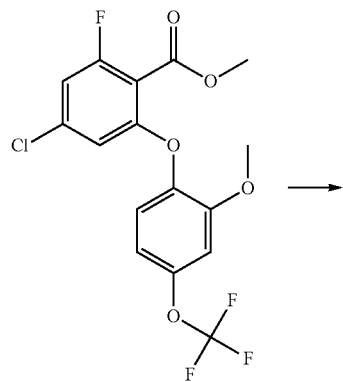

n-Butyllithium (565 μL of 2.5 M, 1.412 mmol) was added to a stirred solution of diisopropylamine (185 μL, 1.320 mmol) in THF (5 mL) at −78° C. and the reaction warmed to 0° C. and stirred for 20 minutes. The LDA formed was added dropwise to a solution of methyl 4-chloro-2-fluoro-6-[2-methoxy-4-(trifluoromethoxy)phenoxy]benzoate (465 mg, 1.18 mmol) in THF (5 mL) at −78° C. The reaction was stirred at this temperature for 10 minutes then methyl iodide (110 μL, 1.77 mmol) was added. The mixture was stirred at −78° C. for 30 minutes then allowed to warm to room temperature. The reaction was quenched by the addition of water and the mixture was extracted with ethyl acetate (3×). The combined organic extracts were dried over MgSO₄, filtered and concentrated in vacuo. The residue was purified by silica gel column chromatography (0-10% ethyl acetate/petroleum ether) to provide methyl 4-chloro-2-fluoro-6-[2-methoxy-4-(trifluoromethoxy)phenoxy]-3-methyl-benzoate (393 mg, 82%) as a colorless oil. ESI-MS m/z calc. 408.04, found 409.1 (M+1)+; retention time (Method F): 1.17 minutes (1.5 minute run). ¹H NMR (400 MHz, CDCl₃) δ 7.06 (d, J=8.6 Hz, 1H), 6.87-6.82 (m, 2H), 6.55 (d, J=1.8 Hz, 1H), 3.92 (s, 3H), 3.84 (s, 3H), 2.28 (d, J=2.4 Hz, 3H) ppm. ¹⁹F NMR (376 MHz, CDCl₃) δ −58.03, −112.16 ppm.

Step 4: 4-Chloro-2-fluoro-6-[2-methoxy-4-(trifluoromethoxy)phenoxy]-3-methyl-benzoic acid

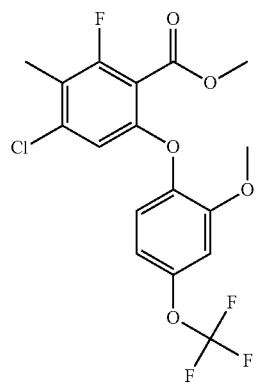

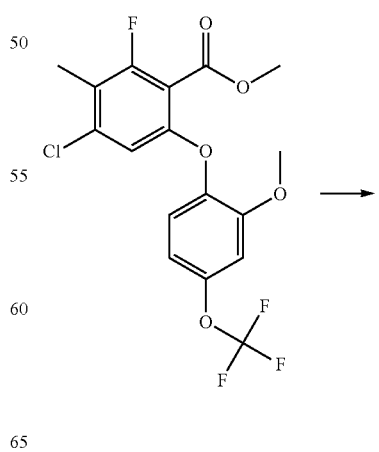

-continued

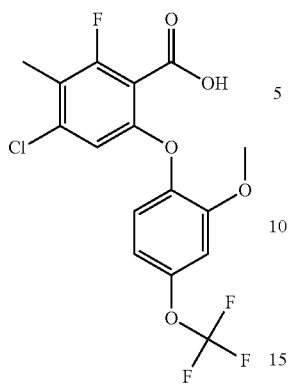

-continued

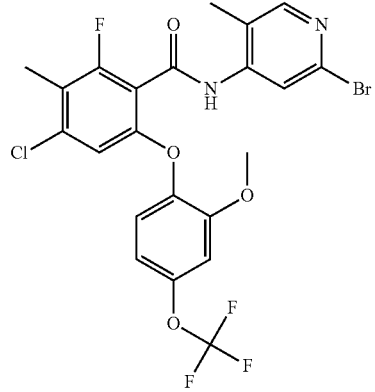

To a slurry of methyl 4-chloro-2-fluoro-6-[2-methoxy-4-(trifluoromethoxy)phenoxy]-3-methyl-benzoate (390 mg, 0.954 mmol) in methanol (10 mL) and water (10 mL) was added NaOH (380 mg, 9.50 mmol). The reaction mixture was stirred at room temperature for 19 hours then the temperature increased to 50° C. for 24 hours. The reaction was cooled to room temperature and concentrated. The residue was taken up in water and acidified with 1M HCl. The mixture was extracted with ethyl acetate (3×) and the combined organic extracts were dried over MgSO$_4$, filtered and concentrated in vacuo to provide 4-chloro-2-fluoro-6-[2-methoxy-4-(trifluoromethoxy)phenoxy]-3-methyl-benzoic acid (363 mg, 96%) as a white solid. ESI-MS m/z calc. 394.02, found 393.1 (M−1)−; retention time (Method F): 0.74 minutes (1.5 minute run). $^1$H NMR (400 MHz, CDCl$_3$) δ 7.20-7.17 (m, 1H), 6.93-6.90 (m, 2H), 6.58 (d, J=1.7 Hz, 1H), 3.85 (s, 3H), 2.30 (d, J=2.5 Hz, 3H) ppm. $^{19}$F NMR (376 MHz, CDCl$_3$) δ −58.00, −109.07 ppm.

Step 5: N-(2-Bromo-5-methyl-4-pyridyl)-4-chloro-2-fluoro-6-[2-methoxy-4-(trifluoromethoxy)phenoxy]-3-methyl-benzamide To a stirring solution of 4-chloro-2-fluoro-6-[2-methoxy-4-(trifluoromethoxy)phenoxy]-3-methyl-benzoic acid (280 mg, 0.709 mmol) in dichloromethane (10 mL) at 0° C. was added DMF (5 μL, 0.06 mmol) and oxalyl chloride (190 μL, 2.18 mmol) dropwise. The reaction mixture was allowed to warm to room temperature over 3.5 hours then concentrated in vacuo. The residue was dissolved in dichloromethane (10 mL) and added dropwise to a solution of 2-bromo-5-methyl-pyridin-4-amine (160 mg, 0.855 mmol) and TEA (500 μL, 3.59 mmol) in dichloromethane (10 mL) at 0° C. The resulting mixture was allowed to warm to room temperature and stirred for 18 hours. The reaction mixture was quenched with water and the layers separated. The aqueous layer was extracted with dichloromethane and the combined organics extracts were dried over MgSO$_4$, filtered and concentrated in vacuo. Silica gel chromatography (0-50% ethyl acetate/petroleum ether) provided N-(2-bromo-5-methyl-4-pyridyl)-4-chloro-2-fluoro-6-[2-methoxy-4-(trifluoromethoxy)phenoxy]-3-methyl-benzamide (150 mg, 37%) as a white solid. ESI-MS m/z calc. 561.99, found 565.1 (M+1)+; 563.0 (M−1)−; retention time (Method F): 1.13 minutes (1.5 minute run). $^1$H NMR (500 MHz, CDCl$_3$) δ 8.62 (s, 1H), 8.30 (s, 1H), 8.12 (s, 1H), 7.19 (d, J=8.7 Hz, 1H), 6.96-6.92 (m, 2H), 6.51 (d, J=1.7 Hz, 1H), 3.82 (s, 3H), 2.32 (d, J=2.5 Hz, 3H), 2.14 (s, 3H) ppm. $^{19}$F NMR (471 MHz, CDCl$_3$) δ −57.97, −110.38 ppm.

Step 6: Methyl 4-[[4-chloro-2-fluoro-6-[2-methoxy-4-(trifluoromethoxy)phenoxy]-3-methyl-benzoyl]amino]-5-methyl-pyridine-2-carboxylate

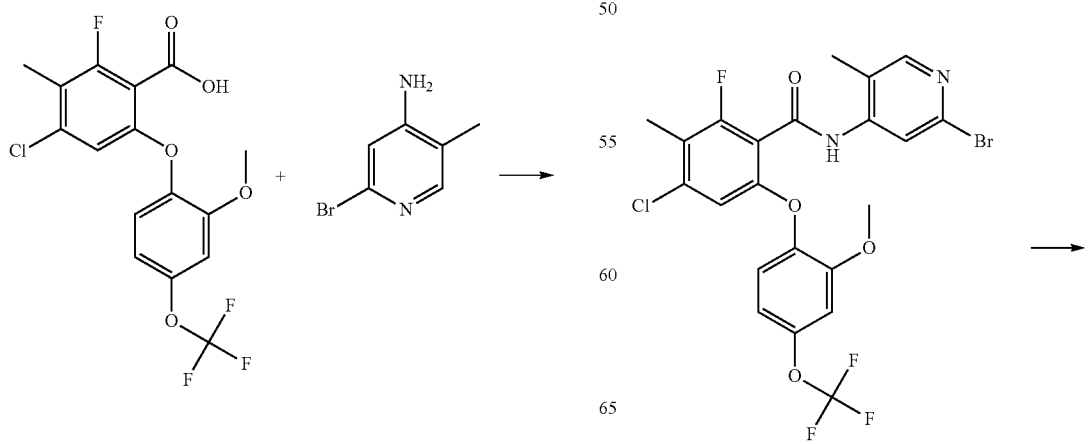

333

-continued

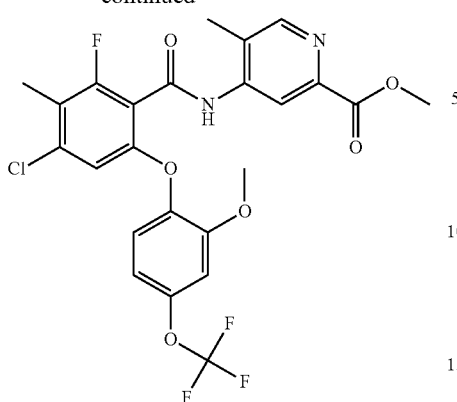

334

-continued

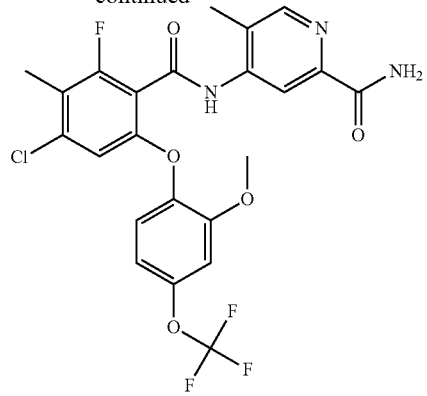

In a pressure tube, N-(2-bromo-5-methyl-4-pyridyl)-4-chloro-2-fluoro-6-[2-methoxy-4-(trifluoromethoxy)phenoxy]-3-methyl-benzamide (149 mg, 0.264 mmol) was dissolved in methanol, (8 mL) and triethylamine (75 µL, 0.54 mmol) and Pd(dppf)Cl₂·DCM (45 mg, 0.055 mmol) were added. Carbon monoxide was bubbled through the vigorously stirred reaction mixture for 5 minutes. The reaction mixture was sealed and heated at 75° C. for 16 hours. The mixture was cooled to room temperature and passed through a pad of Celite. The Celite was rinsed with methanol and the filtrate concentrated in vacuo. Silica gel chromatography (0-100% ethyl acetate/petroleum ether) provided methyl 4-[[4-chloro-2-fluoro-6-[2-methoxy-4-(trifluoromethoxy)phenoxy]-3-methyl-benzoyl]amino]-5-methyl-pyridine-2-carboxylate (105 mg, 73%) as a red solid. ESI-MS m/z calc. 542.09, found 543.3 (M+1)+; 541.2 (M−1)−; retention time (Method F): 1.02 minutes (1.5 minute run). ¹H NMR (500 MHz, CDCl₃) δ 9.08 (s, 1H), 8.51 (s, 1H), 8.34 (s, 1H), 7.20 (d, J=8.6 Hz, 1H), 6.96-6.90 (m, 2H), 6.53 (d, J=1.6 Hz, 1H), 4.02 (s, 3H), 3.83 (s, 3H), 2.33 (d, J=2.4 Hz, 3H), 2.26 (s, 3H) ppm. ¹⁹F NMR (471 MHz, CDCl₃) δ −57.98, −110.38 ppm.

Step 7: 4-[[4-Chloro-2-fluoro-6-[2-methoxy-4-(trifluoromethoxy)phenoxy]-3-methyl-benzoyl]amino]-5-methyl-pyridine-2-carboxamide (211)

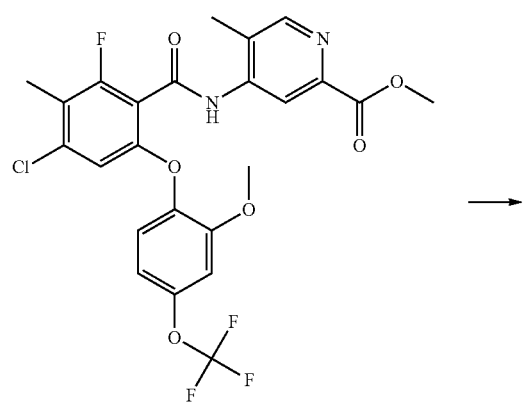

A mixture of methyl 4-[[4-chloro-2-fluoro-6-[2-methoxy-4-(trifluoromethoxy)phenoxy]-3-methyl-benzoyl]amino]-5-methyl-pyridine-2-carboxylate (105 mg, 0.193 mmol) and ammonia (3 mL of 7 M in methanol, 21.00 mmol) was stirred at room temperature for 20 hours. An additional portion of 7M ammonia (3 mL of 7 M in methanol, 21.00 mmol) was added and the reaction was stirred at ambient temperature for 23.5 hours. The reaction mixture was concentrated in vacuo. Silica gel chromatography (0-100% ethyl acetate/petroleum ether) followed by HPLC purification (0-100% acetonitrile/0.1% ammonium hydroxide) and lyophilization of product fractions provided 4-[[4-chloro-2-fluoro-6-[2-methoxy-4-(trifluoromethoxy)phenoxy]-3-methyl-benzoyl]amino]-5-methyl-pyridine-2-carboxamide (22 mg, 22%) as a white solid. ESI-MS m/z calc. 527.09, found 528.2 (M+1)+; 526.2 (M−1)−; retention time (Method C): 3.53 minutes (5 minute run). ¹H NMR (500 MHz, DMSO-d6) δ 10.38 (s, 1H), 8.45 (s, 2H), 8.04-8.03 (m, 1H), 7.58 (s, 1H), 7.27 (d, J=8.8 Hz, 1H), 7.21 (d, J=2.6 Hz, 1H), 7.02-7.00 (m, 1H), 6.67 (s, 1H), 3.81 (s, 3H), 2.28 (s, 6H) ppm. ¹⁹F NMR (471 MHz, DMSO-d6) δ −56.86, −114.46 ppm.

Example 44

4-[[4-Chloro-2-fluoro-6-[2-methoxy-4-(trifluoromethoxy)phenoxy]-3-methyl-benzoyl]amino]pyridine-2-carboxamide (201)

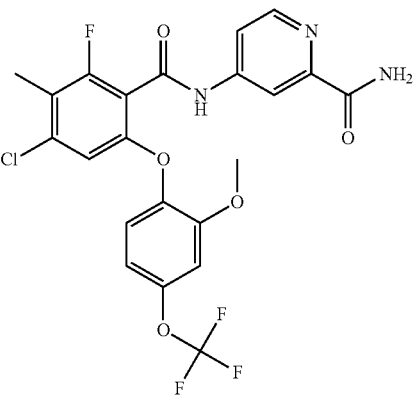

This compound was made in an analogous fashion to Example 43, except employing 4-aminopyridine-2-carbox-

Example 45

N-(3-Carbamoyl-4-fluoro-phenyl)-2-methoxy-6-[2-methoxy-4-(trifluoromethoxy)phenoxy]-3-(trifluoromethyl)benzamide (92)

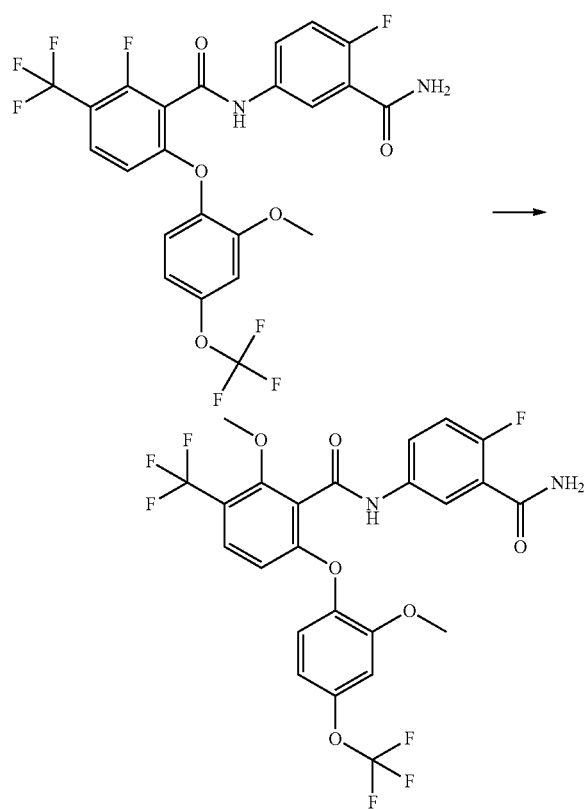

N-(3-Carbamoyl-4-fluoro-phenyl)-2-fluoro-6-[2-methoxy-4-(trifluoromethoxy)phenoxy]-3-(trifluoromethyl)benzamide (Example 2, 54 mg, 0.098 mmol) and sodium methoxide (1 mL of 0.5 M in methanol, 0.5 mmol) were stirred at 80° C. for 3 hours. The reaction mixture was concentrated in vacuo. HPLC purification (1-99% acetonitrile/water) provided N-(3-carbamoyl-4-fluoro-phenyl)-2-methoxy-6-[2-methoxy-4-(trifluoromethoxy)phenoxy]-3-(trifluoromethyl)benzamide (27 mg, 49%). ESI-MS m/z calc. 562.10, found 563.0 (M+1)+; retention time (Method B): 1.82 minutes (3 min run). $^1$H NMR (400 MHz, DMSO-d6) δ 10.88 (s, 1H), 8.03 (dd, J=6.4, 2.8 Hz, 1H), 7.82-7.77 (m, 1H), 7.71 (d, J=17.3 Hz, 2H), 7.66 (d, J=8.9 Hz, 1H), 7.38-7.19 (m, 3H), 7.08-6.98 (m, 1H), 6.51 (d, J=8.8 Hz, 1H), 3.92 (s, 3H), 3.80 (s, 3H) ppm.

amide in the amide formation step (Step 5). The yield of the desired product after purification was 20 mg (19%). ESI-MS m/z calc. 513.07, found 513.9 (M+1)+; 511.7 (M−1)−; retention time (Method E): 3.32 minutes (5 minute run). $^1$H NMR (500 MHz, DMSO-d6) δ 11.25 (s, 1H), 8.54 (d, J=5.5 Hz, 1H), 8.30 (d, J=1.9 Hz, 1H), 8.08 (d, J=2.6 Hz, 1H), 7.81 (dd, J=5.4, 2.1 Hz, 1H), 7.64 (d, J=2.5 Hz, 1H), 7.25 (d, J=8.8 Hz, 1H), 7.18 (d, J=2.7 Hz, 1H), 7.00-6.98 (m, 1H), 6.73-6.65 (m, 1H), 3.78 (s, 3H), 2.27 (d, J=2.0 Hz, 3H) ppm; $^{19}$F NMR (471 MHz, DMSO-d6) δ −56.89, −114.33 ppm.

Example 46

5-[[2-Methoxy-6-[2-methoxy-4-(trifluoromethoxy)phenoxy]-3-(trifluoromethyl)benzoyl]amino]pyridine-2-carboxamide (202)

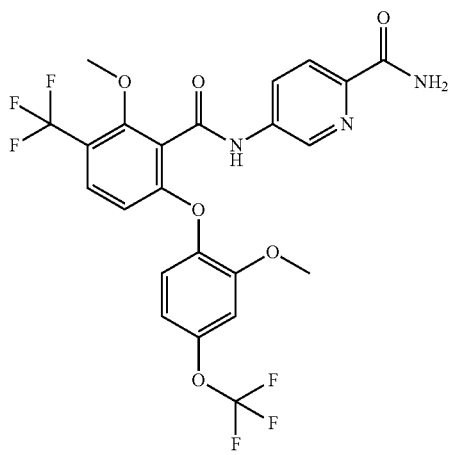 [SMILES: COc1cc(OC(F)(F)F)ccc1Oc1ccc(C(F)(F)F)c(OC)c1C(=O)Nc1ccc(C(N)=O)nc1]

This compound was made in an analogous fashion to Example 45 from 193. The yield of the desired product after HPLC purification was 22 mg (36%). ESI-MS m/z calc. 545.10, found 546.1 (M+1)+; 544.0 (M−1)−; retention time: 3.29 minutes (Method E). $^1$H NMR (500 MHz, DMSO-d6) δ 11.20 (s, 1H), 8.88 (s, 1H), 8.31 (dd, J=8.7, 2.4 Hz, 1H), 8.04 (d, J=8.5 Hz, 1H), 8.01-7.97 (m, 1H), 7.68 (d, J=8.9 Hz, 1H), 7.55-7.51 (m, 1H), 7.31 (d, J=8.8 Hz, 1H), 7.23 (d, J=2.7 Hz, 1H), 7.02 (ddd, J=8.8, 2.7, 1.3 Hz, 1H), 6.54 (d, J=8.8 Hz, 1H), 3.91 (s, 3H), 3.78 (s, 3H) ppm.

Example 47

5-Fluoro-4-(2-methoxy-6-(2-methoxy-4-(trifluoromethoxy)phenoxy)-3-(trifluoromethyl)benzamido)picolinamide (128)

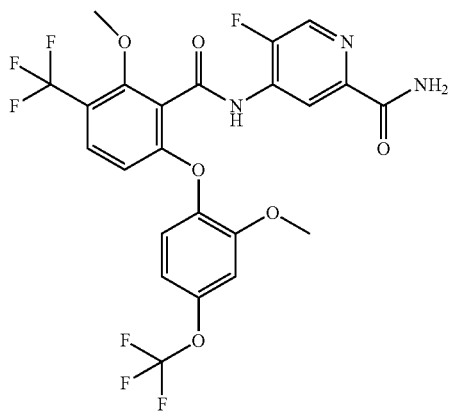 [SMILES: COc1cc(OC(F)(F)F)ccc1Oc1ccc(C(F)(F)F)c(OC)c1C(=O)Nc1cc(C(N)=O)ncc1F]

Compound 128 was prepared according to the experimental described above in Example 33.

Example 48

6-[[2-Methoxy-6-[2-methoxy-4-(trifluoromethoxy)phenoxy]-3-(trifluoromethyl)benzoyl]amino]pyridine-3-carboxamide (205)

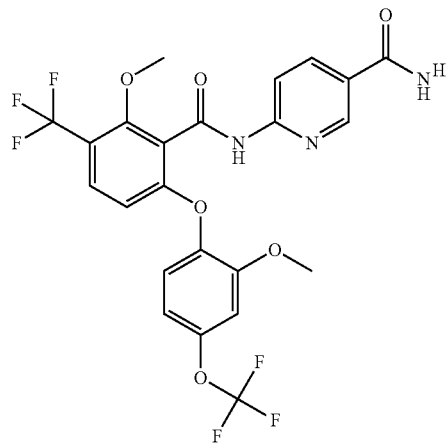

Step 1: Methyl 6-[[2-fluoro-6-[2-methoxy-4-(trifluoromethoxy)phenoxy]-3-(trifluoromethyl)benzoyl]amino]pyridine-3-carboxylate

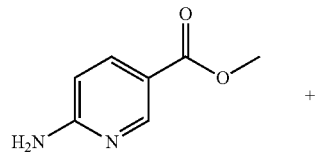

+

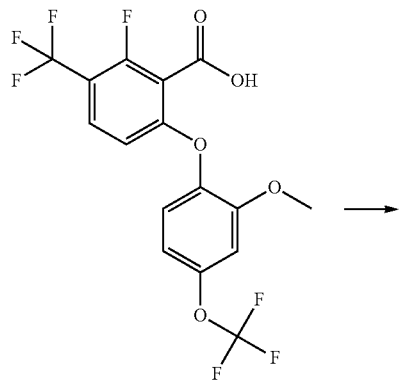

→

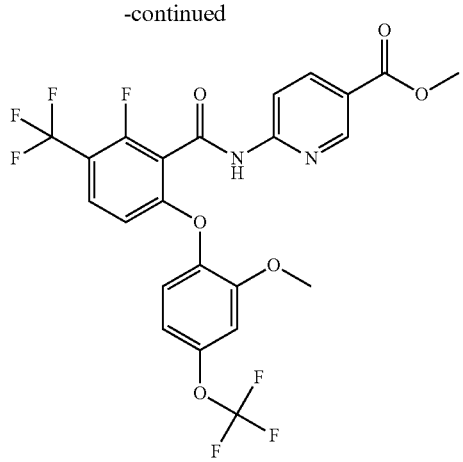

To an ice-cooled solution of 2-fluoro-6-[2-methoxy-4-(trifluoromethoxy)phenoxy]-3-(trifluoromethyl)benzoic acid (100 mg, 0.241 mmol) in dichloromethane (2 mL) was added DMF (10 μL, 0.13 mmol) and oxalyl chloride (70 μL, 0.8024 mmol) dropwise. The reaction mixture was stirred for 2 hours then concentrated in vacuo to afford the acid chloride as a pale yellow oil. The product was dissolved in dichloromethane (2 mL) and added dropwise to a solution of methyl 6-aminopyridine-3-carboxylate (33 mg, 0.22 mmol) and TEA (210 μL, 1.507 mmol) in dichloromethane (3 mL) at 0° C. The mixture was allowed to warm to room temperature and stirred for 16 hours. The reaction mixture was concentrated in vacuo and purified by silica gel chromatography (0-100% ethyl acetate/petroleum ether) to afford methyl 6-[[2-fluoro-6-[2-methoxy-4-(trifluoromethoxy)phenoxy]-3-(trifluoromethyl)benzoyl]amino]pyridine-3-carboxylate (15 mg, 11%) as an off-white waxy solid. ESI-MS m/z calc. 548.08, found 549.0 (M+1)+; retention time (Method F): 1.11 minutes (1.5 minute run). $^1$H NMR (400 MHz, CDCl$_3$) δ 9.35 (s, 1H), 8.87 (dd, J=2.3, 0.8 Hz, 1H), 8.52-8.45 (m, 1H), 8.37 (ddd, J=8.3, 4.8, 2.3 Hz, 1H), 7.62-7.52 (m, 1H), 7.41 (t, J=8.3 Hz, 1H), 7.28-7.20 (m, 1H), 7.24-7.09 (m, 1H), 6.96-6.86 (m, 3H), 6.88-6.81 (m, 2H), 6.58 (d, J=8.9 Hz, 1H), 6.36 (d, J=8.9 Hz, 1H), 3.74 (s, 2H), 1.38-1.21 (m, 3H) ppm.

Step 2: 6-[[2-Methoxy-6-[2-methoxy-4-(trifluoromethoxy)phenoxy]-3-(trifluoromethyl)benzoyl]amino]pyridine-3-carboxamide (205)

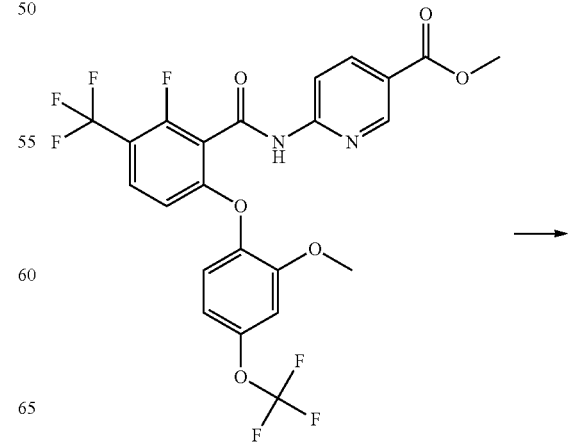

→

-continued

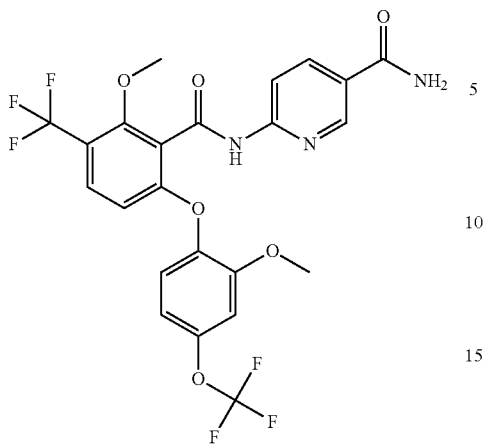

Methyl 6-[[2-fluoro-6-[2-methoxy-4-(trifluoromethoxy)phenoxy]-3-(trifluoromethyl)benzoyl]amino]pyridine-3-carboxylate (15 mg, 0.027 mmol) was dissolved in ammonia (2 mL of 7 M in methanol, 14 mmol) in a sealed tube and stirred at 45° C. for 16 hours. Additional ammonia was added (1 mL of 7 M in methanol, 7 mmol) and the mixture was heated for an additional 48 hours. The reaction mixture was concentrated in vacuo and purified by HPLC (37-100% acetonitrile/0.1% ammonium hydroxide) to provide 6-[[2-methoxy-6-[2-methoxy-4-(trifluoromethoxy)phenoxy]-3-(trifluoromethyl)benzoyl]amino]pyridine-3-carboxamide (0.4 mg, 2%). ESI-MS m/z calc. 545.10, found 545.96 (M+1)+; 543.96 (M−1)−; retention time (Method E): 3.24 minutes (5 minute run). $^1$H NMR (400 MHz, CD$_3$OD) δ 8.85 (s, 1H), 8.49-8.24 (m, 2H), 7.62 (d, J=8.9 Hz, 1H), 7.29 (d, J=8.8 Hz, 1H), 7.08 (s, 1H), 6.95 (d, J=9.4 Hz, 1H), 6.55 (d, J=8.8 Hz, 1H), 3.99 (s, 3H), 3.83 (s, 3H) ppm.

Example 49

2-Fluoro-5-[[2-fluoro-6-[2-methoxy-4-(trifluoromethoxy)phenoxy]-4-(trifluoromethyl)benzoyl]amino]-4-methyl-benzamide (139)

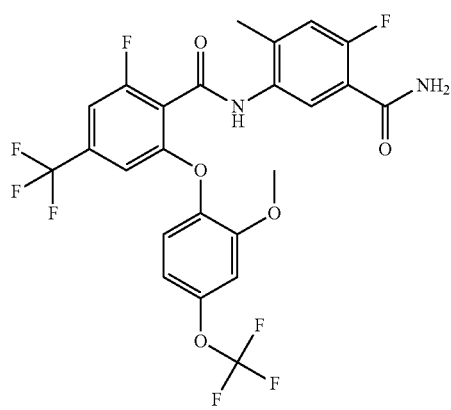 [SMILES: COc1cc(OC(F)(F)F)ccc1Oc1cc(C(F)(F)F)cc(F)c1C(=O)Nc1cc(C(N)=O)c(F)cc1C]

Step 1: Methyl 2-fluoro-6-[2-methoxy-4-(trifluoromethoxy)phenoxy]-4-(trifluoromethyl)benzoate

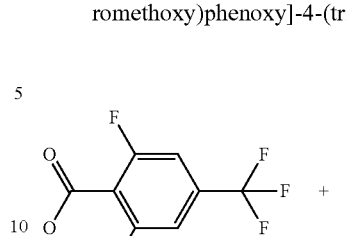

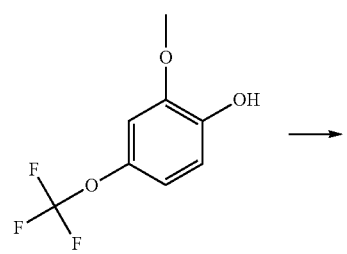

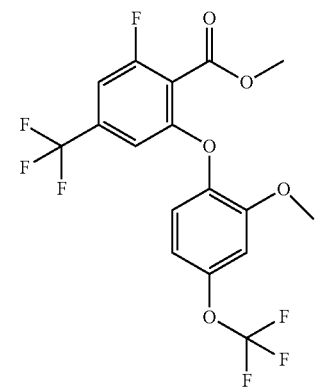

To a solution of methyl 2,6-difluoro-4-(trifluoromethyl)benzoate (1.173 g, 4.885 mmol) in DMF (15 mL), was added 2-methoxy-4-(trifluoromethoxy)phenol (1.017 g, 4.886 mmol) and Cs$_2$CO$_3$ (4.816 g, 14.78 mmol) and the mixture was heated at 80° C. for 1 hour. The reaction was cooled and diluted with ethyl acetate and saturated aqueous sodium chloride solution and the layers were separated. The organic layer was washed with additional sodium chloride solution, dried over MgSO$_4$, filtered and concentrated in vacuo. Silica gel chromatography (0-5% ethyl acetate/hexanes) provided methyl 2-fluoro-6-[2-methoxy-4-(trifluoromethoxy)phenoxy]-4-(trifluoromethyl)benzoate (2.168 g, 104%) containing 0.3 equivalents of DMF by NMR. ESI-MS m/z calc. 428.05, found 429.0 (M+1)+; retention time (Method F): 1.14 minutes (1.5 minute run).

Step 2: 2-Fluoro-6-[2-methoxy-4-(trifluoromethoxy)phenoxy]-4-(trifluoromethyl)benzoic acid

Step 3: 2-Fluoro-5-[[2-fluoro-6-[2-methoxy-4-(trifluoromethoxy)phenoxy]-4-(trifluoromethyl)benzoyl]amino]-4-methyl-benzamide (139)

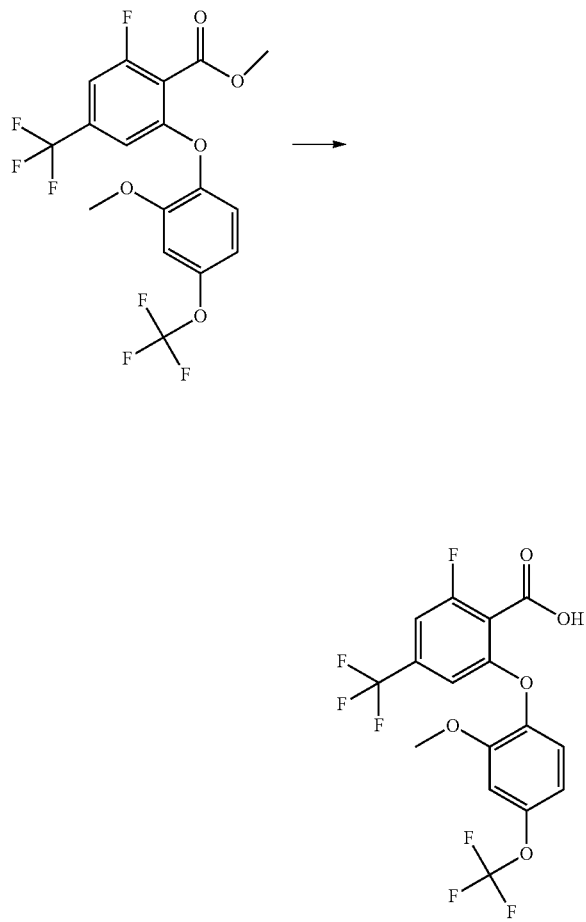

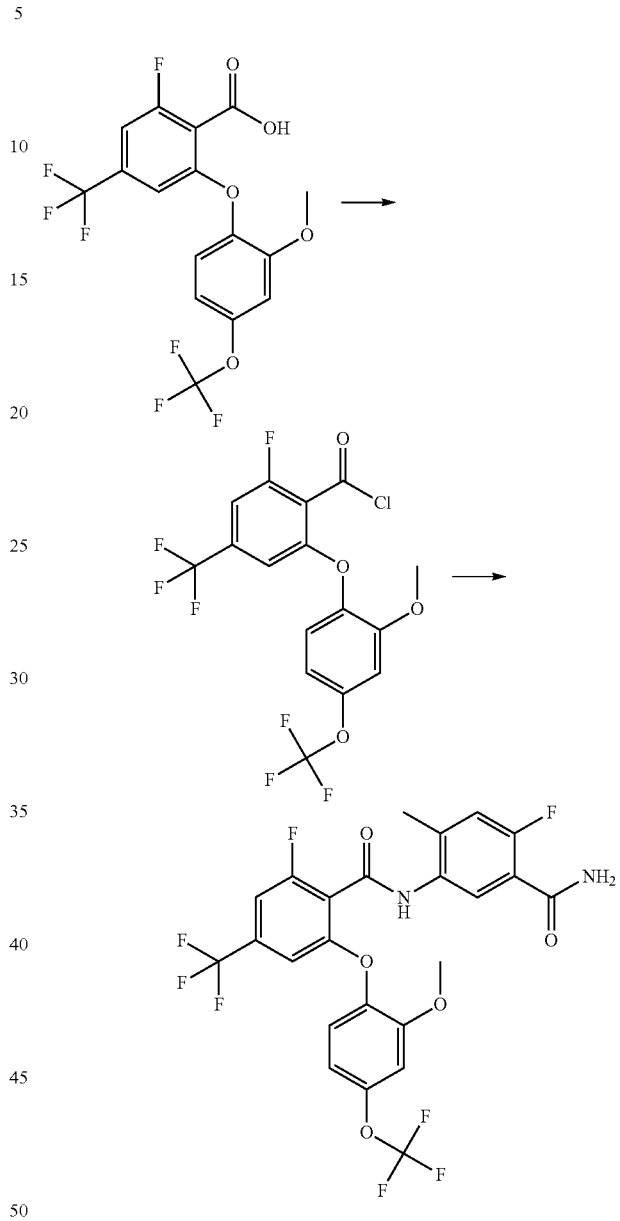

To a flask charged with methyl 2-fluoro-6-[2-methoxy-4-(trifluoromethoxy)phenoxy]-4-(trifluoromethyl)benzoate (5.71 g, 13.3 mmol) in THF (60 mL) was added aqueous NaOH (58 mL of 2 M, 116 mmol). The reaction mixture was stirred for 1 hour at room temperature then refluxed for 16 hours. The solvent was evaporated and the residue was cooled to 0° C., acidified with 2 M HCl and extracted with dichloromethane (3×). The organic layer was dried over MgSO$_4$, filtered and concentrated to provide 2-fluoro-6-[2-methoxy-4-(trifluoromethoxy)phenoxy]-4-(trifluoromethyl)benzoic acid (5.3 g, 96%) as a white solid. ESI-MS m/z calc. 414.03, found 412.9 (M−1)−; retention time (Method F): 0.73 minutes (1.5 minute run). $^1$H NMR (400 MHz, CDCl$_3$) δ 7.12-7.08 (m, 1H), 7.08-7.03 (m, 1H), 6.82 (m, 2H), 6.63 (s, 1H), 3.73 (s, 3H) ppm. $^{19}$F NMR (376 MHz, CDCl$_3$) δ −58.44, −63.89, −108.83 (d, J=9.0 Hz) ppm.

To a solution of 2-fluoro-6-[2-methoxy-4-(trifluoromethoxy)phenoxy]-4-(trifluoromethyl)benzoic acid (100 mg, 0.227 mmol) in dichloromethane (2 mL) at 0° C. was added DMF (12 µL, 0.16 mmol) followed by careful addition of oxalyl chloride (36 µL, 0.41 mmol). The ice-bath was removed after 5 minutes and the reaction was allowed to warm to room temperature over 40 minutes. The solution was concentrated in vacuo and azeotroped with dichloromethane (2×) to provide 2-fluoro-6-(2-methoxy-4-(trifluoromethoxy)phenoxy)-4-(trifluoromethyl)benzoyl chloride. The residue was taken up in THF (1.8 mL) and cooled to 0° C. DIEA (123 µL, 0.706 mmol) was added followed by 5-amino-2-fluoro-4-methyl-benzamide (prepared as described in Preparation 4, 40 mg, 0.24 mmol). The resulting solution was stirred at 0° C. for 30 minutes and then at room temperature for 2 hours. HPLC purification (0-100% acetonitrile/0.1% NH₃ in water) followed by lyophilization of product fractions provided 2-fluoro-5-[[2-fluoro-6-[2-methoxy-4-(trifluoromethoxy)phenoxy]-4-(trifluoromethyl)benzoyl]amino]-4-methyl-benzamide (45 mg, 35%) as a white solid. ESI-MS m/z calc. 564.09, found 565.0 (M+1)+; retention time (Method E): 3.37 minutes (5 minute run). ¹H NMR (400 MHz, DMSO-d6) δ 10.38 (s, 1H), 7.73 (d, J=7.1 Hz, 1H), 7.71-7.62 (m, 3H), 7.32 (d, J=8.8 Hz, 1H), 7.31-7.20 (m, 2H), 7.05 (ddd, J=8.8, 2.7, 1.3 Hz, 1H), 6.82 (1H, s), 3.83 (s, 3H), 2.27 (s, 3H) ppm. ¹⁹F NMR (376 MHz, DMSO-d6) δ −57.34, −62.02, −112.85 (d, J=8.6 Hz), −116.80 (td, J=9.7, 8.5, 4.6 Hz) ppm.

Example 50

N-(3-Carbamoyl-4-fluoro-phenyl)-2-fluoro-6-[2-methoxy-4-(trifluoromethoxy)phenoxy]-4-(trifluoromethyl)benzamide (140)

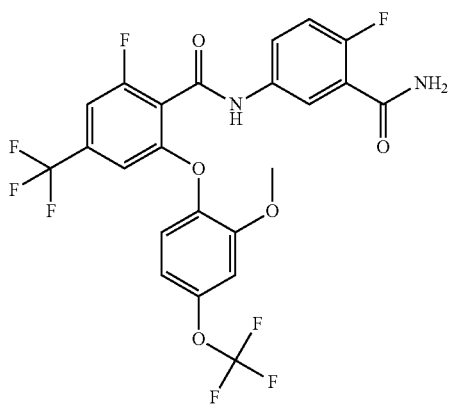 [SMILES: COc1cc(OC(F)(F)F)ccc1Oc1cc(C(F)(F)F)cc(F)c1C(=O)Nc1ccc(F)c(C(N)=O)c1]

This compound was made in an analogous fashion to Example 49 from 2-fluoro-6-(2-methoxy-4-(trifluoromethoxy)phenoxy)-4-(trifluoromethyl)benzoyl chloride and 5-amino-2-fluoro-benzamide. The yield of the desired product after HPLC purification was (70 mg, 56%). ESI-MS m/z calc. 550.08, found 551.0 (M+1)+; retention time (Method E): 3.35 minutes (5 minute run). ¹H NMR (400 MHz, DMSO-d6) δ 11.00 (s, 1H), 7.99 (dd, J=6.4, 2.8 Hz, 1H), 7.79-7.75 (m, 2H), 7.70 (s, 1H), 7.68-7.62 (m, 1H), 7.35-7.26 (m, 2H), 7.24 (d, J=2.7 Hz, 1H), 7.03 (ddd, J=8.8, 2.7, 1.3 Hz, 1H), 6.82 (d, J=1.4 Hz, 1H), 3.79 (s, 3H) ppm. ¹⁹F NMR (376 MHz, DMSO-d6) δ −57.35, −62.04, −112.69 (d, J=8.6 Hz), −119.00 (d, J=3.0 Hz) ppm.

Example 51

5-[[2-Fluoro-6-[2-methoxy-4-(trifluoromethoxy)phenoxy]-4-(trifluoromethyl)benzoyl]amino]pyridine-2-carboxamide (187)

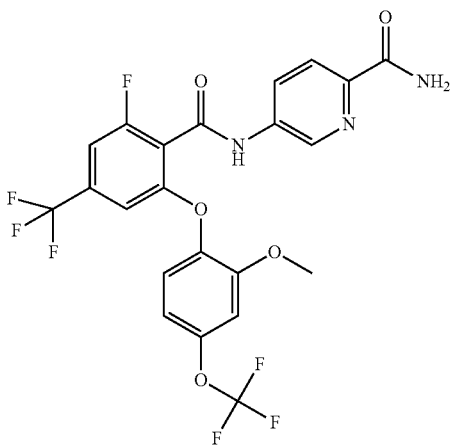 [SMILES: COc1cc(OC(F)(F)F)ccc1Oc1cc(C(F)(F)F)cc(F)c1C(=O)Nc1ccc(C(N)=O)nc1]

This compound was made in an analogous fashion to Example 49 from 2-fluoro-6-(2-methoxy-4-(trifluoromethoxy)phenoxy)-4-(trifluoromethyl)benzoyl chloride and 5-aminopyridine-2-carboxamide. The yield of the desired product after HPLC purification was (30 mg, 23%). ESI-MS m/z calc. 533.08, found 534.0 (M+1)+; 531.8 (M−1)−; retention time (Method E): 3.28 minutes (5 minute run). ¹H NMR (400 MHz, DMSO-d6) δ 11.33 (s, 1H), 8.85 (d, J=2.3 Hz, 1H), 8.27 (dd, J=8.6, 2.5 Hz, 1H), 8.10-8.00 (m, 2H), 7.69 (d, J=8.6 Hz, 1H), 7.57 (s, 1H), 7.33 (d, J=8.9 Hz, 1H), 7.23 (d, J=2.8 Hz, 1H), 7.06-6.98 (m, 1H), 6.88 (s, 1H), 3.78 (s, 3H), 3.30 (s, 17H) ppm.

Example 52

4-[[2-Fluoro-6-[2-methoxy-4-(trifluoromethoxy)phenoxy]-4-(trifluoromethyl)benzoyl]amino]pyridine-2-carboxamide (163)

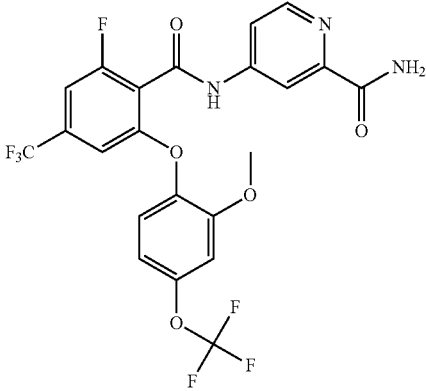 [SMILES: COc1cc(OC(F)(F)F)ccc1Oc1cc(C(F)(F)F)cc(F)c1C(=O)Nc1ccnc(C(N)=O)c1]

345

Step 1: Methyl 4-[[2-fluoro-6-[2-methoxy-4-(trifluoromethoxy)phenoxy]-4-(trifluoromethyl)benzoyl]amino]pyridine-2-carboxylate

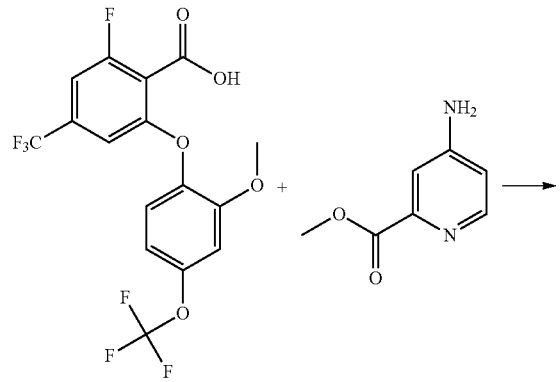

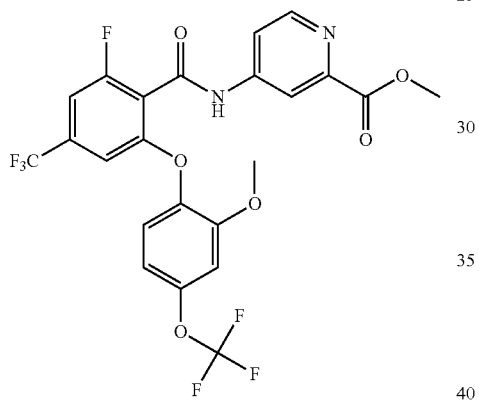

To a solution of 2-fluoro-6-[2-methoxy-4-(trifluoromethoxy)phenoxy]-4-(trifluoromethyl)benzoic acid (200 mg, 0.483 mmol) in dichloromethane (3.5 mL) at 0° C. was added DMF (4 μL, 0.05 mmol) and oxalyl chloride (145 μL, 1.66 mmol) dropwise. The reaction was allowed to warm to room temperature over 3 hours. The reaction mixture was concentrated in vacuo, dissolved in dichloromethane (3.5 mL) and cooled to 0° C. Methyl 4-aminopyridine-2-carboxylate (95 mg, 0.62 mmol) was added followed by triethylamine (360 μL, 2.58 mmol). The resulting mixture was stirred and warmed to room temperature over 16 hours. The reaction mixture was diluted with water (10 mL) and extracted with dichloromethane (2×10 mL). The combined organics were dried over MgSO₄, filtered and concentrated in vacuo. Silica gel chromatography (30-70% ethyl acetate/petroleum ether) provided methyl 4-[[2-fluoro-6-[2-methoxy-4-(trifluoromethoxy)phenoxy]-4-(trifluoromethyl)benzoyl]amino]pyridine-2-carboxylate (129 mg, 49%). ESI-MS m/z calc. 548.08, found 549.0 (M+1)+; retention time: 1.04 minutes (1.5 min run).

346

Step 2: 4-[[2-Fluoro-6-[2-methoxy-4-(trifluoromethoxy)phenoxy]-4-(trifluoromethyl)benzoyl]amino]pyridine-2-carboxamide (163)

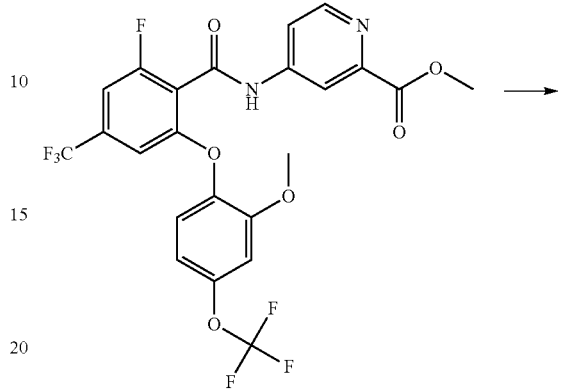

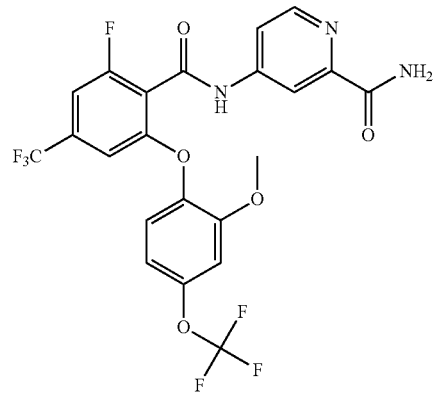

A solution of methyl 4-[[2-fluoro-6-[2-methoxy-4-(trifluoromethoxy)phenoxy]-4-(trifluoromethyl)benzoyl]amino]pyridine-2-carboxylate (129 mg, 0.235 mmol) in ammonia (3.8 mL of 7 M in methanol, 26.6 mmol) was stirred at room temperature for 16 hours. The reaction mixture was concentrated in vacuo and purified by HPLC (37-100% acetonitrile/ 0.1% ammonium hydroxide) to provide 4-[[2-fluoro-6-[2-methoxy-4-(trifluoromethoxy)phenoxy]-4-(trifluoromethyl)benzoyl]amino]pyridine-2-carboxamide (44 mg, 35%) as a white solid. ESI-MS m/z calc. 533.08, found 534.0 (M+1)+; retention time (Method E): 3.42 minute (5 minute run). $^1$H NMR (400 MHz, DMSO-d6) δ 11.41 (s, 1H), 8.68-8.48 (m, 1H), 8.31 (d, J=2.1 Hz, 1H), 8.11 (d, J=2.8 Hz, 1H), 7.82 (dd, J=5.5, 2.2 Hz, 1H), 7.73-7.63 (m, 2H), 7.33 (d, J=8.8 Hz, 1H), 7.23 (d, J=2.8 Hz, 1H), 7.02 (ddd, J=8.8, 2.7, 1.3 Hz, 1H), 6.86 (d, J=1.4 Hz, 1H), 3.78 (s, 3H) ppm.

Example 53

4-[[2-Fluoro-6-[2-methoxy-4-(trifluoromethoxy) phenoxy]-4-(trifluoromethyl)benzoyl]amino]-5-methyl-pyridine-2-carboxamide (153)

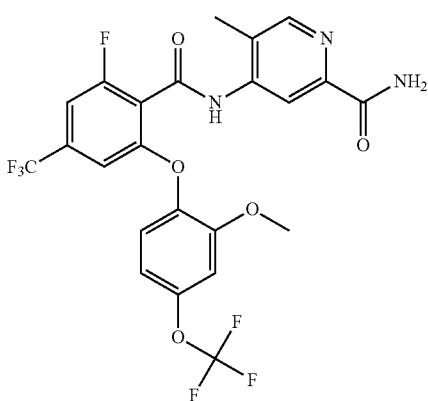 [SMILES: COc1cc(OC(F)(F)F)ccc1Oc1cc(C(F)(F)F)cc(F)c1C(=O)Nc1cc(C(N)=O)ncc1C]

Step 1: N-(2-Bromo-5-methyl-4-pyridyl)-2-fluoro-6-[2-methoxy-4-(trifluoromethoxy)phenoxy]-4-(trifluoromethyl)benzamide

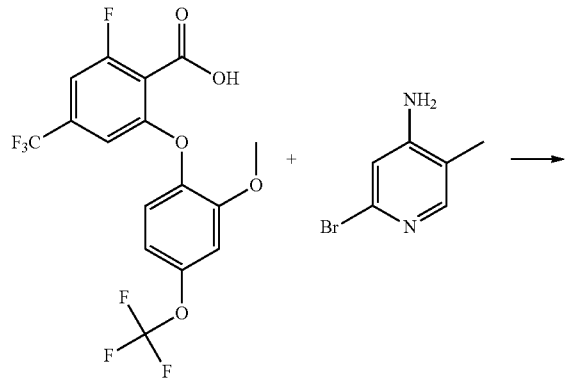

To a solution of 2-fluoro-6-[2-methoxy-4-(trifluoromethoxy)phenoxy]-4-(trifluoromethyl)benzoic acid (1.80 g, 4.35 mmol) in dichloromethane (25 mL) was added DMF (36 μL, 0.47 mmol) and oxalyl chloride (1.30 mL, 14.9 mmol) dropwise. The reaction mixture was allowed to warm to room temperature over 3 hours. The reaction mixture was concentrated in vacuo, dissolved in dichloromethane (25 mL) and cooled to 0° C. 2-Bromo-5-methyl-pyridin-4-amine (1.10 g, 5.88 mmol) was added followed by triethylamine (3.2 mL, 23 mmol). The resulting mixture was stirred and warmed to ambient temperature over 16 hours. The reaction mixture was diluted with water (10 mL) and extracted with dichloromethane (2×10 mL). The combined organics were dried over MgSO₄, filtered and concentrated in vacuo. The residue was purified by silica gel chromatography (0-60% ethyl acetate/petroleum ether) to provide N-(2-bromo-5-methyl-4-pyridyl)-2-fluoro-6-[2-methoxy-4-(trifluoromethoxy)phenoxy]-4-(trifluoromethyl)benzamide (618 mg, 24%). ESI-MS m/z calc. 582.00, found 585.0 (M+1)+; retention time (Method F): 1.15 minutes (1.5 minute run).

Step 2: Methyl 4-[[2-fluoro-6-[2-methoxy-4-(trifluoromethoxy)phenoxy]-4-(trifluoromethyl)benzoyl]amino]-5-methyl-pyridine-2-carboxylate To a solution of N-(2-bromo-5-methyl-4-pyridyl)-2-fluoro-6-[2-methoxy-4-(trifluoromethoxy)phenoxy]-4-(trifluoromethyl)benzamide (618 mg, 1.06 mmol) in methanol (11 mL) and triethylamine (337 μL, 2.42 mmol) was added Pd(dppf)Cl₂·DCM (180 mg, 0.2204 mmol). Carbon monoxide was bubbled through the vigorously stirring reaction mixture for 5 minutes. The reaction mixture was then heated at 75° C. under carbon monoxide atmosphere for 16 hours. The reaction mixture was cooled, filtered through a pad of Celite eluting with methanol and the filtrate was concentrated in vacuo. Silica gel chromatography (30-80% ethyl acetate/petroleum ether) provided methyl 4-[[2-fluoro-6-[2-methoxy-4-(trifluoromethoxy)phenoxy]-4-(trifluoromethyl)benzoyl]amino]-5-methyl-pyridine-2-carboxylate (346 mg, 58%) as a pale yellow oil. ESI-MS m/z calc. 562.10, found 563.0 (M+1)+; retention time (Method F): 1.05 minutes (1.5 minute run).

Step 3: 4-[[2-Fluoro-6-[2-methoxy-4-(trifluoromethoxy)phenoxy]-4-(trifluoromethyl)benzoyl]amino]-5-methyl-pyridine-2-carboxamide (153)

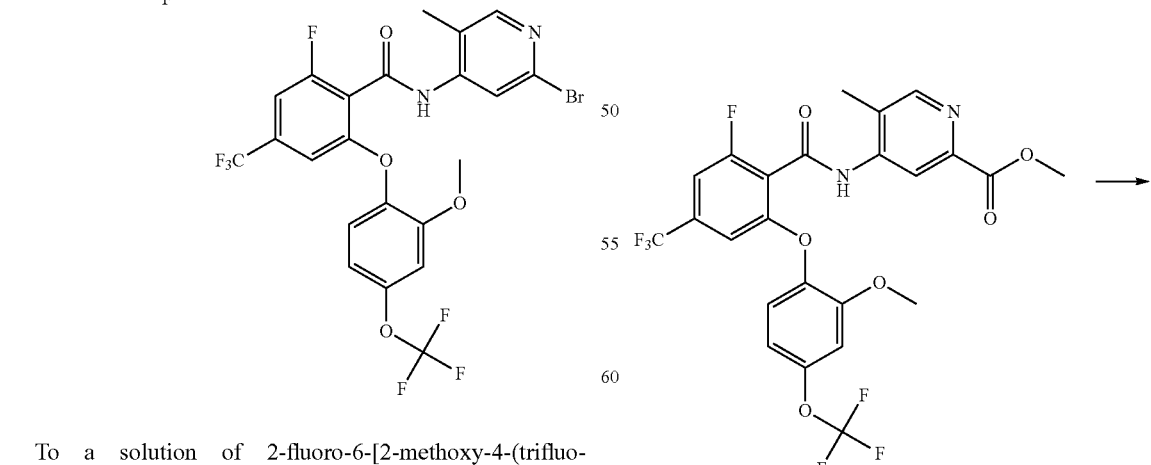

349
-continued

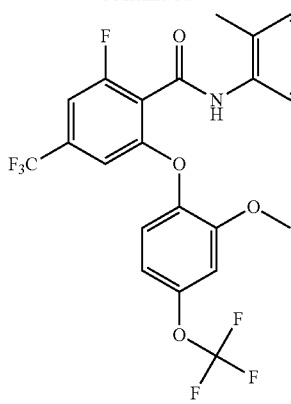

A mixture of methyl 4-[[2-fluoro-6-[2-methoxy-4-(trifluoromethoxy)phenoxy]-4-(trifluoromethyl)benzoyl]amino]-5-methyl-pyridine-2-carboxylate (28.5 mg, 0.051 mmol) and ammonia (1.4 mL of 4 M in methanol, 5.6 mmol) was stirred at room temperature for 72 hours. The reaction mixture was concentrated in vacuo and purified by HPLC (37-100% acetonitrile/0.1% ammonium hydroxide) to provide 4-[[2-fluoro-6-[2-methoxy-4-(trifluoromethoxy)phenoxy]-4-(trifluoromethyl)benzoyl]amino]-5-methyl-pyridine-2-carboxamide (5 mg, 18%) as a white solid. ESI-MS m/z calc. 547.10, found 548.0 (M+1)+; retention time (Method E): 3.45 minutes (5 minute run). $^1$H NMR (400 MHz, DMSO-d6) δ 10.55 (s, 1H), 8.48 (s, 2H), 8.06 (d, J=2.8 Hz, 1H), 7.79-7.55 (m, 2H), 7.45-7.22 (m, 2H), 7.05 (ddd, J=8.9, 2.8, 1.3 Hz, 1H), 6.84 (s, 1H), 3.81 (s, 3H), 2.31 (s, 3H) ppm.

Example 54

5-[[2,4-Dichloro-6-[2-(trideuteriomethoxy)-4-(trifluoromethoxy)phenoxy]benzoyl]amino]pyridine-2-carboxamide (183)

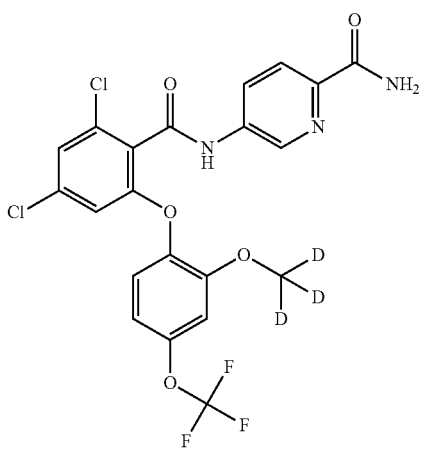 [SMILES: [2H]C([2H])([2H])Oc1cc(OC(F)(F)F)ccc1Oc1cc(Cl)cc(Cl)c1C(=O)Nc1ccc(C(N)=O)nc1]

350

Step 1: 2,4-Dichloro-6-fluoro-benzoic acid

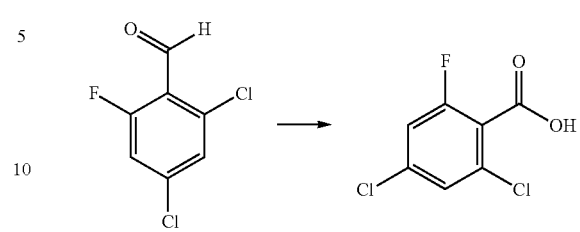

To a solution of 2,4-dichloro-6-fluoro-benzaldehyde (1.0 g, 5.2 mmol), 2-methyl-2-butene (1.8 g, 2.7 mL, 26 mmol) and sodium dihydrogen phosphate hydrate (2.14 g, 15.5 mmol) in tert-BuOH (5.0 mL)/acetonitrile (3.25 mL)/water (5.0 mL) at 0° C. was added sodium chlorite (1.41 g, 15.5 mmol). The reaction mixture was at this temperature for 1 hour, then acidified with 1 M HCl (50 mL) and extracted with ethyl acetate (3×). The combined organics were washed with 1 M HCl and brine, dried over $Na_2SO_4$, filtered and concentrated in vacuo. Then solid was triturated with 20% diethyl ether/hexane, filtered and washing with additional 20% diethyl ether/hexane to provide 2,4-dichloro-6-fluoro-benzoic acid (700 mg, 65%) as a white solid. $^1$H NMR (400 MHz, DMSO-d6) δ 14.29 (br s, 1H), 7.70-7.63 (m, 2H) ppm.

Step 2: 2,4-Dichloro-6-fluoro-benzoyl chloride

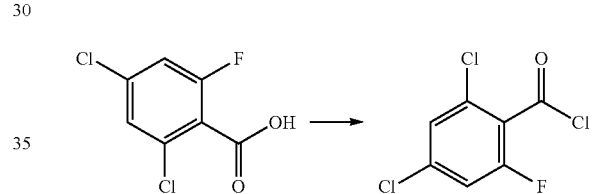

To a solution of 2,4-dichloro-6-fluoro-benzoic acid (5.1 g, 24.4 mmol) and DMF (173 μL, 2.23 mmol) in dichloromethane (51 mL) at 0° C. was added oxalyl chloride (10.2 mL, 117 mmol) dropwise. The mixture was stirred at room temperature for 5 hours under $N_2$ atmosphere. Conversion was monitored by UPLC via test for morpholine adduct formation. The solvent was evaporated in vacuo to provide 2,4-dichloro-6-fluoro-benzoyl chloride.

Step 3: 5-[(2,4-Dichloro-6-fluoro-benzoyl)amino]pyridine-2-carboxamide

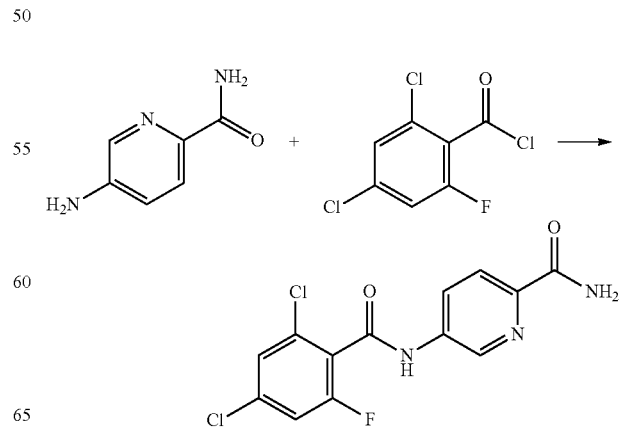

To a solution of 2,4-dichloro-6-fluoro-benzoyl chloride (2.5 g, 11.0 mmol) and DIEA (4.8 mL, 27 mmol) in 1-methyl-pyrrolidin-2-one (25 mL) at 0° C. was added a solution of 5-aminopyridine-2-carboxamide (1.51 g, 11.0 mmol) in dichloromethane (12.5 mL) dropwise. The reaction was allowed to warm to room temperature and stirred for 16 hours. The reaction mixture was diluted with water (20 mL) and the resulting suspension was filtered to provide 5-[(2,4-dichloro-6-fluoro-benzoyl)amino]pyridine-2-carboxamide (1.2 g, 33%). ESI-MS m/z calc. 326.99, found 328.1 (M+1)+; retention time (Method B): 1.16 minutes (3 minute run). $^1$H NMR (400 MHz, DMSO-d6) δ 11.34 (s, 1H), 8.88-8.82 (m, 1H), 8.29 (dd, J=8.5, 2.5 Hz, 1H), 8.12-8.01 (m, 2H), 7.76 (dq, J=4.2, 2.0 Hz, 2H), 7.58 (s, 1H) ppm.

Step 4: 5-[[2,4-Dichloro-6-[2-(trideuteriomethoxy)-4-(trifluoromethoxy)phenoxy]benzoyl]amino]pyridine-2-carboxamide (183)

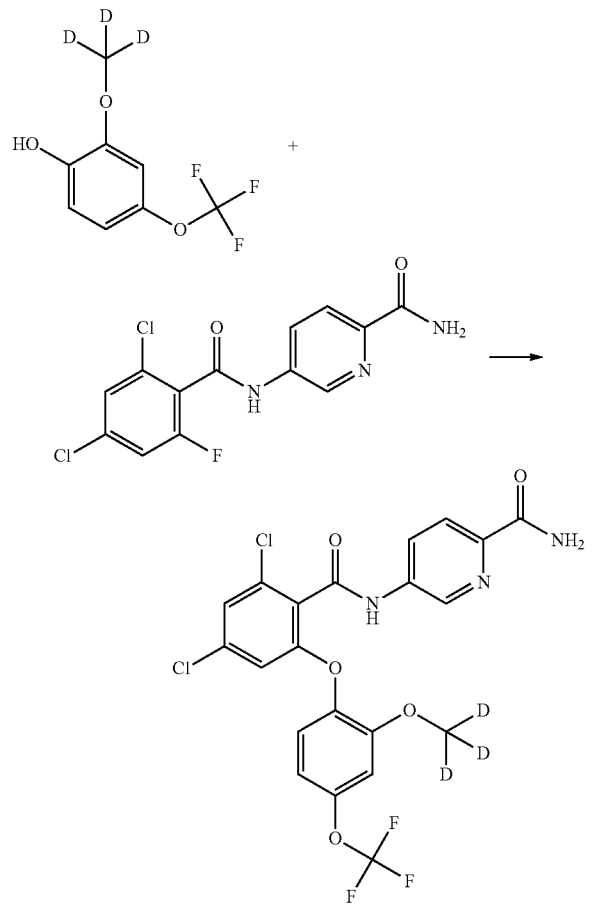

To a solution of 5-[(2,4-dichloro-6-fluoro-benzoyl) amino]pyridine-2-carboxamide (44 mg, 0.13 mmol) in DMF (1 mL) was added 2-(trideuteriomethoxy)-4-(trifluoromethoxy)phenol (28 mg, 0.13 mmol) followed by K$_2$CO$_3$ (56 mg, 0.40 mmol). The reaction was heated at 80° C. for 1 hour. The reaction was diluted with DMSO (0.5 mL), filtered and purified by HPLC (1-99% acetonitrile/5 mM HCl) to provide 5-[[2,4-dichloro-6-[2-(trideuteriomethoxy)-4-(trifluoromethoxy)phenoxy]benzoyl]amino]pyridine-2-carboxamide (41 mg, 58%). ESI-MS m/z calc. 518.05, found 518.9 (M+1)+; retention time (Method B): 1.83 minutes (3 minute run). $^1$H NMR (400 MHz, DMSO-d6) δ 11.23 (s, 1H), 8.86 (dd, J=2.5, 0.7 Hz, 1H), 8.27 (dd, J=8.6, 2.5 Hz, 1H), 8.13-7.99 (m, 2H), 7.61-7.48 (m, 2H), 7.27 (d, J=8.8 Hz, 1H), 7.19 (d, J=2.8 Hz, 1H), 7.00 (m, 1H) 6.76 (d, J=1.8 Hz, 1H) ppm.

Example 55

4-[[2,4-Dichloro-6-[2-(trideuteriomethoxy)-4-(trifluoromethoxy)phenoxy]benzoyl]amino]pyridine-2-carboxamide (179)

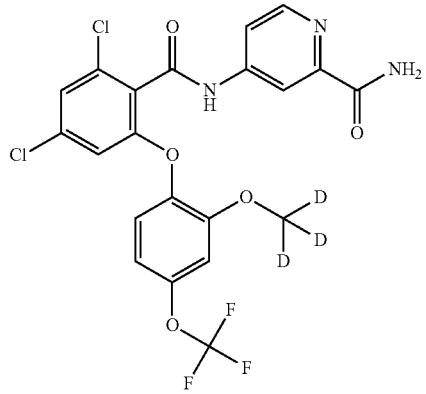 [SMILES: [2H]C([2H])([2H])Oc1cc(OC(F)(F)F)ccc1Oc1cc(Cl)cc(Cl)c1C(=O)Nc1ccnc(C(N)=O)c1]

This compound was made in an analogous fashion to Example 54 from 4-[(2,4-dichloro-6-fluoro-benzoyl)amino]pyridine-2-carboxamide and 2-(trideuteriomethoxy)-4-(trifluoromethoxy)phenol. The yield of the desired product after HPLC purification was 10 mg (13%). ESI-MS m/z calc. 518.04, found 518.9 (M+1)+; retention time (Method B): 1.6 minutes (3 minute run). $^1$H NMR (400 MHz, DMSO-d6) δ 11.31 (s, 1H), 8.54 (d, J=5.5 Hz, 1H), 8.32 (d, J=2.1 Hz, 1H), 8.10 (d, J=2.8 Hz, 1H), 7.82 (dd, J=5.5, 2.2 Hz, 1H), 7.66 (d, J=2.9 Hz, 1H), 7.54 (d, J=1.8 Hz, 1H), 7.28 (d, J=8.8 Hz, 1H), 7.20 (d, J=2.7 Hz, 1H), 7.01 (ddd, J=8.8, 2.7, 1.2 Hz, 1H), 6.76 (d, J=1.8 Hz, 1H) ppm.

Example 56

N-(3-Carbamoyl-4-fluoro-phenyl)-3-fluoro-5-[4-(trifluoromethoxy)phenoxy]-2-(trifluoromethyl)pyridine-4-carboxamide (62)

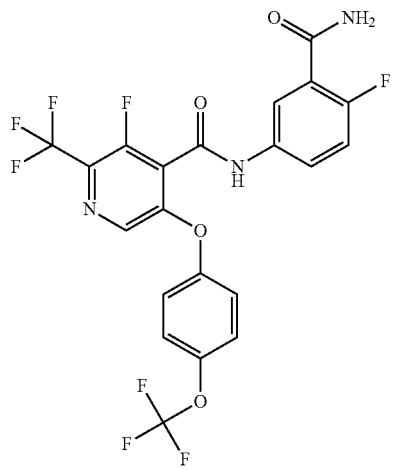 [SMILES: NC(=O)c1cc(NC(=O)c2c(Oc3ccc(OC(F)(F)F)cc3)cnc(C(F)(F)F)c2F)ccc1F]

Step 1: Ethyl 3,5-difluoro-2-(trifluoromethyl)pyridine-4-carboxylate

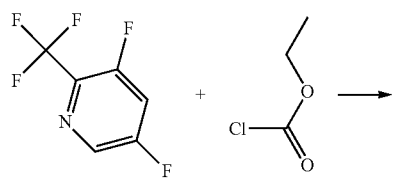

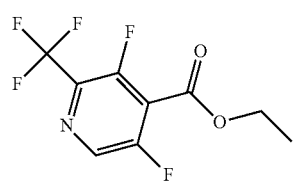

A solution of 3,5-difluoro-2-(trifluoromethyl)pyridine (9.0 g, 49 mmol) in THF (100 mL) was cooled to −78° C. and treated with LDA (27 mL of 2 M in ethylbenzene/THF/heptane, 54.00 mmol) while maintaining the internal reaction temperature below −65° C. The reaction mixture was stirred at −78° C. for 40 minutes followed by the dropwise addition of chloroethylformate (6.1 mL, 63.8 mmol) over 10 minutes while maintaining internal reaction temperature below −65° C. The mixture was stirred at −78° C. for 30 minutes then allowed to warm to room temperature over 1 hour. The mixture was quenched by addition of saturated aqueous NH$_4$Cl and diluted with ethyl acetate (100 mL). The organic layer was separated and washed with water and brine, dried over MgSO$_4$, filtered and concentrated in vacuo. Silica gel chromatography (0-5% ethyl acetate/petroleum ether) provided ethyl 3,5-difluoro-2-(trifluoromethyl)pyridine-4-carboxylate (7.4 g, 59%) as a pale yellow oil. $^1$H NMR (400 MHz, DMSO-d6) δ 8.89 (s, 1H), 4.46 (q, J=7.1 Hz, 2H), 1.33 (t, J=7.1 Hz, 3H) ppm.

Step 2: Ethyl 3-fluoro-5-[4-(trifluoromethoxy)phenoxy]-2-(trifluoromethyl)pyridine-4-carboxylate

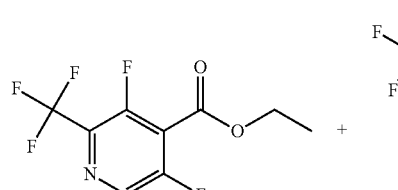

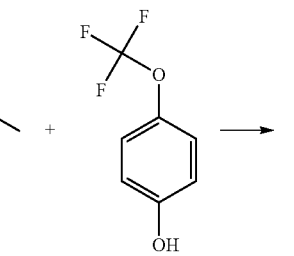

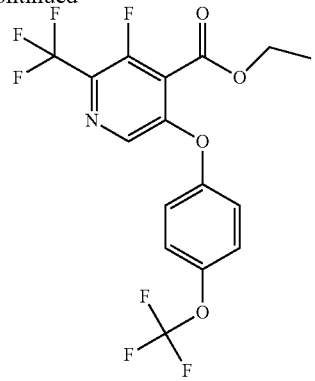

A flask charged with ethyl 3,5-difluoro-2-(trifluoromethyl)pyridine-4-carboxylate (1.87 g, 7.33 mmol) and 4-(trifluoromethoxy)phenol (950 μL, 7.33 mmol) in DMA (20 mL) was cooled to 0° C. and treated with Cs$_2$CO$_3$ (4.78 g, 14.7 mmol) in one portion. The reaction mixture was allowed to warm to room temperature and stirred for 1 hour. The reaction mixture was diluted with water and extracted with ethyl acetate. The organic layer was washed with brine, dried over MgSO$_4$, filtered and concentrated in vacuo. Silica gel chromatography (0-10% ethyl acetate/hexanes) provided ethyl 3-fluoro-5-[4-(trifluoromethoxy)phenoxy]-2-(trifluoromethyl)pyridine-4-carboxylate (2.22 g, 73%) ESI-MS m/z calc. 413.05, found 414.2 (M+1)+; retention time (Method B): 2.16 minutes (3 minute run). $^1$H NMR (400 MHz, DMSO-d6) δ 8.50 (s, 1H), 7.47 (d, J=8.9 Hz, 2H), 7.38-7.31 (m, 2H), 4.31 (q, J=7.1 Hz, 2H), 1.18 (t, J=7.1 Hz, 3H) ppm.

Step 3: 3-Fluoro-5-[4-(trifluoromethoxy)phenoxy]-2-(trifluoromethyl)pyridine-4-carboxylic acid

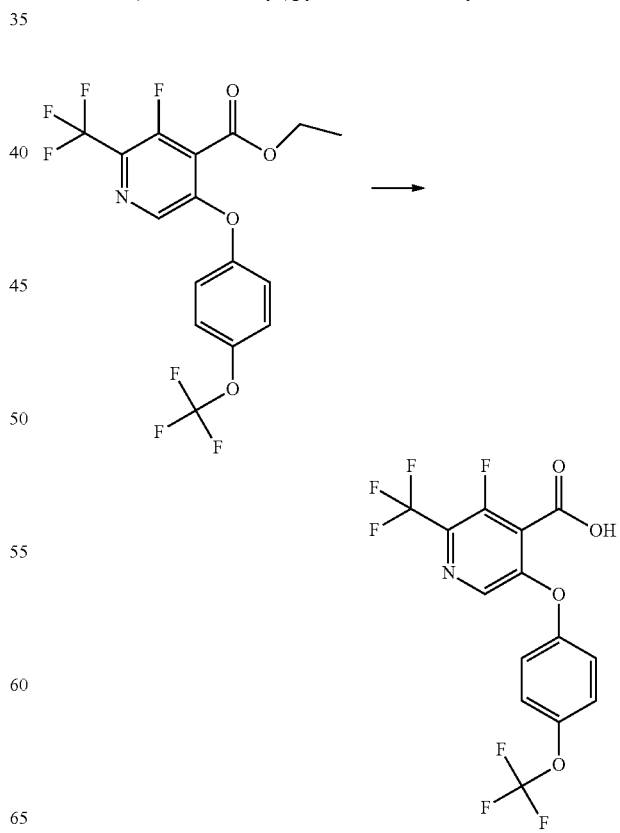

To a solution of ethyl 3-fluoro-5-[4-(trifluoromethoxy)phenoxy]-2-(trifluoromethyl)pyridine-4-carboxylate (2.22 g, 5.37 mmol) in THF (22 mL) was added aqueous NaOH (20 mL of 3 M, 60 mmol) followed by solid NaOH (500 mg, 12.5 mmol). The reaction mixture was stirred for 4 hours at room temperature then cooled to 0° C. and slowly acidified with 6 M HCl. The resulting precipitate was filtered and washed with water. The aqueous filtrated was extracted with dichloromethane and combined with the precipitate. The organic layer was dried over MgSO$_4$, filtered and concentrated in vacuo to obtain 3-fluoro-5-[4-(trifluoromethoxy)phenoxy]-2-(trifluoromethyl)pyridine-4-carboxylic acid (1.97 g, 95%) ESI-MS m/z calc. 385.02, found 386.0 (M+1)+; retention time (method B): 1.73 minutes (3 minute run).

Step 4: 3-Fluoro-5-[4-(trifluoromethoxy)phenoxy]-2-(trifluoromethyl)pyridine-4-carbonyl chloride

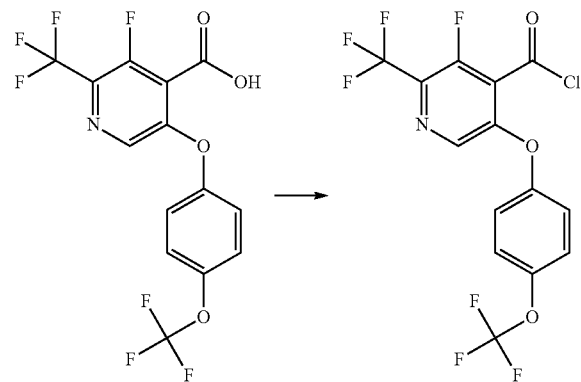 [SMILES: O=C(O)c1c(Oc2ccc(OC(F)(F)F)cc2)cnc(C(F)(F)F)c1F ; O=C(Cl)c1c(Oc2ccc(OC(F)(F)F)cc2)cnc(C(F)(F)F)c1F]

To a solution of 3-fluoro-5-[4-(trifluoromethoxy)phenoxy]-2-(trifluoromethyl)pyridine-4-carboxylic acid (200 mg, 0.519 mmol) and DMF (10 μL, 0.13 mmol) in dichloromethane (2 mL) at 0° C. was added oxalyl chloride (70 μL, 0.80 mmol) dropwise. The reaction mixture was stirred at room temperature for 30 minutes. Conversion was monitored by UPLC via test for morpholine adduct formation. The solvent was evaporated under reduced pressure to afford 3-fluoro-5-[4-(trifluoromethoxy)phenoxy]-2-(trifluoromethyl)pyridine-4-carbonyl chloride.

Step 5: N-(3-Carbamoyl-4-fluoro-phenyl)-3-fluoro-5-[4-(trifluoromethoxy)phenoxy]-2-(trifluoromethyl)pyridine-4-carboxamide (62)

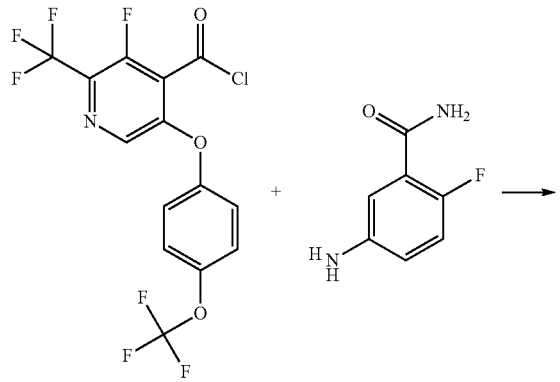

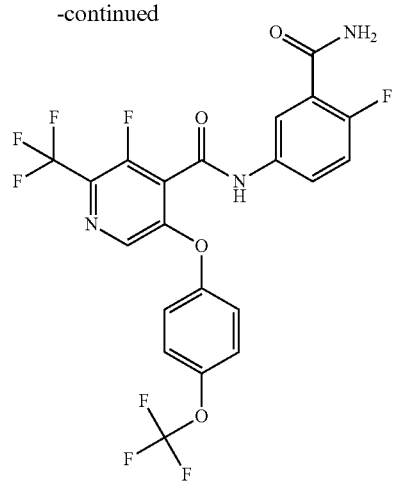

A solution of 5-amino-2-fluoro-benzamide (78 mg, 0.51 mmol) and DIEA (250 μL, 1.44 mmol) in THF (3 mL) at 0° C. was treated with a solution of 3-fluoro-5-[4-(trifluoromethoxy)phenoxy]-2-(trifluoromethyl)pyridine-4-carbonyl chloride (200 mg, 0.496 mmol) in THF (3 mL)/dichloromethane (2 mL) under N$_2$ atmosphere. The reaction mixture was allowed to warm to room temperature and stirred for 1 hour. The mixture was diluted with water and extracted with dichloromethane. The organic layer was washed with 1 M HCl (2×), dried over MgSO$_4$, filtered and concentrated in vacuo. Silica gel chromatography (0-80% ethyl acetate/hexanes) provided N-(3-carbamoyl-4-fluoro-phenyl)-3-fluoro-5-[4-(trifluoromethoxy)phenoxy]-2-(trifluoromethyl)pyridine-4-carboxamide (68 mg, 26%). ESI-MS m/z calc. 521.06, found 522.1 (M+1)+; retention time (Method B): 1.74 minutes (3 minute run). $^1$H NMR (400 MHz, DMSO-d6) δ 11.18 (s, 1H), 8.43 (s, 1H), 7.90 (dd, J=6.4, 2.8 Hz, 1H), 7.78-7.67 (m, 3H), 7.50-7.43 (m, 2H), 7.41-7.35 (m, 2H), 7.30 (dd, J=10.1, 8.9 Hz, 1H) ppm.

Example 57

N-(2-Carbamoyl-4-pyridyl)-3-fluoro-5-[4-(trifluoromethoxy)phenoxy]-2-(trifluoromethyl)pyridine-4-carboxamide (61)

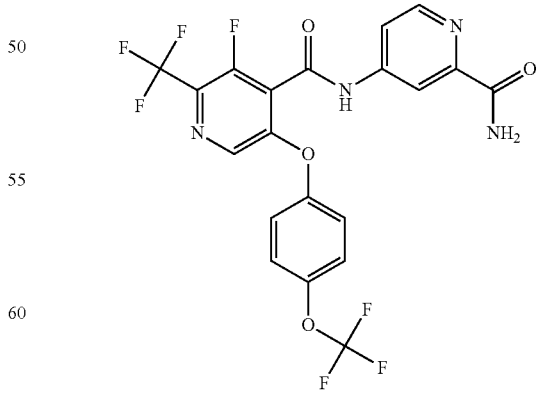

This compound was made in an analogous fashion to Example 56, except employing 4-aminopyridine-2-carboxamide in the amide formation step (Step 5). The yield of the desired product after purification was 76 mg (30%). ESI-MS m/z calc. 504.07, found 505.1 (M+1)+; retention time (Method B): 1.74 minutes (3 minute run). ¹H NMR (400 MHz, DMSO-d6) δ 11.59 (s, 1H), 8.57 (d, J=5.5 Hz, 1H), 8.46 (s, 1H), 8.24 (d, J=2.1 Hz, 1H), 8.12 (d, J=2.8 Hz, 1H), 7.74 (dd, J=5.5, 2.2 Hz, 1H), 7.69 (d, J=2.7 Hz, 1H), 7.49-7.42 (m, 2H), 7.42-7.34 (m, 2H) ppm.

Example 58

5-[[2-Fluoro-6-[2-(trideuteriomethoxy)-4-(trifluoromethoxy)phenoxy]-4-(trifluoromethoxy)benzoyl]amino]pyridine-2-carboxamide (173)

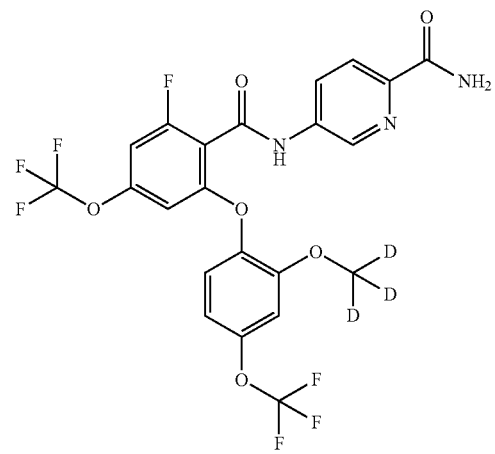 [SMILES: [2H]C([2H])([2H])Oc1cc(OC(F)(F)F)ccc1Oc1cc(OC(F)(F)F)cc(F)c1C(=O)Nc1ccc(C(N)=O)nc1]

Step 1: Methyl 2,6-difluoro-4-(trifluoromethoxy)benzoate

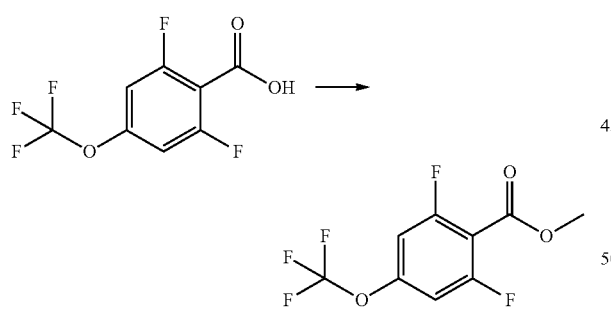

Sulfuric acid (300 µL, 5.63 mmol) was added to a solution of 2,6-difluoro-4-(trifluoromethoxy)benzoic acid (677 mg, 2.80 mmol) in methanol (6.5 mL) and the reaction was stirred at 65° C. for 14 hours. Additional sulfuric acid (300 µL, 5.628 mmol) was added to the reaction and stirred at 65° C. for an additional 17 hours. The reaction was cooled to room temperature and partitioned between water and dichloromethane. The organic layer was washed with saturated aqueous NaHCO₃ and brine dried over Na₂SO₄, filtered and carefully concentrated in vacuo at low temperature (caution: product is volatile) to provide methyl 2,6-difluoro-4-(trifluoromethoxy)benzoate (580 mg, 81%) as a colorless liquid. ¹H NMR (400 MHz, DMSO-d6) δ 7.56-7.45 (m, 2H), 3.91 (s, 3H) ppm.

Step 2: Methyl 2-fluoro-6-[2-(trideuteriomethoxy)-4-(trifluoromethoxy)phenoxy]-4-(trifluoromethoxy)benzoate

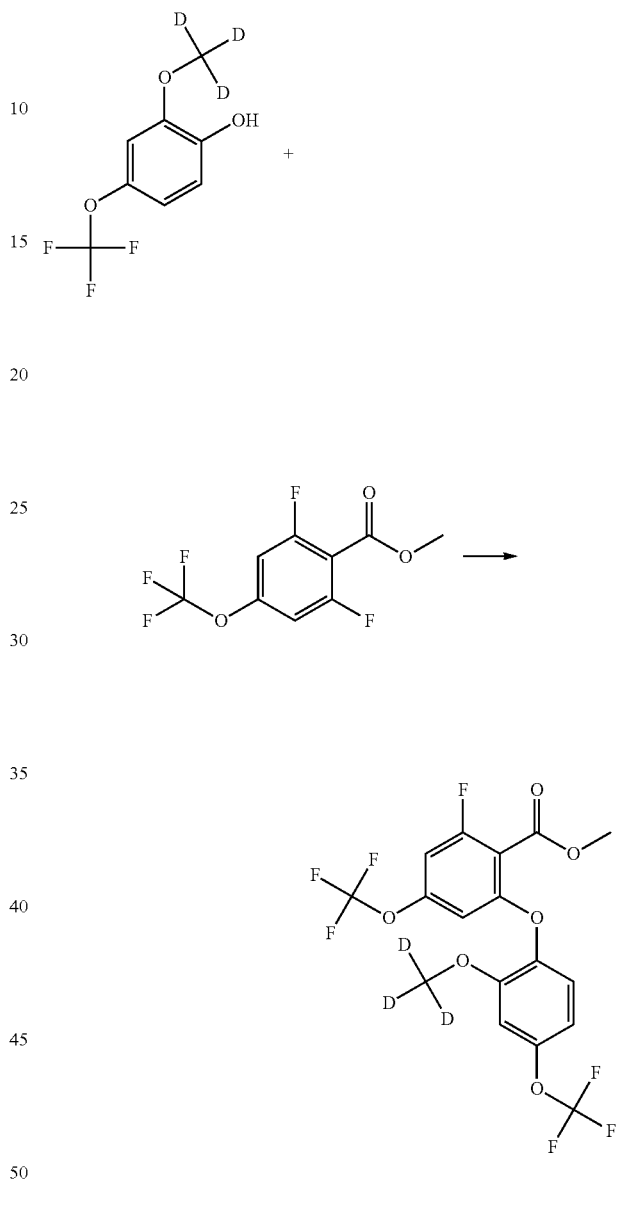

Methyl 2,6-difluoro-4-(trifluoromethoxy)benzoate (550 mg, 2.15 mmol), 2-(trideuteriomethoxy)-4-(trifluoromethoxy)phenol (461 mg, 2.18 mmol) and Cs₂CO₃ (2.38 g, 7.29 mmol) in DMF (7 mL) were stirred at 75° C. for 20 minutes. The reaction was diluted with ethyl acetate and washed with water and brine, dried over Na₂SO₄, filtered and concentrated in vacuo. Silica gel chromatography (0-30% ethyl acetate/hexanes) provided methyl 2-fluoro-6-[2-(trideuteriomethoxy)-4-(trifluoromethoxy)phenoxy]-4-(trifluoromethoxy)benzoate (700 mg, 73%) as a colourless viscous liquid. ESI-MS m/z calc. 447.06, found 448.0 (M+1)+; retention time (Method C): 3.06 minutes (5 minute run).

Step 3: 2-Fluoro-6-[2-(trideuteriomethoxy)-4-(trifluoromethoxy)phenoxy]-4-(trifluoromethoxy)benzoic acid

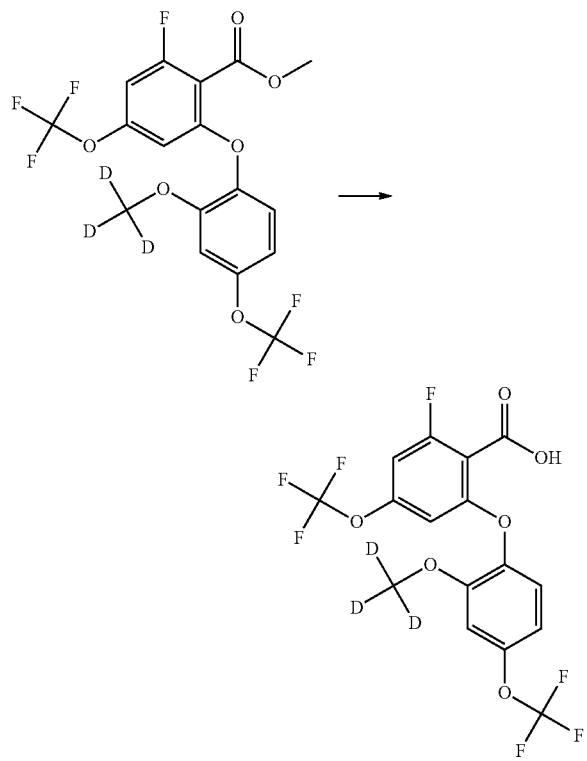

A solution of methyl 2-fluoro-6-[2-(trideuteriomethoxy)-4-(trifluoromethoxy)phenoxy]-4-(trifluoromethoxy)benzoate (660 mg, 1.48 mmol) in methanol (6 mL) was treated with aqueous NaOH (6 mL of 1 M, 6 mmol). The reaction was stirred at room temperature for 2 hours. Additional aqueous NaOH was added (4.5 mL of 1 M, 4.5 mmol) and the reaction was heated at 60° C. for 4.5 hours. The reaction was acidified to pH-1 with 12 M HCl, then diluted with water and extracted with ethyl acetate. The organic layer was washed with brine, dried over $Na_2SO_4$, filtered and concentrated in vacuo to provide 2-fluoro-6-[2-(trideuteriomethoxy)-4-(trifluoromethoxy)phenoxy]-4-(trifluoromethoxy)benzoic acid (592 mg, 92%) as a viscous yellow liquid. ESI-MS m/z calc. 433.05, found 434.1 (M+1)+; retention time (Method A): 0.71 minutes (1 minute run).

Step 4: 2-Fluoro-6-[2-(trideuteriomethoxy)-4-(trifluoromethoxy)phenoxy]-4-(trifluoromethoxy)benzoyl chloride

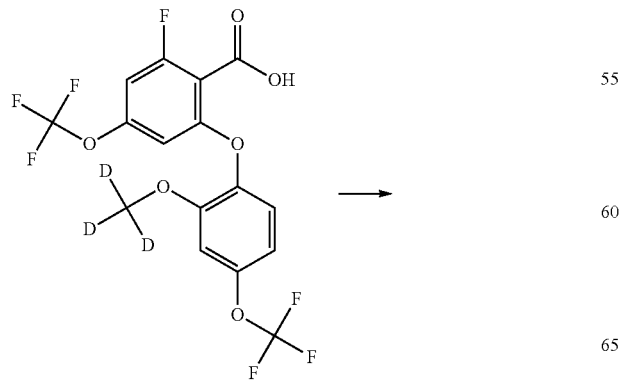

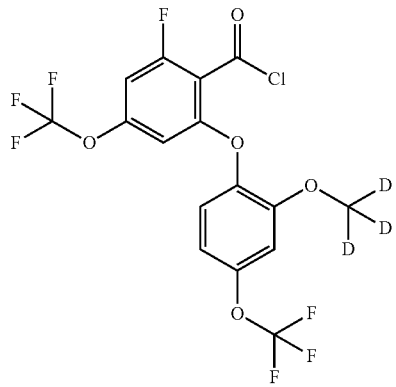

To a solution of 2-fluoro-6-[2-(trideuteriomethoxy)-4-(trifluoromethoxy)phenoxy]-4-(trifluoromethoxy)benzoic acid (200 mg, 0.462 mmol) and DMF (20 μL, 0.26 mmol) in dichloromethane (2 mL) at 0° C. was added oxalyl chloride (300 μL, 3.44 mmol) dropwise under $N_2$ atmosphere. The ice bath was removed after 10 minutes and the reaction allowed to warm to room temperature over 20 minutes. Conversion was monitored by UPLC via test for piperidine adduct formation. The solvent was evaporated under reduced pressure to afford 2-fluoro-6-[2-(trideuteriomethoxy)-4-(trifluoromethoxy)phenoxy]-4-(trifluoromethoxy)benzoyl chloride.

Step 5: 5-[[2-Fluoro-6-[2-(trideuteriomethoxy)-4-(trifluoromethoxy)phenoxy]-4-(trifluoromethoxy)benzoyl]amino]pyridine-2-carboxamide (173)

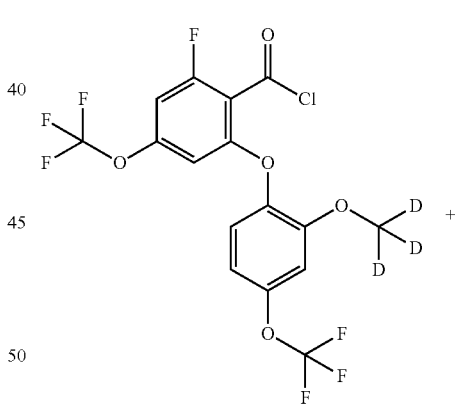

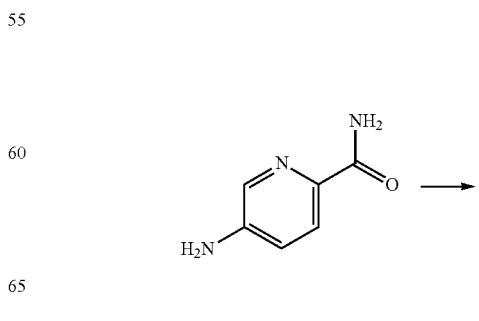

-continued

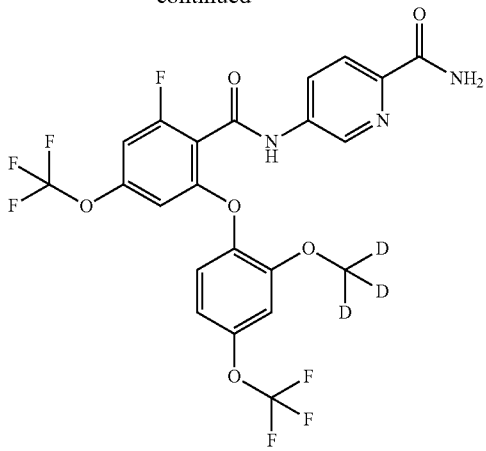

To a stirring slurry of 5-aminopyridine-2-carboxamide (47 mg, 0.35 mmol) in dichloromethane (1 mL) and DIEA (80 µL, 0.46 mmol) at 0° C. was added a slurry of cold 2-fluoro-6-[2-(trideuteriomethoxy)-4-(trifluoromethoxy) phenoxy]-4-(trifluoromethoxy)benzoyl chloride (104 mg, 0.230 mmol) in dichloromethane (1 mL) dropwise. The reaction mixture was removed from ice bath after 10 minutes and stirred at room temperature for 18 hours. The reaction was concentrated in vacuo and purified by HPLC (10-99% acetonitrile/5 mM HCl) to provide 5-[[2-fluoro-6-[2-(trideuteriomethoxy)-4-(trifluoromethoxy)phenoxy]-4-(trifluoromethoxy)benzoyl]amino]pyridine-2-carboxamide (24 mg, 19%). ESI-MS m/z calc. 552.10, found 552.9 (M+1)+; retention time (Method C): 2.57 minutes. $^1$H NMR (400 MHz, DMSO-d6) δ 11.26 (s, 1H), 8.84 (s, 1H), 8.26 (dd, J=8.7, 2.5 Hz, 1H), 8.07-7.95 (m, 2H), 7.55 (s, 1H), 7.43-7.25 (m, 2H), 7.21 (d, J=2.8 Hz, 1H), 7.08-6.93 (m, 1H), 6.56 (s, 1H) ppm.

Example 59

4-[[2-Fluoro-6-[2-(trideuteriomethoxy)-4-(trifluoromethoxy)phenoxy]-4-(trifluoromethoxy)benzoyl]amino]pyridine-2-carboxamide (172)

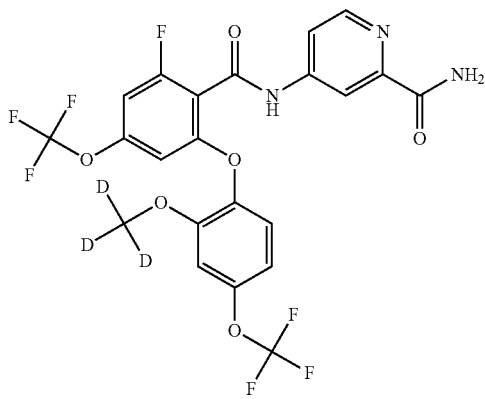 [SMILES: [2H]C([2H])([2H])Oc1cc(OC(F)(F)F)ccc1Oc1cc(OC(F)(F)F)cc(F)c1C(=O)Nc1ccnc(C(N)=O)c1]

A vial was charged with 2-fluoro-6-[2-(trideuteriomethoxy)-4-(trifluoromethoxy)phenoxy]-4-(trifluoromethoxy)benzoic acid (prepared as described in Example 58, 100 mg, 0.231 mmol), 4-[(Z)-[(tert-butylamino)-phenylsulfanyl-methylene]amino]pyridine-2-carboxamide (prepared as described in Preparation 1, 81 mg, 0.25 mmol), and tris[(Z)-1-methyl-3-oxo-but-1-enoxy]iron (8.5 mg, 0.024 mmol) in 2-propanol (1.5 mL), and was heated at 80° C. under an atmosphere of air for 15 hours. The reaction mixture was cooled to room temperature, diluted with ethyl acetate and 1 M HCl. The two layers were separated and the aqueous layer was extracted with again with ethyl acetate. The combined organic layers was dried over Na$_2$SO$_4$, filtered and concentrated in vacuo. HPLC purification (1-99% acetonitrile/5 mM HCl) provided 4-[[2-fluoro-6-[2-(trideuteriomethoxy)-4-(trifluoromethoxy)phenoxy]-4-(trifluoromethoxy)benzoyl]amino]pyridine-2-carboxamide (40 mg, 31%) as a white solid. ESI-MS m/z calc. 552.10, found 553.0 (M+1)+; retention time (Method C): 2.56 minutes (5 minutes run). $^1$H NMR (400 MHz, DMSO-d6) δ 11.34 (s, 1H), 8.54 (d, J=5.4 Hz, 1H), 8.30 (d, J=2.2 Hz, 1H), 8.09 (d, J=2.6 Hz, 1H), 7.82 (dd, J=5.5, 2.2 Hz, 1H), 7.65 (d, J=2.8 Hz, 1H), 7.48-7.27 (m, 2H), 7.21 (d, J=2.8 Hz, 1H), 7.08-6.93 (m, 1H), 6.56 (s, 1H) ppm.

Example 60

4-[[4-Chloro-2-fluoro-6-[2-methoxy-4-(trifluoromethoxy)phenoxy]benzoyl]amino]-5-methyl-pyridine-2-carboxamide (130)

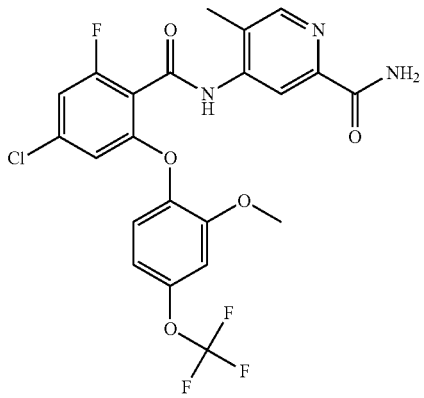 [SMILES: COc1cc(OC(F)(F)F)ccc1Oc1cc(Cl)cc(F)c1C(=O)Nc1cc(C(N)=O)ncc1C]

Step 1: 4-Chloro-2-fluoro-6-[2-methoxy-4-(trifluoromethoxy)phenoxy]benzaldehyde

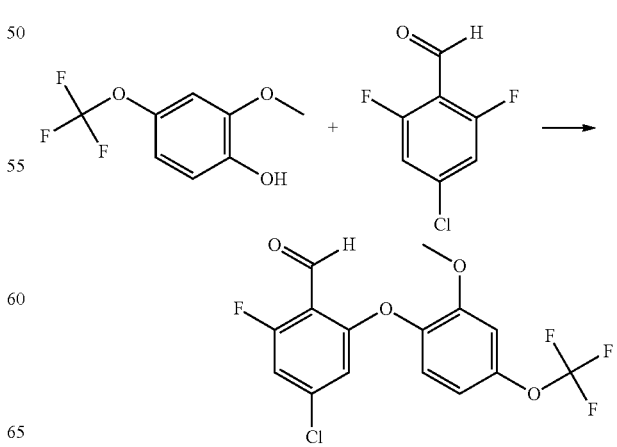

2-Methoxy-4-(trifluoromethoxy)phenol (2.3 g, 11.1 mmol), Cs$_2$CO$_3$ (4.8 g, 14.7 mmol) and 4-chloro-2,6-difluoro-benzaldehyde (2.0 g, 11.3 mmol) were combined in DMF (12 mL) and stirred for 16 hours. The mixture was concentrated in vacuo and the residue was partitioned between water and dichloromethane. The organic layer was concentrated and purified by silica gel chromatography (0-50% ethyl acetate/petroleum ether) to provide 4-chloro-2-fluoro-6-[2-methoxy-4-(trifluoromethoxy)phenoxy]benzaldehyde (3.4 g, 84%) as a colorless oil. ESI-MS m/z calc. 364.01, found 365.1 (M+1)+; retention time (Method F): 1.08 minutes (1.5 minute run).

Step 2: 4-Chloro-2-fluoro-6-[2-methoxy-4-(trifluoromethoxy)phenoxy]benzoic acid

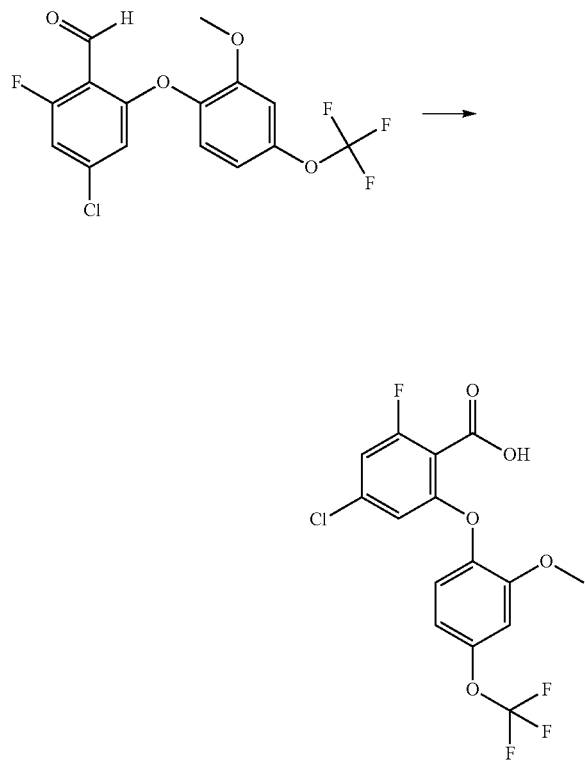

A suspension of 4-chloro-2-fluoro-6-[2-methoxy-4-(trifluoromethoxy)phenoxy]benzaldehyde (3.40 g, 9.32 mmol) and sodium dihydrogen phosphate hydrate (1.3 g, 10.8 mmol) in tert-butyl alcohol (20 mL)/water (10 mL) was cooled to 0° C. and treated with a solution of 2-methyl-2-butene (14 mL of 2 M in THF, 28 mmol) followed by the portionwise addition of sodium chlorite (1.3 g, 11.50 mmol) over 30 minutes. The mixture was allowed to warm to room temperature and stirred for 16 hours. The reaction mixture was acidified to pH1-2 using 2 M HCl and partitioned with dichloromethane. The organic layer was dried (phase separation cartridge) and concentrated in vacuo to afford 4-chloro-2-fluoro-6-[2-methoxy-4-(trifluoromethoxy)phenoxy]benzoic acid (3.82 g, 108%) as a white solid. ESI-MS m/z calc. 380.01, found 379.1 (M−1)−; retention time (Method F): 0.71 minutes (1.5 minutes).

Step 3: 4-Chloro-2-fluoro-6-(2-methoxy-4-(trifluoromethoxy)phenoxy)benzoyl chloride

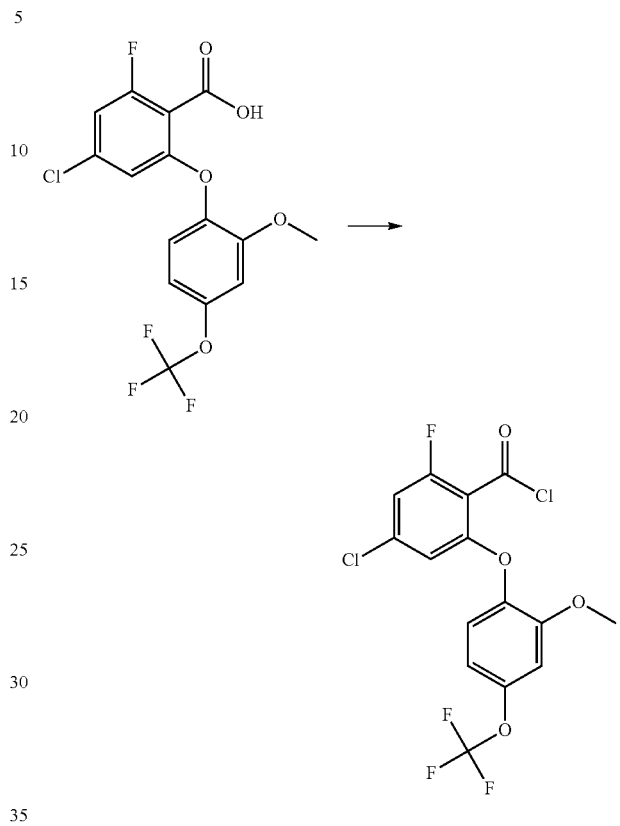

To an ice-cooled solution of 4-chloro-2-fluoro-6-[2-methoxy-4-(trifluoromethoxy)phenoxy]benzoic acid (1.5 g, 3.7 mmol) in dichloromethane (20 mL) was added DMF (33 µL, 0.43 mmol) and oxalyl chloride (1.1 mL, 12.6 mmol). The reaction was warmed to room temperature and stirred for 3.5 hours. The reaction mixture was concentrated in vacuo to provide 4-chloro-2-fluoro-6-(2-methoxy-4-(trifluoromethoxy)phenoxy)benzoyl chloride.

Step 4: N-(2-Bromo-5-methyl-4-pyridyl)-4-chloro-2-fluoro-6-[2-methoxy-4-(trifluoromethoxy)phenoxy]benzamide

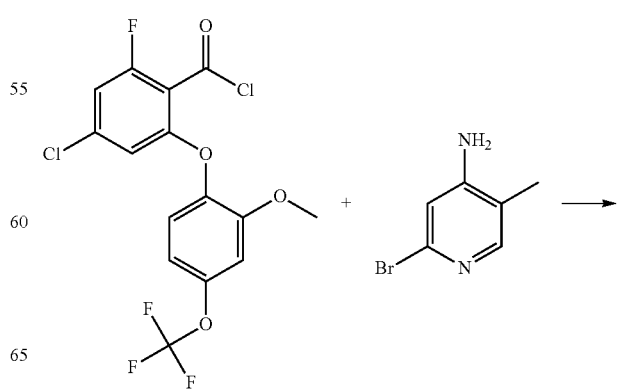

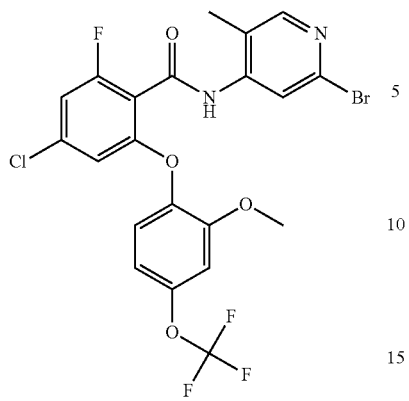

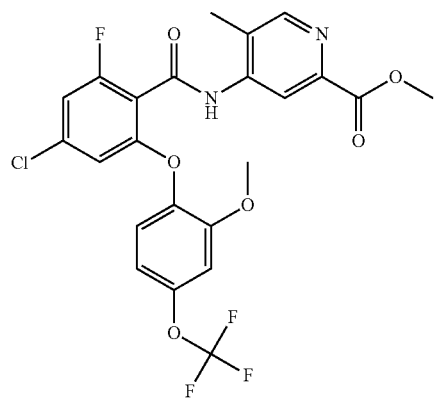

To a solution of 4-chloro-2-fluoro-6-(2-methoxy-4-(trifluoromethoxy)phenoxy)benzoyl chloride (3.7 mmol) in dichloromethane (20 mL) at 0° C. were added 2-bromo-5-methyl-pyridin-4-amine (900 mg, 4.81 mmol) and triethylamine (2.7 mL, 19 mmol). The reaction mixture was allowed to warm to room temperature and stirred for 16 hours. The mixture was diluted with water and extracted with dichloromethane. The combined organics were dried over MgSO$_4$, filtered and concentrated in vacuo. Silica gel chromatography (0-20% ethyl acetate/petroleum ether) provided N-(2-bromo-5-methyl-4-pyridyl)-4-chloro-2-fluoro-6-[2-methoxy-4-(trifluoromethoxy)phenoxy]benzamide (742 mg, 36%) as a white solid. ESI-MS m/z calc. 547.98, found 551.0 (M+1)+; retention time (Method F): 1.13 minutes (1.5 minute run).

To a solution of N-(2-bromo-5-methyl-4-pyridyl)-4-chloro-2-fluoro-6-[2-methoxy-4-(trifluoromethoxy)phenoxy]benzamide (742 mg, 1.35 mmol) in methanol (13 mL) and triethylamine (430 μL, 3.09 mmol) was added Pd(dppf)Cl$_2$·DCM (229 mg, 0.280 mmol). Carbon monoxide was bubbled through the vigorously stirring mixture for 5 minutes. The reaction mixture was heated at 75° C. under carbon monoxide atmosphere for 16 hours. The reaction mixture was filtered through a pad of Celite. The Celite was rinsed with methanol and the filtrate concentrated in vacuo. Silica gel chromatography (30-80% ethyl acetate/petroleum ether) provided methyl 4-[[4-chloro-2-fluoro-6-[2-methoxy-4-(trifluoromethoxy)phenoxy]benzoyl]amino]-5-methyl-pyridine-2-carboxylate (593 mg, 83%) as a pale yellow clear oil. ESI-MS m/z calc. 528.07, found 529.0 (M+1)+; retention time (Method F): 1.03 minutes (1.5 minute run).

Step 5: Methyl 4-[[4-chloro-2-fluoro-6-[2-methoxy-4-(trifluoromethoxy)phenoxy]benzoyl]amino]-5-methyl-pyridine-2-carboxylate Step 6: 4-[[4-Chloro-2-fluoro-6-[2-methoxy-4-(trifluoromethoxy)phenoxy]benzoyl]amino]-5-methyl-pyridine-2-carboxamide (130)

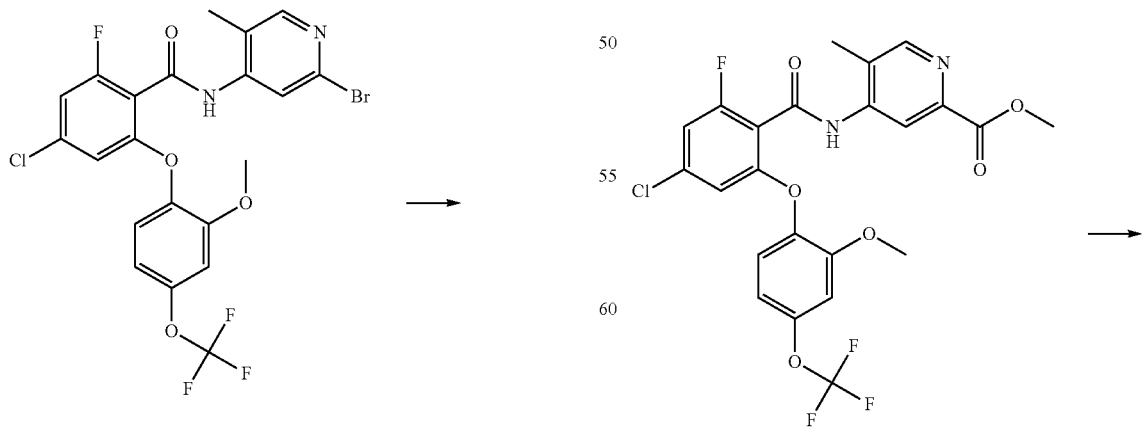

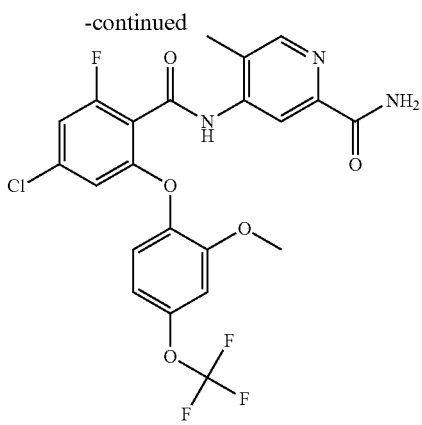

A mixture of methyl 4-[[4-chloro-2-fluoro-6-[2-methoxy-4-(trifluoromethoxy)phenoxy]benzoyl]amino]-5-methyl-pyridine-2-carboxylate (35 mg, 0.07 mmol) and ammonia (1.83 mL of 7 M in methanol, 12.81 mmol) was stirred at room temperature for 16 hours. SPM32 silica metal scavenger (150 mg) was added and the reaction was stirred for 15 minutes. The mixture was filtered and the filtrate concentrated in vacuo. Silica gel chromatography (0-100% ethyl acetate/petroleum ether) provided 4-[[4-chloro-2-fluoro-6-[2-methoxy-4-(trifluoromethoxy)phenoxy]benzoyl]amino]-5-methyl-pyridine-2-carboxamide (6.8 mg, 20%) as a white solid. ESI-MS m/z calc. 513.07, found 514.0 (M+1)+; retention time (Method E): 3.37 minutes (5 minute run). $^1$H NMR (500 MHz, DMSO-d6) δ 10.42 (s, 1H), 8.46 (s, 2H), 8.04 (d, J=2.8 Hz, 1H), 7.59 (s, 1H), 7.35 (dd, J=29.9, 8.8 Hz, 2H), 7.23 (d, J=2.7 Hz, 1H), 7.12-6.95 (m, 1H), 6.61 (s, 1H), 3.82 (s, 3H), 2.29 (s, 3H) ppm.

Example 61

5-[[4-Chloro-2-fluoro-6-[2-methoxy-4-(trifluoromethoxy)phenoxy]benzoyl]amino]pyridine-2-carboxamide (185)

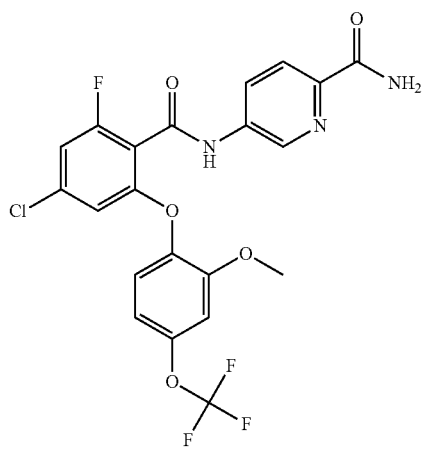 [SMILES: COc1cc(OC(F)(F)F)ccc1Oc1cc(Cl)cc(F)c1C(=O)Nc1ccc(C(N)=O)nc1]

This compound was made in an analogous fashion to N-(2-bromo-5-methyl-4-pyridyl)-4-chloro-2-fluoro-6-[2-methoxy-4-(trifluoromethoxy)phenoxy]benzamide (Example 60, step 4) except employing 5-aminopyridine-2-carboxamide in the amide formation step. The yield of the desired product after purification was 65 mg (45%). ESI-MS m/z calc. 499.06, found 499.9 (M+1)+; 497.9 (M−1)−; retention time (Method E): 3.15 minutes (5 minute run). $^1$H NMR (400 MHz, DMSO-d6) δ 11.20 (s, 1H), 8.83 (d, J=2.4 Hz, 1H), 8.24 (dd, J=8.6, 2.5 Hz, 1H), 8.06-7.97 (m, 2H), 7.54 (s, 1H), 7.39 (dd, J=8.8, 1.8 Hz, 1H), 7.28 (d, J=8.9 Hz, 1H), 7.19 (d, J=2.7 Hz, 1H), 7.03-6.95 (m, 1H), 6.64 (t, J=1.5 Hz, 1H), 3.77 (s, 3H) ppm.

Example 62

4-[[4-Chloro-2-fluoro-6-[2-methoxy-4-(trifluoromethoxy)phenoxy]benzoyl]amino]pyridine-2-carboxamide (170)

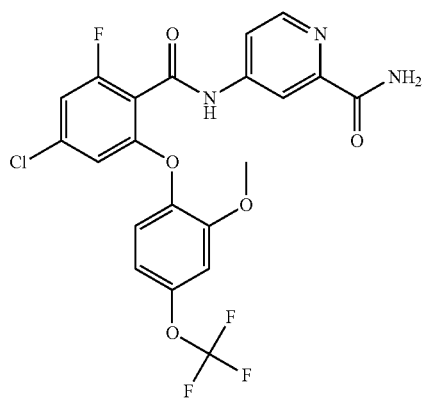 [SMILES: COc1cc(OC(F)(F)F)ccc1Oc1cc(Cl)cc(F)c1C(=O)Nc1ccnc(C(N)=O)c1]

Step 1: Methyl 4-[[4-chloro-2-fluoro-6-[2-methoxy-4-(trifluoromethoxy)phenoxy]benzoyl]amino]pyridine-2-carboxylate

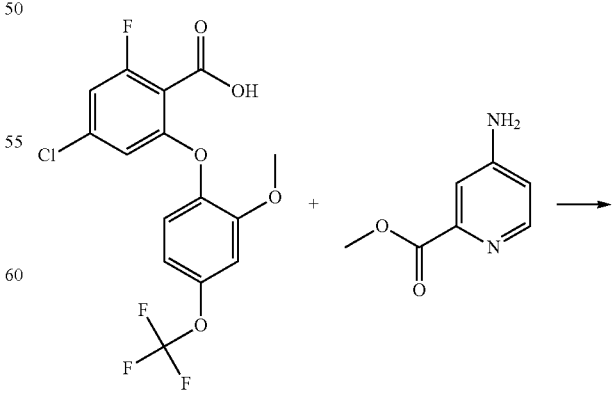

-continued

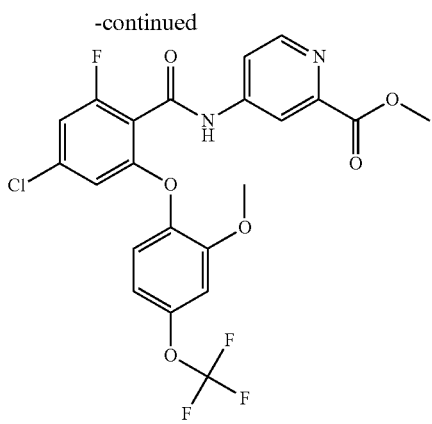

This compound was made in an analogous fashion to N-(2-bromo-5-methyl-4-pyridyl)-4-chloro-2-fluoro-6-[2-methoxy-4-(trifluoromethoxy)phenoxy]benzamide (Example 60, step 4) except employing methyl 4-aminopyridine-2-carboxylate in the amide formation step. The yield of the desired product after purification was 280 mg (69%). ESI-MS m/z calc. 514.06, found 515.2 (M+1)+; retention time (Method F): 1.01 minutes (1.5 minute run).

Step 2: 4-[[4-Chloro-2-fluoro-6-[2-methoxy-4-(trifluoromethoxy)phenoxy]benzoyl]amino]pyridine-2-carboxamide (170)

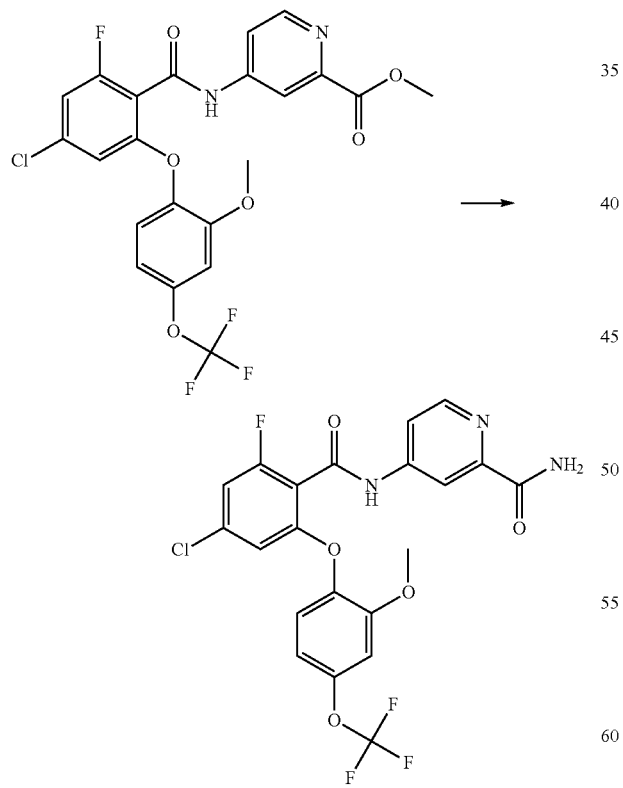

Methyl 4-[[4-chloro-2-fluoro-6-[2-methoxy-4-(trifluoromethoxy)phenoxy]benzoyl]amino]pyridine-2-carboxylate (270 mg, 0.525 mmol) was stirred in ammonia (8.4 mL of 7 M in methanol, 58.8 mmol) for 16 hours under N₂ atmo-sphere. The reaction mixture was concentrated in vacuo. The residue was triturated with ethyl acetate and ether to provide 4-[[4-chloro-2-fluoro-6-[2-methoxy-4-(trifluoromethoxy)phenoxy]benzoyl]amino]pyridine-2-carboxamide (212 mg, 78%). ESI-MS m/z calc. 499.06, found 500.0 (M+1)+; retention time (Method E): 3.32 minutes (5 minute run). $^1$H NMR (500 MHz, DMSO-d6) δ 11.30 (s, 1H), 8.64-8.48 (m, 1H), 8.30 (d, J=2.2 Hz, 1H), 8.09 (d, J=2.8 Hz, 1H), 7.83 (dd, J=5.5, 2.2 Hz, 1H), 7.64 (d, J=2.8 Hz, 1H), 7.49-7.15 (m, 3H), 7.01 (ddd, J=8.7, 2.7, 1.2 Hz, 1H), 6.64 (t, J=1.5 Hz, 1H), 3.79 (s, 3H) ppm.

Example 63

4-[[3-(Difluoromethoxy)-2-fluoro-6-[2-(trideuteriomethoxy)-4-(trifluoromethoxy)phenoxy]benzoyl]amino]pyridine-2-carboxamide (155)

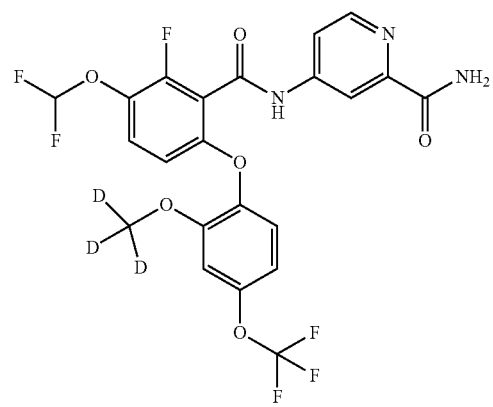 [SMILES: [2H]C([2H])([2H])Oc1cc(OC(F)(F)F)ccc1Oc1ccc(OC(F)F)c(F)c1C(=O)Nc1ccnc(C(N)=O)c1]

Step 1: 6-Bromo-2-fluoro-3-hydroxy-benzaldehyde

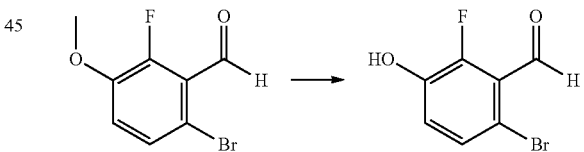

A solution of 6-bromo-2-fluoro-3-methoxy-benzaldehyde (2.0 g, 8.6 mmol) in dichloromethane (45 mL) under a N₂ balloon was cooled to −78° C. Boron tribromide (10 mL of 1 M, 10 mmol) was added dropwise under N₂ atmosphere. The reaction was stirred at room temperature for 16 hours. The mixture was cooled to 0° C. and the excess boron tribromide was quenched with saturated NaHCO₃ solution. Water was added and the solution was extracted with dichloromethane (3×). The combined organic layers were washed with brine, dried over Na₂SO₄, and filtered and concentrated in vacuo to provide 6-bromo-2-fluoro-3-hydroxy-benzaldehyde (1.26 g, 67%). ESI-MS m/z calc. 217.94, found 220.9 (M+2)+; retention time (Method A): 0.41 minutes (1 minute run).

Step 2:
6-Bromo-3-(difluoromethoxy)-2-fluoro-benzaldehyde

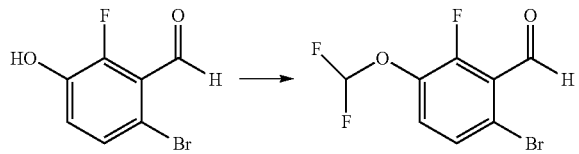 [SMILES: O=Cc1c(Br)ccc(O)c1F ; O=Cc1c(Br)ccc(OC(F)F)c1F]

A flask charged with 6-bromo-2-fluoro-3-hydroxy-benzaldehyde (610 mg, 2.79 mmol), sodium chlorodifluoroacetate (910 mg, 5.97 mmol), $K_2CO_3$ (385 mg, 2.79 mmol), DMF (10 mL) and water (1 mL) was heated under $N_2$ atmosphere at 100° C. for 2 hours. The reaction mixture was cooled to room temperature and partitioned between water and ethyl acetate. The organic layer was washed with brine, dried over $MgSO_4$, filtered and concentrated in vacuo. Silica gel chromatography (0-20% ethyl acetate/hexanes) provided 6-bromo-3-(difluoromethoxy)-2-fluoro-benzaldehyde (280 mg, 37%). ESI-MS m/z calc. 267.93, found 270.9 (M+1)+; retention time (Method A): 0.57 minutes (1 minute run). $^1$H NMR (400 MHz, DMSO-d6) δ 10.17 (d, J=0.9 Hz, 1H), 7.70 (dd, J=8.9, 1.7 Hz, 1H), 7.62 (ddt, J=8.9, 8.0, 0.8 Hz, 1H), 7.31 (t, J=72.6 Hz, 1H) ppm.

Step 3:
6-Bromo-3-(difluoromethoxy)-2-fluoro-benzoic acid

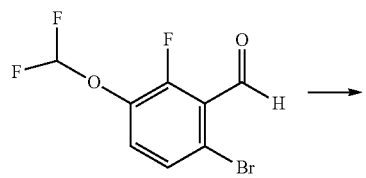

To a solution of 6-bromo-3-(difluoromethoxy)-2-fluoro-benzaldehyde (580 mg, 2.16 mmol) in tert-BuOH (6 mL), water (3 mL) and acetonitrile (3 mL) was added sodium dihydrogen phosphate hydrate (395 mg, 3.29 mmol) followed by 2-methyl-2-butene (1.7 mL, 16 mmol) and the portionwise addition of sodium chlorite (300 mg, 3.312 mmol). The reaction mixture was stirred at room temperature for 45 minutes. The reaction was adjusted to pH-2 with 1 M HCl solution. The layers were separated and the aqueous layer was extracted with ethyl acetate. The combined organic layers were dried over $MgSO_4$, filtered and concentrated in vacuo to provide 6-bromo-3-(difluoromethoxy)-2-fluoro-benzoic acid (575 mg, 94%) as a white solid. ESI-MS m/z calc. 283.93, found 287.0 (M+1)+; retention time (Method A): 0.43 minutes (1 minute run).

Step 4: 3-(Difluoromethoxy)-2-fluoro-6-[2-(trideuteriomethoxy)-4-(trifluoromethoxy)phenoxy]benzoic acid

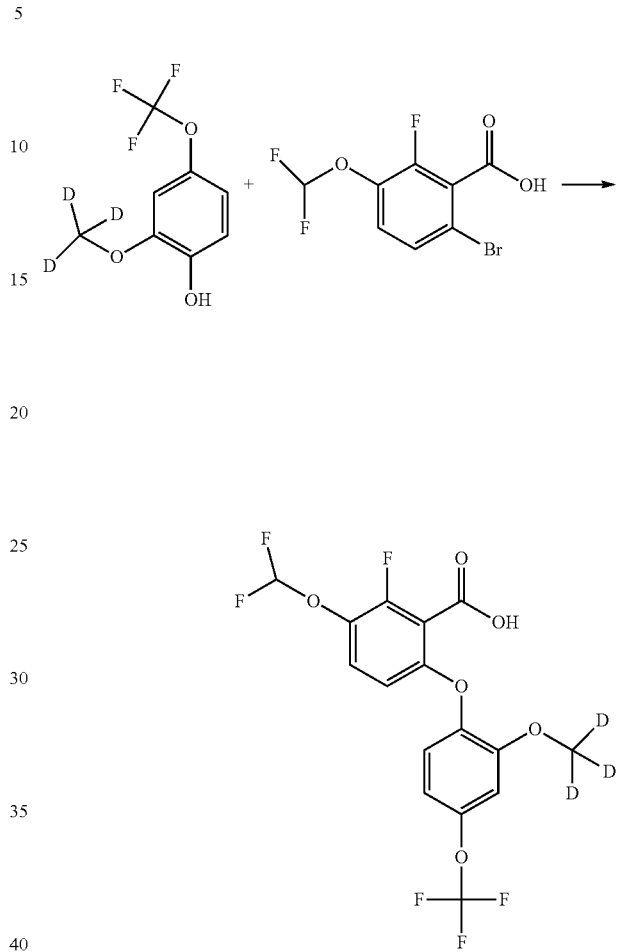

To a pressure flask was added 6-bromo-3-(difluoromethoxy)-2-fluoro-benzoic acid (570 mg, 2.00 mmol), 2-(trideuteriomethoxy)-4-(trifluoromethoxy)phenol (423 mg, 2.00 mmol) and $Cs_2CO_3$ (820 mg, 2.51 mmol), and toluene (7 mL). The reaction mixture was bubbled with $N_2$ for 10 min, then copper (I) iodide (170 mg, 0.893 mmol) was added. The flask was flushed with $N_2$, sealed and heated at 100° C. with vigorous stirring for 4 hours. The mixture was allowed to cool then diluted with ethyl acetate and water. The water layer was acidified with HCl and the product extracted into the ethyl acetate. The organic layer was washed with brine, dried over $Na_2SO_4$, filtered and concentrated. Silica gel chromatography (0-100% ethyl acetate/hexanes) provided 3-(difluoromethoxy)-2-fluoro-6-[2-(trideuteriomethoxy)-4-(trifluoromethoxy)phenoxy]benzoic acid (280 mg, 34%). ESI-MS m/z calc. 415.06, found 416.1 (M+1)+; retention time (Method B): 1.69 minutes (3 minute run).

373

Step 5: 4-[[3-(Difluoromethoxy)-2-fluoro-6-[2-(tri-deuteriomethoxy)-4-(trifluoromethoxy)phenoxy]benzoyl]amino]pyridine-2-carboxamide (155)

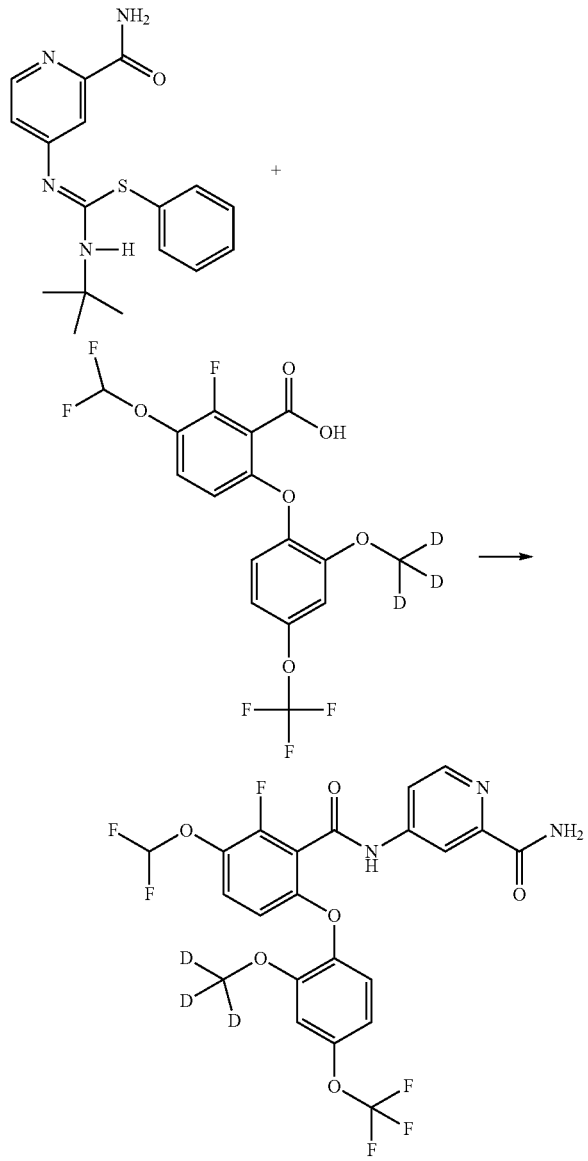

A vial was charged with 3-(difluoromethoxy)-2-fluoro-6-[2-(trideuteriomethoxy)-4-(trifluoromethoxy)phenoxy]benzoic acid (75 mg, 0.18 mmol), 4-[(Z)-[(tert-butylamino)-phenylsulfanyl-methylene]amino]pyridine-2-carboxamide (prepared as described in Preparation 1, 62 mg, 0.19 mmol), tris[(Z)-1-methyl-3-oxo-but-1-enoxy]iron (3.1 mg, 0.0088 mmol) in 2-propanol (1.25 mL) and heated at 83° C. under an air atmosphere for 24 hours. The reaction mixture was cooled to room temperature and concentrated in vacuo. The residue was partitioned between dichloromethane and 1N HCl. The organic layer was dried over MgSO$_4$, filtered and concentrated. Silica gel chromatography (0-60% ethyl acetate/hexanes) provided 4-[[3-(difluoromethoxy)-2-fluoro-6-[2-(trideuteriomethoxy)-4-(trifluoromethoxy)phenoxy]benzoyl]amino]pyridine-2-carboxamide (20 mg, 21%). ESI-MS m/z calc. 534.10, found 535.2 (M+1)+; retention time (Method B): 1.63 minutes (3 minute run). $^1$H NMR (400 MHz, DMSO-d6) δ 11.35 (s, 1H), 8.54 (d, J=5.5 Hz, 1H), 8.31 (d, J=2.1 Hz, 1H), 8.09 (s, 1H), 7.82 (dd, J=5.5, 2.2 Hz, 1H), 7.65 (s, 1H), 7.50-7.22 (m, 3H), 7.19 (d, J=2.8 Hz, 1H), 7.07-6.92 (m, 1H), 6.62 (dd, J=9.1, 1.6 Hz, 1H) ppm.

Example 64

5-[[3-(Difluoromethoxy)-2-fluoro-6-[2-(trideuteriomethoxy)-4-(trifluoromethoxy)phenoxy]benzoyl]amino]pyridine-2-carboxamide (198)

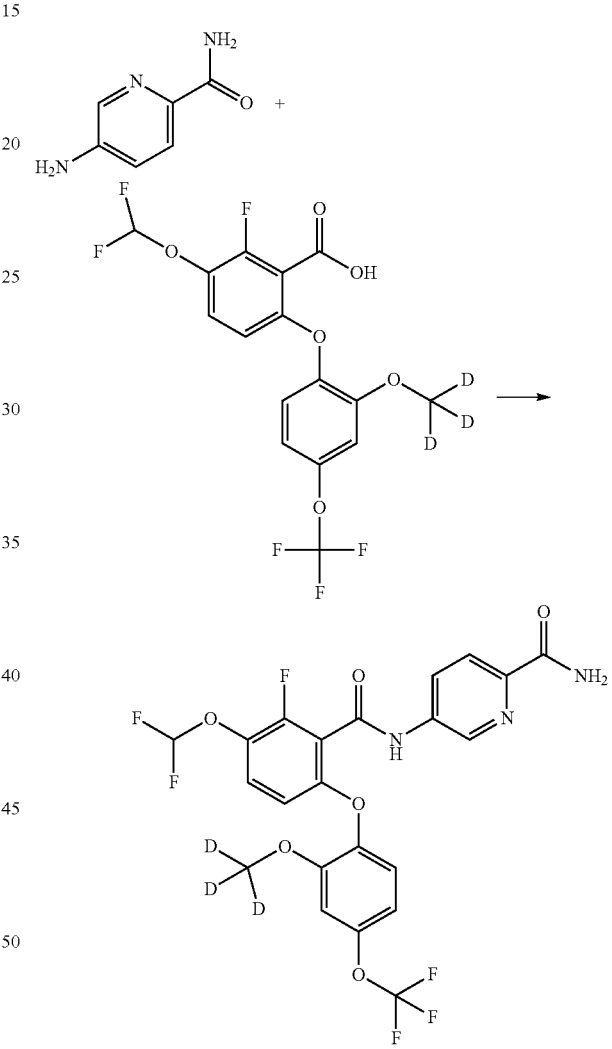

To a solution of 3-(difluoromethoxy)-2-fluoro-6-[2-(trideuteriomethoxy)-4-(trifluoromethoxy)phenoxy]benzoic acid (100 mg, 0.241 mmol) in dichloromethane (3 mL) and DMF (19 µL, 0.24 mmol) at 0° C. was added oxalyl chloride (21 µL, 0.24 mmol) dropwise under N$_2$ atmosphere. The reaction mixture was allowed to warm to room temperature then stirred for 30 minutes. The solution was then added dropwise to a stirring solution of 5-aminopyridine-2-carboxamide (50 mg, 0.36 mmol) in dichloromethane (3 mL) and DIEA (210 µL, 1.20 mmol) at 0° C. The reaction mixture was allowed to warm to room temperature and stirred for 16 hours. The reaction mixture was diluted with water and extracted with ethyl acetate. The organic layer was washed with 1 M HCl, dried over MgSO$_4$, filtered and concentrated in vacuo. HPLC purification (1-99% acetonitrile/5 mM HCl) provided 5-[[3-(difluoromethoxy)-2-fluoro-6-[2-(trideuteriomethoxy)-4-(trifluoromethoxy)phenoxy]benzoyl]amino]pyridine-2-carboxamide (36 mg, 27%). ESI-MS m/z calc. 534.11, found 535.3 (M+1)+; retention time (Method B): 1.63 minutes (3 minute run). $^1$H NMR (400 MHz, DMSO-d6) δ 11.27 (s, 1H), 8.91-8.74 (m, 1H), 8.27 (dd, J=8.6, 2.5 Hz, 1H), 8.10-7.96 (m, 2H), 7.56 (s, 1H), 7.49-7.01 (m, 4H), 6.99 (ddt, J=8.8, 2.4, 1.2 Hz, 1H), 6.63 (dd, J=9.2, 1.6 Hz, 1H) ppm.

Example 65

Racemic trans-N-(3-Carbamoyl-4-fluoro-phenyl)-4-[2-methoxy-4-(trifluoromethoxy)phenoxy]-6-(2-methylcyclopropyl)pyridine-3-carboxamide (106)

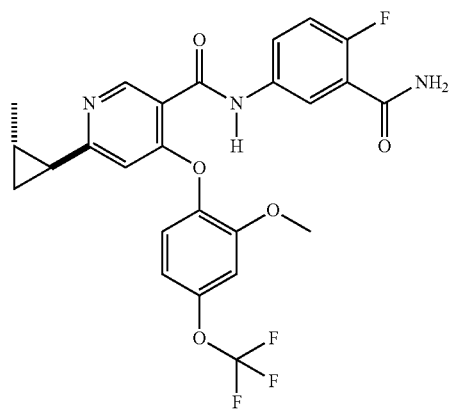

Step 1: Methyl 6-bromo-4-[2-methoxy-4-(trifluoromethoxy)phenoxy]pyridine-3-carboxylate

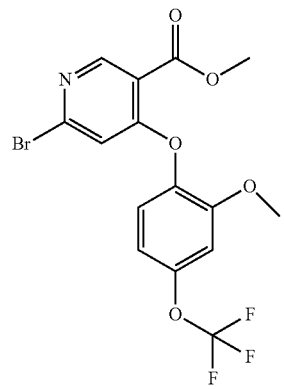

To a solution of methyl 6-bromo-4-chloro-pyridine-3-carboxylate (8.48 g, 33.9 mmol) was dissolved in anhydrous DMF (85 mL) under N$_2$ atmosphere at 0° C. was added 2-methoxy-4-(trifluoromethoxy)phenol (7.05 g, 33.9 mmol) in one portion followed by Cs$_2$CO$_3$ (33.1 g, 102 mmol). The reaction was stirred for 10 minutes then allowed to warm to room temperature and stirred for 2 hours. The mixture was partitioned between ethyl acetate and brine and the layers were separated. The organic layer was washed with brine, dried over Na$_2$SO$_4$, filtered and concentrated in vacuo. Silica gel chromatography (0-10% ethyl acetate/hexanes) provided methyl 6-bromo-4-[2-methoxy-4-(trifluoromethoxy)phenoxy]pyridine-3-carboxylate (11.5 g, 80%) as a white solid. ESI-MS m/z calc. 420.98, found 422.06 (M+1)+; retention time (Method A): 0.75 minutes (1 minute run). $^1$H NMR (500 MHz, DMSO-d6) δ 8.69 (s, 1H), 7.37 (d, J=8.8 Hz, 1H), 7.27 (d, J=2.2 Hz, 1H), 7.04 (d, J=10.0 Hz, 1H), 6.78 (s, 1H), 3.84 (s, 3H), 3.78 (s, 3H) ppm.

Step 2: Methyl 4-[2-methoxy-4-(trifluoromethoxy)phenoxy]-6-[(E)-prop-1-enyl]pyridine-3-carboxylate

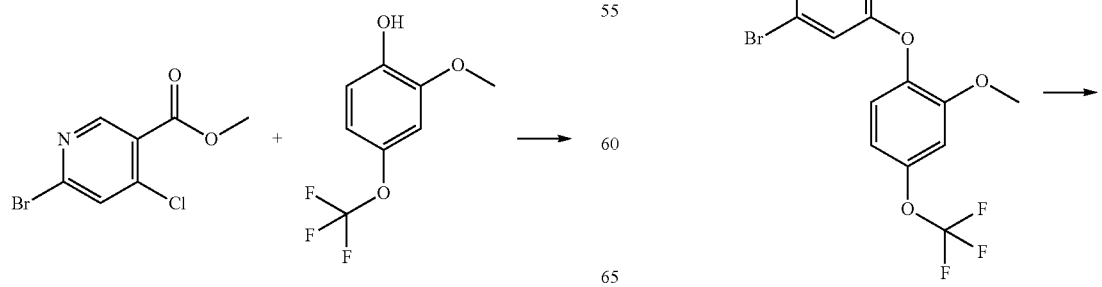

377
-continued

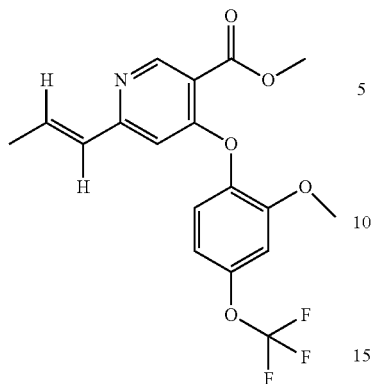

Methyl 6-bromo-4-[2-methoxy-4-(trifluoromethoxy)phenoxy]pyridine-3-carboxylate (2.0 g, 4.74 mmol), trans-1-propenylboronic acid pinacol ester (955 mg, 5.68 mmol), and Pd(dppf)Cl$_2$·DCM (170 mg, 0.232 mmol) were brought up in acetonitrile (20 mL), aqueous K$_2$CO$_3$ solution (12 mL of 2 M, 24 mmol) and DMF (7 mL). The reaction stirred at 60° C. for 1 hour, then the heat was reduced to 40° C. and stirring continued for 16 hours. The reaction was cooled, diluted with ether and washed with 50% saturated aqueous NaHCO$_3$ solution and brine. The organic layer was dried over Na$_2$SO$_4$, filtered and concentrated in vacuo. Silica gel chromatography (80 g silica, 0-40% ethyl acetate/hexanes) provided methyl 4-[2-methoxy-4-(trifluoromethoxy)phenoxy]-6-[(E)-prop-1-enyl]pyridine-3-carboxylate (1.325 g, 73%). ESI-MS m/z calc. 383.10, found 384.2 (M+1)+; retention time (Method A): 0.6 minutes (1 minute run). $^1$H NMR (400 MHz, DMSO-d6) δ 8.82 (s, 1H), 7.31 (d, J=8.7 Hz, 1H), 7.27 (d, J=2.7 Hz, 1H), 7.04 (ddd, J=8.8, 2.7, 1.2 Hz, 1H), 6.89-6.77 (m, 1H), 6.49 (s, 1H), 6.46 (dd, J=15.4, 1.7 Hz, 1H), 3.83 (s, 3H), 3.77 (s, 3H), 1.84 (dd, J=6.9, 1.7 Hz, 3H) ppm.

Step 3: Racemic Methyl trans-4-[2-methoxy-4-(trifluoromethoxy)phenoxy]-6-(2-methylcyclopropyl)pyridine-3-carboxylate

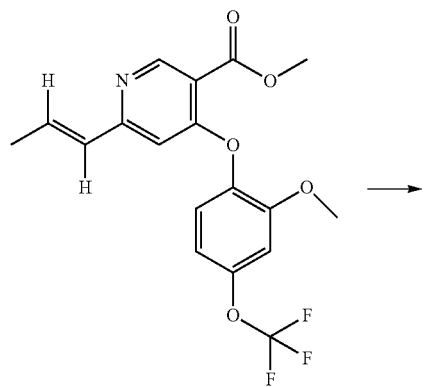

378
-continued

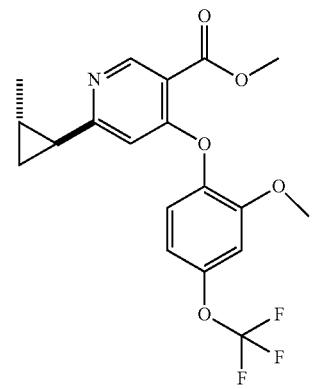

To a stirring suspension of trimethylsulfoxonium iodide (1.15 g, 5.23 mmol) in DMSO (10 mL) and THF (10 mL) was added potassium tert-butoxide (600 mg, 5.35 mmol) in one portion under N$_2$ atmosphere. After 30 minutes a solution of methyl 4-[2-methoxy-4-(trifluoromethoxy)phenoxy]-6-[(E)-prop-1-enyl]pyridine-3-carboxylate (1000 mg, 2.609 mmol) in THF (10 mL) was added. The mixture was stirred at room temperature for 3 hours. The reaction was diluted with water and extracted with ethyl acetate. The organic layer was washed with brine, dried over Na$_2$SO$_4$, filtered and concentrated in vacuo. Silica gel chromatography (0-50% ethyl acetate/hexanes) provided racemic methyl trans-4-[2-methoxy-4-(trifluoromethoxy)phenoxy]-6-(2-methylcyclopropyl)pyridine-3-carboxylate (750 mg, 72%). ESI-MS m/z calc. 397.11, found 398.3 (M+1)+; retention time (Method A): 0.61 minutes (1 minute run). $^1$H NMR (400 MHz, DMSO-d6) δ 8.72 (s, 1H), 7.31 (d, J=8.8 Hz, 1H), 7.28 (d, J=2.7 Hz, 1H), 7.04 (ddd, J=8.8, 2.7, 1.2 Hz, 1H), 6.52 (s, 1H), 3.81 (s, 3H), 3.80 (s, 3H), 1.80 (dt, J=8.4, 4.4 Hz, 1H), 1.40-1.27 (m, 1H), 1.15-1.09 (m, 1H), 1.08 (d, J=6.0 Hz, 3H), 0.76 (ddd, J=8.2, 6.0, 3.5 Hz, 1H) ppm.

Step 4: Racemic trans-4-[2-Methoxy-4-(trifluoromethoxy)phenoxy]-6-(2-methylcyclopropyl)pyridine-3-carboxylic acid

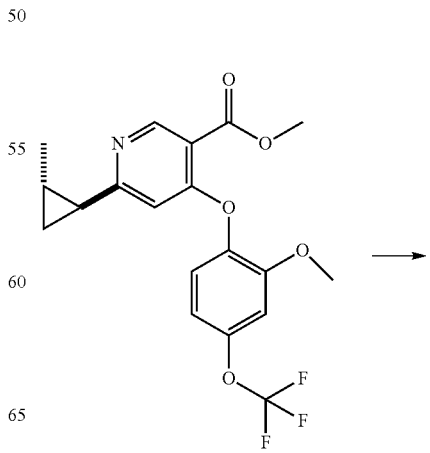

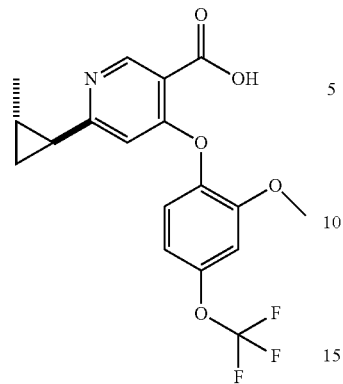

A solution of racemic methyl trans-4-[2-methoxy-4-(trifluoromethoxy)phenoxy]-6-(2-methylcyclopropyl)pyridine-3-carboxylate (750 mg, 1.89 mmol) in methanol (5 mL) at 0° C. was treated with cold aqueous NaOH (3.8 mL of 1 M, 3.8 mmol). The reaction mixture was allowed to come to room temperature and stirred for 2 hours, then concentrated. The crude reaction was partitioned between 1 N HCl and dichloromethane. The dichloromethane was dried over $Na_2SO_4$, filtered and concentrated to provide racemic trans-4-[2-methoxy-4-(trifluoromethoxy)phenoxy]-6-(2-methylcyclopropyl)pyridine-3-carboxylic acid (720 mg, 99%). ESI-MS m/z calc. 383.10, found 384.3 (M+1)+; retention time (Method A): 0.51 minutes (1 minute). $^1$H NMR (400 MHz, DMSO-d6) δ 8.76 (s, 1H), 7.37 (d, J=8.8 Hz, 1H), 7.31 (d, J=2.7 Hz, 1H), 7.07 (ddd, J=8.8, 2.7, 1.2 Hz, 1H), 6.68 (s, 1H), 3.81 (s, 3H), 2.00 (dt, J=8.8, 4.6 Hz, 1H), 1.54-1.40 (m, 1H), 1.28 (dt, J=8.8, 4.5 Hz, 1H), 1.12 (d, J=6.0 Hz, 3H), 1.03-0.91 (m, 1H) ppm.

Step 5: Racemic trans-N-(3-Carbamoyl-4-fluorophenyl)-4-[2-methoxy-4-(trifluoromethoxy)phenoxy]-6-(2-methylcyclopropyl)pyridine-3-carboxamide (106)

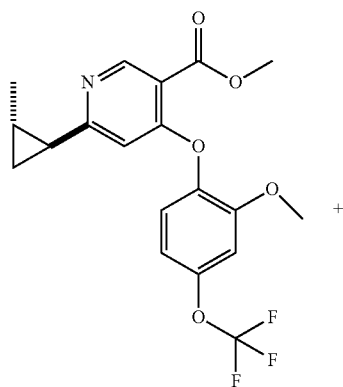

+

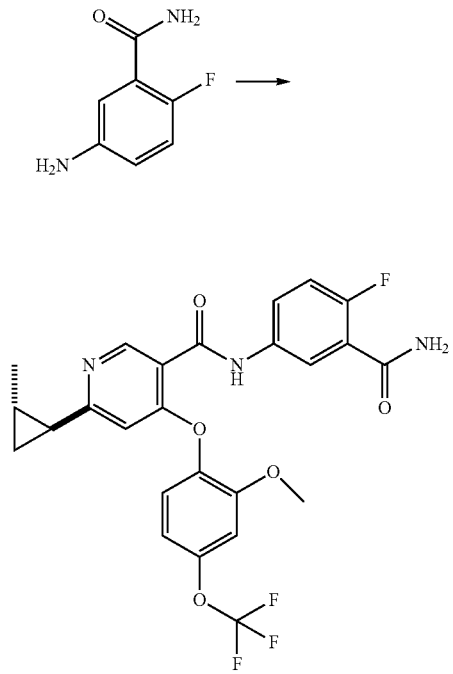

Racemic trans-4-[2-Methoxy-4-(trifluoromethoxy)phenoxy]-6-(2-methylcyclopropyl)pyridine-3-carboxylic acid (103 mg, 0.269 mmol) and HATU (103 mg, 0.271 mmol) were combined in DMF (1 mL) and DIEA (94 µL, 0.54 mmol) and stirred for 5 minutes. 5-Amino-2-fluoro-benzamide (62 mg, 0.40 mmol) was added in one portion and the reaction stirred at 45° C. for 1 hour. The reaction was diluted with ethyl acetate and washed with 50% saturated aqueous $NaHCO_3$ and brine, dried over $Na_2SO_4$, filtered, and concentrated in vacuo. Silica gel chromatography (0-15% methanol/dichloromethane) provided racemic trans-N-(3-carbamoyl-4-fluoro-phenyl)-4-[2-methoxy-4-(trifluoromethoxy)phenoxy]-6-(2-methylcyclopropyl)pyridine-3-carboxamide (135 mg, 95%). ESI-MS m/z calc. 519.14, found 520.2 (M+1)+; retention time (Method B): 1.36 minutes (3 minute run). $^1$H NMR (400 MHz, DMSO-d6) δ 10.38 (s, 1H), 8.54 (s, 1H), 7.99 (dd, J=6.4, 2.8 Hz, 1H), 7.82 (ddd, J=8.9, 4.4, 2.8 Hz, 1H), 7.70 (s, 1H), 7.67 (s, 1H), 7.45 (d, J=8.8 Hz, 1H), 7.32-7.21 (m, 2H), 7.07 (ddd, J=8.8, 2.7, 1.3 Hz, 1H), 6.55 (s, 1H), 3.80 (s, 3H), 1.81 (dt, J=8.5, 4.4 Hz, 1H), 1.38-1.25 (m, 1H), 1.16-1.11 (m, 1H), 1.10 (d, J=6.0 Hz, 3H), 0.74 (ddd, J=9.0, 5.9, 3.6 Hz, 1H) ppm. SFC purification (36% methanol/64% $CO_2$, ChiralPak IG (250× 21.2 mm) 5 µm column, flow=70 mL/min) provided separated enantiomers rel-N-(3-carbamoyl-4-fluoro-phenyl)-4-[2-methoxy-4-(trifluoromethoxy)phenoxy]-6-((1S,2S)-2-methylcyclopropyl)pyridine-3-carboxamide (113) and rel-N-(3-carbamoyl-4-fluoro-phenyl)-4-[2-methoxy-4-(trifluoromethoxy)phenoxy]-6-((1R,2R)-2-methylcyclopropyl)pyridine-3-carboxamide (114). The absolute stereochemistry of enantiomers 113 and 114 was not determined.

Example 66

Racemic trans-4-(4-(2-Methoxy-4-(trifluoromethoxy)phenoxy)-6-(2-methylcyclopropyl)nicotinamido)picolinamide (109)

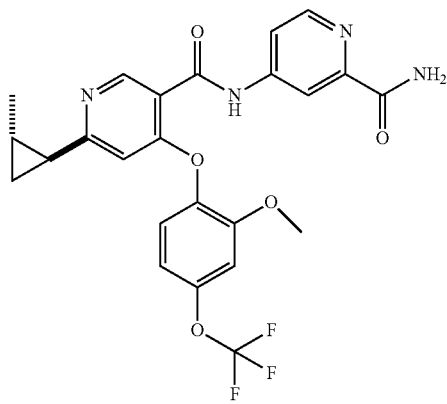

Step 1: Racemic trans-4-[2-Methoxy-4-(trifluoromethoxy)phenoxy]-6-(2-methylcyclopropyl)pyridine-3-carbonyl chloride

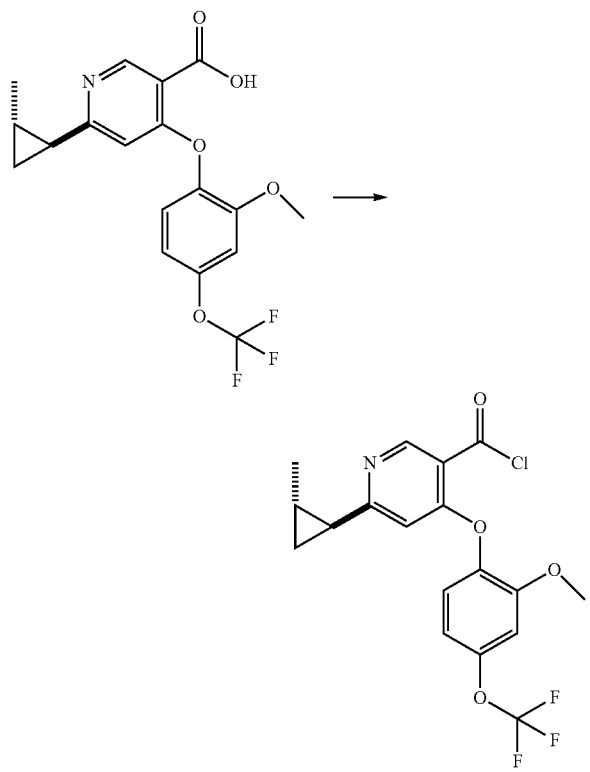

To a suspension of racemic trans-4-[2-methoxy-4-(trifluoromethoxy)phenoxy]-6-(2-methylcyclopropyl)pyridine-3-carboxylic acid (460 mg, 1.20 mmol) and DMF (9 μL, 0.1162 mmol) in dichloromethane (7 mL) at 0° C. was added oxalyl chloride (315 μL, 3.61 mmol) dropwise. The reaction was allowed to come to room temperature and stirred for 30 minutes. Conversion to the desired acid chloride was monitored by UPLC via test for morpholine adduct formation. The reaction mixture was concentrated in vacuo then evaporated with dichloromethane (3×55 mL) to provide racemic trans-4-[2-methoxy-4-(trifluoromethoxy)phenoxy]-6-(2-methylcyclopropyl)pyridine-3-carbonyl chloride.

Step 2: Racemic trans-N-(2-Carbamoyl-4-pyridyl)-4-[2-methoxy-4-(trifluoromethoxy)phenoxy]-6-(2-methylcyclopropyl)pyridine-3-carboxamide (109)

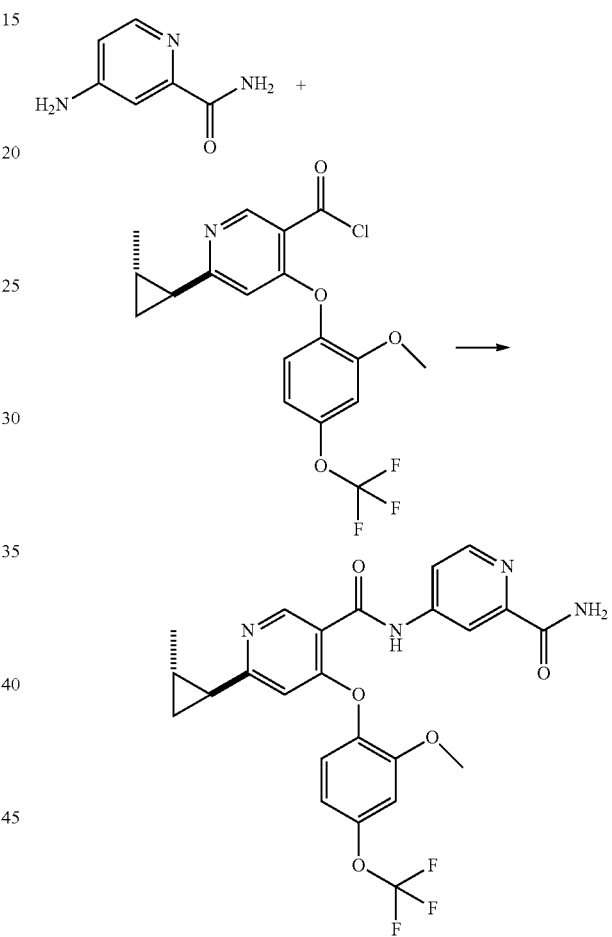

4-Aminopyridine-2-carboxamide (102 mg, 0.744 mmol) was dissolved in dichloromethane (2.5 mL) and DIEA (260 μL, 1.49 mmol) and cooled to −10° C. A solution of cold (−10° C.) racemic trans-4-[2-methoxy-4-(trifluoromethoxy)phenoxy]-6-(2-methylcyclopropyl)pyridine-3-carbonyl chloride (240 mg, 0.597 mmol) in dichloromethane (2.5 mL) was added dropwise to the stirring amine solution. The resulting suspension was slowly allowed to warm to room temperature over 1 hour. DMF (0.5 mL) was added and the reaction was stirred for 1 additional hour. The reaction was diluted with ethyl acetate and washed with 50% saturated sodium carbonate, water, and brine. The reaction mixture was concentrated in vacuo and purified by silica gel chromatography (40 g silica, 0-10% methanol/dichloromethane). Additional silica gel chromatography (40 g silica, 0-40% ethyl acetate/dichloromethane) provided racemic trans-N-

(2-carbamoyl-4-pyridyl)-4-[2-methoxy-4-(trifluoromethoxy)phenoxy]-6-(2-methylcyclopropyl)pyridine-3-carboxamide (85 mg, 27%). ESI-MS m/z calc. 502.15, found 503.4 (M+1)+; retention time (Method B): 1.41 minutes (3 minute run). $^1$H NMR (400 MHz, DMSO-d6) δ 10.82 (s, 1H), 8.56 (s, 1H), 8.52 (d, J=5.4 Hz, 1H), 8.30 (d, J=2.1 Hz, 1H), 8.11 (d, J=2.8 Hz, 1H), 7.90 (dd, J=5.5, 2.2 Hz, 1H), 7.65 (d, J=3.0 Hz, 1H), 7.46 (d, J=8.8 Hz, 1H), 7.26 (d, J=2.7 Hz, 1H), 7.07 (ddd, J=8.8, 2.7, 1.3 Hz, 1H), 6.58 (s, 1H), 3.79 (s, 3H), 1.83 (dt, J=8.4, 4.4 Hz, 1H), 1.39-1.28 (m, 1H), 1.16-1.12 (m, 1H), 1.10 (d, J=5.9 Hz, 3H), 0.80-0.70 (m, 1H) ppm. SFC purification (36% methanol/64% $CO_2$, ChiralPak IG (250×21.2 mm) 5 μm column, flow=70 mL/min) provided separated enantiomers rel-N-(2-carbamoyl-4-pyridyl)-4-[2-methoxy-4-(trifluoromethoxy)phenoxy]-6-((1S,2S)-2-methylcyclopropyl)pyridine-3-carboxamide (111) and rel-N-(2-carbamoyl-4-pyridyl)-4-[2-methoxy-4-(trifluoromethoxy)phenoxy]-6-((1R,2R)-2-methylcyclopropyl)pyridine-3-carboxamide (112). The absolute stereochemistry of enantiomers 111 and 112 was not determined.

Example 67

6-tert-Butyl-N-(2-carbamoyl-4-pyridyl)-4-[2-methoxy-4-(trifluoromethoxy)phenoxy]pyridine-3-carboxamide (93)

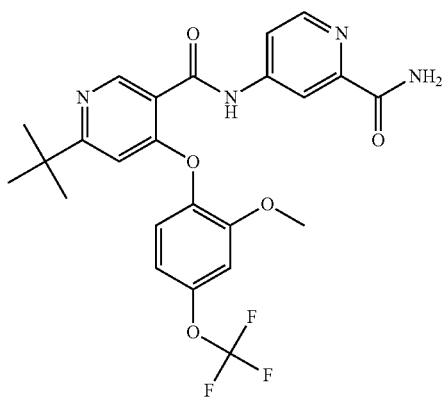 [SMILES: COc1cc(OC(F)(F)F)ccc1Oc1cc(C(C)(C)C)ncc1C(=O)Nc1ccnc(C(N)=O)c1]

Step 1: ethyl 6-tert-butyl-4-[2-methoxy-4-(trifluoromethoxy)phenoxy]pyridine-3-carboxylate

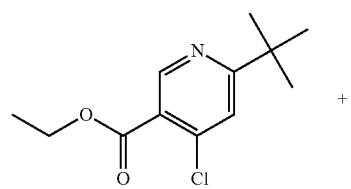

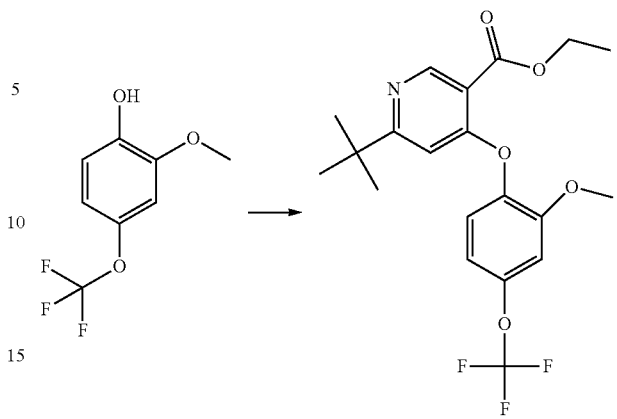

A vial charged with ethyl 6-tert-butyl-4-chloro-pyridine-3-carboxylate (1.56 g, 6.45 mmol), 2-methoxy-4-(trifluoromethoxy)phenol (1.5 g, 7.2 mmol) and $Cs_2CO_3$ (6.3 g, 19 mmol) in DMF (15 mL) was heated at 80° C. for 16 hours. The reaction mixture was quenched with 1N HCl and the aqueous layer was extracted with ethyl acetate. The organic layer was dried over $MgSO_4$, filtered and concentrated in vacuo. Silica gel chromatography (0-30% ethyl acetate/hexanes) provided ethyl 6-tert-butyl-4-[2-methoxy-4-(trifluoromethoxy)phenoxy]pyridine-3-carboxylate (1.92 g, 72%). ESI-MS m/z calc. 413.15, found 414.1 (M+1)+; retention time (Method A): 0.7 minutes (1 minute run).

Step 2: 6-tert-Butyl-4-[2-methoxy-4-(trifluoromethoxy)phenoxy]pyridine-3-carboxylic acid

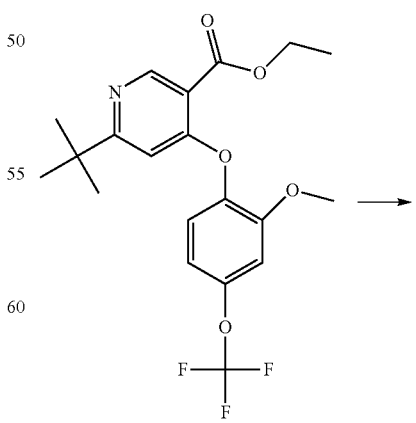

-continued

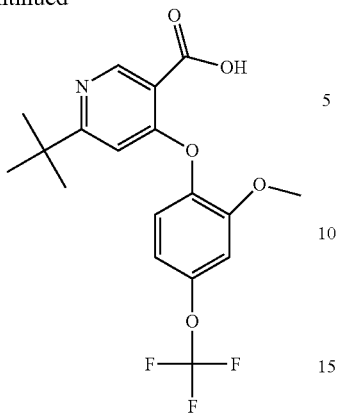

To a solution of ethyl 6-tert-butyl-4-[2-methoxy-4-(trifluoromethoxy)phenoxy]pyridine-3-carboxylate (1.90 g, 4.60 mmol) in methanol (20 mL) and water (15 mL) was added solid NaOH (1.8 g, 45.00 mmol). The reaction mixture was stirred at room temperature for 2 hours then cooled to 0° C. and slowly acidified with 6N HCl. The mixture was extracted with ethyl acetate, and the organic layer was dried over MgSO₄, filtered and concentrated in vacuo to obtain 6-tert-butyl-4-[2-methoxy-4-(trifluoromethoxy)phenoxy]pyridine-3-carboxylic acid (1.64 g, 93%). ESI-MS m/z calc. 385.1137, found 386.2 (M+1)+; retention time (Method B): 1.41 minutes (3 minute run).

Step 3: 6-tert-Butyl-N-(2-carbamoyl-4-pyridyl)-4-[2-methoxy-4-(trifluoromethoxy)phenoxy]pyridine-3-carboxamide (93)

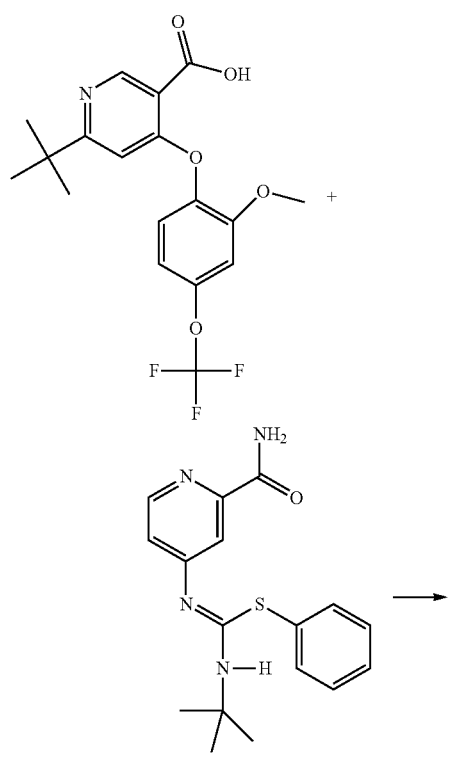

-continued

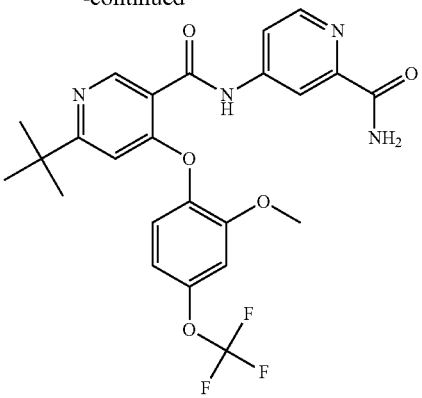

A pressure flask was charged with 6-tert-butyl-4-[2-methoxy-4-(trifluoromethoxy)phenoxy]pyridine-3-carboxylic acid (200 mg, 0.519 mmol), 4-[(Z)-[(tert-butylamino)-phenylsulfanyl-methylene]amino]pyridine-2-carboxamide (prepared as described in Preparation 1, 188 mg, 0.572 mmol), tris[(Z)-1-methyl-3-oxo-but-1-enoxy]iron (5.3 mg, 0.015 mmol) in 2-propanol (2 mL) and heated at 83° C. under an atmosphere of air for 20 hours. The reaction mixture was cooled to room temperature and the solvent was evaporated. Silica gel chromatography (0-60% ethyl acetate/hexanes) provided 6-tert-butyl-N-(2-carbamoyl-4-pyridyl)-4-[2-methoxy-4-(trifluoromethoxy)phenoxy]pyridine-3-carboxamide (83 mg, 32%). ESI-MS m/z calc. 504.16, found 505.2 (M+1)+; retention time (Method B): 1.5 minutes (3 minute run). ¹H NMR (400 MHz, DMSO-d6) δ 10.97 (s, 1H), 8.69 (s, 1H), 8.52 (d, J=5.5 Hz, 1H), 8.32 (d, J=2.1 Hz, 1H), 8.10 (d, J=2.8 Hz, 1H), 7.89 (dd, J=5.5, 2.2 Hz, 1H), 7.65 (d, J=2.9 Hz, 1H), 7.43 (d, J=8.8 Hz, 1H), 7.25 (d, J=2.7 Hz, 1H), 7.06 (ddd, J=8.8, 2.8, 1.3 Hz, 1H), 6.58 (s, 1H), 3.77 (s, 3H), 1.22 (s, 9H) ppm.

Example 68

6-tert-Butyl-N-(3-carbamoyl-4-fluoro-phenyl)-4-[2-methoxy-4-(trifluoromethoxy)phenoxy]pyridine-3-carboxamide (94)

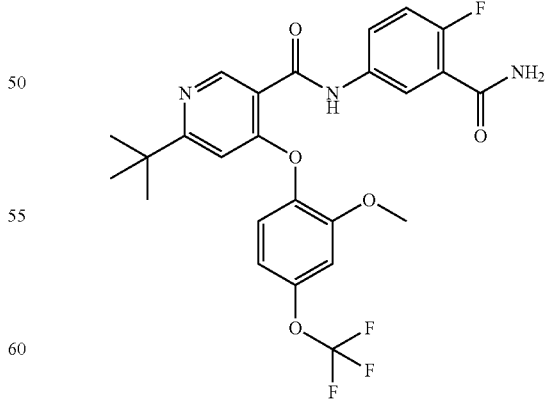

To a solution of 6-tert-butyl-4-[2-methoxy-4-(trifluoromethoxy)phenoxy]pyridine-3-carboxylic acid (prepared as described in Example 67, Step 2, 200 mg, 0.519 mmol), 5-amino-2-fluoro-benzamide (80 mg, 0.52 mmol) and HATU (218 mg, 0.573 mmol) in DMF (2 mL) was added 4-methylmorpholine (200 µL, 1.82 mmol) and the reaction mixture was stirred for 20 hours. The reaction mixture was diluted with water and the aqueous layer was extracted by ethyl acetate. The organic layer was washed with brine, dried over MgSO$_4$, filtered and concentrated in vacuo. The crude material was purified by HPLC (1-99% acetonitrile/5 mM HCl)). The product fractions were neutralized with saturated aqueous NaHCO$_3$ and extracted with dichloromethane. The organic layer was dried over MgSO$_4$, filtered and concentrated to obtain 6-tert-butyl-N-(3-carbamoyl-4-fluoro-phenyl)-4-[2-methoxy-4-(trifluoromethoxy)phenoxy]pyridine-3-carboxamide (155 mg, 57%). ESI-MS m/z calc. 521.16, found 522.2 (M+1)+; retention time (Method B): 1.49 minutes (3 minute run). $^1$H NMR (400 MHz, DMSO-d6) δ 10.54 (s, 1H), 8.66 (s, 1H), 8.00 (dd, J=6.5, 2.8 Hz, 1H), 7.84-7.78 (m, 1H), 7.69 (d, J=14.6 Hz, 2H), 7.42 (d, J=8.8 Hz, 1H), 7.30-7.22 (m, 2H), 7.06 (dd, J=9.0, 2.6 Hz, 1H), 6.55 (s, 1H), 3.78 (s, 3H), 1.21 (s, 9H) ppm.

Example 69

N-(3-Carbamoyl-4-fluoro-phenyl)-4-[2-methoxy-4-(trifluoromethoxy)phenoxy]-6-(1-methylcyclopropyl)pyridine-3-carboxamide (102)

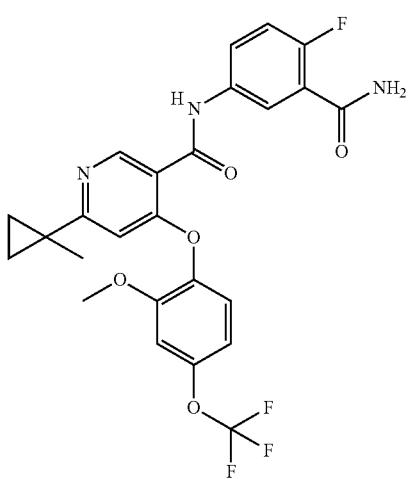

Step 1: Methyl 6-isopropenyl-4-[2-methoxy-4-(trifluoromethoxy)phenoxy]pyridine-3-carboxylate

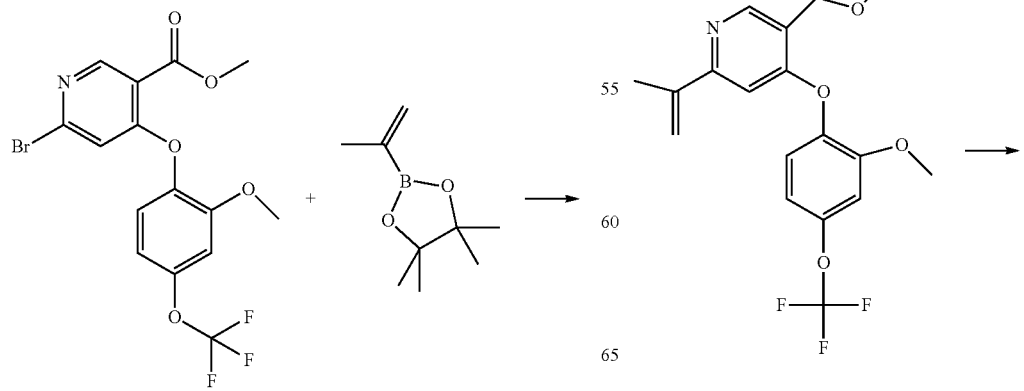

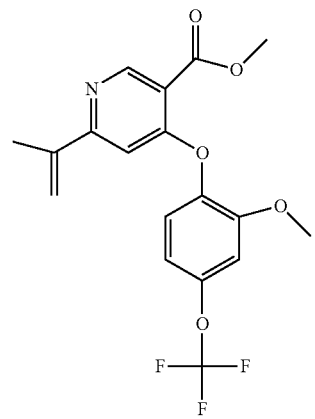

A flask charged with methyl 6-bromo-4-[2-methoxy-4-(trifluoromethoxy)phenoxy]pyridine-3-carboxylate (1.96 g, 4.64 mmol), isopropenylboronic acid pinacol ester (1.04 g, 6.19 mmol), Pd(dppf)Cl$_2$·DCM (380 mg, 0.465 mmol) and aqueous K$_2$CO$_3$ (5 mL of 2 M, 10 mmol) in acetonitrile (20 mL) was flushed with argon and heated at 80° C. for 2 hours. The reaction mixture was cooled to room temperature and partitioned between water and ethyl acetate. The organic layer was dried over MgSO$_4$, filtered and concentrated in vacuo. Silica gel chromatography (0-30% ethyl acetate/hexanes) provided methyl 6-isopropenyl-4-[2-methoxy-4-(trifluoromethoxy)phenoxy]pyridine-3-carboxylate (1.09 g, 61%). ESI-MS m/z calc. 383.10, found 384.2 (M+1)+; retention time (Method B): 1.65 minutes (3 minute run).

Step 2: Methyl 4-[2-methoxy-4-(trifluoromethoxy)phenoxy]-6-(1-methylcyclopropyl)pyridine-3-carboxylate

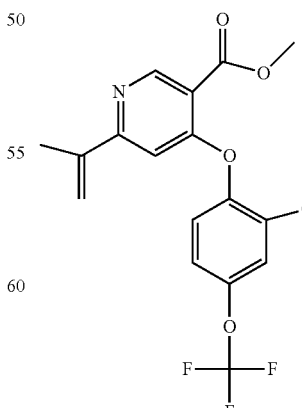

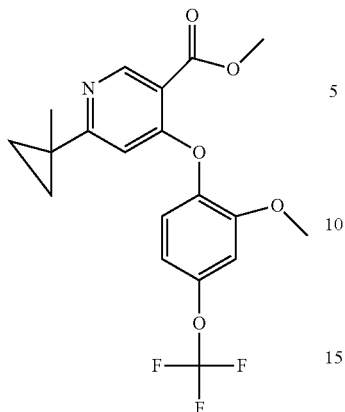

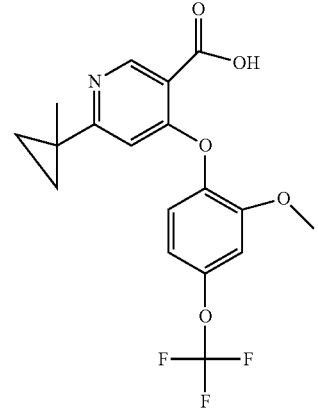

To a stirred suspension of trimethylsulfoxonium iodide (1.38 g, 6.26 mmol) in DMSO (12 mL) and THF (12 mL) was added potassium tert-butoxide (703 mg, 6.26 mmol) in one portion under $N_2$ atmosphere. After 30 minutes a solution of methyl 6-isopropenyl-4-[2-methoxy-4-(trifluoromethoxy)phenoxy]pyridine-3-carboxylate (1.20 g, 3.13 mmol)methyl in THF (1 mL) was added. The mixture was stirred for 3 hours then partitioned between water and with ethyl acetate. The organic layer was washed with water and brine, dried over $MgSO_4$ and concentrated in vacuo. Silica gel chromatography (0-30% ethyl acetate/hexanes) provided methyl 4-[2-methoxy-4-(trifluoromethoxy)phenoxy]-6-(1-methylcyclopropyl)pyridine-3-carboxylate (486 mg, 39%). ESI-MS m/z calc. 397.11, found 398.2 (M+1)+; retention time (Method B): 1.72 minutes (3 minute run). $^1$H NMR (400 MHz, DMSO-d6) δ 8.77 (s, 1H), 7.34-7.26 (m, 2H), 7.09-7.01 (m, 1H), 6.44 (s, 1H), 3.81 (s, 3H), 3.79 (s, 3H), 1.22 (s, 3H), 1.17 (q, J=3.5 Hz, 2H), 0.83 (q, J=3.6 Hz, 2H) ppm.

To a flask charged with methyl 4-[2-methoxy-4-(trifluoromethoxy)phenoxy]-6-(1-methylcyclopropyl)pyridine-3-carboxylate (500 mg, 1.26 mmol) in methanol (5 mL), THF (5 mL) and water (5 mL) was added solid NaOH (510 mg, 12.8 mmol) and the reaction mixture was stirred at room temperature for 45 minutes. The solvent was evaporated and the residue was taken up in water, cooled in an ice bath and quenched slowly with 6 M HCl. The resulting suspension was extracted with ethyl acetate, dried over $MgSO_4$, filtered and concentrated in vacuo to obtain 4-[2-methoxy-4-(trifluoromethoxy)phenoxy]-6-(1-methylcyclopropyl)pyridine-3-carboxylic acid (469 mg, 97%). ESI-MS m/z calc. 383.10, found 384.1 (M+1)+; retention time (Method B): 1.34 minutes (3 minute run). $^1$H NMR (400 MHz, DMSO-d6) δ 8.77 (s, 1H), 7.29 (d, J=8.8 Hz, 2H), 7.05 (ddq, J=8.7, 2.4, 1.2 Hz, 1H), 6.44 (d, J=1.0 Hz, 1H), 3.80 (s, 3H), 1.23 (s, 3H), 1.16 (q, J=3.5 Hz, 2H), 0.83 (q, J=3.6 Hz, 2H) ppm.

Step 3: 4-[2-Methoxy-4-(trifluoromethoxy)phenoxy]-6-(1-methylcyclopropyl)pyridine-3-carboxylic acid Step 4: N-(3-Carbamoyl-4-fluoro-phenyl)-4-[2-methoxy-4-(trifluoromethoxy)phenoxy]-6-(1-methylcyclopropyl)pyridine-3-carboxamide (102)

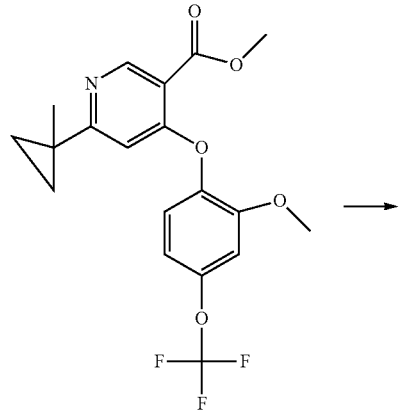

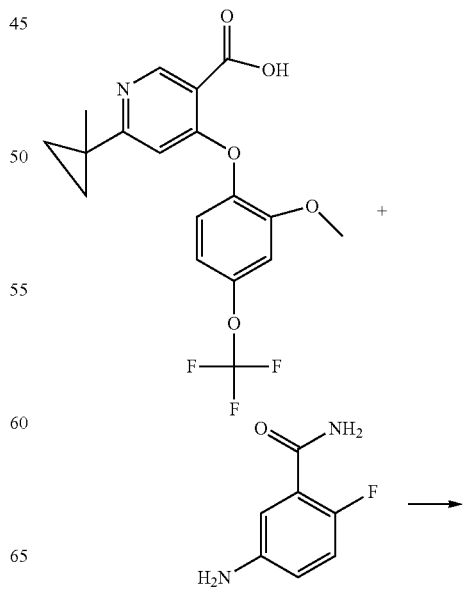

391
-continued

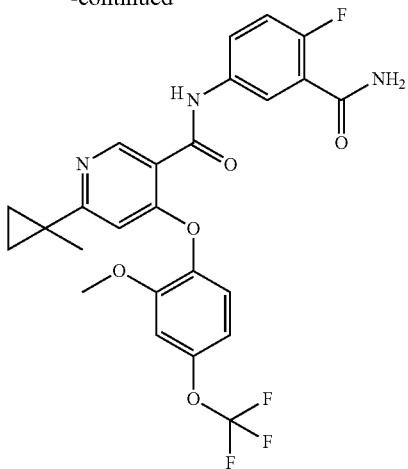

To a solution of 4-[2-methoxy-4-(trifluoromethoxy)phenoxy]-6-(1-methylcyclopropyl)pyridine-3-carboxylic acid (127 mg, 0.331 mmol), 5-amino-2-fluoro-benzamide, (51 mg, 0.33 mmol) and HATU (139 mg, 0.364 mmol) in DMF (1.3 mL) was added 4-methylmorpholine (109 μL, 0.994 mmol) and the reaction mixture was stirred for 1 hour. The reaction mixture was filtered and purified by HPLC (1-99% acetonitrile/5 mM HCl). Product fractions were neutralized with saturated aqueous NaHCO$_3$. The fractions were extracted with dichloromethane, dried over MgSO$_4$, filtered and concentrated to provide N-(3-carbamoyl-4-fluoro-phenyl)-4-[2-methoxy-4-(trifluoromethoxy)phenoxy]-6-(1-methylcyclopropyl)pyridine-3-carboxamide (100 mg, 58%). ESI-MS m/z calc. 519.14, found 520.1 (M+1)+; retention time (Method B): 1.52 minutes (3 minute run). $^1$H NMR (400 MHz, DMSO-d6) δ 10.43 (s, 1H), 8.60 (s, 1H), 7.98 (dd, J=6.5, 2.8 Hz, 1H), 7.81 (ddd, J=7.6, 4.4, 2.8 Hz, 1H), 7.69 (d, J=13.0 Hz, 2H), 7.44 (d, J=8.8 Hz, 1H), 7.33-7.22 (m, 2H), 7.07 (ddd, J=8.7, 2.7, 1.3 Hz, 1H), 6.49 (s, 1H), 3.79 (s, 3H), 1.27 (s, 3H), 1.15 (q, J=3.4 Hz, 2H), 0.82 (q, J=3.6 Hz, 2H) ppm.

Example 70

N-(2-Carbamoyl-4-pyridyl)-4-[2-methoxy-4-(trifluoromethoxy)phenoxy]-6-(1-methylcyclopropyl)pyridine-3-carboxamide (105)

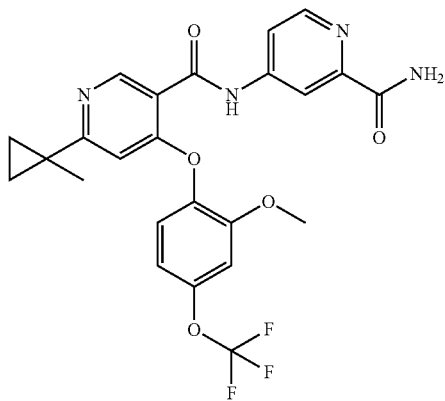 [SMILES: COc1cc(OC(F)(F)F)ccc1Oc1cc(C2(C)CC2)ncc1C(=O)Nc1ccnc(C(N)=O)c1]

392

A solution of 4-[2-methoxy-4-(trifluoromethoxy)phenoxy]-6-(1-methylcyclopropyl)pyridine-3-carboxylic acid (102 mg, 0.266 mmol), 4-[(Z)-[(tert-butylamino)-phenylsulfanyl-methylene]amino]pyridine-2-carboxamide (prepared as described in Preparation 1, 88 mg, 0.27 mmol), tris[(Z)-1-methyl-3-oxo-but-1-enoxy]iron (2.6 mg, 0.007 mmol) in 2-propanol (1.5 mL) was heated at 80° C. under an atmosphere of air for 20 hours. The reaction mixture was cooled to room temperature and concentrated in vacuo. Silica gel chromatography (0-60% ethyl acetate/hexanes) provided N-(2-carbamoyl-4-pyridyl)-4-[2-methoxy-4-(trifluoromethoxy)phenoxy]-6-(1-methylcyclopropyl)pyridine-3-carboxamide (26 mg, 19%). ESI-MS m/z calc. 502.15, found 503.2 (M+1)+; retention time (Method B): 1.44 minutes (3 minute run). $^1$H NMR (400 MHz, DMSO-d6) δ 10.86 (s, 1H), 8.62 (s, 1H), 8.52 (d, J=5.5 Hz, 1H), 8.30 (d, J=2.1 Hz, 1H), 8.10 (d, J=2.8 Hz, 1H), 7.89 (dd, J=5.5, 2.2 Hz, 1H), 7.64 (d, J=3.0 Hz, 1H), 7.44 (d, J=8.8 Hz, 1H), 7.25 (d, J=2.8 Hz, 1H), 7.06 (ddd, J=8.8, 2.7, 1.2 Hz, 1H), 6.52 (s, 1H), 3.78 (s, 3H), 1.28 (s, 3H), 1.17 (q, J=3.5 Hz, 2H), 0.84 (q, J=3.6 Hz, 2H) ppm.

Example 71

4-[[4-[2-Methoxy-4-(trifluoromethoxy)phenoxy]-6-(trifluoromethyl)pyridine-3-carbonyl]amino]-6-methyl-pyridine-2-carboxamide (84)

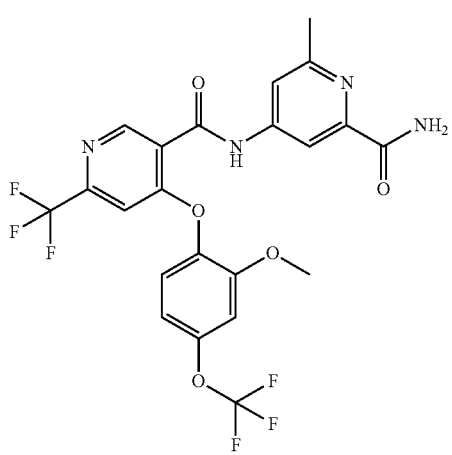 [SMILES: COc1cc(OC(F)(F)F)ccc1Oc1cc(C(F)(F)F)ncc1C(=O)Nc1cc(C)nc(C(N)=O)c1]

Step 1: 4-[2-Methoxy-4-(trifluoromethoxy)phenoxy]-6-(trifluoromethyl)pyridine-3-carboxylic acid

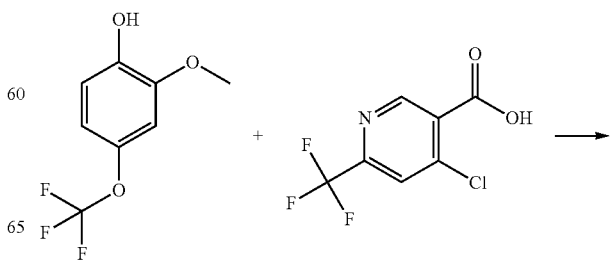

393

-continued

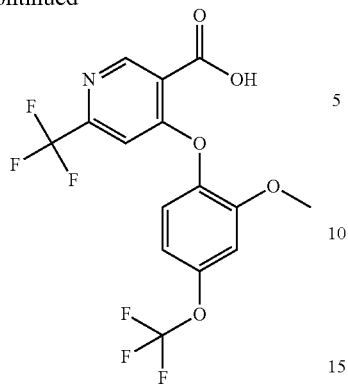

4-Chloro-6-(trifluoromethyl)pyridine-3-carboxylic acid (8.00 g, 35.5 mmol), finely ground K$_2$CO$_3$ (14.7 g, 106 mmol) and 2-methoxy-4-(trifluoromethoxy)phenol (7.35 g, 35.3 mmol) were combined in DMF (65 mL) in a 150-mL pressure vessel and heated at 90° C. for 16 hours. The reaction mixture was cooled to room temperature, diluted with ethyl acetate, and washed with aqueous HCl (180 mL of 1 M, 180.0 mmol), water and brine. The organic phase was dried over Na$_2$SO$_4$, filtered, and concentrated in vacuo. The resulting solid was slurried in approximately 1:30 dichloromethane/hexane. The slurry was filtered and washed with the same dichloromethane/hexane solvent mix. The resulting solid was dried under vacuum to provide 4-[2-methoxy-4-(trifluoromethoxy)phenoxy]-6-(trifluoromethyl)pyridine-3-carboxylic acid (8.83 g, 63%). ESI-MS m/z calc. 397.04, found 398.0 (M+1)+; retention time (Method A): 0.68 minutes (1 minute run). $^1$H NMR (400 MHz, DMSO-d6) δ 13.80 (br s, 1H), 9.02 (s, 1H), 7.42 (d, J=8.8 Hz, 1H), 7.31 (d, J=2.8 Hz, 1H), 7.08 (ddd, J=8.8, 2.7, 1.2 Hz, 1H), 6.93 (s, 1H), 3.78 (s, 3H) ppm.

Step 2: 4-[[4-[2-Methoxy-4-(trifluoromethoxy)phenoxy]-6-(trifluoromethyl)pyridine-3-carbonyl]amino]-6-methyl-pyridine-2-carboxamide (84)

394

-continued

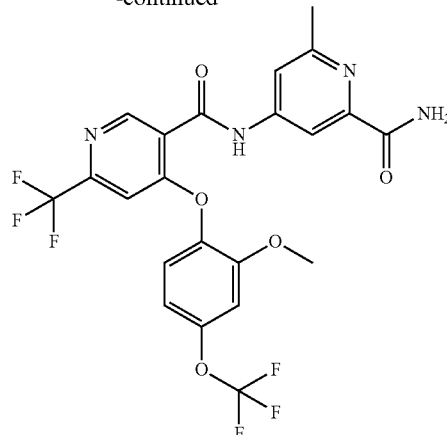

To a solution of 4-[2-methoxy-4-(trifluoromethoxy)phenoxy]-6-(trifluoromethyl)pyridine-3-carboxylic acid (75 mg, 0.17 mmol) in dichloromethane (3.6 mL) at 0° C. was added DMF (7.5 µL, 0.097 mmol) and oxalyl chloride (68 µL, 0.78 mmol). The mixture was warmed to room temperature over 30 minutes and stirred for 1 hour. The reaction mixture was concentrated in vacuo. The residue was dissolved in dichloromethane (3.6 mL) and 4-amino-6-methyl-pyridine-2-carboxamide (40 mg, 0.26 mmol) was added followed by triethylamine (120 µL, 0.86 mmol). The resulting mixture was stirred at room temperature for 45 minutes then concentrated in vacuo. The residue was dissolved in DMSO and purified by HPLC (10-95% acetonitrile/0.05% TFA in water). Product fractions were combined and lyophilized to provide 4-[[4-[2-methoxy-4-(trifluoromethoxy)phenoxy]-6-(trifluoromethyl)pyridine-3-carbonyl]amino]-6-methyl-pyridine-2-carboxamide trifluoroacetate (2 mg, 2%) as a white powder. ESI-MS m/z calc. 530.10, found 531.1 (M+1)+; 529.0 (M−1)−; retention time (Method E): 3.24 minutes (5 minute run). $^1$H NMR (500 MHz, Methanol-d4) δ 8.96 (d, J=0.7 Hz, 1H), 8.22-8.16 (m, 1H), 7.96 (d, J=2.1 Hz, 1H), 7.48-7.42 (m, 1H), 7.23-7.16 (m, 1H), 7.09-7.01 (m, 2H), 3.84 (s, 3H), 2.64 (m, 3H) ppm.

Example 72

N-(2-Carbamoyl-4-pyridyl)-4-[2-methoxy-4-(trifluoromethoxy)phenoxy]-6-(trifluoromethyl)pyridine-3-carboxamide (34)

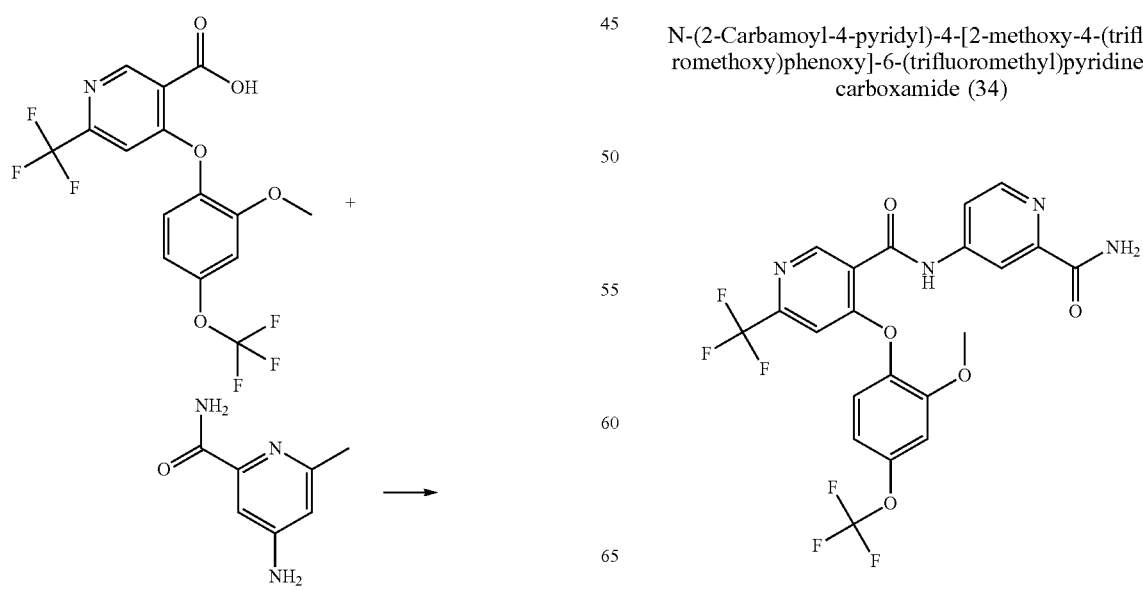

This compound was made in an analogous fashion to Example 71, except employing 4-aminopyridine-2-carboxamide in the amide formation step (Step 2). The yield of the desired product after purification was 550 mg (34%). ESI-MS m/z calc. 516.09, found 517.2 (M+1)+; retention time (Method B): 1.67 minutes (3 minute run). ¹H NMR (400 MHz, DMSO-d6) δ 11.29 (s, 1H), 8.96 (s, 1H), 8.57 (d, J=5.5 Hz, 1H), 8.34 (d, J=2.1 Hz, 1H), 8.15 (s, 1H), 7.93-7.86 (m, 1H), 7.70 (s, 1H), 7.51 (d, J=8.8 Hz, 1H), 7.28 (d, J=2.8 Hz, 1H), 7.10-7.03 (m, 2H), 3.78 (s, 3H) ppm.

Example 73

N-(3-Carbamoyl-4-fluoro-phenyl)-4-[2-methoxy-4-(trifluoromethoxy)phenoxy]-6-(trifluoromethyl)pyridine-3-carboxamide (30)

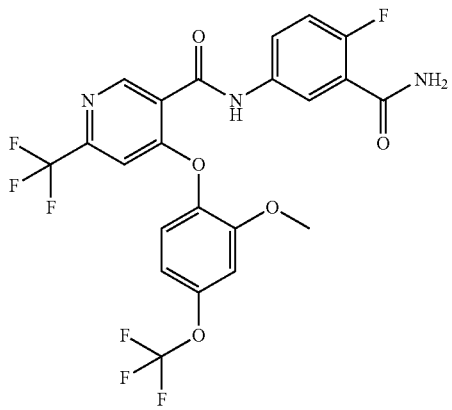 [SMILES: COc1cc(OC(F)(F)F)ccc1Oc1cc(C(F)(F)F)ncc1C(=O)Nc1ccc(F)c(C(N)=O)c1]

This compound was made in an analogous fashion to Example 71 except employing 5-amino-2-fluoro-benzamide in the amide formation step (Step 2). The yield of the desired product after purification was 2.2 g (66%). ESI-MS m/z calc. 533.08, found 534.1 (M+1)+; retention time (Method B): 1.78 minutes (3 minute run). ¹H NMR (400 MHz, DMSO-d6) δ 10.81 (s, 1H), 8.92 (s, 1H), 8.00 (dd, J=6.5, 2.8 Hz, 1H), 7.82 (ddd, J=8.9, 4.4, 2.8 Hz, 1H), 7.72 (s, 1H), 7.69 (s, 1H), 7.49 (d, J=8.8 Hz, 1H), 7.34-7.26 (m, 2H), 7.09 (ddd, J=8.8, 2.7, 1.3 Hz, 1H), 7.02 (s, 1H), 3.79 (s, 3H) ppm.

Example 74

N-(3-Carbamoylphenyl)-4-[2-methoxy-4-(trifluoromethoxy)phenoxy]-6-(trifluoromethyl)pyridine-3-carboxamide (29)

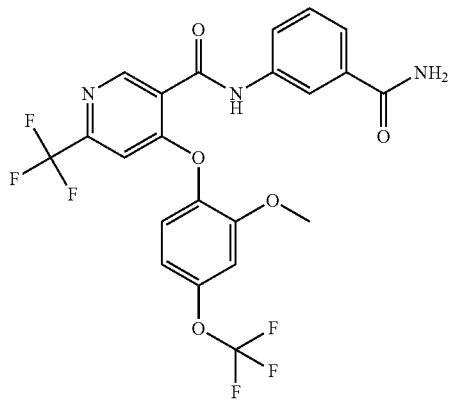 [SMILES: COc1cc(OC(F)(F)F)ccc1Oc1cc(C(F)(F)F)ncc1C(=O)Nc1cccc(C(N)=O)c1]

This compound was made in an analogous fashion to Example 71 except employing 3-aminobenzamide in the amide formation step (Step 2). The yield of the desired product after purification was 43 mg (58%). ESI-MS m/z calc. 515.09, found 516.1 (M+1)+; retention time (Method B): 1.66 minutes (3 minute run). ¹H NMR (400 MHz, DMSO-d₆) δ 10.77 (s, 1H), 8.92 (s, 1H), 8.17 (t, J=1.9 Hz, 1H), 7.98 (s, 1H), 7.85 (ddd, J=8.2, 2.3, 1.0 Hz, 1H), 7.62 (dt, J=7.8, 1.3 Hz, 1H), 7.51 (d, J=8.8 Hz, 1H), 7.44 (t, J=7.9 Hz, 1H), 7.39 (s, 1H), 7.29 (d, J=2.7 Hz, 1H), 7.09 (ddd, J=8.8, 2.7, 1.3 Hz, 1H), 7.02 (s, 1H), 3.79 (s, 3H) ppm.

Example 75

N-(3-Carbamoyl-4-fluoro-phenyl)-3-(difluoromethyl)-2-fluoro-6-[4-(trifluoromethoxy)phenoxy]benzamide (74)

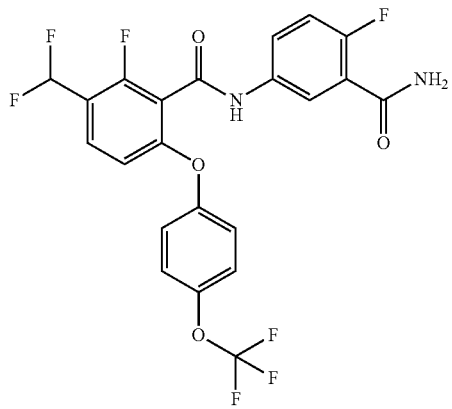 [SMILES: NC(=O)c1cc(NC(=O)c2c(Oc3ccc(OC(F)(F)F)cc3)ccc(C(F)F)c2F)ccc1F]

Step 1: Ethyl 6-bromo-3-(difluoromethyl)-2-fluoro-benzoate

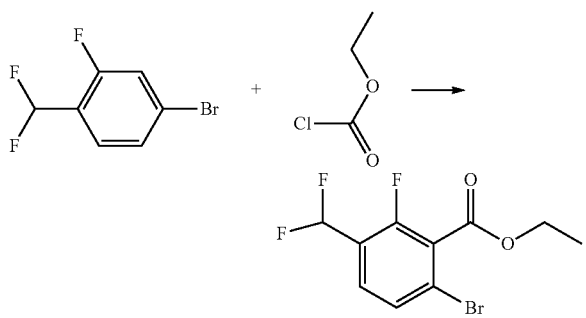

4-Bromo-1-(difluoromethyl)-2-fluoro-benzene (4.90 g, 21.8 mmol) was dissolved in anyhdrous THF (20 mL) under N₂ atmosphere and cooled to −78° C. A solution of LDA (11 mL of 2 M in THF/heptane/benzene, 22 mmol) was further diluted with anyhdrous THF (500 mL) and this solution was added dropwise to the reaction mixture over a period of 1 hour while maintaining the internal temperature below −70° C. Stirring was continued at −78° C. for 1 hour. Ethyl chloroformate (4.2 mL, 44 mmol) as a solution in THF (6 mL) was then added dropwise to the reaction mixture while maintaining internal temperature below −70° C. The reaction was allowed to warm to room temperature and stirred for 16 hours. The reaction was then quenched with saturated aqueous NH₄Cl and extracted with ethyl acetate (2×). The combined organics were dried over Na₂SO₄, filtered and concentrated in vacuo. Silica gel chromatography (0-3% ethyl acetate/hexanes) provided ethyl 6-bromo-3-(difluoromethyl)-2-fluoro-benzoate (2.77 g, 43%). ESI-MS m/z calc. 295.97, found 299.0 (M+1)+; retention time (Method B): 1.72 minutes (3 minute run). ¹H NMR (500 MHz, DMSO-d6) δ 7.72 (h, J=8.2, 7.6 Hz, 2H), 7.23 (t, J=53.9 Hz, 1H), 4.40 (q, J=7.1 Hz, 2H), 1.31 (t, J=7.1 Hz, 3H) ppm.

Step 2: 6-Bromo-3-(difluoromethyl)-2-fluoro-benzoic acid

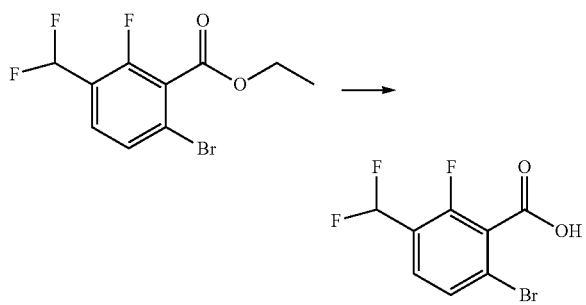

To a solution of ethyl 6-bromo-3-(difluoromethyl)-2-fluoro-benzoate (2.5 g, 8.4 mmol) in methanol (25 mL) and water (25 mL) was added NaOH (3.4 g, 85 mmol). The reaction mixture was stirred at room temperature for 2 hours. The reaction mixture was cooled to 0° C., quenched slowly with 6N HCl and the mixture was extracted with ethyl acetate. The organic layer was dried over MgSO₄, filtered and concentrated in vacuo to provide 6-bromo-3-(difluoromethyl)-2-fluoro-benzoic acid (1.4 g, 62%). ESI-MS m/z calc. 267.95, found 271.0 (M+1)+; retention time (Method A): 0.42 minutes (1 minute run). ¹H NMR (400 MHz, DMSO-d6) δ 14.37 (s, 1H), 7.72 (d, J=8.4 Hz, 1H), 7.69-7.60 (m, 1H), 7.24 (t, J=53.9 Hz, 1H) ppm.

Step 3: 3-(Difluoromethyl)-2-fluoro-6-[4-(trifluoromethoxy)phenoxy]benzoic acid

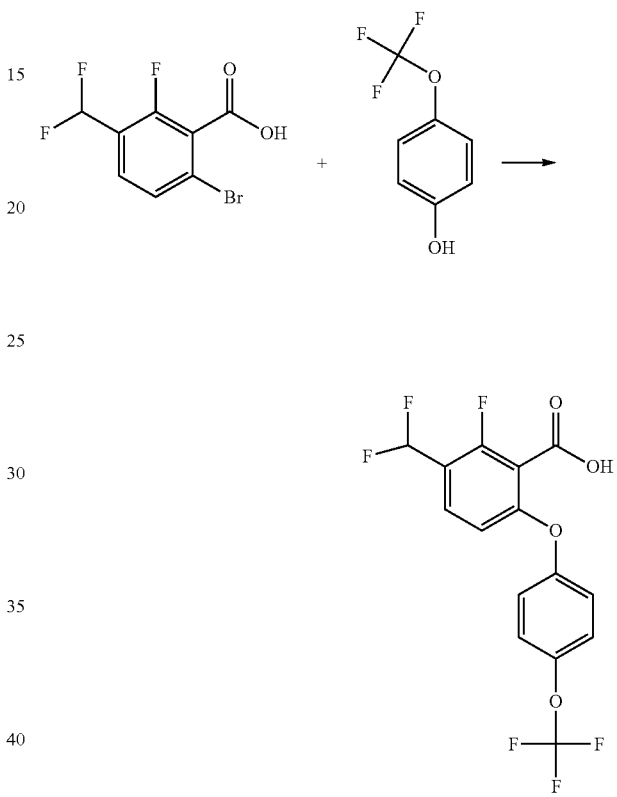

To a pressure flask was added 6-bromo-3-(difluoromethyl)-2-fluoro-benzoic acid (1.00 g, 3.72 mmol), 4-(trifluoromethoxy)phenol (485 μL, 3.74 mmol) and Cs₂CO₃ (1.5 g, 4.6 mmol) and toluene (12 mL). The reaction mixture was bubbled with N₂ for 10 min, and then copper (I) iodide (285 mg, 1.50 mmol) was added. The flask was flushed with N₂, capped, and heated at 100° C. with vigorous stirring for 5 hours. The mixture was allowed to cool then partitioned between ethyl acetate and water. The water layer was acidified with HCl and the product was extracted into the ethyl acetate. The organic layer was washed with brine, dried over Na₂SO₄, filtered and concentrated in vacuo. Silica gel chromatography (0-100% ethyl acetate/hexanes) provided 3-(difluoromethyl)-2-fluoro-6-[4-(trifluoromethoxy)phenoxy]benzoic acid (760 mg, 56%). ESI-MS m/z calc. 366.03, found 367.0 (M+1)+; retention time (Method B): 1.75 minutes (3 minute run). ¹H NMR (400 MHz, DMSO-d6) δ 13.99 (s, 1H), 7.71 (t, J=8.4 Hz, 1H), 7.49-7.39 (m, 2H), 7.39-7.06 (m, 3H), 6.92 (d, J=8.7 Hz, 1H) ppm.

399

Step 4: 3-(Difluoromethyl)-2-fluoro-6-[4-(trifluoromethoxy)phenoxy]benzoyl chloride

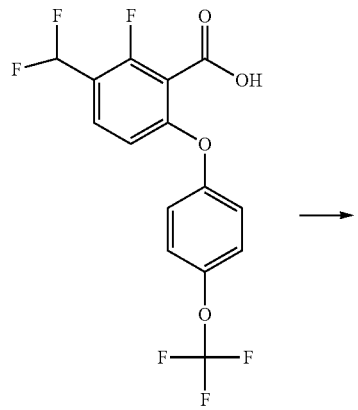

To a solution of 3-(difluoromethyl)-2-fluoro-6-[4-(trifluoromethoxy)phenoxy]benzoic acid (170 mg, 0.464 mmol) and DMF (35 µL, 0.45 mmol) in dichloromethane (2 mL) at 0° C. was added oxalyl chloride (70 µL, 0.80 mmol) dropwise. The mixture was stirred at room temperature for 20 minutes. Conversion was monitored by UPLC via test for morpholine adduct formation. The solvent was evaporated under reduced pressure to afford 3-(difluoromethyl)-2-fluoro-6-[4-(trifluoromethoxy)phenoxy]benzoyl chloride.

400

Step 5: N-(3-Carbamoyl-4-fluoro-phenyl)-3-(difluoromethyl)-2-fluoro-6-[4-(trifluoromethoxy)phenoxy]benzamide (74)

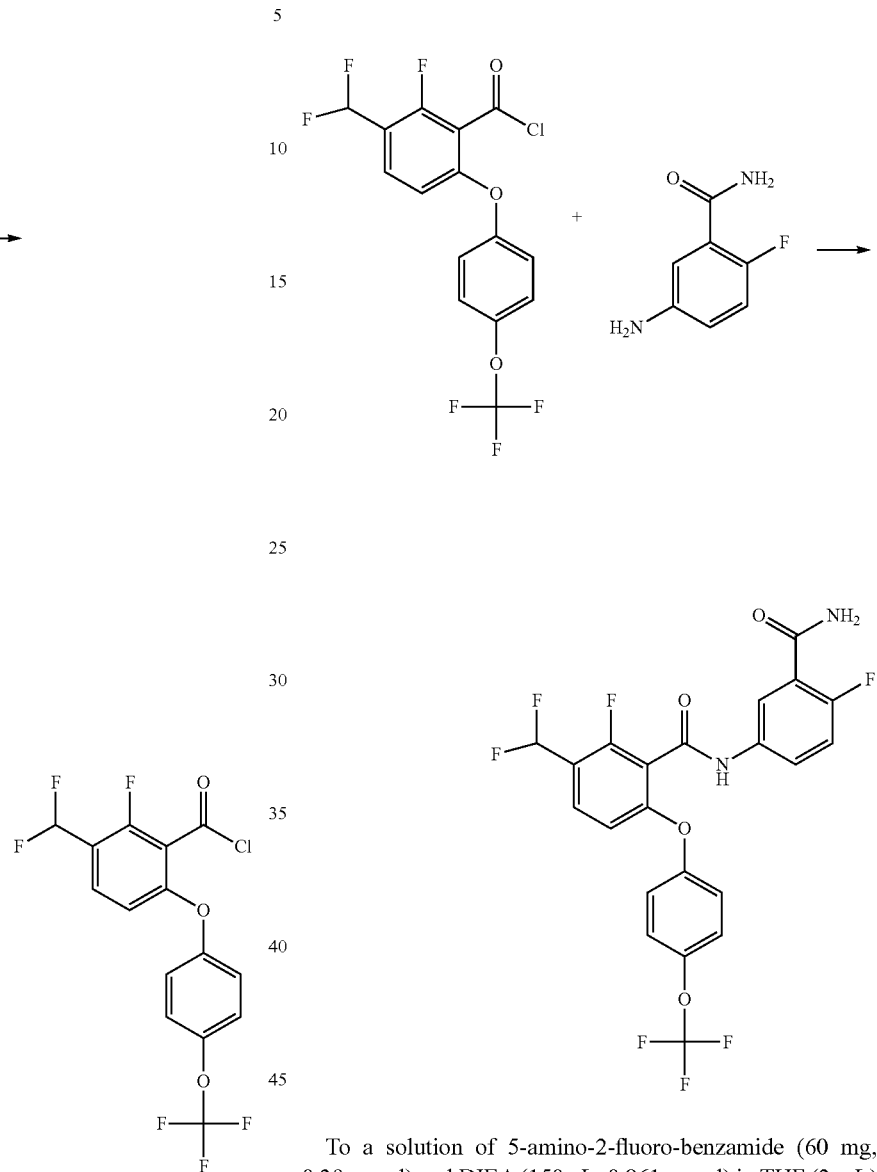

To a solution of 5-amino-2-fluoro-benzamide (60 mg, 0.39 mmol) and DIEA (150 µL, 0.861 mmol) in THF (2 mL) at 0° C. was added a suspension of 3-(difluoromethyl)-2-fluoro-6-[4-(trifluoromethoxy)phenoxy]benzoyl chloride (150 mg, 0.390 mmol) in dichloromethane (1 mL). The reaction mixture was allowed to warm to room temperature and stirred for 16 hours. The reaction mixture was partitioned between water and dichloromethane. The organic layer was washed with 1 M HCl (2×), dried over $MgSO_4$, filtered and concentrated in vacuo. Silica gel chromatography (0-50% ethyl acetate/hexanes) provided N-(3-carbamoyl-4-fluoro-phenyl)-3-(difluoromethyl)-2-fluoro-6-[4-(trifluoromethoxy)phenoxy]benzamide (75 mg, 38%). ESI-MS m/z calc. 502.08, found 503.1 (M+1)+; retention time (Method B): 1.72 minutes (3 minute run). $^1$H NMR (400 MHz, DMSO-d6) δ 10.98 (s, 1H), 7.96 (dd, J=6.4, 2.8 Hz, 1H), 7.78-7.66 (m, 4H), 7.46 (dq, J=7.7, 1.0 Hz, 2H), 7.42-7.10 (m, 4H), 6.89 (d, J=8.7 Hz, 1H) ppm.

Example 76

4-[[3-(Difluoromethyl)-2-fluoro-6-[4-(trifluoromethoxy)phenoxy]benzoyl]amino]pyridine-2-carboxamide (83)

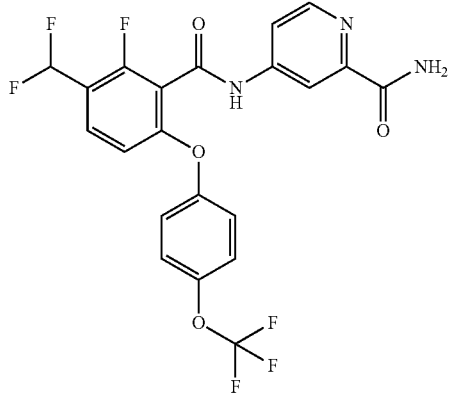 [SMILES: NC(=O)c1cc(NC(=O)c2c(Oc3ccc(OC(F)(F)F)cc3)ccc(C(F)F)c2F)ccn1]

A microwave vial charged with 4-[(Z)-[(tert-butylamino)-phenylsulfanyl-methylene]amino]pyridine-2-carboxamide (prepared as described in Preparation 1, 99 mg, 0.30 mmol), tris[(Z)-1-methyl-3-oxo-but-1-enoxy]iron (2.4 mg, 0.007 mmol) and 3-(difluoromethyl)-2-fluoro-6-[4-(trifluoromethoxy)phenoxy]benzoic acid (prepared as described in Example 75, step 3, 100 mg, 0.273 mmol) in 2-propanol (2 mL) was heated at 83° C. for 16 hours. The reaction mixture was cooled to room temperature and concentrated in vacuo. The crude material was taken up in dichloromethane and washed with 1 M HCl. The organic layer was dried over MgSO₄, filtered and concentrated in vacuo. Silica gel chromatography (0-60% ethyl acetate/hexanes) provided 4-[[3-(difluoromethyl)-2-fluoro-6-[4-(trifluoromethoxy)phenoxy]benzoyl]amino]pyridine-2-carboxamide (82 mg, 62%). ESI-MS m/z calc. 485.08, found 486.2 (M+1)+; retention time (Method B): 1.84 minutes (3 minute run). ¹H NMR (400 MHz, DMSO-d6) δ 11.42 (s, 1H), 8.54 (d, J=5.5 Hz, 1H), 8.29 (d, J=2.1 Hz, 1H), 8.11 (s, 1H), 7.83-7.71 (m, 2H), 7.66 (d, J=2.9 Hz, 1H), 7.46 (dq, J=7.8, 1.0 Hz, 2H), 7.41-7.11 (m, 3H), 6.91 (d, J=8.7 Hz, 1H) ppm.

Example 77

4-[[2-fluoro-3-(trifluoromethoxy)-6-[4-(trifluoromethoxy)phenoxy]benzoyl]amino]pyridine-2-carboxamide (243)

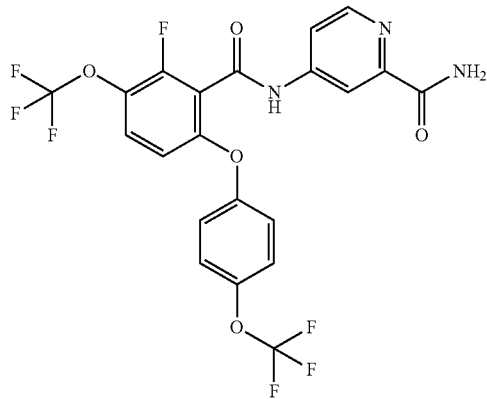 [SMILES: NC(=O)c1cc(NC(=O)c2c(Oc3ccc(OC(F)(F)F)cc3)ccc(OC(F)(F)F)c2F)ccn1]

Step 1: 2-fluoro-3-(trifluoromethoxy)-6-[4-(trifluoromethoxy)phenoxy]benzoic acid

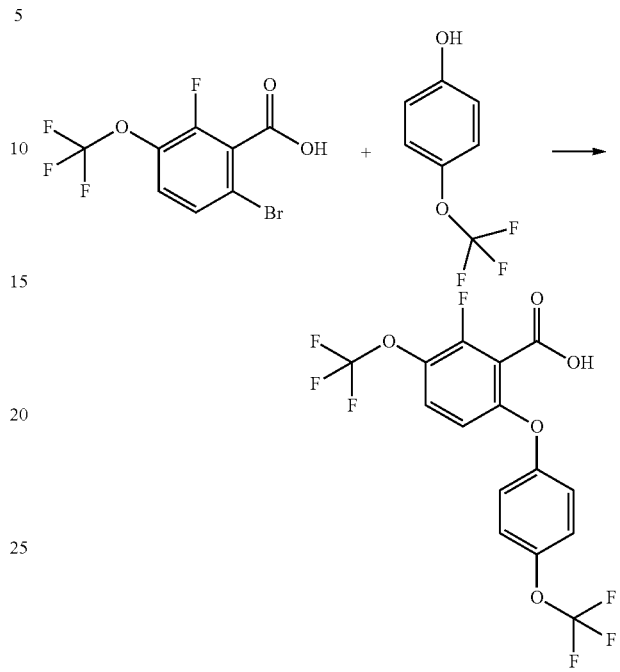

A suspension of 6-bromo-2-fluoro-3-(trifluoromethoxy)benzoic acid (400 mg, 1.32 mmol), 4-(trifluoromethoxy)phenol (190 μL, 1.47 mmol) and cesium carbonate (950 mg, 2.92 mmol) in toluene (8 mL) was heated to 100° C. and then copper (I) iodide (53 mg, 0.28 mmol) was added. The mixture was heated at 100° C. overnight. The reaction mixture was cooled to room temperature then acidified to pH 2 with 2 M HCl. The mixture was extracted with ethyl acetate (2×100 mL). The organics were combined and washed with water (2×100 mL), brine (100 mL), dried over MgSO₄, filtered and concentrated in vacuo to afford 2-fluoro-3-(trifluoromethoxy)-6-[4-(trifluoromethoxy)phenoxy]benzoic acid (500 mg, 95%) as a brown gummy solid, which was used in the next step without purification.

Step 2: methyl 4-[[2-fluoro-3-(trifluoromethoxy)-6-[4-(trifluoromethoxy)phenoxy]benzoyl]amino]pyridine-2-carboxylate

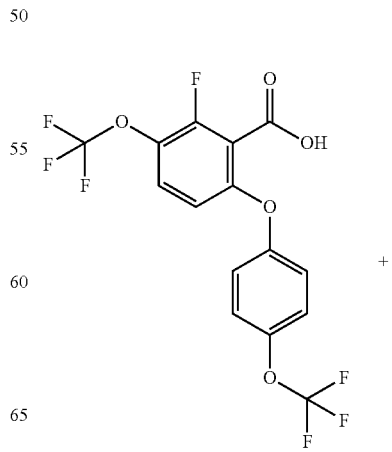

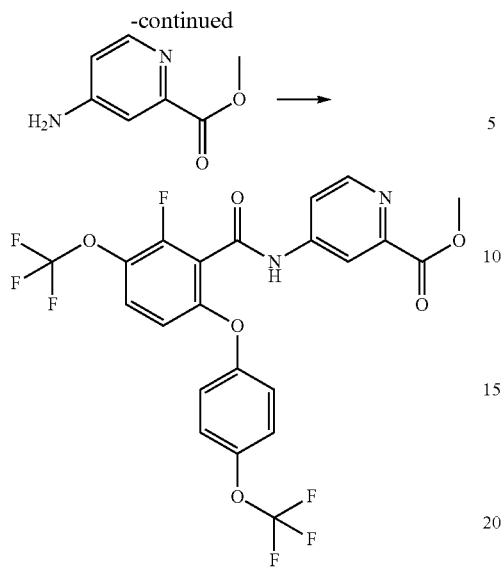

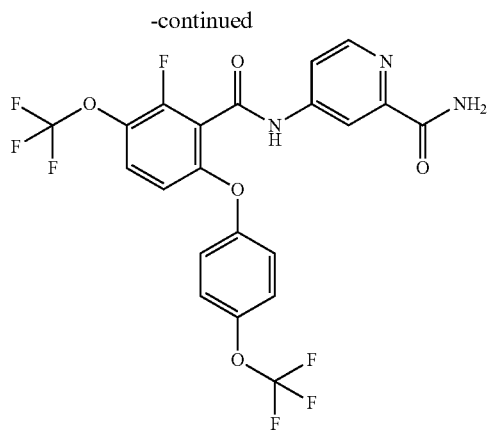

To an ice-cooled solution of 2-fluoro-3-(trifluoromethoxy)-6-[4-(trifluoromethoxy)phenoxy]benzoic acid (400 mg, 1.0 mmol) in DCM (6 mL) was added DMF (13 µL, 0.17 mmol) and dropwise oxalyl dichloride (420 µL, 4.82 mmol) and was stirred for 2 hours. The reaction mixture was concentrated in vacuo to afford the acid chloride as a pale yellow oil. The residue was dissolved in DCM (6 mL) and added dropwise to a solution of methyl 4-aminopyridine-2-carboxylate (275 mg, 1.81 mmol) and triethylamine (1.3 mL, 9.33 mmol) in DCM (6 mL) in an ice bath. The resulting mixture was stirred and warmed to room temperature overnight. The reaction mixture was concentrated in vacuo and purified by silica gel chromatography (ethyl acetate/heptane) to afford methyl 4-[[2-fluoro-3-(trifluoromethoxy)-6-[4-(trifluoromethoxy)phenoxy]benzoyl]amino]pyridine-2-carboxylate (65 mg, 12%) as a clear waxy solid. ESI-MS m/z calc. 534.07, found 535.6 (M+1)+; 533.6 (M−1)−; Retention time (Method F): 0.97 minutes (1.5 minutes run). $^1$H NMR (400 MHz, CDCl3) δ 9.13 (s, 1H), 8.51 (d, J=5.5 Hz, 1H), 8.14 (d, J=2.2 Hz, 1H), 7.94 (dd, J=5.6, 2.2 Hz, 1H), 7.21 (ddq, J=9.5, 8.4, 1.2 Hz, 1H), 7.14 (dtd, J=8.5, 2.3, 1.3 Hz, 2H), 7.06-6.94 (m, 2H), 6.58 (dd, J=9.2, 1.8 Hz, 1H), 3.82 (s, 3H) ppm.

Step 3: 4-[[2-fluoro-3-(trifluoromethoxy)-6-[4-(trifluoromethoxy)phenoxy]benzoyl]amino]pyridine-2-carboxamide (243)

Methyl 4-[[2-fluoro-3-(trifluoromethoxy)-6-[4-(trifluoromethoxy)phenoxy]benzoyl]amino]pyridine-2-carboxylate (100 mg, 0.19 mmol) was dissolved in ammonia (5 mL of 7 M in methanol, 35 mmol) and stirred at room temperature overnight. The reaction mixture was concentrated in vacuo to afford 4-[[2-fluoro-3-(trifluoromethoxy)-6-[4-(trifluoromethoxy)phenoxy]benzoyl]amino]pyridine-2-carboxamide (243, 58 mg, 50%). ESI-MS m/z calc. 519.07, found 520.3 (M+1)+; Retention time (Method E): 3.29 minutes (5 minutes run). $^1$H NMR (400 MHz, Chloroform-d) δ 10.10 (s, 1H), 8.42 (s, 2H), 8.13 (t, J=1.4 Hz, 1H), 7.79 (d, J=4.5 Hz, 1H), 7.28 (ddd, J=9.4, 8.1, 1.2 Hz, 1H), 7.13-7.07 (m, 2H), 7.04-6.98 (m, 2H), 6.62 (dd, J=9.2, 1.7 Hz, 1H), 4.92 (d, J=4.6 Hz, 1H) ppm.

Example 78

N-(2-Carbamoyl-5-methyl-4-pyridyl)-3-methoxy-5-[2-methoxy-4-(trifluoromethoxy)phenoxy]-2-(trifluoromethyl)pyridine-4-carboxamide (144) and
N-(2-Carbamoyl-5-methyl-4-pyridyl)-3-fluoro-5-[2-methoxy-4-(trifluoromethoxy)phenoxy]-2-(trifluoromethyl)pyridine-4-carboxamide (143)

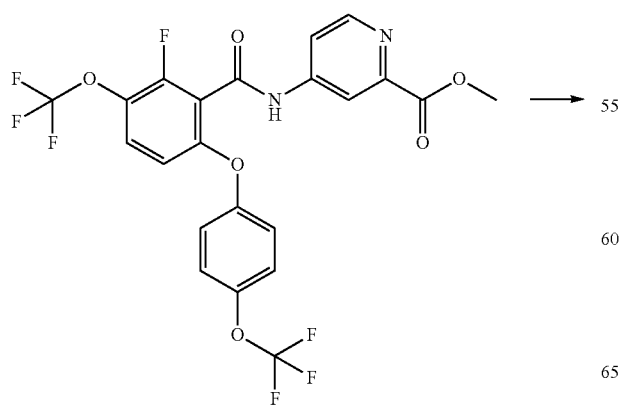

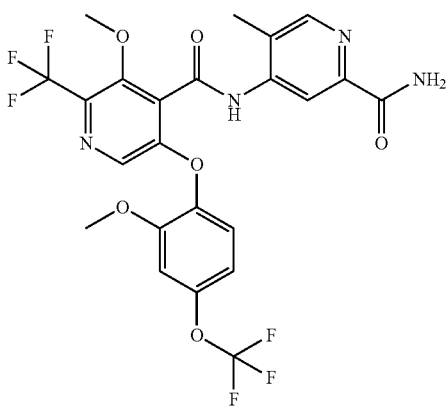

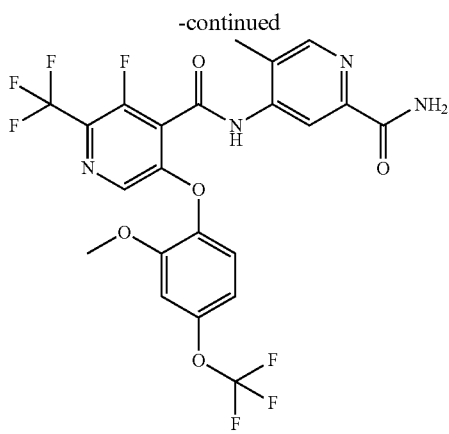

Step 1: N-(2-Bromo-5-methyl-4-pyridyl)-3-fluoro-5-[2-methoxy-4-(trifluoromethoxy)phenoxy]-2-(trifluoromethyl)pyridine-4-carboxamide

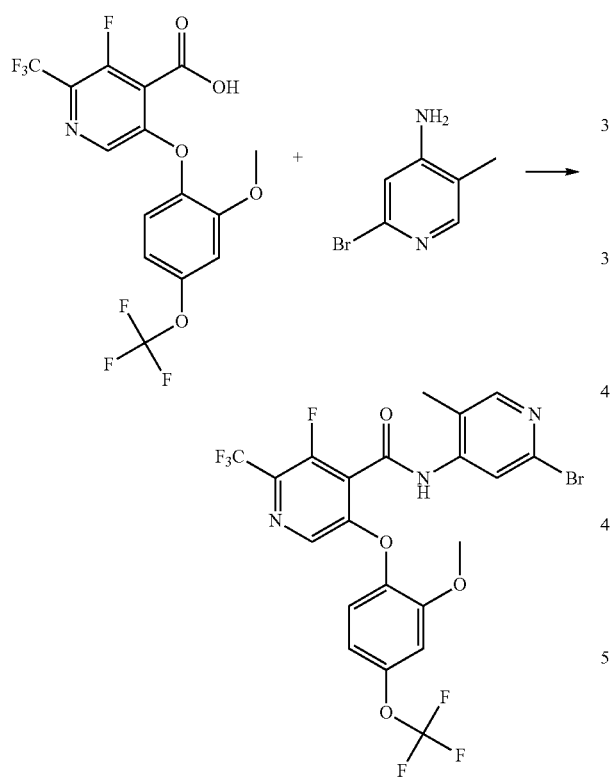

This compound was made in an analogous fashion to methyl 4-[[3-fluoro-5-[2-methoxy-4-(trifluoromethoxy)phenoxy]-2-(trifluoromethyl)pyridine-4-carbonyl]amino]pyridine-2-carboxylate (Example 12, Step 4), except employing 2-bromo-5-methyl-pyridin-4-amine in the amide formation step. The yield of the desired product after purification was 282 mg (670%). ESI-MS m/z calc. 583.00, found 585.0 (M+1)+; retention time (Method F): 1.14 minutes (1.5 minute run).

Step 2: Methyl 4-[[3-Fluoro-5-[2-methoxy-4-(trifluoromethoxy)phenoxy]-2-(trifluoromethyl)pyridine-4-carbonyl]amino]-5-methyl-pyridine-2-carboxylate and methyl 4-[[3-Methoxy-5-[2-methoxy-4-(trifluoromethoxy)phenoxy]-2-(trifluoromethyl)pyridine-4-carbonyl]amino]-5-methyl-pyridine-2-carboxylate

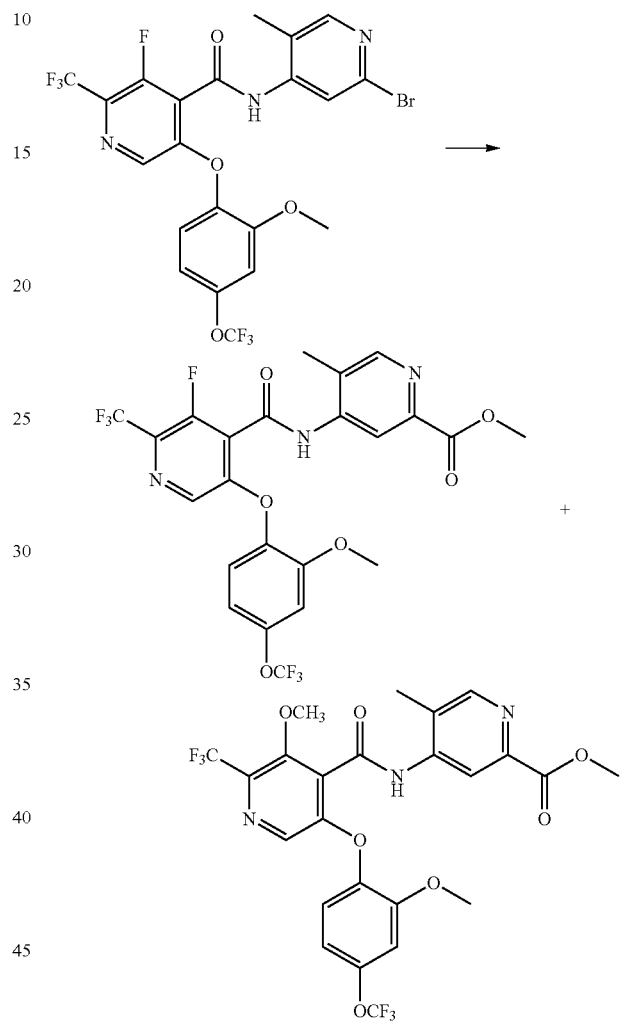

N-(2-bromo-5-methyl-4-pyridyl)-3-fluoro-5-[2-methoxy-4-(trifluoromethoxy)phenoxy]-2-(trifluoromethyl)pyridine-4-carboxamide (282 mg, 0.483 mmol) was dissolved in methanol (5 mL), and triethylamine (143 μL, 1.03 mmol) and Pd(dppf)Cl$_2$·DCM (80 mg, 0.0980 mmol) were added. Carbon monoxide was bubbled through the vigorously stirring reaction mixture for 5 minutes. The reaction mixture was then heated to 75° C. under carbon monoxide atmosphere for 7 hours. The reaction was cooled, then filtered through a pad of Celite eluting with methanol, and concentrated in vacuo. Silica gel chromatography (30-80% ethyl acetate/petroleum ether) provided a 1:1 mixture (378 mg) of methyl 4-[[3-fluoro-5-[2-methoxy-4-(trifluoromethoxy)phenoxy]-2-(trifluoromethyl)pyridine-4-carbonyl]amino]-5-methyl-pyridine-2-carboxylate; ESI-MS m/z calc. 563.09, found 564.0 (M+1) retention time (Method F): 1.02 minutes (1.5 minute run) and methyl 4-[[3-methoxy-5-[2-methoxy-4-(trifluoromethoxy)phenoxy]-2-(trifluoromethyl)pyridine-4-carbonyl]amino]-5-methyl-pyridine-2-carboxylate. ESI-MS m/z calc. 575.11, found 576.0 (M+1)+; retention time (Method F): 1.01 minutes.

Step 3: N-(2-Carbamoyl-5-methyl-4-pyridyl)-3-fluoro-5-[2-methoxy-4-(trifluoromethoxy)phenoxy]-2-(trifluoromethyl)pyridine-4-carboxamide (143) and N-(2-Carbamoyl-5-methyl-4-pyridyl)-3-methoxy-5-[2-methoxy-4-(trifluoromethoxy)phenoxy]-2-(trifluoromethyl)pyridine-4-carboxamide (144)

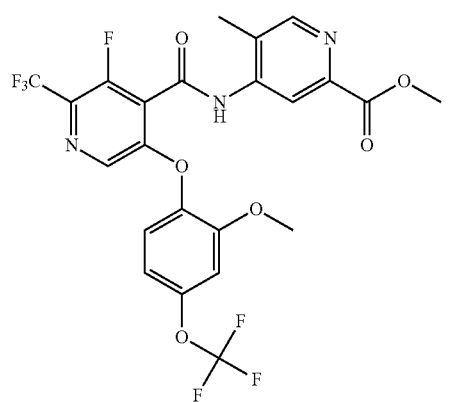

+

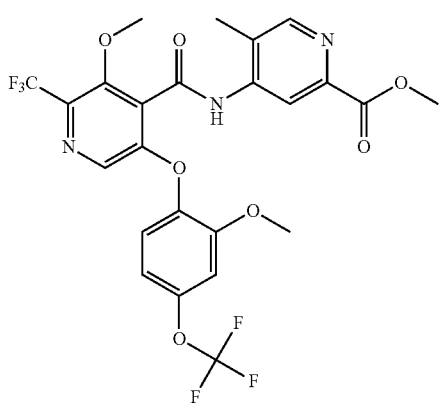

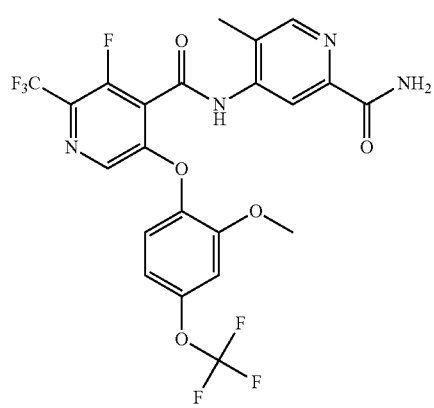

+

-continued

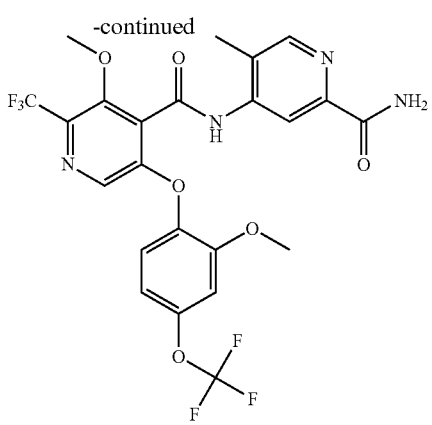

A mixture of methyl 4-[[3-methoxy-5-[2-methoxy-4-(trifluoromethoxy)phenoxy]-2-(trifluoromethyl)pyridine-4-carbonyl]amino]-5-methyl-pyridine-2-carboxylate (approximately 195 mg, 0.34 mmol), methyl 4-[[3-fluoro-5-[2-methoxy-4-(trifluoromethoxy)phenoxy]-2-(trifluoromethyl)pyridine-4-carbonyl]amino]-5-methyl-pyridine-2-carboxylate (approximately 189 mg, 0.34 mmol) and ammonia (9.4 mL of 4 M in methanol, 37.6 mmol) was stirred at ambient temperature for 16 hours. SPM32 silica metal scavenger (150 mg) was added and the reaction was stirred at ambient temperature for 15 minutes. The mixture was filtered and the filtrate was concentrated in vacuo. HPLC purification (37-100% acetonitrile/0.1% ammonium hydroxide) followed by SFC purification (Daicel Chiralpak AD-H column (250×10 mm, 5 m particle), isocratic run of 15% methanol with 20 mM ammonia solution (anhydrous) (mobile phase B). Mobile phase A=Supercritical carbon dioxide. Mobile phase B=Methanol with 20 mM Ammonia. Flow rate=10 mL/min. Detection: UV @ 280 nm. Column temperature=35° C.) provided:

143: N-(2-carbamoyl-5-methyl-4-pyridyl)-3-fluoro-5-[2-methoxy-4-(trifluoromethoxy)phenoxy]-2-(trifluoromethyl)pyridine-4-carboxamide (83, 7.0 mg, 4%). ESI-MS m/z calc. 548.0931, found 549.0 (M+1)+; retention time (Method E): 3.23 minutes (5 minute run). $^1$H NMR (400 MHz, DMSO-d6) δ 10.73 (s, 1H), 8.49 (d, J=4.4 Hz, 2H), 8.26-8.05 (m, 2H), 7.64 (s, 1H), 7.43 (d, J=8.8 Hz, 1H), 7.28 (d, J=2.7 Hz, 1H), 7.05 (ddd, J=8.9, 2.8, 1.3 Hz, 1H), 3.83 (s, 3H), 2.32 (s, 3H) ppm; and 144: N-(2-carbamoyl-5-methyl-4-pyridyl)-3-methoxy-5-[2-methoxy-4-(trifluoromethoxy)phenoxy]-2-(trifluoromethyl)pyridine-4-carboxamide (82, 53.9 mg, 28%). ESI-MS m/z calc. 560.11304, found 561.0 (M+1)+; retention time (Method E): 3.19 minutes (5 minute run). $^1$H NMR (400 MHz, DMSO-d6) δ 10.67 (s, 1H), 8.58-8.42 (m, 2H), 8.10 (d, J=2.8 Hz, 1H), 7.93 (s, 1H), 7.65 (d, J=2.8 Hz, 1H), 7.38 (d, J=8.8 Hz, 1H), 7.27 (d, J=2.8 Hz, 1H), 7.05 (ddd, J=8.8, 2.7, 1.2 Hz, 1H), 4.04 (s, 3H), 3.83 (s, 3H), 2.33 (s, 3H) ppm.

Example 79

N-(6-Carbamoyl-3-pyridyl)-3-methoxy-5-[2-methoxy-4-(trifluoromethoxy)phenoxy]-2-(trifluoromethyl)pyridine-4-carboxamide (203)

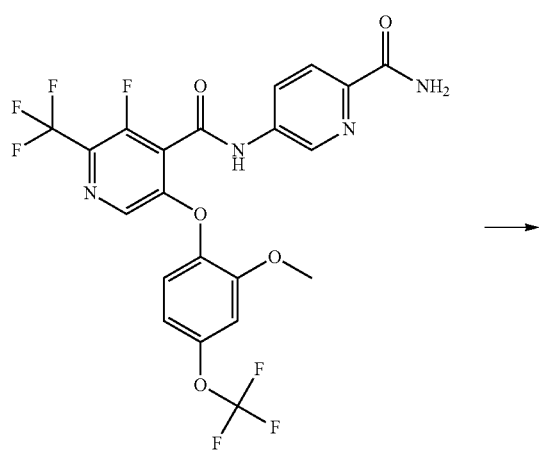

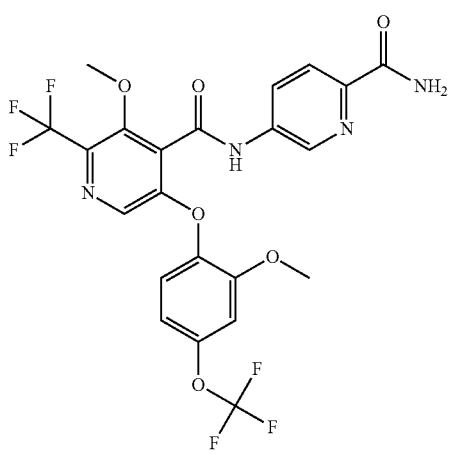

To a microwave vial was added N-(6-carbamoyl-3-pyridyl)-3-fluoro-5-[2-methoxy-4-(trifluoromethoxy)phenoxy]-2-(trifluoromethyl)pyridine-4-carboxamide (194, prepared as described in Example 12, 54 mg, 0.010 mmol) followed by sodium methoxide (1 mL of 0.5 M, 0.5 mmol). The reaction vial was sealed and heated at 80° C. overnight. The reaction mixture was cooled, treated with 2 drops of trifluoroacetic acid to quench and diluted with DMSO. HPLC purification (37-100% acetonitrile/0.1% ammonium hydroxide) provided N-(6-carbamoyl-3-pyridyl)-3-methoxy-5-[2-methoxy-4-(trifluoromethoxy)phenoxy]-2-(trifluoromethyl)pyridine-4-carboxamide (8.5 mg, 14%). ESI-MS m/z calc. 546.10, found 547.1 (M+1)+; 545.0 (M−1)−; retention time: 3.14 minutes (Method E). $^1$H NMR (500 MHz, CDCl$_3$) δ 8.71 (d, J=2.5 Hz, 1H), 8.36-8.28 (m, 2H), 8.26 (d, J=8.4 Hz, 1H), 7.91 (s, 1H), 7.71 (s, 1H), 7.26 (1H, obscured by solvent peak), 6.98-6.90 (m, 2H), 5.52 (s, 1H), 4.10 (s, 3H), 3.87 (s, 3H) ppm.

Example 80

N-(2-Carbamoyl-4-pyridyl)-3-ethoxy-5-[2-methoxy-4-(trifluoromethoxy)phenoxy]-2-(trifluoromethyl)pyridine-4-carboxamide (206)

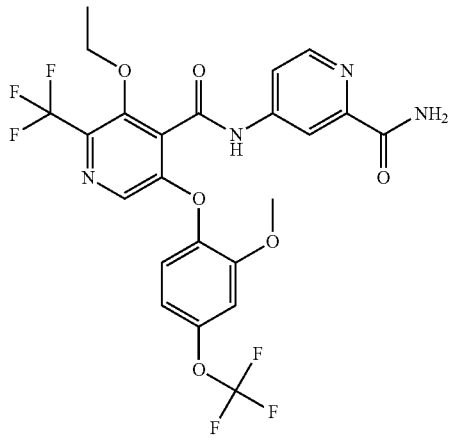 [SMILES: CCOc1c(C(F)(F)F)ncc(Oc2ccc(OC(F)(F)F)cc2OC)c1C(=O)Nc1ccnc(C(N)=O)c1]

Step 1: Ethyl 4-[[3-ethoxy-5-[2-methoxy-4-(trifluoromethoxy)phenoxy]-2-(trifluoromethyl)pyridine-4-carbonyl]amino]pyridine-2-carboxylate

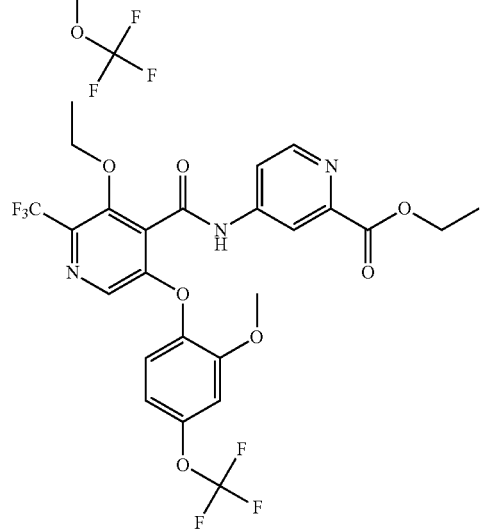

Methyl 4-[[3-fluoro-5-[2-methoxy-4-(trifluoromethoxy)phenoxy]-2-(trifluoromethyl)pyridine-4-carbonyl]amino]

pyridine-2-carboxylate (prepared as described in Example 12, Step 4, 190 mg, 0.346 mmol) was dissolved in ethanol (2.0 mL, 35 mmol) and treated with sodium ethoxide (35 mg, 0.51 mmol). The reaction mixture was heated at 75° C. for 72 hours. Additional sodium ethoxide (35 mg, 0.5143 mmol) was added and the reaction heated for an additional 72 hours. The reaction mixture was concentrated in vacuo to provide crude ethyl 4-[[3-ethoxy-5-[2-methoxy-4-(trifluoromethoxy)phenoxy]-2-(trifluoromethyl)pyridine-4-carbonyl]amino]pyridine-2-carboxylate (150 mg, 74% crude yield). ESI-MS m/z calc. 589.13, found 590.0 (M+1)+; retention time (Method F): 1.02 minutes (1.5 minute run).

Step 2: N-(2-Carbamoyl-4-pyridyl)-3-ethoxy-5-[2-methoxy-4-(trifluoromethoxy)phenoxy]-2-(trifluoromethyl)pyridine-4-carboxamide (206)

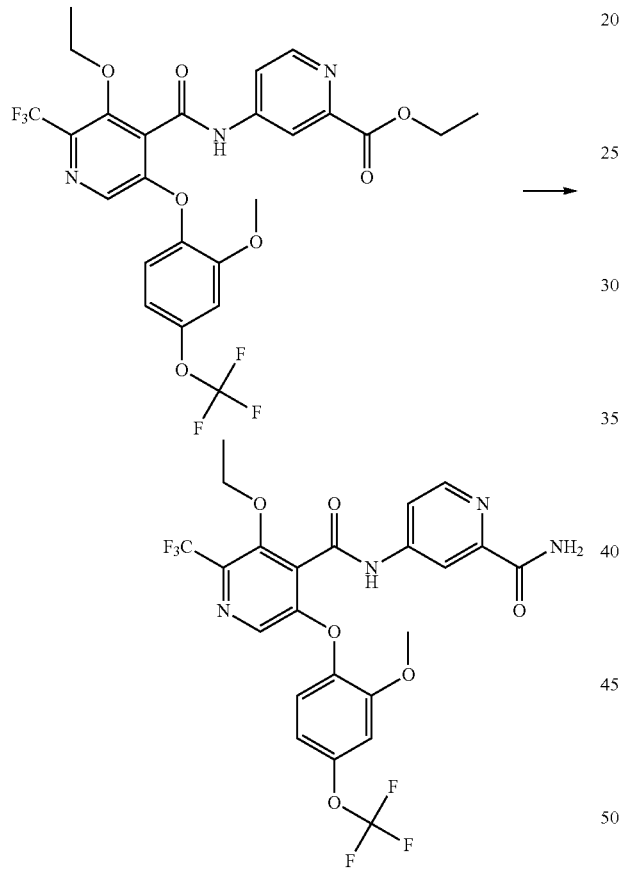

Ethyl 4-[[3-ethoxy-5-[2-methoxy-4-(trifluoromethoxy)phenoxy]-2-(trifluoromethyl)pyridine-4-carbonyl]amino]pyridine-2-carboxylate (150 mg, 0.254 mmol) was dissolved in an ammonia solution (4.1 mL of 7 M, 28.70 mmol) and was stirred for 72 hours under $N_2$. The reaction mixture was concentrated in vacuo and purified by HPLC (0-100% acetonitrile/0.1% ammonium hydroxide) to provide N-(2-carbamoyl-4-pyridyl)-3-ethoxy-5-[2-methoxy-4-(trifluoromethoxy)phenoxy]-2-(trifluoromethyl)pyridine-4-carboxamide (45 mg, 31%) as a white solid. ESI-MS m/z calc. 560.11, found 561.0 (M+1)+; retention time (Method E): 3.4 minutes (5 minute run). $^1$H NMR (500 MHz, DMSO-d6) δ 11.47 (s, 1H), 8.57 (dd, J=5.5, 0.7 Hz, 1H), 8.32 (dd, J=2.2, 0.7 Hz, 1H), 8.11 (d, J=2.9 Hz, 1H), 7.97 (s, 1H), 7.81 (dd, J=5.5, 2.2 Hz, 1H), 7.67 (d, J=2.8 Hz, 1H), 7.35 (d, J=8.8 Hz, 1H), 7.30-7.08 (m, 1H), 7.11-6.89 (m, 1H), 4.19 (q, J=7.0 Hz, 2H), 3.80 (s, 3H), 1.28 (t, J=7.0 Hz, 3H) ppm.

Example 81

N-(2-Carbamoyl-5-methyl-4-pyridyl)-3-ethoxy-5-[2-methoxy-4-(trifluoromethoxy)phenoxy]-2-(trifluoromethyl)pyridine-4-carboxamide (210)

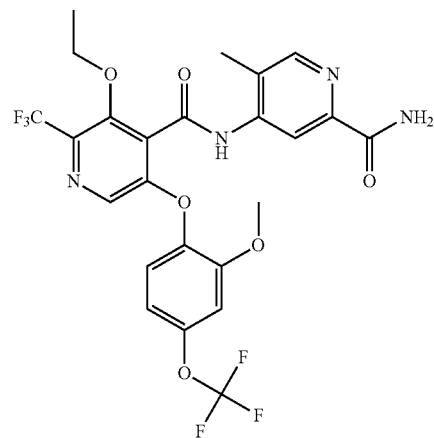 [SMILES: CCOc1c(C(F)(F)F)ncc(Oc2ccc(OC(F)(F)F)cc2OC)c1C(=O)Nc1cc(C(N)=O)ncc1C]

Step 1: N-(2-Bromo-5-methyl-4-pyridyl)-3-ethoxy-5-[2-methoxy-4-(trifluoromethoxy)phenoxy]-2-(trifluoromethyl)pyridine-4-carboxamide

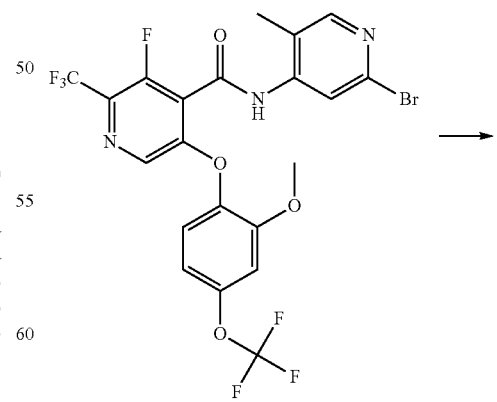

413
-continued

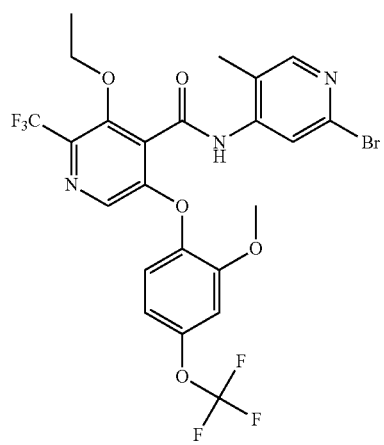

N-(2-Bromo-5-methyl-4-pyridyl)-3-fluoro-5-[2-methoxy-4-(trifluoromethoxy)phenoxy]-2-(trifluoromethyl)pyridine-4-carboxamide (prepared as described in Example 83, Step 1, 180 mg, 0.308 mmol) was dissolved in ethanol (1.8 mL) and treated with sodium ethoxide (31 mg, 0.4555 mmol). The reaction was heated at 75° C. for 72 hours, then treated with additional sodium ethoxixde (31 mg, 0.4555 mmol) and heated for an additional 72 hours. The reaction mixture was concentrated in vacuo to afford crude N-(2-bromo-5-methyl-4-pyridyl)-3-ethoxy-5-[2-methoxy-4-(trifluoromethoxy)phenoxy]-2-(trifluoromethyl)pyridine-4-carboxamide. ESI-MS m/z calc. 609.03, found 612.0 (M+1)+; retention time (Method F): 1.13 minutes (1.5 minute run).

Step 2: Methyl 4-[[3-Ethoxy-5-[2-methoxy-4-(trifluoromethoxy)phenoxy]-2-(trifluoromethyl)pyridine-4-carbonyl]amino]-5-methyl-pyridine-2-carboxylate

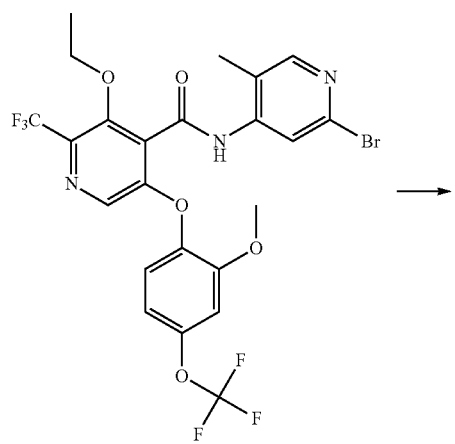

414
-continued

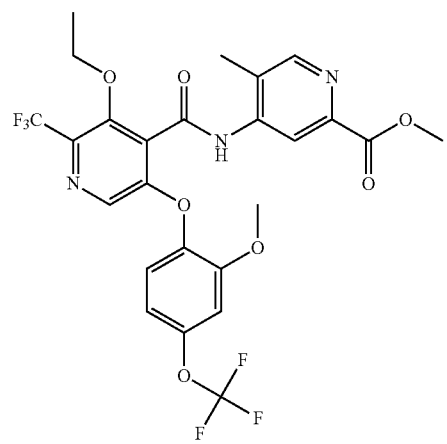

N-(2-bromo-5-methyl-4-pyridyl)-3-ethoxy-5-[2-methoxy-4-(trifluoromethoxy)phenoxy]-2-(trifluoromethyl)pyridine-4-carboxamide (150 mg, 0.246 mmol) was dissolved in methanol (3 mL), and triethylamine (80 µL, 0.5740 mmol) and Pd(dppf)Cl$_2$·DCM (42 mg, 0.051 mmol) were added. Carbon monoxide was bubbled through the vigorously stirring reaction mixture for 5 minutes. The reaction mixture was heated at 75° C. under carbon monoxide atmosphere for 16 hours. The reaction was cooled, filtered through a pad of Celite eluting with methanol and concentrated in vacuo. The residue was purified by silica gel chromatography (30-80% ethyl acetate/petroleum ether) to provide methyl 4-[[3-ethoxy-5-[2-methoxy-4-(trifluoromethoxy)phenoxy]-2-(trifluoromethyl)pyridine-4-carbonyl]amino]-5-methyl-pyridine-2-carboxylate (40 mg, 28%) as a pale yellow oil. ESI-MS m/z calc. 589.13, found 590.0 (M+1)+; retention time (Method F): 0.98 minutes (1.5 minute run).

Step 3: N-(2-Carbamoyl-5-methyl-4-pyridyl)-3-ethoxy-5-[2-methoxy-4-(trifluoromethoxy)phenoxy]-2-(trifluoromethyl)pyridine-4-carboxamide (210)

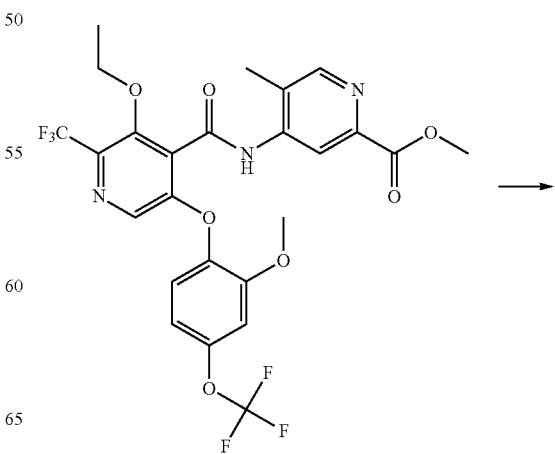

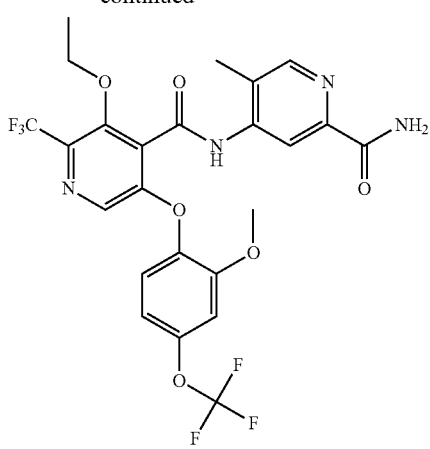

A solution of methyl 4-[[3-ethoxy-5-[2-methoxy-4-(trifluoromethoxy)phenoxy]-2-(trifluoromethyl)pyridine-4-carbonyl]amino]-5-methyl-pyridine-2-carboxylate (40 mg, 0.068 mmol) in ammonia (1.5 mL of 7 M in methanol, 10.50 mmol) was stirred at room temperature for 48 hours. The reaction mixture was concentrated in vacuo and purified by HPLC (37-100% acetonitrile/0.1% ammonium hydroxide) to provide N-(2-carbamoyl-5-methyl-4-pyridyl)-3-ethoxy-5-[2-methoxy-4-(trifluoromethoxy)phenoxy]-2-(trifluoromethyl)pyridine-4-carboxamide (19 mg, 49%). ESI-MS m/z calc. 574.13, found 575.0 (M+1)+; retention time (Method E): 3.4 minutes (5 minute run). $^1$H NMR (500 MHz, DMSO-d6) δ 10.63 (s, 1H), 8.48 (s, 2H), 8.06 (s, 1H), 7.92 (s, 1H), 7.60 (s, 1H), 7.36 (d, J=8.8 Hz, 1H), 7.25 (d, J=2.7 Hz, 1H), 7.11-6.98 (m, 1H), 4.26 (q, J=7.0 Hz, 2H), 3.83 (s, 3H), 2.31 (s, 3H), 1.34 (t, J=7.0 Hz, 3H) ppm.

Example 82

4-[[3-Chloro-2-fluoro-6-[4-(trifluoromethoxy)phenoxy]benzoyl]amino]pyridine-2-carboxamide (70)

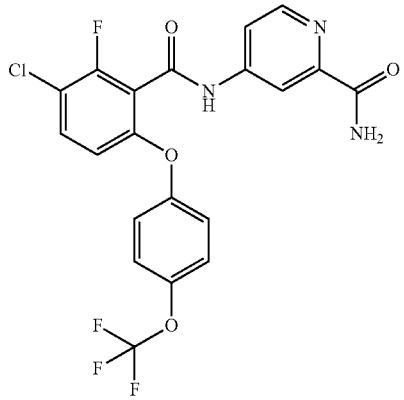 [SMILES: NC(=O)c1cc(NC(=O)c2c(Oc3ccc(OC(F)(F)F)cc3)ccc(Cl)c2F)ccn1]

Step 1: 6-Bromo-3-chloro-2-fluoro-benzoic acid

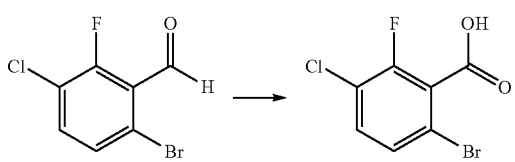 [SMILES: O=Cc1c(Br)ccc(Cl)c1F ; O=C(O)c1c(Br)ccc(Cl)c1F]

To a solution of 6-bromo-3-chloro-2-fluoro-benzaldehyde (1.00 g, 4.211 mmol) in a mixture of tert-BuOH (7 mL) and water (5 mL) was added sodium dihydrogen phosphate hydrate (0.600 g, 5.00 mmol) and 2-methyl-2-butene (9.5 mL of 2 M, 19 mmol). Sodium chlorite (0.600 g, 5.307 mmol) was then added in one portion and the reaction stirred for 2 hours. The reaction mixture was acidified using 1M HCl, and partitioned with ethyl acetate. The organic layer was dried over MgSO$_4$, filtered and concentrated in vacuo to afford 6-bromo-3-chloro-2-fluoro-benzoic acid (0.900 g, 84%) as a white solid. ESI-MS m/z calc. 251.90, found 209.0 (M+1)+(mass of the decarboxylation fragment); retention time (Method F): 0.36 minutes (1.5 minute run).

Step 2: 3-Chloro-2-fluoro-6-[4-(trifluoromethoxy)phenoxy]benzoic acid

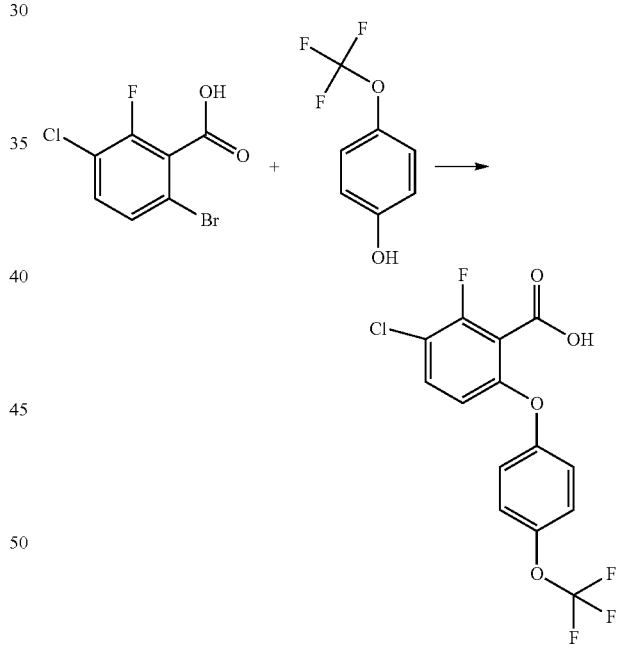

To a pressure flask was added 6-bromo-3-chloro-2-fluoro-benzoic acid (1.00 g, 3.95 mmol), 4-(trifluoromethoxy)phenol (0.705 g, 3.96 mmol), Cs$_2$CO$_3$ (1.29 g, 3.94 mmol) and toluene (12 mL). The reaction mixture was bubbled with N$_2$ for 10 minutes, and then copper (I) iodide (0.375 g, 1.97 mmol) added. The flask was flushed with N$_2$, capped, and heated at 100° C. with vigorous stirring for 1 hour. The mixture was allowed to cool, then diluted with ethyl acetate and water. The water layer was acidified with HCl and the product was extracted into ethyl acetate. The organic layer was washed with brine, dried over Na$_2$SO$_4$, filtered and concentrated in vacuo. Silica gel chromatography (0-5% methanol/dichloromethane) provided 3-chloro-2-fluoro-6-[4-(trifluoromethoxy)phenoxy]benzoic acid (0.820 g, 59%) as a white solid. ESI-MS m/z calc. 349.9969, found 351.0 (M+1)+; retention time (Method B): 1.82 minutes (3 minute run). $^1$H NMR (400 MHz, DMSO-d6) δ 14.02 (s, 1H), 7.69 (t, J=8.7 Hz, 1H), 7.46-7.38 (m, 2H), 7.20-7.13 (m, 2H), 6.92 (dd, J=9.0, 1.5 Hz, 1H) ppm.

Step 3: 3-Chloro-2-fluoro-6-[4-(trifluoromethoxy)phenoxy]benzoyl chloride

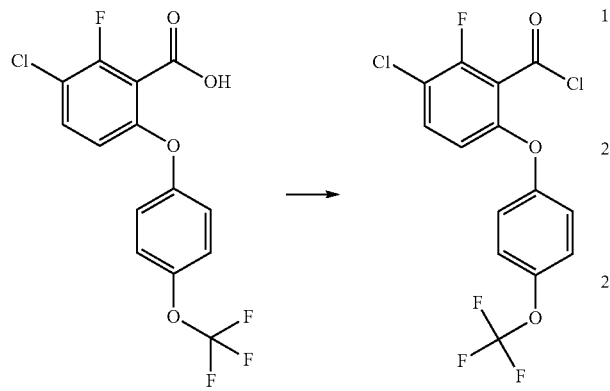

To a solution of 3-chloro-2-fluoro-6-[4-(trifluoromethoxy)phenoxy]benzoic acid (300 mg, 0.856 mmol) and DMF (23 μL, 0.29 mmol) in dichloromethane (4 mL) at 0° C. was added oxalyl chloride (164 mg, 113 μL, 1.30 mmol) dropwise. The mixture was stirred at room temperature for 30 minutes. Conversion was monitored by UPLC via test for morpholine adduct formation. The solvent was evaporated in vacuo to afford 3-chloro-2-fluoro-6-[4-(trifluoromethoxy)phenoxy]benzoyl chloride.

Step 4: 4-[[3-Chloro-2-fluoro-6-[4-(trifluoromethoxy)phenoxy]benzoyl]amino]pyridine-2-carboxamide (70)

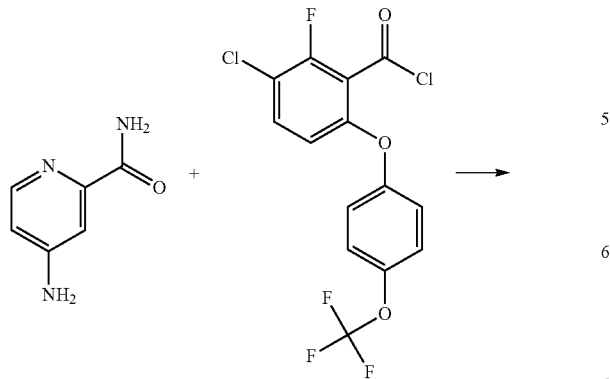

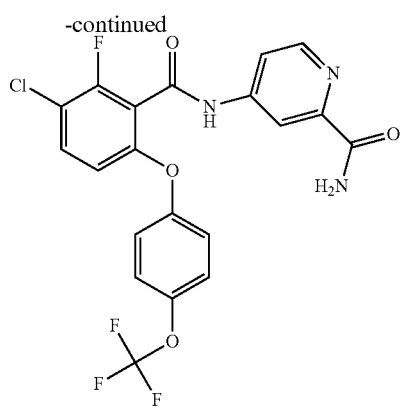

To a solution of 4-aminopyridine-2-carboxamide (37 mg, 0.27 mmol) and DIEA (94 μL, 0.54 mmol) in THF (1 mL) at 0° C. was added a solution of 3-chloro-2-fluoro-6-[4-(trifluoromethoxy)phenoxy]benzoyl chloride (100 mg, 0.271 mmol) in THF (1.0 mL) and dichloromethane (1.0 mL) at 0° C. The reaction mixture was allowed to warm to room temperature and stirred for 16 hours. The mixture was quenched with water and extracted with dichloromethane. The organic layer was dried over MgSO$_4$, filtered and concentrated in vacuo. Silica gel column chromatography (0-60% ethyl acetate/hexanes) provided 4-[[3-chloro-2-fluoro-6-[4-(trifluoromethoxy)phenoxy]benzoyl]amino]pyridine-2-carboxamide (15 mg, 11%). ESI-MS m/z calc. 469.05, found 470.1 (M+1)+; retention time (Method B): 1.74 minutes (3 minute run). $^1$H NMR (400 MHz, DMSO-d6) δ 11.39 (s, 1H), 8.53 (d, J=5.5 Hz, 1H), 8.26 (d, J=2.1 Hz, 1H), 8.10 (s, 1H), 7.77 (dd, J=5.7, 2.3 Hz, 1H), 7.73 (d, J=8.8 Hz, 1H), 7.66 (d, J=2.8 Hz, 1H), 7.41 (dq, J=7.8, 1.0 Hz, 2H), 7.28-7.21 (m, 2H), 6.93 (d, J=9.0, 1.4 Hz, 1H) ppm.

Example 83

N-(3-Carbamoyl-4-fluoro-phenyl)-3-chloro-2-fluoro-6-[4-(trifluoromethoxy)phenoxy]benzamide (73)

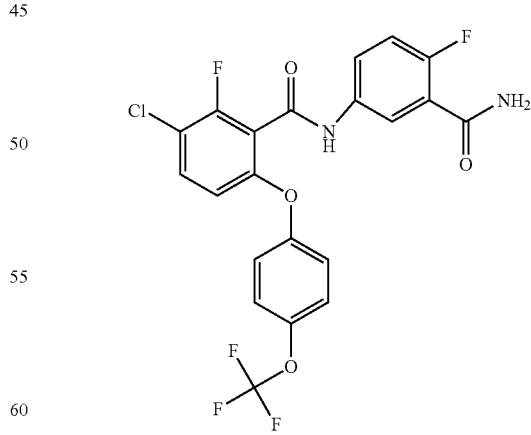

This compound was made in an analogous fashion to Example 82 except employing 5-amino-2-fluoro-benzamide in the amide formation step (Step 4). The yield of the desired product after purification was 57 mg (43%). ESI-MS m/z calc. 486.04, found 487.1 (M+1)+; retention time (Method B): 1.76 minutes (3 minute run). $^1$H NMR (500 MHz, DMSO-d6) δ 10.95 (s, 1H), 7.92 (dd, J=6.4, 2.8 Hz, 1H), 7.74-7.64 (m, 4H), 7.41 (d, J=8.7 Hz, 2H), 7.29-7.18 (m, 3H), 6.89 (dd, J=9.1, 1.4 Hz, 1H) ppm.

Example 84

N-(3-Carbamoyl-4-fluoro-phenyl)-1,1-difluoro-5-[4-(trifluoromethoxy)phenoxy]indane-4-carboxamide (190)

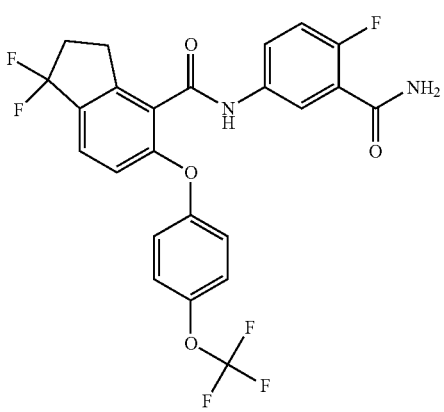 [SMILES: NC(=O)c1cc(NC(=O)c2c(Oc3ccc(OC(F)(F)F)cc3)ccc3c2CCC3(F)F)ccc1F]

Step 1: 2-bromo-6-(4-(trifluoromethoxy)phenoxy)benzaldehyde

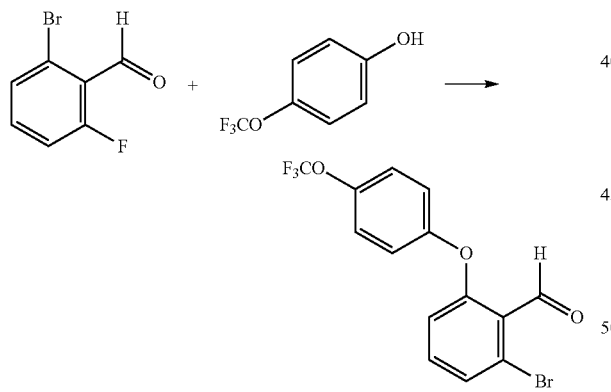

A mixture of 2-bromo-6-fluorobenzaldehyde (10.2 g, 50 mmol), 4-(trifluoromethoxy)phenol (6.5 mL, 50 mmol), K$_2$CO$_3$ (13.8 g, 100 mmol) in DMF (100 mL) was purged with N$_2$ and heated at 70° C. for 2 hours. Water (300 mL) was added and the reaction mixture was extracted with diethyl ether (2×100 mL). The combined organics were washed with brine, dried over Na$_2$SO$_4$, concentrated and the residue was purified by silica gel column chromatography using dichloromethane to afford 2-bromo-6-(4-(trifluoromethoxy)phenoxy)benzaldehyde (16.2 g, 89%) as a yellow oil. ESI-MS m/z calc. 361.96, found 363.0 (M+1)+; retention time (Method G): 3.49 minutes (6 minute run time).

Step 2: (E)-tert-butyl 3-(2-formyl-3-(4-(trifluoromethoxy)phenoxy)phenyl)acrylate

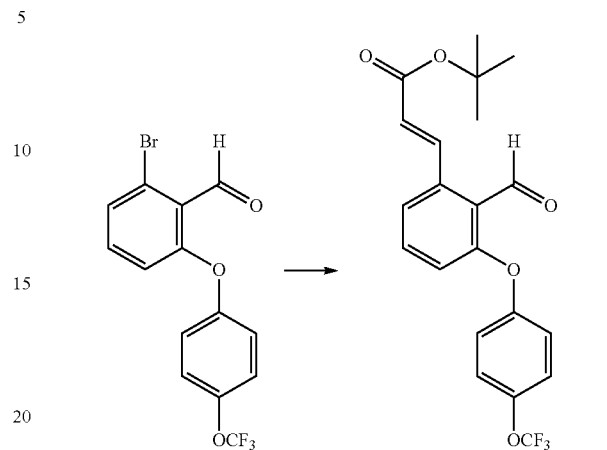

A mixture of 2-bromo-6-(4-(trifluoromethoxy)phenoxy)benzaldehyde (15.0 g, 41.5 mmol), palladium acetate (466 mg, 2.08 mmol), tri-o-tolylphosphine (1.26 g, 4.15 mmol) and tert-butyl acrylate (9.0 mL, 62 mmol) in triethylamine (17 mL) and toluene (85 mL) was heated at reflux for 2.5 hours. Water (100 mL) and 1 M aqueous HCl (100 mL) were added and the reaction was extracted with hexane (100 mL) and ethyl acetate (100 mL). The combined organics was dried over Na$_2$SO$_4$, concentrated in vacuo and purified by silica gel column chromatography (0-30% ethyl acetate/hexanes) to afford (E)-tert-butyl 3-(2-formyl-3-(4-(trifluoromethoxy)phenoxy)phenyl)acrylate (9.02 g, 53%) as a yellow solid. ESI-MS m/z calc. 408.12, found 408.8 (M+1)+; retention time (Method G): 4.07 minutes (6 minute run).

Step 3: (E)-2-(3-tert-Butoxy-3-oxoprop-1-enyl)-6-(4-(trifluoromethoxy)phenoxy)benzoic acid

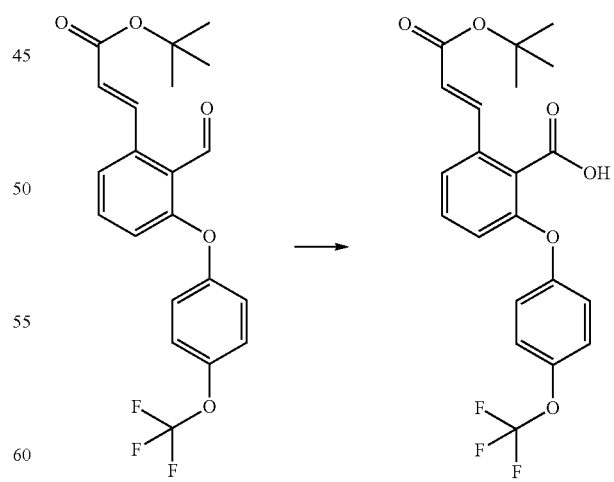

To a mixture of (E)-tert-butyl 3-(2-formyl-3-(4-(trifluoromethoxy)phenoxy)phenyl)acrylate (7.52 g, 18.4 mmol) and 2-methyl-2-butene (23.5 mL, 221 mmol) in tert-BuOH (235 mL) was added a solution of sodium chlorite (11.1 g, 123 mmol) and monobasic sodium phosphate (14.0 g, 101 mmol) in water (80 mL) over 30 minutes. The reaction mixture was stirred for 1 hour at room temperature and then diluted with 2:1 water:brine solution (750 mL). The mixture was extracted with ethyl acetate (750 mL). The organic layer was washed with brine, dried over Na₂SO₄ and concentrated in vacuo to afford (E)-2-(3-tert-butoxy-3-oxoprop-1-enyl)-6-(4-(trifluoromethoxy)phenoxy)benzoic acid (7.88 g, 101%) as a yellow solid. Retention time (Method G): 3.59 minutes (6 minute run).

Step 4: (E)-methyl 2-(3-tert-butoxy-3-oxoprop-1-enyl)-6-(4-(trifluoromethoxy)phenoxy)benzoate Step 5: Methyl 2-(3-tert-butoxy-3-oxopropyl)-6-(4-(trifluoromethoxy)phenoxy)benzoate

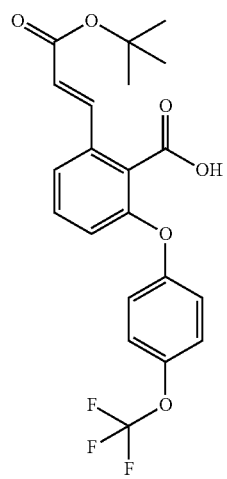

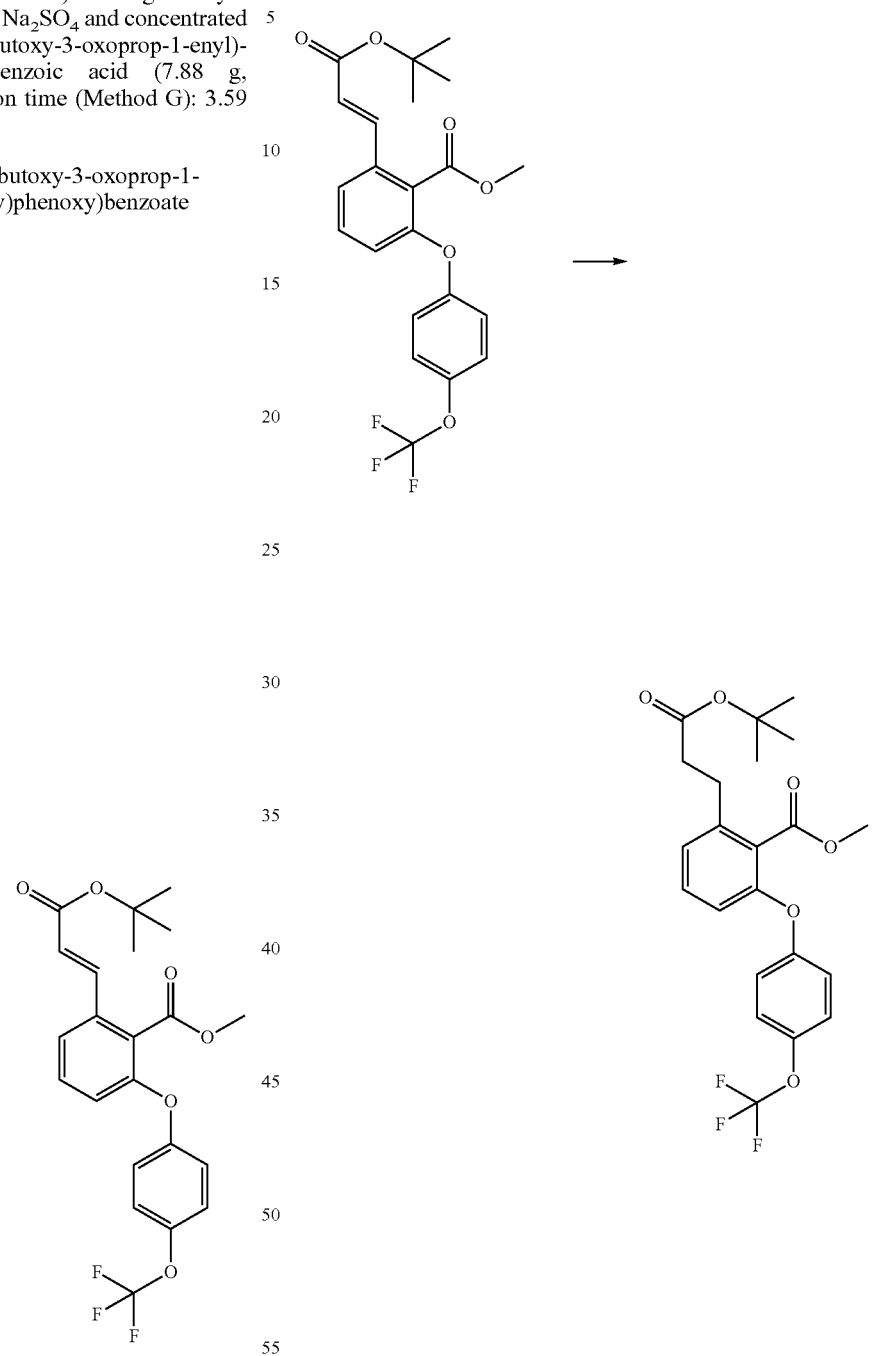

To (E)-2-(3-tert-butoxy-3-oxoprop-1-enyl)-6-(4-(trifluoromethoxy)phenoxy)benzoic acid (7.88 g, 18.4 mmol) and K₂CO₃ (2.54 g, 18.4 mmol) in acetone (75 mL) was added methyl iodide (3.4 mL, 55 mmol) and the reaction was heated at 40° C. for 45 minutes. The reaction was cooled, diluted with ethyl acetate (450 mL) and washed with water and brine (2×). The organic layer was dried over Na₂SO₄, filtered and concentrated in vacuo to afford (E)-methyl 2-(3-tert-butoxy-3-oxoprop-1-enyl)-6-(4-(trifluoromethoxy) phenoxy)benzoate (7.36 g, 91%) as an amber oil. Retention time (Method G): 4.06 minutes (6 minute run).

To (E)-methyl 2-(3-tert-butoxy-3-oxoprop-1-enyl)-6-(4-(trifluoromethoxy)phenoxy)benzoate (7.36 g, 16.8 mmol) and 10% palladium on carbon (2 g) was added methanol (75 mL), and the reaction was heated at 40° C. under hydrogen atmosphere for 3 hours. The reaction mixture was filtered through a pad of Celite and rinsed with methanol. The filtrate was concentrated in vacuo to afford methyl 2-(3-tert-butoxy-3-oxopropyl)-6-(4-(trifluoromethoxy)phenoxy)benzoate (6.70 g, 91%) as an amber oil. ESI-MS m/z calc. 440.14, found 441.3 (M+1)+; retention time (Method H): 4.19 minutes (12 minute run).

423

Step 6: 3-(2-(methoxycarbonyl)-3-(4-(trifluoromethoxy)phenoxy)phenyl)propanoic acid

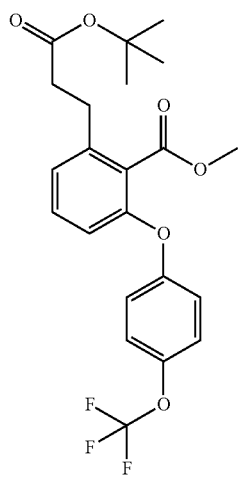

424

Step 7: Methyl 2-(3-chloro-3-oxopropyl)-6-(4-(trifluoromethoxy)phenoxy)benzoate

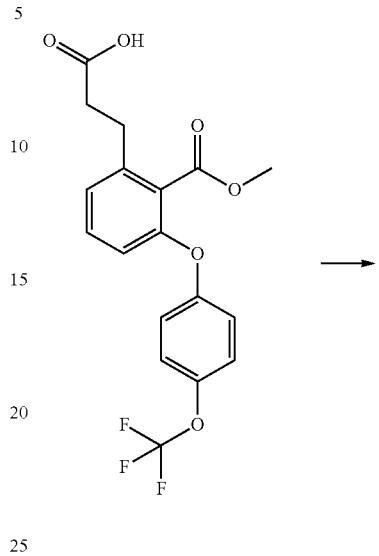

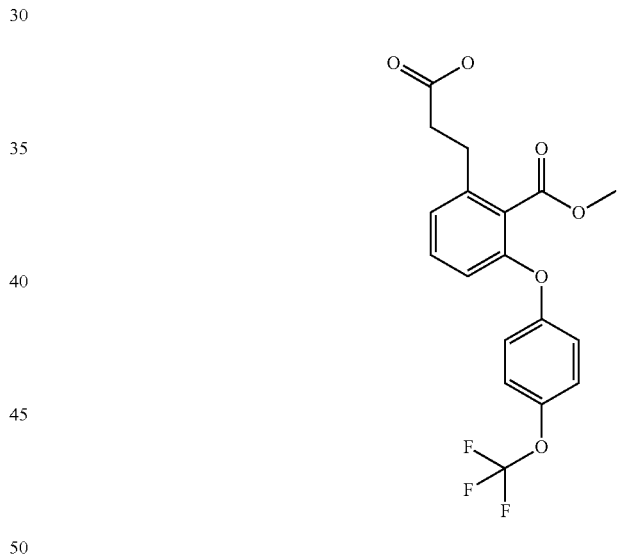

To 2-(3-tert-butoxy-3-oxopropyl)-6-(4-(trifluoromethoxy)phenoxy)benzoate (6.70 g, 15.2 mmol) in dichloromethane (30 mL) was added trifluoroacetic acid (10 mL, 152 mmol). The reaction was stirred for 18 hours at room temperature before the mixture was concentrated twice with 1,2-dichloroethane (2×15 mL). The crude reaction mixture was purified via silica gel column chromatography (0-60% ethyl acetate/hexanes) to afford 3-(2-(methoxycarbonyl)-3-(4-(trifluoromethoxy)phenoxy)phenyl)propanoic acid (5.14 g, 88%) as a white solid. ESI-MS m/z calc. 384.08, found 384.9 (M+1)+); retention time (Method G): 3.16 minutes (6 minute run).

To a solution of 3-(2-(methoxycarbonyl)-3-(4-(trifluoromethoxy)phenoxy)phenyl)propanoic acid (4.17 g, 10.8 mmol) in dichloromethane (44 mL) was added oxalyl chloride (1.8 mL, 21.7 mmol) followed by DMF (5 μL). The reaction mixture was stirred for 3 hours at room temperature and then concentrated twice with 1,2-dichloroethane (10 mL) to afford methyl 2-(3-chloro-3-oxopropyl)-6-(4-(trifluoromethoxy)phenoxy)benzoate (4.24 g, 97%) as an oil, which was used directly in the next step.

Step 8: methyl 1-oxo-5-(4-(trifluoromethoxy)phenoxy)-2,3-dihydro-1H-indene-4-carboxylate

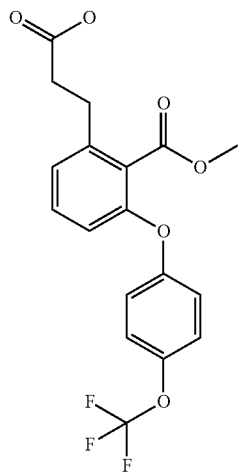

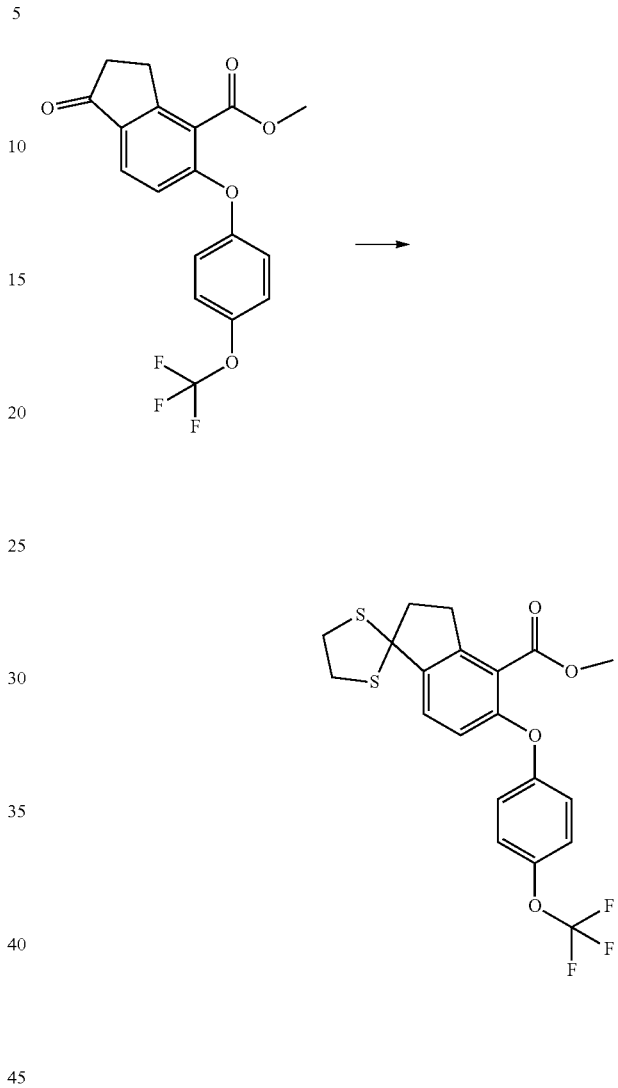

Step 9: Methyl 5-(4-(trifluoromethoxy)phenoxy)-2,3-dihydrospiro[indene-1,2'-[1,3]dithiolane]-4-carboxylate A suspension of aluminum trichloride (2.96 g, 22.2 mmol) in dichloromethane (100 mL) was cooled to 0° C. and a solution of methyl 2-(3-chloro-3-oxopropyl)-6-(4-(trifluoromethoxy)phenoxy)benzoate (3.57 g, 8.87 mmol) in dichloromethane (17 mL) was added over 5 minutes. The reaction mixture was stirred for 20 minutes then poured into ice water (200 mL). The mixture was extracted with dichloromethane (2×100 mL), and the organics were dried over $Na_2SO_4$ and concentrated in vacuo. The residue was purified by silica gel column chromatography (0-50% ethyl acetate/hexanes) to afford methyl 1-oxo-5-(4-(trifluoromethoxy)phenoxy)-2,3-dihydro-1H-indene-4-carboxylate (2.76 g, 85%) as an off-white solid. ESI-MS m/z calc. 366.07, found 366.7 (M+1)+; retention time (Method G): 3.28 minutes (6 minute run). $^1$H NMR (250 MHz, DMSO-d6) δ (ppm): 2.62-2.76 (m, 2H) 3.14-3.28 (m, 2H) 3.80 (s, 3H) 7.06 (d, J=8.35 Hz, 1H) 7.19 (d, J=9.01 Hz, 2H) 7.44 (d, J=9.01 Hz, 2H) 7.80 (d, J=8.46 Hz, 1H) ppm.

A solution of methyl 1-oxo-5-(4-(trifluoromethoxy)phenoxy)-2,3-dihydro-1H-indene-4-carboxylate (1.59 g, 4.35 mmol) and ethane-1,2-dithiol (550 uL, 6.52 mmol) in dichloromethane (17 mL) was cooled in an ice bath and boron trifluoride etherate (2.0 mL, 17 mmol) was added. The reaction mixture was stirred for 18 hours at room temperature. 2 M aqueous NaOH (25 mL) was added and the mixture was extracted with dichloromethane (2×25 mL). The combined organic layers were dried over $Na_2SO_4$, concentrated in vacuo and purified by silica gel chromatography (0-30% ethyl acetate/hexanes) to afford methyl 5-(4-(trifluoromethoxy)phenoxy)-2,3-dihydrospiro[indene-1,2'-[1,3]dithiolane]-4-carboxylate (1.57 g, 82%) as a white solid. ESI-MS m/z calc. 442.05, found 442.8 (M+1)+; retention time (Method G): 3.98 minutes (6 minute run).

427

Step 10: Methyl 2-bromo-1,1-difluoro-5-(4-(trifluoromethoxy)phenoxy)-2,3-dihydro-1H-indene-4-carboxylate

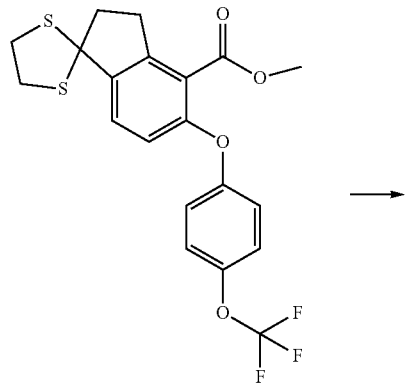

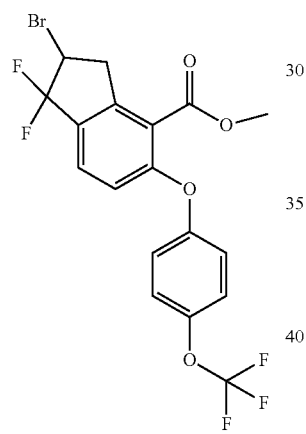

To a solution of dibromantin (2.9 g, 10.2 mmol) in dichloromethane (12 mL) at −78° C. was added 70% HF/pyridine (3.0 mL, 1173 mmol) and the mixture was stirred for 30 minutes. A solution of methyl 5-(4-(trifluoromethoxy)phenoxy)-2,3-dihydrospiro[indene-1,2'-[1,3]dithiolane]-4-carboxylate (1.13 g, 2.55 mmol) in dichloromethane (2.5 mL) was added dropwise. After 1 hour the dry ice bath was removed and the reaction was allowed to warm to room temperature, and then poured onto a mixture of 2 M aqueous NaOH (50 mL) and saturated aqueous sodium bisulfite solution (7.5 mL). The mixture was basified with the addition of 2 M aqueous NaOH and extracted with dichloromethane (2×50 mL). The combined organic layer was dried over Na$_2$SO$_4$, concentrated in vacuo and purified by silica gel chromatography (0-10% ethyl acetate/hexanes) to afford methyl 2-bromo-1,1-difluoro-5-(4-(trifluoromethoxy)phenoxy)-2,3-dihydro-1H-indene-4-carboxylate (779 mg, 47%) as a colorless oil. Retention time (Method G): 3.30 minutes (6 minute run).

428

Step 11: Methyl 1,1-difluoro-5-(4-(trifluoromethoxy)phenoxy)-1H-indene-4-carboxylate

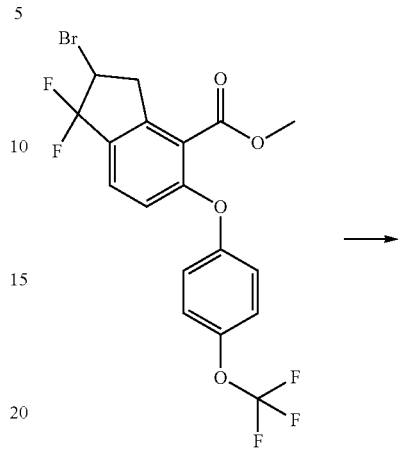

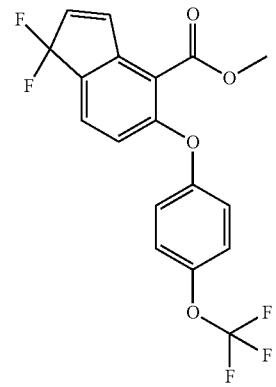

To a solution of methyl 2-bromo-1,1-difluoro-5-(4-(trifluoromethoxy)phenoxy)-2,3-dihydro-1H-indene-4-carboxylate (779 mg, 1.67 mmol) in dichloromethane (6 mL) was added 2,3,4,6,7,8,9,10-octahydropyrimido[1,2-a]azepine (0.38 mL, 2.50 mmol). After stirring for 30 minutes at room temperature, 2 M aqueous HCl (25 mL) was added. The mixture was extracted with dichloromethane (2×25 mL). The combined organic layers were dried over Na$_2$SO$_4$, concentrated in vacuo and purified by silica gel chromatography (0-50% dichloromethane/hexanes) to afford methyl 1,1-difluoro-5-(4-(trifluoromethoxy)phenoxy)-1H-indene-4-carboxylate (595 mg, 92%) as a yellow oil. Retention time (Method G): 3.15 minutes (6 minute run).

Step 12: Methyl 1,1-difluoro-5-(4-(trifluoromethoxy)phenoxy)-2,3-dihydro-1H-indene-4-carboxylate

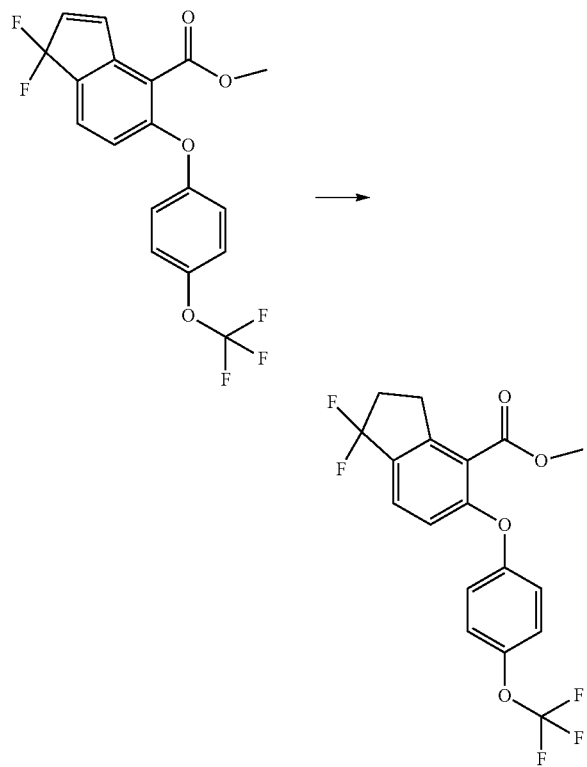

To a solution of methyl 1,1-difluoro-5-(4-(trifluoromethoxy)phenoxy)-1H-indene-4-carboxylate (484 mg, 1.25 mmol) in methanol (15 mL) was added 10% palladium on carbon (100 mg) and the reaction mixture was hydrogenated in a Parr shaker at 60 PSI for 18 hours. The mixture was filtered over Celite pad and the filtrate was concentrated in vacuo. Silica gel chromatography (0-40% dichloromethane/hexanes) provided methyl 1,1-difluoro-5-(4-(trifluoromethoxy)phenoxy)-2,3-dihydro-1H-indene-4-carboxylate (461 mg, 91%) as a colorless oil. ESI-MS m/z calc. 388.07, found 389.0 (M+1)+; retention time (Method G): 3.71 minutes (6 minute run).

Step 13: 1,1-Difluoro-5-[4-(trifluoromethoxy)phenoxy]indane-4-carboxylic acid

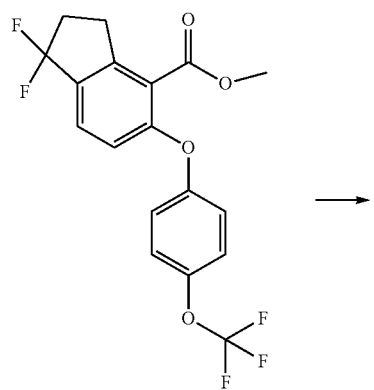

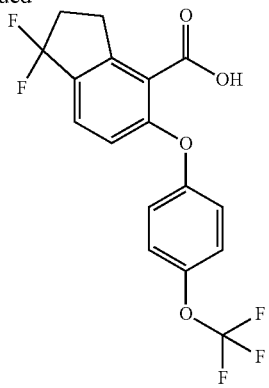

A mixture of methyl 1,1-difluoro-5-(4-(trifluoromethoxy)phenoxy)-2,3-dihydro-1H-indene-4-carboxylate (393 mg, 1.01 mmol), lithium hydroxide hydrate (168 mg, 4.00 mmol), THF (2 mL), methanol (2 mL) and water (2 mL) was stirred at room temperature for 4 hours. The reaction was diluted with saturated NH₄Cl (50 mL) and extracted with ethyl acetate (2×25 mL). The combined organic layers were concentrated to provide 1,1-difluoro-5-(4-(trifluoromethoxy)phenoxy)-2,3-dihydro-1H-indene-4-carboxylic acid (417 mg, 96%) as an off-white solid. ESI-MS m/z calc. 374.06, found 374.9 (M+1)+; retention time (Method G): 3.25 minutes (6 minute run). $^1$H NMR (250 MHz, DMSO-d6) δ (ppm): 2.63 (dd, J=13.95, 6.81 Hz, 2H) 3.09 (bs, 2H) 6.88-7.15 (m, 3H) 7.36 (d, J=8.46 Hz, 2H) 7.59 (d, J=7.80 Hz, 1H) ppm.

Step 14: 1,1-Difluoro-5-[4-(trifluoromethoxy)phenoxy]indane-4-carbonyl chloride

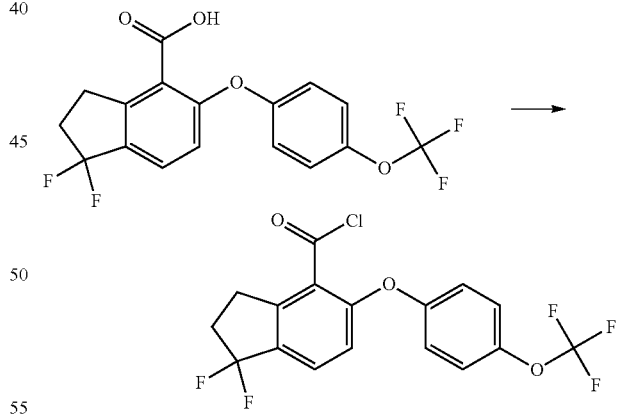

To a solution of 1,1-difluoro-5-[4-(trifluoromethoxy)phenoxy]indane-4-carboxylic acid (272 mg, 0.726 mmol) and DMF (20 μL, 0.26 mmol) in dichloromethane (3 mL) at 0° C. was added oxalyl chloride (400 μL, 4.59 mmol) dropwise under N₂ atmosphere. The ice bath was removed after 10 minutes and the reaction was stirred at room temperature for 30 minutes. Conversion was monitored by UPLC via test for piperidine adduct formation. The solvent was evaporated under reduced pressure to afford 1,1-difluoro-5-[4-(trifluoromethoxy)phenoxy]indane-4-carbonyl chloride.

Step 15: N-(3-Carbamoyl-4-fluoro-phenyl)-1,1-difluoro-5-[4-(trifluoromethoxy)phenoxy]indane-4-carboxamide (190)

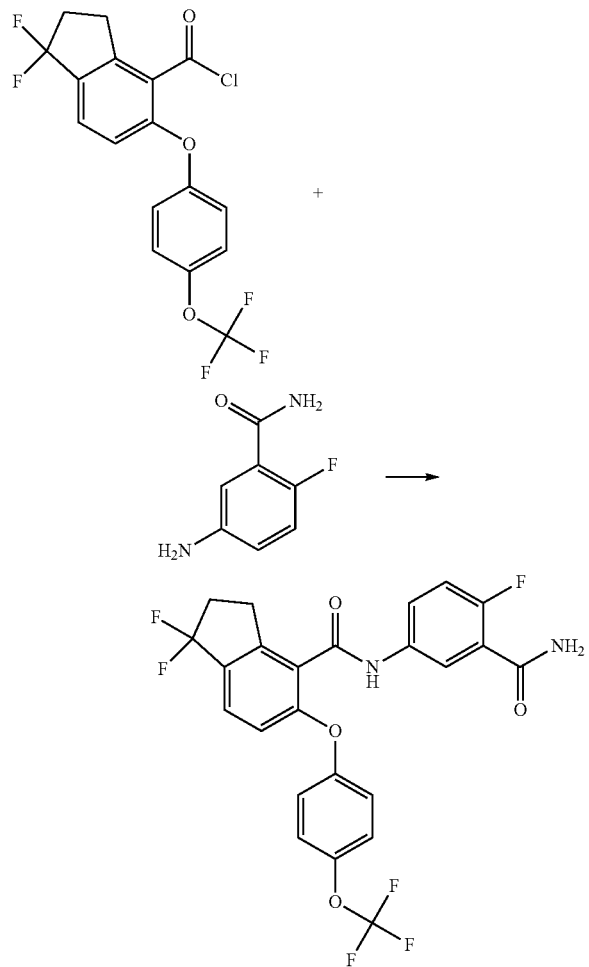

A slurry of 5-amino-2-fluoro-benzamide (42 mg, 0.27 mmol) in dichloromethane (1 mL) and DIEA (63 µL, 0.36 mmol) was cooled to 0° C. A slurry of cold 1,1-difluoro-5-[4-(trifluoromethoxy)phenoxy]indane-4-carbonyl chloride (71 mg, 0.18 mmol) in dichloromethane (1 mL) was added dropwise to the stirring amine solution. The reaction mixture was stirred at 0° C. for 10 minutes then allowed to warm to room temperature over 2 hours. The reaction was concentrated in vacuo and purified by HPLC (10-99% acetonitrile/5 mM HCl) to provide N-(3-carbamoyl-4-fluoro-phenyl)-1,1-difluoro-5-[4-(trifluoromethoxy)phenoxy]indane-4-carboxamide (42.5 mg, 46%). ESI-MS m/z calc. 510.10, found 511.0 (M+1)+; retention time (Method C): 2.51 minutes (5 minute run). ¹H NMR (400 MHz, DMSO-d6) δ 10.69 (s, 1H), 7.96 (dd, J=6.4, 2.8 Hz, 1H), 7.77-7.70 (m, 1H), 7.70-7.62 (m, 3H), 7.55-7.31 (m, 2H), 7.29-7.17 (m, 3H), 7.01 (d, J=8.5 Hz, 1H), 3.21-2.98 (m, 2H), 2.78-2.59 (m, 2H) ppm.

Example 85

4-[[1,1-Difluoro-5-[4-(trifluoromethoxy)phenoxy]indane-4-carbonyl]amino]pyridine-2-carboxamide (191)

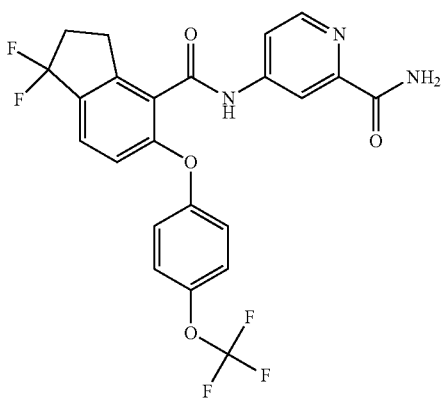

This compound was made in an analogous fashion to Example 84 except employing 4-aminopyridine-2-carboxamide in the amide formation step (Step 15). The yield of the desired product after purification was 30 mg (41%). ESI-MS m/z calc. 493.1061, found 494.0 (M+1)+; retention time (Method C): 2.46 minutes (5 minute run). ¹H-NMR (400 MHz, DMSO-d6) δ 11.15 (s, 1H), 8.51 (d, J=5.5 Hz, 1H), 8.30 (d, J=2.1 Hz, 1H), 8.11 (d, J=2.8 Hz, 1H), 7.81 (dd, J=5.5, 2.2 Hz, 1H), 7.71 (dd, J=8.5, 1.5 Hz, 1H), 7.66 (d, J=2.9 Hz, 1H), 7.41 (dd, J=9.2, 1.0 Hz, 2H), 7.27-7.19 (m, 2H), 7.02 (d, J=8.5 Hz, 1H), 3.19-3.06 (m, 2H), 2.68 (tt, J=13.3, 7.0 Hz, 2H) ppm.

Example 86

5-[[1,1-Difluoro-5-[4-(trifluoromethoxy)phenoxy]indane-4-carbonyl]amino]pyridine-2-carboxamide (192)

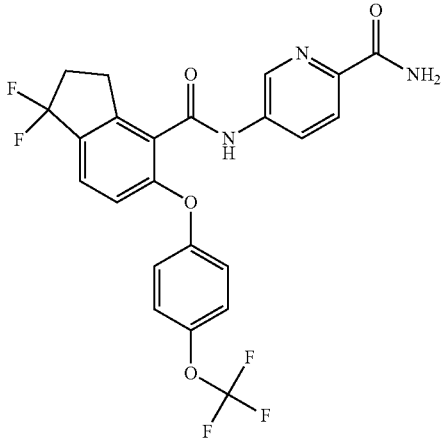 [SMILES: NC(=O)c1ccc(NC(=O)c2c(Oc3ccc(OC(F)(F)F)cc3)ccc3c2CCC3(F)F)cn1]

This compound was made in an analogous fashion to Example 84 except employing 5-aminopyridine-2-carboxamide in the amide formation step (Step 15). The yield of the desired product after purification was 34 mg (43%). ESI-MS m/z calc. 493.11, found 494.0 (M+1)+; retention time (Method C): 2.45 minutes (5 minute run). $^1$H-NMR (400 MHz, DMSO-d6) δ 11.06 (s, 1H), 8.82 (dd, J=2.5, 0.7 Hz, 1H), 8.24 (dd, J=8.6, 2.5 Hz, 1H), 8.06-7.98 (m, 2H), 7.71 (dd, J=8.5, 1.5 Hz, 1H), 7.56 (d, J=2.8 Hz, 1H), 7.41 (dt, J=8.0, 1.0 Hz, 2H), 7.27-7.16 (m, 2H), 7.05 (d, J=8.4 Hz, 1H), 3.17-3.07 (m, 2H), 2.68 (tt, J=14.2, 6.9 Hz, 2H) ppm.

Example 87

4-[[2,4-Dichloro-6-[4-(trifluoromethoxy)phenoxy] benzoyl]amino]pyridine-2-carboxamide (180)

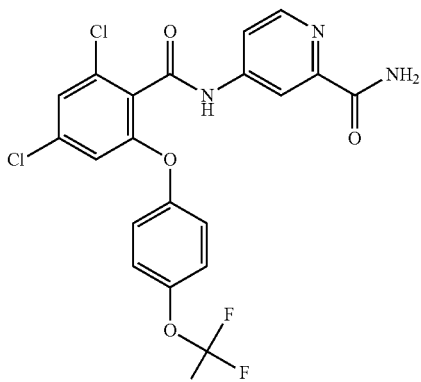

Step 1: 2,4-Dichloro-6-fluoro-benzoic acid

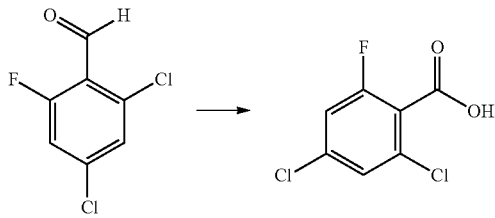 [SMILES: O=Cc1c(F)cc(Cl)cc1Cl ; O=C(O)c1c(F)cc(Cl)cc1Cl]

To a solution of 2,4-dichloro-6-fluoro-benzaldehyde (1.00 g, 5.18 mmol), 2-methyl-2-butene (1.82 g, 2.74 mL, 25.9 mmol) and sodium dihydrogen phosphate hydrate (2.14 g, 15.5 mmol) in tert-BuOH (5 mL)/acetonitrile (3.25 mL)/water (5 mL) at 0° C. was added sodium chlorite (1.41 g, 15.5 mmol) and the reaction mixture stirred at 0° C. for 1 hour. The reaction mixture was acidified with 1N HCl and extracted with ethyl acetate. The organic layer was washed with 1N HCl and brine, dried over Na$_2$SO$_4$, filtered and concentrated. Trituration with 20% diethyl ether/hexane and filtration provided 2,4-dichloro-6-fluoro-benzoic acid (700 mg, 65%) as a white solid. $^1$H NMR (400 MHz, DMSO-d6) δ 14.29 (br s, 1H), 7.70-7.63 (m, 2H) ppm.

Step 2: 2,4-Dichloro-6-fluoro-benzoyl chloride

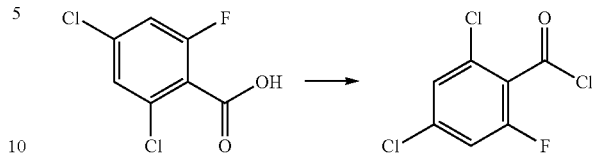

To 2,4-dichloro-6-fluoro-benzoic acid (5.10 g, 24.4 mmol) and DMF (173 µL, 2.23 mmol) in dichloromethane (50 mL) at 0° C. was added oxalyl chloride (10.2 mL, 117 mmol) dropwise. The mixture was stirred at room temperature for 5 hours under N$_2$ atmosphere. Conversion was monitored by UPLC via test for morpholine adduct formation. The solvent was evaporated under reduced pressure to afford 2,4-dichloro-6-fluoro-benzoyl chloride.

Step 3: 4-[(2,4-Dichloro-6-fluoro-benzoyl)amino] pyridine-2-carboxamide

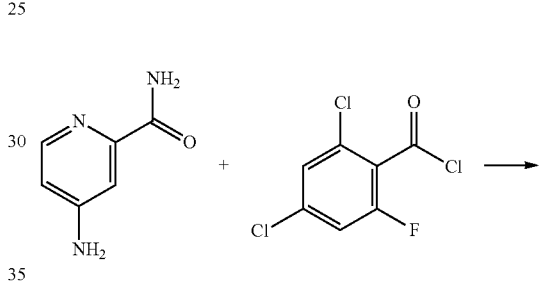

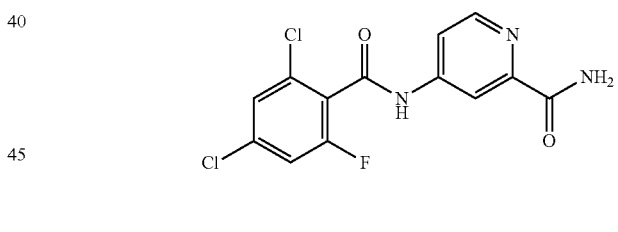

To 4-aminopyridine-2-carboxamide (1.51 g, 11.0 mmol) and DIEA (4.8 mL, 27.5 mmol) in 1-methyl-pyrrolidin-2-one (25 mL) cooled at 0° C. was added a solution of 2,4-dichloro-6-fluoro-benzoyl chloride (2.5 g, 11 mmol) in dichloromethane (12.5 mL) dropwise. The reaction was stirred at room temperature for 16 hours. Water was added to the reaction mixture and the resulting precipitate was filtered and dried to obtain 4-[(2,4-dichloro-6-fluoro-benzoyl)amino]pyridine-2-carboxamide (1.05 g, 29%). ESI-MS m/z calc. 327.00, found 328.1 (M+1)+; retention time (Method B): 1.16 minutes (3 minute run). $^1$H NMR (400 MHz, DMSO-d6) δ 11.42 (s, 1H), 8.58 (d, J=5.4 Hz, 1H), 8.33 (d, J=2.2 Hz, 1H), 8.12 (d, J=2.8 Hz, 1H), 7.88-7.51 (m, 4H) ppm.

Step 4: 4-[[2,4-Dichloro-6-[4-(trifluoromethoxy)phenoxy]benzoyl]amino]pyridine-2-carboxamide (180)

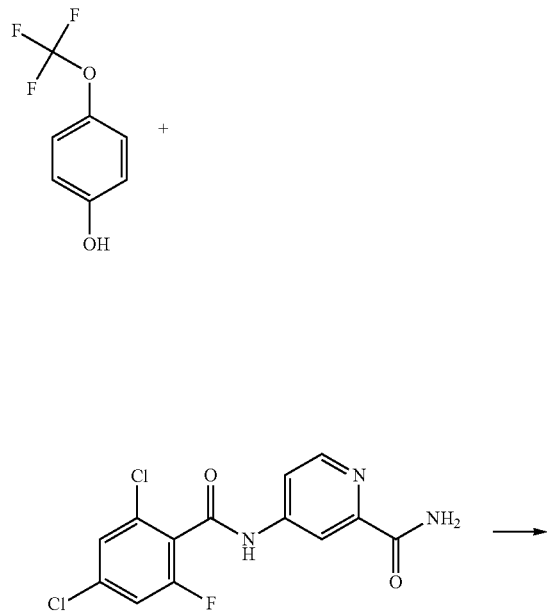

To 4-[(2,4-dichloro-6-fluoro-benzoyl)amino]pyridine-2-carboxamide (45 mg, 0.14 mmol) in DMF (1 mL) was added 4-(trifluoromethoxy)phenol (24 mg, 18 μL, 0.14 mmol) followed by $K_2CO_3$ (57 mg, 0.41 mmol). The reaction was heated at 80° C. for 30 minutes. HPLC purification (1-99% acetonitrile/5 mM HCl) provided 4-[[2,4-dichloro-6-[4-(trifluoromethoxy)phenoxy]benzoyl]amino]pyridine-2-carboxamide (38 mg, 57%). ESI-MS m/z calc. 485.02, found 485.85 (M+1)+; retention time (Method B): 1.82 minutes (3 minute run). $^1$H NMR (400 MHz, DMSO-d6) δ 11.36 (s, 1H), 8.53 (d, J=5.5 Hz, 1H), 8.28 (d, J=2.1 Hz, 1H), 8.12 (d, J=2.7 Hz, 1H), 7.78 (dd, J=5.5, 2.2 Hz, 1H), 7.68 (s, 1H), 7.67 (d, J=1.8 Hz, 1H), 7.43 (dd, J=9.2, 1.0 Hz, 2H), 7.26 (d, J=9.1 Hz, 2H), 7.13 (d, J=1.8 Hz, 1H) ppm. $^{19}$F NMR (376 MHz, DMSO-d6) δ −57.13 ppm.

Example 88

5-[[2,4-Dichloro-6-[4-(trifluoromethoxy)phenoxy]benzoyl]amino]pyridine-2-carboxamide (184)

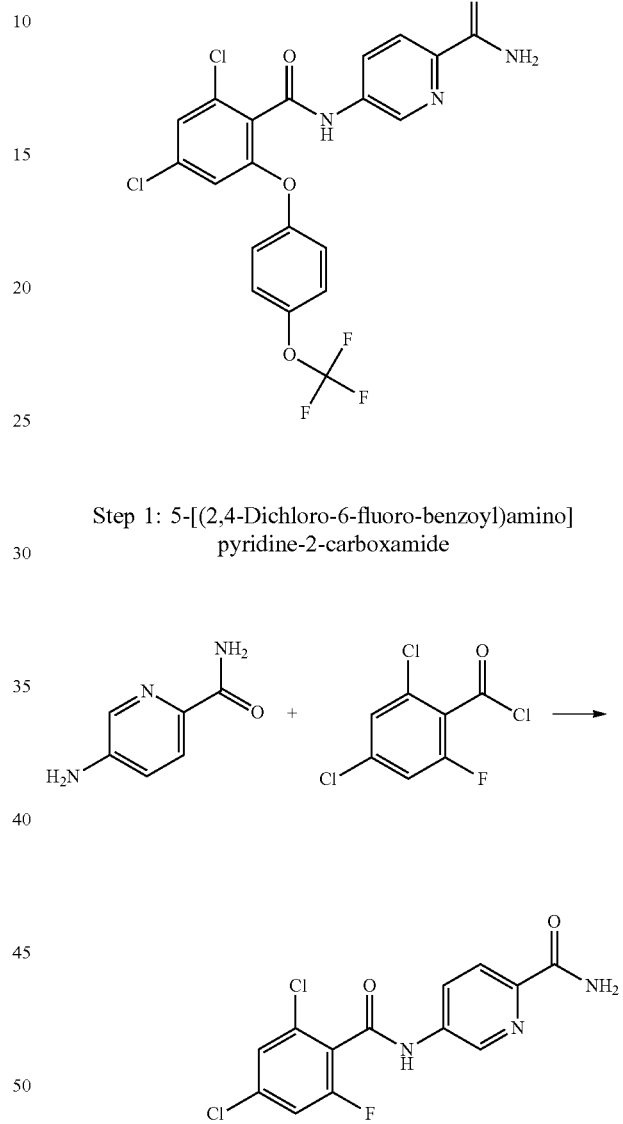

Step 1: 5-[(2,4-Dichloro-6-fluoro-benzoyl)amino]pyridine-2-carboxamide

This compound was made in an analogous fashion to Example 87, step 3, except employing 5-aminopyridine-2-carboxamide in the amide formation step. The yield of the desired product after purification was 1.2 g (33%). ESI-MS m/z calc. 327.00, found 328.1 (M+1)+; retention time (Method B): 1.16 minutes (3 minute run). $^1$H NMR (400 MHz, DMSO-d6) δ 11.34 (s, 1H), 8.88-8.82 (m, 1H), 8.29 (dd, J=8.5, 2.5 Hz, 1H), 8.12-8.01 (m, 2H), 7.76 (dq, J=4.2, 2.0 Hz, 2H), 7.58 (s, 1H) ppm.

437

Step 2: 5-[[2,4-Dichloro-6-[4-(trifluoromethoxy)phenoxy]benzoyl]amino]pyridine-2-carboxamide (184)

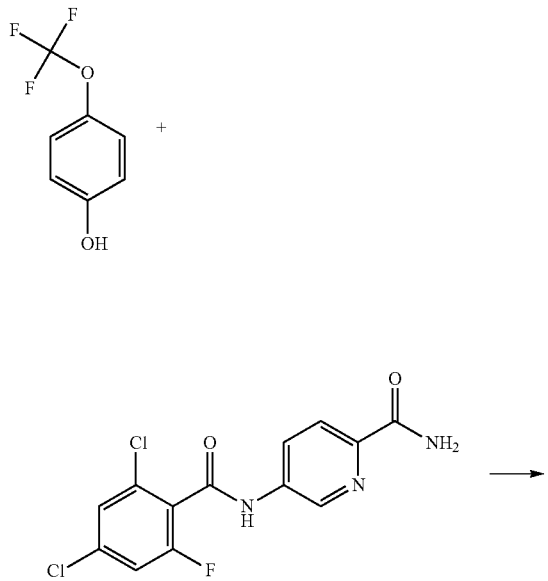

To a solution of 5-[(2,4-dichloro-6-fluoro-benzoyl)amino]pyridine-2-carboxamide (44 mg, 0.13 mmol) in DMF was added 4-(trifluoromethoxy)phenol (24 mg, 17 μL, 0.13 mmol) followed by K₂CO₃ (56 mg, 0.40 mmol). The reaction was heated at 80° C. for 1 hour. The reaction was diluted with DMSO (0.5 mL), filtered, and purified by HPLC (1-99% acetonitrile/5 mM HCl) to provide 5-[[2,4-dichloro-6-[4-(trifluoromethoxy)phenoxy]benzoyl]amino]pyridine-2-carboxamide (36 mg, 53%). ESI-MS m/z calc. 485.02, found 485.8 (M+1)+; retention time (Method B): 1.81 minutes (3 minute run). ¹H NMR (400 MHz, DMSO-d6) δ 11.23 (s, 1H), 8.86 (dd, J=2.5, 0.7 Hz, 1H), 8.27 (dd, J=8.6, 2.5 Hz, 1H), 8.13-7.99 (m, 2H), 7.61-7.48 (m, 2H), 7.27 (d, J=8.8 Hz, 1H), 7.19 (d, J=2.8 Hz, 1H), 7.00 (m, 1H) 6.76 (d, J=1.8 Hz, 1H) ppm.

438

Example 89

N-(3-Carbamoyl-4-fluoro-phenyl)-6-(1-fluoro-1-methyl-ethyl)-4-[2-methoxy-4-(trifluoromethoxy)phenoxy]pyridine-3-carboxamide (103)

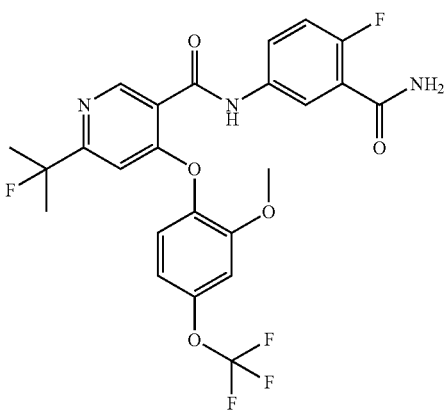 [SMILES: COc1cc(OC(F)(F)F)ccc1Oc1cc(C(C)(C)F)ncc1C(=O)Nc1ccc(F)c(C(N)=O)c1]

Step 1: Methyl 6-isopropenyl-4-[2-methoxy-4-(trifluoromethoxy)phenoxy]pyridine-3-carboxylate

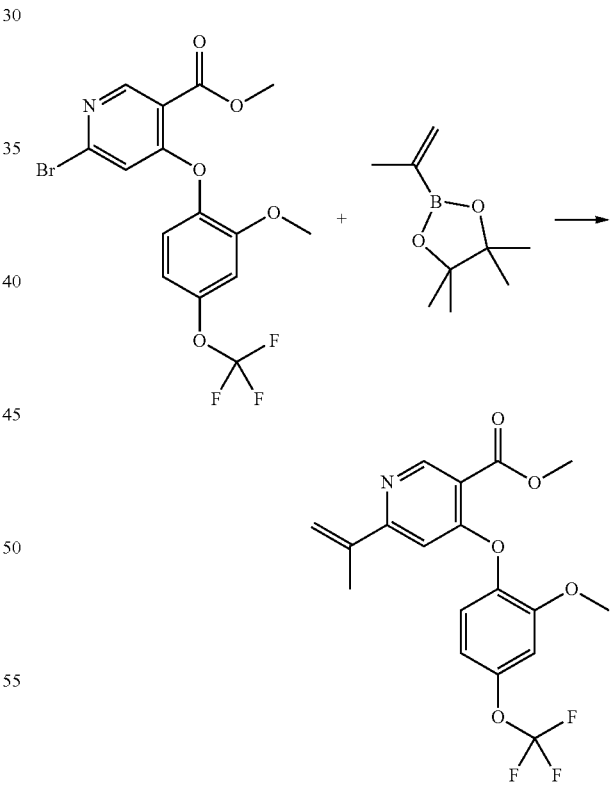

A mixture of methyl 6-bromo-4-[2-methoxy-4-(trifluoromethoxy)phenoxy]pyridine-3-carboxylate (prepared as described in Example 65, Step 1, 12.0 g, 28.4 mmol) and Pd(dppf)Cl₂·DCM (1.86 g, 2.28 mmol) was suspended in anhydrous acetonitrile (120 mL) under a N₂ atmosphere. Isopropenylboronic acid pinacol ester (4.93 g, 28.5 mmol) was added to the reaction mixture followed by an aqueous K₂CO₃ (29 mL of 2 M, 57 mmol). The reaction mixture was heated at 80° C. for 6 hours. The mixture was cooled, partitioned between water and dichloromethane, and the layers separated. The aqueous layer was extracted with additional dichloromethane (2×), and the combined organics were dried over Na₂SO₄, filtered and concentrated in vacuo. Silica gel chromatography (0-25% ethyl acetate/hexanes) provided methyl 6-isopropenyl-4-[2-methoxy-4-(trifluoromethoxy)phenoxy]pyridine-3-carboxylate (8.1 g, 74%) as a white solid. ESI-MS m/z calc. 383.10, found 384.1 (M+1)+; retention time (Method A): 0.69 minutes (1 minute run).

Step 2: Methyl 6-acetyl-4-[2-methoxy-4-(trifluoromethoxy)phenoxy]pyridine-3-carboxylate

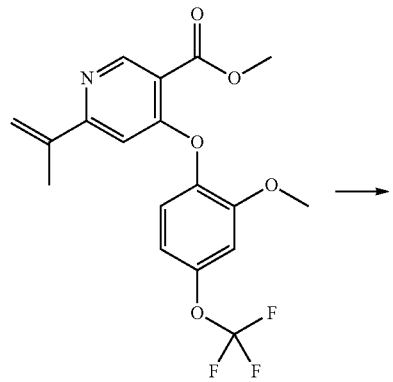

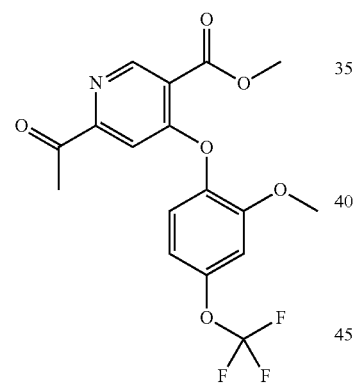

Methyl 6-isopropenyl-4-[2-methoxy-4-(trifluoromethoxy)phenoxy]pyridine-3-carboxylate (4.0 g, 10 mmol) was dissolved in THF (20 mL)/acetone (20 mL) and then water (20 mL) was added. The solution was cooled to 0° C. then treated with trichlororuthenium hydrate (150 mg, 0.665 mmol) followed by portionwise addition of sodium periodate (9.0 g, 42 mmol). The cooling bath was removed and the reaction was allowed to warm to room temperature over 1 hour. The reaction mixture was filtered through a pad of Celite and the filter cake was rinsed with dichloromethane. The filtrate was then diluted with water and the layers separated. The aqueous layer was extracted dichloromethane (2×) and the combined organics were dried over Na₂SO₄, filtered and concentrated in vacuo. Silica gel chromatography (0-30% ethyl acetate/hexanes) provided methyl 6-acetyl-4-[2-methoxy-4-(trifluoromethoxy)phenoxy]pyridine-3-carboxylate (3.1 g, 76%) as a white solid. ESI-MS m/z calc. 385.08, found 386.1 (M+1)+; retention time (method A): 0.70 minutes (1 minute run). ¹H NMR (400 MHz, DMSO-d6) δ 9.01 (d, J=0.4 Hz, 1H), 7.41 (d, J=8.8 Hz, 1H), 7.33 (d, J=2.6 Hz, 1H), 7.09 (ddq, J=8.8, 2.4, 1.2 Hz, 1H), 6.99 (d, J=0.4 Hz, 1H), 3.90 (s, 3H), 3.76 (s, 3H), 2.60 (s, 3H) ppm.

Step 3: Methyl 6-(1-hydroxy-1-methyl-ethyl)-4-[2-methoxy-4-(trifluoromethoxy)phenoxy]pyridine-3-carboxylate

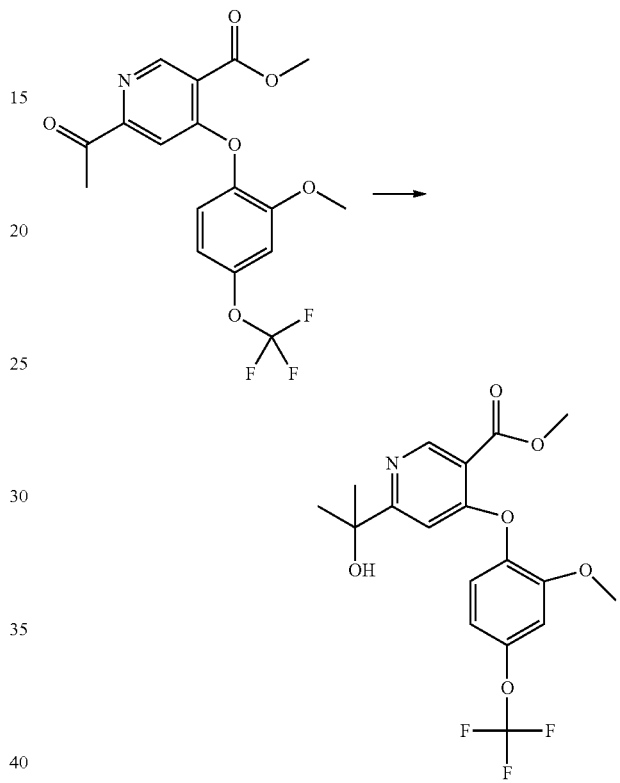

Methyl 6-acetyl-4-[2-methoxy-4-(trifluoromethoxy)phenoxy]pyridine-3-carboxylate (1.56 g, 4.05 mmol) was dissolved in anhydrous THF (40 mL) under N₂ atmosphere and the solution cooled to −78° C. A solution of methylmagnesium bromide (1.5 mL of 3 M in THF, 4.500 mmol) was then added dropwise. The reaction was stirred for an additional 10 minutes and then allowed to warm to room temperature over 2 hours. The reaction mixture was quenched with saturated aqueous NH₄Cl solution and diluted with ethyl acetate. The layers were separated and the aqueous layer was extracted with ethyl acetate (2×). The combined organics were dried over Na₂SO₄, filtered and concentrated in vacuo. Silica gel chromatography (0-60% ethyl acetate/hexanes) provided methyl 6-(1-hydroxy-1-methyl-ethyl)-4-[2-methoxy-4-(trifluoromethoxy)phenoxy]pyridine-3-carboxylate (590 mg, 36%). ESI-MS m/z calc. 401.11, found 402.2 (M+1)+; retention time (Method A): 0.56 minutes (1 minute run). ¹H NMR (400 MHz, DMSO-d6) δ 8.81 (s, 1H), 7.35 (d, J=8.8 Hz, 1H), 7.30 (d, J=2.8 Hz, 1H), 7.06 (ddd, J=8.8, 2.7, 1.3 Hz, 1H), 6.88 (s, 1H), 5.26 (s, 1H), 3.84 (s, 3H), 3.77 (s, 3H), 1.35 (s, 6H) ppm.

Step 4: Methyl 6-(1-fluoro-1-methyl-ethyl)-4-[2-methoxy-4-(trifluoromethoxy)phenoxy]pyridine-3-carboxylate

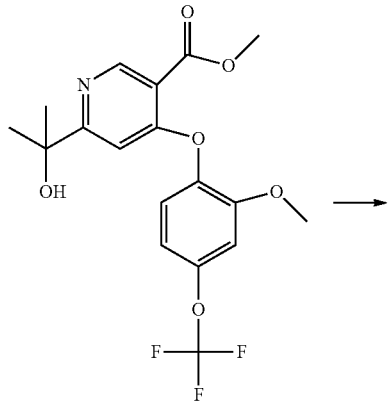

Step 5: 6-(1-Fluoro-1-methyl-ethyl)-4-[2-methoxy-4-(trifluoromethoxy)phenoxy]pyridine-3-carboxylic acid

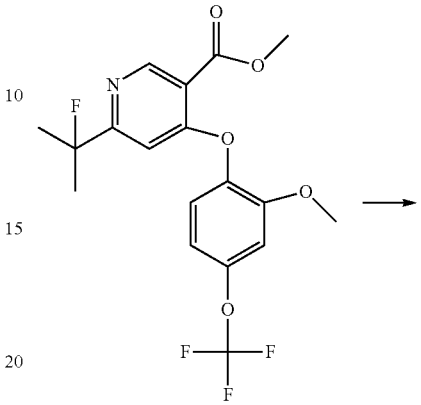

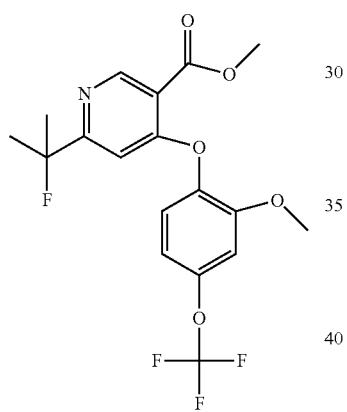

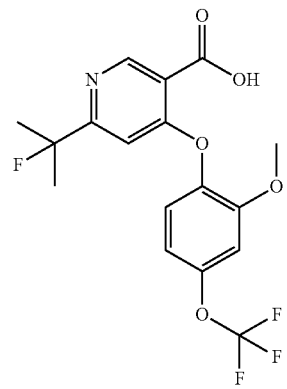

Methyl 6-(1-hydroxy-1-methyl-ethyl)-4-[2-methoxy-4-(trifluoromethoxy)phenoxy]pyridine-3-carboxylate (574 mg, 1.43 mmol) was dissolved in anhydrous dichloromethane (6 mL) under N₂ atmosphere and cooled to −78° C. Deoxo-fluor (320 μL, 1.74 mmol) as a solution in dichloromethane (1.2 mL) was then added dropwise to the reaction mixture. The reaction mixture was stirred for 5 minutes then allowed to warm to room temperature and stirred for 30 minutes. The reaction was quenched with saturated aqueous NaHCO₃ solution and extracted with dichloromethane (2×). The combined organic layers were dried over Na₂SO₄, filtered and concentrated in vacuo. Silica gel chromatography (0-20% ethyl acetate/hexanes) provided methyl 6-(1-fluoro-1-methyl-ethyl)-4-[2-methoxy-4-(trifluoromethoxy)phenoxy]pyridine-3-carboxylate (375 mg, 65%). ESI-MS m/z calc. 403.10, found 404.2 (M+1)+; retention time (Method A): 0.75 minutes (1 minute run).

Methyl 6-(1-fluoro-1-methyl-ethyl)-4-[2-methoxy-4-(trifluoromethoxy)phenoxy]pyridine-3-carboxylate (375 mg, 0.930 mmol) was dissolved in methanol (1.5 mL)/THF (1 mL) at room temperature and solution of NaOH (200 mg, 5.00 mmol) in water (1 mL) was then added. The reaction mixture was stirred at room temperature for 1 hour. The solvents were removed in vacuo and the resulting white slurry was dissolved in water and cooled to 0° C. The solution was treated with 6 M aqueous HCl until pH2. The resulting white suspension was filtered and the filter cake washed with water. The filter cake was then dried in a desiccator filled with DrieRite under high vacuum to provide 6-(1-fluoro-1-methyl-ethyl)-4-[2-methoxy-4-(trifluoromethoxy)phenoxy]pyridine-3-carboxylic acid (285 mg, 79%) as a white solid. ESI-MS m/z calc. 389.09, found 390.1 (M+1)+; retention time (Method A): 0.65 minutes (1 minute run).

Step 6: N-(3-Carbamoyl-4-fluoro-phenyl)-6-(1-fluoro-1-methyl-ethyl)-4-[2-methoxy-4-(trifluoromethoxy)phenoxy]pyridine-3-carboxamide (103)

A mixture of 6-(1-fluoro-1-methyl-ethyl)-4-[2-methoxy-4-(trifluoromethoxy)phenoxy]pyridine-3-carboxylic acid (142 mg, 0.365 mmol), 5-amino-2-fluoro-benzamide (56 mg, 0.37 mmol), HATU (140 mg, 0.368 mmol) and 4-methylmorpholine (111 mg, 1.10 mmol) in DMF (1.5 mL) was stirred at room temperature for 20 minutes. The reaction mixture was partitioned between ethyl acetate and water. The layers were separated and the organic layer was washed with a saturated aqueous sodium chloride solution (2×). The organic layer was dried over Na₂SO₄, filtered and concentrated in vacuo. Silica gel chromatography (0-60% ethyl acetate/hexanes) provided N-(3-carbamoyl-4-fluoro-phenyl)-6-(1-fluoro-1-methyl-ethyl)-4-[2-methoxy-4-(trifluoromethoxy)phenoxy]pyridine-3-carboxamide (134 mg, 69%). ESI-MS m/z calc. 525.13, found 526.2 (M+1)+; retention time (method B): 1.71 minutes (3 minute run). ¹H NMR (400 MHz, DMSO-d6) δ 10.65 (s, 1H), 8.70 (d, J=1.0 Hz, 1H), 8.03 (dd, J=6.4, 2.8 Hz, 1H), 7.83 (ddd, J=9.0, 4.4, 2.8 Hz, 1H), 7.70 (d, J=14.6 Hz, 2H), 7.49 (d, J=8.8 Hz, 1H), 7.34-7.23 (m, 2H), 7.10 (ddt, J=7.7, 2.7, 1.3 Hz, 1H), 6.64 (d, J=1.5 Hz, 1H), 3.79 (s, 3H), 1.61 (d, J=22.3 Hz, 6H) ppm. ¹⁹F NMR (376 MHz, DMSO-d6) δ −56.86, −119.01 (dt, J=8.9, 5.5 Hz), −140.24--143.39 (m) ppm.

Example 90

N-(2-Carbamoyl-4-pyridyl)-6-(1-fluoro-1-methyl-ethyl)-4-[2-methoxy-4-(trifluoromethoxy)phenoxy]pyridine-3-carboxamide (104)

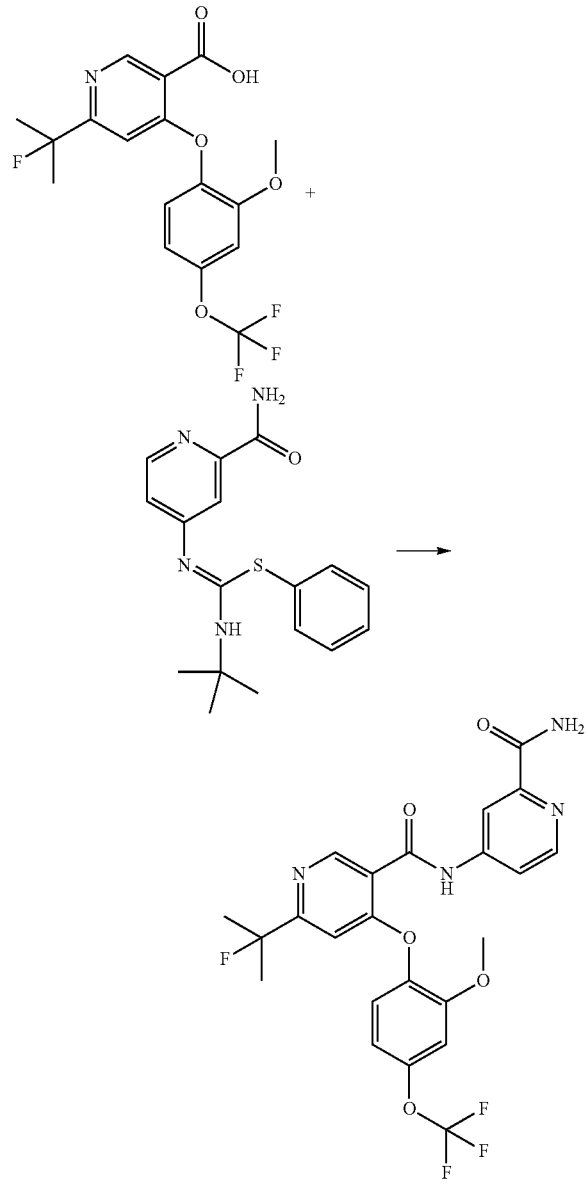

To a pressure vial were added 6-(1-fluoro-1-methyl-ethyl)-4-[2-methoxy-4-(trifluoromethoxy)phenoxy]pyridine-3-carboxylic acid (prepared as described in Example 95, Step 5, 143 mg, 0.367 mmol), 4-[(Z)-[(tert-butylamino)-phenylsulfanyl-methylene]amino]pyridine-2-carboxamide (prepared as described in Preparation 1, 121 mg, 0.368 mmol) and tris[(Z)-1-methyl-3-oxo-but-1-enoxy]iron (3.9 mg, 0.011 mmol) and 2-propanol (1.4 mL). The reaction vessel was sealed and stirred at 80° C. for 20 hours. The reaction mixture was cooled to room temperature and concentrated in vacuo. Silica gel chromatography (0-50% ethyl acetate/dichloromethane) provided N-(2-carbamoyl-4-pyridyl)-6-(1-fluoro-1-methyl-ethyl)-4-[2-methoxy-4-(trifluoromethoxy)phenoxy]pyridine-3-carboxamide (93 mg, 49%). ESI-MS m/z calc. 508.14, found 509.2 (M+1)+; retention time (Method B): 1.59 minutes (3 minute run). ¹H NMR (400 MHz, DMSO-d6) δ 11.07 (s, 1H), 8.74 (d, J=1.1 Hz, 1H), 8.54 (d, J=5.5 Hz, 1H), 8.34 (d, J=2.2 Hz, 1H), 8.11 (d, J=2.8 Hz, 1H), 7.90 (dd, J=5.5, 2.2 Hz, 1H), 7.66 (d, J=2.9 Hz, 1H), 7.49 (d, J=8.8 Hz, 1H), 7.29 (d, J=2.7 Hz, 1H), 7.10 (ddt, J=7.6, 2.8, 1.4 Hz, 1H), 6.66 (d, J=1.4 Hz, 1H), 3.78 (s, 3H), 1.61 (d, J=22.4 Hz, 6H) ppm. ¹⁹F NMR (376 MHz, DMSO-d6) δ −56.87, −142.08 (p, J=22.5 Hz) ppm.

Example 91

4-[[2-[2-(Trideuteriomethoxy)-4-(trifluoromethoxy)phenoxy]-4,6-bis(trifluoromethyl)benzoyl]amino]pyridine-2-carboxamide (175)

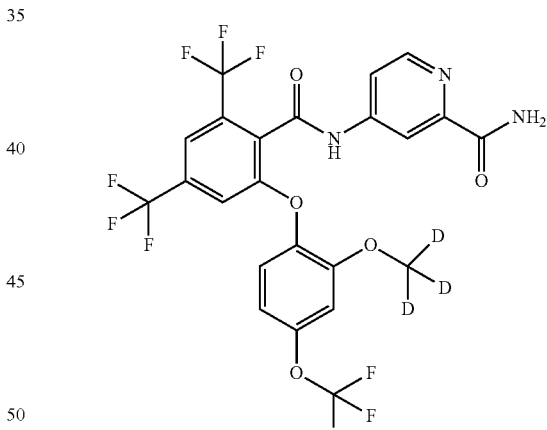

Step 1: 4-[[2-Fluoro-4,6-bis(trifluoromethyl)benzoyl]amino]pyridine-2-carboxamide

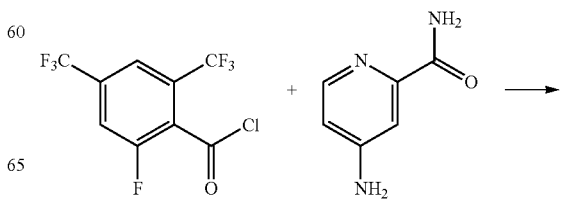

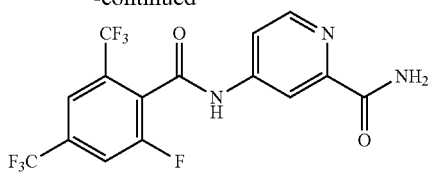

To 2-fluoro-4,6-bis(trifluoromethyl)benzoyl chloride (1.20 g, 4.08 mmol) and DIEA (1.8 mL, 10 mmol) in 1-methyl-pyrrolidin-2-one (12 mL) at 0° C. was added a solution of 4-aminopyridine-2-carboxamide (560 mg, 4.08 mmol) in dichloromethane (6 mL) dropwise. The reaction was stirred at room temperature for 16 hours. The reaction mixture was diluted with ethyl acetate and washed with water. Organic layer was concentrated to dryness. Silica gel chromatography (1-5% methanol/dichloromethane) provided 4-[[2-fluoro-4,6-bis(trifluoromethyl)benzoyl]amino]pyridine-2-carboxamide (400 mg, 11%). ESI-MS m/z calc. 395.05, found 396.6 (M+1)+; retention time (Method A): 0.55 minutes (1 minute run).

Step 2: 4-[[2-[2-(Trideuteriomethoxy)-4-(trifluoromethoxy)phenoxy]-4,6-bis(trifluoromethyl)benzoyl]amino]pyridine-2-carboxamide (175)

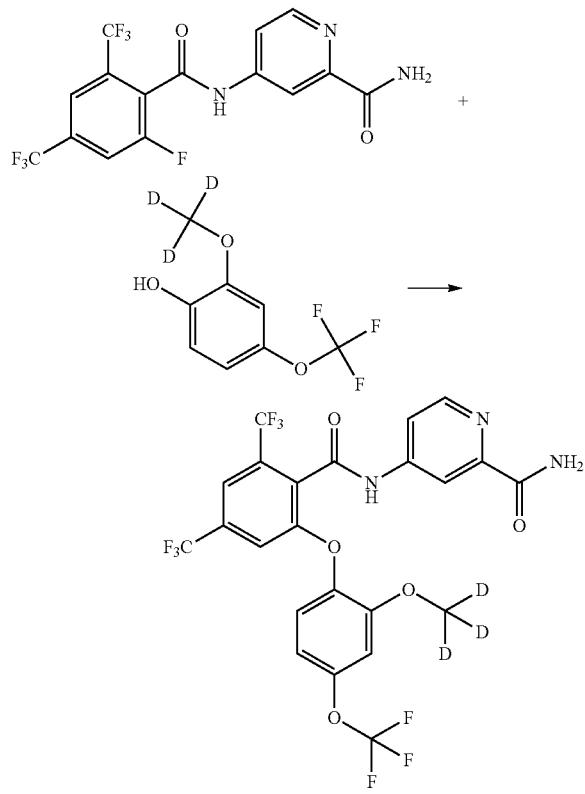

A mixture of 4-[[2-fluoro-4,6-bis(trifluoromethyl)benzoyl]amino]pyridine-2-carboxamide (57 mg, 0.10 mmol), 2-(trideuteriomethoxy)-4-(trifluoromethoxy)phenol (20 mg, 0.10 mmol), K$_2$CO$_3$ (40 mg, 0.29 mmol) in DMF (380 µL) was heated at 100° C. The reaction mixture was filtered and diluted with DMSO (1 mL). HPLC purification (1-99% acetonitrile/5 mM HCl) provided 4-[[2-[2-(trideuteri-omethoxy)-4-(trifluoromethoxy)phenoxy]-4,6-bis(trifluoromethyl)benzoyl]amino]pyridine-2-carboxamide (42 mg, 75%) as a white solid. ESI-MS m/z calc. 586.10, found 587.2 (M+1)+; retention time (method B): 1.84 minutes (3 minute run). $^1$H NMR (400 MHz, DMSO-d6) δ 11.46 (s, 1H), 8.60-8.52 (m, 1H), 8.29 (dd, J=2.2, 0.6 Hz, 1H), 8.12 (d, J=2.7 Hz, 1H), 7.99-7.92 (m, 1H), 7.79 (dd, J=5.5, 2.2 Hz, 1H), 7.66 (d, J=2.8 Hz, 1H), 7.35-7.27 (m, 2H), 7.23 (dd, J=2.8, 0.7 Hz, 1H), 7.09-6.99 (m, 1H) ppm. $^{19}$F NMR (376 MHz, DMSO-d6) δ −56.87, −58.50, −61.65 ppm.

Example 92

5-[[2-[2-(Trideuteriomethoxy)-4-(trifluoromethoxy)phenoxy]-4,6-bis(trifluoromethyl)benzoyl]amino]pyridine-2-carboxamide (176)

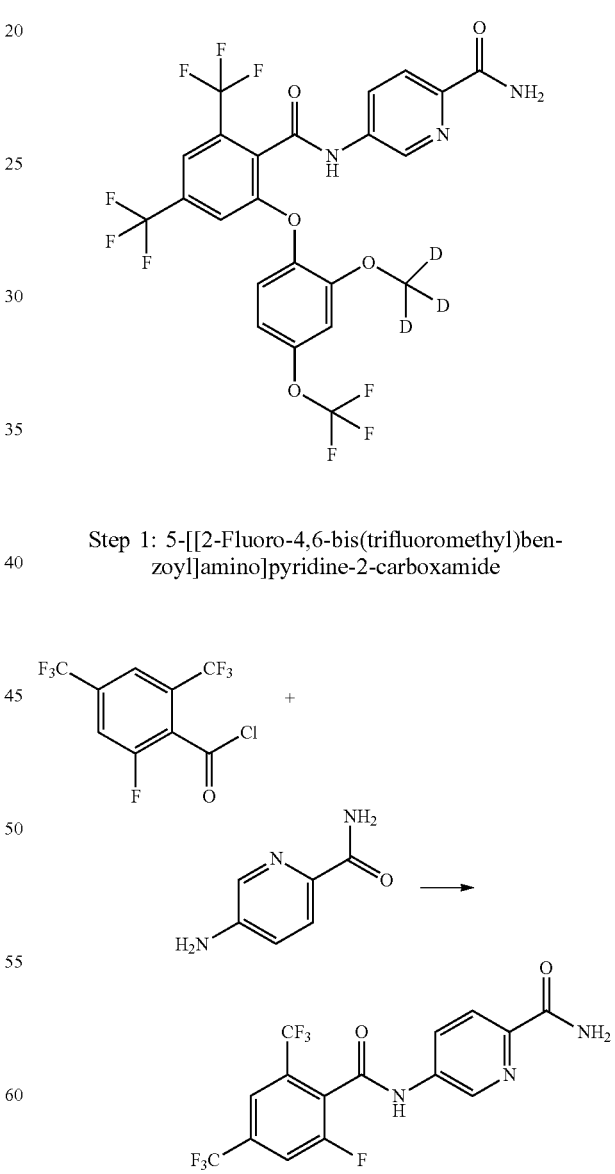

Step 1: 5-[[2-Fluoro-4,6-bis(trifluoromethyl)benzoyl]amino]pyridine-2-carboxamide This compound was made in an analogous fashion to Example 91, Step 1, except employing 5-aminopyridine-2-carboxamide in the amide formation step. The yield of the

447 desired product after purification was 560 mg (49%). ESI-MS m/z calc. 395.05, found 396.2 (M+1)+; retention time (Method B): 0.55 minutes (3 minute run).

Step 2: 5-[[2-[2-(Trideuteriomethoxy)-4-(trifluoromethoxy)phenoxy]-4,6-bis(trifluoromethyl)benzoyl]amino]pyridine-2-carboxamide (176)

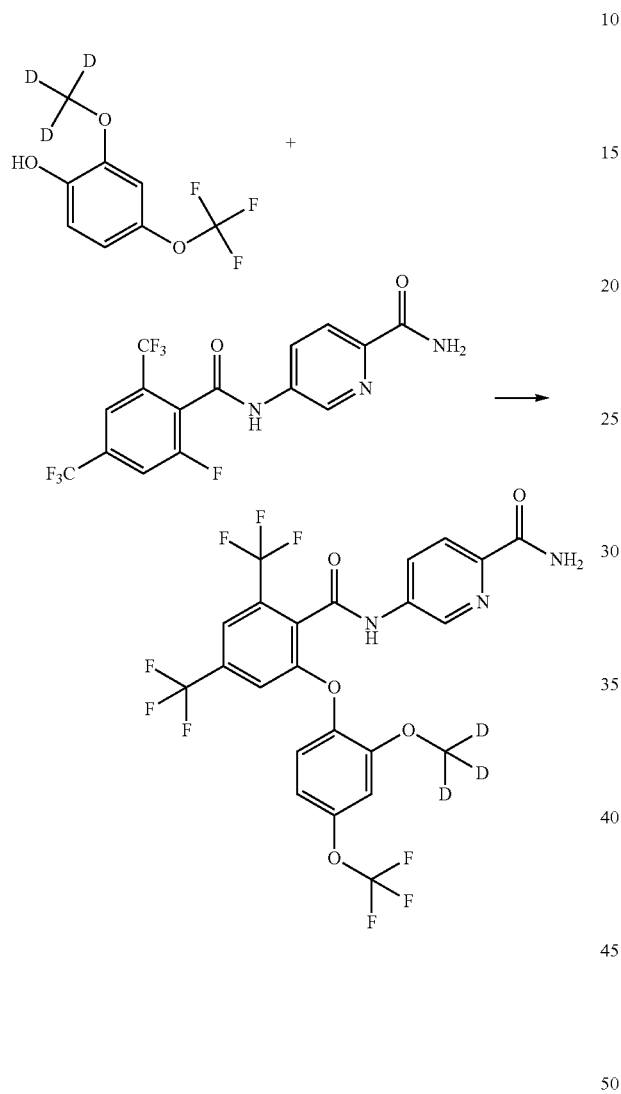

A mixture of 5-[[2-fluoro-4,6-bis(trifluoromethyl)benzoyl]amino]pyridine-2-carboxamide (50 mg, 0.13 mmol), 2-(trideuteriomethoxy)-4-(trifluoromethoxy)phenol (27 mg, 0.13 mmol) and $K_2CO_3$ (52 mg, 0.38 mmol) in DMF (0.5 mL) was heated at 100° C. for 16 hours. The reaction was filtered, diluted with DMSO (1 mL) and purified by HPLC (1-99% acetonitrile/5 mM HCl) to obtain 5-[[2-[2-(trideuteriomethoxy)-4-(trifluoromethoxy)phenoxy]-4,6-bis(trifluoromethyl)benzoyl]amino]pyridine-2-carboxamide (39 mg, 52%) as a white solid. ESI-MS m/z calc. 586.10, found 587.2 (M+1)+; retention time (Method B): 1.84 minutes (3 minute run). $^1$H NMR (400 MHz, DMSO-d6) δ 11.34 (s, 1H), 8.82 (d, J=2.8 Hz, 1H), 8.25 (dd, J=8.6, 2.5 Hz, 1H), 8.06 (d, J=8.6 Hz, 1H), 8.02 (d, J=2.7 Hz, 1H), 7.97 (d, J=1.4 Hz, 1H), 7.58 (d, J=2.8 Hz, 1H), 7.35-7.30 (m, 2H), 7.25 (d, J=2.8 Hz, 1H), 7.07-7.01 (m, 1H) ppm.

448

Example 93

5-[[2-Chloro-3-fluoro-6-[2-methoxy-4-(trifluoromethoxy)phenoxy]benzoyl]amino]pyridine-2-carboxamide (186)

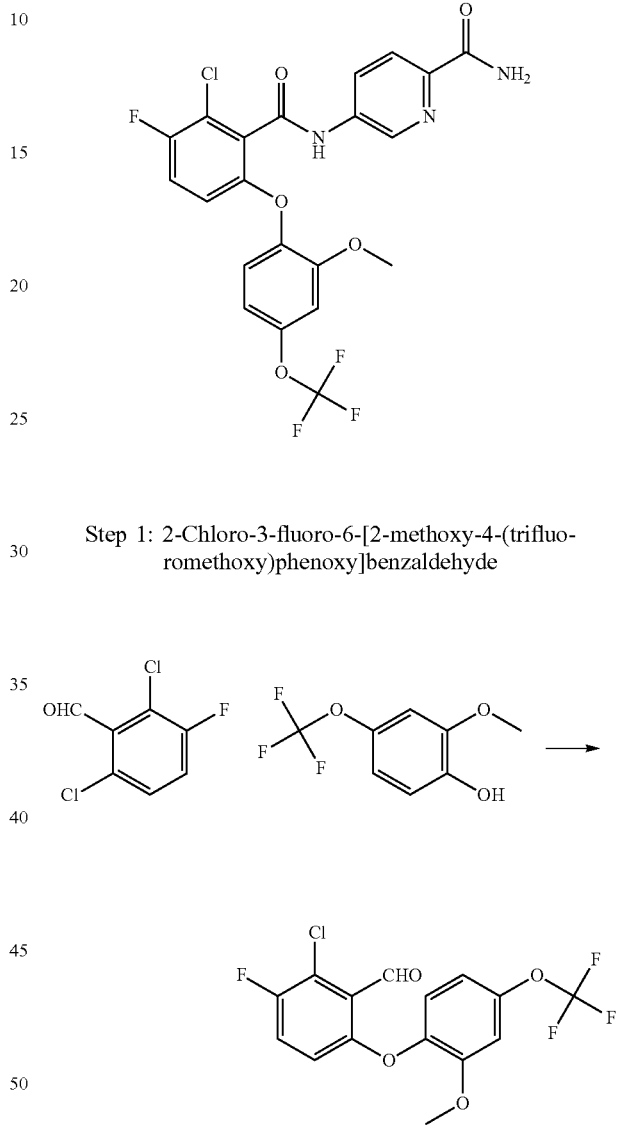

Step 1: 2-Chloro-3-fluoro-6-[2-methoxy-4-(trifluoromethoxy)phenoxy]benzaldehyde

A mixture of 2-chloro-3,6-difluoro-benzaldehyde (2.0 g, 11.3 mmol), 2-methoxy-4-(trifluoromethoxy)phenol (2.4 g, 11.5 mmol) and $Cs_2CO_3$ (4.5 g, 13.8 mmol) in DMF (15 mL) was stirred for 16 hours at room temperature. The mixture was concentrated in vacuo and the residue was purified by silica gel chromatography (0-50% ethyl acetate/petroleum ether) to provide 2-chloro-3-fluoro-6-[2-methoxy-4-(trifluoromethoxy)phenoxy]benzaldehyde (3.6 g, 87%) as a pale yellow oil. ESI-MS m/z calc. 364.01, found 365.0 (M+1)+; retention time (Method F): 1.09 minutes (1.5 minute run).

Step 2: 2-Chloro-3-fluoro-6-[2-methoxy-4-(trifluoromethoxy)phenoxy]benzoic acid

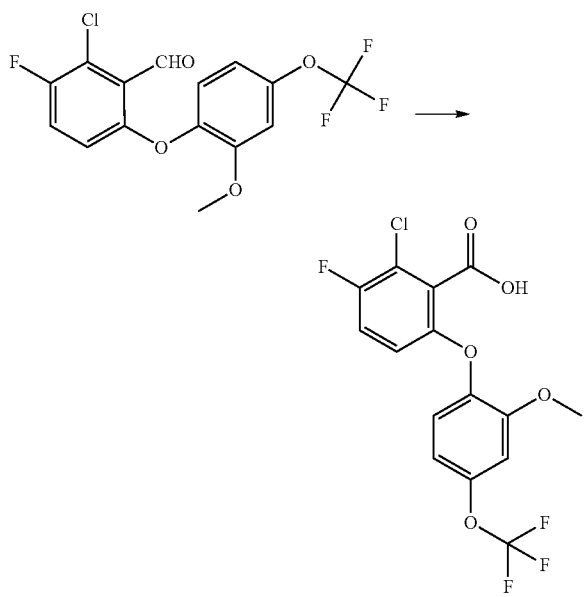

To a suspension of 2-chloro-3-fluoro-6-[2-methoxy-4-(trifluoromethoxy)phenoxy]benzaldehyde (3.60 g, 9.87 mmol) and sodium dihydrogen phosphate hydrate (1.40 g, 11.7 mmol) in tert-BuOH (20 mL)/water (10 mL) at 0° C. was added a solution of 2-methyl-2-butene (15 mL of 2 M in THF, 30 mmol). Sodium chlorite (1.40 g, 12.4 mmol) was then added portionwise over 30 minutes. The mixture was allowed to warm to room temperature and stirred for 16 hours. The reaction mixture was acidified to pH1-2 using 2M HCl, and extracted with dichloromethane. The organic layer was separated, dried by passing through a phase separation cartridge and concentrated in vacuo to afford 2-chloro-3-fluoro-6-[2-methoxy-4-(trifluoromethoxy)phenoxy]benzoic acid (3.76 g, 100%) as a white solid. ESI-MS m/z calc. 380.01, found 379.1 (M−1)−; retention time (Method F): 0.71 minutes (1.5 minute run).

Step 3: 2-Chloro-3-fluoro-6-[2-methoxy-4-(trifluoromethoxy)phenoxy]benzoyl chloride

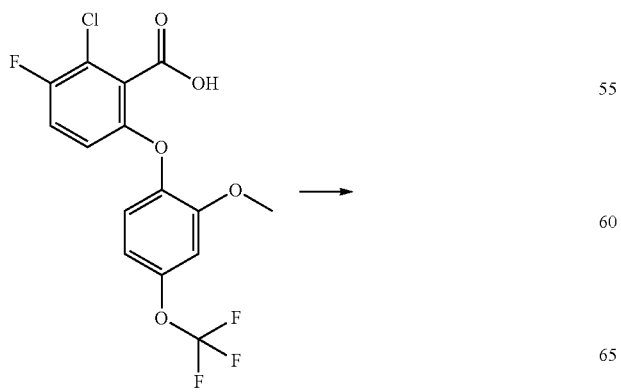

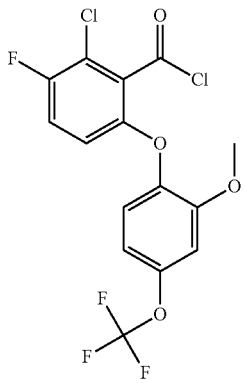

A solution of 2-chloro-3-fluoro-6-[2-methoxy-4-(trifluoromethoxy)phenoxy]benzoic acid (100 mg, 0.263 mmol) in dichloromethane (2 mL) was cooled to 0° C. To the solution was added DMF (2 μL, 0.03 mmol) followed by careful addition of oxalyl chloride (35 μL, 0.40 mmol). The ice-bath removed after 5 minutes and the reaction stirred at room temperature for 20 minutes. The reaction was concentrated in vacuo and azeotroped with dichloromethane to afford 2-chloro-3-fluoro-6-[2-methoxy-4-(trifluoromethoxy)phenoxy]benzoyl chloride.

Step 4: 5-[[2-Chloro-3-fluoro-6-[2-methoxy-4-(trifluoromethoxy)phenoxy]benzoyl]amino]pyridine-2-carboxamide (186)

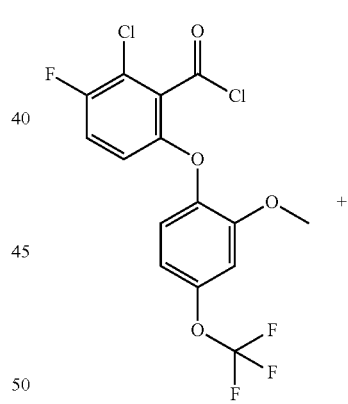

+

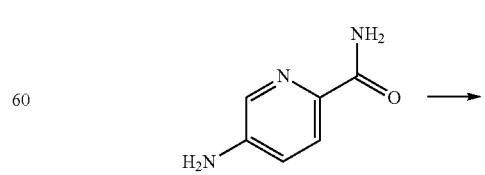

451
-continued

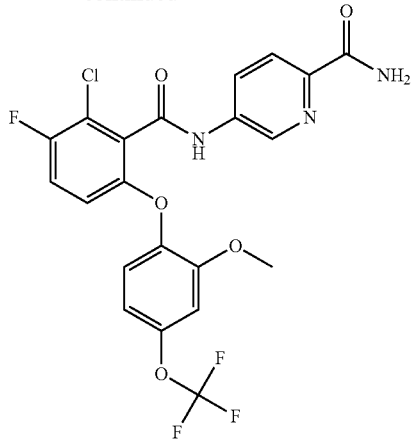 [SMILES: COc1cc(OC(F)(F)F)ccc1Oc1ccc(F)c(Cl)c1C(=O)Nc1ccc(C(N)=O)nc1]

2-Chloro-3-fluoro-6-[2-methoxy-4-(trifluoromethoxy)phenoxy]benzoyl chloride was dissolved in THF (2 mL) and cooled to 0° C. DIEA (138 µL, 0.792 mmol) and 5-aminopyridine-2-carboxamide (40 mg, 0.29 mmol) were added and the resulting suspension was stirred at 0° C. for 30 minutes and then allowed to warmed to room temperature and stirred for 16 hours. The reaction mixture was diluted with ethyl acetate and washed with water and brine. The organic later was separated, dried by passing through a phase separation cartridge and concentrated in vacuo. Silica gel chromatography (0-100% ethyl acetate/petroleum ether) provided 5-[[2-chloro-3-fluoro-6-[2-methoxy-4-(trifluoromethoxy)phenoxy]benzoyl]amino]pyridine-2-carboxamide (85 mg, 64%). ESI-MS m/z calc. 499.06, found 500.0 (M+1)+; 497.9 (M−1)−; retention time (Method E): 3.01 minutes (5 minute run). $^1$H NMR (400 MHz, DMSO-d6) δ 11.25 (s, 1H), 8.86 (d, J=2.4 Hz, 1H), 8.28 (dd, J=8.6, 2.5 Hz, 1H), 8.09-7.99 (m, 2H), 7.56 (s, 1H), 7.49 (t, J=9.0 Hz, 1H), 7.23-7.16 (m, 2H), 6.98 (ddd, J=8.9, 2.8, 1.3 Hz, 1H), 6.84 (dd, J=9.3, 3.9 Hz, 1H), 3.77 (s, 3H) ppm.

Example 94

4-[[2-Chloro-3-fluoro-6-[2-methoxy-4-(trifluoromethoxy)phenoxy]benzoyl]amino]pyridine-2-carboxamide (171)

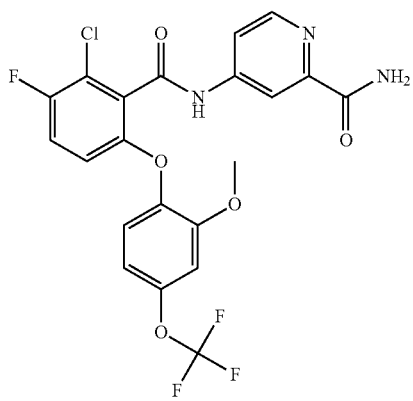 [SMILES: COc1cc(OC(F)(F)F)ccc1Oc1ccc(F)c(Cl)c1C(=O)Nc1ccnc(C(N)=O)c1]

Step 1: Methyl 4-[[2-chloro-3-fluoro-6-[2-methoxy-4-(trifluoromethoxy)phenoxy]benzoyl]amino]pyridine-2-carboxylate

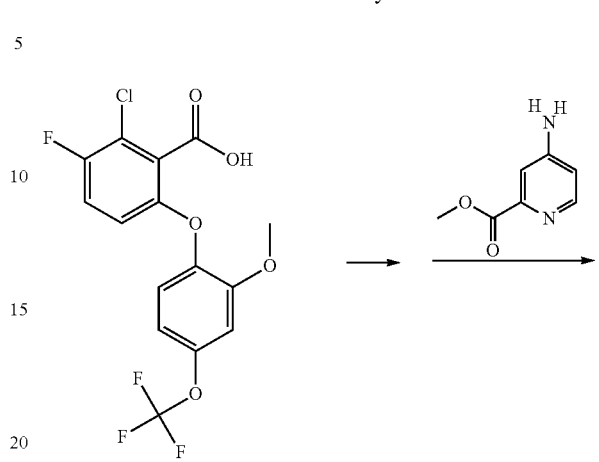

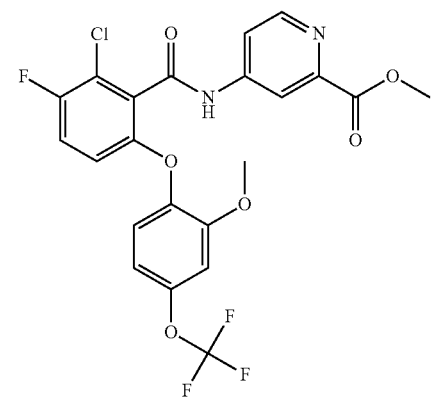

To a solution of 2-chloro-3-fluoro-6-[2-methoxy-4-(trifluoromethoxy)phenoxy]benzoic acid (300 mg, 0.788 mmol) in dichloromethane (5 mL) at 0° C. was added DMF (7 µL, 0.08 mmol) and oxalyl chloride (235 µL, 2.69 mmol) dropwise. The reaction was allowed to warm to room temperature over 3 hours. The reaction mixture was concentrated in vacuo, dissolved in dichloromethane (5 mL) and cooled to 0° C. Methyl 4-aminopyridine-2-carboxylate (159 mg, 1.05 mmol) was added followed by triethylamine (422 µL, 3.03 mmol). The resulting mixture was allowed to warm to room temperature over 16 hours. The reaction mixture was diluted with water (10 mL) and extracted with dichloromethane (2×10 mL). The combined organic layers were dried over MgSO$_4$, filtered and concentrated in vacuo. Silica gel chromatography (0-60% ethyl acetate/petroleum ether) provided methyl 4-[[2-chloro-3-fluoro-6-[2-methoxy-4-(trifluoromethoxy)phenoxy]benzoyl]amino]pyridine-2-carboxylate (204 mg, 50%). ESI-MS m/z calc. 514.06, found 515.0 (M+1)+; retention time (Method F): 0.97 minutes (1.5 minute run).

453

Step 2: 4-[[2-Chloro-3-fluoro-6-[2-methoxy-4-(trifluoromethoxy)phenoxy]benzoyl]amino]pyridine-2-carboxamide (171)

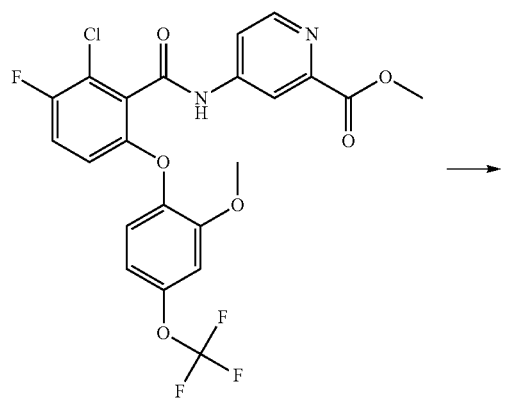

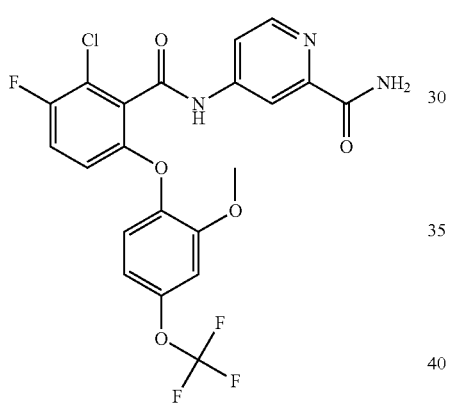

A solution of methyl 4-[[2-chloro-3-fluoro-6-[2-methoxy-4-(trifluoromethoxy)phenoxy]benzoyl]amino]pyridine-2-carboxylate (204 mg, 0.3963 mmol) in ammonia (6.4 mL of 7 M in methanol, 44.80 mmol) was stirred for 16 hours at room temperature. The reaction mixture was concentrated in vacuo and purified by HPLC (37-100% acetonitrile/0.1% ammonium hydroxide) to provide 4-[[2-chloro-3-fluoro-6-[2-methoxy-4-(trifluoromethoxy)phenoxy]benzoyl]amino]pyridine-2-carboxamide (142.3 mg, 70%). ESI-MS m/z calc. 499.056, found 500.0 (M+1)+; retention time: 3.2 minutes (5 minute run). $^1$H NMR (400 MHz, DMSO-d6) δ 11.36 (s, 1H), 8.56 (d, J=5.5 Hz, 1H), 8.33 (d, J=2.2 Hz, 1H), 8.11 (d, J=2.9 Hz, 1H), 7.84 (dd, J=5.5, 2.2 Hz, 1H), 7.74-7.55 (m, 2H), 7.39-7.12 (m, 2H), 7.00 (ddd, J=8.8, 2.7, 1.3 Hz, 1H), 6.64 (dd, J=9.0, 1.4 Hz, 1H), 3.78 (s, 3H) ppm.

454

Example 95

4-[[2-Chloro-3-fluoro-6-[2-methoxy-4-(trifluoromethoxy)phenoxy]benzoyl]amino]-5-methyl-pyridine-2-carboxamide (129)

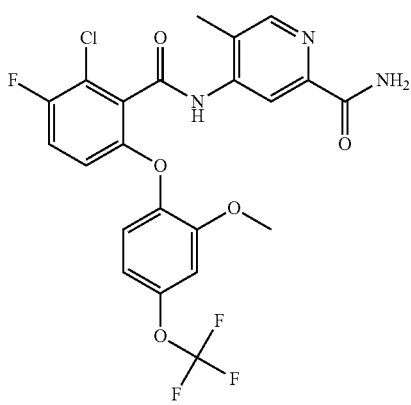 [SMILES: COc1cc(OC(F)(F)F)ccc1Oc1ccc(F)c(Cl)c1C(=O)Nc1cc(C(N)=O)ncc1C]

Step 1: N-(2-Bromo-5-methyl-4-pyridyl)-2-chloro-3-fluoro-6-[2-methoxy-4-(trifluoromethoxy)phenoxy]benzamide

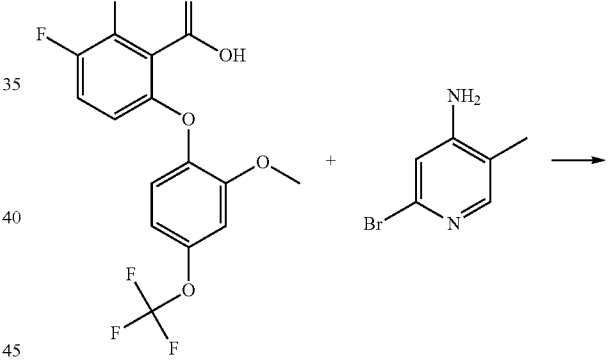

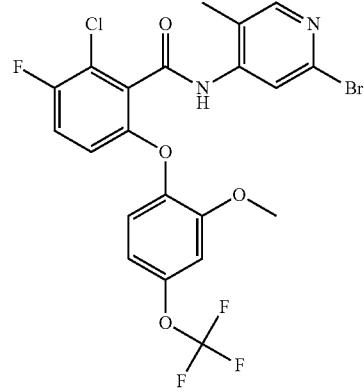

This compound was made in an analogous fashion to Example 94, Step 1, except employing 2-bromo-5-methyl-pyridin-4-amine in the amide formation step. The yield of the desired product after purification was 179 mg (29%). ESI-MS m/z calc. 547.98, found 551.0 (M+1)+; retention time (Method F): 1.10 minutes (1.5 minute run).

Step 2: Methyl 4-[[2-chloro-3-fluoro-6-[2-methoxy-4-(trifluoromethoxy)phenoxy]benzoyl]amino]-5-methyl-pyridine-2-carboxylate

Step 3: 4-[[2-Chloro-3-fluoro-6-[2-methoxy-4-(trifluoromethoxy)phenoxy]benzoyl]amino]-5-methyl-pyridine-2-carboxamide (129)

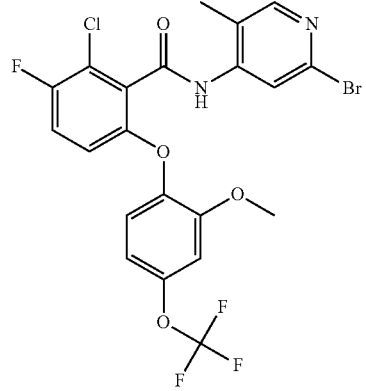

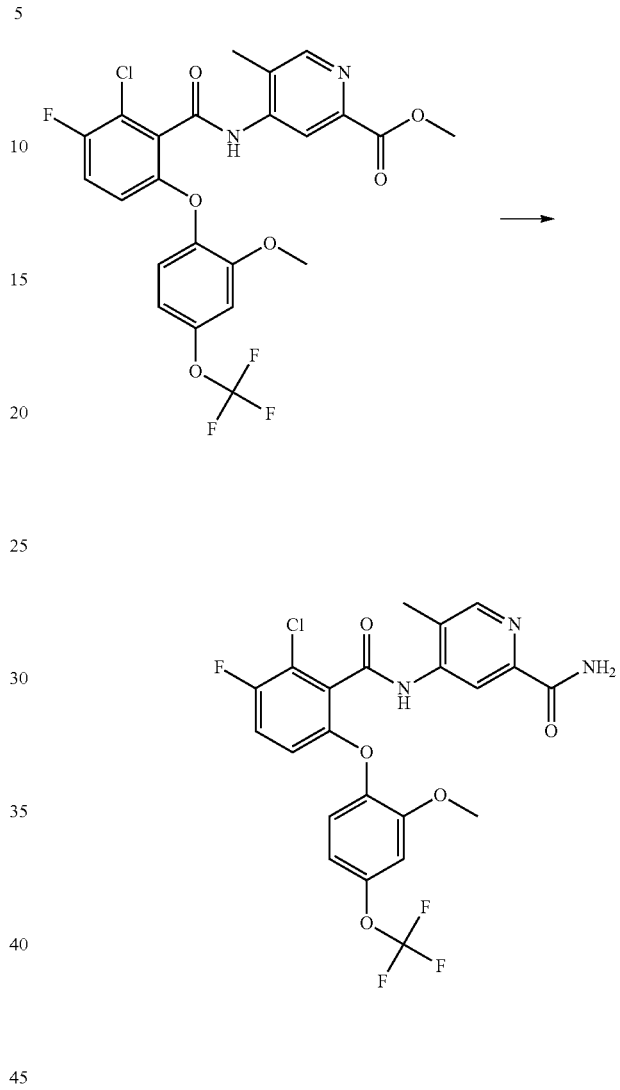

To a solution of N-(2-bromo-5-methyl-4-pyridyl)-2-chloro-3-fluoro-6-[2-methoxy-4-(trifluoromethoxy)phenoxy]benzamide (179 mg, 0.186 mmol) in methanol (5 mL) and triethylamine (40 mg, 0.3953 mmol) in a pressure tube was added Pd(dppf)Cl₂·DCM (30 mg, 0.03674 mmol). Carbon monoxide was bubbled through the vigorously stirring reaction mixture for 5 minutes. The reaction mixture was sealed and heated to 75° C. for 16 hours. The reaction mixture was cooled and passed through a pad of Celite eluting with methanol. The filtrate was concentrated in vacuo and purified by silica gel chromatography (0-100% ethyl acetate/petroleum ether) to provide methyl 4-[[2-chloro-3-fluoro-6-[2-methoxy-4-(trifluoromethoxy)phenoxy]benzoyl]amino]-5-methyl-pyridine-2-carboxylate (87 mg, 89%). ESI-MS m/z calc. 528.07, found 529.0 (M+1)+; retention time (Method F): 0.99 minutes (1.5 minute run).

A mixture of methyl 4-[[2-chloro-3-fluoro-6-[2-methoxy-4-(trifluoromethoxy)phenoxy]benzoyl]amino]-5-methyl-pyridine-2-carboxylate (87 mg, 0.16 mmol) and ammonia (4.5 mL of 7 M in methanol, 31.5 mmol) was stirred at room temperature for 16 hours. SPM32 silica metal scavenger (150 mg) was added and the reaction was stirred for 15 minutes. The mixture was filtered and the filtrate concentrated in vacuo. Silica gel chromatography (0-100% ethyl acetate/petroleum ether) provided 4-[[2-chloro-3-fluoro-6-[2-methoxy-4-(trifluoromethoxy)phenoxy]benzoyl]amino]-5-methyl-pyridine-2-carboxamide (54 mg, 62%) as a white solid. ESI-MS m/z calc. 513.07, found 514.0 (M+1)+; retention time (Method E): 3.21 minutes (5 minute run). $^1$H NMR (500 MHz, DMSO-d6) δ 10.52 (s, 1H), 8.61-8.34 (m, 2H), 8.16-7.97 (m, 1H), 7.60 (d, J=2.9 Hz, 1H), 7.48 (t, J=9.0 Hz, 1H), 7.28-7.12 (m, 2H), 6.99 (ddd, J=8.8, 2.7, 1.2 Hz, 1H), 6.83 (dd, J=9.2, 3.9 Hz, 1H), 3.81 (s, 3H), 2.29 (s, 3H) ppm.

Example 96

N-(4-Carbamoyl-3-fluoro-phenyl)-2-methoxy-6-[4-(trifluoromethoxy)phenoxy]-3-(trifluoromethyl)benzamide (132)

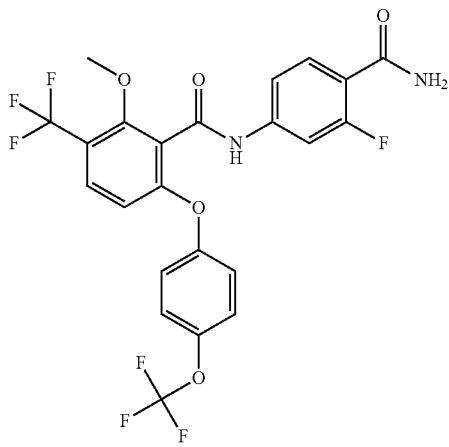 [SMILES: COc1c(C(F)(F)F)ccc(Oc2ccc(OC(F)(F)F)cc2)c1C(=O)Nc1ccc(C(N)=O)c(F)c1]

Step 1: N-(4-Carbamoyl-3-fluoro-phenyl)-2-fluoro-6-[4-(trifluoromethoxy)phenoxy]-3-(trifluoromethyl)benzamide (65)

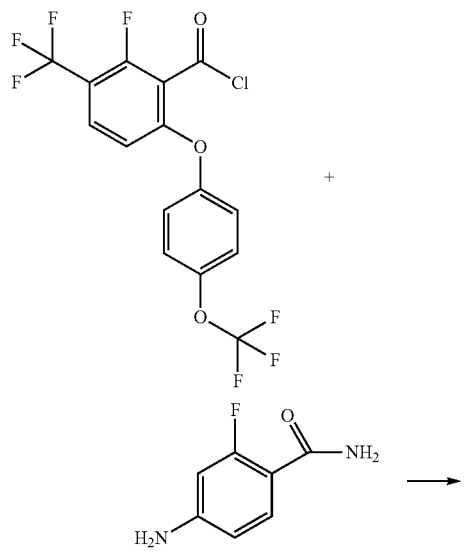

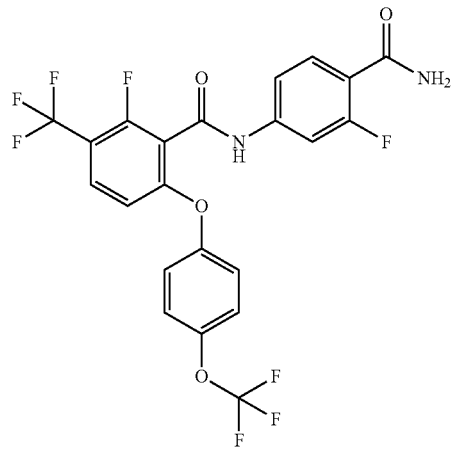

A slurry of 4-amino-2-fluoro-benzamide (122 mg, 0.790 mmol) in dichloromethane (2 mL) and DIEA (272 µL, 1.56 mmol) was cooled to 0° C. A slurry of cold 2-fluoro-6-[4-(trifluoromethoxy)phenoxy]-3-(trifluoromethyl)benzoyl chloride (prepared as described in Example 15, Step 2, 314 mg, 0.780 mmol) in dichloromethane (2 mL) was added dropwise to the stirring amine solution. The reaction mixture was removed from ice bath after 10 min and stirred at room temperature for 2 hours. The solvent was evaporated under a stream of $N_2$ and the residue was purified by HPLC (1-99% acetonitrile/5 mM HCl) to provide N-(4-carbamoyl-3-fluoro-phenyl)-2-fluoro-6-[4-(trifluoromethoxy)phenoxy]-3-(trifluoromethyl)benzamide (298 mg, 74%). ESI-MS m/z calc. 520.07, found 521.0 (M+1)+; retention time (Method A): 2.56 minutes (1 minute run); retention time (Method B): 1.85 minutes (3 minute run); $^1$H NMR (400 MHz, DMSO-d6) δ 11.28 (s, 1H), 7.88 (t, J=8.7 Hz, 1H), 7.73 (d, J=8.5 Hz, 1H), 7.66 (dd, J=13.0, 2.0 Hz, 1H), 7.60 (s, 1H), 7.56 (s, 1H), 7.49 (dd, J=9.1, 1.0 Hz, 2H), 7.41 (dd, J=8.5, 2.0 Hz, 1H), 7.35 (d, J=9.1 Hz, 2H), 6.92 (d, J=8.8 Hz, 1H).

Step 2: N-(4-Carbamoyl-3-fluoro-phenyl)-2-methoxy-6-[4-(trifluoromethoxy)phenoxy]-3-(trifluoromethyl)benzamide (132)

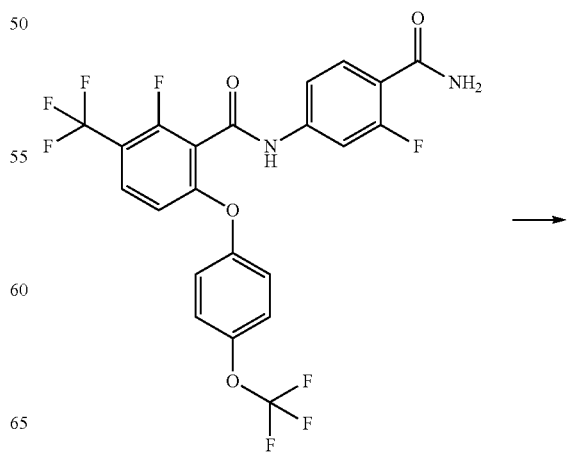

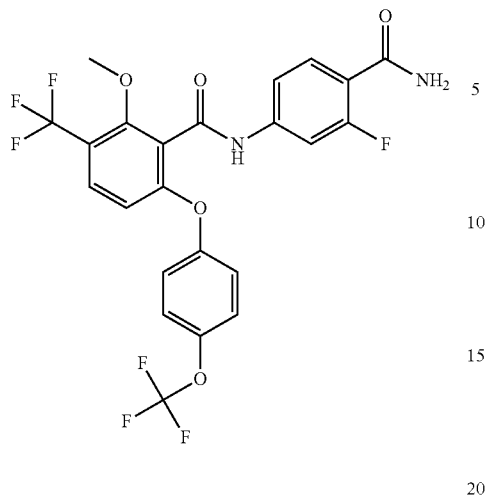

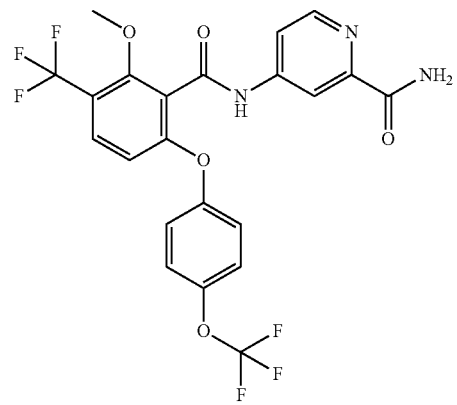

N-(4-Carbamoyl-3-fluoro-phenyl)-2-fluoro-6-[4-(trifluoromethoxy)phenoxy]-3-(trifluoromethyl)benzamide (65 mg, 0.12 mmol) was dissolved in a solution of sodium methoxide (1 mL of 0.5 M in methanol, 0.5 mmol) and heated at 80° C. for 16 hours. The reaction mixture was filtered and purified by HPLC (1-99% acetonitrile/5 mM HCl) to provide N-(4-carbamoyl-3-fluoro-phenyl)-2-methoxy-6-[4-(trifluoromethoxy)phenoxy]-3-(trifluoromethyl)benzamide (14.6 mg, 22%). ESI-MS m/z calc. 532.09, found 533.0 (M+1)+; retention time (Method C): 2.59 minutes (5 minute run). $^1$H NMR (400 MHz, DMSO-d6) δ 11.13 (s, 1H), 7.75 (d, J=8.9 Hz, 1H), 7.73-7.65 (m, 2H), 7.54 (d, J=16.9 Hz, 2H), 7.48-7.44 (m, 2H), 7.42 (dd, J=8.6, 2.0 Hz, 1H), 7.32-7.26 (m, 2H), 6.79 (d, J=8.8 Hz, 1H), 3.92 (s, 3H) ppm.

This compound was made in an analogous fashion to Example 96, Step 2, except employing 4-[[2-fluoro-6-[4-(trifluoromethoxy)phenoxy]-3-(trifluoromethyl)benzoyl]amino]pyridine-2-carboxamide 48. The yield of the desired product after purification was 8 mg (14%). ESI-MS m/z calc. 515.09, found 516.0 (M+1)+; retention time (Method B): 1.79 minutes (3 min run). $^1$H NMR (400 MHz, DMSO-d6) δ 11.37 (s, 1H), 8.54 (d, J=5.5 Hz, 1H), 8.34 (d, J=2.2 Hz, 1H), 8.11 (d, J=2.9 Hz, 1H), 7.82 (dd, J=5.5, 2.2 Hz, 1H), 7.77 (d, J=8.9 Hz, 1H), 7.67 (d, J=3.0 Hz, 1H), 7.54-7.42 (m, 2H), 7.35-7.26 (m, 2H), 6.79 (d, J=8.8 Hz, 1H), 3.92 (s, 3H) ppm.

Example 97

4-[[2-Methoxy-6-[4-(trifluoromethoxy)phenoxy]-3-(trifluoromethyl)benzoyl]amino]pyridine-2-carboxamide (91)

Example 98

N-(3-Carbamoyl-4-fluoro-phenyl)-3-cyclopropyl-2-fluoro-6-[4-(trifluoromethoxy)phenoxy]benzamide (71)

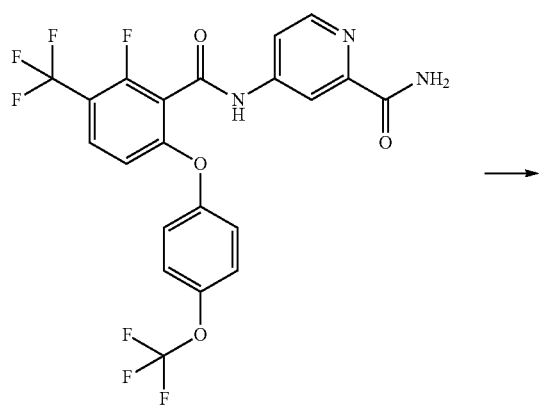

→

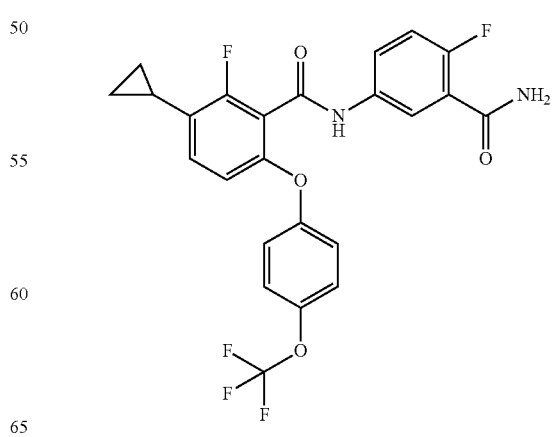

461

Step 1: Methyl 3-chloro-2-fluoro-6-[4-(trifluoromethoxy)phenoxy]benzoate

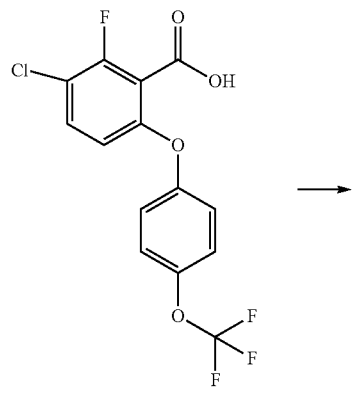

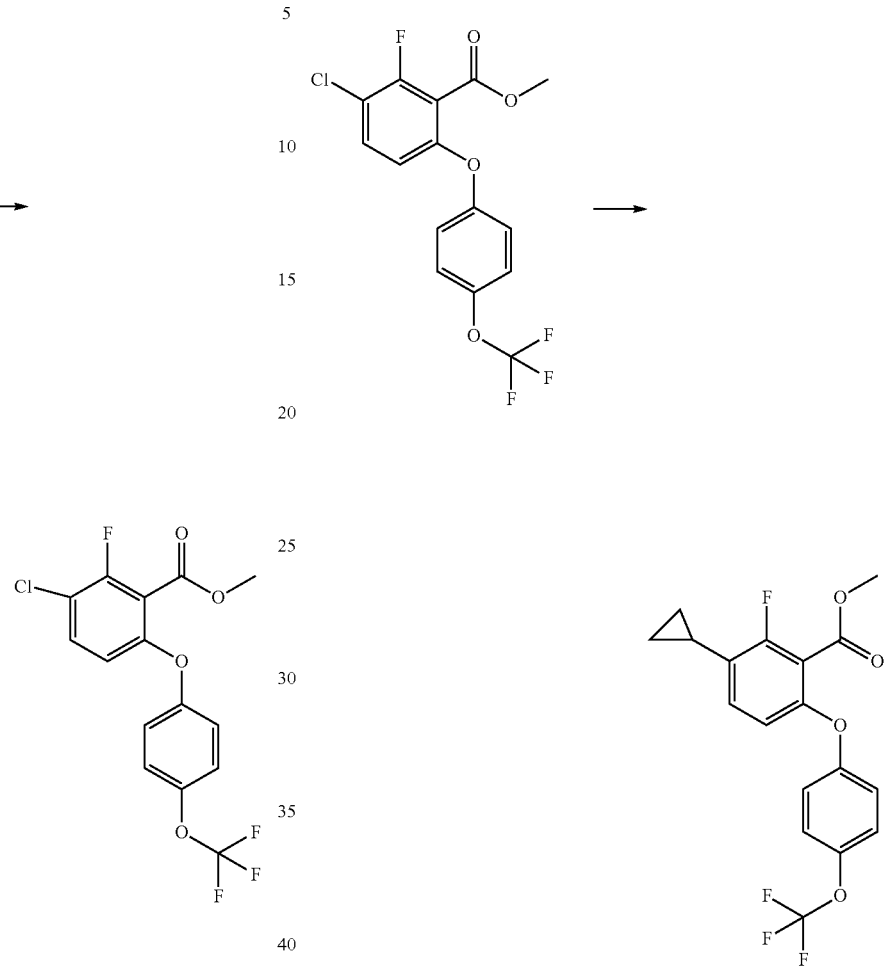

462

Step 2: Methyl 3-cyclopropyl-2-fluoro-6-[4-(trifluoromethoxy)phenoxy]benzoate

To a suspension of 3-chloro-2-fluoro-6-[4-(trifluoromethoxy)phenoxy]benzoic acid (prepared as described Example 88, Step 2, in 390 mg, 1.11 mmol) in dichloromethane (2.5 mL) and methanol (600 µL, 14.8 mmol) stirred under $N_2$ at 0° C. was added (trimethylsilyl)diazomethane (1 mL of 2 M in hexanes, 2.000 mmol) dropwise until a faint yellow color persisted. The mixture was stirred 10 minutes then several drops of acetic acid were added to quench excess reagent (turns colorless). The mixture was concentrated, dissolved in dichloromethane and washed with saturated aqueous $NaHCO_3$, dried over $MgSO_4$, filtered and concentrated in vacuo. Silica gel chromatography (0-5% ethyl acetate/hexanes) provided methyl 3-chloro-2-fluoro-6-[4-(trifluoromethoxy)phenoxy]benzoate (400 mg, 99%). ESI-MS m/z calc. 364.01, found 365.0 (M+1)+; retention time (Method B): 2.12 minutes (3 minute run). $^1$H NMR (400 MHz, DMSO-d6) δ 7.76 (t, J=8.8 Hz, 1H), 7.45-7.39 (m, 2H), 7.22-7.14 (m, 2H), 6.96 (dd, J=9.0, 1.6 Hz, 1H), 3.81 (s, 3H) ppm.

To a vial charged with methyl 3-chloro-2-fluoro-6-[4-(trifluoromethoxy)phenoxy]benzoate (400 mg, 1.10 mmol) and bis(tri-tert-butylphosphine)palladium (0) (340 mg, 0.665 mmol) under an atmosphere of $N_2$ at 0° C. was added cyclopropylzinc bromide (635 mL of 0.5 M in THF, 318 mmol). The reaction mixture was warmed to room temperature and stirred at 60° C. for 12 hours. The reaction was diluted with 1N HCl and extracted with dichloromethane. The organic layer was dried over $MgSO_4$, filtered and concentrated in vacuo. Silica gel chromatography (0-4% ethyl acetate/hexanes) provided methyl 3-cyclopropyl-2-fluoro-6-[4-(trifluoromethoxy)phenoxy]benzoate (336 mg, 83%). ESI-MS m/z calc. 370.08, found 371.2 (M+1)+; retention time (Method B): 2.2 minutes (3 minute run). $^1$H NMR (400 MHz, DMSO-d6) δ 7.43-7.35 (m, 2H), 7.18 (t, J=8.7 Hz, 1H), 7.13-7.06 (m, 2H), 6.83 (dd, J=8.6, 1.2 Hz, 1H), 3.76 (s, 3H), 2.03 (ddd, J=13.6, 8.6, 5.2 Hz, 1H), 1.07-0.91 (m, 2H), 0.83-0.61 (m, 2H) ppm.

Step 3: 3-Cyclopropyl-2-fluoro-6-[4-(trifluoromethoxy)phenoxy]benzoic acid

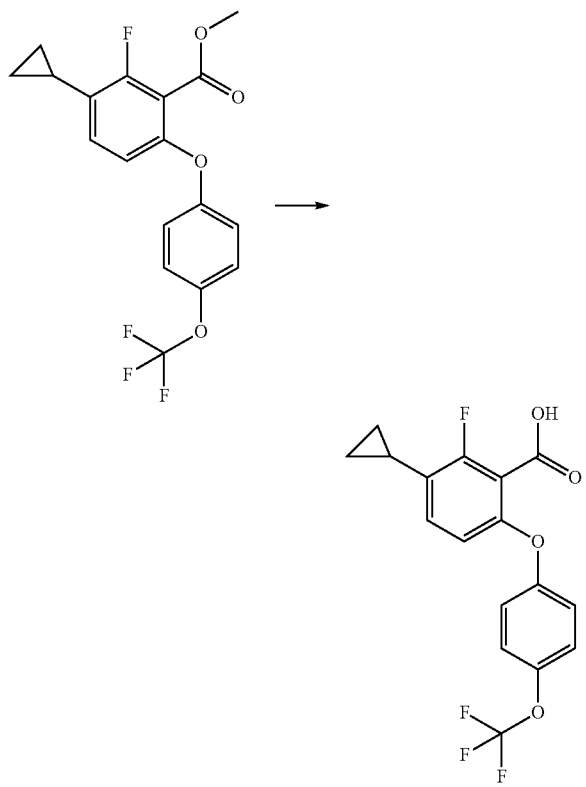

To a solution of methyl 3-cyclopropyl-2-fluoro-6-[4-(trifluoromethoxy)phenoxy]benzoate (360 mg, 0.972 mmol) in methanol (5 mL) and THF (5 mL) was added aqueous NaOH (5 mL of 3 M, 15 mmol) followed by solid NaOH (500 mg, 12.5 mmol). The reaction mixture was stirred at room temperature for 16 hours, then cooled to 0° C. and quenched with carefully with 6 M HCl. The suspension was extracted with ethyl acetate and the organic layer was dried over MgSO$_4$, filtered and concentrated in vacuo to obtain 3-cyclopropyl-2-fluoro-6-[4-(trifluoromethoxy)phenoxy]benzoic acid (329 mg, 95%). ESI-MS m/z calc. 356.07, found 357.1 (M+1)+; retention time (Method A): 0.76 minutes (1 minute run).

Step 4: 3-Cyclopropyl-2-fluoro-6-[4-(trifluoromethoxy)phenoxy]benzoyl chloride

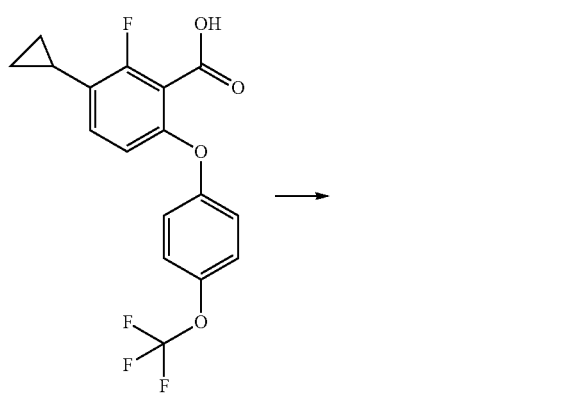

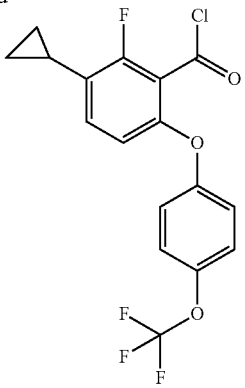

To a solution of 3-cyclopropyl-2-fluoro-6-[4-(trifluoromethoxy)phenoxy]benzoic acid (235 mg, 0.660 mmol) and DMF (30 μL, 0.39 mmol) in dichloromethane (2 mL) at 0° C. was added oxalyl chloride (100 μL, 1.15 mmol) dropwise. The mixture was stirred at room temperature for 30 minutes. Conversion was monitored by UPLC via test for morpholine adduct formation. The solvent was evaporated in vacuo to provide 3-cyclopropyl-2-fluoro-6-[4-(trifluoromethoxy)phenoxy]benzoyl chloride.

Step 5: N-(3-carbamoyl-4-fluoro-phenyl)-3-cyclopropyl-2-fluoro-6-[4-(trifluoromethoxy)phenoxy]benzamide (71)

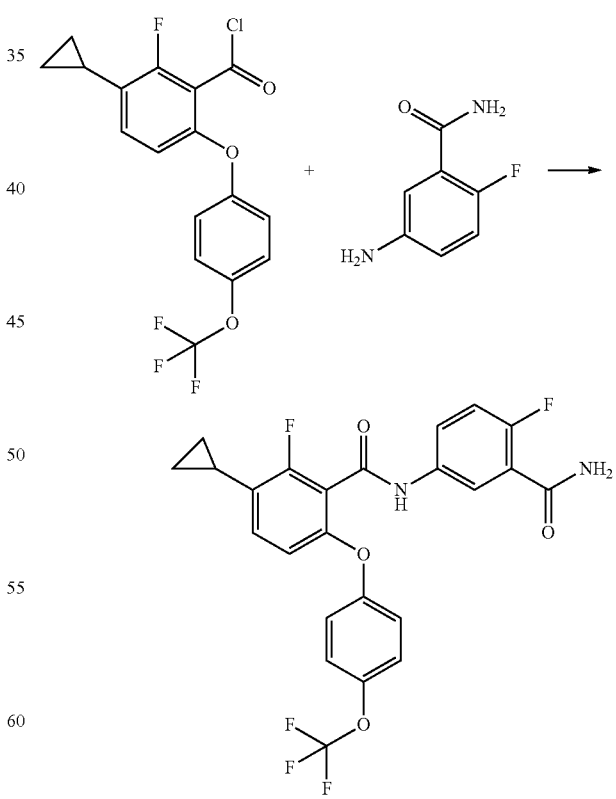

A solution of 5-amino-2-fluoro-benzamide (50 mg, 0.32 mmol) and DIEA (200 μL, 1.15 mmol) in THF (2 mL) was cooled to 0° C. and treated with a suspension of 3-cyclopropyl-2-fluoro-6-[4-(trifluoromethoxy)phenoxy]benzoyl chloride (120 mg, 0.3202 mmol) in THF (1 mL)/dichloromethane (1 mL). The reaction mixture was warmed to room temperature and stirred for 16 hours. The reaction was diluted with water and extracted with dichloromethane. The organic layer was washed with 1 M HCl, dried over MgSO$_4$, filtered and concentrated in vacuo. Silica gel chromatography (0-60% ethyl acetate/hexanes) provided N-(3-carbamoyl-4-fluoro-phenyl)-3-cyclopropyl-2-fluoro-6-[4-(trifluoromethoxy)phenoxy]benzamide (24 mg, 14%). ESI-MS m/z calc. 492.11, found 493.1 (M+1)+; retention time (Method B): 1.83 minutes (3 minute run). $^1$H NMR (500 MHz, DMSO-d6) δ 10.83 (s, 1H), 7.94 (dd, J=6.6, 2.8 Hz, 1H), 7.74-7.62 (m, 3H), 7.36 (d, J=8.5 Hz, 2H), 7.23 (t, J=9.5 Hz, 1H), 7.15-7.05 (m, 3H), 6.76 (d, J=8.7 Hz, 1H), 2.05 (tt, J=8.9, 5.2 Hz, 1H), 1.08-0.92 (m, 2H), 0.72 (p, J=4.9, 4.4 Hz, 2H) ppm.

Example 99

4-[[3-Cyclopropyl-2-fluoro-6-[4-(trifluoromethoxy)phenoxy]benzoyl]amino]pyridine-2-carboxamide (72)

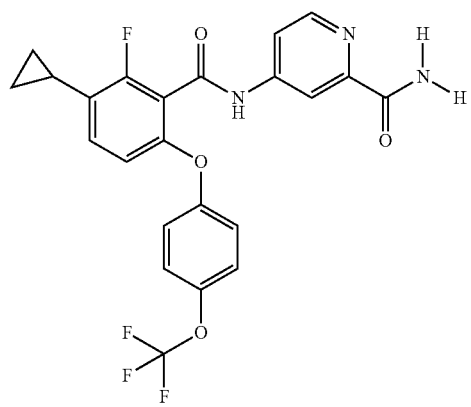 [SMILES: NC(=O)c1cc(NC(=O)c2c(Oc3ccc(OC(F)(F)F)cc3)ccc(C3CC3)c2F)ccn1]

This compound was made in an analogous fashion to Example 98, except employing 4-aminopyridine-2-carboxamide in the amide formation step (Step 5). The yield of the desired product after purification was 7 mg (4%). ESI-MS m/z calc. 475.12, found 476.2 (M+1)+; retention time (Method B): 1.79 minutes (3 minute run). $^1$H NMR (500 MHz, DMSO-d6) δ 11.27 (s, 1H), 8.50 (d, J=5.5 Hz, 1H), 8.27 (d, J=2.2 Hz, 1H), 8.08 (d, J=2.8 Hz, 1H), 7.76 (dd, J=5.6, 2.2 Hz, 1H), 7.64 (d, J=2.9 Hz, 1H), 7.35 (d, J=8.6 Hz, 2H), 7.20-7.02 (m, 3H), 6.78 (d, J=8.7 Hz, 1H), 2.06 (tt, J=8.7, 5.1 Hz, 1H), 1.00 (h, J=4.4 Hz, 2H), 0.78-0.61 (m, 2H) ppm.

Example 100

N-(3-Carbamoyl-4-fluoro-phenyl)-6-cyclopropyl-4-[2-methoxy-4-(trifluoromethoxy)phenoxy]pyridine-3-carboxamide (43)

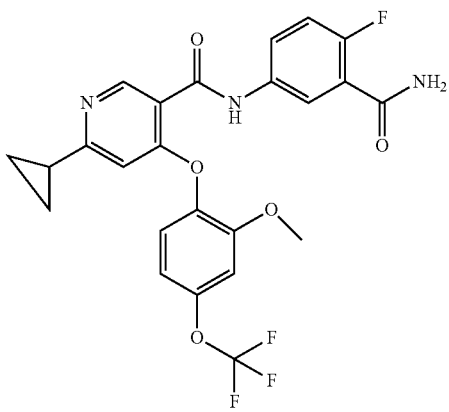 [SMILES: COc1cc(OC(F)(F)F)ccc1Oc1cc(C2CC2)ncc1C(=O)Nc1ccc(F)c(C(N)=O)c1]

Step 1: Methyl 6-cyclopropyl-4-[2-methoxy-4-(trifluoromethoxy)phenoxy]pyridine-3-carboxylate

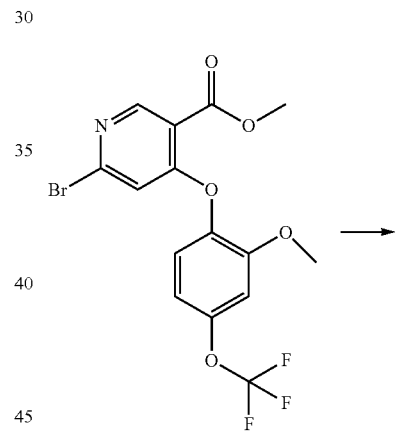

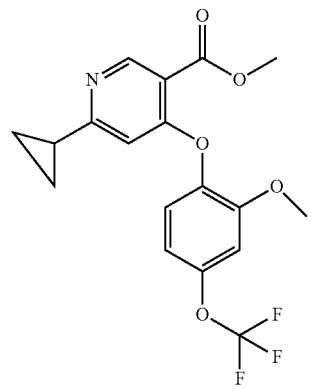

A two neck round bottom flask equipped with addition funnel was charged with methyl 6-bromo-4-[2-methoxy-4-(trifluoromethoxy)phenoxy]pyridine-3-carboxylate (prepared as described in Example 65, Step 1, 10.0 g, 23.7 mmol) and bis(tri-t-butylphosphine)palladium (0) (1.98 g, 3.87 mmol), sealed with a septum and placed under a N$_2$ atmosphere, and THF (24 mL) was added, resulting in a slurry. The reaction mixture was cooled to 0° C. and the addition funnel was charged with cyclopropylzinc bromide (57 mL of 0.5 M in THF, 28.5 mmol) as a solution in THF, which was then added dropwise to the reaction mixture over 30 minutes. The reaction was stirred for an additional 30 minutes, then diluted with saturated aqueous NH₄Cl solution and extracted with ethyl acetate. The layers were separated and the organic layer was dried over Na₂SO₄, filtered and concentrated in vacuo. Silica gel chromatography (0-10% ethyl acetate/hexanes) provided methyl 6-cyclopropyl-4-[2-methoxy-4-(trifluoromethoxy)phenoxy]pyridine-3-carboxylate (7.3 g, 80%) and an off white solid after drying under high vacuum. ESI-MS m/z calc. 383.10, found 384.1 (M+1)+; retention time (Method A): 0.63 minutes (1 minute). ¹H NMR (500 MHz, DMSO-d6) δ 8.72 (s, 1H), 7.30 (d, J=8.7 Hz, 1H), 7.25 (d, J=2.7 Hz, 1H), 7.02 (ddd, J=8.9, 2.7, 1.3 Hz, 1H), 6.54 (s, 1H), 3.80 (s, 3H), 3.78 (s, 3H), 2.01 (tt, J=7.9, 4.9 Hz, 1H), 0.91 (tt, J=8.0, 2.9 Hz, 4H) ppm.

Step 2: 6-Cyclopropyl-4-[2-methoxy-4-(trifluoromethoxy)phenoxy]pyridine-3-carboxylic acid Methyl 6-cyclopropyl-4-[2-methoxy-4-(trifluoromethoxy)phenoxy]pyridine-3-carboxylate (7.30 g, 19.0 mmol) was dissolved in methanol (110 mL) and treated with a solution of NaOH (11.4 g, 285 mmol) in water (37 mL). The reaction mixture was stirred at room temperature for 1 hour. The solvents were removed in vacuo and the resulting slurry was dissolved in water (100 mL). The solution was cooled to 0° C. and treated dropwise with aqueous 6 M HCl until pH2. The resulting precipitate was collected by vacuum filtration. The filter cake was washed with water and dried under vacuum for 16 hours to provide 6-cyclopropyl-4-[2-methoxy-4-(trifluoromethoxy)phenoxy]pyridine-3-carboxylic acid (7.0 g, 100%) as a white powder. ESI-MS m/z calc. 369.08, found 370.1 (M+1)+; retention time (Method A): 0.51 minutes (1 minute run). ¹H NMR (400 MHz, DMSO-d6) δ 8.73 (s, 1H), 7.30 (d, J=8.8 Hz, 1H), 7.28 (d, J=2.8 Hz, 1H), 7.04 (ddq, J=8.7, 2.3, 1.2 Hz, 1H), 6.55 (s, 1H), 3.80 (s, 3H), 2.06 (p, J=6.4 Hz, 1H), 0.95 (d, J=6.4 Hz, 4H) ppm.

Step 3: 6-Cyclopropyl-4-[2-methoxy-4-(trifluoromethoxy)phenoxy]pyridine-3-carbonyl chloride

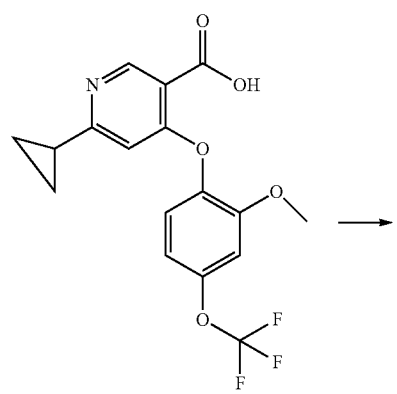

To a solution of 6-cyclopropyl-4-[2-methoxy-4-(trifluoromethoxy)phenoxy]pyridine-3-carboxylic acid (2.1 g, 5.7 mmol) and DMF (400 µL, 5.17 mmol) in dichloromethane (20 mL) at 0° C. was added oxalyl chloride (500 µL, 5.73 mmol) dropwise. The mixture was stirred at room temperature for 30 minutes. Conversion was monitored by UPLC via test for morpholine adduct formation. The reaction was concentrated in vacuo to provide 6-cyclopropyl-4-[2-methoxy-4-(trifluoromethoxy)phenoxy]pyridine-3-carbonyl chloride.

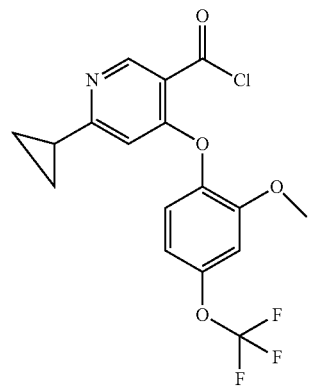

Step 4: N-(3-Carbamoyl-4-fluoro-phenyl)-6-cyclopropyl-4-[2-methoxy-4-(trifluoromethoxy)phenoxy]pyridine-3-carboxamide (43)

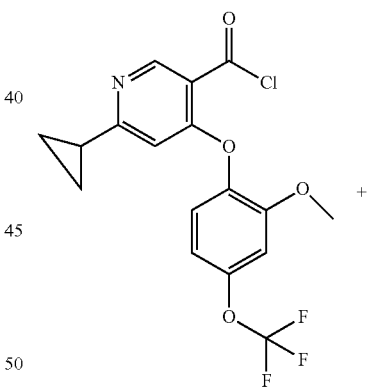

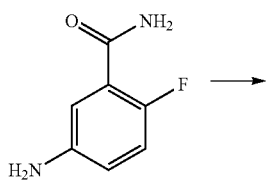

469

-continued

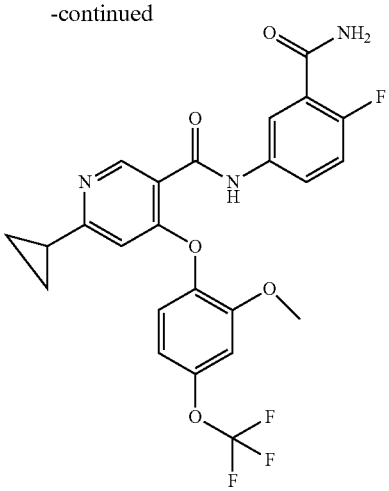

To a solution of 5-amino-2-fluoro-benzamide (0.88 g, 5.7 mmol) and DIEA (3.0 mL, 17 mmol) in THF (20 mL) and dichloromethane (10 mL) at 0° C. was added a solution of 6-cyclopropyl-4-[2-methoxy-4-(trifluoromethoxy)phenoxy] pyridine-3-carbonyl chloride (2.1 g, 5.4 mmol) in dichloromethane. The reaction mixture was removed from the ice bath and stirred at room temperature for 1 hour. The reaction mixture was diluted with water and extracted with dichloromethane. The organic layer was concentrated in vacuo and the resulting solid was purified using silica gel chromatography (0-60% ethyl acetate/hexanes) to provide N-(3-carbamoyl-4-fluoro-phenyl)-6-cyclopropyl-4-[2-methoxy-4-(trifluoromethoxy)phenoxy]pyridine-3-carboxamide (1.1 g, 40%). ESI-MS m/z calc. 505.13, found 506.2 (M+1)+; retention time (Method B): 1.4 minutes (3 minute run). $^1$H NMR (400 MHz, DMSO-d6) δ 10.41 (s, 1H), 8.55 (s, 1H), 7.99 (dd, J=6.5, 2.8 Hz, 1H), 7.87-7.76 (m, 1H), 7.69 (d, J=14.5 Hz, 2H), 7.45 (d, J=8.8 Hz, 1H), 7.32-7.18 (m, 2H), 7.07 (ddd, J=8.8, 2.8, 1.3 Hz, 1H), 6.59 (s, 1H), 3.80 (s, 3H), 2.07 (p, J=6.7 Hz, 1H), 0.99-0.87 (m, 4H) ppm.

Example 101

N-(2-Carbamoyl-4-pyridyl)-6-cyclopropyl-4-[2-methoxy-4-(trifluoromethoxy)phenoxy]pyridine-3-carboxamide (372)

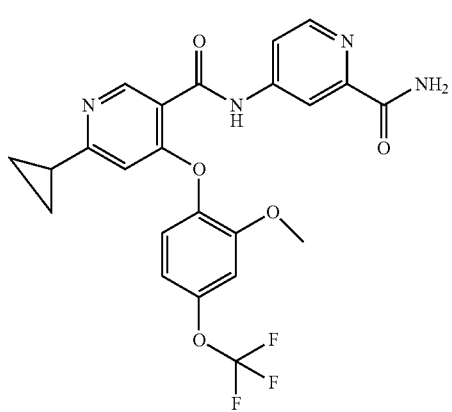 [SMILES: COc1cc(OC(F)(F)F)ccc1Oc1cc(C2CC2)ncc1C(=O)Nc1ccnc(C(N)=O)c1]

470

This compound was made in an analogous fashion to Example 100 except employing 4-aminopyridine-2-carboxamide in the amide formation step (Step 4). The yield of the desired product after purification was 296 mg (21%). ESI-MS m/z calc. 488.13, found 489.2 (M+1)+; retention time (Method B): 1.39 minutes (3 minute run). $^1$H NMR (400 MHz, DMSO-d6) δ 10.84 (s, 1H), 8.58 (s, 1H), 8.52 (d, J=5.5 Hz, 1H), 8.31 (d, J=2.1 Hz, 1H), 8.09 (d, J=2.9 Hz, 1H), 7.90 (dd, J=5.5, 2.2 Hz, 1H), 7.64 (d, J=2.9 Hz, 1H), 7.46 (d, J=8.8 Hz, 1H), 7.26 (d, J=2.7 Hz, 1H), 7.07 (ddt, J=8.7, 2.4, 1.2 Hz, 1H), 6.62 (s, 1H), 3.79 (s, 3H), 2.13-2.01 (m, 1H), 0.97-0.91 (m, 4H) ppm.

Example 102

N-(2-Carbamoyl-4-pyridyl)-6-(2,2-difluorocyclopropyl)-4-[2-methoxy-4-(trifluoromethoxy)phenoxy] pyridine-3-carboxamide (107)

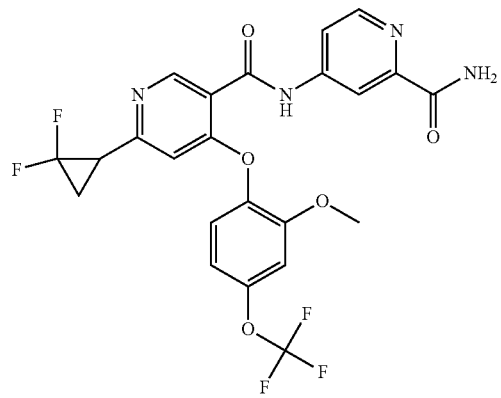 [SMILES: COc1cc(OC(F)(F)F)ccc1Oc1cc(C2CC2(F)F)ncc1C(=O)Nc1ccnc(C(N)=O)c1]

Step 1: Methyl 4-[2-methoxy-4-(trifluoromethoxy) phenoxy]-6-vinyl-pyridine-3-carboxylate

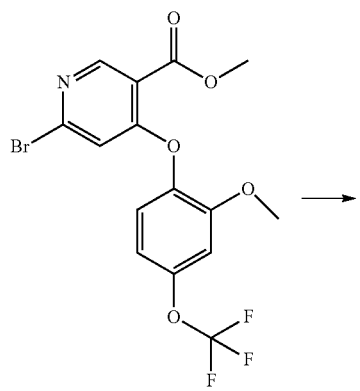

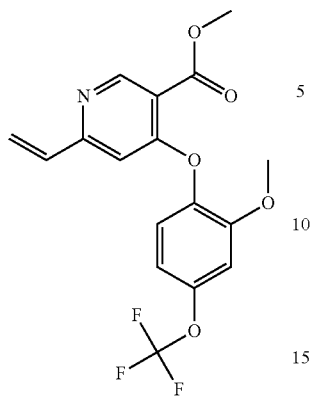

Methyl 6-bromo-4-[2-methoxy-4-(trifluoromethoxy)phenoxy]pyridine-3-carboxylate (3.0 g, 7.1 mmol) was dissolved in acetonitrile (30 mL) and degassed with N₂ for 10 minutes. To the solution was added vinylboronic acid pinacol ester (2.8 g, 18 mmol), aqueous K₂CO₃ (10.7 mL of 2 M, 21.3 mmol) and Pd(dppf)Cl₂·DCM (0.260 g, 0.355 mmol). The reaction was heated under N₂ atmosphere at 80° C. for 40 minutes. The reaction was diluted with ethyl acetate (100 mL) and washed with aqueous NaHCO₃ solution, water, 10% citric acid and brine. The organic layer was dried over Na₂SO₄, filtered and concentrated in vacuo. Silica gel chromatography (0-40% ethyl acetate/hexanes) provided 4-[2-methoxy-4-(trifluoromethoxy)phenoxy]-6-vinyl-pyridine-3-carboxylate (2.8 g, 85%). ESI-MS m/z calc. 369.08, found 370.3 (M+1)+; retention time (Method B): 1.5 minutes (3 minute run). ¹H NMR (400 MHz, DMF-d7) δ 8.90 (s, 1H), 7.36 (d, J=8.8 Hz, 1H), 7.30 (d, J=2.7 Hz, 1H), 6.88-6.71 (m, 1H), 6.68 (s, 1H), 6.31 (dd, J=17.3, 1.7 Hz, 1H), 5.55 (dd, J=10.6, 1.7 Hz, 1H), 3.87 (s, 3H), 3.80 (s, 3H) ppm.

Step 2: Methyl 6-(2,2-difluorocyclopropyl)-4-[2-methoxy-4-(trifluoromethoxy)phenoxy]pyridine-3-carboxylate

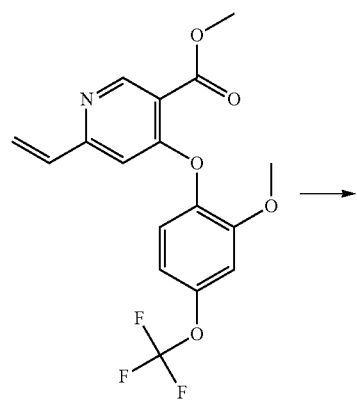

A solution of methyl 4-[2-methoxy-4-(trifluoromethoxy)phenoxy]-6-vinyl-pyridine-3-carboxylate (235 mg, 0.636 mmol) in THF (2.4 mL) was treated with sodium iodide (48 mg, 0.32 mmol) and trimethyl(trifluoromethyl)silane (362 mg, 2.55 mmol) and heated at 65° C. Additional sodium iodide (24 mg, 0.16 mmol) and trimethyl(trifluoromethyl)silane (362 mg, 2.55 mmol) were added after 1 hour, and the reaction again charged with trimethyl(trifluoromethyl)silane (362 mg, 2.55 mmol) added after 2 hours. The reaction was stirred for 1 additional hour, then cooled and partitioned between ethyl acetate and water. The layers were separated and the aqueous layer was extracted with additional ethyl acetate. The combined organic layers were washed with brine, dried over MgSO₄ and concentrated in vacuo. Silica gel chromatography (0-100% ethyl acetate/hexanes) provided 6-(2,2-difluorocyclopropyl)-4-[2-methoxy-4-(trifluoromethoxy)phenoxy]pyridine-3-carboxylate (82 mg, 28%) as a yellow solid. ESI-MS m/z calc. 419.08, found 420.2 (M+1)+; retention time (Method A): 0.74 minutes (1 minute run).

Step 3: 6-(2,2-Difluorocyclopropyl)-4-[2-methoxy-4-(trifluoromethoxy)phenoxy]pyridine-3-carboxylic acid

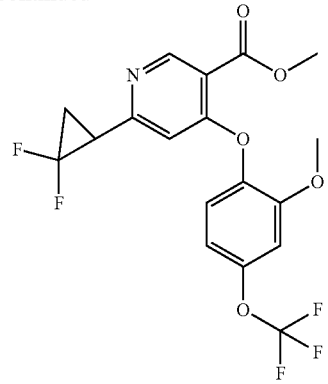

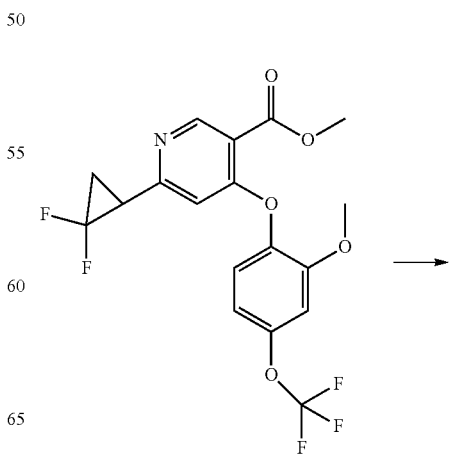

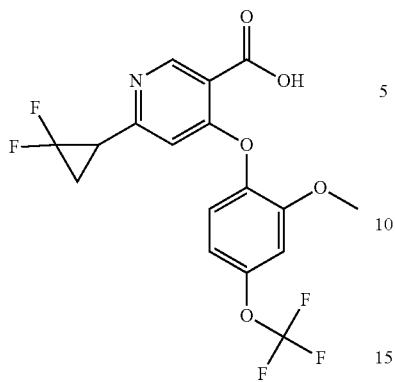

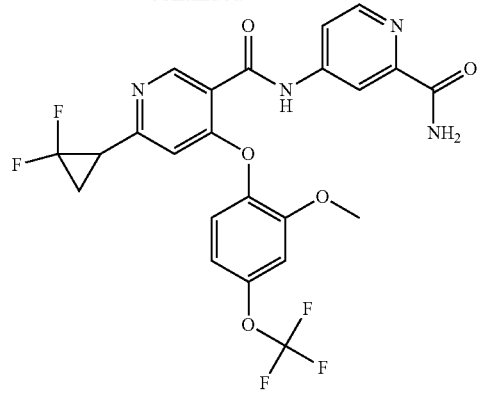

To a solution of methyl 6-(2,2-difluorocyclopropyl)-4-[2-methoxy-4-(trifluoromethoxy)phenoxy]pyridine-3-carboxylate (82 mg, 0.18 mmol) in methanol (738 µL) was added sodium hydroxide (574 µL of 3 M, 1.72 mmol), followed by THF (1 mL). The reaction mixture was stirred at room temperature for 2 hours, then cooled to 0° C. and quenched dropwise with 6N HCl. The mixture was extracted with ethyl acetate and the organic layer was dried over MgSO₄, filtered and concentrated in vacuo to obtain 6-(2,2-difluorocyclopropyl)-4-[2-methoxy-4-(trifluoromethoxy)phenoxy]pyridine-3-carboxylic acid (60 mg, 84%). ESI-MS m/z calc. 405.06, found 406.1 (M+1)+; retention time (Method A): 0.52 minutes (1 minute run).

Step 4: N-(2-Carbamoyl-4-pyridyl)-6-(2,2-difluorocyclopropyl)-4-[2-methoxy-4-(trifluoromethoxy)phenoxy]pyridine-3-carboxamide (107)

A vial was charged with 6-(2,2-difluorocyclopropyl)-4-[2-methoxy-4-(trifluoromethoxy)phenoxy]pyridine-3-carboxylic acid (55 mg, 0.14 mmol), 4-[(Z)-[(tert-butylamino)-phenylsulfanyl-methylene]amino]pyridine-2-carboxamide (49 mg, 0.15 mmol), iron (III) acetylacetonate (3 mg, 0.008 mmol) in 2-propanol (550 µL) and heated at 83° C. under air atmosphere for 20 hours. The reaction mixture was concentrated in vacuo and purified using silica gel chromatography (0-60% ethyl acetate/hexanes) to obtain N-(2-carbamoyl-4-pyridyl)-6-(2,2-difluorocyclopropyl)-4-[2-methoxy-4-(trifluoromethoxy)phenoxy]pyridine-3-carboxamide (4 mg, 5%). ESI-MS m/z calc. 524.11, found 525.1 (M+1)+; retention time (Method B): 1.54 minutes (3 minute run). ¹H NMR (400 MHz, DMSO-d6) δ 11.01 (s, 1H), 8.68 (s, 1H), 8.54 (d, J=5.5 Hz, 1H), 8.33 (d, J=2.2 Hz, 1H), 8.11 (d, J=2.9 Hz, 1H), 7.90 (dd, J=5.5, 2.2 Hz, 1H), 7.65 (d, J=2.9 Hz, 1H), 7.47 (d, J=8.8 Hz, 1H), 7.27 (d, J=2.8 Hz, 1H), 7.08 (ddd, J=8.9, 2.8, 1.3 Hz, 1H), 6.82 (s, 1H), 3.79 (s, 3H), 3.31-3.22 (m, 1H), 2.30 (dq, J=13.4, 7.3, 6.7 Hz, 1H), 2.08-1.87 (m, 1H) ppm. ¹⁹F NMR (376 MHz, DMSO-d6) δ −56.80, −122.59, −122.99, −141.98, −142.36 ppm.

Example 103

N-(3-Carbamoyl-4-fluoro-phenyl)-6-(2,2-difluorocyclopropyl)-4-[2-methoxy-4-(trifluoromethoxy)phenoxy]pyridine-3-carboxamide (108)

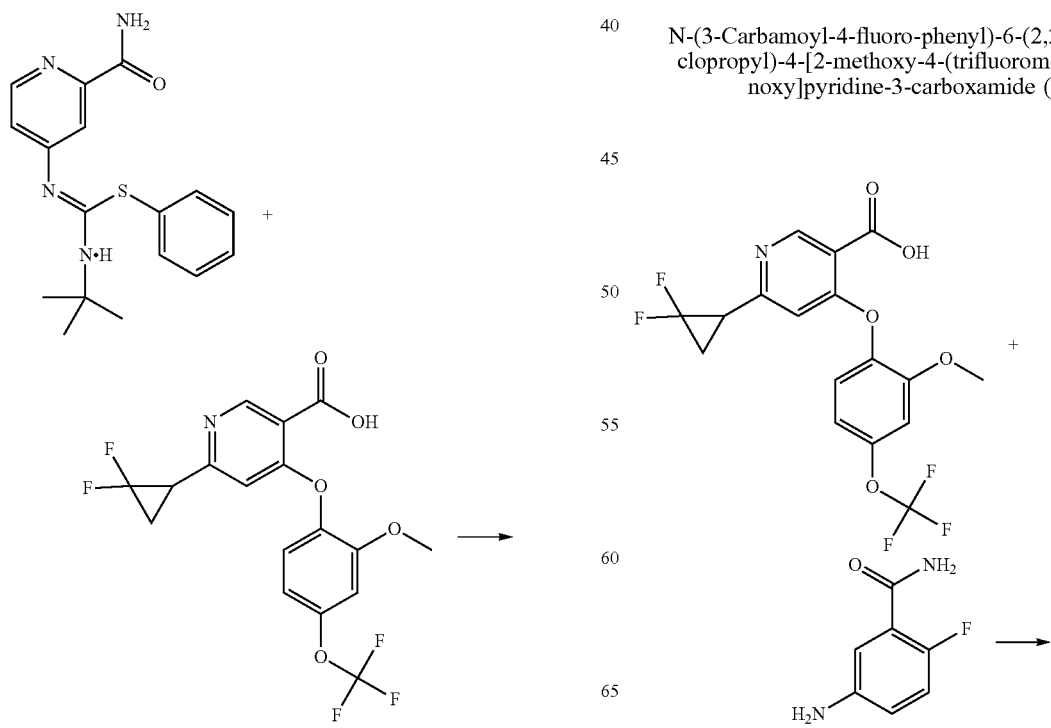

475
-continued

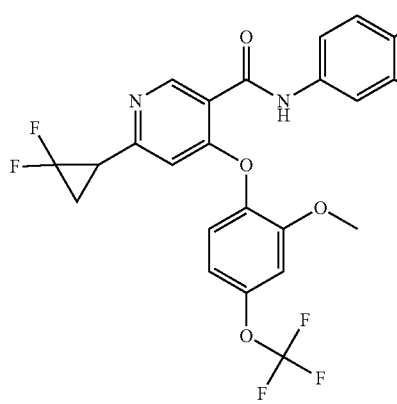

A solution of 5-amino-2-fluoro-benzamide (7.0 mg, 0.04 mmol), 6-(2,2-difluorocyclopropyl)-4-[2-methoxy-4-(trifluoromethoxy)phenoxy]pyridine-3-carboxylic acid (15 mg, 0.04 mmol) and HATU (15 mg, 0.04 mmol) in DMF (225 µL) was treated with triethylamine (16 µL, 0.11 mmol) and stirred at room temperature for 2 hours. The reaction mixture was diluted with DMSO (1 mL) and purified by HPLC (1-99% acetonitrile/5 mM HCl) to obtain N-(3-carbamoyl-4-fluoro-phenyl)-6-(2,2-difluorocyclopropyl)-4-[2-methoxy-4-(trifluoromethoxy)phenoxy]pyridine-3-carboxamide (5 mg, 24%). ESI-MS m/z calc. 541.11, found 542.1 (M+1)+; retention time (Method B): 1.56 minutes (3 minute run).

Example 104

N-(3-Carbamoyl-4-fluoro-phenyl)-3-[2-methoxy-4-(trifluoromethoxy)phenoxy]-5-(trifluoromethyl)pyridine-2-carboxamide (32)

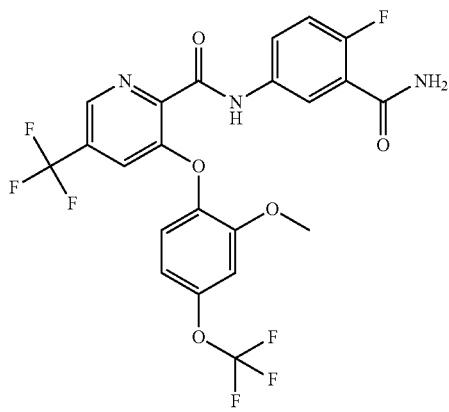

476

Step 1: 3-[2-Methoxy-4-(trifluoromethoxy)phenoxy]-5-(trifluoromethyl)pyridine-2-carboxylic acid

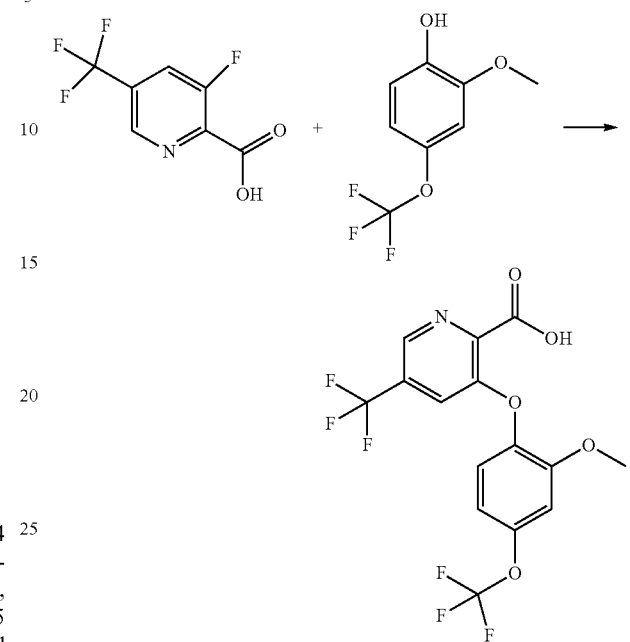

To 3-fluoro-5-(trifluoromethyl)pyridine-2-carboxylic acid (1.40 g, 6.70 mmol) in DMF (14 mL) was added 2-methoxy-4-(trifluoromethoxy)phenol (1.39 g, 6.69 mmol) and Cs$_2$CO$_3$ (6.54 g, 20.1 mmol). The reaction was stirred at 90° C. for 72 hours. The reaction was filtered through a pad of Celite and the filtrate was partitioned between water and ethyl acetate. The organic layer was washed with water, aqueous NaHCO$_3$ and brine, dried over Na$_2$SO$_4$, filtered and concentrated in vacuo. Silica gel chromatography (10-100% ethyl acetate/hexanes) provided 3-[2-methoxy-4-(trifluoromethoxy)phenoxy]-5-(trifluoromethyl)pyridine-2-carboxylic acid (1.80 g, 68%) as a white solid. ESI-MS m/z calc. 397.04, found 398.2 (M+1)+; retention time (Method A): 0.61 minutes (1 minute run).

Step 2: 3-[2-Methoxy-4-(trifluoromethoxy)phenoxy]-5-(trifluoromethyl)pyridine-2-carbonyl chloride

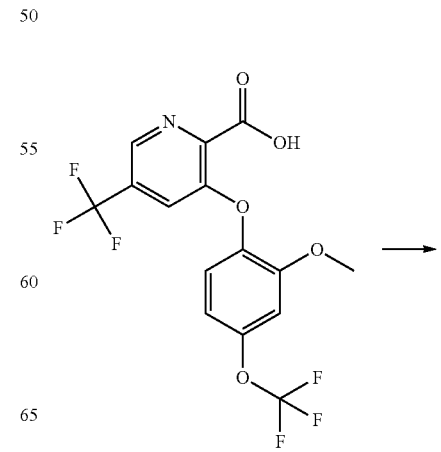

477
-continued

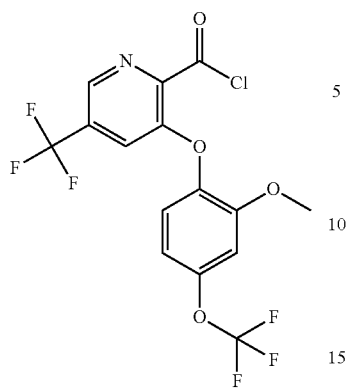

478
-continued

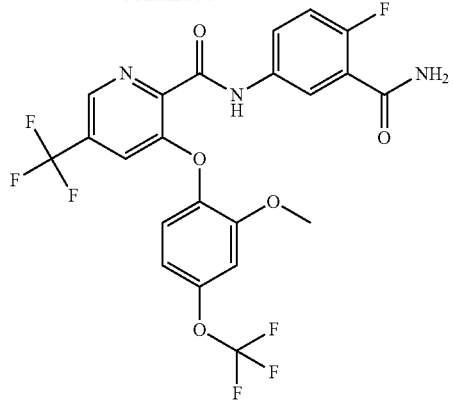 [SMILES: COc1cc(OC(F)(F)F)ccc1Oc1cc(C(F)(F)F)cnc1C(=O)Nc1ccc(F)c(C(N)=O)c1]

To a solution of 3-[2-methoxy-4-(trifluoromethoxy)phenoxy]-5-(trifluoromethyl)pyridine-2-carboxylic acid (600 mg, 1.51 mmol) and DMF (12 µL, 0.15 mmol) in dichloromethane (9 mL) at 0° C. was added oxalyl chloride (0.50 mL, 5.7 mmol) dropwise. The mixture was heated to 50° C. for 10 minutes. Conversion was monitored by UPLC via test for the morpholine adduct. The reaction mixture was concentrated, then evaporated with dichloromethane (3×50 mL) to provide 3-[2-methoxy-4-(trifluoromethoxy)phenoxy]-5-(trifluoromethyl)pyridine-2-carbonyl chloride (625 mg, 100%).

Step 3: N-(3-Carbamoyl-4-fluoro-phenyl)-3-[2-methoxy-4-(trifluoromethoxy)phenoxy]-5-(trifluoromethyl)pyridine-2-carboxamide (32)

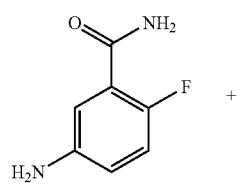 +

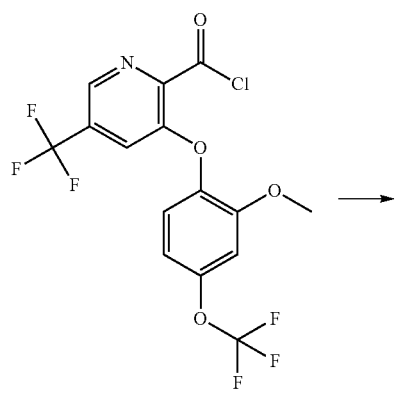 →

5-amino-2-fluoro-benzamide (19 mg, 0.12 mmol) was dissolved in dichloromethane (1 mL) and DIEA (63 µL, 0.36 mmol) and treated with a solution of 3-[2-methoxy-4-(trifluoromethoxy)phenoxy]-5-(trifluoromethyl)pyridine-2-carbonyl chloride (50 mg, 0.12 mmol) in dichloromethane (1 mL). The reaction was stirred for 30 minutes then concentrated in vacuo. The residue was dissolved in DMSO (1 mL) and treated with water to afford a precipitate. The precipitate was filtered, then triturated and filtered sequentially with acetonitrile and diethyl ether. The resulting solid was dried under vacuum to provide N-(3-carbamoyl-4-fluoro-phenyl)-3-[2-methoxy-4-(trifluoromethoxy)phenoxy]-5-(trifluoromethyl)pyridine-2-carboxamide (22 mg, 34%). ESI-MS m/z calc. 533.08, found 534.2 (M+1)+; retention time (Method B): 1.71 minutes (3 minute run). $^1$H NMR (400 MHz, DMSO-d6) δ 10.90 (s, 1H), 8.82 (dd, J=1.9, 0.9 Hz, 1H), 8.05 (dd, J=6.5, 2.8 Hz, 1H), 7.81 (ddd, J=8.9, 4.5, 2.8 Hz, 1H), 7.72 (s, 1H), 7.68 (s, 1H), 7.62 (d, J=1.8 Hz, 1H), 7.28 (dt, J=8.9, 5.1 Hz, 2H), 7.23 (d, J=2.7 Hz, 1H), 7.01 (ddd, J=8.9, 2.7, 1.3 Hz, 1H), 3.78 (s, 3H) ppm.

Example 105

N-(3-Carbamoylphenyl)-3-[2-methoxy-4-(trifluoromethoxy)phenoxy]-5-(trifluoromethyl)pyridine-2-carboxamide (31)

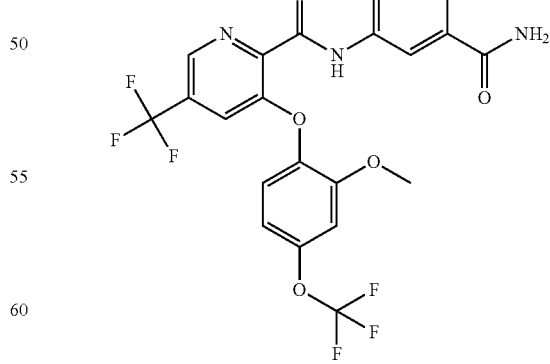

This compound was made in an analogous fashion to Example 104 except employing 3-aminobenzamide in the amide formation step (Step 3). The yield of the desired product after purification was 18 mg (29%). ESI-MS m/z calc. 515.09, found 516.2 (M+1)+; retention time (Method B): 0.67 minutes (3 minute run). ¹H NMR (400 MHz, DMSO-d6) δ 10.85 (s, 1H), 8.82 (dd, J=1.8, 0.9 Hz, 1H), 8.21 (t, J=1.9 Hz, 1H), 7.97 (s, 1H), 7.83 (ddd, J=8.0, 2.2, 1.0 Hz, 1H), 7.64-7.59 (m, 2H), 7.43 (t, J=7.9 Hz, 1H), 7.38 (s, 1H), 7.29 (d, J=8.8 Hz, 1H), 7.23 (d, J=2.7 Hz, 1H), 7.01 (ddd, J=8.8, 2.7, 1.3 Hz, 1H), 3.78 (s, 3H) ppm.

Example 106

N-(3-Carbamoyl-4-fluoro-phenyl)-2,2-difluoro-6-[2-methoxy-4-(trifluoromethoxy)phenoxy]-1,3-benzodioxole-5-carboxamide (122)

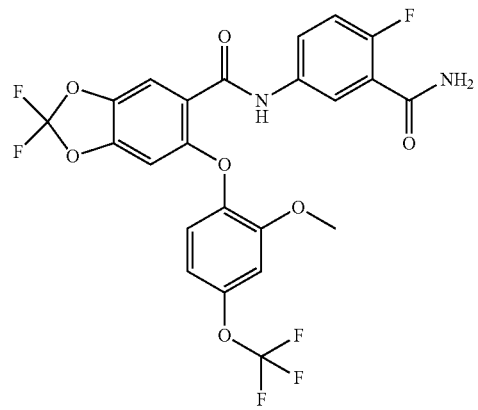 [SMILES: COc1cc(OC(F)(F)F)ccc1Oc1cc2c(cc1C(=O)Nc1ccc(F)c(C(N)=O)c1)OC(F)(F)O2]

Step 1: Methyl 6-chloro-2,2-difluoro-1,3-benzodioxole-5-carboxylate

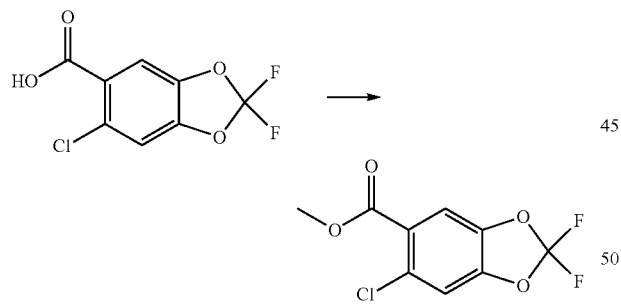

Sulfuric acid (693 μL, 13.0 mmol) was added to a solution of 6-chloro-2,2-difluoro-1,3-benzodioxole-5-carboxylic acid (2.05 g, 8.67 mmol) in methanol (50 mL) and the resulting mixture was heated at 65° C. for 18 hours. The reaction mixture was cooled to room temperature and concentrated in vacuo. The residue was taken up in ethyl acetate and water and the layers were separated. The organic layer was washed with a saturated aqueous NaHCO₃ and brine, dried over Na₂SO₄, filtered and concentrated to provide methyl 6-chloro-2,2-difluoro-1,3-benzodioxole-5-carboxylate (1.96 g, 90%) as a brown solid. ESI-MS m/z calc. 249.98, found 250.9 (M+1)+; retention time (Method A): 0.64 minutes (1 minute run). ¹H NMR (400 MHz, DMSO-d6) δ 7.89 (s, 1H), 7.83 (s, 1H), 3.86 (s, 3H) ppm.

Step 2: Methyl 2,2-difluoro-6-[2-methoxy-4-(trifluoromethoxy)phenoxy]-1,3-benzodioxole-5-carboxylate

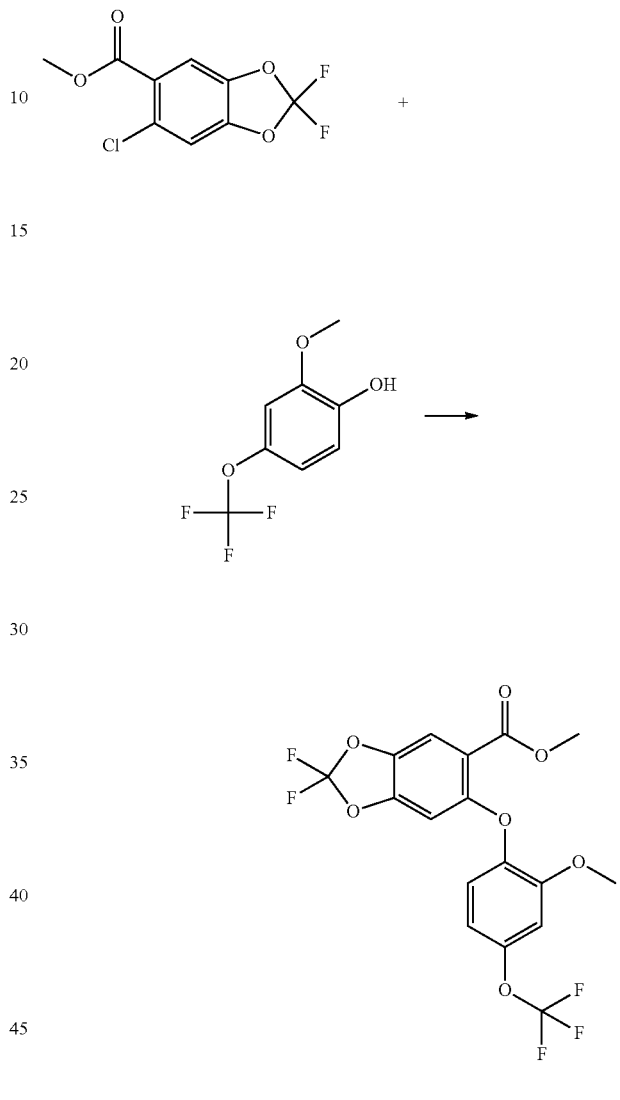

A mixture of methyl 6-chloro-2,2-difluoro-1,3-benzodioxole-5-carboxylate (3.0 g, 12 mmol), 2-methoxy-4-(trifluoromethoxy)phenol (5.0 g, 24 mmol), K₂CO₃ (3.4 g, 24 mmol), Cu (950 mg, 15.0 mmol), and copper iodide (364 mg, 1.91 mmol) in nitrobenzene (41 mL) was stirred at 170° C. for 25 minutes. The reaction was cooled to room temperature and filtered through a pad of Celite and rinsed with ethyl acetate. The filtrate was evaporated in vacuo and purified using silica gel chromatography (0-15% ethyl acetate/hexanes) to provide methyl 2,2-difluoro-6-[2-methoxy-4-(trifluoromethoxy)phenoxy]-1,3-benzodioxole-5-carboxylate (540 mg, 11%) as a yellow solid. ESI-MS m/z calc. 422.04, found 423.0 (M+1)+; retention time (Method C): 2.97 minutes (5 minute run).

Step 3: 2,2-Difluoro-6-[2-methoxy-4-(trifluoromethoxy)phenoxy]-1,3-benzodioxole-5-carboxylic acid

Step 4: N-(3-Carbamoyl-4-fluoro-phenyl)-2,2-difluoro-6-[2-methoxy-4-(trifluoromethoxy)phenoxy]-1,3-benzodioxole-5-carboxamide (122)

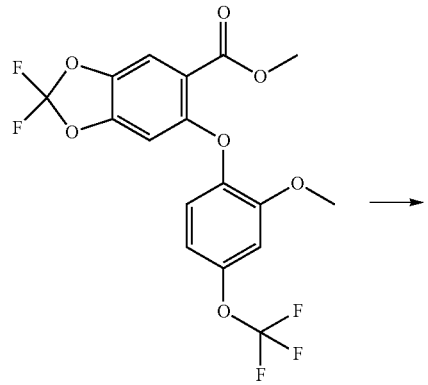

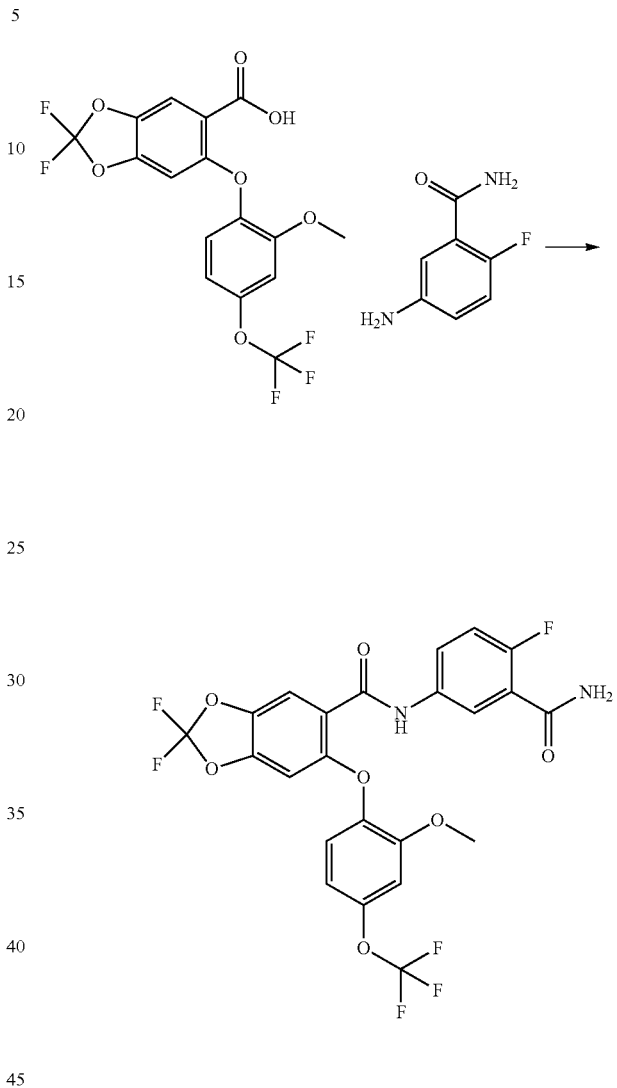

A solution of methyl 2,2-difluoro-6-[2-methoxy-4-(trifluoromethoxy)phenoxy]-1,3-benzodioxole-5-carboxylate (140 mg, 0.332 mmol) in methanol (3 mL) was treated with aqueous NaOH (1.5 mL of 1 M, 1.5 mmol). The reaction mixture was stirred at 60° C. for 75 minutes. The reaction was cooled and acidified to pH1 with 12 M HCl. The mixture was partitioned between water and ethyl acetate. The organic layer was washed with brine, dried over $Na_2SO_4$, filtered and concentrated to provide 2,2-difluoro-6-[2-methoxy-4-(trifluoromethoxy)phenoxy]-1,3-benzodioxole-5-carboxylic acid (135 mg, 100%) as a light yellow solid. ESI-MS m/z calc. 408.03, found 409.0 (M+1)+; retention time (Method B): 0.71 minutes (3 minute run).

2,2-Difluoro-6-[2-methoxy-4-(trifluoromethoxy)phenoxy]-1,3-benzodioxole-5-carboxylic acid (30 mg, 0.07 mmol) and HATU (34 mg, 0.09 mmol) were combined in DMF (500 µL) and DIEA (27 µL, 0.16 mmol), and stirred for 5 minutes. 5-Amino-2-fluoro-benzamide (12 mg, 0.08 mmol) was added in one portion and the reaction was stirred for 1 hour. HPLC purification (10-99% acetonitrile/5 mM HCl) provided N-(3-carbamoyl-4-fluoro-phenyl)-2,2-difluoro-6-[2-methoxy-4-(trifluoromethoxy)phenoxy]-1,3-benzodioxole-5-carboxamide (19 mg, 48%) as a white solid. ESI-MS m/z calc. 544.07, found 544.8 (M+1)+; retention time (Method C): 2.7 minutes (5 minute run). $^1$H NMR (400 MHz, DMSO-d6) δ 10.44 (s, 1H), 7.95 (dd, J=6.4, 2.8 Hz, 1H), 7.80-7.60 (m, 4H), 7.24 (dd, J=10.2, 9.0 Hz, 1H), 7.18-7.10 (m, 3H), 7.00-6.80 (m, 1H), 3.77 (s, 3H) ppm.

Example 107

5-[[2,2-Difluoro-6-[2-methoxy-4-(trifluoromethoxy)phenoxy]-1,3-benzodioxole-5-carbonyl]amino]pyridine-2-carboxamide (197)

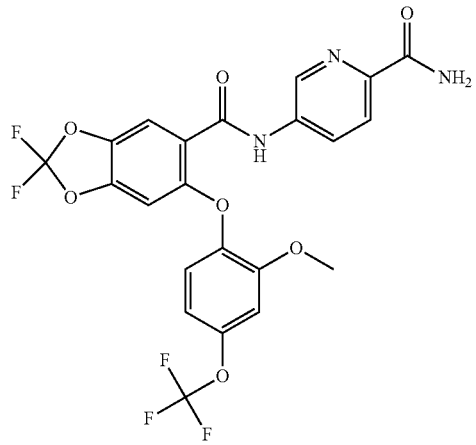 [SMILES: COc1cc(OC(F)(F)F)ccc1Oc1cc2c(cc1C(=O)Nc1ccc(C(N)=O)nc1)OC(F)(F)O2]

This compound was made in an analogous fashion to Example 106 except employing 5-aminopyridine-2-carboxamide in the amide formation step (Step 4). The yield of the desired product after purification was 18 mg (21%). ESI-MS m/z calc. 527.08, found 527.9 (M+1)+; retention time (Method C): 2.64 minutes (5 minute run). $^1$H-NMR (400 MHz, DMSO-d6) δ 10.82 (s, 1H), 8.84 (d, J=2.4 Hz, 1H), 8.21 (dd, J=8.5, 2.5 Hz, 1H), 8.02 (d, J=8.7 Hz, 2H), 7.82 (s, 1H), 7.56 (s, 1H), 7.20-7.12 (m, 3H), 6.94 (ddd, J=8.9, 2.8, 1.3 Hz, 1H), 3.74 (s, 3H) ppm.

Example 108

4-[[2,2-Difluoro-6-[2-methoxy-4-(trifluoromethoxy)phenoxy]-1,3-benzodioxole-5-carbonyl]amino]pyridine-2-carboxamide (121)

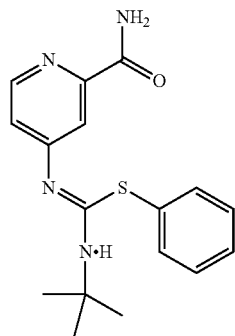

+

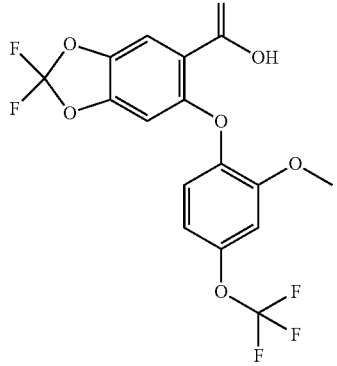

→

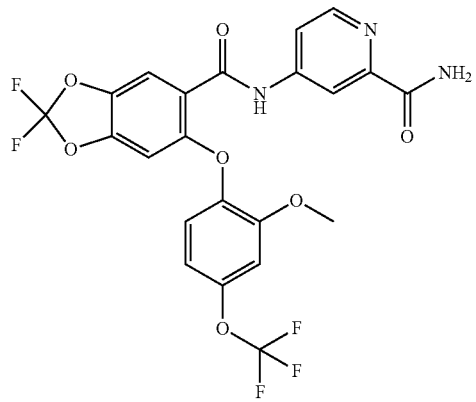

A vial charged with 2,2-difluoro-6-[2-methoxy-4-(trifluoromethoxy)phenoxy]-1,3-benzodioxole-5-carboxylic acid (27 mg, 0.066 mmol), 4-[(Z)-[(tert-butylamino)-phenylsulfanyl-methylene]amino]pyridine-2-carboxamide (prepared as described in Preparation 1, 25 mg, 0.075 mmol) and tris[(Z)-1-methyl-3-oxo-but-1-enoxy]iron (2 mg, 0.006 mmol) in 2-propanol (0.4 mL) was heated at 80° C. under an atmosphere of air for 20 hours. The reaction mixture was cooled to room temperature and diluted with ethyl acetate and 1 M HCl. The two layers were separated and the aqueous layer was extracted with ethyl acetate. The combined organic layers were dried over Na$_2$SO$_4$, filtered and concentrated in vacuo. Silica gel chromatography (0-30% ethyl acetate/dichloromethane) provided 4-[[2,2-difluoro-6-[2-methoxy-4-(trifluoromethoxy)phenoxy]-1,3-benzodioxole-5-carbonyl]amino]pyridine-2-carboxamide (18.5 mg, 53%) as a white solid. ESI-MS m/z calc. 527.08, found 528.0 (M+1)+; retention time (Method C): 2.62 minutes (5 minutes run). $^1$H NMR (400 MHz, DMSO-d6) δ 10.88 (s, 1H), 8.50 (d, J=5.5 Hz, 1H), 8.27 (d, J=2.2 Hz, 1H), 8.07 (d, J=2.8 Hz, 1H), 7.84-7.79 (m, 2H), 7.62 (d, J=3.0 Hz, 1H), 7.18-7.14 (m, 2H), 7.13 (d, J=2.9 Hz, 1H), 7.03-6.66 (m, 1H), 3.75 (s, 3H) ppm.

Example 109

4-[[5-(1,1,2,2,2-pentafluoroethyl)-2-[4-(trifluoromethoxy)phenoxy]benzoyl]amino]pyridine-2-carboxamide (80)

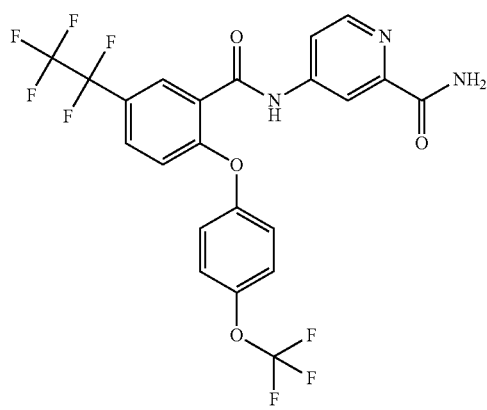 [SMILES: NC(=O)c1cc(NC(=O)c2cc(C(F)(F)C(F)(F)F)ccc2Oc2ccc(OC(F)(F)F)cc2)ccn1]

Step 1:
2-Fluoro-5-(1,1,2,2,2-pentafluoroethyl)benzoic acid

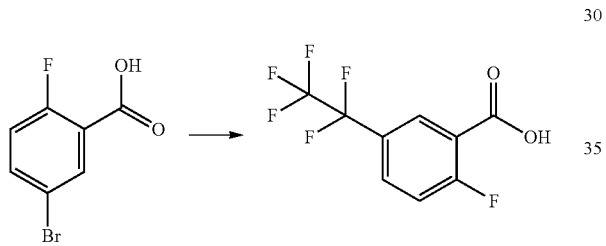

Activation of copper reagent: 20 g of bronze copper powder was stirred in ~250 mL of a solution of 4 g iodine in acetone for 15 minutes until the iodine solution was decolorized (purple turning to colorless). The product was collected in a filter funnel and added to a solution of 12 M HCl in acetone (1:1, v/v, 80 mL). After stirring for 5 minutes the solid was filtered, washed with acetone (8×40 mL) and air dried for 30 minutes. The activation was carried out directly prior to reaction.

5-Bromo-2-fluoro-benzoic acid (5.0 g, 22.8 mmol) was dissolved in DMSO (100 mL) under $N_2$ atmosphere and cooled to 0° C. The 1,1,1,2,2-pentafluoro-2-iodo-ethane canister was cooled to 0° C. and then 1,1,1,2,2-pentafluoro-2-iodo-ethane (39.3 g, 160 mmol) was poured into reaction flask under $N_2$ followed by the activated copper reagent (12.3 g, 193 mmol). The flask was sealed under $N_2$ and heated for 30 minutes at 100° C. and then the temperature was raised to 120° C. and stirred for 48 hours. The reaction was cooled to room temperature, filtered and the filter cake was rinsed with DMSO (60 mL). The filtrate was diluted with ethyl acetate (450 mL) and filtered through a pad of Celite. To the filtrate was added 1 N HCl and the layers separated. The aqueous layer was extracted with additional ethyl acetate, and the combined organic layers were dried over $Na_2SO_4$, filtered and concentrated in vacuo. Silica gel chromatography (0-30% ethyl acetate/dichloromethane) provided 2-fluoro-5-(1,1,2,2,2-pentafluoroethyl)benzoic acid (2.0606 g, 35%) as a light brown solid. ESI-MS m/z calc. 258.01, found 259.2 (M+1)+; retention time (Method B): 1.36 minutes (3 minute run). $^1$H NMR (400 MHz, DMSO-d6) δ 13.84 (s, 1H), 8.11 (dd, J=6.6, 2.7 Hz, 1H), 8.07-7.96 (m, 1H), 7.81-7.41 (m, 1H) ppm.

Step 2: 5-(1,1,2,2,2-Pentafluoroethyl)-2-[4-(trifluoromethoxy)phenoxy]benzoic acid

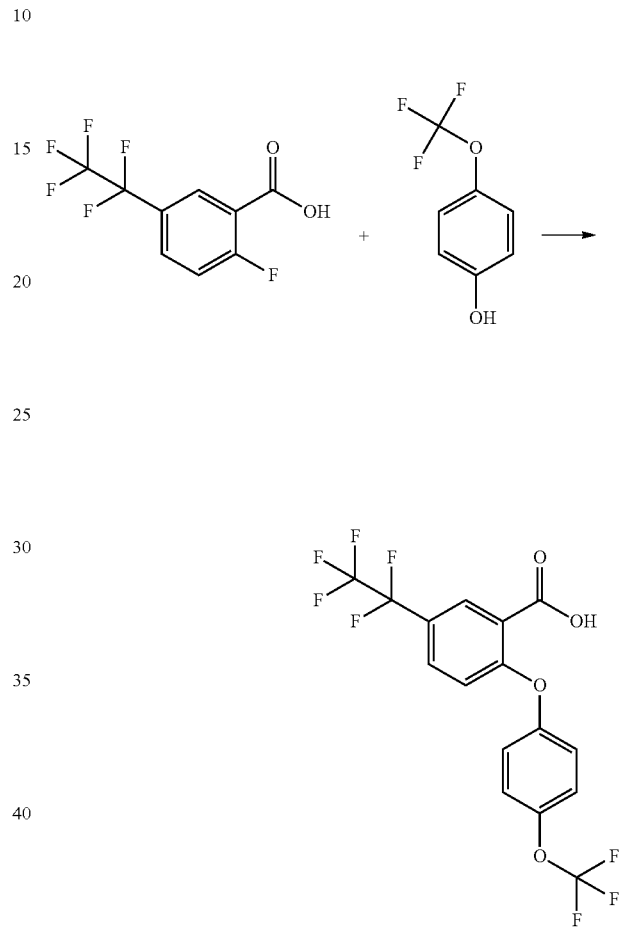

2-Fluoro-5-(1,1,2,2,2-pentafluoroethyl)benzoic acid (500 mg, 1.94 mmol), $Cs_2CO_3$ (1.36 g, 4.17 mmol), 4-(trifluoromethoxy)phenol (459 mg, 2.58 mmol) and DMF (10 mL) were combined in a sealed vial and heated at 150° C. for 14 hours. The reaction was cooled, diluted with 1 N HCl and extracted with ethyl acetate. The organic layer was washed with water and brine, dried over $Na_2SO_4$, filtered and concentrated in vacuo. Silica gel chromatography (0-15% ethyl acetate/dichloromethane) provided 5-(1,1,2,2,2-pentafluoroethyl)-2-[4-(trifluoromethoxy)phenoxy]benzoic acid (116 mg, 14%) as a brown solid. ESI-MS m/z calc. 416.03, found 417.1 (M+1)+; retention time (Method B): 1.92 minutes (3 minute run).

Step 3: 5-(1,1,2,2,2-Pentafluoroethyl)-2-[4-(trifluoromethoxy)phenoxy]benzoyl chloride

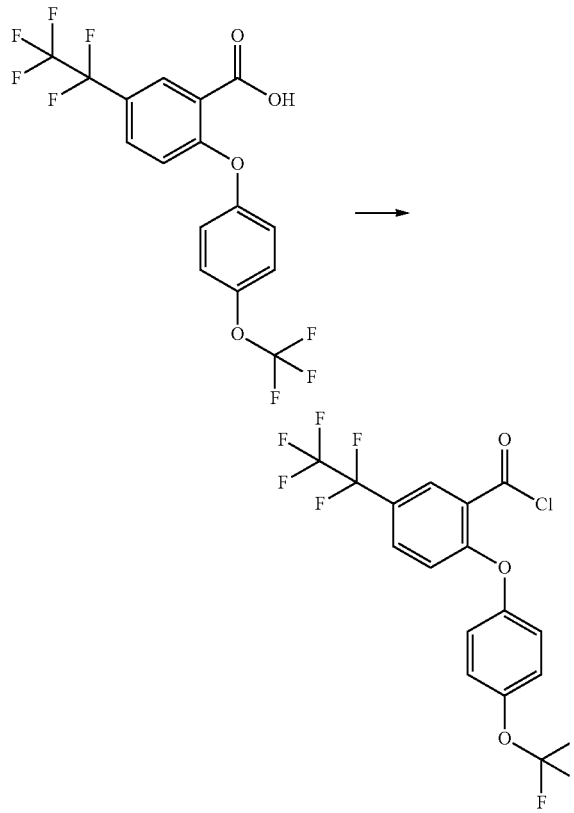

To a solution of 5-(1,1,2,2,2-pentafluoroethyl)-2-[4-(trifluoromethoxy)phenoxy]benzoic acid (114 mg, 0.274 mmol) and DMF (10 μL, 0.13 mmol) in dichloromethane (1.5 mL) at 0° C. was added oxalyl chloride (150 μL, 1.72 mmol) dropwise. The reaction was then allowed to warm to room temperature. Conversion was monitored via test for piperidine adduct formation. After 35 minutes the reaction mixture was concentrated to provide 5-(1,1,2,2,2-pentafluoroethyl)-2-[4-(trifluoromethoxy)phenoxy]benzoyl chloride.

Step 4: 4-[[5-(1,1,2,2,2-Pentafluoroethyl)-2-[4-(trifluoromethoxy)phenoxy]benzoyl]amino]pyridine-2-carboxamide (80)

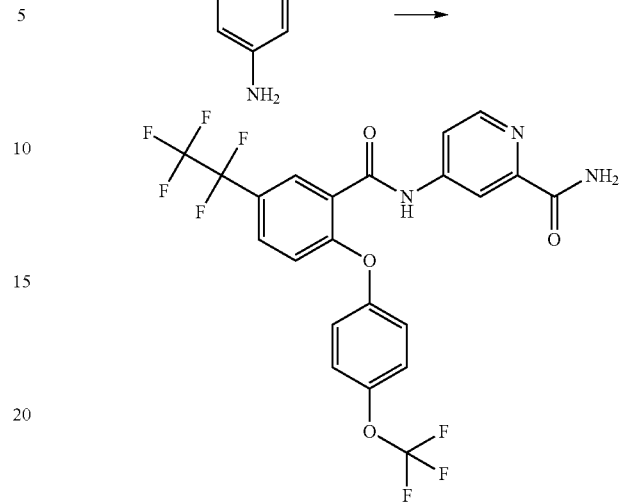

To a solution of 4-aminopyridine-2-carboxamide (19 mg, 0.14 mmol) in THF (1 mL) and DIEA (72 μL, 0.41 mmol) at 0° C. was added a slurry of 5-(1,1,2,2,2-pentafluoroethyl)-2-[4-(trifluoromethoxy)phenoxy]benzoyl chloride (60 mg, 0.14 mmol) in THF (1 mL) dropwise. The reaction was allowed to come to room temperature and stirred for 4 hours. The solvent was evaporated under a stream of $N_2$. HPLC purification (1-99% acetonitrile/5 mM HCl) provided 4-[[5-(1,1,2,2,2-pentafluoroethyl)-2-[4-(trifluoromethoxy)phenoxy]benzoyl]amino]pyridine-2-carboxamide (10 mg, 13%). ESI-MS m/z calc. 535.08, found 535.9 (M+1)+; retention time (Method B): 1.95 minutes (3 minute run). $^1$H NMR (400 MHz, DMSO-d6) δ 11.12 (s, 1H), 8.53 (d, J=5.5 Hz, 1H), 8.31 (d, J=2.2 Hz, 1H), 8.10 (d, J=2.8 Hz, 1H), 8.01 (d, J=2.5 Hz, 1H), 7.96-7.76 (m, 2H), 7.65 (d, J=2.8 Hz, 1H), 7.56-7.39 (m, 2H), 7.39-7.24 (m, 2H), 7.14 (d, J=8.8 Hz, 1H) ppm.

Example 110

N-(3-Carbamoyl-4-fluoro-phenyl)-5-(1,1,2,2,2-pentafluoroethyl)-2-[4-(trifluoromethoxy)phenoxy]benzamide (79)

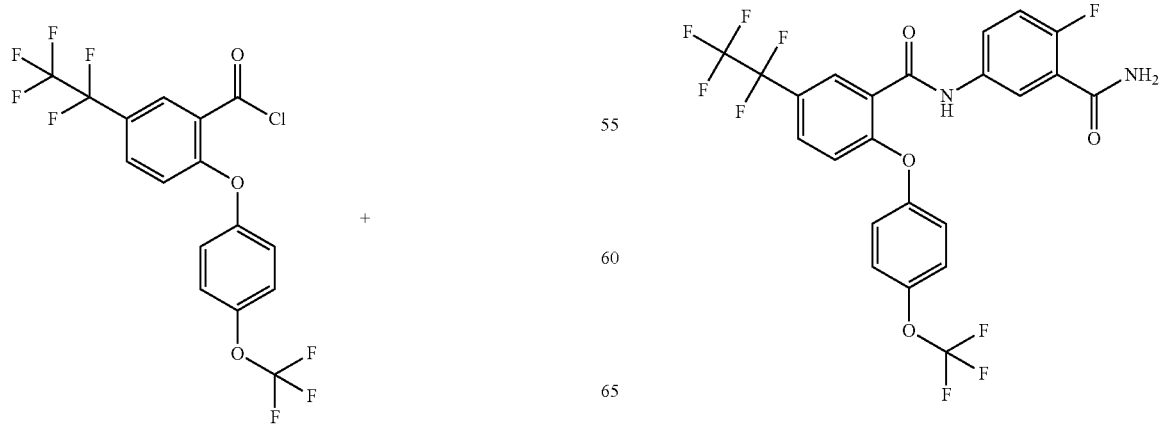

This compound was made in an analogous fashion to Example 109 except employing 5-amino-2-fluoro-benzamide in the amide formation step (Step 4). The yield of the desired product after purification was 28 mg (36%). ESI-MS m/z calc. 552.07, found 553.0 (M+1)+; retention time (Method B): 2.0 minutes (3 minute run). $^1$H NMR (400 MHz, DMSO-d6) δ 10.68 (s, 1H), 8.07-7.91 (m, 2H), 7.87-7.75 (m, 2H), 7.69 (d, J=8.4 Hz, 2H), 7.54-7.40 (m, 2H), 7.37-7.31 (m, 2H), 7.27 (dd, J=10.1, 8.9 Hz, 1H), 7.12 (d, J=8.7 Hz, 1H) ppm.

Example 111

5-[[2,4-Dichloro-6-(4-fluoro-2-methoxy-phenoxy)benzoyl]amino]pyridine-2-carboxamide (182)

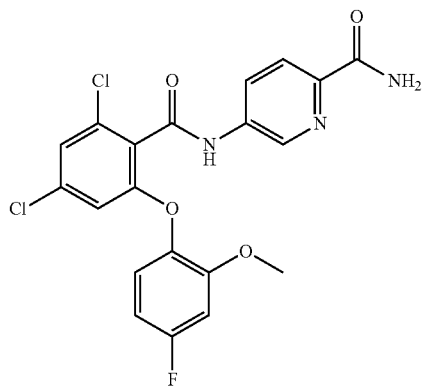 [SMILES: COc1cc(F)ccc1Oc1cc(Cl)cc(Cl)c1C(=O)Nc1ccc(C(N)=O)nc1]

Step 1: 2,4-Dichloro-6-fluoro-benzoic acid

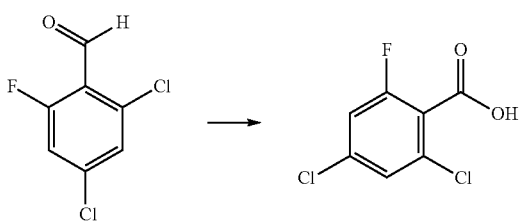 [SMILES: O=Cc1c(F)cc(Cl)cc1Cl ; O=C(O)c1c(F)cc(Cl)cc1Cl]

To a solution of 2,4-dichloro-6-fluoro-benzaldehyde (1.0 g, 5.2 mmol), 2-methyl-2-butene (1.8 g, 2.7 mL, 26 mmol) and sodium dihydrogen phosphate hydrate (2.1 g, 16 mmol) in tert-BuOH (5.0 mL)/acetonitrile (3.25 mL)/water (5.0 mL) at 0° C. was added sodium chlorite (1.4 g, 16 mmol) and the reaction mixture was stirred for 1 hour. The cold reaction mixture was then acidified with 1 M HCl (50 mL) and extracted with ethyl acetate (3×). The combined organics were washed with 1 M HCl and brine, dried over Na$_2$SO$_4$, filtered and evaporated to dryness. The residue was triturated in 20% diethyl ether/hexanes and filtered to provide 2,4-dichloro-6-fluoro-benzoic acid (700 mg, 65%) as a white solid. $^1$H NMR (400 MHz, DMSO-d6) δ 14.29 (br s, 1H), 7.70-7.63 (m, 2H) ppm.

Step 2: 2,4-Dichloro-6-fluoro-benzoyl chloride

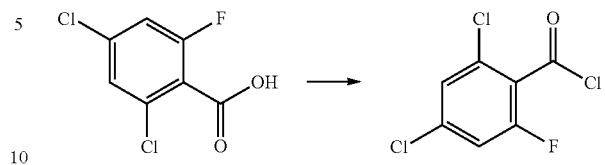

To a solution of 2,4-dichloro-6-fluoro-benzoic acid (5.1 g, 24 mmol) and DMF (173 µL, 2.23 mmol) in dichloromethane (50 mL) at 0° C. was added oxalyl chloride (10.2 mL, 117 mmol) dropwise. The mixture was stirred at room temperature for 5 hours under N$_2$ atmosphere. Conversion was monitored by UPLC via test for morpholine adduct formation. The solvent was evaporated under reduced pressure to afford 2,4-dichloro-6-fluoro-benzoyl chloride.

Step 3: 5-[(2,4-Dichloro-6-fluoro-benzoyl)amino]pyridine-2-carboxamide

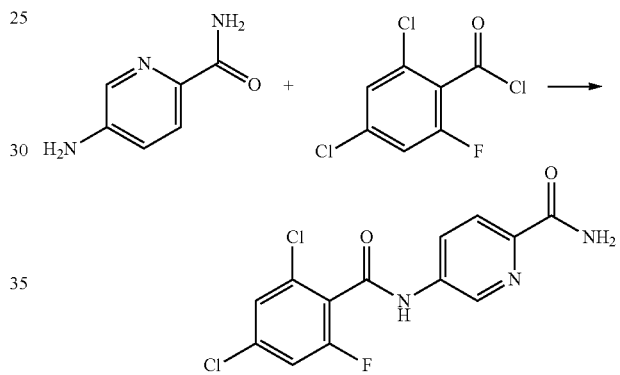

To 2,4-dichloro-6-fluoro-benzoyl chloride (2.5 g, 11 mmol) and DIEA (4.8 mL, 27.5 mmol) in NMP (25 mL) at 0° C. was added a solution of 5-aminopyridine-2-carboxamide (1.5 g, 11 mmol) in dichloromethane (12.5 mL) dropwise. The reaction was stirred at room temperature for 16 hours. Water (20 mL) was added to the reaction mixture and the resulting solid was filtered to provide 5-[(2,4-dichloro-6-fluoro-benzoyl)amino]pyridine-2-carboxamide (1.2 g, 33%). ESI-MS m/z calc. 327.00, found 328.1 (M+1)+; retention time (Method B): 1.16 minutes (3 minute run). $^1$H NMR (400 MHz, DMSO-d6) δ 11.34 (s, 1H), 8.88-8.82 (m, 1H), 8.29 (dd, J=8.5, 2.5 Hz, 1H), 8.12-8.01 (m, 2H), 7.76 (dq, J=4.2, 2.0 Hz, 2H), 7.58 (s, 1H) ppm.

Step 4: 5-[[2,4-Dichloro-6-(4-fluoro-2-methoxyphenoxy)benzoyl]amino]pyridine-2-carboxamide (182)

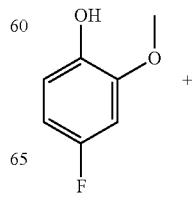

491
-continued

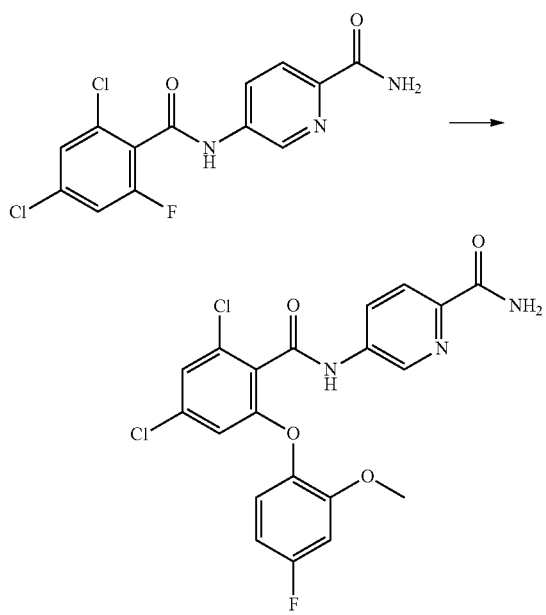

To 5-[(2,4-dichloro-6-fluoro-benzoyl)amino]pyridine-2-carboxamide (44 mg, 0.13 mmol) in DMF (1 mL) was added 4-fluoro-2-methoxy-phenol (19 mg, 15 µL, 0.13 mmol) followed by $K_2CO_3$ (56 mg, 0.40 mmol). The reaction was heated at 80° C. for 1 hour. The reaction was diluted with DMSO and purified by HPLC (1-99% acetonitrile/5 mM HCl) to provide 5-[[2,4-dichloro-6-(4-fluoro-2-methoxy-phenoxy)benzoyl]amino]pyridine-2-carboxamide (39 mg, 63%). ESI-MS m/z calc. 449.03, found 449.95 (M+1)+; retention time (Method B): 1.66 minutes (3 minute run). $^1$H NMR (400 MHz, DMSO-d6) δ 11.23 (s, 1H), 8.88 (d, J=2.6 Hz, 1H), 8.31 (dd, J=8.6, 2.5 Hz, 1H), 8.06 (d, J=8.7 Hz, 1H), 8.04 (s, 1H), 7.58 (d, J=2.6 Hz, 1H), 7.51 (d, J=1.8 Hz, 1H), 7.23 (dd, J=8.9, 5.9 Hz, 1H), 7.15 (dd, J=10.7, 2.9 Hz, 1H), 6.85 (td, J=8.4, 2.9 Hz, 1H), 6.64 (d, J=1.8 Hz, 1H), 3.78 (s, 3H) ppm.

Example 112

4-[[2,4-Dichloro-6-(4-fluoro-2-methoxy-phenoxy)benzoyl]amino]pyridine-2-carboxamide (178)

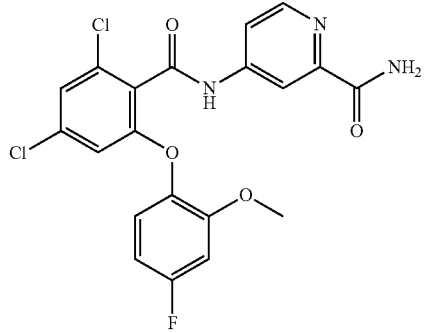 [SMILES: COc1cc(F)ccc1Oc1cc(Cl)cc(Cl)c1C(=O)Nc1ccnc(C(N)=O)c1]

492

Step 1: 4-[(2,4-Dichloro-6-fluoro-benzoyl)amino]pyridine-2-carboxamide

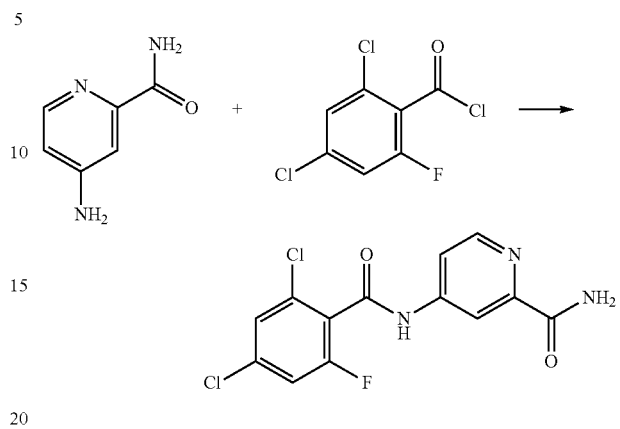

This compound was made in an analogous fashion to Example 111, step 3, except employing 4-aminopyridine-2-carboxamide in the amide formation step. The yield of the desired product after purification was 1.05 g (29%). ESI-MS m/z calc. 327.00, found 328.1 (M+1)+; retention time (Method B): 1.16 minutes (3 minute run). $^1$H NMR (400 MHz, DMSO-d6) δ 11.42 (s, 1H), 8.58 (d, J=5.4 Hz, 1H), 8.33 (d, J=2.2 Hz, 1H), 8.12 (d, J=2.8 Hz, 1H), 7.88-7.51 (m, 4H) ppm.

Step 2: 4-[[2,4-Dichloro-6-(4-fluoro-2-methoxy-phenoxy)benzoyl]amino]pyridine-2-carboxamide (178)

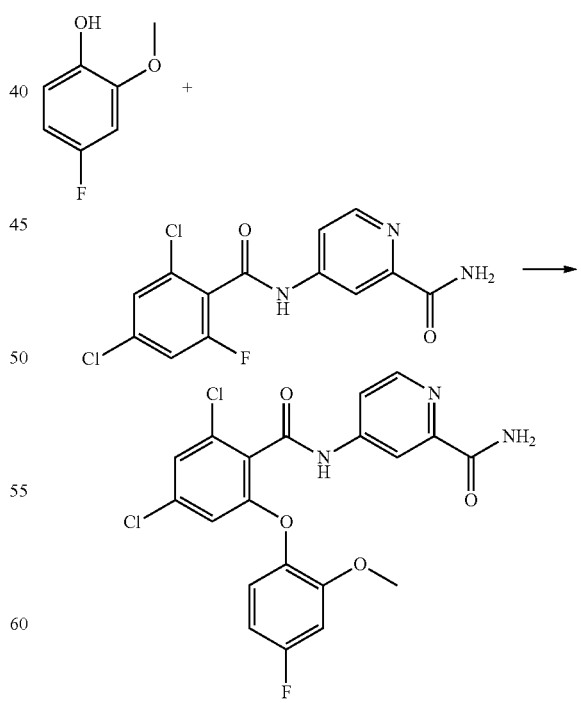

To 4-[(2,4-dichloro-6-fluoro-benzoyl)amino]pyridine-2-carboxamide (45 mg, 0.14 mmol) in DMF was added 4-fluoro-2-methoxy-phenol (20 mg, 16 µL, 0.14 mmol)

followed by K₂CO₃ (57 mg, 0.41 mmol). The reaction was heated at 80° C. for 30 minutes, then diluted with DMSO (0.5 mL), filtered, and purified by HPLC (1-99% acetonitrile/5 mM HCl) to provide 4-[[2,4-dichloro-6-(4-fluoro-2-methoxy-phenoxy)benzoyl]amino]pyridine-2-carboxamide (34 mg, 54%). ESI-MS m/z calc. 449.03, found 449.95 (M+1)+; retention time (Method B): 1.65 minutes (3 minute run). ¹H NMR (400 MHz, DMSO-d6) δ 11.34 (s, 1H), 8.55 (d, J=5.5 Hz, 1H), 8.35 (d, J=2.1 Hz, 1H), 8.13 (d, J=2.7 Hz, 1H), 7.85 (dd, J=5.5, 2.2 Hz, 1H), 7.68 (s, 1H), 7.50 (d, J=1.8 Hz, 1H), 7.22 (dd, J=8.9, 5.8 Hz, 1H), 7.14 (dd, J=10.7, 2.9 Hz, 1H), 6.84 (ddd, J=8.9, 8.1, 2.9 Hz, 1H), 6.63 (d, J=1.8 Hz, 1H), 3.77 (s, 3H) ppm.

Example 113

N-(3-Carbamoylphenyl)-2-[2-methoxy-4-(trifluoromethoxy)phenoxy]-4-(trifluoromethyl)benzamide (28)

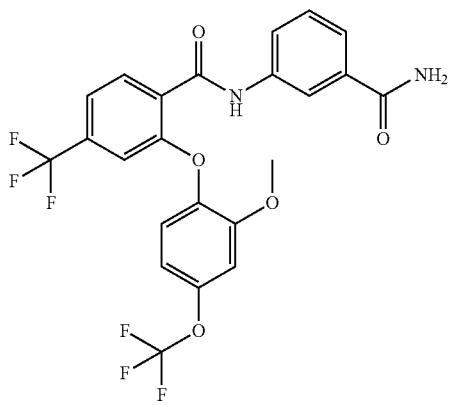 [SMILES: COc1cc(OC(F)(F)F)ccc1Oc1cc(C(F)(F)F)ccc1C(=O)Nc1cccc(C(N)=O)c1]

Step 1: 2-[2-Methoxy-4-(trifluoromethoxy)phenoxy]-4-(trifluoromethyl)benzaldehyde

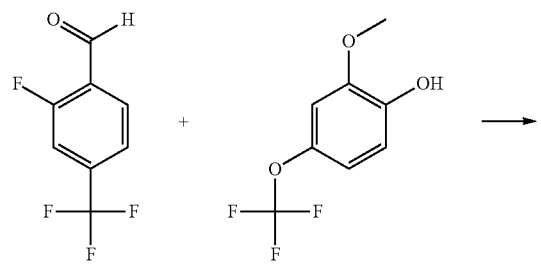

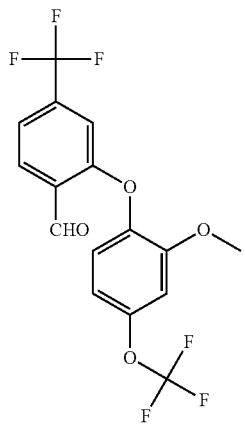

To a solution of 2-fluoro-4-(trifluoromethyl)benzaldehyde (923 mg, 655 μL, 4.81 mmol) in DMF (5 mL) was added 2-methoxy-4-(trifluoromethoxy)phenol (1000 mg, 655 μL, 4.81 mmol) and Cs₂CO₃ (1.57 g, 4.81 mmol). The mixture was heated at 100° C. for 2 hours. The reaction mixture was diluted with water and extracted with ethyl acetate (3×). The combined organic layers were dried over MgSO₄, filtered and concentrated in vacuo. Silica gel chromatography (1-50% ethyl acetate/hexanes) provided 2-[2-methoxy-4-(trifluoromethoxy)phenoxy]-4-(trifluoromethyl)benzaldehyde (1.83 g, 91%). ESI-MS m/z calc. 380.05, found 381.1 (M+1)+; retention time (Method A): 0.77 minutes (1 minute run).

Step 2: 2-[2-Methoxy-4-(trifluoromethoxy)phenoxy]-4-(trifluoromethyl)benzoic acid

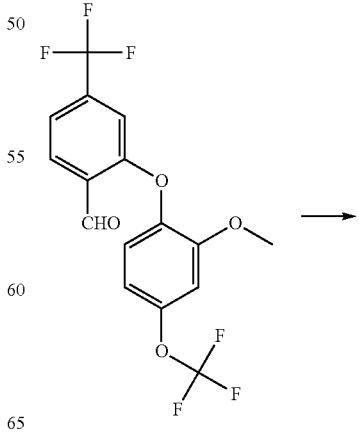

495

-continued

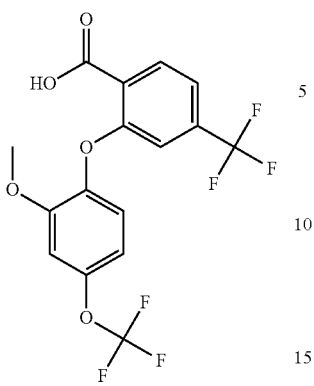

496

-continued

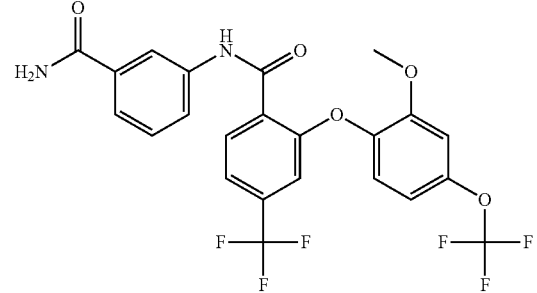

To a solution of 2-[2-methoxy-4-(trifluoromethoxy)phenoxy]-4-(trifluoromethyl)benzaldehyde (1.83 g, 4.81 mmol) in tert-BuOH (18 mL), water (12 mL) and acetonitrile (12 mL) was added sodium dihydrogen phosphate hydrate (577 mg, 4.81 mmol) and 2-methyl-2-butene (1.5 g, 2.3 mL, 22 mmol). Sodium chlorite (522 mg, 5.78 mmol) was then added portionwise and the reaction mixture was stirred for 1 hour at room temperature. The reaction was adjusted to pH2 by the addition of 1 M HCl solution and the reaction mixture was extracted with ethyl acetate (3×). The combined organic layers were dried over MgSO₄, filtered, and concentrated in vacuo to provide 2-[2-methoxy-4-(trifluoromethoxy)phenoxy]-4-(trifluoromethyl)benzoic acid (1.65 g, 87%) as an off-white solid. ESI-MS m/z calc. 396.04, found 397.1 (M+1)+; retention time (Method B): 1.81 minutes (3 minute run). $^{1}$H NMR (400 MHz, DMSO-d6) δ 13.43 (s, 1H), 7.99 (dd, J=8.1, 0.9 Hz, 1H), 7.59-7.52 (m, 1H), 7.24 (d, J=2.8 Hz, 1H), 7.14 (d, J=8.7 Hz, 1H), 6.99 (qd, J=3.7, 3.2, 1.3 Hz, 2H), 3.80 (s, 3H) ppm.

Step 3: N-(3-Carbamoylphenyl)-2-[2-methoxy-4-(trifluoromethoxy)phenoxy]-4-(trifluoromethyl)benzamide (28)

To a solution of 2-[2-methoxy-4-(trifluoromethoxy)phenoxy]-4-(trifluoromethyl)benzoic acid (50 mg, 0.13 mmol), 3-aminobenzamide (17 mg, 0.13 mmol) and HATU (62 mg, 0.16 mmol) in DMF (1 mL) was added DIEA (66 µL, 0.38 mmol). The reaction was stirred at room temperature for 16 hours. HPLC purification (1-99% acetonitrile/5 mM HCl) afforded N-(3-carbamoylphenyl)-2-[2-methoxy-4-(trifluoromethoxy)phenoxy]-4-(trifluoromethyl)benzamide (34 mg, 52%). ESI-MS m/z calc. 514.10, found 515.2 (M+1)+; retention time (Method B): 1.91 minutes (3 minute run). $^{1}$H NMR (400 MHz, DMSO-d6) δ 10.60 (s, 1H), 8.17 (t, J=1.9 Hz, 1H), 7.97 (s, 1H), 7.90-7.84 (m, 1H), 7.82 (ddd, J=8.1, 2.3, 1.0 Hz, 1H), 7.60 (dt, J=7.9, 1.3 Hz, 2H), 7.42 (t, J=7.9 Hz, 1H), 7.38 (s, 1H), 7.34 (d, J=8.8 Hz, 1H), 7.23 (d, J=2.7 Hz, 1H), 7.04 (ddd, J=8.8, 2.7, 1.3 Hz, 1H), 6.98 (d, J=1.6 Hz, 1H), 3.78 (s, 3H) ppm.

Example 114

N-(3-Carbamoyl-4-fluoro-phenyl)-2-[2-methoxy-4-(trifluoromethoxy)phenoxy]-4-(trifluoromethyl)benzamide (27)

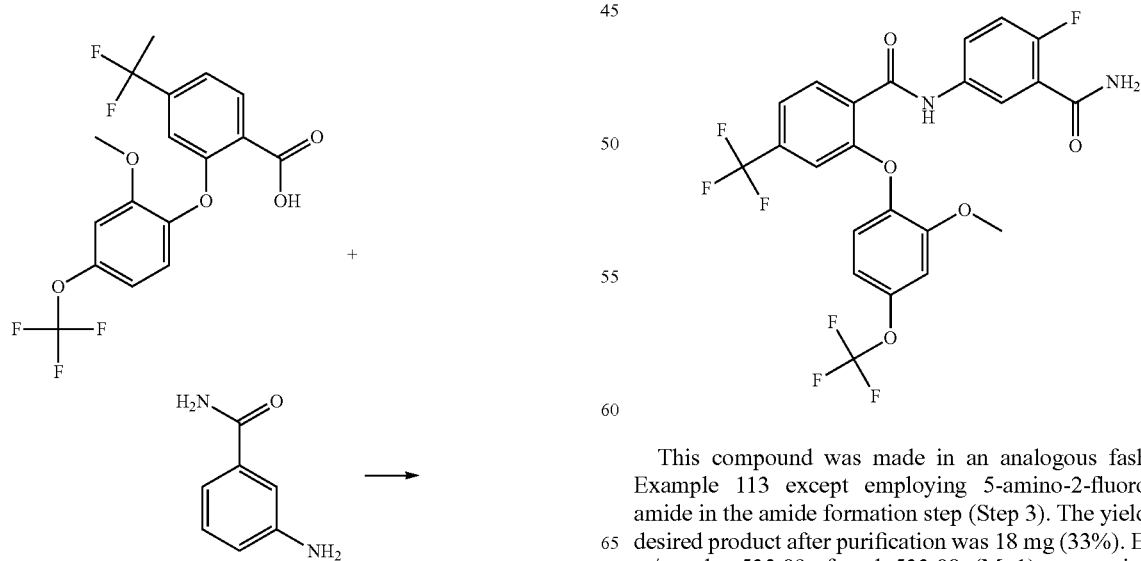

This compound was made in an analogous fashion to Example 113 except employing 5-amino-2-fluoro-benzamide in the amide formation step (Step 3). The yield of the desired product after purification was 18 mg (33%). ESI-MS m/z calc. 532.09, found 533.08 (M+1)+; retention time (Method B): 1.76 minutes (3 minute run).

Example 115

4-[[2,3-Difluoro-6-[4-(trifluoromethoxy)phenoxy]benzoyl]amino]pyridine-2-carboxamide (64)

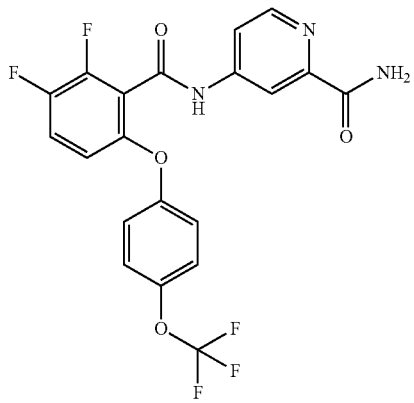 [SMILES: NC(=O)c1cc(NC(=O)c2c(Oc3ccc(OC(F)(F)F)cc3)ccc(F)c2F)ccn1]

Step 1: 2,3-Difluoro-6-[4-(trifluoromethoxy)phenoxy]benzoic acid

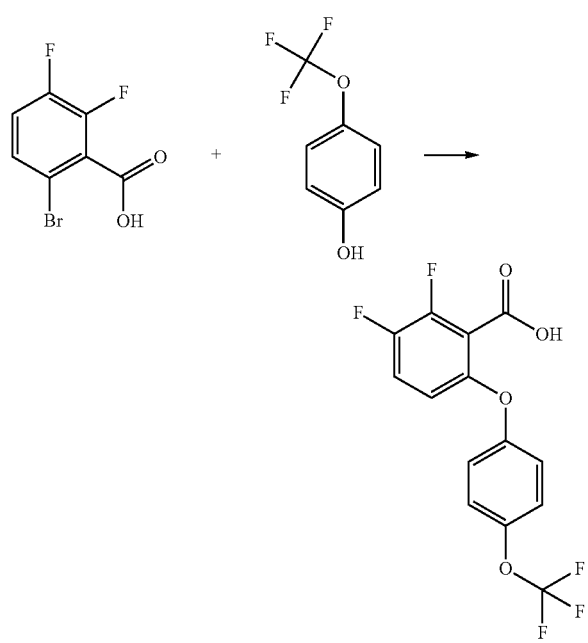

To a pressure flask was added 6-bromo-2,3-difluorobenzoic acid (5.0 g, 21 mmol), 4-(trifluoromethoxy)phenol (3.8 g, 21 mmol), $Cs_2CO_3$ (7.0 g, 21.5 mmol) and toluene (150 mL). The reaction mixture was bubbled with $N_2$ for 10 minutes, and then copper iodide (840 mg, 4.41 mmol) was added. The flask was flushed with $N_2$, capped, and heated at 100° C. with vigorous stirring for 22 hours. The mixture was allowed to cool and was diluted with ethyl acetate and water. The water layer was acidified with 12 M HCl to pH1 and the product was extracted into ethyl acetate. The organic layer was washed with 1 M HCl and brine, dried over $Na_2SO_4$, filtered and concentrated in vacuo. Silica gel chromatography (0-30% ethyl acetate/hexanes) provided 2,3-difluoro-6-[4-(trifluoromethoxy)phenoxy]benzoic acid (3.4 g, 48%). ESI-MS m/z calc. 334.03, found 335.1 (M+1)+; retention time (Method C): 2.23 minutes (5 minute run).

Step 2: 2,3-Difluoro-6-[4-(trifluoromethoxy)phenoxy]benzoyl chloride

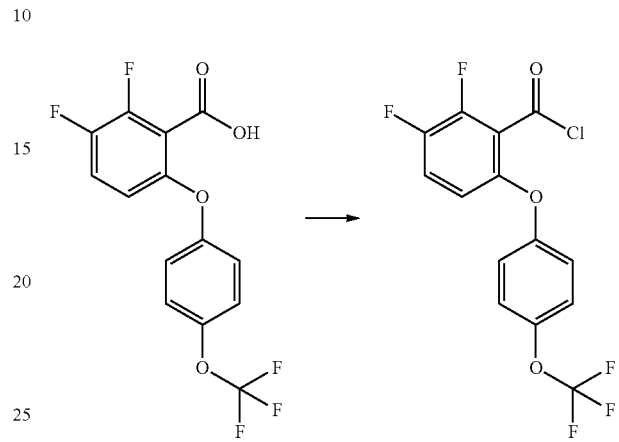

To a solution of 2,3-difluoro-6-[4-(trifluoromethoxy)phenoxy]benzoic acid (1.35 g, 4.04 mmol) and DMF (20 μL, 0.26 mmol) in dichloromethane (12 mL) at 0° C. was added oxalyl chloride (2.0 mL, 23 mmol) dropwise. The reaction was removed from the ice bath and was stirred under $N_2$ atmosphere for 50 minutes. Conversion was monitored by UPLC via test for piperidine adduct formation. The solvent was evaporated under reduced pressure to afford 2,3-difluoro-6-[4-(trifluoromethoxy)phenoxy]benzoyl chloride (1.4 g, 98%).

Step 3: 4-[[2,3-Difluoro-6-[4-(trifluoromethoxy)phenoxy]benzoyl]amino]pyridine-2-carboxamide (64)

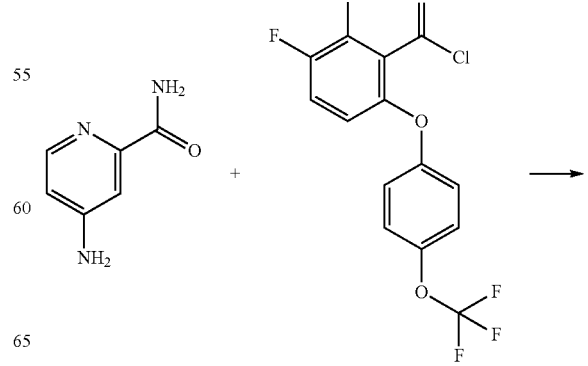

-continued

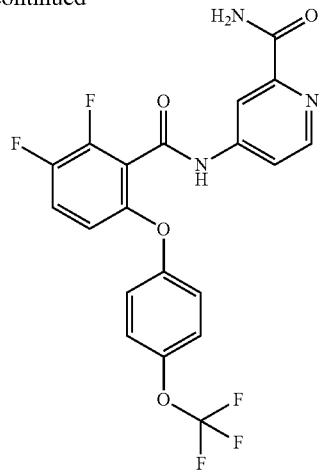

To a solution of 4-aminopyridine-2-carboxamide (58 mg, 0.43 mmol) and DIEA (222 µL, 1.28 mmol) in dichloromethane (1 mL) at 0° C. was added a slurry of 2,3-difluoro-6-[4-(trifluoromethoxy)phenoxy]benzoyl chloride (150 mg, 0.425 mmol) in dichloromethane (1 mL) slowly and the reaction was stirred at room temperature for 2 hours. The solvent was evaporated under a stream of $N_2$. HPLC purification (1-99% acetonitrile/5 mM HCl) provided 4-[[2,3-difluoro-6-[4-(trifluoromethoxy)phenoxy]benzoyl]amino]pyridine-2-carboxamide (33 mg, 17%). ESI-MS m/z calc. 453.08, found 454.1 (M+1)+; retention time (Method B): 1.55 minutes (3 minute run). $^1$H NMR (400 MHz, DMSO-d6) δ 11.39 (s, 1H), 8.53 (d, J=5.5 Hz, 1H), 8.25 (d, J=2.1 Hz, 1H), 8.10 (d, J=2.7 Hz, 1H), 7.76 (dd, J=5.5, 2.2 Hz, 1H), 7.70-7.59 (m, 2H), 7.42-7.35 (m, 2H), 7.21-7.13 (m, 2H), 7.02-6.92 (m, 1H) ppm.

Example 116

N-(3-Carbamoyl-4-fluoro-phenyl)-2,3-difluoro-6-[4-(trifluoromethoxy)phenoxy]benzamide (63)

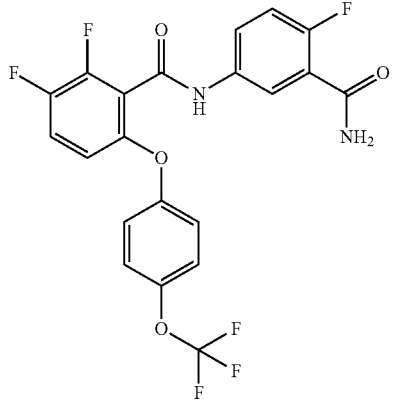 [SMILES: NC(=O)c1cc(NC(=O)c2c(Oc3ccc(OC(F)(F)F)cc3)ccc(F)c2F)ccc1F]

This compound was made in an analogous fashion to Example 115 except employing 5-amino-2-fluoro-benzamide in the amide formation step (Step 3). The yield of the desired product after purification was 84 mg (42%). ESI-MS m/z calc. 470.07, found 471.1 (M+1)+; retention time (Method B): 1.6 minutes (3 minute run). $^1$H NMR (400 MHz, DMSO-d6) δ 10.96 (s, 1H), 7.92 (dd, J=6.4, 2.8 Hz, 1H), 7.74-7.65 (m, 3H), 7.65-7.55 (m, 1H), 7.43-7.36 (m, 2H), 7.26 (dd, J=10.1, 9.0 Hz, 1H), 7.22-7.11 (m, 2H), 7.00-6.90 (m, 1H) ppm.

Example 117

4-[[5-Fluoro-2-[4-(trifluoromethoxy)phenoxy]-4-(trifluoromethyl)benzoyl]amino]pyridine-2-carboxamide (76)

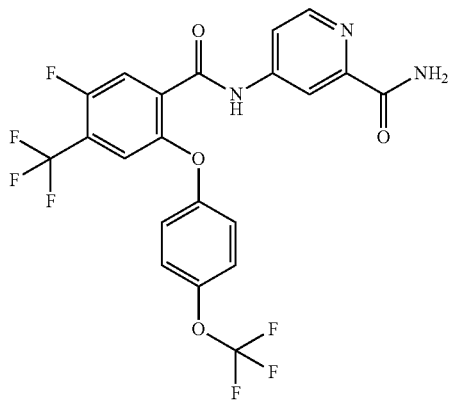 [SMILES: NC(=O)c1cc(NC(=O)c2cc(F)c(C(F)(F)F)cc2Oc2ccc(OC(F)(F)F)cc2)ccn1]

Step 1: 2,5-Difluoro-4-(trifluoromethyl)benzoyl chloride

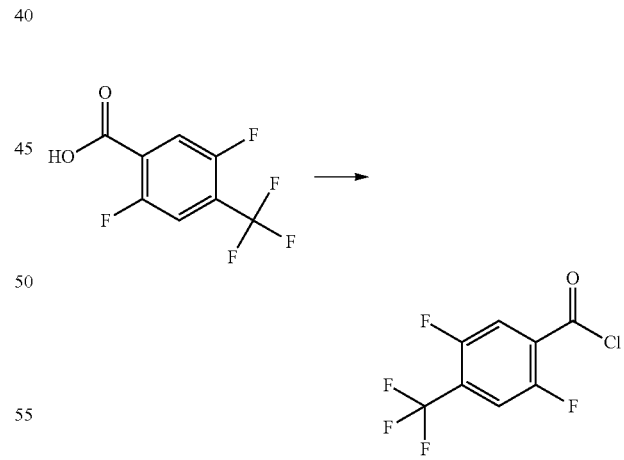

To a solution of 2,5-difluoro-4-(trifluoromethyl)benzoic acid (2.00 g, 8.85 mmol) and DMF (63 µL, 0.81 mmol) in dichloromethane (23 mL) at 0° C. was added oxalyl chloride (5.5 g, 3.8 mL, 43 mmol) dropwise. The mixture was stirred at 50° C. for 40 minutes under $N_2$ atmosphere and the conversion was monitored by UPLC via test for piperidine adduct formation. The solvent was evaporated under reduced pressure to afford 2,5-difluoro-4-(trifluoromethyl)benzoyl chloride (1.90 g, 88%).

Step 2: 4-[[2,5-Difluoro-4-(trifluoromethyl)benzoyl]amino]pyridine-2-carboxamide

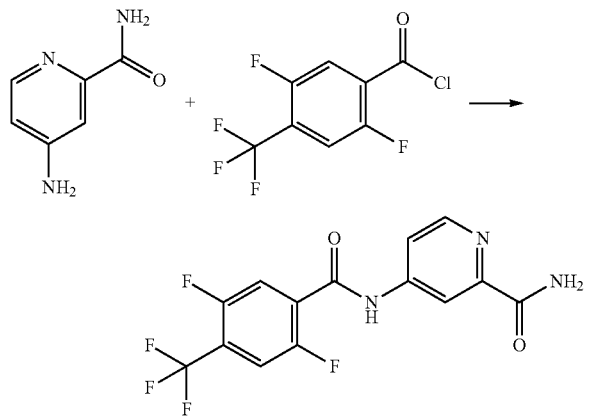 [SMILES: NC(=O)c1cc(N)ccn1 ; O=C(Cl)c1cc(F)c(C(F)(F)F)cc1F ; NC(=O)c1cc(NC(=O)c2cc(F)c(C(F)(F)F)cc2F)ccn1]

To a solution of 4-aminopyridine-2-carboxamide (0.73 g, 5.3 mmol), DMAP (0.13 g, 1.1 mmol) and DIEA (2.1 g, 2.8 mL, 16 mmol) in dichloromethane (13 mL) at 0° C. was added a solution of 2,5-difluoro-4-(trifluoromethyl)benzoyl chloride (1.3 g, 5.3 mmol) in THF (13 mL) dropwise. The reaction was stirred at room temperature for 16 hours. The reaction was diluted with ethyl acetate and washed with aqueous NaHCO$_3$, water and brine. The organic layer was dried over Na$_2$SO$_4$, filtered and concentrated in vacuo. Silica gel chromatography (0-40% ethyl acetate/hexanes) provided 4-[[2,5-difluoro-4-(trifluoromethyl)benzoyl]amino]pyridine-2-carboxamide (1.7 g, 85%). ESI-MS m/z calc. 345.05, found 346.2 (M+1)+; retention time (Method A): 0.53 minutes (1 minute run).

Step 3: 4-[[5-Fluoro-2-[4-(trifluoromethoxy)phenoxy]-4-(trifluoromethyl)benzoyl]amino]pyridine-2-carboxamide (76)

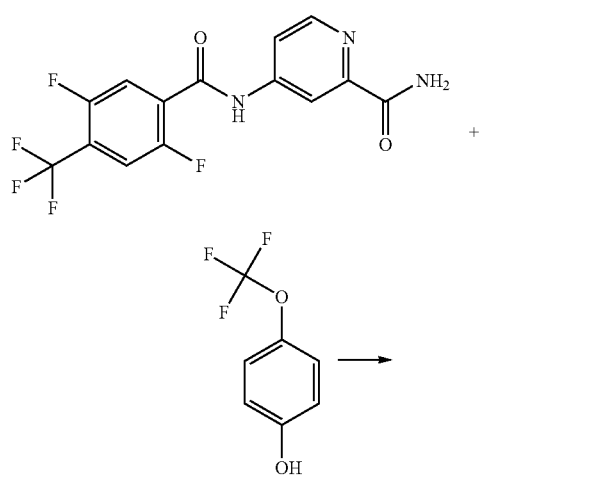

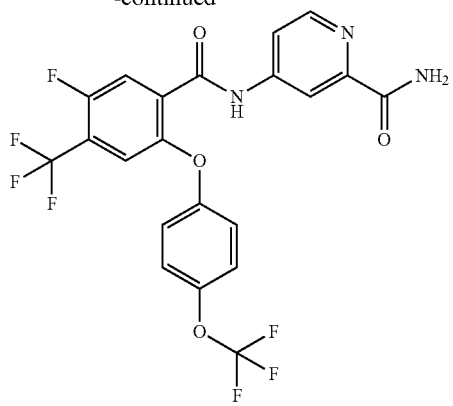

A mixture of 4-[[2,5-difluoro-4-(trifluoromethyl)benzoyl]amino]pyridine-2-carboxamide (100 mg, 0.27 mmol), 4-(trifluoromethoxy)phenol (47 mg, 34 µL, 0.27 mmol), K$_2$CO$_3$ (111 mg, 0.80 mmol) and DMF (1 mL) was heated at 80° C. for 16 hours. HPLC purification (1-99% acetonitrile/5 mM HCl) provided 4-[[5-fluoro-2-[4-(trifluoromethoxy)phenoxy]-4-(trifluoromethyl)benzoyl]amino]pyridine-2-carboxamide (40 mg, 30%) as a white solid. ESI-MS m/z calc. 503.07, found 504.2 (M+1)+; retention time (Method B): 1.77 minutes (3 minute run). $^1$H NMR (400 MHz, DMSO-d6) δ 11.17 (s, 1H), 8.52 (d, J=5.5 Hz, 1H), 8.26 (d, J=2.2 Hz, 1H), 8.10 (d, J=2.8 Hz, 1H), 8.02 (d, J=10.1 Hz, 1H), 7.77 (dd, J=5.6, 2.2 Hz, 1H), 7.66 (d, J=2.8 Hz, 1H), 7.59 (d, J=5.8 Hz, 1H), 7.40-7.32 (m, 2H), 7.21-7.09 (m, 2H) ppm. $^{19}$F NMR (376 MHz, DMSO-d6) δ −57.22, −60.39, −120.34 ppm.

Example 118

N-(3-Carbamoyl-4-fluoro-phenyl)-5-fluoro-2-[4-(trifluoromethoxy)phenoxy]-4-(trifluoromethyl)benzamide (77)

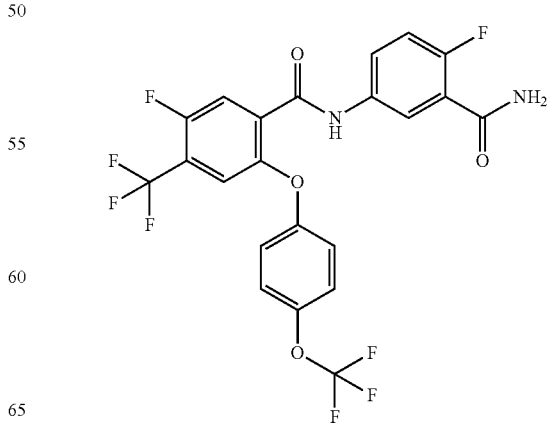

Step 1: N-(3-Carbamoyl-4-fluoro-phenyl)-2,5-difluoro-4-(trifluoromethyl)benzamide

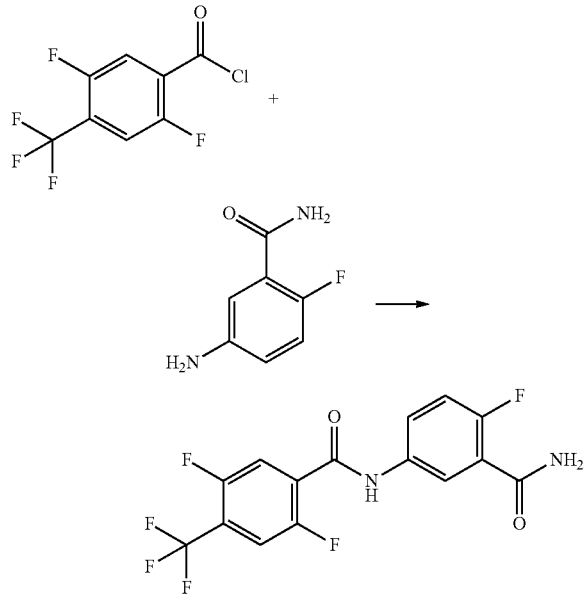

This compound was made in an analogous fashion to Example 117, Step 2, except employing 5-amino-2-fluoro-benzamide in the amide formation step. The yield of the desired product after purification was 1.0 g (89%). ESI-MS m/z calc. 362.05, found 363.2 (M+1)+; retention time (Method A): 0.55 minutes (1 minute run).

Step 2: N-(3-Carbamoyl-4-fluoro-phenyl)-5-fluoro-2-[4-(trifluoromethoxy)phenoxy]-4-(trifluoromethyl)benzamide (77)

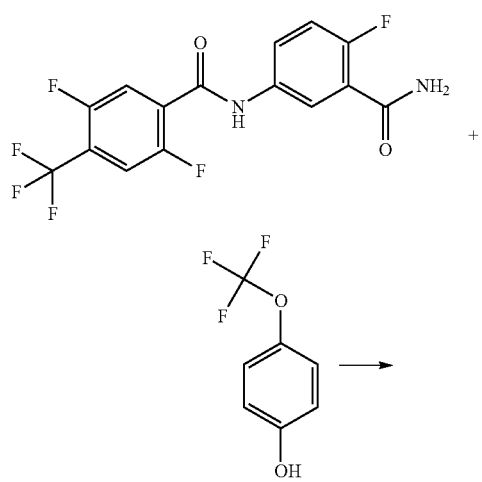

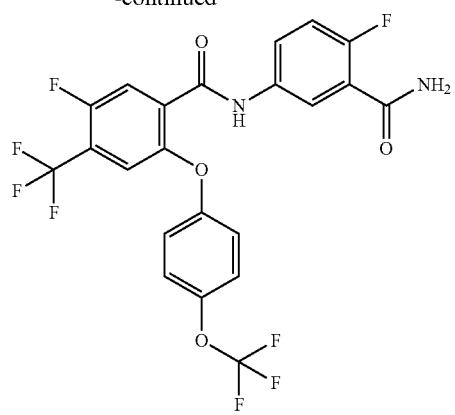

A mixture of N-(3-carbamoyl-4-fluoro-phenyl)-2,5-difluoro-4-(trifluoromethyl)benzamide (100 mg, 0.254 mmol), 4-(trifluoromethoxy)phenol (45 mg, 0.25 mmol), $K_2CO_3$ (105 mg, 0.762 mmol) in DMF (1 mL) was heated at 100° C. for 2 hours. The reaction mixture was filtered, diluted with DMSO and purified by HPLC (1-99% acetonitrile/5 mM HCl) to provide N-(3-carbamoyl-4-fluoro-phenyl)-5-fluoro-2-[4-(trifluoromethoxy)phenoxy]-4-(trifluoromethyl)benzamide (19 mg, 14%) as a white solid. ESI-MS m/z calc. 520.07, found 521.1 (M+1)+; retention time (Method B): 1.9 minutes (3 minute run). $^1$H NMR (400 MHz, DMSO-d6) δ 10.74 (s, 1H), 8.07-7.87 (m, 2H), 7.78-7.63 (m, 3H), 7.56 (d, J=5.8 Hz, 1H), 7.44-7.32 (m, 2H), 7.32-7.24 (m, 1H), 7.22-7.05 (m, 2H) ppm. $^{19}$F NMR (376 MHz, DMSO-d6) δ −57.19, −60.36, −118.49, −120.43 ppm.

Example 119

3-Fluoro-6-[[3-fluoro-5-[2-methoxy-4-(trifluoromethoxy)phenoxy]pyridine-4-carbonyl]amino]pyridine-2-carboxamide (164)

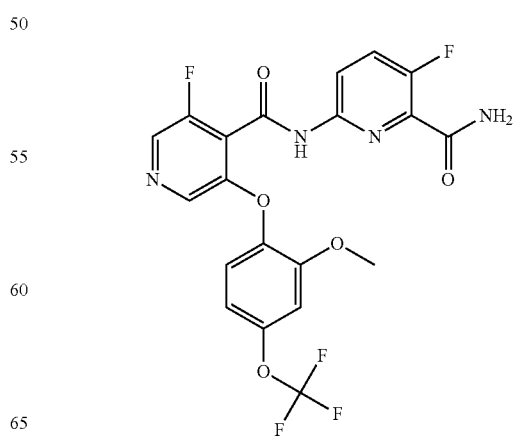

Step 1: Methyl 3,5-difluoropyridine-4-carboxylate

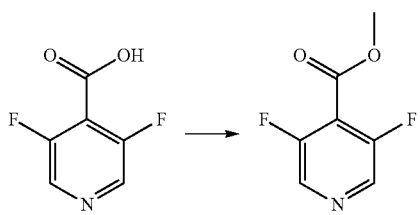

3,5-Difluoropyridine-4-carboxylic acid (5.39 g, 33.9 mmol) was suspended in methanol (50 mL) and stirred vigorously with heating (71° C.) as thionyl chloride (5.4 mL, 74 mmol) was added dropwise. The reaction was heated for 24 hours, and then the heat was removed and the reaction was stirred at room temperature for 48 hours. The reaction mixture was concentrated in vacuo and the residue was purified by silica gel chromatography (0-50% ethyl acetate/hexanes) to provide methyl 3,5-difluoropyridine-4-carboxylate (2.332 g, 40%) as a clear, colorless oil. $^1$H NMR (400 MHz, CDCl$_3$) δ 8.46 (s, 2H), 4.01 (s, 3H) ppm.

Step 2: Methyl 3-fluoro-5-[2-methoxy-4-(trifluoromethoxy)phenoxy]pyridine-4-carboxylate

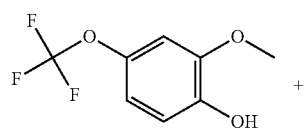

Methyl 3,5-difluoropyridine-4-carboxylate (1.012 g, 5.846 mmol), 2-methoxy-4-(trifluoromethoxy)phenol (1.354 g, 6.505 mmol) and cesium carbonate (2.48 g, 7.61 mmol) were combined in DMF (22 mL). The mixture was stirred at 50° C. for 3 hours. The reaction mixture was cooled, diluted with water and extracted with ethyl acetate. The organic layer was washed with water (2×), dried by passing through a phase separation cartridge, and concentrated in vacuo. Silica gel chromatography (0-70% ethyl acetate/hexanes) provided methyl 3-fluoro-5-[2-methoxy-4-(trifluoromethoxy)phenoxy]pyridine-4-carboxylate (2.02 g, 96%) as a clear oil. ESI-MS m/z calc. 361.06, found 362.0 (M+1)+; retention time (Method F): 0.98 minutes (1.5 minute run). $^1$H NMR (400 MHz, DMSO-d6) δ 8.53 (d, J=0.4 Hz, 1H), 8.04 (s, 1H), 7.34-7.22 (m, 3H), 7.00 (ddq, J=8.9, 2.4, 1.2 Hz, 2H), 3.87 (s, 4H), 3.80 (d, J=12.8 Hz, 1H), 3.80 (s, 4H), 3.34 (s, OH), 2.89 (s, 1H), 2.74 (d, J=0.7 Hz, 1H) ppm.

Step 3: 3-Fluoro-5-[2-methoxy-4-(trifluoromethoxy)phenoxy]pyridine-4-carboxylic acid

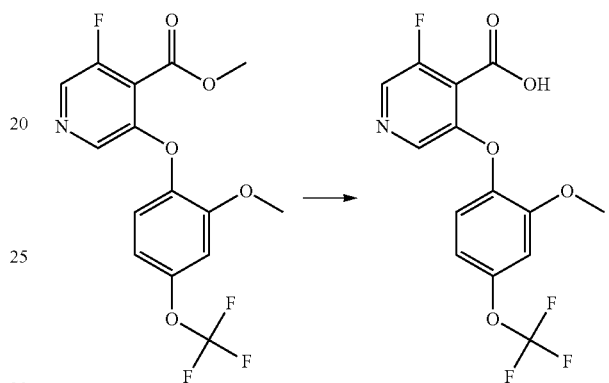

Methyl 3-fluoro-5-[2-methoxy-4-(trifluoromethoxy)phenoxy]pyridine-4-carboxylate (250 mg, 0.692 mmol) and aqueous NaOH (370 µL of 2 M, 0.7400 mmol) in THF (7 mL) were stirred at 71° C. for 72 hours. The reaction mixture was concentrated in vacuo to provide 3-fluoro-5-[2-methoxy-4-(trifluoromethoxy)phenoxy]pyridine-4-carboxylic acid (240 mg, 100%). ESI-MS m/z calc. 347.0417, found 347.9 (M+1)+; retention time (Method F): 0.55 minutes (1.5 minute run).

Step 4: N-(6-Bromo-5-fluoro-2-pyridyl)-3-fluoro-5-[2-methoxy-4-(trifluoromethoxy)phenoxy]pyridine-4-carboxamide

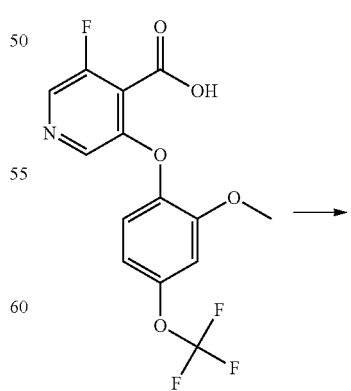

507

-continued

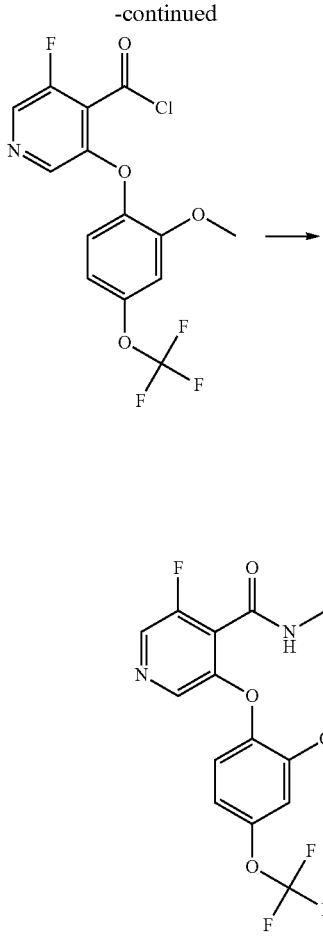

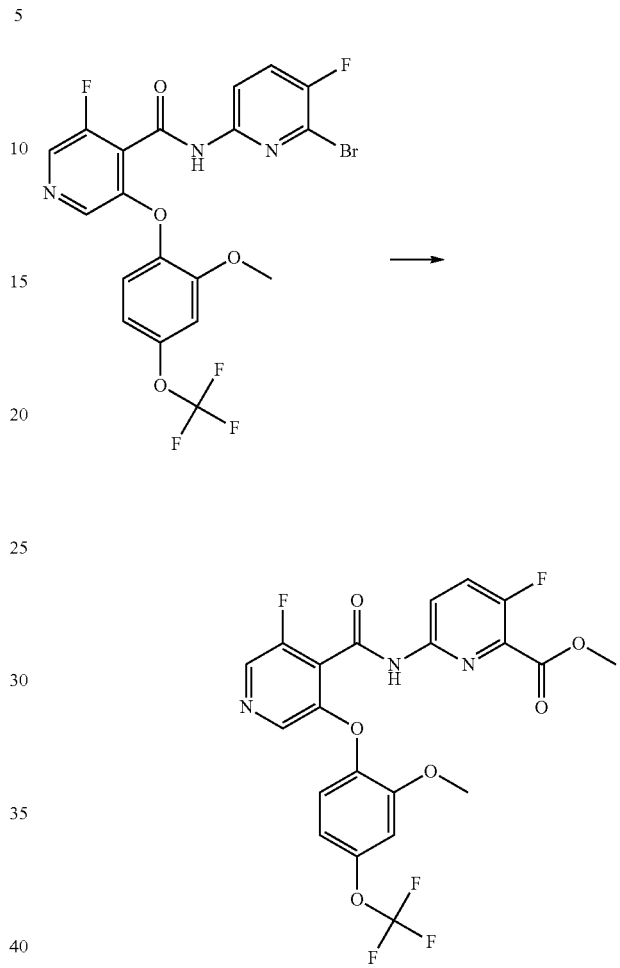

Step 5: Methyl 3-fluoro-6-[[3-fluoro-5-[2-methoxy-4-(trifluoromethoxy)phenoxy]pyridine-4-carbonyl]amino]pyridine-2-carboxylate To a solution of 3-fluoro-5-[2-methoxy-4-(trifluoromethoxy)phenoxy]pyridine-4-carboxylic acid (240 mg, 0.691 mmol) in dichloromethane (5 mL) at 0° C. was added DMF (24 mg, 0.33 mmol) and oxalyl chloride (290 mg, 200 µL, 2.29 mmol) dropwise. The reaction mixture was stirred for 2 hours then concentrated in vacuo to afford 3-fluoro-5-(2-methoxy-4-(trifluoromethoxy)phenoxy)isonicotinoyl chloride as a pale yellow oil Conversion to the acid chloride was monitored through formation of the methyl ester following methanol quench. The oil was dissolved in dichloromethane (5 mL) and added dropwise to a solution of 6-bromo-5-fluoro-pyridin-2-amine (130 mg, 0.681 mmol) and triethylamine (436 mg, 601 µL, 4.31 mmol) in dichloromethane (3 mL) at 0° C. The resulting mixture was allowed to warm to room temperature and stirred for 16 hours. Silica gel chromatography (0-100% ethyl acetate/petroleum ether) provided N-(6-bromo-5-fluoro-2-pyridyl)-3-fluoro-5-[2-methoxy-4-(trifluoromethoxy)phenoxy]pyridine-4-carboxamide (170 mg, 47%) as an off-white waxy solid. ESI-MS m/z calc. 518.99, found 521.9 (M+1)+; 519.8 (M−1)−; retention time (Method F): 1.06 minutes (1.5 minute run). $^1$H NMR (400 MHz, CDCl$_3$) δ 9.47 (s, 1H), 8.35 (dd, J=8.8, 3.3 Hz, 1H), 8.34 (s, 1H), 8.00 (s, 1H), 7.51 (dd, J=8.8, 6.9 Hz, 1H), 7.34-7.26 (m, 1H), 6.93 (dtt, J=3.8, 2.6, 1.3 Hz, 3H), 3.94 (s, 3H) ppm.

In a pressure tube N-(6-bromo-5-fluoro-2-pyridyl)-3-fluoro-5-[2-methoxy-4-(trifluoromethoxy)phenoxy]pyridine-4-carboxamide (50 mg, 0.096 mmol) was dissolved in methanol (2.3 mL) and triethylamine (21 mg, 29 µL, 0.21 mmol) and Pd(dppf)Cl$_2$·DCM (18 mg, 0.022 mmol) were added. Carbon monoxide was bubbled through the reaction mixture for 5 minutes. The reaction mixture was sealed and heated to 75° C. for 16 hours. The mixture was cooled and concentrated in vacuo. Silica gel chromatography (0-90% ethyl acetate/petroleum ether) provided methyl 3-fluoro-6-[[3-fluoro-5-[2-methoxy-4-(trifluoromethoxy)phenoxy]pyridine-4-carbonyl]amino]pyridine-2-carboxylate (20 mg, 42%). ESI-MS m/z calc. 499.08, found 500.2 (M+1)+; 498.2 (M−1)−; retention time (Method F): 0.97 minutes (1.5 minute run). $^1$H NMR (400 MHz, CDCl$_3$) δ 9.35 (s, 1H), 8.63 (dd, J=9.1, 3.2 Hz, 1H), 8.38 (s, 1H), 8.03 (s, 1H), 7.66 (t, J=9.1 Hz, 1H), 7.26 (m, 1H), 6.97-6.89 (m, 1H), 6.92 (s, 1H), 3.98 (d, J=13.4 Hz, 6H) ppm.

Step 6: 3-Fluoro-6-[[3-fluoro-5-[2-methoxy-4-(trifluoromethoxy)phenoxy]pyridine-4-carbonyl]amino]pyridine-2-carboxamide (164)

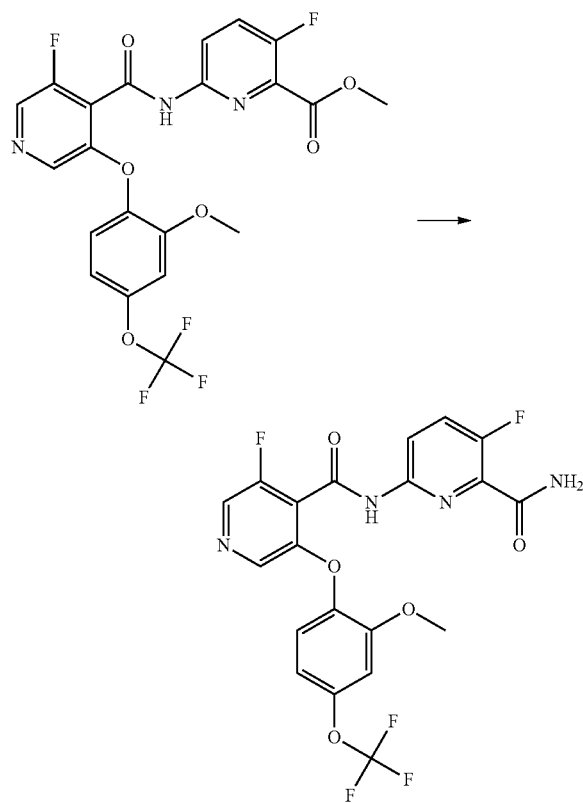

Methyl 3-fluoro-6-[[3-fluoro-5-[2-methoxy-4-(trifluoromethoxy)phenoxy]pyridine-4-carbonyl]amino]pyridine-2-carboxylate (20 mg, 0.04 mmol) was dissolved in a solution of ammonia (2 mL of 7 M in methanol, 14 mmol) and stirred at 45° C. in a sealed tube overnight. The reaction mixture was cooled and concentrated in vacuo. HPLC purification (37-100% acetonitrile/0.1% ammonium hydroxide) and lyophilization of product fractions provided 3-fluoro-6-[[3-fluoro-5-[2-methoxy-4-(trifluoromethoxy)phenoxy]pyridine-4-carbonyl]amino]pyridine-2-carboxamide (3 mg, 15%). ESI-MS m/z calc. 484.08, found 484.91 (M+1)+; 482.96 (M−1)−; retention time (Method E): 2.66 minutes (5 minute run). ¹H NMR (400 MHz, CD₃OD) δ 8.44 (dd, J=9.1, 3.1 Hz, 1H), 8.39 (s, 1H), 7.97 (s, 1H), 7.81 (t, J=9.5 Hz, 1H), 7.31 (d, J=8.8 Hz, 1H), 7.08 (d, J=2.6 Hz, 1H), 6.93 (ddt, J=8.8, 2.0, 1.0 Hz, 1H), 3.82 (s, 3H) ppm.

Example 120

N-(2-Carbamoyl-4-pyridyl)-3-fluoro-5-[2-methoxy-4-(trifluoromethoxy)phenoxy]pyridine-4-carboxamide (165)

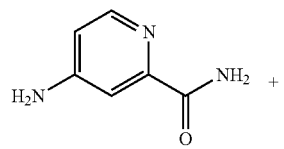

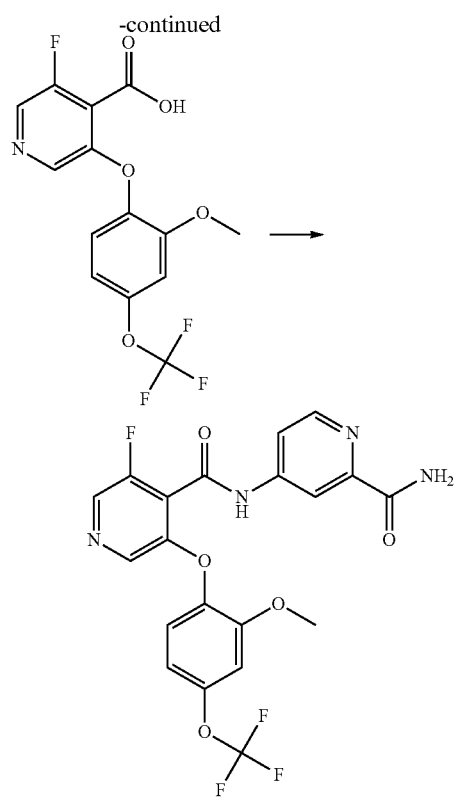

This compound was made in an analogous fashion to Example 119, step 4, except employing 4-aminopyridine-2-carboxamide in the amide formation step. The yield of the desired product after purification was 4 mg (3%). ESI-MS m/z calc. 466.09, found 467.05 (M+1)+; retention time (Method E): 2.64 minutes (5 minute run). ¹H NMR (400 MHz, DMSO-d6) δ 11.49 (s, 1H), 8.55 (d, J=10.9 Hz, 2H), 8.27 (d, J=2.2 Hz, 1H), 8.08 (d, J=14.7 Hz, 2H), 7.81-7.75 (m, 1H), 7.66 (s, 1H), 7.31 (d, J=8.8 Hz, 1H), 7.19 (d, J=2.7 Hz, 1H), 6.98 (ddq, J=8.7, 2.4, 1.2 Hz, 1H), 3.78 (s, 3H) ppm.

Example 121

N-(3-Carbamoyl-4-fluoro-phenyl)-3-fluoro-5-[2-methoxy-4-(trifluoromethoxy)phenoxy]pyridine-4-carboxamide (117)

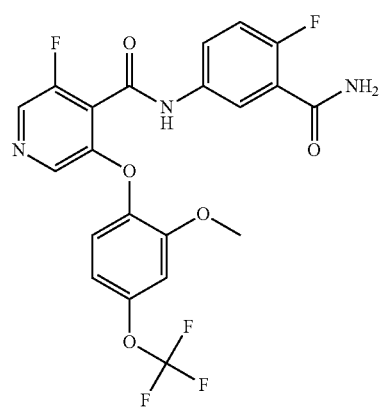 [SMILES: COc1cc(OC(F)(F)F)ccc1Oc1cncc(F)c1C(=O)Nc1ccc(F)c(C(N)=O)c1]

511

Step 1: N-(3-carbamoyl-4-fluoro-phenyl)-3,5-difluoro-pyridine-4-carboxamide

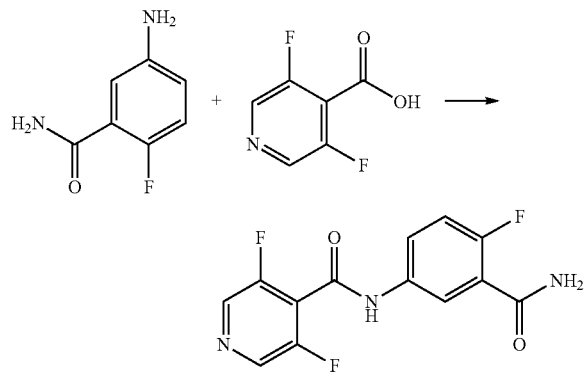

To a solution of 3,5-difluoropyridine-4-carboxylic acid (200 mg, 0.880 mmol) in dichloromethane (2.6 mL) at 0° C. was added DMF (21 μL, 0.27 mmol) and oxalyl chloride (250 μL, 2.87 mmol) dropwise. The reaction was stirred for 2 hours then concentrated in vacuo. The residue was dissolved in dichloromethane (2.6 mL), cooled to 0° C. and treated with 5-amino-2-fluoro-benzamide hydrochloride (280 mg, 1.23 mmol) and triethylamine (740 μL, 5.28 mmol). The reaction mixture was allowed to come to room temperature over 2 hours, then was diluted with water and extracted with dichloromethane (2×10 mL). The combined organics were dried using a phase separation cartridge and concentrated in vacuo to provide N-(3-carbamoyl-4-fluoro-phenyl)-3,5-difluoro-pyridine-4-carboxamide (130 mg, 50%). ESI-MS m/z calc. 295.06, found 295.9 (M+1)+; 293.9 (M−1)−; retention time (Method F): 0.53 minutes (1.5 minute run).

Step 2: N-(3-Carbamoyl-4-fluoro-phenyl)-3-fluoro-5-[2-methoxy-4-(trifluoromethoxy)phenoxy]pyridine-4-carboxamide (117)

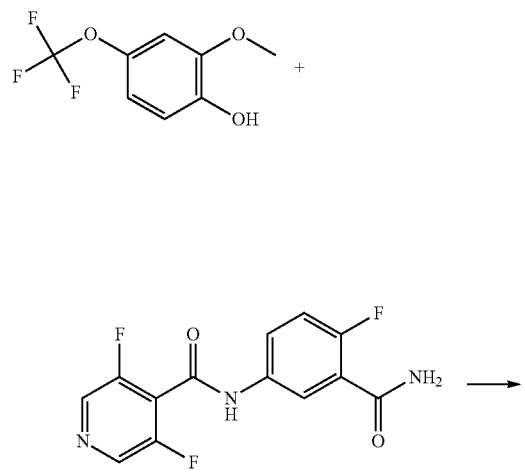

512

-continued

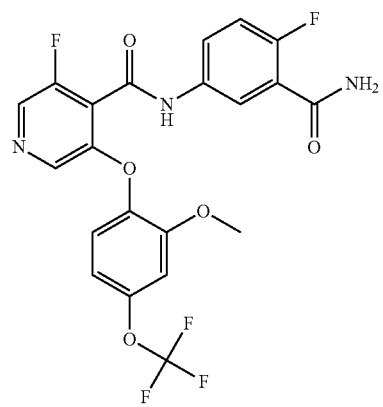

N-(3-carbamoyl-4-fluoro-phenyl)-3,5-difluoro-pyridine-4-carboxamide (130 mg, 0.440 mmol), 2-methoxy-4-(trifluoromethoxy)phenol (102 mg, 0.492 mmol) and $Cs_2CO_3$ (185 mg, 0.570 mmol) were combined in DMF (1.3 mL). The mixture was stirred at room temperature for 30 days. The reaction mixture was diluted with water and extracted with ethyl acetate. The organic layer was washed further with water, dried by passing through a phase separation cartridge and concentrated in vacuo. HPLC purification (37-100% acetonitrile/0.1% ammonium hydroxide) provided N-(3-carbamoyl-4-fluoro-phenyl)-3-fluoro-5-[2-methoxy-4-(trifluoromethoxy)phenoxy]pyridine-4-carboxamide (6.2 mg, 1%). ESI-MS m/z calc. 483.09, found 483.76 (M+1)+; retention time (Method E): 2.65 minutes (5 minute run). $^1$H NMR (400 MHz, $CD_3OD$) δ 8.38 (s, 1H), 8.04 (dd, J=6.4, 2.8 Hz, 1H), 7.97 (s, 1H), 7.89 (ddd, J=9.0, 4.4, 2.8 Hz, 1H), 7.32-7.20 (m, 2H), 7.08 (d, J=2.6 Hz, 1H), 6.98-6.89 (m, 1H), 3.82 (s, 3H) ppm.

Example 122

4-[[3-Fluoro-5-[2-methoxy-4-(trifluoromethoxy)phenoxy]pyridine-4-carbonyl]amino]-5-methyl-pyridine-2-carboxamide (151)

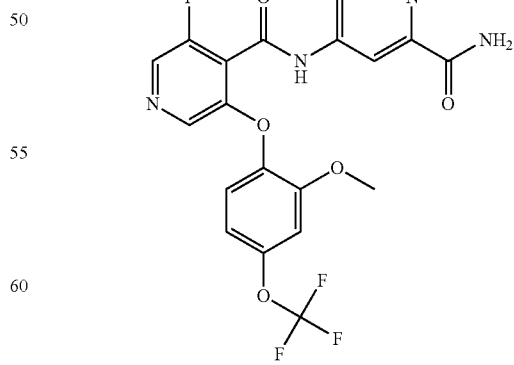

Step 1: N-(2-Bromo-5-methyl-4-pyridyl)-3,5-difluoro-pyridine-4-carboxamide

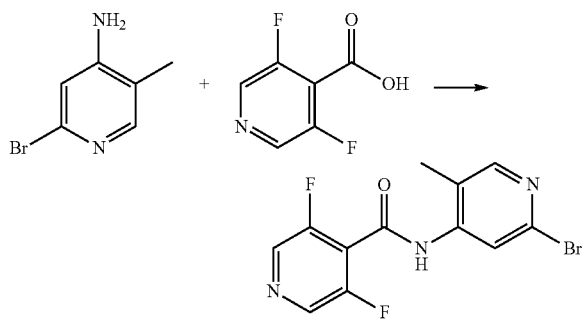

This compound was made in an analogous fashion to Example 121, Step 1, except employing 2-bromo-5-methyl-pyridin-4-amine in the amide formation step. The yield of the desired product after purification was 430 mg (60%). ESI-MS m/z calc. 326.98, found 329.9 (M+1)+; 325.8 (M−1)−; retention time (Method E): 1.51 minutes (5 minute run). $^1$H NMR (400 MHz, DMSO-d6) δ 10.77 (s, 1H), 8.76 (s, 2H), 8.33-8.27 (m, 1H), 8.10 (s, 1H), 2.23 (d, J=0.8 Hz, 3H) ppm.

Step 2: N-(2-Bromo-5-methyl-4-pyridyl)-3-fluoro-5-[2-methoxy-4-(trifluoromethoxy)phenoxy]pyridine-4-carboxamide

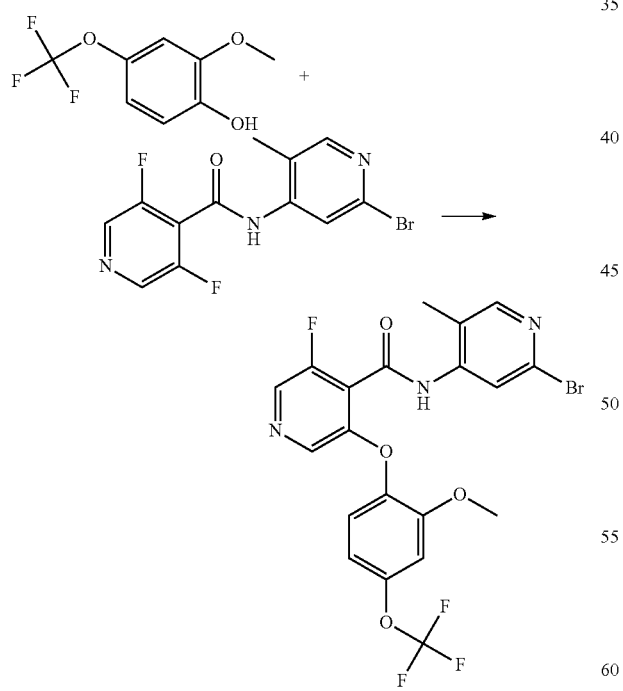

N-(2-bromo-5-methyl-4-pyridyl)-3,5-difluoro-pyridine-4-carboxamide (125 mg, 0.381 mmol), 2-methoxy-4-(trifluoromethoxy)phenol (90 mg, 0.43 mmol) and Cs$_2$CO$_3$ (160 mg, 0.491 mmol) were combined in DMF (3 mL) and stirred at 61° C. for 72 hours. The reaction mixture was concentrated in vacuo and purified by silica gel chromatography (0-90% ethyl acetate/hexanes) to provide N-(2-bromo-5-methyl-4-pyridyl)-3-fluoro-5-[2-methoxy-4-(trifluoromethoxy)phenoxy]pyridine-4-carboxamide (108 mg, 55%). ESI-MS m/z calc. 515.01, found 518.1 (M+1)+; retention time (Method F): 1.0 minutes (1.5 minute run). $^1$H NMR (400 MHz, CDCl$_3$) δ 8.54 (s, 1H), 8.48 (s, 1H), 8.37 (s, 1H), 8.11 (s, 1H), 7.94 (s, 1H), 7.25 (dd, J=25.6, 9.0 Hz, 1H), 7.00-6.86 (m, 2H), 3.81 (s, 3H), 2.15 (t, J=1.9 Hz, 3H) ppm.

Step 3: Methyl 4-[[3-fluoro-5-[2-methoxy-4-(trifluoromethoxy)phenoxy]pyridine-4-carbonyl]amino]-5-methyl-pyridine-2-carboxylate

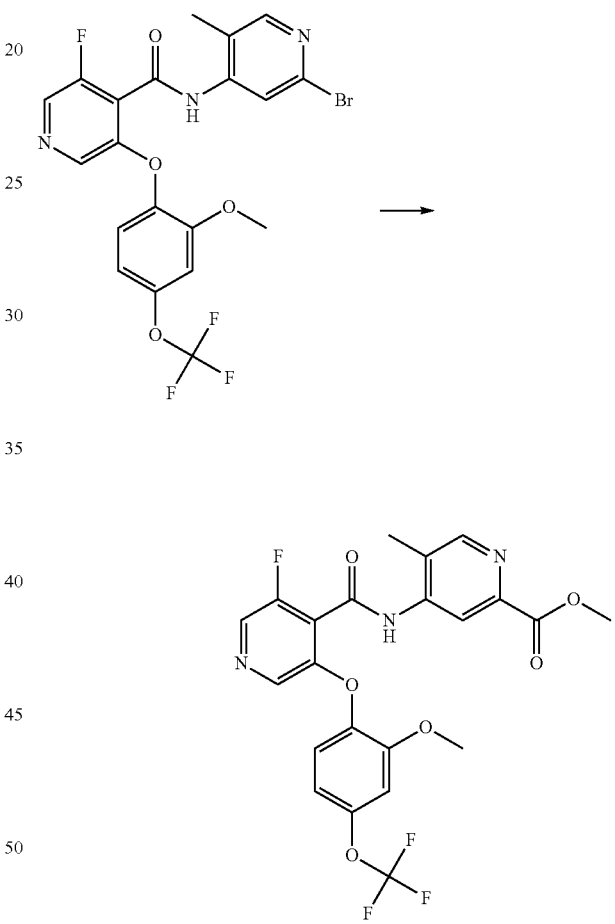

This compound was made in an analogous fashion to Example 119, Step 5, except employing N-(2-bromo-5-methyl-4-pyridyl)-3-fluoro-5-[2-methoxy-4-(trifluoromethoxy)phenoxy]pyridine-4-carboxamide in the carbonylation step. The yield of the desired product after purification was 15 mg (30%). ESI-MS m/z calc. 495.10, found 496.0 (M+1)+; 493.9 (M−1)−; retention time (Method F): 0.88 minutes (1.5 minute run time).

Step 4: 4-[[3-Fluoro-5-[2-methoxy-4-(trifluoromethoxy)phenoxy]pyridine-4-carbonyl]amino]-5-methyl-pyridine-2-carboxamide (151)

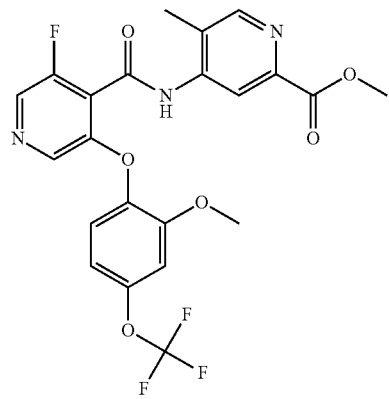

This compound was made in an analogous fashion to Example 119, Step 6, except employing methyl 4-[[3-fluoro-5-[2-methoxy-4-(trifluoromethoxy)phenoxy]pyridine-4-carbonyl]amino]-5-methyl-pyridine-2-carboxylate in the carboxamide formation step. The yield of the desired product after purification was 2 mg (13%). ESI-MS m/z calc. 480.11, found 481.21 (M+1)+; retention time (Method E): 2.66 minutes (5 minute run). $^1$H NMR (400 MHz, DMSO-d6) δ 10.63 (s, 1H), 8.56 (s, 1H), 8.45 (d, J=19.7 Hz, 2H), 8.04 (d, J=11.0 Hz, 2H), 7.61 (s, 1H), 7.32 (d, J=8.7 Hz, 1H), 7.23 (s, 1H), 7.01 (d, J=9.1 Hz, 1H), 3.82 (s, 3H), 2.28 (d, J=8.9 Hz, 3H) ppm.

Example 123

5-[[4-Chloro-2-methoxy-6-[2-methoxy-4-(trifluoromethoxy)phenoxy]benzoyl]amino]pyridine-2-carboxamide (204)

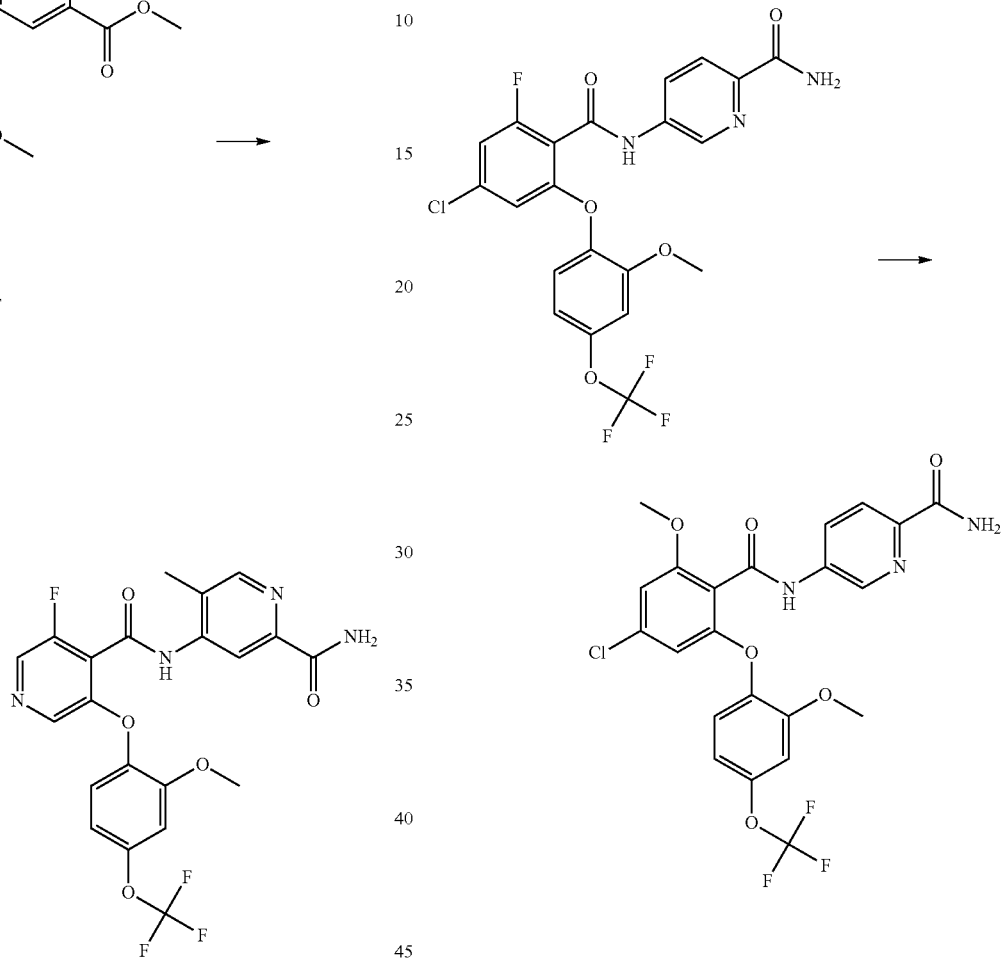

5-[[4-Chloro-2-fluoro-6-[2-methoxy-4-(trifluoromethoxy)phenoxy]benzoyl]amino]pyridine-2-carboxamide (185, 45 mg, 0.089 mmol) and sodium methoxide (900 μL of 0.5 M in methanol, 0.45 mmol) were combined in a microwave vial and the sealed reaction mixture heated at 80° C. for 16 hours. The reaction was cooled, treated with 2 drops of trifluoroacetic acid, and diluted with DMSO (2 mL). HPLC purification (1-99% acetonitrile/0.1% ammonia hydroxide) and freeze-drying of product fractions provided 5-[[4-chloro-2-methoxy-6-[2-methoxy-4-(trifluoromethoxy)phenoxy]benzoyl]amino]pyridine-2-carboxamide (20 mg, 42%) as an off-white solid. ESI-MS m/z calc. 511.08, found 512.0 (M+1)+; 510.0 (M−1)−; retention time (Method E): 3.12 minutes (5 minute run). $^1$H NMR (500 MHz, DMSO-d6) δ 13.21 (s, 1H), 11.13 (d, J=2.4 Hz, 1H), 10.55 (dd, J=8.6, 2.5 Hz, 1H), 10.33-10.24 (m, 2H), 9.80 (d, J=2.8 Hz, 1H), 9.53-9.44 (m, 2H), 9.33-9.23 (m, 2H), 8.62 (d, J=1.7 Hz, 1H), 6.15 (s, 3H), 6.07 (s, 3H) ppm.

Example 124

4-[[4-Chloro-2-methoxy-6-[2-methoxy-4-(trifluoromethoxy)phenoxy]benzoyl]amino]-5-methyl-pyridine-2-carboxamide (133)

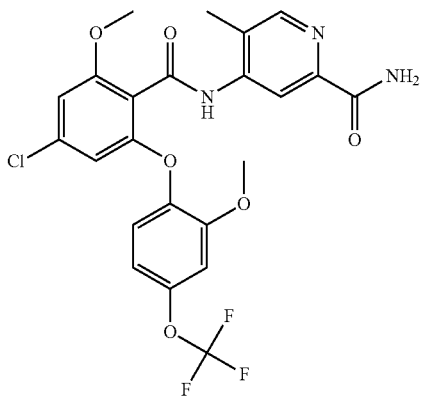 [SMILES: COc1cc(OC(F)(F)F)ccc1Oc1cc(Cl)cc(OC)c1C(=O)Nc1cc(C(N)=O)ncc1C]

Step 1: 4-Chloro-2-methoxy-6-[2-methoxy-4-(trifluoromethoxy)phenoxy]benzaldehyde

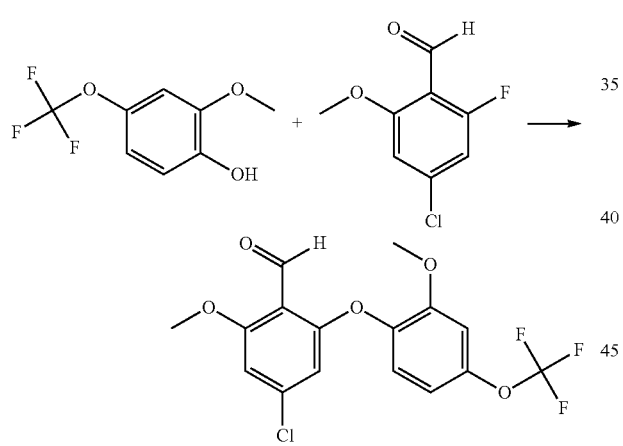

A mixture of 2-methoxy-4-(trifluoromethoxy)phenol (1.15 g, 5.53 mmol), Cs$_2$CO$_3$ (2.20 g, 6.75 mmol) and 4-chloro-2-fluoro-6-methoxy-benzaldehyde (1.00 g, 5.30 mmol) in DMF (9 mL) was stirred for 16 hours at room temperature. The reaction mixture was concentrated and the residue was partitioned between water and dichloromethane. The organic layer was dried over MgSO$_4$, filtered and concentrated in vacuo. Silica gel chromatography (0-50% ethyl acetate/petroleum ether) provided 4-chloro-2-methoxy-6-[2-methoxy-4-(trifluoromethoxy)phenoxy]benzaldehyde (1.880 g, 94%) as a white solid. ESI-MS m/z calc. 376.03, found 377.1 (M+1)+; retention time (Method F): 1.07 minutes (1.5 minute run). $^1$H NMR (500 MHz, DMSO-d6) δ 10.39 (s, 1H), 7.28-7.21 (m, 2H), 7.06-6.98 (m, 2H), 6.26 (d, J=1.8 Hz, 1H), 3.92 (s, 3H), 3.80 (s, 3H) ppm.

Step 2: 4-Chloro-2-methoxy-6-[2-methoxy-4-(trifluoromethoxy)phenoxy]benzoic acid

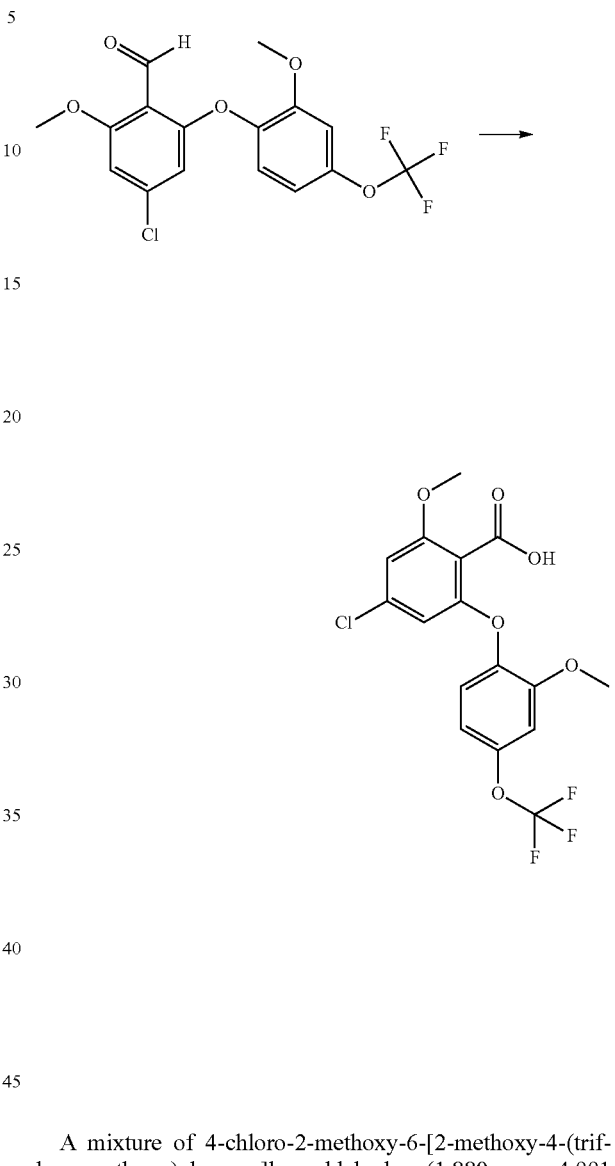

A mixture of 4-chloro-2-methoxy-6-[2-methoxy-4-(trifluoromethoxy)phenoxy]benzaldehyde (1.880 g, 4.991 mmol), sodium dihydrogenphosphate hydrate (0.630 g, 5.25 mmol) and 2-methyl-2-butene (10 mL of 2 M in THF, 20 mmol) in tert-butyl alcohol (17 mL)/water (8.5 mL) at 0° C. was treated with sodium chlorite (0.670 g, 5.926 mmol) portionwise over 30 minutes. The mixture was allowed to warm to room temperature then stirred for 16 hours. The reaction mixture was acidified to pH1-2 using 2 M HCl and partitioned with dichloromethane. The organic layer was separated, dried using a phase separation cartridge and concentrated in vacuo to afford 4-chloro-2-methoxy-6-[2-methoxy-4-(trifluoromethoxy)phenoxy]benzoic acid (1.890 g, 96%) as a white solid. ESI-MS m/z calc. 392.03, found 393.1 (M+1)+; 391.1 (M−1)−; retention time (Method F): 0.69 minutes (1.5 minute run). $^1$H NMR (500 MHz, DMSO-d6) δ 13.14 (s, 1H), 7.21 (d, J=2.7 Hz, 1H), 7.12 (d, J=8.8 Hz, 1H), 6.98 (ddq, J=8.8, 2.4, 1.1 Hz, 1H), 6.95 (d, J=1.7 Hz, 1H), 6.28 (d, J=1.7 Hz, 1H), 3.85 (s, 3H), 3.81 (s, 3H) ppm.

Step 3: N-(2-Bromo-5-methyl-4-pyridyl)-4-chloro-2-methoxy-6-[2-methoxy-4-(trifluoromethoxy)phenoxy]benzamide

Step 4: Methyl 4-[[4-chloro-2-methoxy-6-[2-methoxy-4-(trifluoromethoxy)phenoxy]benzoyl]amino]-5-methyl-pyridine-2-carboxylate

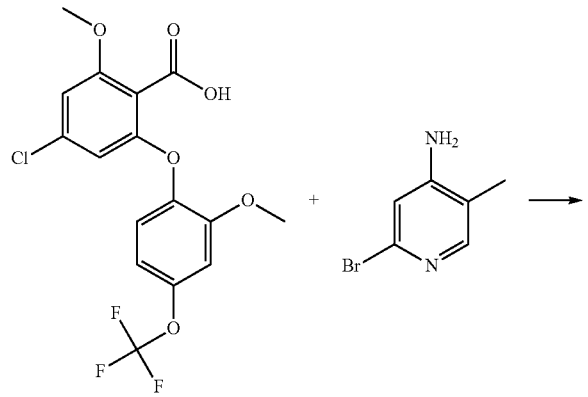

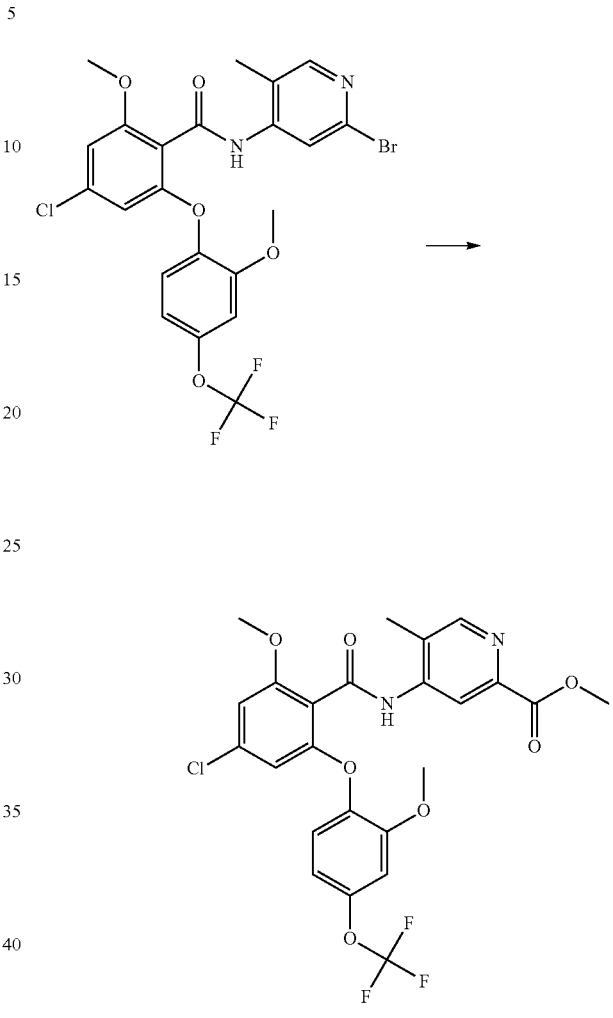

To a solution of 4-chloro-2-methoxy-6-[2-methoxy-4-(trifluoromethoxy)phenoxy]benzoic acid (320 mg, 0.766 mmol) in dichloromethane (5.3 mL) at 0° C. was added DMF (7 μL, 0.09 mmol) and oxalyl chloride (225 μL, 2.58 mmol) dropwise. The reaction mixture was allowed to warm to room temperature over 3.5 hours then concentrated in vacuo. The residue was dissolved in dichloromethane (5.3 mL), cooled to 0° C. and treated with 2-bromo-5-methyl-pyridin-4-amine (186 mg, 0.995 mmol) and triethylamine (565 μL, 4.05 mmol). The resulting mixture was allowed to warm to room temperature and stirred for 16 hours. The reaction mixture was diluted with water (10 mL) and extracted with dichloromethane (2×10 mL). The combined organic layers were dried over MgSO$_4$, filtered and concentrated in vacuo. Silica gel chromatography (20-50% ethyl acetate/petroleum ether) provided N-(2-bromo-5-methyl-4-pyridyl)-4-chloro-2-methoxy-6-[2-methoxy-4-(trifluoromethoxy)phenoxy]benzamide (300 mg, 70%) as a yellow oil. ESI-MS m/z calc. 560.00, found 563.0 (M+1)+; retention time (Method F): 1.1 minutes (1.5 minute run).

In a pressure tube N-(2-bromo-5-methyl-4-pyridyl)-4-chloro-2-methoxy-6-[2-methoxy-4-(trifluoromethoxy)phenoxy]benzamide (300 mg, 0.497 mmol) was dissolved in methanol (10 mL) and triethylamine (107 mg, 1.06 mmol) and Pd(dppf)Cl$_2$·DCM (82 mg, 0.10 mmol) was added. Carbon monoxide was bubbled through the vigorously stirring reaction mixture for 5 minutes. The reaction vessel was sealed and heated to 75° C. for 16 hours. The reaction mixture was filtered through a pad of Celite eluting with methanol and concentrated in vacuo. Silica gel chromatography (30-80% ethyl acetate/petroleum ether) provided methyl 4-[[4-chloro-2-methoxy-6-[2-methoxy-4-(trifluoromethoxy)phenoxy]benzoyl]amino]-5-methyl-pyridine-2-carboxylate (98 mg, 36%) as a yellow oil. ESI-MS m/z calc. 540.09, found 541.0 (M+1)+; retention time (Method F): 1.02 minutes (1.5 minute run).

Step 5: 4-[[4-Chloro-2-methoxy-6-[2-methoxy-4-(trifluoromethoxy)phenoxy]benzoyl]amino]-5-methyl-pyridine-2-carboxamide (133)

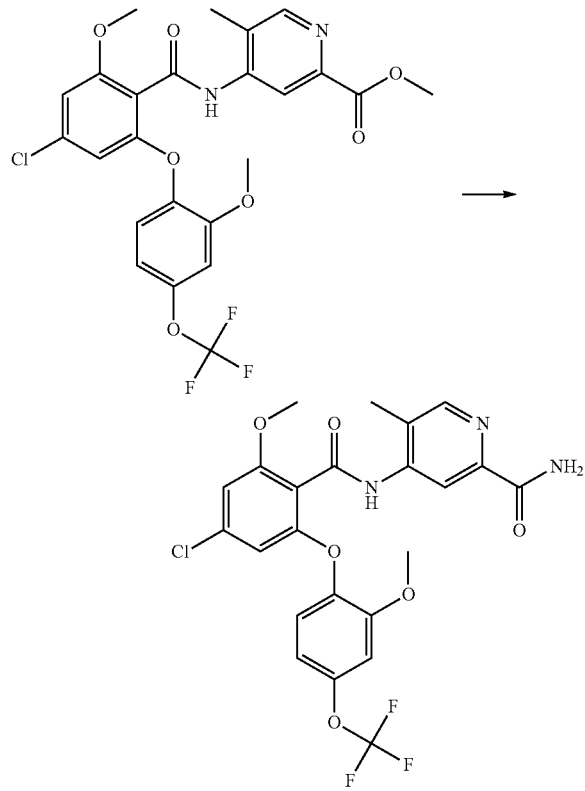

A mixture of methyl 4-[[4-chloro-2-methoxy-6-[2-methoxy-4-(trifluoromethoxy)phenoxy]benzoyl]amino]-5-methyl-pyridine-2-carboxylate (98 mg, 0.18 mmol) and ammonia (5 mL of 4 M in methanol, 20 mmol) was stirred at room temperature for 16 hours then concentrated in vacuo. HPLC purification (37-100% acetonitrile/0.1% ammonium hydroxide) provided 4-[[4-chloro-2-methoxy-6-[2-methoxy-4-(trifluoromethoxy)phenoxy]benzoyl]amino]-5-methyl-pyridine-2-carboxamide (39.1 mg, 41%) as a white solid. ESI-MS m/z calc. 525.09, found 526.0 (M+1)+; retention time (Method E): 3.31 minutes (5 minute run). $^1$H NMR (500 MHz, DMSO-d6) δ 10.13 (s, 1H), 8.44 (d, J=13.2 Hz, 2H), 8.03 (d, J=2.9 Hz, 1H), 7.56 (d, J=2.9 Hz, 1H), 7.32-6.91 (m, 4H), 6.33 (d, J=1.7 Hz, 1H), 3.89 (s, 3H), 3.82 (s, 3H), 2.27 (s, 3H) ppm.

Example 125

4-[[2,4-Dichloro-6-(4-fluorophenoxy)benzoyl]amino]pyridine-2-carboxamide (177)

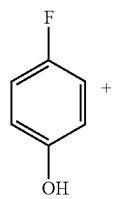

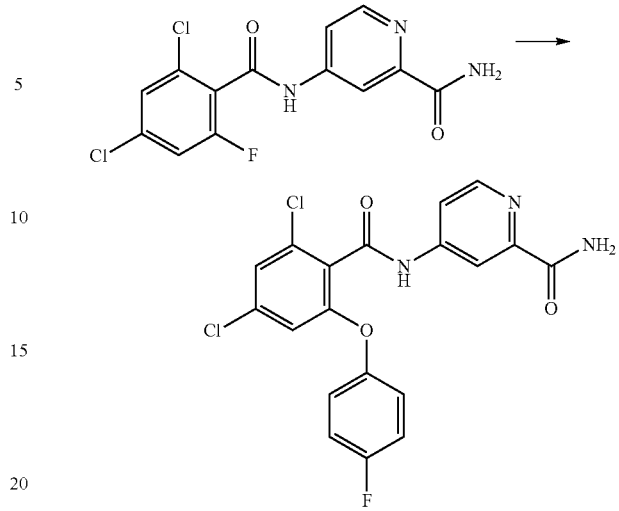

To 4-[(2,4-dichloro-6-fluoro-benzoyl)amino]pyridine-2-carboxamide (prepared as described in Example 112, step 1, 45 mg, 0.14 mmol) in DMF (1 mL) was added 4-fluorophenol (15 mg, 0.13 mmol) followed by K$_2$CO$_3$ (57 mg, 0.41 mmol). The reaction was heated at 80° C. for 30 minutes. HPLC purification (1-99% acetonitrile/5 mM HCl) provided 4-[[2,4-dichloro-6-(4-fluorophenoxy)benzoyl]amino]pyridine-2-carboxamide (38 mg, 66%). ESI-MS m/z calc. 419.02, found 419.95 (M+1)+; retention time (Method B): 1.63 minutes (3 minute run). $^1$H NMR (400 MHz, DMSO-d6) δ 11.35 (s, 1H), 8.54 (d, J=5.5 Hz, 1H), 8.30 (d, J=2.2 Hz, 1H), 8.11 (d, J=2.8 Hz, 1H), 7.81 (dd, J=5.5, 2.2 Hz, 1H), 7.67 (d, J=2.8 Hz, 1H), 7.60 (d, J=1.8 Hz, 1H), 7.33-7.25 (m, 2H), 7.25-7.18 (m, 2H), 6.93 (d, J=1.8 Hz, 1H) ppm.

Example 126

5-[[2,4-Dichloro-6-(4-fluorophenoxy)benzoyl]amino]pyridine-2-carboxamide (181)

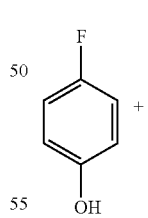

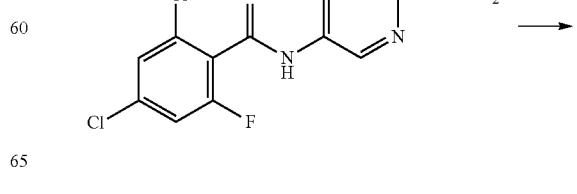

-continued

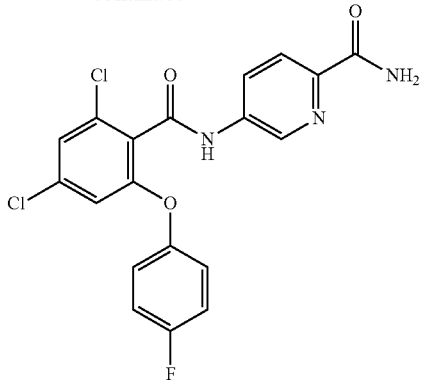

To a solution of 5-[(2,4-dichloro-6-fluoro-benzoyl)amino]pyridine-2-carboxamide (prepared as described in Example 111, Step 3, 44 mg, 0.134 mmol) in DMF (0.5 mL) was added 4-fluorophenol (15 mg, 0.13 mmol) followed by $K_2CO_3$ (56 mg, 0.40 mmol). The reaction was heated at 80° C. for 1 hour, then diluted with DMSO (0.5 mL) and filtered. Purification by HPLC (1-99% acetonitrile/5 mM HCl) provided 5-[[2,4-dichloro-6-(4-fluorophenoxy)benzoyl]amino]pyridine-2-carboxamide (26.7 mg, 47%). ESI-MS m/z calc. 419.02, found 419.9 (M+1)+; retention time (Method B): 1.63 minutes (3 minutes). $^1$H NMR (400 MHz, DMSO-d6) δ 11.25 (s, 1H), 8.83 (d, J=2.5 Hz, 1H), 8.26 (dd, J=8.5, 2.5 Hz, 1H), 8.04 (d, J=8.6 Hz, 1H), 8.02 (d, J=2.7 Hz, 1H), 7.60 (d, J=1.7 Hz, 1H), 7.57 (d, J=3.2 Hz, 0H), 7.28 (t, J=8.7 Hz, 2H), 7.21 (dd, J=9.2, 4.5 Hz, 2H), 6.94 (d, J=1.7 Hz, 1H) ppm.

Example 127

4-[[2-Methoxy-6-[2-(trideuteriomethoxy)-4-(trifluoromethoxy)phenoxy]-3-(trifluoromethyl)benzoyl]amino]-5-methyl-pyridine-2-carboxamide (146)

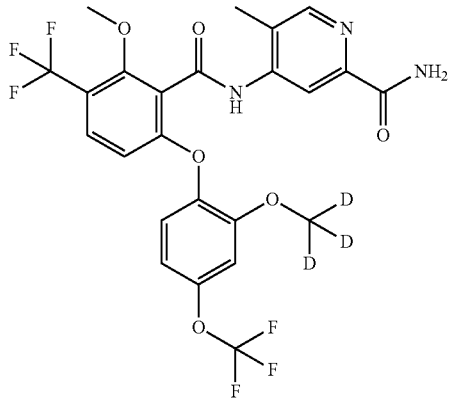 [SMILES: [2H]C([2H])([2H])Oc1cc(OC(F)(F)F)ccc1Oc1ccc(C(F)(F)F)c(OC)c1C(=O)Nc1cc(C(N)=O)ncc1C]

To 4-[[2-fluoro-6-[2-(trideuteriomethoxy)-4-(trifluoromethoxy)phenoxy]-3-(trifluoromethyl)benzoyl]amino]-5-methyl-pyridine-2-carboxamide (59 mg, 0.11 mmol, prepared as described in Example 28) was added a solution of sodium methoxide (1 mL of 0.5 M in methanol, 0.5 mmol) and the reaction was heated at 80° C. for 23 hours. The reaction mixture was filtered and the resulting solid was purified by HPLC (10-99% acetonitrile/water) to provide 4-[[2-methoxy-6-[2-(trideuteriomethoxy)-4-(trifluoromethoxy)phenoxy]-3-(trifluoromethyl)benzoyl]amino]-5-methyl-pyridine-2-carboxamide (32.6 mg, 55%). ESI-MS m/z calc. 562.13, found 563.0 (M+1)+; retention time (Method C): 2.51 minutes (5 minute run). $^1$H NMR (400 MHz, DMSO-d6) δ 10.48 (s, 1H), 8.48 (s, 1H), 8.46 (s, 1H), 8.09-8.01 (m, 1H), 7.68 (d, J=9.0 Hz, 1H), 7.65-7.57 (m, 1H), 7.33 (d, J=8.8 Hz, 1H), 7.25 (d, J=2.8 Hz, 1H), 7.10-7.00 (m, 1H), 6.52 (d, J=8.9 Hz, 1H), 3.98 (s, 3H), 2.32 (s, 3H) ppm.

Example 128

N-(3-Carbamoyl-4-fluoro-phenyl)-6-[(6-chloro-2-methoxy-3-pyridyl)oxy]-2-fluoro-3-(trifluoromethyl)benzamide (54)

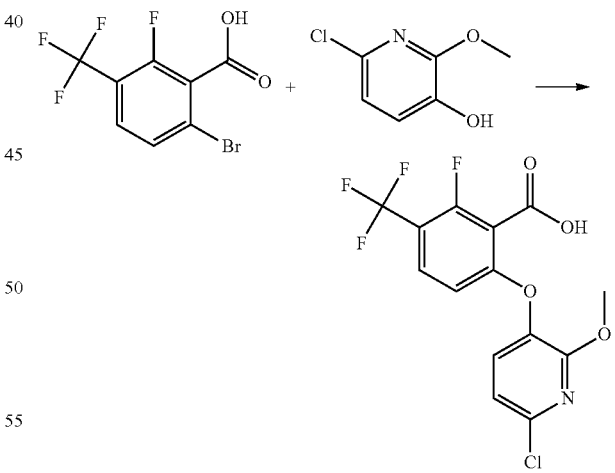

Step 1: 6-[(6-Chloro-2-methoxy-3-pyridyl)oxy]-2-fluoro-3-(trifluoromethyl)benzoic acid To a pressure flask was added 6-bromo-2-fluoro-3-(trifluoromethyl)benzoic acid (1.80 g, 6.27 mmol), 6-chloro-2-methoxy-pyridin-3-ol (1.00 g, 6.27 mmol), cesium carbonate (4.0 g, 12 mmol) and toluene (30 mL). The reaction mixture was bubbled with $N_2$ for 10 minutes, then copper (I) iodide (240 mg, 1.26 mmol) was added. The flask was flushed with $N_2$, sealed, and heated at 100° C. with vigorous stirring for 1 hour. The mixture was allowed to cool to room temperature then diluted with ethyl acetate and water. The water layer was acidified with 1 M HCl (30 mL) and the product extracted into the ethyl acetate. The organic layer was washed with brine, dried over Na₂SO₄, filtered and concentrated in vacuo to a dark green oil. To the oil was added minimal amount of dichloromethane and hexanes to form a precipitate. The solid was filtered, washed with hexanes and dried to provide 6-[(6-chloro-2-methoxy-3-pyridyl)oxy]-2-fluoro-3-(trifluoromethyl)benzoic acid (1.3 g, 57%). ESI-MS m/z calc. 365.01, found 365.9 (M+1)+; retention time (Method A): 0.67 minutes (1.2 minute run). ¹H NMR (400 MHz, DMSO-d6) δ 14.20 (br s, 1H), 7.86-7.57 (m, 2H), 7.19 (d, 1H), 6.86-6.78 (m, 1H), 3.86 (s, 3H) ppm.

Step 2: 6-[(6-Chloro-2-methoxy-3-pyridyl)oxy]-2-fluoro-3-(trifluoromethyl)benzoyl chloride

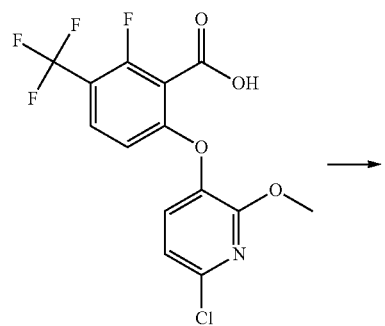

To a suspension of 6-[(6-chloro-2-methoxy-3-pyridyl)oxy]-2-fluoro-3-(trifluoromethyl)benzoic acid (600 mg, 1.64 mmol) and DMF (5 μL, 0.06 mmol) in dichloromethane (9 mL) at 0° C. was added oxalyl chloride (0.7 mL, 8 mmol) dropwise. The reaction was allowed to come to room temperature and stirred for 30 minutes. Conversion to the desired acid chloride was monitored by UPLC via test for morpholine adduct formation. The reaction mixture was concentrated under reduced pressure then co-evaporated with dichloromethane (3×55 mL) to afford 6-[(6-chloro-2-methoxy-3-pyridyl)oxy]-2-fluoro-3-(trifluoromethyl)benzoyl chloride.

Step 3: N-(3-Carbamoyl-4-fluoro-phenyl)-6-[(6-chloro-2-methoxy-3-pyridyl)oxy]-2-fluoro-3-(trifluoromethyl)benzamide (54)

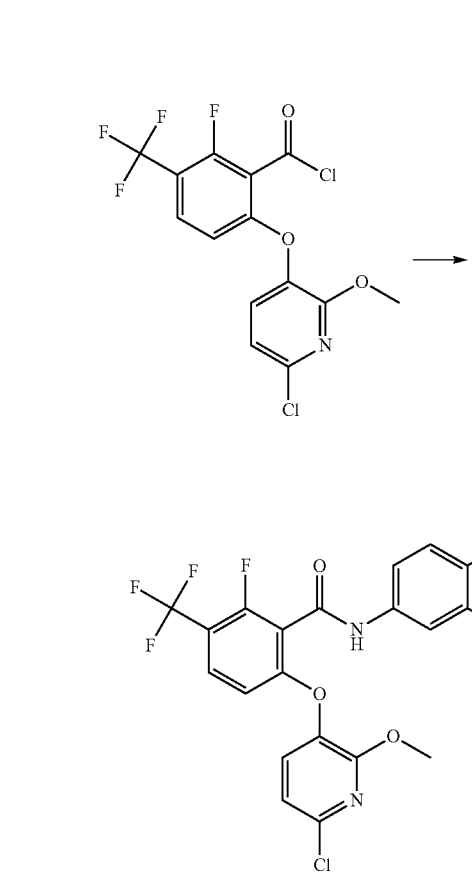

5-Amino-2-fluoro-benzamide (40 mg, 0.26 mmol) was suspended in dichloromethane (1 mL) and DIEA (101 mg, 136 μL, 0.781 mmol) and cooled to 0° C., then treated with a cold solution of 6-[(6-chloro-2-methoxy-3-pyridyl)oxy]-2-fluoro-3-(trifluoromethyl)benzoyl chloride (100 mg, 0.260 mmol) in dichloromethane (1 mL). The reaction was then allowed to warm to room temperature and stirred for 16 hours. The reaction was concentrated in vacuo, dissolved in DMSO and purified by HPLC (10-99% acetonitrile/5 mM HCl) to provide N-(3-carbamoyl-4-fluoro-phenyl)-6-[(6-chloro-2-methoxy-3-pyridyl)oxy]-2-fluoro-3-(trifluoromethyl)benzamide (5.3 mg, 4.06%). ESI-MS m/z calc. 501.05, found 502.0 (M+1)+; retention time (Method B): 1.66 minutes (3 minute run). ¹H NMR (400 MHz, DMSO-d6) δ 11.03 (s, 1H), 7.98 (dd, J=6.3, 2.8 Hz, 1H), 7.82-7.74 (m, 3H), 7.72 (d, J=8.1 Hz, 1H), 7.69 (s, 1H), 7.30 (dd, J=10.1, 8.9 Hz, 1H), 7.19 (d, J=8.1 Hz, 1H), 6.84 (d, J=8.9 Hz, 1H), 3.86 (s, 3H) ppm.

Example 129

N-(3-Carbamoyl-4-fluoro-phenyl)-2-fluoro-4-methoxy-6-[4-(trifluoromethoxy)phenoxy]-3-(trifluoromethyl)benzamide (216)

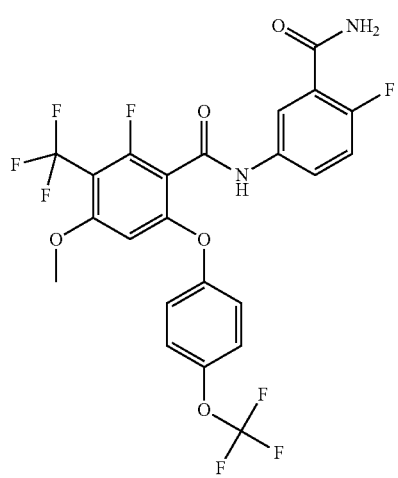 [SMILES: COc1cc(Oc2ccc(OC(F)(F)F)cc2)c(C(=O)Nc2ccc(F)c(C(N)=O)c2)c(F)c1C(F)(F)F]

Step 1: 5-Bromo-1-fluoro-3-methoxy-2-(trifluoromethyl)benzene

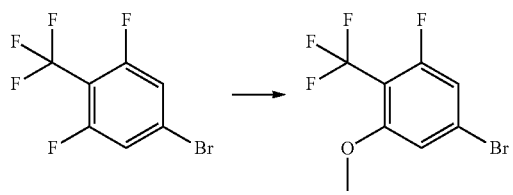

To a solution of 5-bromo-1,3-difluoro-2-(trifluoromethyl)benzene (1.0 g, 3.8 mmol) in DMF (10 mL) at 0° C. was added a solution of sodium methoxide (12 mL of 0.5 M in methanol, 6 mmol) dropwise. The cooling bath was removed and the reaction mixture was stirred for 2 days at room temperature. The reaction mixture was diluted with dichloromethane and washed with water. The separated organic layer was washed with brine, dried over MgSO$_4$, filtered and concentrated in vacuo. Silica gel chromatography using hexanes as eluent provided 5-bromo-1-fluoro-3-methoxy-2-(trifluoromethyl)benzene (600 mg, 57%) as a colorless oil. $^1$H NMR (400 MHz, DMSO-d6) δ 7.49-7.29 (m, 2H), 3.94 (s, 3H) ppm. $^{19}$F NMR (376 MHz, DMSO-d6) δ −55.27 (d, J=29.6 Hz), −111.65−−112.01 (m) ppm.

Step 2: Ethyl 6-bromo-2-fluoro-4-methoxy-3-(trifluoromethyl)benzoate

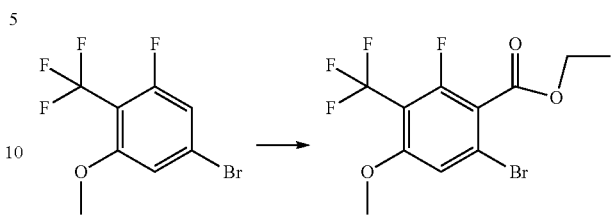

A solution of 5-bromo-1-fluoro-3-methoxy-2-(trifluoromethyl)benzene (1.19 g, 4.36 mmol) in THF (12 mL) was cooled to −78° C. (dry ice/acetone bath) and a solution of LDA (2.1 mL of 2 M, 4.2 mmol) was added dropwise while maintaining the internal temperature below −70° C. The reaction mixture was stirred at −70° C. for 30 minutes, then ethyl carbonochloridate (1 mL, 10 mmol) was added dropwise maintaining the internal temperature below −70° C. The reaction mixture was allowed to warm to room temperature and was stirred for 1 hour. The reaction mixture was quenched with saturate aqueous NH$_4$Cl solution and extracted with ethyl acetate. The organic layer was dried over MgSO$_4$, filtered and concentrated in vacuo. Silica gel chromatography (0-5% ethyl acetate/hexanes) provided ethyl 6-bromo-2-fluoro-4-methoxy-3-(trifluoromethyl)benzoate (585 mg, 39%). ESI-MS m/z calc. 343.96, found 347.0 (M+1)+; retention time (Method B): 1.58 minutes (3 minute run). $^1$H NMR (400 MHz, DMSO-d6) δ 7.53 (dd, J=1.7, 0.8 Hz, 1H), 4.38 (q, J=7.1 Hz, 2H), 3.99 (s, 3H), 1.31 (t, J=7.1 Hz, 3H) ppm.

Step 3: 6-Bromo-2-fluoro-4-methoxy-3-(trifluoromethyl)benzoic acid

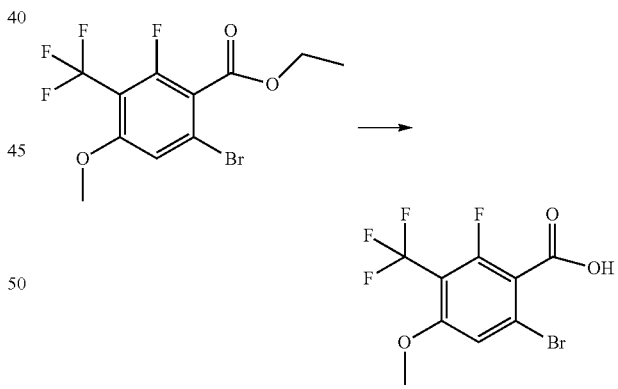

To a solution of ethyl 6-bromo-2-fluoro-4-methoxy-3-(trifluoromethyl)benzoate (580 mg, 1.68 mmol) in methanol (6 mL) was added an aqueous NaOH (6 mL of 6 M, 36 mmol) and the reaction mixture was stirred for 24 hours. The reaction mixture was cooled to 0° C. and quenched with 6 M HCl. The resulting precipitate was filtered and washed with water. The solid was dissolved in dichloromethane, dried over MgSO$_4$, filtered and concentrated in vacuo to provide 6-bromo-2-fluoro-4-methoxy-3-(trifluoromethyl)benzoic acid (456 mg, 86%). ESI-MS m/z calc. 315.93, found 319.0 (M+2)+; retention time (Method B): 1.03 minutes (3 minute run).

Step 4: 2-Fluoro-4-methoxy-6-[4-(trifluoromethoxy)phenoxy]-3-(trifluoromethyl)benzoic acid

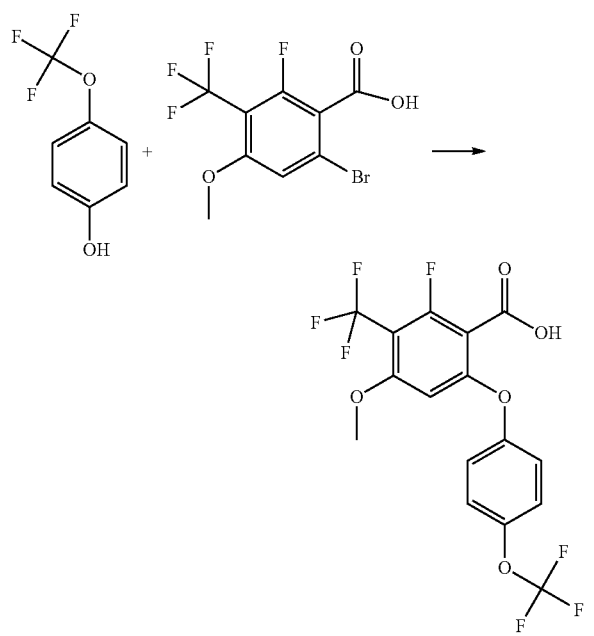

To a pressure vessel were added 6-bromo-2-fluoro-4-methoxy-3-(trifluoromethyl)benzoic acid (285 mg, 0.899 mmol), 4-(trifluoromethoxy)phenol (145 mg, 0.814 mmol), Cs₂CO₃ (313 mg, 0.961 mmol) and toluene (3 mL). The reaction mixture was bubbled with N₂ for 10 minutes then treated with copper (I) iodide (60 mg, 0.32 mmol). The flask was flushed with N₂, sealed, and heated at 100° C. with vigorous stirring for 4 hours. The mixture was cooled to room temperature, acidified with 1 M HCl, filtered and the aqueous layer was extracted with ethyl acetate. The organic layer was washed with brine, dried over Na₂SO₄, filtered and concentrated in vacuo. Silica gel column chromatography (0-100% ethyl acetate/hexanes) provided 2-fluoro-4-methoxy-6-[4-(trifluoromethoxy)phenoxy]-3-(trifluoromethyl)benzoic acid (213 mg, 57%) ESI-MS m/z calc. 414.03, found 415.1 (M+1)+; retention time (Method B): 1.79 minutes (3 minute run). ¹H NMR (400 MHz, DMSO-d6) δ 13.69 (s, 1H), 7.42 (dq, J=7.7, 1.0 Hz, 2H), 7.26-7.17 (m, 2H), 6.72 (s, 1H), 3.82 (s, 3H) ppm.

Step 5: N-(3-Carbamoyl-4-fluoro-phenyl)-2-fluoro-4-methoxy-6-[4-(trifluoromethoxy)phenoxy]-3-(trifluoromethyl)benzamide (216)

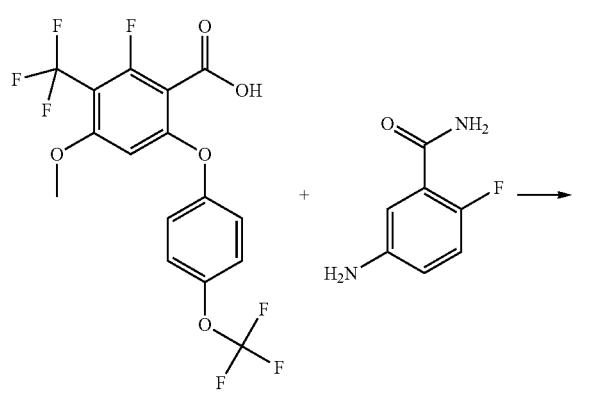

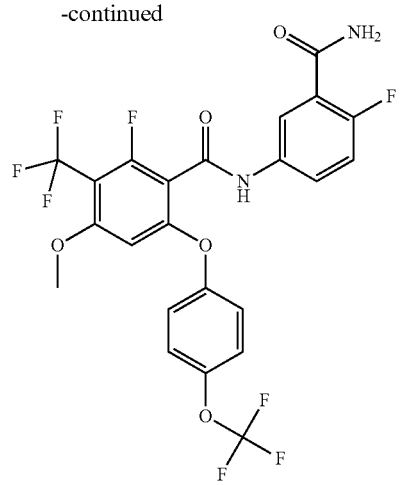

To a flask charged with 2-fluoro-4-methoxy-6-[4-(trifluoromethoxy)phenoxy]-3-(trifluoromethyl)benzoic acid (205 mg, 0.495 mmol), 5-amino-2-fluoro-benzamide (81 mg, 0.53 mmol) and HATU (230 mg, 0.605 mmol) in DMF (2.5 mL) was added DIEA (300 μL, 1.72 mmol) and the reaction mixture was stirred overnight at room temperature. The reaction mixture was diluted with water and the aqueous layer was extracted with ethyl acetate. The organic layer was washed with brine, dried over MgSO₄, filtered and concentrated in vacuo. The crude material was purified by HPLC (1-99% acetonitrile/5 mM HCl) to provide N-(3-carbamoyl-4-fluoro-phenyl)-2-fluoro-4-methoxy-6-[4-(trifluoromethoxy)phenoxy]-3-(trifluoromethyl)benzamide (110 mg, 38%). ESI-MS m/z calc. 550.07, found 551.3 (M+1)+; retention time (Method B): 1.54 minutes (3 minute run). ¹H NMR (400 MHz, DMSO-d6) δ 10.82 (s, 1H), 7.90 (dd, J=6.4, 2.8 Hz, 1H), 7.76-7.62 (m, 3H), 7.44-7.35 (m, 2H), 7.30-7.19 (m, 3H), 6.69 (s, 1H), 3.83 (s, 3H) ppm.

Example 130

4-Benzyloxy-N-(3-carbamoyl-4-fluoro-phenyl)-2-fluoro-6-[4-(trifluoromethoxy)phenoxy]-3-(trifluoromethyl)benzamide (215)

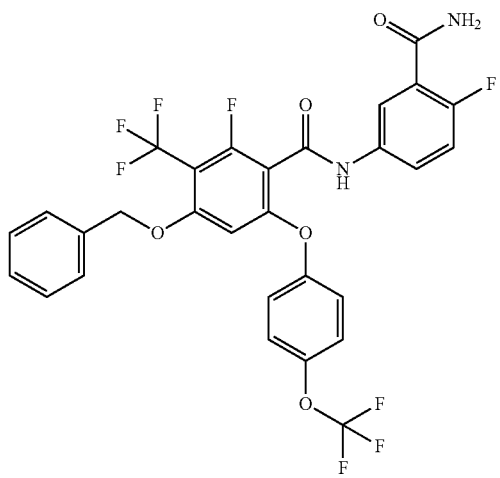 [SMILES: NC(=O)c1cc(NC(=O)c2c(Oc3ccc(OC(F)(F)F)cc3)cc(OCc3ccccc3)c(C(F)(F)F)c2F)ccc1F]

Step 1: 1-Benzyloxy-5-bromo-3-fluoro-2-(trifluoromethyl)benzene

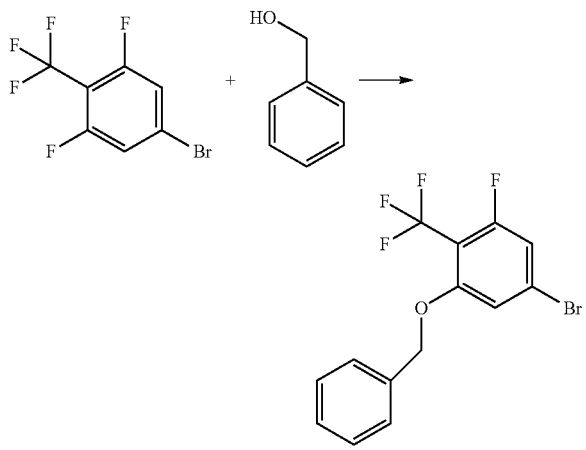

To a solution of phenylmethanol (0.800 mL, 7.73 mmol) in THF (12 mL) was added NaH (0.310 g of 60% w/w, 7.75 mmol) portionwise at 0° C. The reaction mixture was stirred for 1 hour and then a solution of 5-bromo-1,3-difluoro-2-(trifluoromethyl)benzene (2.00 g, 7.66 mmol) in THF (12 mL) was added slowly while maintaining the internal temperature below 40° C. The reaction mixture was stirred for 2 hours. The reaction mixture was quenched with water and the aqueous layer was extracted with dichloromethane. The organic layer was dried over MgSO$_4$, filtered and concentrated in vacuo. Silica gel column chromatography using hexanes as eluent provided 1-benzyloxy-5-bromo-3-fluoro-2-(trifluoromethyl)benzene (1.31 g, 49%). $^1$H NMR (400 MHz, DMSO-d6) δ 7.49 (s, 1H), 7.46-7.32 (m, 6H), 5.32 (s, 2H) ppm.

Step 2: Ethyl 4-benzyloxy-6-bromo-2-fluoro-3-(trifluoromethyl)benzoate

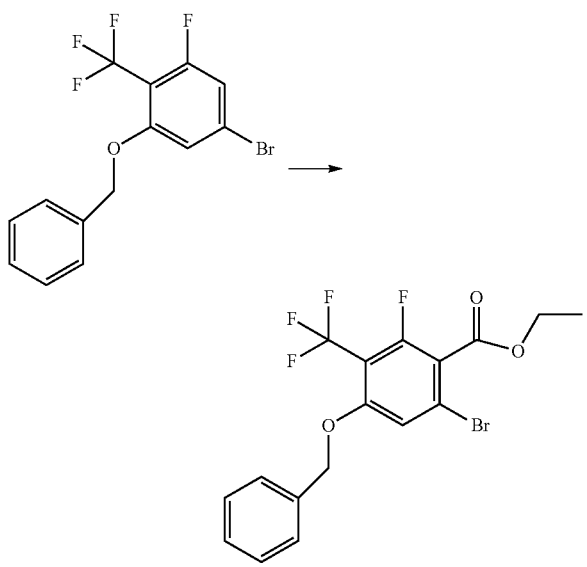

To a solution of 1-benzyloxy-5-bromo-3-fluoro-2-(trifluoromethyl)benzene (1.30 g, 3.72 mmol) in THF (13 mL) at −78° C. was added a solution of LDA (1.9 mL of 2 M, 3.8 mmol) dropwise while maintaining the internal temperature below −70° C., and the reaction mixture was stirred at −70° C. for 30 minutes. Ethyl chloroformate (0.900 mL, 9.41 mmol) was added dropwise maintaining the internal temperature below −70° C. The resultant reaction mixture was allowed to warm to room temperature and stirred for 1 hour. The reaction mixture was quenched with a saturated aqueous NH$_4$Cl solution and the aqueous layer was extracted with ethyl acetate. The organic layer was dried over MgSO$_4$, filtered and concentrated in vacuo. Silica gel chromatography (0-5% ethyl acetate/hexanes) provided ethyl 4-benzyloxy-6-bromo-2-fluoro-3-(trifluoromethyl)benzoate (860 mg, 55%). ESI-MS m/z calc. 419.99, found 423.0 (M+1)+; retention time (Method B): 2.16 minutes (3 minute run). $^1$H NMR (400 MHz, DMSO-d6) δ 7.66 (d, J=1.5 Hz, 1H), 7.46-7.40 (m, 4H), 7.37 (ddt, J=5.5, 4.5, 3.6 Hz, 1H), 5.38 (s, 2H), 4.38 (q, J=7.1 Hz, 2H), 1.31 (t, J=7.1 Hz, 3H) ppm.

Step 3: 4-Benzyloxy-6-bromo-2-fluoro-3-(trifluoromethyl)benzoic acid

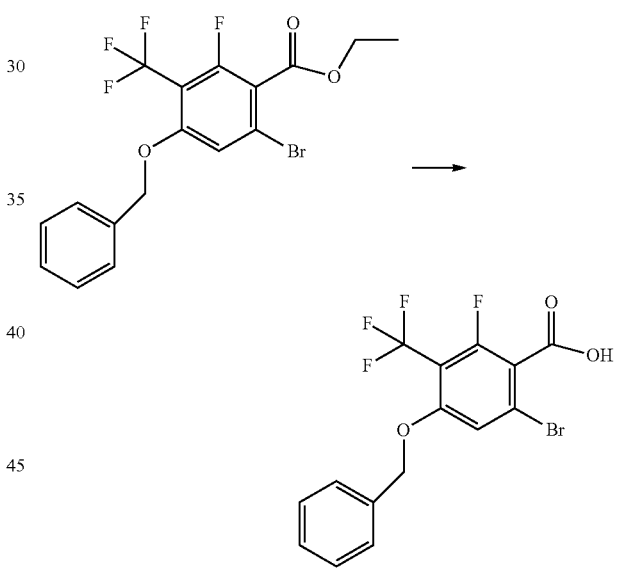

To a solution of ethyl 4-benzyloxy-6-bromo-2-fluoro-3-(trifluoromethyl)benzoate (0.900 g, 2.14 mmol) in methanol (10 mL) and water (10 mL) was added NaOH (2.0 g, 50 mmol) and the reaction mixture was stirred at room temperature for 20 hours. The solvent was evaporated and the crude material was taken up in water, cooled to 0° C. and acidified with 6 M HCl. The aqueous layer was extracted with ethyl acetate. The organic layer was dried over MgSO$_4$, filtered and concentrated in vacuo. Silica gel column chromatography (0-50% ethyl acetate/hexanes) provided 4-benzyloxy-6-bromo-2-fluoro-3-(trifluoromethyl)benzoic acid (170 mg, 20%). ESI-MS m/z calc. 391.96, found 395.0 (M+1)+; retention time (Method B): 1.72 minutes (3 minute run). $^1$H NMR (400 MHz, DMSO-d6) δ 14.16 (s, 1H), 7.61 (s, 1H), 7.45-7.34 (m, 5H), 5.37 (s, 2H) ppm.

533

Step 4: 4-Benzyloxy-2-fluoro-6-[4-(trifluoromethoxy)phenoxy]-3-(trifluoromethyl)benzoic

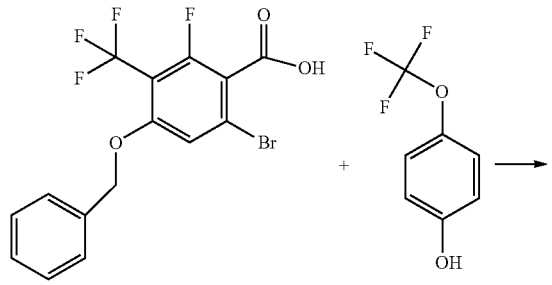

534

Step 5: 4-Benzyloxy-N-(3-carbamoyl-4-fluoro-phenyl)-2-fluoro-6-[4-(trifluoromethoxy)phenoxy]-3-(trifluoromethyl)benzamide (215)

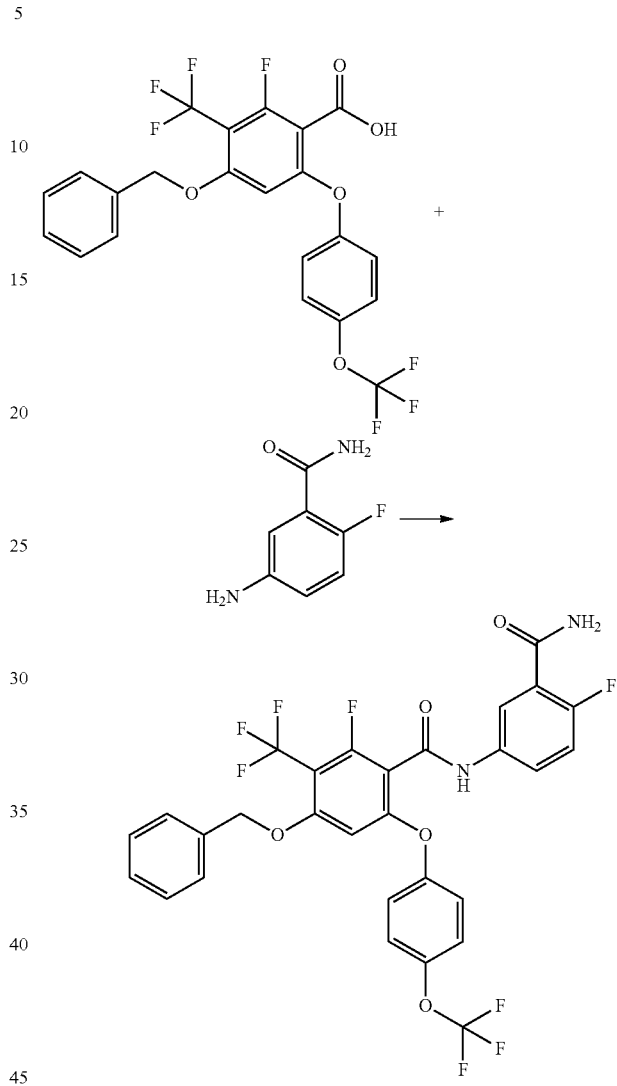

To a microwave vial was added 4-benzyloxy-6-bromo-2-fluoro-3-(trifluoromethyl)benzoic acid (165 mg, 0.420 mmol), 4 4-(trifluoromethoxy)phenol (0.07 mL, 0.54 mmol), $Cs_2CO_3$ (150 mg, 0.460 mmol) and toluene (4 mL). The reaction mixture was bubbled with $N_2$ for 10 minutes then treated with copper (I) iodide (35 mg, 0.18 mmol). The flask was flushed with $N_2$, sealed, and heated at 100° C. with vigorous stirring for 4 hours. The mixture acidified with 1 M HCl, filtered and the aqueous layer was extracted with ethyl acetate. The organic layer was washed with brine, dried over $Na_2SO_4$, filtered and concentrated in vacuo. Silica gel chromatography (0-50% ethyl acetate/hexanes) provided 4-benzyloxy-2-fluoro-6-[4-(trifluoromethoxy)phenoxy]-3-(trifluoromethyl)benzoic acid (93 mg, 45%). ESI-MS m/z calc. 490.06, found 491.1 (M+1)+; retention time (Method B): 2.06 minutes (3 minute run). $^1$H NMR (400 MHz, DMSO-d6) δ 13.70 (s, 1H), 7.44-7.32 (m, 5H), 7.29 (dd, J=7.7, 1.9 Hz, 2H), 7.18-7.10 (m, 2H), 6.75 (s, 1H), 5.22 (s, 2H) ppm.

To a flask charged with 4-benzyloxy-2-fluoro-6-[4-(trifluoromethoxy)phenoxy]-3-(trifluoromethyl)benzoic acid (90 mg, 0.18 mmol), 5-amino-2-fluoro-benzamide (34 mg, 0.22 mmol) and HATU (86 mg, 0.23 mmol) in DMF (1 mL) was added DIEA (0.100 mL, 0.574 mmol) and the reaction mixture was stirred at room temperature for 20 hours. The reaction mixture was diluted with water and the resulting precipitate was filtered and washed with water. The residue was dissolved in dichloromethane, dried over $MgSO_4$, filtered and concentrated in vacuo. Silica gel chromatography (0-50% ethyl acetate/hexanes) provided 4-benzyloxy-N-(3-carbamoyl-4-fluoro-phenyl)-2-fluoro-6-[4-(trifluoromethoxy)phenoxy]-3-(trifluoromethyl)benzamide (100 mg, 87%). ESI-MS m/z calc. 626.10, found 627.3 (M+1)+; retention time (Method B): 2.01 minutes (3 minute run). $^1$H NMR (400 MHz, DMSO-d6) δ 10.82 (s, 1H), 7.90 (dd, J=6.4, 2.8 Hz, 1H), 7.73-7.63 (m, 3H), 7.44-7.32 (m, 5H), 7.29-7.15 (m, 5H), 6.68 (s, 1H), 5.25 (s, 2H) ppm.

Example 131

4-[[6-(2,4-Dimethoxyphenoxy)-2-fluoro-3-(trifluoromethyl)benzoyl]amino]pyridine-2-carboxamide (195)

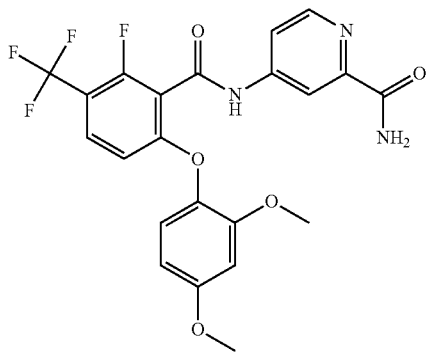 [SMILES: COc1ccc(Oc2ccc(C(F)(F)F)c(F)c2C(=O)Nc2ccnc(C(N)=O)c2)c(OC)c1]

Step 1: 6-Bromo-2-fluoro-3-(trifluoromethyl)benzoyl chloride

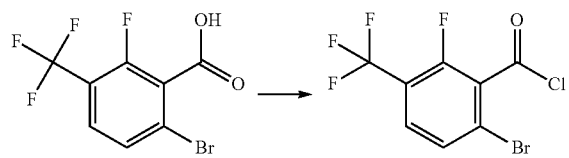 [SMILES: O=C(O)c1c(Br)ccc(C(F)(F)F)c1F ; O=C(Cl)c1c(Br)ccc(C(F)(F)F)c1F]

To a solution of 6-bromo-2-fluoro-3-(trifluoromethyl)benzoic acid (5.40 g, 18.8 mmol) and DMF (126 mg, 1.72 mmol) in dichloromethane (54 mL) at 0° C. was added oxalyl chloride (11.5 g, 90.3 mmol) dropwise. The mixture was allowed to warm to room temperature and stirred for 5 hours under N₂ atmosphere. The solvent was evaporated in vacuo to afford 6-bromo-2-fluoro-3-(trifluoromethyl)benzoyl chloride. The intermediate was used in the next step without further purification.

Step 2: 4-[[6-bromo-2-fluoro-3-(trifluoromethyl)benzoyl]amino]pyridine-2-carboxamide

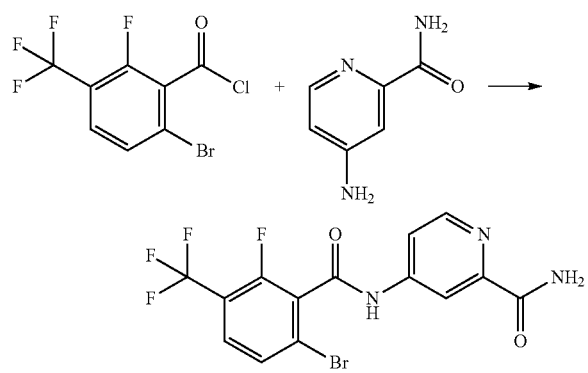

To a solution of 4-aminopyridine-2-carboxamide (2.56 g, 18.7 mmol) and DIEA (6.03 g, 46.7 mmol) in dichloromethane (29 mL) at 0° C. was added a solution of 6-bromo-2-fluoro-3-(trifluoromethyl)benzoyl chloride (5.7 g, 18.7 mmol) in dichloromethane (29 mL) dropwise. The reaction mixture was allowed to warm to room temperature and stirred for 16 hours. Ethyl acetate (150 mL) was added to the reaction mixture followed by the addition of water. The organic layer was separated, dried over $Na_2SO_4$, and concentrated in vacuo. Silica gel chromatography (1-10% methanol/dichloromethane) provided 4-[[6-bromo-2-fluoro-3-(trifluoromethyl)benzoyl]amino]pyridine-2-carboxamide (800 mg, 11%). ESI-MS m/z calc. 404.97, found 408.2 (M+1)+; retention time Method (B): 0.58 minutes (3 minute run).

Step 3: 4-[[6-(2,4-Dimethoxyphenoxy)-2-fluoro-3-(trifluoromethyl)benzoyl]amino]pyridine-2-carboxamide (195)

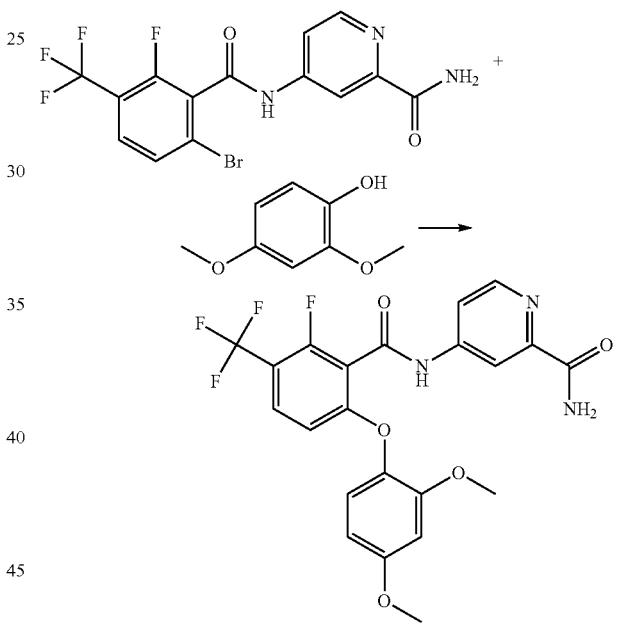

To a microwave vial were added 4-[[6-bromo-2-fluoro-3-(trifluoromethyl)benzoyl]amino]pyridine-2-carboxamide (50 mg, 0.12 mmol), $Cs_2CO_3$ (80 mg, 0.25 mmol), 2,4-dimethoxyphenol (19 mg, 0.12 mmol) and toluene (500 µL, degassed via bubbling with N₂). The mixture was bubbled with N₂ and then treated with copper (I) iodide (13 mg, 0.066 mmol). The vial was sealed and the reaction stirred at 100° C. for 20 minutes. The reaction was diluted with ethyl acetate and water. The organic layer was separated, dried over $Na_2SO_4$ and concentrated in vacuo. HPLC purification (1-99% acetonitrile/5 mM HCl) provided 4-[[6-(2,4-dimethoxyphenoxy)-2-fluoro-3-(trifluoromethyl)benzoyl]amino] pyridine-2-carboxamide (9.6 mg, 16%). ESI-MS m/z calc. 479.11, found 480.2 (M+1)+; retention time (Method B): 1.55 minutes (3 minute run).

Example 132

4-[[2-Fluoro-6-[4-methoxy-2-(trifluoromethoxy)phenoxy]-3-(trifluoromethyl)benzoyl]amino]pyridine-2-carboxamide (196)

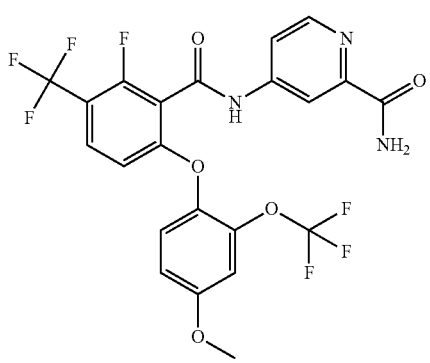 [SMILES: COc1ccc(Oc2ccc(C(F)(F)F)c(F)c2C(=O)Nc2ccnc(C(N)=O)c2)c(OC(F)(F)F)c1]

In a microwave vial were combined 4-[[6-bromo-2-fluoro-3-(trifluoromethyl)benzoyl]amino]pyridine-2-carboxamide (prepared as described in Example 131, 50 mg, 0.12 mmol), $Cs_2CO_3$ (80 mg, 0.25 mmol), 4-methoxy-2-(trifluoromethoxy)phenol (26 mg, 0.12 mmol) and toluene (0.5 mL, degassed by $N_2$ bubbling). The mixture was further bubbled with $N_2$, then copper (I) iodide (14 mg, 0.074 mmol) was added and the reaction was stirred at 100° C. for 20 minutes. The reaction was diluted with ethyl acetate and water. The layers were separated and the organic layer was concentrated in vacuo. The crude material was dissolved in DMSO (2 mL) and purified by HPLC (1-99% acetonitrile/5 mM HCl) to obtain 4-[[2-fluoro-6-[4-methoxy-2-(trifluoromethoxy)phenoxy]-3-(trifluoromethyl)benzoyl]amino]pyridine-2-carboxamide (17.6 mg, 27%). ESI-MS m/z calc. 533.08, found 534.4 (M+1)+; retention time (Method B): 1.69 minutes (3 minute run). $^1$H NMR (400 MHz, DMSO-d6) δ 11.45 (s, 1H), 8.57 (d, J=5.5 Hz, 1H), 8.32 (d, J=2.1 Hz, 1H), 8.11 (d, J=2.9 Hz, 1H), 7.99-7.73 (m, 2H), 7.67 (d, J=2.9 Hz, 1H), 7.42 (d, J=9.0 Hz, 1H), 7.29-6.94 (m, 2H), 6.77 (d, J=8.9 Hz, 1H), 3.82 (s, 3H) ppm. $^{19}$F NMR (376 MHz, DMSO) δ -57.29, -59.21, -59.25, -117.27, -117.30, -117.33, -117.34, -117.36 ppm.

Example 133

4-[[6-[2-(Difluoromethoxy)-4-fluoro-phenoxy]-2-fluoro-3-(trifluoromethyl)benzoyl]amino]pyridine-2-carboxamide (208)

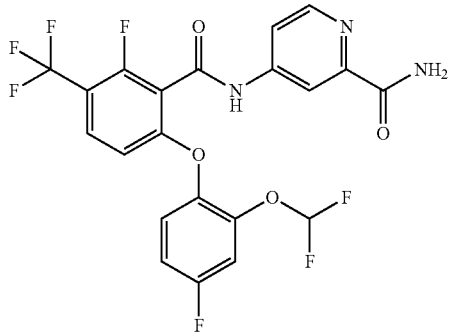 [SMILES: NC(=O)c1cc(NC(=O)c2c(Oc3ccc(F)cc3OC(F)F)ccc(C(F)(F)F)c2F)ccn1]

Step 1: 2-(Difluoromethoxy)-4-fluoro-1-methoxy-benzene

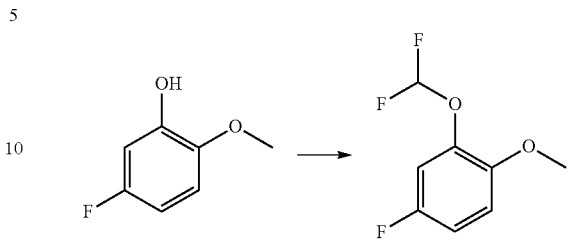

A mixture of 5-fluoro-2-methoxy-phenol (1.00 g, 7.04 mmol), sodium 2-chloro-2,2-difluoro-acetate (2.68 g, 17.6 mmol) and cesium carbonate (4.58 g, 14.1 mmol) in DMF (14 mL) and water (1.5 mL) was heated at 100° C. for 16 hours. The reaction mixture was diluted with dichloromethane, filtered, and the filtrate was washed with water and brine. The organic layer was dried over $MgSO_4$, concentrated in vacuo and purified by silica gel chromatography (0-20% ethyl acetate/hexanes) to provide 2-(difluoromethoxy)-4-fluoro-1-methoxy-benzene (590 mg, 44%) as a colorless liquid. $^1$H NMR (400 MHz, CDCl$_3$) δ 6.99-6.86 (m, J=6.5, 5.1 Hz, 3H), 6.56 (t, J=74.7 Hz, 1H), 3.86 (s, 3H) ppm.

Step 2: 4-[[2,6-Difluoro-3-(trifluoromethyl)benzoyl]amino]pyridine-2-carboxamide

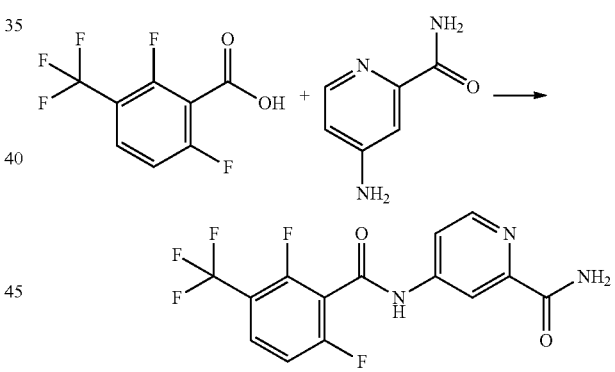

To a solution of 2,6-difluoro-3-(trifluoromethyl)benzoic acid (250 mg, 1.11 mmol) in dichloromethane (4 mL) at 0° C. was added DMF (10 μL, 0.13 mmol) followed by the dropwise addition of oxalyl chloride (0.250 mL, 2.87 mmol). The reaction mixture was stirred at 0° C. for 40 minutes. The solvent was removed in vacuo to afford a gummy solid. The solid was dissolved in dichloromethane and added dropwise to a solution of 4-aminopyridine-2-carboxamide (152 mg, 1.11 mmol) and DIEA (0.40 mL, 2.3 mmol) in NMP (3 mL) at 0° C. The reaction mixture was allowed to warm to room temperature slowly with ice-bath in place and stirred for 16 hours. The reaction mixture was poured onto ice, diluted with dichloromethane and stirred for 30 minutes. The organic layer was separated, concentrated in vacuo, and the resulting brown oil was partitioned between ethyl acetate and water. The layers were separated and the organic layer was further washed with water. The organic layer was dried (by passing through a phase separation cartridge) and concentrated in vacuo. Purification by silica gel chromatography (0-100% ethyl acetate/petroleum ether) provided 4-[[2,6-difluoro-3-(trifluoromethyl)benzoyl]amino]pyridine-2-carboxamide (77 mg, 20%). ESI-MS m/z calc. 345.05, found 346.0 (M+1)+; 344.0 (M−1)−; retention time (Method F): 0.76 minutes (1.5 minute run).

Step 3: 2-(Difluoromethoxy)-4-fluoro-phenol

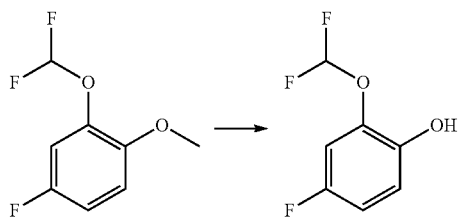

To sodium iodide (2.24 g, 15.0 mmol) in acetonitrile (10 mL) under a N₂ atmosphere was added TMSCl (1.63 g, 1.90 mL, 15.0 mmol) and the mixture was stirred 20 minutes. 2-(Difluoromethoxy)-4-fluoro-1-methoxy-benzene (575 mg, 2.99 mmol) was added and the mixture was heated at 80° C. for 6 hours, then the heat was reduced to 70° C. for 16 hours. The reaction was concentrated in vacuo and the residue was partitioned between dichloromethane and 1 M aqueous sodium thiosulfate. The organic layer was separated and the aqueous layer was further extracted with dichloromethane. The combined organics were dried over MgSO₄, concentrated and purified by silica gel chromatography (0-30% ethyl acetate/hexanes) to provide 2-(difluoromethoxy)-4-fluoro-phenol (325 mg, 61%) as a pale yellow oil. ESI-MS retention time (Method A): 0.45 minutes (1.2 minute run). ¹H NMR (400 MHz, CDCl₃) δ 7.04-6.79 (m, 3H), 6.53 (t, J=73.0 Hz, 1H), 5.22 (s, 1H) ppm.

Step 4: 4-[[6-[2-(Difluoromethoxy)-4-fluoro-phenoxy]-2-fluoro-3-(trifluoromethyl)benzoyl]amino]pyridine-2-carboxamide (208)

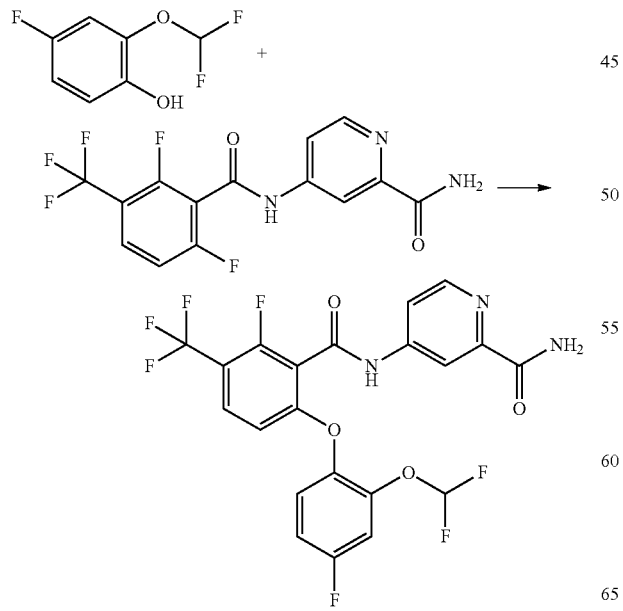

In a microwave vial were combined 4-[[2,6-difluoro-3-(trifluoromethyl)benzoyl]amino]pyridine-2-carboxamide (40 mg, 0.12 mmol), 2-(difluoromethoxy)-4-fluoro-phenol (52 mg, 0.29 mmol) and Cs₂CO₃ (57 mg, 0.18 mmol) in DMF (1 mL). The resulting suspension was heated to 90° C. for 30 minutes using microwave irradiation. The reaction mixture was cooled, filtered and diluted with DMSO. Two sequential HPLC purifications (initial purification using acetonitrile/0.1% ammonium hydroxide gradient followed by final purification using acetonitrile/0.05% TFA gradient) provided 4-[[6-[2-(difluoromethoxy)-4-fluoro-phenoxy]-2-fluoro-3-(trifluoromethyl)benzoyl]amino]pyridine-2-carboxamide trifluoroacetate (11 mg, 15%) as a white solid. ESI-MS m/z calc. 503.07, found 504.0 (M+1)+; 502.0 (M−1)−; retention time (Method E): 3.07 minutes (4.45 minute run). ¹H NMR (500 MHz, DMSO-d6) δ 11.47 (s, 1H), 8.57 (d, J=5.5 Hz, 1H), 8.34 (d, J=2.2 Hz, 1H), 8.12 (d, J=2.7 Hz, 1H), 7.90-7.81 (m, 2H), 7.68 (d, J=2.6 Hz, 1H), 7.50-7.39 (m, 2H), 7.38-7.06 (m, 2H), 6.77 (d, J=8.9 Hz, 1H) ppm.

Example 134

N-(3-Carbamoyl-4-fluoro-phenyl)-5-[2-methoxy-4-(trifluoromethoxy)phenoxy]-2-(trifluoromethyl)pyridine-4-carboxamide (68)

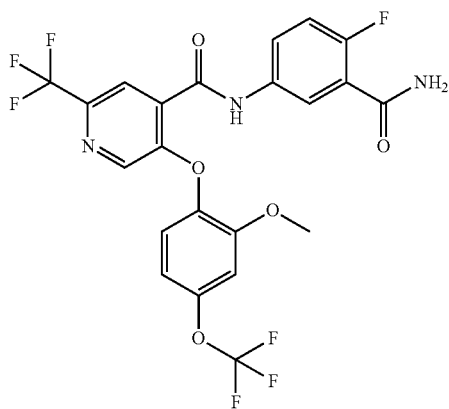

Step 1: 5-[2-Methoxy-4-(trifluoromethoxy)phenoxy]-2-(trifluoromethyl)pyridine-4-carboxylic acid

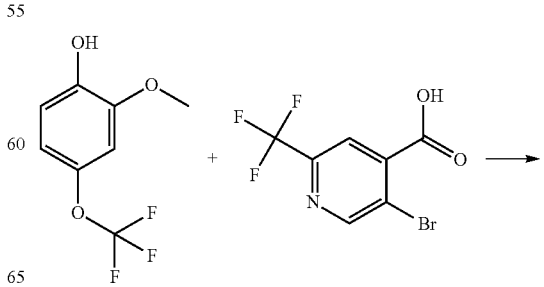

541

-continued

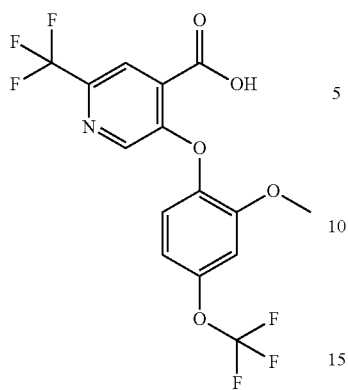

2-Methoxy-4-(trifluoromethoxy)phenol (prepared as described in Example 2, 1.01 g, 4.48 mmol), 5-bromo-2-(trifluoromethyl)pyridine-4-carboxylic acid (1.00 g, 3.70 mmol), $Cs_2CO_3$ (2.60 g, 7.98 mmol) and toluene (20 mL) were combined and heated at 100° C. After 10 minutes, copper (I) iodide (140 mg, 0.735 mmol) was added and the reaction was stirred at 100° C. for 2.5 hours. The reaction mixture was cooled to room temperature and partitioned between ethyl acetate and 1 M HCl. The organic phase was separated and washed with water and brine, dried over $Na_2SO_4$, filtered and concentrated. The residue was triturated in dichloromethane and filtered to provide 5-[2-methoxy-4-(trifluoromethoxy)phenoxy]-2-(trifluoromethyl)pyridine-4-carboxylic acid (620 mg, 42%) as a white solid. ESI-MS m/z calc. 397.04, found 398.0 (M+1)+; retention time (Method A): minutes 0.71 (1.2 minute run).

Step 2: N-(3-Carbamoyl-4-fluoro-phenyl)-5-[2-methoxy-4-(trifluoromethoxy)phenoxy]-2-(trifluoromethyl)pyridine-4-carboxamide (68)

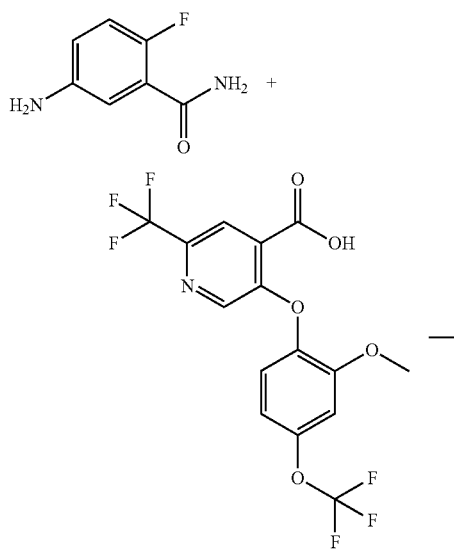

542

-continued

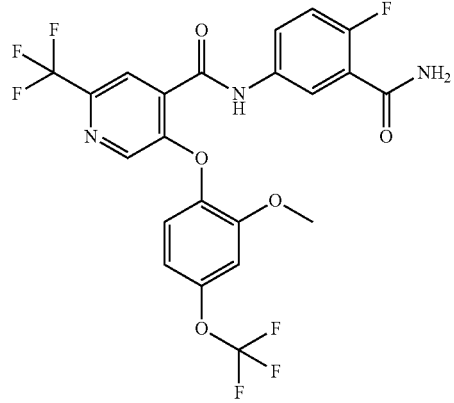 [SMILES: COc1cc(OC(F)(F)F)ccc1Oc1cnc(C(F)(F)F)cc1C(=O)Nc1ccc(F)c(C(N)=O)c1]

5-[2-Methoxy-4-(trifluoromethoxy)phenoxy]-2-(trifluoromethyl)pyridine-4-carboxylic acid (150 mg, 0.378 mmol) and HATU (144 mg, 0.379 mmol) were combined in DMF (2 mL) and DIEA (0.165 mL, 0.947 mmol) and stirred for 10 minutes, followed by the addition of 5-amino-2-fluorobenzamide (116 mg, 0.753 mmol). The reaction was stirred for 1 hour, then diluted with dichloromethane and washed with water and brine. The organic layer was dried over $Na_2SO_4$, filtered and concentrated in vacuo. HPLC purification (10-99% acetonitrile/5 mM HCl) provided N-(3-carbamoyl-4-fluoro-phenyl)-5-[2-methoxy-4-(trifluoromethoxy)phenoxy]-2-(trifluoromethyl)pyridine-4-carboxamide (21.8 mg, 10%). ESI-MS m/z calc. 533.08, found 534.1 (M+1)+; retention time (Method B): 1.84 minutes (3 minute run). $^1$H NMR (400 MHz, DMSO-d6) δ 10.83 (s, 1H), 8.28 (s, 1H), 8.20 (s, 1H), 7.99-7.95 (m, 1H), 7.78 (ddd, J=9.0, 4.4, 2.8 Hz, 1H), 7.70 (br s, 2H), 7.38 (d, J=8.8 Hz, 1H), 7.29 (dd, J=10.1, 9.0 Hz, 1H), 7.23 (d, J=2.7 Hz, 1H), 7.02 (ddd, J=8.8, 2.7, 1.2 Hz, 1H), 3.78 (s, 3H) ppm.

Example 135

N-(2-Carbamoyl-4-pyridyl)-4-[2-methoxy-4-(trifluoromethoxy)phenoxy]-6-[1-(trifluoromethyl)cyclopropyl]pyridine-3-carboxamide (119)

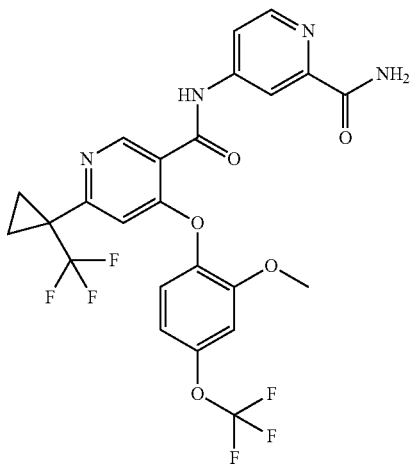 [SMILES: COc1cc(OC(F)(F)F)ccc1Oc1cc(C2(C(F)(F)F)CC2)ncc1C(=O)Nc1ccnc(C(N)=O)c1]

Step 1: Methyl 6-bromo-4-chloro-pyridine-3-carboxylate

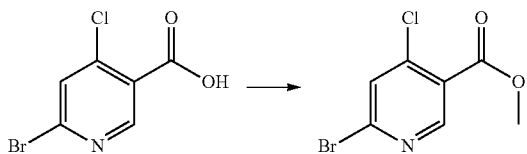

A 5000-mL 3-neck round bottom flask was fitted with a mechanical stirrer, a cooling bath, an addition funnel, a J-Kem temperature probe and a $N_2$ inlet/outlet. The vessel was charged under a $N_2$ atmosphere with 6-bromo-4-chloro-pyridine-3-carboxylic acid (250 g, 1.06 mol) and 1-methyl-pyrrolidin-2-one (1.250 L) which provided a clear pale amber solution (internal temperature 19° C.). Potassium carbonate (146.1 g, 1.057 mol) was added to the stirring solution as a solid in one portion and the mixture was stirred for 30 minutes. Neat dimethyl sulfate (133.3 g, 100.0 mL, 1.057 mol) was added dropwise over 30 minutes resulting in an exotherm to 26° C. The mixture was stirred at room temperature for 2 hours and then cooled to 0° C. Ice cold water (3000 mL) was added dropwise to the reaction mixture over 1 hour resulting in a thick suspension. The cooling bath was removed and the suspension was stirred for 1 hour. The solid was collected by vacuum filtration and the filter cake was washed with water (3×500 mL) and air dried for 1 hour. The material was further dried in a vacuum oven at 45° C. for 24 hours to provide methyl 6-bromo-4-chloro-pyridine-3-carboxylate (255 g, 96%) as an off-white solid. $^1$H NMR (400 MHz, DMSO-d6) δ 8.80 (d, J=0.4 Hz, 1H), 8.13 (d, J=0.5 Hz, 1H), 3.90 (s, 3H) ppm.

Step 2: Methyl 6-bromo-4-[2-methoxy-4-(trifluoromethoxy)phenoxy]pyridine-3-carboxylate

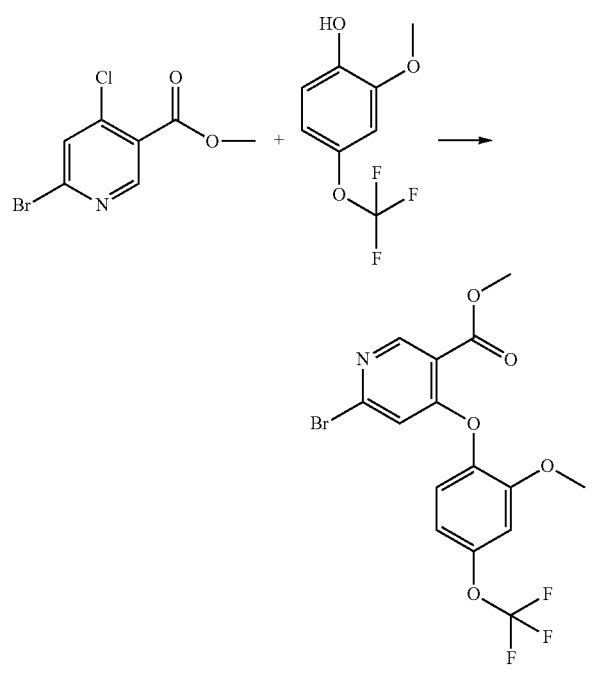

A 5000-mL 3-neck round bottom flask was fitted with a mechanical stirrer, a cooling bath, a J-Kem temperature probe and a $N_2$ inlet/outlet. The vessel was charged under a $N_2$ atmosphere with methyl 6-bromo-4-chloro-pyridine-3-carboxylate (175 g, 698.7 mmol) and DMF (1.750 L) (10 ml/g) which provided a clear pale yellow solution. The stirring solution was cooled to 0° C. then charged with 2-methoxy-4-(trifluoromethoxy)phenol (prepared as described in Example 2, 145.4 g, 698.6 mmol) added as a solid in one portion followed by cesium carbonate (341.5 g, 1.048 mol) added as a solid in one portion. The reaction mixture was stirred in the ice bath for 10 minutes then allowed to warm to room temperature and stirred for 2 hours. The resulting suspension was then added slowly to 4 L of stirring cold water and the resulting slurry was continued to stir at room temperature for 30 minutes. The material was collected by vacuum filtration and the filter cake was washed with water (3×250 mL) and air dried for 16 hours to provide an off-white solid (160 g). The material was suspended in heptane (1500 mL) and heated to reflux. The solution was clarified by vacuum filtration through a glass frit Buchner funnel. The filtrate was then heated to reflux and the resulting clear solution was allowed to slowly cool to room temperature during which time a solid formed. The material was collected by vacuum filtration and the filter cake was washed with cold heptane (2×50 mL). Vacuum was pulled in the funnel for 30 minutes and the material further dried in the vacuum oven at 45° C. for 12 hours to provide methyl 6-bromo-4-[2-methoxy-4-(trifluoromethoxy)phenoxy]pyridine-3-carboxylate (275 g, 93%) as of a white solid. ESI-MS m/z calc. 420.97, found 424.0 (M+1)+; retention time (Method B): 1.84 minutes (3 minute run). $^1$H NMR (400 MHz, DMSO-d6) δ 8.71 (s, 1H), 7.39 (d, J=8.8 Hz, 1H), 7.29 (d, J=2.7 Hz, 1H), 7.06 (ddd, J=8.8, 2.7, 1.2 Hz, 1H), 6.80 (s, 1H), 3.86 (s, 3H), 3.80 (s, 3H) ppm.

Step 3: Methyl 4-[2-methoxy-4-(trifluoromethoxy)phenoxy]-6-[1-(trifluoromethyl)vinyl]pyridine-3-carboxylate

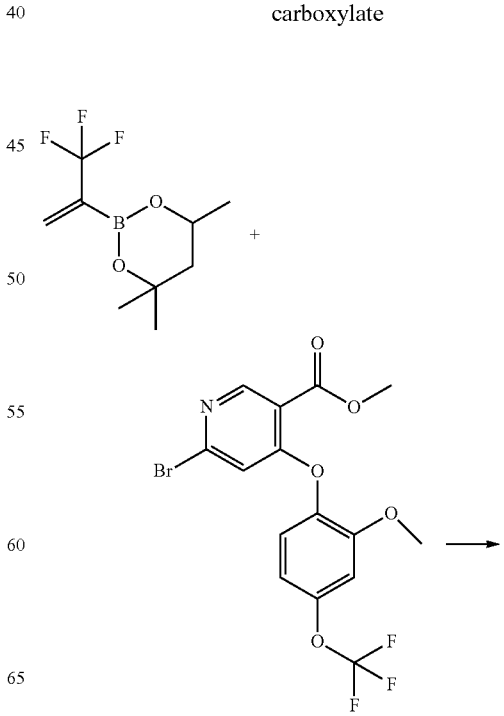

-continued

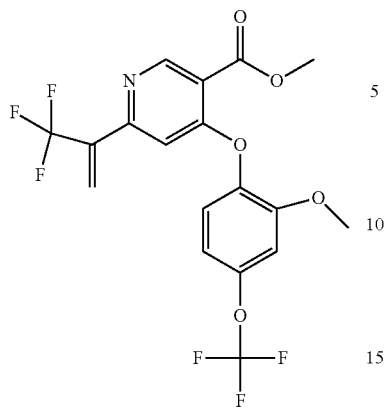

-continued

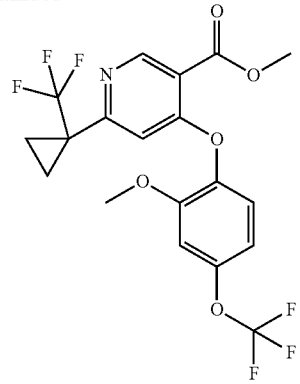

A vial was charged with methyl 6-bromo-4-[2-methoxy-4-(trifluoromethoxy)phenoxy]pyridine-3-carboxylate (800 mg, 1.90 mmol), 4,4,6-trimethyl-2-[1-(trifluoromethyl)vinyl]-1,3,2-dioxaborinane (550 mg, 2.48 mmol), Pd(dppf)Cl$_2$·DCM (155 mg, 0.190 mmol), K$_2$CO$_3$ (2 mL of 2 M in water, 4 mmol) and acetonitrile (8 mL). The vial was flushed with argon, sealed and heated at 80° C. for 90 minutes. The reaction mixture was cooled to room temperature and partitioned between water and ethyl acetate. The organic layer was dried over MgSO$_4$, filtered and concentrated in vacuo. Silica gel column chromatography (0-20% ethyl acetate/hexanes) provided methyl 4-[2-methoxy-4-(trifluoromethoxy)phenoxy]-6-[1-(trifluoromethyl)vinyl]pyridine-3-carboxylate (340 mg, 41%). ESI-MS m/z calc. 437.06, found 438.2 (M+1)+; retention time (Method B): 2.07 minutes (3 minute run).

Step 4: Methyl 4-[2-methoxy-4-(trifluoromethoxy)phenoxy]-6-[1-(trifluoromethyl)cyclopropyl]pyridine-3-carboxylate

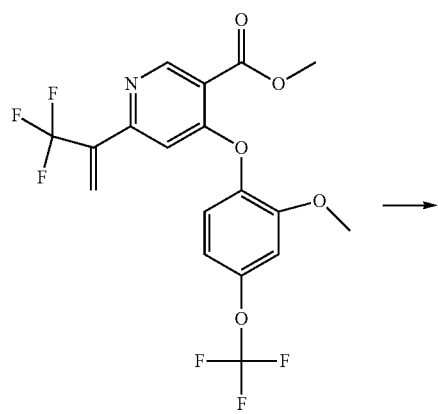

Preparation of a solution of diazomethane in ethyl ether: To 1-methyl-1-nitroso-urea (1.00 g, 9.70 mmol) was added a biphasic mixture of 40% aqueous KOH (2.0 mL of 40% w/v, 14.3 mmol) and diethyl ether (2 mL) cooled in an ice-bath. The mixture was stirred in the ice-bath for 10 minutes (turns yellow), and then cooled to −78° C. The ether layer was decanted from the frozen aqueous layer and the yellow solution was used directly in the next step.

The diazomethane solution was added dropwise to a solution of methyl 4-[2-methoxy-4-(trifluoromethoxy)phenoxy]-6-[1-(trifluoromethyl)vinyl]pyridine-3-carboxylate (470 mg, 1.08 mmol) in diethyl ether (7 mL) at 0° C. The yellow color of the diazomethane disappeared upon addition. The reaction was stirred at 0° C. for 5 minutes. Acetic acid (3 mL) was added to quench the excess diazomethane until the reaction mixture was colorless and gas evolution had ceased. The mixture was diluted with ethyl acetate (10 mL), washed with saturated aqueous NaHCO$_3$ (20 mL), brine (20 mL), dried over anhydrous Na$_2$SO$_4$ and concentrated in vacuo to provide the intermediate methyl 4-[2-methoxy-4-(trifluoromethoxy)phenoxy]-6-[5-(trifluoromethyl)-3,4-dihydropyrazol-5-yl]pyridine-3-carboxylate (500 mg, 97%) as a yellow oil. ESI-MS m/z calc. 479.09, found 480.2 (M+1)+; retention time (Method B): 2.04 minutes (3 minute run). $^1$H NMR (400 MHz, DMSO-d6) δ 8.84 (s, 1H), 7.41-7.29 (m, 2H), 7.08 (ddq, J=8.8, 2.5, 1.2 Hz, 1H), 6.64 (s, 1H), 3.86 (s, 3H), 3.76 (s, 3H), 1.46-1.37 (m, 4H) ppm.

The 4-[2-methoxy-4-(trifluoromethoxy)phenoxy]-6-[5-(trifluoromethyl)-3,4-dihydropyrazol-5-yl]pyridine-3-carboxylate was dissolved in p-xylene (7 mL) and heated at reflux (125° C.) open to air for 2 hours. The solvent was evaporated and the crude material was purified by silica gel column chromatography (0-10% ethyl acetate/hexanes) to obtain methyl 4-[2-methoxy-4-(trifluoromethoxy)phenoxy]-6-[1-(trifluoromethyl)cyclopropyl]pyridine-3-carboxylate (135 mg, 56%). ESI-MS m/z calc. 451.08, found 452.3 (M+1)+; retention time (Method B): 1.9 minutes (3 minute run). $^1$H NMR (400 MHz, DMSO-d6) δ 8.84 (s, 1H), 7.41-7.29 (m, 2H), 7.08 (ddq, J=8.8, 2.5, 1.2 Hz, 1H), 6.64 (s, 1H), 3.86 (s, 3H), 3.76 (s, 3H), 1.46-1.37 (m, 4H) ppm.

Step 5: 4-[2-Methoxy-4-(trifluoromethoxy)phenoxy]-6-[1-(trifluoromethyl)cyclopropyl]pyridine-3-carboxylic acid

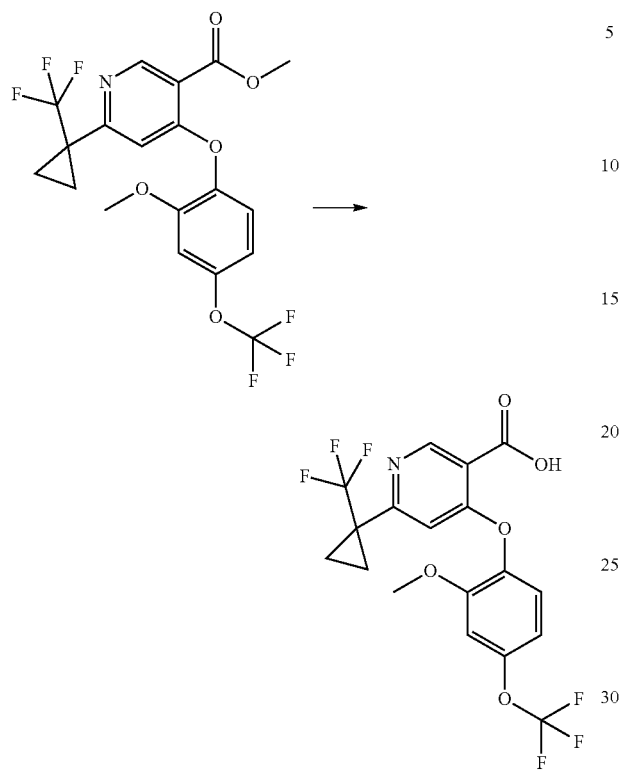

To a solution of methyl 4-[2-methoxy-4-(trifluoromethoxy)phenoxy]-6-[1-(trifluoromethyl)cyclopropyl] pyridine-3-carboxylate (128 mg, 0.284 mmol) in methanol (1.2 mL) was added NaOH (270 mg, 6.75 mmol) in water (1.2 mL). The reaction mixture was stirred at room temperature for 1 hour. The solvent was evaporated and the reaction mixture was quenched with 6 M HCl. The aqueous layer was extracted with ethyl acetate, dried over MgSO$_4$, filtered and concentrated in vacuo to provide 4-[2-methoxy-4-(trifluoromethoxy)phenoxy]-6-[1-(trifluoromethyl)cyclopropyl]pyridine-3-carboxylic acid (120 mg, 97%). ESI-MS m/z calc. 437.06, found 438.5 (M+1)+; retention time (Method B): 1.88 minutes (3 minute run).

Step 6: N-(2-Carbamoyl-4-pyridyl)-4-[2-methoxy-4-(trifluoromethoxy)phenoxy]-6-[1-(trifluoromethyl)cyclopropyl]pyridine-3-carboxamide (119)

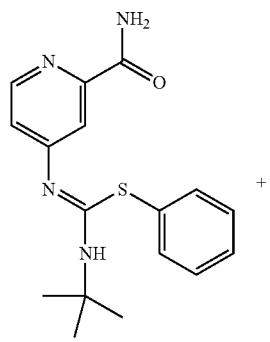

A vial was charged with 4-[2-methoxy-4-(trifluoromethoxy)phenoxy]-6-[1-(trifluoromethyl)cyclopropyl] pyridine-3-carboxylic acid (19 mg, 0.043 mmol), 4-[(Z)-[(tert-butylamino)-phenylsulfanyl-methylene]amino] pyridine-2-carboxamide (prepared as described in Preparation 1, 15 mg, 0.04567 mmol), tris[(Z)-1-methyl-3-oxo-but-1-enoxy]iron (2 mg, 0.006 mmol) in 2-propanol (0.5 mL) and heated at 83° C. under an air atmosphere for 20 hours. The reaction mixture was cooled to room temperature and concentrated in vacuo. The residue was purified by silica gel column chromatography (0-60% ethyl acetate/hexanes) followed by HPLC purification (10-99% acetonitrile/5 mM HCl). The desired fractions were quenched with saturated NaHCO$_3$ and extracted with dichloromethane, dried over MgSO$_4$ and concentrated in vacuo to obtain N-(2-carbamoyl-4-pyridyl)-4-[2-methoxy-4-(trifluoromethoxy)phenoxy]-6-[1-(trifluoromethyl)cyclopropyl] pyridine-3-carboxamide (8 mg, 33%). ESI-MS m/z calc. 556.11, found 557.2 (M+1)+; retention time (Method B): 1.86 minutes (3 minute run). $^1$H NMR (400 MHz, DMF-d7) δ 11.46 (s, 1H), 9.15 (s, 1H), 8.97 (d, J=5.5 Hz, 1H), 8.75 (d, J=2.2 Hz, 1H), 8.52 (s, 1H), 8.32 (dd, J=5.5, 2.2 Hz, 1H), 8.07 (d, J=2.8 Hz, 1H), 7.91 (d, J=8.8 Hz, 1H), 7.72 (d, J=2.7 Hz, 1H), 7.59-7.43 (m, 1H), 7.13 (s, 1H), 4.20 (s, 3H), 1.85 (d, J=4.3 Hz, 4H) ppm.

Example 136

N-(3-Carbamoyl-4-fluoro-phenyl)-2,3-difluoro-6-[2-methoxy-4-(trifluoromethoxy)phenoxy]benzamide (55)

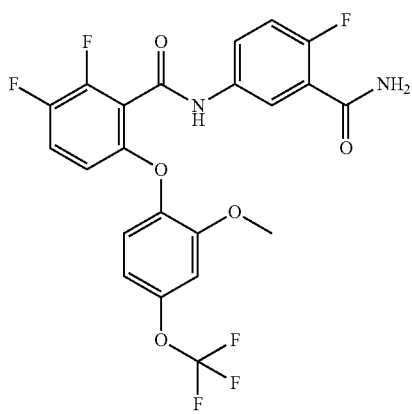 [SMILES: COc1cc(OC(F)(F)F)ccc1Oc1ccc(F)c(F)c1C(=O)Nc1ccc(F)c(C(N)=O)c1]

Step 1: 2,3-Difluoro-6-[2-methoxy-4-(trifluoromethoxy)phenoxy]benzoic acid

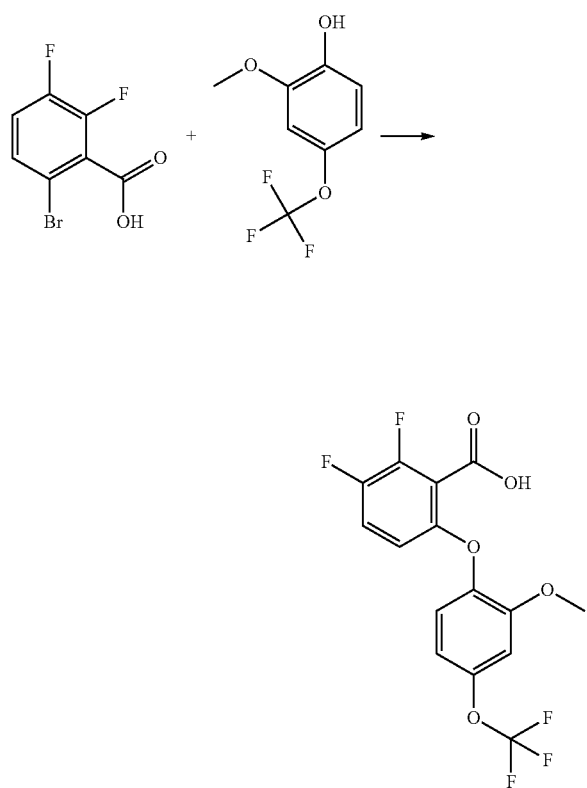

6-Bromo-2,3-difluoro-benzoic acid (1.00 g, 4.22 mmol), 2-methoxy-4-(trifluoromethoxy)phenol (prepared as described in Example 2, 1.02 g, 4.91 mmol) and Cs$_2$CO$_3$ (2.76 g, 8.46 mmol) in toluene (10 mL) were combined in a pressure vessel and the mixture was bubbled with N$_2$ for 3 minutes. Copper (I) iodide (168 mg, 0.881 mmol) was added and the reaction was stirred at 100° C. for 1.5 hours in the sealed vessel. The reaction mixture was cooled then partitioned between ethyl acetate and water. The aqueous layer was acidified to pH~1 and extracted with ethyl acetate (3×). The combined organic layers were dried over Na$_2$SO$_4$, filtered and concentrated in vacuo to yield 2,3-difluoro-6-[2-methoxy-4-(trifluoromethoxy)phenoxy]benzoic acid (336 mg, 22%). ESI-MS m/z calc. 364.04, found 365.1 (M+1)+; retention time (Method C): 2.23 minutes (5 minute run).

Step 2: 2,3-Difluoro-6-[2-methoxy-4-(trifluoromethoxy)phenoxy]benzoyl chloride

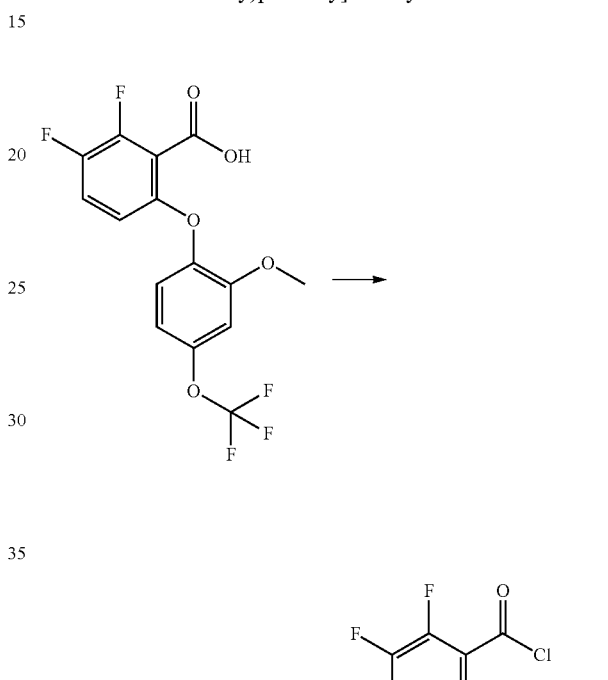

To a solution of 2,3-difluoro-6-[2-methoxy-4-(trifluoromethoxy)phenoxy]benzoic acid (326 mg, 0.895 mmol) and DMF (10 µL, 0.13 mmol) in dichloromethane (3 mL) at 0° C. was added oxalyl chloride (500 µL, 5.73 mmol) dropwise. The ice bath was removed and the reaction was stirred under a N$_2$ atmosphere for 35 minutes. Conversion was monitored by UPLC via test for piperidine adduct formation. The solvent was evaporated in vacuo to afford 2,3-difluoro-6-[2-methoxy-4-(trifluoromethoxy)phenoxy] benzoyl chloride which was used directly for the next step.

551

Step 3: N-(3-Carbamoyl-4-fluoro-phenyl)-2,3-difluoro-6-[2-methoxy-4-(trifluoromethoxy)phenoxy]benzamide (55)

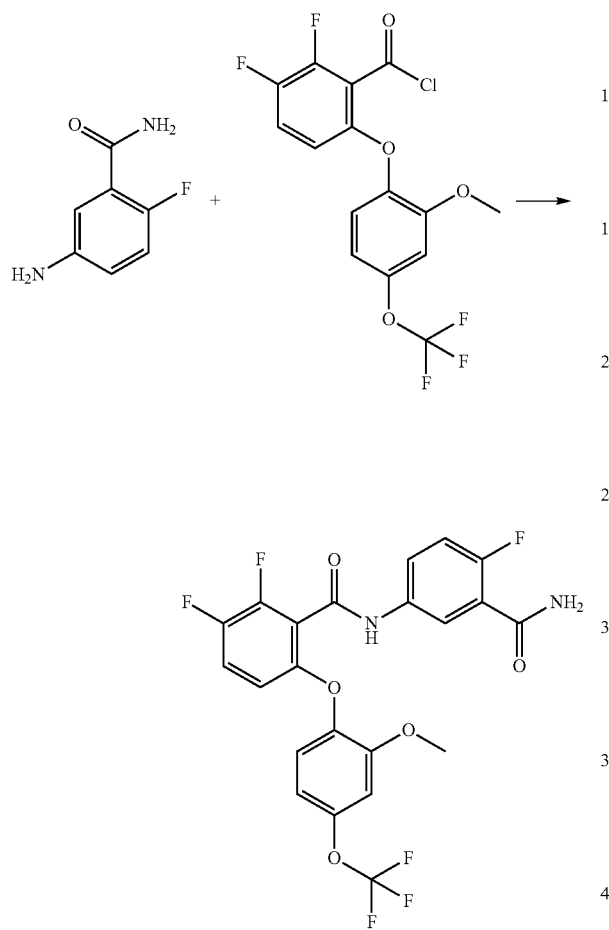

To a solution of 5-amino-2-fluoro-benzamide (60 mg, 0.39 mmol) and DIEA (0.204 mL, 1.18 mmol) in dichloromethane (1 mL) at 0° C. was added a solution of 2,3-difluoro-6-[2-methoxy-4-(trifluoromethoxy)phenoxy]benzoyl chloride (150 mg, 0.392 mmol) in dichloromethane (1 mL) dropwise. The reaction was allowed to warm to room temperature and stirred for 2 hours. The solvent was evaporated under a stream of $N_2$ gas. The crude product was dissolved in DMSO, filtered and purified by HPLC (1-99% acetonitrile/5 mM HCl) to provide N-(3-carbamoyl-4-fluoro-phenyl)-2,3-difluoro-6-[2-methoxy-4-(trifluoromethoxy)phenoxy]benzamide (22.3 mg, 11%). ESI-MS m/z calc. 500.08, found 501.1 (M+1)+; retention time (Method C): 2.22 minutes (5 minute run). $^1$H NMR (400 MHz, DMSO-d6) δ 10.94 (s, 1H), 7.98 (dd, J=6.4, 2.8 Hz, 1H), 7.82-7.64 (m, 3H), 7.54-7.41 (m, 1H), 7.28 (dd, J=10.0, 8.9 Hz, 1H), 7.23-7.17 (m, 2H), 7.09-6.81 (m, 1H), 6.81-6.43 (m, 1H), 3.77 (s, 3H) ppm.

552

Example 137

4-[[4-Cyclopropyl-2-[2-methoxy-4-(trifluoromethoxy)phenoxy]-5-(trifluoromethyl)benzoyl]amino]pyridine-2-carboxamide (125)

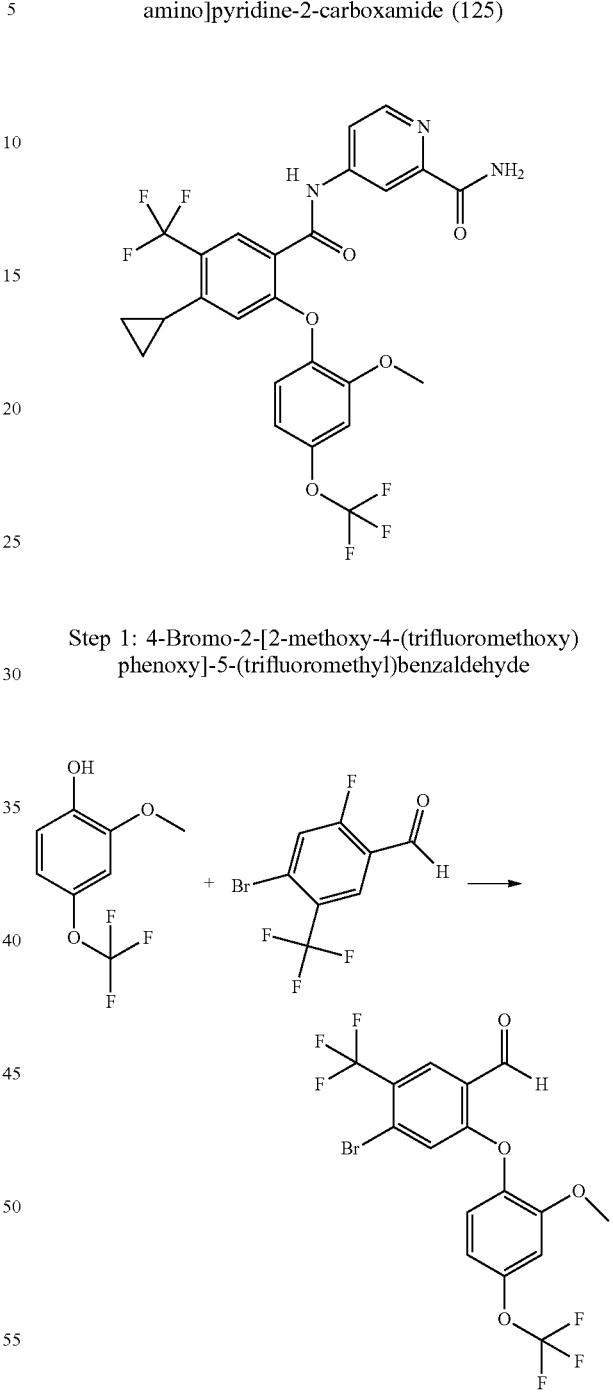

Step 1: 4-Bromo-2-[2-methoxy-4-(trifluoromethoxy)phenoxy]-5-(trifluoromethyl)benzaldehyde A vial charged with 2-methoxy-4-(trifluoromethoxy)phenol (prepared as described in Example 2, 768 mg, 3.69 mmol), 4-bromo-2-fluoro-5-(trifluoromethyl)benzaldehyde (1.00 g, 3.69 mmol), $Cs_2CO_3$ (3.01 g, 9.23 mmol) and DMF (3 mL) was heated at 80° C. for 2 hours. The reaction mixture was diluted with water and the resulting precipitate was filtered and washed with water. The solid was dissolved in dichloromethane, dried over $MgSO_4$, filtered and concentrated in vacuo. The crude material was purified by silica gel chromatography (0-5% ethyl acetate/hexanes) to provide 4-bromo-2-[2-methoxy-4-(trifluoromethoxy)phenoxy]-5-(trifluoromethyl)benzaldehyde (725 mg, 43%). ESI-MS m/z calc. 457.95, found 461.1 (M+1)+; retention time (Method B): 2.26 minutes (3 minute run). H NMR (400 MHz, DMSO-d6) δ 10.43 (s, 1H), 8.12 (s, 1H), 7.47 (d, J=8.8 Hz, 1H), 7.31 (d, J=2.7 Hz, 1H), 7.12 (s, 1H), 7.09 (ddq, J=8.8, 2.4, 1.2 Hz, 1H), 3.81 (s, 3H) ppm.

Step 2: 4-Cyclopropyl-2-[2-methoxy-4-(trifluoromethoxy)phenoxy]-5-(trifluoromethyl)benzaldehyde

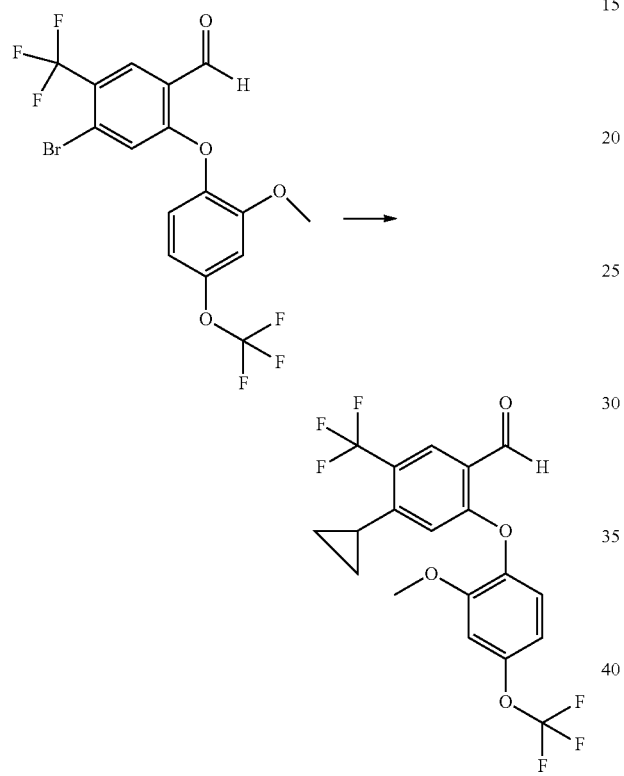

To a round bottom flask equipped with a stir bar were added 4-bromo-2-[2-methoxy-4-(trifluoromethoxy)phenoxy]-5-(trifluoromethyl)benzaldehyde (725 mg, 1.58 mmol) and bis(tri-tert-butylphosphine)palladium(0) (245 mg, 0.479 mmol). The flask was sealed with a septum, placed under a N$_2$ atmosphere and THF (7.5 mL) added. The reaction mixture was cooled to 0° C. and a solution of bromo(cyclopropyl)zinc (6.4 mL of 0.5 M in THF, 3.2 mmol) was added dropwise to the reaction mixture. After 30 minutes the reaction was quenched with saturated aqueous NH$_4$Cl solution and extracted with ethyl acetate. The organic layer was separated and dried over Na$_2$SO$_4$, filtered and concentrated in vacuo. Silica gel column chromatography (0-5% ethyl acetate/hexanes) provided 4-cyclopropyl-2-[2-methoxy-4-(trifluoromethoxy)phenoxy]-5-(trifluoromethyl)benzaldehyde (390 mg, 59%) as an off-white solid. ESI-MS m/z calc. 420.07, found 421.2 (M+1)+; retention time (Method B): 2.3 minutes (3 minute run). $^1$H NMR (400 MHz, DMSO-d6) δ 10.38 (s, 1H), 8.03 (s, 1H), 7.36 (d, J=8.8 Hz, 1H), 7.28 (d, J=2.8 Hz, 1H), 7.05 (ddq, J=8.8, 2.4, 1.1 Hz, 1H), 6.27 (s, 1H), 3.79 (s, 3H), 2.18-2.06 (m, 1H), 1.21-0.98 (m, 2H), 0.64-0.35 (m, 2H) ppm.

Step 3: 4-Cyclopropyl-2-[2-methoxy-4-(trifluoromethoxy)phenoxy]-5-(trifluoromethyl)benzoic acid

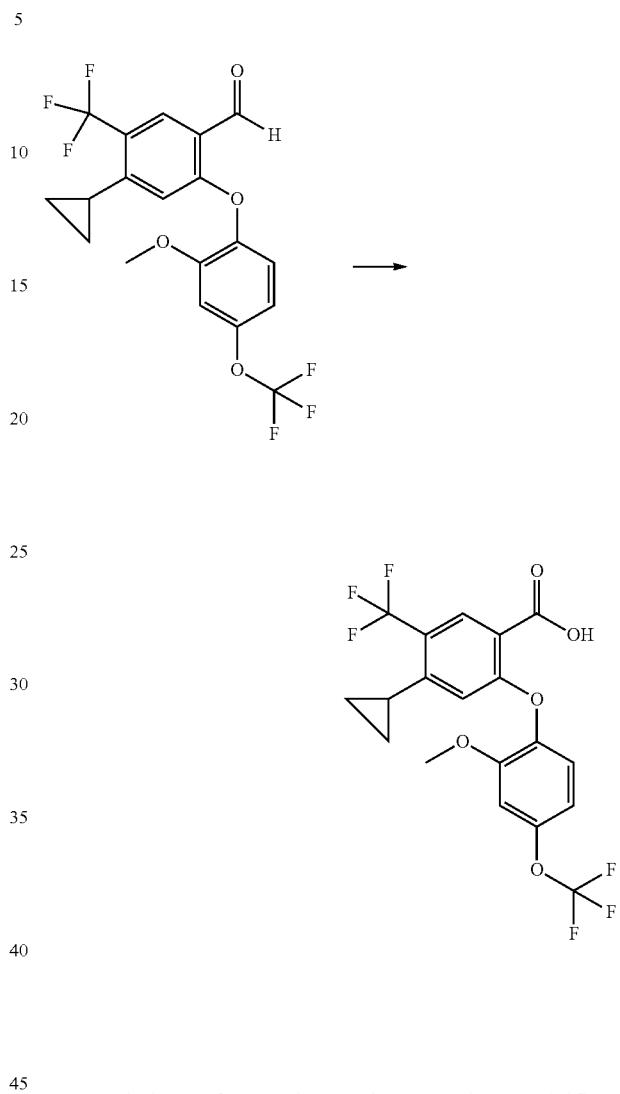

A solution of 4-cyclopropyl-2-[2-methoxy-4-(trifluoromethoxy)phenoxy]-5-(trifluoromethyl)benzaldehyde (390 mg, 0.928 mmol) in tert-butyl alcohol (4 mL), water (2.5 mL) and acetonitrile (2.5 mL) was treated with sodium dihydrogen phosphate (144 mg, 1.20 mmol) added in one portion followed by 2-methyl-2-butene (0.50 mL, 4.73 mmol). Sodium chlorite (100 mg, 1.11 mmol) was then added portion wise (exotherm to 33° C., internal temperature) and the reaction mixture was stirred at room temperature for 16 hours. The reaction mixture was adjusted to pH-2 by the addition of 1 M HCl solution. The organic phase was separated and the aqueous layer was extracted with ethyl acetate (3×10 mL). The combined organics were dried over MgSO$_4$, filtered and concentrated in vacuo. The resulting solid was further dried under high vacuum for 24 hours to provide 4-cyclopropyl-2-[2-methoxy-4-(trifluoromethoxy)phenoxy]-5-(trifluoromethyl)benzoic acid (320 mg, 79%) as an off-white solid. ESI-MS m/z calc. 436.07, found 437.3 (M+1)+; retention time (Method A): 0.81 minutes (1.2 minute run).

Step 4: 4-[[4-Cyclopropyl-2-[2-methoxy-4-(trifluoromethoxy)phenoxy]-5-(trifluoromethyl)benzoyl]amino]pyridine-2-carboxamide (125)

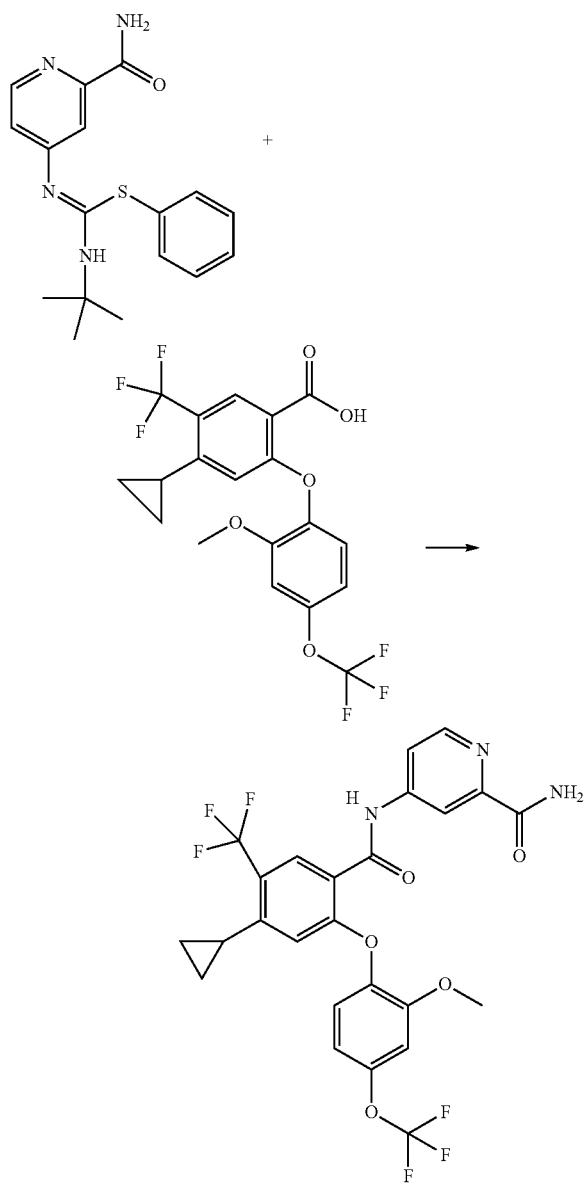

A vial was charged with 4-cyclopropyl-2-[2-methoxy-4-(trifluoromethoxy)phenoxy]-5-(trifluoromethyl)benzoic acid (50 mg, 0.12 mmol), 4-[(Z)-[(tert-butylamino)-phenylsulfanyl-methylene]amino]pyridine-2-carboxamide (prepared as described in preparation 1, 37 mg, 0.11 mmol), tris[(Z)-1-methyl-3-oxo-but-1-enoxy]iron (3 mg, 0.008 mmol) in 2-propanol (0.7 mL) and heated at 83° C. under an atmosphere of air for 20 hours. The reaction mixture was cooled to room temperature and concentrated in vacuo. Purification by silica gel chromatography (0-60% ethyl acetate/hexanes) was followed by HPLC purification (10-99% acetonitrile/5 mM HCl). The product HPLC fractions were basified with saturated NaHCO₃, extracted with dichloromethane, dried over MgSO₄ and concentrated in vacuo to provide 4-[[4-cyclopropyl-2-[2-methoxy-4-(trifluoromethoxy)phenoxy]-5-(trifluoromethyl)benzoyl]amino]pyridine-2-carboxamide (8 mg, 13%). ESI-MS m/z calc. 555.12, found 556.3 (M+1)+; retention time (Method B): 2.12 minutes (3 minute run). $^1$H NMR (400 MHz, DMSO-d6) δ 10.87 (s, 1H), 8.51 (d, J=5.5 Hz, 1H), 8.28 (d, J=2.1 Hz, 1H), 8.07 (d, J=2.9 Hz, 1H), 7.95 (s, 1H), 7.84 (dd, J=5.5, 2.2 Hz, 1H), 7.62 (d, J=2.8 Hz, 1H), 7.26 (d, J=8.8 Hz, 1H), 7.18 (d, J=2.7 Hz, 1H), 6.99 (ddd, J=8.7, 2.8, 1.3 Hz, 1H), 6.41 (s, 1H), 3.75 (s, 3H), 2.14 (s, 1H), 1.11-0.99 (m, 2H), 0.59 (dd, J=6.7, 4.7 Hz, 2H) ppm.

Example 138

N-(3-Carbamoyl-4-fluoro-phenyl)-2-[2-methoxy-4-(trifluoromethoxy)phenoxy]-6-(trifluoromethyl)benzamide (40)

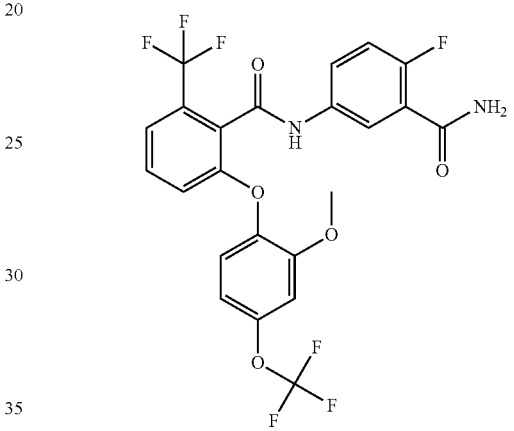

Step 1: N-(3-Carbamoyl-4-fluoro-phenyl)-2-fluoro-6-(trifluoromethyl)benzamide

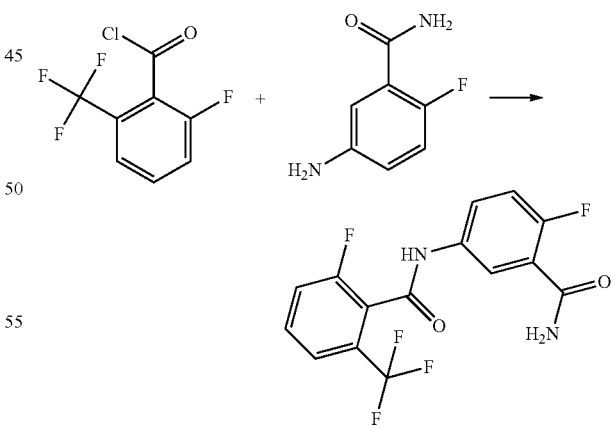

To a solution of 2-fluoro-6-(trifluoromethyl)benzoyl chloride (1.00 mL, 6.49 mmol) and DIEA (3.28 mL, 18.8 mmol) in dichloromethane (15 mL) at 0° C. was added a solution of 5-amino-2-fluoro-benzamide (1.00 g, 6.49 mmol) in dichloromethane (10 mL) dropwise. The reaction mixture was allowed to warm to room temperature, stirred for 20 minutes then concentrated in vacuo. Silica gel chromatography (0-50% ethyl acetate/hexanes) provided N-(3-carbamoyl-4-fluoro-phenyl)-2-fluoro-6-(trifluoromethyl)benzamide (1.3 g, 58%). ESI-MS m/z calc. 344.05, found 345.2 (M+1)+; retention time (Method A): 0.46 minutes (1.2 minute run).

Step 2: N-(3-Carbamoyl-4-fluoro-phenyl)-2-[2-methoxy-4-(trifluoromethoxy)phenoxy]-6-(trifluoromethyl)benzamide (40)

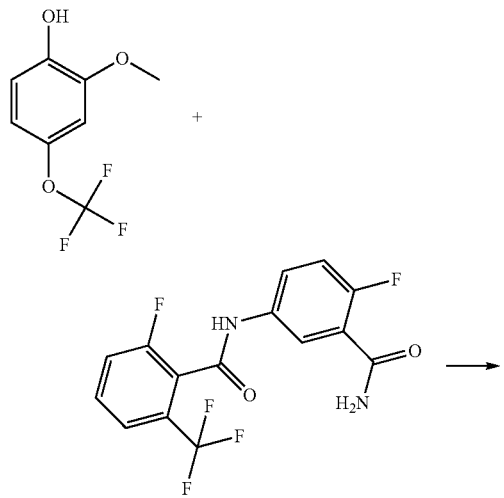

N-(3-carbamoyl-4-fluoro-phenyl)-2-fluoro-6-(trifluoromethyl)benzamide (50 mg, 0.15 mmol), 2-methoxy-4-(trifluoromethoxy)phenol (prepared as described in Example 2, 60 mg, 0.29 mmol) and $Cs_2CO_3$ (95 mg, 0.29 mmol) were combined in DMF (1 mL) and heated at 100° C. for 1 hour. The reaction was cooled to room temperature, diluted with DMSO (0.5 mL) and purified by HPLC (1-70% acetonitrile/5 mM HCl) to provide N-(3-carbamoyl-4-fluoro-phenyl)-2-[2-methoxy-4-(trifluoromethoxy)phenoxy]-6-(trifluoromethyl)benzamide (14.8 mg, 18%). ESI-MS m/z calc. 532.08, found 533.2 (M+1)+; retention time (Method B): 1.66 minutes (3 minute run). $^1$H NMR (400 MHz, DMSO-d6) δ 10.84 (s, 1H), 7.97 (dd, J=6.4, 2.8 Hz, 1H), 7.77-7.72 (m, 2H), 7.69 (s, 1H), 7.60 (td, J=8.0, 0.9 Hz, 1H), 7.57-7.53 (m, 1H), 7.31-7.21 (m, 3H), 7.06-6.98 (m, 2H), 3.80 (s, 3H) ppm.

Example 139

N-(3-Carbamoyl-4-fluoro-phenyl)-6-cyclopropyl-4-[2-(trideuteriomethoxy)-4-(trifluoromethoxy)phenoxy]pyridine-3-carboxamide (88)

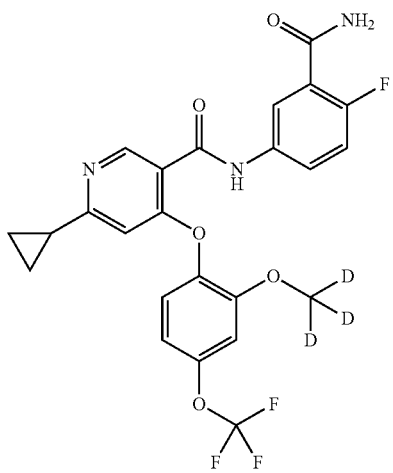 [SMILES: [2H]C([2H])([2H])Oc1cc(OC(F)(F)F)ccc1Oc1cc(C2CC2)ncc1C(=O)Nc1ccc(F)c(C(N)=O)c1]

Step 1: Methyl 6-bromo-4-[2-(trideuteriomethoxy)-4-(trifluoromethoxy)phenoxy]pyridine-3-carboxylate

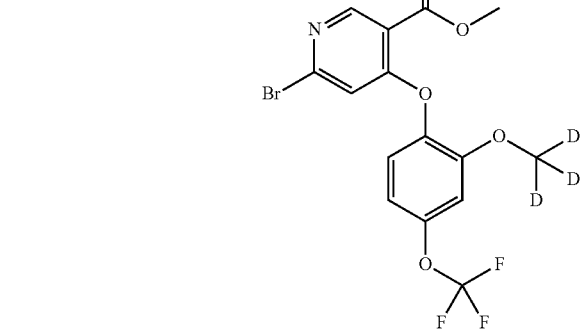

Methyl 6-bromo-4-chloro-pyridine-3-carboxylate (prepared as described in Example 135, step 1, 757 mg, 3.02 mmol) was dissolved in anhydrous DMF (7.6 mL) under a N₂ atmosphere and cooled to 0° C. 2-(Trideuteriomethoxy)-4-(trifluoromethoxy)phenol (prepared as described in Example 1, step 1, 0.638 g, 3.02 mmol) was added in one portion followed by Cs₂CO₃ (2.95 g, 9.05 mmol). The reaction mixture was stirred for 10 minutes at 0° C. then the cooling bath was removed and the reaction mixture was stirred for an additional 2 hours at room temperature. The reaction mixture was partitioned between ethyl acetate and brine and the layers separated. The organic layer was washed with brine, dried over Na₂SO₄, filtered and concentrated in vacuo. Silica gel chromatography (0-10% ethyl acetate/hexanes) provided methyl 6-bromo-4-[2-(trideuteriomethoxy)-4-(trifluoromethoxy)phenoxy]pyridine-3-carboxylate (1 g, 78%). ESI-MS m/z calc. 423.99, found 425.1 (M+1)+; retention time (Method A): 0.75 minutes (1.2 minute run).

Step 2: Methyl 6-cyclopropyl-4-[2-(trideuteriomethoxy)-4-(trifluoromethoxy)phenoxy]pyridine-3-carboxylate

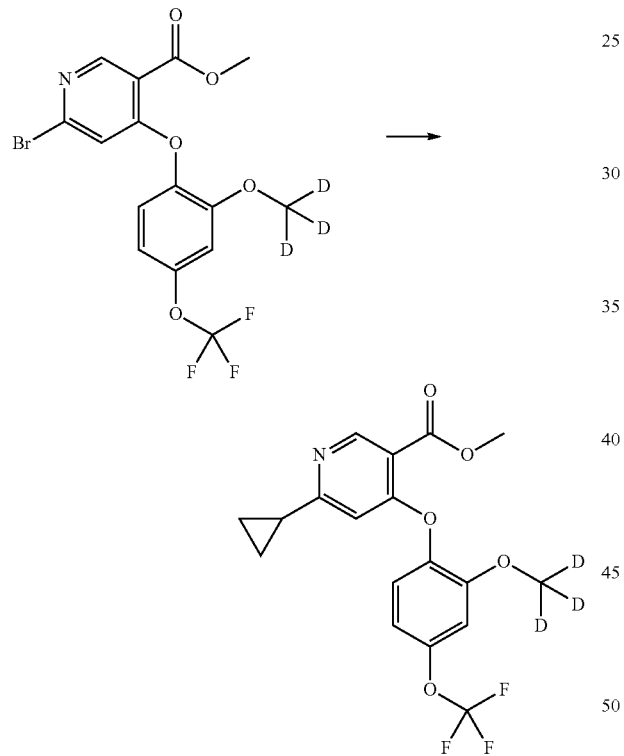

A flask was charged with a stir bar, methyl 6-bromo-4-[2-(trideuteriomethoxy)-4-(trifluoromethoxy)phenoxy]pyridine-3-carboxylate (1.00 g, 2.35 mmol) and bis(tri-t-butylphosphine)palladium(0) (144 mg, 0.282 mmol). The flask was sealed with a septum, placed under a N₂ atmosphere, and anhydrous THF (2.4 mL) was added. The resulting slurry was cooled to 0° C. and treated dropwise with a solution of bromo(cyclopropyl)zinc (5.6 mL of 0.5 M in THF, 2.8 mmol) over 30 minutes. The reaction was stirred for 30 minutes then quenched with saturated aqueous NH₄Cl solution and extracted with ethyl acetate. The organic layer was dried over Na₂SO₄, filtered and concentrated in vacuo. Silica gel chromatography (0-10% ethyl acetate/hexanes) provided methyl 6-cyclopropyl-4-[2-(trideuteriomethoxy)-4-(trifluoromethoxy)phenoxy]pyridine-3-carboxylate (710 mg, 78%). ESI-MS m/z calc. 386.11, found 387.2 (M+1)+; retention time (Method A): 0.61 minutes (1.2 minute run).

Step 3: 6-Cyclopropyl-4-[2-(trideuteriomethoxy)-4-(trifluoromethoxy)phenoxy]pyridine-3-carboxylic acid

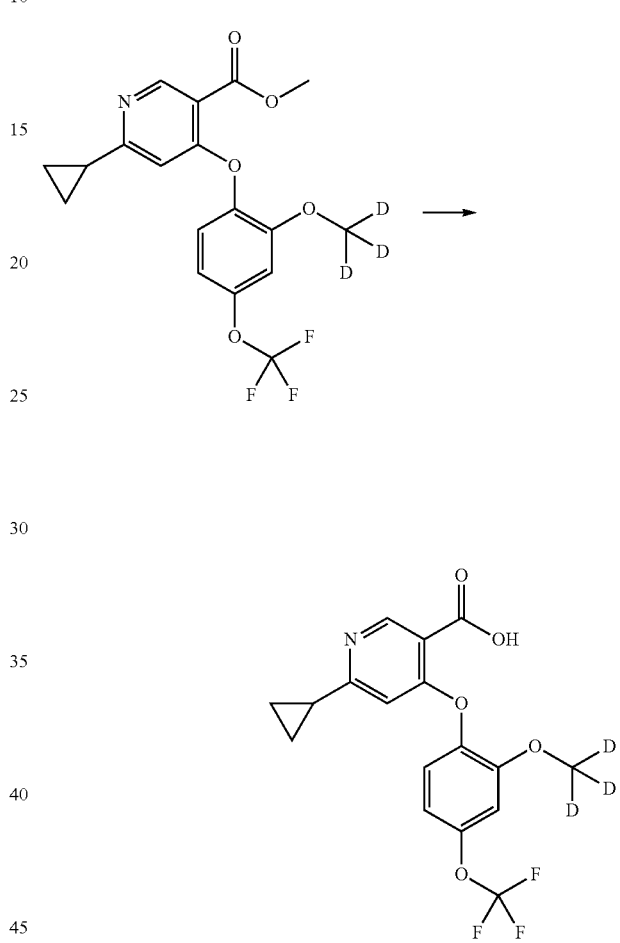

Methyl 6-cyclopropyl-4-[2-(trideuteriomethoxy)-4-(trifluoromethoxy)phenoxy]pyridine-3-carboxylate (710 mg, 1.84 mmol) was dissolved in methanol (10 mL) and treated with a solution of NaOH (735 mg, 18.4 mmol) in water (4 mL). The reaction mixture was stirred at room temperature for 1 hour. The solvents were removed under reduced pressure and the resulting white slurry was dissolved in water (100 mL), cooled to 0° C. and treated dropwise with 6 M HCl until pH2 was reached. The resulting precipitate was collected by vacuum filtration and the filter cake was further washed with water. The filter cake was then dried in a desiccator filled with Drierite® under high vacuum for 16 hours to obtain 6-cyclopropyl-4-[2-(trideuteriomethoxy)-4-(trifluoromethoxy)phenoxy]pyridine-3-carboxylic acid (630 mg, 92%) as a white solid. ESI-MS m/z calc. 372.10, found 373.2 (M+1)+; retention time (Method A): 0.5 minutes (1.2 minute run).

561

Step 4: N-(3-Carbamoyl-4-fluoro-phenyl)-6-cyclopropyl-4-[2-(trideuteriomethoxy)-4-(trifluoromethoxy)phenoxy]pyridine-3-carboxamide (88)

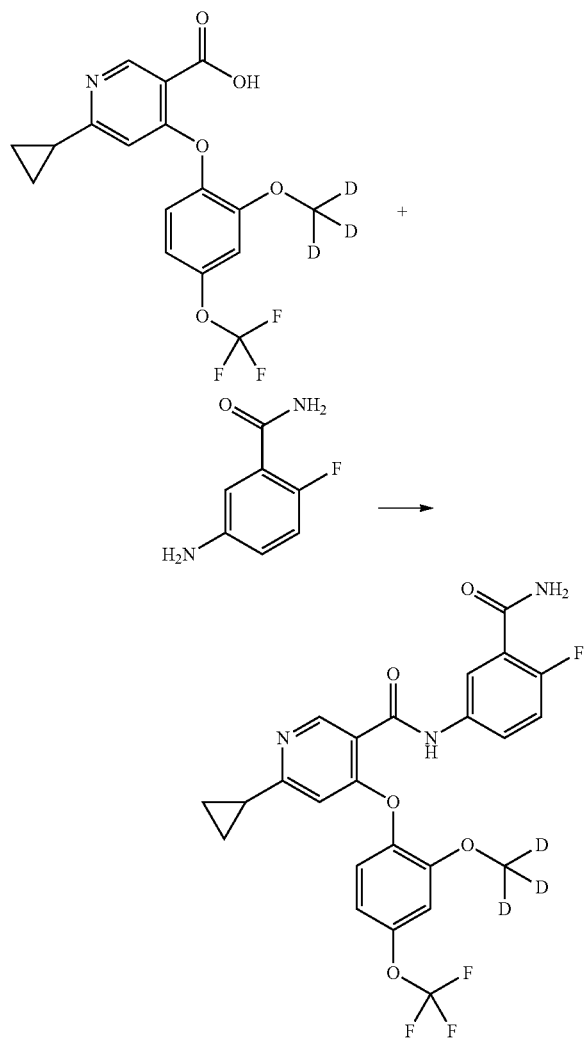

A mixture of 6-cyclopropyl-4-[2-(trideuteriomethoxy)-4-(trifluoromethoxy)phenoxy]pyridine-3-carboxylic acid (100 mg, 0.269 mmol), HATU (103 mg, 0.270 mmol) and 4-methylmorpholine (0.06 mL, 0.55 mmol) in DMF (0.5 mL) was stirred at room temperature for 5 minutes and then 5-amino-2-fluoro-benzamide (41 mg, 0.27 mmol) was added in one portion. The reaction was stirred for 30 minutes, then diluted to a total volume of 1 mL with DMF, filtered and purified by HPLC (30-99% acetonitrile/5 mM HCl) to provide N-(3-carbamoyl-4-fluoro-phenyl)-6-cyclopropyl-4-[2-(trideuteriomethoxy)-4-(trifluoromethoxy)phenoxy]pyridine-3-carboxamide (72 mg, 52%). ESI-MS m/z calc. 508.15, found 509.2 (M+1)+; retention time (Method B): 1.35 minutes (3 minute run). $^1$H NMR (400 MHz, DMSO-d6) δ 10.61 (s, 1H), 8.67 (s, 1H), 8.00 (dd, J=6.4, 2.8 Hz, 1H), 7.83 (ddd, J=8.9, 4.4, 2.8 Hz, 1H), 7.70 (d, J=10.7 Hz, 2H), 7.49 (d, J=8.8 Hz, 1H), 7.32-7.24 (m, 2H), 7.08 (ddq, J=8.9, 2.4, 1.2 Hz, 1H), 6.69 (s, 1H), 2.18 (dt, J=7.7, 4.6 Hz, 1H), 1.09-0.97 (m, 4H) ppm.

562

Example 140

N-(3-Carbamoyl-4-fluoro-phenyl)-2-fluoro-6-[3-methoxy-4-(trifluoromethoxy)phenoxy]-3-(trifluoromethyl)benzamide (126)

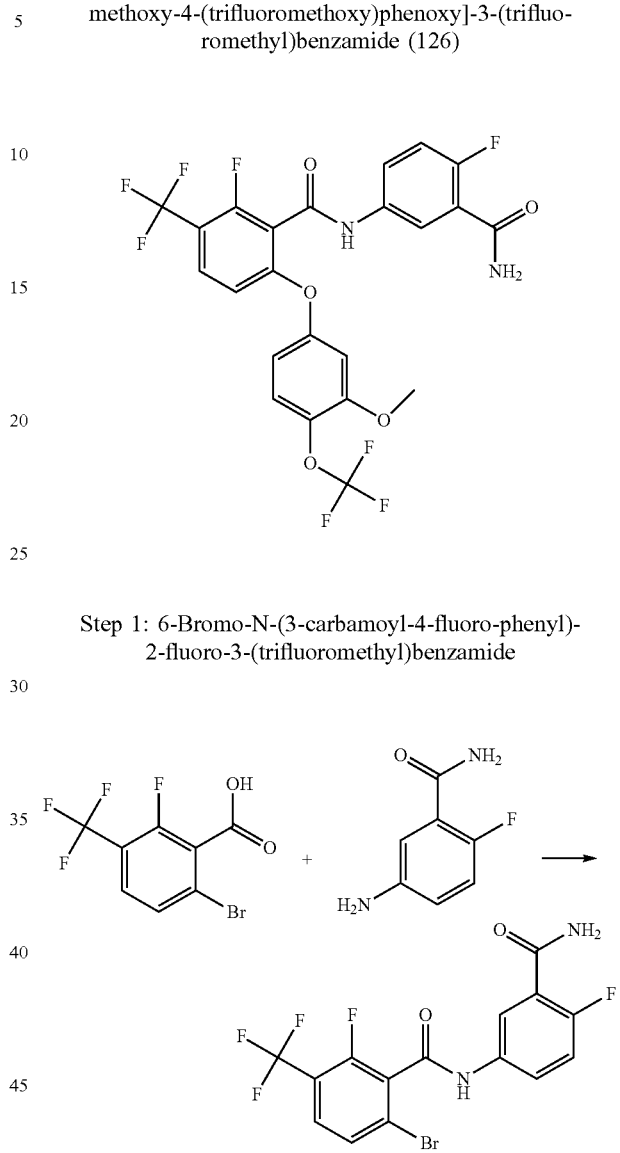

Step 1: 6-Bromo-N-(3-carbamoyl-4-fluoro-phenyl)-2-fluoro-3-(trifluoromethyl)benzamide 6-Bromo-2-fluoro-3-(trifluoromethyl)benzoic acid (2.00 g, 6.97 mmol) and HATU (2.65 g, 6.97 mmol) were combined in DMF (20 mL) and treated with DIEA (3.6 mL, 21 mmol). The mixture was stirred for 5 minutes then treated with 5-amino-2-fluoro-benzamide (1.08 g, 6.97 mmol). The reaction mixture was stirred for 1 hour then diluted with ethyl acetate and washed with 50% saturated NaHCO$_3$ solution, water, and brine. The organic layer was dried over Na$_2$SO$_4$, filtered, and concentrated in vacuo. The resulting solid was triturated with dichloromethane, and filtered to provide crop 1 of the desired product (1.91 g). The mother liquor was concentrated and purified by silica gel chromatography (0-100% ethyl acetate/hexanes) to provide an additional 470 mg of product. Total yield of 6-bromo-N-(3-carbamoyl-4-fluoro-phenyl)-2-fluoro-3-(trifluoromethyl) benzamide (2.38 g, 81%). ESI-MS m/z calc. 421.96, found 425.0 (M+1)+; retention time (Method B): 1.34 minutes (3 minute run). $^1$H NMR (400 MHz, DMSO-d6) δ 11.08 (s, 1H), 7.98 (dd, J=6.3, 2.8 Hz, 1H), 7.92-7.83 (m, 2H), 7.80-7.73 (m, 2H), 7.72 (br s, 1H), 7.32 (dd, J=10.1, 8.9 Hz, 1H) ppm.

Step 2: 3-Methoxy-4-(trifluoromethoxy)phenol

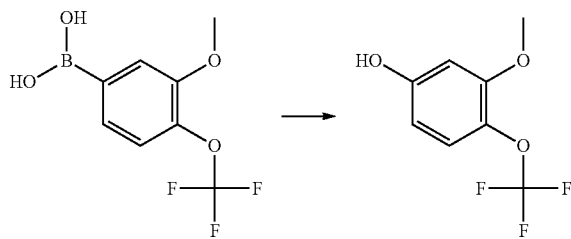 [SMILES: COc1cc(B(O)O)ccc1OC(F)(F)F ; COc1cc(O)ccc1OC(F)(F)F]

To a solution of [3-methoxy-4-(trifluoromethoxy)phenyl] boronic acid (1.00 g, 4.24 mmol) in ethanol (12 mL) was added hydrogen peroxide (1.37 g of 35% w/v, 12.7 mmol) and the reaction was stirred at room temperature for 16 hours. The reaction mixture was partitioned between water (15 mL) and ethyl acetate (30 mL). The organic layer was washed with saturated aqueous $NaHCO_3$ solution, dried over $Na_2SO_4$, and concentrated in vacuo to provide 3-methoxy-4-(trifluoromethoxy)phenol (350 mg, 40%). ESI-MS m/z calc. 208.03, found 209.1 (M+1)+; retention time (Method B): 1.27 minutes (3 minute run).

Step 3: N-(3-Carbamoyl-4-fluoro-phenyl)-2-fluoro-6-[3-methoxy-4-(trifluoromethoxy)phenoxy]-3-(trifluoromethyl)benzamide (126)

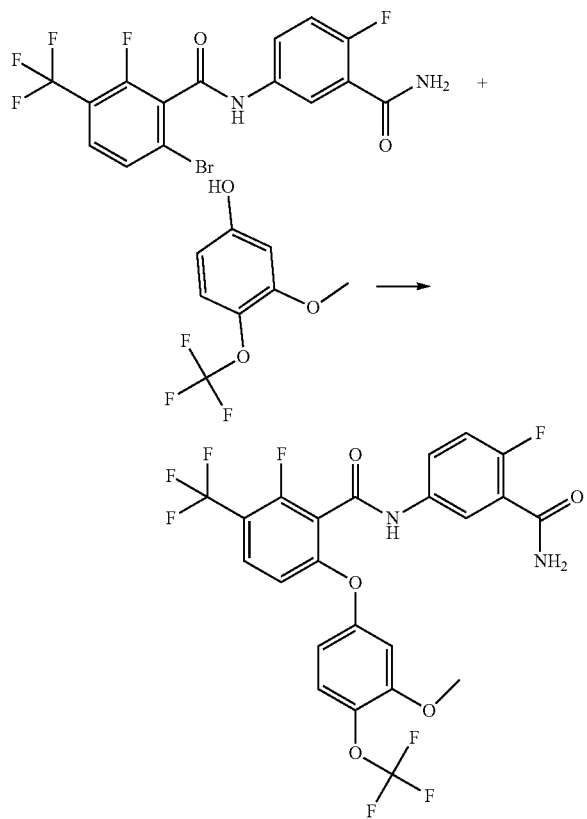

To a microwave vial was added 6-bromo-N-(3-carbamoyl-4-fluoro-phenyl)-2-fluoro-3-(trifluoromethyl)benzamide (200 mg, 0.473 mmol), $Cs_2CO_3$ (308 mg, 0.945 mmol), 3-methoxy-4-(trifluoromethoxy)phenol (98 mg, 0.47 mmol) and toluene (2 mL, degassed with $N_2$ bubbling). The mixture was bubbled with $N_2$ gas, then copper (I) iodide (18 mg, 0.095 mmol) was added and the reaction was stirred at 100° C. for 20 minutes. The reaction was diluted with ethyl acetate and water, and the layers separated. The organic layer was washed with brine, dried over $Na_2SO_4$, filtered and concentrated in vacuo. The residue was triturated in hexane and filtered to obtain N-(3-carbamoyl-4-fluoro-phenyl)-2-fluoro-6-[3-methoxy-4-(trifluoromethoxy)phenoxy]-3-(trifluoromethyl)benzamide (50 mg, 19%). ESI-MS m/z calc. 550.07, found 551.2 (M+1)+; retention time (Method B): 1.9 minutes (3 minute run).

Example 141

5-[[4-(Difluoromethoxy)-2-fluoro-6-[2-(trideuteriomethoxy)-4-(trifluoromethoxy)phenoxy]benzoyl]amino]pyridine-2-carboxamide (174)

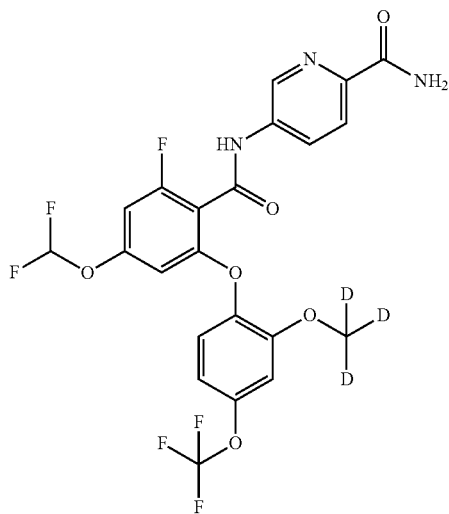 [SMILES: [2H]C([2H])([2H])Oc1cc(OC(F)(F)F)ccc1Oc1cc(OC(F)F)cc(F)c1C(=O)Nc1ccc(C(N)=O)nc1]

Step 1: Methyl 4-(difluoromethoxy)-2,6-difluoro-benzoate

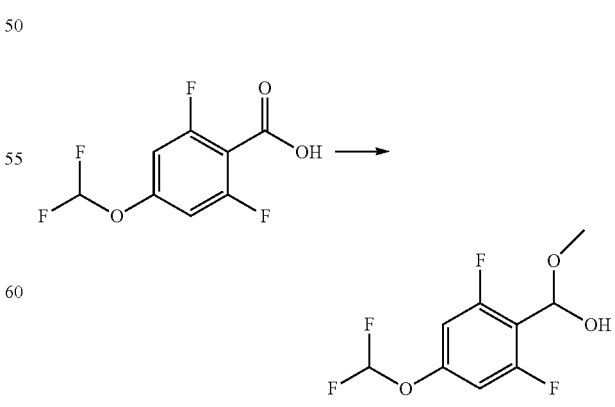

To a suspension of 4-(difluoromethoxy)-2,6-difluoro-benzoic acid (900 mg, 4.02 mmol) in dichloromethane (10 mL)

and methanol (3.5 mL, 86 mmol) at 0° C. under N₂ atmosphere was added a solution of diazomethyl(trimethyl)silane (3.4 mL of 2 M in hexanes, 6.8 mmol) dropwise (persistent yellow color). The mixture was stirred 10 minutes then several drops of acetic acid were added to quench excess reagent (until colorless). The reaction mixture was concentrated in vacuo, dissolved in dichloromethane and washed with saturated aqueous NaHCO₃, dried over MgSO₄ and concentrated. Silica gel chromatography (0-10% ethyl acetate/dichloromethane) provided methyl 4-(difluoromethoxy)-2,6-difluoro-benzoate (746 mg, 74%). ¹H NMR (400 MHz, DMSO-d6) δ 7.43 (t, J=72.6 Hz, 1H), 7.23 (d, J=1.8 Hz, 1H), 7.21 (d, J=1.9 Hz, 1H), 3.88 (s, 3H) ppm.

Step 2: Methyl 4-(difluoromethoxy)-2-fluoro-6-[2-(trideuteriomethoxy)-4-(trifluoromethoxy)phenoxy]benzoate

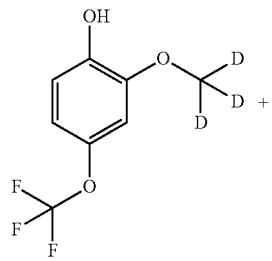

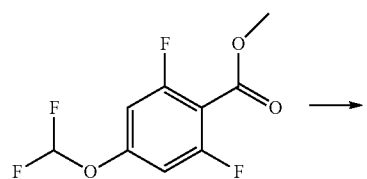

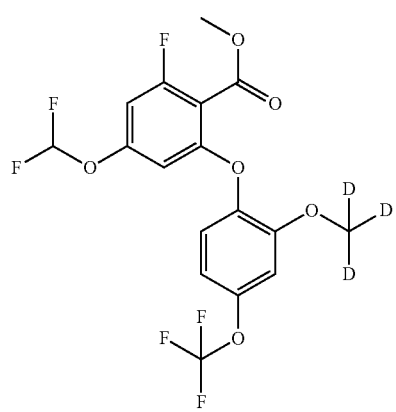

A vial charged with 2-(trideuteriomethoxy)-4-(trifluoromethoxy)phenol (prepared as described in Example 1, step 1, 630 mg, 2.98 mmol), methyl 4-(difluoromethoxy)-2,6-difluoro-benzoate (750 mg, 2.99 mmol), Cs₂CO₃ (2.10 g, 6.45 mmol) in DMF (8 mL) was heated at 80° C. for 90 minutes. The reaction mixture was cooled to room temperature and partitioned between water and ethyl acetate. The organic layer was washed with brine, dried over MgSO₄, filtered and concentrated in vacuo. Silica gel chromatography (0-5% ethyl acetate/hexanes) provided methyl 4-(difluoromethoxy)-2-fluoro-6-[2-(trideuteriomethoxy)-4-(trifluoromethoxy)phenoxy]benzoate (780 mg, 61%). ESI-MS m/z calc. 429.07, found 430.2 (M+1)+; retention time (Method B): 1.95 minutes (3 minute run). ¹H NMR (400 MHz, DMSO-d6) δ 7.50-7.10 (m, 3H), 7.04-6.97 (m, 2H), 6.34-6.30 (m, 1H), 3.82 (s, 3H) ppm.

Step 3: 4-(Difluoromethoxy)-2-fluoro-6-[2-(trideuteriomethoxy)-4-(trifluoromethoxy)phenoxy]benzoic acid

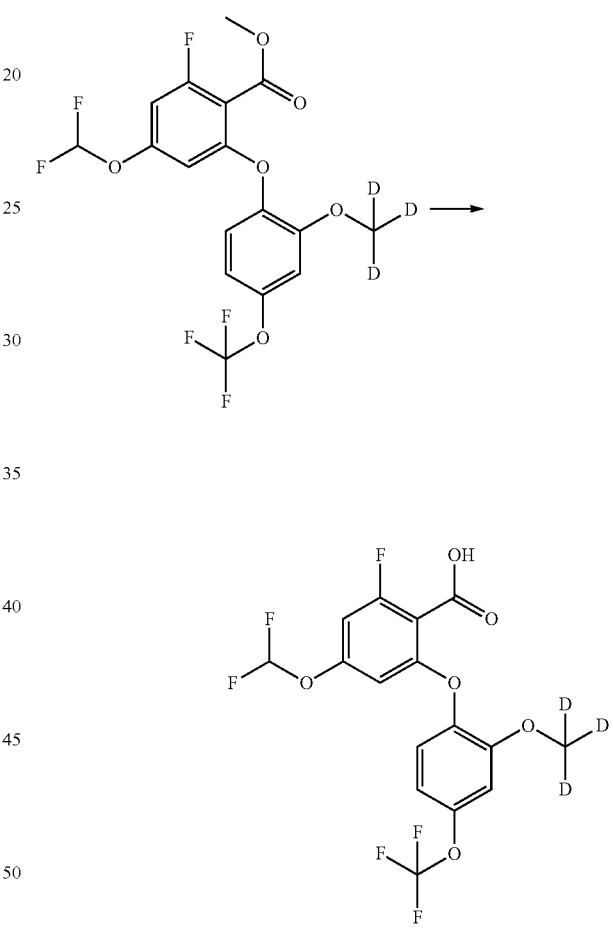

To a solution of methyl 4-(difluoromethoxy)-2-fluoro-6-[2-(trideuteriomethoxy)-4-(trifluoromethoxy)phenoxy]benzoate (575 mg, 1.34 mmol) in methanol (1 mL) was added NaOH (800 mg, 20.0 mmol) and water (1 mL). The reaction mixture was stirred at room temperature for 15 hours. The solvent was evaporated and the reaction mixture was quenched with 6 M HCl. The aqueous layer was extracted by ethyl acetate, dried over MgSO₄, filtered and concentrated in vacuo to provide 4-(difluoromethoxy)-2-fluoro-6-[2-(trideuteriomethoxy)-4-(trifluoromethoxy)phenoxy]benzoic acid (347 mg, 62%). ESI-MS m/z calc. 415.05, found 416.2 (M+1)+; retention time (Method B): 1.68 minutes (3 minute run).

Step 4: 4-(Difluoromethoxy)-2-fluoro-6-[2-(trideuteriomethoxy)-4-(trifluoromethoxy)phenoxy]benzoyl chloride To a solution of 4-(difluoromethoxy)-2-fluoro-6-[2-(trideuteriomethoxy)-4-(trifluoromethoxy)phenoxy]benzoic acid (200 mg, 0.482 mmol) and DMF (35 µL, 0.45 mmol) in dichloromethane (3 mL) at 0° C. was added oxalyl chloride (0.045 mL, 0.52 mmol) dropwise. The mixture was stirred at room temperature for 90 minutes and conversion was monitored by UPLC via test for morpholine adduct formation. The acid chloride was used as a solution for the next step.

Step 5: 5-[[4-(Difluoromethoxy)-2-fluoro-6-[2-(trideuteriomethoxy)-4-(trifluoromethoxy)phenoxy]benzoyl]amino]pyridine-2-carboxamide (174)

To a flask charged with 5-aminopyridine-2-carboxamide (48 mg, 0.35 mmol) and DIEA (0.150 mL, 0.861 mmol) in dichloromethane (1 mL) was added a solution of 4-(difluoromethoxy)-2-fluoro-6-[2-(trideuteriomethoxy)-4-(trifluoromethoxy)phenoxy]benzoyl chloride (100 mg, 0.231 mmol) in dichloromethane (1.5 mL) at 0° C. dropwise under an $N_2$ atmosphere. The reaction mixture was stirred for 16 hours at room temperature then diluted with water and extracted with dichloromethane. The organic layer was dried over $MgSO_4$, filtered and concentrated in vacuo. Silica gel chromatography (0-60% ethyl acetate/hexanes) provided 5-[[4-(difluoromethoxy)-2-fluoro-6-[2-(trideuteriomethoxy)-4-(trifluoromethoxy)phenoxy]benzoyl]amino]pyridine-2-carboxamide (22 mg, 18%). ESI-MS m/z calc. 534.10, found 535.2 (M+1)+; retention time (Method B): 1.67 minutes (3 minute run). $^1$H NMR (400 MHz, DMSO-d6) δ 11.18 (s, 1H), 8.85 (dd, J=2.5, 0.7 Hz, 1H), 8.25 (dd, J=8.6, 2.5 Hz, 1H), 8.08-7.97 (m, 2H), 7.60-6.93 (m, 6H), 6.37 (t, J=1.7 Hz, 1H) ppm.

Example 142

N-(3-Carbamoyl-4-fluoro-phenyl)-2-fluoro-6-[3-hydroxy-4-(trifluoromethoxy)phenoxy]-3-(trifluoromethyl)benzamide (141)

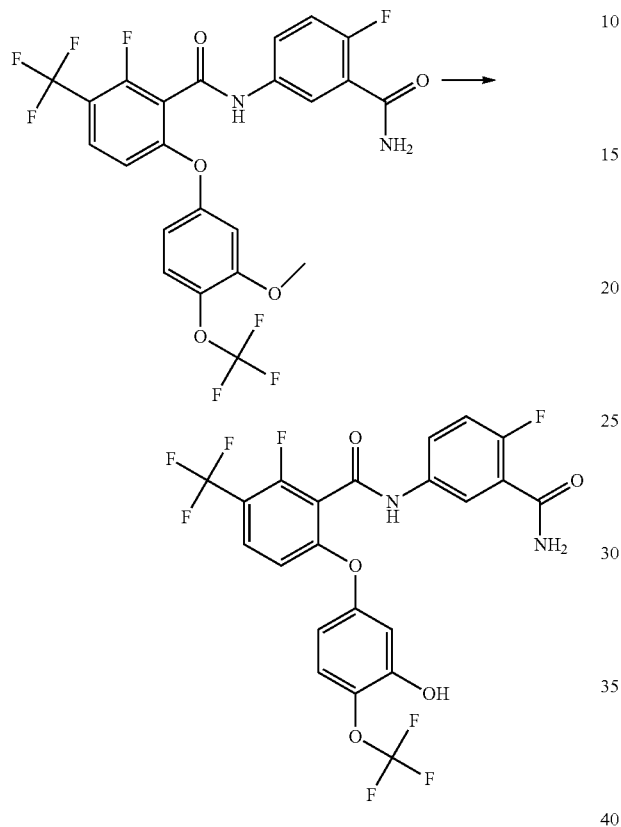

N-(3-carbamoyl-4-fluoro-phenyl)-2-fluoro-6-[3-methoxy-4-(trifluoromethoxy)phenoxy]-3-(trifluoromethyl)benzamide (26, prepared as described in Example 140, 30 mg, 0.055 mmol) was dissolved in dichloromethane (0.6 mL) and cooled to −78° C. (dry ice/acetone bath). The solution was treated dropwise with a solution of BBr$_3$ (0.27 mL of 1.0 M in dichloromethane, 0.27 mmol) and stirred for 10 minutes. The reaction mixture was removed from the dry ice bath and allowed to come to room temperature and stirred for 20 minutes. The reaction mixture was diluted with dichloromethane and washed with saturated NaHCO$_3$ and brine, dried over Na$_2$SO$_4$, filtered and concentrated in vacuo. Silica gel chromatography (0-25% ethyl acetate/dichloromethane) provided N-(3-carbamoyl-4-fluoro-phenyl)-2-fluoro-6-[3-hydroxy-4-(trifluoromethoxy)phenoxy]-3-(trifluoromethyl)benzamide (17 mg, 57%) as a pale yellow solid. ESI-MS m/z calc. 536.06, found 537.2 (M+1)+; retention time (Method B): 1.6 minutes (3 minute run). $^1$H NMR (400 MHz, DMSO-d6) δ 11.03 (s, 1H), 10.62 (s, 1H), 7.96 (dd, J=6.4, 2.8 Hz, 1H), 7.86 (t, J=8.7 Hz, 1H), 7.76 (ddd, J=8.9, 4.4, 2.9 Hz, 1H), 7.70 (d, J=17.4 Hz, 2H), 7.36 (dq, J=8.8, 1.2 Hz, 1H), 7.29 (dd, J=10.1, 8.9 Hz, 1H), 6.92 (d, J=8.8 Hz, 1H), 6.80 (d, J=2.9 Hz, 1H), 6.68 (dd, J=8.9, 2.8 Hz, 1H) ppm. 19F NMR (376 MHz, DMSO-d6) δ −57.33, −59.25, −59.28, −117.44, −118.46 ppm.

Example 143

4-[[2-[2-(Trideuteriomethoxy)-4-(trifluoromethoxy)phenoxy]-4-(trifluoromethoxy)benzoyl]amino]pyridine-2-carboxamide (147)

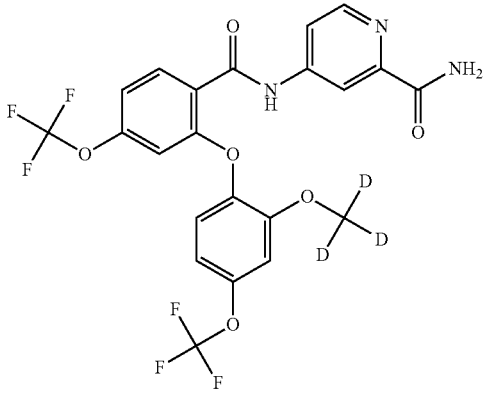 [SMILES: [2H]C([2H])([2H])Oc1cc(OC(F)(F)F)ccc1Oc1cc(OC(F)(F)F)ccc1C(=O)Nc1ccnc(C(N)=O)c1]

Step 1: 2-Fluoro-4-(trifluoromethoxy)benzoyl chloride

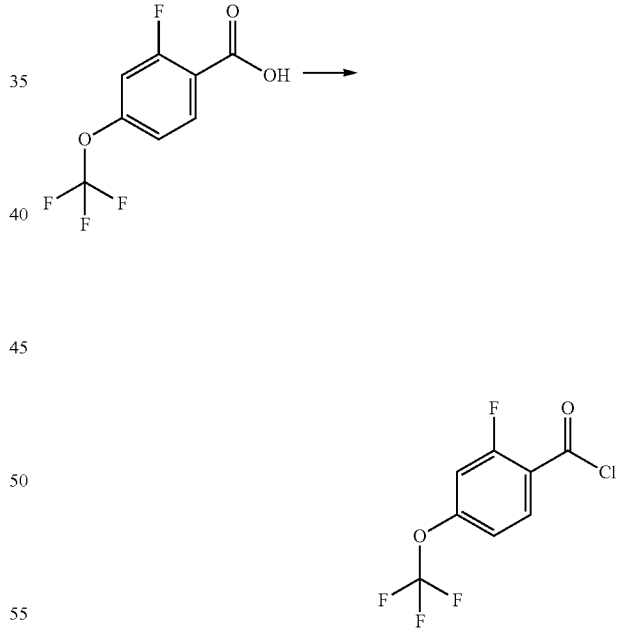

To a solution of 2-fluoro-4-(trifluoromethoxy)benzoic acid (13.86 g, 109.2 mmol) and DMF (161 μL, 2.08 mmol) in dichloromethane (51 mL) at 0° C. was added oxalyl chloride (9.53 mL, 109 mmol) dropwise. The mixture was stirred at room temperature for 5 hours under N$_2$ atmosphere with conversion to product monitored by UPLC via test for [2-fluoro-4-(trifluoromethoxy)phenyl]-morpholino-methanone piperidine adduct formation. The solvent was evaporated in vacuo to afford 2-fluoro-4-(trifluoromethoxy)benzoyl chloride (3.5 g, 63%).

Step 2: 4-[[2-Fluoro-4-(trifluoromethoxy)benzoyl]amino]pyridine-2-carboxamide

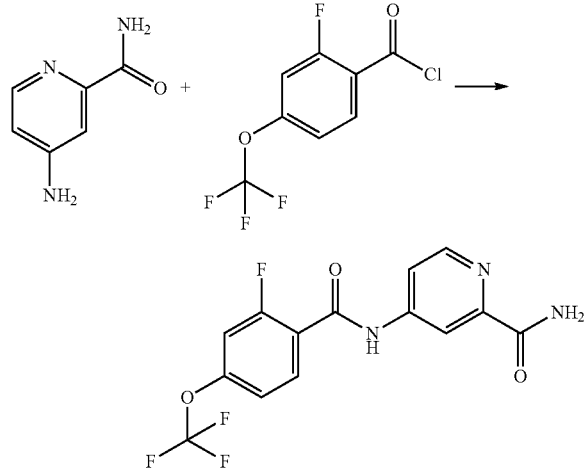

To a solution of 4-aminopyridine-2-carboxamide (2.90 g, 21.2 mmol) and DIEA (7.19 g, 55.7 mmol) in NMP (27 mL) at 0° C. was added dropwise a solution of 2-fluoro-4-(trifluoromethoxy)benzoyl chloride (5.40 g, 22.3 mmol) in dichloromethane (27 mL). The reaction mixture was removed from the ice bath and stirred at room temperature for 16 hours. The reaction mixture was partitioned between water and ethyl acetate. The layers were separated and the aqueous layer was extracted with additional ethyl acetate. The combined organic layers were dried over Na$_2$SO$_4$, filtered and concentrated in vacuo. The crude material was triturated with a mixture of hexanes/dichloromethane and the solid was collected by vacuum filtration to obtain 4-[[2-fluoro-4-(trifluoromethoxy)benzoyl]amino]pyridine-2-carboxamide (650 mg, 9%). ESI-MS m/z calc. 343.05, found 344.1 (M+1)+; retention time (Method B): 1.65 minutes (3 minute run). $^1$H NMR (400 MHz, DMSO-d6) δ 11.09 (s, 1H), 8.56 (d, J=5.6 Hz, 1H), 8.36 (d, J=2.2 Hz, 1H), 8.11 (d, J=2.7 Hz, 1H), 7.95-7.80 (m, 2H), 7.74-7.54 (m, 2H), 7.50-7.32 (m, 1H) ppm.

Step 3: 4-[[2-[2-(Trideuteriomethoxy)-4-(trifluoromethoxy)phenoxy]-4-(trifluoromethoxy)benzoyl]amino]pyridine-2-carboxamide (147)

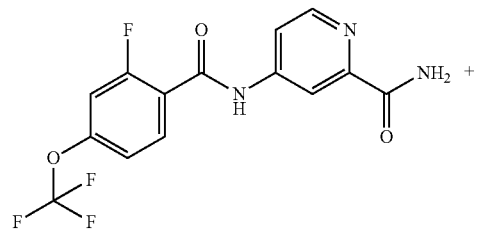

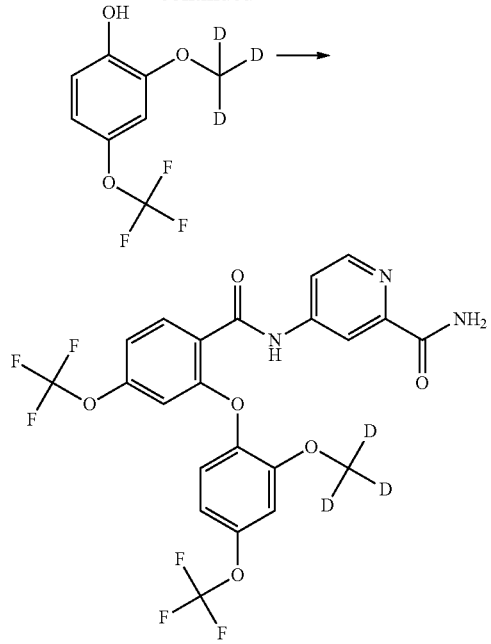

A mixture of 4-[[2-fluoro-4-(trifluoromethoxy)benzoyl]amino]pyridine-2-carboxamide (75 mg, 0.22 mmol), 2-(trideuteriomethoxy)-4-(trifluoromethoxy)phenol (prepared as described in Example 1 step 1, 46 mg, 0.22 mmol) and K$_2$CO$_3$ (91 mg, 0.66 mmol) in DMF (0.75 mL) was heated at 100° C. for 2 hours. The reaction mixture was cooled to room temperature, filtered and diluted with DMSO (1 mL). HPLC purification (10-99% acetonitrile/5 mM HCl) provided 4-[[2-[2-(trideuteriomethoxy)-4-(trifluoromethoxy)phenoxy]-4-(trifluoromethoxy)benzoyl]amino]pyridine-2-carboxamide (46.5 mg, 39%) as a white solid. ESI-MS m/z calc. 534.10, found 535.5 (M+1)+; retention time (Method B): 1.83 minutes (3 minute run). $^1$H NMR (400 MHz, DMSO-d6) δ 10.98 (s, 1H), 8.52 (d, J=5.4 Hz, 1H), 8.32 (d, J=2.0 Hz, 1H), 8.11 (d, J=2.8 Hz, 1H), 7.86 (dd, J=5.5, 2.2 Hz, 1H), 7.81 (d, J=8.5 Hz, 1H), 7.63 (d, J=2.7 Hz, 1H), 7.33 (d, J=8.8 Hz, 1H), 7.24 (ddd, J=8.5, 2.3, 1.2 Hz, 1H), 7.18 (dd, J=2.8, 0.7 Hz, 1H), 7.02 (ddq, J=8.8, 2.4, 1.2 Hz, 1H), 6.69 (dd, J=2.2, 0.9 Hz, 1H) ppm. $^{19}$F NMR (376 MHz, DMSO-d6) δ −56.8, −56.93, ppm.

Example 144

4-[[6-[4-(Difluoromethoxy)-2-fluoro-phenoxy]-2-fluoro-3-(trifluoromethyl)benzoyl]amino]pyridine-2-carboxamide (136)

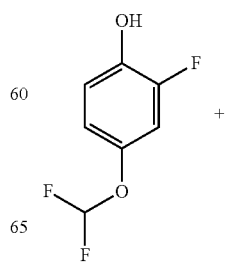

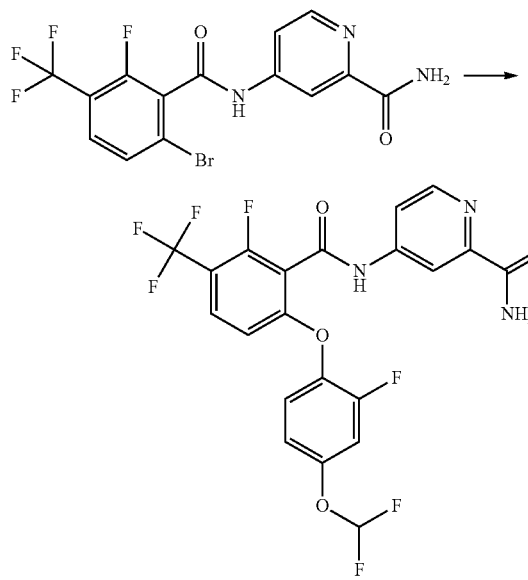

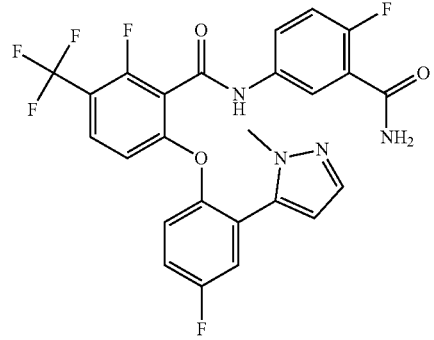

To a microwave vial was added 4-[[6-bromo-2-fluoro-3-(trifluoromethyl)benzoyl]amino]pyridine-2-carboxamide (prepared as described in Example 136, step 2, 50 mg, 0.12 mmol), Cs₂CO₃ (80 mg, 0.25 mmol), 4-(difluoromethoxy)-2-fluoro-phenol (22 mg, 0.12 mmol) and toluene (0.5 mL, degassed by N₂ bubbling). The mixture was bubbled with N₂ gas, treated with copper (I) iodide (13 mg, 0.07 mmol) and stirred at 100° C. for 20 minutes. The reaction was partitioned between ethyl acetate and water and the layers separated. The organic layer was concentrated in vacuo. The residue was dissolved in DMSO (2 mL) and purified by HPLC (10-99% acetonitrile/5 mM HCl) to provide 4-[[6-[4-(difluoromethoxy)-2-fluoro-phenoxy]-2-fluoro-3-(trifluoromethyl)benzoyl]amino]pyridine-2-carboxamide (35 mg, 56%). ESI-MS m/z calc. 503.07, found 504.3 (M+1)+; retention time (Method B): 1.61 minutes (3 minute run).

Example 145

N-(3-Carbamoyl-4-fluoro-phenyl)-2-fluoro-6-[4-fluoro-2-(2-methylpyrazol-3-yl)phenoxy]-3-(trifluoromethyl)benzamide (135)

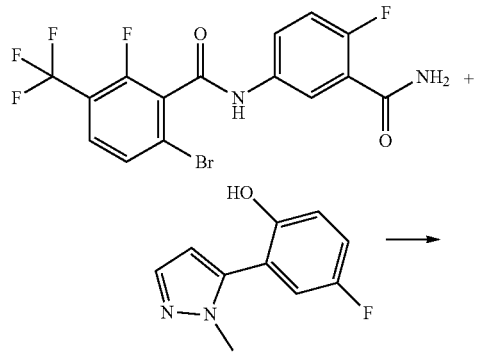

To a microwave vial was added 6-bromo-N-(3-carbamoyl-4-fluoro-phenyl)-2-fluoro-3-(trifluoromethyl)benzamide (75 mg, 0.18 mmol, prepared as described in Example 140, step 1), Cs₂CO₃ (116 mg, 0.36 mmol), 4-fluoro-2-(2-methylpyrazol-3-yl)phenol (34 mg, 0.18 mmol) and toluene (0.34 mL, degassed with N₂ bubbling). The mixture was bubbled with N₂ gas then treated with copper (I) iodide (18 mg, 0.10 mmol) and stirred at 100° C. for 20 minutes. The reaction was partitioned between ethyl acetate and water, and the layers separated. The organic layer was concentrated in vacuo. The residue was dissolved DMSO (2 mL) and purified by HPLC (10-99% acetonitrile/5 mM HCl) to provide N-(3-carbamoyl-4-fluoro-phenyl)-2-fluoro-6-[4-fluoro-2-(2-methylpyrazol-3-yl)phenoxy]-3-(trifluoromethyl)benzamide (10.3 mg, 11%). ESI-MS m/z calc. 534.11, found 535.2 (M+1)+; retention time (Method B): 1.52 minutes (3 minute run).

Example 146

4-[[4-Cyclopropyl-5-fluoro-2-[2-methoxy-4-(trifluoromethoxy)phenoxy]benzoyl]amino]pyridine-2-carboxamide (116)

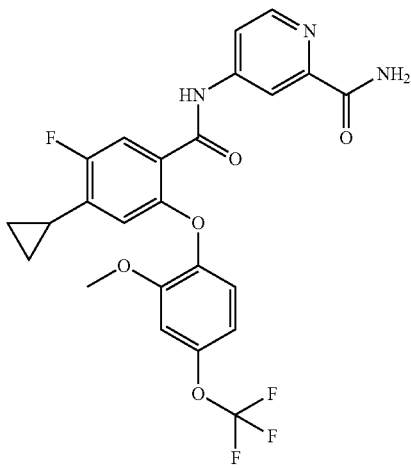

Step 1: Methyl 4-bromo-5-fluoro-2-[2-methoxy-4-(trifluoromethoxy)phenoxy]benzoate

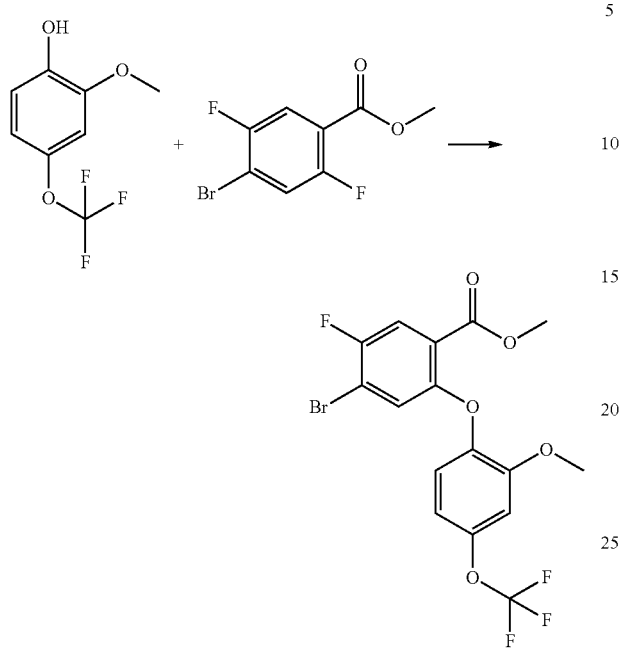

A vial charged with 2-methoxy-4-(trifluoromethoxy)phenol (647 mg, 3.11 mmol), methyl 4-bromo-2,5-difluorobenzoate (780 mg, 3.11 mmol), Cs₂CO₃ (2.5 g, 7.7 mmol) and DMF (6.5 mL) was heated at 80° C. for 2 hours. The reaction mixture was cooled to room temperature and diluted with ethyl acetate and brine. The layers were separated and the organic layer was washed with brine (3×), dried over Na₂SO₄, filtered and concentrated in vacuo. Silica gel chromatography (0-5% ethyl acetate/hexanes) provided methyl 4-bromo-5-fluoro-2-[2-methoxy-4-(trifluoromethoxy)phenoxy]benzoate (350 mg, 26%). ESI-MS m/z calc. 437.97, found 441.2 (M+2)+; retention time (Method B): 2.13 minutes (3 minute run). ¹H NMR (400 MHz, DMSO-d6) δ 7.79 (d, J=8.7 Hz, 1H), 7.22-7.16 (m, 2H), 7.06 (d, J=8.8 Hz, 1H), 6.97-6.91 (m, 1H), 3.81 (s, 3H), 3.77 (s, 3H) ppm.

Step 2: Methyl 4-cyclopropyl-5-fluoro-2-[2-methoxy-4-(trifluoromethoxy)phenoxy]benzoate

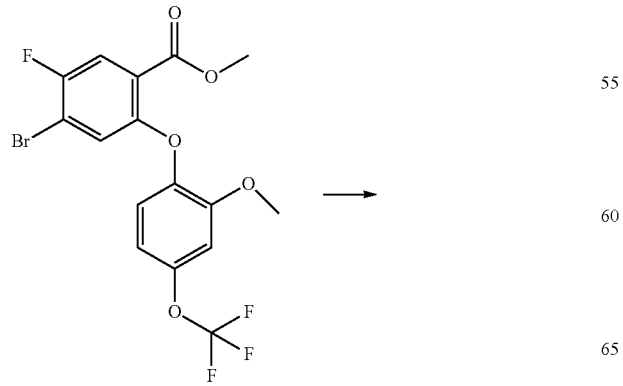

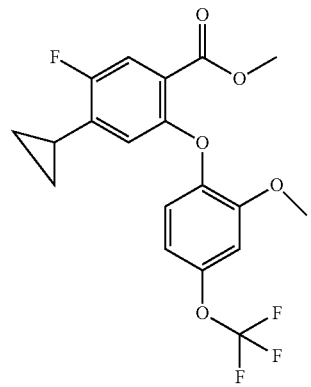

To a round bottom flask equipped with a stir bar was added methyl 4-bromo-5-fluoro-2-[2-methoxy-4-(trifluoromethoxy)phenoxy]benzoate (345 mg, 0.786 mmol) and bis(tri-t-butylphosphine)palladium(0) (210 mg, 0.411 mmol). The flask was sealed with a septum, placed under N₂ atmosphere and THF (5 mL) was added. The mixture was cooled to 0° C. and a solution of bromo(cyclopropyl)zinc (3.2 mL of 0.5 M in THF, 1.6 mmol) was added dropwise. After 30 minutes the reaction was quenched with saturated aqueous NH₄Cl solution and diluted with ethyl acetate. The layers were separated and the organic layer was dried over anhydrous Na₂SO₄, filtered and concentrated in vacuo. Silica gel chromatography (0-5% ethyl acetate/hexanes) provided methyl 4-cyclopropyl-5-fluoro-2-[2-methoxy-4-(trifluoromethoxy)phenoxy]benzoate (221 mg, 70%) and an off white solid. ESI-MS m/z calc. 400.09, found 401.3 (M+1)+; retention time (Method B): 2.18 minutes (3 minute run).

Step 3: 4-Cyclopropyl-5-fluoro-2-[2-methoxy-4-(trifluoromethoxy)phenoxy]benzoic acid

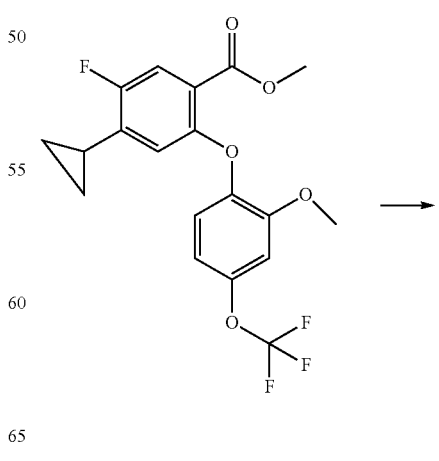

577

-continued

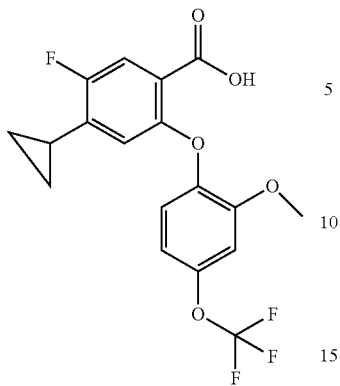

To a solution of methyl 4-cyclopropyl-5-fluoro-2-[2-methoxy-4-(trifluoromethoxy)phenoxy]benzoate (220 mg, 0.550 mmol) in THF (3 mL) and water (2 mL) was added NaOH (223 mg, 5.58 mmol) and the reaction mixture was stirred at room temperature for 2 hours. The reaction mixture was cooled in an ice bath and quenched with 1 M HCl. The aqueous layer was extracted with dichloromethane, dried over MgSO₄, filtered and concentrated in vacuo to obtain 4-cyclopropyl-5-fluoro-2-[2-methoxy-4-(trifluoromethoxy)phenoxy]benzoic acid (173 mg, 81%). ESI-MS m/z calc. 386.07, found 387.1 (M+1)+; retention time (Method B): 1.95 minutes (3 minute run).

Step 4: 4-[[4-Cyclopropyl-5-fluoro-2-[2-methoxy-4-(trifluoromethoxy)phenoxy]benzoyl]amino]pyridine-2-carboxamide (116)

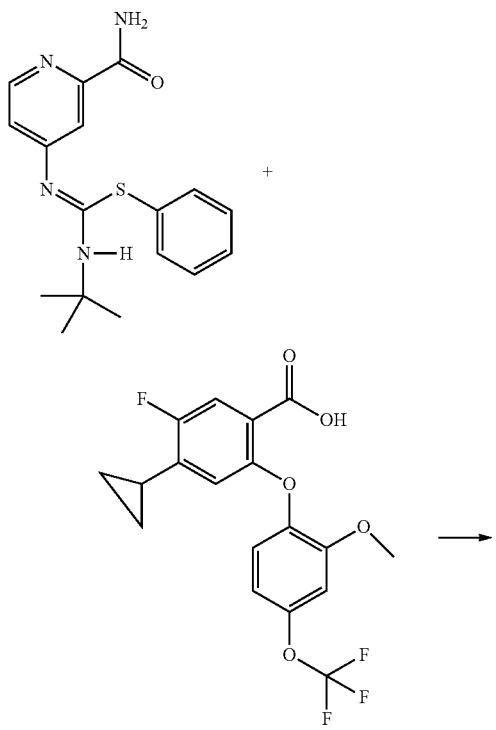

578

-continued

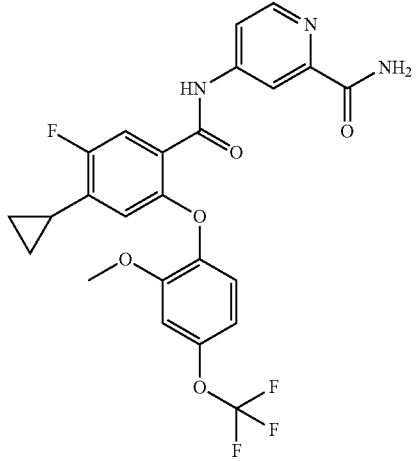 [SMILES: COc1cc(OC(F)(F)F)ccc1Oc1cc(C2CC2)c(F)cc1C(=O)Nc1ccnc(C(N)=O)c1]

A vial was charged with 4-cyclopropyl-5-fluoro-2-[2-methoxy-4-(trifluoromethoxy)phenoxy]benzoic acid (76 mg, 0.20 mmol), 4-[(Z)-[(tert-butylamino)-phenylsulfanyl-methylene]amino]pyridine-2-carboxamide (prepared as described in Preparation 1, 65 mg, 0.20 mmol), tris[(Z)-1-methyl-3-oxo-but-1-enoxy]iron (2 mg, 0.005 mmol) in 2-propanol (1.1 mL) and heated at 80° C. under an atmosphere of air for 20 hours. The reaction mixture was cooled to room temperature and concentrated in vacuo. The residue was dissolved in dichloromethane and washed with 1 M HCl. The organic layer was dried over MgSO₄, filtered and concentrated. Silica gel chromatography (0-60% ethyl acetate-hexanes) provided 4-[[4-cyclopropyl-5-fluoro-2-[2-methoxy-4-(trifluoromethoxy)phenoxy]benzoyl]amino]pyridine-2-carboxamide (44 mg, 44%). ESI-MS m/z calc. 505.12, found 506.3 (M+1)+; retention time (Method B): 1.93 minutes (3 minute run). ¹H NMR (400 MHz, DMSO-d6) δ 10.77 (s, 1H), 8.48 (d, J=5.5 Hz, 1H), 8.24 (d, J=2.1 Hz, 1H), 8.06 (d, J=2.8 Hz, 1H), 7.79 (dd, J=5.6, 2.2 Hz, 1H), 7.61 (s, 1H), 7.52 (d, J=10.0 Hz, 1H), 7.08 (d, J=2.7 Hz, 1H), 6.97 (d, J=8.8 Hz, 1H), 6.89 (ddd, J=8.8, 2.7, 1.2 Hz, 1H), 6.58 (d, J=6.3 Hz, 1H), 3.73 (s, 3H), 2.07 (ddd, J=13.6, 8.7, 5.2 Hz, 1H), 1.09-0.95 (m, 2H), 0.77-0.62 (m, 2H) ppm.

Example 147

4-[[2-[2-(Trideuteriomethoxy)-4-(trifluoromethoxy)phenoxy]-5-(trifluoromethoxy)benzoyl]amino]pyridine-2-carboxamide (158)

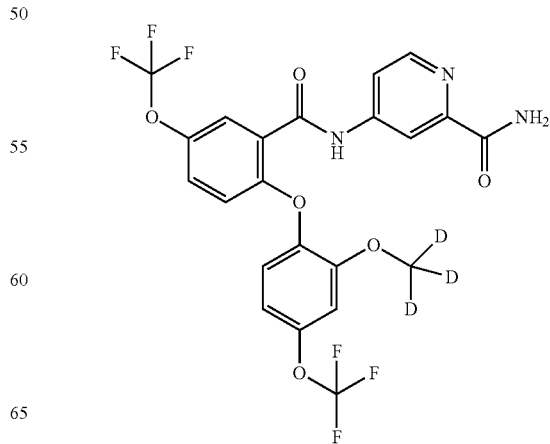

Step 1: 4-[[2-Fluoro-5-(trifluoromethoxy)benzoyl]amino]pyridine-2-carboxamide

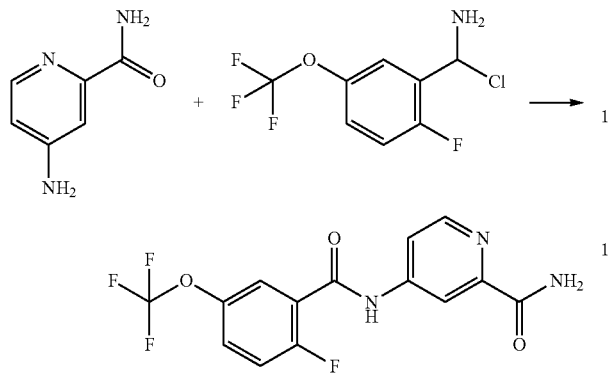

To a solution of 4-aminopyridine-2-carboxamide (565 mg, 4.12 mmol) and DIEA (1.33 g, 10.3 mmol) in NMP (10 mL) at 0° C. was added a solution of 2-fluoro-5-(trifluoromethoxy)benzoyl chloride (1.00 g, 4.123 mmol) in dichloromethane (5 mL) dropwise. The reaction was allowed to warm to room temperature and stirred for 16 hours. The reaction mixture was partitioned between ethyl acetate and water, and the layers separated. The organic layer was dried over $Na_2SO_4$, filtered and concentrated in vacuo to obtain 4-[[2-fluoro-5-(trifluoromethoxy)benzoyl]amino]pyridine-2-carboxamide (850 mg, 60%). ESI-MS m/z calc. 343.05, found 344.1 (M+1)+; retention time (Method B): 0.51 minutes (3 minute run).

Step 2: 4-[[2-[2-(Trideuteriomethoxy)-4-(trifluoromethoxy)phenoxy]-5-(trifluoromethoxy)benzoyl]amino]pyridine-2-carboxamide (158)

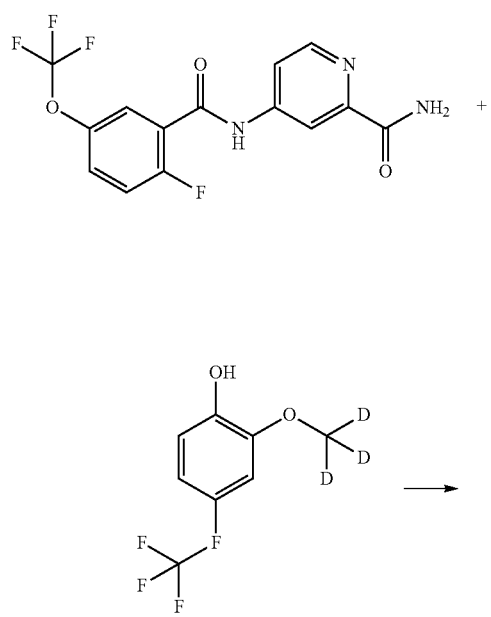

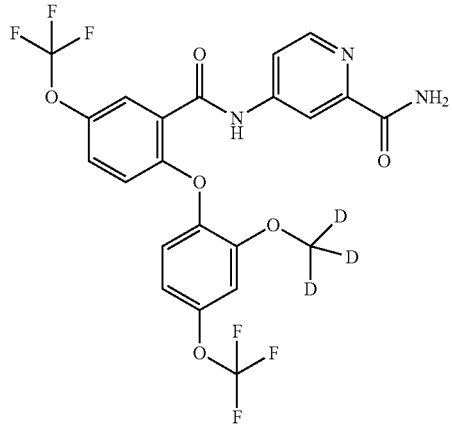 [SMILES: [2H]C([2H])([2H])Oc1cc(OC(F)(F)F)ccc1Oc1ccc(OC(F)(F)F)cc1C(=O)Nc1ccnc(C(N)=O)c1]

A mixture of 4-[[2-fluoro-5-(trifluoromethoxy)benzoyl]amino]pyridine-2-carboxamide (75 mg, 0.22 mmol), 2-(trideuteriomethoxy)-4-(trifluoromethoxy)phenol (prepared as described in Example 1, step 2, 46 mg, 0.22 mmol), $K_2CO_3$ (91 mg, 0.66 mmol) in DMF (0.75 mL) was heated at 100° C. for 2 hours. The reaction mixture was cooled to room temperature, filtered and diluted with DMSO (1 mL). HPLC purification (10-99% acetonitrile/5 mM HCl) provided 4-[[2-[2-(trideuteriomethoxy)-4-(trifluoromethoxy)phenoxy]-5-(trifluoromethoxy)benzoyl]amino]pyridine-2-carboxamide (58 mg, 49%) as a white solid. ESI-MS m/z calc. 534.10, found 535.1 (M+1)+; retention time (Method B): 1.84 minutes (3 minute run). $^1$H NMR (400 MHz, DMSO-d6) δ 11.00 (s, 1H), 8.53 (d, J=5.5 Hz, 1H), 8.32 (d, J=2.1 Hz, 1H), 8.10 (d, J=2.8 Hz, 1H), 7.88 (dd, J=5.5, 2.2 Hz, 1), 7.67 (dd, J=22.1, 2.9 Hz, 2H), 7.53-7.44 (m, 1H), 7.32 (d, J=8.8 Hz, 1H), 7.20 (d, J=2.8 Hz, 1H), 7.02 (ddq, J=8.8, 2.5, 1.2 Hz, 1H), 6.87 (d, J=9.0 Hz, 1H) ppm.

Example 148

N-(2-Carbamoyl-5-methyl-4-pyridyl)-3-methoxy-5-[4-(trifluoromethoxy)phenoxy]-2-(trifluoromethyl)pyridine-4-carboxamide (131)

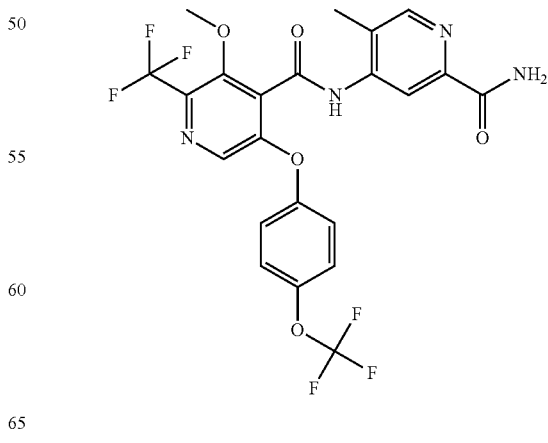

Step 1: Ethyl 3,5-difluoro-2-(trifluoromethyl)pyridine-4-carboxylate

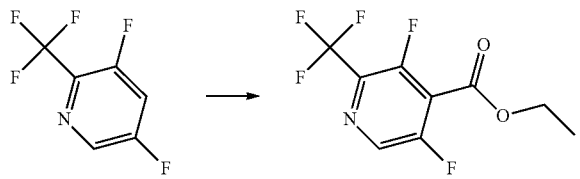 [SMILES: Fc1cnc(C(F)(F)F)c(F)c1 ; CCOC(=O)c1c(F)cnc(C(F)(F)F)c1F]

A solution of 3,5-difluoro-2-(trifluoromethyl)pyridine (9.00 g, 49.16 mmol) in THF (100 mL) was cooled to −78° C. A solution of LDA (27 mL of 2 M in ethylbenzene/THF/heptane, 54 mmol) was added dropwise while maintaining the reaction internal temperature below −65° C. The mixture was stirred at −78° C. for 40 minutes after the completion of the LDA addition. The reaction mixture was then treated with ethyl chloroformate (6.1 mL, 64 mmol) dropwise over 10 minutes while keeping the internal temperature below −65° C. The mixture was stirred at −78° C. for 30 minutes then allowed to warm to room temperature over 1 hour. The mixture was quenched by addition of saturated aqueous NH$_4$Cl and diluted with ethyl acetate (100 mL). The organic layer was separated and washed with water (2×) and brine, dried over MgSO$_4$, filtered and concentrated in vacuo. Purification by silica gel chromatography (0-5% ethyl acetate/petroleum ether) provided ethyl 3,5-difluoro-2-(trifluoromethyl)pyridine-4-carboxylate (7.4 g, 59%) as a pale yellow oil. ESI-MS m/z calc. 255.03, retention time (Method F): 0.94 minutes (1.5 minute run). $^1$H NMR (400 MHz, DMSO-d6) δ 8.89 (s, 1H), 4.46 (q, J=7.1 Hz, 2H), 1.33 (t, J=7.1 Hz, 3H) ppm. $^{19}$F NMR (376 MHz, DMSO-d6) δ −64.15 (d, J=15.2 Hz), −116.78−−118.04 (m), −121.70 (qd, J=15.6, 5.8 Hz) ppm.

Step 2: Ethyl 3-fluoro-5-[4-(trifluoromethoxy)phenoxy]-2-(trifluoromethyl)pyridine-4-carboxylate

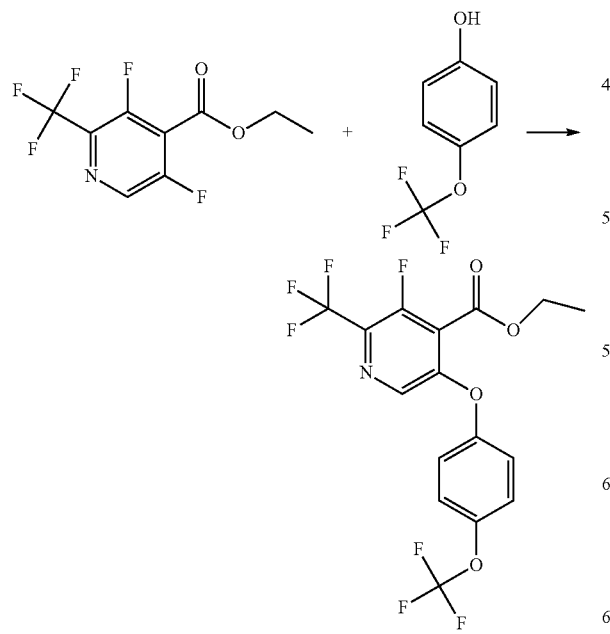

To a solution of ethyl 3,5-difluoro-2-(trifluoromethyl)pyridine-4-carboxylate (1.87 g, 7.33 mmol) and 4-(trifluoromethoxy)phenol (0.950 mL, 7.33 mmol) in DMA (20 mL) at 0° C. was added Cs$_2$CO$_3$ (4.78 g, 14.7 mmol) in one portion. The reaction mixture was allowed to warm to room temperature and stirred for 1 hour. The mixture was diluted with water and extracted with ethyl acetate. The organic layer was washed with brine, dried over MgSO$_4$, filtered and concentrated in vacuo. Purification by silica gel column chromatography (0-10% ethyl acetate/hexanes) provided ethyl 3-fluoro-5-[4-(trifluoromethoxy)phenoxy]-2-(trifluoromethyl)pyridine-4-carboxylate (2.223 g, 73%). ESI-MS m/z calc. 413.04, found 414.2 (M+1)+; retention time (Method B): 2.16 minutes (3 minute run). $^1$H NMR (400 MHz, DMSO-d6) δ 8.50 (s, 1H), 7.47 (d, J=8.9 Hz, 2H), 7.38-7.31 (m, 2H), 4.31 (q, J=7.1 Hz, 2H), 1.18 (t, J=7.1 Hz, 3H) ppm.

Step 3: 3-Fluoro-5-[4-(trifluoromethoxy)phenoxy]-2-(trifluoromethyl)pyridine-4-carboxylic acid

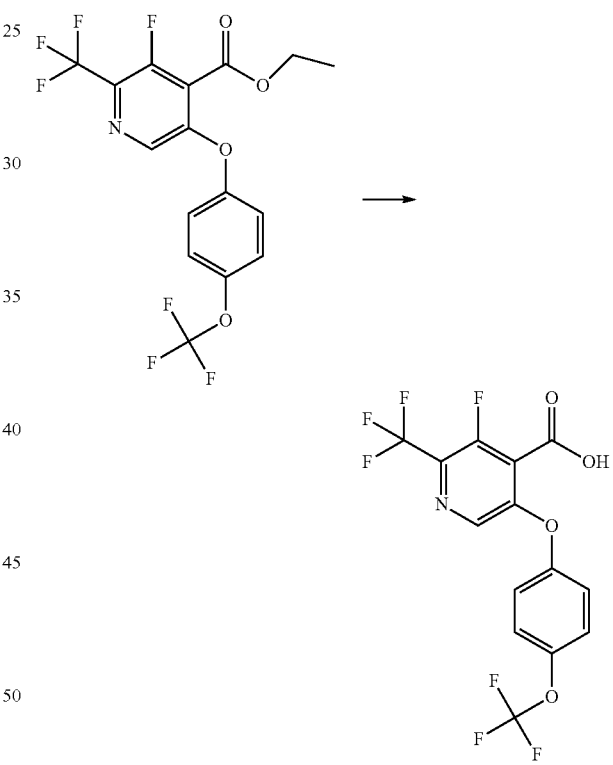

To a flask charged with ethyl 3-fluoro-5-[4-(trifluoromethoxy)phenoxy]-2-(trifluoromethyl)pyridine-4-carboxylate (2.22 g, 5.37 mmol) in THF (22 mL) was added NaOH (20 mL of 3 M, 60 mmol) and 500 mg of solid NaOH. The reaction mixture was stirred for 4 hours at room temperature then cooled to 0° C. and quenched slowly with 6 M HCl. The resulting precipitate was filtered and washed with water. The filtrate was extracted with dichloromethane and combined with the filtered solid. The combined solution was dried over MgSO$_4$, filtered and concentrated in vacuo to obtain 3-fluoro-5-[4-(trifluoromethoxy)phenoxy]-2-(trifluoromethyl)pyridine-4-carboxylic acid (1.967 g, 95%). ESI-MS m/z calc. 385.01, found 386.0 (M+1)+; retention time (Method B): 1.73 minutes (3 minute run). $^1$H NMR (400 MHz, DMSO-d6) δ 8.40 (s, 1H), 7.50-7.43 (m, 2H), 7.38-7.30 (m, 2H) ppm.

Step 4: N-(2-Bromo-5-methyl-4-pyridyl)-3-fluoro-5-[4-(trifluoromethoxy)phenoxy]-2-(trifluoromethyl)pyridine-4-carboxamide

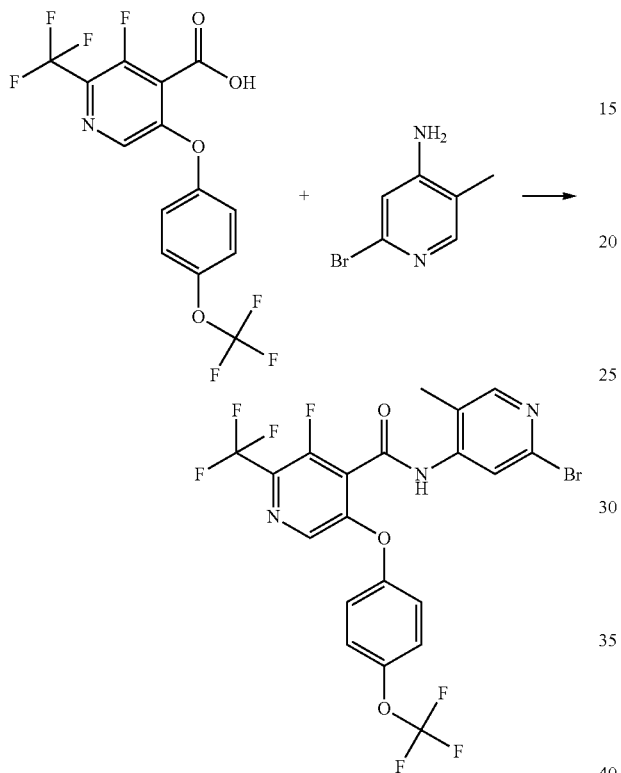

To a solution of 3-fluoro-5-[4-(trifluoromethoxy)phenoxy]-2-(trifluoromethyl)pyridine-4-carboxylic acid (250 mg, 0.649 mmol) in dichloromethane (4 mL) at 0° C. was added DMF (6 μL, 0.07 mmol) and oxalyl chloride (278 mg, 0.190 mL, 2.19 mmol). The reaction was allowed to warm to room temperature and stirred for 3.5 hours. The reaction mixture was concentrated in vacuo, dissolved in dichloromethane (4.4 mL) and the solution was cooled to 0° C. 2-Bromo-5-methyl-pyridin-4-amine (157 mg, 0.841 mmol) was added followed by triethylamine (346 mg, 0.477 μL, 3.42 mmol). The resulting mixture was allowed to warm to room temperature over 16 hours. The reaction mixture was quenched with water (10 mL) and extracted with dichloromethane (2×10 mL). The combined organics were dried over MgSO$_4$, filtered and concentrated in vacuo. Purification by silica gel chromatography (0-20% ethyl acetate/petroleum ether) provided N-(2-bromo-5-methyl-4-pyridyl)-3-fluoro-5-[4-(trifluoromethoxy)phenoxy]-2-(trifluoromethyl)pyridine-4-carboxamide (181 mg, 47%). ESI-MS m/z calc. 552.98, found 554.0 (M+1)+; retention time (Method E): 1.33 minutes (5 minute run).

Step 5: Methyl 4-[[3-methoxy-5-[4-(trifluoromethoxy)phenoxy]-2-(trifluoromethyl)pyridine-4-carbonyl]amino]-5-methyl-pyridine-2-carboxylate

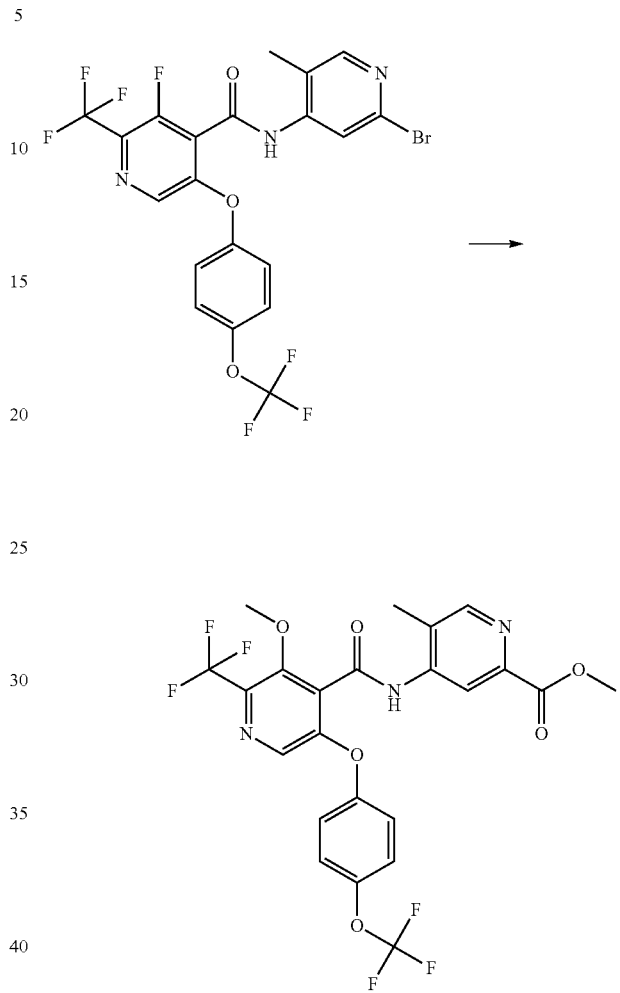

To a solution of N-(2-bromo-5-methyl-4-pyridyl)-3-fluoro-5-[4-(trifluoromethoxy)phenoxy]-2-(trifluoromethyl)pyridine-4-carboxamide (181 mg, 0.304 mmol) in methanol (8 mL) and triethylamine (65 mg, 0.64 mmol) in a pressure vessel was added Pd(dppf)Cl$_2$·DCM (50 mg, 0.061 mmol). Carbon monoxide was bubbled through the vigorously stirring reaction mixture for 5 minutes. The reaction vessel was sealed and heated at 75° C. for 16 hours. The reaction mixture was cooled to room temperature, filtered through a pad of Celite eluting with methanol and concentrated in vacuo. Purification by silica gel chromatography (0-100% ethyl acetate/petroleum ether) provided methyl 4-[[3-methoxy-5-[4-(trifluoromethoxy)phenoxy]-2-(trifluoromethyl)pyridine-4-carbonyl]amino]-5-methyl-pyridine-2-carboxylate (51 mg, 31%) as a red solid. ESI-MS m/z calc. 545.10, found 546.0 (M+1)+; retention time (Method F): 1.01 minutes (1.5 minute run). $^{19}$F NMR (471 MHz, CDCl$_3$) δ −58.01, −60.82 (d, J=12.9 Hz), −112.16--112.24 (m) ppm.

585

Step 6: N-(2-Carbamoyl-5-methyl-4-pyridyl)-3-methoxy-5-[4-(trifluoromethoxy)phenoxy]-2-(trifluoromethyl)pyridine-4-carboxamide (131)

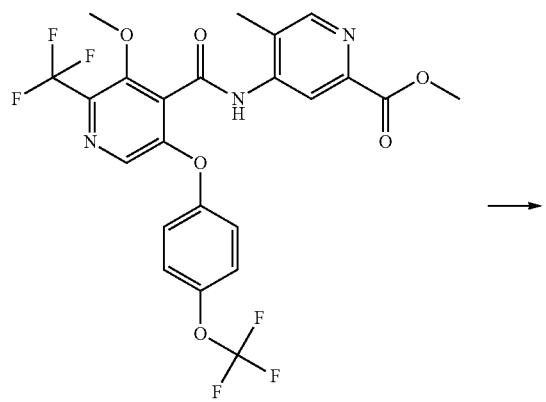

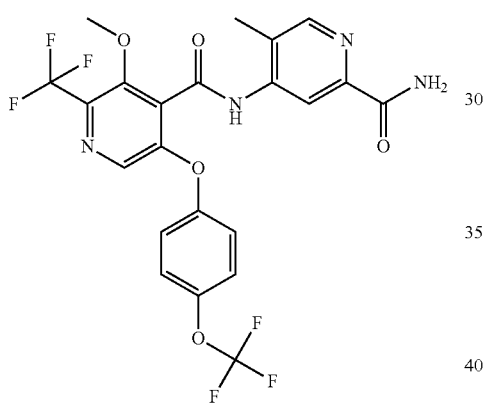

A mixture of methyl 4-[[3-methoxy-5-[4-(trifluoromethoxy)phenoxy]-2-(trifluoromethyl)pyridine-4-carbonyl]amino]-5-methyl-pyridine-2-carboxylate (51 mg, 0.094 mmol) and ammonia (2.6 mL of 4 M in methanol, 10.40 mmol) was stirred at room temperature for 16 hours. SPM32 silica metal scavenger (150 mg) was added and the reaction was stirred for 15 minutes. The mixture was filtered and the filtrate was concentrated in vacuo. Purification by silica gel chromatography (0-100% ethyl acetate/petroleum ether) provided N-(2-carbamoyl-5-methyl-4-pyridyl)-3-methoxy-5-[4-(trifluoromethoxy)phenoxy]-2-(trifluoromethyl)pyridine-4-carboxamide (33.2 mg, 62%) as a white solid. ESI-MS m/z calc. 530.10, found 531.0 (M+1)+; retention time (Method E): 3.26 minutes (5 minute run). $^1$H NMR (500 MHz, DMSO-d6) δ 10.63 (s, 1H), 8.46 (d, J=4.0 Hz, 2H), 8.20 (s, 1H), 8.13-7.91 (m, 1H), 7.60 (s, 1H), 7.59-7.43 (m, 2H), 7.36 (d, J=9.1 Hz, 2H), 4.04 (s, 3H), 2.08 (s, 3H) ppm.

586

Example 149

N-(3-Carbamoyl-4-fluoro-phenyl)-2-cyclopropyl-3-fluoro-5-[2-methoxy-4-(trifluoromethoxy)phenoxy]pyridine-4-carboxamide (46)

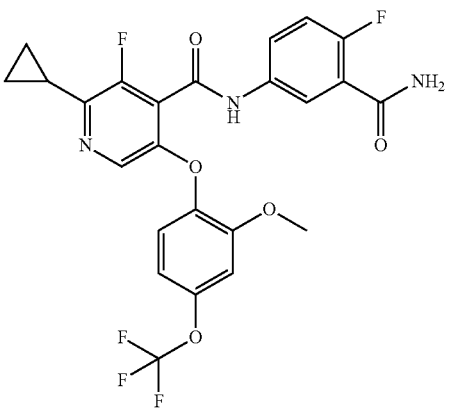 [SMILES: COc1cc(OC(F)(F)F)ccc1Oc1cnc(C2CC2)c(F)c1C(=O)Nc1ccc(F)c(C(N)=O)c1]

Step 1: Ethyl 2-bromo-3,5-difluoro-pyridine-4-carboxylate

2-Bromo-3,5-difluoro-pyridine (4.9 g, 25 mmol) was dissolved in anhydrous THF (20 mL) under a N$_2$ atmosphere and cooled to −78° C. in a dry ice/acetone bath. A solution of LDA (2.7 g, 3.3 mL of 2 M THF/heptane/benzene, 25 mmol) was further diluted with anhydrous THF (49 mL) and this solution was added dropwise to the reaction mixture over a period of 1 hour while maintaining the internal temperature below −70° C. The reaction mixture was stirred at −78° C. for 1 hour, and was then treated dropwise with a solution of ethyl chloroformate (7.5 g, 6.6 mL, 69 mmol) in THF (6 mL) while maintaining the internal temperature below −70° C. The reaction mixture was then allowed to warm to room temperature. After 10 minutes at room temperature the reaction mixture went from a clear solution to a slurry, which was then quenched with a saturated aqueous solution of NH$_4$Cl. The mixture was extracted with ethyl acetate (2×), and the combined organics were dried over Na$_2$SO$_4$, filtered and concentrated to an orange oil in vacuo. Silica gel chromatography (0-3% ethyl acetate/hexanes) provided ethyl 2-bromo-3,5-difluoro-pyridine-4-carboxylate (1.96 g, 29%) as a clear liquid. ESI-MS m/z calc. 264.95, found 267.9 (M+1); retention time (Method B): 1.49 minutes (3 minute run). $^1$H NMR (400 MHz, DMSO-d6) δ 8.62 (d, J=3.2 Hz, 1H), 4.44 (q, J=7.1 Hz, 2H), 1.32 (t, J=7.1 Hz, 3H) ppm.

Step 2: Ethyl 2-cyclopropyl-3,5-difluoro-pyridine-4-carboxylate

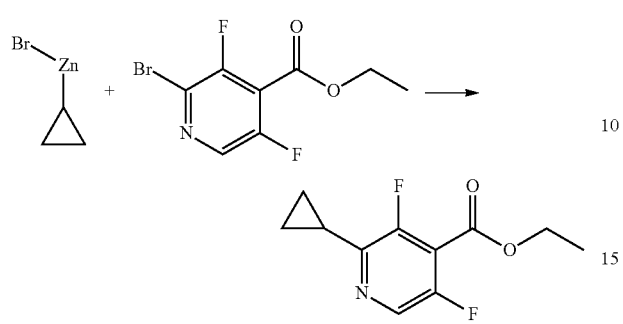

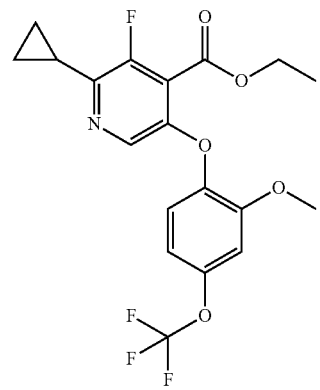

To a flask charged with ethyl 2-bromo-3,5-difluoro-pyridine-4-carboxylate (1.95 g, 7.33 mmol) and bis(tri-t-butylphosphine)palladium(0) (188 mg, 0.368 mmol) under an atmosphere of $N_2$ at 0° C. was added a solution of bromo(cyclopropyl)zinc (15 mL of 0.5 M in THF, 7.5 mmol) and the reaction mixture was allowed to gradually warmed to room temperature and stirred for 1 hour. Another 100 mg of the catalyst and 2 mL of the bromo(cyclopropyl)zinc solution were added and stirred for 30 minutes at room temperature. The reaction mixture was quenched with 1 M HCl and the aqueous layer was extracted with dichloromethane (3×). The combined organic layers were dried over $MgSO_4$, filtered and concentrated in vacuo. Silica gel chromatography (0-5% ethyl acetate/hexanes) provided ethyl 2-cyclopropyl-3,5-difluoro-pyridine-4-carboxylate (917 mg, 55%). ESI-MS m/z calc. 227.075, found 228.1 (M+1)+; retention time (Method B): 1.7 minutes (3 minute run). $^1$H NMR (400 MHz, DMSO-d6) δ 8.52 (s, 1H), 4.43 (q, J=7.1 Hz, 2H), 2.33 (dddd, J=12.8, 8.0, 4.8, 2.2 Hz, 1H), 1.32 (t, J=7.1 Hz, 3H), 1.10-1.02 (m, 2H), 0.98 (ddt, J=7.2, 4.6, 2.5 Hz, 2H) ppm.

Step 3: Ethyl 2-cyclopropyl-3-fluoro-5-[2-methoxy-4-(trifluoromethoxy)phenoxy]pyridine-4-carboxylate A mixture of ethyl 2-cyclopropyl-3,5-difluoro-pyridine-4-carboxylate (520 mg, 2.29 mmol) and 2-methoxy-4-(trifluoromethoxy)phenol (prepared as described in Example 2, step 2, 476 mg, 2.29 mmol) in DMF (5.2 mL) at 0° C. was treated with $Cs_2CO_3$ (1.20 g, 3.68 mmol) in one portion. The mixture was gradually warmed to room temperature and stirred for 3 days. The mixture was diluted with water and extracted with ethyl acetate (3×20 mL). The combined organic layers were dried over $MgSO_4$ and concentrated in vacuo. Silica gel chromatography (1-5% ethyl acetate/hexanes) provided ethyl 2-cyclopropyl-3-fluoro-5-[2-methoxy-4-(trifluoromethoxy)phenoxy]pyridine-4-carboxylate (520 mg, 55%). ESI-MS m/z calc. 415.10, found 416.2 (M+1)+; retention time (Method A): 0.82 minutes (1.2 minute run). $^1$H NMR (400 MHz, DMSO-d6) δ 8.53 (s, 1H), 7.17 (d, J=2.7 Hz, 1H), 6.87 (ddq, J=8.9, 2.3, 1.1 Hz, 1H), 6.73 (d, J=8.9 Hz, 1H), 4.08 (q, J=7.1 Hz, 2H), 3.85 (s, 3H), 2.09 (tt, J=8.0, 4.9 Hz, 1H), 1.01 (t, J=7.1 Hz, 3H), 0.94-0.84 (m, 4H) ppm.

Step 4: 2-Cyclopropyl-3-fluoro-5-[2-methoxy-4-(trifluoromethoxy)phenoxy]pyridine-4-carboxylic acid

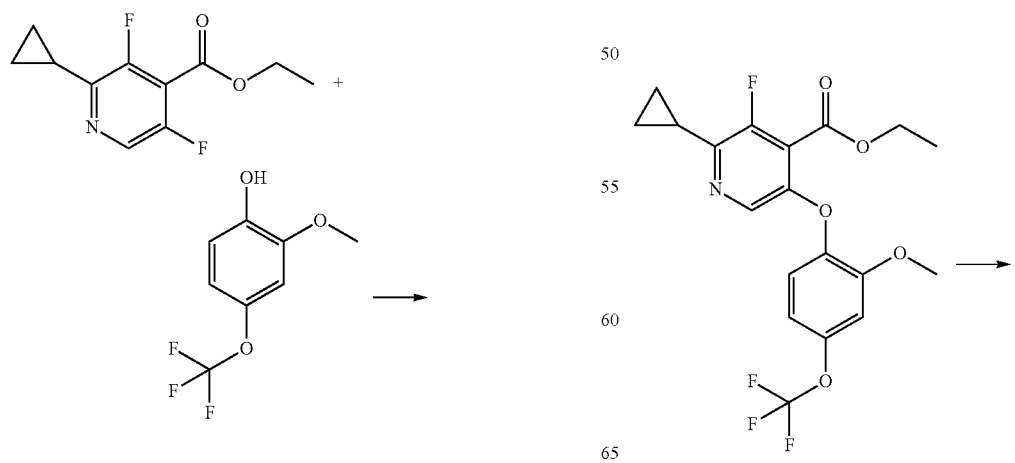

-continued

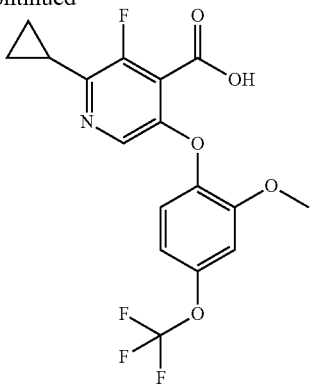

To a solution of ethyl 2-cyclopropyl-3-fluoro-5-[2-methoxy-4-(trifluoromethoxy)phenoxy]pyridine-4-carboxylate (225 mg, 0.542 mmol) in methanol (2.5 mL) was added NaOH (1 mL of 6 M, 6 mmol) at 0° C. and the reaction mixture was gradually warmed to room temperature and stirred for 30 minutes. The solvent was evaporated and the residue taken up in water and cooled to 0° C. A solution of 6 M HCl was added slowly and the resulting precipitate was filtered and washed with water. The residue was taken up in dichloromethane/ethyl acetate, dried over MgSO$_4$, filtered and concentrated in vacuo to provide 2-cyclopropyl-3-fluoro-5-[2-methoxy-4-(trifluoromethoxy)phenoxy]pyridine-4-carboxylic acid (171 mg, 82%). ESI-MS m/z calc. 387.07, found 388.2 (M+1)+; retention time (Method A): 0.7 minutes (1.2 minute run).

Step 5: 2-Cyclopropyl-3-fluoro-5-[2-methoxy-4-(trifluoromethoxy)phenoxy]pyridine-4-carbonyl chloride

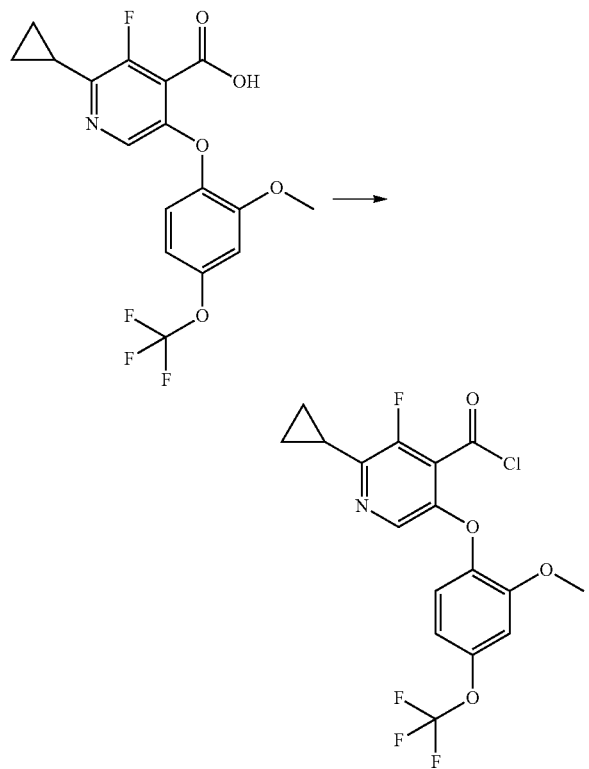

To a suspension of 2-cyclopropyl-3-fluoro-5-[2-methoxy-4-(trifluoromethoxy)phenoxy]pyridine-4-carboxylic acid (167 mg, 0.431 mmol) and DMF (10 μL, 0.13 mmol) in dichloromethane (2 mL) at 0° C. under N$_2$ atmosphere was added oxalyl chloride (0.115 mL, 1.32 mmol) dropwise over 1 minute. The ice bath was removed and replaced with a room-temperature water bath. The reaction mixture was stirred at room temperature for 30 minutes. The reaction mixture was concentrated in vacuo. The product 2-cyclopropyl-3-fluoro-5-(2-methoxy-4-(trifluoromethoxy)phenoxy)isonicotinoyl chloride was used directly for the next step.

Step 6: N-(3-Carbamoyl-4-fluoro-phenyl)-2-cyclopropyl-3-fluoro-5-[2-methoxy-4-(trifluoromethoxy)phenoxy]pyridine-4-carboxamide (46)

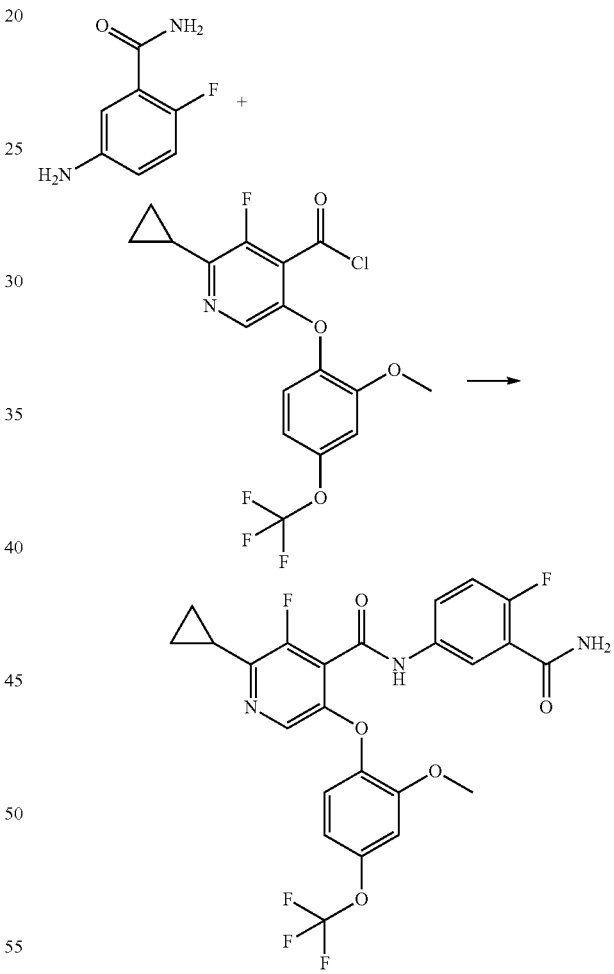

To a vial charged with 5-amino-2-fluoro-benzamide (23 mg, 0.15 mmol) and DIEA (38 mg, 0.052 mL, 0.30 mmol) in THF (0.2 mL) at 0° C. was added a solution of 2-cyclopropyl-3-fluoro-5-[2-methoxy-4-(trifluoromethoxy)phenoxy]pyridine-4-carbonyl chloride (60 mg, 0.15 mmol) in dichloromethane dropwise. The reaction mixture was gradually warmed to room temperature and stirred for 18 hours. The reaction mixture was quenched with water and the aqueous layer was extracted with dichloromethane. The organic layer was dried over MgSO$_4$, filtered and concentrated in vacuo. The crude material was dissolved in DMF/methanol, filtered (syringe filter) and purified by HPLC (10-99% acetonitrile/5 mM HCl) to provide N-(3-carbamoyl-4-fluoro-phenyl)-2-cyclopropyl-3-fluoro-5-[2-methoxy-4-(trifluoromethoxy)phenoxy]pyridine-4-carboxamide (27 mg, 34%). ESI-MS m/z calc. 523.11, found 524.2 (M+1)+; retention time (Method B): 1.69 minutes (3 minute run). $^1$H NMR (400 MHz, DMSO-d6) δ 10.93 (s, 1H), 8.54 (s, 1H), 7.79 (dd, J=6.4, 2.8 Hz, 1H), 7.69 (s, 2H), 7.55 (ddd, J=9.0, 4.4, 2.8 Hz, 1H), 7.23 (dd, J=10.1, 8.9 Hz, 1H), 7.03 (d, J=2.7 Hz, 1H), 6.82 (ddd, J=8.9, 2.5, 1.2 Hz, 1H), 6.75 (d, J=8.9 Hz, 1H), 3.71 (s, 3H), 2.09 (ddd, J=13.1, 8.0, 4.9 Hz, 1H), 0.93 (qd, J=6.2, 2.4 Hz, 2H), 0.88-0.82 (m, 2H) ppm.

Example 150

N-(3-Carbamoyl-4-fluoro-phenyl)-6-(2,3-dihydrobenzofuran-7-yloxy)-2-fluoro-3-(trifluoromethyl)benzamide (58)

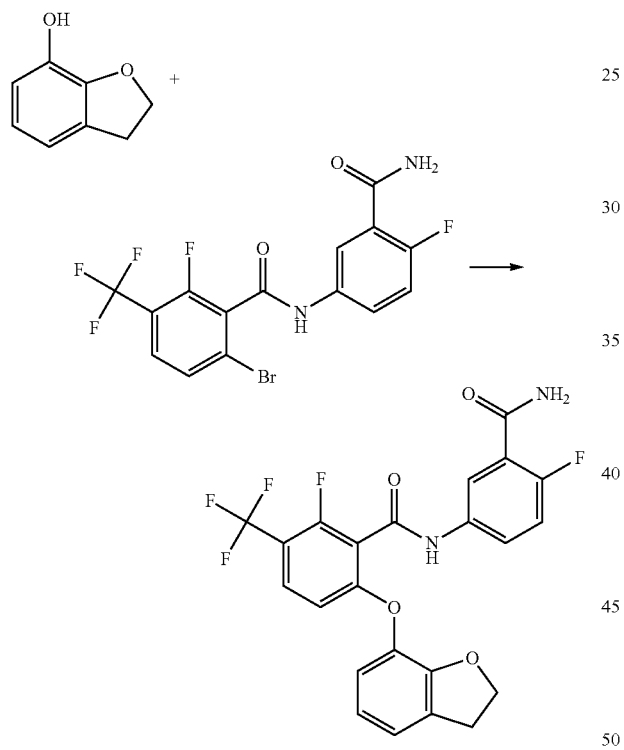

To a pressure flask was added 6-bromo-N-(3-carbamoyl-4-fluoro-phenyl)-2-fluoro-3-(trifluoromethyl)benzamide (prepared as described in Example 140, step 1, 100 mg, 0.236 mmol)), 2,3-dihydrobenzofuran-7-ol (34 mg, 0.25 mmol), Cs$_2$CO$_3$ (105 mg, 0.323 mmol) and toluene (3 mL). The reaction mixture was bubbled with N$_2$ gas for 5 minutes then treated with copper (I) iodide (34 mg, 0.18 mmol). The flask was flushed with N$_2$, sealed and heated at 100° C. with vigorous stirring for 1.5 hours. The mixture was cooled and diluted with ethyl acetate and water. The two layers were separated and the aqueous layer was extracted with additional ethyl acetate (3×). The combined organic layers were dried over Na$_2$SO$_4$, filtered and concentrated in vacuo. HPLC purification (1-99% acetonitrile/5 mM HCl) provided N-(3-carbamoyl-4-fluoro-phenyl)-6-(2,3-dihydrobenzofuran-7-yloxy)-2-fluoro-3-(trifluoromethyl)benzamide (5.1 mg, 4%). ESI-MS m/z calc. 478.09, found 479.1 (M+1)+; retention time (Method C): 2.17 minutes (5 minute run). $^1$H NMR (400 MHz, DMSO-d6) δ 11.04 (s, 1H), 8.00 (dd, J=6.5, 2.8 Hz, 1H), 7.84-7.67 (m, 4H), 7.36-7.23 (m, 1H), 7.20 (dd, J=7.3, 1.2 Hz, 1H), 7.08-6.96 (m, 1H), 6.96-6.84 (m, 1H), 6.69 (d, J=8.8 Hz, 1H), 4.56 (t, J=8.7 Hz, 2H), 3.25 (t, J=8.7 Hz, 2H) ppm.

Example 151

N-(3-Carbamoyl-4-fluoro-phenyl)-2-[4-(trifluoromethoxy)phenoxy]-6-(trifluoromethyl)benzamide (39)

N-(3-carbamoyl-4-fluoro-phenyl)-2-fluoro-6-(trifluoromethyl)benzamide (prepared as described in Example 138, step 1, 50 mg, 0.15 mmol), 4-(trifluoromethoxy)phenol (53 mg, 0.038 mL, 0.30 mmol) and Cs$_2$CO$_3$ (98 mg, 0.30 mmol) were combined in DMF (1.0 mL) and heated at 100° C. for 1 hour. The reaction was cooled to room temperature, filtered and diluted with DMSO (0.5 mL). HPLC purification (1-70% acetonitrile/5 mM HCl) provided N-(3-carbamoyl-4-fluorophenyl)-2-(4-(trifluoromethoxy)phenoxy)-6-(trifluoromethyl)benzamide (17 mg, 21%). ESI-MS m/z calc. 502.07, found 503.2 (M+1)+; retention time (Method B): 1.64 minutes (3 minute run).

Example 152

4-[[2-[4-(Trifluoromethoxy)phenoxy]-4,6-bis(trifluoromethyl)benzoyl]amino]pyridine-2-carboxamide (160)

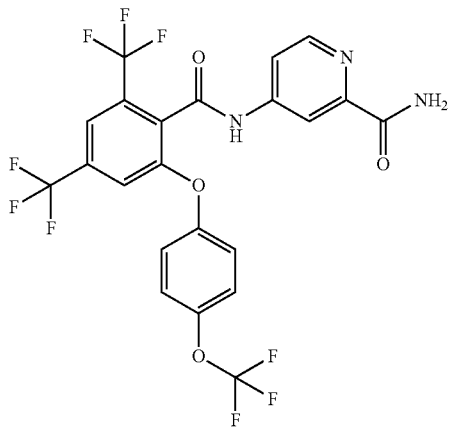 [SMILES: NC(=O)c1cc(NC(=O)c2c(Oc3ccc(OC(F)(F)F)cc3)cc(C(F)(F)F)cc2C(F)(F)F)ccn1]

This compound was made in an analogous fashion to Example 91 above, except employing 4-(trifluoromethoxy)phenol in the displacement step (Step 2). The yield of the desired product after purification was 14 mg (20%). ESI-MS m/z calc. 553.33, found 554.1 (M+1)+; retention time (Method B): 1.84 minutes (3 minute run). $^1$H NMR (400 MHz, DMSO-d6) δ 11.47 (s, 1H), 8.55 (d, J=5.5 Hz, 1H), 8.26 (d, J=2.1 Hz, 1H), 8.10 (d, J=18.6 Hz, 2H), 7.80-7.71 (m, 2H), 7.69 (d, J=2.7 Hz, 1H), 7.55-7.39 (m, 2H), 7.39-7.24 (m, 2H) ppm.

Example 153

N-(3-Carbamoyl-4-fluoro-phenyl)-4-[3-chloro-4-(trifluoromethoxy)phenoxy]-6-cyclopropyl-pyridine-3-carboxamide (36)

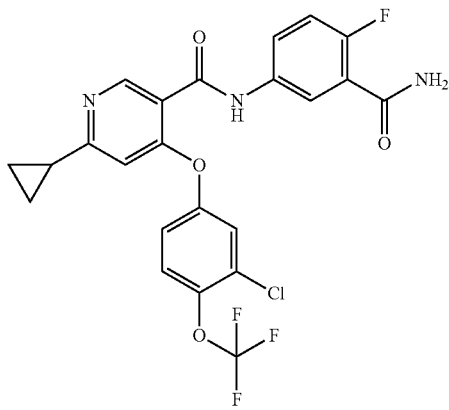

Step 1: Methyl 6-bromo-4-[3-chloro-4-(trifluoromethoxy)phenoxy]pyridine-3-carboxylate

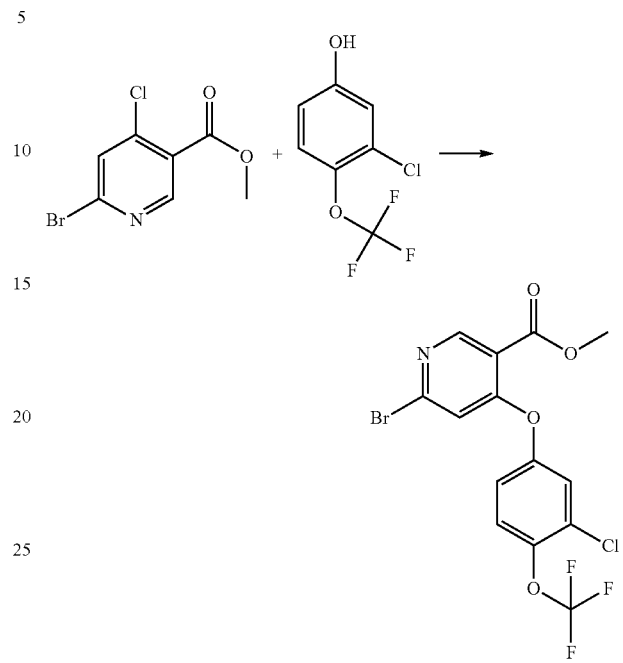

To a flask charged with methyl 6-bromo-4-chloro-pyridine-3-carboxylate (2.80 g, 11.2 mmol) and Cs$_2$CO$_3$ (9.5 g, 29 mmol) in DMF (28 mL) at 0° C. was added 3-chloro-4-(trifluoromethoxy)phenol (2.37 g, 11.2 mmol). The reaction mixture was gradually warmed to room temperature, stirred for 3 hours and quenched with water. The aqueous layer was extracted with ethyl acetate (3×). The combined organic layers were washed with brine, dried over MgSO$_4$, filtered and concentrated in vacuo. Silica gel chromatography (0-10% ethyl acetate/hexanes) provided methyl 6-bromo-4-[3-chloro-4-(trifluoromethoxy)phenoxy]pyridine-3-carboxylate (2.52 g, 53%). ESI-MS m/z calc. 424.92, found 428.1 (M+2)+; retention time (Method B): 2.01 minutes (3 minute run). $^1$H NMR (400 MHz, DMSO-d6) δ 8.77 (s, 1H), 7.71-7.65 (m, 2H), 7.35-7.30 (m, 2H), 3.82 (s, 3H) ppm.

Step 2: Methyl 4-[3-chloro-4-(trifluoromethoxy)phenoxy]-6-cyclopropyl-pyridine-3-carboxylate

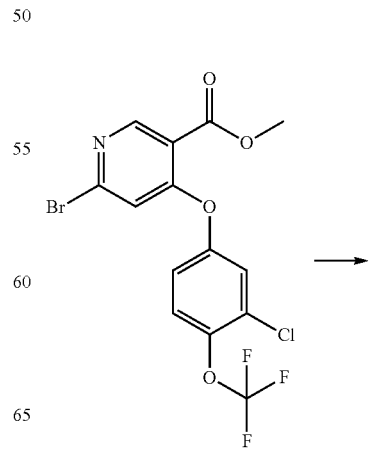

-continued

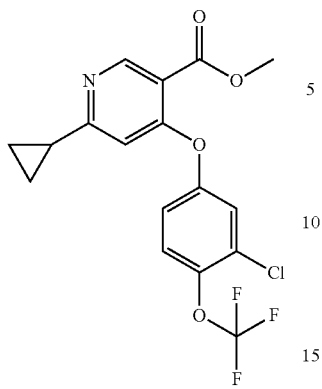

To a vial containing methyl 6-bromo-4-[3-chloro-4-(trifluoromethoxy)phenoxy]pyridine-3-carboxylate (490 mg, 1.15 mmol) and bis(tri-t-butylphosphine)palladium (0) (209 mg, 0.409 mmol) at 0° C. under N₂ atmosphere was added a solution of bromo(cyclopropyl)zinc (2.7 mL of 0.5 M in THF, 1.350 mmol) dropwise. The reaction mixture was stirred for 10 minutes then quenched with saturated aqueous NH₄Cl solution. The mixture was extracted with ethyl acetate (2×) and the combined organics were dried over Na₂SO₄, filtered and concentrated in vacuo. Silica gel chromatography (0-15% ethyl acetate/hexanes) provided methyl 4-[3-chloro-4-(trifluoromethoxy)phenoxy]-6-cyclopropyl-pyridine-3-carboxylate (348 mg, 78%) as a yellow oil. ESI-MS m/z calc. 387.04, found 388.2 (M+1)+; retention time (Method A): 0.71 minutes (1.2 minute run). ¹H NMR (400 MHz, DMSO-d6) δ 8.81 (s, 1H), 7.67-7.62 (m, 1H), 7.59 (d, J=2.9 Hz, 1H), 7.23 (dd, J=9.0, 2.9 Hz, 1H), 7.02 (s, 1H), 3.77 (s, 3H), 2.15 (p, J=6.4 Hz, 1H), 0.99 (d, J=6.4 Hz, 4H) ppm.

Step 3: 4-[3-Chloro-4-(trifluoromethoxy)phenoxy]-6-cyclopropyl-pyridine-3-carboxylic acid

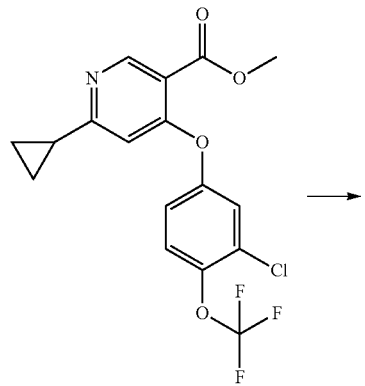

-continued

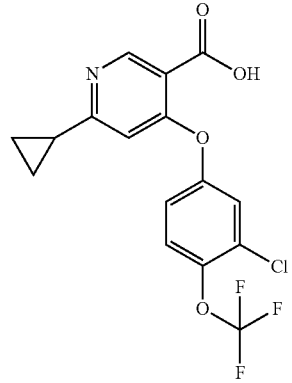

To a solution of methyl 4-[3-chloro-4-(trifluoromethoxy)phenoxy]-6-cyclopropyl-pyridine-3-carboxylate (348 mg, 0.898 mmol) in methanol (4 mL) and water (2 mL) was added NaOH (580 mg, 14.5 mmol) and the reaction mixture was stirred at room temperature for 40 minutes. The solvents were removed under reduced pressure and the residue was dissolved in water. The solution was cooled to 0° C. and treated dropwise with 6 M HCl until a white precipitate formed. The solid was collected by vacuum filtration, washed with water and then dried in a desiccator filled with DrieRite® under high vacuum for 16 hours to provide 4-[3-chloro-4-(trifluoromethoxy)phenoxy]-6-cyclopropyl-pyridine-3-carboxylic acid (308 mg, 92%). ESI-MS m/z calc. 373.03, found 374.1 (M+1)+; retention time (Method A): 0.58 minutes (1.2 minute run).

Step 4: 4-[3-Chloro-4-(trifluoromethoxy)phenoxy]-6-cyclopropyl-pyridine-3-carbonyl chloride

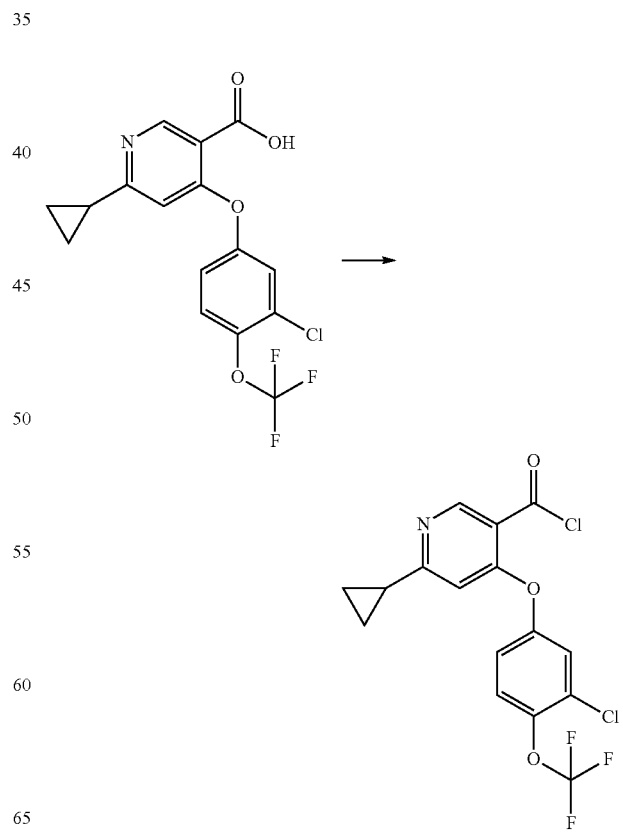

To a solution of 4-[3-chloro-4-(trifluoromethoxy)phenoxy]-6-cyclopropyl-pyridine-3-carboxylic acid (308 mg, 0.824 mmol) and DMF (7 μL, 0.08 mmol) in dichloromethane (3 mL) at 0° C. under a N₂ atmosphere was added oxalyl chloride (0.072 mL, 0.83 mmol) as a solution in dichloromethane (1 mL) dropwise. After 5 minutes the reaction was allowed to warm to room temperature and stirred for 30 minutes. This reaction solution 4-[3-chloro-4-(trifluoromethoxy)phenoxy]-6-cyclopropyl-pyridine-3-carbonyl chloride was used directly in the next step.

Step 5: N-(3-Carbamoyl-4-fluoro-phenyl)-4-[3-chloro-4-(trifluoromethoxy)phenoxy]-6-cyclopropyl-pyridine-3-carboxamide (36)

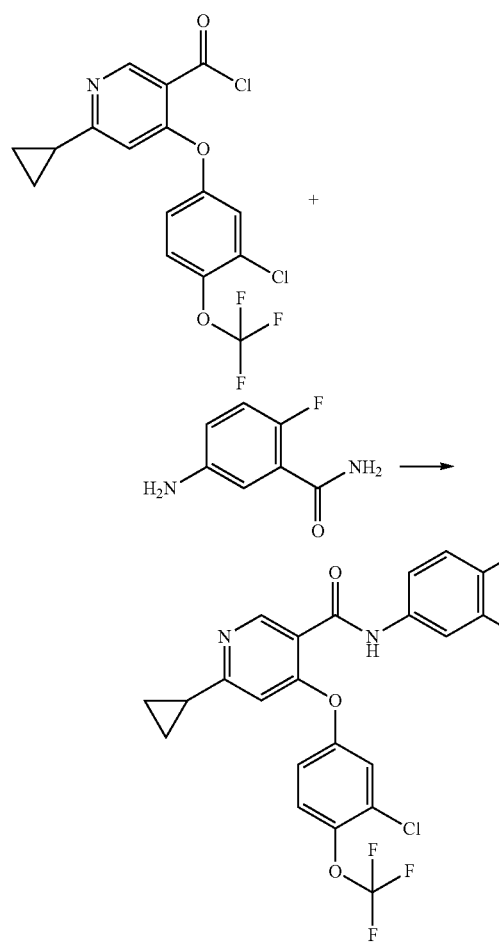

To a solution of 5-amino-2-fluoro-benzamide (48 mg, 0.31 mmol) and DIEA (0.137 mL, 0.787 mmol) in anhydrous THF (1.5 mL) at 0° C. under a N₂ atmosphere was added a solution of 4-[3-chloro-4-(trifluoromethoxy)phenoxy]-6-cyclopropyl-pyridine-3-carbonyl chloride (103 mg, 0.262 mmol) in dichloromethane (1.3 mL) dropwise. The reaction mixture was allowed to slowly warm to room temperature and continued to stir at room temperature for 16 hours. The reaction mixture was partitioned between dichloromethane and water. The layers were separated and the aqueous layer was extracted once more with dichloromethane. The combined organics were dried over Na₂SO₄, filtered and concentrated in vacuo. Silica gel chromatography (0-60% ethyl acetate/dichloromethane) provided N-(3-carbamoyl-4-fluoro-phenyl)-4-[3-chloro-4-(trifluoromethoxy)phenoxy]-6-cyclopropyl-pyridine-3-carboxamide (28.4 mg, 21%). ESI-MS m/z calc. 509.07, found 510.2 (M+1)+; retention time (Method B): 1.46 minutes (3 minute run).

Example 154

4-[[5-Chloro-2-[2-methoxy-4-(trifluoromethoxy)phenoxy]benzoyl]amino]-5-methyl-pyridine-2-carboxamide (150)

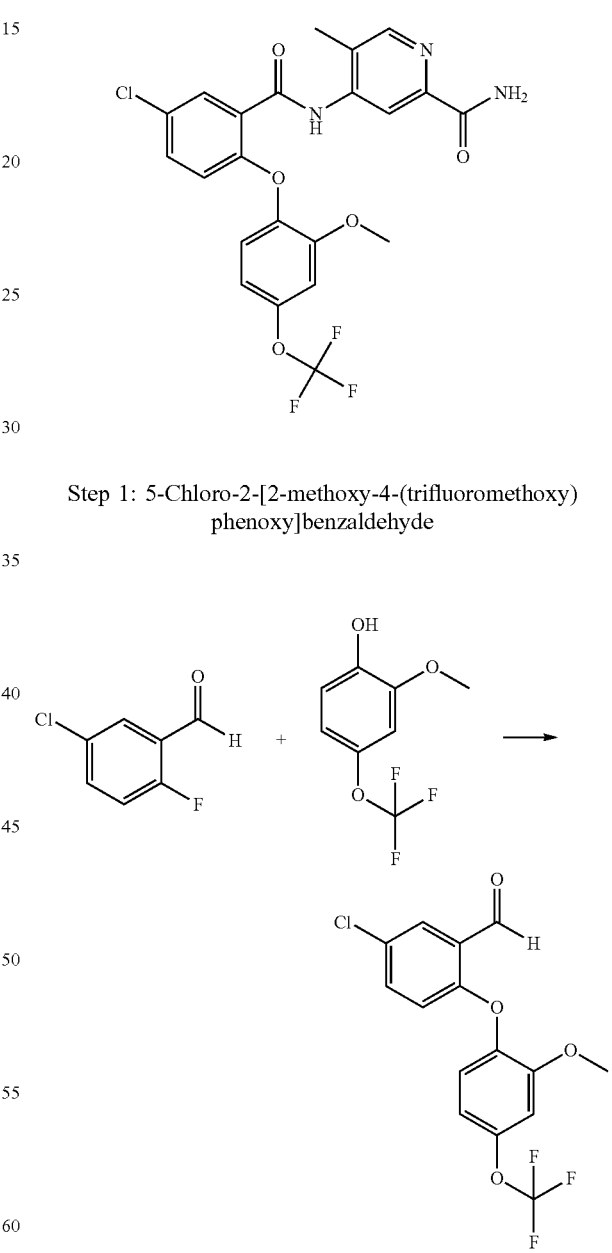

Step 1: 5-Chloro-2-[2-methoxy-4-(trifluoromethoxy)phenoxy]benzaldehyde

A mixture of 2-methoxy-4-(trifluoromethoxy)phenol (prepared as described in Example 2, step 2, 2.00 g, 8.42 mmol), 5-chloro-2-fluoro-benzaldehyde (1.34 g, 8.45 mmol) and Cs₂CO₃ (3.29 g, 10.1 mmol) in DMF (10 mL) was heated at 100° C. for 4 hours. The reaction mixture was cooled to room temperature and partitioned between ethyl acetate (50 mL) and water (30 mL). The organic layer was separated and washed with water (2×30 mL) and brine, dried over MgSO₄, filtered and concentrated in vacuo. Silica gel column chromatography (0-5% ethyl acetate/petroleum ether) provided 5-chloro-2-[2-methoxy-4-(trifluoromethoxy)phenoxy]benzaldehyde (2.2 g, 73%) as a yellow solid. ¹H NMR (400 MHz, DMSO-d6) δ 10.42 (s, 1H), 7.75 (d, J=2.8 Hz, 1H), 7.62 (dd, J=8.9, 2.8 Hz, 1H), 7.37 (d, J=8.8 Hz, 1H), 7.27 (d, J=2.7 Hz, 1H), 7.04 (ddd, J=8.7, 2.7, 1.2 Hz, 1H), 6.77 (d, J=8.9 Hz, 1H), 3.79 (s, 3H) ppm.

Step 2: 5-Chloro-2-[2-methoxy-4-(trifluoromethoxy)phenoxy]benzoic acid

Step 3: N-(2-Bromo-5-methyl-4-pyridyl)-5-chloro-2-[2-methoxy-4-(trifluoromethoxy)phenoxy]benzamide

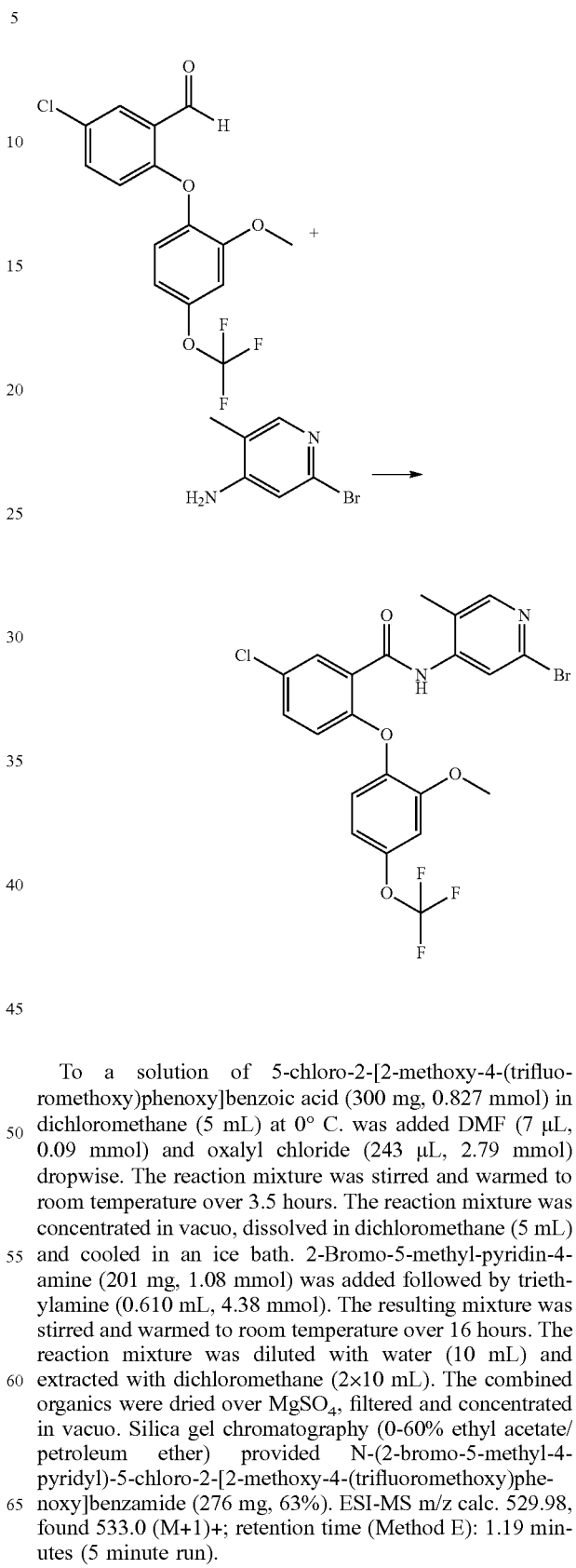

To a mixture of 5-chloro-2-[2-methoxy-4-(trifluoromethoxy)phenoxy]benzaldehyde (2.2 g, 6.2 mmol), sodium dihydrogenphosphate (740 mg, 6.17 mmol) and 2-methyl-2-butene (13.8 mL of 2 M in THF, 27.6 mmol) in tert-butyl alcohol (20 mL) and water (14 mL) at −5° C. (ice/brine bath) was added sodium chlorite (835 mg, 7.39 mmol) portionwise over 30 minutes. The mixture was allowed to warm to room temperature and stirred for 1 hour. The reaction mixture was acidified to pH1-2 using 2 M HCl and partitioned with ethyl acetate. The organic layer was separated, dried over MgSO₄, filtered and concentrated in vacuo to afford 5-chloro-2-[2-methoxy-4-(trifluoromethoxy)phenoxy]benzoic acid (2.24 g, 100%) as a white solid. ESI-MS m/z calc. 362.01, found 364.9 (M+1)+; 361.0 (M−1)−; retention time (Method E): 0.68 minutes (5 minute run). ¹H NMR (500 MHz, DMSO-d6) δ 12.90 (s, 1H), 7.77 (d, J=2.8 Hz, 1H), 7.52 (dd, J=8.9, 2.8 Hz, 1H), 7.20 (d, J=2.7 Hz, 1H), 7.06 (d, J=8.8 Hz, 1H), 6.95 (ddd, J=8.8, 2.7, 1.2 Hz, 1H), 6.77 (d, J=8.9 Hz, 1H), 3.79 (s, 3H) ppm.

To a solution of 5-chloro-2-[2-methoxy-4-(trifluoromethoxy)phenoxy]benzoic acid (300 mg, 0.827 mmol) in dichloromethane (5 mL) at 0° C. was added DMF (7 μL, 0.09 mmol) and oxalyl chloride (243 μL, 2.79 mmol) dropwise. The reaction mixture was stirred and warmed to room temperature over 3.5 hours. The reaction mixture was concentrated in vacuo, dissolved in dichloromethane (5 mL) and cooled in an ice bath. 2-Bromo-5-methyl-pyridin-4-amine (201 mg, 1.08 mmol) was added followed by triethylamine (0.610 mL, 4.38 mmol). The resulting mixture was stirred and warmed to room temperature over 16 hours. The reaction mixture was diluted with water (10 mL) and extracted with dichloromethane (2×10 mL). The combined organics were dried over MgSO₄, filtered and concentrated in vacuo. Silica gel chromatography (0-60% ethyl acetate/petroleum ether) provided N-(2-bromo-5-methyl-4-pyridyl)-5-chloro-2-[2-methoxy-4-(trifluoromethoxy)phenoxy]benzamide (276 mg, 63%). ESI-MS m/z calc. 529.98, found 533.0 (M+1)+; retention time (Method E): 1.19 minutes (5 minute run).

601

Step 4: Methyl 4-[[5-chloro-2-[2-methoxy-4-(trifluoromethoxy)phenoxy]benzoyl]amino]-5-methyl-pyridine-2-carboxylate

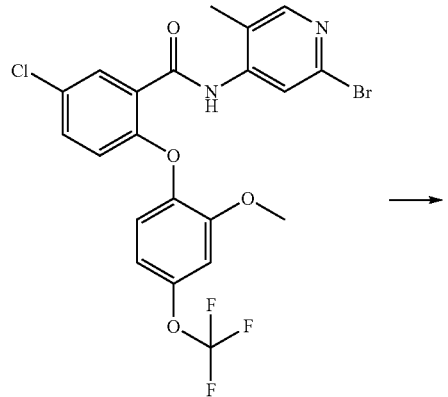

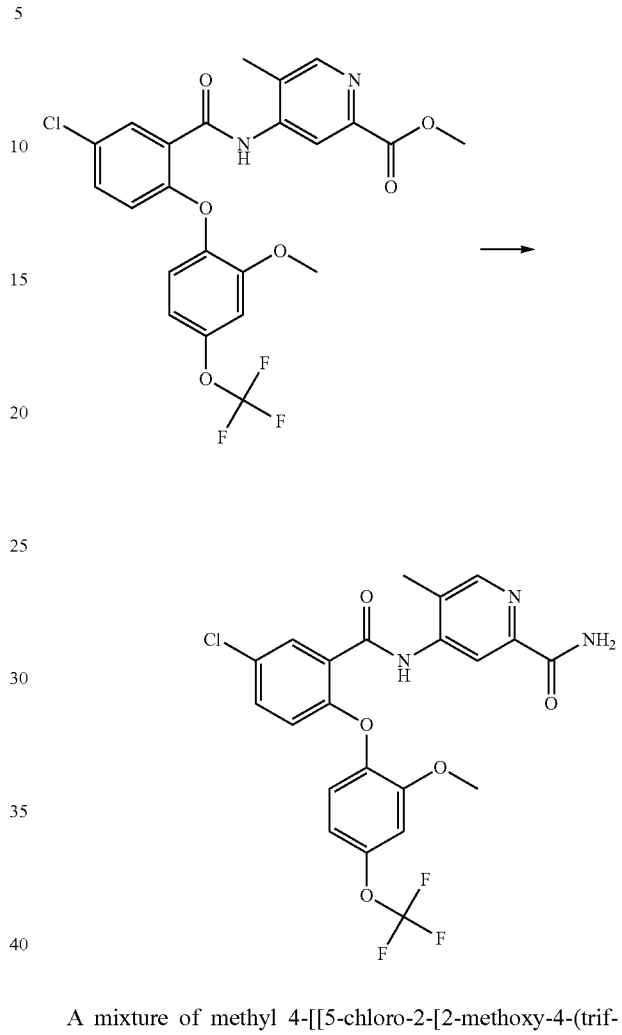

To a solution of N-(2-bromo-5-methyl-4-pyridyl)-5-chloro-2-[2-methoxy-4-(trifluoromethoxy)phenoxy]benzamide (276 mg, 0.519 mmol) in methanol (5 mL) and triethylamine (112 mg, 1.11 mmol) was added Pd(dppf)Cl$_2$·DCM (86 mg, 0.11 mmol). Carbon monoxide gas was bubbled through the vigorously stirring reaction mixture for 5 minutes. The reaction mixture was then heated at 75° C. under carbon monoxide atmosphere (balloon) for 16 hours. The reaction was cooled to room temperature, filtered through a pad of Celite eluting with methanol and concentrated in vacuo. Silica gel chromatography (30-80% ethyl acetate/petroleum ether) provided methyl 4-[[5-chloro-2-[2-methoxy-4-(trifluoromethoxy)phenoxy]benzoyl]amino]-5-methyl-pyridine-2-carboxylate (229 mg, 86%) as a yellow oil. ESI-MS m/z calc. 510.08, found 511.0 (M+1)+; retention time (Method E): 1.08 minutes (5 minute run).

602

Step 5: 4-[[5-Chloro-2-[2-methoxy-4-(trifluoromethoxy)phenoxy]benzoyl]amino]-5-methyl-pyridine-2-carboxamide (150)

A mixture of methyl 4-[[5-chloro-2-[2-methoxy-4-(trifluoromethoxy)phenoxy]benzoyl]amino]-5-methyl-pyridine-2-carboxylate (229 mg, 0.448 mmol) and ammonia (12.6 mL of 4 M in methanol, 50.4 mmol) was stirred at room temperature for 16 hours. The reaction was filtered and concentrated in vacuo. The residue was purified by HPLC (acetonitrile/0.1% ammonium hydroxide) to provide the product as a white solid (140 mg). Further purification by normal phase SFC (Chiralpak IB (250×20 mm ID) 5 m particle (Chiral Technologies Europe pn: 81445) with a Gemini-NX (10×10 mm) guard column (Phenomenex pn: AJ0-8369), and an isocratic run 15% of methanol with 20 mM ammonia solution (mobile phase B) over 6 minutes; Mobile phase A=Supercritical Liquid Carbon Dioxide (58-60 bar); Mobile phase B=Methanol with 20 mM Ammonium hydroxide; Flow rate=100 mL/min, column temperature=40° C.) provided 4-[[5-chloro-2-[2-methoxy-4-(trifluoromethoxy)phenoxy]benzoyl]amino]-5-methyl-pyridine-2-carboxamide (87.6 mg, 39%) as a white solid. ESI-MS m/z calc. 495.08, found 496.0 (M+1)+; retention time (Method E): 3.58 minutes (5 minute run). $^1$H NMR (400 MHz, DMSO-d6) δ 10.07 (s, 1H), 8.71 (s, 1H), 8.43 (s, 1H), 8.05 (d, J=2.9 Hz, 1H), 7.90 (d, J=2.7 Hz, 1H), 7.68-7.37 (m, 3H), 7.26 (d, J=2.8 Hz, 1H), 7.06 (ddd, J=8.8, 2.7, 1.3 Hz, 1H), 6.78 (d, J=8.9 Hz, 1H), 3.79 (s, 3H), 2.25 (s, 3H) ppm.

Example 155

N-(3-Carbamoyl-4-fluoro-phenyl)-2-fluoro-6-[2-hydroxy-4-(trifluoromethoxy)phenoxy]-3-(trifluoromethyl)benzamide (142)

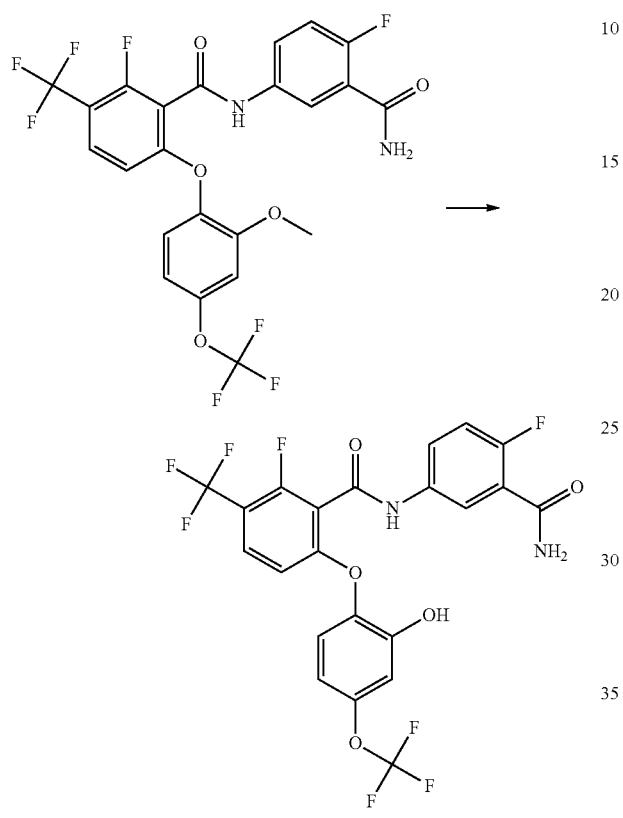

N-(3-carbamoyl-4-fluoro-phenyl)-2-fluoro-6-[2-methoxy-4-(trifluoromethoxy)phenoxy]-3-(trifluoromethyl)benzamide (2, 40 mg, 0.073 mmol) was dissolved in dichloromethane (0.8 mL) and cooled to −78° C. (dry ice/acetone bath). The solution was treated dropwise with a solution of BBr$_3$ (363 µL of 1 M in dichloromethane, 0.363 mmol) forming a yellow precipitate. Stirring was continued for 10 minutes, then the cooling bath was removed and the reaction mixture was allowed to warm to room temperature and stirred for 20 minutes (precipitate forms). The reaction mixture was quenched with a 1:1 solution of methanol (0.7 mL)/1 M NaOH NaOH (0.7 mL). The reaction mixture was diluted with dichloromethane and washed with saturated NaHCO$_3$ and brine, dried over Na$_2$SO$_4$, filtered and concentrated in vacuo. Purification by HPLC (1-99% acetonitrile/5 mM HCl) provided N-(3-carbamoyl-4-fluoro-phenyl)-2-fluoro-6-[2-hydroxy-4-(trifluoromethoxy)phenoxy]-3-(trifluoromethyl)benzamide (13 mg, 33%) as a pale yellow solid. ESI-MS m/z calc. 536.06, found 537.1 (M+1)+; retention time (Method B): 1.71 minutes (3 minute run). $^1$H NMR (400 MHz, DMSO-d6) δ 10.98 (s, 1H), 10.60 (s, 1H), 8.00 (dd, J=6.4, 2.8 Hz, 1H), 7.86-7.76 (m, 2H), 7.70 (d, J=20.9 Hz, 2H), 7.30 (dt, J=9.5, 5.1 Hz, 2H), 6.97 (d, J=2.9 Hz, 1H), 6.89 (dd, J=8.7, 2.8 Hz, 1H), 6.64 (d, J=8.9 Hz, 1H) ppm.

Example 156

4-[[2-Fluoro-6-[2-hydroxy-4-(trifluoromethoxy)phenoxy]-3-(trifluoromethyl)benzoyl]amino]pyridine-2-carboxamide (214)

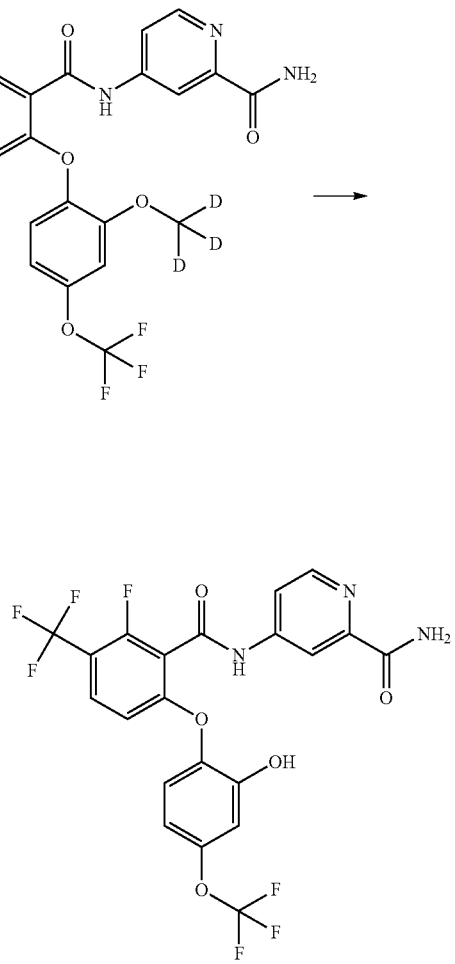

To a solution of 4-[[2-fluoro-6-[2-(trideuteriomethoxy)-4-(trifluoromethoxy)phenoxy]-3-(trifluoromethyl)benzoyl]amino]pyridine-2-carboxamide (6, 200 mg, 0.373 mmol) in dichloromethane (4 mL) at −78° C. was added a solution of BBr$_3$ (1.5 mL of 1 M in dichloromethane, 1.5 mmol) dropwise. The reaction mixture was stirred at −78° C. for 5 minutes then allowed to warm to room temperature and stirred for 3 hours. The reaction was diluted with dichloromethane and washed with 50% saturated NaHCO$_3$, water, and brine. The organic layer was dried over Na$_2$SO$_4$, filtered and concentrated in vacuo. HPLC purification (10-99% acetonitrile/5 mM HCl) provided 4-[[2-fluoro-6-[2-hydroxy-4-(trifluoromethoxy)phenoxy]-3-(trifluoromethyl)benzoyl]amino]pyridine-2-carboxamide (115.2 mg, 59%). ESI-MS m/z calc. 519.06, found 520.1 (M+1)+; retention time (Method B). 1.67 minutes (3 minute run). $^1$H NMR (400 MHz, DMSO-d6) δ 11.42 (s, 1H), 10.62 (s, 1H), 8.56 (d, J=5.4 Hz, 1H), 8.33 (d, J=2.1 Hz, 1H), 8.10 (d, J=2.9 Hz, 1H), 7.86 (dd, J=5.5, 2.2 Hz, 1H), 7.82 (t, J=8.6 Hz, 1H), 7.66 (d, J=2.8 Hz, 1H), 7.31 (d, J=8.8 Hz, 1H), 6.99-6.92 (m, 1H), 6.91-6.85 (m, 1H), 6.67 (d, J=8.9 Hz, 1H) ppm.

Example 157

N-(3-Carbamoyl-4-fluoro-phenyl)-6-cyclopropyl-4-[3-fluoro-4-(trifluoromethoxy)phenoxy]pyridine-3-carboxamide (42)

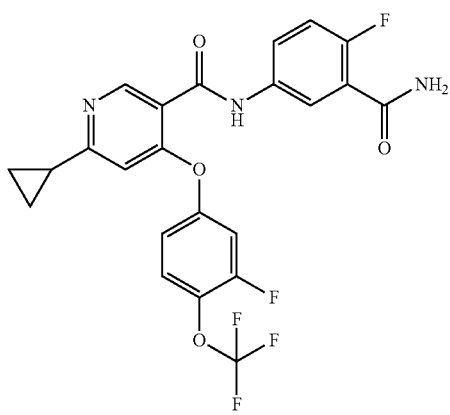 [SMILES: NC(=O)c1cc(NC(=O)c2cnc(C3CC3)cc2Oc2ccc(OC(F)(F)F)c(F)c2)ccc1F]

Step 1: Methyl 6-bromo-4-[3-fluoro-4-(trifluoromethoxy)phenoxy]pyridine-3-carboxylate

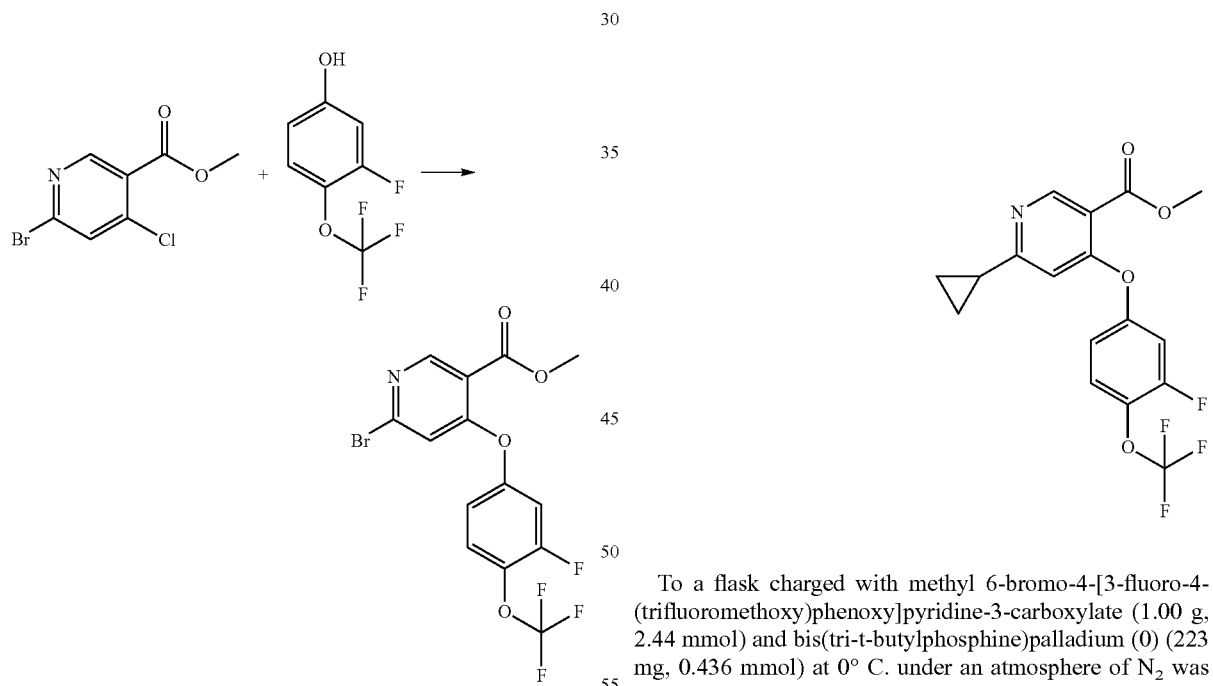

To a flask charged with methyl 6-bromo-4-chloro-pyridine-3-carboxylate (prepared as described in Example 135, step 1, 2.6 g, 10 mmol) and Cs₂CO₃ (8.5 g, 26 mmol) in DMF (26 mL) at 0° C. was added 3-fluoro-4-(trifluoromethoxy)phenol (2.0 g, 10 mmol). The reaction mixture was allowed to warm to room temperature over 3 hours and diluted with water. The resulting precipitate was filtered and washed with water. The solid was dissolved in dichloromethane, dried over MgSO₄, filtered and concentrated in vacuo. Silica gel chromatography (0-20% ethyl acetate/hexanes) provided methyl 6-bromo-4-[3-fluoro-4-(trifluoromethoxy)phenoxy]pyridine-3-carboxylate (2.8 g, 68%). ESI-MS m/z calc. 408.95, found 410.2 (M+1)+; retention time (Method B): 1.88 minutes (3 minute run). ¹H NMR (400 MHz, DMSO-d6) δ 8.77 (s, 1H), 7.69 (tq, J=9.0, 1.1 Hz, 1H), 7.56 (dd, J=11.1, 2.8 Hz, 1H), 7.31 (s, 1H), 7.18 (ddd, J=9.1, 2.9, 1.6 Hz, 1H), 3.82 (s, 3H) ppm.

Step 2: Methyl 6-cyclopropyl-4-[3-fluoro-4-(trifluoromethoxy)phenoxy]pyridine-3-carboxylate

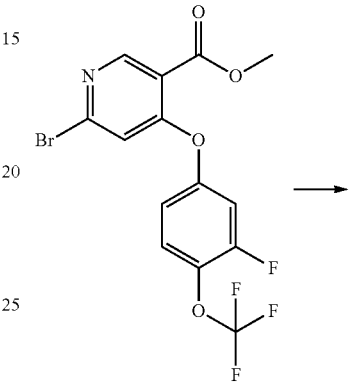

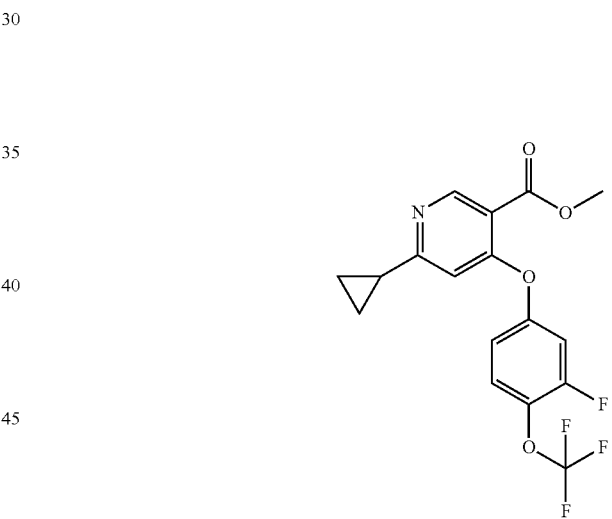

To a flask charged with methyl 6-bromo-4-[3-fluoro-4-(trifluoromethoxy)phenoxy]pyridine-3-carboxylate (1.00 g, 2.44 mmol) and bis(tri-t-butylphosphine)palladium (0) (223 mg, 0.436 mmol) at 0° C. under an atmosphere of N₂ was added a solution of bromo(cyclopropyl)zinc (7.3 mL of 0.5 M in THF, 3.7 mmol). The reaction mixture was gradually warmed to room temperature and stirred for 1 hour. The reaction mixture was quenched with 1 M HCl and the aqueous layer was extracted with dichloromethane (3×). The combined organic layers were dried over MgSO₄, filtered and concentrated in vacuo. Silica gel chromatography (0-10% ethyl acetate/hexanes) provided methyl 6-cyclopropyl-4-[3-fluoro-4-(trifluoromethoxy)phenoxy]pyridine-3-carboxylate (576 mg, 64%). ESI-MS m/z calc. 371.07, found 372.1 (M+1)+; retention time (Method B): 1.66 minutes (3 minute run).

Step 3: 6-Cyclopropyl-4-[3-fluoro-4-(trifluoromethoxy)phenoxy]pyridine-3-carboxylic acid

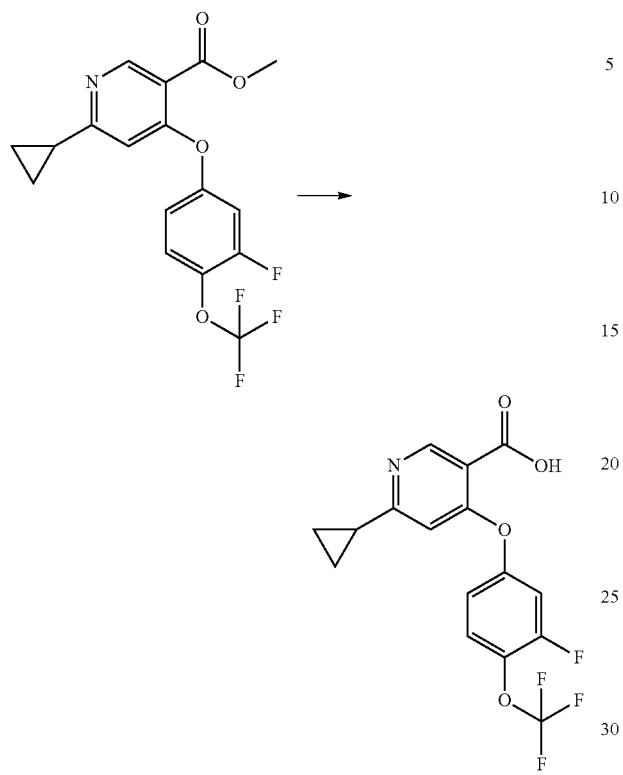

To a solution of methyl 6-cyclopropyl-4-[3-fluoro-4-(trifluoromethoxy)phenoxy]pyridine-3-carboxylate (575 mg, 1.55 mmol) in methanol (6 mL) at 0° C. was added NaOH (2.8 mL of 6 M, 16.8 mmol) and the reaction mixture was gradually warmed to room temperature and stirred for 30 minutes. The solvent was removed in vacuo. The residue was dissolved in water, cooled to 0° C. and treated dropwise with 6 M HCl. The resulting precipitate was filtered and washed with water. The solid was dissolved in dichloromethane/ethyl acetate, dried over MgSO₄, filtered and concentrated to provide 6-cyclopropyl-4-[3-fluoro-4-(trifluoromethoxy)phenoxy]pyridine-3-carboxylic acid (550 mg, 99%). ESI-MS m/z calc. 357.06, found 358.1 (M+1)+; retention time (Method B): 1.28 minutes (3 minute run).

Step 4: 6-Cyclopropyl-4-[3-fluoro-4-(trifluoromethoxy)phenoxy]pyridine-3-carbonyl chloride

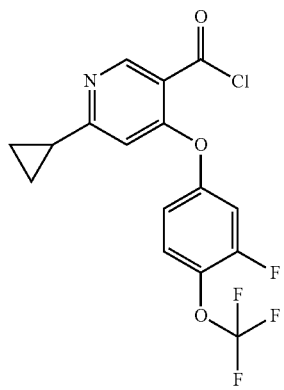

To a mixture of 6-cyclopropyl-4-[3-fluoro-4-(trifluoromethoxy)phenoxy]pyridine-3-carboxylic acid (472 mg, 1.32 mmol) and DMF (10 μL, 0.13 mmol) in dichloromethane (5 mL) at 0° C. under a N₂ atmosphere was added oxalyl chloride (0.115 mL, 1.32 mmol) over 1 minute. The ice bath was removed and replaced with a room-temperature water bath and stirred for 3 hours. The reaction was concentrated in vacuo, dried on high vacuum for 30 minutes and was used directly for the next step.

Step 5: N-(3-Carbamoyl-4-fluoro-phenyl)-6-cyclopropyl-4-[3-fluoro-4-(trifluoromethoxy)phenoxy]pyridine-3-carboxamide (42)

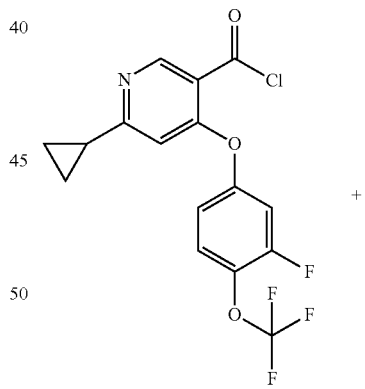

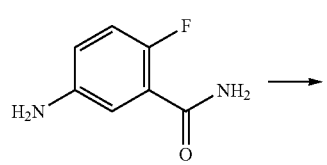

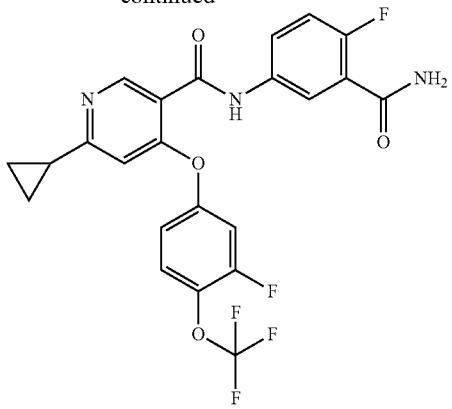

To a mixture of 5-amino-2-fluoro-benzamide (27 mg, 0.18 mmol) and DIEA (62 mg, 0.48 mmol) in dichloromethane (0.6 mL) at 0° C. was added 6-cyclopropyl-4-[3-fluoro-4-(trifluoromethoxy)phenoxy]pyridine-3-carbonyl chloride (60 mg, 0.16 mmol) as a solution in dichloromethane (0.6 mL). The reaction mixture was stirred for 1 hour, then quenched with methanol and purified by HPLC (1-99% acetonitrile/5 mM HCl) to provide N-(3-carbamoyl-4-fluoro-phenyl)-6-cyclopropyl-4-[3-fluoro-4-(trifluoromethoxy)phenoxy]pyridine-3-carboxamide (15.8 mg, 17%). ESI-MS m/z calc. 493.10, found 494.2 (M+1)+; retention time (Method B): 1.38 minutes (3 minute run). $^1$H NMR (400 MHz, DMSO-d6) δ 10.57 (s, 1H), 8.65 (s, 1H), 7.97 (dd, J=6.5, 2.8 Hz, 1H), 7.78 (ddd, J=9.0, 4.4, 2.7 Hz, 1H), 7.73-7.63 (m, 3H), 7.54 (dd, J=11.1, 2.8 Hz, 1H), 7.31-7.17 (m, 2H), 6.99 (s, 1H), 2.25-2.12 (m, 1H), 1.07-0.98 (m, 4H) ppm.

Example 158

N-(3-Carbamoyl-4-fluoro-phenyl)-2-(4-fluoro-2-methyl-phenoxy)-6-(trifluoromethyl)benzamide (41)

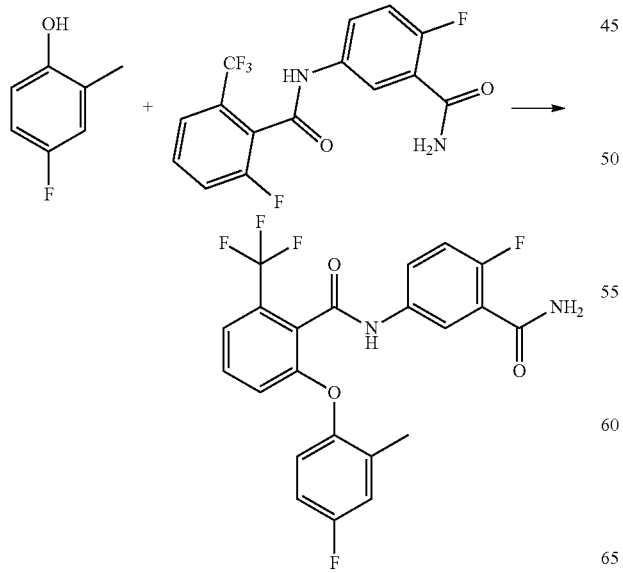

N-(3-Carbamoyl-4-fluoro-phenyl)-2-fluoro-6-(trifluoromethyl)benzamide (prepared as described in Example 138, Step 1, 50 mg, 0.15 mmol), 4-fluoro-2-methyl-phenol (37 mg, 0.29 mmol) and Cs$_2$CO$_3$ (95 mg, 0.29 mmol) were combined in DMF (1.0 mL) and heated at 100° C. for 1 hour. The reaction was cooled to room temperature, diluted with DMSO and filtered. HPLC purification (1-70% acetonitrile/5 mM HCl) provided N-(3-carbamoyl-4-fluoro-phenyl)-2-(4-fluoro-2-methyl-phenoxy)-6-(trifluoromethyl)benzamide (21.8 mg, 33%). ESI-MS m/z calc. 450.10, found 451.2 (M+1)+; retention time (Method B): 1.52 minutes (3 minute run). $^1$H NMR (400 MHz, DMSO-d6) δ 10.86 (s, 1H), 7.96 (dd, J=6.4, 2.8 Hz, 1H), 7.75-7.70 (m, 2H), 7.69 (s, 1H), 7.62-7.53 (m, 2H), 7.27 (dd, J=10.1, 8.9 Hz, 1H), 7.22 (d, J=9.1 Hz, 1H), 7.13-7.09 (m, 2H), 7.01-6.96 (m, 1H), 2.15 (s, 3H) ppm.

Example 159

4-[[5-(Trifluoromethoxy)-2-[4-(trifluoromethoxy)phenoxy]benzoyl]amino]pyridine-2-carboxamide (156)

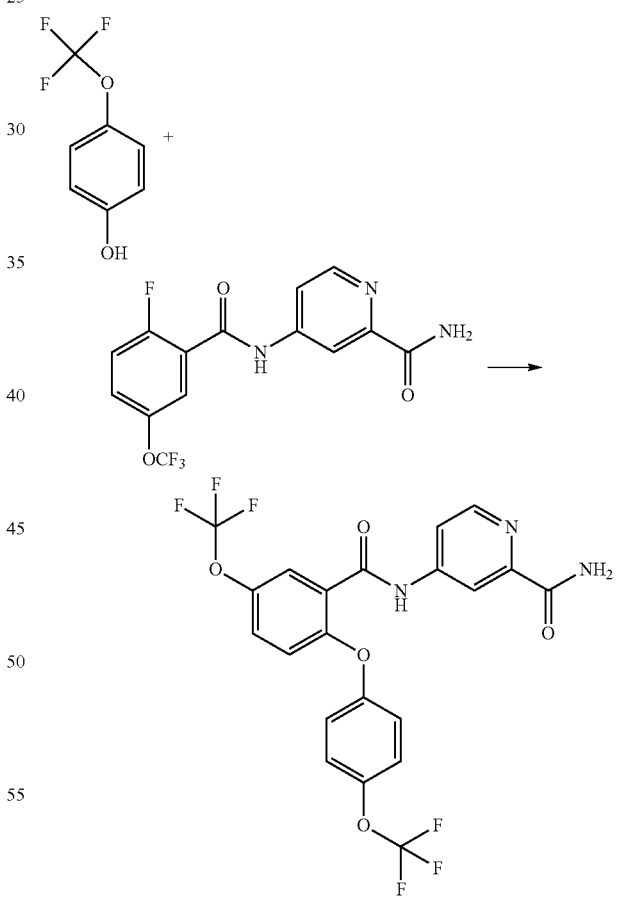

A mixture of 4-[[2-fluoro-5-(trifluoromethoxy)benzoyl]amino]pyridine-2-carboxamide (prepared as described in Example 147, Step 1, 75 mg, 0.22 mmol)), 4-(trifluoromethoxy)phenol (39 mg, 0.22 mmol), K$_2$CO$_3$ (91 mg, 0.66 mmol) in DMF (0.75 mL) was heated at 100° C. for 1 hour. The reaction was filtered, diluted with DMSO (1 mL) and purified by HPLC (1-99% acetonitrile/5 mM HCl) to provide 4-[[5-(trifluoromethoxy)-2-[4-(trifluoromethoxy)phenoxy]benzoyl]amino]pyridine-2-carboxamide (25 mg, 22%) as a white solid. ESI-MS m/z calc. 501.08, found 502.1 (M+1)+; retention time (Method B): 1.79 minutes (3 minute run).

Example 160

N-(3-Carbamoyl-4-fluoro-phenyl)-4-[3-fluoro-4-(trifluoromethoxy)phenoxy]-6-isopropyl-pyridine-3-carboxamide (33)

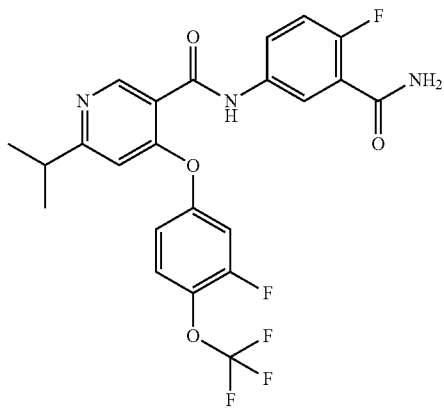 [SMILES: CC(C)c1cc(Oc2ccc(OC(F)(F)F)c(F)c2)c(C(=O)Nc2ccc(F)c(C(N)=O)c2)cn1]

Step 1: Methyl 4-[3-fluoro-4-(trifluoromethoxy)phenoxy]-6-isopropyl-pyridine-3-carboxylate

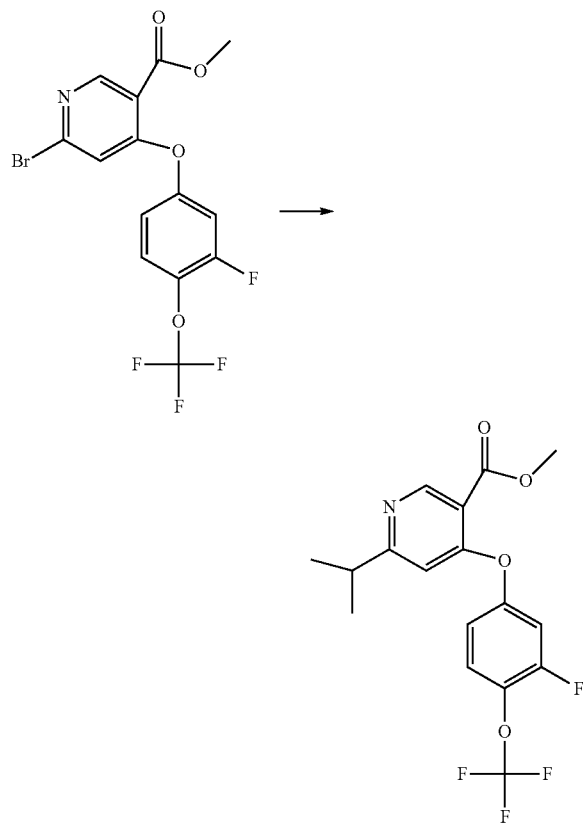

To a flask charged with methyl 6-bromo-4-[3-fluoro-4-(trifluoromethoxy)phenoxy]pyridine-3-carboxylate (prepared as described in Example 157, Step 1, 1 g, 2 mmol) and bis(tri-tert-butylphosphine)palladium(0) (375 mg, 0.734 mmol) at 0° C. under an $N_2$ atmosphere was added a solution of bromo(isopropyl)zinc (7.5 mL of 0.5 M in THF, 3.75 mmol). The reaction mixture was gradually warmed to room temperature and stirred for 1 hour. The reaction mixture was loaded directly onto a silica gel column and eluted using a 0-10% ethyl acetate/hexanes gradient. Product containing fractions were concentrated in vacuo and repurified using silica gel chromatography (0-10% ethyl acetate/hexanes) to obtain methyl 4-[3-fluoro-4-(trifluoromethoxy)phenoxy]-6-isopropyl-pyridine-3-carboxylate (583 mg, 83%). ESI-MS m/z calc. 373.09, found 374.2 (M+1)+; retention time (Method B): 1.66 minutes (3 minute run). $^1$H NMR (400 MHz, DMSO-d6) δ 8.91 (s, 1H), 7.64 (tq, J=8.9, 1.0 Hz, 1H), 7.44 (dd, J=11.3, 2.9 Hz, 1H), 7.04 (ddd, J=9.0, 2.9, 1.6 Hz, 1H), 6.95 (s, 1H), 3.78 (s, 3H), 3.03 (h, J=6.9 Hz, 1H), 1.18 (d, J=6.9 Hz, 6H) ppm.

Step 2: N-(3-Carbamoyl-4-fluoro-phenyl)-4-[3-fluoro-4-(trifluoromethoxy)phenoxy]-6-isopropyl-pyridine-3-carboxamide (33)

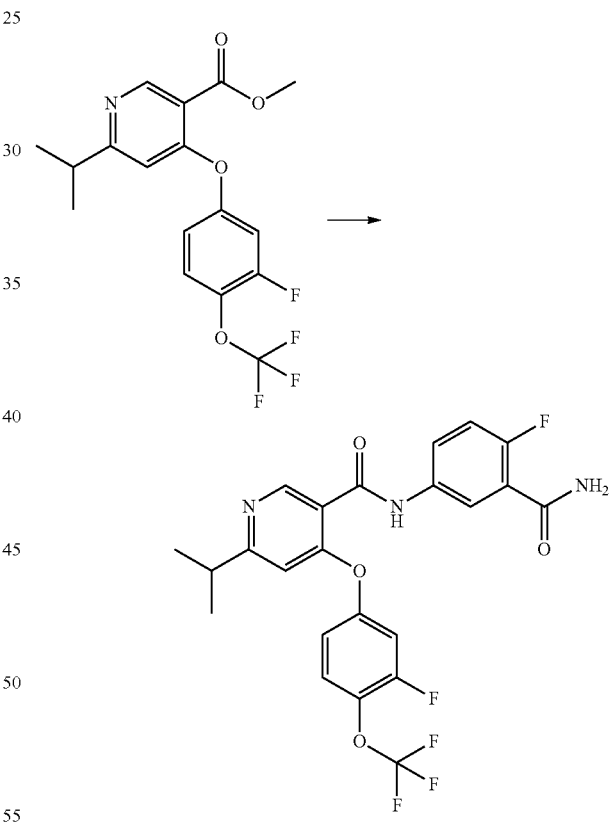

A microwave vial was charged with methyl 4-[3-fluoro-4-(trifluoromethoxy)phenoxy]-6-isopropyl-pyridine-3-carboxylate (40 mg, 0.11 mmol), 1,4-diazabicyclo[2.2.2]octane trimethylalumane (43 mg, 0.17 mmol) and 5-amino-2-fluoro-benzamide (17 mg, 0.11 mmol). The reaction vial was evacuated and flushed with $N_2$. THF (800 μL) was added and the reaction again was evacuated and flushed with $N_2$. The reaction mixture was subjected to microwave irradiation at 120° C. for 60 minutes, then was cooled to room temperature and carefully quenched with 1 M HCl. The aqueous layer was extracted with dichloromethane and the organic layer was dried over MgSO₄, filtered and concentrated in vacuo. Purification by HPLC (1-99% acetonitrile/5 mM HCl) provided N-(3-carbamoyl-4-fluoro-phenyl)-4-[3-fluoro-4-(trifluoromethoxy)phenoxy]-6-isopropyl-pyridine-3-carboxamide (6.1 mg, 11%). ESI-MS m/z calc. 495.12, found 496.3 (M+1)+; retention time (Method B): 1.4 minutes (3 minute run). ¹H NMR (400 MHz, DMSO-d6) δ 10.69 (d, J=5.2 Hz, 1H), 8.79 (d, J=3.1 Hz, 1H), 7.98 (dd, J=6.4, 2.8 Hz, 1H), 7.77 (ddd, J=7.7, 4.4, 2.9 Hz, 1H), 7.70 (t, J=8.0 Hz, 3H), 7.54 (dd, J=11.0, 2.8 Hz, 1H), 7.33-7.13 (m, 2H), 7.00 (d, J=3.9 Hz, 1H), 3.10 (p, J=7.2 Hz, 1H), 1.22 (dd, J=6.9, 1.1 Hz, 6H) ppm.

Example 161

N-(3-Carbamoyl-4-fluoro-phenyl)-2-(2,4-dimethoxyphenoxy)-6-(trifluoromethyl)benzamide (38)

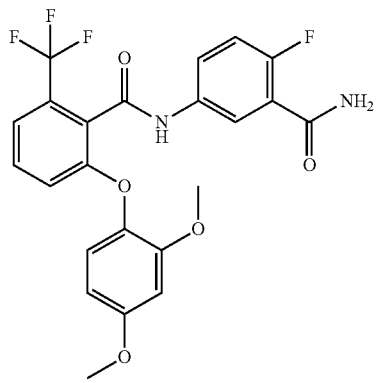 [SMILES: COc1ccc(Oc2cccc(C(F)(F)F)c2C(=O)Nc2ccc(F)c(C(N)=O)c2)c(OC)c1]

This compound was made in an analogous fashion to Example 158 except employing 2,4-dimethoxyphenol in the fluorine-displacement step. The yield of the desired product after purification was 17.7 mg (23%). ESI-MS m/z calc. 478.12, found 479.2 (M+1)+; retention time (Method B): 1.44 minutes (3 minute run).

Example 162

4-[[2-(4-Fluoro-2-methoxy-phenoxy)-4-(trifluoromethoxy)benzoyl]amino]pyridine-2-carboxamide (148)

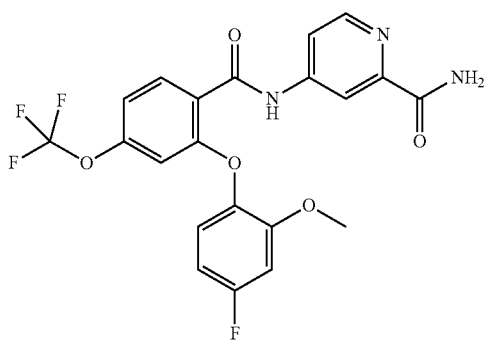 [SMILES: COc1cc(F)ccc1Oc1cc(OC(F)(F)F)ccc1C(=O)Nc1ccnc(C(N)=O)c1]

This compound was made in an analogous fashion to Example 143 except employing 4-fluoro-2-methoxy-phenol in the fluorine-displacement step (Step 3). The yield of the desired product after purification was 44.3 mg (43%) as a white solid. ESI-MS m/z calc. 465.10, found 466.1 (M+1)+; retention time (Method B): 1.66 minutes (3 minute run). ¹H NMR (400 MHz, DMSO-d6) δ 10.98 (s, 1H), 8.54 (d, J=5.5 Hz, 1H), 8.35 (d, J=2.1 Hz, 1H), 8.25-8.06 (m, 1H), 7.90 (dd, J=5.6, 2.2 Hz, 1H), 7.79 (d, J=8.4 Hz, 1H), 7.66 (d, J=2.7 Hz, 1H), 7.33 (dd, J=8.9, 5.9 Hz, 1H), 7.20 (ddq, J=8.4, 2.3, 1.2 Hz, 1H), 7.13 (dd, J=10.6, 2.9 Hz, 1H), 6.86 (td, J=8.5, 2.9 Hz, 1H), 6.56 (dd, J=2.2, 1.0 Hz, 1H), 3.74 (s, 3H) ppm.

Example 163

N-(3-Carbamoyl-4-fluoro-phenyl)-2-(4-fluorophenoxy)-6-(trifluoromethyl)benzamide (37)

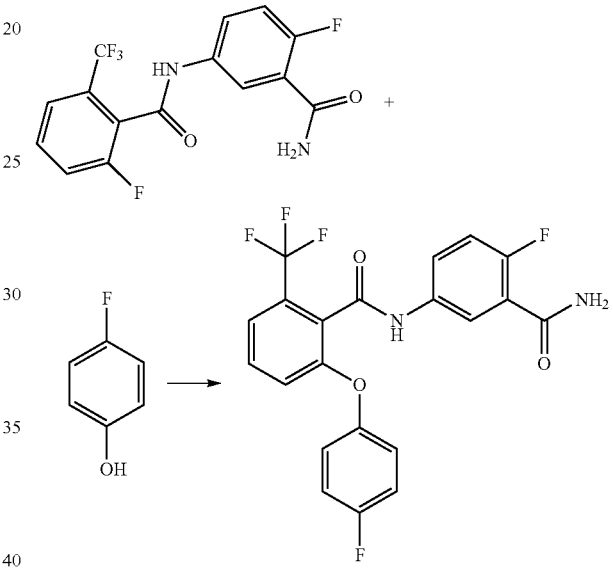

This compound was made in an analogous fashion to Example 138 except employing 4-fluorophenol in the fluorine-displacement step (Step 2). The yield of the desired product after purification was 17.6 mg (27%). ESI-MS m/z calc. 436.08, found 437.2 (M+1)+; retention time (Method B): 1.43 minutes. ESI-MS m/z calc. 465.10, found 466.1 (M+1)+; retention time (Method B): 1.66 minutes (3 minute run).

Example 164

4-[[2-(4-Fluoro-2-methoxy-phenoxy)-5-(trifluoromethoxy)benzoyl]amino]pyridine-2-carboxamide (157)

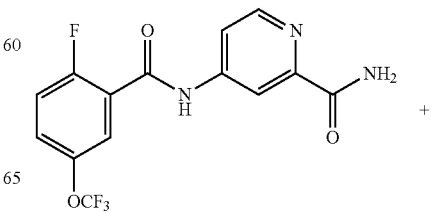

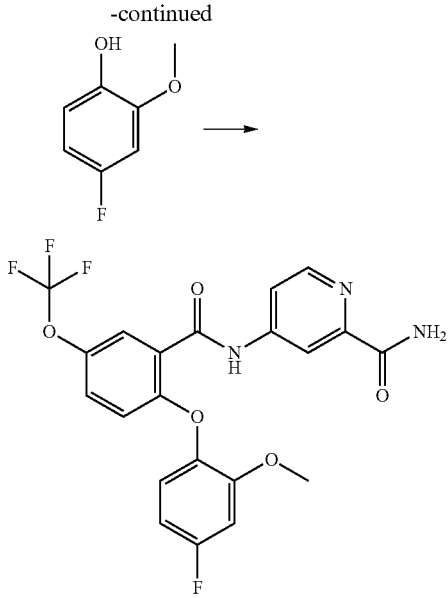

This compound was made in an analogous fashion to Example 147 except employing 4-fluoro-2-methoxy-phenol in the fluorine-displacement step (Step 2). The yield of the desired product after purification was 9.3 mg (9%) as a white solid. ESI-MS m/z calc. 465.10, found 466.3 (M+1)+; retention time (Method B): 1.65 minutes (3 minute run). $^1$H NMR (400 MHz, DMSO-d6) δ 11.03 (s, 1H), 8.54 (d, J=5.5 Hz, 1H), 8.35 (d, J=2.1 Hz, 1H), 8.15 (s, 1H), 7.90 (dd, J=5.6, 2.2 Hz, 1H), 7.73-7.65 (m, 2H), 7.46 (ddd, J=9.1, 3.1, 1.0 Hz, 1H), 7.30 (dd, J=8.9, 5.9 Hz, 1H), 7.13 (dd, J=10.7, 2.9 Hz, 1H), 6.85 (td, J=8.5, 2.9 Hz, 1H), 6.76 (d, J=9.1 Hz, 1H), 3.74 (s, 3H) ppm.

Example 165

N-(3-Carbamoyl-4-fluoro-phenyl)-3-methoxy-5-[2-methoxy-4-(trifluoromethoxy)phenoxy]pyridine-4-carboxamide (138)

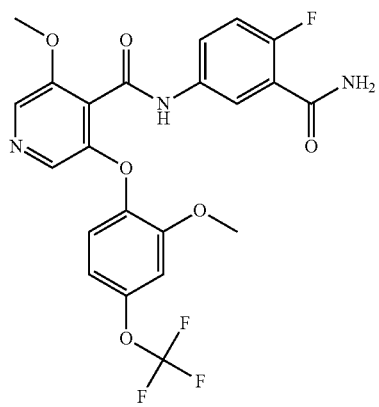 [SMILES: COc1cc(OC(F)(F)F)ccc1Oc1cncc(OC)c1C(=O)Nc1ccc(F)c(C(N)=O)c1]

Step 1: 3-Methoxy-5-[2-methoxy-4-(trifluoromethoxy)phenoxy]pyridine-4-carboxylic acid

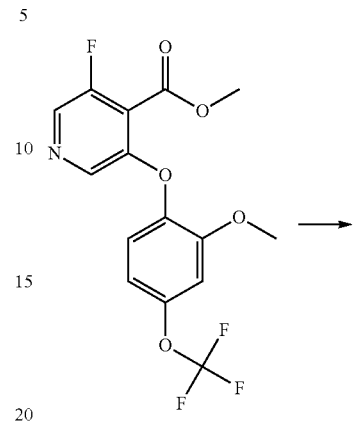

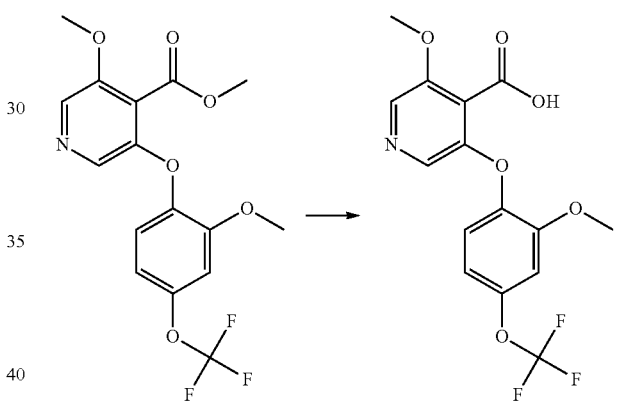

To methyl 3-fluoro-5-[2-methoxy-4-(trifluoromethoxy)phenoxy]pyridine-4-carboxylate (prepared as described in Example 119, Step 2, 300 mg, 0.831 mmol) was added a solution of sodium methoxide (8.5 mL of 0.5 M in methanol, 4.25 mmol) and the mixture was stirred at 80° C. for 2 hours under argon atmosphere. The reaction was concentrated in vacuo to provide crude methyl 3-methoxy-5-[2-methoxy-4-(trifluoromethoxy)phenoxy]pyridine-4-carboxylate as a waxy solid. The solid was taken up in THF (7.6 mL), treated with aqueous NaOH (415 µL of 2 M, 0.83 mmol) and stirred at room temperature for 2 hours. The reaction mixture was concentrated in vacuo to provide 3-methoxy-5-[2-methoxy-4-(trifluoromethoxy)phenoxy]pyridine-4-carboxylic acid (280 mg, 94%) which was taken directly to the next step. ESI-MS m/z calc. 359.06, found 360.0 (M+1)+; retention time (Method F): 0.52 minutes (1.5 minute run).

Step 2: N-(3-Carbamoyl-4-fluoro-phenyl)-3-methoxy-5-[2-methoxy-4-(trifluoromethoxy)phenoxy]pyridine-4-carboxamide (138)

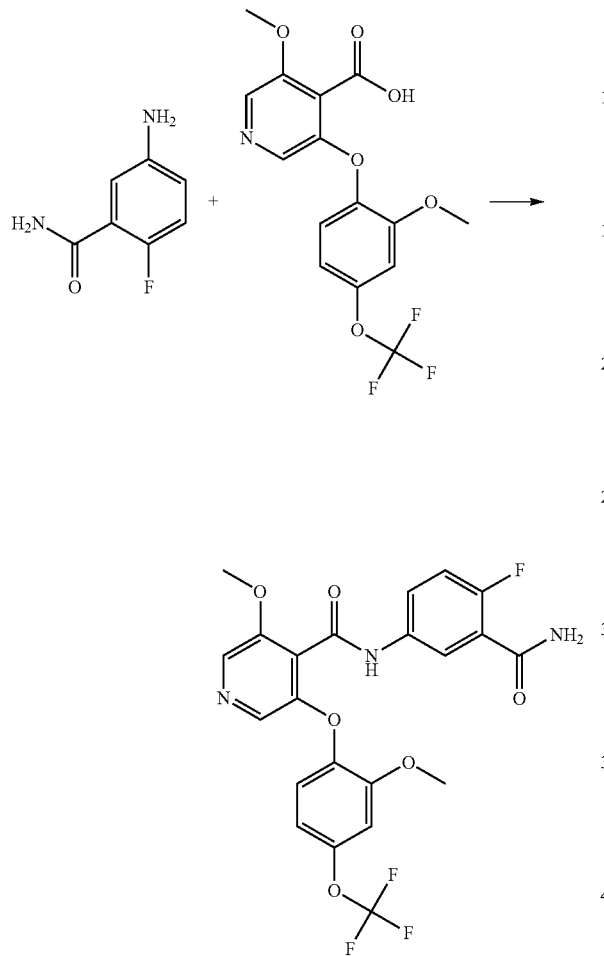

To a solution of 3-methoxy-5-[2-methoxy-4-(trifluoromethoxy)phenoxy]pyridine-4-carboxylic acid (100 mg, 0.278 mmol) in dichloromethane (2 mL) at 0° C. was added DMF (10 µL, 0.13 mmol) and oxalyl chloride (81 µL, 0.93 mmol) dropwise. The reaction mixture was stirred for 2 hours then concentrated in vacuo to afford the acid chloride as a white waxy solid. The solid was dissolved in dichloromethane (2 mL) and added to a solution of 5-amino-2-fluoro-benzamide dihydrochloride (83 mg, 0.37 mmol) and triethylamine (241 µL, 1.73 mmol) in dichloromethane (3 mL) at 0° C. The resulting mixture was allowed to warm to room temperature over 16 hours, then concentrated in vacuo and purified by HPLC to provide N-(3-carbamoyl-4-fluoro-phenyl)-3-methoxy-5-[2-methoxy-4-(trifluoromethoxy)phenoxy]pyridine-4-carboxamide (8.2 mg, 6%) as a white solid. ESI-MS m/z calc. 495.11, found 495.96 (M+1)+; 494.61 (M−1)−; retention time (Method E): 2.57 minutes (5 minute run). $^1$H NMR (400 MHz, DMSO-d6) δ 10.52 (s, 1H), 8.08 (s, 1H), 7.73 (dd, J=6.5, 2.8 Hz, 1H), 7.54-7.39 (m, 4H), 7.06-6.91 (m, 3H), 6.72 (ddq, J=8.9, 2.4, 1.2 Hz, 1H), 3.71 (s, 3H), 3.55 (s, 3H) ppm.

Example 166

4-[[4-(Trifluoromethoxy)-2-[4-(trifluoromethoxy)phenoxy]benzoyl]amino]pyridine-2-carboxamide (149)

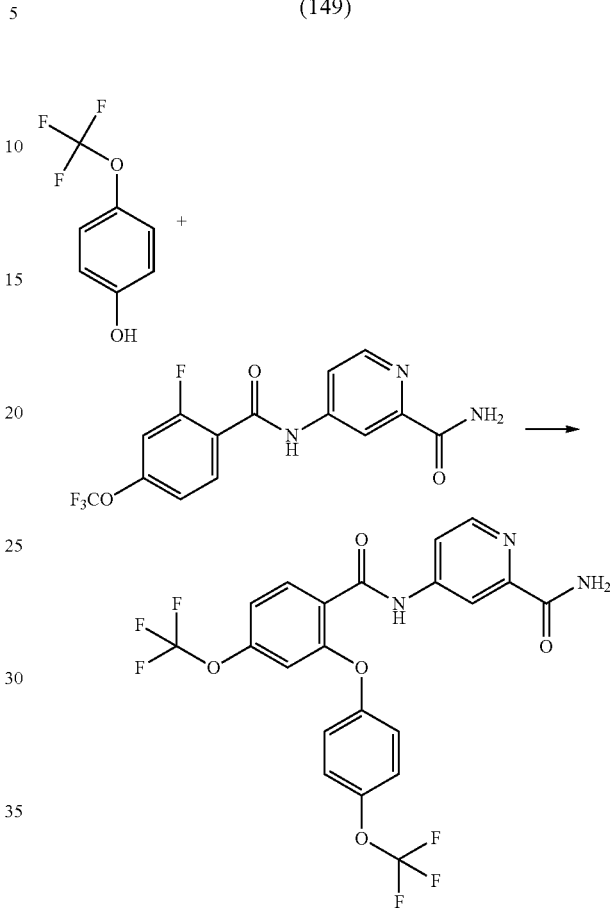

This compound was made in an analogous fashion to Example 143 except employing 4-(trifluoromethoxy)phenol in the fluorine-displacement step (Step 3). The yield of the desired product after purification was 45 mg (38%) as a white solid. ESI-MS m/z calc. 501.08, found 502.1 (M+1)+; retention time (Method B): 1.81 minutes (3 minute run). $^1$H NMR (400 MHz, DMSO-d6) δ 11.07 (s, 1H), 8.51 (d, J=5.5 Hz, 1H), 8.29 (d, J=2.1 Hz, 1H), 8.12 (s, 1H), 7.86 (d, J=8.5 Hz, 1H), 7.82 (dd, J=5.6, 2.2 Hz, 1H), 7.67 (s, 1H), 7.41 (dd, J=9.2, 1.0 Hz, 2H), 7.36 (ddd, J=8.5, 2.4, 1.2 Hz, 1H), 7.25-7.18 (m, 2H), 7.07 (d, J=2.3 Hz, 1H) ppm.

Example 167

5-[[2-(4-Fluoro-2-methoxy-phenoxy)-4,6-bis(trifluoromethyl)benzoyl]amino]pyridine-2-carboxamide (159)

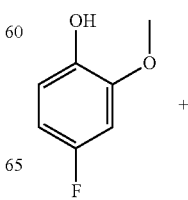

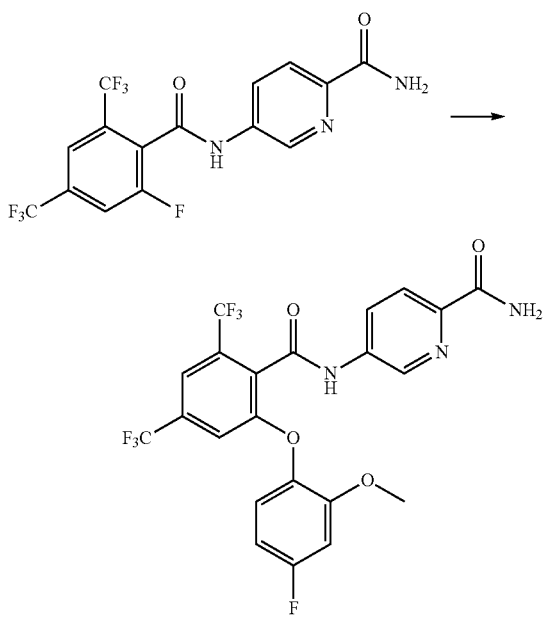

This compound was made in an analogous fashion to Example 92 except employing 4-fluoro-2-methoxy-phenol in the fluorine-displacement step (Step 2). The yield of the desired product after purification was 38.7 mg (58%). ESI-MS m/z calc. 517.09, found 518.2 (M+1)+; retention time (Method B): 1.66 minutes (3 minute run). $^1$H NMR (400 MHz, DMSO-d6) δ 11.35 (s, 1H), 8.84 (dd, J=2.5, 0.7 Hz, 1H), 8.28 (dd, J=8.6, 2.5 Hz, 1H), 8.10-8.05 (m, 1H), 8.04 (d, J=2.7 Hz, 1H), 7.94 (s, 1H), 7.60 (s, 1H), 7.28 (dd, J=8.9, 5.8 Hz, 1H), 7.22-7.15 (m, 2H), 6.88 (ddd, J=8.8, 8.1, 2.9 Hz, 1H), 3.77 (s, 3H) ppm.

Example 168

5-Benzyloxy-N-(3-carbamoyl-4-fluoro-phenyl)-2-fluoro-6-[4-(trifluoromethoxy)phenoxy]-3-(trifluoromethyl)benzamide (217)

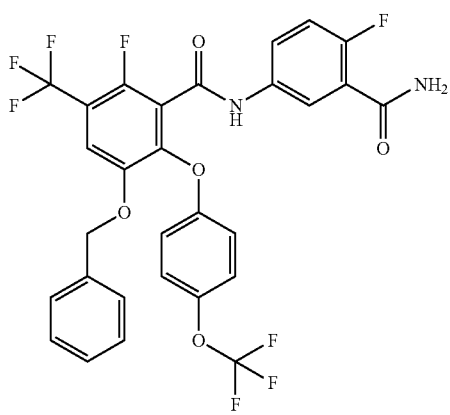 [SMILES: NC(=O)c1cc(NC(=O)c2c(F)c(C(F)(F)F)cc(OCc3ccccc3)c2Oc2ccc(OC(F)(F)F)cc2)ccc1F]

Step 1: 2-Bromo-4-fluoro-5-(trifluoromethyl)phenol

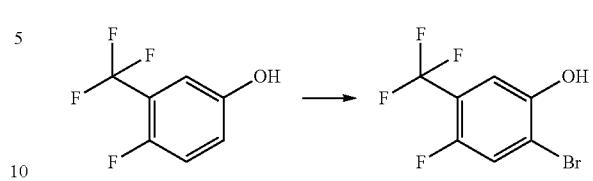

To a mixture of 4-fluoro-3-(trifluoromethyl)phenol (10 g, 55.5 mmol) in acetic acid (50 mL) was added bromine (2.9 mL, 55.5 mmol) and the mixture was stirred at room temperature overnight. Additional bromine (1.4 mL, 27.8 mmol) was added and the reaction mixture was heated at 80° C. for 4 hours. The reaction mixture was diluted with water (10 mL) and diethyl ether (300 mL). The aqueous portion was carefully neutralized with saturated aqueous sodium bicarbonate solution and extracted with dichloromethane (3×50 mL). The organic portions were combined, dried over Na$_2$SO$_4$, filtered and concentrated in vacuo. Product was purified by silica gel chromatography (0-100% ethyl acetate/petroleum ether) to provide 2-bromo-4-fluoro-5-(trifluoromethyl)phenol (2.4 g, 17%). ESI-MS m/z calc. 257.93, found 259.1 (M+1)+; retention time (Method B): 1.48 minutes (3 minutes run).

Step 2: 1-Benzyloxy-2-bromo-4-fluoro-5-(trifluoromethyl)benzene

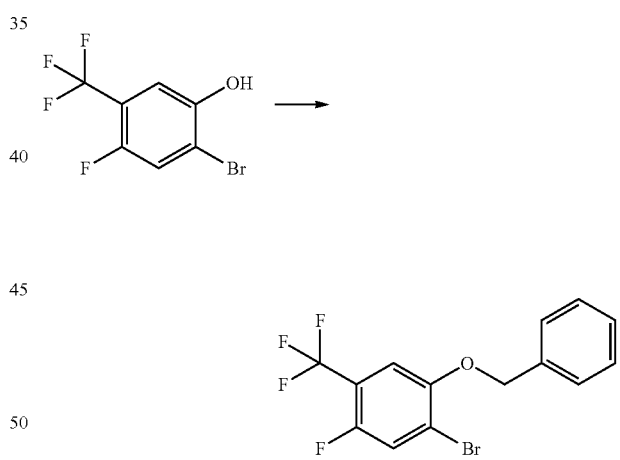

A mixture of 2-bromo-4-fluoro-5-(trifluoromethyl)phenol (1.5 g, 5.79 mmol) and potassium carbonate (2.40 g, 17.4 mmol) in DMF (15 mL) was stirred at room temperature for 5 minutes. Bromomethylbenzene (1.29 g, 7.53 mmol) was added slowly under an atmosphere of nitrogen and was stirred at room temperature for 3 hours. The reaction mixture was quenched with water and the precipitated solid was filtered. The solid was washed with water, taken up in DCM, dried over MgSO$_4$, filtered and concentrated in vacuo. The product was purified by silica gel chromatography (0-10% ethyl acetate/petroleum ether) to provide 1-benzyloxy-2-bromo-4-fluoro-5-(trifluoromethyl)benzene (1.26 g, 62%). ESI-MS m/z calc. 347.98, found 350.0 (M+1)+; retention time (Method A): 0.84 minutes (1 minute run).

Step 3: 3-Benzyloxy-2-bromo-6-fluoro-5-(trifluoromethyl)benzoic acid

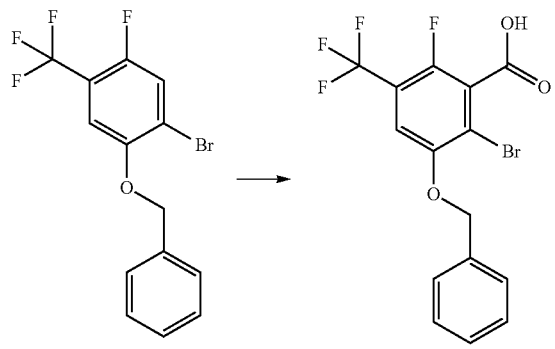 [SMILES: Fc1cc(Br)c(OCc2ccccc2)cc1C(F)(F)F ; O=C(O)c1c(F)c(C(F)(F)F)cc(OCc2ccccc2)c1Br]

To a solution of 1-benzyloxy-2-bromo-4-fluoro-5-(trifluoromethyl)benzene (500 mg, 1.43 mmol) in THF (5 mL) was added LDA dropwise (800 µL of 2 M, 1.6 mmol) while maintaining the temperature below −70° C. and the reaction mixture was stirred at −70° C. for 1 hour. Carbon dioxide (dry ice) was bubbled through the reaction mixture maintaining the temperature below −70° C. The reaction mixture was allowed to warm to room temperature then quenched with saturated ammonium chloride solution. 1 N NaOH was added to make the reaction mixture basic and the aqueous layer was extracted by diethyl ether. The aqueous layer was acidified with 6 N HCl and extracted with DCM, dried over MgSO$_4$, filtered and concentrated in vacuo to provide 3-benzyloxy-2-bromo-6-fluoro-5-(trifluoromethyl)benzoic acid (262 mg, 44%). The product was used crude in next step. ESI-MS m/z calc. 391.97, found 394.9 (M+1)+; retention time (Method B): 1.7 minutes (3 minutes run). $^1$H NMR (400 MHz, DMSO-d6) δ 14.55 (s, 1H), 7.60 (d, J=6.3 Hz, 1H), 7.53-7.47 (m, 2H), 7.46-7.40 (m, 2H), 7.39-7.33 (m, 1H), 5.35 (s, 2H) ppm.

Step 4: 5-Benzyloxy-2-fluoro-6-[4-(trifluoromethoxy)phenoxy]-3-(trifluoromethyl)benzoic acid

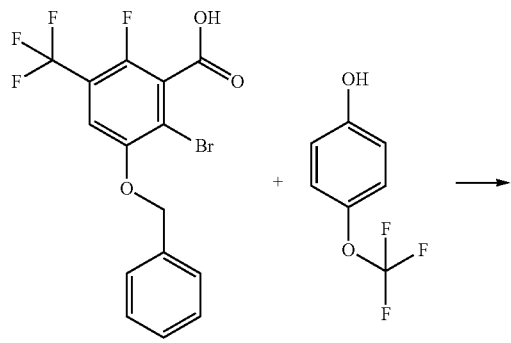

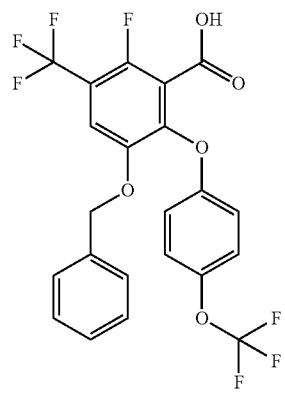

To a mixture of 3-benzyloxy-2-bromo-6-fluoro-5-(trifluoromethyl)benzoic acid (100 mg, 0.25 mmol), 4-(trifluoromethoxy)phenol (40 µL, 0.31 mmol) and cesium carbonate (110 mg, 0.34 mmol) in toluene (1 mL) was added copper (I) iodide (30 mg, 0.16 mmol). The vial was sealed and heated at 100° C. with vigorous stirring for 4 hours. After cooling to room temperature the mixture was acidified with HCl, filtered and the aqueous layer was extracted with DCM. The organic layer was washed with brine, dried over Na$_2$SO$_4$, filtered and concentrated in vacuo. Product was purified by silica gel column chromatography (0-30% ethyl acetate/hexanes) to provide 5-benzyloxy-2-fluoro-6-[4-(trifluoromethoxy)phenoxy]-3-(trifluoromethyl)benzoic acid (45 mg, 36%). ESI-MS m/z calc. 490.07, found 491.1 (M+1)+; retention time (Method B): 2.05 minutes (3 minutes run). $^1$H NMR (400 MHz, DMSO-d6) δ 7.70 (d, J=6.7 Hz, 1H), 7.35-7.30 (m, 2H), 7.28-7.16 (m, 3H), 7.06-7.00 (m, 2H), 6.96-6.90 (m, 2H), 5.14 (s, 2H) ppm.

Step 5: 5-Benzyloxy-N-(3-carbamoyl-4-fluoro-phenyl)-2-fluoro-6-[4-(trifluoromethoxy)phenoxy]-3-(trifluoromethyl)benzamide (217)

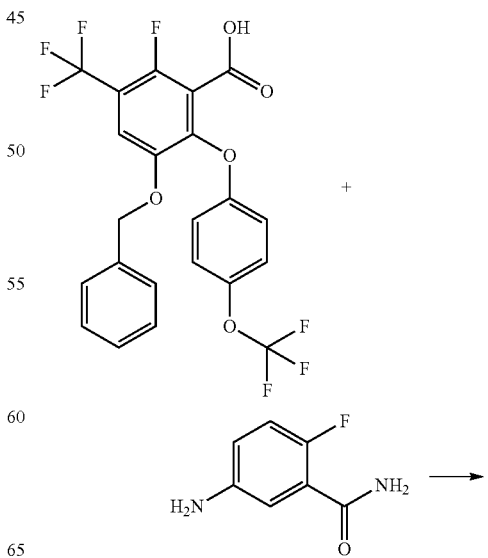

623
-continued

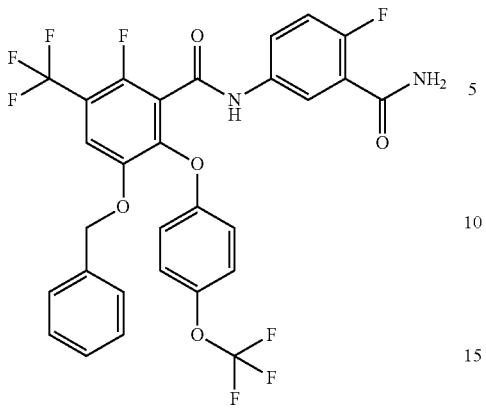

A mixture of 5-benzyloxy-2-fluoro-6-[4-(trifluoromethoxy)phenoxy]-3-(trifluoromethyl)benzoic acid (40 mg, 0.082 mmol), 5-amino-2-fluoro-benzamide (14 mg, 0.09 mmol), HATU (38 mg, 0.10 mmol) and DIPEA (50 µL, 0.2871 mmol) in DMF (700 µL) was stirred at room temperature for 3 hours. The reaction mixture was quenched with water and the precipitated solid was filtered and washed with water. The solid was taken up in DCM, dried over MgSO$_4$, filtered and concentrated in vacuo. Product was purified by silica gel chromatography (0-50% ethyl acetate/hexanes) to afford 5-benzyloxy-N-(3-carbamoyl-4-fluoro-phenyl)-2-fluoro-6-[4-(trifluoromethoxy)phenoxy]-3-(trifluoromethyl)benzamide (28 mg, 52%). ESI-MS m/z calc. 626.11, found 627.2 (M+1)+; retention time (Method B): 2.09 minutes (3 minutes run). $^1$H NMR (400 MHz, DMSO-d6) δ 11.01 (s, 1H), 7.89 (dd, J=6.4, 2.8 Hz, 1H), 7.74 (d, J=6.7 Hz, 1H), 7.71-7.63 (m, 3H), 7.36-7.18 (m, 6H), 7.09-7.04 (m, 2H), 6.97-6.92 (m, 2H), 5.17 (s, 2H) ppm.

Example 169

4-[[2-Fluoro-6-[3-fluoro-2-(trideuteriomethoxy)-4-(trifluoromethoxy)phenoxy]-3-(trifluoromethyl)benzoyl]amino]pyridine-2-carboxamide (218)

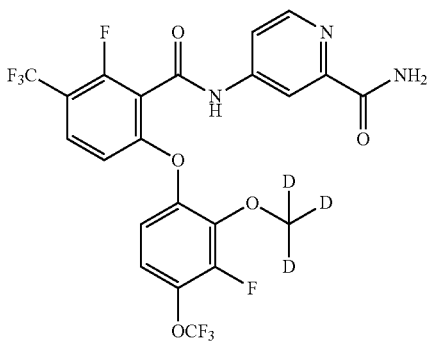 [SMILES: [2H]C([2H])([2H])Oc1c(Oc2ccc(C(F)(F)F)c(F)c2C(=O)Nc2ccnc(C(N)=O)c2)ccc(OC(F)(F)F)c1F]

Step 1: 1-Bromo-3-fluoro-2-(trideuteriomethoxy)-4-(trifluoromethoxy)benzene

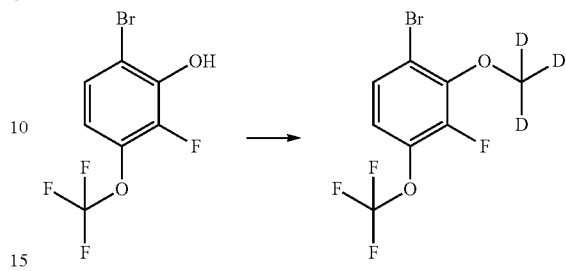

A mixture of 6-bromo-2-fluoro-3-(trifluoromethoxy)phenol (20 g, 72.7 mmol), potassium carbonate (13.1 g, 94.8 mmol) and trideuterio(iodo)methane (14.2 g, 98.0 mmol) in DMF (120 mL) was stirred at room temperature for 2 hours. The reaction mixture was diluted with MTBE (120 mL) and water (120 mL). The aqeuous layer was further extracted with MTBE (50 mL). Combined organic fractions were washed with brine (50 mL), dried over MgSO$_4$, filtered and concentrated in vacuo to provide 1-bromo-3-fluoro-2-(trideuteriomethoxy)-4-(trifluoromethoxy)benzene (20.5 g, 97%). The product was used crude in the next step. $^1$H NMR (500 MHz, CDCl$_3$) δ 7.36 (dd, J=9.0, 2.4 Hz, 1H), 6.97 (ddq, J=9.7, 7.2, 1.3 Hz, 1H) ppm.

Step 2: 3-Fluoro-2-(trideuteriomethoxy)-4-(trifluoromethoxy)phenol

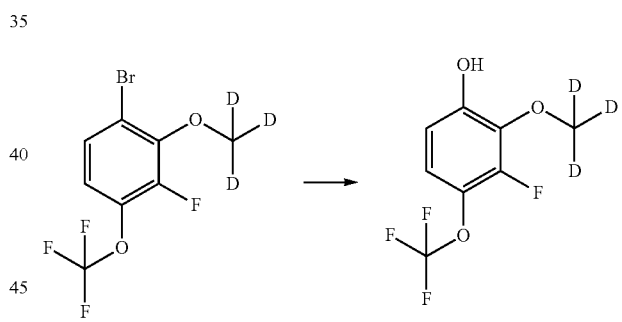

To a mixture of 1-bromo-3-fluoro-2-(trideuteriomethoxy)-4-(trifluoromethoxy)benzene (19.3 g, 66.1 mmol) and Pd$_2$(dba$_3$) (3.02 g, 3.30 mmol) in dioxane (100 mL) was added ditert-butyl-[2-(2,4,6-triisopropylphenyl)phenyl]phosphane (2.92 g, 6.88 mmol) and potassium hydroxide (11.1 g, 198 mmol) in water (50 mL). The mixture was stirred at 100° C. for 2 hours. The reaction mixture was diluted with water (200 mL) and MTBE (200 mL). The aqueous layer was further extracted with MTBE (200 mL). The aqueous layer was acidified with 2 N HCl (200 mL) and extracted with MTBE. The organic layer was washed with brine (300 mL), dried over MgSO$_4$, filtered and concentrated in vacuo to provide 3-fluoro-2-(trideuteriomethoxy)-4-(trifluoromethoxy)phenol (15.9 g, 105%) as an orange liquid. $^1$H NMR (500 MHz, CDCl$_3$) δ 6.92 (ddq, J=9.1, 7.9, 1.2 Hz, 1H), 6.72 (dd, J=9.1, 2.2 Hz, 1H), 5.87 (s, 1H) ppm.

Step 3: Methyl 4-[[2,6-difluoro-3-(trifluoromethyl)benzoyl]amino]pyridine-2-carboxylate

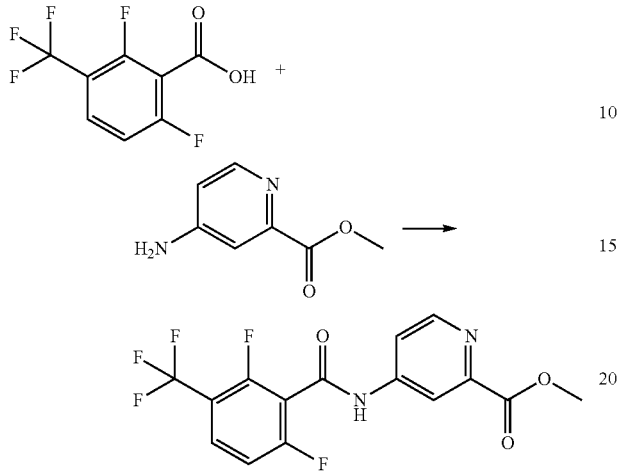

To an ice-cooled solution of 2,6-difluoro-3-(trifluoromethyl)benzoic acid (1 g, 3.1 mmol) in DCM (17 mL) was added DMF (24 µL, 0.31 mmol) and dropwise oxalyl chloride (810 µL, 9.29 mmol) and was stirred for 2 hours. The reaction mixture was concentrated in vacuo to afford the acid chloride as a pale yellow oil. A solution of the acid chloride residue in DCM (17 mL) was added dropwise to an ice-cooled mixture of methyl 4-aminopyridine-2-carboxylate (HCl salt) (820 mg, 4.35 mmol) and triethylamine (2.6 mL, 18.7 mmol) in DCM (17 mL). The mixture was stirred and warmed to room temperature overnight. The reaction mixture was quenched with water (10 mL) and extracted with DCM (2×10 mL). The combined organics were dried by phase separation cartridge and concentrated in vacuo. The product was purified by silica gel chromatography (ethyl acetate/petroleum ether) to provide methyl 4-[[2,6-difluoro-3-(trifluoromethyl)benzoyl]amino]pyridine-2-carboxylate (700 mg, 63%). ESI-MS m/z calc. 360.05, found 361.0 (M+1)+, 359.9 (M−1)−; retention time (Method F): 0.83 minutes (1.5 minutes run). $^1$H NMR (400 MHz, DMSO-d6) δ 11.64 (s, 1H), 8.72 (dd, J=5.4, 0.6 Hz, 1H), 8.42 (dd, J=2.1, 0.6 Hz, 1H), 8.20-8.09 (m, 1H), 7.90 (dd, J=5.4, 2.2 Hz, 1H), 7.66-7.56 (m, 1H), 3.95 (s, 3H) ppm.

Step 4: Methyl 4-[[2-fluoro-6-[3-fluoro-2-(trideuteriomethoxy)-4-(trifluoromethoxy)phenoxy]-3-(trifluoromethyl)benzoyl]amino]pyridine-2-carboxylate

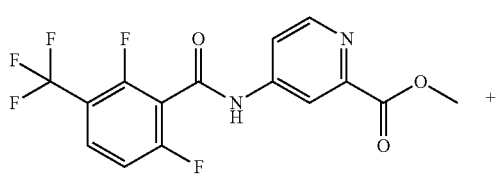

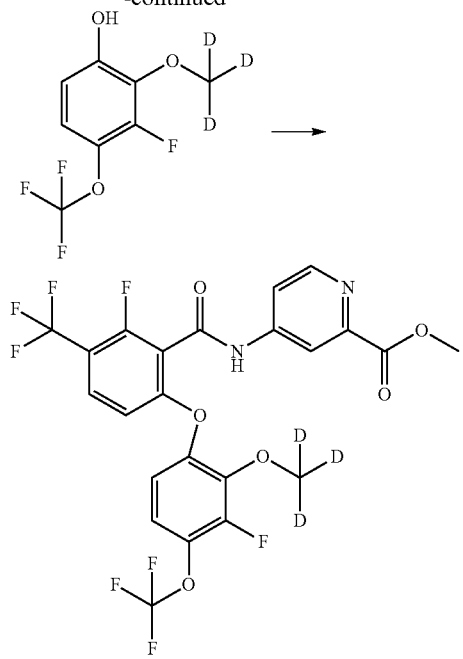

A mixture of methyl 4-[[2,6-difluoro-3-(trifluoromethyl)benzoyl]amino]pyridine-2-carboxylate (430 mg, 1.19 mmol), cesium carbonate (778 mg, 2.39 mmol) and 3-fluoro-2-(trideuteriomethoxy)-4-(trifluoromethoxy)phenol (553 mg, 2.15 mmol) in acetonitrile (3 mL) was heated in the microwave at 90° C. for 1 hour. The cooled reaction mixture was diluted with ethyl acetate (30 mL) and water (30 mL). The aqueous layer was further extracted with ethyl acetate (10 mL). Combined organic portions were washed with brine (20 mL), dried over MgSO4 and concentrated in vacuo to provide methyl 4-[[2-fluoro-6-[3-fluoro-2-(trideuteriomethoxy)-4-(trifluoromethoxy)phenoxy]-3-(trifluoromethyl)benzoyl]amino]pyridine-2-carboxylate (430 mg, 59%). The product was used crude in the next step. ESI-MS m/z calc. 569.09, found 570.0 (M+1)+; retention time (Method F): 1.06 minutes (1.5 minutes run).

Step 5: 4-[[2-Fluoro-6-[3-fluoro-2-(trideuteriomethoxy)-4-(trifluoromethoxy)phenoxy]-3-(trifluoromethyl)benzoyl]amino]pyridine-2-carboxamide (218)

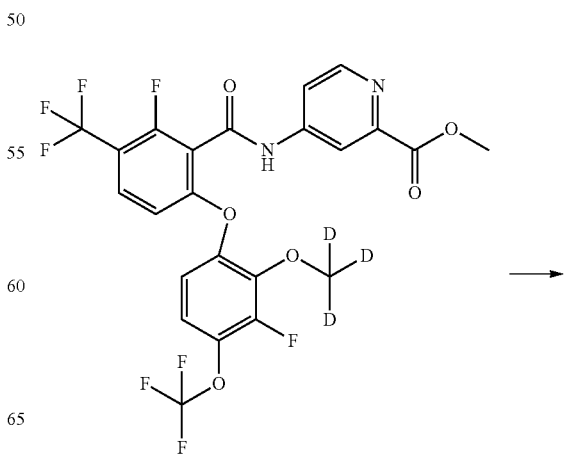

627

-continued

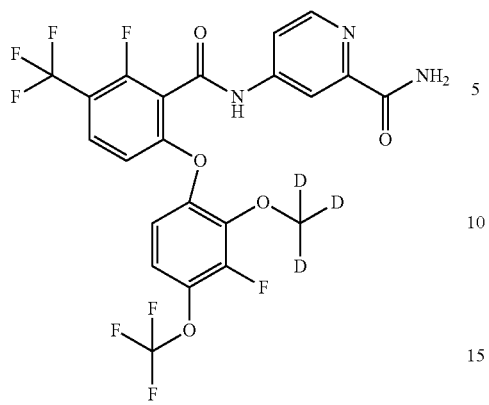

628

-continued

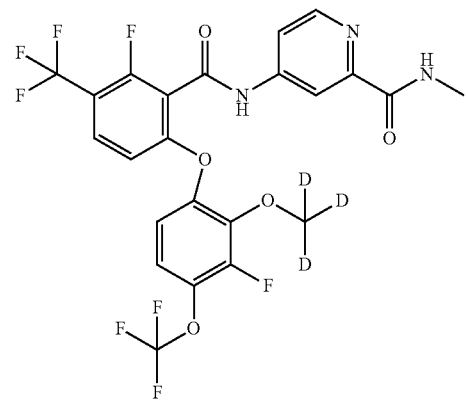

To methyl 4-[[2-fluoro-6-[3-fluoro-2-(trideuteriomethoxy)-4-(trifluoromethoxy)phenoxy]-3-(trifluoromethyl)benzoyl]amino]pyridine-2-carboxylate (900 mg, 0.9800 mmol) was added ammonia (5 mL of 7 M in methanol, 35 mmol) followed by methanol (5 mL) and the mixture was stirred at room temperature overnight. The reaction mixture was concentrated in vacuo. The product was purified by HPLC (0-100% acetonitrile/water/0.1% ammonium hydroxide) to provide 4-[[2-fluoro-6-[3-fluoro-2-(trideuteriomethoxy)-4-(trifluoromethoxy)phenoxy]-3-(trifluoromethyl)benzoyl]amino]pyridine-2-carboxamide (345 mg, 62%) as a white solid. ESI-MS m/z calc. 554.09, found 555.1 (M+1)+; retention time (Method E): 3.38 minutes (5 minutes run). $^1$H NMR (500 MHz, DMSO-d6) δ 11.49 (s, 1H), 8.57 (d, J=5.5 Hz, 1H), 8.33 (d, J=2.2 Hz, 1H), 8.10 (s, 1H), 7.90-7.80 (m, 2H), 7.66 (s, 1H), 7.40 (t, J=8.5 Hz, 1H), 7.23 (dd, J=9.8, 1.9 Hz, 1H), 6.92 (d, J=8.9 Hz, 1H) ppm.

A mixture of methylamine (2.83 mL of 2 M, 5.67 mmol) and methyl 4-[[2-fluoro-6-[3-fluoro-2-(trideuteriomethoxy)-4-(trifluoromethoxy)phenoxy]-3-(trifluoromethyl)benzoyl]amino]pyridine-2-carboxylate (prepared as described in Example 169, step 4, 100 mg, 0.176 mmol) was stirred at room temperature overnight. The reaction mixture was concentrated in vacuo and purified by HPLC (37-100% acetonitrile/water/0.1% ammonium hydroxide) to provide 4-[[2-fluoro-6-[3-fluoro-2-(trideuteriomethoxy)-4-(trifluoromethoxy)phenoxy]-3-(trifluoromethyl)benzoyl]amino]-N-methyl-pyridine-2-carboxamide (13 mg, 12%). ESI-MS m/z calc. 568.11, found 569.2 (M+1)+; 567.4 (M−1)−; Retention time (Method E): 3.49 minutes (5 minutes run). $^1$H NMR (500 MHz, DMSO-d6) δ 11.50 (s, 1H), 8.76 (d, J=5.1 Hz, 1H), 8.56 (dd, J=9.0, 5.4 Hz, 1H), 8.29 (d, J=2.1 Hz, 1H), 7.90-7.83 (m, 2H), 7.40 (t, J=8.7 Hz, 1H), 7.23 (dd, J=9.3, 2.0 Hz, 1H), 6.92 (d, J=8.9 Hz, 1H), 2.82 (d, J=4.8 Hz, 3H) ppm.

Example 170

4-[[2-Fluoro-6-[3-fluoro-2-(trideuteriomethoxy)-4-(trifluoromethoxy)phenoxy]-3-(trifluoromethyl)benzoyl]amino]-N-methyl-pyridine-2-carboxamide (228)

Example 171

N-(3-Carbamoyl-4-fluoro-phenyl)-2-fluoro-6-[3-fluoro-2-methoxy-4-(trifluoromethoxy)phenoxy]-3-(trifluoromethyl)benzamide (219)

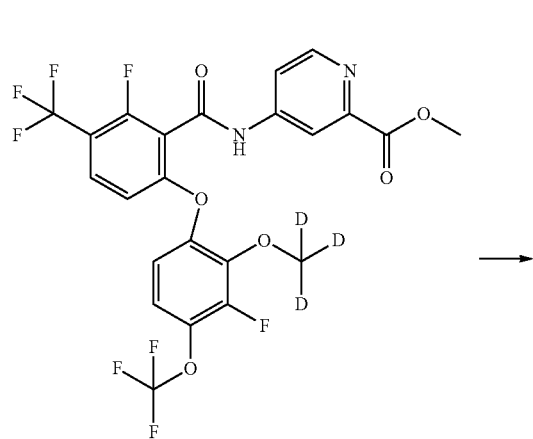

→

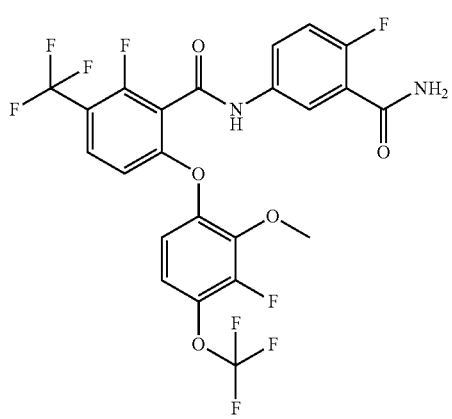 [SMILES: COc1c(Oc2ccc(C(F)(F)F)c(F)c2C(=O)Nc2ccc(F)c(C(N)=O)c2)ccc(OC(F)(F)F)c1F]

Step 1: 1-Bromo-3-fluoro-2-methoxy-4-(trifluoromethoxy)benzene

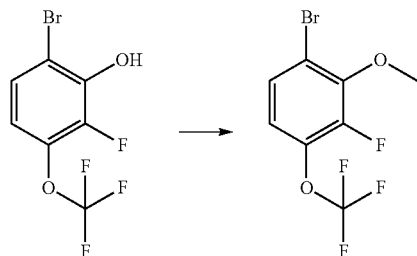

To a solution of 6-bromo-2-fluoro-3-(trifluoromethoxy)phenol (5 g, 18.18 mmol) in DMF (30 mL) was added potassium carbonate (3.27 g, 23.66 mmol) followed by iodomethane (1.47 mL, 23.61 mmol). The mixture was stirred at room temperature for 2.5 hours then partitioned between ethyl acetate (50 mL) and water (50 mL); the organics were collected and the aqueous further extracted with ethyl acetate (2×50 mL). The organics were combined, washed with water (3×50 mL), brine (50 mL), dried over $MgSO_4$, filtered and concentrated in vacuo to provide 1-bromo-3-fluoro-2-methoxy-4-(trifluoromethoxy)benzene (4.6 g, 88%) as an orange oil. $^1H$ NMR (400 MHz, DMSO-d6) δ 7.61 (dd, J=9.1, 2.3 Hz, 1H), 7.31 (ddq, J=8.9, 7.6, 1.3 Hz, 1H), 3.95 (d, J=1.6 Hz, 3H) ppm.

Step 2: 3-Fluoro-2-methoxy-4-(trifluoromethoxy)phenol

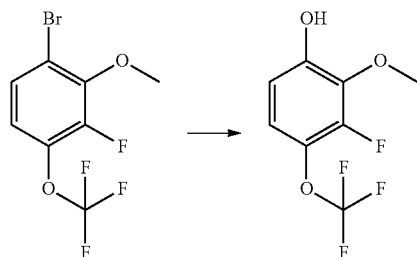

To a solution of 1-bromo-3-fluoro-2-methoxy-4-(trifluoromethoxy)benzene (17.3 g, 59.86 mmol) in dioxane (78 mL) was added (1E,4E)-1,5-diphenylpenta-1,4-dien-3-one; palladium (2.74 g, 2.99 mmol), ditert-butyl-[2-(2,4,6-triisopropylphenyl)phenyl]phosphane (2.54 g, 5.99 mmol) and potassium hydroxide (10.1 g, 180.1 mmol) followed by water (39 mL). The dark red suspension was heated to reflux for 1.25 hours. The reaction mixture was cooled down to room temperature. The reaction mixture was partitioned between MTBE (170 mL) and water (85 mL). The solid was filtered and rinsed with more MTBE and water. The aqueous layer was acidified to pH 1 by addition of HCl (61 mL of 2 M, 122 mmol) then extracted twice with MTBE (50 mL). The combined organic phases were washed with brine (1×20 mL), dried over $MgSO_4$, filtered and concentrated in vacuo to provide 3-fluoro-2-methoxy-4-(trifluoromethoxy)phenol (14.1 g, 89%) as an orange oil. ESI-MS m/z calc. 226.03, found 225.0 (M−1)−; retention time (Method F): 0.79 minutes (1.5 minutes run). $^1H$ NMR (400 MHz, DMSO-d6) δ 10.17 (d, J=1.1 Hz, 1H), 7.07 (dddd, J=9.6, 8.4, 2.4, 1.2 Hz, 1H), 6.73 (dd, J=9.2, 2.2 Hz, 1H), 3.83 (d, J=0.6 Hz, 3H) ppm.

Step 3: N-(3-Carbamoyl-4-fluoro-phenyl)-2,6-difluoro-3-(trifluoromethyl)benzamide

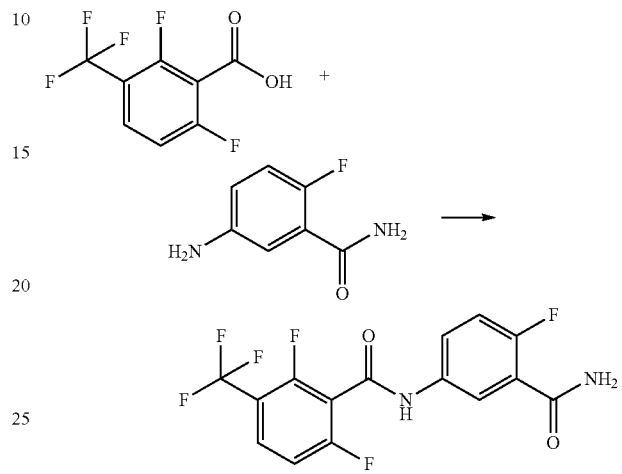

A solution of 2,6-difluoro-3-(trifluoromethyl)benzoic acid (300 mg, 1.33 mmol) in DCM (6 mL) was cooled using an ice-bath. To this was added DMF (10 μL, 0.13 mmol) followed by careful addition of oxalyl chloride (350 μL, 4.012 mmol). The solution was stirred with an ice-bath in place for 2 hours. This solution was concentrated in vacuo and azeotroped with DCM to afford the acid chloride as a cream colored solid. This acid chloride was taken up in DCM (3 mL) and added to an ice-bath cooled solution of 5-amino-2-fluoro-benzamide (208 mg, 1.35 mmol) and DIPEA (700 μL, 4.019 mmol) in DCM (3 mL). The resulting cream suspension was stirred with ice-bath in place for 1 hour and then at room temperature for 18 hours. DCM was removed in vacuo and partitioned with ethyl acetate and water. Layers were separated by phase separation cartridge and the organic layer was concentrated in vacuo to afford N-(3-carbamoyl-4-fluoro-phenyl)-2,6-difluoro-3-(trifluoromethyl)benzamide (489 mg, 95%) as a cream solid. ESI-MS m/z calc. 362.05, found 363.0 (M+1)+; retention time (Method F): 0.79 minutes (1.5 minutes run). $^1H$ NMR (500 MHz, DMSO-d6) δ 11.11 (s, 1H), 8.11-8.02 (m, 1H), 7.98 (dd, J=6.4, 2.8 Hz, 1H), 7.82-7.76 (m, 1H), 7.74 (s, 1H), 7.69 (s, 1H), 7.53 (t, J=8.6 Hz, 1H), 7.33 (dd, J=10.1, 9.0 Hz, 1H) ppm.

Step 4: N-(3-Carbamoyl-4-fluoro-phenyl)-2-fluoro-6-[3-fluoro-2-methoxy-4-(trifluoromethoxy)phenoxy]-3-(trifluoromethyl)benzamide (219)

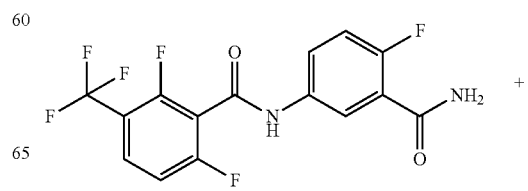

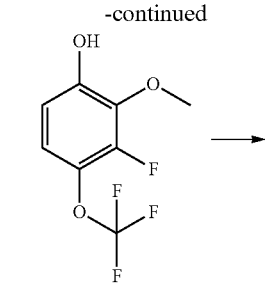

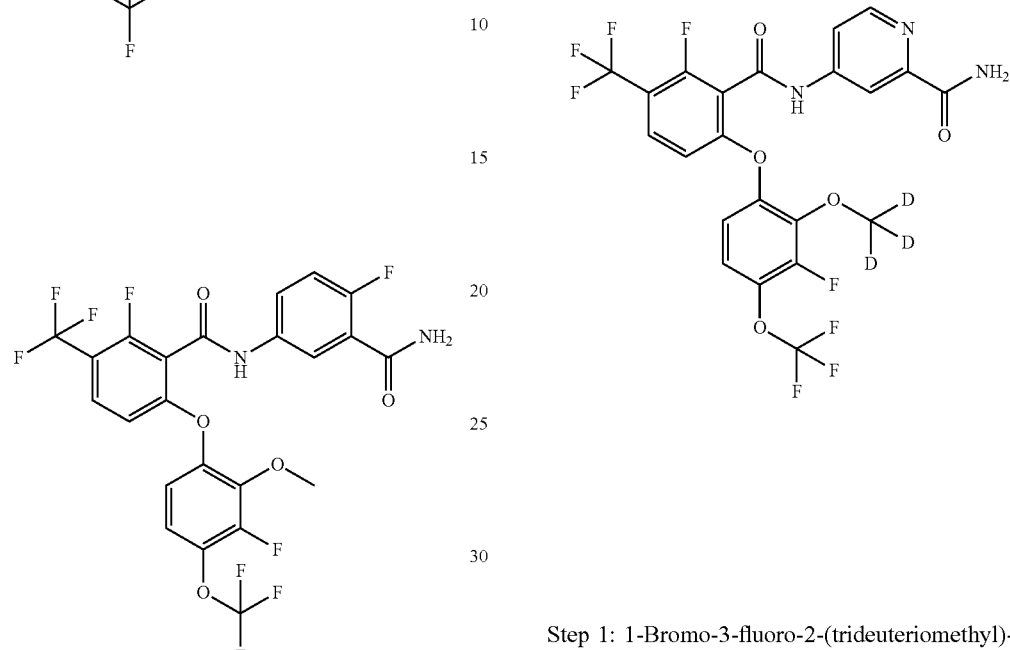

Example 172

4-[[2-Fluoro-6-[3-fluoro-2-(trideuteriomethyl)-4-(trifluoromethoxy)phenoxy]-3-(trifluoromethyl)benzoyl]amino]pyridine-2-carboxamide (232)

Step 1: 1-Bromo-3-fluoro-2-(trideuteriomethyl)-4-(trifluoromethoxy)benzene

In a microwave vial was combined N-(3-carbamoyl-4-fluoro-phenyl)-2,6-difluoro-3-(trifluoromethyl)benzamide (100 mg, 0.26 mmol), 3-fluoro-2-methoxy-4-(trifluoromethoxy)phenol (120 mg, 0.265 mmol) and cesium carbonate (125 mg, 0.384 mmol) in acetonitrile (4 mL). The resulting suspension was heated in the microwave at 90° C. μW for 60 minutes then the mixture was concentrated in vacuo and partitioned with ethyl acetate and water. The layers were separated and the organic phase passed through a phase separation cartridge before concentrating in vacuo and purifying by HPLC (37-100% acetonitrile/water/0.1% ammonium hydroxide) to provide N-(3-carbamoyl-4-fluoro-phenyl)-2-fluoro-6-[3-fluoro-2-methoxy-4-(trifluoromethoxy)phenoxy]-3-(trifluoromethyl)benzamide (18 mg, 12%) as a white solid. ESI-MS m/z calc. 568.07, found 569.0 (M+1)+; 567.0 (M−1)−; Retention time (Method E): 3.38 minutes (5 minutes run). $^1$H NMR (500 MHz, DMSO-d6) δ 11.06 (s, 1H), 7.99 (dd, J=6.4, 2.8 Hz, 1H), 7.84 (t, J=8.6 Hz, 1H), 7.77 (ddd, J=8.9, 4.3, 2.8 Hz, 1H), 7.72 (s, 1H), 7.68 (s, 1H), 7.41 (dd, J=9.3, 7.9 Hz, 1H), 7.30 (dd, J=10.0, 8.9 Hz, 1H), 7.21 (dd, J=9.3, 2.1 Hz, 1H), 6.90 (d, J=8.9 Hz, 1H), 3.87 (s, 3H) ppm.

LDA (6.5 mL of 2 M, 13 mmol) was added dropwise to a solution of 4-bromo-2-fluoro-1-(trifluoromethoxy)benzene (3.03 g, 11.7 mmol) in THF (35 mL) at −78° C. The reaction was stirred at this temperature for 30 minutes then trideuterio(iodo)methane (1.14 mL, 17.9 mmol) was added. The mixture was stirred at −78° C. for 30 minutes then allowed to warm to ambient temperature and stirred for 30 minutes. The reaction was quenched by the addition of aqueous NH$_4$Cl and the mixture was extracted with ethyl acetate (×3). The combined organic extracts were dried over MgSO$_4$, filtered and concentrated in vacuo to afford 1-bromo-3-fluoro-2-(trideuteriomethyl)-4-(trifluoromethoxy)benzene (3.23 mg). The product was used crude in the next step.

Step 2: 3-Fluoro-2-(trideuteriomethyl)-4-(trifluoromethoxy)phenol

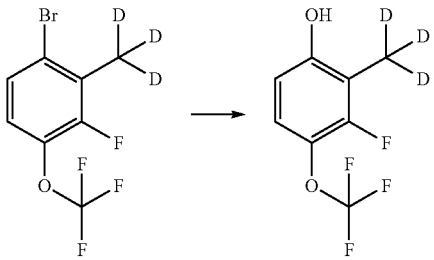 [SMILES: [2H]C([2H])([2H])c1c(Br)ccc(OC(F)(F)F)c1F ; [2H]C([2H])([2H])c1c(O)ccc(OC(F)(F)F)c1F]

To a solution of 1-bromo-3-fluoro-2-(trideuteriomethyl)-4-(trifluoromethoxy)benzene (3.23 g, 11.7 mmol) in dioxane (17 mL) was added Pd$_2$(dba)$_3$ (546 mg, 0.60 mmol) followed by di-tert-butyl-[2-(2,4,6-triisopropylphenyl)phenyl]phosphane (522 mg, 1.23 mmol) and potassium hydroxide (1.97 g, 35.1 mmol) in water (10 mL). The mixture was stirred at 100° C. for 2 hours. The reaction mixture was separated between water (200 mL) and MTBE (200 mL). The aqueous layer was further washed with MTBE (200 mL). The aqueous layer was acidified with 2N HCl (200 mL) and extracted with MTBE. The organic layer was further washed with brine (300 mL) then dried over MgSO$_4$, filtered and concentrated in vacuo to provide 3-fluoro-2-(trideuteriomethyl)-4-(trifluoromethoxy)phenol (631 mg, 25%) as an orange liquid. ESI-MS m/z calc. 213.05, found 212.0 (M−1)−; retention time (Method F): 0.90 minutes (1.5 minutes run). $^1$H NMR (500 MHz, CDCl$_3$) δ 7.01 (t, J=8.7 Hz, 1H), 6.55 (d, J=8.9, 1.9 Hz, 1H) ppm.

Step 3: Methyl 4-[[2,6-difluoro-3-(trifluoromethyl)benzoyl]amino]pyridine-2-carboxylate

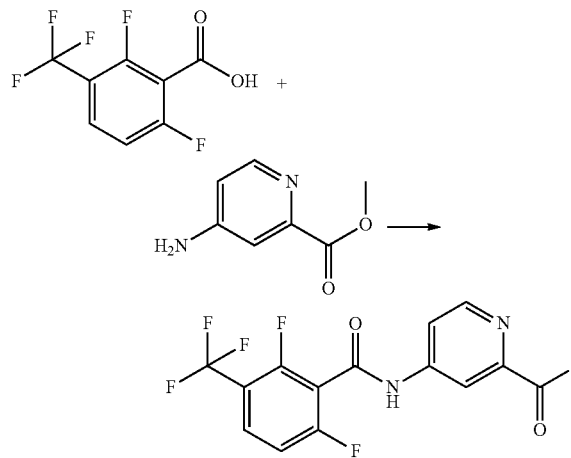

To an ice-cooled solution of 2,6-difluoro-3-(trifluoromethyl)benzoic acid (1 g, 3.1 mmol) in DCM (17 mL) was added DMF (24 μL, 0.31 mmol) and oxalyl chloride (810 μL, 9.285 mmol) dropwise and the mixture stirred for 2 hours. The reaction mixture was concentrated in vacuo to afford the acid chloride as a pale yellow oil. A solution of the residue in DCM (17 mL) was added dropwise to an ice-cooled mixture of methyl 4-aminopyridine-2-carboxylate (HCl salt) (820 mg, 4.348 mmol) and triethylamine (2.6 mL, 18.65 mmol) in DCM (17 mL). The resulting mixture was stirred and warmed to room temperature overnight. The reaction mixture was quenched with water (10 mL) and extracted with DCM (2×10 mL). The combined organics were dried by phase separation cartridge, concentrated in vacuo and purified by column chromatography (ethyl acetate/petroleum ether), to afford methyl 4-[[2,6-difluoro-3-(trifluoromethyl)benzoyl]amino]pyridine-2-carboxylate (700 mg, 63%) as a white solid. ESI-MS m/z calc. 360.05, found 361.0 (M+1)+; 359.9 (M−1)−; retention time (Method F): 0.83 minutes (1.5 minutes run). $^1$H NMR (400 MHz, DMSO-d6) δ 11.64 (s, 1H), 8.72 (dd, J=5.4, 0.6 Hz, 1H), 8.42 (dd, J=2.1, 0.6 Hz, 1H), 8.20-8.09 (m, 1H), 7.90 (dd, J=5.4, 2.2 Hz, 1H), 7.66-7.56 (m, 1H), 3.95 (s, 3H) ppm.

Step 4: Methyl 4-[[2-fluoro-6-[3-fluoro-2-(trideuteriomethyl)-4-(trifluoromethoxy)phenoxy]-3-(trifluoromethyl)benzoyl]amino]pyridine-2-carboxylate

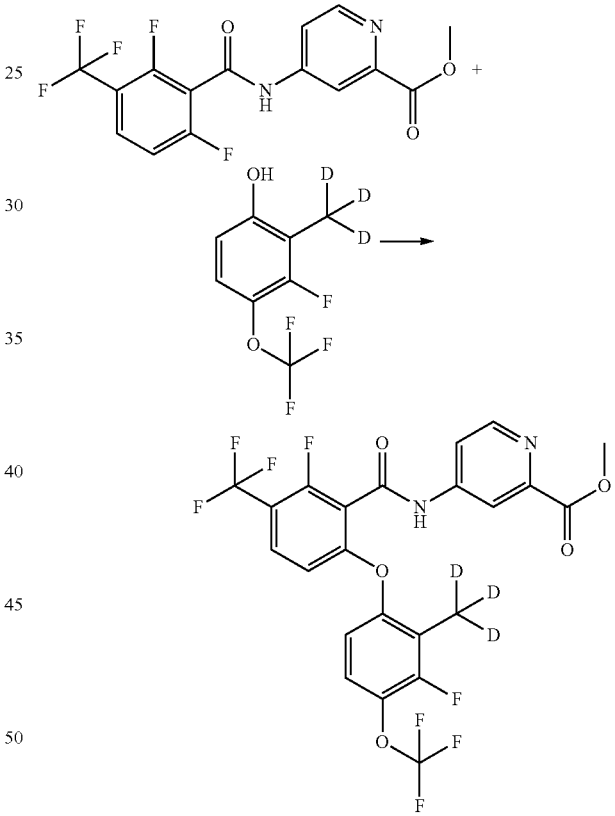

Methyl 4-[[2,6-difluoro-3-(trifluoromethyl)benzoyl]amino]pyridine-2-carboxylate (353 mg, 0.98 mmol), 3-fluoro-2-(trideuteriomethyl)-4-(trifluoromethoxy)phenol (200 mg, 0.94 mmol) and Cs$_2$CO$_3$ (500 mg, 1.54 mmol) were combined in DMF (4 mL) and stirred overnight at 70° C. The reaction mixture was partitioned between ethyl acetate and brine. The organic layer was washed with brine, dried over MgSO$_4$, filtered and evaporated. The product was purified by HPLC (37-100% acetonitrile/water/0.1% ammonium hydroxide) to provide methyl 4-[[2-fluoro-6-[3-fluoro-2-(trideuteriomethyl)-4-(trifluoromethoxy)phenoxy]-3-(trifluoromethyl)benzoyl]amino]pyridine-2-carboxylate (180 mg, 33%). ESI-MS m/z calc. 553.10, found 554.2 (M+1)+;

retention time (Method F): 1.06 minutes (1.5 minutes run). ¹H NMR (500 MHz, CDCl₃) δ 8.83 (s, 1H), 8.65 (d, J=5.5 Hz, 1H), 8.23 (d, J=2.2 Hz, 1H), 8.11-8.00 (m, 1H), 7.59 (t, J=8.3 Hz, 1H), 7.26-7.16 (m, 1H), 6.86 (dd, J=9.0, 1.9 Hz, 1H), 6.58 (d, J=8.8 Hz, 1H), 3.94 (s, 3H) ppm.

Step 5: 4-[[2-Fluoro-6-[3-fluoro-2-(trideuteriomethyl)-4-(trifluoromethoxy)phenoxy]-3-(trifluoromethyl)benzoyl]amino]pyridine-2-carboxamide (232)

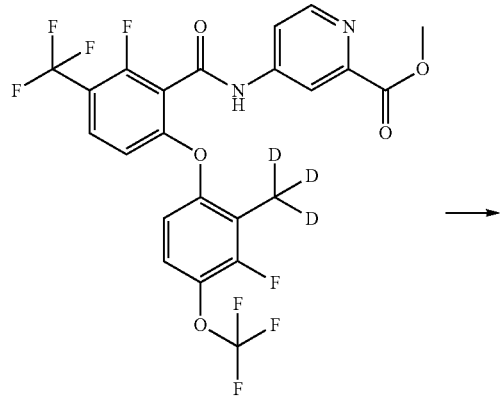

A solution of methyl 4-[[2-fluoro-6-[3-fluoro-2-(trideuteriomethyl)-4-(trifluoromethoxy)phenoxy]-3-(trifluoromethyl)benzoyl]amino]pyridine-2-carboxylate (160 mg, 0.29 mmol) and ammonia (8 mL of 7 M in methanol, 56 mmol) was stirred at room temperature for 24 hours. The reaction mixture was concentrated in vacuo to provide 4-[[2-fluoro-6-[3-fluoro-2-(trideuteriomethyl)-4-(trifluoromethoxy)phenoxy]-3-(trifluoromethyl)benzoyl]amino]pyridine-2-carboxamide (154 mg, 92%). ESI-MS m/z calc. 538.10, found 539.1 (M+1)+; retention time (Method E): 3.44 minutes (5 minutes run). ¹H NMR (500 MHz, DMSO-d6) δ 11.48 (s, 1H), 8.55 (d, J=5.5 Hz, 1H), 8.30 (d, J=2.3 Hz, 1H), 8.09 (d, J=2.8 Hz, 1H), 7.87 (t, J=8.6 Hz, 1H), 7.80 (dd, J=5.5, 2.2 Hz, 1H), 7.65 (d, J=2.9 Hz, 1H), 7.51 (t, J=8.9 Hz, 1H), 7.13 (dd, J=9.1, 1.8 Hz, 1H), 6.89 (d, J=8.9 Hz, 1H) ppm.

Example 173

5-[[2-Fluoro-6-[3-fluoro-2-(trideuteriomethoxy)-4-(trifluoromethoxy)phenoxy]-3-(trifluoromethyl)benzoyl]amino]pyridine-2-carboxamide (221)

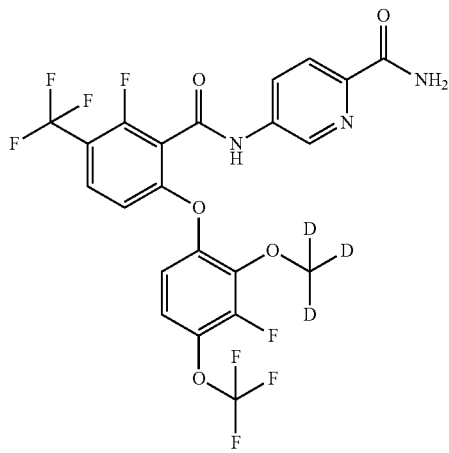 [SMILES: [2H]C([2H])([2H])Oc1c(Oc2ccc(C(F)(F)F)c(F)c2C(=O)Nc2ccc(C(N)=O)nc2)ccc(OC(F)(F)F)c1F]

Step 1: Methyl 5-[[2,6-difluoro-3-(trifluoromethyl)benzoyl]amino]pyridine-2-carboxylate

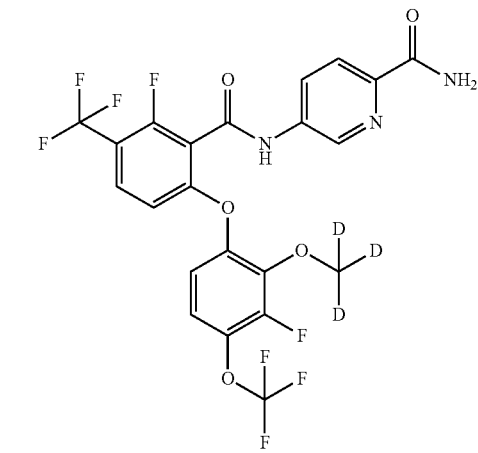

To an ice-cooled solution of 2,6-difluoro-3-(trifluoromethyl)benzoic acid (300 mg, 0.9288 mmol) in DCM (5 mL) was added DMF (7.2 µL, 0.093 mmol) and dropwise oxalyl chloride (245 µL, 2.81 mmol) and the mixture was stirred for 2 hours. The reaction mixture was concentrated in vacuo to afford the acid chloride as a colourless waxy solid. A solution of the acid chloride residue in DCM (5 mL) was added to methyl 5-aminopyridine-2-carboxylate (198 mg, 1.30 mmol) and triethylamine (780 µL, 5.60 mmol) in an ice bath. The resulting mixture was stirred and warmed to room temperature over 2 hours. The reaction mixture was quenched with water (10 mL) and extracted with DCM (2×10 mL). The combined organics were dried by phase separation cartridge and concentrated in vacuo to afford a brown waxy solid. This was purified by silica gel chromatography (0-100% ethyl acetate/petroleum ether) to afford methyl 5-[[2,6-difluoro-3-(trifluoromethyl)benzoyl]amino]pyridine-2-carboxylate (225 mg, 67%) as an off-white gummy solid. ESI-MS m/z calc. 360.05, found 361.0 (M+1)+; 359.0 (M−1)−; retention time (Method F): 0.83 minutes (1.5 minutes run). $^1$H NMR (400 MHz, CDCl$_3$) δ 10.35 (s, 1H), 8.75 (d, J=2.5 Hz, 1H), 8.44 (dd, J=8.6, 2.4 Hz, 1H), 7.99 (d, J=8.6 Hz, 1H), 7.53 (td, J=8.3, 5.9 Hz, 1H), 6.96-6.87 (m, 1H), 3.84 (s, 3H) ppm.

Step 2: Methyl 5-[[2-fluoro-6-[3-fluoro-2-(trideuteriomethoxy)-4-(trifluoromethoxy)phenoxy]-3-(trifluoromethyl)benzoyl]amino]pyridine-2-carboxylate

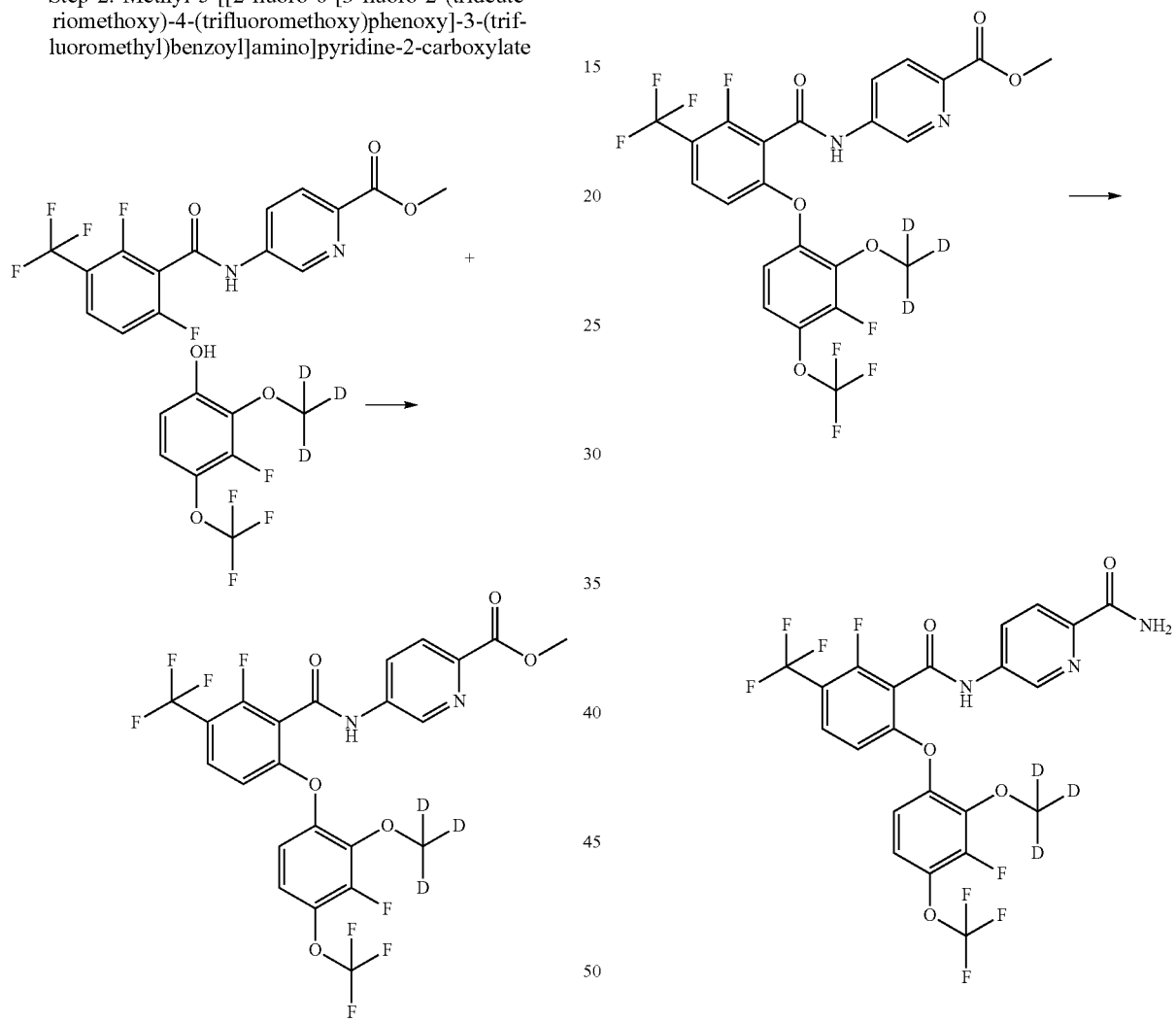

Methyl 5-[[2,6-difluoro-3-(trifluoromethyl)benzoyl]amino]pyridine-2-carboxylate (200 mg, 0.56 mmol), cesium carbonate (283 mg, 0.87 mmol) and 3-fluoro-2-(trideuteriomethoxy)-4-(trifluoromethoxy)phenol (prepared as described in Example 169, step 2, 134 mg, 0.58 mmol) were combined in DMF (5 mL) and stirred over the weekend at 30° C. The reaction mixture was cooled and purified by HPLC (37-100% acetonitrile/water/0.1% ammonium hydroxide) to provide methyl 5-[[2-fluoro-6-[3-fluoro-2-(trideuteriomethoxy)-4-(trifluoromethoxy)phenoxy]-3-(trifluoromethyl)benzoyl]amino]pyridine-2-carboxylate (98 mg, 31%). ESI-MS m/z calc. 569.09, found 570.0 (M+1)+; 568.1 (M−1)−; retention time (Method F): 1.07 minutes (1.5 minutes run). $^1$H NMR (400 MHz, CDCl$_3$) δ 8.69 (dd, J=2.6, 0.7 Hz, 1H), 8.57 (dd, J=8.6, 2.6 Hz, 1H), 8.49 (s, 1H), 8.21 (d, J=8.6 Hz, 1H), 7.64 (t, J=8.3 Hz, 1H), 7.19-7.09 (m, 1H), 7.06 (dd, J=9.2, 2.1 Hz, 1H), 6.67 (d, J=8.9 Hz, 1H), 4.02 (s, 3H) ppm.

Step 3: 5-[[2-Fluoro-6-[3-fluoro-2-(trideuteriomethoxy)-4-(trifluoromethoxy)phenoxy]-3-(trifluoromethyl)benzoyl]amino]pyridine-2-carboxamide (221)

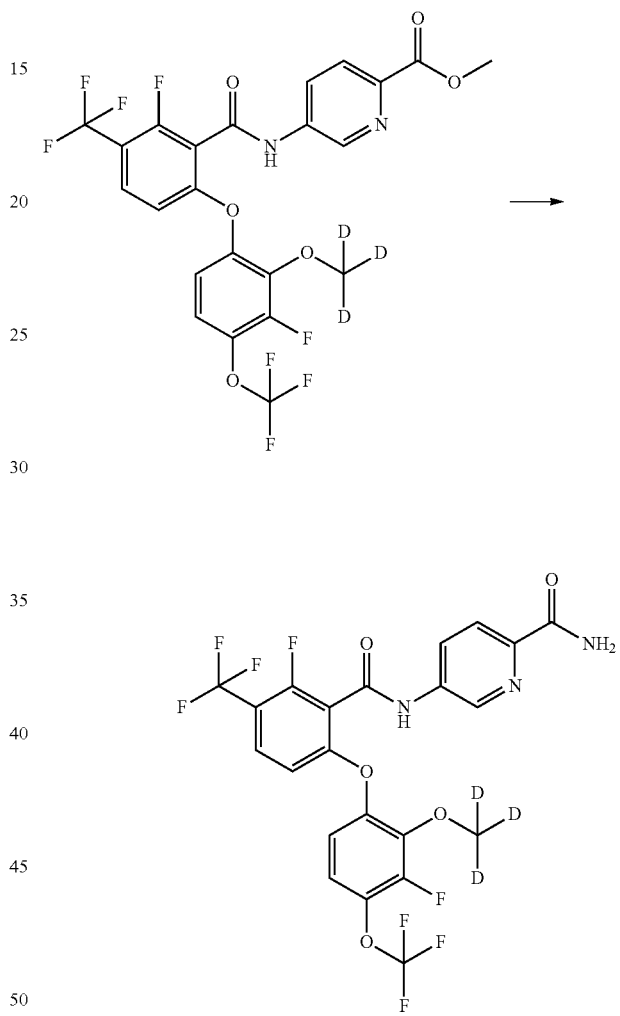

Methyl 5-[[2-fluoro-6-[3-fluoro-2-(trideuteriomethoxy)-4-(trifluoromethoxy)phenoxy]-3-(trifluoromethyl)benzoyl]amino]pyridine-2-carboxylate (98 mg, 0.17 mmol) was dissolved in ammonia (5 mL of 7 M in methanol, 35 mmol) and stirred at ambient temperature for 3 days. The reaction mixture was concentrated in vacuo to afford 5-[[2-fluoro-6-[3-fluoro-2-(trideuteriomethoxy)-4-(trifluoromethoxy)phenoxy]-3-(trifluoromethyl)benzoyl]amino]pyridine-2-carboxamide (94 mg, 81%). ESI-MS m/z calc. 554.09, found 554.9 (M+1)+; 552.7 (M−1)−; retention time (Method E): 3.28 minutes (5 minutes run). $^1$H NMR (400 MHz, CDCl$_3$) δ 9.13 (s, 1H), 8.71 (d, J=2.5 Hz, 1H), 8.22 (dd, J=8.6, 2.5 Hz, 1H), 8.03 (d, J=8.6 Hz, 1H), 7.67-7.61 (m, 1H), 7.48 (t, J=8.3 Hz, 1H), 7.07-6.89 (m, 2H), 6.53 (d, J=8.8 Hz, 1H), 5.73 (s, 1H) ppm.

Example 174

5-[[2-Fluoro-6-[3-fluoro-2-(trideuteriomethoxy)-4-(trifluoromethoxy)phenoxy]-3-(trifluoromethyl)benzoyl]amino]-N-methyl-pyridine-2-carboxamide (229)

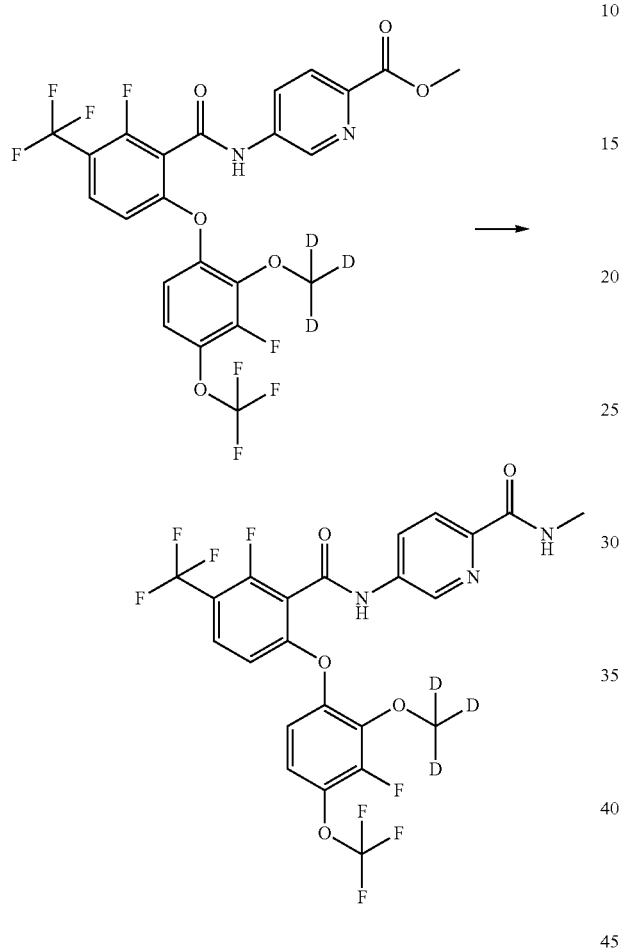

A mixture of methylamine (3.6 mL of 2 M in methanol, 7.20 mmol) and methyl 5-[[2-fluoro-6-[3-fluoro-2-(trideuteriomethoxy)-4-(trifluoromethoxy)phenoxy]-3-(trifluoromethyl)benzoyl]amino]pyridine-2-carboxylate (prepared as described in Example 173, step 2, 126 mg, 0.222 mmol) was stirred at room temperature overnight. The reaction mixture was then concentrated in vacuo and purified by HPLC (37-100% acetonitrile/water/0.1% ammonium hydroxide) to deliver 5-[[2-fluoro-6-[3-fluoro-2-(trideuteriomethoxy)-4-(trifluoromethoxy)phenoxy]-3-(trifluoromethyl)benzoyl]amino]-N-methyl-pyridine-2-carboxamide (11 mg, 8%). ESI-MS m/z calc. 568.11, found 569.2 (M+1)+; 567.3 (M−1)−; retention time (Method E): 3.43 minutes (5 minutes run). $^1$H NMR (500 MHz, DMSO-d6) δ 11.45 (s, 1H), 8.88 (d, J=2.4 Hz, 1H), 8.66 (q, J=5.0 Hz, 1H), 8.29 (dd, J=8.6, 2.5 Hz, 1H), 8.06 (d, J=8.5 Hz, 1H), 7.87 (t, J=8.6 Hz, 1H), 7.40 (tt, J=9.2, 1.3 Hz, 1H), 7.23 (dd, J=9.3, 2.1 Hz, 1H), 6.93 (d, J=8.9 Hz, 1H), 2.82 (d, J=4.8 Hz, 3H) ppm.

Example 175

4-[[6-[3-Fluoro-2-(trideuteriomethoxy)-4-(trifluoromethoxy)phenoxy]-2-methoxy-3-(trifluoromethyl)benzoyl]amino]-5-methyl-pyridine-2-carboxamide (226)

4-[[2-Fluoro-6-[3-fluoro-2-(trideuteriomethoxy)-4-(trifluoromethoxy)phenoxy]-3-(trifluoromethyl)benzoyl]amino]-5-methyl-pyridine-2-carboxamide (227)

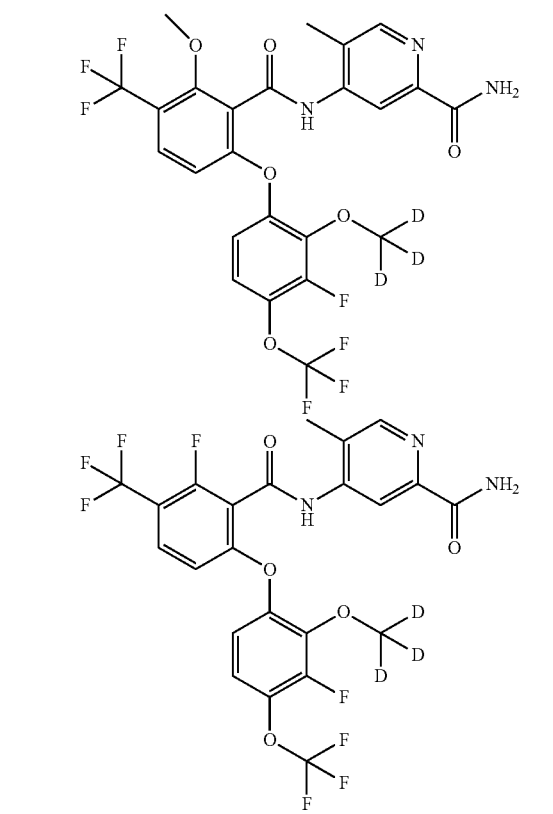

Step 1: N-(2-Bromo-5-methyl-4-pyridyl)-2,6-difluoro-3-(trifluoromethyl)benzamide

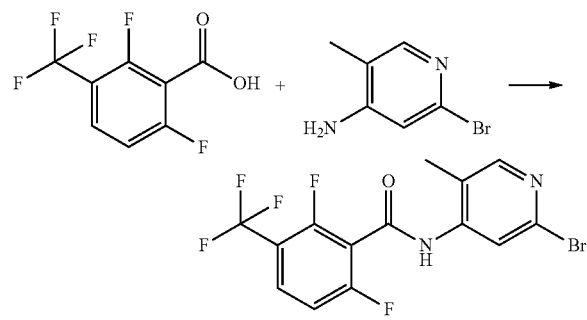

To an ice-cooled solution of 2,6-difluoro-3-(trifluoromethyl)benzoic acid (1 g, 3.1 mmol) in DCM (15 mL) was added DMF (25 μL, 0.32 mmol) followed by dropwise addition of oxalyl chloride (810 μL, 9.29 mmol) and was stirred for 2 hours. The reaction mixture was concentrated in vacuo to afford the acid chloride as a pale yellow oil. To a solution of the acid chloride residue in DCM (15 mL) in an ice bath was added 2-bromo-5-methyl-pyridin-4-amine (HCl salt) (970 mg, 4.34 mmol) followed by triethylamine (2.6 mL, 18.65 mmol). The resulting mixture was stirred and warmed to room temperature over 2 hours. Reaction mixture was quenched with water (10 mL) and extracted with DCM (2×10 mL). The combined organics were dried by phase separation cartridge and concentrated in vacuo to afford a brown waxy solid. The product was purified by silica gel chromatography (0-100% ethyl acetate/hexanes) and triturated with DCM to provide N-(2-bromo-5-methyl-4-pyridyl)-2,6-difluoro-3-(trifluoromethyl)benzamide (320 mg, 26%). ESI-MS m/z calc. 393.97, found 395.0 (M+1)+; 393.0 (M−1)−; retention time (Method F): 0.91 minutes (1.5 minutes run). ¹H NMR (400 MHz, DMSO-d6) δ 10.71 (s, 1H), 8.32-8.26 (m, 1H), 8.13-8.03 (m, 2H), 7.54 (t, J=8.7 Hz, 1H), 2.25-2.16 (m, 3H) ppm.

Step 2: N-(2-Bromo-5-methyl-4-pyridyl)-2-fluoro-6-[3-fluoro-2-(trideuteriomethoxy)-4-(trifluoromethoxy)phenoxy]-3-(trifluoromethyl)benzamide

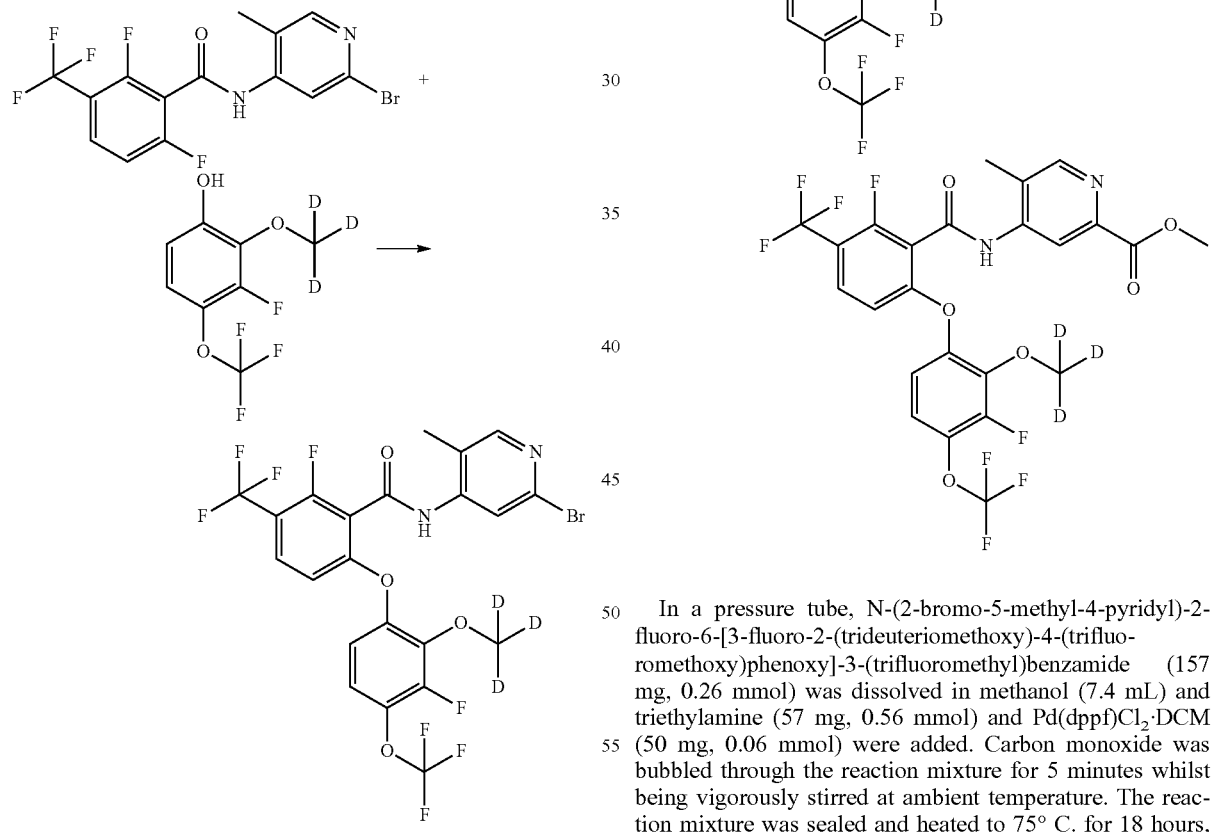

N-(2-Bromo-5-methyl-4-pyridyl)-2,6-difluoro-3-(trifluoromethyl)benzamide (320 mg, 0.81 mmol), cesium carbonate (415 mg, 1.274 mmol) and 3-fluoro-2-(trideuteriomethoxy)-4-(trifluoromethoxy)phenol (prepared as described in Example 169, step 2, 196 mg, 0.86 mmol) were combined in DMF (4.8 mL) and stirred for 10 days at 30° C., then 40° C. for a further 4 days. The mixture was purified by HPLC (37-100% acetonitrile/water/0.1% ammonium hydroxide) and freeze dried to provide N-(2-bromo-5-methyl-4-pyridyl)-2-fluoro-6-[3-fluoro-2-(trideuteriomethoxy)-4-(trifluoromethoxy)phenoxy]-3-(trifluoromethyl)benzamide (157 mg, 32%). ESI-MS m/z calc. 604.26, found 606.0 (M+1)+; 603.9 (M−1)−; retention time (Method F): 1.10 minutes (1.5 minutes run). ¹H NMR (400 MHz, DMSO-d6) δ 10.65 (s, 1H), 8.25 (s, 1H), 8.09 (s, 1H), 7.85 (t, J=8.6 Hz, 1H), 7.42 (t, J=8.4 Hz, 1H), 7.21 (d, J=9.1 Hz, 1H), 6.91 (d, J=8.9 Hz, 1H), 2.21 (s, 3H) ppm.

Step 3: Methyl 4-[[2-fluoro-6-[3-fluoro-2-(trideuteriomethoxy)-4-(trifluoromethoxy)phenoxy]-3-(trifluoromethyl)benzoyl]amino]-5-methyl-pyridine-2-carboxylate

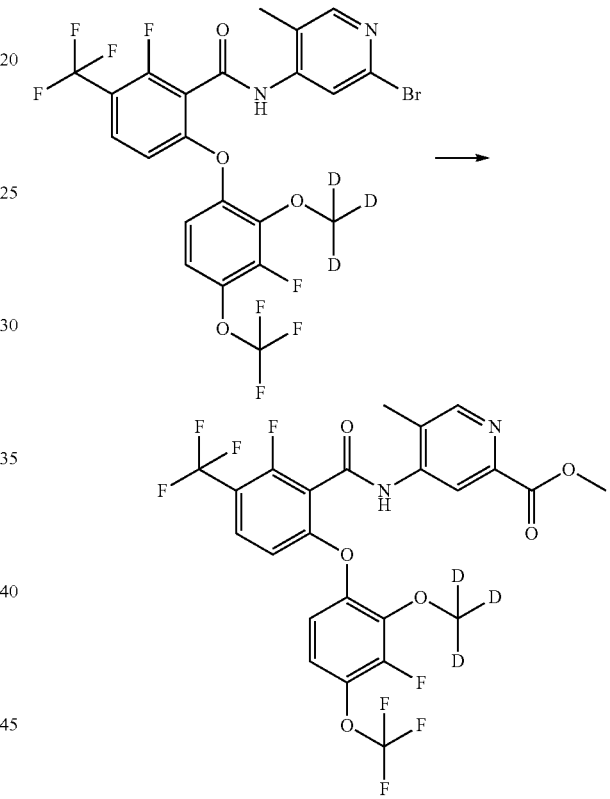

In a pressure tube, N-(2-bromo-5-methyl-4-pyridyl)-2-fluoro-6-[3-fluoro-2-(trideuteriomethoxy)-4-(trifluoromethoxy)phenoxy]-3-(trifluoromethyl)benzamide (157 mg, 0.26 mmol) was dissolved in methanol (7.4 mL) and triethylamine (57 mg, 0.56 mmol) and Pd(dppf)Cl₂·DCM (50 mg, 0.06 mmol) were added. Carbon monoxide was bubbled through the reaction mixture for 5 minutes whilst being vigorously stirred at ambient temperature. The reaction mixture was sealed and heated to 75° C. for 18 hours, then cooled to room temperature before concentrating in vacuo. The product was purified by HPLC (37-100% acetonitrile/water/0.1% ammonium hydroxide) to provide methyl 4-[[2-fluoro-6-[3-fluoro-2-(trideuteriomethoxy)-4-(trifluoromethoxy)phenoxy]-3-(trifluoromethyl)benzoyl]amino]-5-methyl-pyridine-2-carboxylate (86 mg, 57%) as a white solid. ESI-MS m/z calc. 583.11, found 584.2 (M+1)+; retention time (Method F): 1.06 minutes (1.5 minutes run). ¹H NMR (400 MHz, DMSO-d6) δ 10.70 (s, 1H), 8.60-8.49

(m, 2H), 7.87 (t, J=8.6 Hz, 1H), 7.42 (ddd, J=9.4, 8.1, 1.4 Hz, 1H), 7.22 (dd, J=9.3, 2.1 Hz, 1H), 6.93 (d, J=8.8 Hz, 1H), 3.88 (s, 3H), 2.33 (s, 3H) ppm.

Step 4: 4-[[2-Fluoro-6-[3-fluoro-2-(trideuteriomethoxy)-4-(trifluoromethoxy)phenoxy]-3-(trifluoromethyl)benzoyl]amino]-5-methyl-pyridine-2-carboxamide (227) & 4-[[6-[3-Fluoro-2-(trideuteriomethoxy)-4-(trifluoromethoxy)phenoxy]-2-methoxy-3-(trifluoromethyl)benzoyl]amino]-5-methyl-pyridine-2-carboxamide (226)

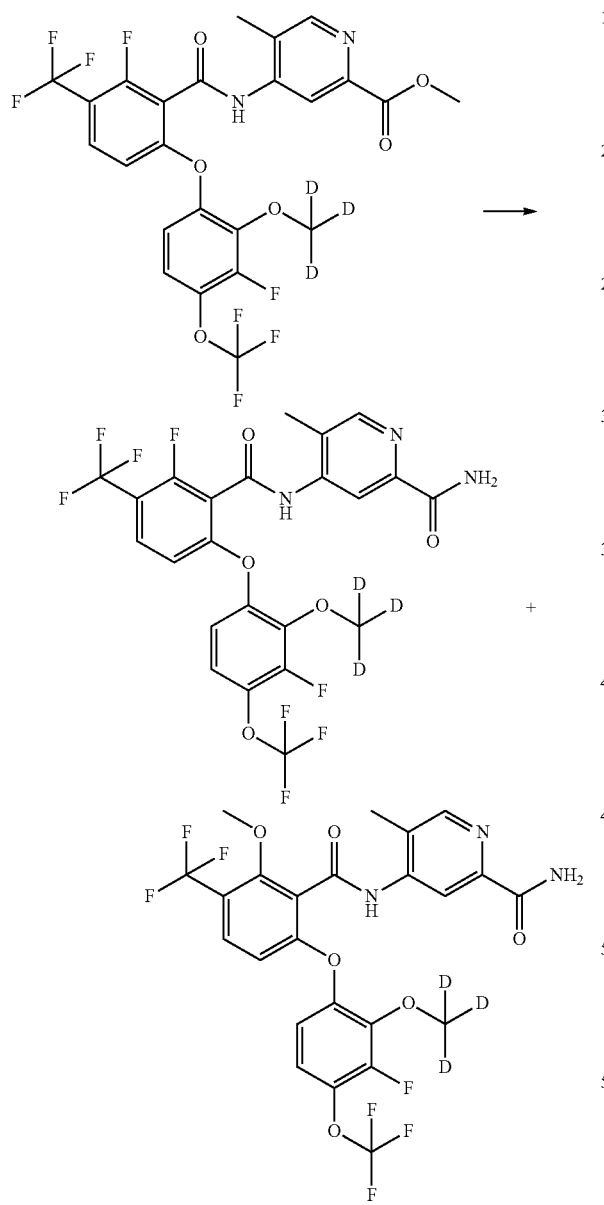

Methyl 4-[[2-fluoro-6-[3-fluoro-2-(trideuteriomethoxy)-4-(trifluoromethoxy)phenoxy]-3-(trifluoromethyl)benzoyl]amino]-5-methyl-pyridine-2-carboxylate (86 mg, 0.15 mmol) was dissolved in ammonia (4 mL of 7 M in methanol, 28 mmol) and stirred at 40° C. over the weekend. Additional ammonia (2 mL of 7 M in methanol, 14 mmol) was added and the mixture was heated to 60° C. in a sealed tube for a further 24 hours. The reaction mixture was concentrated in vacuo and purified by SFC ((R,R)-Whelk-O1 column, 80% CO2/20% methanol with 20 mM ammonia) to afford: 4-[[2-fluoro-6-[3-fluoro-2-(trideuteriomethoxy)-4-(trifluoromethoxy)phenoxy]-3-(trifluoromethyl)benzoyl]amino]-5-methyl-pyridine-2-carboxamide (227, 30 mg, 36%). ESI-MS m/z calc. 568.11, found 569.2 (M+1)+; 567.1 (M−1)−; retention time (Method E): 3.37 minutes (5 minutes run). $^1$H NMR (400 MHz, CD$_3$OD) δ 8.52 (s, 1H), 8.41 (s, 1H), 7.60 (t, J=8.4 Hz, 1H), 7.15-7.05 (m, 1H), 7.03 (dd, J=9.2, 2.0 Hz, 1H), 6.62 (d, J=8.8 Hz, 1H), 2.36 (s, 3H) ppm, and 4-[[6-[3-Fluoro-2-(trideuteriomethoxy)-4-(trifluoromethoxy)phenoxy]-2-methoxy-3-(trifluoromethyl)benzoyl]amino]-5-methyl-pyridine-2-carboxamide (226.16 mg, 19%). ESI-MS m/z calc. 580.13, found 581.2 (M+1)+; 579.1; retention time (Method E): 3.39 minutes (5 minutes run). $^1$H NMR (400 MHz, CD$_3$OD) δ 8.60 (s, 1H), 8.38 (t, J=0.8 Hz, 1H), 7.57 (d, J=8.9 Hz, 1H), 7.07 (ddq, J=8.9, 7.6, 1.2 Hz, 1H), 6.98 (dd, J=9.2, 2.1 Hz, 1H), 6.55 (d, J=8.8 Hz, 1H), 4.01 (s, 3H), 2.34 (s, 3H) ppm.

Example 176

4-[[3-Chloro-2-fluoro-6-[3-fluoro-2-(trideuteriomethoxy)-4-(trifluoromethoxy)phenoxy]benzoyl]amino]pyridine-2-carboxamide (220)

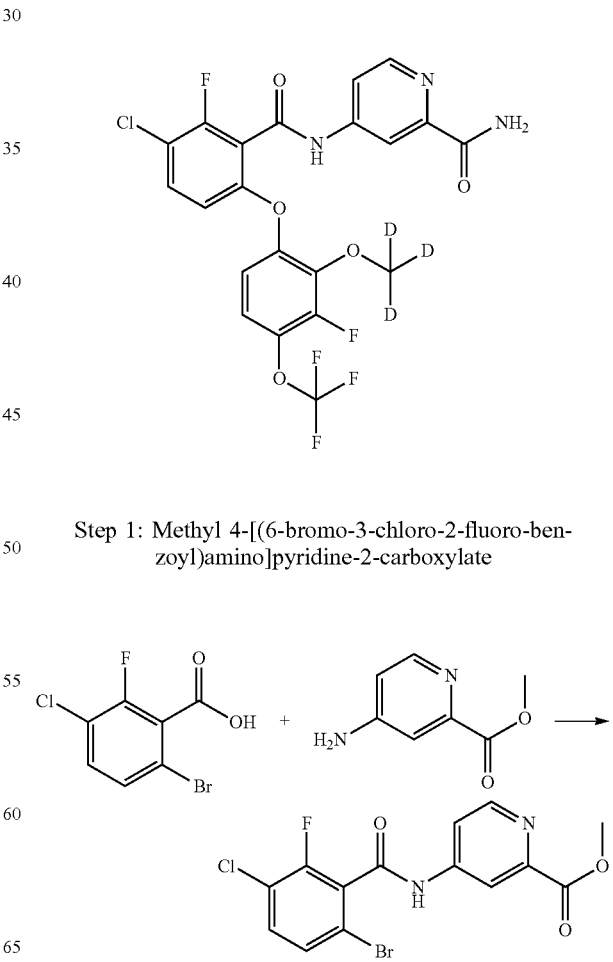

Step 1: Methyl 4-[(6-bromo-3-chloro-2-fluoro-benzoyl)amino]pyridine-2-carboxylate To an ice-cooled solution of 6-bromo-3-chloro-2-fluoro-benzoic acid (1.08 g, 4.27 mmol) in DCM (38 mL) was added DMF (89 µL, 1.15 mmol) followed by dropwise addition of oxalyl chloride (1.15 mL, 13.16 mmol) and was stirred for 1 hour. The reaction mixture was concentrated in vacuo to afford the acid chloride as a white solid. A solution of the acid chloride residue in DCM (38 mL) was then added dropwise to an ice bath cooled solution of methyl 4-amino-pyridine-2-carboxylate (714 mg, 4.69 mmol) and N-ethyl-N-isopropyl-propan-2-amine (4.5 mL, 25.84 mmol). The resulting mixture was stirred at room temperature for 3 hours. The solvent was evaporated and the residue was separated between 2 N NaOH and ethyl acetate. The organic layer was washed with 1 M citric acid, then brine, dried over MgSO₄, filtered and evaporated to provide a crude residue, which was purified by HPLC (26-100% acetonitrile/0.1% ammonium hydroxide) to provide methyl 4-[(6-bromo-3-chloro-2-fluoro-benzoyl)amino]pyridine-2-carboxylate (256 mg, 15%) as a white solid. $^1$H NMR (500 MHz, DMSO-d6) δ 8.67 (dd, J=5.4, 0.6 Hz, 1H), 8.40 (d, J=2.1 Hz, 1H), 7.82 (dd, J=5.4, 2.1 Hz, 1H), 7.76 (dd, J=8.7, 7.8 Hz, 1H), 7.69 (dd, J=8.7, 1.2 Hz, 1H), 3.90 (s, 3H) ppm.

Step 2: Methyl 4-[[3-chloro-2-fluoro-6-[3-fluoro-2-(trideuteriomethoxy)-4-(trifluoromethoxy)phenoxy]benzoyl]amino]pyridine-2-carboxylate

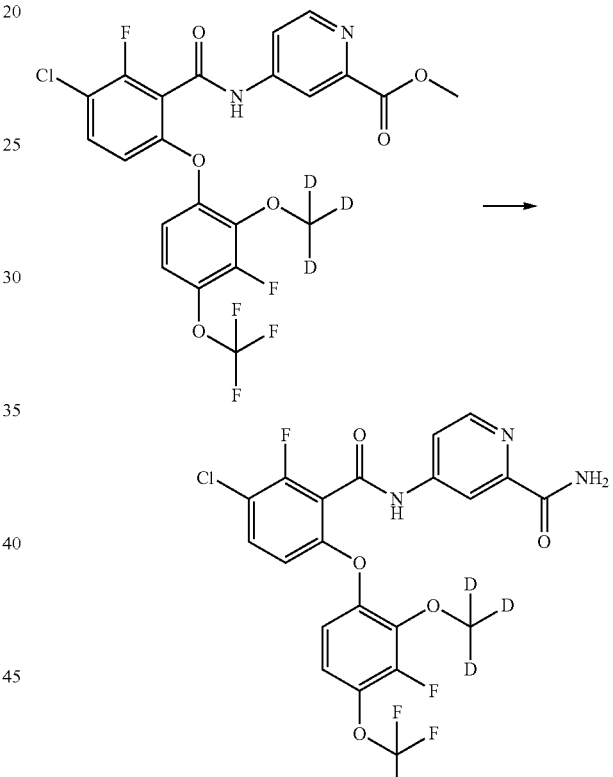

To a mixture of 3-fluoro-2-(trideuteriomethoxy)-4-(trifluoromethoxy)phenol (165 mg, 0.72 mmol), methyl 4-[(6-bromo-3-chloro-2-fluoro-benzoyl)amino]pyridine-2-carboxylate (256 mg, 0.66 mmol) and cesium carbonate (510 mg, 1.565 mmol) in toluene (5 mL) was added copper (I) iodide (45 mg, 0.23 mmol) and the resulting mixture was heated at 100° C. for 4 hours. The mixture was cooled to room temperature and partitioned between 1 M citric acid and ethyl acetate. The organics were washed with water (20 mL), brine (2×20 mL), dried over MgSO₄ and concentrated. The crude product was purified by HPLC (37-100% acetonitrile/0.1% ammonium hydroxide) to afford methyl 4-[[3-chloro-2-fluoro-6-[3-fluoro-2-(trideuteriomethoxy)-4-(trifluoromethoxy)phenoxy]benzoyl]amino]pyridine-2-carboxylate (38 mg, 10%). ESI-MS m/z calc. 535.06, found 535.9 (M+1)+; Retention time (Method F): 1.02 minutes (1.5 minutes run).

Step 3: 4-[[3-Chloro-2-fluoro-6-[3-fluoro-2-(trideuteriomethoxy)-4-(trifluoromethoxy)phenoxy]benzoyl]amino]pyridine-2-carboxamide (220)

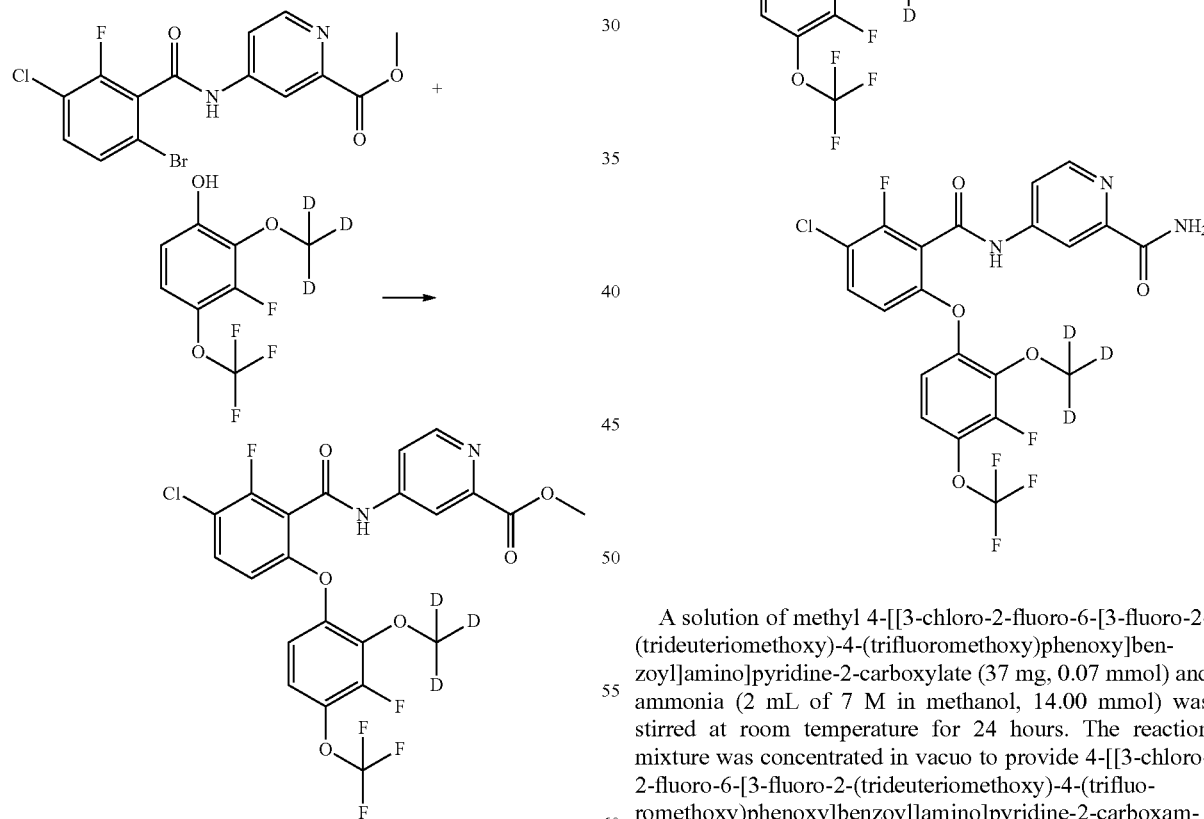

A solution of methyl 4-[[3-chloro-2-fluoro-6-[3-fluoro-2-(trideuteriomethoxy)-4-(trifluoromethoxy)phenoxy]benzoyl]amino]pyridine-2-carboxylate (37 mg, 0.07 mmol) and ammonia (2 mL of 7 M in methanol, 14.00 mmol) was stirred at room temperature for 24 hours. The reaction mixture was concentrated in vacuo to provide 4-[[3-chloro-2-fluoro-6-[3-fluoro-2-(trideuteriomethoxy)-4-(trifluoromethoxy)phenoxy]benzoyl]amino]pyridine-2-carboxamide (35 mg, 92%). ESI-MS m/z calc. 520.07, found 521.2 (M+1)+; Retention time (Method E): 3.34 minutes (5 minutes run). $^1$H NMR (500 MHz, CDCl₃) δ 9.72 (br s, 1H), 8.54 (d, J=5.6 Hz, 1H), 8.46 (d, J=5.5 Hz, 1H), 8.16 (br s, 1H), 7.88 (br s, 1H), 7.43 (t, J=8.4 Hz, 1H), 7.04 (t, J=8.3 Hz, 1H), 7.00-6.94 (m, 1H), 6.59 (d, J=8.9 Hz, 1H), 5.33 (d, J=15.0 Hz, 1H) ppm.

Example 177

4-[[4-Chloro-2-fluoro-6-[3-fluoro-2-(trideuteriomethoxy)-4-(trifluoromethoxy)phenoxy]-3-(trideuteriomethyl)benzoyl]amino]pyridine-2-carboxamide (222)

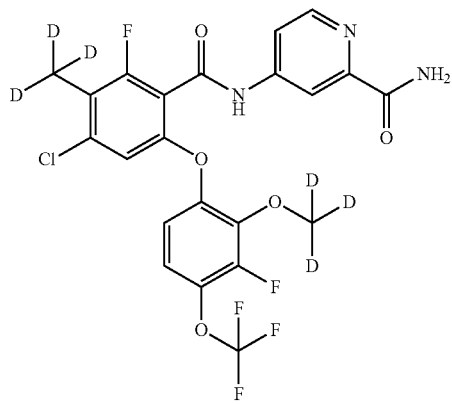 [SMILES: [2H]C([2H])([2H])Oc1c(Oc2cc(Cl)c(C([2H])([2H])[2H])c(F)c2C(=O)Nc2ccnc(C(N)=O)c2)ccc(OC(F)(F)F)c1F]

Step 1: Methyl 4-chloro-2,6-difluoro-benzoate

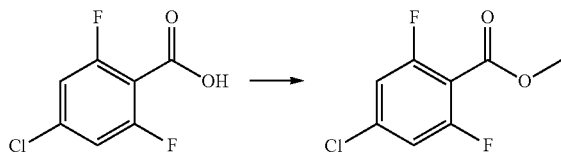

Iodomethane (1.49 mL, 23.93 mmol) was added to a stirred suspension of 4-chloro-2,6-difluoro-benzoic acid (4 g, 20.77 mmol) and cesium carbonate (7.45 g, 22.87 mmol) in DMF (40 mL) and the reaction mixture was stirred at ambient temperature for 18 hours. The mixture was partitioned between water and diethyl ether. The aqueous layer was further extracted with diethyl ether (×2) and the combined organic layers were washed with brine, dried over MgSO$_4$, filtered and evaporated to give methyl 4-chloro-2,6-difluoro-benzoate (4.33 g, 100%). $^1$H NMR (500 MHz, DMSO-d6) δ 7.59-7.53 (m, 2H), 3.90 (s, 3H) ppm.

Step 2: Methyl 4-chloro-2-fluoro-6-[3-fluoro-2-(trideuteriomethoxy)-4-(trifluoromethoxy)phenoxy]benzoate

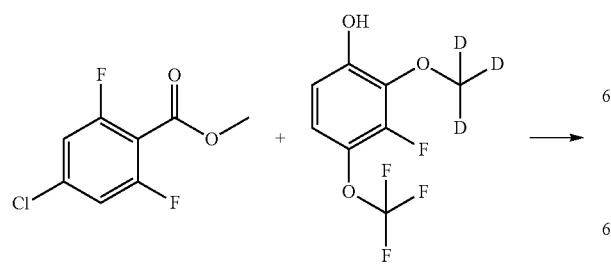

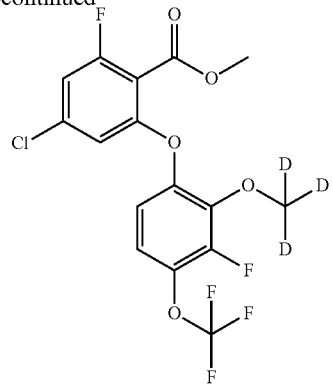

A mixture of cesium carbonate (6.4 g, 19.64 mmol), 3-fluoro-2-(trideuteriomethoxy)-4-(trifluoromethoxy)phenol (3.11 g, 13.57 mmol) and methyl 4-chloro-2,6-difluorobenzoate (2.67 g, 12.92 mmol) in DMF (50 mL) was stirred at ambient temperature for 2 hours, then at 70° C. for 16 hours. The reaction was diluted with ethyl acetate and washed with water (×3) and brine (×2). The organic layer was dried over MgSO$_4$, filtered and concentrated in vacuo to afford methyl 4-chloro-2-fluoro-6-[3-fluoro-2-(trideuteriomethoxy)-4-(trifluoromethoxy)phenoxy]benzoate (4.88 g, 91%) as a yellow oil. ESI-MS m/z calc. 415.03, found 416.0 (M+1)+; Retention time (Method F): 1.14 minutes (1.5 minutes run).

Step 3: Methyl 4-chloro-2-fluoro-6-[3-fluoro-2-(trideuteriomethoxy)-4-(trifluoromethoxy)phenoxy]-3-(trideuteriomethyl)benzoate

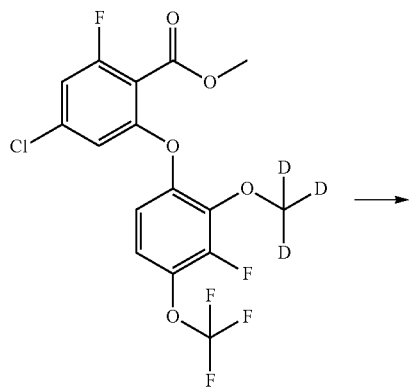

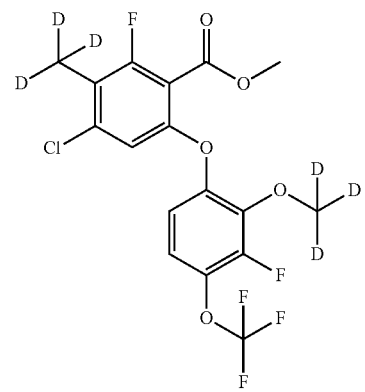

LDA (340 μL of 2 M solution in THF, 0.68 mmol) was added dropwise to a solution of methyl 4-chloro-2-fluoro-6-[3-fluoro-2-(trideuteriomethoxy)-4-(trifluoromethoxy)phenoxy]benzoate (258 mg, 0.62 mmol) in THF (3 mL) at −78° C. The reaction was stirred at this temperature for 10 minutes then trideuterio(iodo)methane (60 μL, 0.94 mmol) was added. The mixture was stirred at −78° C. for 30 minutes then allowed to warm to room temperature. An additional portion of LDA (340 μL of 2 M, 0.68 mmol) was added at −78° C. and the mixture was stirred for 10 minutes at this temperature. Additional trideuterio(iodo)methane (60 μL, 0.94 mmol) was then added and the mixture was stirred at −78° C. for 30 minutes then allowed to warm to room temperature and stirred for 30 minutes. The reaction was quenched by the addition of water and the mixture was extracted with ethyl acetate (×3). The combined organic extracts were dried over MgSO$_4$, filtered and concentrated in vacuo to afford methyl 4-chloro-2-fluoro-6-[3-fluoro-2-(trideuteriomethoxy)-4-(trifluoromethoxy)phenoxy]-3-(trideuteriomethyl)benzoate (277 mg, 100%). $^1$H NMR (500 MHz, CDCl$_3$) δ 6.92 (ddt, J=7.9, 6.5, 1.3 Hz, 1H), 6.73 (dd, J=9.2, 2.3 Hz, 1H), 6.53 (d, J=1.8 Hz, 1H), 3.81 (s, 3H) ppm.

Step 4: 4-Chloro-2-fluoro-6-[3-fluoro-2-(trideuteriomethoxy)-4-(trifluoromethoxy)phenoxy]-3-(trideuteriomethyl)benzoic acid

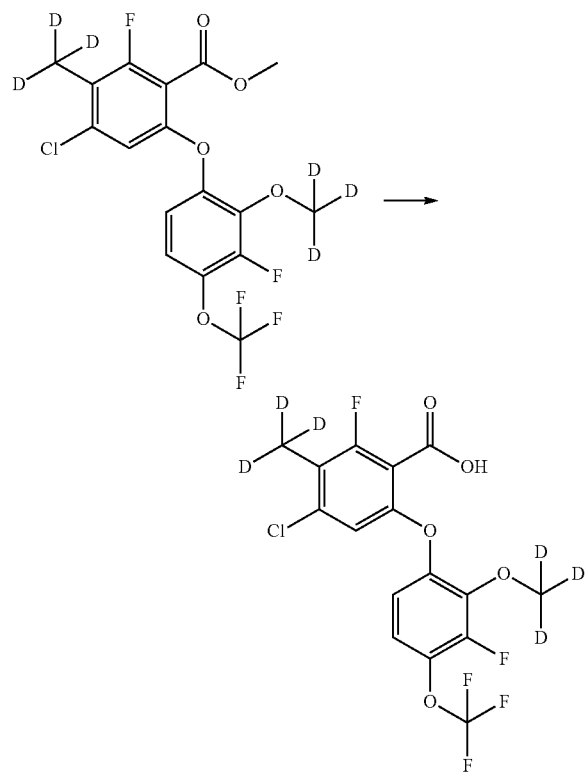

To a slurry of methyl 4-chloro-2-fluoro-6-[3-fluoro-2-(trideuteriomethoxy)-4-(trifluoromethoxy)phenoxy]-3-(trideuteriomethyl)benzoate (277 mg, 0.64 mmol) in methanol (7 mL) and was added NaOH (3.1 mL of 2 M, 6.2 mmol) and the reaction mixture was stirred for 24 hours at 50° C. The reaction was cooled to ambient temperature and the solvent was removed in vacuo. The residue was taken up in water and acidified with 2 M HCL. The mixture was extracted with ethyl acetate (×3) and the combined organic extracts were dried over MgSO$_4$, filtered and concentrated in vacuo to afford 4-chloro-2-fluoro-6-[3-fluoro-2-(trideuteriomethoxy)-4-(trifluoromethoxy)phenoxy]-3-(trideuteriomethyl)benzoic acid (310 mg, 100%) as a yellow solid. ESI-MS m/z calc. 418.05, found 416.9 (M−1)−; Retention time (Method F). 0.76 minutes (1.5 minutes run).

Step 5: Methyl 4-[[4-chloro-2-fluoro-6-[3-fluoro-2-(trideuteriomethoxy)-4-(trifluoromethoxy)phenoxy]-3-(trideuteriomethyl)benzoyl]amino]pyridine-2-carboxylate

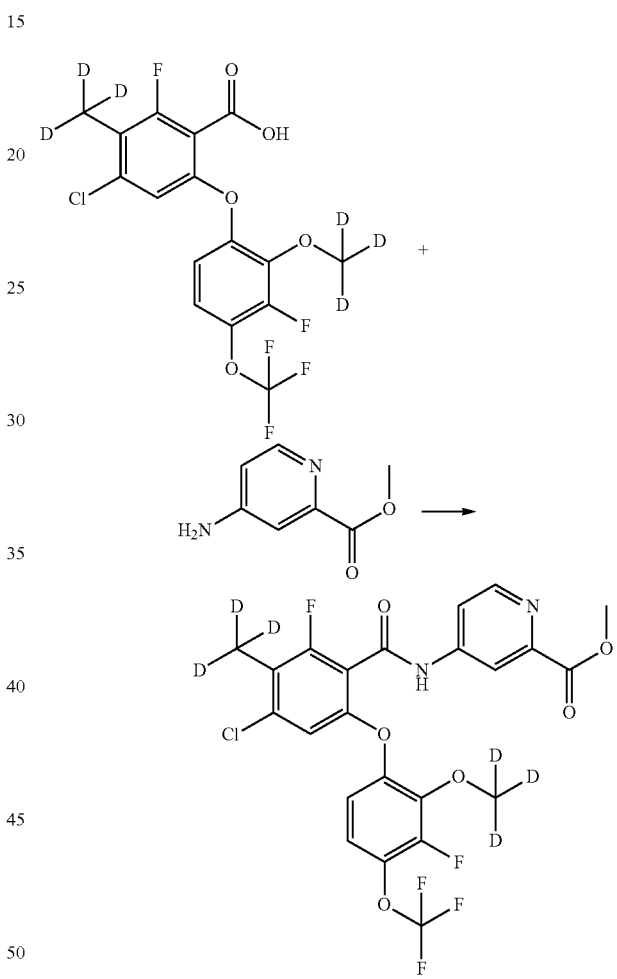

To an ice-cooled solution of 4-chloro-2-fluoro-6-[3-fluoro-2-(trideuteriomethoxy)-4-(trifluoromethoxy)phenoxy]-3-(trideuteriomethyl)benzoic acid (300 mg, 0.71 mmol) in DCM (10 mL) was added DMF (15 μL, 0.19 mmol) followed by dropwise addition of oxalyl chloride (193 μL, 2.21 mmol). The reaction was stirred for 1 hour before concentrating in vacuo to afford the acid chloride. A solution of the acid chloride residue in DCM (10 mL) was then added dropwise to an ice-cooled solution of methyl 4-aminopyridine-2-carboxylate (130 mg, 0.85 mmol) and N-ethyl-N-isopropyl-propan-2-amine (740 μL, 4.28 mmol). The resulting mixture was stirred at room temperature for 3 hours. The solvent was evaporated and the residue was partitioned with 2 N NaOH and ethyl acetate. The organic layer was washed with 1 M citric acid, brine, dried over MgSO₄, filtered and concentrated in vacuo to provide a crude residue, which was purified by HPLC (37-100% acetonitrile/0.1% ammonium hydroxide) to provide methyl 4-[[4-chloro-2-fluoro-6-[3-fluoro-2-(trideuteriomethoxy)-4-(trifluoromethoxy)phenoxy]-3-(trideuteriomethyl)benzoyl]amino]pyridine-2-carboxylate (70 mg, 18%) as a white solid. ESI-MS m/z calc. 552.09, found 553.2 (M+1)+; Retention time (Method F): 1.07 minutes (1.5 minute run).

Step 6: 4-[[4-Chloro-2-fluoro-6-[3-fluoro-2-(trideuteriomethoxy)-4-(trifluoromethoxy)phenoxy]-3-(trideuteriomethyl)benzoyl]amino]pyridine-2-carboxamide (222)

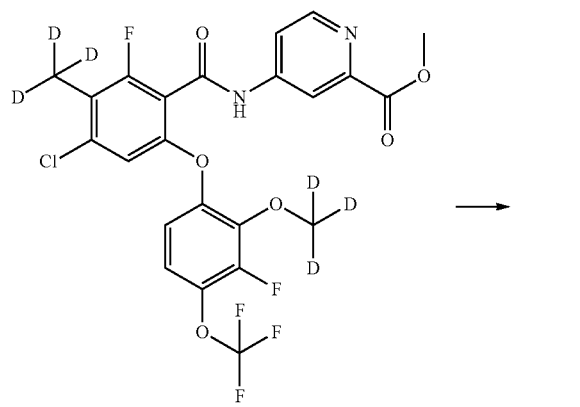

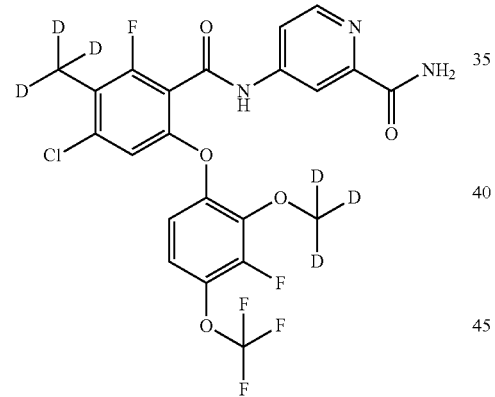

A solution of methyl 4-[[4-chloro-2-fluoro-6-[3-fluoro-2-(trideuteriomethoxy)-4-(trifluoromethoxy)phenoxy]-3-(trideuteriomethyl)benzoyl]amino]pyridine-2-carboxylate (70 mg, 0.126 mmol) and ammonia (4 mL of 7 M in methanol, 28.00 mmol) was stirred at room temperature for 24 hours. The reaction mixture was concentrated in vacuo to provide a crude material which was purified by HPLC (37-100% acetonitrile/0.1% ammonium hydroxide) to afford 4-[[4-chloro-2-fluoro-6-[3-fluoro-2-(trideuteriomethoxy)-4-(trifluoromethoxy)phenoxy]-3-(trideuteriomethyl)benzoyl]amino]pyridine-2-carboxamide (42 mg, 61%). ESI-MS m/z calc. 537.09, found 538.2 (M+1)+; Retention time (Method E): 3.38 minutes (5 minutes run). ¹H NMR (500 MHz, DMSO-d6) δ 11.32 (s, 1H), 8.53 (d, J=5.5 Hz, 1H), 8.29 (d, J=2.1 Hz, 1H), 8.08 (d, J=2.9 Hz, 1H), 7.78 (dd, J=5.5, 2.2 Hz, 1H), 7.64 (s, 1H), 7.32 (ddd, J=9.4, 8.0, 1.2 Hz, 1H), 7.09-7.01 (m, 2H) ppm.

Example 178

4-[[4-Chloro-3-(difluoromethyl)-6-[3-fluoro-2-(trideuteriomethoxy)-4-(trifluoromethoxy)phenoxy]-2-methoxy-benzoyl]amino]pyridine-2-carboxamide (233)

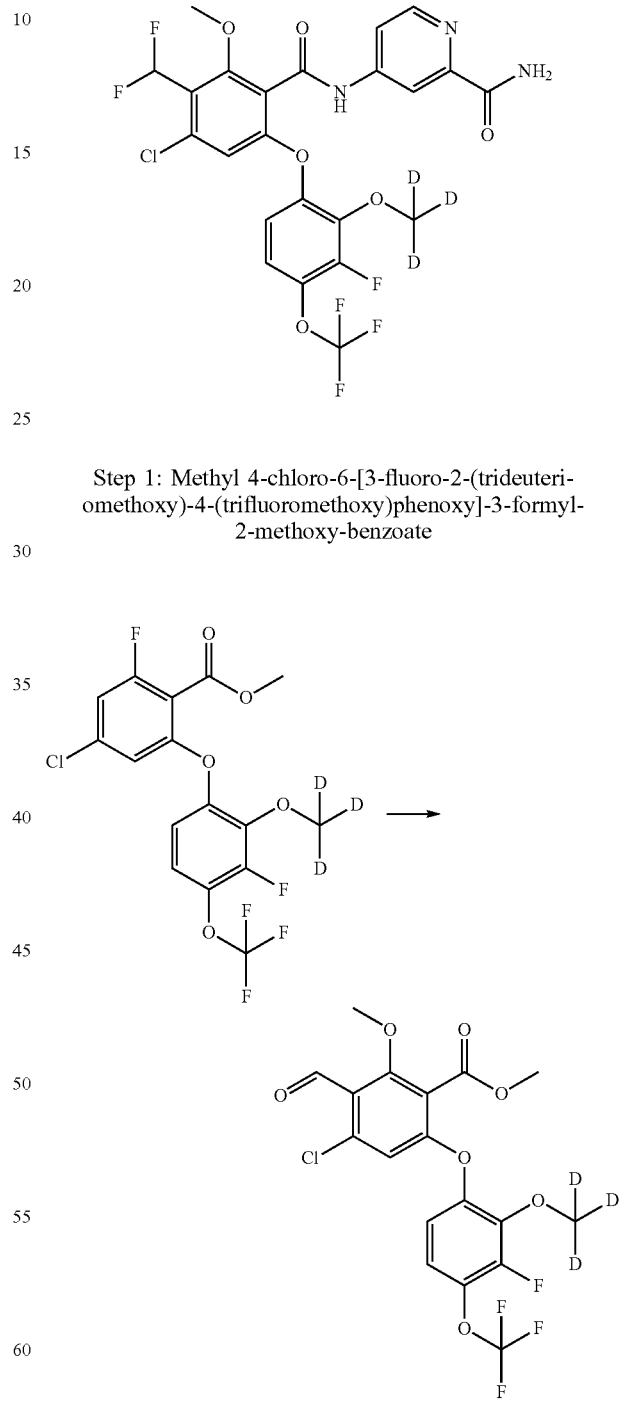

Step 1: Methyl 4-chloro-6-[3-fluoro-2-(trideuteriomethoxy)-4-(trifluoromethoxy)phenoxy]-3-formyl-2-methoxy-benzoate LDA (2.4 mL of 2 M, 4.80 mmol) was added dropwise to a solution of methyl 4-chloro-2-fluoro-6-[3-fluoro-2-(trideuteriomethoxy)-4-(trifluoromethoxy)phenoxy]benzoate (prepared as describe in Example 177, step 2 above, 11.33 g, 3.19 mmol) in THF (15 mL) at −78° C. The reaction was stirred at this temperature for 30 minutes then methyl formate (2 mL, 32.44 mmol) was added. The mixture was stirred at −78° C. for 30 minutes then allowed to warm to ambient temperature over 30 minutes. The reaction was quenched by the addition of water and extracted with ethyl acetate (×3). The combined organic extracts were dried over MgSO₄, filtered and concentrated in vacuo to afford methyl 4-chloro-6-[3-fluoro-2-(trideuteriomethoxy)-4-(trifluoromethoxy)phenoxy]-3-formyl-2-methoxy-benzoate (1.60 g, 100%). ESI-MS m/z calc. 455.05, found 456.0 (M+1)+; Retention time (Method F): 1.05 minutes (1.5 minutes run).

Step 2: Methyl 4-chloro-3-(difluoromethyl)-6-[3-fluoro-2-(trideuteriomethoxy)-4-(trifluoromethoxy)phenoxy]-2-methoxy-benzoate

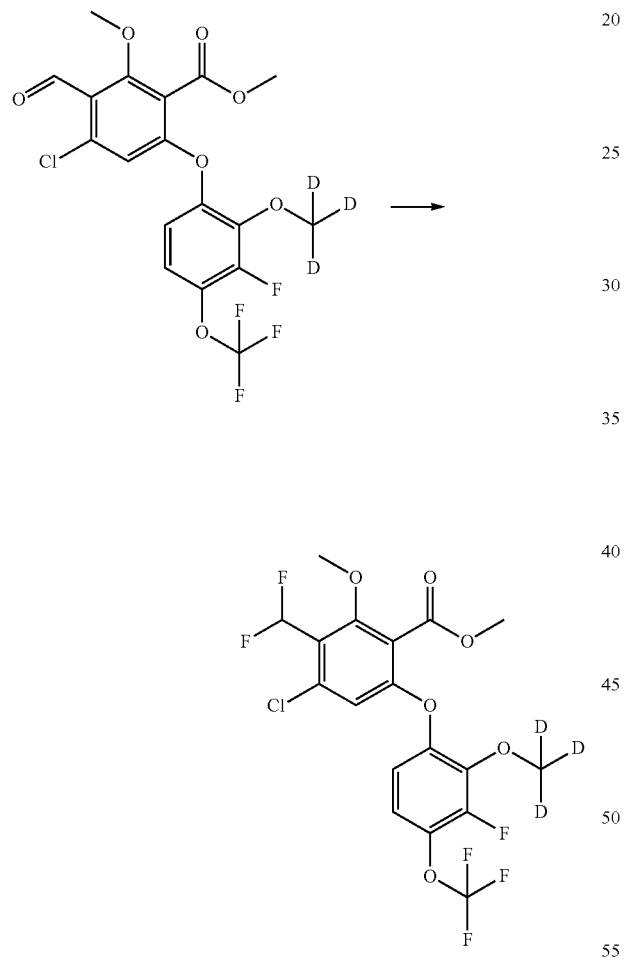

Deoxo-fluor (3.55 g, 16.03 mmol) in DCM (7 mL) was added to a solution of methyl 4-chloro-6-[3-fluoro-2-(trideuteriomethoxy)-4-(trifluoromethoxy)phenoxy]-3-formyl-2-methoxy-benzoate (1.22 g, 2.68 mmol) in DCM (9 mL). The reaction mixture was stirred at room temperature for 18 hours. The reaction was quenched by pouring onto a saturated solution of NaHCO₃ then stirred for 30 minutes at room temperature. The layers were separated and the aqueous layer extracted with DCM (×2). The organic extracts were combined and washed with water then brine to afford crude methyl 4-chloro-3-(difluoromethyl)-6-[3-fluoro-2-(trideuteriomethoxy)-4-(trifluoromethoxy)phenoxy]-2-methoxy-benzoate (1.4 g, 110%) as an orange oil. ESI-MS m/z calc. 477.05, found 478.0 (M+1)+; Retention time (Method F): 1.14 minutes (1.5 minutes run).

Step 3: 4-Chloro-3-(difluoromethyl)-6-[3-fluoro-2-(trideuteriomethoxy)-4-(trifluoromethoxy)phenoxy]-2-methoxy-benzoic acid

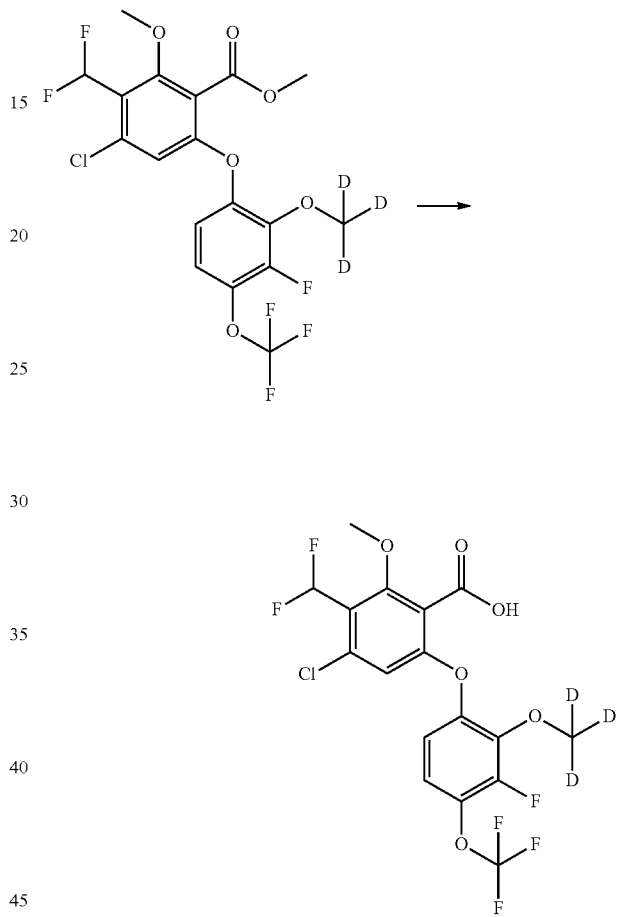

To a solution of methyl 4-chloro-3-(difluoromethyl)-6-[3-fluoro-2-(trideuteriomethoxy)-4-(trifluoromethoxy)phenoxy]-2-methoxy-benzoate (1.28 g, 2.675 mmol) in methanol (30 mL) was added NaOH (13 mL of 2 M, 26.0 mmol) and the reaction mixture was stirred for 4 hours at 50° C. The reaction was cooled to room temperature and the solvent was removed in vacuo. The residue was taken up in water and acidified with 2 M HCl. The mixture was extracted with ethyl acetate (×3) and the combined organic extracts were dried over MgSO₄, filtered and concentrated in vacuo to give the crude 4-chloro-3-(difluoromethyl)-6-[3-fluoro-2-(trideuteriomethoxy)-4-(trifluoromethoxy)phenoxy]-2-methoxy-benzoic acid (1.21 g, 98%) as an orange oil. ESI-MS m/z calc. 463.03, found 464.0 (M+1)+; Retention time (Method F): 0.78 minutes (1.5 minutes run).

Step 4: Methyl 4-[[4-chloro-3-(difluoromethyl)-6-[3-fluoro-2-(trideuteriomethoxy)-4-(trifluoromethoxy)phenoxy]-2-methoxy-benzoyl]amino]pyridine-2-carboxylate

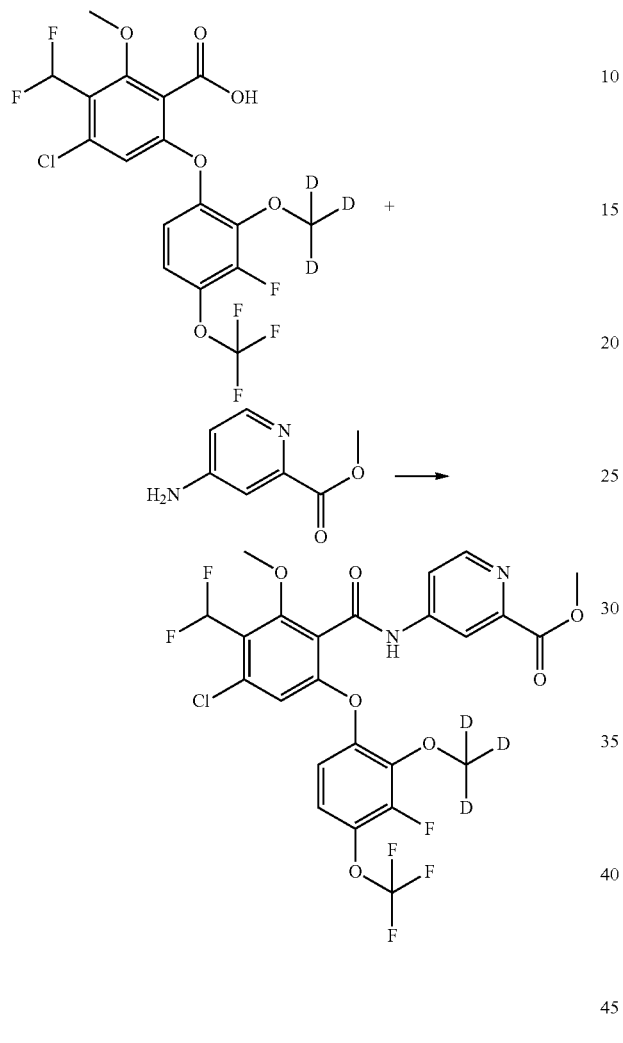

To an ice-cooled solution of 4-chloro-3-(difluoromethyl)-6-[3-fluoro-2-(trideuteriomethoxy)-4-(trifluoromethoxy)phenoxy]-2-methoxy-benzoic acid (402 mg, 0.87 mmol) in DCM (13 mL) was added DMF (18 μL, 0.23 mmol) followed by dropwise addition of oxalyl chloride (235 μL, 2.68 mmol) and the mixture was stirred for 1 hour. The reaction mixture was concentrated in vacuo to afford the acid chloride. A solution of this acid chloride residue in DCM (13 mL) was then added dropwise to an ice bath cooled solution of methyl 4-aminopyridine-2-carboxylate (162 mg, 1.07 mmol) and N-ethyl-N-isopropyl-propan-2-amine (900 μL, 5.18 mmol). The resulting mixture was stirred at room temperature for 3 hours. The solvent was evaporated and the residue was purified by HPLC (37-100% acetonitrile/0.1% ammonium hydroxide) to provide methyl 4-[[4-chloro-3-(difluoromethyl)-6-[3-fluoro-2-(trideuteriomethoxy)-4-(trifluoromethoxy)phenoxy]-2-methoxy-benzoyl]amino]pyridine-2-carboxylate (162 mg, 31%) as a white solid. ESI-MS m/z calc. 597.08, found 598.1 (M+1)+; Retention time (Method F): 1.05 minutes (1.5 minutes run).

Step 5: 4-[[4-Chloro-3-(difluoromethyl)-6-[3-fluoro-2-(trideuteriomethoxy)-4-(trifluoromethoxy)phenoxy]-2-methoxy-benzoyl]amino]pyridine-2-carboxamide (233)

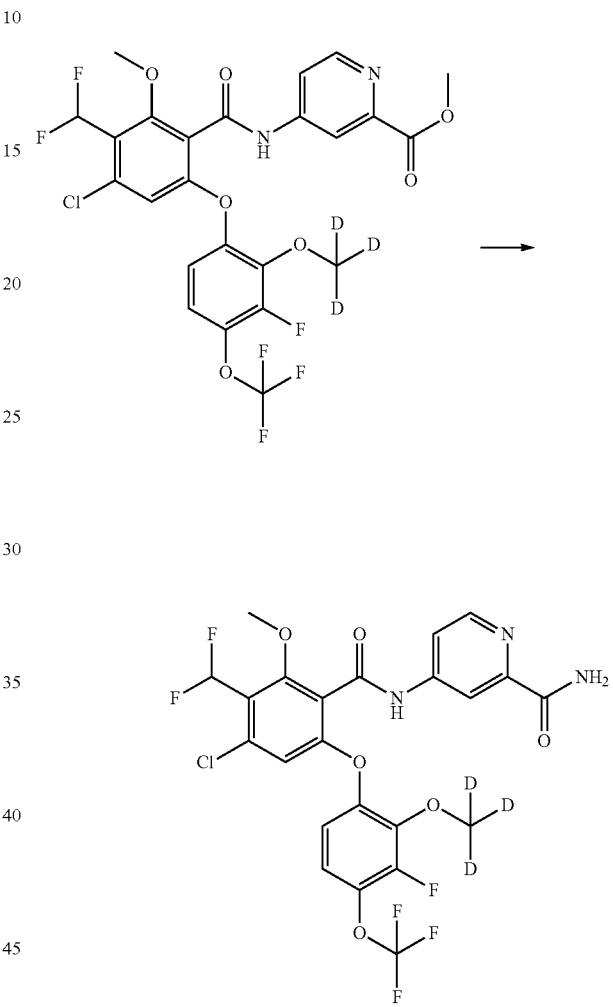

A solution of methyl 4-[[4-chloro-3-(difluoromethyl)-6-[3-fluoro-2-(trideuteriomethoxy)-4-(trifluoromethoxy)phenoxy]-2-methoxy-benzoyl]amino]pyridine-2-carboxylate (162.3 mg, 0.2715 mmol) and ammonia (8.8 mL of 7 M in methanol, 61.6 mmol) was stirred at ambient temperature for 24 hours. The reaction mixture was concentrated in vacuo to provide a crude material which was purified by HPLC (37-100% acetonitrile/0.1% ammonium hydroxide) to afford 4-[[4-chloro-3-(difluoromethyl)-6-[3-fluoro-2-(trideuteriomethoxy)-4-(trifluoromethoxy)phenoxy]-2-methoxy-benzoyl]amino]pyridine-2-carboxamide (74 mg, 44%). ESI-MS m/z calc. 582.08, found 583.2 (M+1)+; Retention time (Method E): 3.39 minutes (5 minutes run). $^1$H NMR (500 MHz, DMSO-d6) δ 11.30 (s, 1H), 8.54 (m, 1H), 8.33 (d, J=2.1 Hz, 1H), 8.09 (d, J=2.7 Hz, 1H), 7.80 (dd, J=5.5, 2.2 Hz, 1H), 7.65 (d, J=2.9 Hz, 1H), 7.36 (m, 1H), 7.28 (t, J=52.7 Hz, 1H), 7.15 (dd, J=9.3, 2.1 Hz, 1H), 6.99 (s, 1H), 3.91 (s, 3H) ppm.

Example 179

4-[[2-Fluoro-6-[3-fluoro-2-(trideuteriomethoxy)-4-(trifluoromethoxy)phenoxy]-4-(trifluoromethyl)benzoyl]amino]pyridine-2-carboxamide (223)

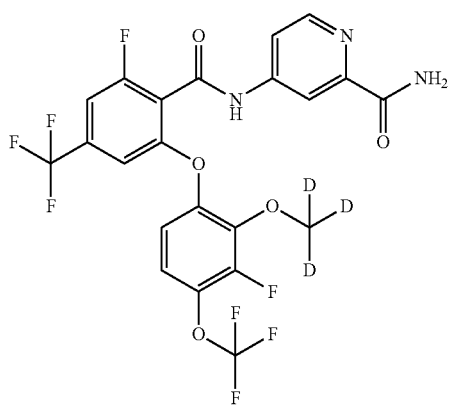 [SMILES: [2H]C([2H])([2H])Oc1c(Oc2cc(C(F)(F)F)cc(F)c2C(=O)Nc2ccnc(C(N)=O)c2)ccc(OC(F)(F)F)c1F]

Step 1: Methyl 4-[[2,6-difluoro-4-(trifluoromethyl)benzoyl]amino]pyridine-2-carboxylate

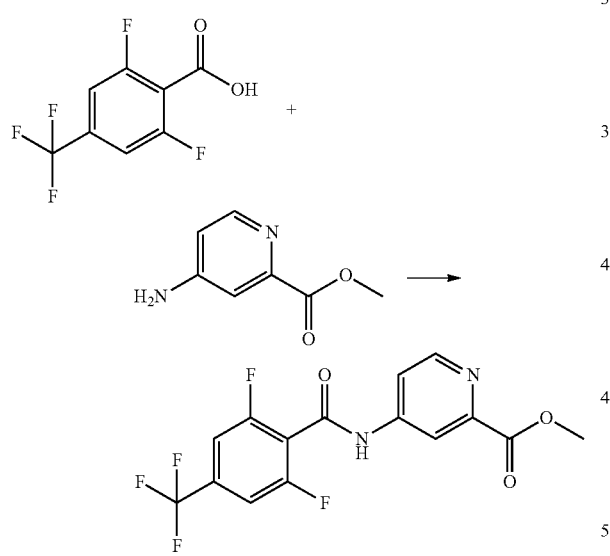

To an ice cooled solution of 2,6-difluoro-4-(trifluoromethyl)benzoic acid (350 mg, 1.08 mmol) in DCM (5 mL) was added DMF (8 µL, 0.11 mmol) followed by dropwise addition of oxalyl chloride (28 µL, 3.25 mmol). The reaction was stirred for 2 hours before concentrating in vacuo to afford the acid chloride as a pale yellow oil. To a solution of this acid chloride in DCM (5 mL) in an ice bath was added methyl 4-aminopyridine-2-carboxylate (HCl salt) (287 mg, 1.52 mmol) followed by triethylamine (900 µL, 6.51 mmol). The resulting mixture was stirred and warmed to room temperature over 2 hours. The reaction mixture was quenched with water (10 mL) and extracted with DCM (2×10 mL). The combined organics were dried by phase separation cartridge and concentrated in vacuo to afford methyl 4-[[2,6-difluoro-4-(trifluoromethyl)benzoyl]amino] pyridine-2-carboxylate (205 mg, 53%) as a brown waxy solid. ESI-MS m/z calc. 360.05, found 361.1 (M+1)+; 359.0 (M−1)−; Retention time (Method F): 0.85 minutes (1.5 minutes run). $^1$H NMR (500 MHz, CD$_3$OD) δ 8.50 (d, J=5.5 Hz, 1H), 8.30 (q, J=2.1 Hz, 1H), 7.89 (dd, J=5.5, 2.1 Hz, 1H), 7.29-7.22 (m, 2H), 4.33 (s, 1H), 3.90 (s, 3H) ppm.

Step 2: Methyl 4-[[2-fluoro-6-[3-fluoro-2-(trideuteriomethoxy)-4-(trifluoromethoxy)phenoxy]-4-(trifluoromethyl)benzoyl]amino]pyridine-2-carboxylate

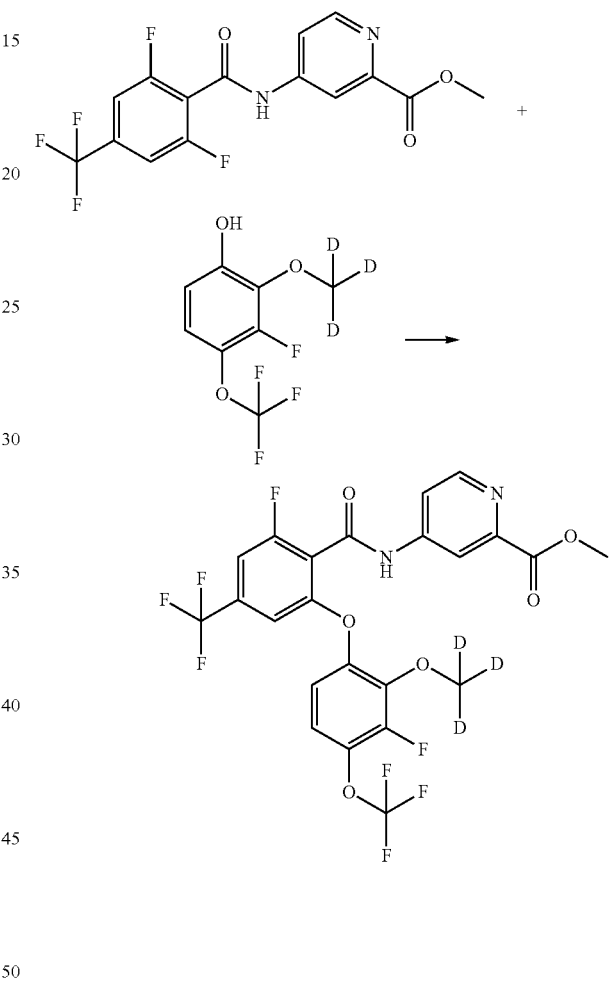

Methyl 4-[[2,6-difluoro-4-(trifluoromethyl)benzoyl]amino]pyridine-2-carboxylate (205 mg, 0.57 mmol), cesium carbonate (291 mg, 0.89 mmol) and 3-fluoro-2-(trideuteriomethoxy)-4-(trifluoromethoxy)phenol (140 mg, 0.61 mmol) were combined in DMF (3 mL) and stirred for 11 days at 30° C. The mixture was purified by HPLC (37-100% acetonitrile/0.1% ammonium hydroxide) to afford methyl 4-[[2-fluoro-6-[3-fluoro-2-(trideuteriomethoxy)-4-(trifluoromethoxy)phenoxy]-4-(trifluoromethyl)benzoyl]amino] pyridine-2-carboxylate (324 mg, 100%). ESI-MS m/z calc. 569.09, found 570.2 (M+1)+; 568.1 (M−1)−; Retention time (Method F): 1.09 minutes (1.5 minutes). $^1$H NMR (400 MHz, DMSO-d6) δ 11.52 (s, 1H), 8.63 (dd, J=5.4, 0.6 Hz, 1H), 8.35 (dd, J=2.1, 0.6 Hz, 1H), 7.83-7.75 (m, 2H), 7.34 (ddt, J=8.1, 6.9, 1.3 Hz, 1H), 7.27 (d, J=1.3 Hz, 1H), 7.11 (dd, J=9.3, 2.2 Hz, 1H), 3.89 (s, 3H) ppm.

659

Step 3: 4-[[2-Fluoro-6-[3-fluoro-2-(trideuteri-omethoxy)-4-(trifluoromethoxy)phenoxy]-4-(trifluoromethyl)benzoyl]amino]pyridine-2-carboxamide (223)

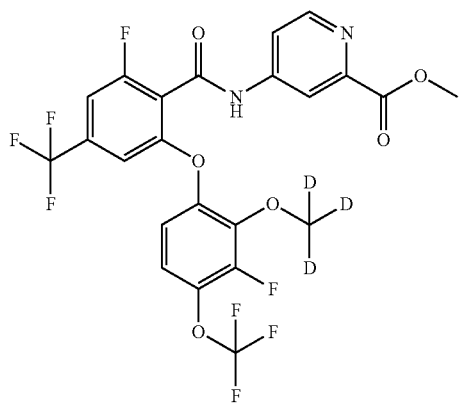

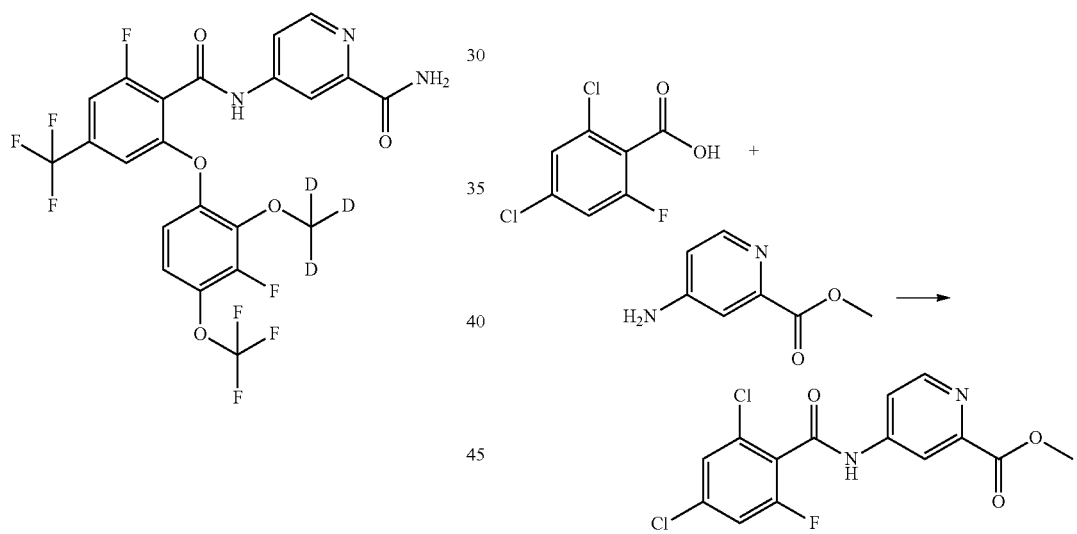

Methyl 4-[[2-fluoro-6-[3-fluoro-2-(trideuteriomethoxy)-4-(trifluoromethoxy)phenoxy]-4-(trifluoromethyl)benzoyl]amino]pyridine-2-carboxylate (100 mg, 0.176 mmol) was dissolved in ammonia (5 mL of 7 M in methanol, 35 mmol) and stirred at 31° C. for 7 hours. The reaction mixture was concentrated in vacuo to afford 4-[[2-fluoro-6-[3-fluoro-2-(trideuteriomethoxy)-4-(trifluoromethoxy)phenoxy]-4-(trifluoromethyl)benzoyl]amino]pyridine-2-carboxamide (53 mg, 45%). ESI-MS m/z calc. 554.09, found 555.1 (M+1)+; 553.0 (M−1)−; Retention time (Method E): 3.42 minutes (5 minutes run). $^1$H NMR (400 MHz, DMSO-d6) δ 11.45 (s, 1H), 8.59-8.52 (m, 1H), 8.37-8.26 (m, 1H), 8.10 (d, J=2.8 Hz, 1H), 7.83-7.74 (m, 2H), 7.66 (d, J=2.9 Hz, 1H), 7.35 (ddt, J=8.1, 6.8, 1.2 Hz, 1H), 7.26 (d, J=1.3 Hz, 1H), 7.12 (dd, J=9.3, 2.2 Hz, 1H) ppm.

660

Example 180

4-[[2,4-Dichloro-6-[3-fluoro-2-(trideuteriomethoxy)-4-(trifluoromethoxy)phenoxy]benzoyl]amino]pyridine-2-carboxamide (224)

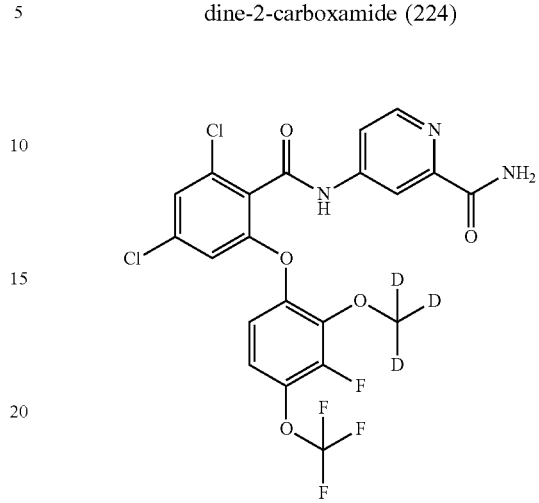

Step 1: Methyl 4-[(2,4-dichloro-6-fluoro-benzoyl)amino]pyridine-2-carboxylate

To an ice-cooled solution of 2,4-dichloro-6-fluoro-benzoic acid (300 mg, 1.01 mmol) in DCM (5 mL) was added DMF (8 μL, 0.10 mmol), followed by dropwise addition of oxalyl chloride (263 μL, 3.015 mmol) and reaction was stirred for 2 hours. The reaction mixture was concentrated in vacuo to afford the acid chloride as a pale yellow oil. A solution of this acid chloride in DCM (5 mL) was added dropwise to a solution of methyl 4-aminopyridine-2-carboxylate (HCl salt) (266 mg, 1.41 mmol) and triethylamine (840 μL, 6.03 mmol) in an ice bath. The resulting mixture was stirred and warmed to room temperature over 2 hours. Reaction mixture was quenched with water (10 mL) and extracted with DCM (2×10 mL). The combined organics were dried by phase separation cartridge and concentrated in vacuo to afford methyl 4-[(2,4-dichloro-6-fluoro-benzoyl)amino]pyridine-2-carboxylate (189 mg, 55%) as a brown waxy solid. ESI-MS m/z calc. 342.00, found 343.0 (M+1)+; 340.9 (M−1)−; Retention time (Method F): 0.82 minutes (1.5 minutes run). $^1$H NMR (400 MHz, CDCl$_3$) δ 10.23 (s, 1H), 8.53 (d, J=5.5 Hz, 1H), 8.30 (d, J=2.1 Hz, 1H), 8.00 (dd, J=5.8, 2.1 Hz, 1H), 7.12 (t, J=1.6 Hz, 1H), 6.99-6.91 (m, 1H), 3.88 (s, 3H) ppm.

Step 2: Methyl 4-[[2,4-dichloro-6-[3-fluoro-2-(trideuteriomethoxy)-4-(trifluoromethoxy)phenoxy]benzoyl]amino]pyridine-2-carboxylate

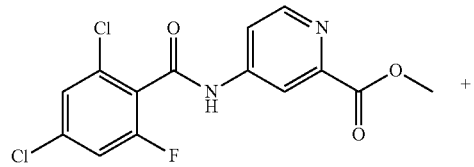

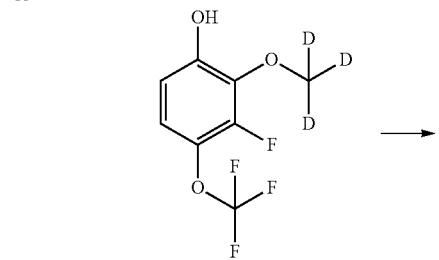

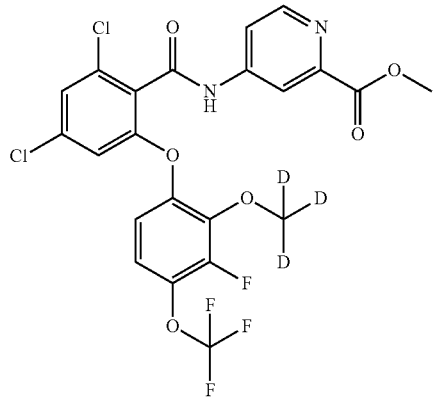

Step 3: [[2,4-Dichloro-6-[3-fluoro-2-(trideuteriomethoxy)-4-(trifluoromethoxy)phenoxy]benzoyl]amino]pyridine-2-carboxamide (224)

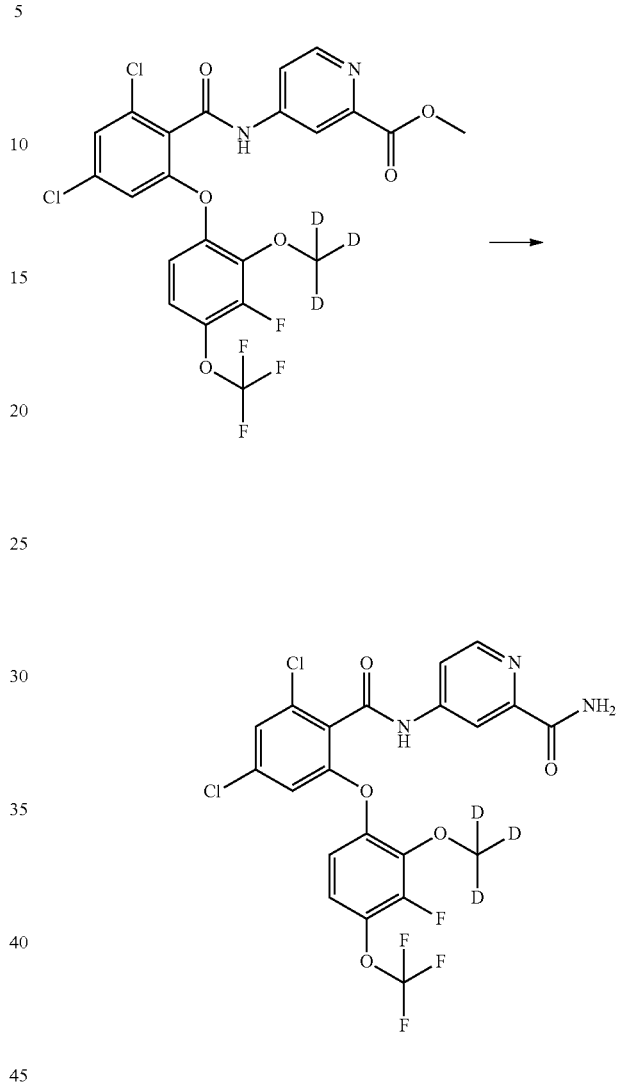

Methyl 4-[(2,4-dichloro-6-fluoro-benzoyl)amino]pyridine-2-carboxylate (189 mg, 0.55 mmol), cesium carbonate (282 mg, 0.87 mmol) and 3-fluoro-2-(trideuteriomethoxy)-4-(trifluoromethoxy)phenol (134 mg, 0.58 mmol) were combined in DMF (3 mL) and stirred for 11 days at 30° C. An additional equivalent of phenol was added and the temperature was raised to 70° C. for 2 hours, then 110° C. overnight. The mixture was purified by HPLC (37-100% acetonitrile/0.1% ammonium hydroxide) to afford methyl 4-[[2,4-dichloro-6-[3-fluoro-2-(trideuteriomethoxy)-4-(trifluoromethoxy)phenoxy]benzoyl]amino]pyridine-2-carboxylate (8.5 mg, 3%). ESI-MS m/z calc. 551.03, found 552.1 (M+1)+; 550.0 (M−1)−; Retention time (Method F): 1.06 minutes (1.5 minutes run). $^1$H NMR (400 MHz, DMSO-d6) δ 11.41 (s, 1H), 8.62 (d, J=5.4 Hz, 1H), 8.37 (d, J=2.1 Hz, 1H), 7.80 (dd, J=5.5, 2.2 Hz, 1H), 7.64 (d, J=1.8 Hz, 1H), 7.34 (ddd, J=9.3, 8.1, 1.3 Hz, 1H), 7.17 (d, J=1.8 Hz, 1H), 7.08 (dd, J=9.4, 2.2 Hz, 1H), 3.88 (s, 3H) ppm.

Methyl 4-[[2,4-dichloro-6-[3-fluoro-2-(trideuteriomethoxy)-4-(trifluoromethoxy)phenoxy]benzoyl]amino]pyridine-2-carboxylate (20 mg, 0.036 mmol) was dissolved in ammonia (1 mL of 7 M in methanol, 7.0 mmol) and stirred at 31° C. for 7 hours. The reaction mixture was concentrated in vacuo and purified by HPLC (37-100% acetonitrile/0.1% ammonium hydroxide) to afford 4-[[2,4-dichloro-6-[3-fluoro-2-(trideuteriomethoxy)-4-(trifluoromethoxy)phenoxy]benzoyl]amino]pyridine-2-carboxamide (3.1 mg, 16%). ESI-MS m/z calc. 536.04, found 537.2 (M+1)+; 537.2 (M−1)−; Retention time (Method E): 3.23 minutes (5 minute method). $^1$H NMR (400 MHz, DMSO-d6) δ 11.35 (s, 1H), 8.54 (d, J=5.5 Hz, 1H), 8.31 (d, J=2.1 Hz, 1H), 8.09 (d, J=2.8 Hz, 1H), 7.80 (dd, J=5.5, 2.2 Hz, 1H), 7.64 (dd, J=6.3, 2.4 Hz, 2H), 7.34 (ddd, J=9.3, 8.1, 1.3 Hz, 1H), 7.16 (d, J=1.8 Hz, 1H), 7.09 (dd, J=9.3, 2.2 Hz, 1H) ppm.

Example 181

4-[[2-Fluoro-6-[3-fluoro-2-(trideuteriomethoxy)-4-(trifluoromethoxy)phenoxy]-3-(trifluoromethoxy)benzoyl]amino]pyridine-2-carboxamide (225)

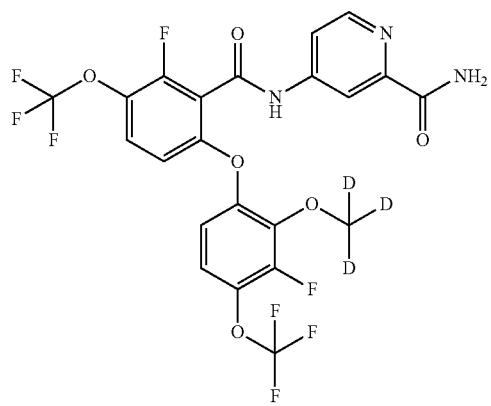 [SMILES: [2H]C([2H])([2H])Oc1c(Oc2ccc(OC(F)(F)F)c(F)c2C(=O)Nc2ccnc(C(N)=O)c2)ccc(OC(F)(F)F)c1F]

Step 1:
6-Bromo-2-fluoro-3-(trifluoromethoxy)benzoic acid

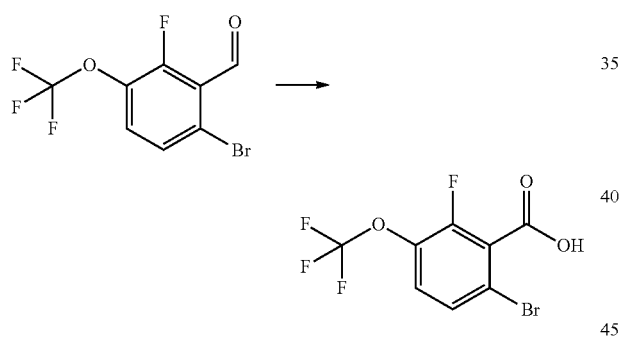

To a suspension of 6-bromo-2-fluoro-3-(trifluoromethoxy)benzaldehyde (2.8 g, 9.76 mmol) in tert-butanol (15 mL), water (15 mL) and acetonitrile (15 mL) was added sodium dihydrogen phosphate (3.53 g, 29.4 mmol) and 2-methyl-2-butene (5.6 mL, 52.9 mmol). Sodium chlorite (2.7 g, 29.9 mmol) was added portionwise and the reaction was cooled in an ice bath as an exotherm was observed during the addition. The reaction was removed from the ice bath and allowed to warm to room temperature. After 20 minutes the reaction mixture was acidified with aqueous HCl (140 mL of 1 M, 140 mmol) and diluted with ethyl acetate. The two layers were separated and the aqueous layer washed with brine, dried over $Na_2SO_4$, filtered and concentrated in vacuo then purified by silica gel chromatography (0-15% methanol/dichloromethane with 0.2% AcOH) to provide 6-bromo-2-fluoro-3-(trifluoromethoxy)benzoic acid (2.10 g, 71%). ESI-MS m/z calc. 301.92, found 304.0 (M+1)+; Retention time (Method A): 0.52 minutes (1 minute run). $^1$H NMR (400 MHz, DMSO-d6) δ 14.52 (br s, 1H), 7.78-7.56 (m, 2H) ppm.

Step 2: 2-Fluoro-6-[3-fluoro-2-(trideuteriomethoxy)-4-(trifluoromethoxy)phenoxy]-3-(trifluoromethoxy)benzoic acid

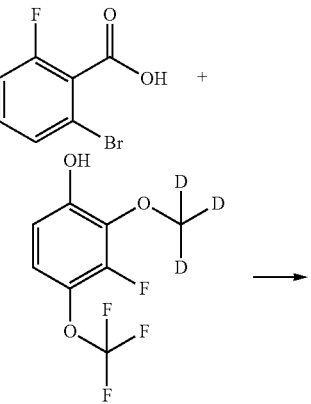

To a mixture of 6-bromo-2-fluoro-3-(trifluoromethoxy)benzoic acid (400 mg, 1.32 mmol), 3-fluoro-2-(trideuteriomethoxy)-4-(trifluoromethoxy)phenol (274 mg, 1.20 mmol) and cesium carbonate (460 mg, 1.41 mmol) in toluene (4.2 mL) was added copper (I) iodide (89 mg, 0.47 mmol) and the mixture was heated at 100° C. with vigorous stirring for 18 hours. Reaction was cooled to room temperature then acidified with 2 M HCl, filtered and the aqueous layer was extracted into ethyl acetate. The organic layer was washed with brine, dried over $Na_2SO_4$, filtered and concentrated in vacuo to afford 2-fluoro-6-[3-fluoro-2-(trideuteriomethoxy)-4-(trifluoromethoxy)phenoxy]-3-(trifluoromethoxy)benzoic acid (580 mg, 97%). ESI-MS m/z calc. 451.04, found 452.0 (M+1)+; Retention time (Method F): 0.78 minutes (1.5 minutes run).

Step 3: Methyl 4-[[2-fluoro-6-[3-fluoro-2-(trideuteriomethoxy)-4-(trifluoromethoxy)phenoxy]-3-(trifluoromethoxy)benzoyl]amino]pyridine-2-carboxylate Step 4: 4-[[2-Fluoro-6-[3-fluoro-2-(trideuteriomethoxy)-4-(trifluoromethoxy)phenoxy]-3-(trifluoromethoxy)benzoyl]amino]pyridine-2-carboxamide (225)

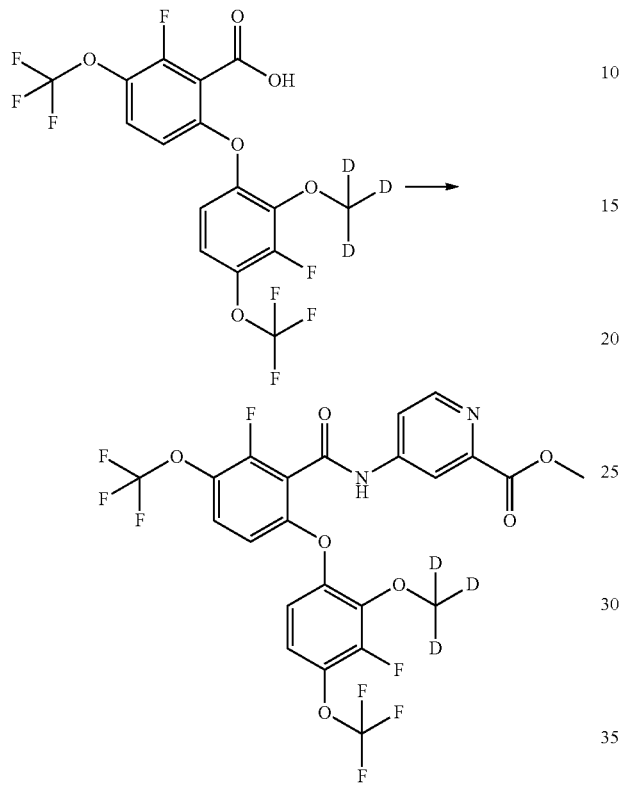

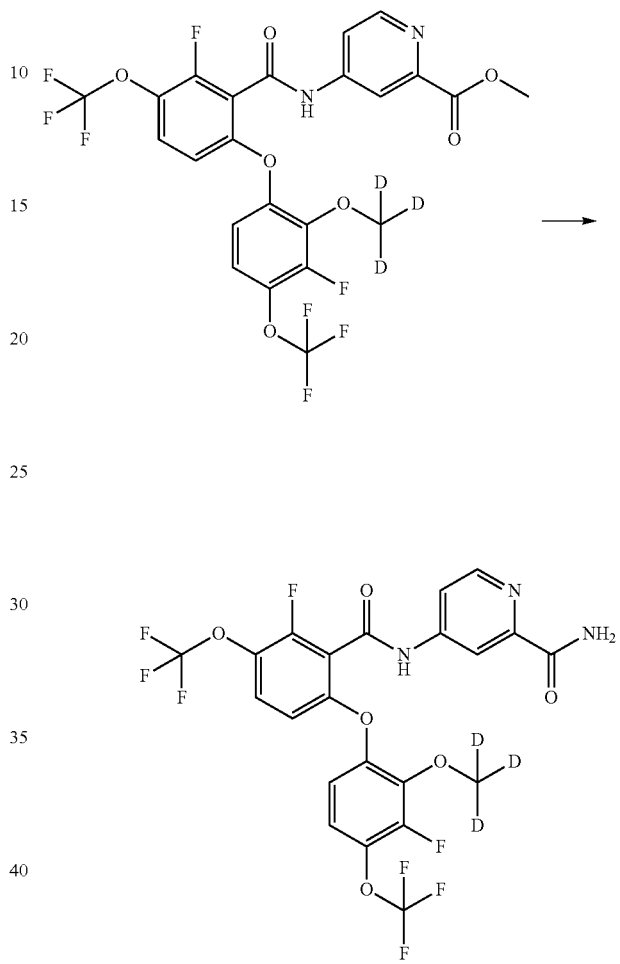

To an ice-cooled solution of 2-fluoro-6-[3-fluoro-2-(trideuteriomethoxy)-4-(trifluoromethoxy)phenoxy]-3-(trifluoromethoxy)benzoic acid (500 mg, 1.11 mmol) in DCM (12 mL) was added DMF (10 µL, 0.12 mmol) followed by dropwise addition of oxalyl chloride (290 µL, 3.324 mmol) and was stirred for 2 hours. The reaction mixture was concentrated in vacuo to afford the acid chloride as a pale yellow waxy solid. A solution of the acid chloride in DCM (12 mL) was added dropwise to a solution of methyl 4-aminopyridine-2-carboxylate (HCl salt) (294 mg, 1.56 mmol) and triethylamine (925 µL, 6.64 mmol) in an ice bath. The resulting mixture was stirred and warmed to room temperature overnight. The reaction mixture was concentrated in vacuo and purified by HPLC (37-100% acetonitrile/0.1% ammonium hydroxide) to afford methyl 4-[[2-fluoro-6-[3-fluoro-2-(trideuteriomethoxy)-4-(trifluoromethoxy)phenoxy]-3-(trifluoromethoxy)benzoyl]amino]pyridine-2-carboxylate (160 mg, 25%) as a pale white solid. ESI-MS m/z calc. 585.09, found 586.2 (M+1)+; 584.0 (M−1)−; Retention time (Method F): 1.05 minutes (1.5 minute run). $^1$H NMR (400 MHz, DMSO-d6) δ 11.53 (s, 1H), 8.64 (dd, J=5.5, 0.6 Hz, 1H), 8.36 (dd, J=2.2, 0.6 Hz, 1H), 7.82 (dd, J=5.5, 2.2 Hz, 1H), 7.76-7.66 (m, 1H), 7.41-7.31 (m, 1H), 7.14 (dd, J=9.3, 2.2 Hz, 1H), 6.93 (dd, J=9.3, 1.7 Hz, 1H), 3.89 (s, 3H) ppm.

Methyl 4-[[2-fluoro-6-[3-fluoro-2-(trideuteriomethoxy)-4-(trifluoromethoxy)phenoxy]-3-(trifluoromethoxy)benzoyl]amino]pyridine-2-carboxylate (80 mg, 0.14 mmol) was dissolved in ammonia (3 mL of 7 M in methanol, 21 mmol) and stirred at 40° C. for 5 hours. The reaction mixture was concentrated in vacuo to afford 4-[[2-fluoro-6-[3-fluoro-2-(trideuteriomethoxy)-4-(trifluoromethoxy)phenoxy]-3-(trifluoromethoxy)benzoyl]amino]pyridine-2-carboxamide (64 mg, 81%). ESI-MS m/z calc. 570.09, found 571.5 (M+1)+; 569.0 (M−1)−; Retention time (Method E): 3.37 minutes (5 minutes run). $^1$H NMR (400 MHz, CDCl$_3$) δ 10.04 (s, 1H), 8.57-8.45 (m, 2H), 8.22 (d, J=2.2 Hz, 1H), 7.87 (d, J=4.5 Hz, 1H), 7.36 (tq, J=8.1, 1.2 Hz, 1H), 7.09-6.92 (m, 2H), 6.62 (dd, J=9.2, 1.7 Hz, 1H), 5.19 (d, J=4.6 Hz, 1H) ppm.

Example 182

4-[[2-Fluoro-6-[3-fluoro-2-(trideuteriomethoxy)-4-(trifluoromethoxy)phenoxy]-3-(trifluoromethoxy)benzoyl]amino]-5-methyl-pyridine-2-carboxamide (231)

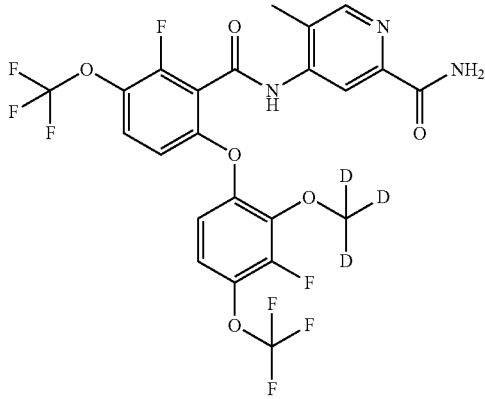 [SMILES: [2H]C([2H])([2H])Oc1c(Oc2ccc(OC(F)(F)F)c(F)c2C(=O)Nc2cc(C(N)=O)ncc2C)ccc(OC(F)(F)F)c1F]

Step 1: N-(2-Bromo-5-methyl-4-pyridyl)-2-fluoro-6-[3-fluoro-2-(trideuteriomethoxy)-4-(trifluoromethoxy)phenoxy]-3-(trifluoromethoxy)benzamide

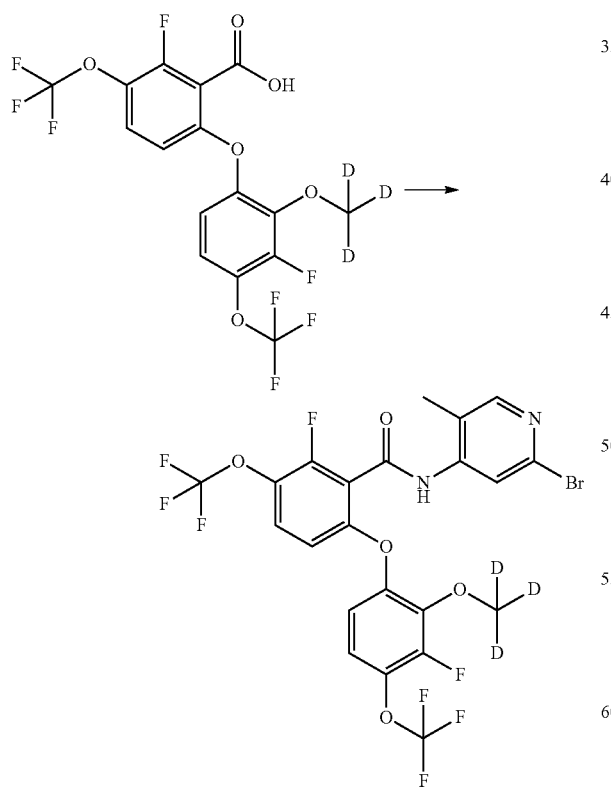

To an ice-cooled solution of 2-fluoro-6-[3-fluoro-2-(trideuteriomethoxy)-4-(trifluoromethoxy)phenoxy]-3-(trifluoromethoxy)benzoic acid (prepared as described in Example 181, step 2, 580 mg, 1.23 mmol) in DCM (14 mL) was added DMF (10 μL, 0.14 mmol) followed by dropwise addition of oxalyl chloride (340 μL, 3.85 mmol). The reaction was stirred for 2 hours then concentrated in vacuo to afford the acid chloride as a pale yellow waxy solid. A solution of this acid chloride in DCM (14 mL) was added dropwise to a solution of 2-bromo-5-methyl-pyridin-4-amine (HCl salt) (404 mg, 1.81 mmol) and triethylamine (1.07 mL, 7.67 mmol) in an ice bath. The resulting mixture was stirred and warmed to room temperature and stirred for 18 hours. The reaction mixture was concentrated in vacuo and purified by HPLC (37-100% acetonitrile/0.1% ammonium hydroxide) to afford N-(2-bromo-5-methyl-4-pyridyl)-2-fluoro-6-[3-fluoro-2-(trideuteriomethoxy)-4-(trifluoromethoxy)phenoxy]-3-(trifluoromethoxy)benzamide (185 mg, 23%) as a pale white solid. ESI-MS m/z calc. 619.01, found 622.1 (M+1)+; 620.1 (M−1)−; Retention time (Method F): 1.15 minutes (1.5 minutes run). $^1$H NMR (400 MHz, DMSO-d6) δ 10.62 (s, 1H), 8.25 (d, J=0.8 Hz, 1H), 8.05 (s, 1H), 7.75-7.65 (m, 1H), 7.38 (ddt, J=9.4, 8.1, 1.2 Hz, 1H), 7.13 (dd, J=9.3, 2.2 Hz, 1H), 6.91 (dd, J=9.3, 1.7 Hz, 1H), 2.19 (d, J=0.7 Hz, 3H) ppm.

Step 2: Methyl 4-[[2-fluoro-6-[3-fluoro-2-(trideuteriomethoxy)-4-(trifluoromethoxy)phenoxy]-3-(trifluoromethoxy)benzoyl]amino]-5-methyl-pyridine-2-carboxylate

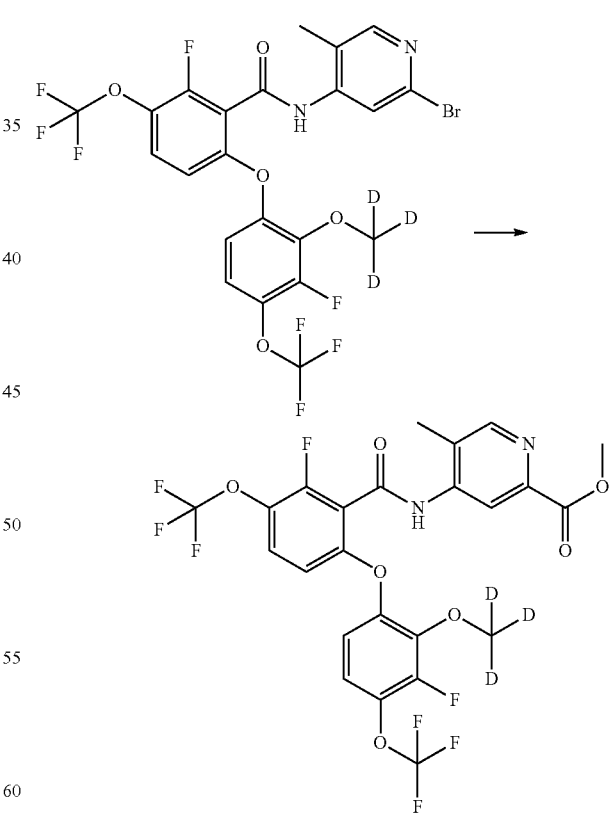

In a pressure tube, N-(2-bromo-5-methyl-4-pyridyl)-2-fluoro-6-[3-fluoro-2-(trideuteriomethoxy)-4-(trifluoromethoxy)phenoxy]-3-(trifluoromethoxy)benzamide (180 mg, 0.29 mmol) was dissolved in methanol (9 mL), and triethylamine (88 μL, 0.63 mmol) and Pd(dppf)Cl$_2$·DCM (56 mg, 0.07 mmol) were added. Carbon monoxide was bubbled through the reaction mixture for 5 minutes at ambient temperature. The reaction mixture was sealed and heated at 75° C. for 18 hours, then cooled to room temperature. The mixture was concentrated in vacuo and purified by HPLC (37-100% acetonitrile/0.1% ammonium hydroxide) to afford methyl 4-[[2-fluoro-6-[3-fluoro-2-(trideuteriomethoxy)-4-(trifluoromethoxy)phenoxy]-3-(trifluoromethoxy)benzoyl]amino]-5-methyl-pyridine-2-carboxylate (84 mg, 48%) as a white solid. ESI-MS m/z calc. 599.10, found 600.2 (M+1)+; 598.1 (M−1)−; Retention time (Method F): 1.05 minutes (1.5 minutes run).

Step 3: 4-[[2-Fluoro-6-[3-fluoro-2-(trideuteriomethoxy)-4-(trifluoromethoxy)phenoxy]-3-(trifluoromethoxy)benzoyl]amino]-5-methyl-pyridine-2-carboxamide (231)

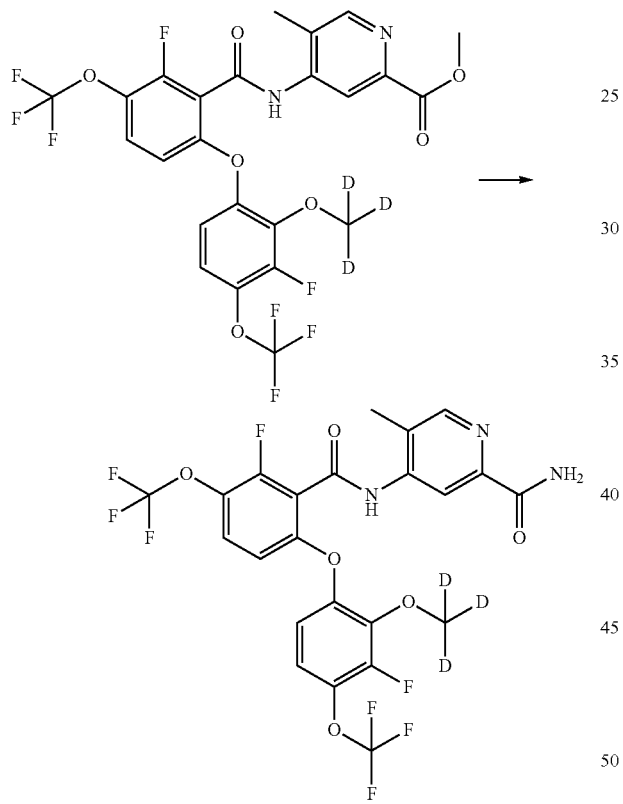

Methyl 4-[[2-fluoro-6-[3-fluoro-2-(trideuteriomethoxy)-4-(trifluoromethoxy)phenoxy]-3-(trifluoromethoxy)benzoyl]amino]-5-methyl-pyridine-2-carboxylate (84 mg, 0.14 mmol) was dissolved in ammonia (3 mL of 7 M in methanol, 21 mmol) and stirred at 40° C. for 18 hours. The reaction mixture was concentrated in vacuo to afford 4-[[2-fluoro-6-[3-fluoro-2-(trideuteriomethoxy)-4-(trifluoromethoxy)phenoxy]-3-(trifluoromethoxy)benzoyl]amino]-5-methyl-pyridine-2-carboxamide (55 mg, 65%). ESI-MS m/z calc. 584.10, found 585.2 (M+1)+; 583.0 (M−1)−; Retention time (Method E): 3.39 minutes (5 minutes run). ¹H NMR (400 MHz, CDCl₃) δ 8.84 (s, 1H), 8.55 (s, 1H), 8.36 (s, 1H), 7.77 (d, J=4.4 Hz, 1H), 7.35-7.22 (m, 1H), 7.15-6.95 (m, 2H), 6.64-6.51 (m, 1H), 5.89 (d, J=4.5 Hz, 1H), 2.32 (s, 3H) ppm.

Example 183

4-[[6-[3-Fluoro-2-(trideuteriomethoxy)-4-(trifluoromethoxy)phenoxy]-2-(methylamino)-3-(trifluoromethoxy)benzoyl]amino]-N-methyl-pyridine-2-carboxamide (230)

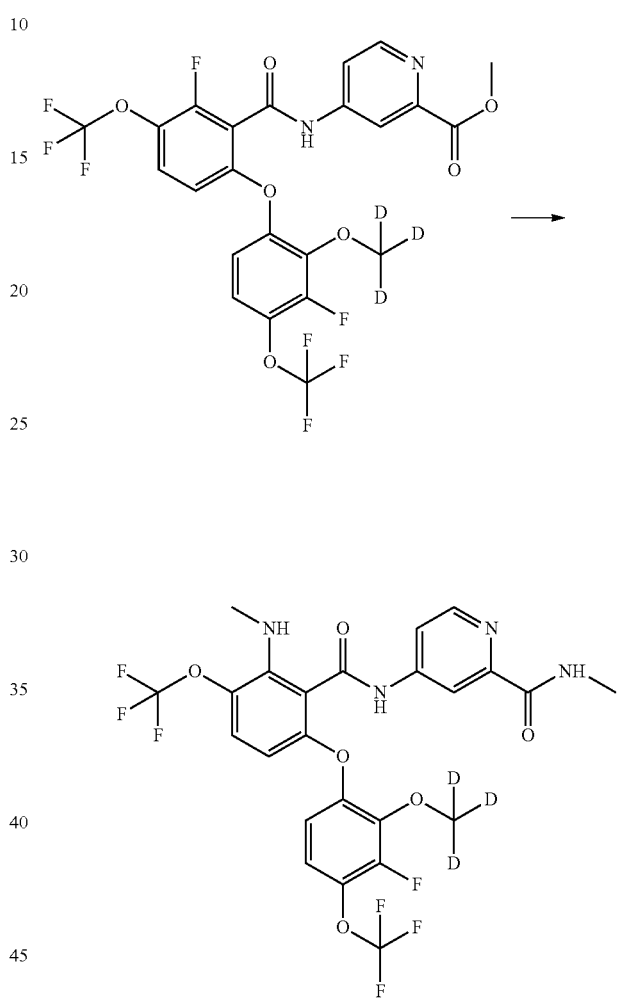

Methyl 4-[[2-fluoro-6-[3-fluoro-2-(trideuteriomethoxy)-4-(trifluoromethoxy)phenoxy]-3-(trifluoromethoxy)benzoyl]amino]pyridine-2-carboxylate (prepared as described in Example 181, step 3, 20 mg, 0.03 mmol) was dissolved in methanamine (35 μL of 2 M, 0.07 mmol) and THF (0.5 mL) and stirred at 50° C. for 18 hours then 40° C. for 4 days. The reaction mixture was concentrated in vacuo to afford 4-[[6-[3-fluoro-2-(trideuteriomethoxy)-4-(trifluoromethoxy)phenoxy]-2-(methylamino)-3-(trifluoromethoxy)benzoyl]amino]-N-methyl-pyridine-2-carboxamide (6.3 mg, 31%). ESI-MS m/z calc. 595.14, found 596.0 (M+1)+; 594.4 (M−1)−; Retention time (Method E): 3.47 minutes (5 minutes run). ¹H NMR (400 MHz, DMSO-d6) δ 11.25 (s, 1H), 8.71 (q, J=4.8 Hz, 1H), 8.50 (d, J=5.5 Hz, 1H), 8.30 (d, J=2.1 Hz, 1H), 7.82 (dd, J=5.5, 2.2 Hz, 1H), 7.36-7.26 (m, 1H), 7.23 (dq, J=8.8, 1.6 Hz, 1H), 6.97 (dd, J=9.4, 2.2 Hz, 1H), 6.13 (d, J=8.9 Hz, 1H), 6.00 (q, J=5.2 Hz, 1H), 2.81 (dd, J=6.5, 5.0 Hz, 6H) ppm.

Example 184

4-[[2-fluoro-6-[4-(trifluoromethoxy)phenoxy]-3-(trifluoromethyl)benzoyl]amino]-5-methyl-pyridine-2-carboxamide (242)

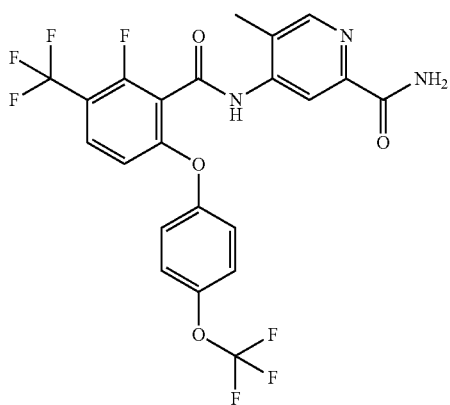 [SMILES: Cc1cnc(C(N)=O)cc1NC(=O)c1c(Oc2ccc(OC(F)(F)F)cc2)ccc(C(F)(F)F)c1F]

Step 1: N-(2-bromo-5-methyl-4-pyridyl)-2-fluoro-6-[4-(trifluoromethoxy)phenoxy]-3-(trifluoromethyl)benzamide

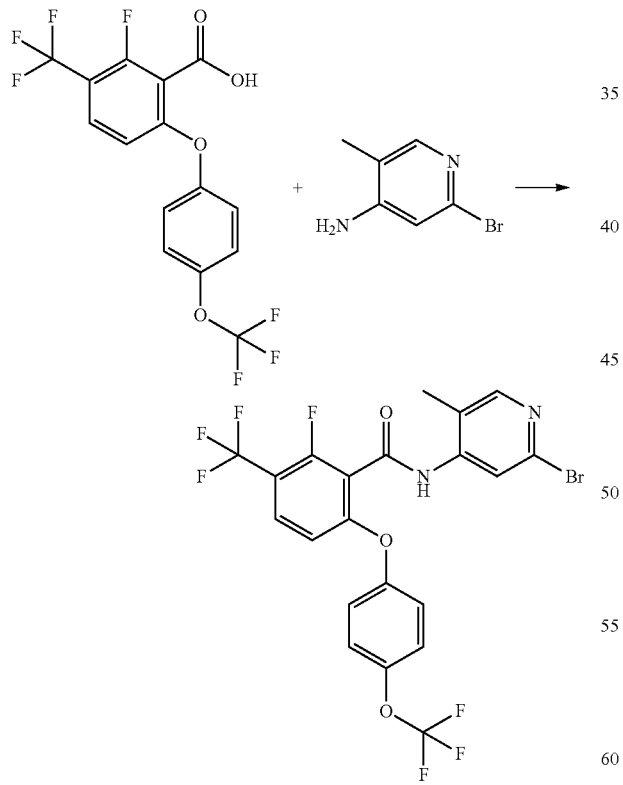

To an ice-cooled solution of 2-fluoro-6-[4-(trifluoromethoxy)phenoxy]-3-(trifluoromethyl)benzoic acid (prepared as described in Example 15, Step 1, 270 mg, 0.70 mmol) in DCM (4 mL) was added DMF (10 μL, 0.13 mmol) and dropwise oxalyl dichloride (295 μL, 3.38 mmol) and was stirred for 2 hours. The reaction mixture was concentrated in vacuo to afford the acid chloride as a pale yellow oil. The residue was dissolved in DCM (4 mL) and added dropwise to a solution of 2-bromo-5-methyl-pyridin-4-amine (237 mg, 1.27 mmol) and triethylamine (925 μL, 6.64 mmol) in DCM (4 mL) in an ice bath. The resulting mixture was stirred and warmed to room temperature overnight. The reaction mixture was concentrated in vacuo and purified by silica gel chromatography (ethyl acetate/heptane) to afford N-(2-bromo-5-methyl-4-pyridyl)-2-fluoro-6-[4-(trifluoromethoxy)phenoxy]-3-(trifluoromethyl)benzamide (100 mg, 26%) as a clear waxy solid. $^1$H NMR (400 MHz, CDCl3) δ 8.90 (s, 1H), 8.31 (s, 1H), 8.07-8.02 (m, 1H), 7.46 (t, J=8.3 Hz, 1H), 7.24-7.16 (m, 2H), 7.09-7.00 (m, 2H), 6.58 (d, J=8.8 Hz, 1H), 2.14 (d, J=0.7 Hz, 3H) ppm.

Step 2: methyl 4-[[2-fluoro-6-[4-(trifluoromethoxy)phenoxy]-3-(trifluoromethyl)benzoyl]amino]-5-methyl-pyridine-2-carboxylate

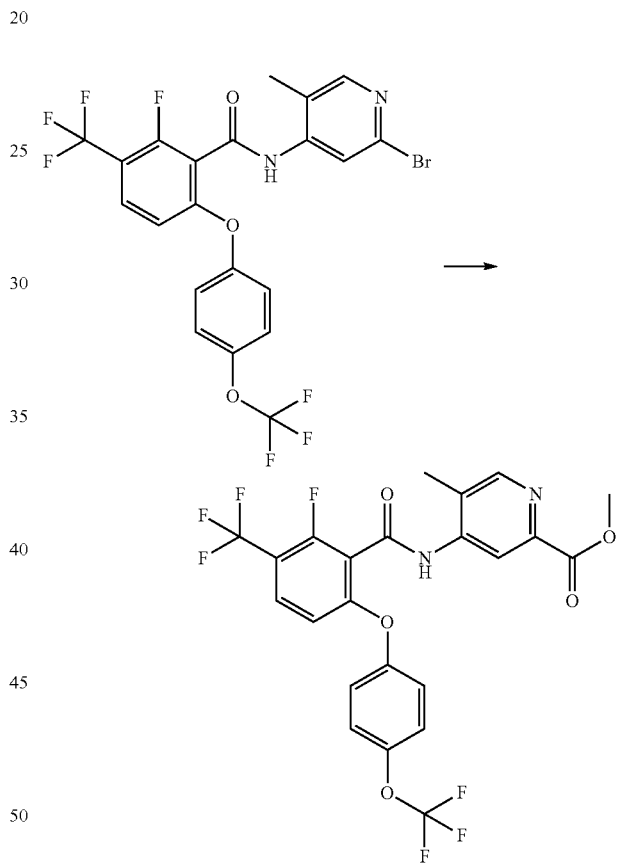

In a pressure tube, N-(2-bromo-5-methyl-4-pyridyl)-2-fluoro-6-[4-(trifluoromethoxy)phenoxy]-3-(trifluoromethyl)benzamide (100 mg, 0.18 mmol) was dissolved in methanol (5 mL) and triethylamine (58 μL, 0.42 mmol) and Pd(dppf)Cl$_2$·DCM (42 mg, 0.05 mmol) were added. CO gas was bubbled through the reaction mixture for 5 minutes whilst being vigorously stirred at room temperature. The reaction mixture was sealed and heated to 75° C. overnight, then cooled to room temperature and concentrated in vacuo to afford methyl 4-[[2-fluoro-6-[4-(trifluoromethoxy)phenoxy]-3-(trifluoromethyl)benzoyl]amino]-5-methyl-pyridine-2-carboxylate (90 mg, 94%). ESI-MS m/z calc. 532.09, found 533.6 (M+1)+; 531.7 (M−1)−; Retention time (Method F): 0.97 minutes (1.5 minutes run).

Step 3: 4-[[2-fluoro-6-[4-(trifluoromethoxy)phenoxy]-3-(trifluoromethyl)benzoyl]amino]-5-methyl-pyridine-2-carboxamide (242)

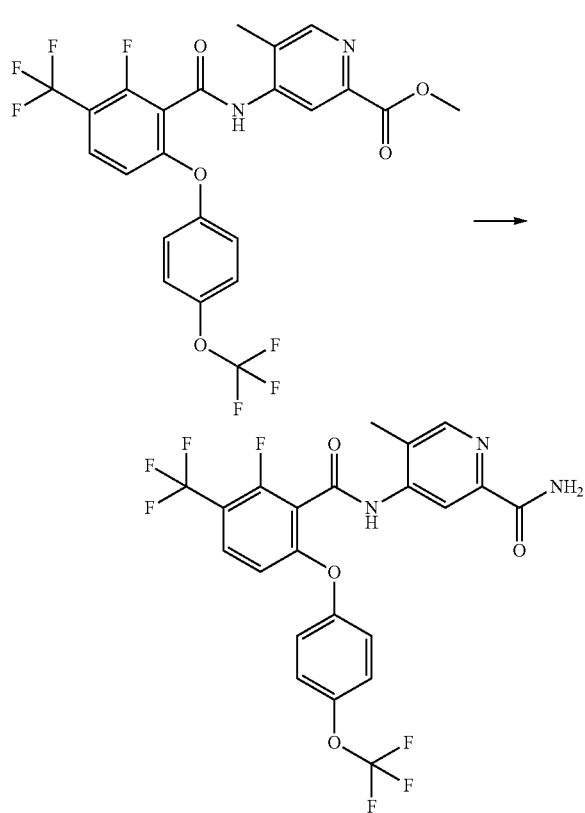

Methyl 4-[[2-fluoro-6-[4-(trifluoromethoxy)phenoxy]-3-(trifluoromethyl)benzoyl]amino]-5-methyl-pyridine-2-carboxylate (90 mg, 0.17 mmol) was dissolved ammonia (5 mL of 7 M in methanol, 35 mmol) and stirred at room temperature overnight. The reaction mixture was concentrated in vacuo and purified by HPLC (37-100% acetonitrile/water/0.1% ammonium hydroxide) to afford 4-[[2-fluoro-6-[4-(trifluoromethoxy)phenoxy]-3-(trifluoromethyl)benzoyl]amino]-5-methyl-pyridine-2-carboxamide (242, 1.8 mg, 2%). ESI-MS m/z calc. 517.09, found 518.6 (M+1)+; 516.7 (M−1)−; Retention time (Method E): 3.24 minutes (5 minutes run). $^1$H NMR (400 MHz, DMSO-d6) δ 10.61 (s, 1H), 8.47 (d, J=1.2 Hz, 2H), 8.05 (s, 1H), 7.89 (t, J=8.6 Hz, 1H), 7.60 (s, 1H), 7.53-7.48 (m, 2H), 7.41-7.36 (m, 2H), 6.91 (d, J=8.8 Hz, 1H), 2.27 (d, J=7.5 Hz, 3H) ppm.

Example 185

N-(3-carbamoyl-4-fluoro-phenyl)-2-fluoro-6-[(6-methoxy-3-pyridyl)oxy]-3-(trifluoromethyl)benzamide (56)

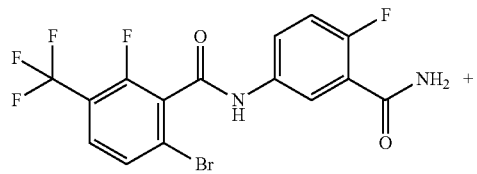

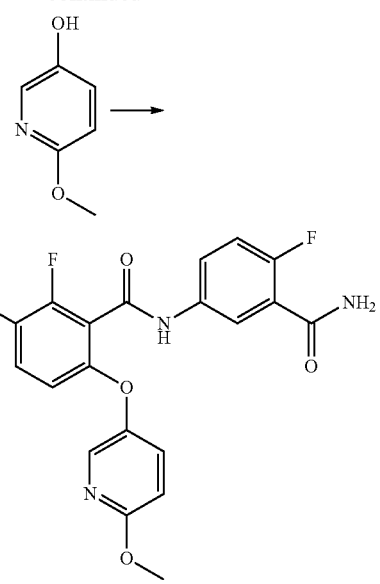

A mixture of 6-bromo-N-(3-carbamoyl-4-fluoro-phenyl)-2-fluoro-3-(trifluoromethyl)benzamide (75 mg, 0.18 mmol, prepared as described in Example 140), cesium carbonate (115 mg, 0.35 mmol) and 6-methoxypyridin-3-ol (22 mg, 0.18 mmol) in toluene (1.9 mL) was bubbled with nitrogen. After 2-3 minutes, copper iodide (7 mg, 0.04 mmol) was added and the reaction mixture was stirred at 100° C. for 20 minutes. The reaction was diluted with ethyl acetate and water. The organic layer was concentrated in vacuo and purified by HPLC (10-99% acetonitrile/5 mM HCl) to provide N-(3-carbamoyl-4-fluoro-phenyl)-2-fluoro-6-[(6-methoxy-3-pyridyl)oxy]-3-(trifluoromethyl)benzamide (6 mg, 7%). $^1$H NMR (400 MHz, DMSO-d6) δ 11.06 (s, 1H), 8.15 (dd, J=3.0, 0.6 Hz, 1H), 7.99 (dd, J=6.4, 2.8 Hz, 1H), 7.87-7.63 (m, 5H), 7.30 (dd, J=10.1, 8.9 Hz, 1H), 6.96 (dd, J=9.0, 0.6 Hz, 1H), 6.82 (d, J=8.9 Hz, 1H), 3.87 (s, 3H) ppm.

Example 186

N-(3-carbamoyl-4-fluoro-phenyl)-4,5-dichloro-2-[(2-methoxy-3-pyridyl)oxy]benzamide (35)

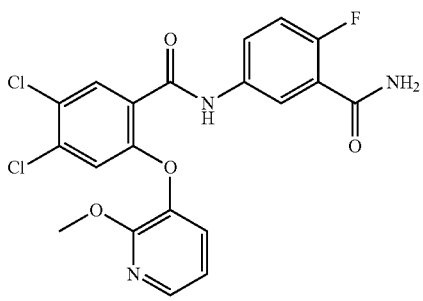 [SMILES: COc1ncccc1Oc1cc(Cl)c(Cl)cc1C(=O)Nc1ccc(F)c(C(N)=O)c1]

Step 1: 4,5-dichloro-2-fluoro-N-methoxy-N-methyl-benzamide

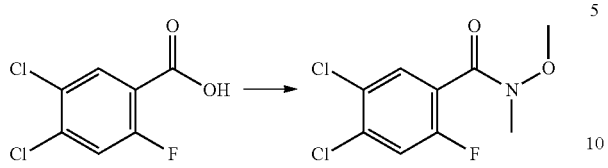

A mixture of 4,5-dichloro-2-fluoro-benzoic acid (10 g, 47.9 mmol), HATU (20 g, 52.6 mmol) and N-methoxymethanamine (HCl salt) (4.67 g, 47.9 mmol) in DMF (150 mL) was treated with N-ethyl-N-isopropyl-propan-2-amine (16.7 mL, 95.7 mmol) and was stirred at room temperature for 18 hours. The reaction mixture was concentrated in vacuo then diluted with diethyl ether and washed with 50% saturated sodium bicarbonate solution (×2) and brine, dried over sodium sulfate, filtered and concentrated in vacuo. The product was purified by silica gel chromatography (0-30% ethyl acetate/hexanes) to provide 4,5-dichloro-2-fluoro-N-methoxy-N-methyl-benzamide (11.5 g, 96%) as a colorless oil. ESI-MS m/z calc. 250.99, found 252.1 (M+1)+; Retention time (Method A): 0.54 minutes (1 minutes run). $^1$H NMR (400 MHz, DMSO-d6) δ 7.87 (d, J=6.4 Hz, 1H), 7.84 (d, J=9.1 Hz, 1H), 3.52 (br s, 3H), 3.27 (br s, 3H) ppm.

Step 2: 4,5-dichloro-2-fluoro-benzaldehyde

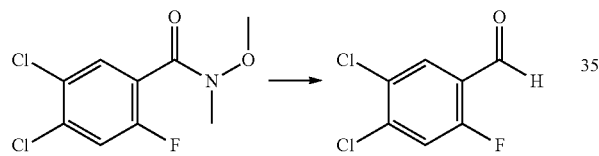

To a stirring solution of lithium aluminum hydride (25 mL of 2 M in THF, 50.1 mmol) in THF (105 mL) at −78° C. was added a solution of 4,5-dichloro-2-fluoro-N-methoxy-N-methyl-benzamide (10.5 g, 41.8 mmol) in anhydrous THF (53 mL) dropwise over 20 minutes whilst maintaining internal reaction temperature less than −65° C. The reaction was stirred at −78° C. for 1 hour then was slowly poured into stirring aqueous 1 N HCl (210 mL of 1 M, 210 mmol) and ice. The mixture was extracted with diethyl ether and the organic layer was washed with 1 N HCl and brine, then dried over sodium sulfate, filtered, and concentrated to provide 4,5-dichloro-2-fluoro-benzaldehyde (7.98 g, 99%) as a white, creamy solid. $^1$H NMR (400 MHz, DMSO-d6) δ 10.11 (d, J=0.5 Hz, 1H), 8.05 (d, J=6.7 Hz, 1H), 7.97 (d, J=10.1 Hz, 1H) ppm.

Step 3: 4,5-dichloro-2-[(2-methoxy-3-pyridyl)oxy]benzaldehyde

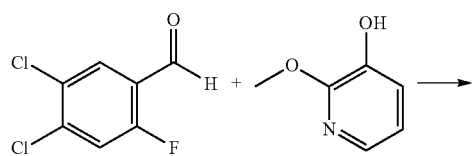

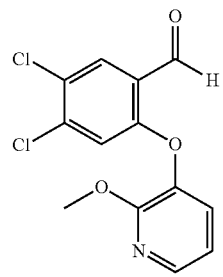

A mixture of 4,5-dichloro-2-fluoro-benzaldehyde (502 mg, 2.60 mmol), 2-methoxypyridin-3-ol (325 mg, 2.60 mmol) and cesium carbonate (1.02 g, 3.12 mmol) in DMF (4 mL) was heated at 75° C. for 10 minutes. The cooled reaction mixture was diluted with ethyl acetate (50 mL) then partitioned with water (50 mL). The aqueous portion was extracted with ethyl acetate (2×25 mL) and the combined organics were washed with saturated sodium chloride solution (2×25 mL), dried over sodium sulfate concentrated in vacuo. The product was purified by silica gel chromatography (0-100% ethyl acetate/hexanes) to provide 4,5-dichloro-2-[(2-methoxy-3-pyridyl)oxy]benzaldehyde (650 mg, 84%). ESI-MS m/z calc. 297.00, found 298.1 (M+1)+; Retention time (Method A): 0.68 minutes (1 minutes run). $^1$H NMR (400 MHz, DMSO-d6) δ 10.35 (s, 1H), 8.12 (dd, J=5.0, 1.6 Hz, 1H), 7.97 (s, 1H), 7.70 (dd, J=7.7, 1.6 Hz, 1H), 7.14-7.08 (m, 2H), 3.87 (s, 3H) ppm

Step 4: 4,5-dichloro-2-[(2-methoxy-3-pyridyl)oxy]benzoic acid

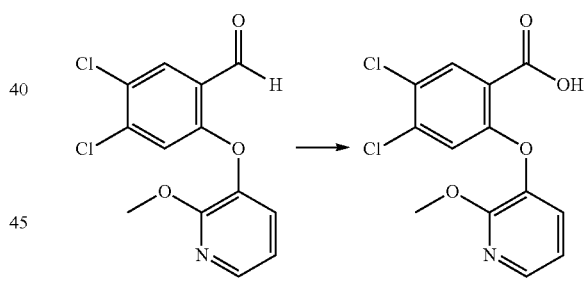

To a suspension of 4,5-dichloro-2-[(2-methoxy-3-pyridyl)oxy]benzaldehyde (775 mg, 2.60 mmol) in t-butanol (5 mL), water (5 mL), acetonitrile (5 mL) was added sodium dihydrogen phosphate (940 mg, 7.84 mmol), 2-methyl-2-butene (1.4 mL, 13 mmol) and sodium chlorite (710 mg, 7.85 mmol) and the mixture was stirred at room temperature for 1 hour. The reaction mixture was acidified with 1 N HCl and diluted with ethyl acetate. The layers were separated and the aqueous was extracted with ethyl acetate (3×25 mL). The combined organics were washed with brine, dried over sodium sulfate and concentrated in vacuo to a light yellow solid. The solid was slurried in hexane and filtered to provide 4,5-dichloro-2-[(2-methoxy-3-pyridyl)oxy]benzoic acid (610 mg, 75%). ESI-MS m/z calc. 312.99, found 314.1 (M+1)+; Retention time (Method A): 0.59 minutes (1 minutes run). $^1$H NMR (400 MHz, DMSO-d6) δ 13.40 (br s, 1H), 8.04-7.97 (m, 2H), 7.38 (dd, J=7.8, 1.6 Hz, 1H), 7.13 (s, 1H), 7.01 (dd, J=7.7, 4.9 Hz, 1H), 3.87 (s, 3H) ppm.

Step 5: 4,5-dichloro-2-[(2-methoxy-3-pyridyl)oxy]
benzoyl chloride

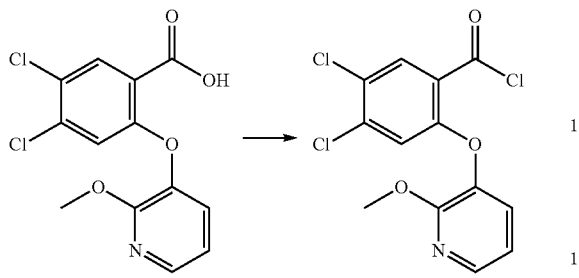

To a solution of 4,5-dichloro-2-[(2-methoxy-3-pyridyl)oxy]benzoic acid (610 mg, 1.94 mmol) and DMF (3 µL, 0.04 mmol) in DCM (9 mL) at room temperature was added oxalyl dichloride (850 µL, 9.74 mmol) dropwise. The reaction mixture was stirred for 10 minutes at room temperature then concentrated in vacuo and azeotroped with DCM (3×25 mL) to provide 4,5-dichloro-2-[(2-methoxy-3-pyridyl)oxy]benzoyl chloride (640 mg, 99%). The product was used in the next step without further purification.

Step 6: N-(3-carbamoyl-4-fluoro-phenyl)-4,5-dichloro-2-[(2-methoxy-3-pyridyl)oxy]benzamide (35)

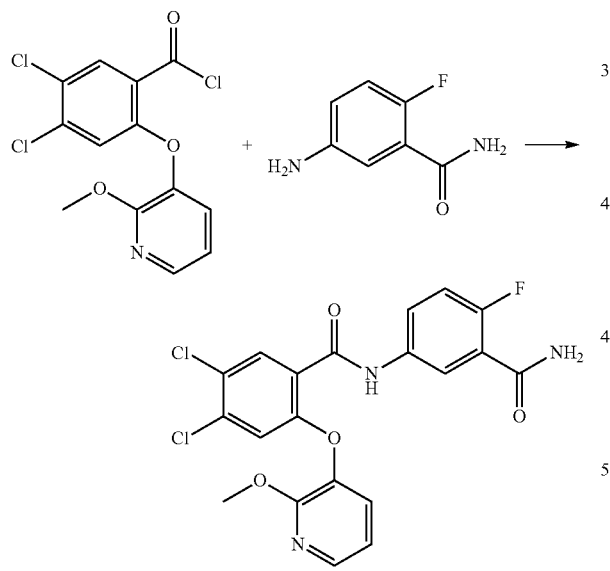

To a solution of 5-amino-2-fluoro-benzamide (23 mg, 0.15 mmol) and N-ethyl-N-isopropyl-propan-2-amine (78 µL, 0.45 mmol) in DCM (500 µL) at 0° C. was added a solution of 4,5-dichloro-2-[(2-methoxy-3-pyridyl)oxy]benzoyl chloride (50 mg, 0.15 mmol) in DCM (500 µL) dropwise. The reaction mixture was warmed to room temperature and stirred for 10 minutes, resulting in a thick slurry. The slurry was filtered and the solid washed with minimal acetonitrile. The resulting solid was re-suspended in water to obtain a white solid which was filtered and air dried. The solid was rinsed with hexanes and dried under vacuum to provide N-(3-carbamoyl-4-fluoro-phenyl)-4,5-dichloro-2-[(2-methoxy-3-pyridyl)oxy]benzamide (30 mg, 45%) as a white solid. ESI-MS m/z calc. 449.03, found 450.1 (M+1)+; Retention time (Method B): 1.59 minutes (3 minutes run). $^1$H NMR (400 MHz, DMSO-d6) δ 10.57 (s, 1H), 8.02 (dd, J=4.9, 1.6 Hz, 1H), 7.97-7.92 (m, 2H), 7.75 (ddd, J=9.0, 4.4, 2.8 Hz, 1H), 7.72-7.62 (m, 2H), 7.52 (dd, J=7.8, 1.6 Hz, 1H), 7.26 (dd, J=10.2, 8.9 Hz, 1H), 7.15 (s, 1H), 7.04 (dd, J=7.7, 4.9 Hz, 1H), 3.83 (s, 3H) ppm.

Example 187

N-(3-carbamoyl-4-fluoro-phenyl)-2-(4-fluoro-2-methoxy-phenyl)-4-(trifluoromethyl)benzamide (162)

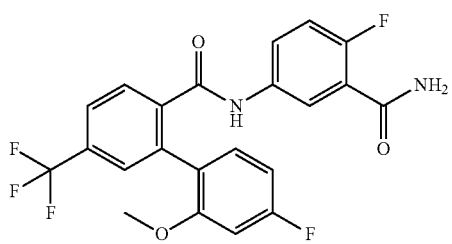 [SMILES: COc1cc(F)ccc1-c1cc(C(F)(F)F)ccc1C(=O)Nc1ccc(F)c(C(N)=O)c1]

Step 1: 2-bromo-N-(3-carbamoyl-4-fluoro-phenyl)-4-(trifluoromethyl)benzamide

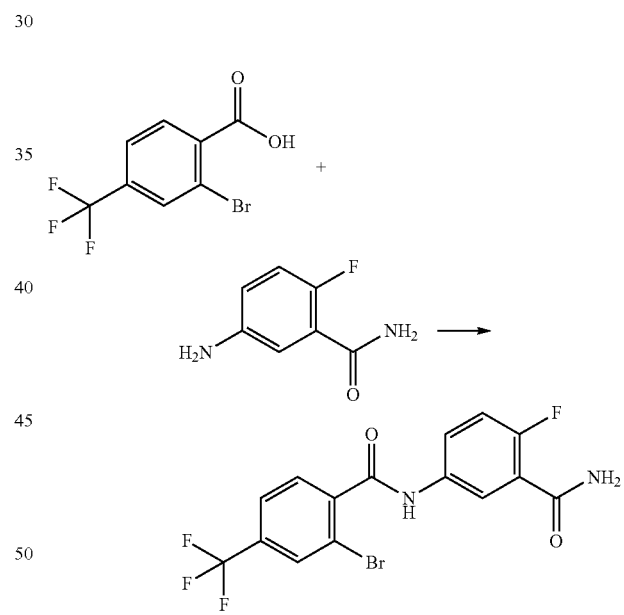

A mixture of 2-bromo-4-(trifluoromethyl)benzoic acid (400 mg, 1.49 mmol), 5-amino-2-fluoro-benzamide (261 mg, 1.69 mmol), triethylamine (1.3 mL, 9.33 mmol) and 2,4,6-tripropyl-1,3,5,2,4,6-trioxatriphosphinane 2,4,6-trioxide (3 mL of 50% w/v, 4.71 mmol) in isopropyl acetate (8 mL) was heated at 100° C. over the weekend. The mixture was concentrated in vacuo and partitioned between DCM and a saturated aqueous solution of sodium bicarbonate. The organic portion was dried over magnesium sulfate and concentrated in vacuo to provide 2-bromo-N-(3-carbamoyl-4-fluoro-phenyl)-4-(trifluoromethyl)benzamide (620 mg, 103%) as a colourless oil. ESI-MS m/z calc. 403.98, found 405.0 (M+1)+; 403.0 (M−1)−; Retention time (Method F): 0.81 minutes (1.5 minutes run)

Step 2: N-(3-carbamoyl-4-fluoro-phenyl)-2-(4-fluoro-2-methoxy-phenyl)-4-(trifluoromethyl)benzamide (162)

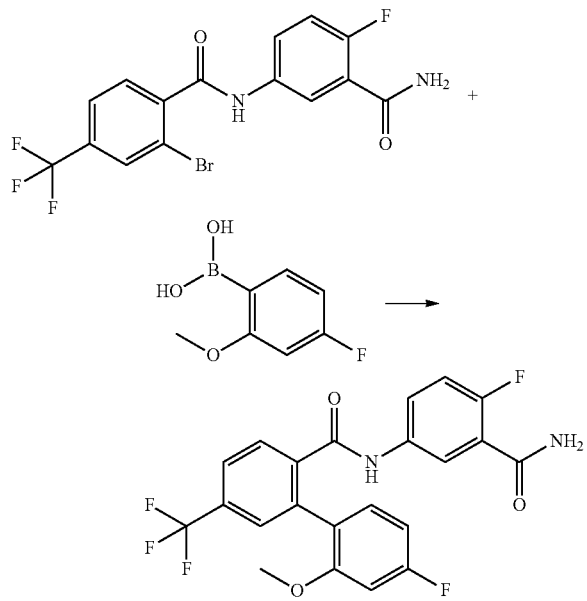

A mixture of 2-bromo-N-(3-carbamoyl-4-fluorophenyl)-4-(trifluoromethyl)benzamide (71 mg, 0.18 mmol), (4-fluoro-2-methoxy-phenyl)boronic acid (50 mg, 0.29 mmol), Pd(PPh₃)₄ (29 mg, 0.03 mmol) and sodium carbonate (300 μL of 2 M, 0.60 mmol) in dioxane (4 mL) was heated for 2 hours at 140° C. in the microwave. The mixture was concentrated in vacuo and purified by HPLC (0-100% acetonitrile/0.05% TFA) to provide N-(3-carbamoyl-4-fluoro-phenyl)-2-(4-fluoro-2-methoxy-phenyl)-4-(trifluoromethyl)benzamide (28 mg, 33%) as a white solid. ESI-MS m/z calc. 450.10, found 451.2 (M+1)+; 449.2 (M−1)−; Retention time (Method E): 3.05 minutes (5 minutes run). ¹H NMR (400 MHz, DMSO-d6) δ 10.43 (s, 1H), 7.94-7.80 (m, 3H), 7.66 (tt, J=4.5, 2.7 Hz, 4H), 7.36 (dd, J=8.4, 6.8 Hz, 1H), 7.23 (dd, J=10.1, 8.9 Hz, 1H), 6.92 (dd, J=11.3, 2.5 Hz, 1H), 6.85 (td, J=8.4, 2.5 Hz, 1H), 3.59 (s, 3H) ppm.

Example 188

N-(4-carbamoyl-3-fluoro-phenyl)-6-[(6-chloro-2-methoxy-3-pyridyl)oxy]-2-fluoro-3-(trifluoromethyl)benzamide (67)

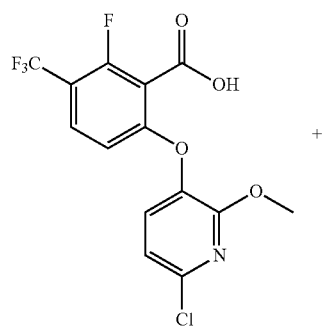

-continued

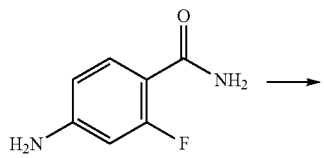

To a mixture of 6-[(6-chloro-2-methoxy-3-pyridyl)oxy]-2-fluoro-3-(trifluoromethyl)benzoic acid (96 mg, 0.26 mmol, prepared as described in Example 128) and HATU (111 mg, 0.29 mmol) in DMF (1.5 mL) was added N-ethyl-N-isopropyl-propan-2-amine (102 μL, 0.58 mmol) and was stirred for 10 minutes. 4-Amino-2-fluoro-benzamide (45 mg, 0.29 mmol) was then added and the reaction was stirred at 45° C. for 16 hours. Product was purified by silica gel chromatography (0-10% methanol/DCM) then purified again by HPLC (10-99% acetonitrile/5 mM HCl) to provide N-(4-carbamoyl-3-fluoro-phenyl)-6-[(6-chloro-2-methoxy-3-pyridyl)oxy]-2-fluoro-3-(trifluoromethyl)benzamide (5 mg, 3%). ESI-MS m/z calc. 501.05, found 502.0 (M+1)+; Retention time (Method B): 3.05 minutes (3 minutes run).

Example 189

6-tert-butyl-N-(3-carbamoyl-4-fluoro-phenyl)-4-(4-fluoro-2-methoxy-phenyl)pyridine-3-carboxamide (199)

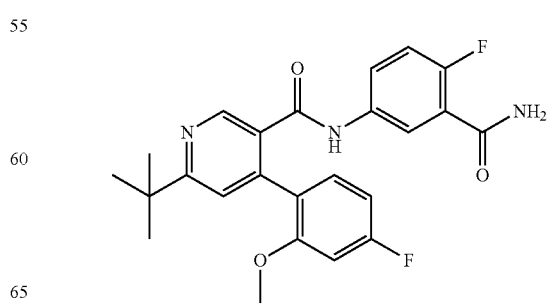

Step 1: 6-tert-butyl-4-chloro-pyridine-3-carboxylic acid

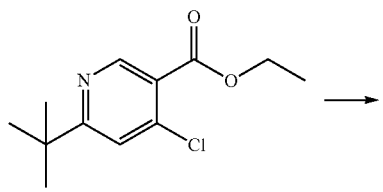 

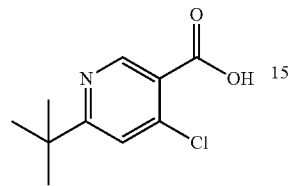

Lithium hydroxide (3 mL of 2 M, 6.0 mmol) was added to a solution of ethyl 6-tert-butyl-4-chloro-pyridine-3-carboxylate (706 mg, 2.9 mmol) in a mixture of THF (8 mL), methanol (2 mL) and water (2 mL). The solution was stirred at room temperature for 18 hours before removing the organic solvents in vacuo. The aqueous residue was acidified with 2 M HCl and the mixture was extracted with DCM (×2). Combined organics were dried over magnesium sulfate, filtered and concentrated in vacuo to afford 6-tert-butyl-4-chloro-pyridine-3-carboxylic acid (625 mg, 100%) as a white solid. ESI-MS m/z calc. 213.06, found 214.1 (M+1)+; 212.1 (M−1)−; Retention time (Method F): 0.47 minutes (1.5 minutes run).

Step 2: 6-tert-butyl-N-(3-carbamoyl-4-fluoro-phenyl)-4-chloro-pyridine-3-carboxamide

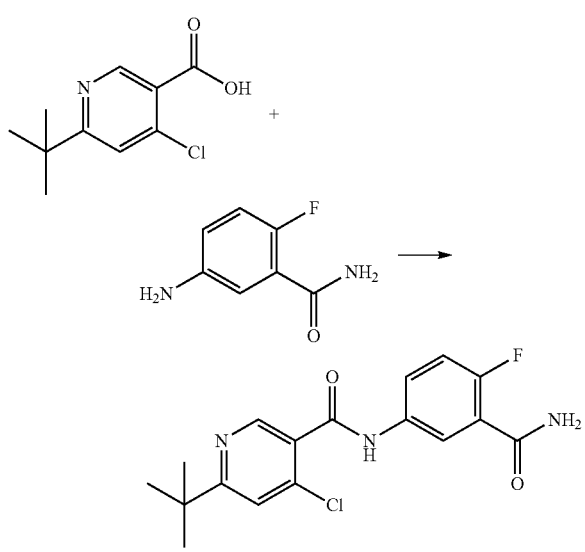

6-tert-Butyl-4-chloro-pyridine-3-carboxylic acid (207 mg, 0.97 mmol), 5-amino-2-fluoro-benzamide (180 mg, 1.17 mmol), triethylamine (900 μL, 6.46 mmol) and 2,4,6-tripropyl-1,3,5,2,4,6-trioxatriphosphinane 2,4,6-trioxide (2 mL of 50% w/v, 3.14 mmol) in isopropyl acetate (5 mL) was stirred at room temperature for 4 hours. The mixture was concentrated in vacuo and residue was partitioned between DCM and saturated aqueous sodium bicarbonate. Layers were separated and the organics dried over magnesium sulfate, filtered and concentrated in vacuo to afford 6-tert-butyl-N-(3-carbamoyl-4-fluoro-phenyl)-4-chloro-pyridine-3-carboxamide (340 mg, 100%) as a colourless oil. ESI-MS m/z calc. 349.10, found 350.2 (M+1)+; 348.2 (M−1)−; Retention time (Method F): 0.8 minutes (1.5 minutes run).

Step 3: 6-tert-butyl-N-(3-carbamoyl-4-fluoro-phenyl)-4-(4-fluoro-2-methoxy-phenyl)pyridine-3-carboxamide (199)

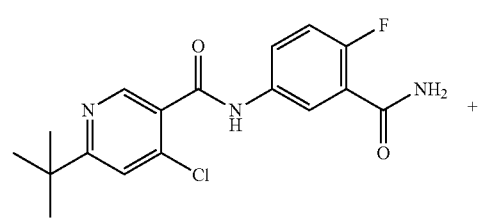

6-tert-Butyl-N-(3-carbamoyl-4-fluoro-phenyl)-4-chloro-pyridine-3-carboxamide (149 mg, 0.43 mmol), (4-fluoro-2-methoxy-phenyl)boronic acid (107 mg, 0.63 mmol), Pd(PPh$_3$)$_4$ (28 mg, 0.02 mmol), sodium carbonate (650 μL of 2 M, 1.30 mmol) in dioxane (4 mL) was heated for 1 hour at 140° C. in a microwave. The mixture was concentrated in vacuo and the residue was purified by HPLC (0-100% acetonitrile/water/0.05% TFA) followed by purification by HPLC (37-100% acetonitrile/water/0.1% ammonium hydroxide) to afford 6-tert-butyl-N-(3-carbamoyl-4-fluoro-phenyl)-4-(4-fluoro-2-methoxy-phenyl)pyridine-3-carboxamide (24 mg, 13%). ESI-MS m/z calc. 439.17, found 440.3 (M+1)+; 438.3 (M−1)−; Retention time (Method E): 2.96 minutes (5 minutes run). $^1$H NMR (500 MHz, DMSO-d6) δ 10.43 (s, 1H), 8.66 (s, 1H), 7.90 (dd, J=6.5, 2.8 Hz, 1H), 7.67 (ddd, J=9.0, 4.4, 2.8 Hz, 2H), 7.61 (s, 1H), 7.42-7.31 (m, 2H), 7.21 (dd, J=10.2, 8.9 Hz, 1H), 6.91-6.81 (m, 2H), 3.55 (s, 3H), 1.36 (s, 9H) ppm.

Example 190

N-(3-carbamoyl-4-fluoro-phenyl)-5-(4-fluoro-2-methoxy-phenyl)-2-(trifluoromethyl)pyridine-4-carboxamide (200)

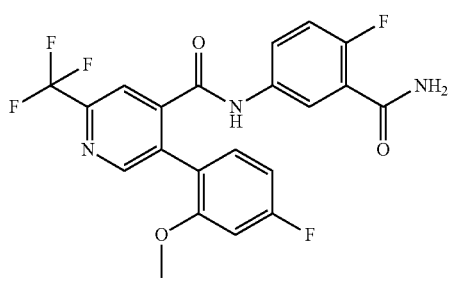 [SMILES: COc1cc(F)ccc1-c1cnc(C(F)(F)F)cc1C(=O)Nc1ccc(F)c(C(N)=O)c1]

Step 1: 5-bromo-N-(3-carbamoyl-4-fluoro-phenyl)-2-(trifluoromethyl)pyridine-4-carboxamide

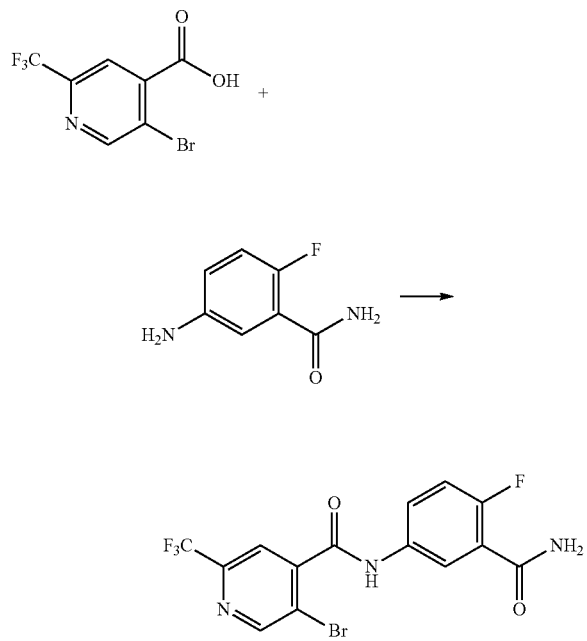

5-Bromo-2-(trifluoromethyl)pyridine-4-carboxylic acid (107 mg, 0.40 mmol), 5-amino-2-fluoro-benzamide (71 mg, 0.46 mmol), triethylamine (350 μL, 2.51 mmol) and 2,4,6-tripropyl-1,3,5,2,4,6-trioxatriphosphinane 2,4,6-trioxide (800 μL of 50% w/v, 1.26 mmol) in isopropyl acetate (2 mL) was stirred at room temperature for 1 hour. The mixture was concentrated in vacuo and the residue was partitioned between DCM and saturated aqueous sodium bicarbonate. Layers were separated and the organic layer dried over magnesium sulfate, filtered and concentrated in vacuo to afford 5-bromo-N-(3-carbamoyl-4-fluoro-phenyl)-2-(trifluoromethyl)pyridine-4-carboxamide (161 mg, 100%) as a colourless oil. ESI-MS m/z calc. 404.97, found 408.1 (M+1)+; Retention time (Method F): 0.74 minutes (1.5 minutes run).

Step 2: N-(3-carbamoyl-4-fluoro-phenyl)-5-(4-fluoro-2-methoxy-phenyl)-2-(trifluoromethyl)pyridine-4-carboxamide (200)

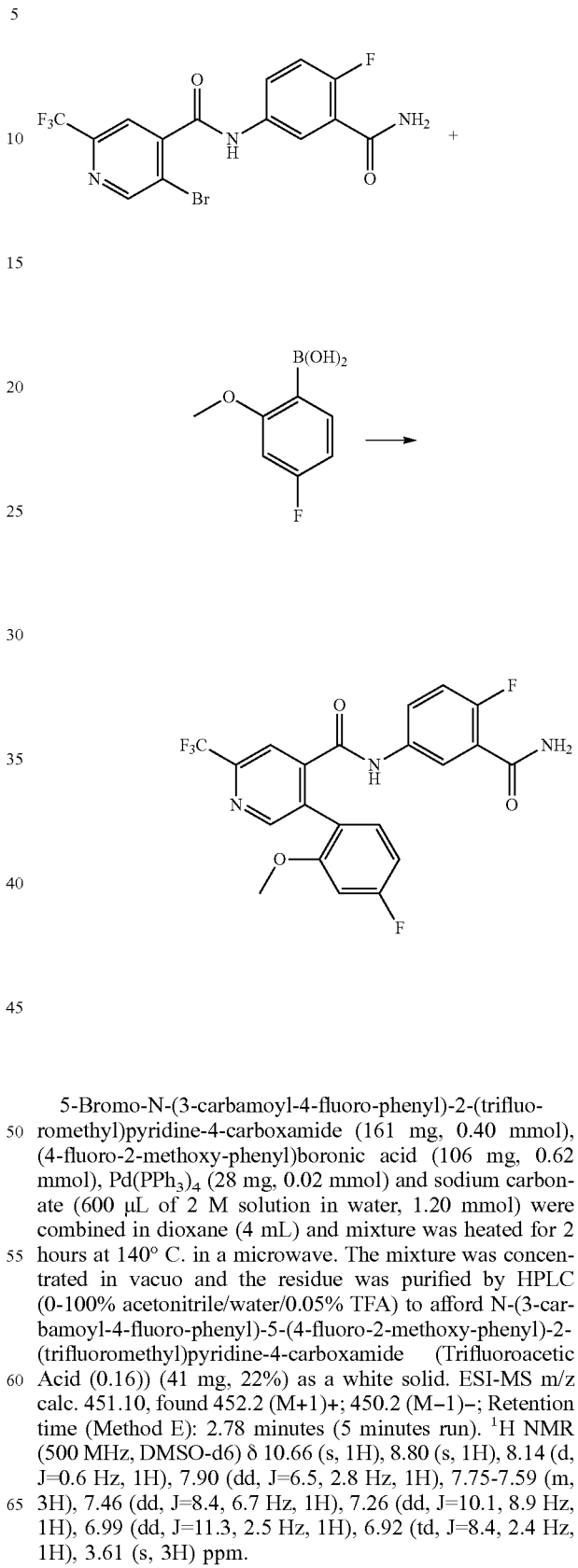

5-Bromo-N-(3-carbamoyl-4-fluoro-phenyl)-2-(trifluoromethyl)pyridine-4-carboxamide (161 mg, 0.40 mmol), (4-fluoro-2-methoxy-phenyl)boronic acid (106 mg, 0.62 mmol), Pd(PPh$_3$)$_4$ (28 mg, 0.02 mmol) and sodium carbonate (600 μL of 2 M solution in water, 1.20 mmol) were combined in dioxane (4 mL) and mixture was heated for 2 hours at 140° C. in a microwave. The mixture was concentrated in vacuo and the residue was purified by HPLC (0-100% acetonitrile/water/0.05% TFA) to afford N-(3-carbamoyl-4-fluoro-phenyl)-5-(4-fluoro-2-methoxy-phenyl)-2-(trifluoromethyl)pyridine-4-carboxamide (Trifluoroacetic Acid (0.16)) (41 mg, 22%) as a white solid. ESI-MS m/z calc. 451.10, found 452.2 (M+1)+; 450.2 (M−1)−; Retention time (Method E): 2.78 minutes (5 minutes run). $^1$H NMR (500 MHz, DMSO-d6) δ 10.66 (s, 1H), 8.80 (s, 1H), 8.14 (d, J=0.6 Hz, 1H), 7.90 (dd, J=6.5, 2.8 Hz, 1H), 7.75-7.59 (m, 3H), 7.46 (dd, J=8.4, 6.7 Hz, 1H), 7.26 (dd, J=10.1, 8.9 Hz, 1H), 6.99 (dd, J=11.3, 2.5 Hz, 1H), 6.92 (td, J=8.4, 2.4 Hz, 1H), 3.61 (s, 3H) ppm.

Example 191

N-(3-carbamoyl-4-fluoro-phenyl)-2-fluoro-6-[[6-(trifluoromethoxy)-3-pyridyl]oxy]-3-(trifluoromethyl)benzamide (69)

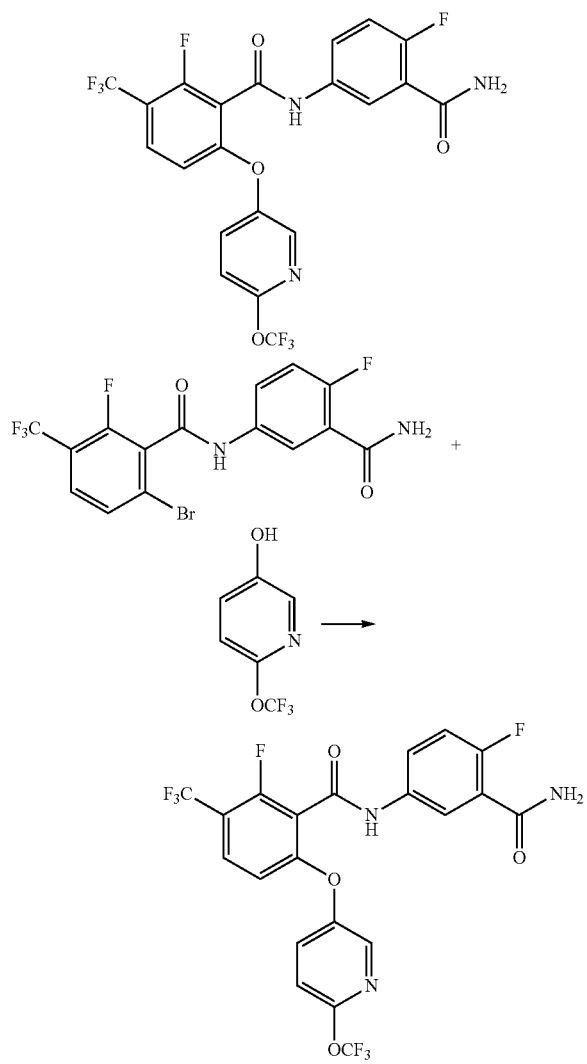

6-Bromo-N-(3-carbamoyl-4-fluoro-phenyl)-2-fluoro-3-(trifluoromethyl)benzamide (150 mg, 0.35 mmol, prepared as described in Example 140), cesium carbonate (231 mg, 0.71 mmol) and 6-(trifluoromethoxy)pyridin-3-ol (74.69 mg, 0.35 mmol) were combined in degassed toluene (1.5 mL). To this mixture was then added copper iodide (14 mg, 0.07 mmol) and the reaction was stirred at 100° C. for 20 minutes in a microwave. The reaction was diluted with ethyl acetate and water. The organic layer was washed with brine and dried over sodium sulfate then concentrated in vacuo. The residue was triturated with hexane and filtered to afford N-(3-carbamoyl-4-fluoro-phenyl)-2-fluoro-6-[[6-(trifluoromethoxy)-3-pyridyl]oxy]-3-(trifluoromethyl)benzamide (44 mg, 23%). ESI-MS m/z calc. 521.06, found 522.1 (M+1)+; Retention time (Method B): 1.69 minutes (3 minutes run). $^1$H NMR (400 MHz, DMSO-d6) δ 11.08 (s, 1H), 8.34 (d, J=3.0 Hz, 1H), 7.97-7.80 (m, 3H), 7.80-7.63 (m, 3H), 7.44 (d, J=8.9 Hz, 1H), 7.30 (dd, J=10.1, 9.0 Hz, 1H), 7.04 (d, J=8.8 Hz, 1H) ppm.

Example 192

4-[[2-fluoro-6-[3-fluoro-4-(trifluoromethoxy)phenoxy]-3-(trifluoromethyl)benzoyl]amino]pyridine-2-carboxamide (57)

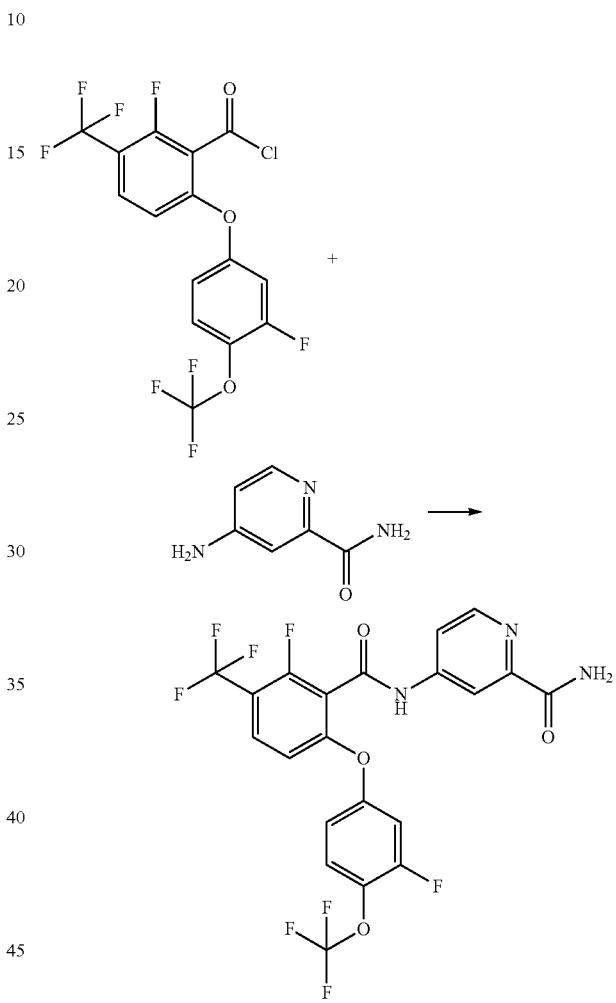

To 4-aminopyridine-2-carboxamide (98 mg, 0.71 mmol), DMAP (17 mg, 0.14 mmol) and N-ethyl-N-isopropyl-propan-2-amine (276 mg, 373 μL, 2.14 mmol) in DCM (3 mL), cooled to 0° C. and was added dropwise a solution of 2-fluoro-6-[3-fluoro-4-(trifluoromethoxy)phenoxy]-3-(trifluoromethyl)benzoyl chloride (300 mg, 0.71 mmol) in DCM (3 mL). The reaction was stirred at room temperature for 18 hours. Mixture was concentrated in vacuo and purified by silica gel chromatography (0-40% ethyl acetate/hexanes) to afford 4-[[2-fluoro-6-[3-fluoro-4-(trifluoromethoxy)phenoxy]-3-(trifluoromethyl)benzoyl]amino]pyridine-2-carboxamide (28 mg, 7%). ESI-MS m/z calc. 521.06, found 522.1 (M+1)+; Retention time (Method B): 1.81 minutes (3 minutes run). $^1$H NMR (400 MHz, DMSO-d6) δ 11.46 (s, 1H), 8.56 (d, J=5.5 Hz, 1H), 8.28 (d, J=2.0 Hz, 1H), 8.12 (d, J=2.7 Hz, 1H), 7.94 (t, J=8.6 Hz, 1H), 7.79 (dd, J=5.5, 2.2 Hz, 1H), 7.73-7.62 (m, 2H), 7.51 (dd, J=11.1, 2.8 Hz, 1H), 7.17 (ddd, J=9.1, 2.9, 1.6 Hz, 1H), 7.10 (d, J=8.9 Hz, 1H) ppm.

Example 193

4-[[4-Chloro-3-(difluoromethyl)-2-fluoro-6-[3-fluoro-2-(trideuteriomethoxy)-4-(trifluoromethoxy)phenoxy]benzoyl]amino]pyridine-2-carboxamide (234)

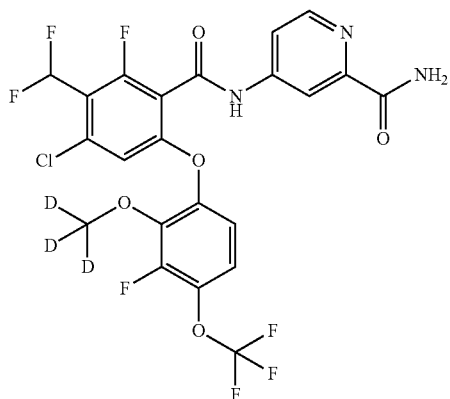

Step 1: Methyl 4-chloro-2-fluoro-6-[3-fluoro-2-(trideuteriomethoxy)-4-(trifluoromethoxy)phenoxy]-3-formyl-benzoate

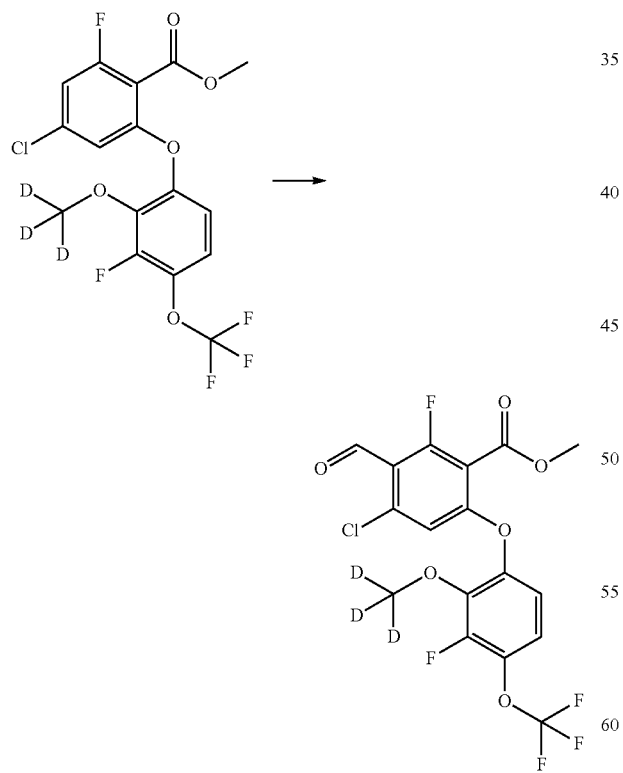

LDA (4.8 mL of 2 M, 9.6 mmol) was added dropwise to a solution of methyl 4-chloro-2-fluoro-6-[3-fluoro-2-(trideuteriomethoxy)-4-(trifluoromethoxy)phenoxy]benzoate (prepared as described in Example 177, Step 2, 3.49 g, 8.41 mmol) in THF (40 mL) at −78° C. The reaction was stirred at this temperature for 30 minutes then DMF (34 mL, 439 mmol) was added dropwise over 15 minutes and the mixture was stirred at −78° C. for 30 minutes. The reaction was quenched by the addition of water and was extracted with ethyl acetate (×3). The combined organic extracts were dried over MgSO$_4$, filtered and concentrated in vacuo to afford methyl 4-chloro-2-fluoro-6-[3-fluoro-2-(trideuteriomethoxy)-4-(trifluoromethoxy)phenoxy]-3-formyl-benzoate (3.92 g, 105%), which was used in the next step without purification. ESI-MS m/z calc. 443.03, found 442.1 (M−1)−; Retention time (Method F): 1.08 minutes (1.5 minutes run).

Step 2: Methyl 4-chloro-3-(difluoromethyl)-2-fluoro-6-[3-fluoro-2-(trideuteriomethoxy)-4-(trifluoromethoxy)phenoxy]benzoate

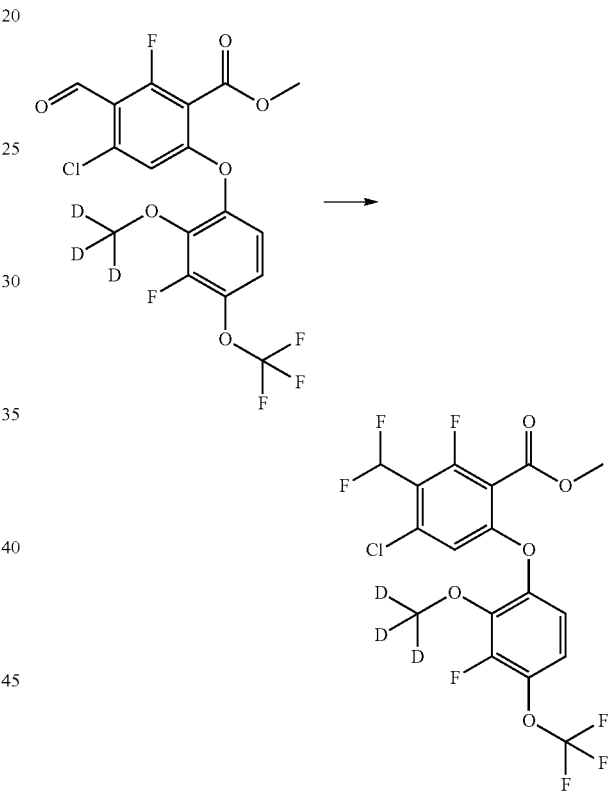

Deoxofluor (11.2 g, 50.7 mmol) in DCM (20 mL) was added to a solution of methyl 4-chloro-2-fluoro-6-[3-fluoro-2-(trideuteriomethoxy)-4-(trifluoromethoxy)phenoxy]-3-formyl-benzoate (3.73 g, 8.40 mmol) in DCM (25 mL) and the reaction mixture was stirred at room temperature overnight. The reaction was quenched by pouring onto saturated aqueous sodium bicarbonate and was stirred for 30 minutes at room temperature. The layers were separated and the aqueous was extracted with DCM (2×). Combined organic extracts were washed with water then brine and concentrated in vacuo to afford methyl 4-chloro-3-(difluoromethyl)-2-fluoro-6-[3-fluoro-2-(trideuteriomethoxy)-4-(trifluoromethoxy)phenoxy]benzoate (3.96 g, 101%) as an orange oil, which was used in the next step without purification.

Step 3: 4-Chloro-3-(difluoromethyl)-2-fluoro-6-[3-fluoro-2-(trideuteriomethoxy)-4-(trifluoromethoxy)phenoxy]benzoic acid

Step 4: Methyl 4-[[4-chloro-3-(difluoromethyl)-2-fluoro-6-[3-fluoro-2-(trideuteriomethoxy)-4-(trifluoromethoxy)phenoxy]benzoyl]amino]pyridine-2-carboxylate

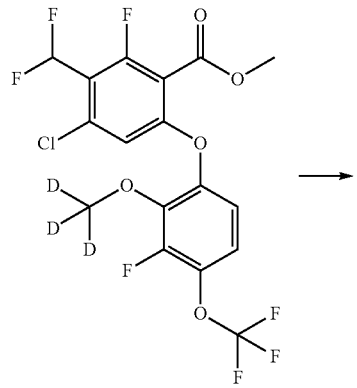

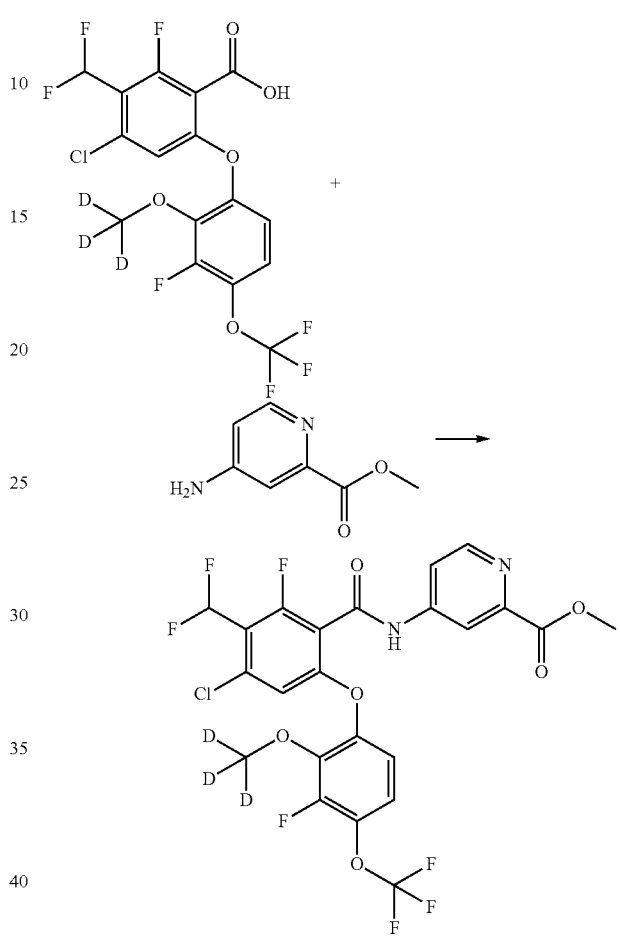

To a solution of methyl 4-chloro-3-(difluoromethyl)-2-fluoro-6-[3-fluoro-2-(trideuteriomethoxy)-4-(trifluoromethoxy)phenoxy]benzoate (3.9 g, 8.37 mmol) in THF (90 mL) was added NaOH (40 mL of 2 M, 80 mmol) and the reaction mixture was stirred at 70° C. overnight. The reaction was cooled to room temperature and concentrated in vacuo. The residue was taken up in water and acidified with 2 M HCl. The mixture was extracted with ethyl acetate (×3) and the combined organic extracts were dried over MgSO$_4$, filtered and concentrated in vacuo to afford 4-chloro-3-(difluoromethyl)-2-fluoro-6-[3-fluoro-2-(trideuteriomethoxy)-4-(trifluoromethoxy)phenoxy]benzoic acid (4.02 g, 106%) as an orange oil, which was used in the next step without purification.

To an ice-cooled solution of 4-chloro-3-(difluoromethyl)-2-fluoro-6-[3-fluoro-2-(trideuteriomethoxy)-4-(trifluoromethoxy)phenoxy]benzoic acid (500 mg, 1.11 mmol) in DCM (17 mL) was added DMF (24 μL, 0.31 mmol) and dropwise oxalyl dichloride (303 μL, 3.47 mmol) and was stirred for 1 hour. The reaction mixture was concentrated in vacuo to afford the acid chloride. A solution of the acid chloride in DCM (17 mL) was then added dropwise to an ice-cooled solution of methyl 4-aminopyridine-2-carboxylate (208 mg, 1.37 mmol) and N-ethyl-N-isopropyl-propan-2-amine (1.3 mL, 7.52 mmol) and was stirred at room temperature for 72 hours. The mixture was concentrated in vacuo and the residue was separated between 2 N aqueous NaOH and ethyl acetate. The organic layer was washed with 1 M citric acid, then brine, dried over MgSO$_4$, filtered and concentrated in vacuo. The product was purified by HPLC (37-100% acetonitrile/water/0.1% ammonium hydroxide) to provide methyl 4-[[4-chloro-3-(difluoromethyl)-2-fluoro-6-[3-fluoro-2-(trideuteriomethoxy)-4-(trifluoromethoxy)phenoxy]benzoyl]amino]pyridine-2-carboxylate (40 mg, 6%) as a white solid. ESI-MS m/z calc. 585.06, found 586.7 (M+1)+; Retention time (Method F): 0.98 minutes (1.5 minutes run)

691

Step 5: 4-[[4-Chloro-3-(difluoromethyl)-2-fluoro-6-[3-fluoro-2-(trideuteriomethoxy)-4-(trifluoromethoxy)phenoxy]benzoyl]amino]pyridine-2-carboxamide (234)

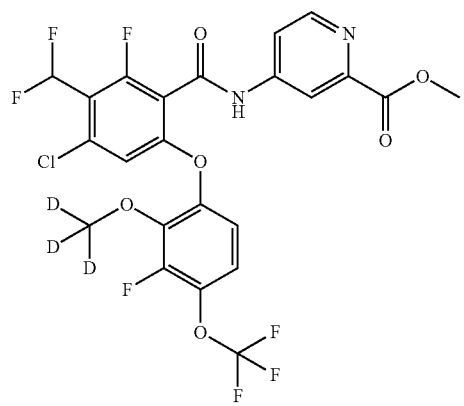

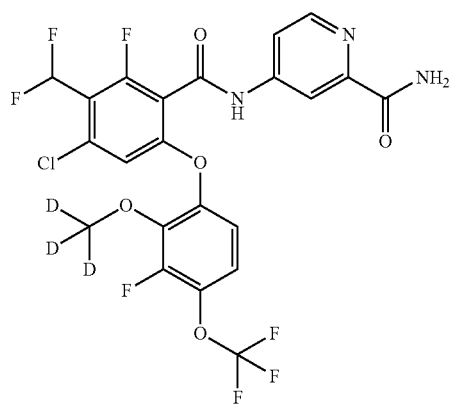 [SMILES: [2H]C([2H])([2H])Oc1c(Oc2cc(Cl)c(C(F)F)c(F)c2C(=O)Nc2ccnc(C(N)=O)c2)ccc(OC(F)(F)F)c1F]

A solution of methyl 4-[[4-chloro-3-(difluoromethyl)-2-fluoro-6-[3-fluoro-2-(trideuteriomethoxy)-4-(trifluoromethoxy)phenoxy]benzoyl]amino]pyridine-2-carboxylate (40 mg, 0.07 mmol) and 7 M ammonia in methanol (2.5 mL of 7 M, 17.5 mmol) was stirred at room temperature for 24 hours. The reaction mixture was concentrated in vacuo and purified by HPLC (37-100% acetonitrile/water/0.1% ammonium hydroxide) to provide 4-[[4-chloro-3-(difluoromethyl)-2-fluoro-6-[3-fluoro-2-(trideuteriomethoxy)-4-(trifluoromethoxy)phenoxy]benzoyl]amino]pyridine-2-carboxamide (234, 9 mg, 23%). ESI-MS m/z calc. 570.06, found 571.7 (M+1)+; Retention time (Method E): 3.34 minutes (5 minutes run). $^1$H NMR (500 MHz, DMSO-d6) δ 11.45 (s, 1H), 8.56 (d, J=5.5 Hz, 1H), 8.30 (d, J=2.1 Hz, 1H), 8.10 (d, J=2.8 Hz, 1H), 7.80 (d, J=5.2 Hz, 1H), 7.66 (s, 1H), 7.38 (t, J=53 Hz, 1H), 7.37 (m, 1H), 7.20 (dd, J=9.4, 2.0 Hz, 1H), 7.13 (m, 1H) ppm.

692

Example 194

4-[[3-(Difluoromethyl)-2-fluoro-6-[3-fluoro-2-(trideuteriomethoxy)-4-(trifluoromethoxy) phenoxy]benzoyl]amino]pyridine-2-carboxamide (235)

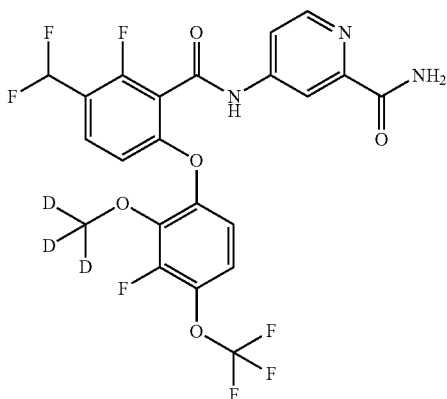

Step 1: 3-(Difluoromethyl)-2-fluoro-6-[3-fluoro-2-(trideuteriomethoxy)-4-(trifluoromethoxy) phenoxy]benzoic acid A suspension of 6-bromo-3-(difluoromethyl)-2-fluorobenzoic acid (prepared as described in Example 75, Step 2, 1 g, 3.7 mmol), 3-fluoro-2-(trideuteriomethoxy)-4-(trifluoromethoxy)phenol (prepared as described in Example 169, Step 2, 941 mg, 4.11 mmol) and cesium carbonate (2.7 g, 8.29 mmol) in toluene (20 mL) was heated to 100° C. and then copper (I) iodide (145 mg, 0.76 mmol) was added. The mixture was heated at 100° C. for 3 hours. The cooled reaction mixture was concentrated in vacuo then diluted with ethyl acetate and water then acidified to pH 2 with 2 M HCl. The mixture was extracted with ethyl acetate (2×100 mL). The combined organics were washed with water (2×100 mL), brine (100 mL), dried over MgSO$_4$, filtered and concentrated in vacuo to provide 3-(difluoromethyl)-2-fluoro-6-[3-fluoro-2-(trideuteriomethoxy)-4-(trifluoromethoxy)phenoxy]benzoic acid (1.48 g, 95%) as a brown gummy solid, which was used in the next step without purification. ESI-MS m/z calc. 417.05, found 416.7 (M−1)−; Retention time (Method F): 0.61 minutes (5 minutes run). Retention time: 0.61 minutes (1.5 minutes run). $^1$H NMR (400 MHz, DMSO-d6) δ 13.90 (s, 1H), 7.71-7.62 (m, 1H), 7.41-7.32 (m, 1H), 7.32-7.14 (m, 1H), 7.15-7.06 (m, 1H), 6.89-6.82 (m, 1H) ppm.

Step 2: Methyl 4-[[3-(difluoromethyl)-2-fluoro-6-[3-fluoro-2-(trideuteriomethoxy)-4-(trifluoromethoxy)phenoxy]benzoyl]amino]pyridine-2-carboxylate

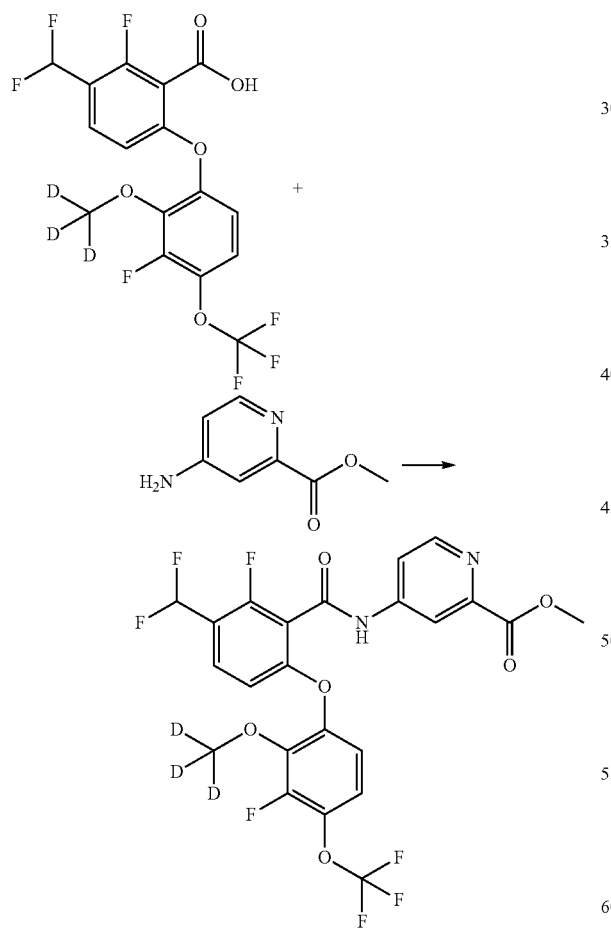

To an ice-cooled solution of 3-(difluoromethyl)-2-fluoro-6-[3-fluoro-2-(trideuteriomethoxy)-4-(trifluoromethoxy)phenoxy]benzoic acid (300 mg, 0.72 mmol) in DCM (5 mL) was added DMF (9.3 µL, 0.12 mmol) and dropwise oxalyl dichloride (295 µL, 3.38 mmol) and was stirred for 2 hours. The reaction mixture was concentrated in vacuo to afford the acid chloride as a pale yellow oil. The residue was dissolved in DCM (5 mL) and added dropwise to a solution of methyl 4-aminopyridine-2-carboxylate (HCl salt) (290 mg, 1.54 mmol) and TEA (950 µL, 6.82 mmol) in DCM (5 mL) in an ice bath. The resulting mixture was stirred and warmed to room temperature overnight. The reaction mixture was concentrated in vacuo to afford methyl 4-[[3-(difluoromethyl)-2-fluoro-6-[3-fluoro-2-(trideuteriomethoxy)-4-(trifluoromethoxy)phenoxy]benzoyl]amino]pyridine-2-carboxylate (380 mg, 96%) as a brown oil, which was used in the next step without purification. ESI-MS m/z calc. 551.10, found 552.3 (M+1)+; Retention time (Method F): 0.93 minutes (1.5 minutes run).

Step 3: 4-[[3-(Difluoromethyl)-2-fluoro-6-[3-fluoro-2-(trideuteriomethoxy)-4-(trifluoromethoxy)phenoxy]benzoyl]amino]pyridine-2-carboxamide (235)

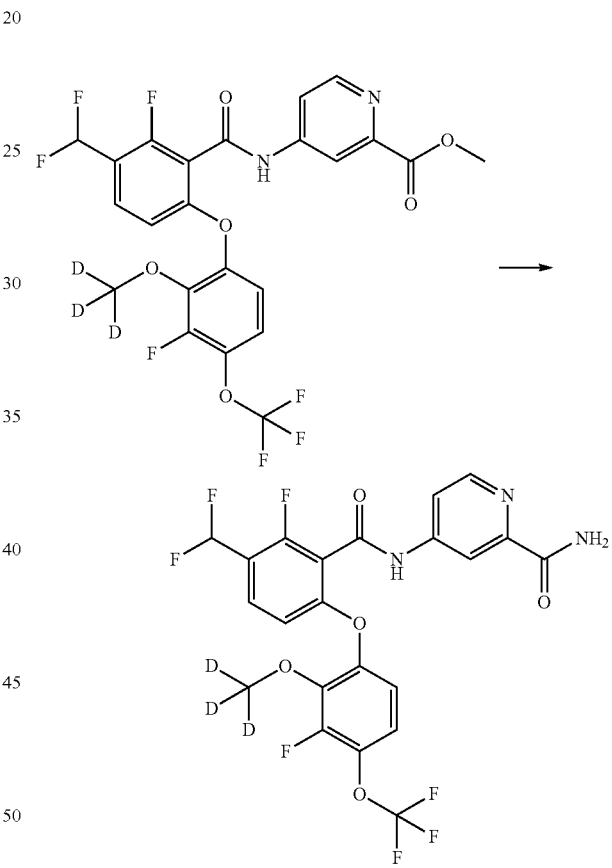

Methyl 4-[[3-(difluoromethyl)-2-fluoro-6-[3-fluoro-2-(trideuteriomethoxy)-4-(trifluoromethoxy)phenoxy]benzoyl]amino]pyridine-2-carboxylate (380 mg, 0.69 mmol) was dissolved in 7 M ammonia in methanol (5 mL of 7 M, 35 mmol) and stirred at room temperature overnight. The reaction mixture was concentrated in vacuo and the residue was purified by HPLC (37-100% acetonitrile/water/0.1% ammonium hydroxide) to provide 4-[[3-(difluoromethyl)-2-fluoro-6-[3-fluoro-2-(trideuteriomethoxy)-4-(trifluoromethoxy)phenoxy]benzoyl]amino]pyridine-2-carboxamide (235, 74 mg, 19%) as a white solid. ESI-MS m/z calc. 536.10, found 537.7 (M+1)+; 535.8 (M−1)−; Retention time (Method E): 3.18 minutes (5 minutes run). $^1$H NMR (400 MHz, DMSO-d6) δ 11.44 (s, 1H), 8.56 (d, J=5.5 Hz, 1H), 8.33 (d, J=2.1 Hz, 1H), 8.10 (d, J=2.7 Hz, 1H), 7.82 (dd, J=5.5, 2.2 Hz, 1H), 7.73 (t, J=8.4 Hz, 1H), 7.66 (d, J=2.9 Hz, 1H), 7.41-7.35 (m, 1H), 7.26 (s, 1H), 7.20-7.10 (m, 1H), 6.89 (d, J=8.7 Hz, 1H) ppm.

Example 195

5-[[3-(Difluoromethyl)-2-fluoro-6-[3-fluoro-2-(trideuteriomethoxy)-4-(trifluoromethoxy) phenoxy] benzoyl]amino]pyridine-2-carboxamide (236)

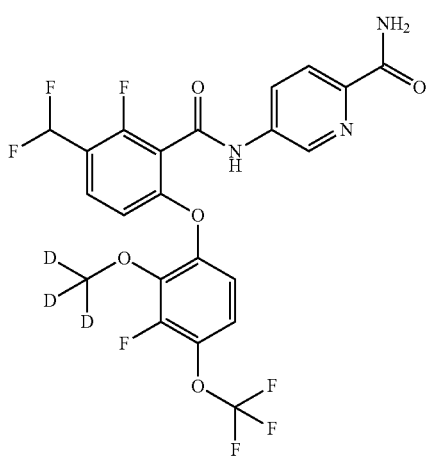 [SMILES: [2H]C([2H])([2H])Oc1c(Oc2ccc(C(F)F)c(F)c2C(=O)Nc2ccc(C(N)=O)nc2)ccc(OC(F)(F)F)c1F]

Step 1: Methyl 5-[[3-(difluoromethyl)-2-fluoro-6-[3-fluoro-2-(trideuteriomethoxy)-4-(trifluoromethoxy)phenoxy]benzoyl]amino]pyridine-2-carboxylate

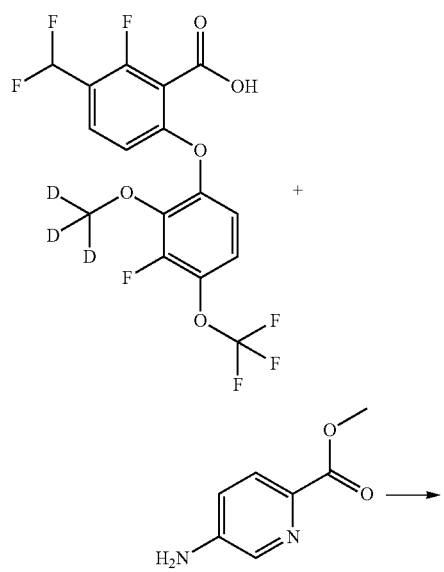

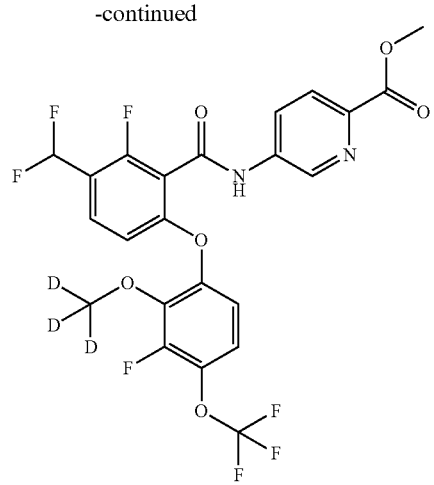

To an ice-cooled solution of 3-(difluoromethyl)-2-fluoro-6-[3-fluoro-2-(trideuteriomethoxy)-4-(trifluoromethoxy)phenoxy]benzoic acid (prepared as described in Example 194, Step 1, 300 mg, 0.72 mmol) in DCM (5 mL) was added DMF (9.3 µL, 0.12 mmol) and dropwise oxalyl dichloride (295 µL, 3.38 mmol) and was stirred for 2 hours. The reaction mixture was concentrated in vacuo to afford the acid chloride as a pale yellow oil. The residue was dissolved in DCM (5 mL) and added dropwise to a solution of methyl 5-aminopyridine-2-carboxylate (HCl salt) (290 mg, 1.54 mmol) and TEA (950 µL, 6.82 mmol) in DCM (5 mL) in an ice bath. The resulting mixture was stirred and warmed to room temperature overnight. The reaction mixture was concentrated in vacuo then partitioned between ethyl acetate and water. The organic portion was dried over MgSO$_4$, filtered and concentrated in vacuo to afford methyl 5-[[3-(difluoromethyl)-2-fluoro-6-[3-fluoro-2-(trideuteriomethoxy)-4-(trifluoromethoxy)phenoxy]benzoyl]amino]pyridine-2-carboxylate (500 mg, 63%) as a brown oil, which was used in the next step without purification. ESI-MS m/z calc. 551.10, found 552.8 (M+1)+; Retention time (Method F): 0.95 minutes (1.5 minutes run).

Step 2: 5-[[3-(Difluoromethyl)-2-fluoro-6-[3-fluoro-2-(trideuteriomethoxy)-4-(trifluoromethoxy)phenoxy]benzoyl]amino]pyridine-2-carboxamide (236)

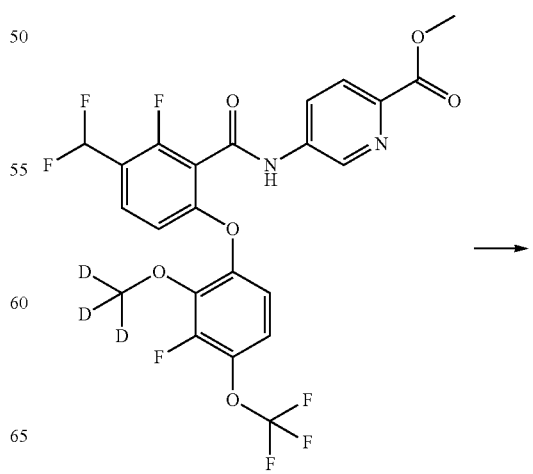

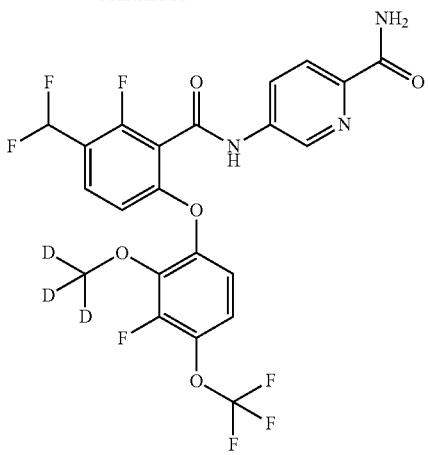

Methyl 5-[[3-(difluoromethyl)-2-fluoro-6-[3-fluoro-2-(trideuteriomethoxy)-4-(trifluoromethoxy)phenoxy]benzoyl]amino]pyridine-2-carboxylate (380 mg, 0.3446 mmol) was dissolved in 7 M ammonia in methanol (6 mL of 7 M, 42 mmol) and stirred at room temperature overnight. The reaction mixture was concentrated in vacuo and the residue was purified by HPLC (37-100% acetonitrile/water/0.1% ammonium hydroxide) to provide 5-[[3-(difluoromethyl)-2-fluoro-6-[3-fluoro-2-(trideuteriomethoxy)-4-(trifluoromethoxy)phenoxy]benzoyl]amino]pyridine-2-carboxamide (236, 63 mg, 34%) as a white solid. ESI-MS m/z calc. 536.10, found 537.7 (M+1)+; 535.7 (M−1)−; Retention time (Method E): 3.12 minutes (5 minutes run). $^1$H NMR (400 MHz, CDCl$_3$) δ 9.32 (s, 1H), 8.80 (d, J=2.4 Hz, 1H), 8.32 (dd, J=8.6, 2.5 Hz, 1H), 8.11 (d, J=8.5 Hz, 1H), 7.73 (d, J=4.1 Hz, 1H), 7.57 (t, J=8.1 Hz, 1H), 7.15-7.00 (m, 2H), 6.84 (t, J=54.8 Hz, 1H), 6.66 (d, J=8.8 Hz, 1H), 5.87 (d, J=4.2 Hz, 1H) ppm.

Example 196

4-[[3-(Difluoromethyl)-2-fluoro-6-[3-fluoro-2-(trideuteriomethoxy)-4-(trifluoromethoxy) phenoxy] benzoyl]amino]-5-methyl-pyridine-2-carboxamide (237)

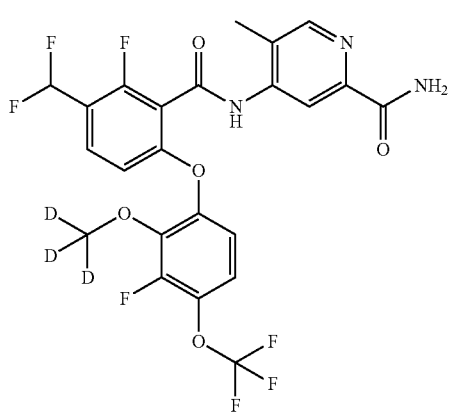

Step 1: N-(2-bromo-5-methyl-4-pyridyl)-3-(difluoromethyl)-2-fluoro-6-[3-fluoro-2-(trideuteriomethoxy)-4-(trifluoromethoxy)phenoxy]benzamide

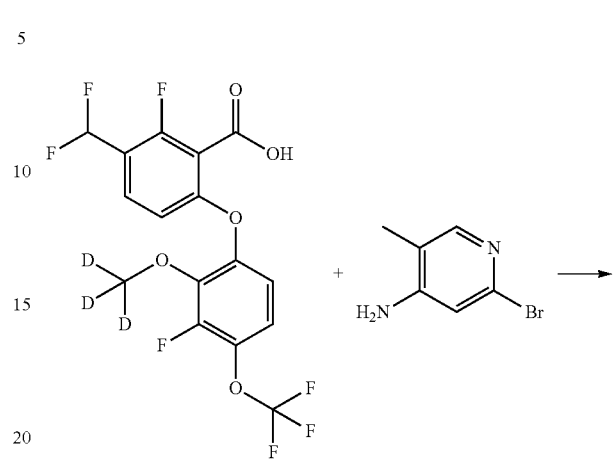

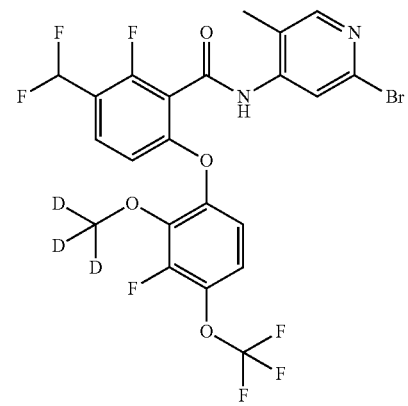

To an ice-cooled solution of 3-(difluoromethyl)-2-fluoro-6-[3-fluoro-2-(trideuteriomethoxy)-4-(trifluoromethoxy) phenoxy]benzoic acid (prepared as described in Example 194, Step 1, 300 mg, 0.72 mmol) in DCM (5 mL) was added DMF (9.3 μL, 0.12 mmol) and dropwise oxalyl dichloride (295 μL, 3.382 mmol) and was stirred for 2 hours. The reaction mixture was concentrated in vacuo to afford the acid chloride as a pale yellow oil. The residue was dissolved in DCM (5 mL) and added dropwise to a solution of 2-bromo-5-methyl-pyridin-4-amine (HCl salt) (290 mg, 1.30 mmol) and triethylamine (950 μL, 6.82 mmol) in DCM (5 mL) in an ice bath. The resulting mixture was stirred and warmed to room temperature overnight. The reaction mixture was concentrated in vacuo then purified by column chromatography (ethyl acetate/heptane) to afford N-(2-bromo-5-methyl-4-pyridyl)-3-(difluoromethyl)-2-fluoro-6-[3-fluoro-2-(trideuteriomethoxy)-4-(trifluoromethoxy)phenoxy]benzamide (100 mg, 24%) as a brown gummy solid. ESI-MS m/z calc. 585.02, found 588.7 (M+1)+; Retention time (Method F): 1.07 minutes (1.5 minutes run). $^1$H NMR (400 MHz, CDCl$_3$) δ 8.45 (s, 1H), 8.16 (s, 1H), 8.07-8.00 (m, 1H), 7.54 (ddt, J=8.6, 7.6, 1.0 Hz, 1H), 7.04 (ddq, J=8.8, 7.5, 1.2 Hz, 1H), 6.97-6.93 (m, 1H), 6.85-6.66 (m, 1H), 6.57 (dd, J=8.7, 1.2 Hz, 1H), 2.09 (d, J=0.8 Hz, 3H) ppm.

Step 2: Methyl 4-[[3-(difluoromethyl)-2-fluoro-6-[3-fluoro-2-(trideuteriomethoxy)-4-(trifluoromethoxy)phenoxy]benzoyl]amino]-5-methyl-pyridine-2-carboxylate Step 3: 4-[[3-(difluoromethyl)-2-fluoro-6-[3-fluoro-2-(trideuteriomethoxy)-4-(trifluoromethoxy)phenoxy]benzoyl]amino]-5-methyl-pyridine-2-carboxamide (37)

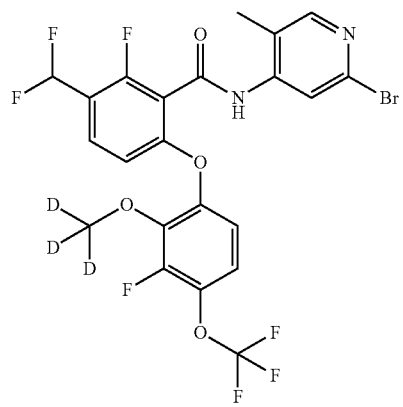

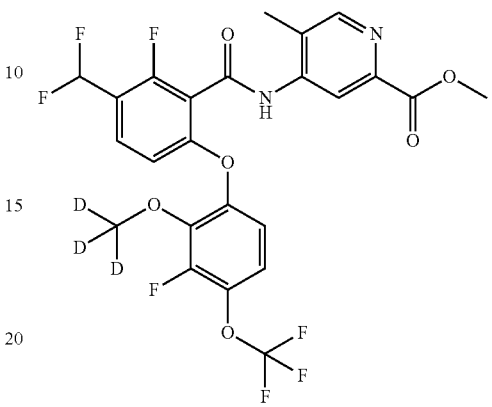

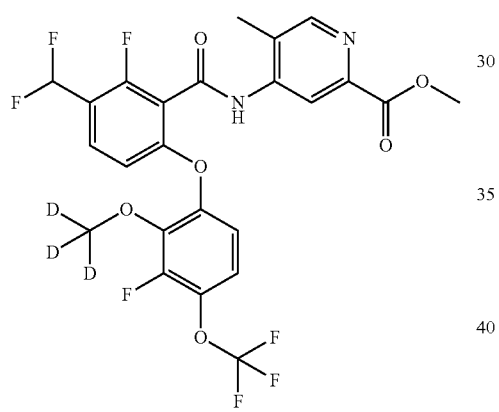

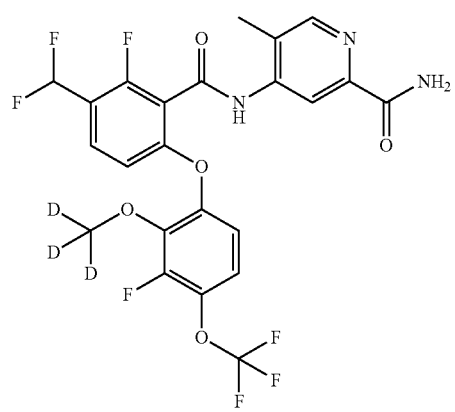 [SMILES: [2H]C([2H])([2H])Oc1c(Oc2ccc(C(F)F)c(F)c2C(=O)Nc2cc(C(N)=O)ncc2C)ccc(OC(F)(F)F)c1F]

In a pressure tube, N-(2-bromo-5-methyl-4-pyridyl)-3-(difluoromethyl)-2-fluoro-6-[3-fluoro-2-(trideuteriomethoxy)-4-(trifluoromethoxy)phenoxy]benzamide (100 mg, 0.17 mmol) was dissolved in methanol (5 mL) and triethylamine (55 µL, 0.39 mmol) and Pd(dppf)Cl$_2$·DCM (40 mg, 0.049 mmol) were added. CO was bubbled through the reaction mixture for 5 minutes whilst being vigorously stirred at room temperature. The reaction mixture was sealed and heated to 75° C. overnight, then cooled to room temperature and concentrated in vacuo to afford methyl 4-[[3-(difluoromethyl)-2-fluoro-6-[3-fluoro-2-(trideuteriomethoxy)-4-(trifluoromethoxy)phenoxy]benzoyl]amino]-5-methyl-pyridine-2-carboxylate (90 mg, 93%), which was used in the next step without purification. ESI-MS m/z calc. 565.12, found 566.7 (M+1)+; 564.7 (M−1)−; Retention time (Method F). 0.95 minutes (1.5 minutes run).

Methyl 4-[[3-(difluoromethyl)-2-fluoro-6-[3-fluoro-2-(trideuteriomethoxy)-4-(trifluoromethoxy)phenoxy]benzoyl]amino]-5-methyl-pyridine-2-carboxylate (90 mg, 0.16 mmol) was dissolved in 7 M ammonia in methanol (5 mL of 7 M, 35 mmol) and stirred at room temperature for 90 minutes, then at 40° C. for 2 hours. The reaction mixture was concentrated in vacuo and the residue was purified by HPLC (37-100% acetonitrile/water/0.1% ammonium hydroxide) to provide 4-[[3-(difluoromethyl)-2-fluoro-6-[3-fluoro-2-(trideuteriomethoxy)-4-(trifluoromethoxy)phenoxy]benzoyl]amino]-5-methyl-pyridine-2-carboxamide (237, 9 mg, 9%). ESI-MS m/z calc. 550.12, found 551.1 (M+1)+; 549.0 (M−1)−; Retention time (Method E): 3.21 minutes (5 minutes run). $^1$H NMR (500 MHz, DMSO-d$_6$) δ 10.61 (s, 1H), 8.46 (d, J=13.4 Hz, 2H), 8.05 (d, J=2.7 Hz, 1H), 7.72 (t, J=8.3 Hz, 1H), 7.60 (s, 1H), 7.43-7.36 (m, 1H), 7.27 (s, 1H), 7.18 (dd, J=9.6, 2.2 Hz, 1H), 6.89 (d, J=8.7 Hz, 1H), 2.30 (s, 3H) ppm.

Example 197

4-[[3-chloro-2-fluoro-6-[3-fluoro-2-(trideuteri-omethoxy)-4-(trifluoromethoxy)phenoxy]benzoyl]amino]-5-methyl-pyridine-2-carboxamide (240)

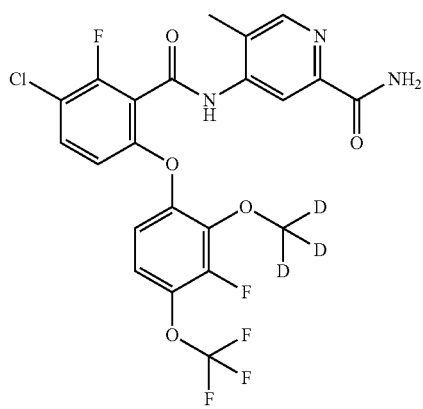 [SMILES: [2H]C([2H])([2H])Oc1c(Oc2ccc(Cl)c(F)c2C(=O)Nc2cc(C(N)=O)ncc2C)ccc(OC(F)(F)F)c1F]

Step 1: 6-Bromo-3-chloro-2-fluoro-benzoic acid

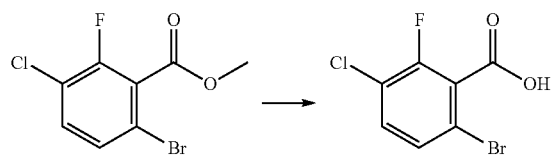

To a solution of methyl 6-bromo-3-chloro-2-fluoro-benzoate (500 mg, 1.87 mmol) in methanol (10 mL) was added lithium hydroxide (5 mL of 2 M, 10 mmol) and the reaction mixture was stirred at 50° C. for 1 hour. The reaction mixture was cooled to room temperature and concentrated in vacuo. The residue was taken up in water and acidified with 2 M HCl. The mixture was extracted with ethyl acetate (×3) and the combined organic extracts were dried over MgSO$_4$, filtered and concentrated in vacuo to provide 6-bromo-3-chloro-2-fluoro-benzoic acid (470 mg, 99%) as a white crystalline solid. $^1$H NMR (400 MHz, DMSO-d6) δ 14.38 (s, 1H), 7.71-7.56 (m, 2H) ppm.

Step 2: 3-chloro-2-fluoro-6-[3-fluoro-2-(trideuteri-omethoxy)-4-(trifluoromethoxy) phenoxy]benzoic acid

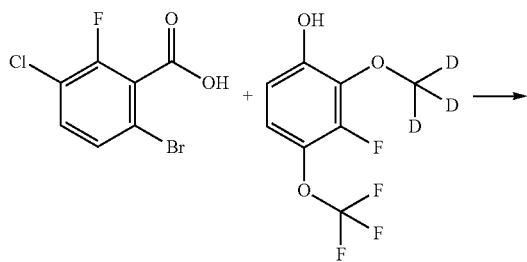

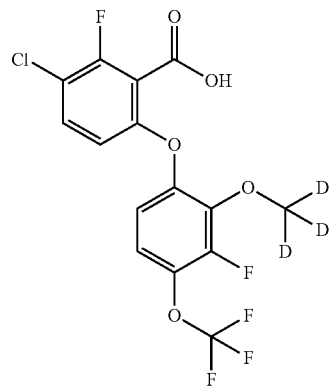

A suspension of 6-bromo-3-chloro-2-fluoro-benzoic acid (245 mg, 0.97 mmol), 3-fluoro-2-(trideuteriomethoxy)-4-(trifluoromethoxy)phenol (235 mg, 1.03 mmol) and cesium carbonate (670 mg, 2.06 mmol) in toluene (5 mL) was heated to 100° C. then copper (I) iodide (36 mg, 0.19 mmol) was added and the mixture was stirred at 100° C. overnight. The reaction mixture was cooled to room temperature then acidified to pH 2 with 2 M HCl. The mixture was extracted with ethyl acetate (2×100 mL). The organics were combined and washed with water (2×100 mL), brine (100 mL), dried over MgSO$_4$, filtered and concentrated in vacuo to afford 3-chloro-2-fluoro-6-[3-fluoro-2-(trideuteriomethoxy)-4-(trifluoromethoxy)phenoxy]benzoic acid (335 mg, 86%) as a brown gummy solid. $^1$H NMR (400 MHz, CDCl3) δ 7.43 (dd, J=9.0, 8.0 Hz, 1H), 7.06 (ddq, J=9.0, 7.7, 1.2 Hz, 1H), 6.90 (dd, J=9.2, 2.3 Hz, 1H), 6.57 (dd, J=9.0, 1.6 Hz, 1H) ppm.

Step 3: N-(2-bromo-5-methyl-4-pyridyl)-3-chloro-2-fluoro-6-[3-fluoro-2-(trideuteriomethoxy)-4-(trifluoromethoxy)phenoxy]benzamide

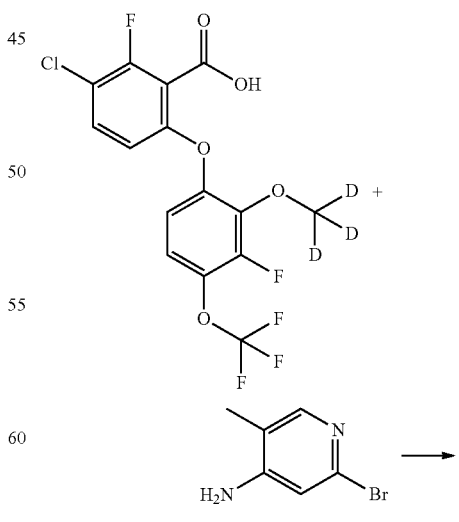

703

-continued

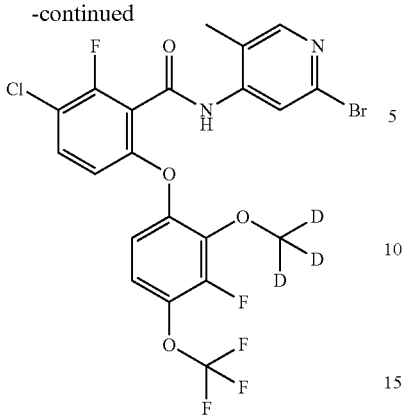

To an ice-cooled solution of 3-chloro-2-fluoro-6-[3-fluoro-2-(trideuteriomethoxy)-4-(trifluoromethoxy)phenoxy]benzoic acid (335 mg, 0.83 mmol) in DCM (6 mL) was added DMF (11 μL, 0.14 mmol) and dropwise oxalyl dichloride (350 μL, 4.01 mmol) and was stirred for 2 hours. The reaction mixture was concentrated in vacuo to afford the acid chloride as a pale yellow oil. The residue was dissolved in DCM (6 mL) and added dropwise to a solution of 2-bromo-5-methyl-pyridin-4-amine (HCl salt) (336 mg, 1.50 mmol) and TEA (1.1 mL, 7.9 mmol) in DCM (6 mL) in an ice bath. The resulting mixture was stirred and warmed to room temperature overnight. The reaction mixture was concentrated in vacuo and purified by silica gel chromatography (ethyl acetate/heptane) to afford N-(2-bromo-5-methyl-4-pyridyl)-3-chloro-2-fluoro-6-[3-fluoro-2-(trideuteriomethoxy)-4-(trifluoromethoxy)phenoxy]benzamide (100 mg, 21%) as a brown waxy solid. ESI-MS m/z calc. 568.99, found 572.5 (M+1)+; 570.5 (M−1)−; Retention time (Method F): 1.05 minutes (1.5 minutes run). $^1$H NMR (400 MHz, CDCl3) δ 8.49 (s, 1H), 8.08 (d, J=6.2 Hz, 2H), 7.35 (dd, J=9.0, 7.9 Hz, 1H), 7.02 (ddd, J=9.0, 7.7, 1.2 Hz, 1H), 6.92 (dd, J=9.2, 2.2 Hz, 1H), 6.48 (ddd, J=9.0, 3.4, 1.6 Hz, 1H), 2.09 (d, J=0.7 Hz, 3H) ppm.

Step 4: methyl 4-[[3-chloro-2-fluoro-6-[3-fluoro-2-(trideuteriomethoxy)-4-(trifluoromethoxy)phenoxy]benzoyl]amino]-5-methyl-pyridine-2-carboxylate In a pressure tube, N-(2-bromo-5-methyl-4-pyridyl)-3-chloro-2-fluoro-6-[3-fluoro-2-(trideuteriomethoxy)-4-(trifluoromethoxy)phenoxy]benzamide (100 mg, 0.17 mmol) was dissolved in methanol (5 mL) and triethylamine (40 mg, 0.39 mmol) and Pd(dppf)Cl$_2$·DCM (40 mg, 0.049 mmol) were added. CO was bubbled through the reaction mixture for 5 minutes whilst being vigorously stirred at room temperature. The reaction mixture was sealed and heated to 75° C. overnight, then cooled to room temperature and concentrated in vacuo to afford methyl 4-[[3-chloro-2-fluoro-6-[3-fluoro-2-(trideuteriomethoxy)-4-(trifluoromethoxy)phenoxy]benzoyl]amino]-5-methyl-pyridine-2-carboxylate (95 mg, 99%). ESI-MS m/z calc. 549.08, found 550.7 (M+1)+; 548.7 (M−1)−; Retention time (Method F): 0.96 minutes (1.5 minutes run).

704

Step 5: 4-[[3-chloro-2-fluoro-6-[3-fluoro-2-(trideuteriomethoxy)-4-(trifluoromethoxy)phenoxy]benzoyl]amino]-5-methyl-pyridine-2-carboxamide (240)

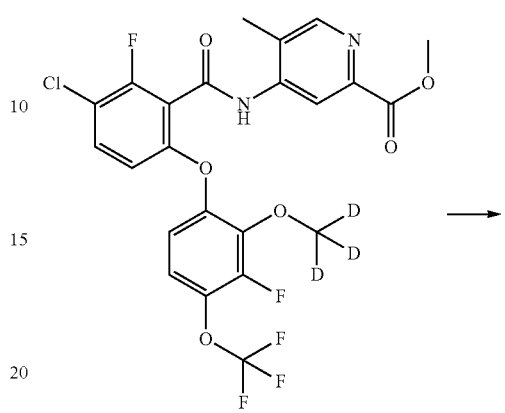

Methyl 4-[[3-chloro-2-fluoro-6-[3-fluoro-2-(trideuteriomethoxy)-4-(trifluoromethoxy)phenoxy]benzoyl]amino]-5-methyl-pyridine-2-carboxylate (95 mg, 0.17 mmol) was dissolved in ammonia (5 mL of 7 M in methanol, 35 mmol) and stirred at room temperature for 90 minutes, then at 40° C. for 2 hours. The reaction mixture was concentrated in vacuo and the residue was purified by HPLC (37-100% acetonitrile/water/0.1% ammonium hydroxide) to afford 4-[[3-chloro-2-fluoro-6-[3-fluoro-2-(trideuteriomethoxy)-4-(trifluoromethoxy)phenoxy]benzoyl]amino]-5-methyl-pyridine-2-carboxamide (240, 5 mg, 5%). ESI-MS m/z calc. 534.08, found 534.9 (M+1)+; 533.2 (M−1)−; Retention time (Method E): 3.21 minutes (5 minutes run). $^1$H NMR (400 MHz, DMSO-d6) δ 10.56 (s, 1H), 8.45 (d, J=16.6 Hz, 2H), 8.05 (s, 1H), 7.70 (t, J=8.7 Hz, 1H), 7.62-7.57 (m, 1H), 7.36 (t, J=8.6 Hz, 1H), 7.09 (dd, J=9.3, 2.1 Hz, 1H), 6.89 (dd, J=9.0, 1.4 Hz, 1H), 2.28 (s, 3H) ppm.

Example 198

4-[[2-fluoro-6-[3-fluoro-4-(trifluoromethoxy)phenoxy]-3-(trifluoromethoxy)benzoyl]amino]pyridine-2-carboxamide (241)

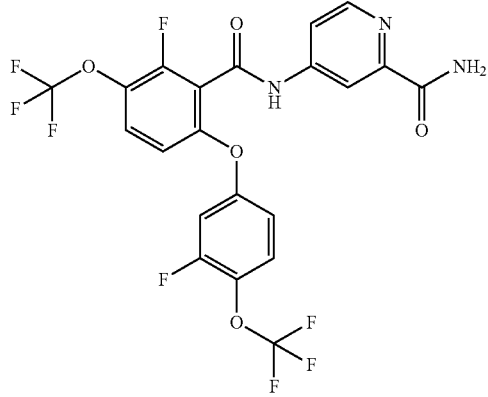 [SMILES: NC(=O)c1cc(NC(=O)c2c(Oc3ccc(OC(F)(F)F)c(F)c3)ccc(OC(F)(F)F)c2F)ccn1]

Step 1: 2-Fluoro-6-[3-fluoro-4-(trifluoromethoxy)phenoxy]-3-(trifluoromethoxy)benzoic acid

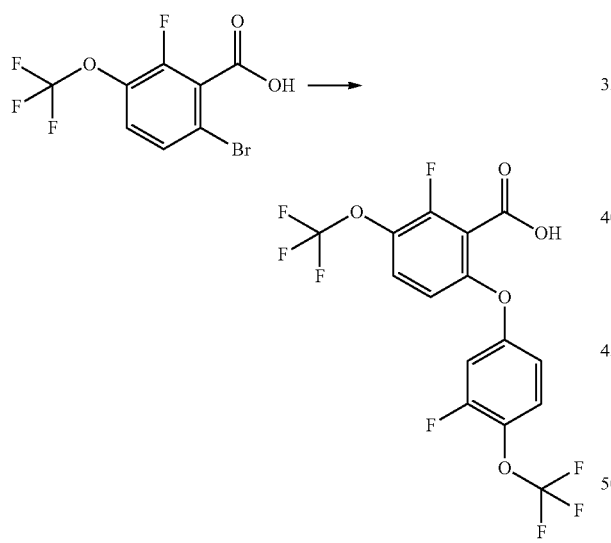

A suspension of 6-bromo-2-fluoro-3-(trifluoromethoxy)benzoic acid (400 mg, 1.32 mmol), 3-fluoro-4-(trifluoromethoxy)phenol (287 mg, 1.46 mmol) and cesium carbonate (950 mg, 2.92 mmol) in toluene (8 mL) was heated to 100° C. then copper (I) iodide (53 mg, 0.28 mmol) was added. The mixture was stirred at 100° C. over the weekend. The reaction mixture was cooled to room temperature then acidified to pH 2 with 2 M HCl. The mixture was extracted with ethyl acetate (2×100 mL). The organics were combined and washed with water (2×100 mL), brine (100 mL), dried over MgSO$_4$, filtered and concentrated in vacuo to afford 2-fluoro-6-[3-fluoro-4-(trifluoromethoxy)phenoxy]-3-(trifluoromethoxy)benzoic acid (500 mg, 91%) as a brown gummy solid. ESI-MS m/z calc. 418.01, found 419.0 (M+1)+; Retention time (Method F): 0.63 minutes (1.5 minutes run).

Step 2: methyl 4-[[2-fluoro-6-[3-fluoro-4-(trifluoromethoxy)phenoxy]-3-(trifluoromethoxy)benzoyl]amino]pyridine-2-carboxylate

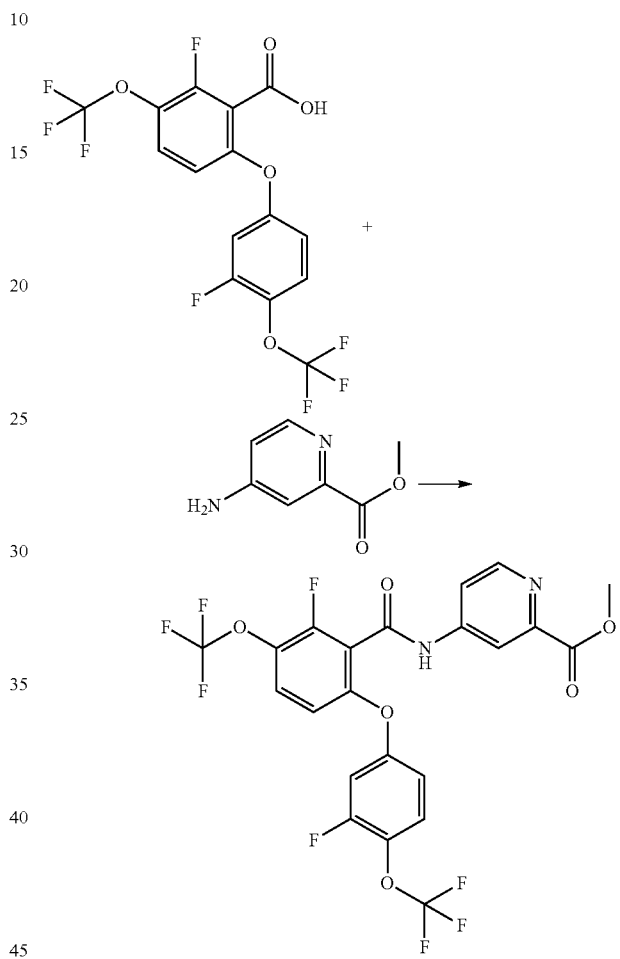

To an ice-cooled solution of 2-fluoro-6-[3-fluoro-4-(trifluoromethoxy)phenoxy]-3-(trifluoromethoxy)benzoic acid (500 mg, 1.20 mmol) in DCM (5 mL) was added DMF (16 µL, 0.21 mmol) and dropwise oxalyl dichloride (500 µL, 5.73 mmol) and the mixture was stirred for 2 hours. The reaction mixture was concentrated in vacuo to afford the acid chloride as a yellow oil. The residue was dissolved in DCM (5 mL) and added dropwise to a solution of methyl 4-aminopyridine-2-carboxylate (330 mg, 2.17 mmol) and triethylamine (1.6 mL, 11.5 mmol) in DCM (5 mL) in an ice bath. The resulting mixture was stirred and warmed to room temperature overnight. The reaction mixture was concentrated in vacuo and purified by silica gel chromatography (ethyl acetate/heptane) to afford methyl 4-[[2-fluoro-6-[3-fluoro-4-(trifluoromethoxy)phenoxy]-3-(trifluoromethoxy)benzoyl]amino]pyridine-2-carboxylate (55 mg, 8%) as a white solid. ESI-MS m/z calc. 552.06, found 553.6 (M+1)+; 551.7 (M−1)−; Retention time (Method F): 0.98 minutes (1.5 minutes run). $^1$H NMR (400 MHz, CDCl3) δ 8.71 (s, 1H), 8.56 (d, J=5.5 Hz, 1H), 8.10 (d, J=2.2 Hz, 1H), 7.94

(dd, J=5.8, 2.1 Hz, 1H), 7.27 (dddt, J=28.5, 9.5, 8.5, 1.1 Hz, 2H), 6.93-6.74 (m, 2H), 6.71 (dd, J=9.2, 1.8 Hz, 1H), 3.87 (s, 3H) ppm.

Step 3: 4-[[2-fluoro-6-[3-fluoro-4-(trifluoromethoxy)phenoxy]-3-(trifluoromethoxy)benzoyl]amino]pyridine-2-carboxamide (241)

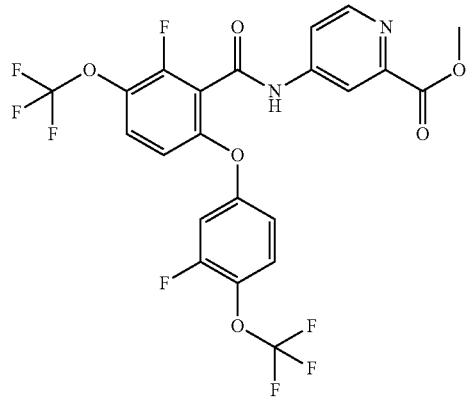

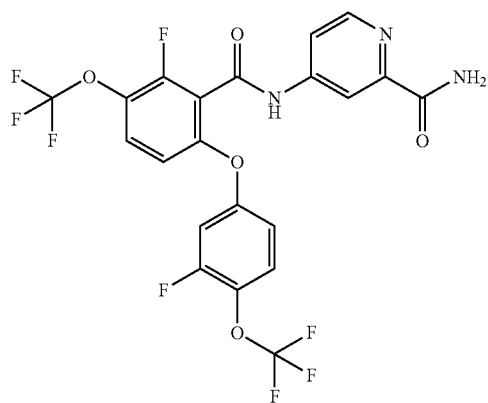

Methyl 4-[[2-fluoro-6-[3-fluoro-4-(trifluoromethoxy)phenoxy]-3-(trifluoromethoxy)benzoyl]amino]pyridine-2-carboxylate (40 mg, 0.07 mmol) was dissolved in ammonia (3 mL of 7 M in methanol, 21 mmol) and stirred at room temperature overnight. The reaction mixture was concentrated in vacuo and the residue was purified by HPLC (37-100% acetonitrile/water/0.1% ammonium hydroxide) to afford 4-[[2-fluoro-6-[3-fluoro-4-(trifluoromethoxy)phenoxy]-3-(trifluoromethoxy)benzoyl]amino]pyridine-2-carboxamide (241, 8.1 mg, 20%). ESI-MS m/z calc. 537.06, found 538.6 (M+1)+; 536.7 (M−1)−; Retention time (Method E): 3.35 minutes (5 minutes run). ¹H NMR (400 MHz, DMSO-d6) δ 11.41 (s, 1H), 8.55 (dd, J=5.4, 0.6 Hz, 1H), 8.26 (dd, J=2.2, 0.6 Hz, 1H), 8.09 (d, J=2.8 Hz, 1H), 7.82-7.72 (m, 2H), 7.69-7.57 (m, 2H), 7.41 (dd, J=11.2, 2.9 Hz, 1H), 7.09 (tt, J=9.0, 2.3 Hz, 2H) ppm.

Example 199

N-(3-carbamoyl-4-methyl-phenyl)-4-[2-methoxy-4-(trifluoromethoxy)phenoxy]-6-(trifluoromethyl)pyridine-3-carboxamide (238)

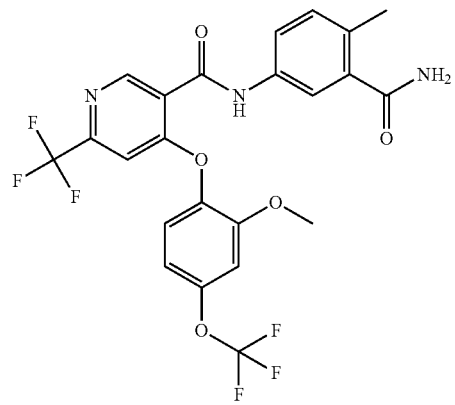 [SMILES: COc1cc(OC(F)(F)F)ccc1Oc1cc(C(F)(F)F)ncc1C(=O)Nc1ccc(C)c(C(N)=O)c1]

This compound was made in an analogous fashion to Example 71, except employing 5-amino-2-methyl-benzamide in the amide formation step (Step 2). The yield of the desired product after purification was 38 mg (60%). ESI-MS m/z calc. 529.11, found 530.2 (M+1)+; retention time (Method B): 1.23 minutes (3 minute run). ¹H NMR (400 MHz, DMSO-d6) δ 10.66 (s, 1H), 8.89 (s, 1H), 7.73 (s, 1H), 7.70 (d, J=2.3 Hz, 1H), 7.64 (dd, J=8.2, 2.4 Hz, 1H), 7.50 (d, J=8.8 Hz, 1H), 7.39 (s, 1H), 7.30 (d, J=2.8 Hz, 1H), 7.22 (d, J=8.3 Hz, 1H), 7.10 (ddd, J=8.8, 2.7, 1.3 Hz, 1H), 6.99 (s, 1H), 3.79 (s, 3H), 2.31 (s, 3H) ppm.

Example 200

N-(3-carbamoyl-4-methoxy-phenyl)-4-[2-methoxy-4-(trifluoromethoxy)phenoxy]-6-(trifluoromethyl)pyridine-3-carboxamide (239)

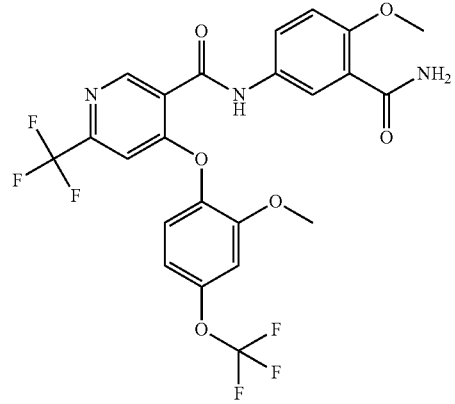 [SMILES: COc1cc(OC(F)(F)F)ccc1Oc1cc(C(F)(F)F)ncc1C(=O)Nc1ccc(OC)c(C(N)=O)c1]

This compound was made in an analogous fashion to Example 71, except employing 5-amino-2-methoxy-benzamide in the amide formation step (Step 2). The yield of the desired product after purification was 34 mg (49%). ESI-MS m/z calc. 545.10, found 546.2 (M+1)+; retention time (Method B): 1.24 minutes (3 minute run). ¹H NMR (400

MHz, DMSO-d6) δ 10.62 (s, 1H), 8.91 (s, 1H), 8.11 (d, J=2.8 Hz, 1H), 7.86 (dd, J=9.0, 2.8 Hz, 1H), 7.68 (s, 1H), 7.59 (s, 1H), 7.50 (d, J=8.8 Hz, 1H), 7.29 (d, J=2.7 Hz, 1H), 7.15 (d, J=9.0 Hz, 1H), 7.09 (ddd, J=8.8, 2.7, 1.3 Hz, 1H), 7.00 (s, 1H), 3.89 (s, 3H), 3.79 (s, 3H) ppm.

Example 201

N-(3-carbamoyl-4-fluoro-phenyl)-3-fluoro-5-[2-methoxy-4-(trifluoromethoxy)phenoxy]-2-(trifluoromethyl)pyridine-4-carboxamide (45)

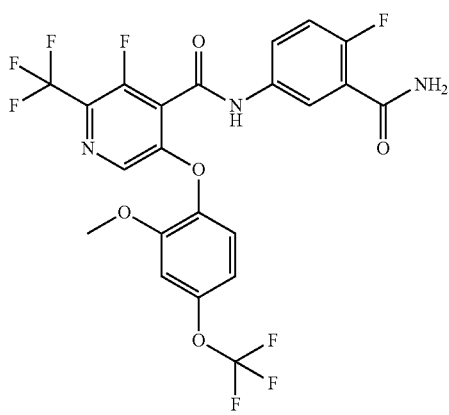 [SMILES: COc1cc(OC(F)(F)F)ccc1Oc1cnc(C(F)(F)F)c(F)c1C(=O)Nc1ccc(F)c(C(N)=O)c1]

This compound was made in an analogous fashion to Example 12, except employing 5-amino-2-fluoro-benzamide in the amide coupling step (Step 4). The yield of the desired product after purification was 40 mg (26%). ESI-MS m/z calc. 551.07, found 552.1 (M+1)+; retention time (Method B): 1.77 minutes (3 minute run). $^1$H NMR (400 MHz, DMSO-d6) δ 11.17 (s, 1H), 8.16 (s, 1H), 7.94 (dd, J=6.3, 2.8 Hz, 1H), 7.79-7.69 (m, 3H), 7.40 (d, J=8.8 Hz, 1H), 7.31 (dd, J=9.9, 9.1 Hz, 1H), 7.25 (d, J=2.6 Hz, 1H), 7.07-6.99 (m, 1H), 3.80 (s, 3H) ppm.

Example 202

4-[[3-chloro-2-fluoro-6-[4-(trifluoromethoxy)phenoxy]benzoyl]amino]-5-methyl-pyridine-2-carboxamide (244)

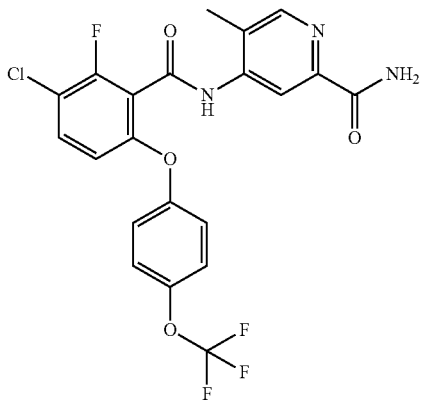 [SMILES: Cc1cnc(C(N)=O)cc1NC(=O)c1c(Oc2ccc(OC(F)(F)F)cc2)ccc(Cl)c1F]

Step 1: N-(2-bromo-5-methyl-4-pyridyl)-3-chloro-2-fluoro-6-[4-(trifluoromethoxy)phenoxy]benzamide

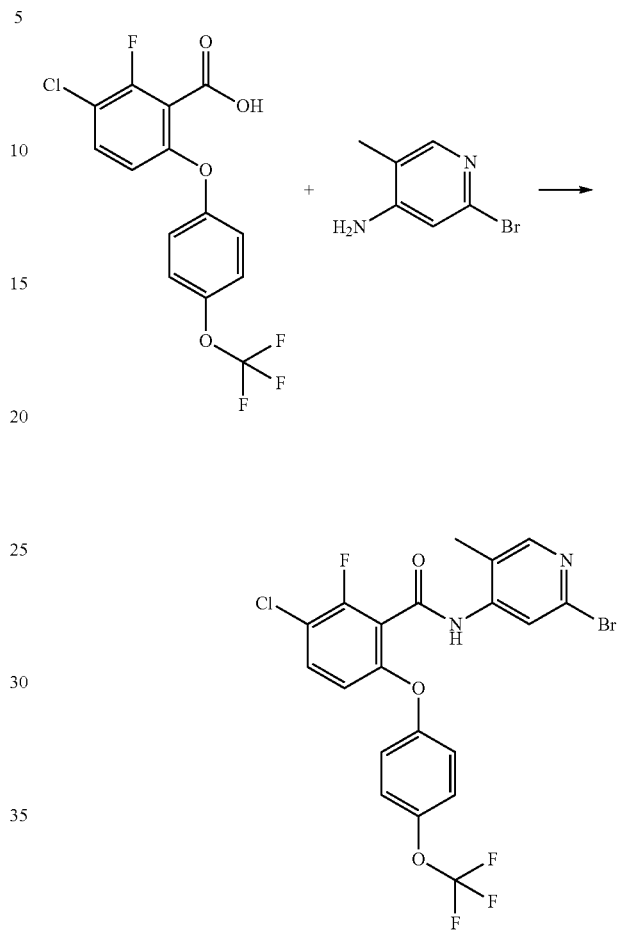

To an ice-cooled solution of 3-chloro-2-fluoro-6-[4-(trifluoromethoxy)phenoxy]benzoic acid (prepared as described in Example 82, Step 2, 300 mg, 0.86 mmol) in DCM (5 mL) was added DMF (12 µL, 0.15 mmol) and dropwise oxalyl dichloride (360 µL, 4.13 mmol) and the mixture was stirred and warmed to room temperature over 2 hours. The reaction mixture was concentrated in vacuo to afford the acid chloride as a pale yellow oil. The residue was dissolved in DCM (5 mL) and added dropwise to a solution of 2-bromo-5-methyl-pyridin-4-amine (HCl salt) (345 mg, 1.54 mmol) and TEA (1.1 mL, 7.9 mmol) in DCM (5 mL) in an ice bath. The resulting mixture was stirred and warmed to room temperature overnight. The reaction mixture was concentrated in vacuo to afford a brown mobile oil, which was purified by silica gel chromatography (ethyl acetate/heptane) to provide a brown gummy solid. The product was re-purified by silica gel chromatography (DCM/methanol) to provide N-(2-bromo-5-methyl-4-pyridyl)-3-chloro-2-fluoro-6-[4-(trifluoromethoxy)phenoxy]benzamide (60 mg, 14%). ESI-MS m/z calc. 517.96, found 521.5 (M+1)+; 519.5 (M−1)−; Retention time (Method F): 1.07 minutes (1.5 minutes run). $^1$H NMR (400 MHz, CDCl$_3$) δ 8.35 (s, 1H), 8.07-7.96 (m, 2H), 7.34 (dd, J=9.0, 8.1 Hz, 1H), 7.22-7.11 (m, 2H), 7.05-6.95 (m, 2H), 6.60 (dd, J=9.0, 1.6 Hz, 1H), 2.09 (d, J=0.8 Hz, 3H) ppm.

Step 2: Methyl 4-[[3-chloro-2-fluoro-6-[4-(trifluoromethoxy)phenoxy]benzoyl]amino]-5-methyl-pyridine-2-carboxylate

Step 3: 4-[[3-chloro-2-fluoro-6-[4-(trifluoromethoxy)phenoxy]benzoyl]amino]-5-methyl-pyridine-2-carboxamide (244)

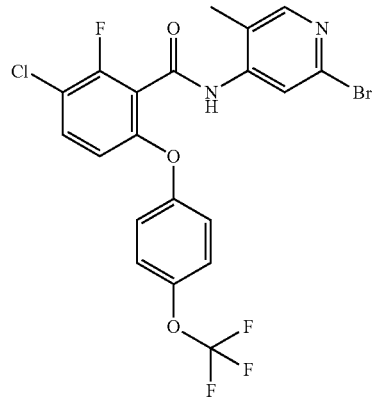

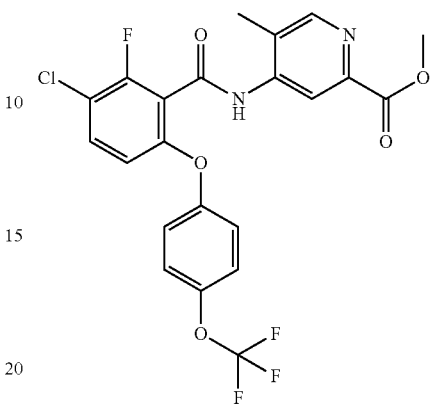

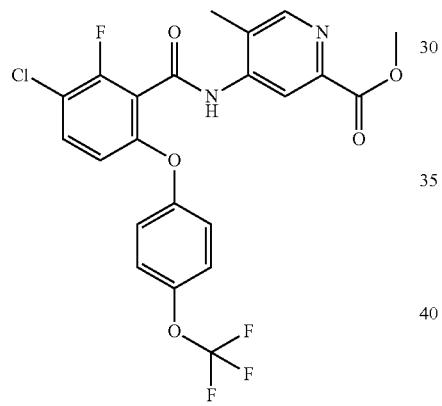

In a pressure tube, N-(2-bromo-5-methyl-4-pyridyl)-3-chloro-2-fluoro-6-[4-(trifluoromethoxy)phenoxy]benzamide (80 mg, 0.15 mmol) was dissolved in methanol (4 mL) and triethylamine (49 µL, 0.35 mmol) and Pd(dppf)Cl$_2$·DCM (35 mg, 0.043 mmol) were added. CO gas was bubbled through the reaction mixture for 5 minutes whilst being vigorously stirred at room temperature. The reaction mixture was sealed and heated to 75° C. overnight, then cooled to room temperature and concentrated in vacuo to afford methyl 4-[[3-chloro-2-fluoro-6-[4-(trifluoromethoxy) phenoxy]benzoyl]amino]-5-methyl-pyridine-2-carboxylate (70 mg, 91%). ESI-MS m/z calc. 498.06, found 499.6 (M+1)+; 497.6 (M−1)−; Retention time (Method F): 0.94 minutes (1.5 minutes run).

Methyl 4-[[3-chloro-2-fluoro-6-[4-(trifluoromethoxy)phenoxy]benzoyl]amino]-5-methyl-pyridine-2-carboxylate (70 mg, 0.14 mmol) was dissolved in ammonia (5 mL of 7 M in methanol, 35 mmol) and was stirred at room temperature overnight. The reaction mixture was concentrated in vacuo and purified by HPLC (37-100% acetonitrile/0.1% ammonium hydroxide) to provide 4-[[3-chloro-2-fluoro-6-[4-(trifluoromethoxy)phenoxy]benzoyl]amino]-5-methyl-pyridine-2-carboxamide (9.4 mg, 13%) as an off-white solid. ESI-MS m/z calc. 483.06, found 484.5 (M+1)+; Retention time (Method E): 3.09 minutes (5 minutes run). $^1$H NMR (400 MHz, DMSO-d$_6$) δ 10.51 (s, 1H), 8.43 (d, J=14.9 Hz, 2H), 8.05 (d, J=2.8 Hz, 1H), 7.73 (t, J=8.8 Hz, 1H), 7.59 (d, J=2.7 Hz, 1H), 7.44 (dq, J=7.7, 1.0 Hz, 2H), 7.31-7.22 (m, 2H), 6.97-6.89 (m, 1H), 2.23 (s, 3H) ppm.

Example 203

4-[[3-chloro-2-fluoro-6-[3-fluoro-4-(trifluoromethoxy)phenoxy]benzoyl]amino]-5-methyl-pyridine-2-carboxamide (245)

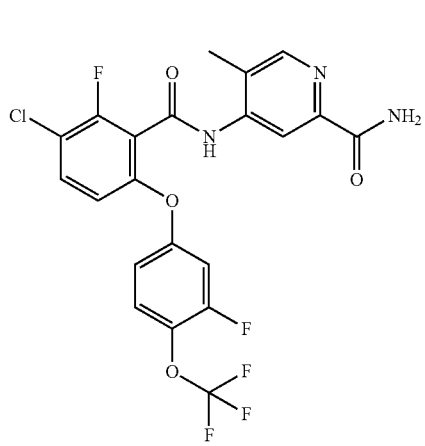 [SMILES: Cc1cnc(C(N)=O)cc1NC(=O)c1c(Oc2ccc(OC(F)(F)F)c(F)c2)ccc(Cl)c1F]

Step 1: 6-bromo-3-chloro-2-fluoro-benzoic acid

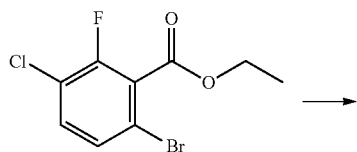

To a solution of methyl 6-bromo-3-chloro-2-fluoro-benzoate (400 mg, 1.50 mmol) in methanol (10 mL) was added lithium hydroxide (5 mL of 2 M, 10 mmol) and the reaction mixture was stirred at 50° C. for 3 hours. The reaction was cooled to ambient temperature and concentrated in vacuo. The residue was taken up in water and acidified with 2 M HCl. The mixture was extracted with ethyl acetate (×3) and the combined organics were dried (MgSO$_4$), filtered and concentrated in vacuo to provide 6-bromo-3-chloro-2-fluoro-benzoic acid (370 mg, 98%) as a white crystalline solid. $^1$H NMR (400 MHz, DMSO-d$_6$) δ 14.38 (s, 1H), 7.66 (dd, J=8.7, 7.7 Hz, 1H), 7.60 (dd, J=8.7, 1.1 Hz, 1H) ppm.

Step 2: 3-chloro-2-fluoro-6-[3-fluoro-4-(trifluoromethoxy)phenoxy]benzoic acid

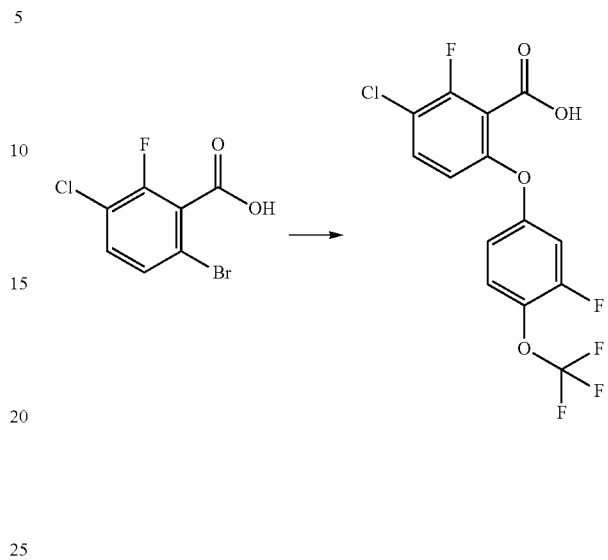

A suspension of 6-bromo-3-chloro-2-fluoro-benzoic acid (370 mg, 1.46 mmol), 3-fluoro-4-(trifluoromethoxy)phenol (337 mg, 1.72 mmol) and cesium carbonate (1.06 g, 3.25 mmol) in toluene (15 mL) was heated to 100° C. Copper (I) iodide (58 mg, 0.30 mmol) was added and the mixture was stirred at 100° C. overnight. The reaction mixture was cooled to room temperature then concentrated in vacuo, taken up in ethyl acetate and water and acidified to pH 2 with 2 M HCl. The mixture was extracted with ethyl acetate (2×100 mL). The organics were combined and washed with water (2×100 mL), brine (100 mL), dried (MgSO$_4$), filtered and concentrated in vacuo to afford 3-chloro-2-fluoro-6-[3-fluoro-4-(trifluoromethoxy) phenoxy]benzoic acid (500 mg, 93%) as a brown gummy solid, which was used in the next step without purification.

Step 3: N-(2-bromo-5-methyl-4-pyridyl)-3-chloro-2-fluoro-6-[3-fluoro-4-(trifluoromethoxy) phenoxy]benzamide

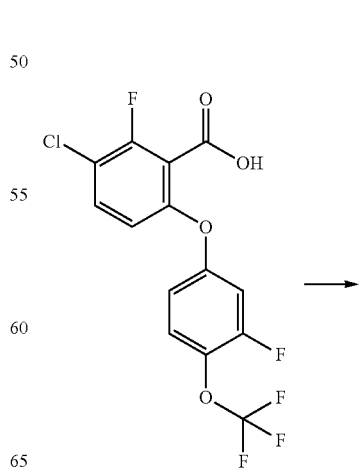

715
-continued

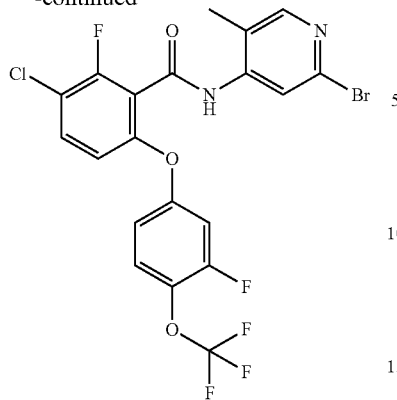

To an ice-cooled solution of 3-chloro-2-fluoro-6-[3-fluoro-4-(trifluoromethoxy)phenoxy]benzoic acid (340 mg, 0.92 mmol) in DCM (5 mL) was added DMF (13 μL, 0.17 mmol) and dropwise oxalyl dichloride (390 μL, 4.47 mmol) and the mixture was stirred for 2 hours. The reaction mixture was concentrated in vacuo to afford the acid chloride as a pale yellow oil. The residue was dissolved in DCM (5 mL) and added dropwise to a solution of 2-bromo-5-methyl-pyridin-4-amine (HCl salt) (370 mg, 1.65 mmol) and triethylamine (1.19 mL, 8.54 mmol) in DCM (5 mL) in an ice bath. The resulting mixture was stirred and warmed to room temperature over the weekend. The reaction mixture was concentrated in vacuo to afford a brown, mobile oil, which was purified by silica gel chromatography (ethyl acetate/heptane) to provide a brown gummy solid. The product was re-purified by silica gel chromatography (DCM/methanol) to provide N-(2-bromo-5-methyl-4-pyridyl)-3-chloro-2-fluoro-6-[3-fluoro-4-(trifluoromethoxy)phenoxy]benzamide (160 mg, 32%). ESI-MS m/z calc. 535.96, found 539.5 (M+1)+; 537.5 (M−1)−; Retention time (Method F): 1.07 minutes (1.5 minutes run). $^1$H NMR (400 MHz, CDCl$_3$) δ 8.81 (d, J=7.6 Hz, 1H), 8.36 (d, J=4.0 Hz, 1H), 8.15-8.10 (m, 1H), 7.45-7.36 (m, 1H), 7.30 (td, J=8.6, 1.2 Hz, 1H), 6.91 (dd, J=10.4, 2.9 Hz, 1H), 6.71 (dd, J=9.0, 1.6 Hz, 1H), 2.21 (d, J=0.7 Hz, 3H) ppm.

Step 4: methyl 4-[[3-chloro-2-fluoro-6-[3-fluoro-4-(trifluoromethoxy)phenoxy]benzoyl]amino]-5-methyl-pyridine-2-carboxylate

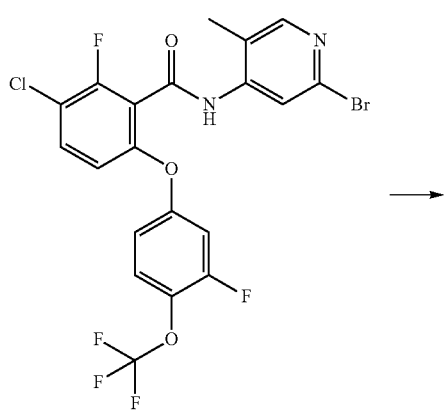

716
-continued

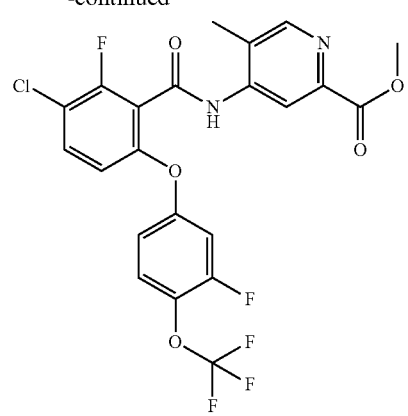

In a pressure tube, N-(2-bromo-5-methyl-4-pyridyl)-3-chloro-2-fluoro-6-[3-fluoro-4-(trifluoromethoxy)phenoxy]benzamide (100 mg, 0.19 mmol) was dissolved in methanol (5 mL) and triethylamine (60 μL, 0.43 mmol) and Pd(dppf)Cl$_2$·DCM (43 mg, 0.053 mmol) were added. CO gas was bubbled through the reaction mixture for 5 minutes whilst being vigorously stirred at room temperature. The reaction mixture was sealed and heated to 75° C. overnight, then cooled to room temperature and concentrated in vacuo. The product was purified by HPLC (37-100% acetonitrile/0.1% ammonium hydroxide) to provide methyl 4-[[3-chloro-2-fluoro-6-[3-fluoro-4-(trifluoromethoxy)phenoxy]benzoyl]amino]-5-methyl-pyridine-2-carboxylate (20 mg, 21%). ESI-MS m/z calc. 516.05, found 517.6 (M+1)+; 515.6 (M−1)−; Retention time (Method F): 0.95 minutes (1.5 minutes run). $^1$H NMR (400 MHz, CDCl$_3$) δ 8.91 (s, 1H), 8.54 (s, 1H), 7.93 (s, 1H), 7.52 (t, J=8.4 Hz, 1H), 7.33 (t, J=8.3 Hz, 1H), 6.95 (d, J=10.3 Hz, 1H), 6.87 (d, J=8.9 Hz, 1H), 6.80 (d, J=8.8 Hz, 1H), 4.00 (s, 3H), 2.34 (s, 3H) ppm.

Step 5: 4-[[3-chloro-2-fluoro-6-[3-fluoro-4-(trifluoromethoxy)phenoxy]benzoyl]amino]-5-methyl-pyridine-2-carboxamide (245)

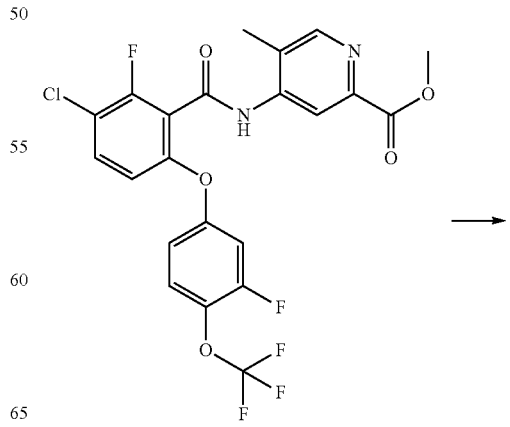

717

-continued

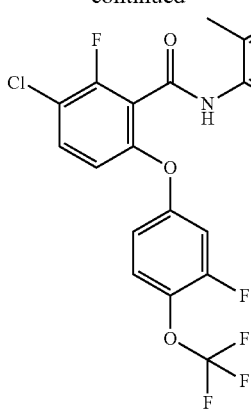

Methyl 4-[[3-chloro-2-fluoro-6-[3-fluoro-4-(trifluoromethoxy)phenoxy]benzoyl]amino]-5-methyl-pyridine-2-carboxylate (20 mg, 0.039 mmol) was dissolved in ammonia (3 mL of 7 M in methanol, 21 mmol) and stirred at room temperature over the weekend. Additional ammonia (2 mL of 7 M in methanol, 14 mmol) was added and the mixture heated to 40° C. overnight. The reaction mixture was concentrated in vacuo and the residue was purified by HPLC (26-100% acetonitrile/0.1% ammonium hydroxide) to provide 4-[[3-chloro-2-fluoro-6-[3-fluoro-4-(trifluoromethoxy)phenoxy]benzoyl]amino]-5-methyl-pyridine-2-carboxamide (10 mg, 50%) as an off-white solid. ESI-MS m/z calc. 501.05, found 502.6 (M+1)+; 500.6 (M−1)−; Retention time (Method E): 3.81 minutes (5 minutes run). $^1$H NMR (400 MHz, DMSO-d$_6$) δ 10.48 (s, 1H), 8.47-8.37 (m, 2H), 8.04 (s, 1H), 7.77 (t, J=8.7 Hz, 1H), 7.68-7.59 (m, 1H), 7.59 (s, 1H), 7.36 (dd, J=11.5, 3.0 Hz, 1H), 7.07 (ddd, J=9.6, 7.2, 1.8 Hz, 2H), 2.19 (d, J=12.2 Hz, 3H) ppm.

Example 204

4-[[3-chloro-2-fluoro-6-[3-fluoro-4-(trifluoromethoxy)phenoxy]benzoyl]amino]-5-methyl-pyridine-2-carboxamide (246)

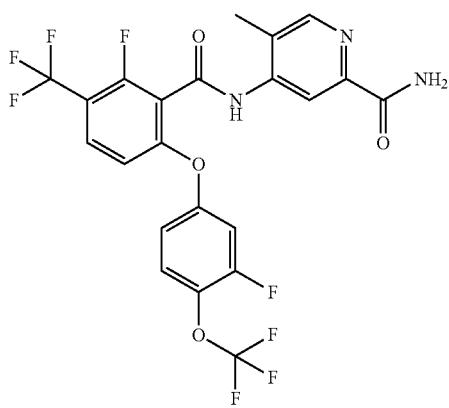 [SMILES: Cc1cnc(C(N)=O)cc1NC(=O)c1c(Oc2ccc(OC(F)(F)F)c(F)c2)ccc(C(F)(F)F)c1F]

718

Step 1: N-(2-bromo-5-methyl-4-pyridyl)-2-fluoro-6-[3-fluoro-4-(trifluoromethoxy) phenoxy]-3-(trifluoromethyl)benzamide

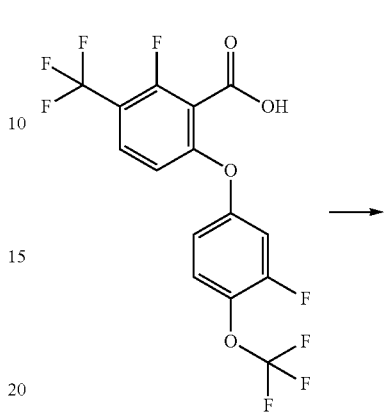

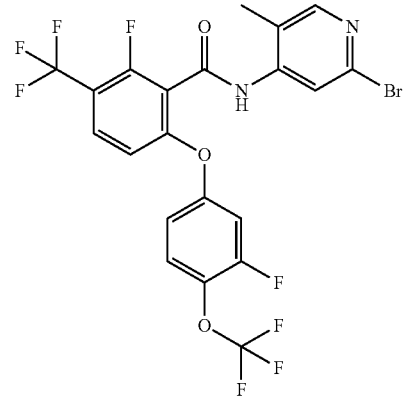

To an ice-cooled solution of 2-fluoro-6-[3-fluoro-4-(trifluoromethoxy)phenoxy]-3-(trifluoromethyl)benzoic acid (prepared as described in Example 18, Step 1, 480 mg, 1.19 mmol) in DCM (7 mL) was added DMF (16 μL, 0.21 mmol) and dropwise oxalyl dichloride (500 μL, 5.73 mmol) and was stirred for 2 hours. The reaction mixture was concentrated in vacuo to afford the acid chloride as a pale yellow oil. The residue was dissolved in DCM (7 mL) and added dropwise to a solution of 2-bromo-5-methyl-pyridin-4-amine (400 mg, 2.14 mmol) and TEA (1.57 mL, 11.3 mmol) in DCM (7 mL) in an ice bath. The resulting mixture was stirred and warmed to room temperature overnight. The reaction mixture was concentrated in vacuo to afford a brown mobile oil, which was purified by silica gel chromatography (ethyl acetate/heptane) to provide N-(2-bromo-5-methyl-4-pyridyl)-2-fluoro-6-[3-fluoro-4-(trifluoromethoxy)phenoxy]-3-(trifluoromethyl)benzamide (170 mg, 25%) as a clear waxy solid. ESI-MS m/z calc. 569.98, found 573.5 (M+1)+; 569.6 (M−1)−; Retention time (Method F): 1.1 minutes (1.5 minutes run).

719

Step 2: methyl 4-[[2-fluoro-6-[3-fluoro-4-(trifluoromethoxy)phenoxy]-3-(trifluoromethyl)benzoyl]amino]-5-methyl-pyridine-2-carboxylate

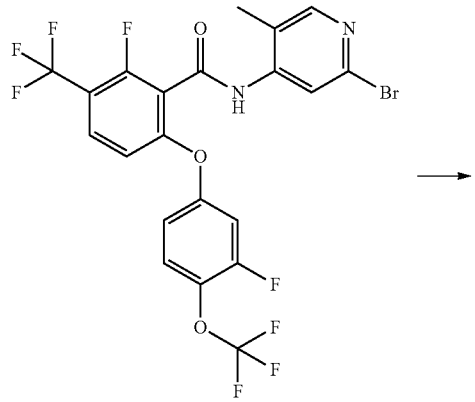

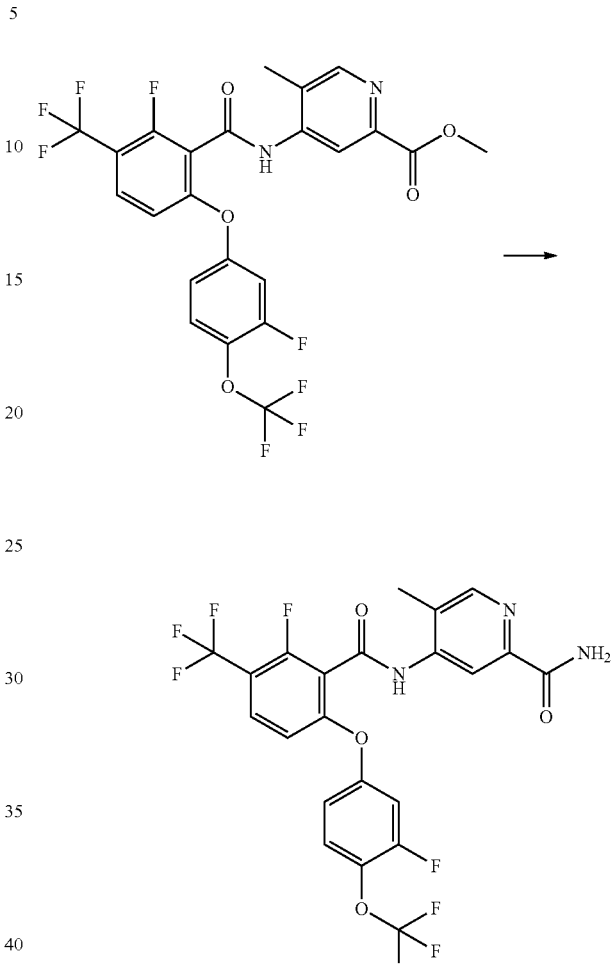

720

Step 3: 4-[[2-fluoro-6-[3-fluoro-4-(trifluoromethoxy)phenoxy]-3-(trifluoromethyl)benzoyl]amino]-5-methyl-pyridine-2-carboxamide (246)

In a pressure tube, N-(2-bromo-5-methyl-4-pyridyl)-2-fluoro-6-[3-fluoro-4-(trifluoromethoxy)phenoxy]-3-(trifluoromethyl)benzamide (100 mg, 0.18 mmol) was dissolved in methanol (5 mL) and triethylamine (55 μL, 0.39 mmol) and Pd(dppf)Cl$_2$·DCM (40 mg, 0.05 mmol) were added. CO gas was bubbled through the reaction mixture for 5 minutes whilst being vigorously stirred at ambient temperature. The reaction mixture was sealed and heated to 75° C. overnight, then cooled to room temperature and concentrated in vacuo. The residue was re-submitted to the same conditions, with more vigorous bubbling of CO gas, then heated overnight. The mixture was concentrated in vacuo, then purified by HPLC (37-100% acetonitrile/0.1% ammonium hydroxide) to provide methyl 4-[[2-fluoro-6-[3-fluoro-4-(trifluoromethoxy)phenoxy]-3-(trifluoromethyl)benzoyl]amino]-5-methyl-pyridine-2-carboxylate (30 mg, 31%). ESI-MS m/z calc. 550.08, found 551.6 (M+1)+; 549.6 (M−1)−; Retention time (Method F): 0.97 minutes (1.5 minutes run). $^1$H NMR (400 MHz, CDCl$_3$) δ 8.97 (s, 1H), 8.61 (s, 1H), 7.90 (s, 1H), 7.72 (s, 1H), 7.40 (s, 1H), 7.05 (s, 1H), 6.96 (s, 1H), 6.85 (d, J=8.4 Hz, 1H), 4.03 (s, 3H), 2.40 (s, 3H) ppm.

Methyl 4-[[2-fluoro-6-[3-fluoro-4-(trifluoromethoxy)phenoxy]-3-(trifluoromethyl)benzoyl]amino]-5-methyl-pyridine-2-carboxylate (30 mg, 0.06 mmol) was dissolved in ammonia (4 mL of 7 M in methanol, 28 mmol) and stirred at room temperature over the weekend. Additional ammonia (2 mL of 7 M in methanol, 14 mmol) was added and the mixture heated to 40° C. overnight. The reaction mixture was concentrated in vacuo and the residue was purified by HPLC (37-100% acetonitrile/0.1% ammonium hydroxide) to provide 4-[[2-fluoro-6-[3-fluoro-4-(trifluoromethoxy)phenoxy]-3-(trifluoromethyl)benzoyl]amino]-5-methyl-pyridine-2-carboxamide (2.6 mg, 8%) as an off-white solid. ESI-MS m/z calc. 535.08, found 536.1 (M+1)+; Retention time (Method E): 3.4 minutes (5 minutes run). $^1$H NMR (400 MHz, DMSO-d$_6$) δ 10.57 (s, 1H), 8.45 (d, J=5.8 Hz, 2H), 8.05 (s, 1H), 7.91 (t, J=8.5 Hz, 1H), 7.68 (q, J=8.3 Hz, 1H), 7.59 (s, 1H), 7.48 (dd, J=19.1, 11.1 Hz, 1H), 7.19 (d, J=9.2 Hz, 1H), 7.08 (d, J=8.9 Hz, 1H), 2.24 (d, J=6.7 Hz, 3H) ppm.

Example 205

N-(3-carbamoylphenyl)-2-(4-chloro-2-methoxyphenoxy)-4-(1,1,2,2,2-pentafluoroethyl)benzamide (247)

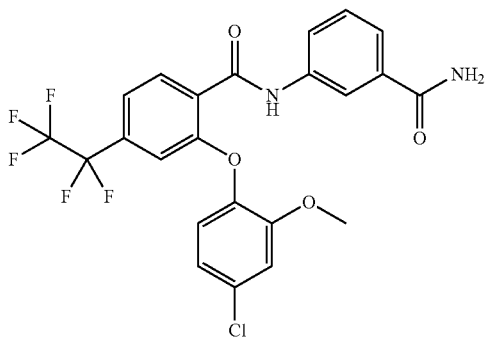 [SMILES: COc1cc(Cl)ccc1Oc1cc(C(F)(F)C(F)(F)F)ccc1C(=O)Nc1cccc(C(N)=O)c1]

Step 1: 2-fluoro-4-(1,1,2,2,2-pentafluoroethyl)benzoic acid

A pressure flask was charged with 4-bromo-2-fluorobenzoic acid (3 g, 13.70 mmol) and copper (approximately 8.706 g, 137.0 mmol) in DMSO (56.25 mL). 1,1,1,2,2-Pentafluoro-2-iodo-ethane (approximately 23.58 g, 95.90 mmol) was bubbled through the stirred solution. The vessel was sealed and heated at 120° C. for 72 hours. The reaction mixture was diluted with water and filtered through a plug of silica and then extracted with ethylacetate (4×). The organic phases were combined, washed with brine, dried over sodium sulfate and evaporated to dryness. Purification by column chromatography (40 g silica; 0-40% ethylacetate in hexane) gave 2-fluoro-4-(1,1,2,2,2-pentafluoroethyl)benzoic acid (1.81 g, 51%) as white solid. ESI-MS m/z calc. 258.01154, found 259.3 (M+1)+; retention time (Method B): 1.45 minutes (3 minute run).

Step 2: 2-fluoro-4-(1,1,2,2,2-pentafluoroethyl)benzoyl chloride

To 2-fluoro-4-(1,1,2,2,2-pentafluoroethyl)benzoic acid (300 mg, 1.162 mmol) in toluene (3 mL) was added pyridine (4.7 µL, 0.058 mmol). The reaction was heated at 60° C. under a nitrogen atmosphere. Sulfonyl chloride (127 µL, 1.743 mmol) was added and the reaction stirred at 60° C. for 2 hours. Further sulfonyl chloride (127 µL, 1.743 mmol) was added. The solvent was then evaporated under reduced pressure. Toluene (1 mL) was added and the mixture was concentrated again to afford 2-fluoro-4-(1,1,2,2,2-pentafluoroethyl)benzoyl chloride (321 mg, 100%), which was used in the next step without further purification.

Step 3: N-(3-carbamoylphenyl)-2-fluoro-4-(1,1,2,2,2-pentafluoroethylbenzamide To 3-aminobenzamide (198 mg, 1.451 mmol) in MTBE (2 mL) and DMF (1 mL) was added potassium carbonate (481 mg, 3.483 mmol) in water (1.822 mL). The reaction was stirred at room temperature and 2-fluoro-4-(1,1,2,2,2-pentafluoroethyl)benzoyl chloride (321 mg, 1.161 mmol) in MTBE (2 mL) was added dropwise. The reaction was stirred at room temperature overnight and then diluted with ethyl acetate (250 mL). The organic layer was separated, washed with brine, and evaporated under reduced pressure to give N-(3-carbamoylphenyl)-2-fluoro-4-(1,1,2,2,2-pentafluoroethyl)benzamide (398 mg, 91%) as a yellow solid, which was used in the next step without further purification. $^1$H NMR (400 MHz, DMSO-d6) δ 10.78 (s, 1H), 8.26-8.12 (m, 1H), 8.04-7.90 (m, 2H), 7.90-7.80 (m, 2H), 7.71 (d, J=7.9 Hz, 1H), 7.63 (d, J=7.8 Hz, 1H), 7.44 (dd, J=18.4, 10.6 Hz, 2H) ppm.

Step 4: N-(3-carbamoylphenyl)-2-(4-chloro-2-methoxyphenoxy)-4-(1,1,2,2,2-pentafluoroethyl)benzamide (247)

To N-(3-carbamoylphenyl)-2-fluoro-4-(1,1,2,2,2-pentafluoroethyl)benzamide (50 mg, 0.13 mmol) and 4-chloro-2-methoxy-phenol (63 mg, 0.40 mmol) in DMF (0.5 mL) was added cesium carbonate (130 mg, 0.040 mmol). The reaction was heated at 70° C. for one hour. The crude material was purified by HPLC (1-99% acetonitrile in water (HCl modifier)) to obtain N-(3-carbamoylphenyl)-2-(4-chloro-2-methoxyphenoxy)-4-(1,1,2,2,2-pentafluoroethyl)benzamide (18.4 mg, 26%). ESI-MS m/z calc. 514.07, found 515.3 (M+1)+; retention time (Method B): 1.64 minutes (3 minute run).

The compounds set forth in Table 13 were prepared by methods analogous to the preparation of compound 247.

TABLE 13

Additional Compounds Prepared By Methods Analogous to Compound 247 in Example 205

| Cmpd No. | Compound Name | LC/MS |
|---|---|---|
| 248 | N-(3-carbamoylphenyl)-2-(4-fluoro-2-methoxyphenoxy)-4-(1,1,2,2,2-pentafluoroethyl)benzamide | ESI-MS m/z calc. 498.10 found 499.2 (M + 1)+; Retention time (Method B): 1.55 minutes (3 minute run). |
| 249 | N-(3-carbamoylphenyl)-2-(4-fluorophenoxy)-4-(1,1,2,2,2-pentafluoroethyl)benzamide | ESI-MS m/z calc. 468.09 found 469.3 (M + 1)+; Retention time (Method B): 1.52 minutes (3 minute run). |
| 250 | N-(3-carbamoylphenyl)-2-(3-fluoro-4-methoxyphenoxy)-4-(1,1,2,2,2-pentafluoroethyl)benzamide | ESI-MS m/z calc. 498.10 found 499.3 (M + 1)+; Retention time (Method B): 1.50 minutes (3 minute run). |

TABLE 13-continued

Additional Compounds Prepared By Methods
Analogous to Compound 247 in Example 205

| Cmpd No. | Compound Name | LC/MS |
|---|---|---|
| 251 | N-(3-carbamoylphenyl)-2-(2-chloro-4-methoxyphenoxy)-4-(1,1,2,2,2-pentafluoroethyl)benzamide | ESI-MS m/z calc. 514.07 found 515.2 (M + 1)+; Retention time (Method B): 1.87 minutes (3 minute run). |
| 252 | N-(3-carbamoylphenyl)-2-(2,4-dimethoxyphenoxy)-4-(1,1,2,2,2-pentafluoroethyl)benzamide | ESI-MS m/z calc. 510.12 found 511.3 (M + 1)+; Retention time (Method B): 1.83 minutes (3 minute run). |

Example 206

N-(3-carbamoyl-4-methoxyphenyl)-2-(2-chloro-4-fluorophenoxy)-6-(trifluoromethyl)benzamide (253)

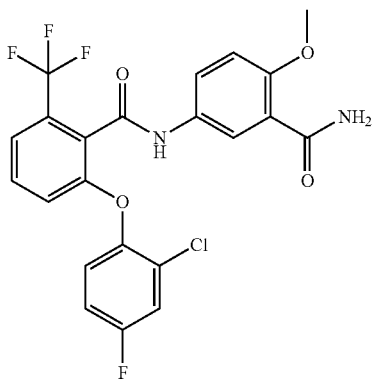 [SMILES: COc1ccc(NC(=O)c2c(Oc3ccc(F)cc3Cl)cccc2C(F)(F)F)cc1C(N)=O]

Step 1: 2-(2-chloro-4-fluoro-phenoxy)-6-(trifluoromethyl)benzaldehyde

To a solution of 2-chloro-4-fluoro-phenol (20.97 g, 143.1 mmol) and 2-fluoro-6-(trifluoromethyl)benzaldehyde (25.0 g, 130.1 mmol) in DMF (125 mL) was added cesium carbonate (46.6 g, 143.1 mmol) and the reaction mixture was stirred at 100° C. for 1 hour. The reaction mixture was poured in to water (500 ml) and extracted with ethyl acetate (3×150 ml). Organics were combined, washed with water, brine (2×), dried over sodium sulfate and evaporated to give a red oil which solidified after standing over night. The material was then triturated with hot hexanes and cooled to room temperature. The slurry was filtered and washed with cold hexanes to give 2-(2-chloro-4-fluoro-phenoxy)-6-(trifluoromethyl)benzaldehyde (32.7 g, 79%) as an off-white solid. $^{1}$H NMR (400 MHz, DMSO-d6) δ 10.61 (s, 1H), 7.84-7.70 (m, 2H), 7.66 (d, J=7.9 Hz, 1H), 7.47 (dd, J=9.0, 5.3 Hz, 1H), 7.42-7.32 (m, 1H), 7.12 (d, J=8.3 Hz, 1H) ppm.

Step 2: 2-(2-chloro-4-fluoro-phenoxy)-6-(trifluoromethyl)benzoic acid

To a solution of 2-(2-chloro-4-fluoro-phenoxy)-6-(trifluoromethyl)benzaldehyde (31 g, 97.29 mmol) in tert-butanol (155.0 mL), water (100.8 mL), acetonitrile (155.0 mL) and 2-methyl-2-butene (51.45 mL, 486.4 mmol) was added sodium dihydrogen phosphate (18.29 mL, 291.9 mmol) and cooled to 0° C. Sodium chlorite (26.40 g, 291.9 mmol) was added in one portion which caused and exotherm and the reaction mixture to reflux. The cooling bath was removed after 15 minutes and the reaction stirred at room temperature for 1 hour. The pH of the reaction mixture was adjusted to 2-3 with 1N HCl and the layers separated. The aqueous layer was extracted with ethylacetate (3×), all organic layers were combined, and in the separation funnel, solid sodium sulfite (~5 g) was added followed by brine (50 ml) and 1N NaOH (10 ml) and shaken until the yellow colour was gone. The layers were separated and the organic was washed with brine, dried over sodium sulfate, filtered through a short plug of silica and evaporated to dryness to give 2-(2-chloro-4-fluoro-phenoxy)-6-(trifluoromethyl)benzoic acid (40 g, 98%) as an oil that was used with out further purification.

Step 3: N-(3-carbamoyl-4-methoxyphenyl)-2-(2-chloro-4-fluorophenoxy)-6-(trifluoromethyl)benzamide (253)

To 5-amino-2-methoxy-benzamide (16.6 mg, 0.1 mmol), 2-(2-chloro-4-fluoro-phenoxy)-6-(trifluoromethyl)benzoic acid (41.8 mg, 0.1 mmol), O-(7-Azabenzotriazol-1-yl)-N,N,N',N'-tetramethyluronium hexafluorophosphate (38.0 mg, 0.1 mmol) in N-methyl pyrrolidinone (1 mL) was added triethylamine (42 µl, 0.3 mmol). The reaction mixture was stirred at room temperature for 18 hours. The compound was filtered and purified by reverse phase preparative chromatography utilizing a gradient of 10-99% acetonitrile in water containing HCl as a modifier to give N-(3-carbamoyl-4-methoxyphenyl)-2-(2-chloro-4-fluorophenoxy)-6-(trifluoromethyl)benzamide (19.1 mg, 40%). ESI-MS m/z calc. 482.07, found 483.3 (M+1)+; retention time (Method B): 1.79 minutes (3 minute run).

The compounds set forth in Table 14 were prepared by methods analogous to the preparation of compound 253.

TABLE 14

Additional Compounds Prepared By Methods Analogous to Compound 253 in Example 206

| Cmpd No. | Compound Name | LC/MS |
|---|---|---|
| 254 | N-(3-carbamoyl-4-chlorophenyl)-2-(2-chloro-4-fluorophenoxy)-6-(trifluoromethyl)benzamide | ESI-MS m/z calc. 486.02 found 487.3 (M + 1)+; Retention time (Method B): 1.83 minutes (3 minute run). |
| 255 | N-(5-carbamoyl-2-methylphenyl)-2-(2-chloro-4-fluorophenoxy)-6-(trifluoromethyl)benzamide | ESI-MS m/z calc. 466.07 found 467.3 (M + 1)+; Retention time (Method B): 1.75 minutes (3 minute run). |

Example 207

5-[[2-(2-chloro-4-fluoro-phenoxy)-6-(trifluoromethyl)benzoyl]amino]pyridine-2-carboxamide (256)

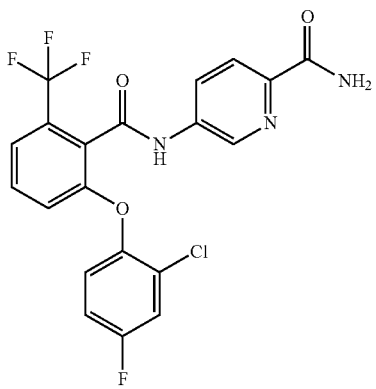 [SMILES: NC(=O)c1ccc(NC(=O)c2c(Oc3ccc(F)cc3Cl)cccc2C(F)(F)F)cn1]

Step 1: 5-aminopyridine-2-carboxylate

To a solution of 5-aminopyridine-2-carboxylic acid (276.2 mg, 2 mmol) in ethanol (3 mL) was added sulphuric acid (53.3 µL, 1.0 mmol) and the reaction mixture was refluxed for 72 hours. The reaction mixture was evaporated, taken up in ethyl acetate, washed with 1N NaOH (3×), dried over sodium sulfate and evaporated to dryness to give ethyl 5-aminopyridine-2-carboxylate (150 mg, 90%) as a tan solid. ESI-MS m/z calc. 166.07 found 167.3 (M+1)+; Retention time (Method B): 0.28 minutes (3 minute run). Used in the following step with out further purification.

Step 2: 5-[[2-(2-chloro-4-fluoro-phenoxy)-6-(trifluoromethyl)benzoyl]amino]pyridine-2-carboxamide (256)

2-(2-Chloro-4-fluoro-phenoxy)-6-(trifluoromethyl)benzoic acid (33.5 mg, 0.10 mmol), ethyl 5-aminopyridine-2-carboxylate (20 mg, 0.12 mmol), N-methylmorpholine (22 µL, 0.2000 mmol) and HATU (42 mg, 0.11 mmol) in N-methyl pyrrolidinone (0.5 mL) were stirred at 80° C. for 8 hours. The reaction mixture was poured into water and extracted with ethyl acetate (3×). The organic layers were combined, dried over sodium sulfate and evaporated to dryness. The material was taken up in ammonia in dioxane (500 µL of 0.5 M, 0.2500 mmol) and heated in a sealed tube at 100° C. for 72 h. The material was cooled, diluted with methanol and purified by HPLC (1-99% acetonitrile in water (HCl modifier)) to give 5-[[2-(2-chloro-4-fluoro-phenoxy)-6-(trifluoromethyl)benzoyl]amino]pyridine-2-carboxamide (2.8 mg, 6%). ESI-MS m/z calc. 453.05 found 454.3 (M+1)+; Retention time (Method B): 1.47 minutes (3 minute run).

Example 208

N-(3-carbamoylphenyl)-2-(4-fluorophenoxy)-6-(trifluoromethyl)benzamide (257)

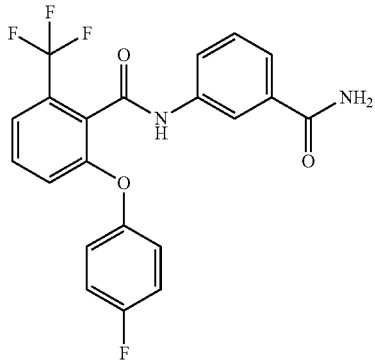 [SMILES: NC(=O)c1cccc(NC(=O)c2c(Oc3ccc(F)cc3)cccc2C(F)(F)F)c1]

Step 1: 2-(4-fluorophenoxy)-6-(trifluoromethyl)benzaldehyde

To a solution of 2-fluoro-6-(trifluoromethyl)benzaldehyde (1.0 g, 5.21 mmol) and 4-fluorophenol (583 mg, 5.21 mmol) in DMF (5 mL) was added cesium carbonate (1.70 g, 5.21 mmol) and the mixture was heated at 100° C. for 1 hour. The reaction was cooled to room temperature. The reaction was diluted with ethyl acetate (5 ml) and water (10 ml). The organic layer was washed with water (2×10 mL), dried over magnesium sulfate, filtered and evaporated to yield yellow oil. The mixture was purified by column chromatography using a gradient of ethyl acetate in hexanes (0-50%) to afford 2-(4-fluorophenoxy)-6-(trifluoromethyl)benzaldehyde (800 mg, 54%) as a colorless oil. $^1$H NMR (400 MHz, CDCl$_3$) δ 10.60 (s, 1H), 7.60-7.50 (m, 2H), 7.17-7.01 (m, 5H) ppm. ESI-MS m/z calc. 284.046, found 284.9 (M+1)+; Retention time (Method B): 2.03 minutes (3 minute run).

Step 2: 2-(4-fluorophenoxy)-6-(trifluoromethyl)benzoic acid

To a solution of 2-(4-fluorophenoxy)-6-(trifluoromethyl)benzaldehyde (2.23 g, 7.846 mmol) in tert-butanol (22.3 mL), water (14 mL) and acetonitrile (14 mL) was added sodium dihydrogen phosphate (1.48 mL, 23.54 mmol), 2-methylbut-2-ene (4.15 mL, 39.25 mmol) and sodium chlorite (2.13 g, 23.54 mmol). The reaction mixture was stirred at 25° C. for 2 h. The reaction was acidified with 1N HCl and was diluted with ethyl acetate. Sodium sulfide was added to remove the faint yellow colour. The two layers were separated and the aqueous layer extracted with ethyl acetate (3×). The organics were combined, dried over sodium sulfate, filtered and concentrated to give 2-(4-fluorophenoxy)-6-(trifluoromethyl)benzoic acid. ESI-MS m/z calc. 300.041, found 301.5 (M+1)+; Retention time (Method B): 1.71 minutes (3 min run).

Step 3: N-(3-carbamoylphenyl)-2-(4-fluorophenoxy)-6-(trifluoromethyl)benzamide (257)

Triethylamine (63 µL, 0.45 mmol) was added to a mixture of 2-(4-fluorophenoxy)-6-(trifluoromethyl)benzoic acid (45 mg, 0.15 mmol), 3-aminobenzamide (20.4 mg, 0.15 mmol), HATU (57 mg, 0.15 mmol) and DMF (0.68 mL) at room temperature. The mixture was heated at 50° C. for 16 hours before it was cooled to room temperature, filtered and subjected to preparatory-HPLC (10-99% acetonitrile/water with 0.01% HCl) to give N-(3-carbamoylphenyl)-2-(4-fluorophenoxy)-6-(trifluoromethyl)benzamide (27 mg, 43%) as a white solid. $^1$H NMR (400 MHz, CDCl$_3$) δ 8.99 (s, 1H), 7.97 (s, 1H), 7.93 (d, J=8.0 Hz, 1H), 7.42-7.33 (m, 3H), 7.27 (t, J=6.3 Hz, 1H), 6.99-6.90 (m, 5H), 6.50 (s, 1H), 5.74 (s, 1H) ppm. ESI-MS m/z calc. 418.09, found 419.3 (M+1)+; retention time (Method B): 1.53 minutes (3 minute run).

Example 209

N-(3-carbamoylphenyl)-2-(4-fluoro-2-methylphenoxy)-6-(trifluoromethyl)benzamide (258)

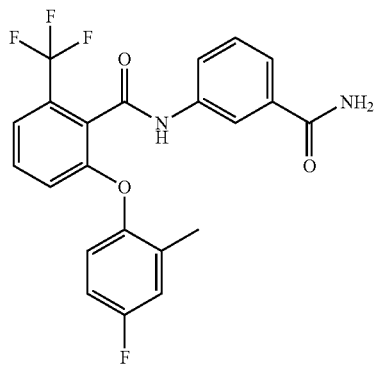 [SMILES: Cc1cc(F)ccc1Oc1cccc(C(F)(F)F)c1C(=O)Nc1cccc(C(N)=O)c1]

Step 1: 2-(4-fluoro-2-methyl-phenoxy)-6-(trifluoromethyl)benzaldehyde

To a solution of 2-fluoro-6-(trifluoromethyl)benzaldehyde (460 mg, 2.394 mmol) and 4-fluoro-2-methyl-phenol (302.0 mg, 2.394 mmol) in DMF (3.942 mL) was added cesium carbonate (780.0 mg, 2.394 mmol) and the mixture was heated at 100° C. for 1 hour. The reaction was cooled to room temperature. The reaction was diluted with ethyl acetate (5 ml) and water (10 ml). The organic layer was washed with water (2×10 mL), dried over magnesium sulfate, filtered and evaporated to yield a light brown oil (740 mg). The mixture was purified by column chromatography using a gradient of ethyl acetate in hexanes (0-50%) over a period of 40 minutes. 2-(4-fluoro-2-methyl-phenoxy)-6-(trifluoromethyl)benzaldehyde (550 mg, 77%) was isolated as a transparent oil. $^1$H NMR (400 MHz, CDCl$_3$) δ 10.59 (s, 1H), 7.46-7.36 (m, 2H), 6.95 (d, J=8.5 Hz, 1H), 6.86 (dd, J=6.1, 1.4 Hz, 2H), 6.80 (d, J=7.8 Hz, 1H), 2.14 (s, 3H) ppm. ESI-MS m/z calc. 298.0617, found 299.3 (M+1)+; Retention time (Method B): 2.12 minutes (3 minute run).

Step 2: 2-(4-fluoro-2-methyl-phenoxy)-6-(trifluoromethyl)benzoic acid

To a solution of 2-(4-fluoro-2-methyl-phenoxy)-6-(trifluoromethyl)benzaldehyde (745 mg, 2.498 mmol) in tert-butanol (7.450 mL), water (4.694 mL) and acetonitrile (4.694 mL) was added sodium dihydrogen phosphate (899 mg, 469.5 µL, 7.494 mmol), 2-methyl-2-butene (876 mg, 1.321 mL, 12.49 mmol) and sodium chlorite (679 mg, 7.494 mmol). The reaction mixture was stirred at 25° C. for 3 h. The mixture was acidified with 1N HCl and was diluted with ethyl acetate. Sodium sulfite was added to remove the slightly yellow color. The two layers were separated and the aqueous layer extracted 3 additional times with ethyl acetate. The organics were combined, washed with brine, dried over sodium sulfate, filtered and concentrated to give 2-(4-fluoro-2-methyl-phenoxy)-6-(trifluoromethyl)benzoic acid (660 mg, 84%). ESI-MS m/z calc. 314.0566, found 315.3 (M+1)+; Retention time (Method B): 1.8 minutes (3 min run).

Step 3: N-(3-carbamoylphenyl)-2-(4-fluoro-2-methylphenoxy)-6-(trifluoromethyl)benzamide (258)

Triethylamine (63 µL, 0.45 mmol) was added to a mixture of 2-(4-fluoro-2-methyl-phenoxy)-6-(trifluoromethyl)benzoic acid (47 mg, 0.15 mmol), 3-aminobenzamide (20.4 mg, 0.15 mmol), HATU (57 mg, 0.15 mmol) and DMF (0.68 mL) at room temperature. The mixture was heated at 50° C. for 16 hours before it was cooled to room temperature, filtered and subjected to preparatory-HPLC (10-99% acetonitrile/water with 0.01% HCl) to give N-(3-carbamoylphenyl)-2-(4-fluoro-2-methylphenoxy)-6-(trifluoromethyl)benzamide (23 mg, 35%) as a white solid. $^1$H NMR (400 MHz, CDCl$_3$) δ 8.74 (s, 1H), 8.05 (s, 1H), 7.96 (d, J=8.0 Hz, 1H), 7.45 (d, J=7.8 Hz, 1H), 7.42-7.30 (m, 3H), 6.95-6.88 (m, 2H), 6.86-6.79 (m, 2H), 6.39 (s, 1H), 5.54 (s, 1H), 2.12 (s, 3H) ppm. ESI-MS m/z calc. 432.11 found 433.3 (M+1)+; Retention time (Method B): 1.58 minutes (3 minute run).

Example 210

N-(3-carbamoylphenyl)-2-(4-fluoro-2-methoxyphenoxy)-6-(trifluoromethyl)benzamide (259)

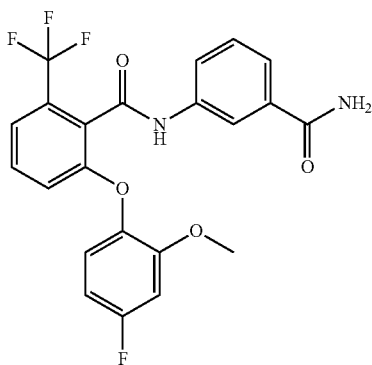 [SMILES: COc1cc(F)ccc1Oc1cccc(C(F)(F)F)c1C(=O)Nc1cccc(C(N)=O)c1]

Step 1: 2-(4-fluoro-2-methoxy-phenoxy)-6-(trifluoromethyl)benzaldehyde

To a solution of 2-fluoro-6-(trifluoromethyl)benzaldehyde (2.00 g, 10.41 mmol) and 4-fluoro-2-methoxy-phenol (1.480 g, 1.187 mL, 10.41 mmol) in DMF (17.14 mL) was added cesium carbonate (3.392 g, 10.41 mmol). The mixture was heated at 100° C. for 3 h. The mixture was cooled to room temperature before it was diluted with ethyl acetate and water. The layers were separated and the aqueous layer was extracted with ethyl acetate (2×). The combined organics were washed with brine, dried over sodium sulfate, filtered and concentrated. The residue was purified by column chromatography using a gradient of ethyl acetate in hexanes (0-100%) to give 2-(4-fluoro-2-methoxy-phenoxy)-6-(trifluoromethyl)benzaldehyde (2.96 g, 89%) as a clear oil that solidified upon standing. $^1$H NMR (400 MHz, DMSO-d6) δ 10.63 (d, J=1.5 Hz, 1H), 7.69 (t, J=8.2 Hz, 1H), 7.56 (d, J=7.8 Hz, 1H), 7.32 (dd, J=8.8, 5.9 Hz, 1H), 7.19 (dd, J=10.7, 2.9 Hz, 1H), 7.01 (d, J=8.5 Hz, 1H), 6.88 (td, J=8.5, 2.9 Hz, 1H), 3.76 (s, 3H) ppm. ESI-MS m/z calc. 314.0566, found 315.3 (M+1)+; Retention time (Method B): 2.0 minutes (3 min run).

Step 2: 2-(4-fluoro-2-methoxy-phenoxy)-6-(trifluoromethyl)benzoic acid

To a solution of 2-(4-fluoro-2-methoxy-phenoxy)-6-(trifluoromethyl)benzaldehyde (2.95 g, 9.200 mmol) in tert-butanol (28.9 mL), water (18.2 mL) and acetonitrile (18.2 mL) was added sodium dihydrogen phosphate (1.73 mL, 27.60 mmol), 2-methylbut-2-ene (4.87 mL, 46.00 mmol) and sodium chlorite (2.50 g, 27.60 mmol). The reaction mixture was stirred at 25° C. for 3 h. The reaction mixture was acidified with 1N HCl and was diluted with ethyl acetate. Sodium sulfite was added to remove the faint yellow color. The two layers were separated and the aqueous layer was extracted with ethyl acetate (3×). The organics were combined, washed with brine, dried over sodium sulfate, filtered and concentrated to give 2-(4-fluoro-2-methoxy-phenoxy)-6-(trifluoromethyl)benzoic acid (3.0 g, 99%). ESI-MS m/z calc. 330.0515, found 331.5 (M+1)+; Retention time (Method B): 1.72 minutes (3 min run).

Step 3: N-(3-carbamoylphenyl)-2-(4-fluoro-2-methoxyphenoxy)-6-(trifluoromethyl)benzamide (259)

Triethylamine (63 μL, 0.45 mmol) was added to a mixture of 2-(4-fluoro-2-methoxy-phenoxy)-6-(trifluoromethyl)benzoic acid (49 mg, 0.15 mmol), 3-aminobenzamide (20.4 mg, 0.15 mmol), HATU (57 mg, 0.15 mmol) and DMF (0.68 mL) at room temperature. The mixture was heated at 50° C. for 16 hours before it was cooled to room temperature, filtered and subjected to preparatory-HPLC (10-99% acetonitrile/water with 0.01% HCl) to give N-(3-carbamoylphenyl)-2-(4-fluoro-2-methoxyphenoxy)-6-(trifluoromethyl)benzamide (22 mg, 33%) as a white solid. $^1$H NMR (400 MHz, CDCl$_3$) δ 8.55 (s, 1H), 8.06 (s, 1H), 7.82 (dd, J=8.1, 1.2 Hz, 1H), 7.51 (d, J=7.8 Hz, 1H), 7.43-7.33 (m, 3H), 7.09 (dd, J=8.8, 5.7 Hz, 1H), 6.90-6.83 (m, 1H), 6.73 (dd, J=10.0, 2.8 Hz, 1H), 6.70-6.62 (m, 1H), 6.45 (s, 1H), 5.84 (s, 1H), 3.77 (s, 3H) ppm. ESI-MS m/z calc. 448.10 found 449.3 (M+1)+; Retention time (Method B): 1.54 minutes (3 minute run).

Example 211

N-(3-carbamoylphenyl)-2-(2-chloro-4-fluorophenoxy)-6-(trifluoromethyl)benzamide (260)

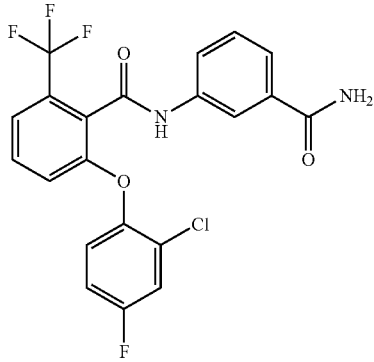 [SMILES: NC(=O)c1cccc(NC(=O)c2c(Oc3ccc(F)cc3Cl)cccc2C(F)(F)F)c1]

Step 1: 2-(2-chloro-4-fluoro-phenoxy)-6-(trifluoromethyl)benzaldehyde

To a solution of 2-fluoro-6-(trifluoromethyl)benzaldehyde (580 mg, 3.019 mmol) and 2-chloro-4-fluoro-phenol (442 mg, 319 μL, 3.02 mmol) in DMF (4.970 mL) was added cesium carbonate (984 mg, 3.019 mmol) and the mixture was heated at 100° C. for 2.5 hours. The mixture was cooled to room temperature before it was diluted with ethyl acetate and water. The layers were separated and the aqueous layer was extracted with ethyl acetate (3×). The combined organics were washed with brine, dried over sodium sulfate, filtered and concentrated. The residue was purified by column chromatography (0-100% ethyl acetate/hexanes) to yield 2-(2-chloro-4-fluoro-phenoxy)-6-(trifluoromethyl)benzaldehyde (623 mg, 65%). $^1$H NMR (400 MHz, DMSO-d6) δ 10.61 (d, J=1.6 Hz, 1H), 7.78-7.70 (m, 2H), 7.66 (d, J=7.7 Hz, 1H), 7.47 (dd, J=9.1, 5.2 Hz, 1H), 7.40-7.33 (m, 1H), 7.12 (d, J=8.4 Hz, 1H) ppm. ESI-MS m/z calc. 318.00708, found 319.3 (M+1)+; Retention time (Method B): 2.07 minutes (3 min run).

Step 2: 2-(2-chloro-4-fluoro-phenoxy)-6-(trifluoromethyl)benzoic acid

To a solution of 2-(2-chloro-4-fluoro-phenoxy)-6-(trifluoromethyl)benzaldehyde (610 mg, 1.914 mmol) in tert-butanol (6.10 mL), water (3.84 mL) and acetonitrile (3.84 mL) was added sodium dihydrogen phosphate (689 mg, 360 µL, 5.742 mmol), 2-methylbut-2-ene (671 mg, 1.01 mL, 9.570 mmol) and sodium chlorite (519 mg, 5.742 mmol). The reaction mixture was stirred at 25° C. for 1 hour. The reaction was acidified with 1N HCl and was diluted with ethyl acetate. Sodium sulfite was added to remove the faint yellow color. The two layers were separated and the aqueous layer was extracted with ethyl acetate (3×). The organics were combined, washed with brine, dried over sodium sulfate, filtered and concentrated to give 2-(2-chloro-4-fluoro-phenoxy)-6-(trifluoromethyl)benzoic acid (483 mg, 75%). ESI-MS m/z calc. 334.00198, found 335.1 (M+1)+; Retention time (Method B): 1.78 minutes (3 min run).

Step 3: N-(3-carbamoylphenyl)-2-(2-chloro-4-fluorophenoxy)-6-(trifluoromethyl)benzamide (260)

Triethylamine (63 µL, 0.45 mmol) was added to a mixture of 2-(4-fluoro-2-methoxy-phenoxy)-6-(trifluoromethyl)benzoic acid (50 mg, 0.15 mmol), 3-aminobenzamide (20.4 mg, 0.15 mmol), HATU (57 mg, 0.15 mmol) and DMF (0.68 mL) at room temperature. The mixture was heated at 50° C. for 16 hours before it was cooled to room temperature, filtered and subjected to preparatory-HPLC (10-99% acetonitrile/water with 0.01% HCl) to give N-(3-carbamoylphenyl)-2-(2-chlorophenoxy)-6-(trifluoromethyl)benzamide (24 mg, 36%) as a white solid. $^1$H NMR (400 MHz, CDCl$_3$) δ 8.57 (s, 1H), 8.06 (s, 1H), 7.88 (dd, J=8.1, 1.1 Hz, 1H), 7.49 (d, J=7.8 Hz, 1H), 7.42 (d, J=4.0 Hz, 2H), 7.41-7.32 (m, 1H), 7.17 (dd, J=7.9, 3.0 Hz, 1H), 7.12 (dd, J=9.0, 5.1 Hz, 1H), 6.97 (ddd, J=9.0, 7.6, 3.0 Hz, 1H), 6.83 (p, J=3.9 Hz, 1H), 6.43 (s, 1H), 5.74 (s, 1H) ppm. ESI-MS m/z calc. 452.06, found 453.3 (M+1)+; Retention time (Method B): 1.56 minutes (3 minute run).

Example 212

5-(4-(tert-butyl)-2-((6-(trifluoromethyl)pyridin-3-yl)oxy)benzamido)nicotinamide (261)

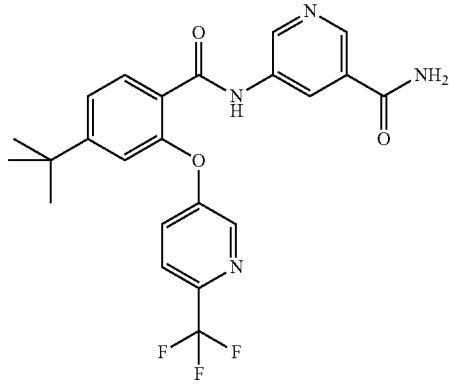 [SMILES: CC(C)(C)c1ccc(C(=O)Nc2cncc(C(N)=O)c2)c(Oc2ccc(C(F)(F)F)nc2)c1]

A solution of 4-tert-butyl-2-[[6-(trifluoromethyl)-3-pyridyl]oxy]benzoic acid (34 mg, 0.1 mmol), 4-aminopyridine-2-carboxamide (15 mg, 0.11 mmol) and HATU (46 mg, 0.12 mmol) in DMF (0.5 mL) with N-methylmorpholine (33 µL, 0.3 mmol) was stirred at room temperature for 16 hours. Purification by HPLC (1-99% acetonitrile in water (HCl modifier)) afforded 4-(4-(tert-butyl)-2-((6-(trifluoromethyl)pyridin-3-yl)oxy)benzamido)picolinamide (23.4 mg, 51%). ESI-MS m/z calc. 458.16, found 459.3 (M+1)+; retention time (Method B): 1.57 minutes (3 minute run).

The compounds set forth in Table 15 were prepared by methods analogous to the preparation of compound 261.

TABLE 15

Additional Compounds Prepared By Methods Analogous to Compound 261 in Example 212

| Cmpd No. | Compound Name | LC/MS |
|---|---|---|
| 262 | N-(3-carbamoylphenyl)-2-(4-fluoro-2-methylphenoxy)-6-(trifluoromethyl)benzamide | ESI-MS m/z calc. 458.16 found 459.5 (M + 1)+; Retention time (Method B): 1.75 minutes (3 minute run). |
| 263 | N-(3-carbamoylphenyl)-2-(4-fluoro-2-methoxyphenoxy)-6-(trifluoromethyl)benzamide | ESI-MS m/z calc. 458.16 found 459.3 (M + 1)+; Retention time (Method B): 1.78 minutes (3 minute run). |

Example 213

4-(4-(tert-butyl)-2-((6-(trifluoromethyl)pyridin-3-yl)oxy)benzamido)picolinamide (266)

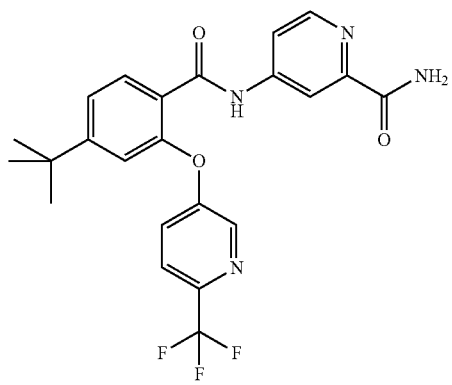 [SMILES: CC(C)(C)c1ccc(C(=O)Nc2ccnc(C(N)=O)c2)c(Oc2ccc(C(F)(F)F)nc2)c1]

A solution of 4-tert-butyl-2-[[6-(trifluoromethyl)-3-pyridyl]oxy]benzoic acid (34 mg, 0.1 mmol), 4-aminopyridine-2-carboxamide (15 mg, 0.11 mmol) and HATU (46 mg, 0.12 mmol) in DMF (0.5 mL) with N-methylmorpholine (33 µL, 0.3 mmol) was stirred at room temperature for 16 hours. After 16 hours, 4-dimethylaminopyridine (12 mg, 0.1 mmol) was added and the reaction mixture stirred at 60° C. for 2 h. Purification by HPLC (1-99% acetonitrile in water (HCl modifier)) afforded 4-(4-(tert-butyl)-2-((6-(trifluoromethyl)pyridin-3-yl)oxy)benzamido)picolinamide (3.11 mg, 7%). ESI-MS m/z calc. 458.16, found 459.5 (M+1)+; retention time (Method B): 1.70 minutes (3 minute run).

Example 214

N-(3-carbamoylphenyl)-4,5-dichloro-2-(4-fluoro-2-methyl-phenoxy)benzamide (267)

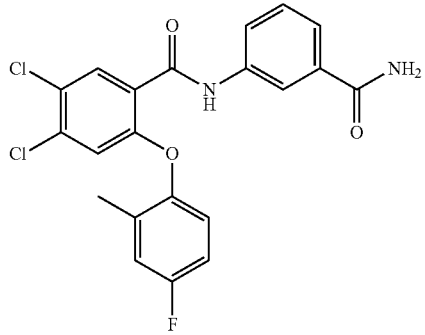 [SMILES: Cc1cc(F)ccc1Oc1cc(Cl)c(Cl)cc1C(=O)Nc1cccc(C(N)=O)c1]

Step 1: 4,5-dichloro-2-fluoro-benzoyl chloride

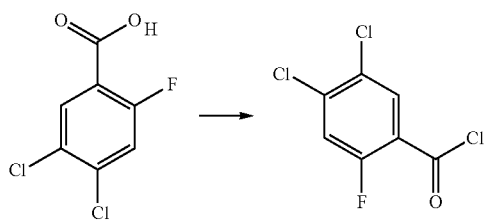

To 4,5-dichloro-2-fluoro-benzoic acid (4 g, 19.14 mmol) in toluene (40.00 mL) was added $SOCl_2$ (approximately 6.83 g, 4.2 mL, 57.42 mmol) and pyridine (approximately 75.7 mg, 77.4 µL, 0.957 mmol) and the reaction was heated to 80° C. under an inert atmosphere. After 4 hours the mixture as concentrated in vacuo, toluene was added and the mixture as concentrated in vacuo (twice) to give 4,5-dichloro-2-fluoro-benzoyl chloride (2.5 g, 57%) as pale solid which was used in the next step without further purification.

Step 2: N-(3-carbamoylphenyl)-4,5-dichloro-2-fluoro-benzamide

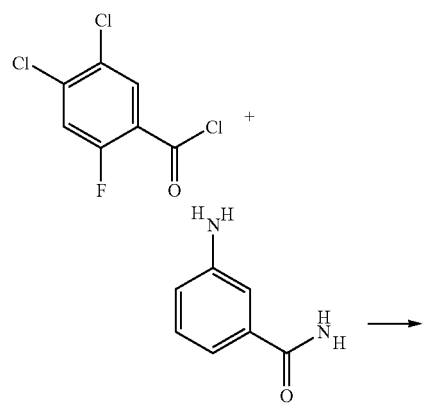

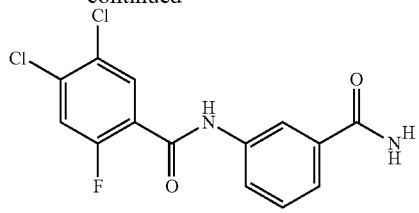

To 3-aminobenzamide (approximately 2.02 g, 14.84 mmol) in MTBE (27 mL) and DMF (16 mL) was added $K_2CO_3$ (approximately 4.92 g, 35.61 mmol) in water (15.33 mL). The reaction was stirred at room temperature, and 4,5-dichloro-2-fluoro-benzoyl chloride (2.7 g, 11.87 mmol) in MTBE (27 mL) was added drop wise. The mixture was stirred at room temperature overnight. Ethyl acetate (250 mL) was added, and the organic layer was washed with brine, and concentrated in vacuo to afford N-(3-carbamoylphenyl)-4,5-dichloro-2-fluoro-benzamide (1.2 g, 31%) as a yellow solid, which was used without further purification. $^1$H NMR (400 MHz, DMSO-d6) δ 10.69 (s, 1H), 8.28-8.11 (m, 1H), 8.03-7.96 (m, 2H), 7.88 (dd, J=26.2, 8.9 Hz, 2H), 7.63 (d, J=7.7 Hz, 1H), 7.51-7.32 (m, 2H).

Step 3: N-(3-carbamoylphenyl)-4,5-dichloro-2-(4-fluoro-2-methyl-phenoxy)benzamide (267)

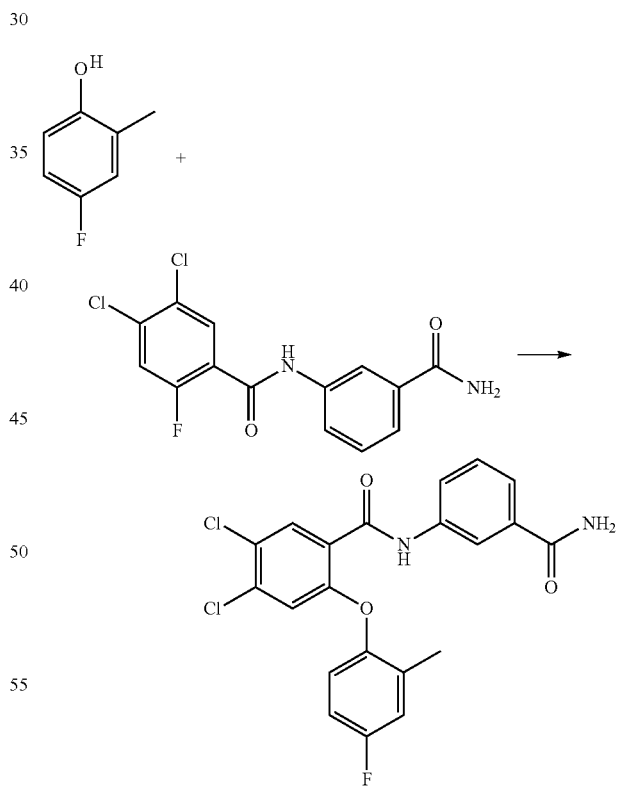

To a solution of N-(3-carbamoylphenyl)-4,5-dichloro-2-fluoro-benzamide (60 mg, 0.183 mmol) and 4-fluoro-2-methyl-phenol (approximately 25 mg, 0.201 mmol) in DMF (0.3 mL) was added $K_2CO_3$ (approximately 76 mg, 0.550 mmol). The mixture was stirred at 70° C. for 40 min, then at room temperature overnight. The mixture was purified by HPLC to provide N-(3-carbamoylphenyl)-4,5-dichloro-2-

(4-fluoro-2-methyl-phenoxy)benzamide (2 mg, 2.5%). ESI-MS m/z calc. 432.04, found 433.16 (M+1)+; Retention time (Method B): 1.89 minutes (3 minutes run).

The compounds set forth in Table 16 were prepared by methods analogous to the preparation of compound 267.

TABLE 16

Additional Compounds Prepared By Methods Analogous to Example 214

| Cmpd No. | Compound Name | LC/MS |
|---|---|---|
| 268 | N-(3-carbamoylphenyl)-4,5-dichloro-2-(4-fluorophenoxy)benzamide | ESI-MS m/z calc. 418.03, found 419.13 (M + 1)+; Retention time (Method B): 1.77 minutes (3 minute run). |
| 269 | N-(3-carbamoylphenyl)-4,5-dichloro-2-(2,4-dimethoxyphenoxy)benzamide | ESI-MS m/z calc. 460.06, found 461.18 (M + 1)+; Retention time (Method B): 1.87 minutes (3 minute run). |
| 270 | N-(3-carbamoylphenyl)-4,5-dichloro-2-(4-fluoro-2-methoxy-phenoxy)benzamide | ESI-MS m/z calc. 448.04, found 449.15 (M + 1)+; Retention time (Method B): 1.83 minutes (3 minute run). |
| 271 | N-(3-carbamoylphenyl)-4,5-dichloro-2-(3-fluoro-4-methoxy-phenoxy)benzamide | ESI-MS m/z calc. 448.04, found 449.15 (M + 1)+; Retention time (Method B): 1.79 minutes (3 minute run). |
| 272 | N-(3-carbamoylphenyl)-4,5-dichloro-2-[4-(trifluoromethoxy)phenoxy]benzamide | ESI-MS m/z calc. 484.02, found 485.16 (M + 1)+; Retention time (Method B): 1.95 minutes (3 minute run). |
| 273 | N-(3-carbamoylphenyl)-4,5-dichloro-2-(2-fluoro-4-methoxy-phenoxy)benzamide | ESI-MS m/z calc. 448.04, found 449.15 (M + 1)+; Retention time (Method B): 1.81 minutes (3 minute run). |

Example 215

N-(4-carbamoylphenyl)-4,5-dichloro-2-(4-fluoro-2-methoxy-phenoxy)benzamide (274)

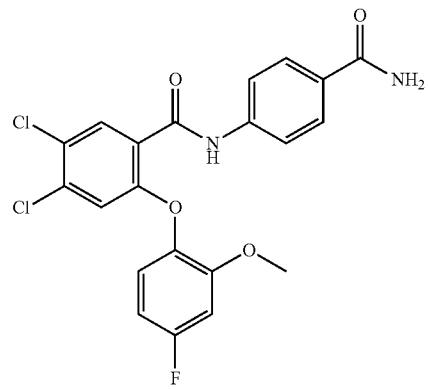 [SMILES: COc1cc(F)ccc1Oc1cc(Cl)c(Cl)cc1C(=O)Nc1ccc(C(N)=O)cc1]

Step 1: 4,5-dichloro-2-(4-fluoro-2-methoxy-phenoxy)benzaldehyde

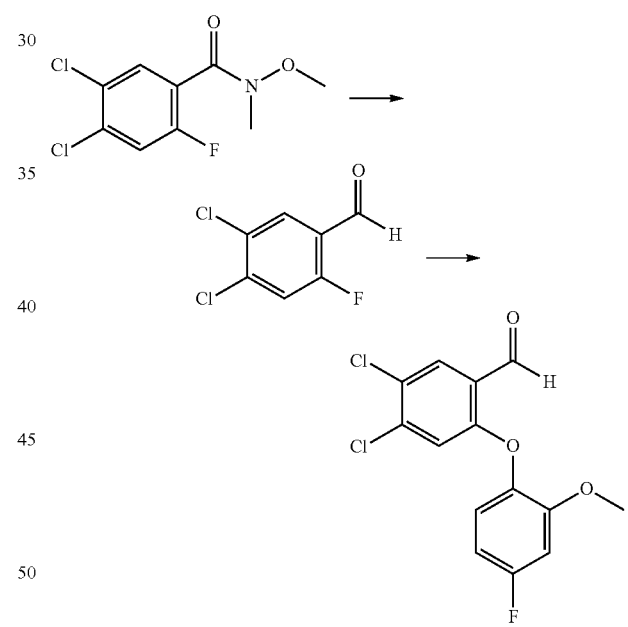

To a stirring solution of 4,5-dichloro-2-fluoro-N-methoxy-N-methyl-benzamide (5.1 g, 20.23 mmol, prepared as described in Example 286) in THF (100 mL) at −78° C. was added a solution of lithium aluminum hydride in THF (approximately 12.14 mL of 2 M, 24.28 mmol). After 3 hours at −78° C., 50 mL of water was added followed by 50 mL of 1 N HCl. The reaction was allowed to warm to room temperature and stirred for 1 hour. The reaction was diluted with water and extracted with diethyl ether. The ether layer was dried over Na$_2$SO$_4$, filtered, and concentrated to provide crude 4,5-dichloro-2-fluoro-benzaldehyde. The aldehyde was taken directly to the next step.

Crude 4,5-dichloro-2-fluoro-benzaldehyde, 4-fluoro-2-methoxy-phenol (approximately 2.875 g, 2.306 mL, 20.23 mmol) and K₂CO₃ (approximately 5.592 g, 40.46 mmol) were combined in DMF (100 mL) and heated for 30 min at 70° C., then at 55° C. overnight. The reaction was cooled, diluted with water (500 mL) and extracted with diethyl ether. The ether layer was dried over Na₂SO₄, filtered, and concentrated. Silica gel chromatography (120 g silica, 0-40% ethyl acetate/hexane) provided 4,5-dichloro-2-(4-fluoro-2-methoxy-phenoxy)benzaldehyde (3.30 g, 52%) as a crystalline white solid. ¹H NMR (400 MHz, DMSO-d6) δ 10.39 (s, 1H), 7.93 (s, 1H), 7.35 (dd, J=8.8, 5.8 Hz, 1H), 7.19 (dd, J=10.7, 2.9 Hz, 1H), 6.92-6.85 (m, 2H), 3.78 (s, 3H).

Step 2:
4,5-dichloro-2-(4-fluoro-2-methoxy-phenoxy)benzoic acid

Step 3: 4,5-dichloro-2-(4-fluoro-2-methoxy-phenoxy)benzoic acid-(4-carbamoylphenyl)-4,5-dichloro-2-(4-fluoro-2-methoxy-phenoxy)benzamide (274)

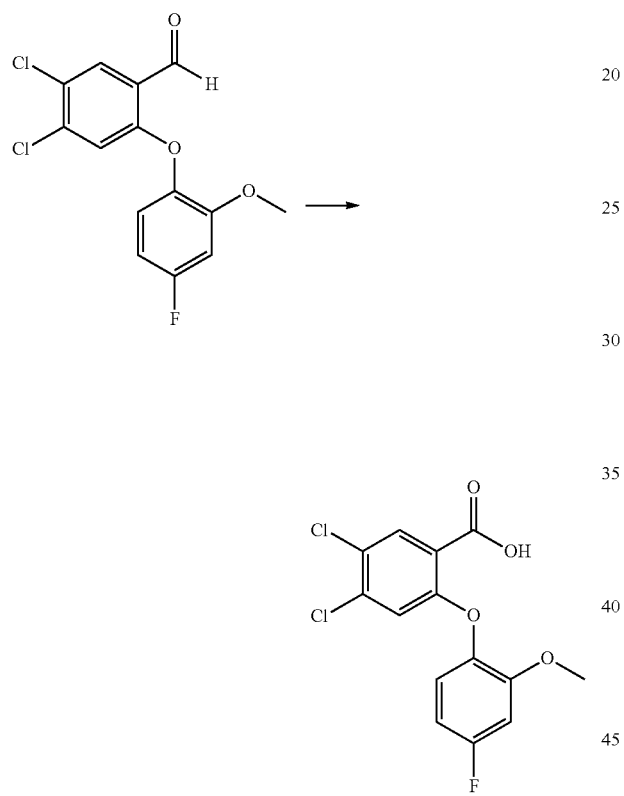

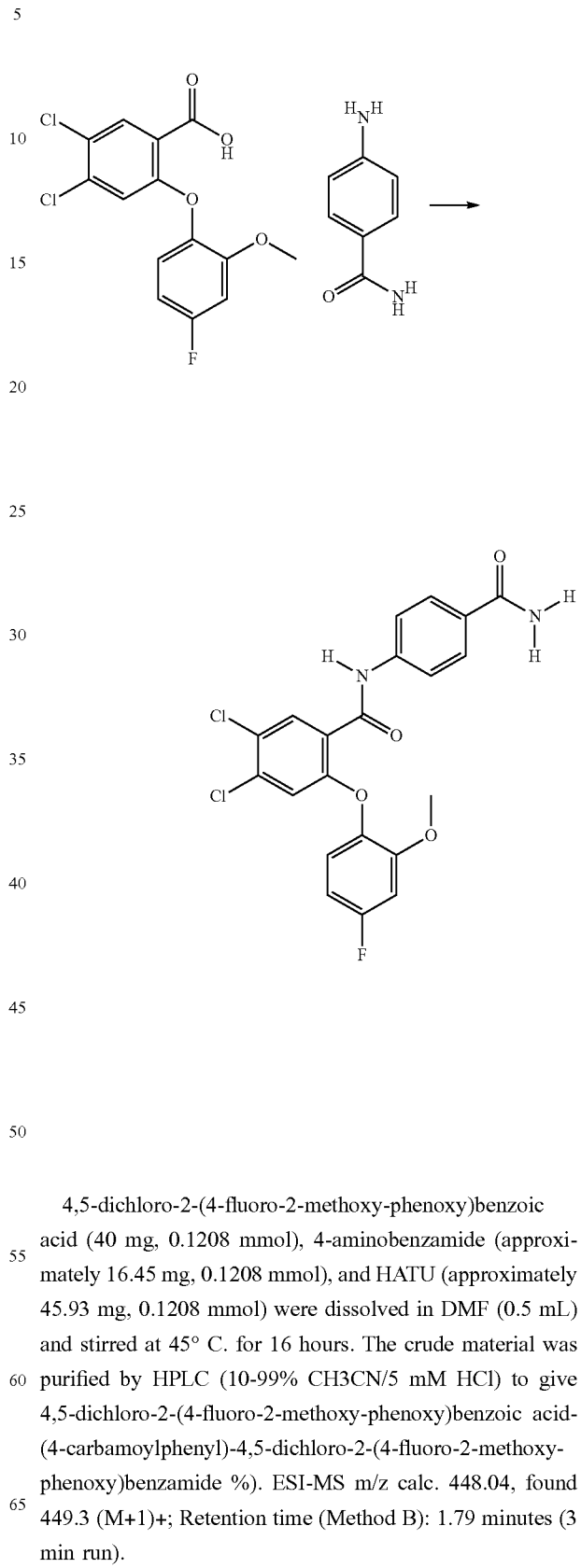

To a solution of 4,5-dichloro-2-(4-fluoro-2-methoxy-phenoxy)benzaldehyde (3.3 g, 10.47 mmol) in tert-butyl alcohol (33 mL), water (19.8 mL) and acetonitrile (19.8 mL) was added sodium dihydrogen phosphate (approximately 1.256 g, 656 µL, 10.47 mmol), 2-methylbut-2-ene (approximately 3.671 g, 5.54 mL, 52.35 mmol) and sodium chlorite (approximately 2.841 g, 31.41 mmol). The reaction mixture was stirred at room temperature for 1 hour. The reaction mixture was acidified with 1N HCl and diluted with ethyl acetate. Sodium sulfite was added to remove the faint yellow color. The two layers were separated and the aqueous layer was extracted with ethyl acetate (3×25 mL). The combined organics were washed with brine, dried over sodium sulfate, filtered and concentrated in vacuo. The solid was triturated with hexane and filtered to provide 4,5-dichloro-2-(4-fluoro-2-methoxy-phenoxy)benzoic acid (2.94 g, 85%) as a white solid. ¹H NMR (400 MHz, DMSO-d6) δ 13.37 (br s, 1H), 7.96 (s, 1H), 7.18-7.12 (m, 2H), 6.86-6.80 (m, 2H), 3.76 (s, 3H).

4,5-dichloro-2-(4-fluoro-2-methoxy-phenoxy)benzoic acid (40 mg, 0.1208 mmol), 4-aminobenzamide (approximately 16.45 mg, 0.1208 mmol), and HATU (approximately 45.93 mg, 0.1208 mmol) were dissolved in DMF (0.5 mL) and stirred at 45° C. for 16 hours. The crude material was purified by HPLC (10-99% CH3CN/5 mM HCl) to give 4,5-dichloro-2-(4-fluoro-2-methoxy-phenoxy)benzoic acid-(4-carbamoylphenyl)-4,5-dichloro-2-(4-fluoro-2-methoxy-phenoxy)benzamide %). ESI-MS m/z calc. 448.04, found 449.3 (M+1)+; Retention time (Method B): 1.79 minutes (3 min run).

Example 216

N-(3-carbamoylphenyl)-2-(2-chloro-4-fluoro-phenoxy)-6-methyl-benzamide (275)

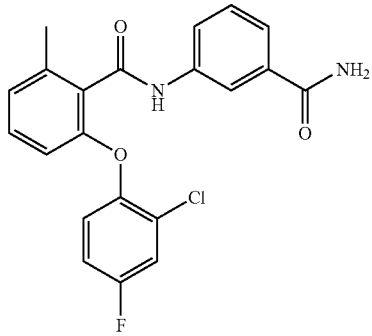 [SMILES: Cc1cccc(Oc2ccc(F)cc2Cl)c1C(=O)Nc1cccc(C(N)=O)c1]

Step 1: 2-(2-chloro-4-fluoro-phenoxy)-6-methyl-benzaldehyde

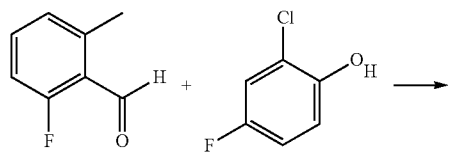

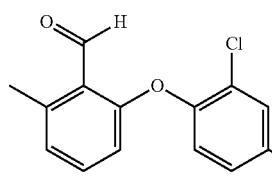

To a solution of 2-fluoro-6-methyl-benzaldehyde (1.07 g, 7.746 mmol) and 2-chloro-4-fluoro-phenol (approximately 1.135 g, 817.7 µL, 7.746 mmol) in DMF (9.169 mL) was added cesium carbonate (approximately 2.524 g, 7.746 mmol), and the mixture was heated at 100° C. for 1 hour. The mixture was cooled to room temperature before it was diluted with ethyl acetate and water. The layers were separated and the aqueous layer was extracted with ethyl acetate (3×). The combined organics were washed with brine, dried over sodium sulfate, filtered and concentrated. The residue was purified by column chromatography using a gradient of ethyl acetate in hexanes (0-100%) to yield 2-(2-chloro-4-fluoro-phenoxy)-6-methyl-benzaldehyde (1.05 g, 51%). ESI-MS m/z calc. 264.03534, found 265.1 (M+1)+; Retention time (Method B): 2.02 minutes (3 min run).

Step 2: 2-(2-chloro-4-fluoro-phenoxy)-6-methyl-benzoic acid

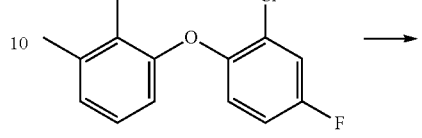

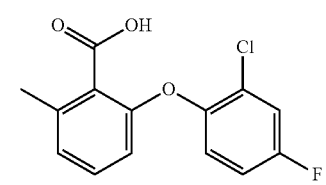

To a solution of 2-(2-chloro-4-fluoro-phenoxy)-6-methyl-benzaldehyde (1.05 g, 3.967 mmol) in tBuOH (10.50 mL), water (6.615 mL) and acetonitrile (6.615 mL) was added sodium dihydrogen phosphate (approximately 1.428 g, 745.7 µL, 11.90 mmol), 2-methylbut-2-ene (approximately 1.391 g, 2.098 mL, 19.83 mmol) and sodium chlorite (approximately 1.076 g, 11.90 mmol). The reaction mixture was stirred at room temperature for 1 hour. The reaction mixture was acidified with 1N HCl and was diluted with ethyl acetate. Sodium sulfite was added to remove the faint yellow color. The two layers were separated and the aqueous layer was extracted with ethyl acetate (3×). The organics were combined, washed with brine, dried over sodium sulfate, filtered and concentrated to give 2-(2-chloro-4-fluoro-phenoxy)-6-methyl-benzoic acid (1.06 g, 95%). ESI-MS m/z calc. 280.03024, found 281.5 (M+1)+; Retention time (Method B): 1.7 minutes (3 min run).

Step 3: N-(3-carbamoylphenyl)-2-(2-chloro-4-fluoro-phenoxy)-6-methyl-benzamide (275)

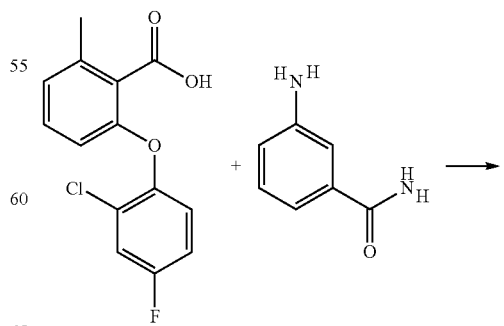

-continued

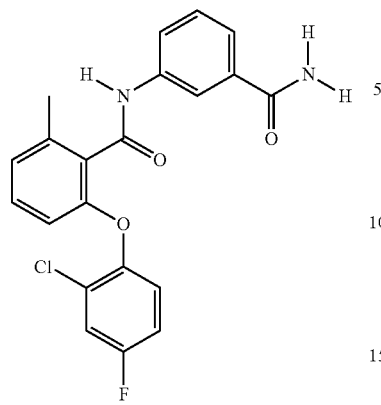

Triethyl amine (approximately 109.9 mg, 151.4 μL, 1.086 mmol) was added to a mixture of 2-(2-chloro-4-fluoro-phenoxy)-6-methyl-benzoic acid (61 mg, 0.217 mmol), 3-aminobenzamide (approximately 29.59 mg, 0.217 mmol), HATU (approximately 82.62 mg, 0.217 mmol) and DMF (1.220 mL) at room temperature. The mixture was heated at 50° C. for 5 hours before it was cooled to room temperature, filtered and subjected to preparatory-HPLC (10-99% ACN/water with 0.01% HCl) to afford N-(3-carbamoylphenyl)-2-(2-chloro-4-fluoro-phenoxy)-6-methyl-benzamide (5.3 mg, 6%). ESI-MS m/z calc. 398.08334, found 399.5 (M+1)+; Retention time (Method B): 1.61 minutes (3 min run). $^1$H NMR (400 MHz, DMSO) δ 10.62 (s, 1H), 8.20 (t, J=1.7 Hz, 1H), 7.95 (s, 1H), 7.78 (dd, J=8.0, 1.4 Hz, 1H), 7.61-7.54 (m, 2H), 7.43-7.34 (m, 2H), 7.33-7.23 (m, 3H), 7.10 (d, J=7.6 Hz, 1H), 6.60 (d, J=8.3 Hz, 1H), 2.35 (s, 3H).

Example 217

N-(3-carbamoylphenyl)-2-(4-fluorophenoxy)-5-(trifluoromethyl)benzamide (276)

Step 1: N-(3-carbamoylphenyl)-2-fluoro-5-(trifluoromethyl)benzamide

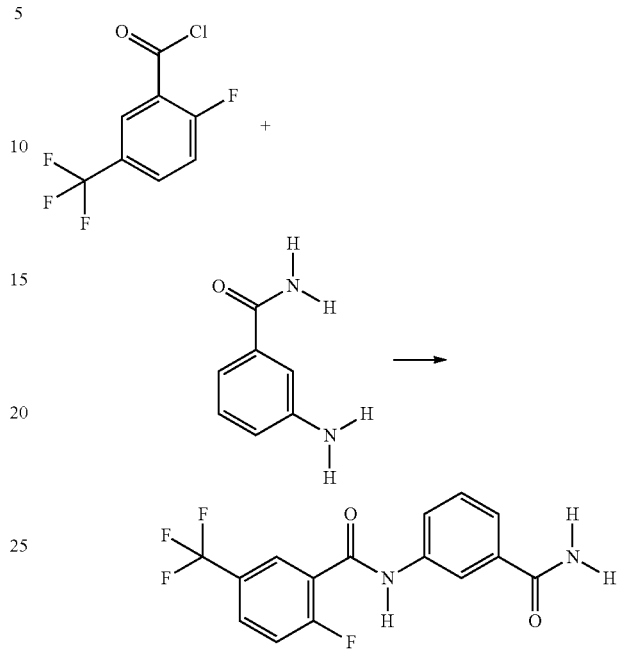

To a stirring solution of 3-aminobenzamide (6.0 g, 44.1 mmol), DCM (100 mL), DMF (30 mL) and pyridine (35 g, 36 mL, 441 mmol), at 0° C. (ice-bath), was added 2-fluoro-5-(trifluoromethyl)benzoyl chloride (10 g, 44.1 mmol) drop-wise over a period of 10 minutes. The reaction mixture was stirred at 0° C. for 1 hour, the ice bath was removed, and the reaction mixture was allowed to stir at room temperature for 4 hours. The reaction mixture was filtered and the solid was washed with a minimum amount of ethyl acetate and water. The obtained solid was dried in a vacuum oven to yield N-(3-carbamoylphenyl)-2-fluoro-5-(trifluoromethyl)benzamide (12.7 g, 88%) as an off-white solid. ESI-MS m/z calc. 326.08, found 327.3 (M+1)+; retention time (Method B): 1.39 (3 minute run). $^1$H NMR (400 MHz, DMSO-d6) δ 10.73 (s, 1H), 8.20-8.14 (m, 1H), 8.08 (dd, J=6.1, 2.4 Hz, 1H), 8.06-7.93 (m, 2H), 7.87 (dd, J=7.9, 2.1 Hz, 1H), 7.69-7.59 (m, 2H), 7.45 (t, J=7.9 Hz, 1H), 7.40 (s, 1H) ppm.

Step 2: N-(3-carbamoylphenyl)-2-(4-fluorophenoxy)-5-(trifluoromethyl)benzamide (276)

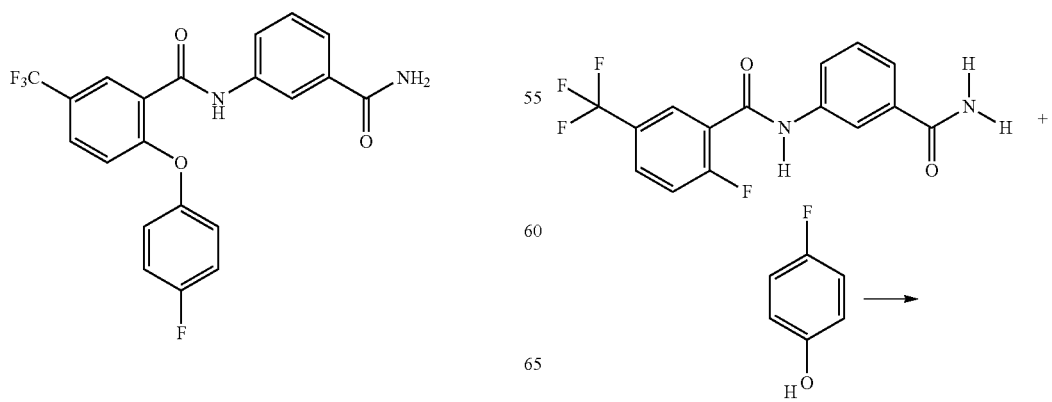

-continued

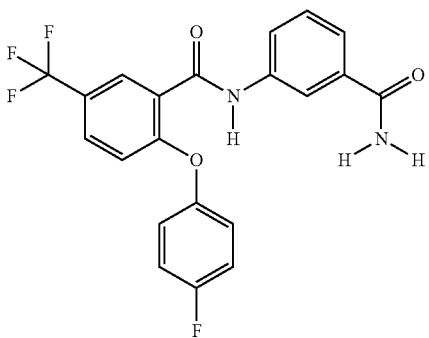

A reaction vial was loaded with N-(3-carbamoylphenyl)-2-fluoro-5-(trifluoromethyl)benzamide (51 mg, 0.15 mmol), 4-fluoro-phenol (17 mg, 0.15 mmol), cesium carbonate (147 mg, 0.45 mmol), and NMP (1 mL), and the reaction mixture was heated at 100° C. for 30 minutes. The reaction mixture was filtered and purified by reverse phase HPLC (gradient of 10-99% acetonitrile in water containing HCl as a modifier) to obtain N-(3-carbamoylphenyl)-2-(4-fluorophenoxy)-5-(trifluoromethyl)benzamide (36 mg, 58I) as a white solid. ESI-MS m/z calc. 418.09, found 419.2 (M+1)+; retention time (Method B): 1.73 (3 minute run). ¹H NMR (400 MHz, DMSO-d6) δ 10.62 (s, 1H), 8.19-8.13 (m, 1H), 8.00 (d, J=2.2 Hz, 1H), 7.96 (s, 1H), 7.89-7.78 (m, 2H), 7.63-7.55 (m, 1H), 7.47-7.35 (m, 2H), 7.35-7.23 (m, 4H), 6.99 (d, J=8.7 Hz, 1H).

The compounds set forth in Table 17 were prepared by methods analogous to the preparation of compound 276.

TABLE 17

Additional Compounds Prepared By Methods Analogous to Example 217

| Cmpd No. | Compound Name | LC/MS | NMR (shifts in ppm) |
|---|---|---|---|
| 277 | N-(3-carbamoylphenyl)-2-phenoxy-5-(trifluoromethyl)benzamide | ESI-MS m/z calc. 400.10, found 401.4 (M + 1)+; Retention time (Method B): 1.72 minutes (3 minute run). | ¹H NMR (400 MHz, DMSO-d6) δ 10.62 (s, 1H), 8.20-8.10 (m, 1H), 8.00 (d, J = 2.3 Hz, 1H), 7.96 (s, 1H), 7.91-7.76 (m, 2H), 7.64-7.54 (m, 1H), 7.52-7.33 (m, 4H), 7.30-7.16 (m, 3H), 7.02 (d, J = 8.8 Hz, 1H). |
| 278 | N-(3-carbamoylphenyl)-2-(3-fluoro-2-methoxyphenoxy)-5-(trifluoromethyl)benzamide | ESI-MS m/z calc. 448.10, found 449.3 (M + 1)+; Retention time (Method B): 1.75 minutes (3 minute run). | ¹H NMR (400 MHz, DMSO-d6) δ 10.64 (s, 1H), 8.24-8.14 (m, 1H), 8.01 (d, J = 2.3 Hz, 1H), 7.96 (s, 1H), 7.89-7.78 (m, 2H), 7.64-7.55 (m, 1H), 7.48-7.31 (m, 2H), 7.30-7.13 (m, 2H), 7.13-7.05 (m, 1H), 6.97 (d, J = 8.7 Hz, 1H), 3.78 (d, J = 1.0 Hz, 3H). |
| 279 | N-(3-carbamoylphenyl)-2-(2-chloro-4-methoxyphenoxy)-5-(trifluoromethyl)benzamide | ESI-MS m/z calc. 464.08, found 465.3 (M + 1)+; Retention time (Method B): 1.82 minutes (3 minute run). | ¹H NMR (400 MHz, DMSO-d6) δ 10.60 (s, 1H), 8.24-8.15 (m, 1H), 8.02-7.94 (m, 2H), 7.90-7.84 (m, 1H), 7.79 (dd, J = 8.9, 2.4 Hz, 1H), 7.65-7.54 (m, 1H), 7.50-7.33 (m, 3H), 7.24 (d, J = 2.9 Hz, 1H), 7.06 (dd, J = 9.0, 3.0 Hz, 1H), 6.80 (d, J = 8.7 Hz, 1H), 3.81 (s, 3H). |
| 280 | N-(3-carbamoylphenyl)-2-(4-methoxy-2-methylphenoxy)-5-(trifluoromethyl)benzamide | ESI-MS m/z calc. 444.13, found 445.4 (M + 1)+; Retention time (Method B): 1.82 minutes (3 minute run). | ¹H NMR (400 MHz, DMSO-d6) δ 10.60 (s, 1H), 8.26-8.14 (m, 1H), 7.97 (d, J = 2.4 Hz, 2H), 7.93-7.81 (m, 1H), 7.76 (dd, J = 8.9, 2.4 Hz, 1H), 7.66-7.57 (m, 1H), 7.48-7.30 (m, 2H), 7.13 (d, J = 8.8 Hz, 1H), 6.94 (d, J = 3.0 Hz, 1H), 6.87 (dd, J = 8.8, 3.0 Hz, 1H), 6.74 (d, J = 8.8 Hz, 1H), 3.76 (s, 3H), 2.11 (s, 3H). |
| 281 | N-(3-carbamoylphenyl)-2-(2,4-dimethoxyphenoxy)-5-(trifluoromethyl)benzamide | ESI-MS m/z calc. 460.12, found 461.2 (M + 1)+; Retention time (Method B): 1.79 minutes (3 minute run). | ¹H NMR (400 MHz, DMSO-d6) δ 10.50 (s, 1H), 8.21-8.14 (m, 1H), 8.02-7.92 (m, 2H), 7.92-7.83 (m, 1H), 7.75 (dd, J = 8.9, 2.4 Hz, 1H), 7.66-7.56 (m, 1H), 7.48-7.32 (m, 2H), 7.27 (d, J = 8.8 Hz, 1H), 6.81-6.70 (m, 2H), 6.62 (dd, J = 8.7, 2.8 Hz, 1H), 3.80 (s, 3H), 3.74 (s, 3H). |
| 282 | N-(3-carbamoylphenyl)-2-(2-isopropoxyphenoxy)-5-(trifluoromethyl)benzamide | ESI-MS m/z calc. 458.15, found 459.4 (M + 1)+; Retention time (Method B): 1.88 minutes (3 minute run). | ¹H NMR (400 MHz, DMSO-d6) δ 10.45 (s, 1H), 8.25-8.11 (m, 1H), 8.04-7.92 (m, 2H), 7.92-7.83 (m, 1H), 7.78 (dd, J = 8.8, 2.4 Hz, 1H), 7.67-7.55 (m, 1H), 7.48-7.31 (m, 3H), 7.31-7.16 (m, 2H), 7.13-6.99 (m, 1H), 6.83 (d, J = 8.8 Hz, 1H), 4.65-4.48 (m, 1H), 1.07 (d, J = 6.0 Hz, 6H). |

TABLE 17-continued

Additional Compounds Prepared By Methods Analogous to Example 217

| Cmpd No. | Compound Name | LC/MS | NMR (shifts in ppm) |
|---|---|---|---|
| 283 | N-(3-carbamoylphenyl)-2-(2-chlorophenoxy)-5-(trifluoromethyl)benzamide | ESI-MS m/z calc. 434.06, found 435.3 (M + 1)+; Retention time (Method B): 1.76 minutes (3 minute run). | $^1$H NMR (400 MHz, DMSO-d6) δ 10.63 (s, 1H), 8.20-8.14 (m, 1H), 8.03 (d, J = 2.3 Hz, 1H), 7.96 (s, 1H), 7.91-7.78 (m, 2H), 7.68-7.56 (m, 2H), 7.54-7.24 (m, 5H), 6.91 (d, J = 8.7 Hz, 1H). |
| 284 | N-(3-carbamoylphenyl)-2-(4-chloro-2-methylphenoxy)-5-(trifluoromethyl)benzamide | ESI-MS m/z calc. 448.08, found 449.3 (M + 1)+; Retention time (Method B): 1.92 minutes (3 minute run). | $^1$H NMR (400 MHz, DMSO-d6) δ 10.63 (s, 1H), 8.22-8.13 (m, 1H), 8.00 (d, J = 2.3 Hz, 1H), 7.96 (s, 1H), 7.86-7.73 (m, 2H), 7.64-7.53 (m, 1H), 7.50-7.29 (m, 4H), 7.15 (d, J = 8.7 Hz, 1H), 6.91 (d, J = 8.7 Hz, 1H), 2.16 (s, 3H). |
| 285 | N-(3-carbamoylphenyl)-2-(2-(difluoromethoxy)phenoxy)-5-(trifluoromethyl)benzamide | ESI-MS m/z calc. 466.10, found 467.4 (M + 1)+; Retention time (Method B): 1.77 minutes (3 minute run). | $^1$H NMR (400 MHz, DMSO-d6) δ 10.60 (s, 1H), 8.21-8.12 (m, 1H), 8.02 (d, J = 2.3 Hz, 1H), 7.96 (s, 1H), 7.83 (dd, J = 8.6, 2.2 Hz, 2H), 7.63-7.56 (m, 1H), 7.47-6.89 (m, 8H). |
| 286 | N-(3-carbamoylphenyl)-2-(4-chloro-2-methoxyphenoxy)-5-(trifluoromethyl)benzamide | ESI-MS m/z calc. 464.08, found 465.3 (M + 1)+; Retention time (Method B): 1.84 minutes (3 minute run). | $^1$H NMR (400 MHz, DMSO-d6) δ 10.55 (s, 1H), 8.24-8.12 (m, 1H), 8.05-7.93 (m, 2H), 7.86 (dd, J = 7.7, 2.1 Hz, 1H), 7.76 (dd, J = 8.8, 2.3 Hz, 1H), 7.64-7.55 (m, 1H), 7.47-7.35 (m, 2H), 7.36-7.29 (m, 2H), 7.11 (dd, J = 8.5, 2.4 Hz, 1H), 6.84 (d, J = 8.8 Hz, 1H), 3.77 (s, 3H). |
| 287 | N-(3-carbamoylphenyl)-2-(2-methoxyphenoxy)-5-(trifluoromethyl)benzamide | ESI-MS m/z calc. 430.11, found 431.5 (M + 1)+; Retention time (Method B): 1.78 minutes (3 minute run). | 1H NMR (400 MHz, DMSO-d6) δ 10.53 (s, 1H), 8.22-8.14 (m, 1H), 8.01-7.94 (m, 2H), 7.94-7.82 (m, 1H), 7.77 (dd, J = 8.9, 2.4 Hz, 1H), 7.64-7.56 (m, 1H), 7.47-7.35 (m, 2H), 7.35-7.27 (m, 2H), 7.27-7.18 (m, 1H), 7.12-7.00 (m, 1H), 6.78 (d, J = 8.8 Hz, 1H), 3.75 (s, 3H). |
| 288 | N-(3-carbamoylphenyl)-2-(4-fluoro-2-methoxyphenoxy)-5-(trifluoromethyl)benzamide | ESI-MS m/z calc. 448.10, found 449.5 (M + 1)+; Retention time (Method B): 1.47 minutes (3 minute run). | $^1$H NMR (400 MHz, DMSO) δ 10.54 (s, 1H), 8.18 (s, 1H), 7.97 (d, J = 2.3 Hz, 2H), 7.88 (d, J = 8.1 Hz, 1H), 7.77 (dd, J = 8.8, 2.3 Hz, 1H), 7.61 (d, J = 7.8 Hz, 1H), 7.48-7.34 (m, 3H), 7.18 (dd, J = 10.7, 2.9 Hz, 1H), 6.92-6.85 (m, 1H), 6.80 (d, J = 8.7 Hz, 1H), 3.76 (s, 3H). |
| 289 | N-(3-carbamoylphenyl)-2-(2-chloro-4-fluorophenoxy)-5-(trifluoromethyl)benzamide | ESI-MS m/z calc. 452.06, found 453.3 (M + 1)+; Retention time (Method B): 1.83 minutes (3 minute run). | |
| 290 | N-(3-carbamoylphenyl)-2-(4-fluoro-2-methoxyphenoxy)-5-(trifluoromethyl)benzamide | ESI-MS m/z calc. 448.10, found 449.2 (M + 1)+; Retention time (Method B): 1.69 minutes (3 minute run). | $^1$H NMR (400 MHz, DMSO) δ 10.52 (s, 1H), 8.17 (s, 1H), 7.98 (m, 2H), 7.86 (m, 1H), 7.79 (dd, J = 8.8, 2.3 Hz, 1H), 7.60 (d, J = 7.8 Hz, 1H), 7.43 (t, J = 7.9 Hz, 1H), 7.38 (s, 1H), 7.25 (m, 2H), 7.15 (m, 1H), 6.88 (d, J = 8.7 Hz, 1H), 3.73 (s, 3H). |

Example 218

N-(3-carbamoyl-2-methylphenyl)-2-(4-fluoro-2-methylphenoxy)-5-(trifluoromethyl)benzamide (291)

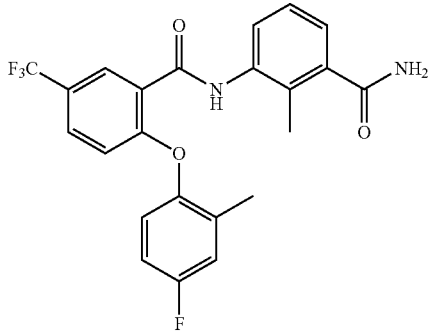 [SMILES: Cc1cc(F)ccc1Oc1ccc(C(F)(F)F)cc1C(=O)Nc1cccc(C(N)=O)c1C]

Step 1: 2-(4-fluoro-2-methylphenoxy)-5-(trifluoromethyl)benzaldehyde

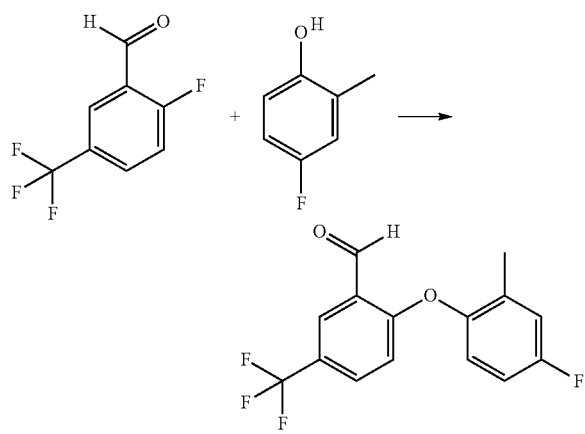

To a solution of 2-fluoro-5-(trifluoromethyl)benzaldehyde (11.6 mL, 82.1 mmol) and 4-fluoro-2-methyl-phenol (11.4 g, 90.3 mmol) in DMF (80 mL) was added cesium carbonate (29.4 g, 90.3 mmol), and the mixture was heated at 100° C. for 1.5 hours. The reaction was cooled to room temperature and filtered, washing with ethyl acetate. The solvent was concentrated under reduced pressure. The residue was partitioned between ethyl acetate (200 mL) and water (100 mL). The two layers were separated, and the aqueous layer was extracted with ethyl acetate (2×100 mL). The organic layers were combined, dried over sodium sulfate, and filtered, and the solvent was evaporated under reduced pressure to give a brown liquid. The crude product was purified on 330 g of silica gel utilizing a gradient of 0-15% ethyl acetate in hexane to yield 2-(4-fluoro-2-methyl-phenoxy)-5-(trifluoromethyl)benzaldehyde (16.4 g, 67%) as a yellow solid. ESI-MS m/z calc. 298.06, found 299.3 (M+1)+; Retention time (Method B): 2.22 minutes (3 min run). $^1$H NMR (400 MHz, DMSO) δ 10.53 (s, 1H), 8.09 (d, J=2.3 Hz, 1H), 7.94 (dd, J=8.8, 2.4 Hz, 1H), 7.32 (dd, J=9.3, 3.1 Hz, 1H), 7.30-7.25 (m, 1H), 7.22-7.14 (m, 1H), 6.84 (d, J=8.8 Hz, 1H), 2.18 (s, 3H) ppm.

Step 2: 2-(4-fluoro-2-methyl-phenoxy)-5-(trifluoromethyl)benzoic acid

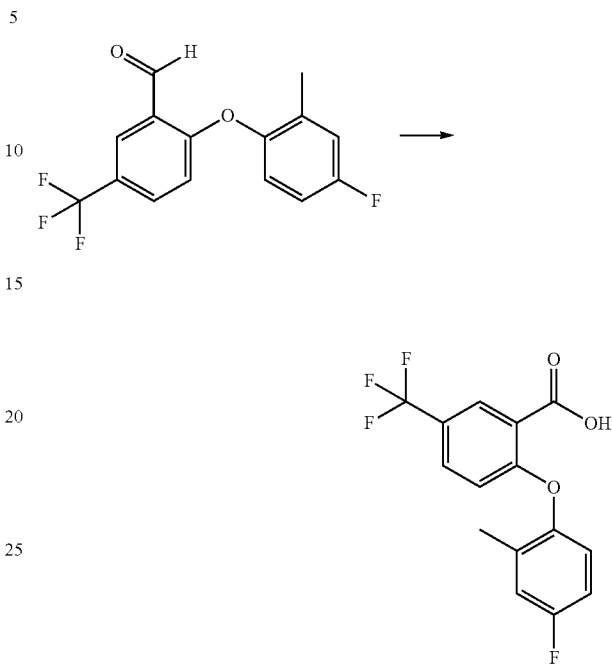

To a solution of 2-(4-fluoro-2-methyl-phenoxy)-5-(trifluoromethyl)benzaldehyde (16.4 g, 55.0 mmol) in tBuOH (164 mL), water (103 mL) and acetonitrile (103 mL) was added sodium dihydrogen phosphate (10.6 g, 5.5 mL, 88.0 mmol), 2-methyl-2-butene (19.3 g, 29.1 mL, 275.1 mmol) and NaClO$_2$ (14.9 g, 165.1 mmol). The reaction mixture was stirred at 25° C. for 2 hours. The mixture was acidified with aqueous 1N HCl and was diluted with ethyl acetate (200 mL). The layers were separated and the aqueous layer was extracted with ethyl acetate (2×100 mL). The organic layers were combined, dried with sodium sulfate, filtered and evaporated to give a pale yellow sticky solid that was titrated with hexanes, then filtered to give 2-(4-fluoro-2-methyl-phenoxy)-5-(trifluoromethyl)benzoic acid (16.5 g, 95%) as a white solid. ESI-MS m/z calc. 314.06, found 315.2 (M+1)+; Retention time (Method B): 1.96 minutes (3 min run). $^1$H NMR (400 MHz, DMSO) δ 12.17 (s, 1H), 8.09 (d, J=2.3 Hz, 1H), 7.83 (dd, J=8.8, 2.2 Hz, 1H), 7.27 (dd, J=9.3, 3.0 Hz, 1H), 7.20-6.99 (m, 2H), 6.84 (d, J=8.7 Hz, 1H), 2.14 (s, 3H) ppm.

Step 3: N-(3-carbamoyl-2-methylphenyl)-2-(4-fluoro-2-methylphenoxy)-5-(trifluoromethyl)benzamide (291)

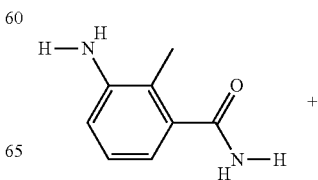 +

749
-continued

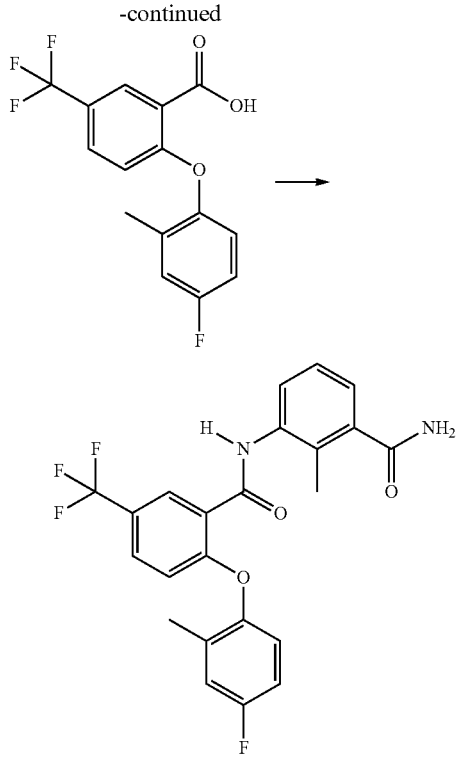

To a reaction vial loaded with 3-amino-2-methylbenzamide (15.0 mg, 0.10 mmol), 2-(4-fluoro-2-methyl-phenoxy)-5-(trifluoromethyl)benzoic acid (63 mg, 0.20 mmol), HATU (38 mg, 0.10 mmol) and NMP (1 mL) was added triethylamine (30 mg, 0.30 mmol), and the reaction was heated at 80° C. for 18 hours. The reaction mixture was filtered and purified by reverse phase HPLC (gradient of 10-99% acetonitrile in water containing HCl as a modifier) to obtain N-(3-carbamoyl-2-methylphenyl)-2-(4-fluoro-2-methylphenoxy)-5-(trifluoromethyl)benzamide acid (9.5 mg, 21%) as a white solid. ESI-MS m/z calc. 446.13, found 447.4 (M+1)+; Retention time (Method B): 1.95 minutes (3 min run). $^1$H NMR (400 MHz, DMSO-d6) δ 10.03 (s, 1H), 8.09 (d, J=2.4 Hz, 1H), 7.80 (dd, J=8.8, 2.4 Hz, 1H), 7.76 (s, 1H), 7.70-7.56 (m, 1H), 7.41 (s, 1H), 7.34-7.06 (m, 5H), 6.83 (d, J=8.8 Hz, 1H), 2.23 (s, 3H), 2.18 (s, 3H) ppm.

The compounds set forth in Table 18 were prepared by methods analogous to the preparation of compound 291.

TABLE 18

Additional Compounds Prepared By Methods Analogous to Example 218

| Cmpd No. | Compound Name | LC/MS | NMR (shifts in ppm) |
|---|---|---|---|
| 292 | N-(3-carbamoyl-4-methoxyphenyl)-2-(4-fluoro-2-methylphenoxy)-5-(trifluoromethyl)benzamide | ESI-MS m/z calc. 462.12, found 467.3 (M + 1)+; Retention time (Method B): 1.98 minutes (3 minute run). | |
| 293 | N-(3-carbamoyl-4-chlorophenyl)-2-(4-fluoro-2-methylphenoxy)-5-(trifluoromethyl)benzamide | ESI-MS m/z calc. 462.12, found 463.3 (M + 1)+; Retention time (Method B): 2.01 minutes (3 minute run). | |
| 294 | N-(3-carbamoyl-4-methylphenyl)-2-(4-fluoro-2-methylphenoxy)-5-(trifluoromethyl)benzamide | ESI-MS m/z calc. 446.13, found 447.1 (M + 1)+; Retention time (Method B): 1.98 minutes (3 minute run). | |
| 296 | N-(3-carbamoylphenyl)-2-(4-fluoro-2-methylphenoxy)-5-(trifluoromethyl)benzamide | ESI-MS m/z calc. 432.11 found 433.3 (M + 1)+; Retention time (Method B): 1.88 minutes (3 minute run). | $^1$H NMR (400 MHz, DMSO) δ 10.62 (s, 1H), 8.18 (s, 1H), 7.98 (m, 2H), 7.85 (d, J = 8.2 Hz, 1H), 7.78 (dd, J = 8.8, 2.1 Hz, 1H), 7.60 (d, J = 7.8 Hz, 1H), 7.41 (dd, J = 16.8, 8.9 Hz, 2H), 7.23 (m, 2H), 7.14 (td, J = 8.6, 3.1 Hz, 1H), 6.82 (d, J = 8.7 Hz, 1H), 2.15 (s, 3H). |
| 297 | N-(4-carbamoylphenyl)-2-(2-chloro-4-fluorophenoxy)-6-(trifluoromethyl)benzamide | ESI-MS m/z calc. 432.11 found 433.3 (M + 1)+; Retention time (Method B): 1.66 minutes (3 minute run). | |

Example 219

N-(3-Carbamoylphenyl)-2-[4-fluoro-2-(methoxy)phenoxy]-4-(trifluoromethyl)benzamide (298)

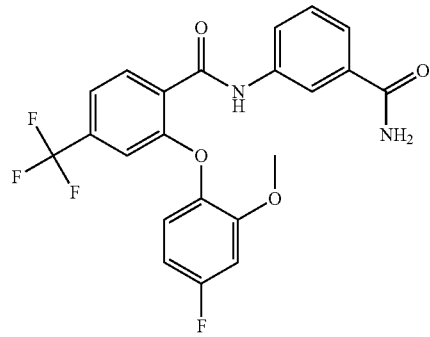 [SMILES: COc1cc(F)ccc1Oc1cc(C(F)(F)F)ccc1C(=O)Nc1cccc(C(N)=O)c1]

Step 1: N-(3-carbamoylphenyl)-2-fluoro-4-(trifluoromethyl)benzamide

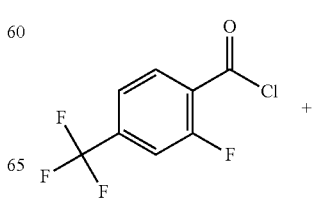

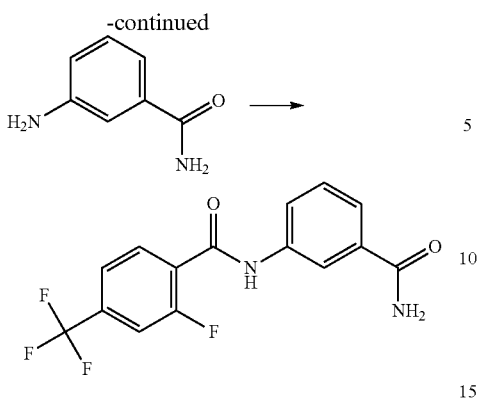

To 3-aminobenzamide (1.20 g, 8.83 mmol) in dichloromethane (20 mL), N,N-dimethylformamide (6 mL), and pyridine (6.98 g, 7.14 mL, 88.3 mmol) at 0° C. was added a solution of 2-fluoro-5-(trifluoromethyl)benzoyl chloride (2.00 g, 8.83 mmol) in dichloromethane (4 mL) drop wise. The resulting precipitate was filtered and washed with minimal dichloromethane. The solid was re-suspended in water, filtered, and dried under vacuum to provide N-(3-carbamoylphenyl)-2-fluoro-4-(trifluoromethyl)benzamide (2.02 g, 70%) as a white solid. ESI-MS m/z calc. 326.07, found 327.3 (M+1)+; retention time (Method B): 1.25 minutes (3 minute run). $^1$H NMR (400 MHz, DMSO-d6) δ 10.75 (s, 1H), 8.19 (t, J=1.8 Hz, 1H), 7.99 (s, 1H), 7.96-7.88 (m, 2H), 7.85 (ddd, J=8.2, 2.1, 1.0 Hz, 1H), 7.75 (d, J=8.2 Hz, 1H), 7.67-7.59 (m, 1H), 7.45 (t, J=7.9 Hz, 1H), 7.39 (s, 1H).

Step 2: N-(3-Carbamoylphenyl)-2-[4-fluoro-2-(methoxy)phenoxy]-4-(trifluoromethyl)benzamide (298)

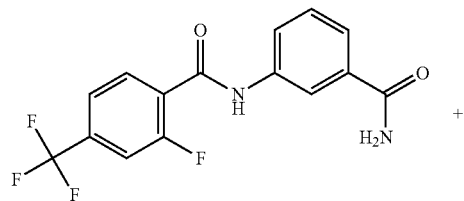

A mixture of N-(3-carbamoylphenyl)-2-fluoro-4-(trifluoromethyl)benzamide (50 mg, 0.15 mmol), 4-fluoro-2-methoxy-phenol (26 mg, 21 μL, 0.18 mmol)) and potassium carbonate (64 mg, 0.46 mmol) was heated in DMF (0.5 mL) at 100° C. for 1 hour. Filtration followed by HPLC purification (1-99% acetonitrile/5 mM HCl) afforded N-(3-carbamoylphenyl)-2-[4-fluoro-2-(methoxy)phenoxy]-4-(trifluoromethyl)benzamide as a white solid (41 mg, 59%). ESI-MS m/z calc. 448.10, found 449.3 (M+1)+; Retention time (Method B): 1.57 minutes (3 minute run). $^1$H NMR (400 MHz, DMSO-d6) δ 10.57 (s, 1H), 8.22-8.16 (m, 1H), 7.97 (br s, 1H), 7.84 (d, J=7.9 Hz, 2H), 7.60 (dd, J=7.7, 1.3 Hz, 1H), 7.55 (d, J=7.2 Hz, 1H), 7.42 (t, J=7.9 Hz, 1H), 7.38 (br s, 1H), 7.33 (dd, J=8.8, 5.8 Hz, 1H), 7.16 (dd, (=10.7, 2.9 Hz, 1H), 6.87 (td, b=8.6, 3.1 Hz, 1H), 6.84 (s, 1H), 3.76 (s, 3H).

The compounds set forth in Table 19 were prepared by methods analogous to the preparation of compound 298.

TABLE 19

Additional Compounds Prepared By Methods Analogous to Example 219

| Cmpd No. | Compound Name | LC/MS | NMR (shifts in ppm) |
|---|---|---|---|
| 299 | N-(3-carbamoylphenyl)-2-[2-chloro-4-(methoxy)phenoxy]-4-(trifluoromethyl)benzamide | ESI-MS m/z calc. 464.08, found 465.5 (M + 1)+; Retention time (Method B): 1.61 minutes (3 minute run). | $^1$H NMR (400 MHz, DMSO-d6) δ 10.64 (s, 1H), 8.19 (t, J = 1.9 Hz, 1H), 7.97 (s, 1H), 7.87 (d, J = 7.9 Hz, 1H), 7.83 (dd, J = 7.9, 1.8 Hz, 1H), 7.64-7.56 (m, 2H), 7.42 (t, J = 7.9 Hz, 1H), 7.39-7.33 (m, 2H), 7.22 (d, J = 3.0 Hz, 1H), 7.04 (dd, J = 9.0, 3.0 Hz, 1H), 6.87 (d, J = 1.8 Hz, 1H), 3.80 (s, 3H). |
| 300 | N-(3-carbamoylphenyl)-2-[4-fluorophenoxy]-4-(trifluoromethyl)benzamide | ESI-MS m/z calc. 418.09, found 419.1 (M + 1)+; | $^1$H NMR (400 MHz, DMSO-d6) δ 10.65 (s, 1H), 8.15 (t, J = 1.9 Hz, 1H), 7.96 (s, 1H), 7.87 (d, J = 8.4 Hz, 1H), 7.80 (ddd, J = 8.3, |

TABLE 19-continued

Additional Compounds Prepared By Methods Analogous to Example 219

| Cmpd No. | Compound Name | LC/MS | NMR (shifts in ppm) |
|---|---|---|---|
| | | Retention time (Method B): 1.54 minutes (3 minute run). | 2.2, 1.1 Hz, 1H), 7.63 (dd, J = 8.1, 1.6 Hz, 1H), 7.59 (dt, J = 7.9, 1.3 Hz, 1H), 7.41 (t, J = 7.9 Hz, 1H), 7.37 (br s, 1H), 7.31-7.25 (m, 2H), 7.25-7.19 (m, 2H), 7.14 (d, J = 1.6 Hz, 1H). |
| 301 | N-(3-carbamoylphenyl)-2-[2,4-(dimethoxy)phenoxy]-4-(trifluoromethyl)benzamide | ESI-MS m/z calc. 460.12, found 461.3 (M + 1)+; Retention time (Method B): 1.58 minutes (3 minute run). | $^1$H NMR (400 MHz, DMSO-d6) δ 10.54 (s, 1H), 8.20 (t, J = 1.9 Hz, 1H), 7.98 (br s, 1H), 7.88-7.80 (m, 2H), 7.60 (dt, J = 7.8, 1.3 Hz, 1H), 7.51 (dd, J = 8.2, 1.6 Hz, 1H), 7.43 (t, J = 7.9 Hz, 1H), 7.38 (br s, 1H), 7.25 (d, J = 8.8 Hz, 1H), 6.78 (d, J = 2.6 Hz, 2H), 6.61 (dd, J = 8.8, 2.8 Hz, 1H), 3.80 (s, 3H), 3.74 (s, 3H). |
| 302 | N-(3-carbamoylphenyl)-2-[4-chloro-2-(methoxy)phenoxy]-4-(trifluoromethyl)benzamide | ESI-MS m/z calc. 464.08, found 465.5 (M + 1)+; Retention time (Method B): 1.65 minutes (3 minute run). | $^1$H NMR (400 MHz, DMSO-d6) δ 10.58 (s, 1H), 8.17 (t, J = 1.9 Hz, 1H), 7.97 (br s, 1H), 7.87-7.79 (m, 2H), 7.59 (t, J = 7.7 Hz, 2H), 7.42 (t, J = 7.9 Hz, 1H), 7.37 (br s, 1H), 7.29 (d, J = 2.4 Hz, 1H), 7.26 (d, J = 8.5 Hz, 1H), 7.09 (dd, J = 8.6, 2.4 Hz, 1H), 6.93 (s, 1H), 3.76 (s, 3H). |

Example 220

4-[[4-[2-methoxy-4-(trifluoromethoxy)phenoxy]-6-(trifluoromethyl)pyridine-3-carbonyl]amino]-N,6-dimethyl-pyridine-2-carboxamide (265)

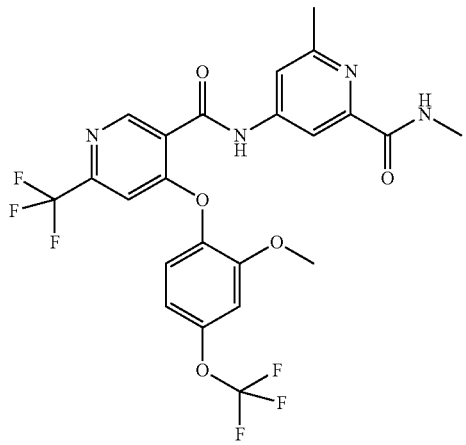 [SMILES: CNC(=O)c1cc(NC(=O)c2cnc(C(F)(F)F)cc2Oc2ccc(OC(F)(F)F)cc2OC)cc(C)n1]

This compound was made in an analogous fashion to Example 71, except employing 4-amino-N,6-dimethyl-pyridine-2-carboxamide in the amide formation step (Step 2). The yield of the desired product after purification was 5 mg (2%). ESI-MS m/z calc. 544.1182, found 545.0 (M+1)+, 543.0 (M−1)−; retention time (Method C): 3.27 minutes (5 minute run). $^1$H NMR (400 MHz, DMSO-d6) δ 11.14 (s, 1H), 8.95 (s, 1H), 8.60 (q, J=4.8 Hz, 1H), 8.12 (d, J=1.9 Hz, 1H), 7.77 (d, J=1.9 Hz, 1H), 7.50 (d, J=8.8 Hz, 1H), 7.28 (d, J=2.7 Hz, 1H), 7.13-7.04 (m, 2H), 3.78 (s, 3H), 2.83 (d, J=4.9 Hz, 3H), 2.54 (s, 3H).

Example 221

N-(3-carbamoyl-4-fluoro-phenyl)-6-(2-cyano-4-fluoro-phenoxy)-2-fluoro-3-(trifluoromethyl)benzamide (295)

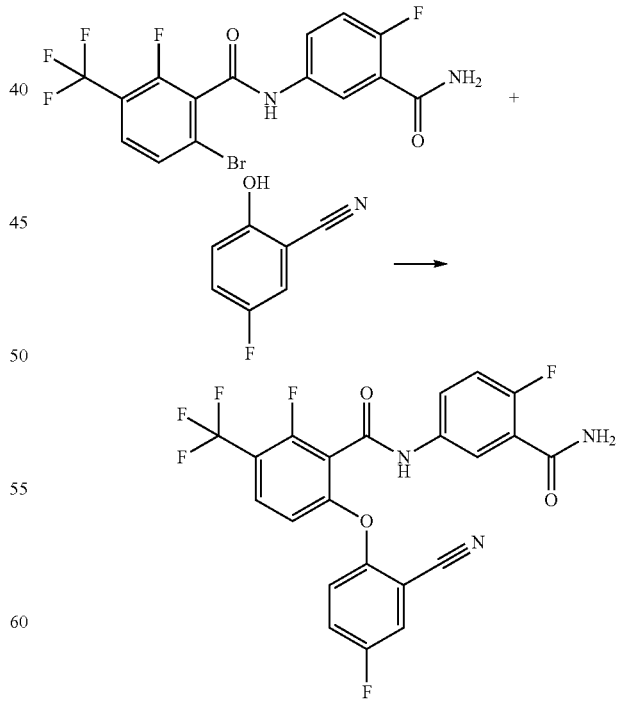

A mixture of 6-bromo-N-(3-carbamoyl-4-fluoro-phenyl)-2-fluoro-3-(trifluoromethyl)benzamide (60 mg, 0.14 mmol, prepared as described in Example 140), cesium carbonate (92 mg, 0.28 mmol) and 5-fluoro-2-hydroxy-benzonitrile (19.44 mg, 0.1418 mmol) in toluene (0.6 mL) was bubbled with nitrogen. After 2-3 minutes, copper iodide (15 mg, 0.07 mmol) was added, and the reaction mixture was stirred at 100° C. for 20 minutes. The reaction was diluted with ethyl acetate and water. The organic layer was concentrated in vacuo and purified by HPLC (10-99% acetonitrile/5 mM HCl) to provide N-(3-carbamoyl-4-fluoro-phenyl)-6-(2-cyano-4-fluoro-phenoxy)-2-fluoro-3-(trifluoromethyl)benzamide (4 mg, 6%). ESI-MS m/z calc. 479.0705, found 480.1 (M+1)+; retention time (Method B). 1.61 minutes (3 minute run).

Example 222

4-(6-((6-chloro-2-methoxypyridin-3-yl)oxy)-2-fluoro-3-(trifluoromethyl)benzamido)picolinamide (303)

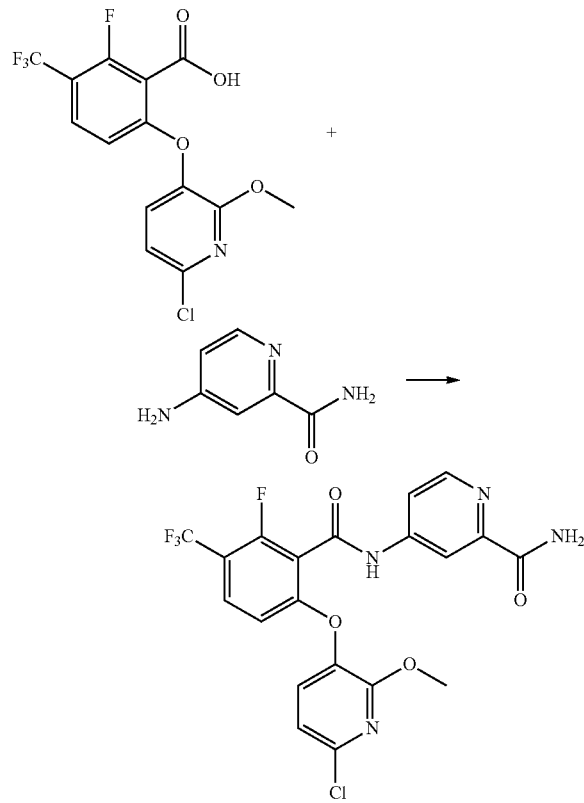

To a suspension of 6-[(6-chloro-2-methoxy-3-pyridyl) oxy]-2-fluoro-3-(trifluoromethyl)benzoic acid (600 mg, 1.641 mmol, prepared as described in Example 128) and DMF (5 µL, 0.06457 mmol) in dichloromethane (9 mL) at 0° C. was added oxalyl chloride (700 µL, 8.024 mmol) dropwise. The reaction was allowed to come to room temperature and stirred for ~30 min. The reaction mixture was concentrated, and the residue was taken up in dichloromethane and concentrated (3×5 mL). A cold solution of the crude 6-[(6-chloro-2-methoxy-3-pyridyl)oxy]-2-fluoro-3-(trifluoromethyl)benzoyl chloride in dichloromethane (1 mL) was then added to 5-aminopyridine-3-carboxamide (35 mg, 0.26 mmol) suspended in dichloromethane (1 mL) and diisopropylethylamine (136 µL, 0.78 mmol) at 0° C. The reaction was then allowed to warm to room temperature and stirred for 16 hours. The reaction was concentrated, dissolved in DMSO and purified by HPLC to afford 4-(6-((6-chloro-2-methoxypyridin-3-yl)oxy)-2-fluoro-3-(trifluoromethyl)benzamido)picolinamide (1.5 mg, 2%). ESI-MS m/z calc. 484.79, found 485.0 (M+1)+; Retention time (Method B): 1.45 minutes (3 minutes run).

Example 223

E-VIPR Assay Method A for Detecting and Measuring Nav Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. *Characterization of voltage-gated sodium channel blockers by electrical stimulation and fluorescence detection of membrane potential*, 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 hours prior to running the assay on E-VIPR, HEK cells expressing a truncated form of human NaV 1.8 with full channel activity were seeded into 384-well plates (Greiner #781091-1B), pre-coated with matrigel, at a density of 25,000 cells per well. 5% KIR2.1 Bacmam virus was added to the final cell suspension before seeding into cell plates. HEK cells were grown in DMEM media (exact composition is specific to each cell type and Nav subtype) supplemented with 10% FBS (Fetal Bovine Serum, qualified; Sigma #F4135), 1% NEAA (Non-Essential Amino Acids, Life Tech #11140), 1% HEPES (Life Tech #15630), 1% Pen-Strep (Penicillin-Streptomycin; Life Tech #15640) and 5 µg/ml Blasticidin (Gibco #R210-01). Cells were expanded in vented cap flasks, with 95% humidity and 5% $CO_2$.

Reagents and Stock Solutions:
   100 mg/mL Pluronic F-127 (Sigma #P2443), in dry DMSO
   Compound Plates: Corning 384-well Polypropylene Round Bottom #3656
   Cell Plates: 384-well tissue culture treated plates. Greiner #781091-1B
   5% KIR 2.1 Bacmam virus (produced in-house), prepared as described in Section 3.3 of J. A. Fornwald et al., *Gene Expression in Mammalian Cells Using BacMam, a Modified Baculovirus System*, 1350 Methods in Molecular Biology 95-116 (2016), the entire contents of which are incorporated by reference.
   5 mM $DiSBAC_6(3)$ (a voltage sensitive oxonol acceptor) (Aurora #00-100-010) in dry DMSO
   5 mM CC2-DMPE (a membrane-bound coumarin phospholipid FRET donor) (Aurora #00-100-008) in dry DMSO
   89 mM VABSC-1 in $H_2O$
   Human Serum (HS, Millipore #S1P1-01KL, lot #2706671A)

Bath1 Buffer:
  Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.
Na/TMA Cl Bath1 Buffer:
  Sodium Chloride 96 mM (5.61 g/L), Potassium Chloride 4.5 mM (0.335 g/L),
  Tetramethylammonium (TMA)-Cl 64 mM (7.01 g/L), Glucose 10 mM (1.8 g/L),
  Magnesium Chloride (Anhydrous) 1 mM (0.095 g/L), Calcium Chloride 2 mM (0.222 g/L)
  HEPES 10 mM (2.38 g/L) in water.
Hexyl Dye Solution (2×):
  Bath1 Buffer containing 0.5% β-cyclodextrin (made fresh prior to each use, Sigma #C4767), 8 µM CC2-DMPE and 2 µM DiSBAC$_6$(3). The solution was made by adding 10% Pluronic F127 stock equal to combined volumes of CC2-DMPE and DiSBAC$_6$(3). The order of preparation was first mix Pluronic and CC2-DMPE, then add DiSBAC$_6$(3), then while vortexing add Bath1/β-Cyclodextrin.
  Compound Loading Buffer (2×): Na/TMA Cl Bath1 Buffer containing HS 50% (omitted in experiments run in the absence of HS), VABSC-1 1 mM, BSA 0.2% (in Bath-1), KCl 9 mM, DMSO 0.75%.
Assay Protocol:
  1) 400 nL of each compound was pre-spotted (in neat DMSO) into polypropylene compound plates at 400× desired final concentration, in an 11 point dose response, 3-fold dilution, resulting in a top dose of 3 µM final concentration in the cell plate. Vehicle control (neat DMSO), and positive control (an established Nav1.8 inhibitor, 25 µM final in assay in DMSO) were added manually to the outermost columns of each plate respectively. The compound plate was backfilled with 80 ul per well of Compound Loading Buffer resulting in a 400 fold dilution of compound following a 1:1 transfer of compound into the cell plate (Step 6). Final DMSO concentration for all wells in the assay was 0.625% (0.75% DMSO was supplemented to the Compound Loading Buffer for a final DMSO concentration of 0.625%).
  2) Hexyl Dye Solution was prepared.
  3) Cell plates were prepared. On the day of the assay, the media was aspirated, and the cells were washed three times with 80 µL of Bath-1 buffer, maintaining 25 µL residual volume in each well.
  4) 25 µL per well of Hexyl Dye Solution was dispensed into the cell plates. The cells were incubated for 20 minutes at room temp or ambient conditions in darkness.
  5) 80 µL per well of Compound Loading Buffer was dispensed into compound plates.
  6) The cell plates were washed three times with 80 µL per well of Bath-1 Buffer, leaving 25 L of residual volume. Then 25 uL per well from compound plate was transferred to each cell plate. The mixture was incubated for 30 minutes at room temp/ambient conditions.
  7) The plate was read on E-VIPR using the current-controlled amplifier to deliver stimulation wave pulses using the following protocol: 1.25 Amps, 2.5 ms pulse width biphasic waveform, 10 Hz for 10 seconds at a scan rate of 200 Hz. A pre-stimulus recording was performed for 0.5 seconds to obtain the un-stimulated intensities baseline. The stimulatory waveform was followed by 0.5 seconds of post-stimulation recording to examine the relaxation to the resting state.

Data Analysis:
Data were analyzed and reported as normalized ratios of emission intensities measured in the 460 nm and 580 nm channels. The response as a function of time was reported as the ratios obtained using the following formula:

$$R(t) = \frac{(\text{intensity}_{460\ nm})}{(\text{intensity}_{580\ nm})}$$

The data were further reduced by calculating the initial ($R_i$) and final ($R_f$) ratios. These were the average ratio values during part or all of the pre-stimulation period and during sample points during the stimulation period. The fluorescence ratio ($R_f/R_i$) was then calculated and reported as a function of time.

Control responses were obtained by performing assays in the presence of the positive control, and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the ratio response of the test compound. Using this analysis Method A protocol, dose response curves were plotted and IC$_{50}$ values were generated for various compounds of the present invention as reported below in Tables 20 and 20A.

E-VIPR Assay Method B for Detecting and Measuring Nav Inhibition Properties

Sodium ion channels are voltage-dependent proteins that can be activated by inducing membrane voltage changes by applying electric fields. The electrical stimulation instrument and methods of use, referred to as E-VIPR, are described in International Publication No. WO 2002/008748 A3 and C.-J. Huang et al. *Characterization of voltage-gated sodium channel blockers by electrical stimulation and fluorescence detection of membrane potential*, 24 Nature Biotech. 439-46 (2006), both of which are incorporated by reference in their entirety. The instrument comprises a microtiter plate handler, an optical system for exciting the coumarin dye while simultaneously recording the coumarin and oxonol emissions, a waveform generator, a current- or voltage-controlled amplifier, and parallel electrode pairs that are inserted into assay plate wells. Under integrated computer control, this instrument passes user-programmed electrical stimulus protocols to cells within the wells of the microtiter plate.

16-20 hours prior to running the assay on E-VIPR, HEK cells expressing a truncated form of human Na$_V$1.8 with full channel activity were seeded into 384-well plates (Greiner #781091-1B), pre-coated with matrigel, at a density of 25,000 cells per well. 5% KIR2.1 Bacmam virus was added to the final cell suspension before seeding into cell plates. HEK cells were grown in DMEM media (exact composition is specific to each cell type and Nav subtype) supplemented with 10% FBS (Fetal Bovine Serum, qualified; Sigma #F4135), 1% NEAA (Non-Essential Amino Acids, Life Tech #11140), 1% HEPES (Life Tech #15630), 1% Pen-Strep (Penicillin-Streptomycin; Life Tech #15640) and 5 µg/ml Blasticidin (Gibco #R210-01). Cells were expanded in vented cap flasks, with 95% humidity and 5% $CO_2$.

Reagents and Stock Solutions:
- 100 mg/mL Pluronic F-127 (Sigma #P2443), in dry DMSO
- Compound Plates: Corning 384-well Polypropylene Round Bottom #3656
- Cell Plates: 384-well tissue culture treated plates. Greiner #781091-1B
- 5% KIR 2.1 Bacmam virus (produced in-house), prepared as described in Section 3.3 of J. A. Fornwald et al., *Gene Expression in Mammalian Cells Using BacMam, a Modified Baculovirus System*, 1350 Methods in Molecular Biology 95-116 (2016), the entire contents of which are incorporated by reference.
- 5 mM DiSBAC$_6$(3) (a voltage sensitive oxonol acceptor) (Aurora #00-100-010) in dry DMSO
- 5 mM CC2-DMPE (a membrane-bound coumarin phospholipid FRET donor) (Aurora #00-100-008) in dry DMSO
- 89 mM VABSC-1 in H$_2$O. VABSC-1 (Aurora #00-100-390, Voltage Assay Background Suppression Compound) suppress background signal to provide optimal assay performance
- Human Serum (HS, Millipore #S1P1-01KL, lot #2706671A)

Bath1 Buffer:
- Sodium Chloride 160 mM (9.35 g/L), Potassium Chloride, 4.5 mM (0.335 g/L), Glucose 10 mM (1.8 g/L), Magnesium Chloride (Anhydrous) 1 mM (0.095 g/L), Calcium Chloride 2 mM (0.222 g/L), HEPES 10 mM (2.38 g/L) in water.

Na/TMA Cl Bath1 Buffer:
- Sodium Chloride 96 mM (5.61 g/L), Potassium Chloride 4.5 mM (0.335 g/L), Tetramethylammonium (TMA)-Cl 64 mM (7.01 g/L), Glucose 10 mM (1.8 g/L), Magnesium Chloride (Anhydrous) 1 mM (0.095 g/L), Calcium Chloride 2 mM (0.222 g/L) HEPES 10 mM (2.38 g/L) in water.

Hexyl Dye Solution (2×):
- Bath1 Buffer containing 0.5% β-cyclodextrin (made fresh prior to each use, Sigma #C4767), 8 μM CC2-DMPE and 2 μM DiSBAC$_6$(3). The solution was made by adding 10% Pluronic F127 stock equal to combined volumes of CC2-DMPE and DiSBAC$_6$(3). The order of preparation was first mix Pluronic and CC2-DMPE, then add DiSBAC$_6$(3), then while vortexing add Bath1/β-Cyclodextrin.

Compound Loading Buffer (2×): Na/TMA Cl Bath1 Buffer, VABSC-1 1 mM, BSA 0.2% (in Bath-1), KCl 9 mM, DMSO 0.75%.

Assay Protocol:
1) 400 nL of each compound was pre-spotted (in neat DMSO) into polypropylene compound plates at 400× desired final concentration. Vehicle control (neat DMSO), and positive control (an established Nav1.8 inhibitor, 25 μM final in assay in DMSO) were added to the outermost columns of each plate respectively. The compound plate was backfilled with 80 uL per well of Compound Loading Buffer resulting in a 400 fold dilution of compound following a 1:1 transfer of compound into the cell plate (Step 6). Final DMSO concentration for all wells in the assay was 0.625% (0.75% DMSO was supplemented to the Compound Loading Buffer for a final DMSO concentration of 0.625%).

2) Hexyl Dye Solution was prepared.

3) Cell plates were prepared. On the day of the assay, the media was aspirated, and the cells were washed three times with 80 μL of Bath-1 buffer, maintaining 25 μL residual volume in each well.

4) 25 μL per well of Hexyl Dye Solution was dispensed into the cell plates. The cells were incubated for 20 minutes at room temp or ambient conditions in darkness.

5) 80 μL per well of Compound Loading Buffer was dispensed into compound plates.

6) The cell plates were washed three times with 80 μL per well of Bath-1 Buffer, leaving 25 L of residual volume. Then 25 uL per well from compound plate was transferred to each cell plate. The mixture was incubated for 30 minutes at room temp/ambient conditions.

7) The plate was read on E-VIPR using the current-controlled amplifier to deliver stimulation wave pulses using the following protocol: 1.25 Amps, 2.5 ms pulse width biphasic waveform, 10 Hz for 10 seconds at a scan rate of 200 Hz. A pre-stimulus recording was performed for 0.5 seconds to obtain the un-stimulated intensities baseline. The stimulatory waveform was followed by 0.5 seconds of post-stimulation recording to examine the relaxation to the resting state.

Data Analysis:

Data were analyzed and reported as normalized ratios of emission intensities measured in the 460 nm and 580 nm channels. The response as a function of time was reported as the ratios obtained using the following formula:

$$R(t) = \frac{(\text{intensity}_{460\ nm})}{(\text{intensity}_{580\ nm})}$$

The data were further reduced by calculating the initial ($R_i$) and final ($R_f$) ratios. These were the average ratio values during part or all of the pre-stimulation period and during sample points during the stimulation period. The fluorescence ratio ($R_f/R_i$) was then calculated and reported as a function of time.

Control responses were obtained by performing assays in the presence of the positive control, and in the absence of pharmacological agents (DMSO vehicle negative control). Responses to the negative (N) and positive (P) controls were calculated as above. The compound antagonist % activity A was then defined as:

$$A = \frac{X - N}{P - N} \times 100$$

where X is the ratio response of the test compound. Using this analysis Method B protocol, dose response curves were plotted and IC$_{50}$ values were generated for various compounds of the present invention as reported below in Table 20B.

Results:

The IC$_{50}$ values determined for the compounds of the invention are reported in Tables 20, 20A, and 20B.

TABLE 20

IC$_{50}$ Values of Compounds 1-26 of the Invention in E-VIPR Assay Method A

| Compound Number | Nav 1.8 MedChem Optical Assay EVIPR Assay Method A HS IC$_{50}$ (uM) |
|---|---|
| 1 | 0.0007 |
| 2 | 0.001 |
| 3 | 0.001 |

TABLE 20-continued

IC$_{50}$ Values of Compounds 1-26 of the
Invention in E-VIPR Assay Method A

| Compound Number | Nav 1.8 MedChem Optical Assay EVIPR Assay Method A HS IC$_{50}$ (uM) |
|---|---|
| 4 | 0.002 |
| 5 | 0.002 |
| 6 | 0.003 |
| 7 | 0.003 |
| 8 | 0.003 |
| 9 | 0.003 |
| 10 | 0.003 |
| 11 | 0.004 |
| 12 | 0.004 |
| 13 | 0.004 |
| 14 | 0.006 |
| 15 | 0.007 |
| 16 | 0.007 |
| 17 | 0.008 |
| 18 | 0.009 |
| 19 | 0.01 |
| 20 | 0.01 |
| 21 | 0.01 |
| 22 | 0.011 |
| 23 | 0.014 |
| 24 | 0.018 |
| 25 | 0.018 |
| 26 | 0.002 |

TABLE 20A

IC$_{50}$ Values of Compounds 27-246, 264, 265, 295, and 303 of the Invention in E-VIPR Assay Method A

| Compound Number | Nav 1.8 MedChem Optical Assay EVIPR Assay Method A HS IC$_{50}$ (uM) |
|---|---|
| 27 | 0.087 |
| 28 | 0.108 |
| 29 | 0.112 |
| 30 | 0.02 |
| 31 | 0.155 |
| 32 | 0.055 |
| 33 | 0.52 |
| 34 | 0.083 |
| 35 | 0.25 |
| 36 | 0.215 |
| 37 | 0.89 |
| 38 | 0.7 |
| 39 | 0.21 |
| 40 | 0.034 |
| 41 | 0.56 |
| 42 | 0.4 |
| 43 | 0.04 |
| 44 | 0.005 |
| 45 | 0.001 |
| 46 | 1.2 |
| 47 | 0.022 |
| 48 | 0.023 |
| 49 | 0.13 |
| 50 | 0.051 |
| 51 | 0.009 |
| 52 | 0.014 |
| 53 | 0.017 |
| 54 | 0.007 |
| 55 | 0.018 |
| 56 | 0.26 |
| 57 | 0.017 |
| 58 | 0.19 |
| 59 | 0.007 |
| 60 | 0.185 |
| 61 | 0.038 |
| 62 | 0.011 |
| 63 | 0.14 |

TABLE 20A-continued

IC$_{50}$ Values of Compounds 27-246, 264, 265, 295, and 303 of the Invention in E-VIPR Assay Method A

| Compound Number | Nav 1.8 MedChem Optical Assay EVIPR Assay Method A HS IC$_{50}$ (uM) |
|---|---|
| 64 | 0.185 |
| 65 | 0.079 |
| 66 | 0.038 |
| 67 | 0.042 |
| 68 | 0.021 |
| 69 | 0.056 |
| 70 | 0.053 |
| 71 | 0.04 |
| 72 | 0.175 |
| 73 | 0.023 |
| 74 | 0.022 |
| 75 | 0.026 |
| 76 | 0.35 |
| 77 | 0.15 |
| 78 | 0.097 |
| 79 | 0.069 |
| 80 | 0.127 |
| 81 | 0.038 |
| 82 | 0.092 |
| 83 | 0.048 |
| 84 | 0.58 |
| 85 | 0.32 |
| 86 | 0.032 |
| 87 | 0.15 |
| 88 | 0.049 |
| 89 | 0.044 |
| 90 | 0.038 |
| 91 | 0.04 |
| 92 | 0.002 |
| 93 | 0.063 |
| 94 | 0.018 |
| 95 | 0.045 |
| 96 | 0.054 |
| 97 | 0.02 |
| 98 | 0.015 |
| 99 | 0.003 |
| 100 | 0.009 |
| 101 | 0.135 |
| 102 | 0.022 |
| 103 | 0.034 |
| 104 | 0.064 |
| 105 | 0.044 |
| 106 | 0.015 |
| 107 | 0.123 |
| 108 | 0.05 |
| 109 | 0.065 |
| 110 | 0.055 |
| 111 | 0.2 |
| 112 | 0.043 |
| 113 | 0.084 |
| 114 | 0.017 |
| 115 | 0.006 |
| 116 | 0.145 |
| 117 | 0.18 |
| 118 | 0.1 |
| 119 | 0.048 |
| 120 | 0.005 |
| 121 | 0.18 |
| 122 | 0.056 |
| 123 | 0.005 |
| 124 | 0.22 |
| 125 | 0.034 |
| 126 | 0.047 |
| 127 | 0.004 |
| 128 | 0.018 |
| 129 | 0.069 |
| 130 | 0.027 |
| 131 | 0.17 |
| 132 | 0.14 |
| 133 | 0.43 |
| 134 | 0.068 |
| 135 | 0.14 |
| 136 | 0.14 |

TABLE 20A-continued

IC$_{50}$ Values of Compounds 27-246, 264, 265, 295, and 303 of the Invention in E-VIPR Assay Method A

| Compound Number | Nav 1.8 MedChem Optical Assay EVIPR Assay Method A HS IC$_{50}$ (uM) |
|---|---|
| 137 | 0.005 |
| 138 | 1.4 |
| 139 | 0.085 |
| 140 | 0.005 |
| 141 | 0.103 |
| 142 | 0.31 |
| 143 | 0.01 |
| 144 | 0.023 |
| 145 | 0.009 |
| 146 | 0.039 |
| 147 | 0.13 |
| 148 | 0.85 |
| 149 | 1.5 |
| 150 | 0.29 |
| 151 | 0.52 |
| 152 | 0.017 |
| 153 | 0.022 |
| 154 | 0.055 |
| 155 | 0.017 |
| 156 | 0.56 |
| 157 | 1 |
| 158 | 0.15 |
| 159 | 1.7 |
| 160 | 0.41 |
| 161 | 0.15 |
| 162 | 0.17 |
| 163 | 0.011 |
| 164 | 1.6 |
| 165 | 0.34 |
| 166 | 0.005 |
| 167 | 0.045 |
| 168 | 0.14 |
| 169 | 0.113 |
| 170 | 0.014 |
| 171 | 0.035 |
| 172 | 0.012 |
| 173 | 0.052 |
| 174 | 0.088 |
| 175 | 0.038 |
| 176 | 0.19 |
| 177 | 0.46 |
| 178 | 0.076 |
| 179 | 0.01 |
| 180 | 0.075 |
| 181 | 2.1 |
| 182 | 0.41 |
| 183 | 0.099 |
| 184 | 0.5 |
| 185 | 0.066 |
| 186 | 0.19 |
| 187 | 0.053 |
| 188 | 0.16 |
| 189 | 0.006 |
| 190 | 0.032 |
| 191 | 0.12 |
| 192 | 0.42 |
| 193 | 0.016 |
| 194 | 0.021 |
| 195 | 0.011 |
| 196 | 0.044 |
| 197 | 0.46 |
| 198 | 0.15 |
| 199 | 0.17 |
| 200 | >3.1 |
| 201 | 0.001 |
| 202 | 0.04 |
| 203 | 0.046 |
| 204 | 0.6 |
| 205 | 0.15 |
| 206 | 0.045 |
| 207 | 0.027 |
| 208 | 0.013 |
| 209 | 0.05 |
| 210 | 0.14 |
| 211 | 0.006 |
| 212 | 0.054 |
| 213 | 0.009 |
| 214 | 0.66 |
| 215 | 0.018 |
| 216 | 0.008 |
| 217 | 1.1 |
| 218 | 0.002 |
| 219 | 0.0009 |
| 220 | 0.005 |
| 221 | 0.014 |
| 222 | 0.003 |
| 223 | 0.008 |
| 224 | 0.009 |
| 225 | 0.003 |
| 226 | 0.01 |
| 227 | 0.002 |
| 228 | 0.007 |
| 229 | 0.047 |
| 230 | 0.25 |
| 231 | 0.009 |
| 232 | 0.017 |
| 233 | 0.004 |
| 234 | 0.004 |
| 235 | 0.005 |
| 236 | 0.045 |
| 237 | 0.012 |
| 238 | 0.400 |
| 239 | 2.7 |
| 240 | 0.011 |
| 241 | 0.038 |
| 242 | 0.044 |
| 243 | 0.024 |
| 244 | 0.073 |
| 245 | 0.036 |
| 246 | 0.021 |
| 264 | 0.054 |
| 265 | 1.45 |
| 295 | 0.2 |
| 303 | 0.19 |

TABLE 20B

IC$_{50}$ Values of Compounds 247-263, 266-294, and 296-302 of the Invention in E-VIPR Assay Method B

| Compound Number | Nav 1.8 MedChem Optical Assay EVIPR Assay Method B HS IC$_{50}$ (uM) |
|---|---|
| 247 | 0.033 |
| 248 | 0.011 |
| 249 | 0.06 |
| 250 | 0.065 |
| 251 | 0.091 |
| 252 | 0.036 |
| 253 | 0.88 |
| 254 | 0.26 |
| 255 | 7.2 |
| 256 | 0.55 |
| 257 | 0.415 |
| 258 | 0.085 |
| 259 | 0.065 |
| 260 | 0.166 |
| 261 | 1.2 |
| 262 | >25 |
| 263 | >25 |
| 266 | 17 |
| 267 | 0.007 |

TABLE 20B-continued

IC$_{50}$ Values of Compounds 247-263, 266-294, and 296-302 of the Invention in E-VIPR Assay Method B

| Compound Number | Nav 1.8 MedChem Optical Assay EVIPR Assay Method B HS IC$_{50}$ (uM) |
|---|---|
| 268 | 0.014 |
| 269 | 0.009 |
| 270 | 0.009 |
| 271 | 0.02 |
| 272 | 0.008 |
| 273 | 0.03 |
| 274 | 0.002 |
| 275 | 0.165 |
| 276 | 0.098 |
| 277 | 0.25 |
| 278 | 0.021 |
| 279 | 0.056 |
| 280 | 0.042 |
| 281 | 0.039 |
| 282 | 0.13 |
| 283 | 0.082 |
| 284 | 0.043 |
| 285 | 0.072 |
| 286 | 0.02 |
| 287 | 0.084 |
| 288 | 0.034 |
| 289 | 0.036 |
| 290 | 0.1 |
| 291 | 1.4 |
| 292 | 0.27 |
| 293 | 0.033 |
| 294 | 0.037 |
| 296 | 0.018 |
| 297 | 0.04 |
| 298 | 0.014 |
| 299 | 0.13 |
| 300 | 0.061 |
| 301 | 0.057 |
| 302 | 0.026 |

The IC$_{50}$ values for the compounds described previously in U.S. Pat. No. 8,779,197 were also determined by Method A and are reported in Table 21. The compound numbers C1-C8 and C11 referenced in Table 21 refer to the corresponding compounds 1-8 and 11 in U.S. Pat. No. 8,779,197. As evidenced by a comparison of the data in Tables 20, 20A, and 20B with the data in Table 21, the compounds of the invention are more potent than the compounds described in U.S. Pat. No. 8,779,197.

TABLE 21

Comparative IC$_{50}$ Values of Compounds Described in U.S. Pat. No. 8,779,197 in E-VIPR Assay Method A.

| Compound Number | IC$_{50}$ (μM) |
|---|---|
| C1 | >3.1 |
| C2 | >3.1 |
| C3 | >3.1 |
| C4 | >3.1 |
| C5 | >3.1 |
| C6 | >3.1 |
| C7 | 2.8 |
| C8 | 0.985 |
| C11 | 2.65 |

Many modifications and variations of the embodiments described herein may be made without departing from the scope, as is apparent to those skilled in the art. The specific embodiments described herein are offered by way of example only.

What is claimed is:
1. A compound of formula (II)

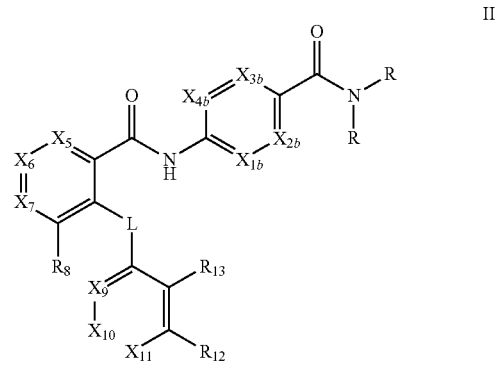

or a pharmaceutically acceptable salt thereof, wherein:
L is O;
$X_{1b}$ is N or $CR_{1b}$;
$X_{2b}$ is N or $CR_{2b}$;
$X_{3b}$ is N or $CR_{3b}$;
$X_{4b}$ is N or $CR_{4b}$;
$X_5$ is N or $CR_5$;
$X_6$ is N or $CR_6$;
$X_7$ is N or $CR_7$;
$X_9$ is N or $CR_9$;
$X_{10}$ is N or $CR_{10}$;
$X_{11}$ is N or $CR_{11}$;
each R is independently H or $CH_3$;
$R_{1b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{2b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{3b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_{4b}$ is H, halo, OH, $C_1$-$C_6$ alkyl, $C_1$-$C_6$ haloalkyl, $C_1$-$C_6$ alkoxy, or $C_1$-$C_6$ haloalkoxy;
$R_5$, $R_6$, and $R_7$ are defined as follows:
(i) $R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$;
(ii) $R_5$ is H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_6$ and $R_7$, together with the carbon atoms to which they are attached, form a ring of formula:

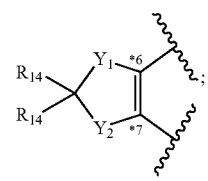

or
(iii) $R_5$ and $R_6$, together with the carbon atoms to which they are attached, form a ring of formula:

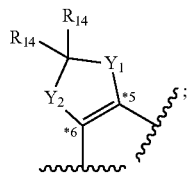

and $R_7$ is H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_8$ is H or —O—$(CH_2)_n$—$R_w$;

$R_9$, $R_{10}$, and $R_{11}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$;

$R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$; or $R_{12}$ and $R_{13}$, together with the carbon atoms to which they are attached, form a ring of formula:

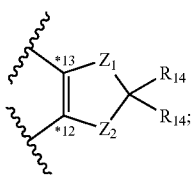

$Y_1$, $Y_2$, $Z_1$, and $Z_2$ are each independently O or C$(R_{14})_2$;

each $R_{14}$ is independently H, halo, $C_1$-$C_4$ alkyl, or $C_1$-$C_4$ haloalkyl;

each W is independently O or a single bond;

each $R_w$ is independently 3-6 membered cycloalkyl, phenyl, or 5-6 membered heteroaryl, wherein said 3-6 membered cycloalkyl, phenyl, or 5-6 membered heteroaryl may be unsubstituted or may be substituted with 1-3 substituents selected from a group consisting of halo, $C_1$-$C_6$ alkyl, and $C_1$-$C_6$ haloalkyl; and n is 0 or 1;

wherein when $R_8$ is H, then at least one of $X_5$, $X_6$, and $X_7$ is not N or CH;

wherein no more than two of $X_{1b}$, $X_{2b}$, $X_{3b}$, and $X_{4b}$ is N;

wherein no more than one of $X_5$, $X_6$, and $X_7$ is N;

wherein no more than one of $X_9$, $X_{10}$, and $X_{11}$ is N.

2. The compound of claim 1, wherein the compound has formula (II-B-1)

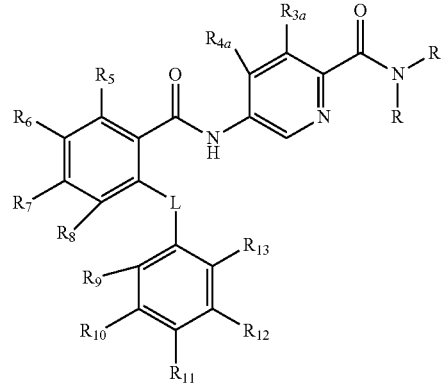

or a pharmaceutically acceptable salt thereof, wherein:

L, R, $R_{1b}$, $R_{3b}$, $R_{4b}$, $R_8$, $R_9$, $R_{10}$, and $R_{11}$ are as defined in claim 1;

$R_5$, $R_6$, and $R_7$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, $C_1$-$C_6$ alkylamino, or —W—$(CH_2)_n$—$R_w$; and $R_{12}$ and $R_{13}$ are each independently H, halo, CN, OH, $C_1$-$C_6$ alkyl, $C_1$-$C_6$ haloalkyl, $C_1$-$C_6$ alkoxy, $C_1$-$C_6$ haloalkoxy, or —W—$(CH_2)_n$—$R_w$.

3. The compound of claim 1, or a pharmaceutically acceptable salt thereof, wherein:

$R_{1b}$ is H, halo, or $C_1$-$C_6$ alkyl; and/or $R_{2b}$ is H or halo; and/or $R_{3b}$ is H; and/or $R_{4b}$ is H or $C_1$-$C_6$ alkyl.

4. The compound of claim 2, or a pharmaceutically acceptable salt thereof, wherein:

$R_{1b}$ is H, halo, or $C_1$-$C_6$ alkyl; and/or $R_{2b}$ is H or halo; and/or $R_{3b}$ is H; and/or $R_{4b}$ is H or $C_1$-$C_6$ alkyl.

5. The compound of claim 1, or a pharmaceutically acceptable salt thereof, wherein:

$R_5$ is H, halo, $C_1$-$C_6$ alkyl, $C_1$-$C_6$ haloalkyl, or $C_1$-$C_6$ alkoxy; and/or $R_6$ is H, halo, $C_1$-$C_6$ alkyl, $C_1$-$C_6$ haloalkyl, $C_1$-$C_6$ alkoxy, or $C_1$-$C_6$ haloalkoxy; and/or $R_7$ is H, halo, $C_1$-$C_6$ alkyl, $C_1$-$C_6$ haloalkyl, $C_1$-$C_6$ alkoxy, or $C_1$-$C_6$ haloalkoxy; and/or $R_8$ is H.

6. The compound of claim 2, or a pharmaceutically acceptable salt thereof, wherein:

$R_5$ is H, halo, $C_1$-$C_6$ alkyl, $C_1$-$C_6$ haloalkyl, or $C_1$-$C_6$ alkoxy; and/or $R_6$ is H, halo, $C_1$-$C_6$ alkyl, $C_1$-$C_6$ haloalkyl, $C_1$-$C_6$ alkoxy, or $C_1$-$C_6$ haloalkoxy; and/or $R_7$ is H, halo, $C_1$-$C_6$ alkyl, $C_1$-$C_6$ haloalkyl, $C_1$-$C_6$ alkoxy, or $C_1$-$C_6$ haloalkoxy; and/or $R_8$ is H.

7. The compound of claim 1, or a pharmaceutically acceptable salt thereof, wherein:

$R_9$ is H, $C_1$-$C_6$ alkyl, or $C_1$-$C_6$ alkoxy; and/or $R_{10}$ is H or halo; and/or $R_{11}$ is halo, $C_1$-$C_6$ alkoxy, or $C_1$-$C_6$ haloalkoxy; and/or $R_{12}$ is H, and $R_{13}$ is H.

8. The compound of claim 2, or a pharmaceutically acceptable salt thereof, wherein:
$R_9$ is H, $C_1$-$C_6$ alkyl, or $C_1$-$C_6$ alkoxy; and/or
$R_{10}$ is H or halo; and/or
$R_{11}$ is halo, $C_1$-$C_6$ alkoxy, or $C_1$-$C_6$ haloalkoxy; and/or
$R_{12}$ is H, and $R_{13}$ is H.
9. The compound of claim 1, wherein the compound is selected from:
16
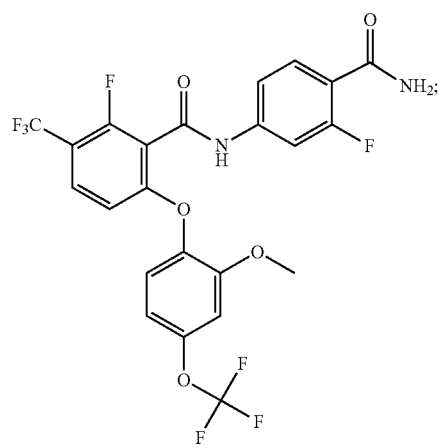
24
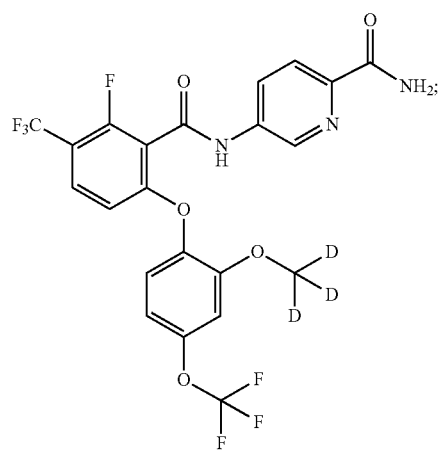
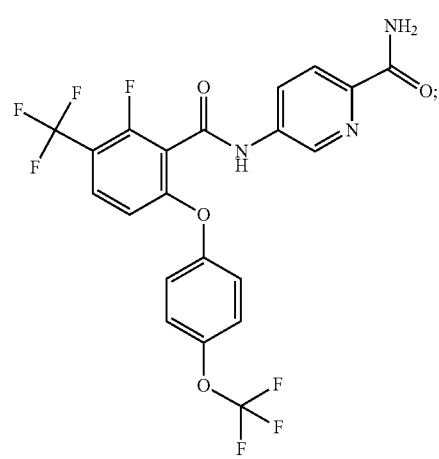
65
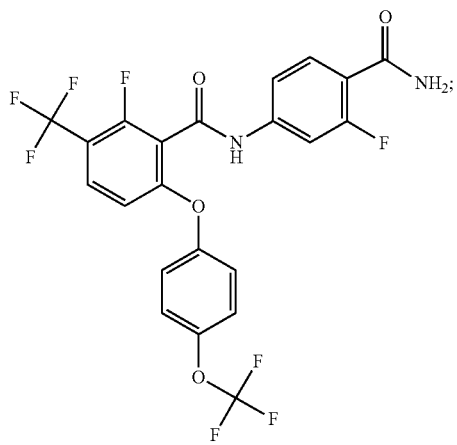
66
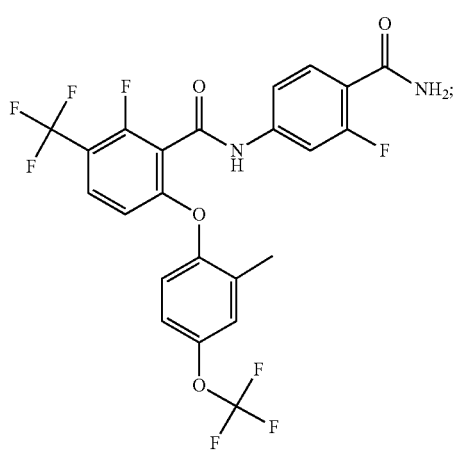
67
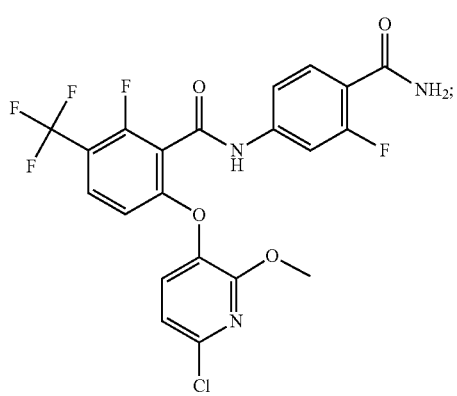

-continued
82
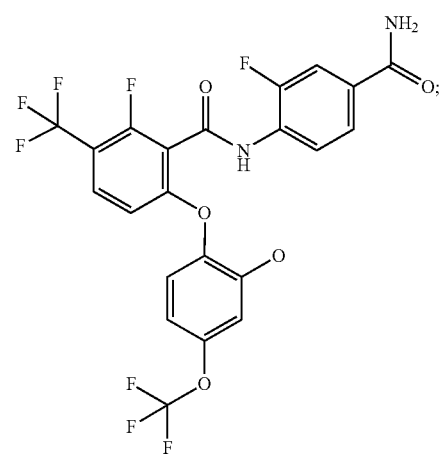
127
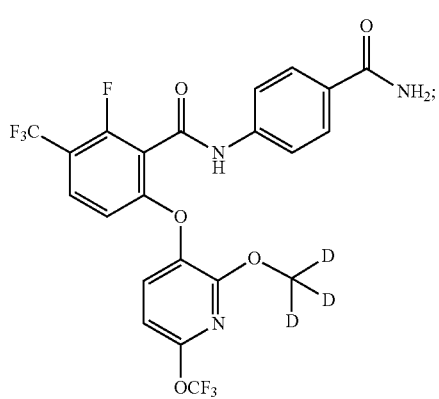
132
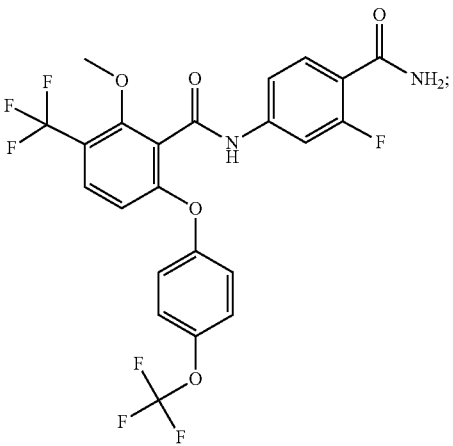
-continued
154
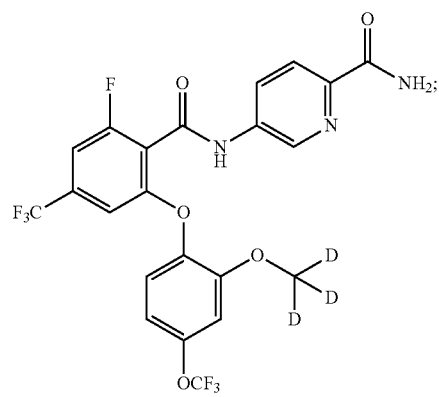
159
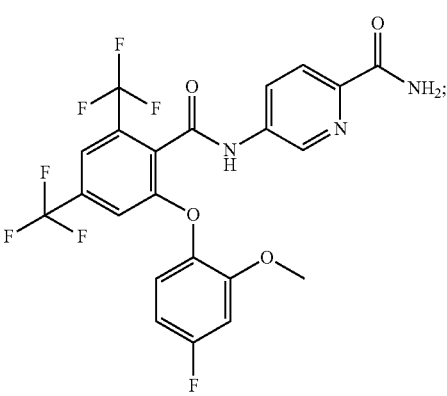
161
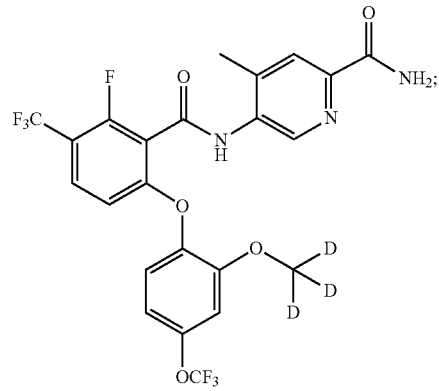
167
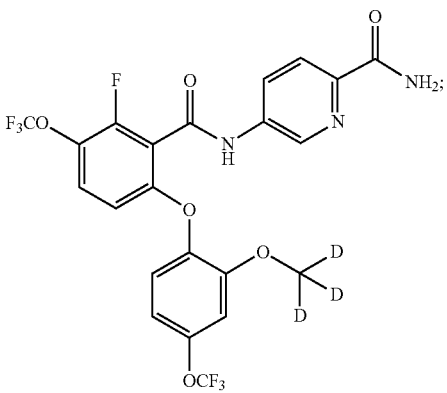

773
-continued
173
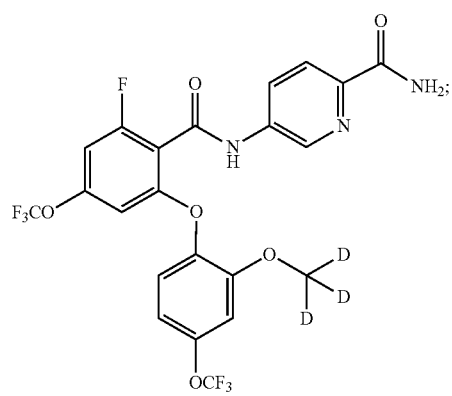
174
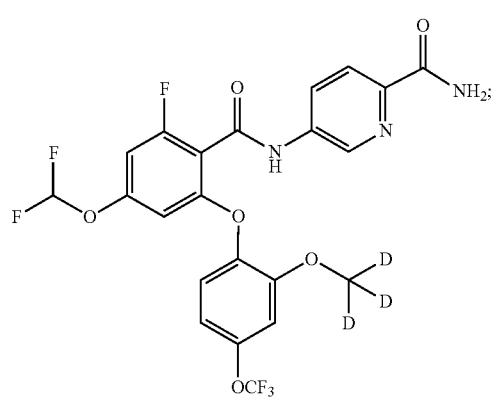
176
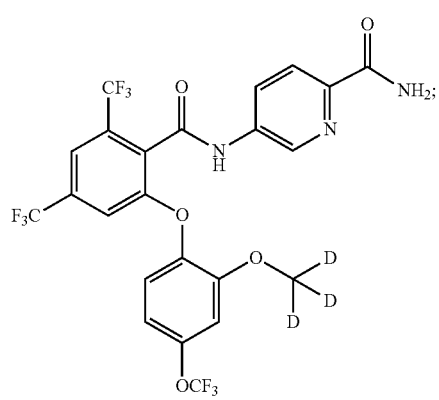
181
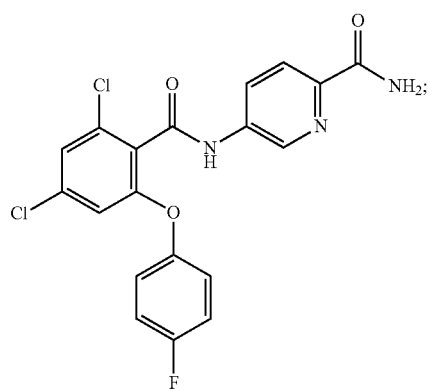
774
-continued
182
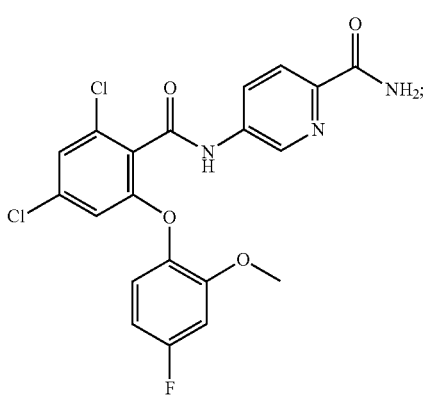
183
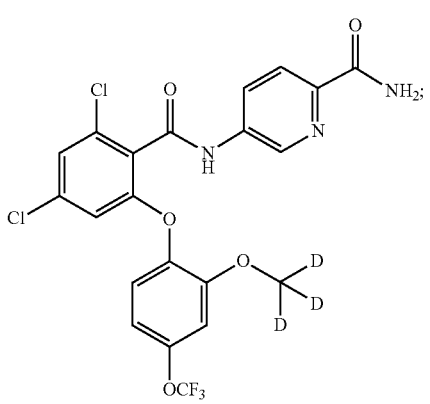
184
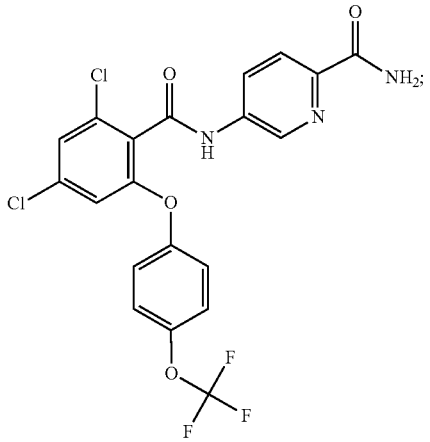

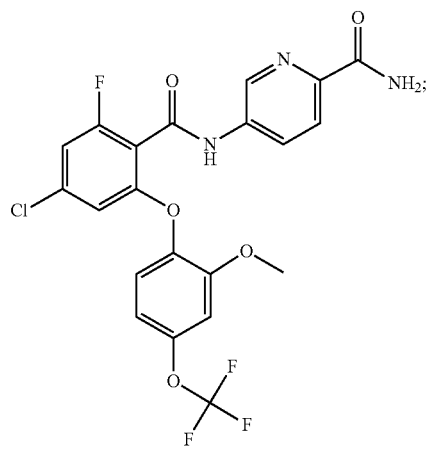
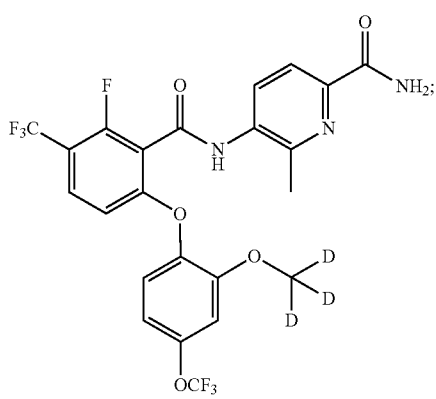
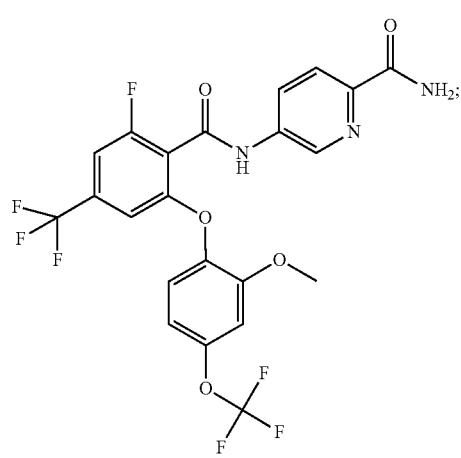

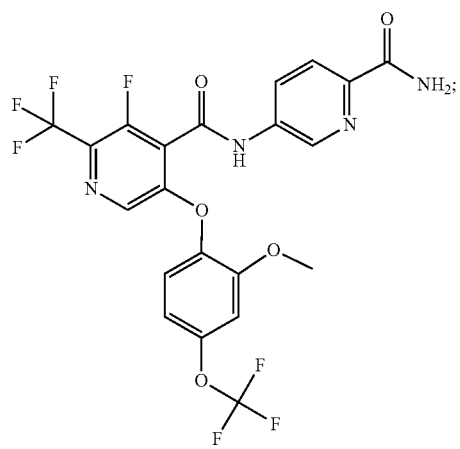
194
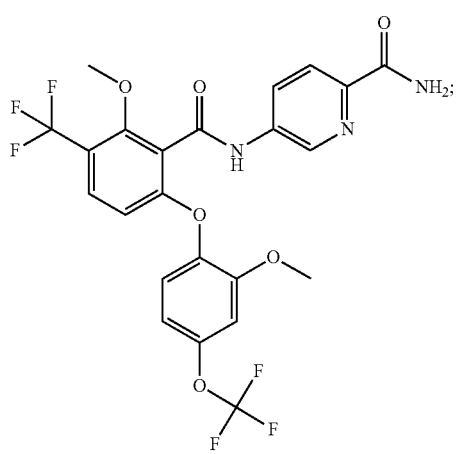
202
197
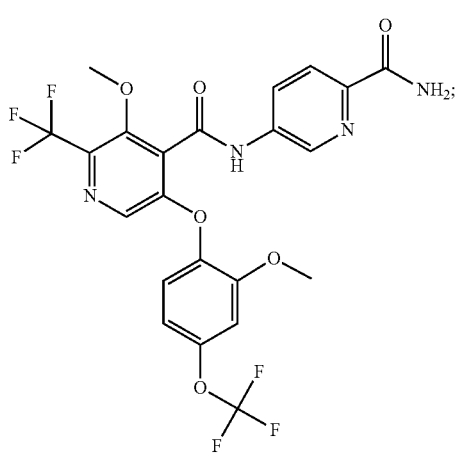
203
198
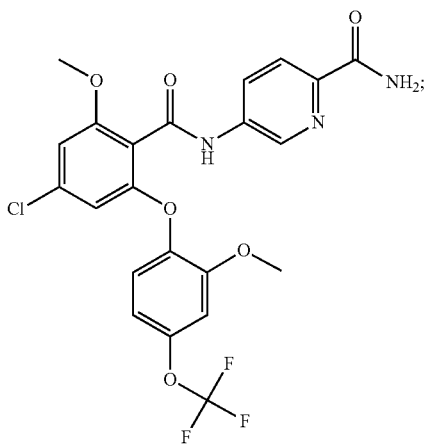
204

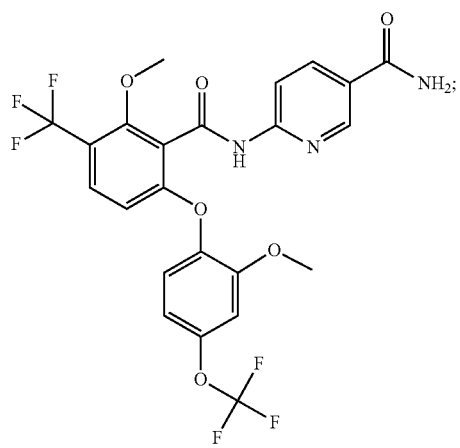
205
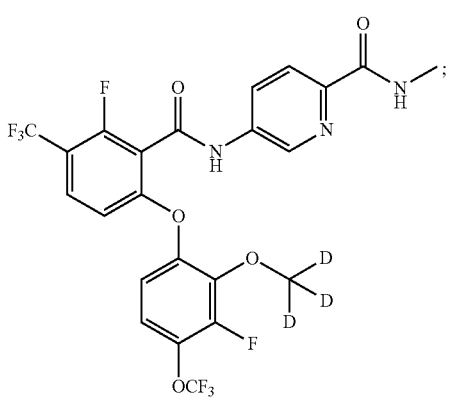
229
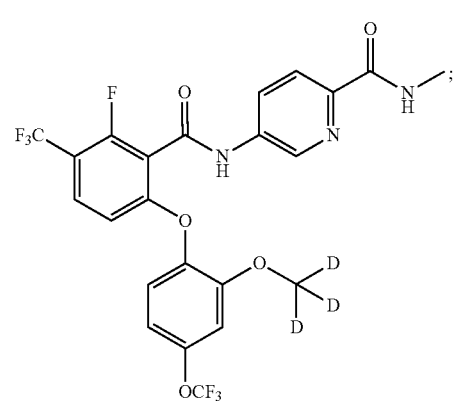
209
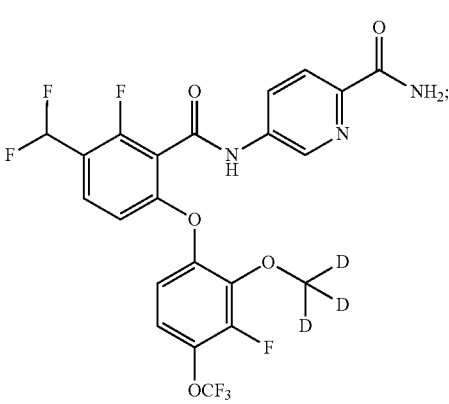
236
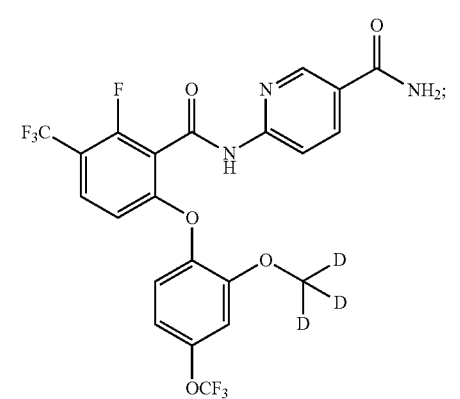
212
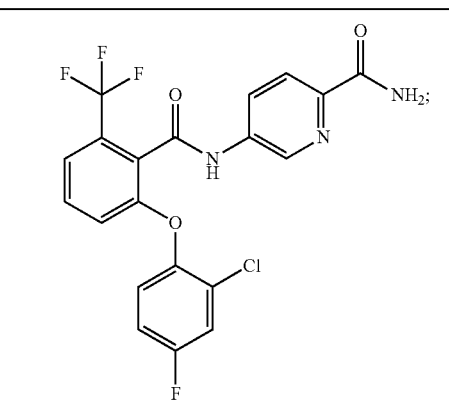
256
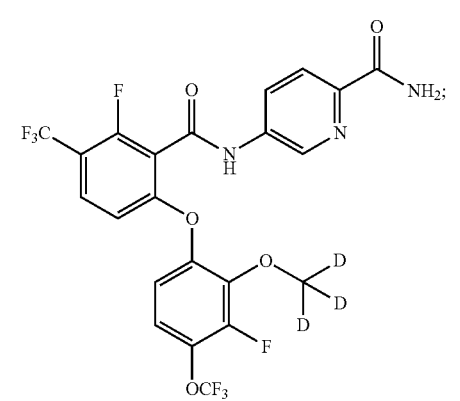
221

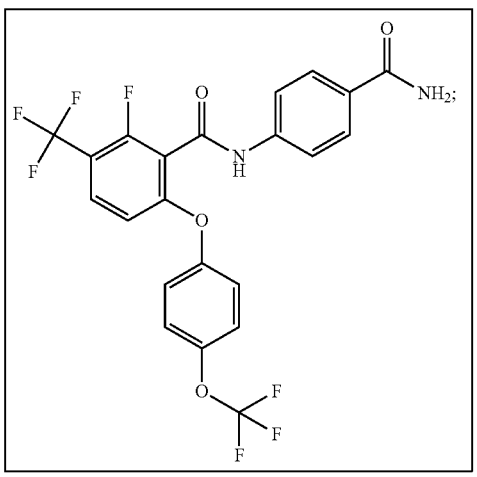

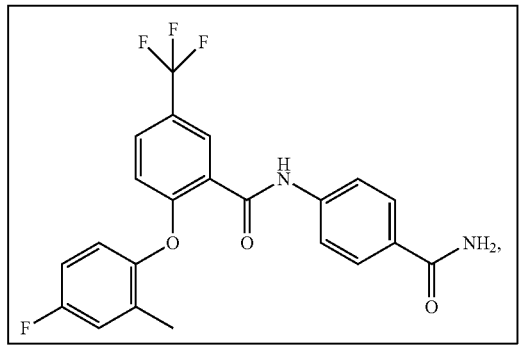

or a pharmaceutically acceptable salt thereof.

10. The compound of claim 1.

11. A pharmaceutical composition comprising the compound of claim 1, or a pharmaceutically acceptable salt thereof.

12. A method of inhibiting a voltage-gated sodium channel in a subject comprising administering to the subject the compound of claim 1, or a pharmaceutically acceptable salt thereof;
  optionally wherein the voltage-gated sodium channel is Nav1.8.

13. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of the compound of claim 1, or a pharmaceutically acceptable salt thereof.

14. The method of claim 13, wherein the method comprises treating or lessening the severity in the subject of:
  (i) neuropathic pain, optionally wherein the neuropathic pain comprises post-herpetic neuralgia, small-fiber neuropathy, or diabetic neuropathy; or
  (ii) musculoskeletal pain, optionally wherein the musculoskeletal pain comprises osteoarthritis pain; or
  (iii) acute pain, optionally wherein the acute pain comprises acute post-operative pain; or
  (iv) postsurgical pain, optionally wherein the postsurgical pain comprises bunionectomy pain or abdominoplasty pain; or
  (v) visceral pain.

15. The method of claim 13, wherein said subject is treated with one or more additional therapeutic agents administered concurrently with, prior to, or subsequent to treatment with the compound, or pharmaceutically acceptable salt.

* * * * *